United States Patent
Chovatia et al.

(10) Patent No.: US 12,018,021 B2
(45) Date of Patent: Jun. 25, 2024

(54) THIOPHENE DERIVATIVES FOR THE TREATMENT OF DISORDERS CAUSED BY IGE

(71) Applicant: UCB Biopharma SRL, Brussels (BE)

(72) Inventors: Pfrafulkumar Tulshibhai Chovatia, Oxfordshire (GB); Rickki Lee Connelly, Oxfordshire (GB); Richard Jeremy Franklin, Berkshire (GB); Gregory William Haslett, Berkshire (GB); Alistair James Henry, Berkshire (GB); James Madden, Oxfordshire (GB); Judi Charlotte Neuss, Berkshire (GB); Timothy John Norman, Berkshire (GB); Oliver Philps, Oxfordshire (GB); William Ross Pitt, Berkshire (GB); Konstantinos Rampalakos, Oxfordshire (GB); Matthew Duncan Selby, Berkshire (GB); Selvaratnam Suganthan, Oxfordshire (GB); Giancarlo Trani, Oxfordshire (GB); Zhaoning Zhu, Berkshire (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 16/973,701

(22) PCT Filed: Jun. 20, 2019

(86) PCT No.: PCT/EP2019/066414
§ 371 (c)(1),
(2) Date: Dec. 9, 2020

(87) PCT Pub. No.: WO2019/243550
PCT Pub. Date: Dec. 26, 2019

(65) Prior Publication Data
US 2022/0332709 A1    Oct. 20, 2022

(30) Foreign Application Priority Data

Jun. 21, 2018 (EP) .................................. 18179126

(51) Int. Cl.
| | |
|---|---|
| C07D 409/14 | (2006.01) |
| C07D 333/50 | (2006.01) |
| C07D 333/78 | (2006.01) |
| C07D 409/04 | (2006.01) |
| C07D 409/06 | (2006.01) |
| C07D 409/12 | (2006.01) |
| C07D 413/04 | (2006.01) |
| C07D 413/12 | (2006.01) |
| C07D 417/12 | (2006.01) |
| C07D 487/04 | (2006.01) |
| C07D 495/04 | (2006.01) |

(Continued)

(52) U.S. Cl.
CPC ......... *C07D 409/14* (2013.01); *C07D 333/50* (2013.01); *C07D 333/78* (2013.01); *C07D 409/04* (2013.01); *C07D 409/06* (2013.01); *C07D 409/12* (2013.01); *C07D 413/04* (2013.01); *C07D 413/12* (2013.01); *C07D 417/12* (2013.01); *C07D 487/04* (2013.01); *C07D 495/04* (2013.01); *C07D 495/10* (2013.01); *C07D 498/10* (2013.01)

(58) Field of Classification Search
CPC .. C07D 409/14; C07D 333/50; C07D 333/78; C07D 409/04; C07D 409/06; C07D 409/12; C07D 413/04; C07D 413/12; C07D 417/12; C07D 487/04; C07D 495/04; C07D 495/10; C07D 498/10
See application file for complete search history.

(56) References Cited

U.S. PATENT DOCUMENTS

| 6,414,013 B1 | 7/2002 | Fancelli et al. |
| 2004/0171603 A1 | 9/2004 | Pato et al. |

(Continued)

FOREIGN PATENT DOCUMENTS

| EP | 0 317 295 | 5/1989 |
| JP | 2001 151780 | 6/2001 |

(Continued)

OTHER PUBLICATIONS

Mkrtchyan et al., "-Substituted Tetra-Hydrobenzo[b] Thieno[2,3-d] Pyrimidin-4-Ones and Their Anticonvulsant Activity", Helv. Chim. Acta. J. Am. Chem. Soc. J. Am. Chem. Soc., Jan. 1, 1963, pp. 2658-2666.

(Continued)

*Primary Examiner* — Jared Barsky
(74) *Attorney, Agent, or Firm* — McDonnell Boehnen Hulbert & Berghoff LLP

(57) ABSTRACT

Thiophene derivatives of formula (I) and a pharmaceutically acceptable salt thereof are provided. These compounds have utility for the treatment or prevention of disorders caused by IgE, such as allergy, type 1 hypersensitivity or familiar sinus inflammation.

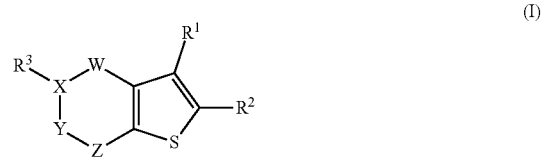

15 Claims, No Drawings

(51) Int. Cl.
    *C07D 495/10*     (2006.01)
    *C07D 498/10*     (2006.01)

(56) References Cited

U.S. PATENT DOCUMENTS

| | | | | |
|---|---|---|---|---|
| 2005/0085531 | A1* | 4/2005 | Hodge | A61P 37/00 514/444 |
| 2009/0018114 | A1 | 1/2009 | Carroll | |
| 2009/0176773 | A1 | 7/2009 | Klussmann et al. | |
| 2015/0045327 | A1 | 2/2015 | Van Der Plas et al. | |

FOREIGN PATENT DOCUMENTS

| | | |
|---|---|---|
| JP | 2001151780 | 6/2001 |
| JP | 2004501146 | 1/2004 |
| JP | 2004520296 | 7/2004 |
| JP | 20076507530 | 3/2007 |
| JP | 2008540586 | 11/2008 |
| JP | 2010533194 | 10/2010 |
| JP | 2016527296 | 9/2016 |
| WO | WO 01/17516 | 7/2001 |
| WO | WO 01/47874 | 7/2001 |
| WO | WO 01/98290 | 12/2001 |
| WO | WO 2002/47762 | 6/2002 |
| WO | WO 2005/023818 | 3/2005 |
| WO | WO 2005/033102 | 4/2005 |
| WO | WO 2005/044008 | 5/2005 |
| WO | WO 2006/122546 | 11/2006 |
| WO | WO 2009/079373 | 6/2009 |
| WO | WO 2015/018823 | 2/2015 |

OTHER PUBLICATIONS

Gupta et al., "Discovery of dual binding site acetylcholinesterase inhibitors identified by pharmacophore modeling and sequential virtual screening techniques", Bioorganic & Medicinal Chemistry Letters, Pergamon, Amsterdam, NL, vol. 21, No. 4, Dec. 28, 2010, pp. 1105-1112.

Hung The Dang et al., "Syntheses and biological evaluation of 2-amino-3-acyl-tetrahydrobenzothiophene derivatives; antibacgterial agents with antivirulence activity", Organic & Biomolecular Chemistry, vol. 12, No. 12, Jan. 1, 2014, pp. 1942-1956.

Van Der Plas et al., "Discovery of N-(3-Carboaoyl-5,5,7,7-tetramethyl-5,7-dihydro-4 H -thieno[2,3- c]pyran-2-yl)-1 H-pyrazole-5-carboxamide (GLPG1837), a Novel Potentiator Which Can Open Class III Mutant Cystic Fibrosis Transmembrane Condutcance Regulator (CFTR) Channels to a High Extent", Journal Of Medicinal Chemistry, vol. 61, No. 4, Nov. 17, 2017, pp. 1425-1435.

Andersen et al., "Discovery and SAR of a Novel Selective and orally Bioavailable Nonpeptide Classical Competitive Inhibitor Class of Protein-Tyrosine Phosphatase 1B", Journal of Medicinal Chemistry, American Chemical Society, US, vol. 45, Jan. 1, 2002, pp. 4443-4459.

International Search Report and Written Opinion dated Sep. 2, 2019 for International Application No. PCT/EP2019/0664, 23 pages.

Extended European Search Report dated Aug. 10, 2018 for European Application No. 18179126.0, 14 pages.

Fugita et al., "Synthesis and Bioactivities of Novel Bicyclic Thiophenes and 4,5,6,7-Tetrahydrothieno[2,3-c]pyridines as Inhibitors of Tumor Necrosis Factor-ax (TNF-ax) Production", Bioorg. Med. Chem. Lett. 12 (2002) 1897-1900.

Banhegyi et al., "New Method for the Synthesis of 2-Acylamino-1-benzothiophene-3-carboxamide Derivatives from the Corresponding Esters, Synthetic Communications", 2008, vol. 38, pp. 3270-3276, DOI: 10.1080/00397910802116591.

Registry 9STN) [online], 2015, [Search Date: May 31, 2023], CAS registry No. 1798032-57-1.

Registry 9STN) [online], 2015, [Search Date: May 31, 2023], CAS registry No. 1375988-00-3.

Registry 9STN) [online], 2015, [Search Date: May 31, 2023], CAS registry No. 1320130-87-7.

Registry 9STN) [online], 2015, [Search Date: May 31, 2023], CAS registry No. 925569-42-2.

Dyson et al., "Introduction Mechanism of action of the drugs", 1964, Chemistry of Synthetic Drugs, pp. 12-19.

Pokrovskij, "Drugs", Popular Medical Encyclopedia, 1997, Ulyanovsk, p. 317.

Japanese Office Action for Japanese Patent Application No. 2020-570719 mailed Jun. 22, 2023, 7 pages.

* cited by examiner

THIOPHENE DERIVATIVES FOR THE TREATMENT OF DISORDERS CAUSED BY IGE

CROSS-REFERENCE TO RELATED APPLICATIONS

This application is a U.S. national phase of International Application No. PCT/EP2019/066414, filed Jun. 20, 2019, which claims priority from European Patent Application no. 18179126.0, filed Jun. 21, 2018, the disclosure of each of which is hereby incorporated by reference in its entirety.

TECHNICAL FIELD

The present invention relates to thiophene derivatives of formula (I), processes for preparing them, pharmaceutical compositions containing them and their use in treating disorders caused by IgE (such as allergic responses, non-allergic mast cell responses or certain autoimmune responses), and in particular disorders caused by the interaction of IgE with the FcεRI receptor.

BACKGROUND OF THE INVENTION

IgE (immunoglobulin E) is a member of the immuno-globulin family and mediates allergic responses such as asthma, food allergies, type 1 hypersensitivity and the familiar sinus inflammation. IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII). Upon exposure of a mammal to an allergen, B-cells are clonally amplified which synthesize IgE that binds the allergen. This IgE in turn is released into the circulation by the B-cells where it is bound by B-cells (through FcεRII) and by mast cells and basophils through the so-called high affinity receptor (FcεRI) found on the surface of the mast cells and basophils. Such mast cells and basophils are thereby sensitized for allergen. The next exposure to the allergen cross-links the FcεRI on these cells and thus activate their release of histamine and other factors which are responsible for clinical hypersensitivity and ana-phylaxis. Currently, allergic diseases, urticaria, and asthma are usually treated with one or more of the following drugs: (1) antihistamines and antileukotrienes which antagonize the inflammatory mediators histamine and leukotrienes, (2) local or systemic (oral or injectable) corticosteroids or immunosuppressants which suppress a broad spectrum of inflammatory mechanisms, (3) short or long-acting bronchodilators which relax smooth muscle of constricted airway in asthma, or (4) mast cell stabilizers which inhibit the degranulation of mast cells that is normally triggered by IgE-binding at FcεRI, (5) biologicals which prevent the binding of IgE at FcεRI.

However, there is still a need to identify compounds which have therapeutic utility in the treatment or prevention of disorders caused by IgE, particularly disorders caused by the interaction of IgE with the FcεRI receptor.

SUMMARY OF THE INVENTION

Surprisingly, it has been found that compounds of formula (I) and their pharmaceutically acceptable salts can be used for this purpose.

DETAILED DESCRIPTION

The present invention provides compounds of formula (I) and pharmaceutically acceptable salts thereof:

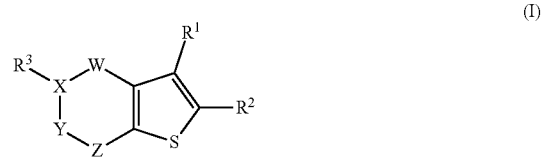

(I)

wherein
X represents CH, N, or C—$R^4$, wherein when X is C—$R^4$, $R^3$ and $R^4$ may be linked to form a 4-6 membered cycloalkyl or heterocyclic ring,
  any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, aryl and heteroaryl, with aryl and heteroaryl optionally substituted by one or more substituents selected from halogen, OH, $C_1$-$C_6$ alkyl, $C_1$-$C_6$ alkoxy and $C_1$-$C_2$ haloalkyl;
when X represents N, then W, Y and Z are C or one of W, Y and Z is a single bond, the other two being C;
when X represents CH or C—$R^4$, then W, Y and Z are C, or one of W, Y or Z is a single bond, O, S, S(O), S(O)$_2$ or N, the other two being C;
  when W, Y, or Z are C, each C may be substituted by 1 or 2 groups which are independently selected from H, halogen, $SF_5$, =O, =NOH, —OH, —CN, —C(O)Me, —C(O)OH, —C(O)$NH_2$, NH—C(O)O—$C_1$-$C_4$ alkyl, —$NO_2$, $NH_2$, NHMe, $NMe_2$, SH, SMe, SOMe, $SO_2$Me, $C_1$-$C_4$ alkyl, $C_3$-$C_4$ cycloalkyl, $C_1$-$C_4$ alkoxy, heterocycle, $C_1$-$C_4$ heteroalkyl, which may be linked to form a 3-6 membered cycloalkyl or 4-6 membered heterocyclic ring,
  any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, which may be linked to form a 3-6 membered cycloalkyl or 4-6 membered heterocyclic ring;
wherein
  when W, Y or Z is N, this N may be independently substituted by H, $C_1$-$C_4$ alkyl, $C_3$-$C_4$ cycloalkyl, heterocycle, —C(O)Me, —C(O)$NH_2$, —C(O)OH, —S(O)Me, —S(O)$_2$Me, —S(O)$_2NH_2$, any of which may be optionally substituted by one or more substituents selected from halogen, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$;
  and W, X, Y and Z may be linked directly or via substituents to form a ring;
$R^1$ is selected from —C(O)O$R^5$, —C(O)N($R^6$)($R^7$), —S(O)$_2$N($R^8$)($R^9$), —S(O)$_2R^{10}$, —S(O)$R^{10}$ and —S(O)(=N$R^{11}$)$R^{10}$;
$R^2$ represents —N($R^{12}$)C(O)$R^{13}$;
$R^3$ is selected from H, —OH, $C_1$-$C_8$ alkyl, —N$R^dR^c$, —NH—$R^{14}$—NH—$R^a$, —NMe-$R^{14}$—NH—$R^a$, —NH—$R^{14}$—NMe-$R^a$, —CO—N$R^dR^c$, —NH—COO—$R^c$, —NH—CO—$R^c$, —COOH, —COO—$C_1$-$C_8$ alkyl, —CO—$C_1$-$C_8$ alkyl, —$C_1$-$C_8$ alkylene-COO—$C_1$-$C_8$ alkyl, —$C_1$-$C_8$ alkylene-N$R^a$—COO—$C_1$-$C_8$ alkyl, —$C_1$-$C_8$ alkylene-NR$^d$R$^c$, —C$_1$-C$_8$ alkylene-NH—R$^{14}$—NH—R$^a$, heteroaryl, —CN, —CH=N—OH, —CF$_3$, alkylamino, amino, —NH—SO—C$_1$-C$_8$ alkyl, —NH—SO$_2$—C$_1$-C$_8$ alkyl, heteroalkyl-amino, aryl, heterocycle, C$_3$-C$_6$ cycloalkyl, —NHS(O)(=NH)Me, —SO$_2$—C$_1$-C$_8$ alkyl, —NH—C(CH$_3$)=N—CN, —NH—CH=N—CN, —NH—S(=O)(=N)—C$_1$-C$_2$ alkyl, any of which may be optionally substituted by one or more substituents selected from halogen, —OH, =O, —COOH, —COH, —CN, SMe, —NR$^d$R$^c$, —OR$^c$, C$_1$-C$_2$ alkoxy, O—C$_1$-C$_2$ haloalkyl, C$_1$-C$_2$ alkyl, C$_1$-C$_2$ heteroalkyl, C$_1$-C$_2$ haloalkyl, C$_1$-C$_2$ alkylene-O—C$_1$-C$_2$ alkyl, C$_1$-C$_2$ alkylene-C$_3$-C$_4$ cycloalkyl, heterocycle, C$_3$-C$_6$ cycloalkyl, aryl, heteroaryl, C$_3$-C$_6$ cycloalkyl-amino, heterocyclo-amino, aryl-amino, heteroaryl-amino, —CONR$^d$R$^c$, —NHCO—R$^a$, —NHCOO—C$_1$-C$_4$ alkyl, —CO—C$_1$-C$_2$ alkyl, —COO—R$^a$, which may be linked to form a ring, and wherein —CONR$^d$R$^c$ and —NR$^d$R$^c$ may be linked to form a seven-membered ring fused to a six-membered aryl group;

with aryl, heteroaryl, heterocycle and cycloalkyl optionally substituted by one or more substituents selected from halogen oxo, cyano, OH, —NOOH, C$_1$-C$_6$ alkyl, C$_1$-C$_6$ alkoxy, halo-C$_1$-C$_6$ alkoxy, C$_3$-C$_6$-cycloalkyl-C$_1$-C$_3$-alkoxy, —O—CO—C$_1$-C$_6$ alkyl, C$_3$-C$_6$ cycloalkyl, C$_1$-C$_2$ haloalkyl, C$_2$-C$_4$ heterocycle, acetyl, acetylphenyl, —CONR$^d$R$^c$, COO—C$_1$-C$_8$ alkyl, —S(O)NH—C$_1$-C$_2$-alkyl, —S(O)$_n$—C$_1$-C$_2$-alkyl, heteroaryl which may be optionally substituted with one or more halogen group, C$_1$-C$_2$-alkyl, with n equal 0, 1 or 2;

R$^4$ is selected from halogen, OH, CN, NO$_2$, NH$_2$, NHMe, NMe$_2$, SH, SMe, SOMe, SO$_2$Me, C$_1$-C$_4$ alkyl, C$_3$-C$_4$ cycloalkyl, C$_1$-C$_3$ alkoxy, C$_1$-C$_3$ heteroalkyl, heterocycle, any of which may be optionally substituted by one or more substituents selected from halogen, =O, OH, SMe, C$_1$-C$_2$ alkoxy, O—C$_1$-C$_2$ haloalkyl, C$_1$-C$_2$ alkyl, C$_1$-C$_2$ heteroalkyl, C$_1$-C$_2$ haloalkyl NH$_2$, NHMe, NMe$_2$, which may be linked to form a ring;

R$^5$ is selected from C$_1$-C$_8$ alkyl, C$_2$-C$_8$ heteroalkyl, C$_2$-C$_8$ alkenyl, C$_2$-C$_8$ heteroalkenyl, C$_2$-C$_8$ alkynyl, C$_2$-C$_8$ heteroalkynyl, C$_3$-C$_8$ cycloalkyl, heterocycle, C$_4$-C$_8$ cycloalkenyl, aryl, heteroaryl, —C$_1$-C$_2$ alkylene-C$_3$-C$_6$ cycloalkyl, —C$_1$-C$_2$ alkylene-heterocycle, —C$_1$-C$_2$ alkylene-aryl, —C$_1$-C$_2$ alkylene-heteroaryl;

any of which may be optionally substituted by one or more substituents selected from halogen, =O, OH, SMe, C$_1$-C$_2$ alkoxy, —O—C$_1$-C$_2$ haloalkyl, C$_1$-C$_2$ alkyl, C$_1$-C$_2$ heteroalkyl, C$_1$-C$_2$ haloalkyl, NH$_2$, NHMe, NMe$_2$ which may be linked to form a ring;

R$^6$, R$^8$ and R$^{12}$ are independently selected from H and C$_1$-C$_3$ alkyl, any of which may be optionally substituted by 1 to 7 halogen;

R$^7$, R$^9$ and R$^{11}$ are independently selected from H, C$_1$-C$_8$ alkyl, C$_2$-C$_8$ heteroalkyl, C$_2$-C$_8$ alkenyl, C$_2$-C$_8$ heteroalkenyl, C$_2$-C$_8$ alkynyl, C$_2$-C$_8$ heteroalkynyl, C$_3$-C$_8$ cycloalkyl, heterocycle, C$_4$-C$_8$ cycloalkenyl, C$_3$-C$_8$ heterocycloalkenyl, aryl, heteroaryl, —C$_1$-C$_2$ alkylene-C$_3$-C$_6$ cycloalkyl, —C$_1$-C$_2$ alkylene-heterocycle, —C$_1$-C$_2$ alkylene-aryl, —C$_1$-C$_2$ alkylene-heteroaryl, —N—C$_1$-C$_7$ alky, —N—C$_3$-C$_8$ cycloalkyl, —N-heterocycle, —N-heteroaryl, C$_1$-C$_7$ alkoxy, —O—C$_3$-C$_8$ cycloalkyl, —O-heterocycle, —O—heteroaryl, any of which may be optionally substituted by one or more substituents selected from halogen, =O, OH, SMe, C$_1$-C$_2$ alkoxy, —O—C$_1$-C$_2$ haloalkyl, C$_1$-C$_2$ alkyl, C$_1$-C$_2$ heteroalkyl, C$_1$-C$_2$ haloalkyl, NH$_2$, NHMe, NMe$_2$, which may be linked to form a ring;

R$^{10}$ is selected from H, C$_1$-C$_8$ alkyl, C$_2$-C$_8$ heteroalkyl, C$_2$-C$_8$ alkenyl, C$_2$-C$_8$ heteroalkenyl, C$_2$-C$_8$ alkynyl, C$_2$-C$_8$ heteroalkynyl, C$_3$-C$_8$ cycloalkyl, heterocycle, C$_4$-C$_8$ cycloalkenyl, C$_3$-C$_8$ heterocycloalkenyl, aryl, heteroaryl, —C$_1$-C$_3$ alkylene-C$_3$-C$_6$ cycloalkyl, —C$_1$-C$_3$ alkylene-heterocycle, —C$_1$-C$_3$ alkylene-aryl, —C$_1$-C$_3$ alkylene-heteroaryl, —N—C$_1$-C$_8$ alkyl, any of which may be optionally substituted by one or more substituents selected from halogen, =O, OH, SMe, C$_1$-C$_2$ alkoxy, —O—C$_1$-C$_2$ haloalkyl, C$_1$-C$_2$ alkyl, C$_1$-C$_2$ heteroalkyl, C$_1$-C$_2$ haloalkyl, NH$_2$, NHMe, NMe$_2$, which may be linked to form a ring;

R$^{13}$ is selected from C$_1$-C$_7$ alkyl, C$_1$-C$_6$ heteroalkyl, C$_3$-C$_8$ cycloalkyl, —C$_1$-C$_2$ alkylene-C$_3$-C$_6$ cycloalkyl, C$_3$-C$_5$ heterocycle, any of which may be optionally substituted by one or more substituents selected from halogen, =O, OH, SMe, C$_1$-C$_2$ alkoxy, O—C$_1$-C$_2$ haloalkyl, C$_1$-C$_2$ alkyl, C$_1$-C$_2$ heteroalkyl, C$_1$-C$_2$ haloalkyl, NH$_2$, NHMe, NMe$_2$, which may be linked to form a cycloalkyl or heterocyclic ring;

R$^6$ and R$^7$ may be linked to one another to form a ring;
R$^8$ and R$^9$ may be linked to one another to form a ring;
R$^{12}$ and R$^{13}$ may be linked to one another to form a ring;
R$^{14}$ is C=O, C=S, C=N—OH, C=NR$^b$, C=CH—NO$_2$, SO$_2$, and C$_3$-C$_6$ cycloalkenyl which may be substituted with 1 or 2 =O;

R$^a$ is selected from H, C$_1$-C$_8$ alkyl, heteroalkyl, C$_1$-C$_8$ alkoxy, heterocycle, C$_3$-C$_8$ cycloalkyl, heteroaryl and aryl, any of which may be optionally substituted by one or more substituents selected from halogen, =O, OH, SMe, C$_1$-C$_2$ alkoxy, —O—C$_1$-C$_2$ haloalkyl, C$_1$-C$_2$ alkyl, C$_3$-C$_6$ cycloalkyl, C$_3$-C$_6$ heterocycloalkyl, C$_1$-C$_2$ heteroalkyl, C$_1$-C$_2$ haloalkyl, aryl, heteroaryl, NH$_2$, NHMe, NMe$_2$ which may be linked to form a ring;

R$^b$ is selected from CN, aryl, heteroaryl, —NO$_2$, —O—C$_1$-C$_2$ alkyl, —CO—O—C$_1$-C$_2$ alkyl, with aryl and heteroaryl optionally substituted by one or more C$_1$-C$_2$ alkyl;

R$^c$ is selected from H, aryl, heteroaryl, C$_3$-C$_6$ cycloalkenyl, C$_3$-C$_8$ cycloalkyl, heterocycle, C$_1$-C$_8$ alkyl, C$_1$-C$_8$ heteroalkyl, C$_1$-C$_4$ alkylene-C$_3$-C$_6$ cycloalkyl;

any of which may be optionally substituted by one or more substituents selected from C(O)(R$^g$), C(O)N(R$^f$)(R$^g$), halogen, SF$_5$, OH, =O, —COH, —COOH, —CO—O—R$^a$, CN, SMe, SO$_2$Me, SO$_2$R$^g$, C$_1$-C$_4$ alkoxy, O—C$_1$-C$_4$ haloalkyl, C$_1$-C$_4$ alkyl, C$_1$-C$_2$ heteroalkyl, C$_1$-C$_4$ haloalkyl, N(R$^f$)(R$^g$), N(R$^f$)SO$_2$(R$^g$), SO$_2$NH$_2$, SO$_2$NHMe, SO$_2$NMe$_2$, S(O)(NR$^f$)R$^g$, C$_3$-C$_6$ cycloalkyl, heterocycle, C$_1$-C$_4$ alkylene-C$_3$-C$_6$ cycloalkyl, aryl and heteroaryl, which may be linked to form a ring with aryl, heteroaryl, heterocycle and cycloalkyl optionally substituted by one or more substituents selected from halogen, =O, =NH, =NMe, OH, C$_1$-C$_2$ alkyl, C$_1$-C$_2$ alkoxy, —COOH, —COO—C$_1$-C$_2$ alkyl, SO$_2$R$^a$, COR$^a$, SOR$^a$, S(O)(NH)R$^a$, CONHR$^a$, which may be linked to form a ring;

R$^d$ represents H or C$_1$-C$_4$ alkyl
and R$^c$ and R$^d$ may be linked to form a heterocycle;
R$^e$ is selected from —C(O)OR$^a$, —C(O)N(R$^f$)(R$^g$), aryl, heteroaryl, C$_1$-C$_2$ haloalkyl, —CN where R$^f$ and R$^g$ may be linked to form a ring, with aryl and heteroaryl optionally substituted with one or more substituents selected from C1-C2 haloalkyl, C1-C2 alkyl;

$R^f$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, $C_1$-$C_4$ alkylene-$C_3$-$C_6$ cycloalkyl, any of which may be optionally substituted by one or more substituents selected from halogen, =O, =NH, =NMe, OH, aryl, heteroaryl, $C_1$-$C_2$ alkyl, $C_1$-$C_2$ haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, S(O)(NH)$R^a$, CONH$R^a$; $R^g$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, $C_1$-$C_4$ alkylene-$C_3$-$C_6$ cycloalkyl, any of which may be optionally substituted by one or more substituents selected from halogen, =O, =NH, =NMe, OH, aryl, heteroaryl, $C_1$-$C_2$ alkyl, $C_1$-$C_2$ haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, S(O)(NH)$R^a$, CONH$R^a$ $R^f$ and $R^g$ may be linked to form a ring.

According to another embodiment, compounds of the invention are according to formula (Ia)

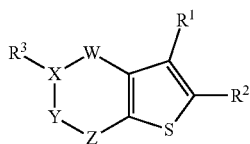

(Ia)

wherein

X represents CH, N, or C—$R^4$, wherein when X is C—$R^4$, $R^3$ and $R^4$ may be linked to form a 4-6 membered cycloalkyl or heterocyclic ring, any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, aryl and heteroaryl, with aryl and heteroaryl optionally substituted by one or more substituents selected from halogen, OH, $C_1$-$C_6$ alkyl, $C_1$-$C_6$ alkoxy and $C_1$-$C_2$ haloalkyl;

when X represents N, then W, Y and Z are C or one of W, Y and Z is a single bond, the other two being C;

when X represents CH or C—$R^4$, then W, Y and Z are C, or one of W, Y or Z is a single bond, O, S, S(O), $S(O)_2$ or N, the other two being C;

when W, Y, or Z are C, each C may be substituted by 1 or 2 groups which are independently selected from H, halogen, $SF_5$, =O, =NOH, —OH, —CN, —C(O)Me, —C(O)OH, —C(O)$NH_2$, NH—C(O)O—$C_1$-$C_4$ alkyl, —$NO_2$, $NH_2$, NHMe, $NMe_2$, SH, SMe, SOMe, $SO_2Me$, $C_1$-$C_4$ alkyl, $C_3$-$C_4$ cycloalkyl, $C_1$-$C_4$ alkoxy, heterocycle, $C_1$-$C_4$ heteroalkyl, which may be linked to form a 3-6 membered cycloalkyl or 4-6 membered heterocyclic ring, any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, which may be linked to form a 3-6 membered cycloalkyl or 4-6 membered heterocyclic ring;

wherein when W, Y or Z is N, this N may be independently substituted by H, $C_1$-$C_4$ alkyl, $C_3$-$C_4$ cycloalkyl, heterocycle, —C(O)Me, —C(O)$NH_2$, —C(O)OH, —S(O)Me, —S(O)$_2$Me, —S(O)$_2$$NH_2$, any of which may be optionally substituted by one or more substituents selected from halogen, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$;

and W, X, Y and Z may be linked directly or via substituents to form a ring;

$R^1$ is selected from —C(O)$OR^5$, —C(O)N($R^6$)($R^7$), —S(O)$_2$N($R^8$)($R^9$), —S(O)$_2$$R^{10}$, —S(O)$R^{10}$ and —S(O)(=N$R^{11}$)$R^{10}$;

$R^2$ represents —N($R^{12}$)C(O)$R^{13}$;

$R^3$ is selected from H, —OH, $C_1$-$C_8$ alkyl, —N$R^dR^c$, —NH—$R^{14}$—NH—$R^a$, —NMe-$R^{14}$—NH—$R^a$, —NH—$R^{14}$—NMe-$R^a$, —CO—N$R^dR^c$, —NH—COO—$R^c$, —NH—CO—$R^c$, —COOH, —COO—$C_1$-$C_8$ alkyl, —CO—$C_1$-$C_8$ alkyl, —$C_1$-$C_8$ alkylene-COO—$C_1$-$C_8$ alkyl, —$C_1$-$C_8$ alkylene-N$R^a$—COO—$C_1$-$C_8$ alkyl, —$C_1$-$C_8$ alkylene-N$R^dR^c$, —$C_1$-$C_8$ alkylene-NH—$R^{14}$—NH—$R^a$, heteroaryl, —CN, —CH=N—OH, —$CF_3$, alkylamino, amino, —NH—SO—$C_1$-$C_8$ alkyl, —NH—$SO_2$—$C_1$-$C_8$ alkyl, heteroalkyl-amino, aryl, heterocycle, $C_3$-$C_6$ cycloalkyl, —NHS(O)(=NH)Me, —$SO_2$—$C_1$-$C_8$ alkyl, —NH—C($CH_3$)=N—CN, —NH—CH=N—CN, —NH—S(=O)(=N)—$C_1$-$C_2$ alkyl, any of which may be optionally substituted by one or more substituents selected from halogen, —OH, =O, —COOH, —COH, —CN, SMe, —N$R^dR^c$, —$OR^c$, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $C_1$-$C_2$ alkylene-O—$C_1$-$C_2$ alkyl, $C_1$-$C_2$ alkylene-$C_3$-$C_4$ cycloalkyl, heterocycle, $C_3$-$C_6$ cycloalkyl, aryl, heteroaryl, $C_3$-$C_6$ cycloalkyl-amino, heterocycle-amino, aryl-amino, heteroaryl-amino, —CONR$^dR^c$, —NHCO—$R^a$, —NHCOO—$C_1$-$C_4$ alkyl, —CO—$C_1$-$C_2$ alkyl, —COO—$R^a$, which may be linked to form a ring, with aryl, heteroaryl, heterocycle and cycloalkyl optionally substituted by one or more substituents selected from halogen, OH, $C_1$-$C_6$ alkyl, $C_1$-$C_6$ alkoxy, —O—CO—$C_1$-$C_6$ alkyl, $C_3$-$C_6$ cycloalkyl, $C_1$-$C_2$ haloalkyl and $C_2$-$C_4$ heterocycle;

$R^4$ is selected from halogen, OH, CN, $NO_2$, $NH_2$, NHMe, $NMe_2$, SH, SMe, SOMe, $SO_2Me$, $C_1$-$C_4$ alkyl, $C_3$-$C_4$ cycloalkyl, $C_1$-$C_3$ alkoxy, $C_1$-$C_3$ heteroalkyl, heterocycle, any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl $NH_2$, NHMe, $NMe_2$, which may be linked to form a ring;

$R^5$ is selected from $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_3$-$C_8$ cycloalkyl, heterocycle, $C_4$-$C_8$ cycloalkenyl, aryl, heteroaryl, —$C_1$-$C_2$ alkylene-$C_3$-$C_6$ cycloalkyl, —$C_1$-$C_2$ alkylene-heterocycle, —$C_1$-$C_2$ alkylene-aryl, —$C_1$-$C_2$ alkylene-heteroaryl, any of which may be optionally substituted by one or more substituents selected from halogen, =O, OH, SMe, $C_1$-$C_2$ alkoxy, —O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$ which may be linked to form a ring;

$R^6$, $R^8$ and $R^{12}$ are independently selected from H and $C_1$-$C_3$ alkyl, any of which may be optionally substituted by 1 to 7 halogen;

$R^7$, $R^9$ and $R^{11}$ are independently selected from H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_3$-$C_8$ cycloalkyl, heterocycle, $C_4$-$C_8$ cycloalkenyl, $C_3$-$C_8$ heterocycloalkenyl, aryl, heteroaryl, —$C_1$-$C_2$ alkylene-$C_3$-$C_6$ cycloalkyl, —$C_1$-$C_2$ alkylene-heterocycle, —$C_1$-$C_2$ alkylene-aryl, —$C_1$-$C_2$ alkylene-heteroaryl, —N—$C_1$-$C_7$ alky, —N—$C_3$-$C_8$ cycloalkyl, —N-heterocycle, —N-heteroaryl, $C_1$-$C_7$ alkoxy, —O—$C_3$-$C_8$ cycloalkyl, —O-heterocycle, —O— heteroaryl, any of which may be optionally substituted by one or more substituents selected from halogen, =O, OH, SMe, $C_1$-$C_2$ alkoxy, —O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, which may be linked to form a ring;

$R^{10}$ is selected from H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_3$-$C_8$ cycloalkyl, heterocycle, $C_4$-$C_8$ cycloalkenyl, $C_3$-$C_8$ heterocycloalkenyl, aryl, heteroaryl, —$C_1$-$C_3$ alkylene-$C_3$-$C_6$ cycloalkyl, —$C_1$-$C_3$ alkylene-heterocycle, —$C_1$-$C_3$ alkylene-aryl, —$C_1$-$C_3$ alkylene-heteroaryl, —N—$C_1$-$C_8$ alkyl, any of which may be optionally substituted by one or more substituents selected from halogen, =O, OH, SMe, $C_1$-$C_2$ alkoxy, —O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, which may be linked to form a ring;

$R^{13}$ is selected from $C_1$-$C_7$ alkyl, $C_1$-$C_6$ heteroalkyl, $C_3$-$C_8$ cycloalkyl, —$C_1$-$C_2$ alkylene-$C_3$-$C_6$ cycloalkyl, $C_3$-$C_5$ heterocycle, any of which may be optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, $NMe_2$, which may be linked to form a cycloalkyl or heterocyclic ring;

$R^6$ and $R^7$ may be linked to one another to form a ring;
$R^8$ and $R^9$ may be linked to one another to form a ring;
$R^{12}$ and $R^{13}$ may be linked to one another to form a ring;
$R^{14}$ is C=O, C=S, C=N—OH, C=$NR^b$, C=CH—$NO_2$, $SO_2$, and $C_3$-$C_6$ cycloalkenyl which may be substituted with 1 or 2 =O;

$R^a$ is selected from H, $C_1$-$C_8$ alkyl, heteroalkyl, $C_1$-$C_8$ alkoxy, heterocycle, $C_3$-$C_8$ cycloalkyl, heteroaryl and aryl, any of which may be optionally substituted by one or more substituents selected from halogen, =O, OH, SMe, $C_1$-$C_2$ alkoxy, —O—$C_1$-$C_2$ haloalkyl, $C_1$-$C_2$ alkyl, $C_3$-$C_6$ cycloalkyl, $C_1$-$C_2$ heteroalkyl, $C_1$-$C_2$ haloalkyl, aryl, heteroaryl, $NH_2$, NHMe, $NMe_2$ which may be linked to form a ring;

$R^b$ is selected from CN, aryl, heteroaryl, —$NO_2$, —O—$C_1$-$C_2$ alkyl, —CO—O—$C_1$-$C_2$ alkyl, with aryl and heteroaryl optionally substituted by one or more $C_1$-$C_2$ alkyl;

$R^c$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, $C_1$-$C_4$ alkylene-$C_3$-$C_6$ cycloalkyl, any of which may be optionally substituted by one or more substituents selected from C(O)($R^g$), C(O)N($R^f$)($R^g$), halogen, $SF_5$, OH, =O, —COH, —COOH, —CO—O—$R^a$, CN, SMe, $SO_2$Me, $SO_2R^g$, $C_1$-$C_4$ alkoxy, O—$C_1$-$C_4$ haloalkyl, $C_1$-$C_4$ alkyl, $C_1$-$C_2$ heteroalkyl, $C_1$-$C_4$ haloalkyl, N($R^f$)($R^g$), N($R^f$)$SO_2$($R^g$), $SO_2NH_2$, $SO_2NHMe$, $SO_2NMe_2$, S(O)(N$R^f$)$R^g$, $C_3$-$C_6$ cycloalkyl, heterocycle, $C_1$-$C_4$ alkylene-$C_3$-$C_6$ cycloalkyl, aryl and heteroaryl, which may be linked to form a ring with aryl, heteroaryl, heterocycle and cycloalkyl optionally substituted by one or more substituents selected from halogen, =O, =NH, =NMe, OH, $C_1$-$C_2$ alkyl, $C_1$-$C_2$ alkoxy, —COOH, —COO—$C_1$-$C_2$ alkyl, $SO_2R^a$, $COR^a$, $SOR^a$, S(O)(NH)$R^a$, $CONHR^a$, which may be linked to form a ring;

$R^d$ represents H or $C_1$-$C_4$ alkyl;

and $R^c$ and $R^d$ may be linked to form a heterocycle;

$R^e$ is selected from —C(O)$OR^a$, —C(O)N($R^f$)($R^g$), aryl, heteroaryl, $C_1$-$C_2$ haloalkyl, —CN where $R^f$ and $R^g$ may be linked to form a ring, with aryl and heteroaryl optionally substituted with one or more substituents selected from C1-C2 haloalkyl, C1-C2 alkyl;

$R^f$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, $C_1$-$C_4$ alkylene-$C_3$-$C_6$ cycloalkyl, any of which may be optionally substituted by one or more substituents selected from halogen, =O, =NH, =NMe, OH, aryl, heteroaryl, $C_1$-$C_2$ alkyl, $C_1$-$C_2$ haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, S(O)(NH)$R^a$, $CONHR^a$;

$R^g$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, $C_1$-$C_4$ alkylene-$C_3$-$C_6$ cycloalkyl, any of which may be optionally substituted by one or more substituents selected from halogen, =O, =NH, =NMe, OH, aryl, heteroaryl, $C_1$-$C_2$ alkyl, $C_1$-$C_2$ haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, S(O)(NH)$R^a$, $CONHR^a$ $R^f$ and $R^g$ may be linked to form a ring.

In a preferred embodiment of the present invention, X, W, Y and Z are preferably C or alternatively, X, W and Y are preferably C and Z is preferably O, all of which may be substituted as described above.

More preferably X is CH and W, Y and Z are independently selected from $CH_2$, CH($C_1$-$C_2$ alkyl), CH($C_1$-$C_2$ haloalkyl), C($C_1$-$C_2$ alkyl)$_2$ and spiro-cyclopropyl. Most preferably, X is CH and W, Y and Z are $CH_2$.

In this case, the preferred compounds are characterized by formula (II):

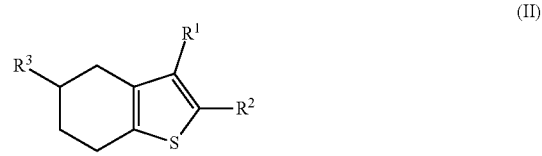

wherein $R^1$, $R^2$ and $R^3$ are as defined in formula (I) or (Ia).

Preferred embodiments according to the invention are compounds of formula (I), (Ia) or (II) and salts thereof wherein $R^1$, $R^2$ and $R^3$ are as defined below. It will be understood by those skilled in the art that the present invention also encompasses compounds of formula (I), (Ia) and (II) and salts thereof wherein various substituents are independently selected from these embodiment, preferred embodiment, more preferred embodiment, preferably, more preferably, even more preferably, most preferably, specific embodiment, preferred specific embodiment, specific preferred embodiment, specific more preferred embodiment, particularly preferred embodiment, best results. This also includes compounds of formula (III) to (XXIV) defined below.

If $R^1$ is selected from —S(O)$_2$R$^{10}$, —S(O)R$^{10}$ and —S(O)(=NR$^{11}$)R$^{10}$, R$^{10}$ is preferably nBu and R$^{11}$ is H.

If $R^1$ represents —C(O)OR$^5$, R$^5$ is preferably

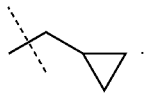

In a more preferred embodiment, $R^1$ is —C(O)N(R$^6$)(R$^7$) or —S(O)$_2$N(R$^8$)(R$^9$) wherein R$^6$, R$^7$, R$^8$ and R$^9$ are as defined above;

more preferably $R^1$ is —C(O)N(R$^6$)(R$^7$) or —S(O)$_2$N(R$^8$)(R$^9$)

wherein $R^6$ and $R^8$ are selected from H and C$_1$-C$_3$ alkyl, and most preferably $R^6$ and $R^8$ are H; and $R^7$ and $R^9$ are selected from C$_1$-C$_8$ alkyl, C$_3$-C$_6$ cycloalkyl and —C$_1$-C$_2$ alkylene-C$_3$-C$_6$ cycloalkyl, any of which groups may be optionally substituted by 1 to 4 halogen and cycloalkyl may be substituted by C$_1$-C$_8$ alkyl, and most preferably $R^7$ is

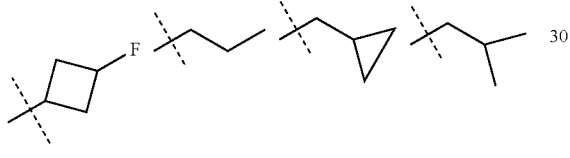

and $R^9$ is

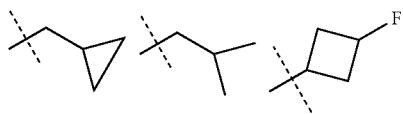

even more preferably $R^1$ is

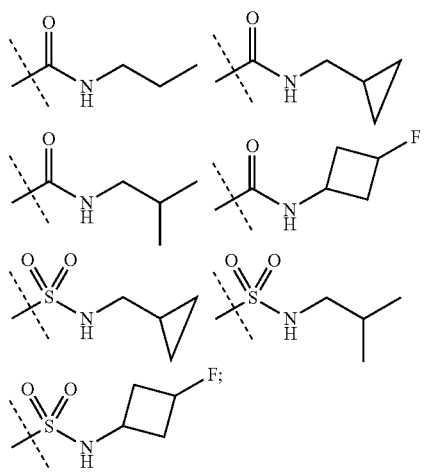

and most preferably $R^1$ is

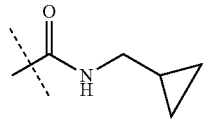

$R^2$ preferably represents —N(R$^{12}$)C(O)R$^{13}$
wherein $R^{12}$ is selected from H and C$_1$-C$_3$ alkyl, and $R^{13}$ is selected from C$_1$-C$_7$ alkyl, C$_3$-C$_8$ cycloalkyl and —C$_1$-C$_2$ alkylene-C$_3$-C$_6$ cycloalkyl, any of which groups may be optionally substituted by 1 to 5 substituents selected from halogen and C$_1$-C$_2$ alkyl, which may be linked to form a cycloalkyl ring, more preferably $R^2$ represents

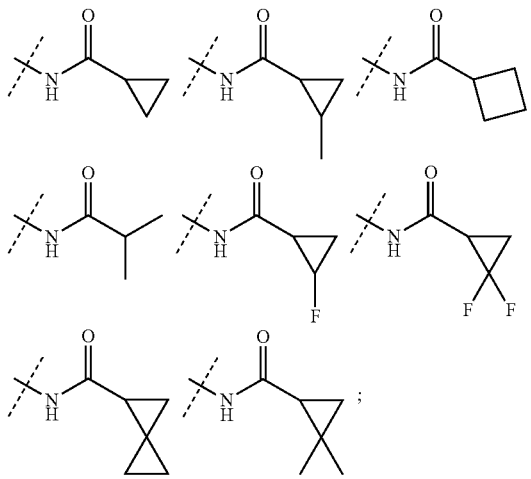

and most preferably $R^2$ represents

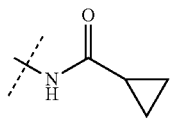

In a preferred embodiment, $R^3$ is selected from —NHR$^c$, —NH—R$^{14}$—NH—R$^a$, and heteroaryl, any of which may be substituted by one or more substituents selected from —NHR$^c$, —C(O)O—R$^a$, —C(O)NR$^d$R$^c$, aryl, heteroaryl, C$_1$-C$_2$ haloalkyl and —CN, where R$^c$ is selected from H, optionally substituted heteroaryl, optionally substituted heterocycle and optionally substituted aryl, wherein substituents of aryl, heterocycle and heteroaryl are selected from halogen, —CN, —C(O)OH, —C(O)O—C$_1$-C$_2$ alkyl, —C(O)Me, —S(O)Me, —S(O)(O)Me, —S(O)(=NH)Me, heterocycle, C$_1$-C$_4$ alkyl, C$_1$-C$_2$ heteroalkyl, C$_1$-C$_2$ haloalkyl, C$_1$-C$_2$ alkoxy, C$_1$-C$_2$ haloalkoxy, aryl, heteroaryl, C$_3$-C$_8$ cycloalkyl.

In a specific preferred embodiment, $R^3$ is heteroaryl, containing at least one nitrogen as heteroatom, which may be substituted by either —NR$^d$R$^c$ or —NR$^d$R$^c$ and —C(O)O—C$_1$-C$_2$ alkyl, $R^c$ is selected from H, optionally substituted heteroaryl, optionally substituted heterocycle and optionally substituted aryl, wherein substituents of aryl, heterocycle and heteroaryl are selected from —CN, —C(O)O—$C_1$-$C_2$ alkyl, $C_1$-$C_4$ alkyl, $C_1$-$C_2$ haloalkyl, $C_3$-$C_6$ cycloalkyl, $C_1$-$C_2$ haloalkoxy, —S(O)Me and —S(O)(O)Me and $R^d$ represents H.

In a specific more preferred embodiment, $R^3$ is heteroaryl, containing at least two nitrogen as heteroatom, which may be substituted by either —$NHR^c$ or —$NHR^c$ and —C(O)O—$C_1$-$C_2$ alkyl, $R^c$ is selected from H or optionally substituted heteroaryl, containing at least one nitrogen as heteroatom, wherein substituents of heteroaryl are selected from $C_1$-$C_3$ alkyl, $C_1$-$C_2$ haloalkyl and $C_1$-$C_2$ haloalkoxy wherein at least one halogen is a fluorine atom.

The best results have been obtained with $R^3$ being heteroaryl, containing three nitrogen as heteroatom, which may be substituted by —$NHR^c$, $R^c$ is optionally substituted heteroaryl, containing at least one nitrogen as heteroatom, wherein substituents of heteroaryl are selected from methyl, ethyl, difluoromethyl or trifluoromethyl.

Most preferably $R^3$ is,

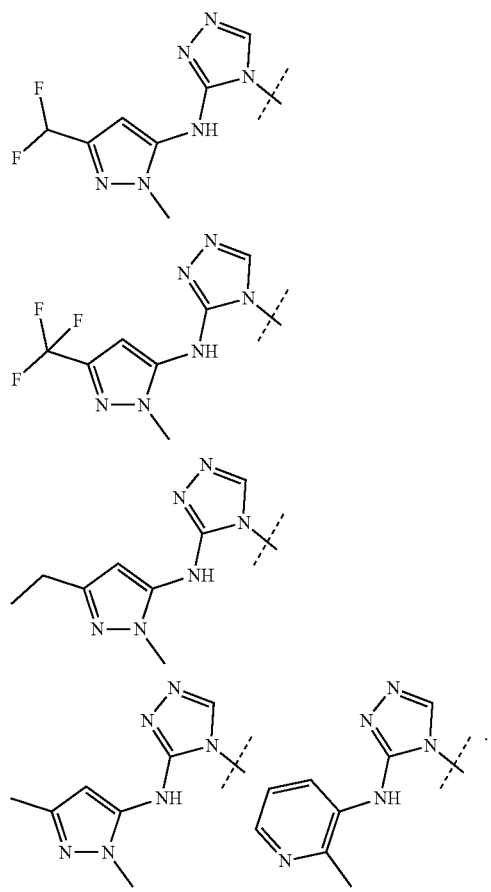

$R^1$ is

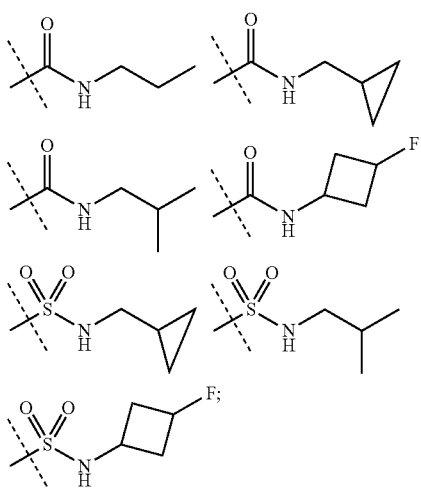

$R^2$ is

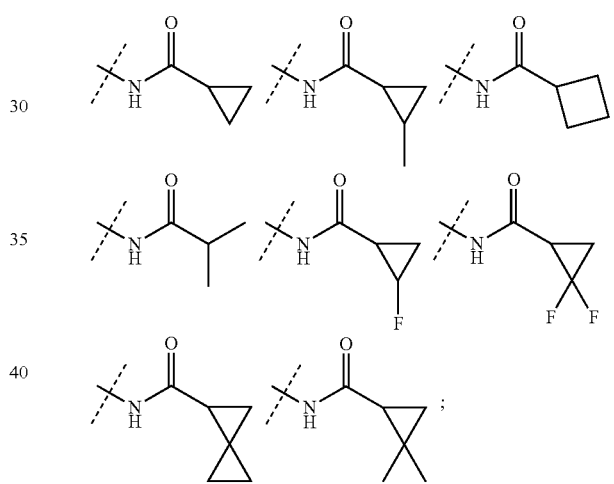

and/or $R^3$ is

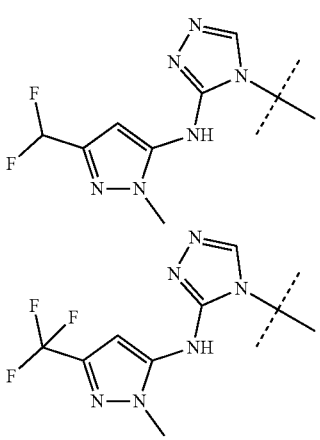

In a particularly preferred embodiment of the present invention, compounds of formula (I) or (Ia) or (XXXVI) and their pharmaceutically acceptable salts are those wherein:

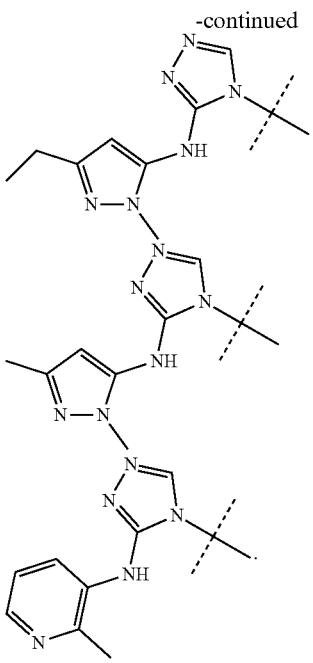

In a further embodiment, the compounds are characterized by formula (I) or (Ia) wherein X is C or N; Z is C, N, O or S; Y is C or S.

In a further embodiment, the compounds are characterized by formula (I) or (Ia) wherein $R^1$ is selected from N-methylaminocarbonyl, (cyclopropylmethyl)aminocarbonyl, cyclopropylcarbonylamino, cyclopropylcarbamoyl, propyl-sulfamoyl, isobutyl-sulfamoyl, [(2-hydroxy-2-methyl)propyl]sulfamoyl, 2-hydroxypropylsulfamoyl, 3-pyrrolidin-1-ylsulfonyl, (3-fluorocyclobutyl)-sulfamoyl, butylsulfonyl, butylsulfinyl, cyclopropylmethylsulfamoyl, butylsulfonimidoyl, 3-fluoropyrrolidine-1-carbonyl, 3-fluoroazetidine-1-carbonyl, piperidine-1-carbonyl, cyclopropylmethoxycarbonyl, ethoxycarbonyl, isobutyl-aminocarbonyl, 5-azaspiro[2.4]heptane-5-carbonyl, (3,3-difluorocyclobutyl)carbamoyl, (3-fluorocyclobutyl)carbamoyl, (2-fluoro-2-methyl-propyl)carbamoyl, isobutylcarbamoyl, 3-methylpyrrolidine-1-carbonyl, propylcarbamoyl, other substituents are as defined below, In another embodiment, the compounds are characterized by formula (I) or (Ia) wherein $R^2$ is selected from cyclopropanecarbonylamino, 2-methylpropanoylamino, cyclobutanecarbonylamino, (2-methylcyclopropanecarbonyl)amino, other substituents are as defined above and below and.

In a further embodiment, the compounds are characterized by formula (I) or (Ia) wherein X Y, W is C and Z is N wherein N is substituted with a group selected from methylsulfonyl, acetyl ethylcarbamoyl, cyano, other substituents are as defined above and below.

In a further embodiment, the compounds are characterized by formula (I) or (Ia) wherein X, Y, W, Z is C and wherein Z is substituted with a group selected from OH, methyl, ethylcarbamoyl, cyano, oxo, tert-butoxycarbonylamino, 1H-pyrazol-3-yl, other substituents are as defined above and below, In a further embodiment, the compounds are characterized by formula (I) or (Ia) wherein X, Y, W, Z is C and wherein W is substituted with a methyl group and $R^3$H or a methy group other substituents are as defined above and below.

In a further embodiment, compounds of the invention are characterized by formula (I) or (Ia) wherein X is C or N and $R^3$ is selected from H, OH, methyl, amino, methylsulfonyl, acetyl, 2-methoxyacetyl, 2-phenylacetyl, 2-(tert-butoxycarbonylamino)ethyl, 2-phenylethyl, pyrimidin-2-ylamino, methanesufonamido, (4-methoxyphenyl)carbamothioylamino, (4-Methoxyphenyl)carbamoylamino, ethylcarbamoyl, [N'-Cyano-N-(p-tolyl)carbamimidoyl]amino, [N'-Cyano-N-ethyl-carbamimidoyl]amino, (1-oxoisoindolin-5-yl)carbamoyl, (3-sulfamoylphenyl)carbamoyl, (3-methylsulfonylphenyl)carbamoyl, 3-isoxazol-5-ylanilino, (2-ethoxy-3,4-dioxo-cyclobuten-1-yl)amino, ethylcarbonyl, carboxy, (1-oxoisoindolin-5-yl)aminocarbonyl, [(5-oxopyrrolidin-3-yl)phenyl]aminocarbonyl, [3-(3-methyl-5-oxo-4H-pyrazol-1-yl)phenyl]carbonylamino, (1H-indazol-4-yl)carbonylamino, 1H-imidazo[4,5-b]pyrazin-2-yl, indan-2-yl, [2-(4-methoxyphenyl)ethylaminocarbonyl, quinoxalin-6-yl, (thiazol-2-yl)aminocarbonyl, (1H-tetrazol-5-yl)aminocarbonyl, (4-pyridyl)aminocarbonyl, pyrazin-2-ylaminocarbonyl, (3-pyridyl)aminocarbonyl, 3-hydroxyazetidine-1-carbonyl, 1,1-dioxo-1,4-thiazinane-4-carbonyl, 2-(4-hydroxyphenyl)ethylaminocarbonyl, hydroxyiminomethyl, [(4-ethyl-1,2,4-triazol-3-yl)amino]methyl, (4-methylanilino)methyl, 2-Amino-3-pyridyl, 5-(p-tolyl)-1H-imidazol-2-yl, cyano, trifluoromethyl, 4-methyloxazol-2-yl, aminomethyl, (p-tolylcarbamoylamino)methyl, 3-methyl-1,2,4-oxadiazol-5-yl, 5-methyl-1,3,4-oxadiazol-2-yl, pyrrolidine-1-carbonyl, 3-pyridylcarbamothioylamino, 3-(3-pyridylamino)-1,2,4-triazol-4-yl, 1H-pyrazol-3-yl, 5-Amino-4-cyano-imidazol-1-yl, 3-(2,2-dimethylpropylamino)-1,2,4-triazol-4-yl, 3-[(2,5-dimethylpyrazol-3-yl)amino]-1,2,4-triazol-4-yl, 4-(2,5-dimethylpyrazol-3-yl)-1,2,4-triazol-3-yl]amino, [(2,5-dimethylpyrazol-3-yl)amino]-1,2,4-triazol-4-yl, N'-Cyano-N-phenyl-carbamimidoylamino, 3-(isobutylamino)-1,2,4-triazol-4-yl, 3-[(1-methylcyclopropyl)methylamino]-1,2,4-triazol-4-yl, 5-Acetamidoimidazol-1-yl, 3-[(5-methyl-3-pyridyl)amino]-1,2,4-triazol-4-yl, 3-(4-pyridylamino)-1,2,4-triazol-4-yl, N'-Cyano-N-(3,4-dimethoxyphenyl)carbamimidoyl]amino, 4-ethoxycarbony-5-(ethylamino)imidazole-1-yl, 3-(2-morpholinoethylamino)-1,2,4-triazol-4-yl, (5-oxo-4H-1,2,4-oxadiazol-3-yl)amino, 2-(ethylamino)-3,4-dioxo-cyclobuten-1-yl]amino, [N'-cyano-N-(2,2,2-trifluoroethyl)carbamimidoyl]amino, 3-(ethylamino)-1,2,4-triazol-4-yl, (N-ethyl-N'-nitro-carbamimidoyl)amino, 3-(3-pyridylamino)-1,2,4-triazol-4-yl, 3-[(1-oxidopyridin-1-ium-3-yl)amino, [N'-nitro-N-(p-tolyl)carbamimidoyl]amino, 2-(3-pyridylamino)imidazol-1-yl, 3-(3-pyridylamino)-1,2,4-triazol-4-yl, 3-(cyclopropylmethylamino, (2,5-dimethylpyrazol-3-yl)carbamothioylamino, 3-(pyrimidin-5-ylamino)-1,2,4-triazol-4-yl, 2-(cyclopropylmethylamino)imidazol-1-yl, [4-(ethylamino)-1,1-dioxo-1,2,5-thiadiazol-3-yl]amino, [1-(4-methylanilino)-2-nitro-vinyl]amino, (N'-cyano-N-ethyl-carbamimidoyl)-methyl-amino, [2-(4-methylanilino)-3,4-dioxo-cyclobuten-1-yl]amino, 3-(2-pyridylamino)-1,2,4-triazol-4-yl, 2-Acetamidoimidazol-1-yl, 5-(N-tert-butyloxycarbonylamino)-triazol-1-yl, 5-(3-pyridylamino)triazol-1-yl, ethylcarbamothioylamino, 3-[[(3S)-tetrahydrofuran-3-yl]amino]-1,2,4-triazol-4-yl, [(E)-N-ethyl-N'-nitro-carbamimidoyl]amino, 2-(ethylamino)imidazol-1-yl, 3-[(3,5-dimethylisoxazol-4-yl)amino], [[N'-ethoxycarbonyl-N-(p-tolyl)carbamimidoyl]amino], [2-[(2-methyl-3-pyridyl)amino]imidazol-1-yl, 1-[(ethylamino)-2-nitro-vinyl]amino, (4-methyl-6-oxo-1H-pyrimidin-2-yl)amino, 5-amino-4-(methylcarbamoyl)imidazol-1-yl, 5-amino-4-carbamoyl-imidazol-1-yl, 2-Anilinoimidazol-1-yl, ethylcarbamoylamino, (4-oxo-1H-pyridin-2-yl)amino,

[6-(5-methyl-1,3,4-oxadiazol-2-yl)-3-pyridyl]amino, 5-(ethylamino)tetrazol-1-yl, 1H-1,2,4-triazol-3-ylamino, 4-(1-methylpyrazol-4-yl)-1,2,4-triazol-3-yl]amino, 4-(ethyloxycarbonyl)imidazol-1-yl, [4-(4-fluorophenyl)-1,2,4-triazol-3-yl]amino, 1H-imidazol-2-ylamino, N'-methoxy-N-(p-tolyl)carbamimidoyl]amino, [4-(4-methylanilino)-1,1-dioxo-1,2,5-thiadiazol-3-yl]amino, [1-(3-pyridyl)imidazol-2-yl]amino, 5-aminotriazol-1-yl, (2-methoxyphenyl)carbamoylamino, 4-pyridine-carbonylamino, benzylamino, 1H-Benzimidazol-2-ylamino, [N'-hydroxycarbamimidoyl]amino, [N'-(1-methylpyrazol-3-yl)-N-(p-tolyl)carbamimidoyl]amino, 3-[(3,5-dimethylpyrazin-2-yl)amino, 3-(ethylamino)-5-(methoxymethyl)-1,2,4-triazol-4-yl, [5-(3-pyridyl)-1H-1,2,4-triazol-3-yl]amino, p-tolylcarbonylamino, quinazolin-2-ylamino, 1,3-Benzoxazol-2-ylamino, 3-(ethylamino)-5-(hydroxymethyl)-1,2,4-triazol-4-yl, 2-aminoimidazol-1-yl, 3-amino-5-oxo-1,2,4-oxadiazol-4-yl, 3-(ethylamino)-5-methyl-1,2,4-triazol-4-yl, (2-ethyl-3,4-dioxo-cyclobuten-1-yl)amino, 1,3,4-oxadiazol-2-ylamino, 5-oxo-1-(p-tolyl)-4H-imidazol-2-yl]amino, [2-[ethyl(methyl)amino]-3,4-dioxo-cyclobuten-1-yl]amino, (methylsulfonimidoyl)amino, [N-Cyano-C-methyl-carbonimidoyl]amino, tetrazol-1-yl, methanesulfinamido, morpholino, 3-(ethylamino)-5-(trifluoromethyl)-1,2,4-triazol-4-yl, (4-oxo-1H-pyrimidin-2-yl)amino, isopropylsulfamoylamino, N'-Cyano-N-morpholino-carbamimidoyl]amino, acetamido, methanesulfonamido, [N'-Cyano-N-methoxy-carbamimidoyl]amino, (4-methoxyphenyl)carbamoylamino, [4-oxo-6-(trifluoromethyl)-1H-pyrimidin-2-yl]amino, [4-(trifluoromethoxy)phenyl]carbamoylamino, 3-(2-methylpropanoylamino)-1,2,4-triazol-4-yl, 3-[(2,5-dimethylpyrazol-3-yl)-methyl-amino]-1,2,4-triazol-4-yl, 5-amino-4-(5-methyl-1,3,4-oxadiazol-2-yl)imidazol-1-yl, 3-[(3-methyl-1H-pyrazol-5-yl)amino]-1,2,4-triazol-4-yl, 3-[(1,3-dimethylpyrazol-4-yl)amino]-1,2,4-triazol-4-yl-[(5-cyclopropyl-2-methyl-pyrazol-3-yl)amino]-1,2,4-triazol-4-yl, 3-[(5-isopropyl-2-methyl-pyrazol-3-yl)amino]-1,2,4-triazol-4-yl, 3-[[2-methyl-5-(trifluoromethyl)pyrazol-3-yl]amino]-1,2,4-triazol-4-yl, 3-[(2-isopropyl-5-methyl-pyrazol-3-yl)amino, 3-[(5-methyl-2-tetrahydrofuran-3-yl-pyrazol-3-yl)amino]-1,2,4-triazol-4-yl, 3-[(2-methylpyrazol-3-yl)amino]-1,2,4-triazol-4-yl, 3-[(2-ethyl-5-methyl-pyrazol-3-yl)amino]-1,2,4-triazol-4-yl, 3-[(2-cyclopropyl-5-methyl-pyrazol-3-yl)amino]-1,2,4-triazol-4-yl, 3-[(3-methoxy-1-methyl-pyrazol-4-yl)amino]-1,2,4-triazol-4-yl, 3-[(5-ethyl-2-methyl-pyrazol-3-yl)amino]-1,2,4-triazol-4-yl, 3-[[5-(difluoromethyl)-2-methyl-pyrazol-3-yl]amino, 3-[(1,4-dimethylpyrazol-3-yl)amino]-1,2,4-triazol-4-yl, [3-[(5-methoxycarbonyl-2-methyl-pyrazol-3-yl)amino]-1,2,4-triazol-4-yl], 2-[[2-methyl-5-(trifluoromethyl)pyrazol-3-yl]amino]imidazol-1-yl, [3-[(5-carboxy-2-methyl-pyrazol-3-yl)amino]-1,2,4-triazol-4-yl], other substituents are as defined above and below.

In a further embodiment, the compounds are characterized by formula (I) or (Ia) wherein W, X, Y, Z is C and Z is optionally substituted with a methyl group, other substituents are as defined above and below.

In a further embodiment, the compounds are characterized by formula (I) or (Ia) wherein $R^1$ is selected from (cyclopropylmethyl)carbamoyl, (3-fluorocyclobutylmethyl)carbamoyl, (2-fluorocyclopropyl)methyl-carbamoyl, (2,2-difluorocyclopropyl)methyl-carbamoyl, (2,2-dimethylcyclopropyl)methylcarbamoyl, (spiro[2.2]pentan-2-yl)carbamoyl, (spiro[2.2]pentan-2-yl)methyl-carbamoyl, (3,3-difluorocyclobutyl)carbamoyl, (3-fluorocyclobutyl)carbamoyl, (2-methylcyclopropyl)methylcarbamoyl, (3,3-difluorocyclobutyl)methyl-carbamoyl, ethoxycarbonyl, (3-fluorocyclobutyl)methyl-carbamoyl, (cyclobutyl)methyl-carbamoyl, (3-methylcyclobutyl)carbamoyl, (2,2-difluorocyclobutyl)methyl-carbamoyl, (3-fluorocyclobutyl)methyl-carbamoyl, (2-fluorocyclobutyl)methyl-carbamoyl, (spiro[2.2]pentan-2-yl)carbamoyl, other substituents are as defined above and below, In a further embodiment, the compounds are characterized by formula (I) or (Ia) wherein $R^2$ is selected from (cyclopropyl)acetylamino, (spiro[2.2]pentan-2-yl)carbonylamino, (2-fluorocyclopropyl)carbonylamino, (2,2-difluorocyclopropyl)carbonylamino, (2-methylcyclopropyl)carbonylamino, (3-fluorocyclobutyl)carbonylamino, (3,3-difluorocyclobutyl)carbonylamino, (oxetan-3-yl)carbonylamino, 3,3-difluoropropanoylamino, (cyclobutyl)carbonylamino, 2-(methylpropanoyl)amino, other substituents are as defined above and below.

In a further embodiment, the compounds are characterized by formula (I) or (Ia) wherein $R^3$ is selected from (1,1-dioxothiolan-3-yl)amino-1,2,4-triazol-4-yl, 3-[3-[methylsulfonimidoyl]anilino]-1,2,4-triazol-4-yl, 3-[(1-acetyl-3-methylpyrrolidin-3-yl)amino]-4H-1,2,4-triazol-4-yl, 3-{[1-(6-methylpyridazin-3-yl)pyrrolidin-3-yl]amino}-4H-1,2,4-triazol-4-yl, 3-[[-1-pyrazin-2-ylpyrrolidin-3-yl]amino]-1,2,4-triazol-4-yl, 3-[(4-methyl-1-methylsulfonyl-pyrrolidin-3-yl)amino]-1,2,4-triazol-4-yl, 3-[(1-oxo-2,3-dihydro-1H-isoindol-4-yl)amino]-4H-1,2,4-triazol-4-yl, 3-[[-1-(6-fluoropyridazin-3-yl)pyrrolidin-3-yl]amino]-1,2,4-triazol-4-yl, 3-[[1-pyrimidin-2-ylpyrrolidin-3-yl]amino]-1,2,4-triazo-4-yl, 5-amino-4-(2-methoxyethoxycarbonyl)imidazol-1-yl, 5-amino-4-(2-morpholinethoxycarbonyl)imidazol-1-yl, 3-(3-methylsulfanylanilino)-1,2,4-triazol-4-yl, 3-(3-methylsulfonylanilino)-1,2,4-triazol-4-yl, 3-(3-methylsulfinylanilino)-1,2,4-triazol-4-yl, 3-[3-(methylsulfonimidoyl)anilino]-1,2,4-triazol-4-yl, 3-[(6-methylsulfinyl-2-pyridyl)amino]-1,2,4-triazol-4-yl, 3-[(6-methylsulfonyl-2-pyridyl)amino]-1,2,4-triazol-4-yl, 8-methoxy-4-oxo-5,10-dihydroimidazo[4,5-c][1,5]benzodiazepin-1-yl, 8-methoxy-5-methyl-4-oxo-10H-imidazo[4,5-c][1,5]benzodiazepin-1-yl, 5-amino-4-[(2S)-2-methylpyrrolidine-1-carbonyl]imidazol-1-yl, 5-amino-4-[(3R)-3-hydroxypyrrolidine-1-carbonyl]imidazol-1-yl, 5-amino-4-[(2S)-2-methylpyrrolidine-1-carbonyl]imidazol-1-yl, 5-[[4-(dihydroxyamino)-2,5-dimethyl-3H-pyrazol-3-yl]amino]-4-ethoxycarbonyl-imidazol-1-yl, 5-[[4-(dihydroxyamino)-2,5-dimethyl-3H-pyrazol-3-yl]amino]-4-ethoxycarbonyl-imidazol-1-yl, 3-(2-methyl-3-methylsulfinyl-anilino)-1,2,4-triazol-4-yl, 3-(2-methyl-3-methylsulfonyl-anilino)-1,2,4-triazol-4-yl, 3-[(2-methyl-5-oxazol-2-yl-pyrazol-3-yl)amino]-1,2,4-triazol-4-yl, 1-acetylpyrrolidin-3-yl]amino]-1,2,4-triazol-4-yl, 1-methylsulfonylpyrrolidin-3-yl]amino]-1,2,4-triazol-4-yl, 3-[(2-methylcyclohexyl)amino]-1,2,4-triazol-4-yl, 3-[(5-oxopyrrolidin-3-yl)amino]-1,2,4-triazol-4-yl, 3-[(2-oxo-4-piperidyl)amino]-1,2,4-triazol-4-yl, 3-[(1-acetyl-2-methyl-pyrrolidin-3-yl)amino]-1,2,4-triazol-4-yl, 3-[(2-methyl-1-methylsulfonyl-pyrrolidin-3-yl)amino]-1,2,4-triazol-4-yl, -[3-[[3-(6-methyl-3-pyridyl)cyclobutyl]amino]-1,2,4-triazol-4-yl, 3-[[5-(difluoromethoxy)-2-methyl-pyrazol-3-yl]amino]-1,2,4-triazol-4-yl, [[1-benzoyl-4,4-difluoro-pyrrolidin-3-yl]amino]-1,2,4-triazol-4-yl, 3-[(1-acetyl-4-piperidyl)amino]-1,2,4-triazol-4-yl, 3-[(1-methoxycarbonylpyrrolidin-3-yl)amino]-1,2,4-triazol-4-yl, 3-[[1-(ethylcarbamoyl)pyrrolidin-3-yl]amino]-1,2,4-triazol-4-yl, 3-{2-(pyrimidin-2-yl)-2-azaspiro[4.4]nonan-7-yl]amino}-4H-1,2,4-triazol-4-yl, 3-[[2-methyl-5-(trifluoromethoxy)pyrazol-3-yl]amino]-1,2,4-triazol-4-yl, 3-[[5-[chloro(difluoro)methoxy]-2-methyl-pyrazol-3-yl]amino]-1,2,4-triazol-4-yl, 3-{[1-methyl-3-(5-methyl-1,3,4- oxadiazol-2-yl)-1H-pyrazol-5-yl]amino}-4H-1,2,4-triazol-4-yl, 3-[(5-methoxy-3-methyl-pyrazin-2-yl)amino]-1,2,4-triazol-4-yl, (5-methylthiazolo[5,4-b]pyridin-2-yl)amino, 3-[(5-cyano-2-methyl-3-pyridyl)amino]-1,2,4-triazol-4-yl, 3-[(6-cyano-2-methyl-3-pyridyl)amino]-1,2,4-triazol-4-yl, 3-[(1-methyl-2-oxo-4-pyridyl)amino]-1,2,4-triazol-4-yl, 3-[(6-chloro-2-methyl-3-pyridyl)amino]-1,2,4-triazol-4-yl, 3-[[2-methyl-6-(trifluoromethyl)-3-pyridyl]amino]-1,2,4-triazol-4-yl, 3-[(3-methylpyridazin-4-yl)amino]-1,2,4-triazol-4-yl, 3-[(5-chloro-2-methyl-pyrazol-3-yl)amino]-1,2,4-triazol-4-yl, 3-[(3-methylisothiazol-4-yl)amino]-1,2,4-triazol-4-yl, 3-[(3-methylisoxazol-4-yl)amino]-1,2,4-triazol-4-yl, 3-[[5-(cyclopropylmethoxy)-2-methyl-pyrazol-3-yl]amino]-1,2,4-triazol-4-yl, 3-[(5-ethoxy-2-methyl-pyrazol-3-yl)amino]-1,2,4-triazol-4-yl, 3-[(2,5-dimethylpyrazol-3-yl)amino]-1,2,4-triazol-4-yl, (5-amino-4-ethoxycarbonyl-imidazol-1-yl), 3-[[5-(difluoromethoxy)-2-methylpyrazol-3-yl]amino]-1,2,4-triazol-4-yl, 3-[[5-(difluoromethyl)-2-methylpyrazol-3-yl]amino]-1,2,4-triazol-4-yl, 3-[(5-methoxy-2-methylpyrazol-3-yl)amino]-1,2,4-triazo-4-yl, 3-[[5-(difluoromethyl)-2-(trideuteriomethyl)pyrazol-3-yl]amino, 3-[(5-Cyano-2-methyl-pyrazol-3-yl)amino]-1,2,4-triazol-4-yl, 3-[(2,2-difluoro-1,3-benzodioxol-5-yl)amino]-1,2,4-triazol-4-yl, 3-[(5-methoxy-2-methyl-pyrazol-3-yl)amino]-1,2,4-triazol-4-yl, 3-[[5-(difluoromethyl)-2-(trideuteriomethyl)pyrazol-3-yl]amino]-1,2,4-triazol-4-yl, 3-[(6-fluoro-2-methyl-3-pyridyl)amino]-1,2,4-triazol-4-yl, 3-[[5-(cyclopropoxy)-2-methyl-pyrazol-3-yl]amino]-1,2,4-triazol-4-yl, 3-[[2-methyl-5-(2,2,2-trifluoroethoxy)pyrazol-3-yl]amino]-1,2,4-triazol-4-yl, 3-[[6-(trifluoromethyl)-3-pyridyl]amino]-1,2,4-triazol-4-yl, 3-[(6-methoxy-3-pyridyl)amino]-1,2,4-triazol-4-yl, 3-[(2-methoxy-4-pyridyl)amino]-1,2,4-triazol-4-yl, 3-[(6-chloro-3-pyridyl)amino]-1,2,4-triazol-4-yl, 3-[(2-chloro-4-pyridyl)amino]-1,2,4-triazol-4-yl, 3-[(6-methoxy-2-methyl-3-pyridyl)amino]-1,2,4-triazol-4-yl, thiazolo[5,4-b]pyridin-2-ylamino, 3-[(3-methyltriazol-4-yl)amino]-1,2,4-triazol-4-yl, other substituents are as defined above and below.

In another specific embodiment, the compounds are characterized by formula (III) or (IV)

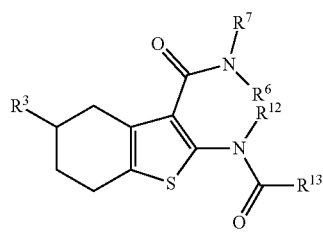

(III)

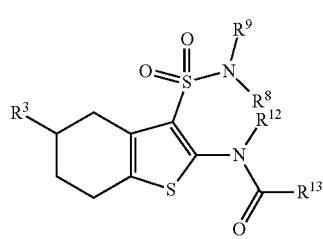

(IV)

wherein $R^3$, $R^6$, $R^7$, $R^8$, $R^9$, $R^{12}$ and $R^{13}$ are as defined in formula (I) or (Ia).

In another specific embodiment, the compounds are characterized by formula (V) or (VI)

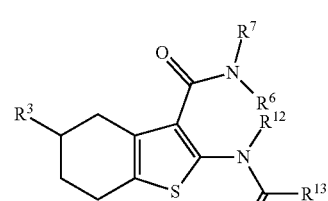

(V)

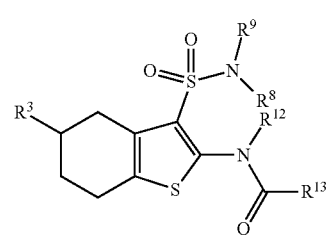

(VI)

wherein $R^a$, $R^c$, $R^d$, $R^6$, $R^7$, $R^8$, $R^9$, $R^{12}$, $R^{13}$ and $R^{14}$ are as defined in formula (I) or (Ia);
$R^3$ is $NR^cR^d$, $NH-R^{14}-NH-R^a$, heteroaryl optionally substituted as defined in formula (I) or (Ia).

In another preferred specific embodiment, the compound are characterized by formula (VII) or (VIII)

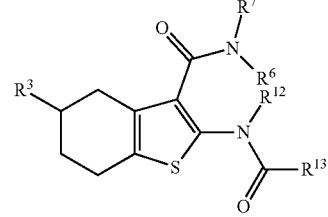

(VII)

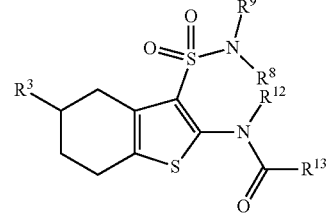

(VIII)

wherein $R^6$, $R^7$, $R^8$, $R^9$, $R^{12}$ and $R^{13}$ are as defined in formula (I) or (Ia);
and $R^3$ is heteroaryl, optionally substituted as defined in formula (I) or (Ia).

In another preferred specific embodiment, the compound are characterized by formula (IX) or (X)

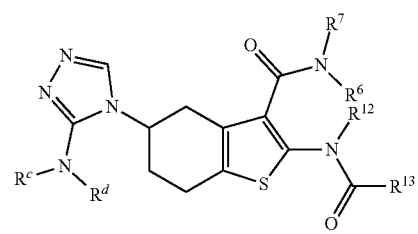

(IX)

-continued

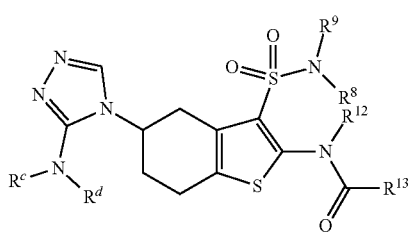
(X)

wherein $R^c$, $R^d$, $R^6$, $R^7$, $R^8$, $R^9$, $R^{12}$ and $R^{13}$ are as defined in formula (I) or (Ia).

In another preferred specific embodiment, the compound are characterized by formula (XI) or (XII)

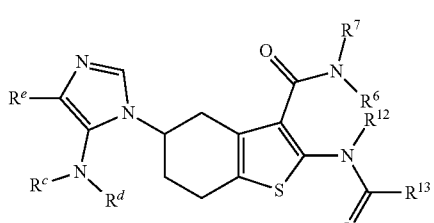
(XI)

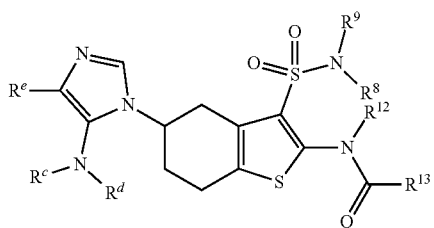
(XII)

wherein $R^c$, $R^d$, $R^e$, $R^6$, $R^7$, $R^8$, $R^9$, $R^{12}$ and $R^{13}$ are as defined in formula (I) or (Ia).

In another preferred specific embodiment, the compound are characterized by formula (XIII) or (XIV)

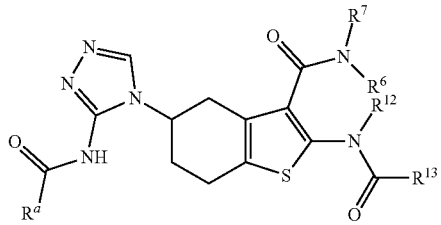
(XIII)

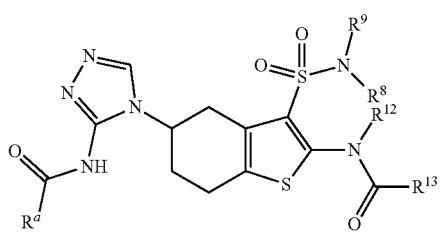
(XIV)

wherein $R^a$, $R^6$, $R^7$, $R^8$, $R^9$, $R^{12}$ and $R^{13}$ are as defined in formula (I) or (Ia).

In another preferred specific embodiment, the compound are characterized by formula (XV) or (XVI)

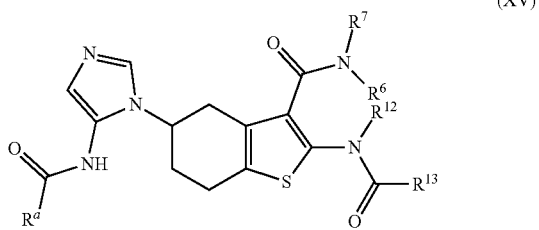
(XV)

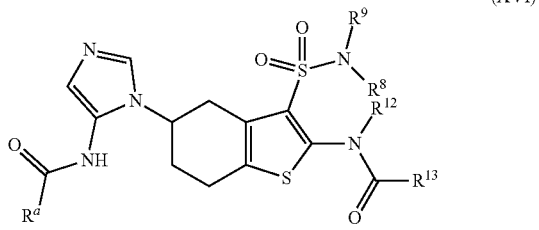
(XVI)

wherein $R^a$, $R^6$, $R^7$, $R^8$, $R^9$, $R^{12}$ and $R^{13}$ are as defined in formula (I) or (Ia).

In another preferred specific embodiment, the compound are characterized by formula (XVII) or (XVIII)

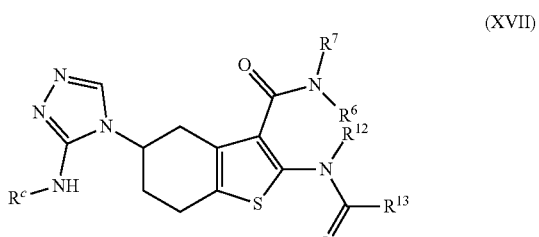
(XVII)

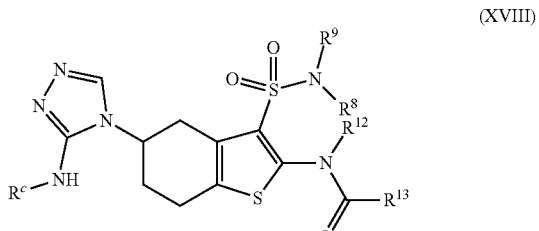
(XVIII)

wherein $R^c$, $R^6$, $R^7$, $R^8$, $R^9$, $R^{12}$ and $R^{13}$ are as defined in formula (I).

In another preferred specific embodiment, the compound are characterized by formula (XIX) or (XX)

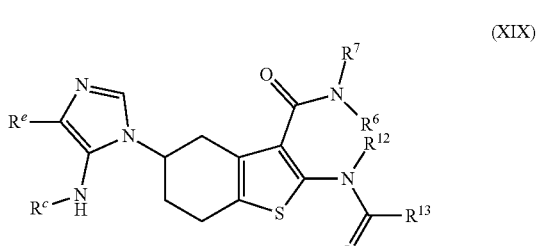
(XIX)

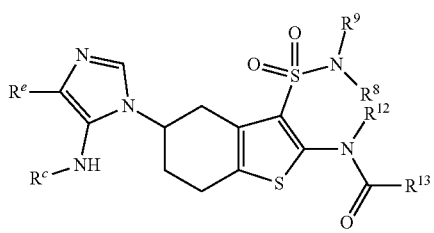
(XX)

wherein $R^c$, $R^e$, $R^6$, $R^7$, $R^8$, $R^9$, $R^{12}$ and $R^{13}$ are as defined in formula (I) or (Ia).

In another preferred specific embodiment, the compound are characterized by formula (XXI) or (XXII)

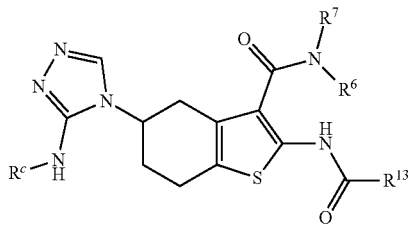
(XXI)

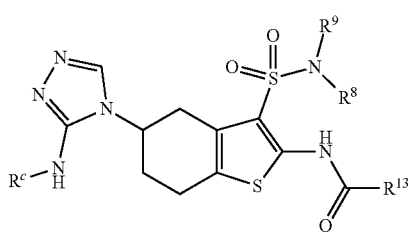
(XXII)

wherein $R^c$, $R^6$, $R^7$, $R^8$, $R^9$, and $R^{13}$ are as defined in formula (I) or (Ia).

In another preferred specific embodiment, the compound are characterized by formula (XXIII) or (XXIV)

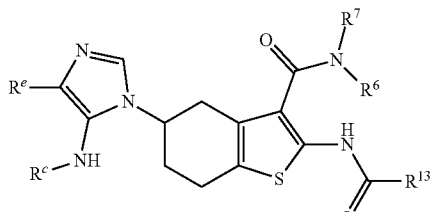
(XXIII)

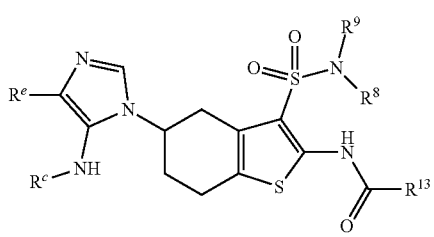
(XXIV)

wherein $R^c$, $R^e$, $R^6$, $R^7$, $R^8$, $R^9$ and $R^{13}$ are as defined in formula (I) or (Ia).

In another preferred specific embodiment, the compound are characterized by formula (XXV) or (XXVI)

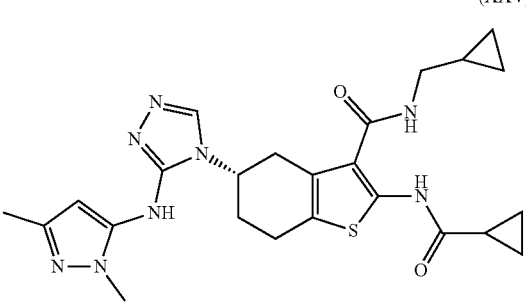
(XXV)

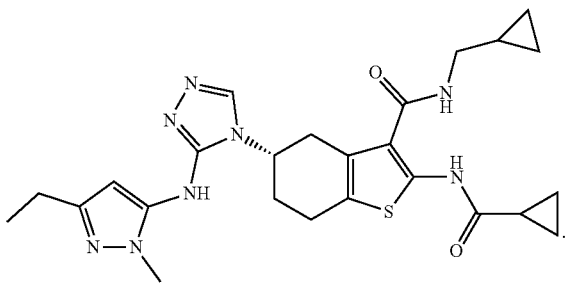
(XXVI)

In another preferred specific embodiment, the compound are characterized by formula (XXVII) or (XXVIII)

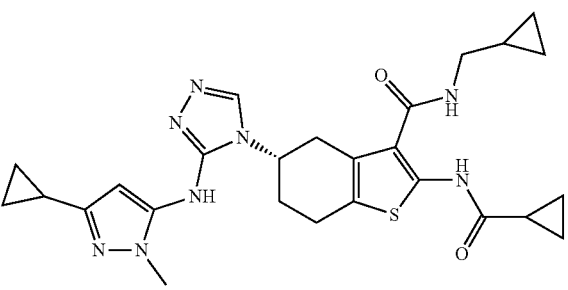
(XXVII)

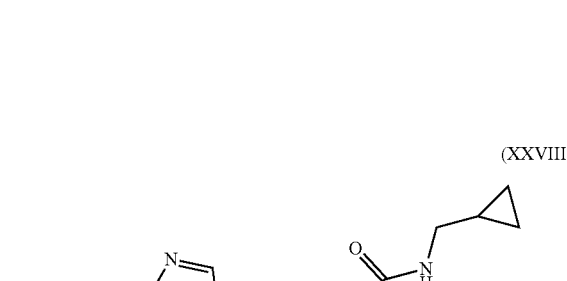
(XXVIII)

In another preferred specific embodiment, the compound are characterized by formula (XXIX) or (XXX)

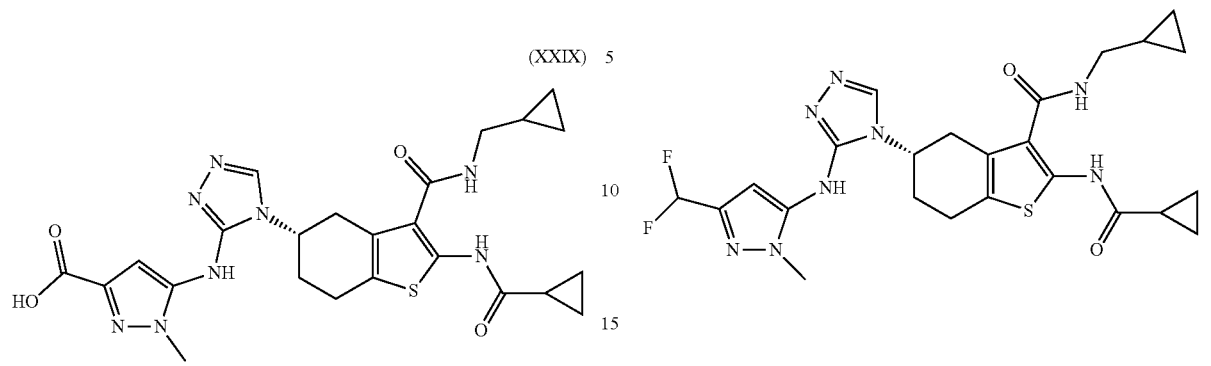

(XXIX)

(XXX)

In another preferred specific embodiment, the compound are characterized by formula (XXXI) or (XXXII)

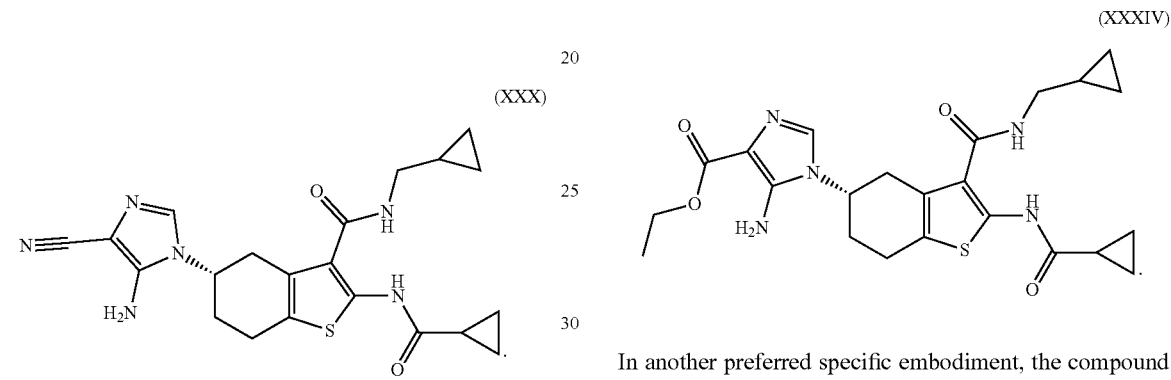

(XXXI)

(XXXII)

In another preferred specific embodiment, the compound are characterized by formula (XXXII) or (XXXIV)

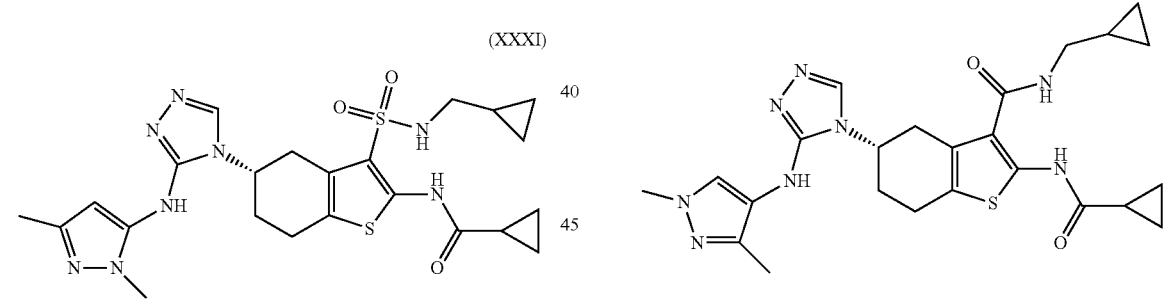

(XXXII)

(XXXIV)

In another preferred specific embodiment, the compound are characterized by formula (XXXV) or (XXXVI)

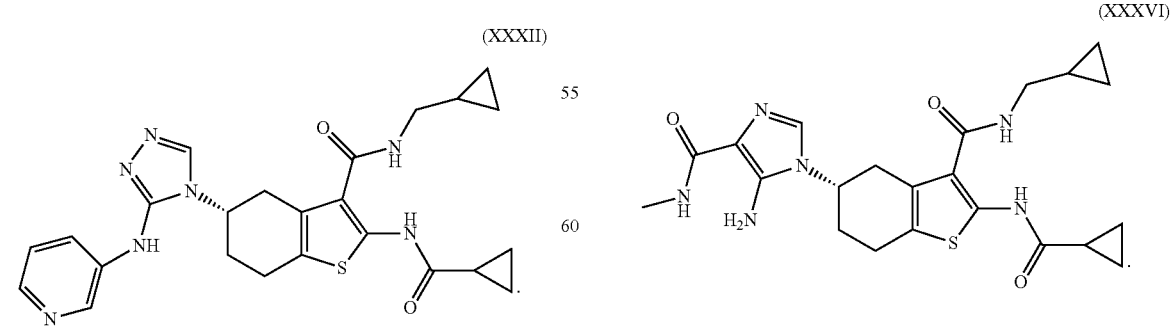

(XXXV)

(XXXVI)

Specific compounds of formula (I) or (XXXVI) according to the present invention are selected from the group consisting of:

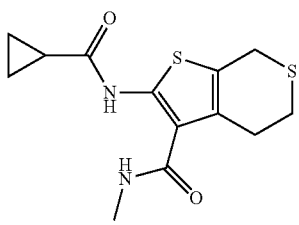 [SMILES: CNC(=O)c1c(NC(=O)C2CC2)sc2c1CCSC2]

2-(Cyclopropanecarbonylamino)-N-methyl-5,7-dihydro-4H-thieno[2,3-c]thiopyran-3-carboxamide

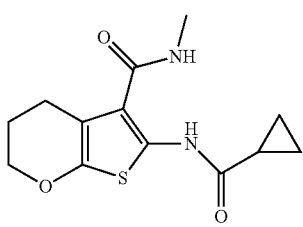 [SMILES: CNC(=O)c1c(NC(=O)C2CC2)sc2c1CCCO2]

6-(Cyclopropanecarbonylamino)-N-methyl-3,4-dihydro-2H-thieno[2,3-b]pyran-5-carboxamide

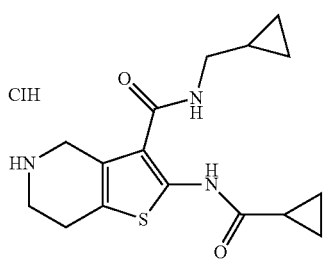 [SMILES: "CIH" ; O=C(NCC1CC1)c1c(NC(=O)C2CC2)sc2c1CNCC2]

2-(Cyclopropanecarbonylamino)-N-(cyclopropylmethyl)-4,5,6,7-tetrahydrothieno[3,2-c]pyridine-3-carboxamide; hydrochloride

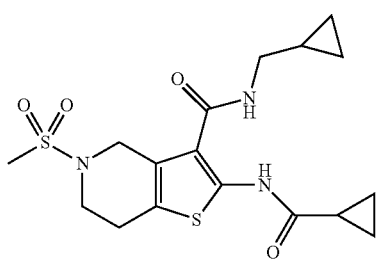 [SMILES: CS(=O)(=O)N1CCc2sc(NC(=O)C3CC3)c(C(=O)NCC3CC3)c2C1]

2-(Cyclopropanecarbonylamino)-N-(cyclopropylmethyl)-5-methylsulfonyl-6,7-dihydro-4H-thieno[3,2-c]pyridine-3-carboxamide

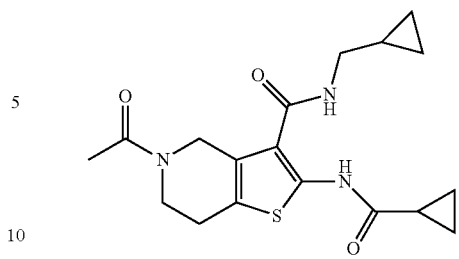

5-Acetyl-2-(cyclopropanecarbonylamino)-N-(cyclopropylmethyl)-6,7-dihydro-4H-thieno[3,2-c]pyridine-3-carboxamide 2-(Cyclopropanecarbonylamino)-N-(cyclopropylmethyl)-7-methylsulfonyl-5,6-dihydro-4H-thieno[2,3-b]pyridine-3-carboxamide 7-Acetyl-2-(cyclopropanecarbonylamino)-N-(cyclopropylmethyl)-5,6-dihydro-4H-thieno[2,3-b]pyridine-3-carboxamide

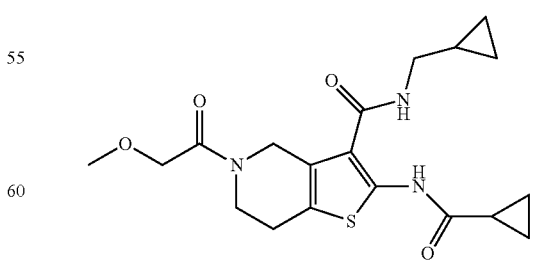

2-(Cyclopropanecarbonylamino)-N-(cyclopropylmethyl)-5-(2-methoxyacetyl)-6,7-dihydro-4H-thieno[3,2-c]pyridine-3-carboxamide

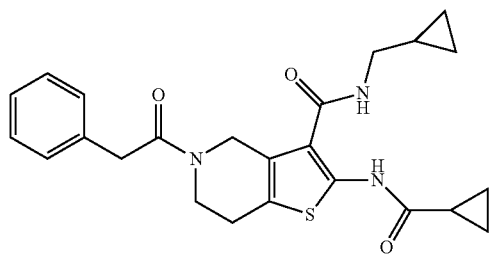 [SMILES: O=C(NCC1CC1)c1c(NC(=O)C2CC2)sc2c1CN(C(=O)Cc1ccccc1)CC2]

2-(Cyclopropanecarbonylamino)-N-(cyclopropylmethyl)-5-(2-methylacetyl)-6,7-dihydro-4H-thieno[3,2-c]pyridine-3-carboxamide

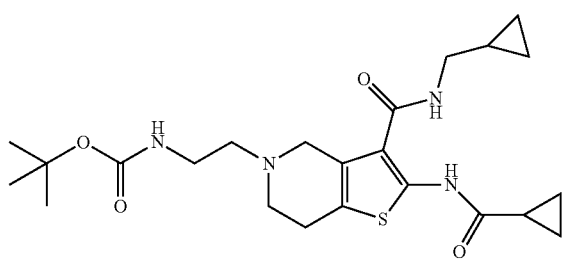 [SMILES: CC(C)(C)OC(=O)NCCN1CCc2sc(NC(=O)C3CC3)c(C(=O)NCC3CC3)c2C1]

Tert-butyl N-[2-[2-(cyclopropanecarbonylamino)-3-(cyclopropylmethylcarbamoyl)-6,7-dihydro-4H-thieno[3,2-c]pyridin-5-yl]ethyl]carbamate

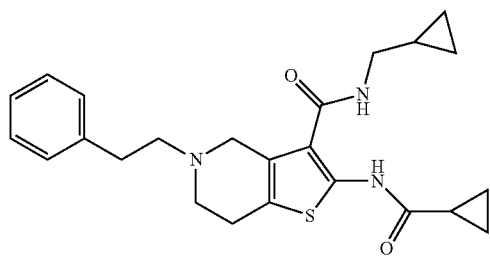 [SMILES: O=C(NCC1CC1)c1c(NC(=O)C2CC2)sc2c1CN(CCc1ccccc1)CC2]

2-(Cyclopropanecarbonylamino)-N-(cyclopropylmethyl)-5-(2-phenylethyl)-6,7-dihydro-4H-thieno[3,2-c]pyridine-3-carboxamide

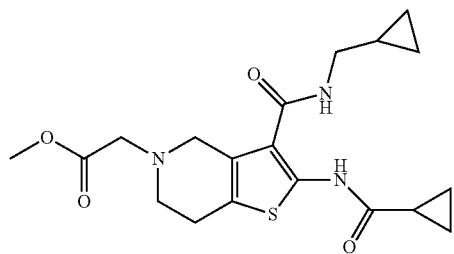 [SMILES: COC(=O)CN1CCc2sc(NC(=O)C3CC3)c(C(=O)NCC3CC3)c2C1]

Methyl 2-[2-(cyclopropanecarbonylamino)-3-(cyclopropylmethylcarbamoyl)-6,7-dihydro-4H-thieno[3,2-c]pyridin-5-yl]acetate

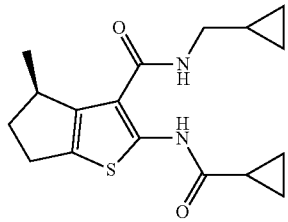

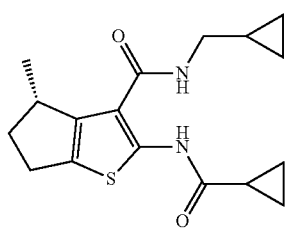

(4R)-2-(Cyclopropanecarbonylamino)-N-(cyclopropylmethyl)-4-methyl-5,6-dihydro-4H-cyclopenta[b]thiophene-3-carboxamide (4S)-2-(Cyclopropanecarbonylamino)-N-(cyclopropylmethyl)-4-methyl-5,6-dihydro-4H-cyclopenta[b]thiophene-3-carboxamide

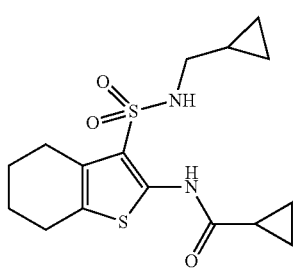 [SMILES: O=C(Nc1sc2c(c1S(=O)(=O)NCC1CC1)CCCC2)C1CC1]

N-[3-(Cyclopropylmethylsulfamoyl)-4,5,6,7-tetrahydrobenzothiophen-2-yl]cyclopropanecarboxamide

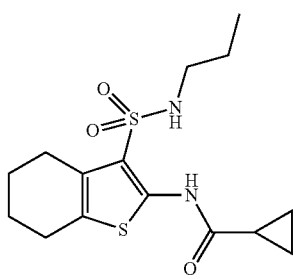 [SMILES: CCCNS(=O)(=O)c1c(NC(=O)C2CC2)sc2c1CCCC2]

N-[3-(Propylsulfamoyl)-4,5,6,7-tetrahydrobenzothiophen-2-yl]cyclopropanecarboxamide

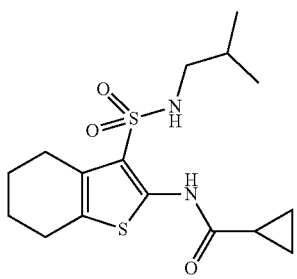 [SMILES: CC(C)CNS(=O)(=O)c1c(NC(=O)C2CC2)sc2c1CCCC2]

N-[3-(Isobutylsulfamoyl)-4,5,6,7-tetrahydrobenzothiophen-2-yl]cyclopropanecarboxamide

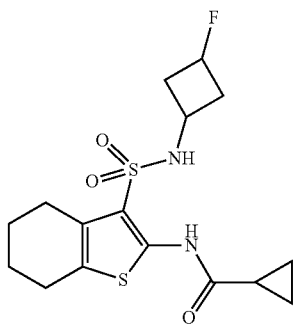

N-[3-[(3-Fluorocyclobutyl)sulfamoyl]-4,5,6,7-tetrahydrobenzothiophen-2-yl]cyclopropanecarboxamide

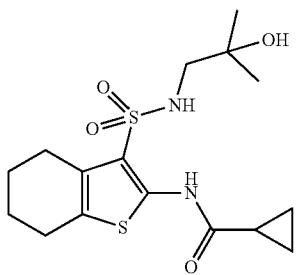 [SMILES: CC(C)(O)CNS(=O)(=O)c1c(NC(=O)C2CC2)sc2c1CCCC2]

N-[3-[(2-Hydroxy-2-methyl-propyl)sulfamoyl]-4,5,6,7-tetrahydrobenzothiophen-2-yl]cyclopropanecarboxamide

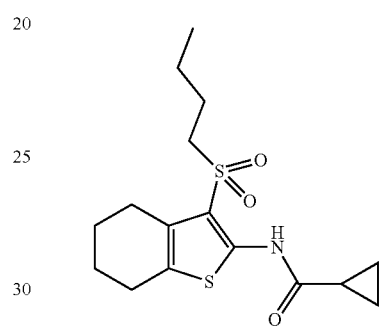

N-(3-Butylsulfonyl-4,5,6,7-tetrahydrobenzothiophen-2-yl)cyclopropanecarboxamide

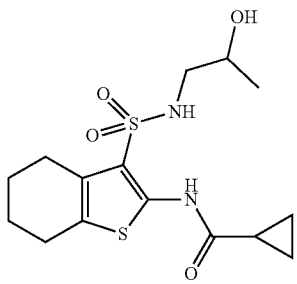 [SMILES: CC(O)CNS(=O)(=O)c1c(NC(=O)C2CC2)sc2c1CCCC2]

N-[3-(2-Hydroxypropylsulfamoyl)-4,5,6,7-tetrahydrobenzothiophen-2-yl]cyclopropanecarboxamide

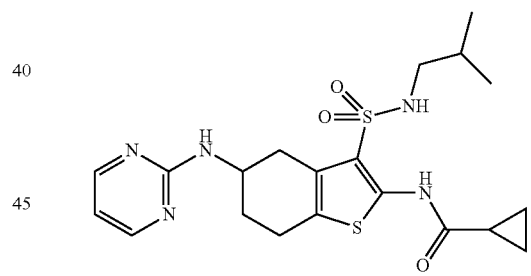

N-[3-(Isobutylsulfamoyl)-5-(pyrimidin-2-ylamino)-4,5,6,7-tetrahydrobenzothiophen-2-yl]cyclopropanecarboxamide

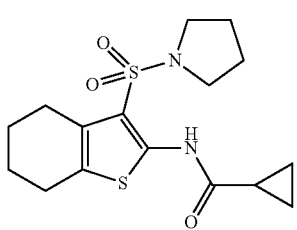 [SMILES: O=C(Nc1sc2c(c1S(=O)(=O)N1CCCC1)CCCC2)C1CC1]

N-(3-Pyrrolidin-1-ylsulfonyl-4,5,6,7-tetrahydrobenzothiophen-2-yl)cyclopropanecarboxamide

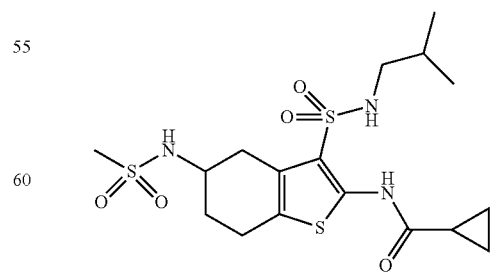

N-[3-(Isobutylsulfamoyl)-5-(methanesulfonamido)-4,5,6,7-tetrahydrobenzothiophen-2-yl]cyclopropanecarboxamide

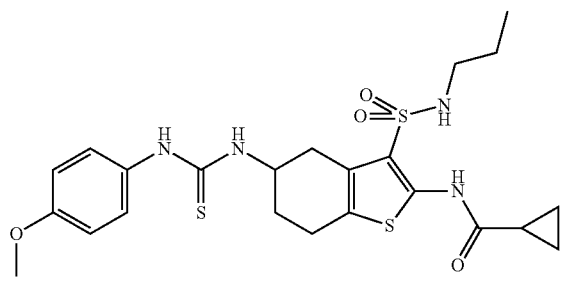 [SMILES: CCCNS(=O)(=O)c1c(NC(=O)C2CC2)sc2c1CC(NC(=O)Nc1ccc(OC)cc1)CC2]

N-[5-[(4-Methoxyphenyl)carbamothioylamino]-3-(propylsulfamoyl)-4,5,6,7-tetrahydrobenzothiophen-2-yl]cyclopropanecarboxamide

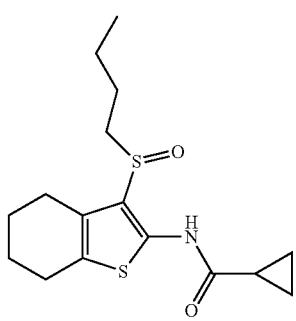

N-(3-Butylsulfinyl-4,5,6,7-tetrahydrobenzothiophen-2-yl)cyclopropanecarboxamide

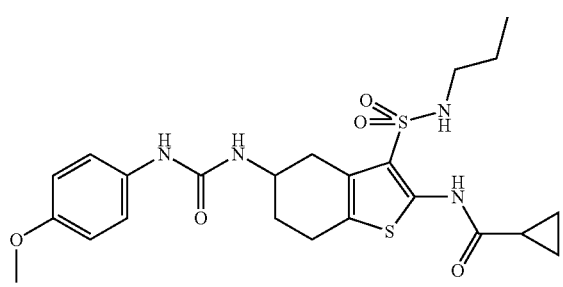

N-[5-[(4-Methoxyphenyl)carbamoylamino]-3-(propylsulfamoyl)-4,5,6,7-tetrahydrobenzothiophen-2-yl]cyclopropanecarboxamide

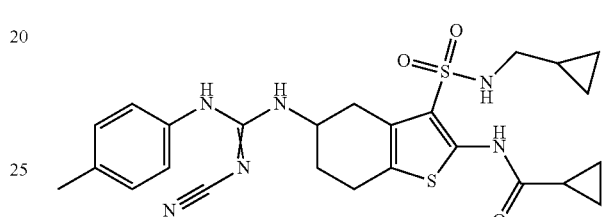

N-[5-[[N'-Cyano-N-(p-tolyl)carbamimidoyl]amino]-3-(cyclopropylmethylsulfamoyl)-4,5,6,7-tetrahydrobenzothiophen-2-yl]cyclopropanecarboxamide

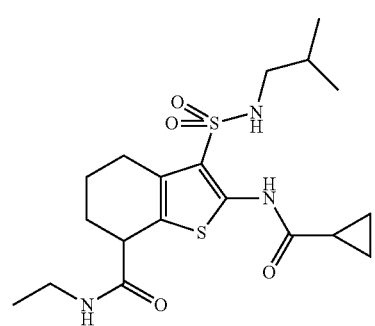 [SMILES: CCNC(=O)C1CCCc2c1sc(NC(=O)C1CC1)c2S(=O)(=O)NCC(C)C]

2-(Cyclopropanecarbonylamino)-N-ethyl-3-(isobutylsulfamoyl)-4,5,6,7-tetrahydrobenzothiophene-7-carboxamide

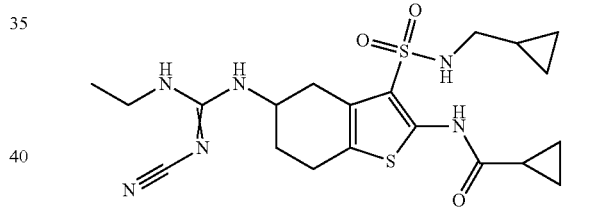

N-[5-[[N'-Cyano-N-ethyl-carbamimidoyl]amino]-3-(cyclopropylmethylsulfamoyl)-4,5,6,7-tetrahydrobenzothiophen-2-yl]cyclopropanecarboxamide

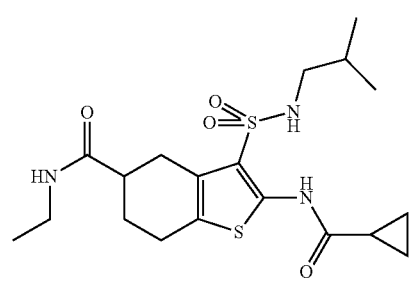 [SMILES: CCNC(=O)C1CCc2sc(NC(=O)C3CC3)c(S(=O)(=O)NCC(C)C)c2C1]

2-(Cyclopropanecarbonylamino)-N-ethyl-3-(isobutylsulfamoyl)-4,5,6,7-tetrahydrobenzothiophene-5-carboxamide

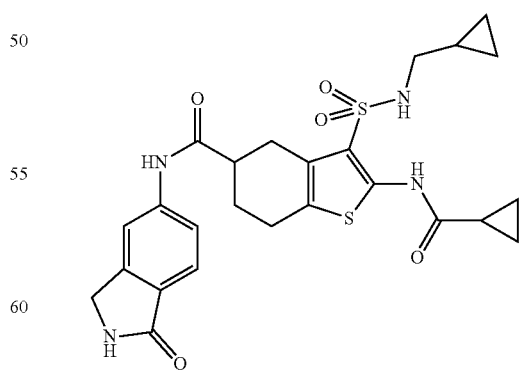

2-(Cyclopropanecarbonylamino)-3-(cyclopropylmethylsulfamoyl)-N-(1-oxoisoindolin-5-yl)-4,5,6,7-tetrahydrobenzothiophene-5-carboxamide

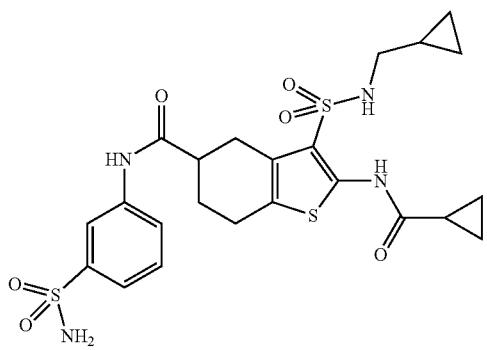 [SMILES: NS(=O)(=O)c1cccc(NC(=O)C2CCc3sc(NC(=O)C4CC4)c(S(=O)(=O)NCC4CC4)c3C2)c1]

2-(Cyclopropanecarbonylamino)-3-(cyclopropylmethylsulfamoyl)-N-(3-sulfamoylphenyl)-4,5,6,7-tetrahydrobenzothiophene-5-carboxamide

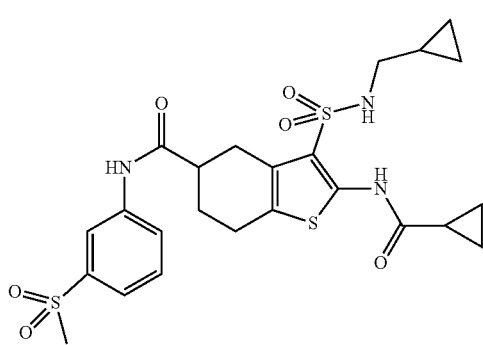 [SMILES: CS(=O)(=O)c1cccc(NC(=O)C2CCc3sc(NC(=O)C4CC4)c(S(=O)(=O)NCC4CC4)c3C2)c1]

2-(Cyclopropanecarbonylamino)-3-(cyclopropylmethylsulfamoyl)-N-(3-methylsulfonylphenyl)-4,5,6,7-tetrahydrobenzothiophene-5-carboxamide

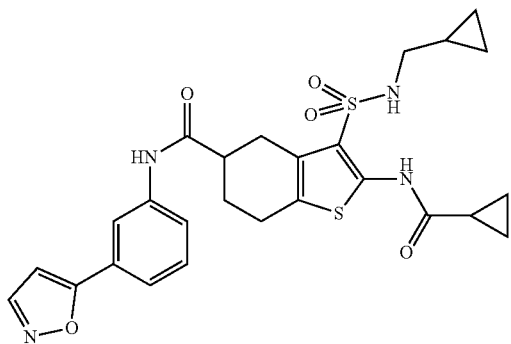 [SMILES: O=C(Nc1cccc(-c2ccno2)c1)C1CCc2sc(NC(=O)C3CC3)c(S(=O)(=O)NCC3CC3)c2C1]

2-(Cyclopropanecarbonylamino)-3-(cyclopropylmethylsulfamoyl)-N-(3-isoxazol-5-ylphenyl)-4,5,6,7-tetrahydrobenzothiophene-5-carboxamide

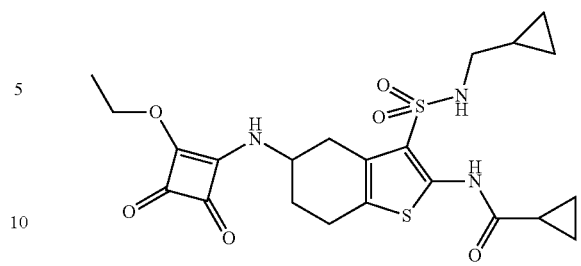

N-[3-(Cyclopropylmethylsulfamoyl)-5-[(2-ethoxy-3,4-dioxo-cyclobuten-1-yl)amino]-4,5,6,7-tetrahydrobenzothiophen-2-yl]cyclopropanecarboxamide

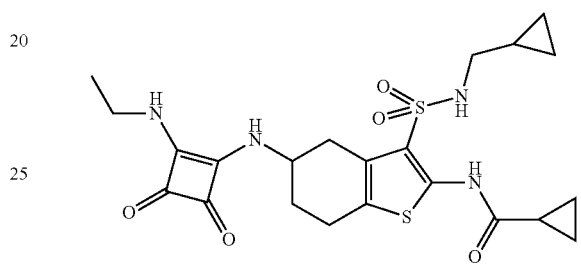

N-[3-(Cyclopropylmethylsulfamoyl)-5-[[2-(ethylamino)-3,4-dioxo-cyclobuten-1-yl]amino]-4,5,6,7-tetrahydrobenzothiophen-2-yl]cyclopropanecarboxamide

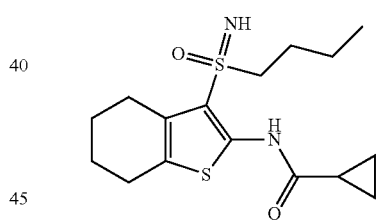

N-[3-(Butylsulfonimidoyl)-4,5,6,7-tetrahydrobenzothiophen-2-yl]cyclopropanecarboxamide

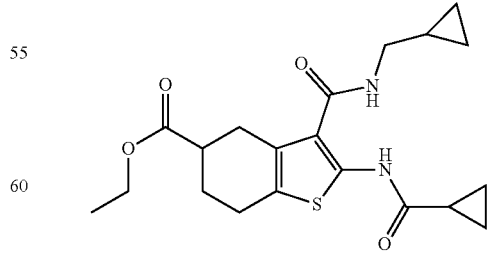

Ethyl 2-(cyclopropanecarbonylamino)-3-(cyclopropylmethylcarbamoyl)-4,5,6,7-tetrahydrobenzothiophene-5-carboxylate

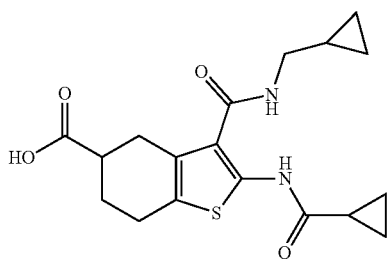

2-(Cyclopropanecarbonylamino)-3-(cyclopropylmethylcarbamoyl)-4,5,6,7-tetrahydrobenzothiophene-5-carboxylic acid

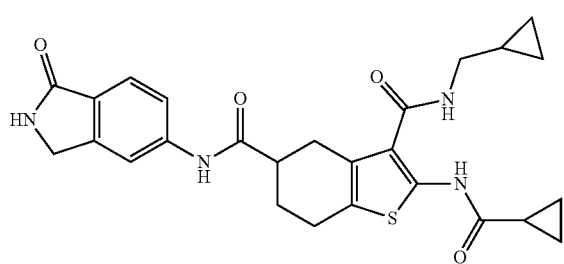

2-(Cyclopropanecarbonylamino)-N3-(cyclopropylmethyl)-N5-(1-oxoisoindolin-5-yl)-4,5,6,7-tetrahydrobenzothiophene-3,5-dicarboxamide

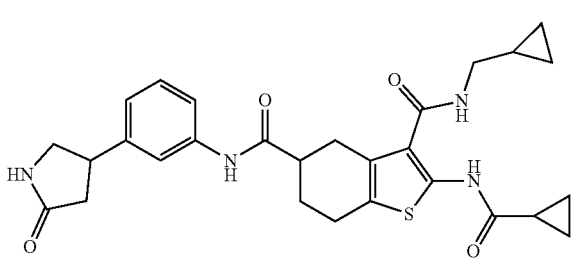

2-(Cyclopropanecarbonylamino)-N3-(cyclopropylmethyl)-N5-[3-(5-oxopyrrolidin-3-yl)phenyl]-4,5,6,7-tetrahydrobenzothiophene-3,5-dicarboxamide

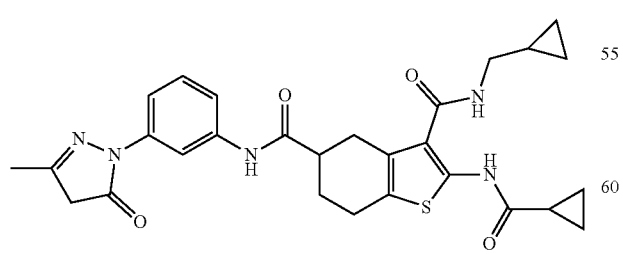

2-(Cyclopropanecarbonylamino)-N3-(cyclopropylmethyl)-N5-[3-(3-methyl-5-oxo-4H-pyrazol-1-yl)phenyl]-4,5,6,7-tetrahydrobenzothiophene-3,5-dicarboxamide

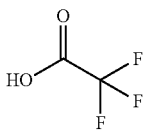
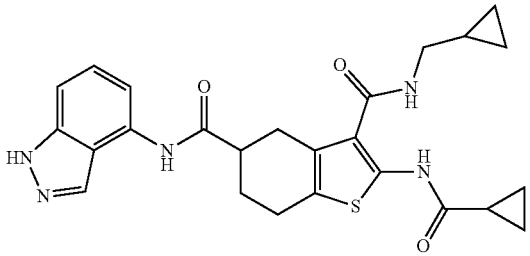

2-(Cyclopropanecarbonylamino)-N3-(cyclopropylmethyl)-N5-(1H-indazol-4-yl)-4,5,6,7-tetrahydrobenzothiophene-3,5-dicarboxamide; 2,2,2-trifluoroacetic acid

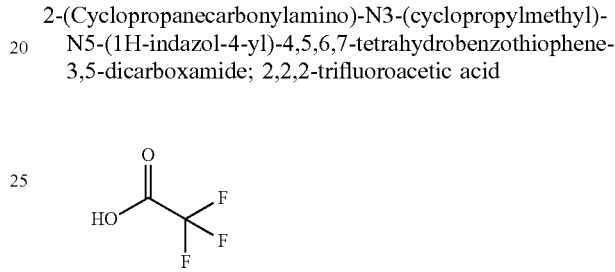

2-(Cyclopropanecarbonylamino)-N3-(cyclopropylmethyl)-N5-(1H-indazol-5-yl)-4,5,6,7-tetrahydrobenzothiophene-3,5-dicarboxamide; 2,2,2-trifluoroacetic acid

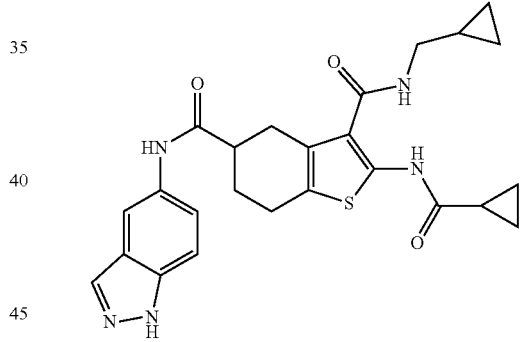

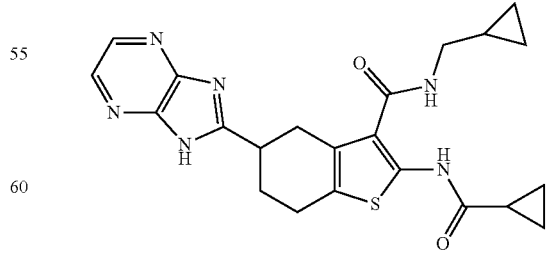

2-(Cyclopropanecarbonylamino)-N-(cyclopropylmethyl)-5-(1H-imidazo[4,5-b]pyrazin-2-yl)-4,5,6,7-tetrahydrobenzothiophene-3-carboxamide

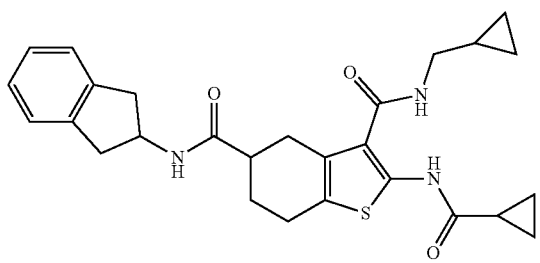

2-(Cyclopropanecarbonylamino)-N3-(cyclopropylmethyl)-N5-indan-2-yl-4,5,6,7-tetrahydrobenzothiophene-3,5-dicarboxamide

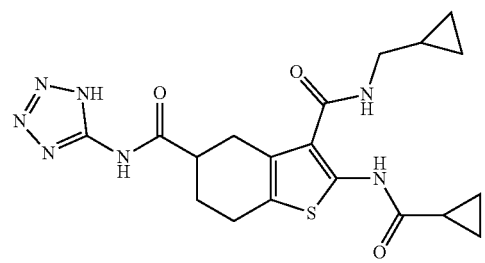

2-(Cyclopropanecarbonylamino)-N3-cyclopropylmethyl)-5-(1H-tetrazol-5-yl)-4,5,6,7-tetrahydrobenzothiophene-3,5-dicarboxamide

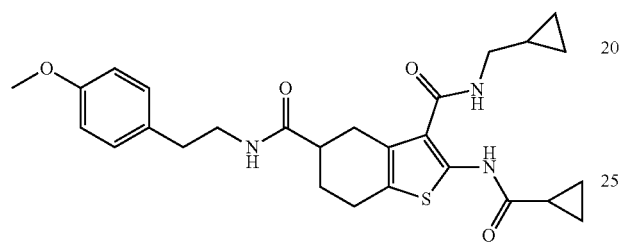

2-(Cyclopropanecarbonylamino)-N3-(cyclopropylmethyl)-N5-[2-(4-methoxyphenyl)ethyl]-4,5,6,7-tetrahydrobenzothiophene-3,5-dicarboxamide

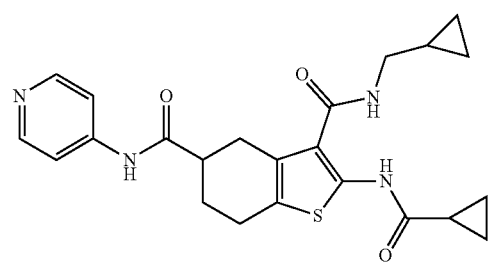

2-(Cyclopropanecarbonylamino)-N3-(cyclopropylmethyl)-N5-(4-pyridyl)-4,5,6,7-tetrahydrobenzothiophene-3,5-dicarboxamide

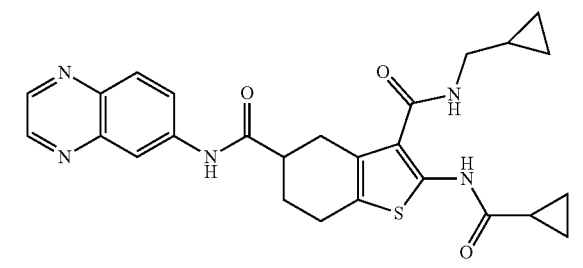

2-(Cyclopropanecarbonylamino)-N3-(cyclopropylmethyl)-N5-quinoxalin-6-yl-4,5,6,7-tetrahydrobenzothiophene-3,5-dicarboxamide

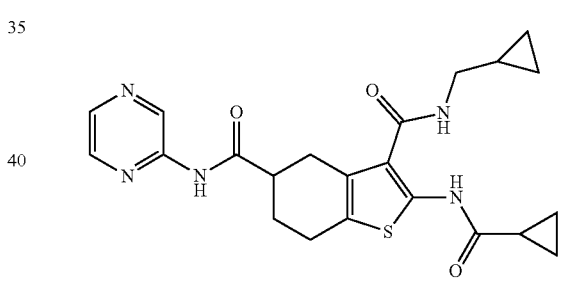

2-(Cyclopropanecarbonylamino)-N3-(cyclopropylmethyl)-N5-pyrazin-2-yl-4,5,6,7-tetrahydrobenzothiophene-3,5-dicarboxamide

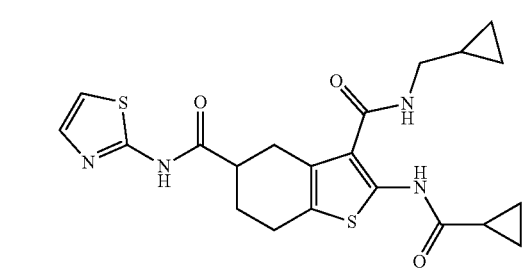

2-(Cyclopropanecarbonylamino)-N3-(cyclopropylmethyl)-N5-thiazol-2-yl-4,5,6,7-tetrahydrobenzothiophene-3,5-dicarboxamide

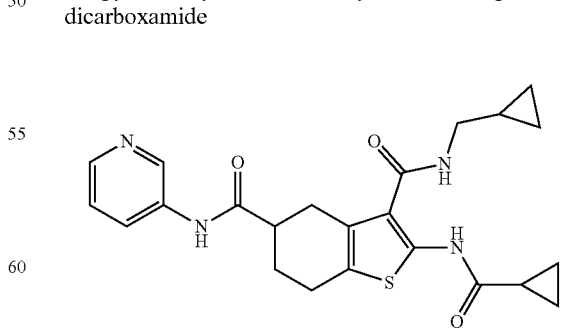

2-(Cyclopropanecarbonylamino)-N3-(cyclopropylmethyl)-N5-(3-pyridyl)-4,5,6,7-tetrahydrobenzothiophene-3,5-dicarboxamide

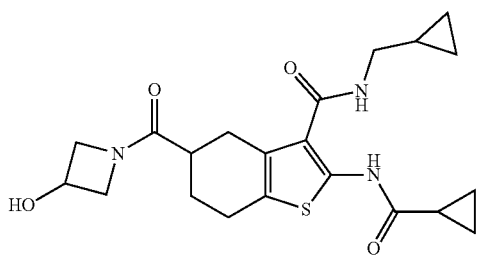 [SMILES: O=C(NCC1CC1)c1c(NC(=O)C2CC2)sc2c1CC(C(=O)N1CC(O)C1)CC2]

2-(Cyclopropanecarbonylamino)-N-(cyclopropylmethyl)-5-(3-hydroxyazetidine-1-carbonyl)-4,5,6,7-tetrahydrobenzothiophene-3-carboxamide

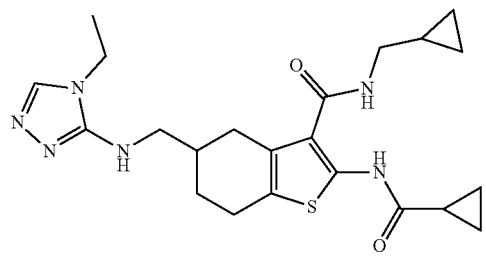

2-(Cyclopropanecarbonylamino)-N-(cyclopropylmethyl)-5-[[(4-ethyl-1,2,4-triazol-3-yl)amino]methyl]-4,5,6,7-tetrahydrobenzothiophene-3-carboxamide

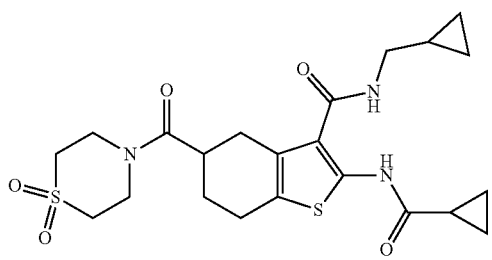 [SMILES: O=C(NCC1CC1)c1c(NC(=O)C2CC2)sc2c1CC(C(=O)N1CCS(=O)(=O)CC1)CC2]

2-(Cyclopropanecarbonylamino)-N-(cyclopropylmethyl)-5-(1,1-dioxo-1,4-thiazinane-4-carbonyl)-4,5,6,7-tetrahydrobenzothiophene-3-carboxamide

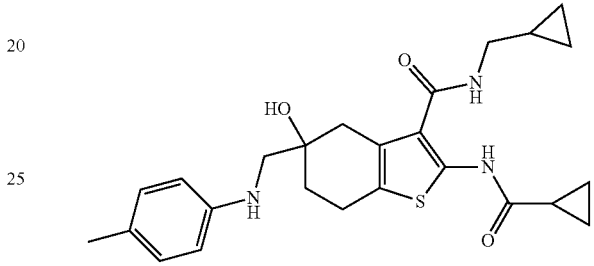

2-(Cyclopropanecarbonylamino)-N-(cyclopropylmethyl)-5-hydroxy-5-[(4-methylanilino)methyl]-6,7-dihydro-4H-benzothiophene-3-carboxamide

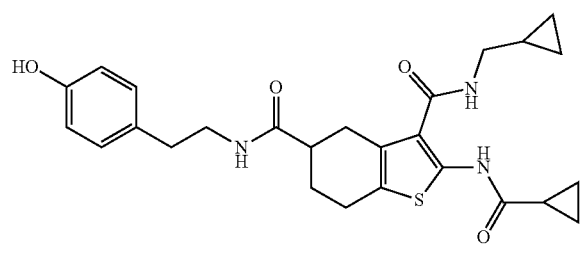 [SMILES: O=C(NCC1CC1)c1c(NC(=O)C2CC2)sc2c1CC(C(=O)NCCc1ccc(O)cc1)CC2]

2-(Cyclopropanecarbonylamino)-N3-(cyclopropylmethyl)-N5-[2-(4-hydroxyphenyl)ethyl]-4,5,6,7-tetrahydrobenzothiophene-3,5-dicarboxamide

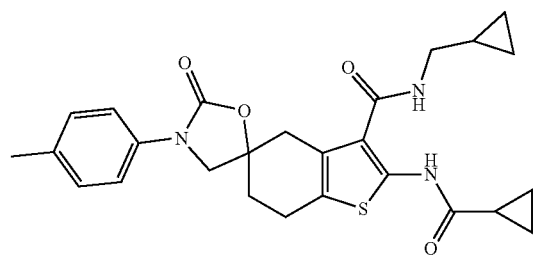

2-(Cyclopropanecarbonylamino)-N-(cyclopropylmethyl)-2'-oxo-3'-(p-tolyl)spiro[6,7-dihydro-4H-benzothiophene-5,5'-oxazolidine]-3-carboxamide

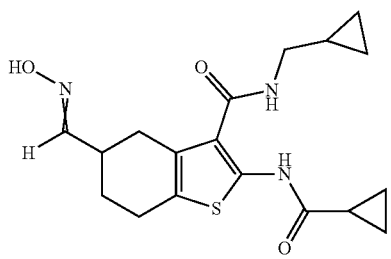 [SMILES: O=C(NCC1CC1)c1c(NC(=O)C2CC2)sc2c1CC(C=NO)CC2]

2-(cyclopropanecarbonylamino)-N-(cyclopropylmethyl)-5-(hydroxyiminomethyl)-4,5,6,7-tetrahydrobenzothiophene-3-carboxamide

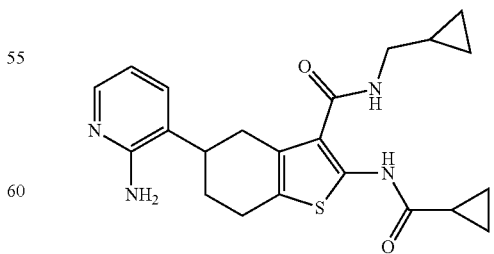

5-(2-Amino-3-pyridyl)-2-(cyclopropanecarbonylamino)-N-(cyclopropylmethyl)-4,5,6,7-tetrahydrobenzothiophene-3-carboxamide

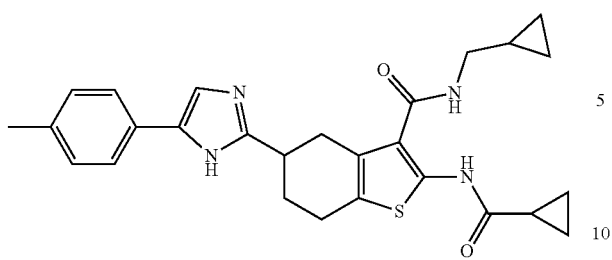

2-(Cyclopropanecarbonylamino)-N-(cyclopropylmethyl)-5-[5-(p-tolyl)-1H-imidazol-2-yl]-4,5,6,7-tetrahydrobenzothiophene-3-carboxamide

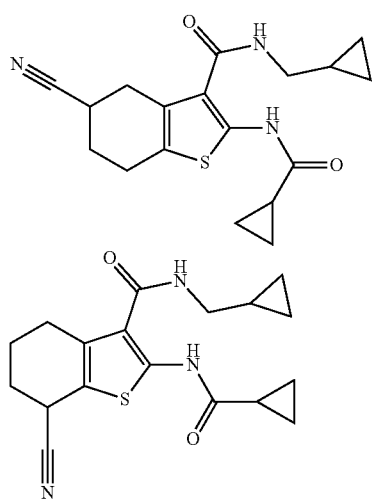

5-Cyano-2-(cyclopropanecarbonylamino)-N-(cyclopropylmethyl)-4,5,6,7-tetrahydrobenzothiophene-3-carboxamide 7-Cyano-2-(cyclopropanecarbonylamino)-N-(cyclopropylmethyl)-4,5,6,7-tetrahydrobenzothiophene-3-carboxamide

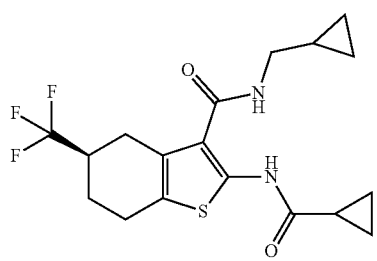

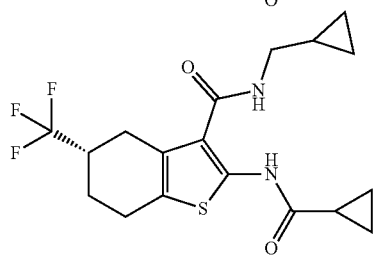

(5R)-2-(Cyclopropanecarbonylamino)-N-(cyclopropylmethyl)-5-(trifluoromethyl)-4,5,6,7-tetrahydrobenzothiophene-3-carboxamide (5S)-2-(Cyclopropanecarbonylamino)-N-(cyclopropylmethyl)-5-(trifluoromethyl)-4,5,6,7-tetrahydrobenzothiophene-3-carboxamide

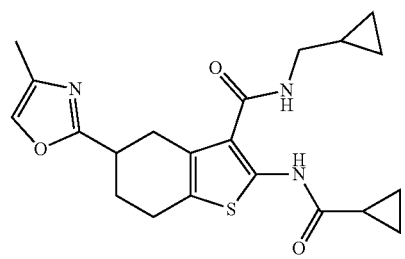 [SMILES: Cc1coc(C2CCc3sc(NC(=O)C4CC4)c(C(=O)NCC4CC4)c3C2)n1]

2-(Cyclopropanecarbonylamino)-N-(cyclopropylmethyl)-5-(4-methyloxazol-2-yl)-4,5,6,7-tetrahydrobenzothiophene-3-carboxamide

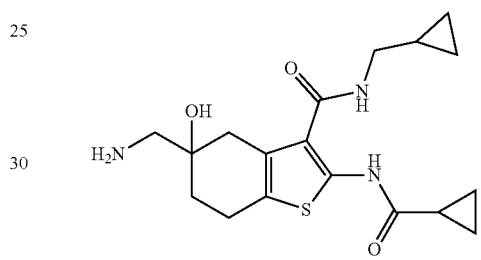

5-(Aminomethyl)-2-(cyclopropanecarbonylamino)-N-(cyclopropylmethyl)-5-hydroxy-6,7-dihydro-4H-tetrahydrobenzothiophene-3-carboxamide

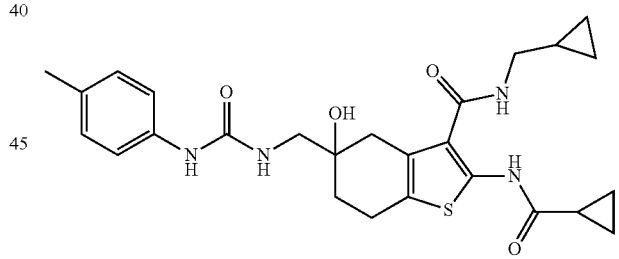

2-(Cyclopropanecarbonylamino)-N-(cyclopropylmethyl)-5-hydroxy-5-[(p-tolylcarbamoylamino)methyl]-6,7-dihydro-4H-benzothiophene-3-carboxamide

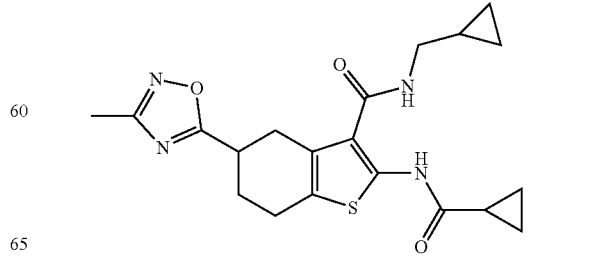

2-(Cyclopropanecarbonylamino)-N-(cyclopropylmethyl)-5-(3-methyl-1,2,4-oxadiazol-5-yl)-4,5,6,7-tetrahydrobenzothiophene-3-carboxamide

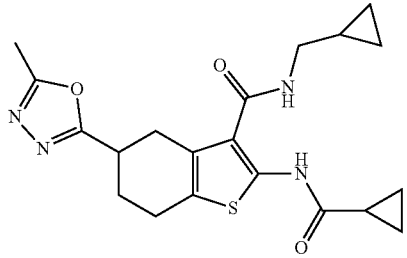 [SMILES: Cc1nnc(C2CCc3sc(NC(=O)C4CC4)c(C(=O)NCC4CC4)c3C2)o1]

2-(Cyclopropanecarbonylamino)-N-(cyclopropylmethyl)-5-(5-methyl-1,3,4-oxadiazol-2-yl)-4,5,6,7-tetrahydrobenzothiophene-3-carboxamide

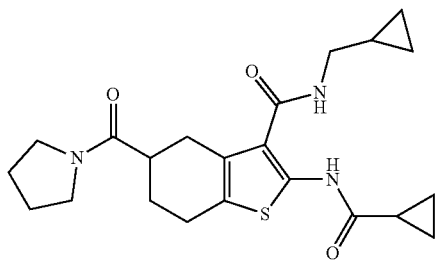 [SMILES: O=C(NCC1CC1)c1c(NC(=O)C2CC2)sc2c1CC(C(=O)N1CCCC1)CC2]

2-(Cyclopropanecarbonylamino)-N-(cyclopropylmethyl)-5-(pyrrolidine-1-carbonyl)-4,5,6,7-tetrahydrobenzothiophene-3-carboxamide

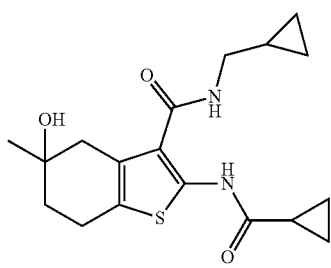 [SMILES: CC1(O)CCc2sc(NC(=O)C3CC3)c(C(=O)NCC3CC3)c2C1]

2-(Cyclopropanecarbonylamino)-N-(cyclopropylmethyl)-5-hydroxy-5-methyl-6,7-dihydro-4H-benzothiophene-3-carboxamide

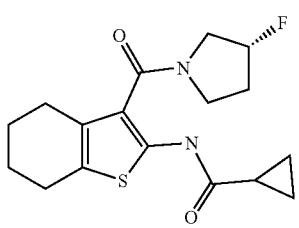 [SMILES: O=C(Nc1sc2c(c1C(=O)N1CC[C@@H](F)C1)CCCC2)C1CC1]

N-[3-[(3R)-3-Fluoropyrrolidine-1-carbonyl]-4,5,6,7-tetrahydrobenzothiophen-2-yl]cyclopropanecarboxamide

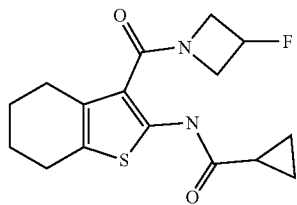 [SMILES: O=C(Nc1sc2c(c1C(=O)N1CC(F)C1)CCCC2)C1CC1]

N-[3-(3-Fluoroazetidine-1-carbonyl)-4,5,6,7-tetrahydrobenzothiophen-2-yl]cyclopropanecarboxamide

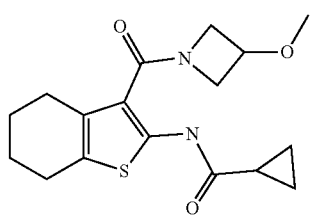

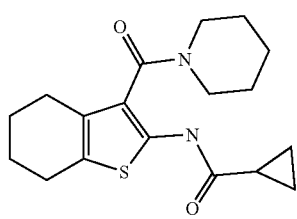

N-[3-(Piperidine-1-carbonyl)-4,5,6,7-tetrahydrobenzothiophen-2-yl]cyclopropanecarboxamide

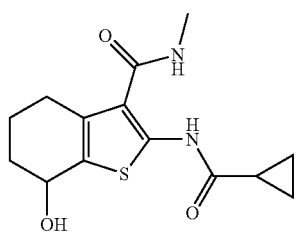 [SMILES: CNC(=O)c1c(NC(=O)C2CC2)sc2c1CCCC2O]

2-(Cyclopropanecarbonylamino)-7-hydroxy-N-methyl-4,5,6,7-tetrahydrobenzothiophene-3-carboxamide

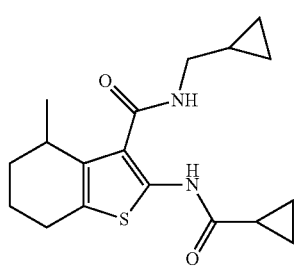 [SMILES: CC1CCCc2sc(NC(=O)C3CC3)c(C(=O)NCC3CC3)c21]

2-(Cyclopropanecarbonylamino)-N-(cyclopropylmethyl)-4-methyl-4,5,6,7-tetrahydrobenzothiophene-3-carboxamide

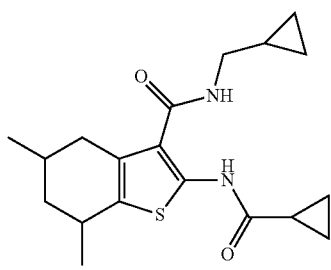 [SMILES: CC1Cc2c(sc(NC(=O)C3CC3)c2C(=O)NCC2CC2)C(C)C1]

2-(Cyclopropanecarbonylamino)-N-(cyclopropylmethyl)-5,7-dimethyl-4,5,6,7-tetrahydrobenzothiophene-3-carboxamide

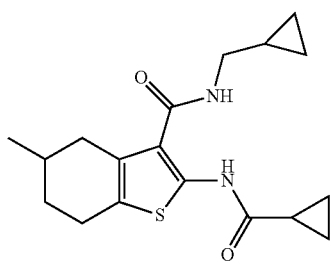

2-(Cyclopropanecarbonylamino)-N-(cyclopropylmethyl)-5-methyl-4,5,6,7-tetrahydrobenzothiophene-3-carboxamide 2-(cyclopropanecarbonylamino)-N-(cyclopropylmethyl)-7-methyl-4,5,6,7-tetrahydrobenzothiophene-3-carboxamide

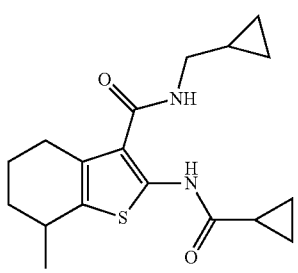

2-(Cyclopropanecarbonylamino)-N-(cyclopropylmethyl)-5,5-dimethyl-6,7-dihydro-4H-benzothiophene-3-carboxamide

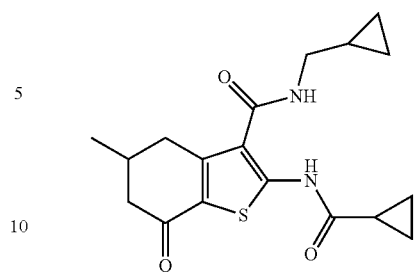

2-(Cyclopropanecarbonylamino)-N-(cyclopropylmethyl)-5-methyl-7-oxo-5,6-dihydro-4H-benzothiophene-3-carboxamide

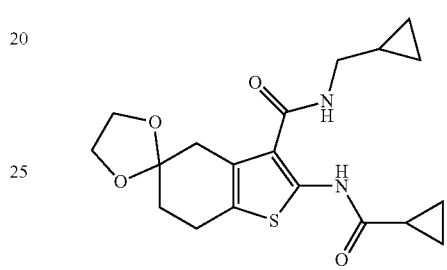

2'-(Cyclopropanecarbonylamino)-N-(cyclopropylmethyl) spiro[1,3-dioxolane-2,5'-6,7-dihydro-4H-benzothiophene]-3'-carboxamide

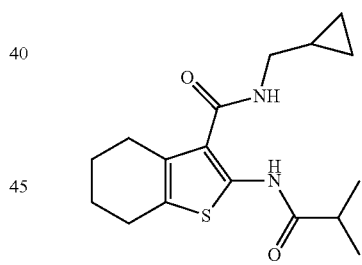

N-(Cyclopropylmethyl)-2-(2-methylpropanoylamino)-4,5,6,7-tetrahydrobenzothiophene-3-carboxamide

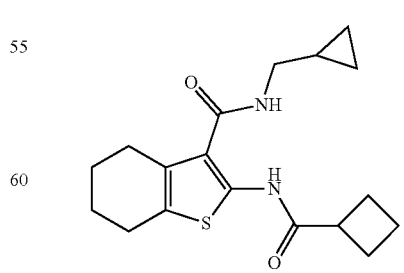

2-(Cyclobutanecarbonylamino)-N-(cyclopropylmethyl)-4,5,6,7-tetrahydrobenzothiophene-3-carboxamide

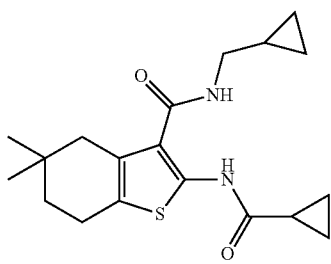 [SMILES: CC1(C)CCc2sc(NC(=O)C3CC3)c(C(=O)NCC3CC3)c2C1]

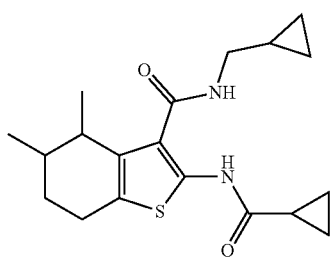 [SMILES: CC1CCc2sc(NC(=O)C3CC3)c(C(=O)NCC3CC3)c2C1C]

2-(Cyclopropanecarbonylamino)-N-(cyclopropylmethyl)-4,5-dimethyl-4,5,6,7-tetrahydrobenzothiophene-3-carboxamide 2-(Cyclopropanecarbonylamino)-4,5-dimethyl-4,5,6,7-tetrahydrobenzothiophene-3-carboxylic acid

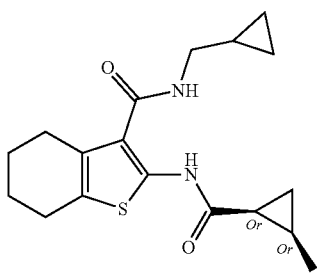

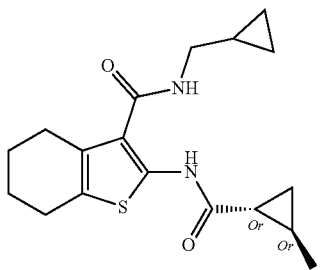

N-(cyclopropylmethyl)-2-[(2-methylcyclopropanecarbonyl)amino]-4,5,6,7-tetrahydrobenzothiophene-3-carboxamide—Diastereomer 1

N-(cyclopropylmethyl)-2-[(2-methylcyclopropanecarbonyl)amino]-4,5,6,7-tetrahydrobenzothiophene-3-carboxamide—Diastereomer 2

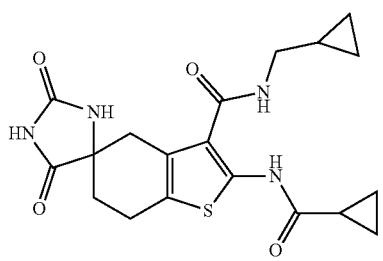 [SMILES: O=C1NC(=O)C2(CCc3sc(NC(=O)C4CC4)c(C(=O)NCC4CC4)c3C2)N1]

2-(Cyclopropanecarbonylamino)-N-(cyclopropylmethyl)-2',5'-dioxo-spiro[6,7-dihydro-4H-benzothiophene-5,4'-imidazolidine]-3-carboxamide

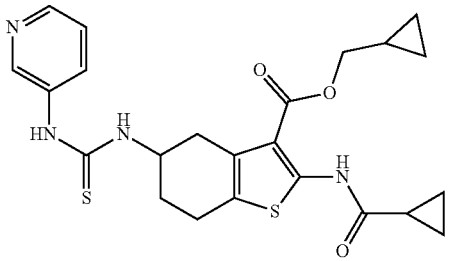 [SMILES: O=C(OCC1CC1)c1c(NC(=O)C2CC2)sc2c1CC(NC(=S)Nc1cccnc1)CC2]

Cyclopropylmethyl 2-(cyclopropanecarbonylamino)-5-(3-pyridylcarbamothioylamino)-4,5,6,7-tetrahydrobenzothiophene-3-carboxylate

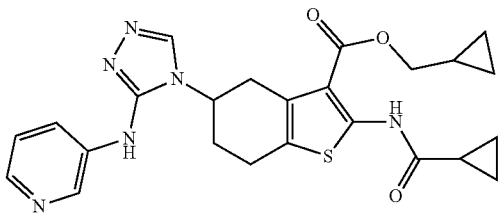 [SMILES: O=C(OCC1CC1)c1c(NC(=O)C2CC2)sc2c1CC(n1cnnc1Nc1cccnc1)CC2]

Cyclopropylmethyl 2-(cyclopropanecarbonylamino)-5-[3-(3-pyridylamino)-1,2,4-triazol-4-yl]-4,5,6,7-tetrahydrobenzothiophene-3-carboxylate

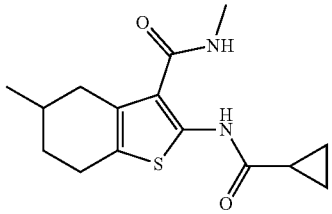

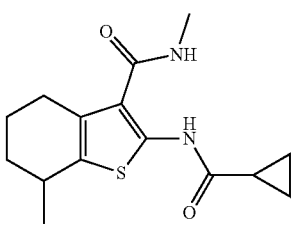

2-(Cyclopropanecarbonylamino)-N,5-dimethyl-4,5,6,7-tetrahydrobenzothiophene-3-carboxamide 2-(Cyclopropanecarbonylamino)-N,7-dimethyl-4,5,6,7-tetrahydrobenzothiophene-3-carboxamide

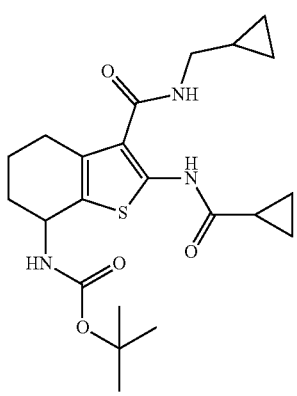 [SMILES: CC(C)(C)OC(=O)NC1CCCc2c1sc(NC(=O)C1CC1)c2C(=O)NCC1CC1]

tert-Butyl N-[2-(cyclopropanecarbonylamino)-3-(cyclopropylmethylcarbamoyl)-4,5,6,7-tetrahydrobenzothiophen-7-yl]carbamate

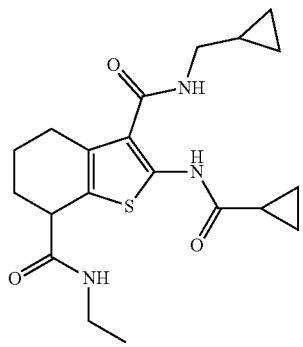

2-(Cyclopropanecarbonylamino)-N3-(cyclopropylmethyl)-N7-ethyl-4,5,6,7-tetrahydrobenzothiophene-3,7-dicarboxamide

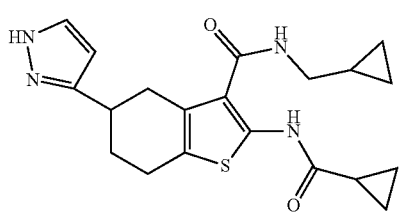

-continued

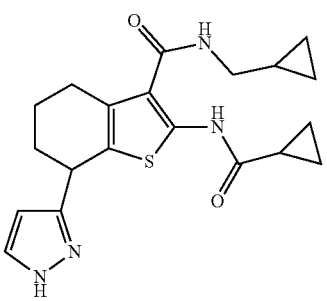

2-(Cyclopropanecarbonylamino)-N-(cyclopropylmethyl)-5-(1H-pyrazol-3-yl)-4,5,6,7-tetrahydrobenzothiophene-3-carboxamide 2-(Cyclopropanecarbonylamino)-N-(cyclopropylmethyl)-7-(1H-pyrazol-3-yl)-4,5,6,7-tetrahydrobenzothiophene-3-carboxamide

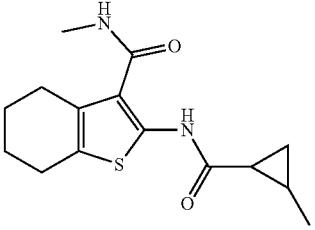 [SMILES: CNC(=O)c1c(NC(=O)C2CC2C)sc2c1CCCC2]

N-Methyl-2-[(2-methylcyclopropanecarbonyl)amino]-4,5,6,7-tetrahydrobenzothiophene-3-carboxamide

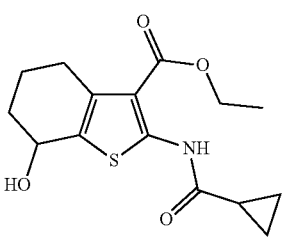 [SMILES: CCOC(=O)c1c(NC(=O)C2CC2)sc2c1CCCC2O]

Ethyl 2-(cyclopropanecarbonylamino)-7-hydroxy-4,5,6,7-tetrahydrobenzothiophene-3-carboxylate

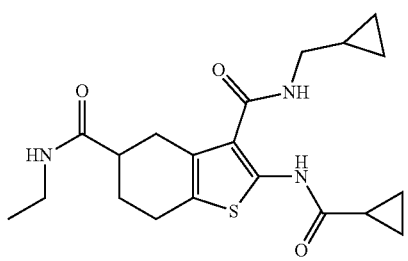

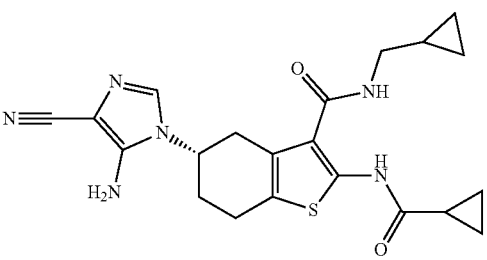 [SMILES: N#Cc1ncn([C@H]2CCc3sc(NC(=O)C4CC4)c(C(=O)NCC4CC4)c3C2)c1N]

(5S)-5-(5-Amino-4-cyano-imidazol-yl)-2-(cyclopropanecarbonylamino)-N-(cyclopropylmethyl)-4,5,6,7-tetrahydrobenzothiophene-3-carboxamide

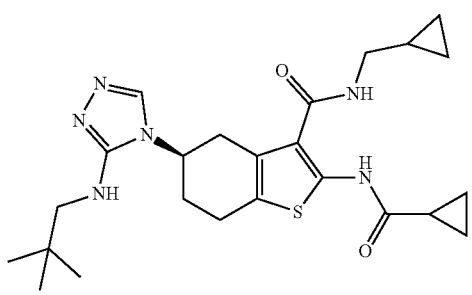 [SMILES: CC(C)(C)CNc1nncn1[C@@H]1CCc2sc(NC(=O)C3CC3)c(C(=O)NCC3CC3)c2C1]

(5S)-2-(Cyclopropanecarbonylamino)-N-(cyclopropylmethyl)-5-[3-(2,2-dimethylpropylamino)-1,2,4-triazol-4-yl]-4,5,6,7-tetrahydrobenzothiophene-3-carboxamide

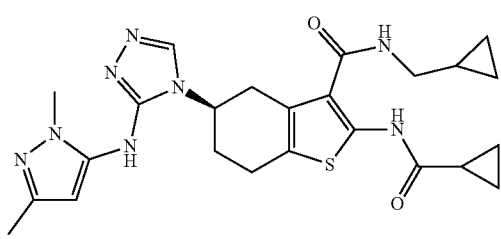

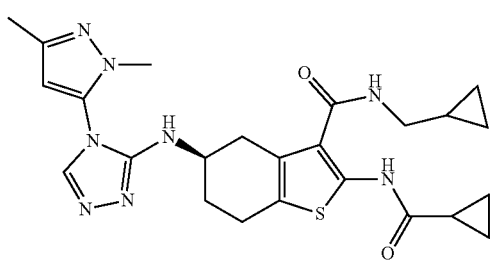

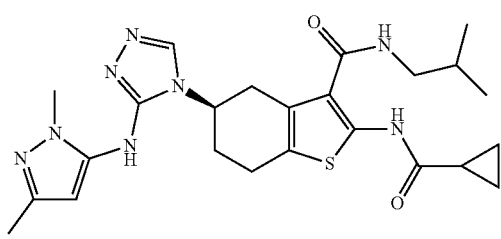

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide (5S)-2-(Cyclopropanecarbonylamino)-N-(cyclopropylmethyl)-5-[[4-(2,5-dimethylpyrazol-3-yl)-1,2,4-triazol-3-yl]amino]-4,5,6,7-tetrahydrobenzothiophene-3-carboxamide (5S)-2-(Cyclopropanecarbonylamino)-5-[3-[(2,5-dimethylpyrazol-3-yl)amino]-1,2,4-triazol-4-yl]-N-isobutyl-4,5,6,7-tetrahydrobenzothiophene-3-carboxamide

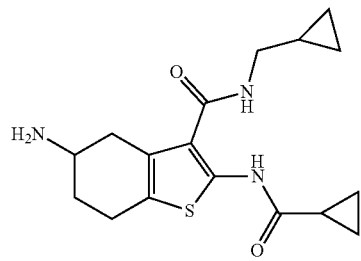

5-Amino-2-(cyclopropanecarbonylamino)-N-(cyclopropylmethyl)-4,5,6,7-tetrahydrobenzothiophene-3-carboxamide

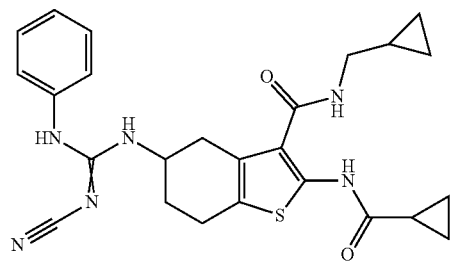

5-[[N'-Cyano-N-phenyl-carbamimidoyl]amino]-2-(cyclopropanecarbonylamino)-N-(cyclopropylmethyl)-4,5,6,7-tetrahydrobenzothiophene-3-carboxamide

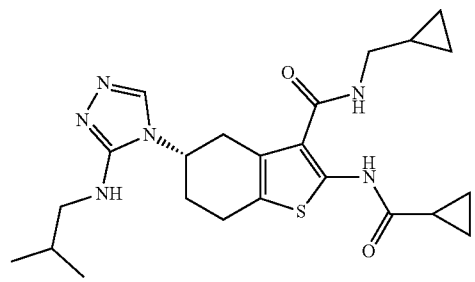

(5S)-2-(Cyclopropanecarbonylamino)-N-(cyclopropylmethyl)-5-[3-(isobutylamino)-1,2,4-triazol-4-yl]-4,5,6,7-tetrahydrobenzothiophene-3-carboxamide

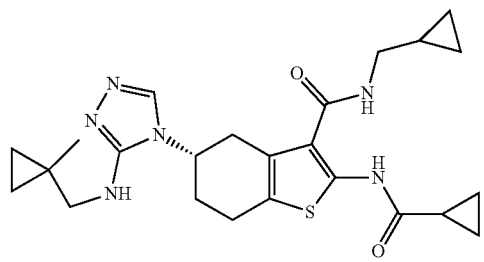

(5S)-2-(Cyclopropanecarbonylamino)-N-(cyclopropylmethyl)-5-[3-[(1-methylcyclopropyl)methylamino]-1,2,4-triazol-4-yl]-4,5,6,7-tetrahydrobenzothiophene-3-carboxamide

53

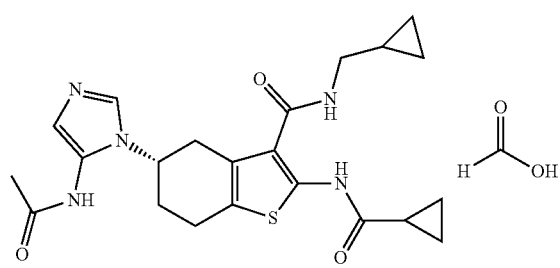

(5S)-5-(5-Acetamidoimidazol-1-yl)-2-(cyclopropanecarbonylamino)-N-(cyclopropylmethyl)-4,5,6,7-tetrahydrobenzothiophene-3-carboxamide

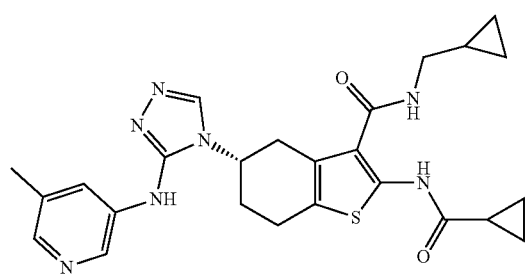

(5S)-2-(cyclopropanecarbonylamino)-N-(cyclopropylmethyl)-5-[3-[(5-methyl-3-pyridyl)amino]-1,2,4-triazol-4-yl]-4,5,6,7-tetrahydrobenzothiophene-3-carboxamide

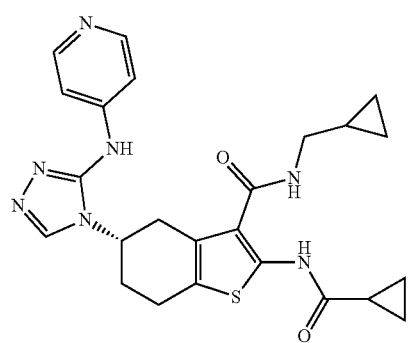

(5S)-2-(Cyclopropanecarbonylamino)-N-(cyclopropylmethyl)-5-[3-(4-pyridylamino)-1,2,4-triazol-4-yl]-4,5,6,7-tetrahydrobenzothiophene-3-carboxamide

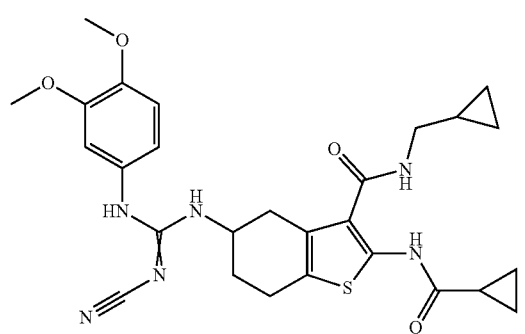

54

5-[[N'-Cyano-N-(3,4-dimethoxyphenyl)carbamimidoyl]amino]-2-(cyclopropanecarbonylamino)-N-(cyclopropylmethyl)-4,5,6,7-tetrahydrobenzothiophene-3-carboxamide

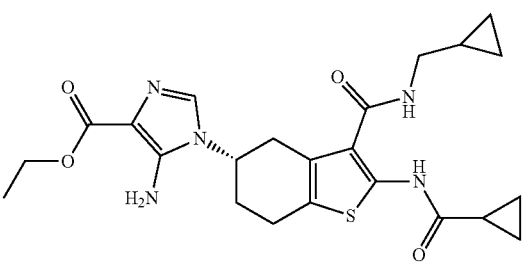

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate

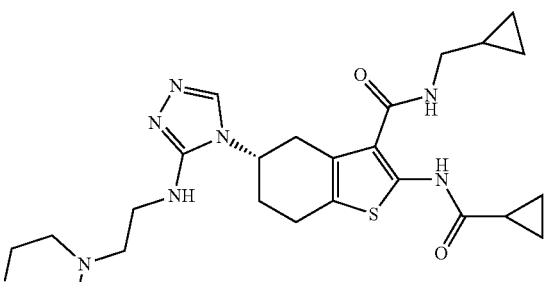

(5S)-2-(Cyclopropanecarbonylamino)-N-(cyclopropylmethyl)-5-[3-(2-morpholinoethylamino)-1,2,4-triazol-4-yl]-4,5,6,7-tetrahydrobenzothiophene-3-carboxamide

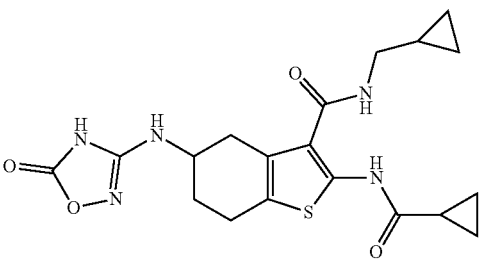

2-(Cyclopropanecarbonylamino)-N-(cyclopropylmethyl)-5-[(5-oxo-4H-1,2,4-oxadiazol-3-yl)amino]-4,5,6,7-tetrahydrobenzothiophene-3-carboxamide

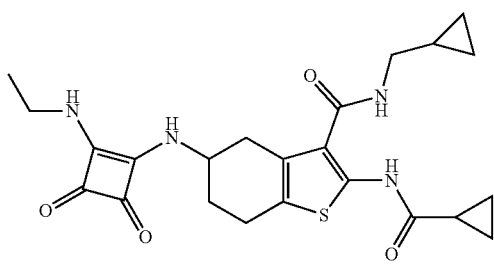

2-(Cyclopropanecarbonylamino)-N-(cyclopropylmethyl)-5-[[2-(ethylamino)-3,4-dioxo-cyclobuten-1-yl]amino]-4,5,6,7-tetrahydrobenzothiophene-3-carboxamide

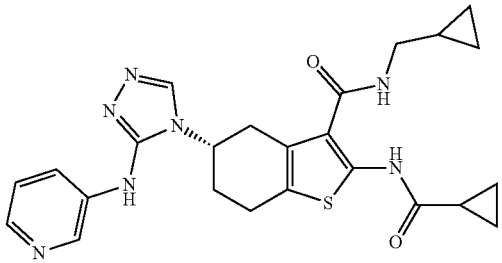

(5S)-2-(Cyclopropanecarbonylamino)-N-(cyclopropylmethyl)-5-[3-(3-pyridylamino)-1,2,4-triazol-4-yl]-4,5,6,7-tetrahydrobenzothiophene-3-carboxamide

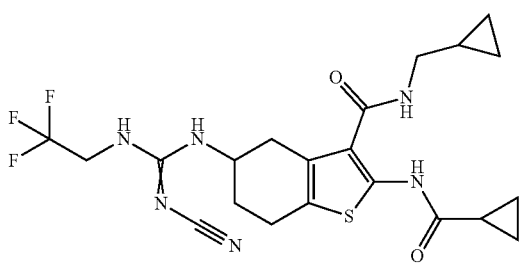

5-[[N'-cyano-N-(2,2,2-trifluoroethyl)carbamimidoyl]amino]-2-(cyclopropanecarbonylamino)-N-(cyclopropylmethyl)-4,5,6,7-tetrahydrobenzothiophene-3-carboxamide

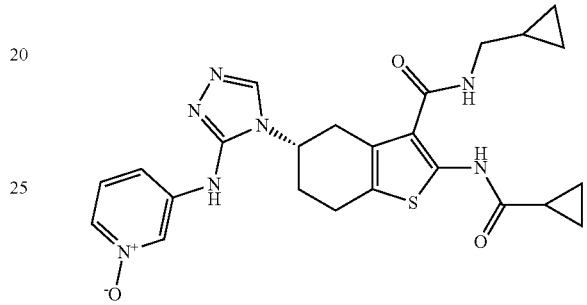

(5S)-2-(Cyclopropanecarbonylamino)-N-(cyclopropylmethyl)-5-[3-[(1-oxidopyridin-1-ium-3-yl)amino]-1,2,4-triazol-4-yl]-4,5,6,7-tetrahydrobenzothiophene-3-carboxamide

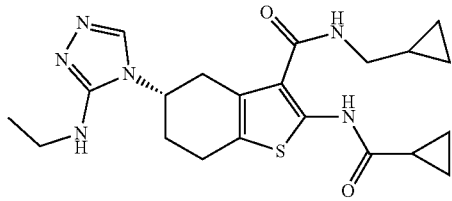

(5S)-2-(cyclopropanecarbonylamino)-N-(cyclopropylmethyl)-5-[3-(ethylamino)-1,2,4-triazol-4-yl]-4,5,6,7-tetrahydrobenzothiophene-3-carboxamide

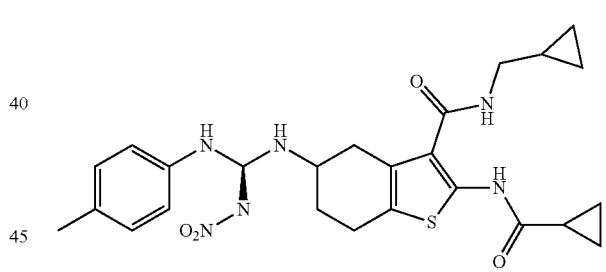

2-(cyclopropanecarbonylamino)-N-(cyclopropylmethyl)-5-[[N'-nitro-N-(p-tolyl)carbamimidoyl]amino]-4,5,6,7-tetrahydrobenzothiophene-3-carboxamide

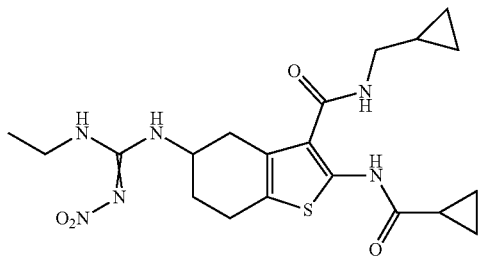

2-(cyclopropanecarbonylamino)-N-(cyclopropylmethyl)-5-[(N-ethyl-N'-nitro-carbamimidoyl)amino]-4,5,6,7-tetrahydrobenzothiophene-3-carboxamide

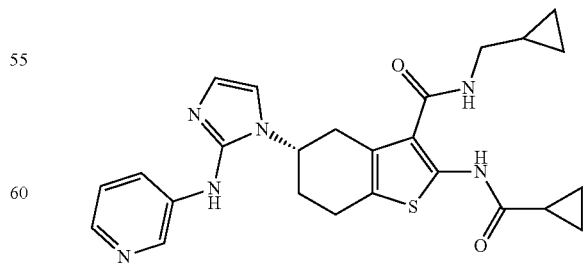

(5S)-2-(Cyclopropanecarbonylamino)-N-(cyclopropylmethyl)-5-[2-(3-pyridylamino)imidazol-1-yl]-4,5,6,7-tetrahydrobenzothiophene-3-carboxamide

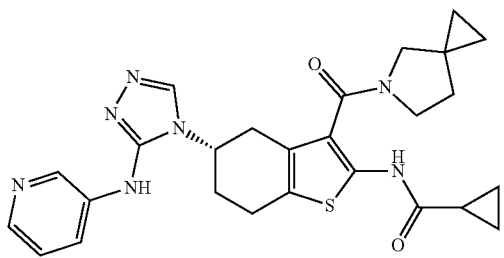

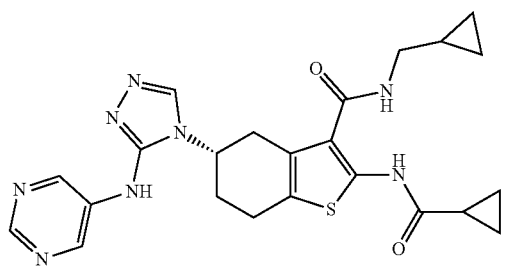 [SMILES: O=C(NCC1CC1)c1c(NC(=O)C2CC2)sc2c1C[C@@H](n1cnnc1Nc1cncnc1)CC2]

(5S)-2-(Cyclopropanecarbonylamino)-N-(cyclopropylmethyl)-5-[3-(pyrimidin-5-ylamino)-1,2,4-triazol-4-yl]-4,5,6,7-tetrahydrobenzothiophene-3-carboxamide

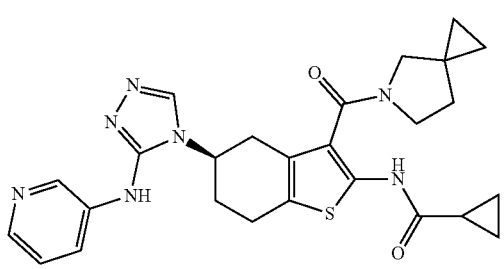

N-[(5S)-3-(5-azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide N-[(5R)-3-(5-Azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide (5S)-2-(Cyclopropanecarbonylamino)-N-(cyclopropylmethyl)-5-[2-(cyclopropylmethylamino)imidazol-1-yl]-4,5,6,7-tetrahydrobenzothiophene-3-carboxamide

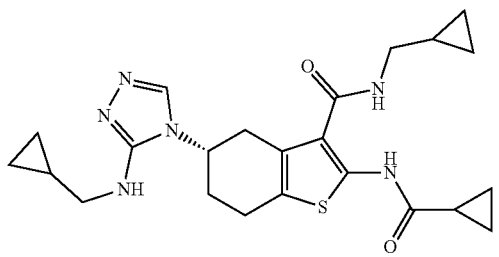 [SMILES: O=C(NCC1CC1)c1c(NC(=O)C2CC2)sc2c1C[C@@H](n1ccnc1NCC1CC1)CC2]

(5S)-2-(Cyclopropanecarbonylamino)-N-(cyclopropylmethyl)-5-[3-(cyclopropylmethylamino)-1,2,4-triazol-4-yl]-4,5,6,7-tetrahydrobenzothiophene-3-carboxamide

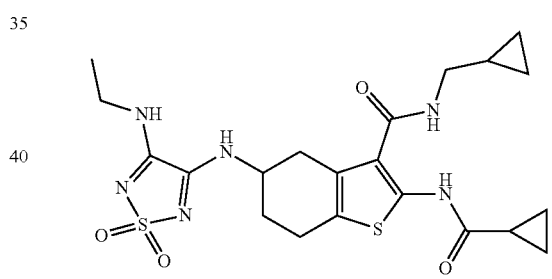

2-(Cyclopropanecarbonylamino)-N-(cyclopropylmethyl)-5-[[4-(ethylamino)-1,1-dioxo-1,2,5-thiadiazol-3-yl]amino]-4,5,6,7-tetrahydrobenzothiophene-3-carboxamide

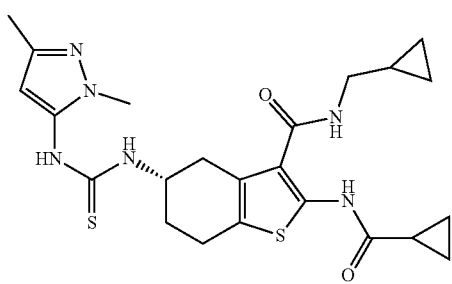

(5S)-2-(Cyclopropanecarbonylamino)-N-(cyclopropylmethyl)-5-[(2,5-dimethylpyrazol-3-yl)carbamothioylamino]-4,5,6,7-tetrahydrobenzothiophene-3-carboxamide

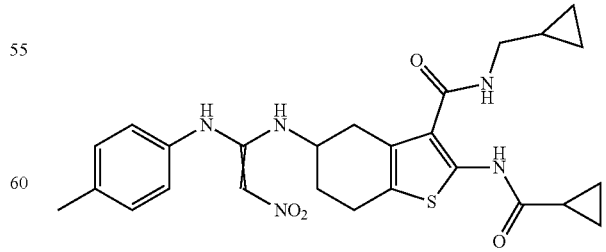

2-(cyclopropanecarbonylamino)-N-(cyclopropylmethyl)-5-[[1-(4-methylanilino)-2-nitro-vinyl]amino]-4,5,6,7-tetrahydrobenzothiophene-3-carboxamide

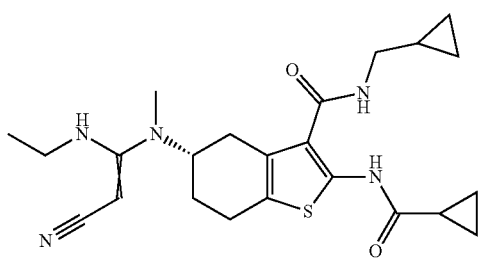 [SMILES: CCNC(=CC#N)N(C)[C@H]1CCc2sc(NC(=O)C3CC3)c(C(=O)NCC3CC3)c2C1]

(5S)-5-[(N'-cyano-N-ethyl-carbamimidoyl)-methyl-amino]-2-(cyclopropanecarbonylamino)-N-(cyclopropylmethyl)-4,5,6,7-tetrahydrobenzothiophene-3-carboxamide

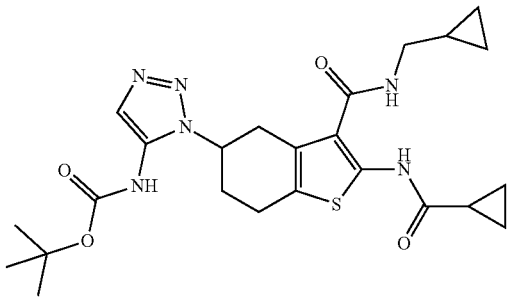

tert-Butyl N-[3-[2-(cyclopropanecarbonylamino)-3-(cyclopropylmethylcarbamoyl)-4,5,6,7-tetrahydrobenzothiophen-5-yl]triazol-4-yl]carbamate

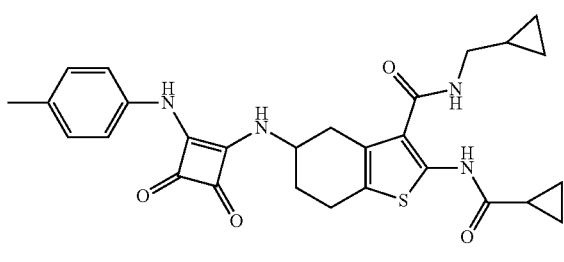 [SMILES: Cc1ccc(Nc2c(NC3CCc4sc(NC(=O)C5CC5)c(C(=O)NCC5CC5)c4C3)c(=O)c2=O)cc1]

2-(Cyclopropanecarbonylamino)-N-(cyclopropylmethyl)-5-[[2-(4-methyl anilino)-3,4-dioxo-cyclobuten-1-yl]amino]-4,5,6,7-tetrahydrobenzothiophene-3-carboxamide

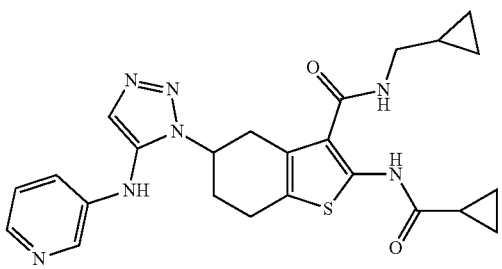

2-(Cyclopropanecarbonylamino)-N-(cyclopropylmethyl)-5-[5-(3-pyridylamino)triazol-1-yl]-4,5,6,7-tetrahydrobenzothiophene-3-carboxamide

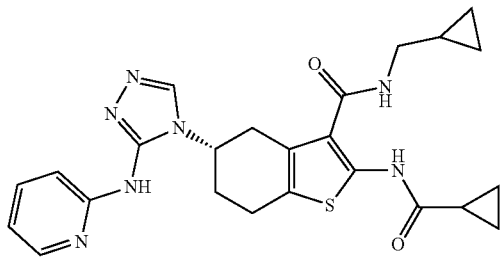 [SMILES: O=C(NCC1CC1)c1c(NC(=O)C2CC2)sc2c1C[C@@H](n1cnnc1Nc1ccccn1)CC2]

(5S)-2-(Cyclopropanecarbonylamino)-N-(cyclopropylmethyl)-5-[3-(2-pyridylamino)-1,2,4-triazol-4-yl]-4,5,6,7-tetrahydrobenzothiophene-3-carboxamide

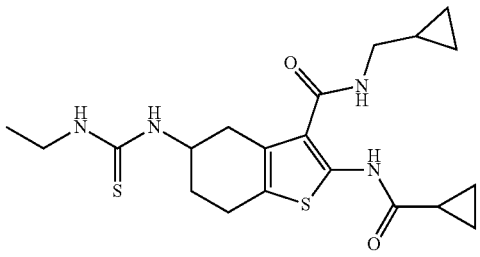

2-(Cyclopropanecarbonylamino)-N-(cyclopropylmethyl)-5-(ethylcarbamothioylamino)-4,5,6,7-tetrahydrobenzothiophene-3-carboxamide

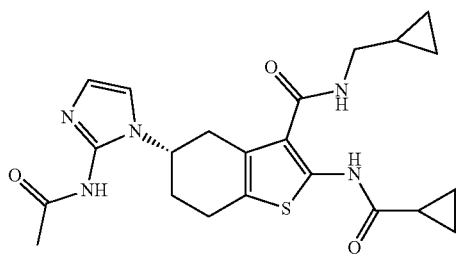 [SMILES: CC(=O)Nc1nccn1[C@H]1CCc2sc(NC(=O)C3CC3)c(C(=O)NCC3CC3)c2C1]

(5S)-5-(2-Acetamidoimidazol-1-yl)-2-(cyclopropanecarbonylamino)-N-(cyclopropylmethyl)-4,5,6,7-tetrahydrobenzothiophene-3-carboxamide

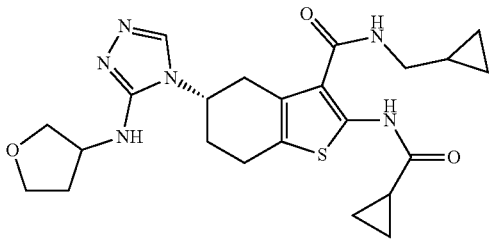 [SMILES: O=C(NCC1CC1)c1c(NC(=O)C2CC2)sc2c1C[C@@H](n1cnnc1NC1CCOC1)CC2]

(5S)-2-(cyclopropanecarbonylamino)-N-(cyclopropylmethyl)-5-[3-[[(3S)-tetrahydrofuran-3-yl]amino]-1,2,4-triazol-4-yl]-4,5,6,7-tetrahydrobenzothiophene-3-carboxamide

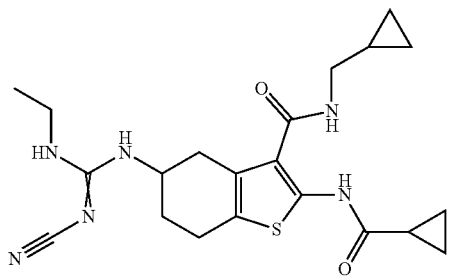 [SMILES: CCNC(=NC#N)NC1CCc2sc(NC(=O)C3CC3)c(C(=O)NCC3CC3)c2C1]

5-[[N'-Cyano-N-ethyl-carbamimidoyl]amino]-2-(cyclopropanecarbonylamino)-N-(cyclopropylmethyl)-4,5,6,7-tetrahydrobenzothiophene-3-carboxamide

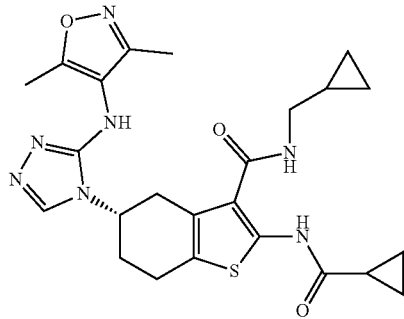

(5S)-2-(Cyclopropanecarbonylamino)-N-(cyclopropylmethyl)-5-[3-[(3,5-dimethylisoxazol-4-yl)amino]-1,2,4-triazol-4-yl]-4,5,6,7-tetrahydrobenzothiophene-3-carboxamide

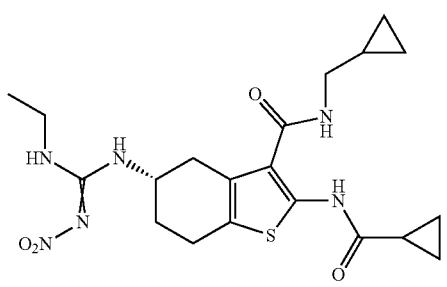

(5S)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide (5R)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide ethyl N-[[[2-(cyclopropanecarbonylamino)-3-(cyclopropylmethylcarbamoyl)-4,5,6,7-tetrahydrobenzothiophen-5-yl]amino]-(4-methylanilino)methylene]carbamate

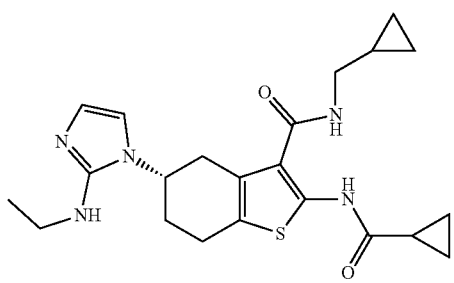 [SMILES: CCNc1nccn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[2-(ethylamino)imidazol-1-yl]-4,5,6,7-tetrahydrobenzothiophene-3-carboxamide

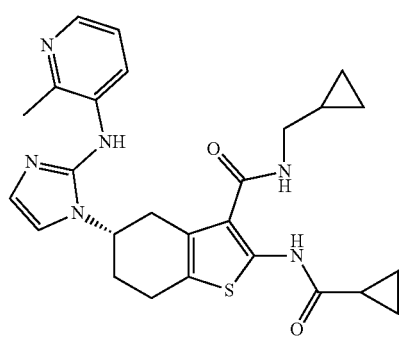 [SMILES: Cc1ncccc1Nc1nccn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[2-[(2-methyl-3-pyridyl)amino]imidazol-1-yl]-4,5,6,7-tetrahydrobenzothiophene-3-carboxamide

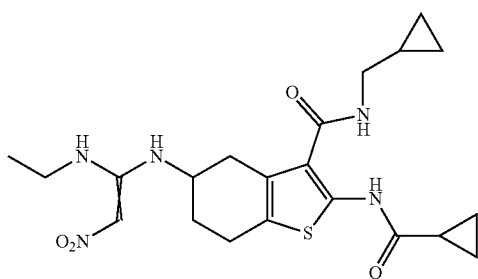 [SMILES: CCNC(=C[N+](=O)[O-])NC1CCc2sc(NC(=O)C3CC3)c(C(=O)NCC3CC3)c2C1]

2-(cyclopropanecarbonylamino)-N-(cyclopropylmethyl)-5-[[1-(ethylamino)-2-nitro-vinyl]amino]-4,5,6,7-tetrahydrobenzothiophene-3-carboxamide

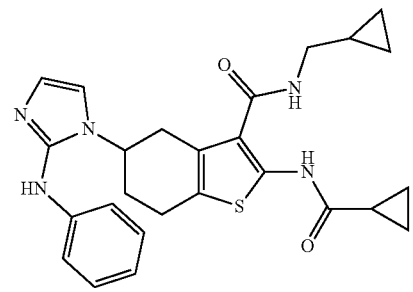

5-(2-Anilinoimidazol-1-yl)-2-(cyclopropanecarbonylamino)-N-(cyclopropylmethyl)-4,5,6,7-tetrahydrobenzothiophene-3-carboxamide

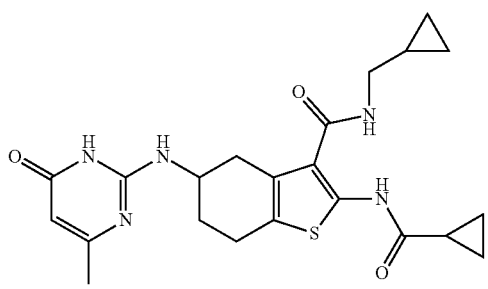 [SMILES: Cc1cc(=O)[nH]c(NC2CCc3sc(NC(=O)C4CC4)c(C(=O)NCC4CC4)c3C2)n1]

2-(Cyclopropanecarbonylamino)-N-(cyclopropylmethyl)-5-[(4-methyl-6-oxo-1H-pyrimidin-2-yl)amino]-4,5,6,7-tetrahydrobenzothiophene-3-carboxamide

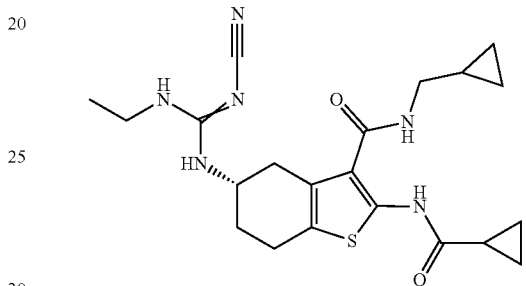

(5S)-5-[[N'-cyano-N-ethyl-carbamimidoyl]amino]-2-(cyclopropanecarbonylamino)-N-(cyclopropylmethyl)-4,5,6,7-tetrahydrobenzothiophene-3-carboxamide

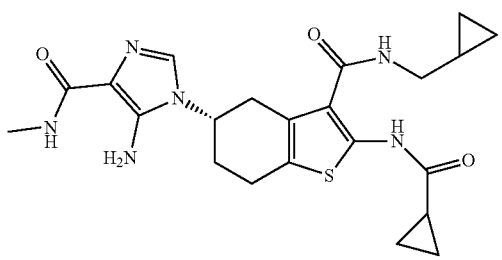 [SMILES: CNC(=O)c1ncn([C@H]2CCc3sc(NC(=O)C4CC4)c(C(=O)NCC4CC4)c3C2)c1N]

5-amino-1-[(5S)-2-cyclopropaneamido-3-[(cyclopropylmethyl)carbamoyl]-4,5,6,7-tetrahydro-1-benzothiophen-5-yl]-N-methyl-1H-imidazole-4-carboxamide

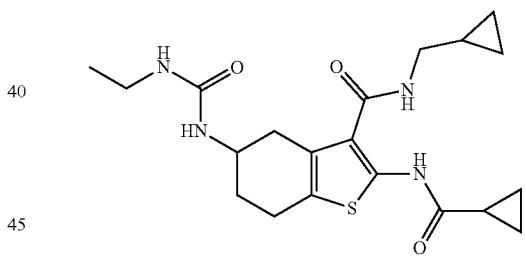

2-(Cyclopropanecarbonylamino)-N-(cyclopropylmethyl)-5-(ethylcarbamoylamino)-4,5,6,7-tetrahydrobenzothiophene-3-carboxamide

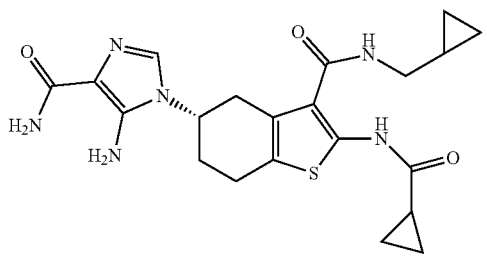 [SMILES: NC(=O)c1ncn([C@H]2CCc3sc(NC(=O)C4CC4)c(C(=O)NCC4CC4)c3C2)c1N]

5-amino-1-[(5S)-2-cyclopropaneamido-3-[(cyclopropylmethyl)carbamoyl]-4,5,6,7-tetrahydro-1-benzothiophen-5-yl]-1H-imidazole-4-carboxamide

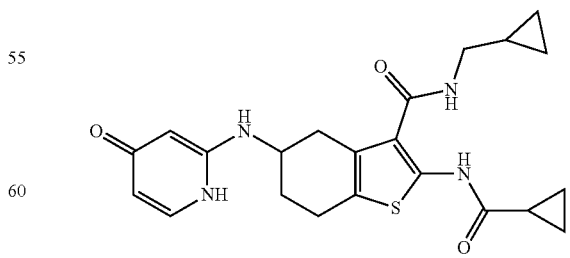

2-(Cyclopropanecarbonylamino)-N-(cyclopropylmethyl)-5-[(4-oxo-1H-pyridin-2-yl)amino]-4,5,6,7-tetrahydrobenzothiophene-3-carboxamide

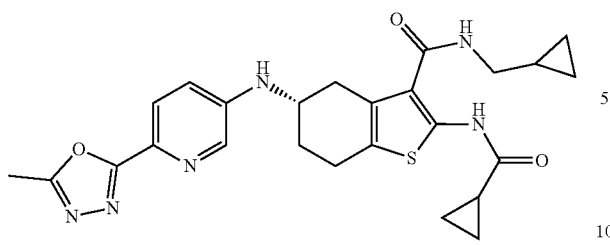

(5S)-2-(cyclopropanecarbonylamino)-N-(cyclopropylmethyl)-5-[[6-(5-methyl-1,3,4-oxadiazol-2-yl)-3-pyridyl]amino]-4,5,6,7-tetrahydrobenzothiophene-3-carboxamide

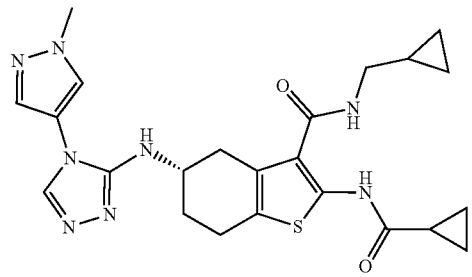

(5S)-2-(Cyclopropanecarbonylamino)-N-(cyclopropylmethyl)-5-[[4-(1-methylpyrazol-4-yl)-1,2,4-triazol-3-yl]amino]-4,5,6,7-tetrahydrobenzothiophene-3-carboxamide

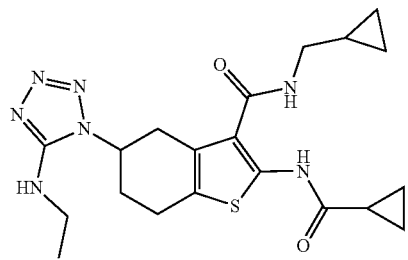 [SMILES: CCNc1nnnn1C1CCc2sc(NC(=O)C3CC3)c(C(=O)NCC3CC3)c2C1]

2-(Cyclopropanecarbonylamino)-N-(cyclopropylmethyl)-5-[5-(ethylamino)tetrazol-1-yl]-4,5,6,7-tetrahydrobenzothiophene-3-carboxamide

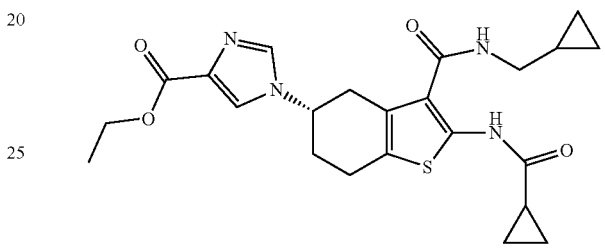

ethyl 1-[(5S)-2-cyclopropaneamido-3-[(cyclopropylmethyl)carbamoyl]-4,5,6,7-tetrahydro-1-benzothiophen-5-yl]-1H-imidazole-4-carboxylate

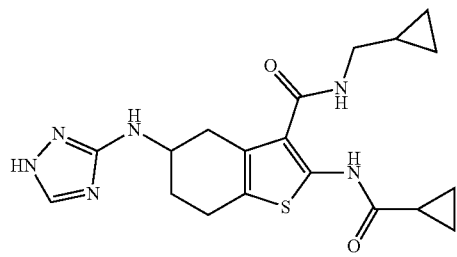 [SMILES: O=C(NCC1CC1)c1c(NC(=O)C2CC2)sc2c1CC(Nc1nc[nH]n1)CC2]

2-(Cyclopropanecarbonylamino)-N-(cyclopropylmethyl)-5-(1H-1,2,4-triazol-3-ylamino)-4,5,6,7-tetrahydrobenzothiophene-3-carboxamide

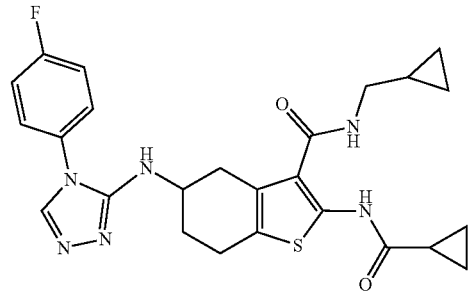

2-(Cyclopropanecarbonylamino)-N-(cyclopropylmethyl)-5-[[4-(4-fluorophenyl)-1,2,4-triazol-3-yl]amino]-4,5,6,7-tetrahydrobenzothiophene-3-carboxamide

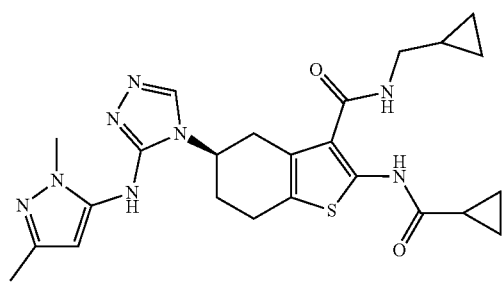 [SMILES: Cc1cc(Nc2nncn2[C@@H]2CCc3sc(NC(=O)C4CC4)c(C(=O)NCC4CC4)c3C2)n(C)n1]

(5R)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide

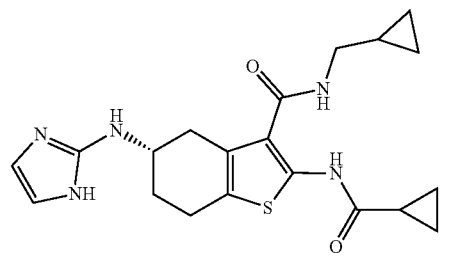 [SMILES: O=C(NCC1CC1)c1c(NC(=O)C2CC2)sc2c1C[C@@H](Nc1ncc[nH]1)CC2]

(5S)-2-(Cyclopropanecarbonylamino)-N-(cyclopropylmethyl)-5-(1H-imidazol-2-ylamino)-4,5,6,7-tetrahydrobenzothiophene-3-carboxamide

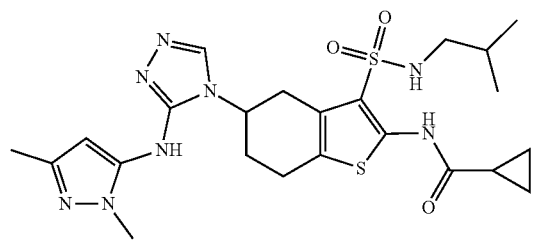 [SMILES: Cc1cc(Nc2nncn2C2CCc3sc(NC(=O)C4CC4)c(S(=O)(=O)NCC(C)C)c3C2)n(C)n1]

N-[3-(isopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide

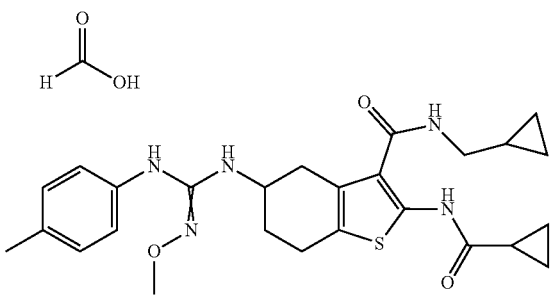

2-(Cyclopropanecarbonylamino)-N-(cyclopropylmethyl)-5-[[N'-methoxy-N-(p tolyl)carbamimidoyl]amino]-4,5,6,7-tetrahydrobenzothiophene-3-carboxamide

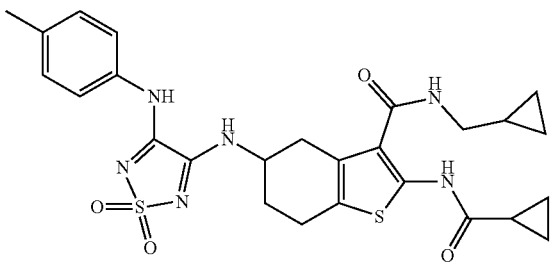 [SMILES: Cc1ccc(NC2=NS(=O)(=O)N=C2NC2CCc3sc(NC(=O)C4CC4)c(C(=O)NCC4CC4)c3C2)cc1]

2-(Cyclopropanecarbonylamino)-N-(cyclopropylmethyl)-5-[[4-(4-methyl anilino)-1,1-dioxo-1,2,5-thiadiazol-3-yl]amino]-4,5,6,7-tetrahydrobenzothiophene-3-carboxamide

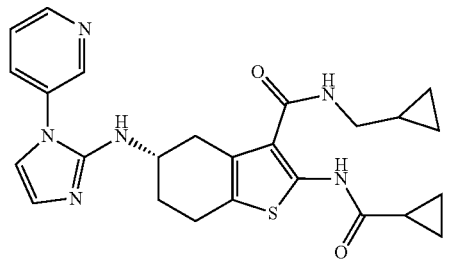 [SMILES: O=C(NCC1CC1)c1c(NC(=O)C2CC2)sc2c1C[C@@H](Nc1nccn1-c1cccnc1)CC2]

(5S)-2-(Cyclopropanecarbonylamino)-N-(cyclopropylmethyl)-5-[[1-(3-pyridyl)imidazol-2-yl]amino]-4,5,6,7-tetrahydrobenzothiophene-3-carboxamide

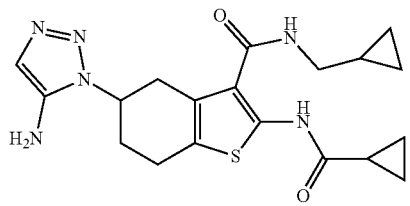 [SMILES: Nc1cnnn1C1CCc2sc(NC(=O)C3CC3)c(C(=O)NCC3CC3)c2C1]

5-(5-Aminotriazol-1-yl)-2-(cyclopropanecarbonylamino)-N-(cyclopropylmethyl)-4,5,6,7-tetrahydrobenzothiophene-3-carboxamide

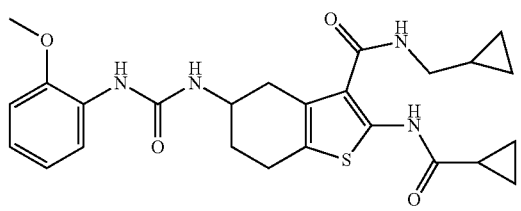 [SMILES: COc1ccccc1NC(=O)NC1CCc2sc(NC(=O)C3CC3)c(C(=O)NCC3CC3)c2C1]

2-(Cyclopropanecarbonylamino)-N-(cyclopropylmethyl)-5-[(2-methoxyphenyl)carbamoylamino]-4,5,6,7-tetrahydrobenzothiophene-3-carboxamide

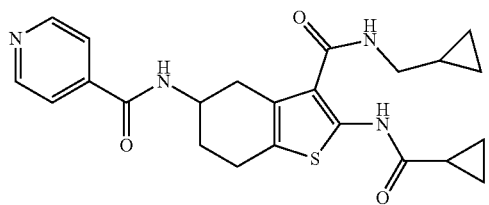 [SMILES: O=C(NC1CCc2sc(NC(=O)C3CC3)c(C(=O)NCC3CC3)c2C1)c1ccncc1]

N-[2-(Cyclopropanecarbonylamino)-3-(cyclopropylmethylcarbamoyl)-4,5,6,7-tetrahydrobenzothiophen-5-yl]pyridine-4-carboxamide

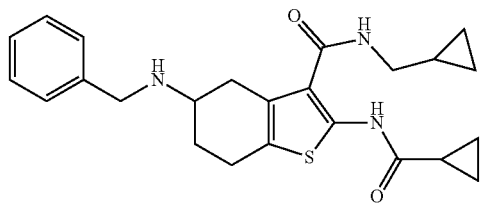 [SMILES: O=C(NCC1CC1)c1c(NC(=O)C2CC2)sc2c1CC(NCc1ccccc1)CC2]

5-(Benzylamino)-2-cyclopropanecarbonylamino)-N-(cyclopropylmethyl)-4,5,6,7-tetrahydrobenzothiophene-3-carboxamide

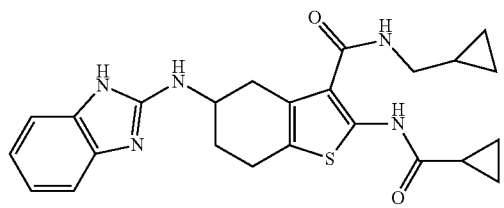 [SMILES: O=C(NCC1CC1)c1c(NC(=O)C2CC2)sc2c1CC(Nc1nc3ccccc3[nH]1)CC2]

5-(1H-Benzimidazol-2-ylamino)-2-(cyclopropanecarbonylamino)-N-(cyclopropylmethyl)-4,5,6,7-tetrahydrobenzothiophene-3-carboxamide

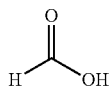

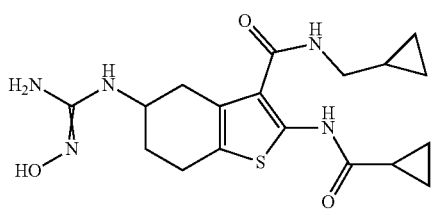

2-(Cyclopropanecarbonylamino)-N-(cyclopropylmethyl)-5-[[N'-hydroxycarbamimidoyl]amino]-4,5,6,7-tetrahydrobenzothiophene-3-carboxamide

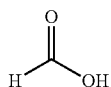

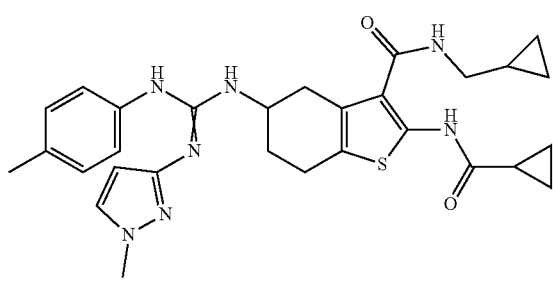

2-(Cyclopropanecarbonylamino)-N-(cyclopropylmethyl)-5-[[N'-(1-methylpyrazol-3-yl)-N-(p-tolyl)carbamimidoyl]amino]-4,5,6,7-tetrahydrobenzothiophene-3-carboxamide; formic acid

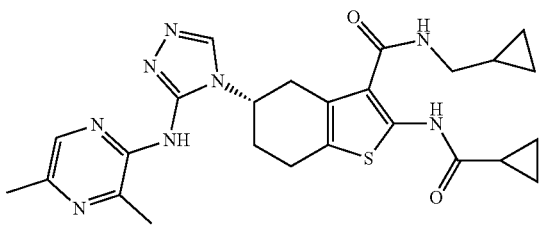 [SMILES: Cc1cnc(Nc2nncn2[C@H]2CCc3sc(NC(=O)C4CC4)c(C(=O)NCC4CC4)c3C2)c(C)n1]

(5S)-2-(Cyclopropanecarbonylamino)-N-(cyclopropylmethyl)-5-[3-[(3,5-dimethylpyrazin-2-yl)amino]-1,2,4-triazol-4-yl]-4,5,6,7-tetrahydrobenzothiophene-3-carboxamide

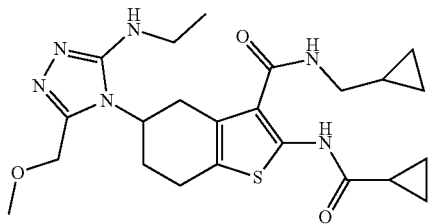 [SMILES: CCNc1nnc(COC)n1C1CCc2sc(NC(=O)C3CC3)c(C(=O)NCC3CC3)c2C1]

2-(Cyclopropanecarbonylamino)-N-(cyclopropylmethyl)-5-[3-(ethylamino)-5-(methoxymethyl)-1,2,4-triazol-4-yl]-4,5,6,7-tetrahydrobenzothiophene-3-carboxamide

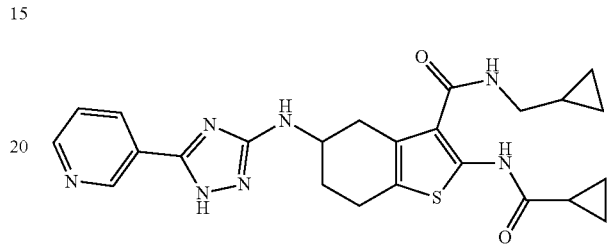

2-(Cyclopropanecarbonylamino)-N-(cyclopropylmethyl)-5-[[5-(3-pyridyl)-1H-1,2,4-triazol-3-yl]amino]-4,5,6,7-tetrahydrobenzothiophene-3-carboxamide

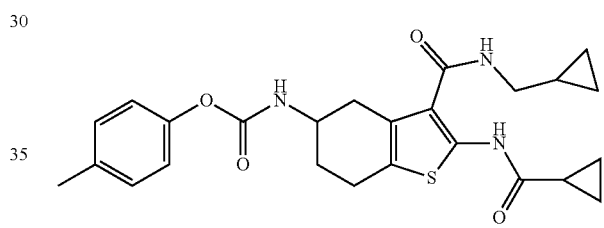

p-Tolyl N-[2-(cyclopropanecarbonylamino)-3-(cyclopropylmethylcarbamoyl)-4,5,6,7-tetrahydrobenzothiophen-5-yl]carbamate

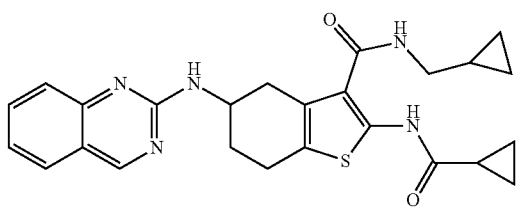 [SMILES: O=C(NCC1CC1)c1c(NC(=O)C2CC2)sc2c1CC(Nc1ncc3ccccc3n1)CC2]

2-(Cyclopropanecarbonylamino)-N-(cyclopropylmethyl)-5-(quinazolin-2-ylamino)-4,5,6,7-tetrahydrobenzothiophene-3-carboxamide

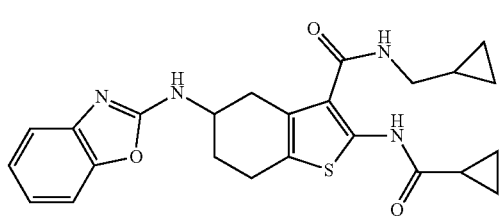 [SMILES: O=C(NCC1CC1)c1c(NC(=O)C2CC2)sc2c1CC(Nc1nc3ccccc3o1)CC2]

71

5-(1,3-Benzoxazol-2-ylamino)-2-(cyclopropanecarbonylamino)-N-(cyclopropylmethyl)-4,5,6,7-tetrahydrobenzothiophene-3-carboxamide

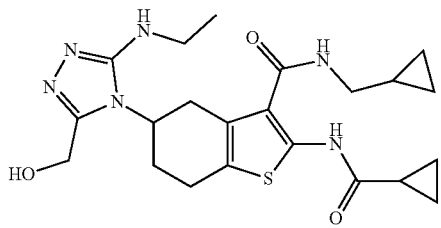 [SMILES: CCNc1nnc(CO)n1C1CCc2sc(NC(=O)C3CC3)c(C(=O)NCC3CC3)c2C1]

2-(Cyclopropanecarbonylamino)-N-(cyclopropylmethyl)-5-[3-(ethylamino)-5-(hydroxymethyl)-1,2,4-triazol-4-yl]-4,5,6,7-tetrahydrobenzothiophene-3-carboxamide

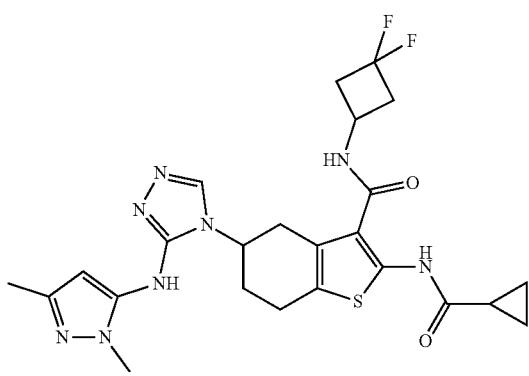 [SMILES: Cc1cc(Nc2nncn2C2CCc3sc(NC(=O)C4CC4)c(C(=O)NC4CC(F)(F)C4)c3C2)n(C)n1]

2-(cyclopropanecarbonylamino)-N-(3,3-difluorocyclobutyl)-5-[3-[(2,5-dimethylpyrazol-3-yl)amino]-1,2,4-triazol-4-yl]-4,5,6,7-tetrahydrobenzothiophene-3-carboxamide

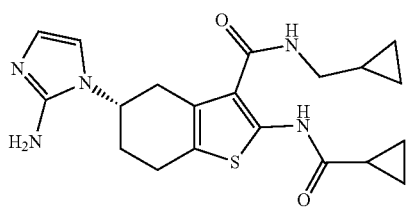 [SMILES: Nc1nccn1[C@H]1CCc2sc(NC(=O)C3CC3)c(C(=O)NCC3CC3)c2C1]

(5S)-5-(2-Aminoimidazol-1-yl)-2-(cyclopropanecarbonylamino)-N-(cyclopropylmethyl)-4,5,6,7-tetrahydrobenzothiophene-3-carboxamide

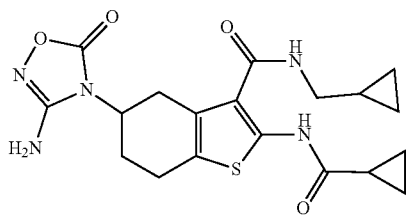 [SMILES: Nc1noc(=O)n1C1CCc2sc(NC(=O)C3CC3)c(C(=O)NCC3CC3)c2C1]

5-(3-Amino-5-oxo-1,2,4-oxadiazol-4-yl)-2-(cyclopropanecarbonylamino)-N-(cyclopropylmethyl)-4,5,6,7-tetrahydrobenzothiophene-3-carboxamide

72

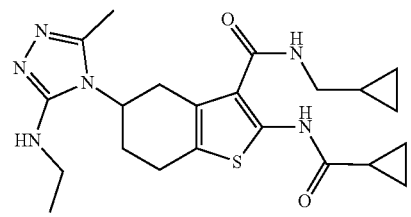 [SMILES: CCNc1nnc(C)n1C1CCc2sc(NC(=O)C3CC3)c(C(=O)NCC3CC3)c2C1]

2-(Cyclopropanecarbonylamino)-N-(cyclopropylmethyl)-5-[3-(ethylamino)-5-methyl-1,2,4-triazol-4-yl]-4,5,6,7-tetrahydrobenzothiophene-3-carboxamide

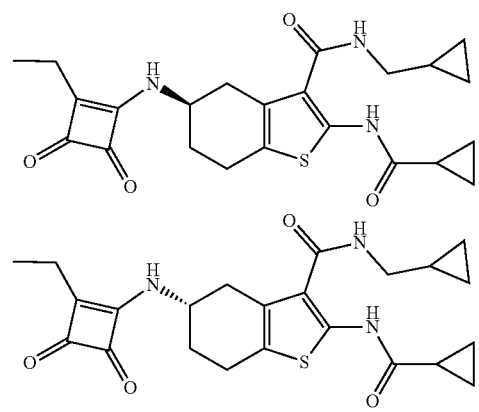

(5R)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide
(5S)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide

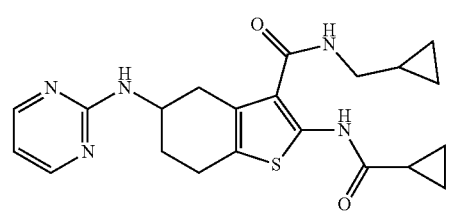 [SMILES: O=C(NCC1CC1)c1c(NC(=O)C2CC2)sc2c1CC(Nc1ncccn1)CC2]

2-(Cyclopropanecarbonylamino)-N-(cyclopropylmethyl)-5-(pyrimidin-2-ylamino)-4,5,6,7-tetrahydrobenzothiophene-3-carboxamide

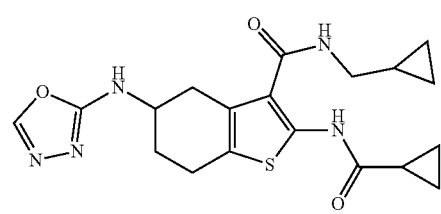 [SMILES: O=C(NCC1CC1)c1c(NC(=O)C2CC2)sc2c1CC(Nc1nnco1)CC2]

2-(Cyclopropanecarbonylamino)-N-(cyclopropylmethyl)-5-(1,3,4-oxadiazol-2-ylamino)-4,5,6,7-tetrahydrobenzothiophene-3-carboxamide

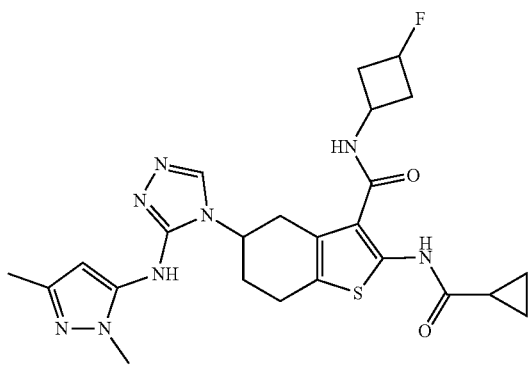 [SMILES: Cc1cc(Nc2nncn2C2CCc3sc(NC(=O)C4CC4)c(C(=O)NC4CC(F)C4)c3C2)n(C)n1]

2-(cyclopropanecarbonylamino)-5-[3-[(2,5-dimethylpyrazol-3-yl)amino]-1,2,4-triazol-4-yl]-N-(3-fluorocyclobutyl)-4,5,6,7-tetrahydrobenzothiophene-3-carboxamide

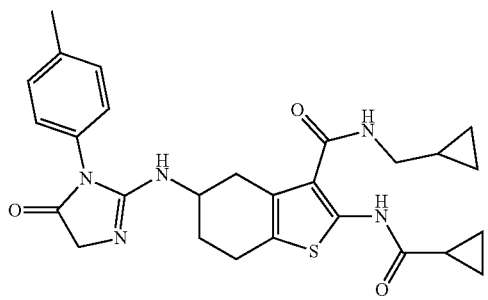 [SMILES: Cc1ccc(N2C(=O)CN=C2NC2CCc3sc(NC(=O)C4CC4)c(C(=O)NCC4CC4)c3C2)cc1]

2-(Cycloprpanecarbonylamino)-N-(cyclopropylmethyl)-5-[5-oxo-1-(p-tolyl)-4H-imidazol-2-yl]amino-4,5,6,7-tetrahydrobenzothiophene-3-carboxamide

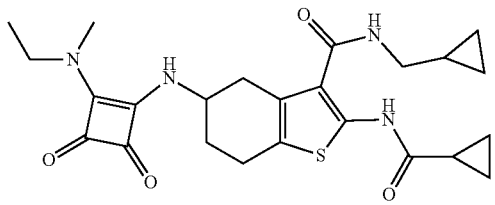 [SMILES: CCN(C)c1c(NC2CCc3sc(NC(=O)C4CC4)c(C(=O)NCC4CC4)c3C2)c(=O)c1=O]

2-(Cyclopropanecarbonylamino)-N-(cyclopropylmethyl)-5-[[2-[ethyl(methyl)amino]-3,4-dioxo-cyclobuten-1-yl]amino]-4,5,6,7-tetrahydrobenzothiophene-3-carboxamide

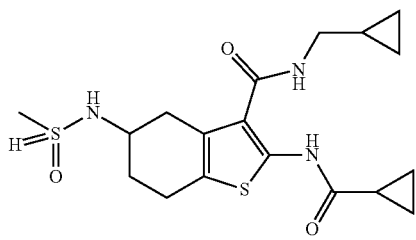

2-(Cyclopropanecarbonylamino)-N-(cyclopropylmethyl)-5-[(methylsulfonimidoyl)amino]-4,5,6,7-tetrahydrobenzothiophene-3-carboxamide

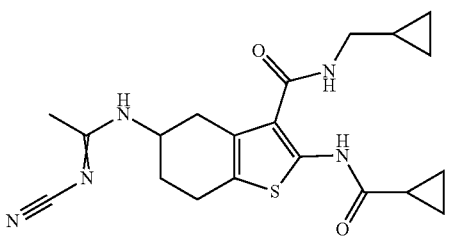 [SMILES: CC(=NC#N)NC1CCc2sc(NC(=O)C3CC3)c(C(=O)NCC3CC3)c2C1]

5-[[N-Cyano-C-methyl-carbonimidoyl]amino]-2-(cyclopropanecarbonylamino)-N-(cyclopropylmethyl)-4,5,6,7-tetrahydrobenzothiophene-3-carboxamide

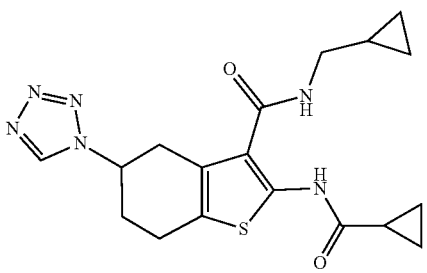 [SMILES: O=C(NCC1CC1)c1c(NC(=O)C2CC2)sc2c1CC(n1cnnn1)CC2]

2-(Cyclopropanecarbonylamino)-N-(cyclopropylmethyl)-5-(tetrazol-1-yl)-4,5,6,7-tetrahydrobenzothiophene-3-carboxamide

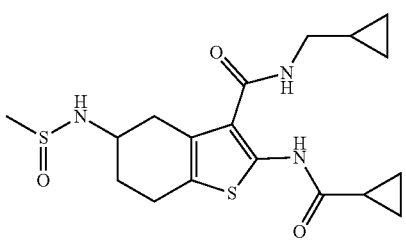 [SMILES: CS(=O)NC1CCc2sc(NC(=O)C3CC3)c(C(=O)NCC3CC3)c2C1]

2-(Cyclopropanecarbonylamino)-N-(cyclopropylmethyl)-5-(methanesulfinamido)-4,5,6,7-tetrahydrobenzothiophene-3-carboxamide

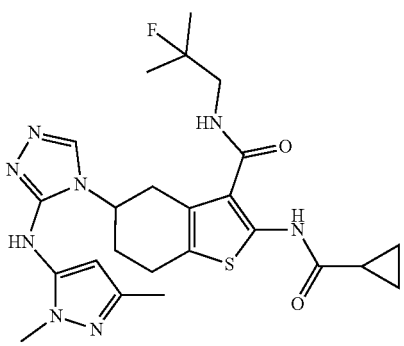 [SMILES: Cc1cc(Nc2nncn2C2CCc3sc(NC(=O)C4CC4)c(C(=O)NCC(C)(C)F)c3C2)n(C)n1]

2-(cyclopropanecarbonylamino)-5-[3-[(2,5-dimethylpyrazol-3-yl)amino]-1,2,4-triazol-4-yl]-N-(2-fluoro-2-methyl-propyl)-4,5,6,7-tetrahydrobenzothiophene-3-carboxamide

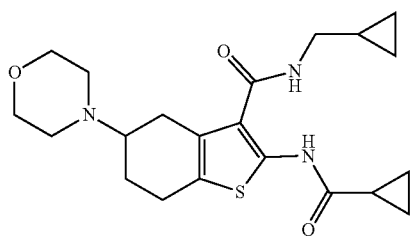 [SMILES: O=C(NCC1CC1)c1c(NC(=O)C2CC2)sc2c1CC(N1CCOCC1)CC2]

2-(Cyclopropanecarbonylamino)-N-(cyclopropylmethyl)-5-morpholino-4,5,6,7-tetrahydrobenzothiophene-3-carboxamide

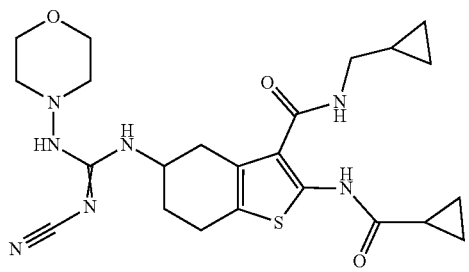

5-[[N'-Cyano-N-morpholino-carbamimidoyl]amino]-2-(cyclopropanecarbonylamino)-N-(cyclopropylmethyl)-4,5,6,7-tetrahydrobenzothiophene-3-carboxamide

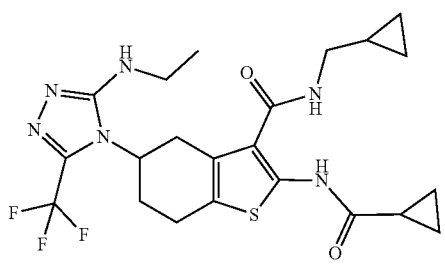 [SMILES: CCNc1nnc(C(F)(F)F)n1C1CCc2sc(NC(=O)C3CC3)c(C(=O)NCC3CC3)c2C1]

2-(Cyclopropanecarbonylamino)-N-(cyclopropylmethyl)-5-[3-(ethylamino)-5-(trifluoromethyl)-1,2,4-triazol-4-yl]-4,5,6,7-tetrahydrobenzothiophene-3-carboxamide

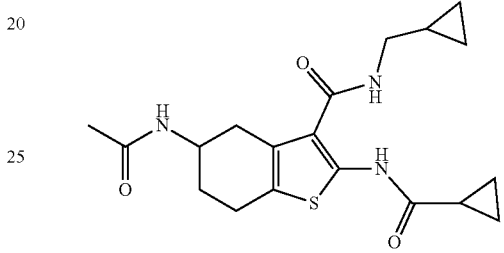

5-Acetamido-2-(cyclopropanecarbonylamino)-N-(cyclopropylmethyl)-4,5,6,7-tetrahydrobenzothiophene-3-carboxamide

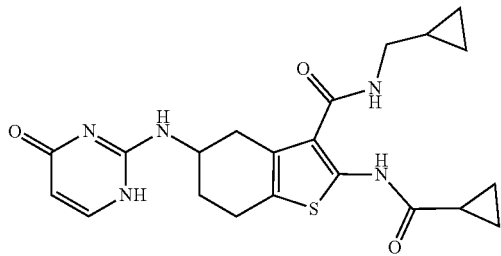 [SMILES: O=C(NCC1CC1)c1c(NC(=O)C2CC2)sc2c1CC(Nc1nc(=O)cc[nH]1)CC2]

2-(Cyclopropanecarbonylamino)-N-(cyclopropylmethyl)-5-[(4-oxo-1H-pyrimidin-2-yl)amino]-4,5,6,7-tetrahydrobenzothiophene-3-carboxamide

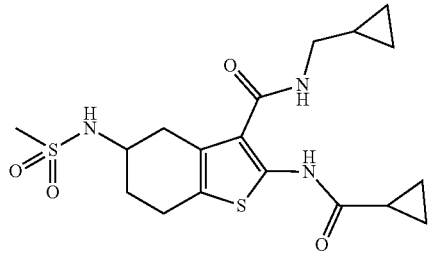

2-(Cyclopropanecarbonylamino)-N-(cyclopropylmethyl)-5-(methanesulfonamido)-4,5,6,7-tetrahydrobenzothiophene-3-carboxamide

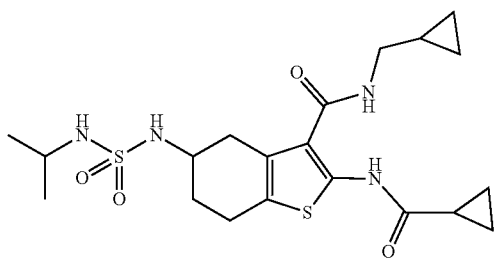 [SMILES: CC(C)NS(=O)(=O)NC1CCc2sc(NC(=O)C3CC3)c(C(=O)NCC3CC3)c2C1]

2-(Cyclopropanecarbonylamino)-N-(cyclopropylmethyl)-5-(isopropylsulfamoylamino)-4,5,6,7-tetrahydrobenzothiophene-3-carboxamide

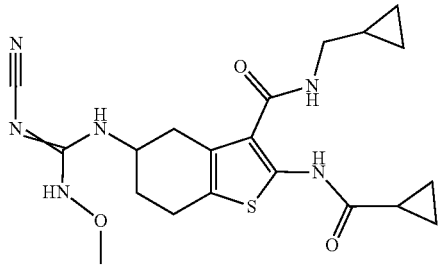 [SMILES: CONC(=NC#N)NC1CCc2sc(NC(=O)C3CC3)c(C(=O)NCC3CC3)c2C1]

5-[[N'-Cyano-N-methoxy-carbamimidoyl]amino]-2-(cyclopropanecarbonylamino)-N-(cyclopropylmethyl)-4,5,6,7-tetrahydrobenzothiophene-3-carboxamide

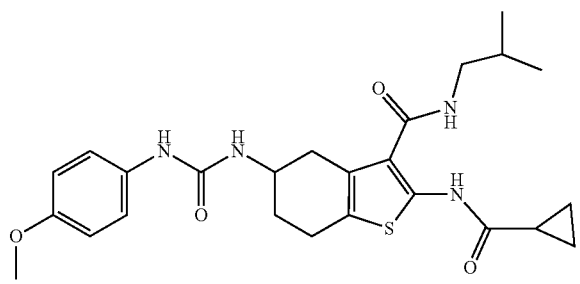 [SMILES: COc1ccc(NC(=O)NC2CCc3sc(NC(=O)C4CC4)c(C(=O)NCC(C)C)c3C2)cc1]

2-(Cyclopropanecarbonylamino)-N-isobutyl-5-[(4-methoxyphenyl)carbamoylamino]-4,5,6,7-tetrahydrobenzothiophene-3-carboxamide

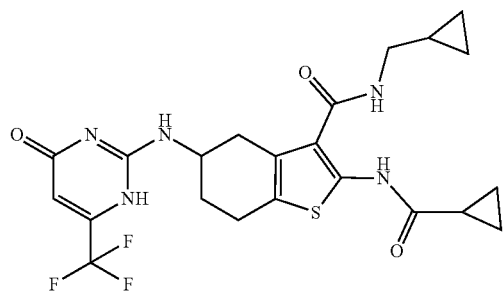 [SMILES: O=C(NCC1CC1)c1c(NC(=O)C2CC2)sc2c1CC(Nc1nc(=O)cc(C(F)(F)F)[nH]1)CC2]

2-(Cyclopropanecarbonylamino)-N-(cyclopropylmethyl)-5-[[4-oxo-6-(trifluoromethyl)-1H-pyrimidin-2-yl]amino]-4,5,6,7-tetrahydrobenzothiophene-3-carboxamide

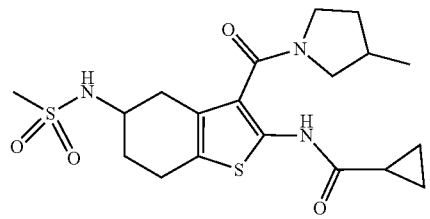 [SMILES: CC1CCN(C(=O)c2c(NC(=O)C3CC3)sc3c2CC(NS(C)(=O)=O)CC3)C1]

N-[5-(Methanesulfonamido)-3-(3-methyl pyrrolidine-1-carbonyl)-4,5,6,7-tetrahydrobenzothiophen-2-yl]cyclopropanecarboxamide

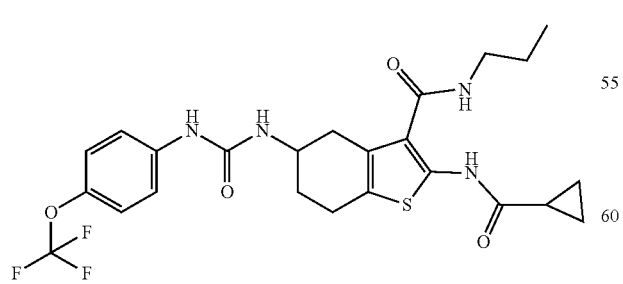

2-(Cyclopropanecarbonylamino)-N-propyl-5-[[4-(trifluoromethoxy)phenyl]carbamoylamino]-4,5,6,7-tetrahydrobenzothiophene-3-carboxamide

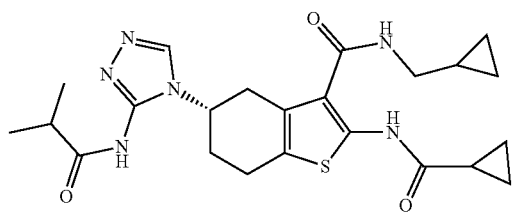

(5S)-2-(cyclopropanecarbonylamino)-N-(cyclopropylmethyl)-5-[3-(2-methylpropanoylamino)-1,2,4-triazol-4-yl]-4,5,6,7-tetrahydrobenzothiophene-3-carboxamide

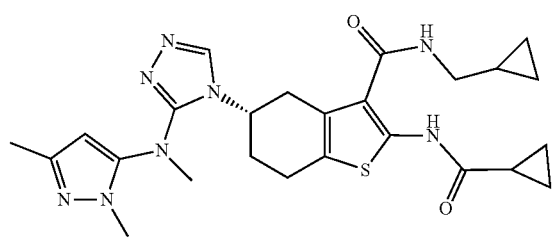

(5S)-2-(cyclopropanecarbonylamino)-N-(cyclopropylmethyl)-5-[3-[(2,5-dimethylpyrazol-3-yl)-methyl-amino]-1,2,4-triazol-4-yl]-4,5,6,7-tetrahydrobenzothiophene-3-carboxamide

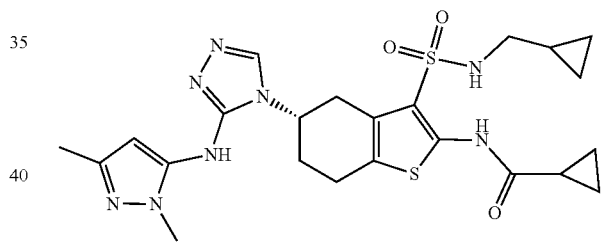

N-[(5S)-3-(cyclopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide

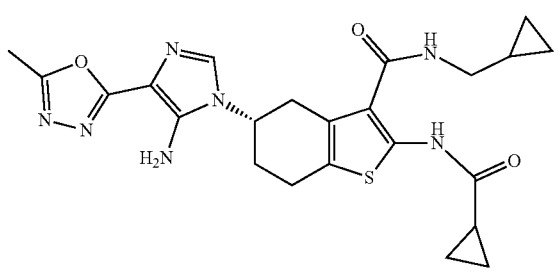

(5S)-5-[5-amino-4-(5-methyl-1,3,4-oxadiazol-2-yl)imidazol-1-yl]-2-(cyclopropanecarbonylamino)-N-(cyclopropylmethyl)-4,5,6,7-tetrahydrobenzothiophene-3-carboxamide

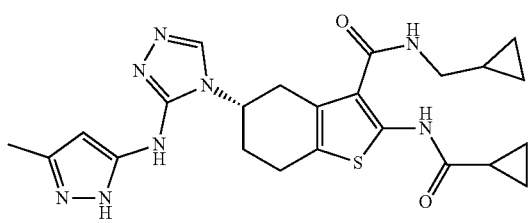 [SMILES: Cc1cc(Nc2nncn2[C@H]2CCc3sc(NC(=O)C4CC4)c(C(=O)NCC4CC4)c3C2)[nH]n1]

(5S)-2-(cyclopropanecarbonylamino)-N-(cyclopropylmethyl)-5-[3-[(3-methyl-1H-pyrazol-5-yl)amino]-1,2,4-triazol-4-yl]-4,5,6,7-tetrahydrobenzothiophene-3-carboxamide

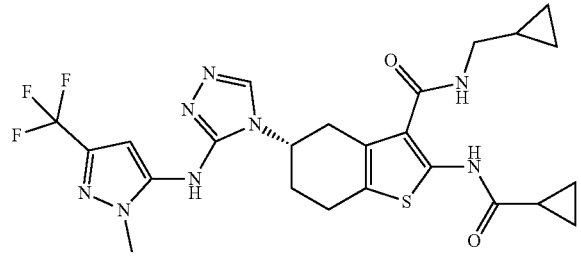 [SMILES: Cn1nc(C(F)(F)F)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide

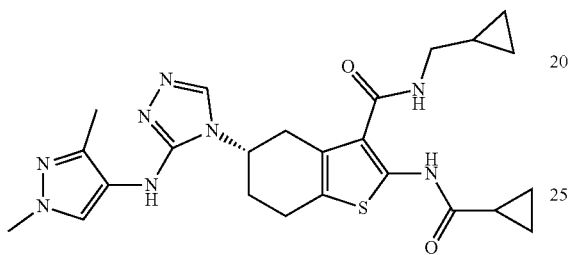

(5S)-2-(cyclopropanecarbonylamino)-N-(cyclopropylmethyl)-5-[3-[(1,3-dimethylpyrazol-4-yl)amino]-1,2,4-triazol-4-yl]-4,5,6,7-tetrahydrobenzothiophene-3-carboxamide

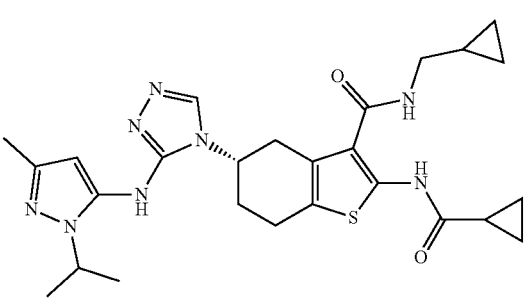 [SMILES: Cc1cc(Nc2nncn2[C@H]2CCc3sc(NC(=O)C4CC4)c(C(=O)NCC4CC4)c3C2)n(C(C)C)n1]

(5S)-2-(cyclopropanecarbonylamino)-N-(cyclopropylmethyl)-5-[3-[(2-isopropyl-5-methyl-pyrazol-3-yl)amino]-1,2,4-triazol-4-yl]-4,5,6,7-tetrahydrobenzothiophene-3-carboxamide

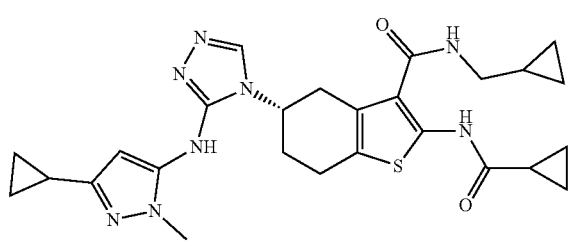

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide

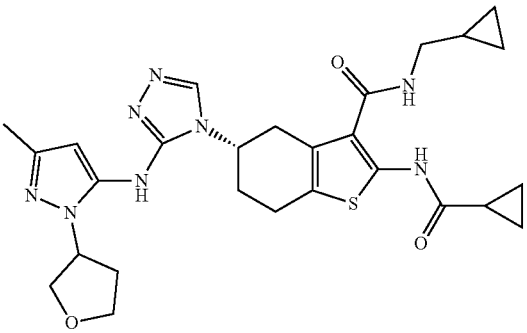 [SMILES: Cc1cc(Nc2nncn2[C@H]2CCc3sc(NC(=O)C4CC4)c(C(=O)NCC4CC4)c3C2)n(C2CCOC2)n1]

(5S)-2-(cyclopropanecarbonylamino)-N-(cyclopropylmethyl)-5-[3-[(5-methyl-2-tetrahydrofuran-3-yl-pyrazol-3-yl)amino]-1,2,4-triazol-4-yl]-4,5,6,7-tetrahydrobenzothiophene-3-carboxamide

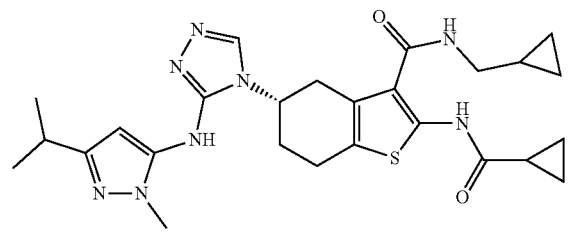

(5S)-2-(cyclopropanecarbonylamino)-N-(cyclopropylmethyl)-5-[3-[(5-isopropyl-2-methyl-pyrazol-3-yl)amino]-1,2,4-triazol-4-yl]-4,5,6,7-tetrahydrobenzothiophene-3-carboxamide

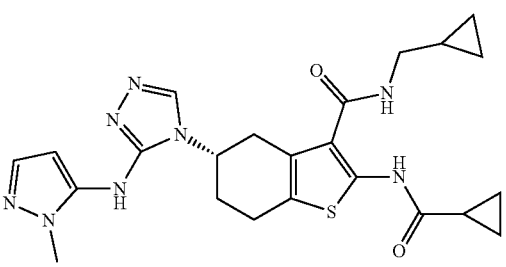 [SMILES: Cn1nccc1Nc1nncn1[C@H]1CCc2sc(NC(=O)C3CC3)c(C(=O)NCC3CC3)c2C1]

81

(5S)-2-(cyclopropanecarbonylamino)-N-(cyclopropylmethyl)-5-[3-[(2-methylpyrazol-3-yl)amino]-1,2,4-triazol-4-yl]-4,5,6,7-tetrahydrobenzothiophene-3-carboxamide

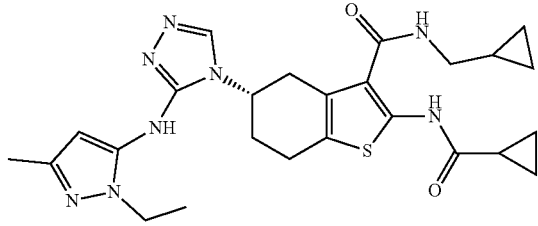 [SMILES: CCn1nc(C)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(2-ethyl-5-methyl-pyrazol-3-yl)amino]-1,2,4-triazol-4-yl]-4,5,6,7-tetrahydrobenzothiophene-3-carboxamide

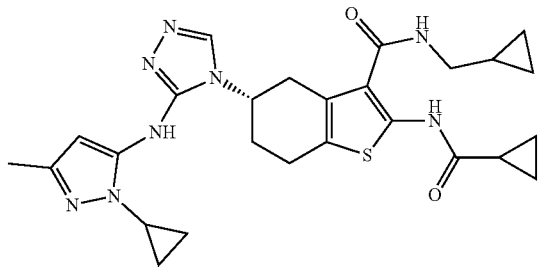 [SMILES: Cc1cc(Nc2nncn2[C@H]2CCc3sc(NC(=O)C4CC4)c(C(=O)NCC4CC4)c3C2)n(C2CC2)n1]

(5S)-2-(cyclopropanecarbonylamino)-N-(cyclopropylmethyl)-5-[3-[(2-cyclopropyl-5-methyl-pyrazol-3-yl)amino]-1,2,4-triazol-4-yl]-4,5,6,7-tetrahydrobenzothiophene-3-carboxamide

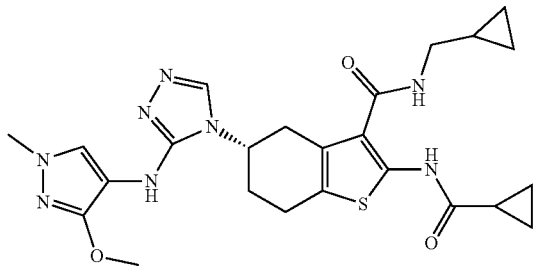 [SMILES: COc1nn(C)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(3-methoxy-1-methyl-pyrazol-4-yl)amino]-1,2,4-triazol-4-yl]-4,5,6,7-tetrahydrobenzothiophene-3-carboxamide

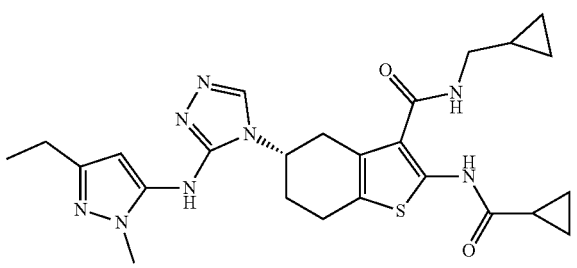 [SMILES: CCc1cc(Nc2nncn2[C@H]2CCc3sc(NC(=O)C4CC4)c(C(=O)NCC4CC4)c3C2)n(C)n1]

82

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide

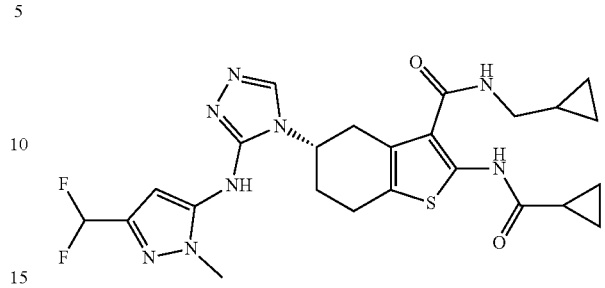

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide

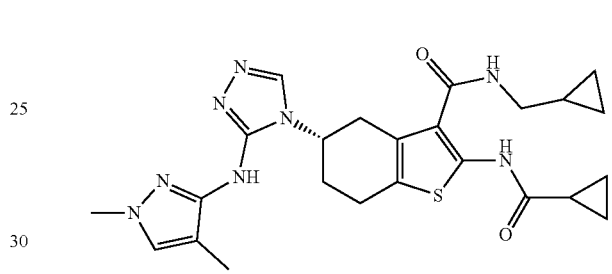

(5S)-2-(Cyclopropanecarbonylamino)-N-(cyclopropylmethyl)-5-[3-[(1,4-dimethylpyrazol-3-yl)amino]-1,2,4-triazol-4-yl]-4,5,6,7-tetrahydrobenzothiophene-3-carboxamide

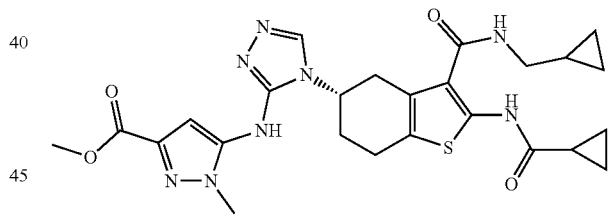

Methyl 5-[[4-[(5S)-2-cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylate

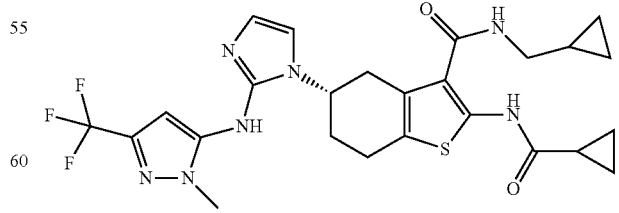

(5S)-2-(Cyclopropanecarbonylamino)-N-(cyclopropylmethyl)-5-[2-[[2-methyl-5-(trifluoromethyl)pyrazol-3-yl]amino]imidazol-1-yl]-4,5,6,7-tetrahydrobenzothiophene-3-carboxamide

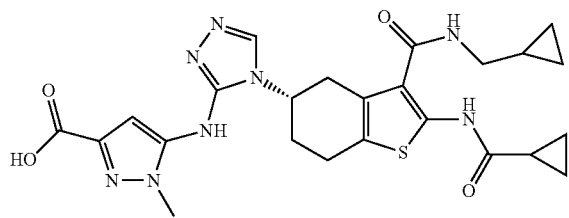 [SMILES: Cn1nc(C(=O)O)cc1Nc1nncn1[C@H]1CCc2sc(NC(=O)C3CC3)c(C(=O)NCC3CC3)c2C1]

5-[[4-[(5S)-2-(Cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylic acid;

their enantiomers and pharmaceutically acceptable salts thereof.

According to an embodiment, the compounds of the invention are selected from:

(5S)-2-(cyclopropanecarbonylamino)-N-(cyclopropylmethyl)-5-[3-[[(3S*)-1,1-dioxothiolan-3-yl]amino]-1,2,4-triazol-4-yl]-4,5,6,7-tetrahydrobenzothiophene-3-carboxamide [*or R];

(5S)-2-cyclopropaneamido-N-(cyclopropylmethyl)-5-[3-({3-[imino(methyl)oxo-lambda6-sulfanyl]-2-methylphenyl}amino)-4H-1,2,4-triazol-4-yl]-4,5,6,7-tetrahydro-1-benzothiophene-3-carboxamide;

(5S)-2-(cyclopropanecarbonylamino)-N-(cyclopropylmethyl)-5-[3-[2-methyl-3-[(S)-methylsulfonimidoyl]anilino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[2-methyl-3-[(R)-methylsulfonimidoyl]anilino]-1,2,4-triazol-4-yl]-4,5,6,7-tetrahydrobenzothiophene-3-carboxamide;

(5S)-5-{3-[(1-acetyl-3-methylpyrrolidin-3-yl)amino]-4H-1,2,4-triazol-4-yl}-2-cyclopropaneamido-N-(cyclopropylmethyl)-4,5,6,7-tetrahydro-1-benzothiophene-3-carboxamide;

(5S)-5-[3-[[(3S*)-1-acetyl-3-methyl-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R];

(5S)-2-cyclopropaneamido-N-(cyclopropylmethyl)-5-(3-{[(3S)-1-(6-methylpyridazin-3-yl)pyrrolidin-3-yl]amino}-4H-1,2,4-triazol-4-yl)-4,5,6,7-tetrahydro-1-benzothiophene-3-carboxamide;

(5S)-2-(cyclopropanecarbonylamino)-N-(cyclopropylmethyl)-5-[3-[[(3S)-1-pyrazin-2-ylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(4-methyl-1-methylsulfonyl-pyrrolidin-3-yl)amino]-1,2,4-triazol-4-yl]-4,5,6,7-tetrahydrobenzothiophene-3-carboxamide;

(5S)-2-cyclopropaneamido-N-(cyclopropylmethyl)-5-{3-[(1-oxo-2,3-dihydro-1H-isoindol-4-yl)amino]-4H-1,2,4-triazol-4-yl}-4,5,6,7-tetrahydro-1-benzothiophene-3-carboxamide;

(5S)-2-(cyclopropanecarbonylamino)-N-(cyclopropylmethyl)-5-[3-[[(3S)-1-(6-fluoropyridazin-3-yl)pyrrolidin-3-yl]amino]-1,2,4-triazol-4-yl]-4,5,6,7-tetrahydrobenzothiophene-3-carboxamide; [Ex 246]

(5S)-2-(cyclopropanecarbonylamino)-N-(cyclopropylmethyl)-5-[3-[[(3S)-1-pyrimidin-2-ylpyrrolidin-3-yl]amino]-1,2,4-triazol-4-yl]-4,5,6,7-tetrahydro-1-benzothiophene-3-carboxamide;

2-methoxyethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate;

2-morpholin-4-ylethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate;

(5S)-2-(cyclopropanecarbonylamino)-N-(cyclopropylmethyl)-5-[3-(3-methylsulfanylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(3-methylsulfonylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(3-methylsulfinylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[3-(methylsulfonimidoyl)anilino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[3-[(S)-methylsulfonimidoyl]anilino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[3-[(R)-methylsulfonimidoyl]anilino]-1,2,4-triazol-4-yl]-4,5,6,7-tetrahydrobenzothiophene-3-carboxamide (5S)—N-(cyclopropylmethyl)-5-[3-[(6-methylsulfinyl-2-pyridyl)amino]-1,2,4-triazol-4-yl]-2-(spiro[2.2]pentane-2-carbonylamino)-4,5,6,7-tetrahydrobenzothiophene-3-carboxamide;

(5S)—N-(cyclopropylmethyl)-5-[3-[(6-methylsulfonyl-2-pyridyl)amino]-1,2,4-triazol-4-yl]-2-[[(2S*)-spiro[2.2]pentane-2-carbonyl]amino]-4,5,6,7-tetrahydrobenzothiophene-3-carboxamide;

(5S)-2-(cyclopropanecarbonylamino)-N-(cyclopropylmethyl)-5-(8-methoxy-4-oxo-5,10-dihydroimidazo[4,5-c][1,5]benzodiazepin-1-yl)-4,5,6,7-tetrahydrobenzothiophene-3-carboxamide;

(5S)-2-(cyclopropanecarbonylamino)-N-(cyclopropylmethyl)-5-(8-methoxy-5-methyl-4-oxo-10H-imidazo[4,5-c][1,5]benzodiazepin-1-yl)-4,5,6,7-tetrahydrobenzothiophene-3-carboxamide;

(5S)-5-[5-amino-4-[(2S)-2-methylpyrrolidine-1-carbonyl]imidazol-1-yl]-N-(cyclopropylmethyl)-2-[[(1R*,2R*)-2-fluorocyclopropanecarbonyl]amino]-4,5,6,7-tetrahydrobenzothiophene-3-carboxamide [* or 1S,2S];

(5S)-5-[5-amino-4-[(3R)-3-hydroxypyrrolidine-1-carbonyl]imidazol-1-yl]-2-(cyclopropanecarbonylamino)-N-(cyclopropylmethyl)-4,5,6,7-tetrahydrobenzothiophene-3-carboxamide;

(5S)-5-[5-amino-4-[(2S)-2-methylpyrrolidine-1-carbonyl]imidazol-1-yl]-2-(cyclopropanecarbonylamino)-N-(cyclopropylmethyl)-4,5,6,7-tetrahydrobenzothiophene-3-carboxamide;

Ethyl 1-[(5S)-2-(cyclopropanecarbonylamino)-3-(cyclopropylmethylcarbamoyl)-4,5,6,7-tetrahydrobenzothiophen-5-yl]-5-[(2,5-dimethyl-4-nitro-pyrazol-3-yl)amino]imidazole-4-carboxylate;

(5S)-2-(cyclopropanecarbonylamino)-N-(cyclopropylmethyl)-5-[3-(2-methyl-3-methylsulfinyl-anilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(2-methyl-3-methylsulfonyl-anilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methyl-5-oxazol-2-yl-pyrazol-3-yl)amino]-1,2,4-triazol-4-yl]-4,5,6,7-tetrahydrobenzothiophene-3-carboxamide;

(5S)-5-[3-[[(3S)-1-acetylpyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[[(3S)-1-methylsulfonylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[(3R)-1-methylsulfonylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methylcyclohexyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-oxopyrrolidin-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[(3R*)-5-oxopyrrolidin-3-yl]amino]-1,2,4-triazol-4-yl]-4,5,6,7-tetrahydrobenzothiophene-3-carboxamide (*or S);

5S)-2-(cyclopropanecarbonylamino)-N-(cyclopropylmethyl)-5-[3-[(2-oxo-4-piperidyl)amino]-1,2,4-triazol-4-yl]-4,5,6,7-tetrahydrobenzothiophene-3-carboxamide;

(5S)-5-[3-[(1-acetyl-2-methyl-pyrrolidin-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(2-methyl-1-methylsulfonyl-pyrrolidin-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamide;

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [*or S];

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-(trans-3-fluorocyclobutyl)-4,5,6,7-tetrahydrobenzothiophene-3-carboxamide (* or S);

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [* or S];

(5S)-2-[[(1S*)-2,2-difluorocyclopropanecarbonyl]amino]-5-[3-[[5-(difluoromethoxy)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R];

(5S)-2-[(2,2-difluorocyclopropanecarbonyl)amino]-N-[(2,2-difluorocyclopropyl)methyl]-5-[3-[[5-(difluoromethyl)-2-methyl-pyrazol-3-yl]amino]-1,2,4-triazol-4-yl]-4,5,6,7-tetrahydrobenzothiophene-3-carboxamide;

(5S)-2-[[(1S*)-2,2-difluorocyclopropanecarbonyl]amino]-5-[3-[[5-(difluoromethyl)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R];

(5S)-5-[3-[[(3S*)-1-benzoyl-4,4-difluoro-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R];

(5S)-5-[3-[(1-acetyl-4-piperidyl)amino]-1,2,4-triazol-4-yl]-2-(cyclopropanecarbonylamino)-N-(cyclopropylmethyl)-4,5,6,7-tetrahydrobenzothiophene-3-carboxamide;

Methyl (3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]pyrrolidine-1-carboxylate;

(3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-N-ethyl-pyrrolidine-1-carboxamide;

(5S)-2-cyclopropaneamido-N-(cyclopropylmethyl)-5-(3-{[2-(pyrimidin-2-yl)-2-azaspiro[4.4]nonan-7-yl]amino}-4H-1,2,4-triazol-4-yl)-4,5,6,7-tetrahydro-1-benzothiophene-3-carboxamide;

(5S)—N-(cyclopropylmethyl)-2-[[(1R,2R)-2-fluorocyclopropanecarbonyl]amino]-5-[3-[[2-methyl-5-(trifluoromethoxy)pyrazol-3-yl]amino]-1,2,4-triazol-4-yl]-4,5,6,7-tetrahydrobenzothiophene-3-carboxamide;

(5S)-5-[3-[[5-[chloro(difluoro)methoxy]-2-methyl-pyrazol-3-yl]amino]-1,2,4-triazol-4-yl]-N-(cyclopropylmethyl)-2-[[(1R,2R)-2-fluorocyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethoxy)pyrazol-3-yl]amino]-1,2,4-triazol-4-yl]-4,5,6,7-tetrahydrobenzothiophene-3-carboxamide;

(5S)-5-[3-[[5-[chloro(difluoro)methoxy]-2-methyl-pyrazol-3-yl]amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-cyclopropaneamido-N-(cyclopropylmethyl)-5-(3-{[1-methyl-3-(5-methyl-1,3,4-oxadiazol-2-yl)-1H-pyrazol-5-yl]amino}-4H-1,2,4-triazol-4-yl)-4,5,6,7-tetrahydro-1-benzothiophene-3-carboxamide;

(5S)-2-(cyclopropanecarbonylamino)-N-(cyclopropylmethyl)-5-[3-[(5-methoxy-3-methyl-pyrazin-2-yl)amino]-1,2,4-triazol-4-yl]-4,5,6,7-tetrahydrobenzothiophene-3-carboxamide (5S)-2-(cyclopropanecarbonylamino)-N-(cyclopropylmethyl)-5-[(5-methylthiazolo[5,4-b]pyridin-2-yl)amino]-4,5,6,7-tetrahydrobenzothiophene-3-carboxamide;

(5S)-5-[3-[(5-cyano-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-5-[3-[(6-cyano-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(1-methyl-2-oxo-4-pyridyl)amino]-1,2,4-triazol-4-yl]-4,5,6,7-tetrahydrobenzothiophene-3-carboxamide;

(5S)-5-[3-[(6-chloro-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[[2-methyl-6-(trifluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methylpyridazin-4-yl)amino]-1,2,4-triazol-4-yl]-4,5,6,7-tetrahydrobenzothiophene-3-carboxamide;

(5S)-5-[3-[(5-chloro-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-N-(cyclopropylmethyl)-5-[3-[[5-(difluoromethoxy)-2-methyl-pyrazol-3-yl]amino]-1,2,4-triazol-4-yl]-2-[[(1S,2R)-2-methylcyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[(3-methylisothiazol-4-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methylisoxazol-4-yl)amino]-1,2,4-triazol-4-yl]-4,5,6,7-tetrahydrobenzothiophene-3-carboxamide;

(5S)-5-[3-[[5-(cyclopropylmethoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide;

(5S)—N-(cyclopropylmethyl)-5-[3-[(5-ethoxy-2-methyl-pyrazol-3-yl)amino]-1,2,4-triazol-4-yl]-2-[[(1R,2S)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(2R*)-spiro[2.2]pentane-2-carbonyl]amino]-4,5,6,7-tetrahydrobenzothiophene-3-carboxamide [* or S];

(5S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide;

N-[(5S)-3-(cyclopropylmethylsulfamoyl)-5-[3-[(2,5-dimethylpyrazol-3-yl)amino]-1,2,4-triazol-4-yl]-4,5,6,7-tetrahydro-1-benzothiophen-2-yl]cyclopropanecarboxamide;

ethyl 5-amino-1-[(5S*)-2-(cyclopropanecarbonylamino)-3-(cyclopropylmethylsulfamoyl)-4,5,6,7-tetrahydrobenzothiophen-5-yl]imidazole-4-carboxylate (* or R);

N-[(5S*)-3-(cyclopropylmethylsulfamoyl)-5-[3-[[5-(difluoromethoxy)-2-methyl-pyrazol-3-yl]amino]-1,2,4-triazol-4-yl]-4,5,6,7-tetrahydrobenzothiophen-2-yl]cyclopropanecarboxamide (* or R);

N-[(5S*)-3-(cyclopropylmethylsulfamoyl)-5-[3-[(2-methylpyrazol-3-yl)amino]-1,2,4-triazol-4-yl]-4,5,6,7-tetrahydrobenzothiophen-2-yl]cyclopropanecarboxamide (* or R);

(1R,2S)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluoro-cyclopropanecarboxamide;

(1R,2S)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluoro-cyclopropanecarboxamide;

(1S*)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R];

(1S*)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R];

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1S,2S)-2-fluorocyclopropyl]methyl]-4,5,6,7-tetrahydro-1-benzothiophene-3-carboxamide;

N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]cyclopropanecarboxamide;

N-[(5S)-5-[3-[[5-(difluoromethyl)-2-methyl-pyrazol-3-yl]amino]-1,2,4-triazol-4-yl]-3-[trans-(3-fluorocyclobutyl)sulfamoyl]-4,5,6,7-tetrahydrobenzothiophen-2-yl]cyclopropanecarboxamide;

(1R,2S)—N-[(5S)-3-[(3,3-difluorocyclobutyl)sulfamoyl]-5-[3-[[5-(difluoromethoxy)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R,2S)—N-[(5S)-3-[(3,3-difluorocyclobutyl)sulfamoyl]-5-[3-[[5-(difluoromethyl)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R*)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S);

(1R*)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S);

(5S)—N-(cyclopropylmethyl)-5-[3-[(3-methyl-1,2-thiazol-4-yl)amino]-1,2,4-triazol-4-yl]-2-(spiro[2.2]pentane-2-carbonylamino)-4,5,6,7-tetrahydro-1-benzothiophene-3-carboxamide;

N-[(5S)-3-[(3,3-difluorocyclobutyl)sulfamoyl]-5-[3-[(2,5-dimethylpyrazol-3-yl)amino]-1,2,4-triazol-4-yl]-4,5,6,7-tetrahydro-1-benzothiophen-2-yl]cyclopropanecarboxamide;

N-[(5S)-5-[3-[[5-(difluoromethoxy)-2-methylpyrazol-3-yl]amino]-1,2,4-triazol-4-yl]-3-[cis-(3-fluorocyclobutyl)sulfamoyl]-4,5,6,7-tetrahydro-1-benzothiophen-2-yl]cyclopropanecarboxamide;

N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]cyclopropanecarboxamide N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]cyclopropanecarboxamide;

(1R,2S)—N-[(5S)-3-(cyclopropylmethylsulfamoyl)-5-[3-[[5-(difluoromethyl)-2-methylpyrazol-3-yl]amino]-1,2,4- triazol-4-yl]-4,5,6,7-tetrahydro-1-benzothiophen-2-yl]-2-fluorocyclopropane-1-carboxamide;

(1R,2S)—N-[(5S)-3-(cyclopropylmethylsulfamoyl)-5-[3-[[5-(difluoromethoxy)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R,2S)—N-[(5S)-3-(cyclopropylmethylsulfamoyl)-5-[3-[(5-methoxy-2-methylpyrazol-3-yl)amino]-1,2,4-triazol-4-yl]-4,5,6,7-tetrahydro-1-benzothiophen-2-yl]-2-fluorocyclopropane-1-carboxamide;

(5S)-2-(cyclopropanecarbonylamino)-N-(cyclopropylmethyl)-5-[3-[(5-methoxy-2-methylpyrazol-3-yl)amino]-1,2,4-triazol-4-yl]-4,5,6,7-tetrahydro-1-benzothiophene-3-carboxamide;

N-[(5S)-3-(cyclopropylmethylsulfamoyl)-5-[3-[[5-(difluoromethyl)-2-methylpyrazol-3-yl]amino]-1,2,4-triazol-4-yl]-4,5,6,7-tetrahydro-1-benzothiophen-2-yl]cyclopropanecarboxamide;

(1R,2S)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide;

(1R,2S)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide;

(1R*)—N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]-2,2-difluorocyclopropane-1-carboxamide (* or S)

N-[(5S)-3-(cyclopropylmethylsulfamoyl)-5-[3-[[2-methyl-5-(trifluoromethyl) pyrazol-3-yl]amino]-1,2,4-triazol-4-yl]-4,5,6,7-tetrahydro-1-benzothiophen-2-yl]cyclopropanecarboxamide;

(5S)—N-(cyclopropylmethyl)-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)—N-(cyclopropylmethyl)-2-[(2,2-difluorocyclopropanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-2-[[(1R*)-2,2-difluorocyclopropanecarbonyl]amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide (* or S);

(5S)—N-(cyclopropylmethyl)-2-[(3,3-difluorocyclobutanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[cis-(3-fluorocyclobutanecarbonyl)amino]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[(3-fluorocyclobutanecarbonyl)amino]-4,5,6,7-tetrahydro-1-benzothiophene-3-carboxamide;

(5S)—N-(cyclopropylmethyl)-5-[3-[[5-(difluoromethyl)-2-methyl pyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)—N-(cyclopropylmethyl)-2-[[(1RS,2RS)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

N-[(5S)-3-(cyclopropylmethylcarbamoyl)-5-[3-[[5-(difluoromethyl)-2-methylpyrazol-3-yl]amino]-1,2,4-triazol-4-yl]-4,5,6,7-tetrahydro-1-benzothiophen-2-yl]oxetane-3-carboxamide;

(5S)—N-(cyclopropylmethyl)-2-[(3,3-difluorocyclobutanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethyl)-2-methyl pyrazol-3-yl]amino]-1,2,4-triazol-4-yl]-2-(3,3-difluoropropanoylamino)-4,5,6,7-tetrahydro-1-benzothiophene-3-carboxamide;

(5S)-2-(cyclobutanecarbonylamino)-N-(cyclopropylmethyl)-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-(2-methylpropanoylamino)-4,5,6,7-tetrahydro-1-benzothiophene-3-carboxamide;

(5S)—N-(cyclopropylmethyl)-5-[3-[[5-(difluoromethyl)-2-methyl pyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide;

(5S)—N-(cyclopropylmethyl)-2-[(2,2-difluorocyclopropanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide (5S)—N-(cyclopropylmethyl)-2-[[(1R*)-2,2-difluorocyclopropanecarbonyl]amino]-5-[3-[[5-(difluoromethyl)-2-methylpyrazol-3-yl]amino]-1,2,4-triazol-4-yl]-4,5,6,7-tetrahydro-1-benzothiophene-3-carboxamide (* or S);

(5S)—N-(cyclopropylmethyl)-5-[3-[[5-(difluoromethyl)-2-methyl pyrazol-3-yl]amino]-1,2,4-triazol-4-yl]-2-[[(1RS,2SR)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[[(1S, 2R)-2-fluorocyclopropanecarbonyl]amino]-4,5,6,7-tetrahydro-1-benzothiophene-3-carboxamide;
(5S)—N-(cyclopropylmethyl)-5-[3-[[5-(difluoromethyl)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide;
(5S)—N-(cyclopropylmethyl)-5-[3-[[5-(difluoromethyl)-2-methyl pyrazol-3-yl]amino]-1,2,4-triazol-4-yl]-2-[(2-methylcyclopropanecarbonyl)amino]-4,5,6,7-tetrahydro-1-benzothiophene-3-carboxamide;
(5S)—N-(cyclopropylmethyl)-5-[3-[[5-(difluoromethyl)-2-methyl pyrazol-3-yl]amino]-1,2,4-triazol-4-yl]-2-[[(1R*,2R*)-2-methylcyclopropanecarbonyl]amino]-4,5,6,7-tetrahydro-1-benzothiophene-3-carboxamide (* or S);
(5S)—N-(cyclopropylmethyl)-5-[3-[[5-(difluoromethyl)-2-methyl pyrazol-3-yl]amino]-1,2,4-triazol-4-yl]-2-[[(1R*,2S*)-2-methylcyclopropanecarbonyl]amino]-4,5,6,7-tetrahydro-1-benzothiophene-3-carboxamide (*1R,2S or 1S,2R);
(5S)-2-(cyclopropanecarbonylamino)-5-[3-[[5-(difluoromethyl)-2-methylpyrazol-3-yl]amino]-1,2,4-triazol-4-yl]-N-[[(1R*)-2,2-dimethylcyclopropyl]methyl]-4,5,6,7-tetrahydro-1-benzothiophene-3-carboxamide (* or S);
(5S)-2-(cyclopropanecarbonylamino)-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide;
(5S)—N-[[(1R)-2,2-difluorocyclopropyl]methyl]-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-4,5,6,7-tetrahydro-1-benzothiophene-3-carboxamide
(5S)—N-[[(1S)-2,2-difluorocyclopropyl]methyl]-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-4,5,6,7-tetrahydro-1-benzothiophene-3-carboxamide;
(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[(2R*)-spiro[2.2]pentan-2-yl]-4,5,6,7-tetrahydro-1-benzothiophene-3-carboxamide (* or S);
(5S)-5-[3-[[5-(difluoromethoxy)-2-methylpyrazol-3-yl]amino]-1,2,4-triazol-4-yl]-N-[cis-(3-fluorocyclobutyl)methyl]-2-[[(1R,2S)-2-fluorocyclopropanecarbonyl]amino]-4,5,6,7-tetrahydro-1-benzothiophene-3-carboxamide;
(5S)-5-[3-[[5-(difluoromethoxy)-2-methylpyrazol-3-yl]amino]-1,2,4-triazol-4-yl]-N-[trans-(3-fluorocyclobutyl)methyl]-2-[[(1R,2S)-2-fluorocyclopropanecarbonyl]amino]-4,5,6,7-tetrahydro-1-benzothiophene-3-carboxamide;
(5S)-5-[3-[[5-(difluoromethoxy)-2-methylpyrazol-3-yl]amino]-1,2,4-triazol-4-yl]-N-(trans-3-fluorocyclobutyl)-2-[[(1R,2S)-2-fluorocyclopropanecarbonyl]amino]-4,5,6,7-tetrahydro-1-benzothiophene-3-carboxamide;
(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1R,2R)-2-fluorocyclopropyl]methyl]-4,5,6,7-tetrahydro-1-benzothiophene-3-carboxamide;
(5S)-2-(cyclopropanecarbonylamino)-N-[(2,2-difluorocyclopropyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;
(5S)-2-(cyclopropanecarbonylamino)-N-[[(1R)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;
(5S)-2-(cyclopropanecarbonylamino)-N-[[(1S)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;
(5S)-2-(cyclopropanecarbonylamino)-5-[3-[[5-(difluoromethyl)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide;
(5S)-2-(cyclopropanecarbonylamino)-5-[3-[[5-(difluoromethyl)-2-methylpyrazol-3-yl]amino]-1,2,4-triazol-4-yl]-N-[[(2R)-spiro[2.2]pentan-2-yl]methyl]-4,5,6,7-tetrahydro-1-benzothiophene-3-carboxamide;
(5S)-2-(cyclopropanecarbonylamino)-5-[3-[[5-(difluoromethyl)-2-methylpyrazol-3-yl]amino]-1,2,4-triazol-4-yl]-N-[[(2S)-spiro[2.2]pentan-2-yl]methyl]-4,5,6,7-tetrahydro-1-benzothiophene-3-carboxamide;
(5S)-2-(cyclopropanecarbonylamino)-N-(3,3-difluorocyclobutyl)-5-[3-[[5-(difluoromethyl)-2-methylpyrazol-3-yl]amino]-1,2,4-triazol-4-yl]-4,5,6,7-tetrahydro-1-benzothiophene-3-carboxamide;
(5S)-2-(cyclopropanecarbonylamino)-5-[3-[[5-(difluoromethyl)-2-methylpyrazol-3-yl]amino]-1,2,4-triazol-4-yl]-N-(cis-3-fluorocyclobutyl)-4,5,6,7-tetrahydro-1-benzothiophene-3-carboxamide;
(5S)-2-(cyclopropanecarbonylamino)-N-[(3,3-difluorocyclobutyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;
(5S)-2-[[(1R,2R)-2-fluorocyclopropanecarbonyl]amino]-N-[[(1RS,2RS)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (cis);
(5S)-2-[[(1R,2R)-2-fluorocyclopropanecarbonyl]amino]-N-[[(1RS,2SR)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (trans);
5S)-2-[[(1R,2R)-2-fluorocyclopropanecarbonyl]amino]-N-[[(1S,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;
(5S)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-N-[(2R)-spiro[2.2]pentan-2-yl]-4,5,6,7-tetrahydro-1-benzothiophene-3-carboxamide;
5S)-2-[[(1R,2R)-2-fluorocyclopropanecarbonyl]amino]-N-[[(1R,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;
(5S)—N-[(2,2-difluorocyclopropyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;
(5S)—N-[[(1R)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;
(5S)—N-[[(1S)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)-2-[[(1R,2R)-2-fluorocyclopropanecarbonyl]amino]-N-[[(1R,2R)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-[trans-(3-fluorocyclobutyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-(cyclopropylmethyl)-2-[[(1S,2S)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-(trans-3-fluorocyclobutyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)-2-(cyclopropanecarbonylamino)-N-(cyclopropylmethyl)-5-[3-[[5-(difluoromethyl)-2-(trideuteriomethyl)pyrazol-3-yl]amino]-1,2,4-triazol-4-yl]-4,5,6,7-tetrahydrobenzothiophene-3-carboxamide;

(5S)-5-[3-[[5-(Difluoromethyl)-2-methylpyrazol-3-yl]amino]-1,2,4-triazol-4-yl]-N-[trans-(3-fluorocyclobutyl)methyl]-2-[[(2S)-spiro[2.2]pentane-2-carbonyl]amino]-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-(trans-3-fluorocyclobutyl)-2-[[(2S)-spiro[2.2]pentane-2-carbonyl]amino]-4,5,6,7-tetrahydro-1-benzothiophene-3-carboxamide;

(5S)—N-(3,3-Difluorocyclobutyl)-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[(3,3-Difluorocyclobutyl)methyl]-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[(2,2-Difluorocyclopropyl)methyl]-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[[(1S)-2,2-Difluorocyclopropyl]methyl]-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide;

(5S)—N-[[(1R)-2,2-difluorocyclopropyl]methyl]-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide;

(5S)-5-[3-[[5-(Difluoromethyl)-2-methylpyrazol-3-yl]amino]-1,2,4-triazol-4-yl]-2-[[(2S)-spiro[2.2]pentane-2-carbonyl]amino]-N-spiro[2.2]pentan-2-yl-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-[[(1R,2R)-2-fluorocyclopropyl]methyl]-2-[[(2S)-spiro[2.2]pentane-2-carbonyl]amino]-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-[[(1R,2S)-2-fluorocyclopropyl]methyl]-2-[[(2S)-spiro[2.2]pentane-2-carbonyl]amino]-4,5,6,7-tetrahydro-1-benzothiophene-3-carboxamide;

(5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2S)-spiro[2.2]pentan-2-yl]-4,5,6,7-tetrahydrobenzothiophene-3-carboxamide;

(5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2R)-spiro[2.2]pentan-2-yl]-4,5,6,7-tetrahydrobenzothiophene-3-carboxamide;

(5S)—N-(Cyclopropylmethyl)-5-[3-[[5-(difluoromethyl)-2-methyl-pyrazol-3-yl]amino]-1,2,4-triazo-4-yl]-2-[[(2S)-spiro[2.2]pentane-2-carbonyl]amino]-4,5,6,7-tetrahydrobenzothiophene-3-carboxamide;

Ethyl (5S)-5-[3-[[5-(difluoromethyl)-2-methyl-pyrazol-3-yl]amino]-1,2,4-triazol-4-yl]-2-(spiro[2.2]pentane-2-carbonylamino)-4,5,6,7-tetrahydrobenzothiophene-3-carboxylate;

Ethyl (5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxylate;

(5S)-5-[3-[(5-Cyano-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(Cyclopropanecarbonylamino)-N-(cyclopropylmethyl)-5-[3-[(2,2-difluoro-1,3-benzodioxol-5-yl)amino]-1,2,4-triazol-4-yl]-4,5,6,7-tetrahydrobenzothiophene-3-carboxamide;

(5S)-5-[3-[[5-(Difluoromethyl)-2-methyl-pyrazol-3-yl]amino]-1,2,4-triazol-4-yl]-N-[[(1S,2S)-2-fluorocyclopropyl]methyl]-2-[[(2S)-spiro[2.2]pentane-2-carbonyl]amino]-4,5,6,7-tetrahydrobenzothiophene-3-carboxamide;

(4RS,5RS)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide;

(4R*,5R*)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[6-(difluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(6-fluoro-2-methyl-3-pyridyl)amino]-1,2,4-triazol-4-yl]-4,5,6,7-tetrahydrobenzothiophene-3-carboxamide;

(5S)-5-[3-[[5-(cyclopropoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide;

(5S)—N-(cyclopropylmethyl)-2-[[(1R,2S)-2-fluorocyclopropanecarbonyl]amino]-5-[3-[[2-methyl-5-(2,2,2-trifluoroethoxy)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[6-(trifluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(6-methoxy-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methoxy-4-pyridyl)amino]-1,2,4-triazol-4-yl]-4,5,6,7-tetrahydrobenzothiophene-3-carboxamide;

(5S)-5-[3-[(6-chloro-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-5-[3-[(2-chloro-4-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(6-methoxy-2-methyl-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-fluoro-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methyltriazol-4-yl)amino]-1,2,4-triazol-4-yl]-4,5,6,7-tetrahydrobenzothiophene-3-carboxamide;

(5S)-5-[3-[[5-(difluoromethyl)-2-methylpyrazol-3-yl]amino]-1,2,4-triazol-4-yl]-N-[[(1S,2S)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[[(1R,2S)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[trans-(3-fluorocyclobutyl)methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-(trans-3-fluorocyclobutyl)-2-[[(1S,2S)-2-methylcyclopropanecarbonyl]amino]-4,5,6,7-tetrahydro-1-benzothiophene-3-carboxamide;

(5S)—N-(3,3-difluorocyclobutyl)-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[(3,3-difluorocyclobutyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[(2,2-difluorocyclopropyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[cis-(3-fluorocyclobutyl)methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[[(1R,2R)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide;

(5S)—N-(cyclobutylmethyl)-2-(cyclopropanecarbonylamino)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[(3,3-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(cis-3-fluorocyclobutyl)-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(3-methylcyclobutyl)-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-2-(cyclopropanecarbonylamino)-N-(3,3-difluorocyclobutyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[(2,2-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-spiro[2.2]pentan-2-yl-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[(2-methylcyclopropyl)methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[[(1RS,2RS)-2-fluorocyclopropyl]methyl]-4,5,6,7-tetrahydro-1-benzothiophene-3-carboxamide;

(5S)—N-(cyclopropylmethyl)-5-[3-[(5-methoxy-2-methylpyrazol-3-yl)amino]-1,2,4-triazol-4-yl]-2-[[(2R*)-spiro[2.2]pentane-2-carbonyl]amino]-4,5,6,7-tetrahydrobenzothiophene-3-carboxamide (* or S);

(5S)-2-(cyclopropanecarbonylamino)-5-[3-[[5-(difluoromethoxy)-2-methylpyrazol-3-yl]amino]-1,2,4-triazol-4-yl]-N-[trans-(3-fluorocyclobutyl)methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[(2-fluorocyclobutyl)methyl]-4,5,6,7-tetrahydro-1-benzothiophene-3-carboxamide;

(5S)-2-(cyclopropanecarbonylamino)-N-[(2,2-difluorocyclopropyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[[(1R)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[[(1S)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol- 4-yl]-N-[[(1R,2S)-2-fluorocyclopropyl]methyl]-4,5,6,7-tetrahydro-1-benzothiophene-3-carboxamide;

(5S)—N-[[(1R)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide (5S)—N-[[(1S)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide;

(5S)-5-[3-[(5-methoxy-2-methyl-pyrazol-3-yl)amino]-1,2,4-triazol-4-yl]-2-[[(1S,2S)-2-methylcyclopropanecarbonyl]amino]-N-[(2R*)-spiro[2.2]pentan-2-yl]-4,5,6,7-tetrahydrobenzothiophene-3-carboxamide [* or S];

(5S)—N-[[(1R,2S)-2-fluorocyclopropyl]methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[trans-(3-fluorocyclobutyl)methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-(cyclopropylmethyl)-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide (5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide;

(5S)—N-[[(1R*)-2,2-difluorocyclopropyl]methyl]-5-[3-[[5-(difluoromethyl)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxamide [* or S];

(5S)—N-(cyclobutylmethyl)-5-[3-[[5-(difluoromethyl)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-(trans-3-fluorocyclobutyl)-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1S,2S)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1S,2S)-2-fluorocyclopropyl]methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2R)-2-fluorocyclopropyl]methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide;

(5S)—N-[[(1R)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide (5S)—N-[[(1S)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-[[(1S,2S)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-2-[(2,2-difluorocyclopropanecarbonyl)amino]-5-[3-[[5-(difluoromethyl)-2-methyl-pyrazol-3-yl]amino]-1,2,4-triazol-4-yl]-N-(trans-3-fluorocyclobutyl)-4,5,6,7-tetrahydrobenzothiophene-3-carboxamide;

(5S)-2-cyclopropaneamido-5-(3-{[3-(difluoromethyl)-1-methyl-1H-pyrazol-5-yl]amino}-4H-1,2,4-triazol-4-yl)-N-{spiro[2.2]pentan-1-yl}-4,5,6,7-tetrahydro-1-benzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(2S)-spiro[2.2]pentan-2-yl]-4,5,6,7-tetrahydrobenzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(2R)-spiro[2.2]pentan-2-yl]-4,5,6,7-tetrahydrobenzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(3-fluorocyclobutyl)methyl]-4,5,6,7-tetrahydrobenzothiophene-3-carboxamide;

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[[(1R,2R)-2-fluorocyclopropyl]methyl]-4,5,6,7-tetrahydrobenzothiophene-3-carboxamide (* or S);

(5S)—N-(cyclopropylmethyl)-5-[3-[(2,5-dimethylpyrazol-3-yl)amino]-1,2,4-triazol-4-yl]-2-(spiro[2.2]pentane-2-carbonylamino)-4,5,6,7-tetrahydrobenzothiophene-3-carboxamide;

(5S)—N-(cyclopropylmethyl)-5-[3-[(2,5-dimethylpyrazol-3-yl)amino]-1,2,4-triazol-4-yl]-2-[[(2S*)-spiro[2.2]pentane-2-carbonyl]amino]-4,5,6,7-tetrahydrobenzothiophene-3-carboxamide (* or R);

(3R*)-6-(cyclopropanecarbonylamino)-N-(cyclopropylmethyl)-3-[3-[[2-methyl-5-(trifluoromethyl)pyrazol-3-yl]amino]-1,2,4-triazol-4-yl]-3,4-dihydro-2H-thieno[2,3-b]pyran-5-carboxamide (* or S);

their enantiomers and pharmaceutically acceptable salts thereof.

According to an embodiment, the compounds of the invention are selected from:

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide;

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate;

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-isopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide;

(5S)—N-(cyclopropylmethyl)-5-[3-[(5-ethoxy-2-methyl-pyrazol-3-yl)amino]-1,2,4-triazol-4-yl]-2-[[(1R,2S)-2-fluorocyclopropanecarbonyl]amino]-4,5,6,7-tetrahydrobenzothiophene-3-carboxamide;

15S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-5-[3-[(5-methoxy-2-methyl-pyrazol-3-yl)amino]-1,2,4-triazol-4-yl]-2-[[(2R*)-spiro[2.2]pentane-2-carbonyl]amino]-4,5,6,7-tetrahydrobenzothiophene-3-carboxamide (* or S)

(5S)—N-(cyclopropylmethyl)-5-[3-[(5-methoxy-2-methyl-pyrazol-3-yl)amino]-1,2,4-triazol-4-yl]-2-[[(2R*)-spiro[2.2]pentane-2-carbonyl]amino]-4,5,6,7-tetrahydrobenzothiophene-3-carboxamide (* or S).

their enantiomers and pharmaceutically acceptable salts thereof.

The following paragraphs provide definitions of the various chemical moieties that make up the compounds according to the invention and are intended to apply uniformly throughout the specification and claims unless a broader definition is explicitly set out.

The term "halogen" refers to fluorine, chlorine, bromine or iodine, and preferably fluorine.

The term "heterocyclic ring" refers to a saturated ring, containing at least one heteroatom, such as oxygen, sulphur and nitrogen; and includes a heteoaromatic or aromatic ring fused onto the heterocycle.

The term "alkyl" refers to a straight or branched, saturated, aliphatic hydrocarbon group.

The term "cycloalkyl" refers to monovalent groups derived from a saturated cyclic hydrocarbon and includes fused ring cycloalkyl and a heteroaromatic, heterocyclic or aromatic ring fused onto the carbocyle.

The term "fused ring cycloalkyl" refers to a cycloalkyl with two or more rings wherein the rings have at least one bond and two atoms in common. Examples of fused ring cycloalkyl include

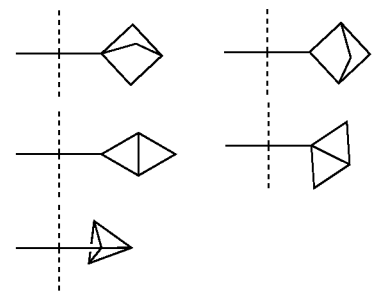

The term "heteroalkyl" refers to an alkyl group, where at least one carbon atom has been replaced with a heteroatom, such as oxygen, sulphur and nitrogen.

The term "heterocycle" refers to a ring structure that has atoms of at least two different elements as members of its ring, so some or all of the atoms in the molecules are joined in rings containing at least one atom of an element other than carbon, so for example oxygen, sulphur and nitrogen; and includes a heteoaromatic or aromatic ring fused onto the heterocycle.

The term "alkylene" refers to a bivalent saturated aliphatic radical derived from an unsaturated aliphatic hydrocarbon.

The term "haloalkyl" refers to an alkyl group as defined above, wherein at least one hydrogen atom is replaced by a halogen atom.

The term "alkenyl" refers to monovalent groups derived from a partially unsaturated, straight or branched carbon chain, such as ethenyl, propenyl, butenyl, pentenyl etc.

The term "cycloalkenyl" refers to monovalent groups derived from a partially unsaturated monocyclic hydrocarbon, such as cyclobutenyl.

The term "heteroalkenyl" refers to monovalent groups derived from a partially unsaturated straight or branched carbon chain containing at least one heteroatom such as oxygen, sulphur and nitrogen.

The term "heterocycloalkenyl" refers to monovalent groups derived from a partially unsaturated monocyclic hydrocarbon containing at least one heteroatom such as oxygen, sulphur and nitrogen.

The term "alkynyl" refers to an unsaturated, straight or branched carbon chain containing at least one carbon-carbon triple bond, such as ethynyl, propinyl and butinyl.

The term "heteroalkynyl" refers to an unsaturated, straight or branched carbon chain containing at least one carbon-carbon triple bond and containing at least one heteroatom such as oxygen, sulphur and nitrogen.

The term "aryl" refers to monovalent carbocyclic aromatic groups derived from a single aromatic ring or multiple condensed aromatic rings; for example phenyl, naphthyl.

The term "heteroaryl" refers to monovalent aromatic groups containing at least 5 atoms derived from a single ring or multiple condensed rings containing at least one heteroatom such as oxygen, sulphur and nitrogen.

The term "alkoxy" refers to a group —O—R' wherein R' is alkyl as defined above

The term "alkylamino" refers to the group —NH-alkyl, wherein alkyl is as defined above. The term "cycloalkyl-amino" refers to the group —NH— cycloalkyl, wherein cycloalkyl is as defined above.

The term "heterocycle-amino" refers to a heterocycle as defined above in which one or more carbon atoms is linked to —NH—, so refers to the group —NH-heterocycle.

The term "aryl-amino" refers to an aryl as defined above in which one or more carbon atoms is linked to —NH—, so refers to the group —NH-aryl.

The term "heteroaryl-amino", refers to a heteroaryl as defined above in which one or more carbon atoms is linked to —NH—, so refers to the group —NH-heteroaryl.

The term "heteroalkyl-amino" refers to the group —NH-heteroalkyl, wherein heteroalkyl is as defined above.

The term "pharmaceutically acceptable salt" according to the invention embraces salts of the compounds of formula (I) to (XXXVI) with a pharmaceutically acceptable acid or base, in particular an acid addition salt. The acid addition salt form of a compound of formula (I) to (XXXVI) that occurs in its free form as a base can be obtained by treating the free base with an appropriate acid such as an inorganic acid, for example, a hydrohalic acid such as hydrochloric acid or hydrobromic acid, sulfuric acid, nitric acid, phosphoric acid and the like; or an organic acid, such as, for example, acetic acid, trifluoroacetic acid, oxalic acid, hydroxyacetic acid, propanoic acid, lactic acid, pyruvic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and the like.

The invention also relates to all stereoisomeric forms such as enantiomeric and diastereoisomeric forms of the compounds of formula (I) to (XXXVI) or mixtures thereof (including all possible mixtures of stereoisomers such as racemates). With respect to the present invention reference to a compound or compounds is intended to encompass that compound in each of its possible isomeric forms and mixtures thereof, unless the particular isomeric form is referred to specifically.

Some of the compounds of formula (I) to (XXXVI) may also exist in tautomeric forms. Such forms although not explicitly indicated in the above formula are intended to be included within the scope of the present invention.

It is to be understood that each individual atom present in formula (I) to (XXXVI), or in formulae depicted herein, may in fact be present in the form of any of its naturally occurring isotopes, with the most abundant isotope(s) being preferred. Thus, by way of example, each individual hydrogen atom present in formula (I) to (XXXVI), or in the formulae depicted herein, may be present as a 1H, 2H (deuterium) or 3H (tritium) atom, preferably 1H. Similarly, by way of example, each individual carbon atom present in formula (I) to (XXXVI), or in the formulae depicted herein, may be present as a 12C, 13C or 14C atom, preferably 12C.

The present invention includes within its scope solvates of the compounds of formula (I) to (XXXVI) above. Such solvates may be formed with common organic solvents or water.

The present invention also includes within its scope co-crystals of the compounds of formula (I) to (XXXVI) above. The technical term "co-crystal" is used to describe the situation where neutral molecular components are present within a crystalline compound in a definite stoichiometric ratio.

The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

The present invention also includes within its scope prodrug of the compounds of formula (I) to (XXXVI) above. The term "prodrug" means a compound metabolised in vivo to a compound of the invention or its salt. A prodrug may be identified by administering the prodrug to a mammal, such as rat, mouse, monkey or man, and identifying the compound or its salt, for example in blood or urine. Another embodiment of the present invention concerns a pharmaceutical composition comprising a detectable amount of a compound of formula (I) to (XXXVI) or a pharmaceutically acceptable salt, solvate or co-crystal thereof in combination with a pharmaceutically acceptable diluent or carrier. In yet another embodiment, the present invention concerns a compound of formula (I) to (XXXVI) a pharmaceutically acceptable salt, solvate or co-crystal thereof for use as a medicament, in particular for use in a method for the treatment or prevention of disorders caused by IgE, including allergy, type 1 hypersensitivity, familiar sinus inflammation, urticaria or related conditions, such as airway constriction in asthma, local inflammation in eczema, increased mucus secretion in allergic rhinitis, increased vascular permeability, eosinophilic granulomatosis with polyangiitis (also known as "Churg Strauss syndrome"), aspirin exacerbated respiratory disease, or cutaneous T-cell lymphoma.

In a further embodiment, the present invention concerns a method for the treatment or prevention of allergy, type 1 hypersensitivity, familiar sinus inflammation, urticaria or related conditions, which comprises the administration of a compound of formula (I) to (XXXVI) in a therapeutically effective amount.

The following examples illustrate how the compounds covered by formula (I) to (XXXVI) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

The following examples illustrate how the compounds covered by formula I may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Abbreviations
  DCM: Dichloromethane
  MTBE: tert-Butylmethyl ether
  $Et_2O$: Diethyl ether
  THF: Tetrahydrofuran
  EtOAc: Ethyl acetate
  MeCN: Acetonitrile
  MeOH: Methanol
  h: Hour
  b s.: Broad singlet
  r.t.: Room temperature
  M: Mass
  Brine: Saturated sodium chloride solution
  HPLC: High performance liquid chromatography
  LCMS: Liquid Chromatography Mass Spectrometry
  ES+: Electrospray positive ionisation
  DIPEA: N,N-di-iso-propylethylamine
  RT: Retention time
  DMF: N,N'-dimethylformamide
  NaOH: Sodium hydroxide
  COMU: (1-Cyano-2-ethoxy-2-oxoethylidenaminooxy)-dimethylamino-morpholino-carbenium hexafluorophosphate
  mCPBA: 3-Chloroperbenzoic acid
  DMAP: 4-Dimethylaminopyridine
  NMP: N-Methyl-2-pyrrolidone
  CV: Column volume
  TFA: Trifluoroacetic acid
  DMSO: Dimethyl sulfoxide
  EDCl: N-(3-Dimethylaminopropyl)-N'-ethylcarbodiimide hydrochloride
  TBTU: O-(Benzotriazol-1-yl)-N,N,N',N'-tetramethyluronium tetrafluoroborate
  CDI: 1,1'-Carbonyldiimidazole
  EtOH: Ethanol Analytical Conditions All NMRs were obtained either at 250 MHz, 300 MHz, 400 MHz or 500 MHz.

All reactions involving air- or moisture-sensitive reagents were performed under a nitrogen atmosphere using dried solvents and glassware.

All compound LCMS data was determined using the methods below.

LCMS Methods

Method 1: 6120B pH10 Long (Slough)
  X-Bridge C18 Waters 2.1×20 mm, 2.5 µM column
  Mobile Phase A: 10 mM Ammonium formate in water+0.1% ammonia solution
  Mobile Phase B: Acetonitrile+5% water+0.1% Ammonia Solution
  Gradient program: Flow rate 1 mL/min

| Time | A % | B % |
|---|---|---|
| 0.00 | 96.00 | 4.00 |
| 4.00 | 5.00 | 95.00 |
| 5.00 | 5.00 | 95.00 |
| 5.10 | 96.00 | 4.00 |

Method 2: 6140 pH3 Registration (Slough)
  X-Bridge C18 Waters 2.1×20 mm, 2.5 µM column
  Mobile Phase A: 10 mM Ammonium formate in water+0.1% Formic acid
  Mobile Phase B: Acetonitrile+5% water+0.1% Formic acid
  Gradient program: Flow rate Pump 1: 1 mL/min, Flow rate Pump 2: 0.5 mL/min

| Time | A % | B % |
|---|---|---|
| Pump 1: | | |
| 0.00 | 95.00 | 5.00 |
| 4.00 | 5.00 | 95.00 |
| 5.00 | 5.00 | 95.00 |
| 5.10 | 95.00 | 5.00 |
| Pump 2: | | |
| 0.10 | 5.00 | 95.00 |
| 1.00 | 5.00 | 95.00 |
| 1.10 | 95.00 | 5.00 |

Method 3: 6140 pH10 Registration (Slough)
  X-Bridge C18 Waters 2.1×20 mm, 2.5 µM column
  Mobile Phase A: 10 mM Ammonium formate in water+0.1% Ammonia solution
  Mobile Phase B: Acetonitrile+5% water+0.1% Ammonia solution
  Gradient program: Flow rate Pump 1: 1 mL/min, Flow rate Pump 2: 0.5 mL/min

| Time | A % | B % |
|---|---|---|
| Pump 1: | | |
| 0.00 | 95.10 | 4.90 |
| 4.00 | 5.00 | 95.00 |
| 5.00 | 5.00 | 95.00 |
| 5.10 | 95.10 | 4.90 |

| Time | A % | B % |
|---|---|---|
| Pump 2: | | |
| 0.10 | 5.00 | 95.00 |
| 1.00 | 5.00 | 95.00 |
| 1.10 | 95.00 | 5.00 |

Method 4: L102 pH10 Short 3 Min (Crude System 1?) (Slough)
 X-Bridge C18 Waters 2.1×20 mm, 2.5 µM column
 Mobile Phase A: 10 mM Ammonium formate in water+0.1% ammonia solution
 Mobile Phase B: Acetonitrile+5% water+0.1% Ammonia solution
 Gradient program: Flow rate 1 mL/min

| Time | A % | B % |
|---|---|---|
| 0.00 | 94.00 | 6.00 |
| 1.50 | 5.00 | 95.00 |
| 2.25 | 5.00 | 95.00 |
| 2.50 | 94.00 | 6.00 |

Method 5: MS17 7 Min HiRes Evotec Shimadzu (Evotec) MET/CR/1416
 Mobile Phase A: 0.1% Formic Acid in water
 Mobile Phase B: 0.1% Formic Acid in Acetonitrile
 Waters Atlantis dC18, Part number 186001295, 2.1 mm×100 mm, 3 µm column
 Flow rate: 0.6 mL/min
 Column temperature: 40° C.
 Injection volume: 3 µL
 Gradient:

| Time (minutes): | % A | % B |
|---|---|---|
| 0.00 | 95 | 5 |
| 5.00 | 0 | 100 |
| 5.40 | 0 | 100 |
| 5.42 | 95 | 5 |
| 7.00 | 95 | 5 |

UV 215 nM, PDA spectrum 210-420 nm, step: 1 nm
MSD Scan Positive 100-1000
Method 6: MS17 METCR1673 Generic 2 Min (Evotec)
 Mobile Phase A: 0.1% Formic Acid in water
 Mobile Phase B: 0.1% Formic Acid in Acetonitrile
 Supelco Ascentis Express, Part Number: 53802-U, 2.1 mm×30 mm, 2.7 µm column
 Flow rate: 1 mL/min
 Column temperature: 40° C.
 Injection volume: 3 µL
 Gradient:

| Time (minutes): | % A | % B |
|---|---|---|
| 0 | 95 | 5 |
| 1.5 | 0 | 100 |
| 1.6 | 0 | 100 |
| 1.61 | 95 | 5 |

UV 215 nM, PDA spectrum 210-420 nm, step: 1 nm
MSD Scan Positive 100-1000
Method 7: pH10 6120B Short (Slough)
 X-Bridge C18 Waters 2.1×20 mm, 2.5 µM column
 Mobile Phase A: 10 mM Ammonium formate in water+0.1% ammonia solution
 Mobile Phase B: Acetonitrile+5% water+0.1% Ammonia solution
 Gradient program: Flow rate 1 mL/min

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Method 8: Braine Acidic QDA (Braine)
 A QDA Waters simple quadrupole mass spectrometer is used for LC-MS analysis.
 This spectrometer is equipped with an ESI source and an UPLC Acquity Hclass with diode array detector (210 to 400 nm).
 Data are acquired in a full MS scan from m/z 50 to 1000 in positive mode with an acidic elution.
 The reverse phase separation is carried out at 45° C. on a Waters Acquity UPLC HSS T3 1.8 µm (2.1×50 mm) column for acidic elution.
 Gradient elution is performed with:
 Mobile Phase A: Water
 Mobile Phase B: MeCN
 Mobile Phase C: Water/MeCN/formic acid 0.5%
 Gradient program:
 HPLC flow rate: 0.6 mL/minute to 0.7 mL/minute
 Injection volume: 1 µL
 Full flow in MS.

| Time (minute) | A (%) | B (%) | C (%) | Flow (mL/minute) |
|---|---|---|---|---|
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

Method 9: Braine Basic QDA (Braine)
 A QDA Waters simple quadrupole mass spectrometer is used for LC-MS analysis.
 This spectrometer is equipped with an ESI source and an UPLC Acquity Classic with diode array detector (210 to 400 nm).
 Data are acquired in a full MS scan from m/z 50 to 1000 in positive mode with a basic elution.
 The reverse phase separation is carried out at 45° C. on a Waters Acquity UPLC BEH C18 1.7 µm (2.1×50 mm) column for basic elution.
 Gradient elution is performed with:
 Mobile Phase A: $H_2O$/acetonitrile/ammonium formate (95/5/63 mg/L)+50 µL $NH_4OH$
 Mobile Phase B: Acetonitrile/$H_2O$/ammonium formate (95/5/63 mg/L)+50 µL $NH_4OH$
 Gradient program:
 HPLC flow rate: 0.4 mL/minute to 0.5 mL/minute
 Injection volume: 1 µL
 Full flow in MS.

| Time (minute) | A (%) | B (%) | Flow (mL/minute) |
| --- | --- | --- | --- |
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 90 | 1 | 0.4 |

Method 10: MSQ1 MET-uPLC-AB-101 7 Min Low pH (Evotec)
  Mobile Phase A: 0.1% Formic Acid in water
  Mobile Phase B: 0.1% Formic Acid in Acetonitrile Phenomenex, Kinetex-XB C18, 2.1 mm×100 mm, 1.7 μm column
  Flow rate: 0.6 mL/min
  Column temperature: 40° C.
  Injection volume: 1 μL
  Gradient:

| Time (minutes): | % A | % B |
| --- | --- | --- |
| 0.00 | 95 | 5 |
| 5.30 | 0 | 100 |
| 5.80 | 0 | 100 |
| 5.82 | 95 | 5 |
| 7.00 | 95 | 5 |

UV 215 nM, PDA spectrum 200-400 nm, step: 1 nm
MSD Scan Positive 150-850

Method 11: MS17 METCR1410 Generic 2 Min (Evotec)
  Mobile Phase A: 0.1% Formic Acid in water
  Mobile Phase B: 0.1% Formic Acid in Acetonitrile
  Kinetex Core-Shell C18 50×2.1 mm, 5 μm column protected by Phenomenex 'Security Guard' column.
  Flow rate: 1.2 mL/min
  Column temperature: 40° C.
  Injection volume: 3 μL
  Gradient:

| Time (minutes): | % A | % B |
| --- | --- | --- |
| 0.00 | 95 | 5 |
| 1.20 | 0 | 100 |
| 1.30 | 0 | 100 |
| 1.31 | 95 | 5 |

UV 215 nM, PDA spectrum 210-420 nm, step: 1 nm
MSD Scan Positive 100-1000

Method 12: Agilent 6120 3 Min pH3 (Evotec Insourcing Lab-UCB Machine)
  Column: Waters X-Bridge, C18, 2.1×20 mm, 2.5 μm silica particle
  Flow Rate: 1.0 mL/min
  Mobile Phase A: 10 mM Ammonium Formate+0.1% formic acid
  Mobile Phase B: Acetonitrile+5% Water+0.1% formic acid
  Column Temp: 40° C.
  Injection Volume: 1-5 μL
  UV Detection: 230 to 400 nm and 215 nm
  Mass Spec Detection: Agilent 6120 Mass Spectrometer (ES) m/z 120 to 800
  Gradient: 5% to 95% B over 1.5 minutes, hold 95% B for 0.5 minute, re-equilibrate at 5% B Method 13: Braine Basic QDA Long
  A QDA Waters simple quadrupole mass spectrometer is used for LC-MS analysis.
  This spectrometer is equipped with an ESI source and an UPLC Acquity Classic with diode array detector (210 to 400 nm.)
  Data are acquired in a full MS scan from m/z 70 to 800 in positive/negative mode with an acidic elution
  The reverse phase separation is carried out at 45° C. on a Waters Acquity UPLC BEH C18 1.7 μm (2.1×100 mm) column for basic elution
  Gradient elution is done with
  $H_2O$/ACN/Ammonium_formate (95/5/63 mg/L)+100 μl/L NH4OH (solvent A)
  ACN/$H_2O$/Ammonium_formate (95/5/63 mg/L)+100 μl/L NH4OH (solvent B)
  HPLC flow rate: 0.4 ml/min to 0.5 ml/min,
  injection volume: 1 μl
  Full flow in MS.

| Time (min) | A (%) | B (%) | Flow (ml/min) |
| --- | --- | --- | --- |
| 0 | 99 | 1 | 0.4 |
| 0.8 | 99 | 1 | 0.4 |
| 5.30 | 0 | 100 | 0.4 |
| 5.35 | 0 | 100 | 0.5 |
| 7.30 | 0 | 100 | 0.5 |
| 7.35 | 99 | 1 | 0.4 |
| 9 | 90 | 1 | 0.4 |

Method 14: METCR 1704 (MSQ2 1 min IPC-Evotec)
  Column: Waters UPLC CSH C18, 2.1×100 mm, 1.7 μm silica particle
  Flow Rate: 0.9 mL/min
  Mobile Phase A: Water+0.1% Formic acid
  Mobile Phase B: Acetonitrile+0.1% Formic acid
  Column Temp: 40° C.
  Injection Volume: 2 μL
  UV Detection: 200 to 400 nm and 215 nm
  Mass Spec Detection: m/z 150 to 850
  Gradient: 5% to 100% B over 1.1 minutes, hold 100% B for 0.25 minute, re-equilibrate at 5% B Method 15: (Slough Crude System pH10 Short)
  Gradient:

| Time | A % | B % |
| --- | --- | --- |
| 0.00 | 95.00 | 5.00 |
| 1.50 | 5.00 | 95.00 |
| 2.25 | 5.00 | 95.00 |
| 2.50 | 95.00 | 5.00 |

Flow: 1 mL/min
  Solvent A: 10 mM Ammonium Formate in water+0.1% Ammonia Solution
  Solvent B: Acetonitrile+5% water+0.1% Ammonia Solution
  Column: XBridge C18, 2.1×20 mm, 2.5 μm Method 16: Agilent 6120 6 Min pH10 (Evotec Insourcing Lab-UCB Machine)
  Column: Waters X-Bridge, C18, 2.1×20 mm, 2.5 μm silica particle
  Flow Rate: 1.0 mL/min
  Mobile Phase A: 10 mM Ammonium Formate+0.1% Ammonia solution
  Mobile Phase B: Acetonitrile+5% Water+0.1% Ammonia solution Column Temp: 40° C.
Injection Volume: 1-5 μL
UV Detection: 230 to 400 nm and 215 nm
Mass Spec Detection: Agilent 6120 Mass Spectrometer (ES) m/z 120 to 800
Gradient: 5% to 95% B over 4 minutes, hold 95% B for 1 minute, re-equilibrate at 5% B Method 17: Agilent 6120 3 Min pH10 (Evotec Insourcing Lab-UCB Machine)
Column: Waters X-Bridge, C18, 2.1×20 mm, 2.5 μm silica particle
Flow Rate: 1.0 mL/min
Mobile Phase A: 10 mM Ammonium Formate+0.1% Ammonia solution
Mobile Phase B: Acetonitrile+5% Water+0.1% Ammonia solution
Column Temp: 40° C.
Injection Volume: 1-5 μL
UV Detection: 230 to 400 nm and 215 nm
Mass Spec Detection: Agilent 6120 Mass Spectrometer (ES) m/z 120 to 800
Gradient: 5% to 95% B over 1.5 minutes, hold 95% B for 0.5 minute, re-equilibrate at 5% B Method 18: MS10 METCR0990 High pH 2.5 Min (Evotec)
Mobile Phase A: 2 mM Ammonium bicarbonate pH10
Mobile Phase B: Acetonitrile
Phenomenex Gemini-NX C18 2.0 mm×50 mm, 3 μm column
Flow rate: 1.0 mL/min
Column temperature: 40° C.
Injection volume: 3 μL
Gradient:

| Time (minutes): | % A | % B |
|---|---|---|
| 0.00 | 99 | 1 |
| 1.80 | 0 | 100 |
| 2.10 | 0 | 100 |
| 2.30 | 99 | 1 |
| 3.50 | 99 | 1 |

UV 215 nM, PDA spectrum 210-420 nm, step: 1 nm
MSD Scan Positive 150-850

Method 19: SFC1AB (Evotec Achiral SFC_1)
Column: Synergi 4u Polar RP, 4.6×250 mm
Mobile phase: 15% Ethanol: 85% CO2
Flow rate: 4 ml/min
Runtime: 15 mins Method 20: Braine TOFA
Column: a Acquity UPLC HSS T3 C18 column (1.7 μm, 2.1×100 mm)
Flow rate: 0.4 ml/min to 0.5 ml/min
Solvent A: Water
Solvent B: Acetonitrile
Solvent C: Formic Acid 5 ml/L in Acetonitrile/water 50/50 (PH3)
Column Temp: 45° C.
Injection Volume: 0.3 μl
Full flow in MS.

| Time (min) | % A | % B | % C | Flow (ml/min) |
|---|---|---|---|---|
| 0 | 88 | 2 | 10 | 0.4 |
| 0.5 | 88 | 2 | 10 | 0.4 |
| 5 | 2.5 | 90 | 7.5 | 0.4 |
| 5.1 | 2.5 | 90 | 7.5 | 0.5 |
| 7.30 | 2.5 | 90 | 7.5 | 0.5 |
| 7.5 | 88 | 2 | 10 | 0.4 |
| 10 | 88 | 2 | 10 | 0.4 |

UV Detection: 210 to 400 nm
Mass Spec detection: LCT Waters Time of flight mass spectrometer m/z 50 to 950 in positive mode Method 21: Braine Acidic QDA Long
A QDA Waters simple quadrupole mass spectrometer is used for LC-MS analysis.
This spectrometer is equipped with an ESI source and an UPLC Acquity Hclass with diode array detector (210 to 400 nm.)
Data are acquired in a full MS scan from m/z 50 to 1000 in positive mode with an acidic elution
The reverse phase separation is carried out at 45° C. on a Waters Acquity UPLC HSS T3 1.8 μm (2.1×100 mm) column for acidic elution
Gradient elution is done with
Water/Formic Ac (solvent A)
Acetonitrile/formic Ac (solvent B)
HPLC flow rate: 0.4 ml/min to 0.5 ml/min,
injection volume: 1 μl
Full flow in MS.

| Time (min) | A (%) | B (%) | Flow(ml/min) |
|---|---|---|---|
| 0 | 99 | 1 | 0.4 |
| 0.8 | 99 | 1 | 0.4 |
| 5.3 | 5 | 95 | 0.4 |
| 5.35 | 5 | 95 | 0.5 |
| 8.30 | 5 | 95 | 0.5 |
| 8.35 | 99 | 1 | 0.4 |
| 10 | 99 | 1 | 0.4 |

Method 22: SFC1AB (Evotec achiral SFC_2)
Column: KR60-5DIOL, 4.6×250 mm
Mobile phase: 25% Methanol: 75% CO2
Flow rate: 4 ml/min
Runtime: 8 mins Method 23: Chiral SFCMS Analysis (Evotec)
Column: Chiralpak AD-H 25 cm
Mobile phase: 15% IPA: 85% CO2
Flow rate: 4 ml/min
Runtime: 20 mins Method 24: pH3 UPLC (Slough)
Low pH (approximately pH 3):
Column: Waters Acquity UPLC BEH, C18, 2.1×50 mm, 1.7 μm
Mobile Phase A: 10 mM Ammonium formate in water+0.1% formic acid
Mobile Phase B: acetonitrile+5% solvent A+0.1% formic acid
Gradient:

| Time | A % | B % |
|---|---|---|
| 0.00 | 98.0 | 2.0 |
| 4.00 | 5.0 | 95.0 |
| 5.00 | 5.0 | 95.0 |
| 5.10 | 98.0 | 2.0 |

System: Waters Classic Acquity-SQD, Acquity PDAc
Column Temperature: 40° C.
PDA wavelength range: 210-400 nm
Mass spec detection: ESI on a Waters SQD
Flow rate: 0.7 mL/min
Method 25: pH10 UPLC (Slough)
High pH (approximately pH 9.5)
Column: Waters Acquity UPLC BEH, C18, 2.1×50 mm, 1.7 μm
Mobile Phase A: 10 mM Ammonium formate in water+0.1% ammonia solution
Mobile Phase B: acetonitrile+5% solvent A+0.1% ammonia solution
Gradient:

| Time | A % | B % |
|---|---|---|
| 0.00 | 98.0 | 2.0 |
| 4.00 | 5.0 | 95.0 |
| 5.00 | 5.0 | 95.0 |
| 5.10 | 98.0 | 2.0 |

System: Waters Classic Acquity-SQD, Acquity PDAc
Column Temperature: 40° C.
PDA wavelength range: 210-400 nm
Mass spec detection: ESI on a Waters SQD
Flow rate: 0.7 mL/min
Method 26: (Slough Registration 6140 pH 10, 2018)
Gradient:

| Time | A % | B % |
|---|---|---|
| 0.00 | 95.10 | 5.00 |
| 4.00 | 5.00 | 95.00 |
| 5.00 | 5.00 | 95.00 |
| 5.10 | 95.10 | 5.00 |

Flow: 1 mL/min
Solvent A: 10 mM Ammonium Formate in water+0.1% Ammonia Solution
Solvent B: Acetonitrile+5% water+0.1% Ammonia Solution
Column: XBridge C18, 2.1×20 mm, 2.5 μm
Method 27: (Slough Registration 6140 pH 3, 2018)
Gradient:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Flow: 1 mL/min
Solvent A: 10 mM Ammonium Formate in water+0.1% Formic Acid
Solvent B: Acetonitrile+5% water+0.1% Formic Acid
Column: XBridge C18, 2.1×20 mm, 2.5 μm
Method 28: (Slough Crude, Long pH 3, 2018)
Gradient:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Flow: 1 mL/min
Solvent A: 10 mM Ammonium Formate in water+0.1% Formic Acid
Solvent B: Acetonitrile+5% water+0.1% Formic Acid
Column: XBridge C18, 2.1×20 mm, 2.5 μm
Method 29: Agilent 6120 6 min pH3
X-Bridge C18 Waters 2.1×20 mm, 2.5 μM column
Mobile Phase A: 10 mM Ammonium formate in water+0.1% formic acid
Mobile Phase B: Acetonitrile+5% water+0.1% Formic acid
Gradient program: Flow rate 1 mL/min

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 30: MET/uPLC/AB102
Waters UPLC® CSH™ C18, 2.1×100 mm, 1.7 m column
Column Temperature 40° C.
Mobile Phase A: 2 mM ammonia bicarbonate, buffered to pH 10
Mobile Phase B: Acetonitrile
Gradient program Flow rate 0.6 mL/Min

| Time | A % | B % |
|---|---|---|
| 0.00 | 95.00 | 5.00 |
| 5.30 | 0 | 100 |
| 5.80 | 0 | 100 |
| 5.82 | 95.00 | 5.00 |

Method 31: MET/CR/1600
Phenomenex Gemini-NX C18, Part No. 00D-4453-B0, 2.0×100 mm, 3 μm column
Column Temperature 40° C.
Mobile Phase A: 2 mM ammonia bicarbonate, buffered to pH 10
Mobile Phase B: Acetonitrile
Gradient program Flow rate 0.5 mL/Min

| Time | A % | B % |
|---|---|---|
| 0.00 | 95.00 | 5.00 |
| 5.50 | 0 | 100 |
| 5.90 | 0 | 100 |
| 5.92 | 95.00 | 5.00 |
| 7.00 | 95.00 | 5.00 |

Method 32: MET-uPLC-AB-105
  Waters UPLC® BEH™ C18, Part No. 186002352, 2.1×100 mm, 1.7 μm
  Column Temperature 40° C.
  Mobile Phase A: 2 mM ammonia bicarbonate, buffered to pH 10
  Mobile Phase B: Acetonitrile
  Gradient program Flow rate 0.6 mL/Min

| Time | A % | B % |
|---|---|---|
| 0.00 | 95.00 | 5.00 |
| 5.30 | 0 | 100 |
| 5.80 | 0 | 100 |
| 5.82 | 95.00 | 5.00 |
| 7.00 | 95.00 | 5.00 |

Method 33: 6140 pH10 Short pH 3
  X-Bridge C18 Waters 2.1×20 mm, 2.5 μM column
  Mobile Phase A: 10 mM Ammonium formate in water+0.1% Ammonia solution
  Mobile Phase B: Acetonitrile+5% water+0.1% Ammonia solution
  Gradient program: Flow rate 1 mL/min

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Method 34: Agilent 1260-6120B
  X-Bridge C18 Waters 2.1×20 mm, 2.5 μM column
  Mobile Phase A: 10 mM Ammonium formate in water+0.1% Ammonia solution
  Mobile Phase B: Acetonitrile+5% water+0.1% Ammonia solution
  Gradient program: Flow rate 1 mL/min

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Chiral SFC Analytical Methods

Method 1: Using Conditions Below Unless Otherwise Stated in Procedure
  Column: ChiralPak IC-3, 150×4.6 mm, 3 μm
  Mobile Phase A: $CO_2$
  Mobile Phase B: Methanol+0.1% Ammonium hydroxide
  ABPR Pressure: 120 bar
  Detection Signal: UV 210-600 nm, DAD
  Gradient Program: Flow rate 3 mL/min

| Time | A % | B % |
|---|---|---|
| 0 | 97 | 3 |
| 5 | 60 | 40 |
| 5.1 | 97 | 3 |
| 6.5 | 97 | 3 |

HPLC Methods

Method 1: Generic High pH Prep Method (Standard Method)
  Column: Waters Xbridge C18 Part no. 186003930, 30×100 mm, 10 um
  Column Temp: Room temperature
  Mobile Phase A: Water+0.2% Ammonium hydroxide
  Mobile Phase B: Acetonitrile+0.2% Ammonium hydroxide
  Flow rate: 40 ml/min
  Injection Volume: 1500 μl
  Detection Signal: UV 715, Variable
  Gradient:

| Time (minutes): | % A | % B |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 2: Generic High pH Prep Method (Early Elute Method)
  Column: Waters Xbridge C18 Part no. 186003930, 30×100 mm, 10 um
  Column Temp: Room temperature
  Mobile Phase A: Water+0.2% Ammonium hydroxide
  Mobile Phase B: Acetonitrile+0.2% Ammonium hydroxide
  Flow rate: 40 ml/min
  Injection Volume: 1500 μl
  Detection Signal: UV 215, Variable
  Gradient:

| Time (minutes): | % A | % B |
|---|---|---|
| 0.00 | 90 | 10 |
| 0.55 | 90 | 10 |
| 14.44 | 5 | 95 |
| 16.55 | 5 | 95 |
| 16.75 | 90 | 10 |

Method 3: Generic Low pH Prep Method (Standard Method)
  Column: Waters Sunfire C18, Part no. 186003971, 30×100 mm, 10 um
  Column Temp: Room temperature
  Mobile Phase A: Water+0.1% formic acid
  Mobile Phase B: Acetonitrile+0.1% formic acid
  Flow rate: 40 ml/min
  Injection Volume: 1500 μl
  Detection Signal: UV 215, Variable
  Gradient:

| Time (minutes): | % A | % B |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 4: Generic Low pH Prep Method (Early Elute Method)
Column: Waters Sunfire C18, Part no. 186003971, 30×100 mm, 10 um
Column Temp: Room temperature
Mobile Phase A: Water+0.1% formic acid
Mobile Phase B: Acetonitrile+0.1% formic acid
Flow rate: 40 ml/min
Injection Volume: 1500 µl
Detection Signal: UV 215, Variable
Gradient:

| Time (minutes): | % A | % B |
|---|---|---|
| 0.00 | 90 | 10 |
| 0.55 | 90 | 10 |
| 14.44 | 5 | 95 |
| 16.55 | 5 | 95 |
| 16.75 | 90 | 10 |

Method 5: UCB pH10 Gilson Standard Method
Column: Waters XBridge C18, Part no. 186003896, 30×150 mm, 10 um
Column Temp: Room temperature
Mobile Phase A: Water+0.1% NH$_4$OH
Mobile Phase B: Acetonitrile+0.1% NH$_4$OH
Flow rate: 40 ml/min
Injection Volume: 500 µl
Detection Signal: UV 215, Variable
Gradient:

| Time (minutes): | % A | % B |
|---|---|---|
| 0.00 | 70 | 30 |
| 1.95 | 70 | 30 |
| 12.95 | 5 | 95 |
| 15.42 | 5 | 95 |
| 15.75 | 70 | 30 |

General Experimental Methods

General Method 1

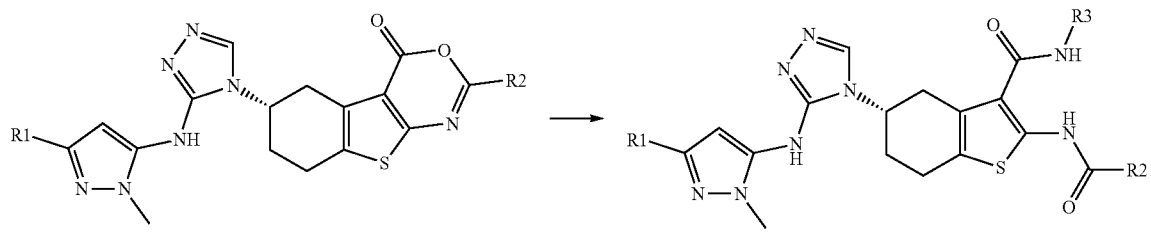

A mixture the tricycle and amine (1-10 equivalents) with or without an excess of base (triethylamine or DIPEA) was dissolved/suspended in either anhydrous DMF or acetonitrile. The reaction was then heated at 70° C., 90° C., or 140° C. for a period of 15 min to 1 hour in a sealed vial or under an atmosphere of N$_2$. The reaction mixture was then cooled to room temperature and either (1) filtered and purified by reverse phase HPLC or (2) worked up and purified by reverse phase HPLC or normal phase column chromatography unless otherwise noted.

General Method 2

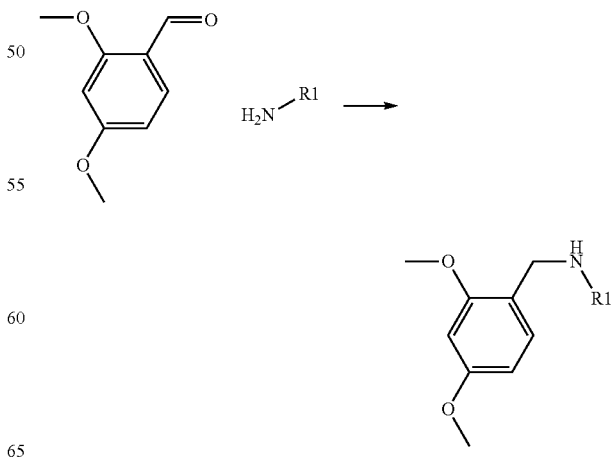

To a solution of amine (1 equivalent) in DCM was added 2,4-dimethoxybenzaldehyde (1 equivalent), followed by STAB (1.5 equivalent). The mixture was stirred at room temperature for 4 hours. The mixture was then quenched with saturated sodium bicarbonate. The aqueous layer was extracted with DCM and the organic fractions combined, dried (Na$_2$SO$_4$) and concentrated under vacuum. The resulting residue was purified by column chromatography.

General Method 3

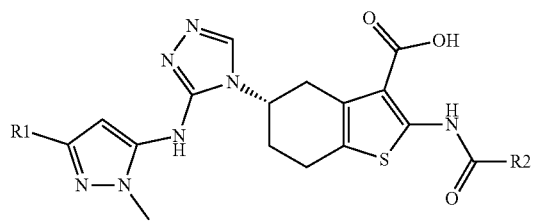

To a stirred solution of the acid (1 equivalent) in anhydrous DMF were added DIPEA (5-7 equivalents), relevant amine (2-6 equivalents), and HATU (1-3 equivalents). The reaction mixture was heated at 70° C. (unless otherwise stated) for a period of 1-7 hours (unless otherwise stated). Note: in some cases, the reagents were added in two or three portions throughout the duration of the reaction. The reaction mixture was then cooled to room temperature and either (1) purified by reverse phase HPLC or (2) worked up and purified by column chromatography.

General Method 4

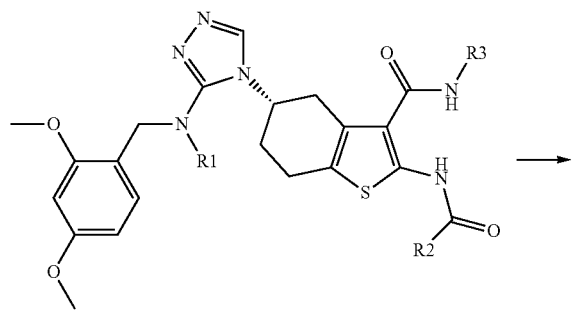

reaction mixture was used in the next stage as a HCl salt. Alternatively, the residue was dissolved in saturated aqueous NaHCO$_3$ and DCM, organic layer was separated and extracted with further DCM. Organic layers were combined, dried (Na$_2$SO$_4$) and concentrated under vacuum. Then purified either by column chromatography or reverse phase HPLC.

General Method 5

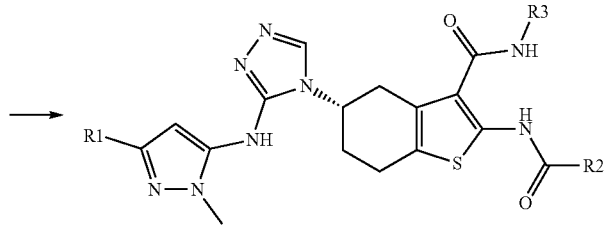

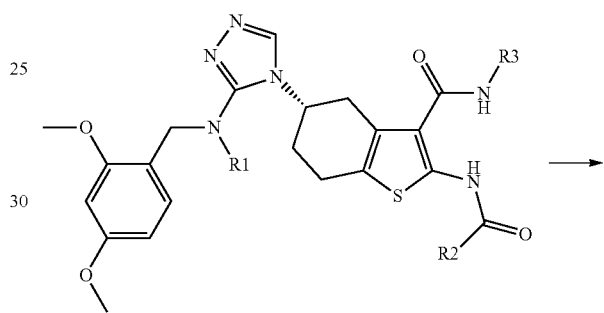

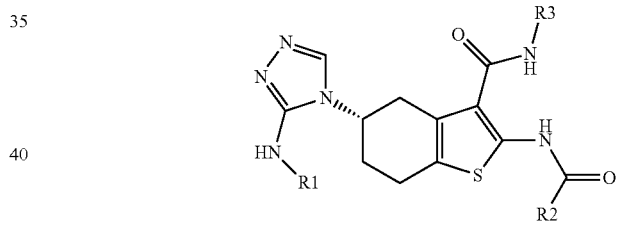

To a stirred solution of the 2,4-Dimethoxylbenzyl-protected amine (1 equivalent) in anhydrous DCM was added TFA (10 equivalents). The reaction mixture was stirred at RT for 16 hrs. After removing solvent, crude reaction mixture was used in the next stage as a TFA salt. Alternatively, the residue was dissolved in saturated aqueous NaHCO$_3$ and DCM, organic layer was separated and extracted with further DCM. Organics layers were combined, dried (Na$_2$SO$_4$) and concentrated under vacuum. Then purified either by column chromatography or reverse phase HPLC.

General Method 6

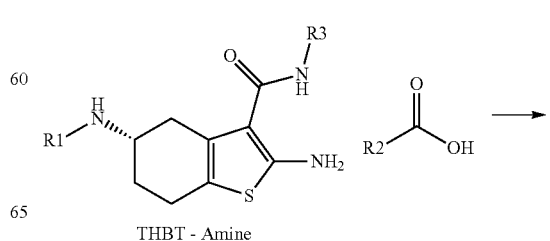

THBT - Amine

To a stirred solution of the 2,4-Dimethoxylbenzyl-protected amine (1 equivalent) in anhydrous dioxane was added 4 M HCl in dioxane (20 equivalents). The reaction mixture was stirred at RT for 16 hrs. After removing solvent, crude -continued

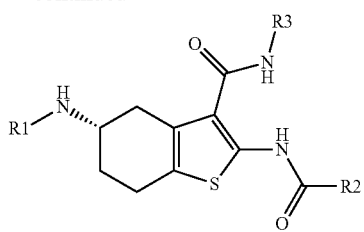

To a mixture of the THBT-amine (1 equivalent), acid (1 equivalent) and pyridine (5 equivalents) in DCM (5 mL), T3P (1-2 equivalents) was slowly added at 0° C. The reaction mixture was slowly allowed to warm to RT and stirred for a period of several hours. Reaction mixture was worked up and purified by reverse phase HPLC.

General Method 7

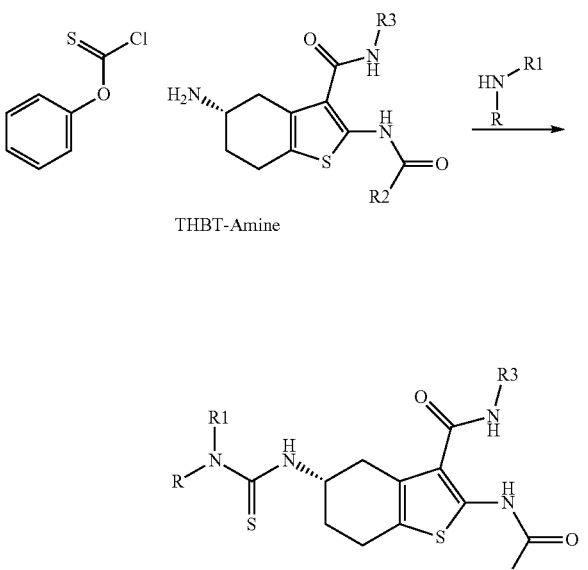

To a stirred solution of phenyl chloromethanethioate (1.1 equivalents) in DCM, at 0° C. was added THBT-amine (1 equivalent) and triethylamine (2-3 equivalents). The reaction was stirred whilst warming to room temperature for 1 hour, the relevant amine (1-2 equivalents) was then added as a solution in DCM. The mixture was stirred at room temperature until LCMS showed completion of the reaction. The mixture was then concentrated in vacuo and the residue purified.

General Method 8

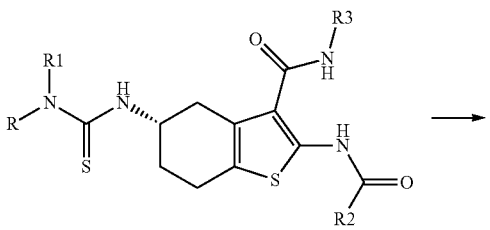

-continued

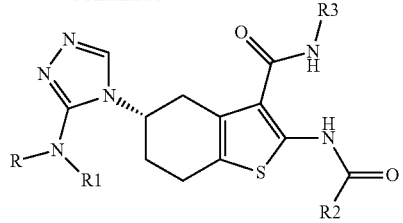

Thiourea (1 equivalent) was dissolved in DMF and formic hydrazide (2-3 equivalents) was added, followed by mercury dichloride (2-3 equivalents). The reaction mixture was stirred at room temperature for 5 minutes, then triethylamine (3 equivalents) was added. The mixture was stirred at 90° C. until reaction was complete. The mixture was cooled to room temperature, diluted with DCM and filtered through kieselguhr/Celite, washing with DCM. The solvent was removed in vacuo and the residue purified.

General Method 9

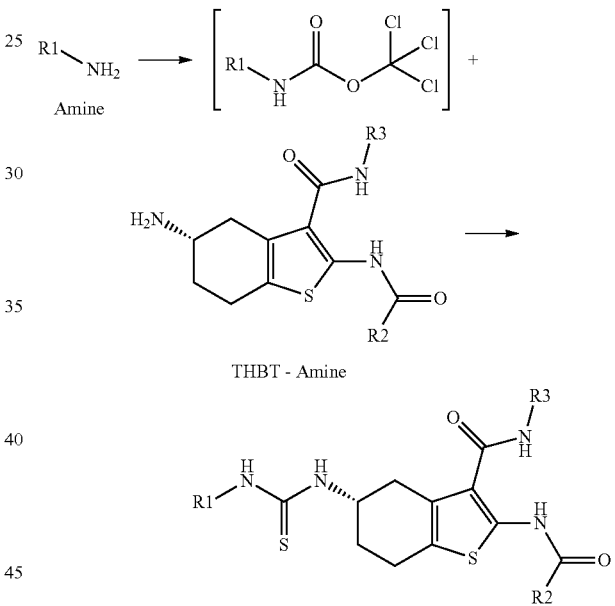

Sodium carbonate (5 equivalents) was stirred in mixture of DCM:Water (2:1, respectively) at 0° C. Thiophosgene (1 equivalent) was added, followed by amine (1 equivalent). The reaction mixture was stirred at 0° C. for 5 minutes, then at room temperature for 1 hour. The mixture was then extracted using DCM, dried over sodium or magnesium sulphate, or passed through a hydrophobic frit. The solvent was removed in vacuo and the residue re-dissolved in DCM. THBT-amine (1.1 equivalents) was added and the mixture stirred at room temperature until the reaction was complete.

Abbreviations sat. saturated
aq. aqueous
BOC tert-Butoxycarbonyl
tBuXPhos Pd G3 [(2-Di-tert-butylphosphino-2',4',6'-triisopropyl-1,1'-biphenyl)-2-(2'-amino-1,1' biphenyl)] palladium(II) methanesulfonate DCE 1,2-Dichloroethane TEA Triethylamine THBT 4,5,6,7-tetrahydrobenzothiophene T3P 2,4,6-Tripropyl-1,3,5,2,4,6-trioxatriphosphorinane-2,4,6-trioxide EDC N-(3-Dimethylaminopropyl)-N'-ethylcarbodiimide hydrochloride STAB Sodium triacetoxyborohydride HATU 1-[Bis(dimethylamino)methylene]-1H-1,2,3-triazolo[4,5-b]pyridinium 3-oxid hexafluorophosphate DPPA Diphenyl phosphoryl azide PTSA para toluene sulfonic acid DEA diethylamine DMA N,N-dimethylacetamide TBME tert-Butylmethyl ether (also abbreviated to MTBE)

hr or hrs hours

KP-NH Biotage® SNAP KP-NH, Flash Chromatography Cartridge mCPBA 3-Chloroperoxybenzoic acid o/n overnight It will be apparent to the person skilled in the art that different retention times (RT) may be obtained for LCMS if different analytical conditions are used.

Intermediate 2

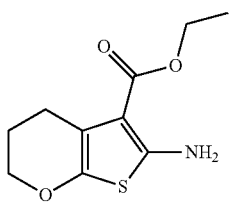

Ethyl 6-amino-3,4-dihydro-2H-thieno[2,3-b]pyran-5-carboxylate

To sulfur [7704-34-9] (0.36 g, 11.2 mmol) was added dihydro-2H-pyran-3(4H)-one [23462-75-1] (1.04 g, 10.4 mmol), EtOH (30 mL), ethyl cyanoacetate [105-56-6] (1.2 mL, 11 mmol) and morpholine [110-91-8] (1.4 mL, 16 mmol). The reaction mixture was stirred at r.t. for 15 minutes under nitrogen before heating to 50° C. overnight. The reaction mixture was cooled to r.t. and filtered, washing with EtOAc. The crude residue was purified by flash column chromatography on silica (gradient elution with 100% isohexane/EtOAc to 30% EtOAc/isohexane) to afford the title compound (1.41 g, 60%) as a pale brown crystalline solid. $\delta_H$ (300 MHz, DMSO-$d_6$) 7.00 (s, 2H), 4.13 (q, J 7.1 Hz, 2H), 4.09-4.03 (m, 2H), 2.56 (t, J 6.4 Hz, 2H), 1.94-1.79 (m, 2H), 1.23 (t, J 7.1 Hz, 3H).

Intermediate 2

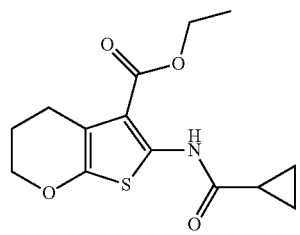 [SMILES: CCOC(=O)c1c(NC(=O)C2CC2)sc2c1CCCO2]

ethyl 6-(cyclopropanecarbonylamino)-3,4-dihydro-2H-thieno[2,3-b]pyran-5-carboxylate To intermediate 1 (1.41 g, 6.20 mmol) dissolved in DCM (45 mL) was added DIPEA (3.2 mL, 18 mmol) and cyclopropanecarbonyl chloride [4023-34-1] (0.63 mL, 6.8 mmol) and the reaction mixture was stirred under nitrogen at r.t. for ~2 h before quenching with water (15 mL) and diluting with DCM (25 mL). The reaction mixture was filtered through a phase separation cartridge and the mixture was concentrated in vacuo to afford the title compound (2.16 g, 118%) which was carried through crude to the following step. LCMS (ES+) [M+H]$^+$ 296.1, RT 3.280 minutes, 94.2% purity (Method 1).

Intermediate 3

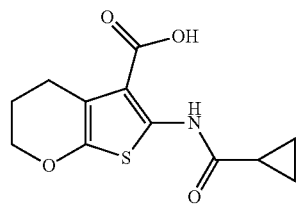 [SMILES: O=C(O)c1c(NC(=O)C2CC2)sc2c1CCCO2]

6-(Cyclopropanecarbonylamino)-3,4-dihydro-2H-thieno[2,3-b]pyran-5-carboxylic acid To intermediate 2 (2.16 g, 7.31 mmol) in 1,4-dioxane (20 mL) and water (4 mL) was added lithium hydroxide monohydrate [1310-66-3] (483 mg, 11.5 mmol) and the reaction mixture was heated to 70° C. under nitrogen for 3 h. Further lithium hydroxide monohydrate [1310-66-3] (179 mg, 4.25 mmol) was added and the mixture was heated to 70° C. under nitrogen for 2 h and cooled to r.t. overnight. The mixture was concentrated in vacuo and the residue left at r.t. for 2 nights. The residue was diluted with water (50 mL) and was washed with DCM (2×50 mL). The aqueous phase was acidified to ~pH 4 with 2M aqueous hydrochloric acid solution and the solid formed was filtered and washed with water to afford the title compound (1.28 g, 65%) as a pale brown/orange solid. $\delta_H$ (300 MHz, DMSO-$d_6$) 13.06 (s, 1H), 11.31 (s, 1H), 4.14 (dd, J 5.9, 4.2 Hz, 2H), 2.67 (t, J 6.4 Hz, 2H), 2.03-1.78 (m, 3H), 0.98-0.77 (m, 4H).

Intermediate 4 and Intermediate 5

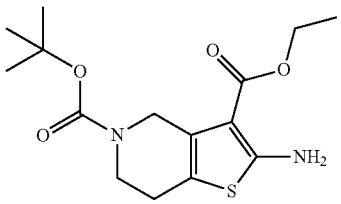

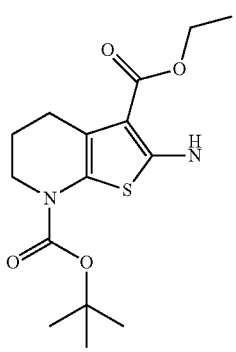

Intermediate 4

O5-Tert-butyl O3-ethyl 2-amino-6,7-dihydro-4H-thieno[3,2-c]pyridine-3,5-dicarboxylate and

Intermediate 5

O7-Tert-butyl O3-ethyl 2-amino-5,6-dihydro-4H-thieno[2,3-b]pyridine-3,7-dicarboxylate 1-Boc-3-piperidone [98977-36-7] (10.0 g, 48.7 mmol) was dissolved in EtOH (30 mL) and ethyl cyanoacetate [105-56-6] (6.06 g, 53.6 mmol), morpholine [110-91-8] (6.43 g, 73.0 mmol) and sulphur [7704-34-9] (1.72 g, 53.6 mmol) were added. The reaction mixture was stirred at r.t. for 16 h and heated at 50° C. for 24 h, before filtering and washing with EtOH. The filtrate was partitioned between DCM and water and the organic phase was washed with saturated sodium chloride solution and passed through a phase separation cartridge. The crude material was purified by flash column chromatography on silica (gradient elution with 10-50% EtOAc/hexane) to afford the title compound intermediate 4 (2.28 g, 14%) as a yellow gum and title compound intermediate 5 (1.74 g, 11%) as a pale yellow solid. Intermediate 4 LCMS [M–H]⁻ 325.0, RT 2.613 minutes, 83.6% purity (Method 1).

Intermediate 5 LCMS [M–H]⁻ 325.0, RT 2.774 minutes, 91.5% purity (Method 1).

Intermediate 6

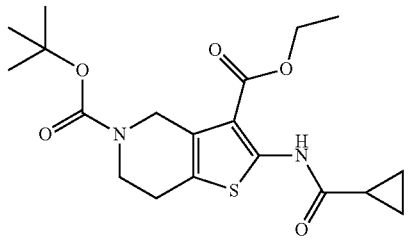 [SMILES: CCOC(=O)c1c(NC(=O)C2CC2)sc2c1CN(C(=O)OC(C)(C)C)CC2]

O5-Tert-butyl O3-ethyl 2-(cyclopropanecarbonylamino)-6,7-dihydro-4H-thieno[3,2-c]pyridine-3,5-dicarboxylate Intermediate 4 (2.28 g, 6.99 mmol) was dissolved in DCM (50 mL) and DIPEA (1.81 g, 14.0 mmol) and cyclopropanecarbonyl chloride [4023-34-1] (0.820 g, 7.68 mmol) was added. The reaction mixture was stirred at r.t. for 16 h. The mixture was washed with water, passed through a phase separation cartridge and the organic phase concentrated in vacuo. The crude residue was purified by flash column chromatography on silica (gradient elution with 5-60% EtOAc/hexane) to afford the title compound (2.55 g, 93%) as an off-white solid. $\delta_H$ (400 MHz, DMSO-$d_6$) 11.20 (s, 1H), 4.54 (s, 2H), 4.32 (q, J=7.3 Hz, 2H), 3.60 (t, J=5.7 Hz, 2H), 2.66 (t, J=5.8 Hz, 2H), 2.12-2.02 (m, 1H), 1.43 (s, 9H), 1.35 (t, J=7.1 Hz, 3H), 1.01-0.83 (m, 4H). LCMS [M-Boc+H]⁺ 295.8, RT 2.904 minutes (Method 2).

Intermediate 7

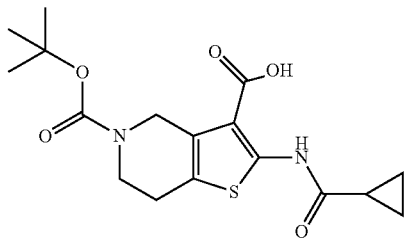 [SMILES: CC(C)(C)OC(=O)N1CCc2sc(NC(=O)C3CC3)c(C(=O)O)c2C1]

5-Tert-butoxycarbonyl-2-(cyclopropanecarbonylamino)-6,7-dihydro-4H-thieno[3,2-c]pyridine-3-carboxylic acid Intermediate 6 (2.55 g, 6.46 mmol) was dissolved in 1,4-dioxane (100 mL) and a solution of lithium hydroxide monohydrate [1310-66-3] (0.73 g, 17.3 mmol) in water (5 mL) was added. The reaction mixture was stirred at 70° C. for 16 h before cooling to r.t. and concentrating in vacuo. The reaction was partitioned between water and DCM and the organic phase was separated and the aqueous phase extracted with DCM (2×). The aqueous phase was acidified to pH<4.5 by addition of aqueous citric acid solution and the resulting precipitate was filtered off washing with water (3×) to afford the title compound (1.82 g, 77%) as an off-white solid. $\delta_H$ (400 MHz, DMSO-$d_6$) 13.31 (s, 1H), 11.54 (s, 1H), 4.53 (s, 2H), 3.60 (t, J 5.6 Hz, 2H), 2.72-2.60 (m, 2H), 2.07-1.93 (m, 1H), 1.42 (s, 9H), 0.99-0.81 (m, 4H).

Intermediate 8

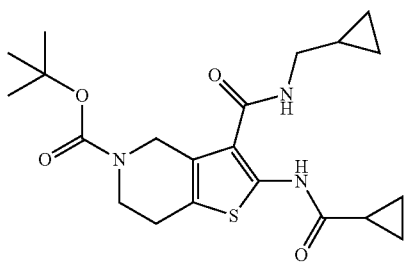 [SMILES: CC(C)(C)OC(=O)N1CCc2sc(NC(=O)C3CC3)c(C(=O)NCC3CC3)c2C1]

Tert-butyl 2-(cyclopropanecarbonylamino)-3-(cyclopropylmethylcarbamoyl)-6,7-dihydro-4H-thieno[3,2-c]pyridine-5-carboxylate Intermediate 7 (1.82 g, 4.97 mmol) was suspended in DCM (50 mL) and cyclopropylmethylamine [2516-47-4] (0.53 g, 7.5 mmol) and EDCl (1.18 g, 5.96 mmol) were added and the reaction mixture was stirred at r.t. for 16 h. The reaction mixture was washed with water and saturated sodium chloride solution, passed through a phase separation cartridge and the filtrate concentrated in vacuo. The crude residue was purified by flash column chromatography on silica (gradient elution with 10-60% EtOAc/hexane) to afford the title compound (873 mg, 42%) as an off-white solid. $\delta_H$ (400 MHz, DMSO-$d_6$) 10.75 (s, 1H), 7.60 (s, 1H), 4.23 (s, 2H), 3.36 (t, J 5.7 Hz, 2H), 2.91 (t, J 6.2 Hz, 2H), 2.52-2.31 (m, 2H), 1.81-1.60 (m, 1H), 1.17 (s, 9H), 0.87-0.69 (m, 1H), 0.68-0.48 (m, 4H), 0.26-0.11 (m, 2H), 0.07-−0.10 (m, 2H). LCMS [M+H]$^+$ 420.8, RT 2.582 minutes (Method 2). LCMS [M−H]$^-$ 418.0, RT 2.471 minutes (Method 3).

Intermediate 9

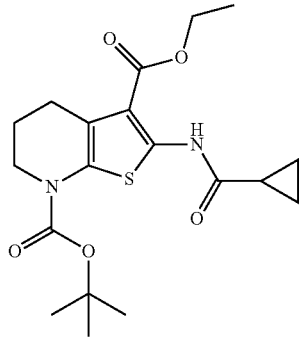 [SMILES: CCOC(=O)c1c(NC(=O)C2CC2)sc2c1CCCN2C(=O)OC(C)(C)C]

O7-tert-Butyl O3-ethyl 2-(cyclopropanecarbonylamino)-5,6-dihydro-4H-thieno[2,3-b]pyridine-3,7-dicarboxylate Intermediate 5 (2.74 g, 8.39 mmol) was dissolved in DCM (50 mL) and DIPEA (2.17 g, 16.8 mmol) and cyclopropanecarbonyl chloride (0.99 g, 9.23 mmol) was added. The reaction mixture was stirred at r.t. for 16 h. The reaction mixture was washed with water and passed through a phase separation cartridge. The organic phase was concentrated in vacuo to give the crude residue which was purified by flash column chromatography on silica (gradient elution with 5-50% EtOAc/hexane) to afford the title compound (3.28 g, 99%) as an off-white solid. $\delta_H$ (400 MHz, DMSO-$d_6$) 11.09 (s, 1H), 4.30 (q, J 7.1 Hz, 2H), 3.69 (s, 2H), 2.77 (t, J 6.3 Hz, 2H), 2.06-1.93 (m, 1H), 1.93-1.82 (m, 2H), 1.49 (s, 9H), 1.33 (t, J 7.1 Hz, 3H), 1.01-0.82 (m, 4H). LCMS [M+H]$^+$ 395.8, RT 3.141 minutes, 100.0% purity (Method 2).

Intermediate 10

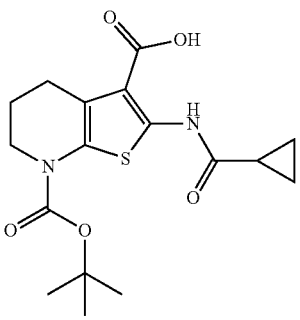 [SMILES: CC(C)(C)OC(=O)N1CCCc2c1sc(NC(=O)C1CC1)c2C(=O)O]

7-Tert-butoxycarbonyl-2-(cyclopropanecarbonylamino)-5,6-dihydro-4H-thieno[2,3-b]pyridine-3-carboxylic acid Intermediate 9 (3.28 g, 8.31 mmol) was dissolved in 1,4-dioxane (100 mL) and a solution of lithium hydroxide monohydrate [1310-66-3] (0.934 g, 12.5 mmol) in water (5 mL) was added. The reaction mixture was heated to 70° C. and was stirred for 16 h before cooling to r.t. and concentrating in vacuo. The reaction mixture was partitioned between water and DCM and the organic phase was separated and the aqueous phase extracted with further DCM (2×). The aqueous phase was acidified to pH<4.5 using aqueous citric acid solution and the resulting precipitated gum was extracted into EtOAc (3×). The combined organic phases were washed with saturated sodium chloride solution and passed through a phase separation cartridge and the filtrate was concentrated in vacuo to afford the title compound (2.85 g, 94%) as a yellow sticky solid. $\delta_H$ (400 MHz, DMSO-$d_6$) 11.35 (s, 1H), 3.69 (br. s, J 6.2 Hz, 2H), 2.77 (t, J 6.4 Hz, 3H), 1.96-1.76 (m, 3H), 1.49 (s, 9H), 0.99-0.83 (m, 4H). LCMS [M+H]$^+$ 367.2, RT 1.088 minutes (Method 4). LCMS [M−H]$^-$ 365.0, RT 2.351 minutes, 100.0% purity (Method 2).

Intermediate 11

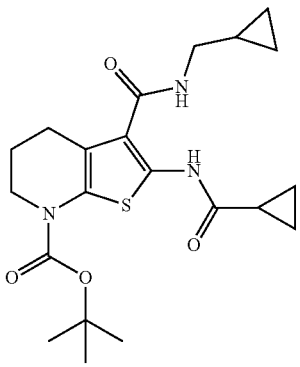 [SMILES: CC(C)(C)OC(=O)N1CCCc2c1sc(NC(=O)C1CC1)c2C(=O)NCC1CC1]

tert-Butyl 2-(cyclopropanecarbonylamino)-3-(cyclo-propylmethylcarbamoyl)-5,6-dihydro-4H-thieno[2,3-b]pyridine-7-carboxylate Intermediate 10 (1.43 g, 3.89 mmol) was suspended in DCM (50 mL) and cyclopropylmethylamine [2516-47-4] (0.42 g, 5.83 mmol) and EDCl (0.92 g, 4.67 mmol) were added and the reaction was stirred at r.t. for 16 h. The reaction mixture was partitioned between water and saturated sodium chloride solution, passed through a phase separator and the filtrate was concentrated in vacuo to yield the crude reaction mixture which was purified by flash column chromatography on silica (gradient elution with 20-80% EtOAc/isohexane) to afford the title compound (434 mg, 27%) as a pale yellow gum. $\delta_H$ (400 MHz, DMSO-$d_6$) 10.76 (s, 1H), 7.44 (s, 1H), 3.46 (s, 2H), 2.90 (t, J 6.2 Hz, 2H), 2.53-2.37 (m, 2H), 1.74-1.53 (m, 3H), 1.26 (s, 9H), 0.90-0.72 (m, 1H), 0.72-0.52 (m, 4H), 0.26-0.13 (m, 2H), 0.06--0.06 (m, 2H). LCMS $[M+H]^+$ 420.8, $[M+Na]^+$ 442.8, RT 2.645 minutes, 100.0% purity (Method 3).

Intermediate 12

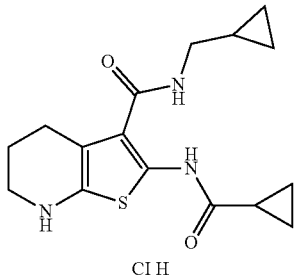 [SMILES: O=C(NCC1CC1)c1c(NC(=O)C2CC2)sc2c1CCCN2 ; "CI H"]

2-(Cyclopropanecarbonylamino)-N-(cyclopropylm-ethyl)-4,5,6,7-tetrahydrothieno[2,3-b]pyridine-3-carboxamide; hydrochloride Intermediate 11 (0.43 g, 1.03 mmol) was dissolved in 4 N hydrochloric acid solution in 1,4-dioxane (20 mL) and the reaction mixture was stirred at r.t. for 3 h, before concentrating in vacuo to afford the title compound (370 mg, 101%) as an off white solid. $\delta_H$ (400 MHz, DMSO-$d_6$) 10.98 (s, 1H), 7.41 (s, 1H), 3.05-2.94 (m, 2H), 2.90 (t, J 6.2 Hz, 2H), 2.43 (t, J 6.2 Hz, 2H), 1.73-1.53 (m, 3H), 0.86-0.69 (m, 1H), 0.68-0.51 (m, 4H), 0.25-0.16 (m, 2H), 0.05--0.06 (m, 2H), NH$_2$ not observed.

Intermediate 13

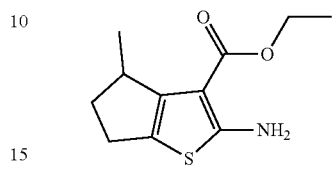

Ethyl 2-amino-4-methyl-5,6-dihydro-4H-cyclopenta[b]thiophene-3-carboxylate

To a solution of 2-methylcyclopentanone [1120-72-5] (3.40 g, 34.6 mmol) in EtOH (10 mL) was added ethyl cyanoacetate [105-56-6] (4.31 g, 38.1 mmol), sulphur [7704-34-9] (1.22 g, 38.0 mmol) and diethylamine (3.82 g, 52.0 mmol). The reaction mixture was stirred at r.t. for 18 h and the mixture concentrated in vacuo to give the crude product which was purified by flash column chromatography on silica (gradient elution with 0-15% EtOAc in hexane) to afford the title compound (3.33 g, 43%) as a yellow solid. $\delta_H$ (400 MHz, DMSO-$d_6$) 7.21 (s, 2H), 4.26-4.04 (m, 2H), 3.14 (ddt, J 8.5, 6.6, 3.3 Hz, 1H), 2.72 (dtd, J 14.3, 8.1, 2.3 Hz, 1H), 2.55 (dd, J 9.3, 2.1 Hz, 1H), 2.44 (ddt, J 12.4, 9.3, 8.1 Hz, 1H), 1.85 (ddt, J 12.2, 8.1, 1.8 Hz, 1H), 1.25 (t, J 7.1 Hz, 3H), 1.09 (d, J 6.8 Hz, 3H).

Intermediate 14

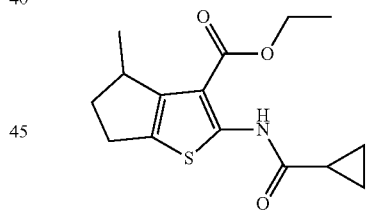

Ethyl 2-(cyclopropanecarbonylamino)-4-methyl-5,6-dihydro-4H-cyclopenta[b]thiophene-3-carboxylate To a solution of intermediate 13 (1 g, 4.44 mmol) and triethylamine (1.0 mL, 7.18 mmol) in DCM (10 mL) at 0° C. was added cyclopropanecarbonyl chloride [4023-34-1] (0.6 mL, 6.61 mmol). The reaction mixture was stirred at 0° C. for 2 h, before diluting with DCM (20 mL). 1 M Aqueous hydrochloric acid solution (20 mL) was added and the aqueous phase was separated and extracted with DCM (2×10 mL) and washed with water (10 mL). The organic phases were combined, dried (MgSO$_4$), filtered and concentrated in vacuo to afford the title compound (1.45 g, 89%) as a brown oil which was utilised without further purification. $\delta_H$ (500 MHz, Chloroform-d) 11.27 (s, 1H), 4.42-4.35 (m, 1H), 4.31 (dq, J 10.8, 7.2 Hz, 1H), 3.39-3.28 (m, 1H), 2.91 (dtd, J 15.2, 8.7, 1.8 Hz, 1H), 2.72 (ddd, J 15.1, 9.4, 2.0 Hz, 1H), 2.58 (dq, J 12.6, 8.8 Hz, 1H), 2.00 (ddt, J 12.3, 7.9, 1.9 Hz, 1H), 1.66 (ddd, J 12.5, 7.9, 4.5 Hz, 1H), 1.39 (t, J 7.1 Hz, 3H), 1.16 (d, J 6.8 Hz, 3H), 1.13 (q, J 3.7, 3.2 Hz, 2H), 0.92 (dq, J 6.9, 3.7 Hz, 2H). 80% purity.

Intermediate 15

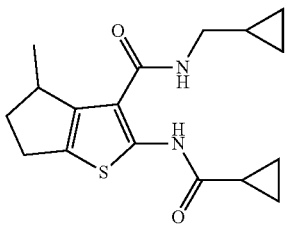 [SMILES: CC1CCc2sc(NC(=O)C3CC3)c(C(=O)NCC3CC3)c21]

2-(Cyclopropanecarbonylamino)-N-(cyclopropylmethyl)-4-methyl-5,6-dihydro-4H-cyclopenta[b]thiophene-3-carboxamide Intermediate 14 (80% purity, 1.31 g, 3.57 mmol) was dissolved in a solution of MeOH (10 mL) and 2M aqueous NaOH solution (3.5 mL) was added. The reaction mixture was heated to reflux for 2 h and the reaction was cooled to r.t. and concentrated in vacuo. The reaction mixture was acidified with 1 M aqueous hydrochloric acid solution and the mixture was extracted with EtOAc (2×20 mL). The combined organic phases were washed with water (10 mL), dried (MgSO$_4$), filtered and concentrated in vacuo to afford the acid: 2-(cyclopropanecarbonylamino)-4-methyl-5,6-dihydro-4H-cyclopenta[b]thiophene-3-carboxylic acid (1 g, 74%, 70% purity) which was utilised without further purification.

EDCl (180 mg, 0.94 mmol) was added to a solution of 2-(cyclopropanecarbonylamino)-4-methyl-5,6-dihydro-4H-cyclopenta[b]thiophene-3-carboxylic acid (200 mg, 0.75 mmol) and 1-cyclopropylmethanamine [2516-47-4] (100 µL, 1.15 mmol) in DCM (5 mL). The reaction mixture was stirred at r.t. for 4 h before diluting with DCM (10 mL) and washing with 1 M aqueous hydrochloric acid solution (10 mL). The organic phase was separated, dried (MgSO$_4$), filtered and concentrated in vacuo to give the crude product which was purified by flash column chromatography on silica (gradient elution with 0-30% EtOAc/heptane) to afford the title compound (40 mg, 16%) as a light brown solid. LCMS [M+H]$^+$ 319.1, RT 4.58 minutes (Method 5).

Intermediate 16

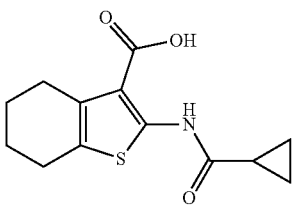 [SMILES: O=C(O)c1c(NC(=O)C2CC2)sc2c1CCCC2]

2-(Cyclopropanecarbonylamino)-4,5,6,7-tetrahydrobenzothiophene-3-carboxylic acid Cyclopropanecarbonyl chloride [4023-34-1] (5.44 g, 51.0 mmol) was added to a solution of 2-amino-4,5,6,7-tetrahydro-benzo[B]thiophene-3-carboxylic acid methyl ester [108354-78-5] (10.0 g, 46.4 mmol) and DIPEA (15.0 g, 116 mmol) in DCM (100 mL) and the reaction was stirred at r.t. overnight. The reaction mixture was washed with water and brine, passed through a phase separator and evaporated in vacuo to yield a yellow sticky solid which was dissolved in 1,4-dioxane (100 mL). A solution of lithium hydroxide monohydrate [1310-66-3] (2.92 g, 69.6 mmol) in water (30 mL) was added and the mixture was heated at 70° C. for ~3 h. The reaction mixture was cooled to r.t. and was left to stand overnight and the 1,4-dioxane was removed in vacuo. The aqueous residue was diluted with water and washed with DCM (2×). The aqueous phase was acidified to pH<4 by addition of concentrated hydrochloric acid. The resulting precipitate was filtered, washed with water (3×) and was allowed to air dry to afford the title compound (12.1 g, 99%) as a cream solid. δ$_H$ (400 MHz, DMSO-d$_6$) 13.04 (s, 1H), 11.46 (s, 1H), 2.81-2.63 (m, 2H), 2.63-2.54 (m, 2H), 1.95 (h, J 5.6 Hz, 1H), 1.80-1.60 (m, 4H), 1.02-0.76 (m, 4H).

Intermediate 17

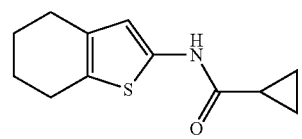 [SMILES: O=C(Nc1cc2c(s1)CCCC2)C1CC1]

N-(4,5,6,7-Tetrahydrobenzothiophen-2-yl)cyclopropanecarboxamide

A suspension of intermediate 16 (500 mg, 1.89 mmol) in toluene (5 mL) was heated at 180° C. in a microwave for 8 h. The solvent was removed in vacuo and the residues were dissolved in hot EtOAc (20 mL). The mixture was filtered to afford the title compound (403 mg, 97%). δ$_H$ (400 MHz, DMSO-d$_6$) 11.05 (s, 1H), 6.29 (s, 1H), 2.57 (t, J 5.8 Hz, 2H), 2.45 (t, J 5.9 Hz, 2H), 1.82-1.54 (m, 5H), 0.79 (d, J 6.2 Hz, 4H).

Intermediate 18

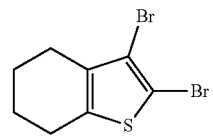 [SMILES: Brc1sc2c(c1Br)CCCC2]

2,3-Dibromo-4,5,6,7-tetrahydrobenzothiophene

To a stirred solution of 4,5,6,7-tetrahydro-1-benzothiophene [13129-17-4] (3 g, 21.7 mmoL) in acetic acid (15 mL) and chloroform (15 mL) cooled to −5° C. was added N-bromosuccinimide [128-08-5] (8.5 g, 47.8 mmoL) portionwise over 1.5 h and the resulting yellow/orange solution was stirred at −5° C. The reaction mixture was quenched with 10% aqueous sodium sulphite (10 mL) and extracted with DCM (3×15 mL). The combined organic phases were washed with saturated aqueous sodium hydrogen carbonate solution (15 mL), brine (15 mL) and dried (MgSO$_4$) and filtered. The crude material was purified by filtration through silica (gradient elution with 0 to 10% DCM in heptane) to afford the title compound (260 mg, 64%) as a colourless oil. $\delta_H$ (250 MHz, Chloroform-d) 2.79-2.59 (m, 2H), 2.57-2.42 (m, 2H), 1.91-1.70 (m, 4H).

Intermediate 19

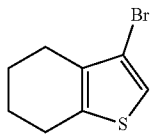

3-Bromo-4,5,6,7-tetrahydrobenzothiophene

To a stirred solution of intermediate 18 (3.9 g, 13.2 mmoL) in Et$_2$O (100 mL) cooled to −78° C. was added n-butyllithium 1.6 M in hexanes (17.3 mL, 27.7 mmoL) dropwise over 20 minutes and the resulting solution was stirred at this temperature for 1.5 h. Water (30 mL) was added, the cooling bath was removed and the reaction mixture was warmed to r.t. over a couple of hours. EtOAc (30 mL) was added, the layers were separated and the aqueous phase was extracted with further EtOAc (40 mL). The combined organic phases were washed with brine (20 mL), dried (MgSO$_4$), filtered and concentrated in vacuo to afford the crude material (2.8 g) as an orange oil which was purified by flash column chromatography on silica (gradient elution with of 0 to 10% DCM in heptane) to afford the title compound (885 mg, 31%). $\delta_H$ (250 MHz, Chloroform-d) 7.03 (s, 1H), 2.81-2.69 (m, 2H), 2.57-2.46 (m, 2H), 1.92-1.73 (m, 4H).

Intermediate 20

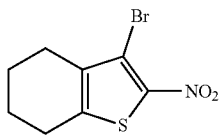 [SMILES: O=[N+]([O-])c1sc2c(c1Br)CCCC2]

3-Bromo-2-nitro-4,5,6,7-tetrahydrobenzothiophene

To a solution of intermediate 19 (660 mg, 3 mmoL) in DCM (15 mL) cooled to −5° C. was added nitronium tetrafluoroborate [13826-86-3] (460 mg, 3.34 mmoL) in three portions (200 mg+200 mg+60 mg at 5 minutes intervals). After 1 h the mixture was poured onto ice, diluted with DCM and warmed to r.t. The layers were separated and the aqueous phase was extracted with DCM (10 mL). The combined organic phases were washed with brine and dried (MgSO$_4$) and filtered. The crude product was combined with the crude material from another experiment (starting material intermediate 17, 200 mg, 0.92 mmoL) concentrated in vacuo and purified by flash column chromatography on silica (gradient elution with 0 to 50% DCM in heptane) to afford the title compound (260 mg, 25%) as a red solid. $\delta_H$ (500 MHz, Chloroform-d) 2.87-2.68 (m, 2H), 2.62-2.49 (m, 2H), 1.96-1.74 (m, 4H).

Intermediate 21

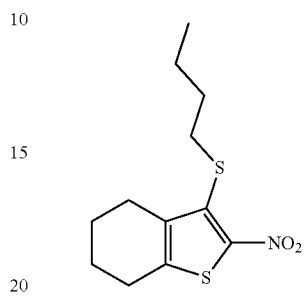

3-Butylsulfanyl-2-nitro-4,5,6,7-tetrahydrobenzothiophene

To a solution of intermediate 20 (260 mg, 0.99 mmoL) in THF (10 mL) and water (5 mL) was added potassium carbonate (150 mg, 1.01 mmoL) followed by dropwise addition of a solution of butane-1-thiol [109-79-5] (0.22 mL, 1.98 mmoL) in THF (3 mL) and the resulting mixture was stirred at r.t. After 2 h further butane-1-thiol [109-79-5] (0.12 mL, 1.01 mmoL) was added and stirring was continued for 1 h. Further butane-1-thiol [109-79-5] (0.12 mL, 1.01 mmoL) was added and stirring was continued overnight. The reaction mixture was partitioned between water (20 mL) and EtOAc (40 mL), the layers were separated and the aqueous phase was extracted with EtOAc (2×30 mL). The combined organic phases were washed with brine (20 mL), dried (MgSO$_4$), filtered and concentrated in vacuo. The crude material was purified by flash column chromatography on silica (gradient elution with 0 to 100% DCM in heptane) to afford the title compound (212 mg, 79%) as a bright yellow solid. $\delta_H$ (250 MHz, Chloroform-d) 3.01 (t, J 7.2 Hz, 2H), 2.86-2.71 (m, 2H), 2.68-2.54 (m, 2H), 1.91-1.80 (m, 4H), 1.60-1.32 (m, 4H, part. obscured by water peak), 0.90 (t, J 7.2 Hz, 3H).

Intermediate 22

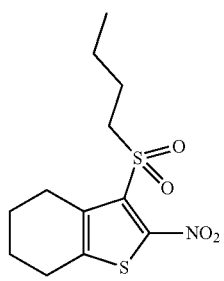 [SMILES: CCCCS(=O)(=O)c1c([N+](=O)[O-])sc2c1CCCC2]

3-Butylsulfonyl-2-nitro-4,5,6,7-tetrahydrobenzothiophene

To a stirred solution of intermediate 21 (195 mg, 0.72 mmoL) in DCM (8 mL) was added a solution of mCPBA (70%, 266 mg, 1.08 mmoL) in DCM (5 mL) dropwise at r.t. The reaction mixture was stirred for 1 h and combined with an additional experiment (15 mg, 0.055 mmol). The reaction was quenched with saturated aqueous sodium sulfite (15 mL) and the layers were separated and the aqueous phase was extracted with DCM (2×30 mL). The combined organic layers were washed with 0.5 M aqueous potassium carbonate solution (30 mL), brine (20 mL), dried (MgSO$_4$), filtered and concentrated in vacuo. The crude material was purified by flash column chromatography on silica (gradient elution with 0 to 100% DCM in heptane) to afford the title compound (107 mg, 51%). $\delta_H$ (250 MHz, Chloroform-d) 3.69-3.47 (m, 2H), 2.95 (t, J 5.4 Hz, 2H), 2.87-2.73 (m, 2H), 1.98-1.71 (m, 6H), 1.59-1.34 (m, 2H, part. obscured by water peak), 0.96 (t, J 7.3 Hz, 3H).

Intermediate 23

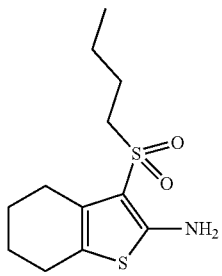 [SMILES: CCCCS(=O)(=O)c1c(N)sc2c1CCCC2]

3-Butylsulfonyl-4,5,6,7-tetrahydrobenzothiophen-2-amine

To a solution of intermediate 22 (35 mg, 0.12 mmoL) in EtOH (3 mL) was added 10% Pd on charcoal (50% wet, 25 mg, 0.012 mmoL) and the mixture was hydrogenated at r.t. and atmospheric pressure. The reaction was left under hydrogen overnight and was filtered through a pad of celite, washing with EtOAc. The reaction mixture was concentrated in vacuo to afford the title compound (32 mg, 93%) as a yellow film. LCMS [M+H]$^+$ 274, RT 1.37 minutes (Method 6).

Intermediate 24

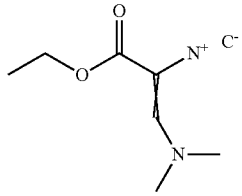

Ethyl 3-(dimethylamino)-2-isocyanoprop-2-enoate

To a brown solution of ethyl isocyanoacetate [2999-46-4] (1 g, 8.84 mmol) in dry ethanol (10 mL) at 0° C. (ice bath) under N$_2$ was added DMF-DMA (1.53 mL, 11.49 mmol) dropwise. Reaction was allowed to warm to room temperature and stirred for 24 hours. The reaction was concentrated in vacuo and the material was purified by flash chromatography on silica (elution gradient using 0-60% ethyl acetate in heptane) to afford the title compound (780 mg, 52%) as a yellow oil which solidified on cooling. $\delta_H$ (500 MHz, Chloroform-d) δ 7.18 (s, 1H), 4.22 (q, J 7.1 Hz, 2H), 3.23 (s, 6H), 1.30 (t, J 7.1 Hz, 3H).

Intermediate 25

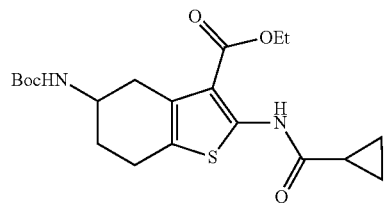 [SMILES: CCOC(=O)c1c(NC(=O)C2CC2)sc2c1CC(NC(=O)OC(C)(C)C)CC2]

Ethyl 5-(tert-butoxycarbonylamino)-2-(cyclopropanecarbonylamino)-4,5,6,7-tetrahydrobenzothiophene-3-carboxylate To a stirred solution of intermediate 102a (15 g, 44.1 mmol) in DCM (250 mL) and triethylamine (12.3 mL, 88.2 mmol) was added cyclopropanecarbonyl chloride [4023-34-1] (6.9 g, 66.2 mmol) dropwise at 0° C. The reaction mixture was stirred at r.t. for 16 h before quenching with 0.5 N aqueous hydrochloric acid solution. The organic phase was separated, washed with brine, dried (Na$_2$SO$_4$), filtered and concentrated in vacuo to give the crude product which was triturated with Et$_2$O and pentane to afford the title compound (14 g, 78%). $\delta_H$ (400 MHz, DMSO-d$_6$) δ 11.17 (s, 1H), 6.92 (d, J 7.3 Hz, 1H), 4.29 (q, J 7.1 Hz, 2H), 3.62 (s, 1H), 3.04 (dd, J 17.0, 4.3 Hz, 1H), 2.74-2.66 (m, 2H), 2.46 (d, J 9.3 Hz, 1H), 2.06-1.88 (m, 2H), 1.68-1.58 (m, 1H), 1.40 (s, 9H), 1.31 (t, J 7.1 Hz, 3H), 0.97-0.84 (m, 4H). LCMS [M-Boc+H]$^+$309.8, RT 2.831 minutes, 96.2% purity (Method 2).

Intermediate 26

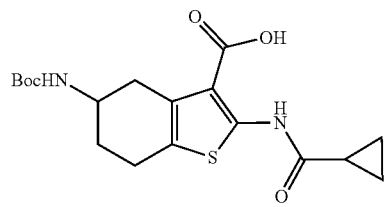

5-(tert-Butoxycarbonylamino)-2-(cyclopropanecarbonylamino)-4,5,6,7-tetrahydrobenzothiophene-3-carboxylic acid To a stirred solution of intermediate 25 (14 g, 34.3 mmol) in 1,4-dioxane (100 mL) and water (100 mL) was added lithium hydroxide (1.64 g, 68.6 mmol) and the reaction mixture was heated at 100° C. for 3 h. The reaction mixture was acidified with 1N hydrochloric acid solution to pH 6, stirred for 15 minutes and filtered. The residue obtained was dried in vacuo to afford the title compound (12 g, 91%). $\delta_H$ (400 MHz, Chloroform-d) 11.31 (s, 1H), 5.80 (s, 1H), 4.70 (s, 1H), 3.99 (s, 1H), 3.22-3.18 (m, 2H), 2.71 (s, 2H), 2.02-2.00 (m, 1H), 1.78-1.67 (m, 2H), 1.45 (s, 9H), 1.18-1.12 (m, 2H), 0.96-0.92 (m, 2H). LCMS [M−H]⁻ 379.0, RT 1.267 minutes, 77.3% purity (Method 7).

Intermediate 27

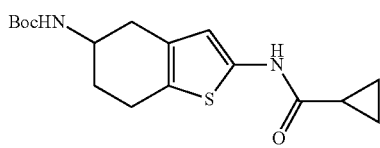 [SMILES: CC(C)(C)OC(=O)NC1CCc2sc(NC(=O)C3CC3)cc2C1]

tert-Butyl N-[2-(cyclopropanecarbonylamino)-4,5,6,7-tetrahydrobenzothiophen-5-yl]carbamate To a suspension of intermediate 26 (1.2 g, 2.71 mmoL, 86% purity) in quinoline [91-22-5] (10 mL) was added copper powder [7440-50-8] (259 mg, 4.0 mmol). The reaction mixture was heated to 150° C. for 1 h in the microwave before diluting with DCM (60 mL) and water (60 mL). The organic phase was washed with 0.75M aqueous hydrochloric acid solution, saturated sodium hydrogen carbonate solution and brine. The organic phase was separated, dried (Na₂SO₄), filtered and concentrated in vacuo. The crude residue was purified by flash column chromatography on silica (gradient elution with 5% to 50% EtOAc in heptane) to afford the 5-substituted title compound (640 mg, 50%) as an off-white solid mixed with the 7-regio isomer (carried through previous synthetic steps, originating from the synthesis of Intermediates 102 and 102a). LCMS [M+H]⁺ 337, RT 1.28 minutes, 71% (5-regio isomer), [M+Na]⁺359.15, [M-tBu+H]⁺280.95, RT 1.38 minutes, 28% (7-regio isomer) (Method 6).

Intermediate 28

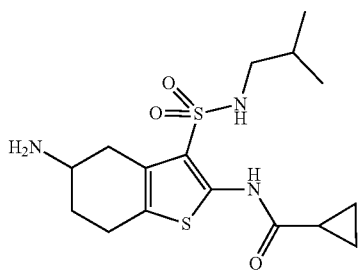 [SMILES: CC(C)CNS(=O)(=O)c1c(NC(=O)C2CC2)sc2c1CC(N)CC2]

N-[5-Amino-3-(isobutylsulfamoyl)-4,5,6,7-tetrahydrobenzothiophen-2-yl]cyclopropanecarboxamide To a suspension of intermediate 27 (1.1 g, 3.3 mmol) in MeCN (9 mL) was added chlorosulfonic acid [7790-94-5] (1 mL, 14.7 mmol). The reaction mixture was stirred at 70° C. for 1 h 40 minutes before cooling to 0° C. To chloroform (5 mL) was added isobutylamine [78-81-9] (3 mL, 29.5 mmol) and triethylamine (2 mL, 14.2 mmol) and the mixture was cooled to 0° C. The two solutions were added together and the mixture was stirred at 30° C. for 30 minutes. To the reaction mixture was added water (25 mL) and the mixture was extracted with Et₂O (1×50 ml, 2×25 ml). The organic phases were combined, dried (MgSO₄), filtered and concentrated in vacuo to yield the crude product (691 mg) as a yellow oil. The aqueous layer was extracted with EtOAc to afford further crude product (0.58 g) as a yellow oil. The crude products were combined and purified by flash column chromatography on silica (gradient elution with 100% DCM to 80/20/2 DCM/MeOH/NH₄OH) to afford a dark solid (1.05 g) which was solubilised in DCM (4 mL) and treated with 60 ml of 80/20 isopropanol/EtOAc. Insoluble residues were removed and the organic phases combined and concentrated in vacuo to afford the title compound (0.67 g, 55%). LCMS [M+H]⁺ 372.13, [M−H]⁻ 370.13, RT 2.52 minutes (Method 9).

Intermediate 29

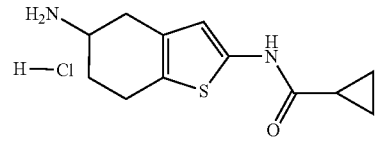

N-(5-Amino-4,5,6,7-tetrahydrobenzothiophen-2-yl)cyclopropanecarboxamide; hydrochloride Intermediate 27 (640 mg, 1.35 mmol) was dissolved in 1,4-dioxane (5 mL) and 4M hydrochloric acid in 1,4-dioxane (10 mL, 40.5 mmol) was added. The reaction mixture was stirred at r.t. for 3 h. The reaction was concentrated in vacuo and the crude material (550 mg) used without further purification. LCMS [M+H]⁺ 236.95, RT 0.66 minutes, purity 31% (Method 6).

Intermediate 30

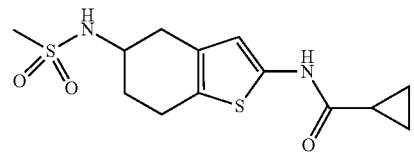 [SMILES: CS(=O)(=O)NC1CCc2sc(NC(=O)C3CC3)cc2C1]

N-[5-(Methanesulfonamido)-4,5,6,7-tetrahydrobenzothiophen-2-yl]cyclopropanecarboxamide Intermediate 29 (550 mg, 2.0 mmol) was dissolved in DCM (5 mL) and DIPEA (0.7 mL, 4.03 mmol) and methanesulfonyl chloride [124-63-0] (0.23 ml, 3.0 mmol) were added. The reaction mixture was stirred at r.t. for 5 h before diluting with DCM (50 mL) and water (50 mL). The organic phase was separated, dried (Na₂SO₄), filtered and concentrated in vacuo. The residue obtained was purified by flash column chromatography on silica (gradient elution with 12% to 100% EtOAc in heptane) to afford the title compound (270 mg) as an off-white solid. $\delta_H$ (500 MHz, CD₃OD) 6.33 (s, 1H), 3.72-3.63 (m, 1H), 2.99 (s, 3H), 2.92 (dd, J 15.9, 5.2 Hz, 1H), 2.83-2.76 (m, 2H), 2.49 (dd, J 15.9, 8.7 Hz, 1H), 2.18-2.10 (m, 1H), 1.88-1.79 (m, 1H), 1.74-1.66 (m, 1H), 0.96-0.91 (m, 2H), 0.86 (m, 2H). 90% purity.

Intermediate 31

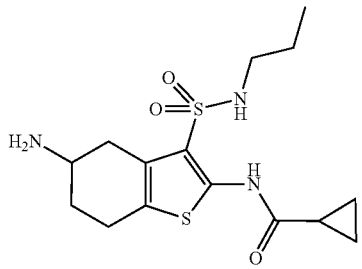 [SMILES: CCCNS(=O)(=O)c1c(NC(=O)C2CC2)sc2c1CC(N)CC2]

N-[5-Amino-3-(propylsulfamoyl)-4,5,6,7-tetrahydrobenzothiophen-2-yl]cyclopropanecarboxamide To a suspension of intermediate 29 (1.21 g, 3.60 mmol) in MeCN (15 mL) was added chlorosulfonic acid [7790-94-5] (1.85 mL, 27.3 mmol). The reaction mixture was stirred at 70° C. for 1 h before cooling to 0° C. This solution was added slowly to a cooled solution of chloroform (15 mL), n-propylamine [107-10-8] (5 mL, 60.21 mmol) and triethylamine (10 mL, 71.0 mmol) and the reaction mixture was stirred at r.t. overnight. To the reaction mixture was added saturated sodium hydrogen carbonate solution (200 mL) and the aqueous phase was extracted with Et₂O (1×100 mL, 2×50 mL). The organic phases were combined and washed with water (2×50 mL), dried (MgSO₄), filtered and concentrated in vacuo to yield the crude material (502 mg) as a sticky yellow oil. The combined aqueous phases were extracted with EtOAc (2×100 mL) and the organic phases were combined, dried (MgSO₄), filtered and concentrated in vacuo to yield a dark yellow oil which was combined with the first batch of crude material. The combined crude material was purified by flash column chromatography on silica (gradient elution with DCM/MeOH/NH₄OH 97.5/2.5/0.25 to 80/20/2) to afford the title compound (230 mg, 19%). LCMS [M+H]⁺ 358.15, [M−H]⁻ 356.12, RT 1.84 minutes (Method 8).

Intermediate 32

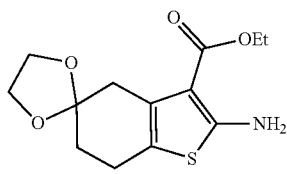 [SMILES: CCOC(=O)c1c(N)sc2c1CC1(CC2)OCCO1]

Ethyl 2'-aminospiro[1,3-dioxolane-2,5'-6,7-dihydro-4H-benzothiophene]-3'-carboxylate To a mixture of 1,4-dioxaspiro[4.5]decan-7-one [4969-01-1] (5 g, 32.0 mmol), sulphur [7664-93-9] (1.23 g, 38.4 mmol) and ethyl cyanoacetate [105-56-6] (4.34 g, 38.4 mmol) in EtOH (50 mL) was added triethylamine (8.92 ml, 64.0 mmol) and the reaction mixture was stirred at r.t. for 5 days before concentrating in vacuo. To the crude product was added water and the aqueous phase was extracted with EtOAc. The combined organic phases were washed with brine, dried (MgSO₄), filtered and concentrated in vacuo to yield a crude residue which was purified by flash column chromatography on silica (gradient elution with 100% DCM followed by 5% to 50% EtOAc in heptane) to afford the title compound (5.47 g, 59%) as yellow gum. δ_H (500 MHz, CD₃OD) 4.23 (q, J 7.1 Hz, 2H), 4.05-3.96 (m, 4H), 2.87 (s, 2H), 2.63 (tt, J 6.5, 1.6 Hz, 2H), 1.89 (t, J 6.5 Hz, 2H), 1.32 (t, J 7.1 Hz, 3H). LCMS [M+H]⁺ 283.95, RT 1.19 minutes (Method 6).

Intermediate 33

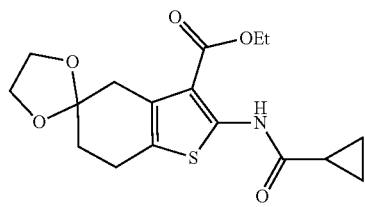 [SMILES: CCOC(=O)c1c(NC(=O)C2CC2)sc2c1CC1(CC2)OCCO1]

Ethyl 2'-(cyclopropanecarbonylamino)spiro[1,3-dioxolane-2,5'-6,7-dihydro-4H-benzothiophene]-3'-carboxylate To a solution of intermediate 32 (5.47 g, 19.3 mmol) and DIPEA (6.7 mL, 38.6 mmol) in DCM (200 mL) at 0° C. was added cyclopropanecarbonyl chloride [4023-34-1] (2.6 ml, 28.9 mmol). The reaction mixture was stirred at r.t. for 2 h before diluting with DCM (200 mL). Water (200 mL) was added and the phases were separated. The aqueous phase was extracted with DCM (2×100 mL) and washed 0.5 M aqueous hydrochloric acid solution (100 mL), saturated sodium hydrogen carbonate solution (100 mL) and brine. The organic phase was dried (MgSO₄), filtered and concentrated in vacuo to yield the crude product, a pale yellow solid which was purified by flash column chromatography on silica (gradient elution with 5% to 50% EtOAc in heptane) to afford the title compound (6.5 g, 96%) as a pale yellow solid. LCMS [M+H]⁺ 352.05, RT 1.38 minutes (Method 6).

Intermediate 34

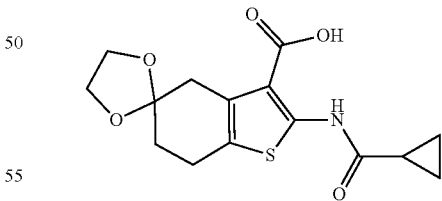

2'-(Cyclopropanecarbonylamino)spiro[1,3-dioxolane-2,5'-6,7-dihydro-4H-benzothiophene]-3'-carboxylic acid To a suspension of intermediate 33 (6.5 g, 18.5 mmoL) in 1,4-dioxane (120 mL) was added 2M lithium hydroxide monohydrate solution [1310-66-3] (18.5 mL, 37.0 mmoL) and the reaction mixture was heated to 90° C. for 2 h. The mixture was concentrated in vacuo and the residue was diluted with water (20 mL). The solution was acidified to pH 4-5 with 0.2M aqueous hydrochloric acid solution and the material was collected by filtration, washed with water and dried in vacuo to afford the title compound (5 g, 84%) as a brown solid. δ$_H$ (500 MHz, CD$_3$OD) 4.03-3.99 (m, 4H), 2.99 (s, 2H), 2.80 (t, J 6.5 Hz, 2H), 1.93 (t, J 6.5 Hz, 2H), 1.85-1.77 (m, 1H), 1.05-0.94 (m, 4H). LCMS [M+H] 323.95, RT 1.14 minutes (Method 6).

Intermediate 35

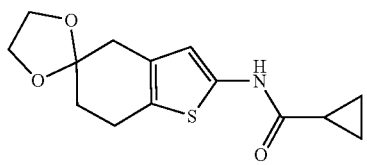 [SMILES: O=C(Nc1cc2c(s1)CCC1(C2)OCCO1)C1CC1]

N-Spiro[1,3-dioxolane-2,5'-6,7-dihydro-4H-benzothiophene]-2'-ylcyclopropanecarboxamide To a suspension of intermediate 34 (1.6 g, 4.94 mmoL) in quinolone [91-22-5] (15 mL) was added copper powder [7440-50-8] (472 mg, 7.42 mmol) and the mixture was heated to 150° C. for 1 h in the microwave. The reaction mixture was diluted with DCM (100 mL) and water (100 mL). The organic phase was washed with 0.75M aqueous hydrochloric acid solution, saturated sodium hydrogen carbonate solution and brine. The organic phase was dried (Na$_2$SO$_4$), filtered and concentrated in vacuo. The residue obtained was purified by flash column chromatography on silica (gradient elution with 5% to 50% EtOAc in heptane) to afford the title compound (1.1 g, 80%) as an off-white solid. LCMS [M+H]+ 279.95, RT 1.10 minutes (Method 6).

Intermediate 36

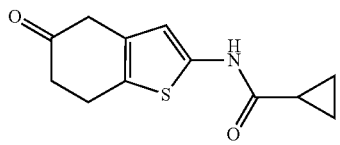 [SMILES: O=C1CCc2sc(NC(=O)C3CC3)cc2C1]

N-(5-Oxo-6,7-dihydro-4H-benzothiophen-2-yl)cyclopropanecarboxamide

To intermediate 35 (2 g, 7.15 mmol) dissolved in THF (80 mL) was added 1M aqueous hydrochloric acid solution (36 mL). The reaction mixture was heated at 50° C. for 5 h whilst stirring under nitrogen. After cooling to r.t. the reaction mixture was basified with saturated sodium hydrogen carbonate solution and diluted with EtOAc. The organic phase was separated, dried (Na$_2$SO$_4$), filtered and concentrated in vacuo to yield a pale yellow solid which was triturated with DCM/Et$_2$O to afford the title compound (1.42 g, 78%) as a pale yellow solid. LCMS [M+H]$^+$ 235.90, RT 1.01 minutes (Method 6).

Intermediate 37

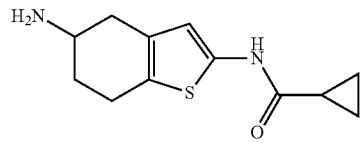 [SMILES: NC1CCc2sc(NC(=O)C3CC3)cc2C1]

N-(5-Amino-4,5,6,7-tetrahydrobenzothiophen-2-yl)cyclopropanecarboxamide

To a mixture of intermediate 36 (1.42 g, 6.0 mmol), ammonium acetate (4.65 g, 60.3 mmol) and Na$_2$SO$_4$ (1.5 g) in MeOH (80 mL) was added sodium triacetoxyborohydride [56553-60-7] (2.55 g, 12.07 mmol). The reaction mixture was stirred at r.t. for 5 h. The mixture was filtered and the filtrate was diluted with EtOAc and washed with saturated sodium bicarbonate solution. The aqueous phase was extracted with isopropanol/chloroform (1:1). The organic phases were dried (MgSO$_4$), filtered and concentrated in vacuo to give the crude residue which was purified by flash column chromatography on silica (gradient elution with 1% to 70% MeOH in DCM) to afford the title compound (270 mg, 19%) as a light brown solid. LCMS [M+H]$^+$ 236.95 (Method 6).

Intermediate 38

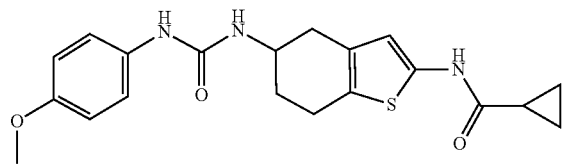 [SMILES: COc1ccc(NC(=O)NC2CCc3sc(NC(=O)C4CC4)cc3C2)cc1]

N-[5-[(4-Methoxyphenyl)carbamoylamino]-4,5,6,7-tetrahydrobenzothiophen-2-yl]cyclopropanecarboxamide To a solution of intermediate 37 (130 mg, 0.55 mmol) in DCM (7 mL) was added 1-isocyanato-4-methoxybenzene [5416-93-3] (78.4 μL, 0.60 mmol). The solution was stirred at r.t. for 30 minutes and the reaction mixture was filtered and washed with DCM to afford the title compound (160 mg, 72%) as an off white solid. LCMS [M+H]$^+$ 386.25, RT 1.17 minutes (Method 6).

Intermediates 39 and 40

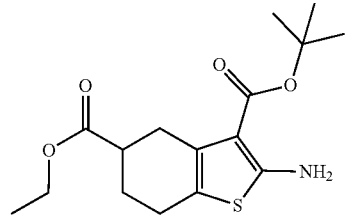

-continued

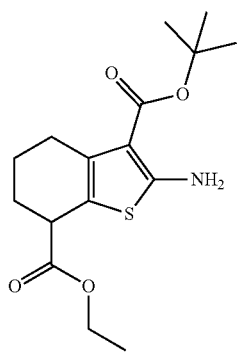

Intermediate 39

O3-tert-Butyl O5-ethyl 2-amino-4,5,6,7-tetrahydrobenzothiophene-3,5-dicarboxylate Intermediate 40

O3-tert-Butyl O7-ethyl 2-amino-4,5,6,7-tetrahydrobenzothiophene-3,7-dicarboxylate To a mixture of ethyl 3-oxocyclohexanecarboxylate [17159-79-4] (2 g, 11.75 mmol), sulfur (0.45 g, 14.1 mmol) and tert-butyl cyanoacetate [1116-98-9] (2.15 g, 15 mmol) in EtOH (20 mL) was added triethylamine (3.27 ml, 2.35 mmol). The reaction mixture was stirred at r.t. for 16 h before concentrating in vacuo. Water was added and the solution was extracted with EtOAc. The organic phases were combined, washed with brine, dried (MgSO$_4$), filtered and concentrated in vacuo. The crude residue was purified by flash column chromatography on silica (gradient elution with 5% to 40% EtOAc in heptane) to afford a 79:21 ratio of regioisomers of title compound intermediate 39 and title compound intermediate 40 (2.84 g, 74%). LCMS [M+H]$^+$ 326.00, RT 1.49 and 1.52 minutes (Method 6).

Intermediates 41 and 42

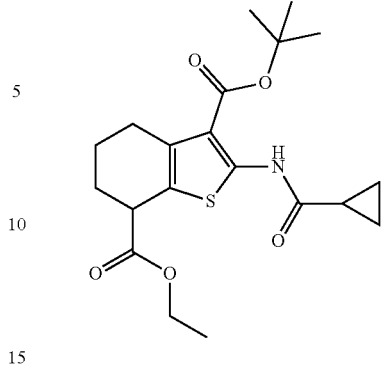

Intermediate 41

O3-tert-Butyl O5-ethyl 2-(cyclopropanecarbonylamino)-4,5,6,7-tetrahydrobenzothiophene-3,5-dicarboxylate Intermediate 42

O3-tert-Butyl O7-ethyl 2-(cyclopropanecarbonylamino)-4,5,6,7-tetrahydrobenzothiophene-3,7-dicarboxylate To a 79: 21 solution of intermediate 39 and intermediate 40 (8 g, 24.5 mmol) and DIPEA (8.56 ml, 16.0 mmol) in DCM (300 mL) at 0° C. was added cyclopropanecarbonyl chloride (1.08 ml, 49.1 mmol). The reaction was stirred at r.t. for 2 h before diluting with DCM (200 mL). Water (200 mL) was added and the phases were separated. The aqueous phase was extracted with DCM (2×100 mL) and washed 0.5 M aqueous hydrochloric acid solution (100 mL), saturated sodium hydrogen carbonate solution (100 mL) and brine. The organic phase was separated, dried (MgSO$_4$), filtered and concentrated in vacuo to give a pale yellow solid as a mixture of regioisomers which was purified by flash column chromatography on silica (gradient elution with 5% to 50% EtOAc in heptane) to afford the solid product as a mixture of regioisomers. The solid was triturated with heptane/Et$_2$O to afford title compound intermediate 41 (7 g, 72%) and the filtrate was concentrated in vacuo to afford the a 40: 60 mixture of title compound intermediate 41 and title compound intermediate 42 (2 g, 21%). Intermediate 41: δ$_H$ (500 MHz, CD$_3$OD) 4.24-4.11 (m, 2H), 3.16 (dd, J 17.2, 5.4 Hz, 1H), 2.87-2.78 (m, 1H), 2.77-2.63 (m, 3H), 2.25-2.16 (m, 1H), 1.89-1.77 (m, 2H), 1.61 (s, 9H), 1.27 (t, J 7.1 Hz, 3H), 1.05-0.94 (m, 4H). LCMS [M+H]$^+$ 394.10, RT 1.63 minutes (Method 6).

Intermediate 43

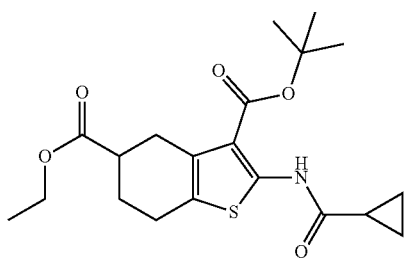

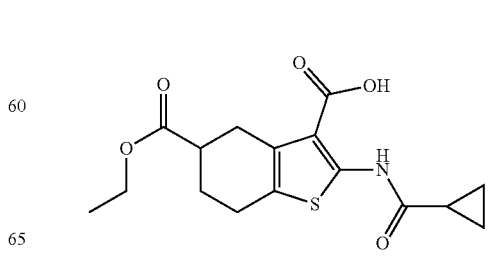

2-(Cyclopropanecarbonylamino)-5-ethoxycarbonyl-4,5,6,7-tetrahydrobenzothiophene-3-carboxylic acid Intermediate 41 (7.0 g, 17.7 mmol) was dissolved in 4M hydrochloric acid in 1,4-dioxane (88.95 mL). The reaction mixture was stirred at 30° C. for 16 h. The solvent was removed in vacuo and the crude product was triturated with Et$_2$O to afford the title compound (5.3 g, 88%) as a white solid. LCMS [M+H]$^+$ 338, RT 1.28 minutes (Method 6).

Intermediate 43 and 44

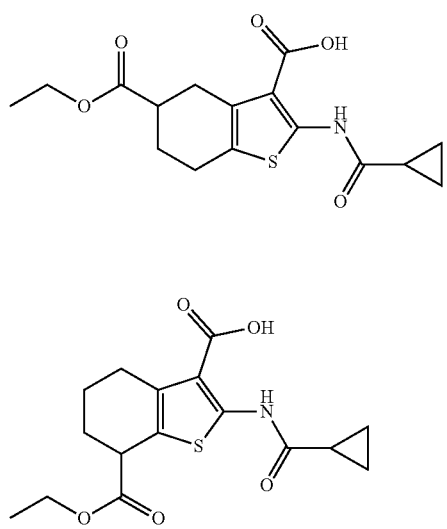

Intermediate 43

2-(Cyclopropanecarbonylamino)-5-ethoxycarbonyl-4,5,6,7-tetrahydrobenzothiophene-3-carboxylic acid Intermediate 44

2-(Cyclopropanecarbonylamino)-7-ethoxycarbonyl-4,5,6,7-tetrahydrobenzothiophene-3-carboxylic acid A 1:2 mixture of intermediate 41 and 42 (90%, 2.7 g, 6.18 mmol) was dissolved in 4M hydrochloric acid in 1,4-dioxane (30 mL) and stirred at r.t. for 2 h, followed by 35° C. for 6 h, then r.t. for 16 h then 35° C. for 3 h. The reaction mixture was concentrated in vacuo and the residue was triturated with Et$_2$O to afford the 5-isomer title compound intermediate 43 (220 mg, 11%) as an off white solid. The filtrate was concentrated in vacuo under reduced pressure to afford a 1:3 mixture of the 5-isomer title compound intermediate 43 and the 7-isomer title compound intermediate 44 (2 g, 88%) as a sticky yellow foam which was utilised without further purification. Title compound intermediate 43: δ$_H$ (500 MHz, Chloroform-d) 11.27 (s, 1H), 4.25-4.12 (m, 2H), 3.24 (dd, J 17.4, 5.4 Hz, 1H), 3.03-2.90 (m, 1H), 2.82-2.63 (m, 3H), 2.28-2.18 (m, 1H), 1.96-1.84 (m, 1H), 1.80-1.71 (m, 2H), 1.29 (t, J 7.1 Hz, 3H), 1.20-1.13 (m, 2H), 1.02-0.94 (m, 2H).

Intermediate 45 and 46

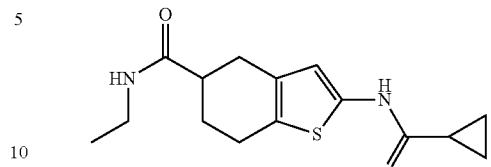

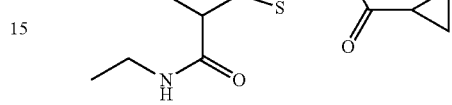

Intermediate 45

2-(Cyclopropanecarbonylamino)-N-ethyl-4,5,6,7-tetrahydrobenzothiophene-5-carboxamide Intermediate 46

2-(Cyclopropanecarbonylamino)-N-ethyl-4,5,6,7-tetrahydrobenzothiophene-7-carboxamide A 1:3 mixture of intermediate 43 and intermediate 44 (2 g, 5.45 mmol, 92% purity) was suspended in quinolone [91-22-5] (15 mL) and copper powder [7440-50-8] (520 mg, 8.18 mmol) was added. The mixture was heated to 150° C. for 1 h in the microwave and the reaction mixture was diluted with DCM (150 mL) and water (150 mL). The organic phase was washed with 1M aqueous hydrochloric acid solution (2×100 mL), followed by saturated aqueous sodium hydrogen carbonate (100 mL), dried (MgSO$_4$), filtered and concentrated in vacuo. Trituration with Et$_2$O afforded a 2:1 mixture of ethyl 2-(cyclopropanecarbonylamino)-4,5,6,7-tetrahydrobenzothiophene-5-carboxylate and ethyl 2-(cyclopropanecarbonylamino)-4,5,6,7-tetrahydrobenzothiophene-7-carboxylate (130 mg, 8%) as a light brown solid. The filtrate was concentrated in vacuo and purified by flash column chromatography on silica (gradient elution with 25-50% EtOAc/heptane) to afford a 1:3 mixture of ethyl 2-(cyclopropanecarbonylamino)-4,5,6,7-tetrahydrobenzothiophene-5-carboxylate and ethyl 2-(cyclopropanecarbonylamino)-4,5,6,7-tetrahydrobenzothiophene-7-carboxylate (1 g, 47%). 5-Isomer: δ$_H$ (500 MHz, CD$_3$OD) 6.35 (s, 1H), 4.16 (q, J 7.1 Hz, 2H), 2.82-2.65 (m, 5H), 2.25-2.17 (m, 1H), 1.92-1.83 (m, 1H), 1.74-1.67 (m, 1H), 1.26 (t, J 7.1 Hz, 3H), 0.96-0.91 (m, 2H), 0.89-0.83 (m, 2H).

To a 1:3 mixture of ethyl 2-(cyclopropanecarbonylamino)-4,5,6,7-tetrahydrobenzothiophene-5-carboxylate and ethyl 2-(cyclopropanecarbonylamino)-4,5,6,7-tetrahydrobenzothiophene-7-carboxylate (1 g, 3.41 mmol, 85% purity) dissolved in THF (20 mL), 2M aqueous lithium hydroxide solution (6 mL, 12 mmol) was added. The reaction mixture was stirred at r.t. for 20 h and the reaction mixture was concentrated in vacuo and the residue was acidified with 1M aqueous hydrochloric acid solution and the precipitate was filtered to afford a 1:3 mixture of 2-(cyclopropanecarbonylamino)-4,5,6,7-tetrahydrobenzothiophene-5-carboxylic acid and 2-(cyclopropanecarbonylamino)-4,5,6,7-tetrahydrobenzothiophene-7-carboxylic acid (600 mg, 60%). The mixture was utilised crude.

A 1:3 mixture of 2-(cyclopropanecarbonylamino)-4,5,6,7-tetrahydrobenzothiophene-5-carboxylic acid and 2-(cyclopropanecarbonylamino)-4,5,6,7-tetrahydrobenzothiophene-7-carboxylic acid (300 mg, 1.13 mmol) in DCM (5 mL) was treated with COMU (530 mg, 1.24 mmol) and DIPEA (240 µL, 1.38 mmol) and the mixture was stirred for 10 minutes at r.t. prior to addition of 2M ethanamine in THF (0.7 mL). The reaction mixture was stirred for a further 30 minutes and was diluted with DCM (20 mL) and washed with water (20 mL) followed by 1 M aqueous hydrochloric acid solution and dried (MgSO$_4$), filtered and concentrated in vacuo. The crude residue was purified by flash column chromatography on silica (gradient elution with 50-100% EtOAc/heptanes) to afford the 5-isomer title compound intermediate 45 (100 mg, 20%, ~65% purity) as a sticky dark brown oil and the 7-isomer title compound intermediate 46 (150 mg, 45%) as a brown solid. 5-Isomer intermediate 45: LCMS [M+H]+ 293.00, RT 1.04 minutes (Method 11). 7-Isomer intermediate 46: $\delta_H$ (500 MHz, DMSO-d$_6$) 11.09 (s, 1H), 7.91 (t, J 5.5 Hz, 1H), 6.29 (s, 1H), 3.47 (t, J 6.7 Hz, 1H), 3.16-3.00 (m, 2H), 2.44 (t, J 5.5 Hz, 2H), 1.97-1.83 (m, 3H), 1.74-1.67 (m, 1H), 1.63-1.51 (m, 1H), 1.03 (t, J 7.2 Hz, 3H), 0.82-0.76 (m, 4H).

Intermediates 47 and 22

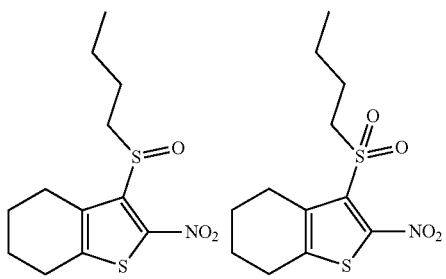

Intermediate 47

3-Butylsulfinyl-2-nitro-4,5,6,7-tetrahydrobenzothiophene

Intermediate 22

3-butylsulfonyl-2-nitro-4,5,6,7-tetrahydrobenzothiophene

To a stirred solution of intermediate 21 (195 mg, 0.72 mmoL) in DCM (8 mL) was added a solution of mCPBA (266 mg, 1.08 mmol, 70%) in DCM (5 mL) dropwise at r.t. The reaction mixture was combined with another experiment (15 mg, 0.055 mmol starting material) and quenched with saturated aqueous Na$_2$SO$_3$ (15 mL). The phases were separated and the aqueous phase was extracted with DCM (2×30 mL). The combined organic phases were washed with 0.5 M potassium carbonate solution (30 mL), brine (20 mL), dried (MgSO$_4$), filtered and concentrated in vacuo. The crude material was purified by flash chromatography on silica (gradient elution with 0 to 100% DCM in heptane) to afford the title compound intermediate 47 (107 mg, 49%) and the title compound intermediate 22 (106 mg, 51%).

Intermediate 47: $\delta_H$ (250 MHz, Chloroform-d) 3.35-3.02 (m, 3H), 2.96-2.75 (m, 3H), 2.12-1.71 (m, 6H), 1.67-1.44 (m, 2H, obscured by water peak), 0.99 (t, J 7.3 Hz, 3H). LCMS [M+H]$^+$ 288, RT 1.38 minutes (Method 6). Intermediate 22: $\delta_H$ (250 MHz, Chloroform-d) 3.69-3.47 (m, 2H), 2.95 (t, J 5.4 Hz, 2H), 2.87-2.73 (m, 2H), 1.98-1.71 (m, 6H), 1.59-1.34 (m, 2H, part. obscured by water peak), 0.96 (t, J 7.3 Hz, 3H). LCMS [M+H]$^+$ 304, RT 4.40 minutes (Method 5).

Intermediate 48

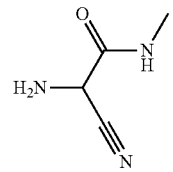

2-amino-2-cyano-N-methylacetamide

To a stirred solution of Intermediate 131 (77%, 691 mg, 4.15 mmol) in TBME (10 mL) cooled in an ice bath was added 2M CH$_3$NH$_2$ in MeOH (7 mL). The reaction was stirred while warming to room temperature for 1.5 hours to give a yellow solution. The reaction was concentrated in vacuo, the orange residue was sonicated in ethanol: diethyl ether (1:9) to give an orange solid which was collected by vacuum filtration and washed with ethanol: diethyl ether (1:9) to afford the title compound (395 mg, 76% at 90% purity) as an orange solid. $\delta_H$ (250 MHz, DMSO-d$_6$) δ 8.09 (s, 1H), 4.47 (s, 1H), 2.81 (br s, 2H), 2.65 (d, J 4.7 Hz, 3H).

Intermediate 49

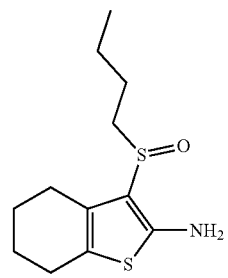 [SMILES: CCCCS(=O)c1c(N)sc2c1CCCC2]

3-Butylsulfinyl-4,5,6,7-tetrahydrobenzothiophen-2-amine

To a solution of intermediate 47 (40 mg, 0.14 mmoL) in EtOH (3 mL) was added 10% palladium on charcoal (50% wet) (30 mg, 0.014 mmoL) and the mixture was hydrogenated at r.t. and atmospheric pressure. Further 10% palladium on charcoal (50% wet) (30 mg, 0.014 mmoL) was added and stirring was continued at r.t. After stirring for a total of 7 h the reaction mixture was filtered through a pad of celite, washed with EtOAc and concentrated in vacuo to afford the title compound (20 mg, 56%) as a yellow film. LCMS [M+H]$^+$ 258, RT 1.31 minutes (Method 6).

Intermediate 50

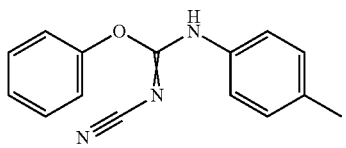 [SMILES: Cc1ccc(NC(=NC#N)Oc2ccccc2)cc1]

3-Cyano-2-phenyl-1-(p-tolyl)isourea

4-Methylaniline [106-49-0] (40 mg, 0.37 mmol) was dissolved in DCM (2 mL) and diphenyl cyanocarbonimidate [79463-77-7] (80.0 mg, 0.33 mmol) was added and the reaction mixture was stirred at r.t. for 6 h. The mixture was concentrated in vacuo and the title compound (94 mg, 84%) was used without further purification. LCMS [M+H]$^+$ 251.95, RT 1.30 minutes, purity 72% (Method 6).

Intermediate 51

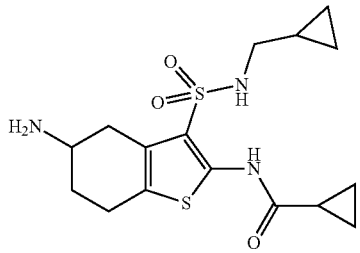 [SMILES: NC1CCc2sc(NC(=O)C3CC3)c(S(=O)(=O)NCC3CC3)c2C1]

N-[5-Amino-3-(cyclopropylmethylsulfamoyl)-4,5,6,7-tetrahydrobenzothiophen-2-yl]cyclopropanecarboxamide To a suspension of intermediate 27 (500 mg, 1.46 mmol) in MeCN (6 mL) was added chlorosulfonic acid [7790-94-5] (0.49 mL, 7.43 mmol). The reaction mixture was stirred at 70° C. for 1 h in a sealed tube and then cooled to r.t. This solution was added slowly to a solution of 1-cyclopropylmethanamine [2516-47-4] (1.0 mL, 11.8 mmol) and triethylamine (0.84 mL, 5.94 mmol) in chloroform (5 mL) cooled to 0° C. The mixture was stirred at r.t. for 3 h before diluting with EtOAc (70 mL) and washing with water. The aqueous phase was extracted with EtOAc (2×40 mL) and the combined organic phases were dried (Na$_2$SO$_4$), filtered and concentrated in vacuo to yield the crude product which was purified by flash column chromatography on silica (gradient elution with 1% to 20% MeOH in DCM) to afford the title compound (210 mg, 38%) as a pale yellow solid. $\delta_H$ (500 MHz, Chloroform-d) 10.49 (s, 1H), 3.44-3.17 (m, 5H), 2.81-2.68 (m, 4H), 2.60 (dd, J 15.7, 9.4 Hz, 1H), 2.22-2.12 (m, 1H), 1.86-1.74 (m, 1H), 1.65-1.57 (m, 1H), 1.15-1.08 (m, 2H), 0.98-0.91 (m, 2H), 0.91-0.81 (m, 1H), 0.48-0.41 (m, 2H), 0.12-0.05 (m, 2H). LCMS [M+H]$^+$ 370.10, RT 0.98 minutes (Method 6).

Intermediate 52

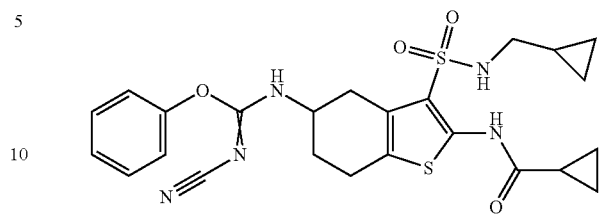

N-[5-[(N-Cyano-C-phenoxy-carbonimidoyl)amino]-3-(cyclopropylmethylsulfamoyl)-4,5,6,7-tetrahydrobenzothiophen-2-yl]cyclopropanecarboxamide Intermediate 51 (100 mg, 0.27 mmol) was dissolved in 2-propanol (5 mL) and diphenyl cyanocarbonimidate [79463-77-7] (70.9 mg, 0.29 mmol) was added and the reaction mixture was stirred at r.t. for 2 h. The solvent was removed in vacuo to yield the crude product (30 mg) which was purified by preparative HPLC (acidic) followed by preparative HPLC (Basic) to afford the title compound (130 mg, 89%) as a white solid, 1:1 mixture of geometrical isomers E and Z. $\delta_H$ (500 MHz, CD$_3$OD) 7.52-7.38 (m, 2H), 7.34-7.26 (m, 1H), 7.24-7.11 (m, 2H), 4.32-4.13 (m, 1H), 3.46-3.36 (m, 1H, isomer 1), 3.31-3.24 (m, 1H, isomer 2), 2.90-2.74 (m, 4H and 1H, isomer 1), 2.70-2.62 (m, 1H, isomer 2), 2.32-2.22 (m, 1H, isomer 1), 2.21-2.13 (m, 1H, isomer 2), 2.06-1.97 (m, 1H, isomer 1), 1.94-1.84 (m, 1H, isomer 2), 1.83-1.75 (m, 1H), 1.06-0.93 (m, 4H), 0.90-0.77 (m, 1H), 0.50-0.35 (m, 2H), 0.16-0.02 (m, 2H). LCMS [M+H]$^+$ 514.3, RT 3.70 minutes (Method 10).

Intermediate 53

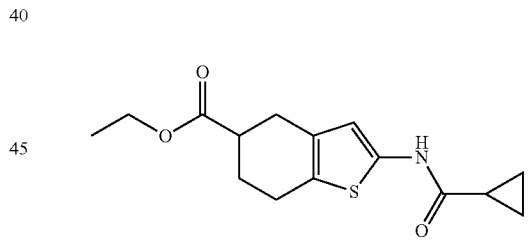

Ethyl 2-(cyclopropanecarbonylamino)-4,5,6,7-tetrahydrobenzothiophene-5-carboxylate Intermediate 43 (4 g, 11.9 mmol) was split into 2 equal portions and each was suspended in quinoline (15 mL) and copper powder (555 mg, 8.73 mmol) was added. The mixtures were heated to 150° C. for 1 h in the microwave. The reaction mixtures were combined and diluted with DCM (250 mL) and washed with 1M aqueous hydrogen chloride solution (2×250 mL), followed by saturated aqueous sodium hydrogen carbonate solution (100 mL), dried (MgSO$_4$), filtered and concentrated in vacuo. The crude product was triturated with EtOAc and filtered afford the title compound (3.07 g, 88%) as a grey solid. $\delta_H$ (500 MHz, DMSO-d$_6$) 11.10 (s, 1H), 6.32 (s, 1H), 4.17-4.01 (m, 2H), 2.81-2.56 (m, 5H), 2.14-2.06 (m, 1H), 1.82-1.66 (m, 2H), 1.20 (t, J 7.1 Hz, 3H), 0.83-0.75 (m, 4H). LCMS [M+H]+ 294.0, RT 1.26 minutes, 98% purity (Method 6).

Intermediate 54

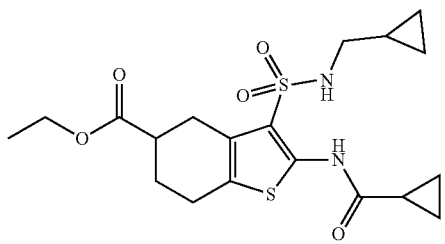 [SMILES: CCOC(=O)C1CCc2sc(NC(=O)C3CC3)c(S(=O)(=O)NCC3CC3)c2C1]

Ethyl 2-(cyclopropanecarbonylamino)-3-(cyclopropylmethylsulfamoyl)-4,5,6,7-tetrahydrobenzothiophene-5-carboxylate Intermediate 53 (2 g, 6.34 mmol, 93% purity) was suspended in MeCN (120 mL) and sulfurochloridic acid [7790-94-5] (1.45 mL, 21.8 mmol) was added. The solution was heated at 50° C. under nitrogen for 18 h. The solution was cooled to 0° C. and cyclopropylmethanamine [2516-47-4] (4 mL, 46.1 mmol) was added dropwise. The ice bath was removed and the solution was stirred for 30 minutes. EtOAc (200 mL) was added and the mixture was washed with 1 M aqueous hydrochloric acid solution (2×100 mL) and brine. The organic phase was separated, dried (MgSO₄), filtered and concentrated in vacuo to give the product which was purified by flash column chromatography on silica (gradient elution with 0-30% EtOAc/heptane) to afford the title compound (1.4 g, 52%) as an amber oil which solidified to form a beige solid. $\delta_H$ (500 MHz, DMSO-d₆) 10.44 (s, 1H), 7.94 (t, J 5.9 Hz, 1H), 4.18-4.02 (m, 2H), 3.08-2.98 (m, 1H), 2.80-2.63 (m, 6H), 2.14-2.05 (m, 1H), 1.94-1.86 (m, 1H), 1.81-1.71 (m, 1H), 1.21 (t, J 7.1 Hz, 3H), 0.96-0.85 (m, 4H), 0.82-0.73 (m, 1H), 0.39-0.32 (m, 2H), 0.10-0.05 (m, 2H). LCMS [M+H]+ 449.0, RT 1.43 minutes, 99% purity (Method 6).

Intermediate 55

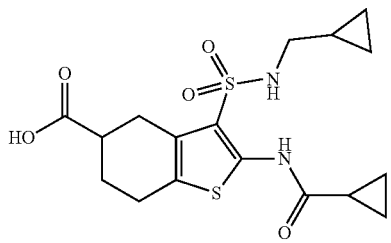 [SMILES: O=C(O)C1CCc2sc(NC(=O)C3CC3)c(S(=O)(=O)NCC3CC3)c2C1]

2-(Cyclopropanecarbonylamino)-3-(cyclopropylmethylsulfamoyl)-4,5,6,7-tetrahydrobenzothiophene-5-carboxylic acid Intermediate 54 (1.8 g, 4.22 mmol) was dissolved in 1,4-dioxane (40 mL) and water (10 mL) and 2M lithium hydroxide monohydrate solution (6 mL) was added. The reaction mixture was heated at 90° C. for 2 h and was then cooled to r.t. The mixture was concentrated in vacuo and the residue was acidified with 1 M aqueous hydrochloric acid solution. The resulting solid was filtered off, washed with water and dried in vacuo to afford the title compound (1.2 g, 71%) as a beige solid. $\delta_H$ (500 MHz, DMSO-d₆) 12.34 (s, 1H), 10.45 (s, 1H), 7.94 (t, J 5.7 Hz, 1H), 3.03 (dd, J 16.7, 5.0 Hz, 1H), 2.78-2.58 (m, 6H), 2.14-2.05 (m, 1H), 1.94-1.86 (m, 1H), 1.80-1.67 (m, 1H), 0.95-0.85 (m, 4H), 0.81-0.72 (m, 1H), 0.39-0.30 (m, 2H), 0.10-0.04 (m, 2H). LCMS [M+H]+ 399.0, RT 1.24 minutes, 97% purity (Method 6).

Intermediate 56

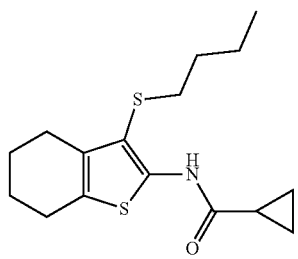 [SMILES: CCCCSc1c(NC(=O)C2CC2)sc2c1CCCC2]

N-(3-Butylsulfanyl-4,5,6,7-tetrahydrobenzothiophen-2-yl)cyclopropanecarboxamide

To a solution of intermediate 21 (930 mg, 3.43 mmoL) and cyclopropanecarboxylic anhydride [33993-24-7] (634 mg, 4.11 mmoL) in EtOAc (120 mL) was added 10% Pd on charcoal (50% wet, 730 mg, 0.34 mmoL) and the reaction mixture was hydrogenated at r.t. and atmospheric pressure for 2 h. Further 10% Pd on charcoal (50% wet, 730 mg, 0.34 mmoL) was added and stirring was continued at r.t. for 1 h. 10% Pd on charcoal (50% wet, 500 mg, 0.24 mmoL) was added and stirring was continued for 1 h. The reaction mixture was filtered through a pad of celite, washed with EtOAc and the resulting solution was treated with triethylamine (1.43 mL, 10.3 mmoL) followed by cyclopropanecarbonyl chloride [4023-34-1] (0.63 mL, 6.9 mmoL) and the reaction mixture was stirred under nitrogen at r.t. for 60 h. The mixture was washed with saturated aqueous ammonium chloride solution (10 mL) and brine (10 mL) and the organic phase was dried (MgSO₄), filtered and concentrated in vacuo. The crude material was purified by flash column chromatography on silica (gradient elution with 0 to 50% DCM/heptane) to give the crude product which was dissolved in EtOAc (15 mL) and washed with saturated aqueous ammonium chloride solution (10 mL), saturated aqueous sodium hydrogen carbonate solution (10 mL) and brine. The organic phase was dried (MgSO₄), filtered and concentrated in vacuo. The crude product was purified by flash column chromatography on silica (gradient elution with 0 to 50% EtOAc/heptane) to afford the title compound (630 mg, 90% purity, 54%) as a light yellow solid. $\delta_H$ (250 MHz, Chloroform-d) 8.73 (s, 1H), 2.72-2.62 (m, 2H), 2.62-2.51 (m, 4H), 1.87-1.74 (m, 4H), 1.62-1.56 (m, 1H), 1.52-1.34 (m, 4H), 1.22-1.07 (m, 2H), 0.96-0.82 (m, 5H). LCMS [M+H]+ 310, RT 1.45 minutes, 94% purity (Method 11).

Intermediate 57

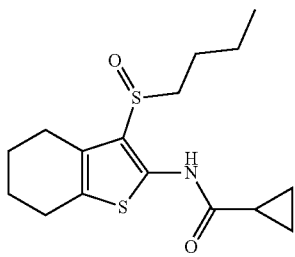 [SMILES: CCCCS(=O)c1c(NC(=O)C2CC2)sc2c1CCCC2]

N-(3-Butylsulfinyl-4,5,6,7-tetrahydrobenzothiophen-2-yl)cyclopropanecarboxamide

To a stirred solution of intermediate 56 (660 mg, 1.9 mmoL) in DCM (12 mL) was added a solution of mCPBA (70% purity, 473 mg, 1.9 mmoL) in DCM (8 mL) at r.t. for 1.5 h. The mixture was quenched with saturated aqueous sodium sulfite (15 mL), the phases were separated and the aqueous phase was extracted with DCM (2×15 mL). The combined organic layers were washed with 1M potassium carbonate solution (20 mL), water (15 mL), brine (15 mL), dried (MgSO₄), filtered and concentrated in vacuo. The crude material was purified by flash column chromatography on silica (gradient elution with 0 to 50% EtOAc/heptane) to afford the title compound as a yellow oil (576 mg, 92%). $\delta_H$ (250 MHz, Chloroform-d) 11.23 (s, 1H), 3.15-2.79 (m, 2H), 2.71-2.58 (m, 2H), 2.58-2.43 (m, 1H), 2.26-2.07 (m, 1H), 1.93-1.64 (m, 6H), 1.68-1.40 (m, 3H), 1.16-1.03 (m, 2H), 0.96 (t, J 7.3 Hz, 3H), 0.94-0.80 (m, 2H). LCMS [M+H]⁺ 326, RT 1.28 minutes, 100% purity (Method 11).

Intermediate 58

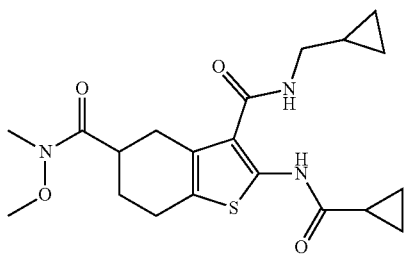 [SMILES: CON(C)C(=O)C1CCc2sc(NC(=O)C3CC3)c(C(=O)NCC3CC3)c2C1]

2-(Cyclopropanecarbonylamino)-N3-(cyclopropylmethyl)-N5-methoxy-N5-methyl-4,5,6,7-tetrahydrobenzothiophene-3,5-dicarboxamide Example 40 (4 g, 11.04 mmol) was suspended in DCM (100 mL) and EDCl (2.12 g, 11.04 mmol), methoxy(methyl) amine (1.35 g, 22.07 mmol), triethylamine (2.23 g, 22.07 mmol) and catalytic DMAP (30 mg) were added to this mixture. The reaction mixture was stirred at r.t. for 16 h and the reaction mixture was concentrated in vacuo. The crude residue was dissolved in saturated sodium hydrogen carbonate solution (2×10 mL) and extracted with DCM (40 mL). The organic phase was concentrated in vacuo and the residue was purified by flash column chromatography on silica (gradient elution with 0-50% DCM/MeOH) to afford the title compound (3.0 g, 60%) as a yellow solid. $\delta_H$ (500 MHz, Methylene Chloride-d₂) 12.11 (s, 1H), 6.00 (s, 1H), 3.70 (s, 3H), 3.29-3.22 (m, 2H), 3.20 (s, 3H), 2.97-2.83 (m, 2H), 2.82-2.70 (m, 2H), 2.13-2.08 (m, 1H), 1.89-1.76 (m, 1H), 1.65 (tt, J 7.9, 4.6 Hz, 1H), 1.09-0.98 (m, 3H), 0.90-0.81 (m, 2H), 0.60-0.44 (m, 2H), 0.29-0.18 (m, 2H). Missing an NH proton. LCMS [M+H]⁺ 406.20, RT 1.78 minutes, 91.76% purity (Method 12).

Intermediate 59

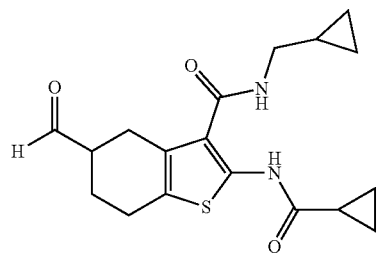 [SMILES: O=CC1CCc2sc(NC(=O)C3CC3)c(C(=O)NCC3CC3)c2C1]

2-(Cyclopropanecarbonylamino)-N-(cyclopropylmethyl)-5-formyl-4,5,6,7-tetrahydrobenzothiophene-3-carboxamide Intermediate 58 (2.27 g, 5.6 mmol) was dissolved in DCM (70 mL) and the reaction mixture was stirred at r.t. for 5 minutes. 1M Hydrido[bis(2-methylpropyl)]aluminium in hexane (11.2 mL, 11.20 mmol) was added dropwise to the reaction mixture and stirred at −78° C. for 1 h. The reaction mixture was removed from the dry ice bath and quenched by addition of saturated sodium potassium tartrate (100 mL) and the combined organic phases were washed with brine (100 mL), dried (MgSO₄), filtered, and the filtrate was concentrated in vacuo to afford the title compound (1.46 g, 75%) which was utilised without further purification. LCMS [M+H]⁺ 347.20, RT 1.79 minutes, 80% purity (Method 12).

Intermediate 60

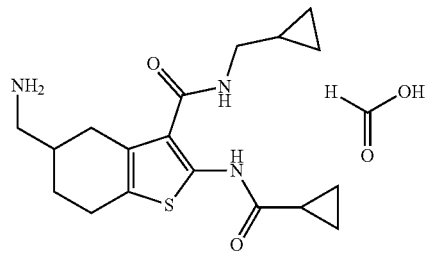

5-(Aminomethyl)-2-(cyclopropanecarbonylamino)-N-(cyclopropylmethyl)-4,5,6,7-tetrahydrobenzothiophene-3-carboxamide; formic acid Example 59 (300 mg, 0.83 mmol) was dissolved in MeOH (6 mL) and water (3 mL) and formic acid [64-18-6] (2.94 ml, 78.0 mmol) was added. The reaction mixture was cooled to 0° C. and zinc [7440-66-6] (109 mg, 1.66 mmol)

was added. The reaction mixture was stirred at 0° C. and warmed to r.t. and stirred for 36 h and the reaction mixture was filtered, and the solid was washed with MeOH. The filtrate was concentrated in vacuo to give the desired product which was purified by flash column chromatography on silica (gradient elution with 0-60% MeOH in DCM) to afford the title compound (300 mg, 92%) as a white solid. $\delta_H$ (250 MHz, Methylene Chloride-$d_2$) 12.07 (s, 1H), 6.46 (t, J 7.5 Hz, 1H), 3.36-3.33 (m, 1H), 3.21-3.08 (m, 1H), 3.07-2.85 (m, 3H), 2.73-2.68 (m, 2H), 2.57-2.40 (m, 1H), 2.18-2.15 (m, 1H), 2.02-1.96 (m, 1H), 1.71-1.46 (m, 2H), 1.14-0.96 (m, 3H), 0.90-0.86 (m, 2H), 0.49-0.45 (m, 2H), 0.29-0.23 (m, 2H), as a formate salt (1 equivalent).

Intermediate 61

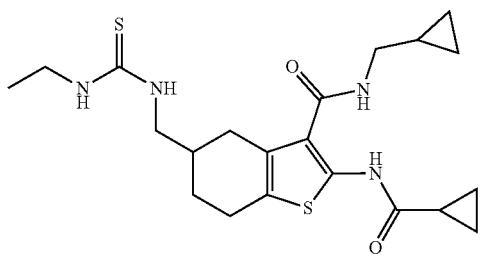 [SMILES: CCNC(=S)NCC1CCc2sc(NC(=O)C3CC3)c(C(=O)NCC3CC3)c2C1]

2-(Cyclopropanecarbonylamino)-N-(cyclopropylmethyl)-5-[(ethylcarbamothioylamino)methyl]-4,5,6,7-tetrahydrobenzothiophene-3-carboxamide A solution of isothiocyanatoethane [542-85-8] (160.5 mg, 1.84 mmol) in DCM (5 mL) was stirred at r.t. prior to the addition of intermediate 60 (320 mg, 0.92 mmol). Triethylamine (128 µl, 0.92 mmol) was added to the reaction mixture and the solution was stirred for 18 h under nitrogen. The reaction mixture was concentrated in vacuo to give a pale yellow solid which was purified by flash column chromatography on silica (gradient elution with 0% to 100% EtOAc in heptane) to afford the title compound (369 mg, 90%) as a white solid. $\delta_H$ (250 MHz, Methylene Chloride-$d_2$) 12.16 (s, 1H), 6.07 (s, 1H), 5.80 (br s, 2H), 3.73-3.70 (m, 1H), 3.64-3.49 (m, 1H), 3.48-3.32 (m, 2H), 3.26 (dd, J 7.0, 5.5 Hz, 2H), 2.90 (dd, J 15.0, 4.9 Hz, 1H), 2.75-2.70 (m, 2H), 2.61-2.43 (m, 1H), 2.13-2.08 (m, 1H), 2.03-1.97 (m, 1H), 1.69-1.66 (m, 1H), 1.22 (t, J 7.5 Hz, 3H), 1.11-0.96 (m, 3H), 0.91-0.81 (m, 2H), 0.63-0.50 (m, 2H), 0.30-0.25 (m, 2H); 1H obscured with solvent.

Intermediate 62

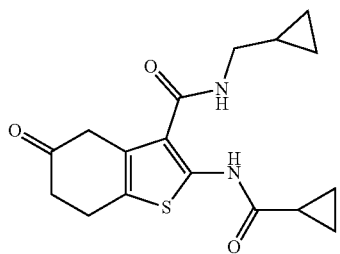 [SMILES: O=C1CCc2sc(NC(=O)C3CC3)c(C(=O)NCC3CC3)c2C1]

2-(Cyclopropanecarbonylamino)-N-(cyclopropylmethyl)-5-oxo-6,7-dihydro-4H-benzothiophene-3-carboxamide Example 86 (420 mg, 1.12 mmol) was dissolved in THF and 1M aqueous hydrochloric acid solution (7.81 mL) was added. The reaction mixture was heated at 70° C. for 3 h and then stirred at r.t. for 18 h. The reaction mixture was heated for a further 1 h and the solution was cooled to r.t. and the pH adjusted to pH 9 with saturated sodium hydrogen carbonate solution. The mixture was extracted with EtOAc (2×15 mL) and the combined organic phases were washed with brine (15 mL), dried ($Na_2SO_4$), filtered and the concentrated in vacuo to give a yellow solid which was purified by flash column chromatography on silica (gradient elution with 0-50% EtOAc/iso-hexane) to afford the title compound (264 mg, 71%) as an off white solid. LCMS [M+H]$^+$ 333.2, RT 1.630 minutes, 92.8% purity (Method 1).

Intermediate 63

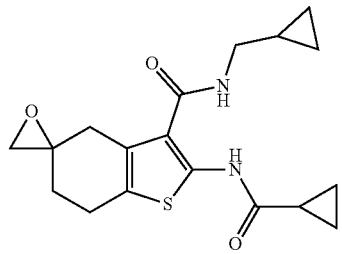 [SMILES: O=C(NCC1CC1)c1c(NC(=O)C2CC2)sc2c1CC1(CC2)CO1]

2-(Cyclopropanecarbonylamino)-N-(cyclopropylmethyl)spiro[6,7-dihydro-4H-benzothiophene-5,2'-oxirane]-3-carboxamide Trimethylsulfoxonium iodide [1774-47-6] (2.00 g, 9.09 mmol) was poured into DMSO (13 mL) and cooled to 0° C. Sodium hydride [7646-69-7] (650 mg, 16.3 mmol) was added and the reaction mixture was stirred at r.t. After 1.5 h, intermediate 62 (1.95 g, 5.87 mmol) and tetrabutylammonium bromide [1643-19-2] (200 mg, 0.620 mmol) was added and the reaction mixture was stirred for 1 h. The reaction mixture was poured into water and ice (50 g) and was extracted with EtOAc (3×50 mL). The combined organic phases were dried ($MgSO_4$), filtered and concentrated in vacuo to afford a yellow solid which was purified by flash column chromatography on silica (gradient elution with 100% DCM to 95/5/0.5% DCM/MeOH/$NH_4OH$) to afford the title compound (1.73 g, 85%) as a yellow solid. LCMS [M+H]$^+$ 347.11, RT 2.31 minutes, purity 96.42% (Method 9).

Intermediate 64

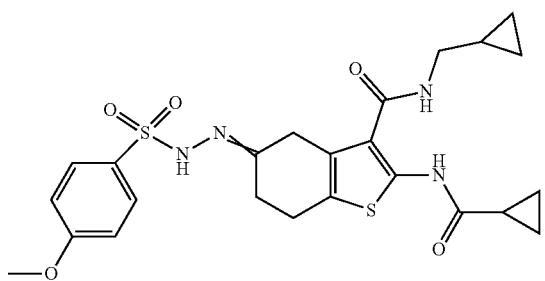 [SMILES: COc1ccc(S(=O)(=O)NN=C2CCc3sc(NC(=O)C4CC4)c(C(=O)NCC4CC4)c3C2)cc1]

2-(cyclopropanecarbonylamino)-N-(cyclopropylmethyl)-5-[(4-methoxyphenyl)sulfonylhydrazono]-6,7-dihydro-4H-benzothiophene-3-carboxamide Intermediate 62 (200 mg, 0.6 mmol) was added to a solution of 4-methoxybenzenesulfonohydrazide [1950-68-1] (122 mg, 0.6 mmol) in MeOH (1.2 mL) and the suspension was stirred under nitrogen for 60 h at 20° C. The reaction mixture was diluted with MeOH (10 mL) and the solids collected by filtration. The solids were washed with MeOH (2×20 mL) and dried in vacuo at 40° C. for 2 h to afford the title compound (146 mg, 44%) as a pale yellow powder. $\delta_H$ (500 MHz, DMSO-$d_6$) 10.96 (s, 1H), 10.16 (s, 1H), 7.90 (t, J 5.5 Hz, 1H), 7.83-7.76 (m, 2H), 7.14-7.08 (m, 2H), 3.83 (s, 3H), 3.54 (s, 2H), 3.17 (t, J 6.2 Hz, 2H), 2.73 (t, J 6.3 Hz, 2H), 2.49-2.44 (obs. m, 2H), 1.97-1.86 (m, 1H), 1.15-1.02 (m, 1H), 0.91-0.75 (m, 4H), 0.52-0.40 (m, 2H), 0.32-0.21 (m, 2H). LCMS [M+H]$^+$ 517.2, RT 1.87 minutes, 95% purity (Method 12).

Intermediate 65

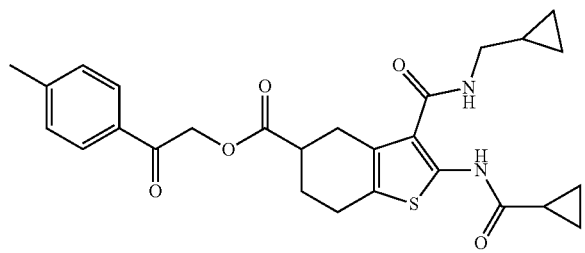 [SMILES: Cc1ccc(C(=O)COC(=O)C2CCc3sc(NC(=O)C4CC4)c(C(=O)NCC4CC4)c3C2)cc1]

[2-Oxo-2-(p-tolyl)ethyl] 2-(cyclopropanecarbonylamino)-3-(cyclopropylmethylcarbamoyl)-4,5,6,7-tetrahydrobenzothiophene-5-carboxylate To a stirred solution of Example 40 (100 mg, 0.28 mmol) in DMF (2 mL) was added potassium carbonate (55 mg, 2.26 mmol). The reaction mixture was stirred for 10 minutes and 2-bromo-1-(4-methylphenyl)ethanone [619-41-0] (65 mg, 0.3 mmol) was added and the mixture was stirred at 40° C. for 1 h. The solvent was removed in vacuo and the remaining residue was quenched with water (50 mL) and extracted with EtOAc (3×50 mL). The organic phases were combined washed with water (3×50 mL), brine (50 mL), separated, dried (Na$_2$SO$_4$) and filtered and the solvent was removed in vacuo to yield the crude title compound (120 mg, 62%) as a yellow solid. LCMS [M+H]$^+$ 517.10, RT 1.33 minutes, purity 70.3% (Method 11).

Intermediate 66

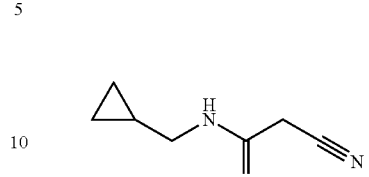

2-Cyano-N-(cyclopropylmethyl)acetamide

To cyclopropylmethylamine [2516-47-4] (3.63 g, 50.0 mmol) at 0° C. was added methyl cyanoacetate [105-34-0] (2.50 g, 25.0 mmol) dropwise. The reaction mixture was stirred for 90 minutes, and after 45 minutes a white solid precipitated. 1:1 Et$_2$O/iso-hexane (40 mL) was added to the reaction mixture which was stirred at 0° C. for 10 minutes. The solid was filtered and washed with a small amount of iso-hexane to afford the title compound (3.25 g, 95%) as a pure white solid. $\delta_H$ (300 MHz, Chloroform-d) 6.19 (s, 1H), 3.40 (s, 2H), 3.19 (dd, J 7.3, 5.4 Hz, 2H), 1.10-0.90 (m, 1H), 0.66-0.52 (m, 2H), 0.26 (dt, J 6.2, 4.7 Hz, 2H).

Intermediate 67

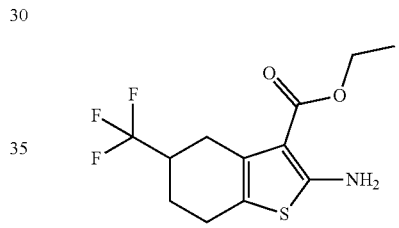

Ethyl 2-amino-5-(trifluoromethyl)-4,5,6,7-tetrahydrobenzothiophene-3-carboxylate To a solution of 3-(trifluoromethyl)cyclohexanone [585-36-4] (0.50 g, 3.0 mmol) in EtOH (3 mL) was added ethyl cyanoacetate [105-56-6] (0.37 g, 3.3 mmol) followed by sulphur [7704-34-9] (0.11 g, 3.4 mmol) and diethylamine (0.33 g, 4.5 mmol). The reaction mixture was stirred at r.t. for 1.5 h and the mixture was concentrated in vacuo and the crude residue was purified by flash column chromatography on silica (gradient elution with 0-15% EtOAc in hexanes) to afford the title compound (717 mg, 81%) as an off-white solid. LCMS [M+H]$^+$ 294.0, RT 1.532 minutes (Method 4).

Intermediate 68

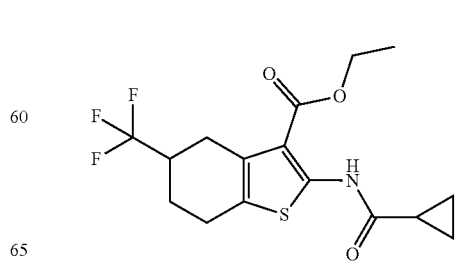

Ethyl 2-(cyclopropanecarbonylamino)-5-(trifluorom-ethyl)-4,5,6,7-tetrahydrobenzothiophene-3-carboxylate Intermediate 67 (717 mg, 2.45 mmol) was dissolved in DCM (10 mL) and DIPEA (0.75 mL, 4.3 mmol) and cyclopropanecarbonyl chloride [4023-34-1] (0.22 mL, 2.4 mmol) were added. The reaction mixture was stirred at r.t. for 1 h before washing with saturated sodium hydrogen carbonate solution and brine. The mixture was passed through a phase separation cartridge and the organic layer was concentrated in vacuo to yield a yellow gum which was purified by flash column chromatography on silica (gradient elution with 10-50% EtOAc/hexane) to afford the title compound (0.75 g, 85%) as a white solid. $\delta_H$ (400 MHz, DMSO-$d_6$) 11.17 (s, 1H), 4.32 (qd, J 7.1, 2.0 Hz, 2H), 3.13 (dd, J 16.6, 5.0 Hz, 1H), 2.85-2.65 (m, 3H), 2.65-2.54 (m, 1H), 2.12 (d, J 12.9 Hz, 1H), 2.04 (tt, J 7.4, 4.9 Hz, 1H), 1.63 (qd, J 11.9, 5.7 Hz, 1H), 1.32 (t, J 7.1 Hz, 3H), 1.04-0.83 (m, 4H).

Intermediate 69

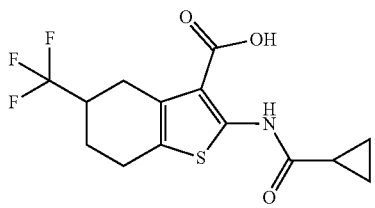 [SMILES: O=C(O)c1c(NC(=O)C2CC2)sc2c1CC(C(F)(F)F)CC2]

2-(Cyclopropanecarbonylamino)-5-(trifluorom-ethyl)-4,5,6,7-tetrahydrobenzothiophene-3-carboxylic acid Intermediate 68 (0.73 g, 2.0 mmol) was dissolved in 1,4-dioxane (7 mL) and a solution of lithium hydroxide monohydrate [1310-66-3] (236 mg, 3.15 mmol, 56 mass %) in water (1.5 mL) was added and the mixture was stirred at 50° C. for 16 h. The mixture was concentrated in vacuo and the residue was dissolved in water and washed with DCM (2×). The aqueous phase was acidified to <pH 2 by addition of 2M aqueous hydrochloric acid solution and the resulting precipitate was filtered off and washed with water (2×) to afford the title compound (665 mg, 99%) as an off white solid which was air dried. LCMS [M−H]⁻ 332.0, RT 2.374 minutes (Method 2).

Intermediate 70

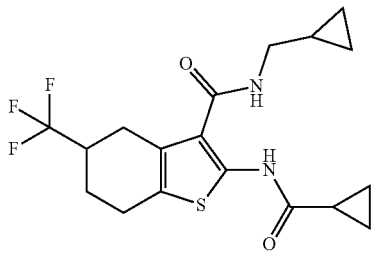 [SMILES: O=C(NCC1CC1)c1c(NC(=O)C2CC2)sc2c1CC(C(F)(F)F)CC2]

2-(Cyclopropanecarbonylamino)-N-(cyclopropylm-ethyl)-5-(trifluoromethyl)-4,5,6,7-tetrahydrobenzo-thiophene-3-carboxamide To intermediate 69 (100 mg, 0.30 mmol) was added cyclopropylmethylamine [2516-47-4] (32 mg, 0.45 mmol) and a suspension of EDCl (71.2 mg, 0.36 mmol) in DCM (1 mL). The reaction mixture was stirred at r.t. overnight before heating at 40° C. for 1 h. The mixture was diluted with DCM (5 mL), washed with water and passed through a phase separation cartridge before concentrating the filtrate in vacuo. The crude product was purified by flash column chromatography on silica (gradient elution with 10-50% EtOAc/hexane) followed by freeze drying from MeCN/water to afford the title compound (35 mg, 30%) as a white solid. LCMS [M+H]⁺ 387.8, RT 2.637 minutes (Method 2).

Intermediate 71

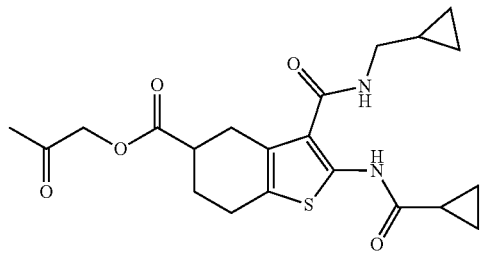 [SMILES: CC(=O)COC(=O)C1CCc2sc(NC(=O)C3CC3)c(C(=O)NCC3CC3)c2C1]

Acetonyl 2-(cyclopropanecarbonylamino)-3-(cyclo-propylmethylcarbamoyl)-4,5,6,7-tetrahydrobenzothi-ophene-5-carboxylate Example 40 was dissolved in DMF (3 mL) and triethyl-amine (0.046 ml, 0.33 mmol) and chloroacetone [78-95-5] (0.026 ml, 0.33 mmol) were added. The reaction mixture was stirred at r.t. for 16 h. The reaction mixture was poured into water and the resulting solid was filtered off to afford the title compound (80 mg, 63%) which was utilised without further purification. LCMS [M+H]⁺ 419.05, RT 1.38 minutes, purity 91% (Method 6).

Intermediate 72

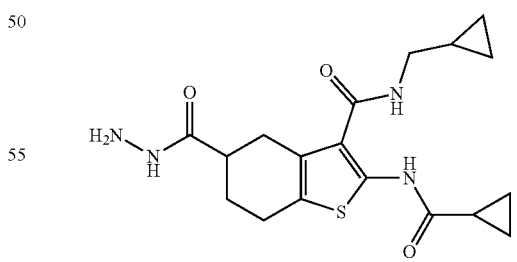

2-(Cyclopropanecarbonylamino)-N-(cyclopropylm-ethyl)-5-(hydrazinecarbonyl)-4,5,6,7-tetrahydroben-zothiophene-3-carboxamide Example 40 (100 mg, 0.26 mmol) was dissolved in EtOH (3 mL) and hydrazine hydrate (0.12 ml, 2.56 mmol) was added. The reaction mixture was stirred at 70° C. for 20 h. The mixture was concentrated in vacuo to afford the title compound (95 mg, 99%) as a white solid. LCMS [M+H]+ 377.05, RT 1.13 minutes, purity 100% (Method 6).

Intermediate 73

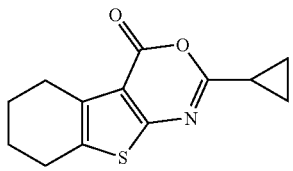 [SMILES: O=c1oc(C2CC2)nc2sc3c(c12)CCCC3]

2-Cyclopropyl-5,6,7,8-tetrahydrobenzothiopheno[2,3-d][1,3]oxazin-4-one

To intermediate 16 (200 mg, 0.75 mmol), DCM (4 mL) and DMF (0.01 mL) was added oxalyl chloride [79-37-8] (105 mg, 0.83 mmol). The reaction mixture was stirred at r.t. for 3 h before concentrating in vacuo to yield the crude product which was purified by LCMS reverse phase (basic mode) to afford the title compound (200 mg, 107%) as a beige solid. $\delta_H$ (400 MHz, DMSO-$d_6$) 2.75 (dt, J 11.2, 6.0 Hz, 4H), 2.05-1.95 (m, 1H), 1.87-1.70 (m, 4H), 1.17-1.07 (m, 4H).

Intermediate 74

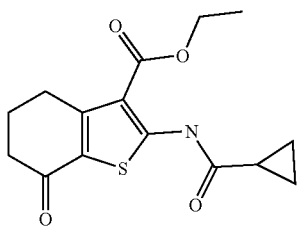 [SMILES: CCOC(=O)c1c(NC(=O)C2CC2)sc2c1CCCC2=O]

Ethyl 2-(cyclopropanecarbonylamino)-7-oxo-5,6-dihydro-4H-benzothiophene-3-carboxylate To ethyl 2-amino-7-oxo-4,5,6,7-tetrahydro-1-benzothiophene-3-carboxylate [96334-44-0] (506 mg, 2.12 mmol) was added DCM (15 mL) and DIPEA (1.1 mL, 6.3 mmol). The reaction mixture was stirred under nitrogen prior to the addition of cyclopropanecarbonyl chloride [4023-34-1] (0.21 mL, 2.30 mmol). The reaction mixture was stirred under nitrogen at r.t. overnight. Further DCM (24 mL) was added to solubilise the mixture, followed by a further cyclopropanecarbonyl chloride [4023-34-1](0.21 mL, 2.30 mmol) and the reaction mixture was stirred for 1 h before adding further cyclopropanecarbonyl chloride [4023-34-1] (0.21 mL, 2.30 mmol), the mixture was left to stir under nitrogen overnight. Further cyclopropanecarbonyl chloride [4023-34-1] (0.21 mL, 2.30 mmol) was added and the reaction mixture was stirred for 2 h before addition of further cyclopropanecarbonyl chloride [4023-34-1] (0.85 mL, 9.19 mmol) and the reaction mixture was stirred at r.t. for 2 h. Water (25 mL) was added to the reaction mixture, which was stirred vigorously for 10 minutes. Further water (25 mL) and DCM (25 mL) was added and the organic layer was separated before washing with brine (50 mL). The organic layer was separated, passed through a phase separation frit and was concentrated in vacuo to yield a dark brown oil which was purified by flash column chromatography on silica (gradient elution with 20% EtOAc/isohexane to 95% EtOAc/isohexane) to afford the title compound (253 mg, 39%) as a pale yellow solid. LCMS [M+H]+ 308.8, RT 2.162 minutes, 100.0% purity (Method 2). LCMS [M+H]+ 308.8, RT 2.205 minutes, 100.0% purity (Method 3).

Intermediates 74 and 75

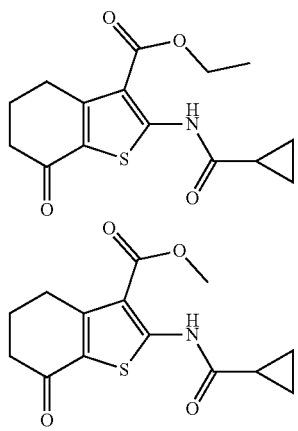

Intermediate 74

Ethyl 2-(cyclopropanecarbonylamino)-7-oxo-5,6-dihydro-4H-benzothiophene-3-carboxylate Intermediate 75

Methyl 2-(cyclopropanecarbonylamino)-7-oxo-5,6-dihydro-4H-benzothiophene-3-carboxylate To a stirred solution of cyclopropanecarboxylic acid [1759-53-1] (1.00 g, 11.6 mmol) in DCM (3 mL) was added oxalyl chloride [79-37-8] (1.50 g, 11.61 mmol) followed by DMF (1 drop). The reaction immediately evolved gas and was stirred at r.t. for 1 h to form cyclopropane carbonyl chloride [4023-34-1]. A mixture of ethyl 2-amino-7-oxo-5,6-dihydro-4H-benzothiophene-3-carboxylate and methyl 2-amino-7-oxo-5,6-dihydro-4H-benzothiophene-3-carboxylate [96334-44-0] (commercially available ASINEX compound 73% ethyl and 27% methyl) (Ratio 0.73:0.27, 2.736 g) was dissolved with heating in 1,4-dioxane (40 mL) and triethylamine (2.38 g, 23.2 mmol) was added. On cooling the amino ester crashes out of solution and the crude cyclopropane carbonyl chloride solution was added dropwise over 1 minute to this stirred, 30° C. solution. After 2 h at r.t., further commercial cyclopropane carbonyl chloride [4023-34-1] (364 mg, 3.48 mmol) was added and the mixture was stirred for 1 h at r.t. The mixture was concentrated in vacuo and the residues suspended in EtOAc, washed with water (2×), 0.5 M aqueous hydrochloric acid solution, saturated sodium hydrogen carbonate solution (2×) and water (2×). The organic layer was separated, dried (MgSO₄), filtered and the mixture concentrated in vacuo to yield a crude mixture of title products intermediate 74 and intermediate 75 (2.84 g, 59%) as a yellow solid in ~3:1 ratio. 200 mg was separated by prep HPLC to give 45 mg and 15 mg of intermediates 74 & 75 respectively. Intermediate 74: LCMS [M+H]⁺ 308.8, RT 2.162 minutes, 100.0% purity (Method 2). LCMS [M+H]⁺ 308.8, RT 2.205 minutes, 100.0% purity (Method 3). Intermediate 75: LCMS [M+H]⁺ 294.6, RT 1.940 minutes, 100.0% purity (Method 2). LCMS [M+H]⁺ 294.6, RT 1.868 minutes, 100.0% purity (Method 3).

Intermediate 76

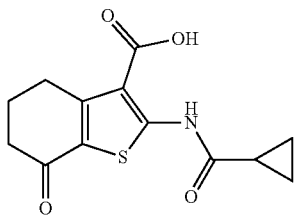 [SMILES: O=C1CCCc2c1sc(NC(=O)C1CC1)c2C(=O)O]

2-(Cyclopropanecarbonylamino)-7-oxo-5,6-dihydro-4H-benzothiophene-3-carboxylic acid A mix of Intermediates 74 and 75 (3:1 ratio) (2.63 g, 8.66 mmol) were dissolved with heating in 1,4-dioxane (40 mL). Lithium hydroxide monohydrate [1310-66-3] (0.55 g, 13.0 mmol) was dissolved with heating in water (3 mL) and this solution was added to the stirred solution of intermediates 74 and 75. The stirred solution was heated at 60° C. for 2 h followed by 18 h at r.t. The reaction mixture was heated at 70° C. for 2 h followed by 40° C. for 5 h. Further lithium hydroxide monohydrate [1310-66-3] (0.18 g, 4.33 mmol, 0.5 eq) dissolved in water (1 mL) was added and the solution stirred for 3 days at r.t. The reaction was heated for 4 h at 70° C. before removing the 1,4-dioxane under vacuum. The mixture was diluted with dilute sodium carbonate solution and the suspension was partitioned with EtOAc. The aqueous phase was separated and the organic phase extracted with dilute sodium carbonate solution and the aqueous extracts combined. 2M Aqueous hydrochloric acid solution was added to the aqueous extracts until the acid precipitated out of solution. The resulting suspension was filtered and the solids washed with 0.2 M aqueous hydrochloric acid solution and dried under vacuum to afford the title compound (890 mg, 37%) as a beige solid. δ$_H$ (400 MHz, DMSO-d₆) 13.68 (s, 1H), 11.81 (s, 1H), 3.05 (t, J 6.0 Hz, 2H), 2.49-2.45 (m, 2H), 2.19-1.98 (m, 3H), 1.02-0.91 (m, 4H). LCMS [M+H]⁺ 280.7, RT 1.452 minutes, 96.8% purity (Method 2). LCMS [M+H]⁺ 280.6, RT 0.600 minutes, 96.9% purity (Method 3).

Intermediate 77

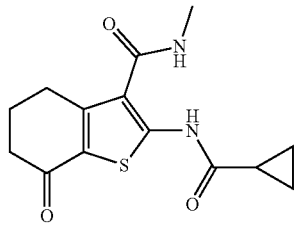 [SMILES: CNC(=O)c1c(NC(=O)C2CC2)sc2c1CCCC2=O]

2-(Cyclopropanecarbonylamino)-N-methyl-7-oxo-5,6-dihydro-4H-benzothiophene-3-carboxamide To a suspension of intermediate 76 (320 mg, 1.15 mmol) in DCM (12 mL) was added 1-hydroxybenzotriazole hydrate [123333-53-9] (263 mg, 1.72 mmol) followed by EDCl (340 mg, 1.72 mmol). After stirring for 10 minutes 2M methylamine in THF (773 mg, 1.72 mmol, 0.86 mL) was added and the reaction stirred at r.t. overnight. The reaction mixture was concentrated in vacuo and the crude residue purified by flash column chromatography on silica (gradient elution with 0-100% EtOAc in hexane) to afford the title compound (250 mg, 75%) as a yellow solid. LCMS [M+H]⁺ 293.0, RT 1.092 minutes, 94.0% purity (Method 4).

Intermediate 78

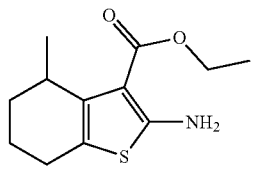 [SMILES: CCOC(=O)c1c(N)sc2c1C(C)CCC2]

Ethyl 2-amino-4-methyl-4,5,6,7-tetrahydrobenzothiophene-3-carboxylate

To a solution of 2-methylcyclohexanone [583-60-8] (1 g, 8.83 mmol) in EtOH (4 mL) was added ethyl cyanoacetate [105-56-6] (1.10 g, 9.71 mmol), sulphur [7704-34-9] (0.31 g, 9.71 mmol) and diethylamine [109-89-7] (0.973 g, 13.24 mmol). The reaction mixture was stirred at r.t. for 18 h, followed by heating at 50° C. for 7 h and then left at r.t. overnight. The solvent was removed in vacuo and the residue purified by flash column chromatography on silica (gradient elution with 0-10% EtOAc in hexane) to afford the title compound (520 mg, 25%) as a yellow solid. δ$_H$ (400 MHz, DMSO-d₆) 7.23 (s, 2H), 4.27-4.07 (m, 2H), 3.22-3.10 (m, 1H), 2.47-2.32 (m, 2H), 1.87-1.62 (m, 3H), 1.61-1.47 (m, 1H), 1.26 (t, J 7.1 Hz, 3H), 1.09 (d, J 6.7 Hz, 3H).

Intermediate 79

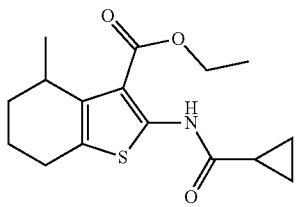 [SMILES: CCOC(=O)c1c(NC(=O)C2CC2)sc2c1C(C)CCC2]

Ethyl 2-(cyclopropanecarbonylamino)-4-methyl-4,5,6,7-tetrahydrobenzothiophene-3-carboxylate Cyclopropanecarbonyl chloride [4023-34-1] (0.22 mL, 2.4 mmol) was added to a solution of intermediate 78 (520 mg, 2.17 mmol) and DIPEA (0.75 mL, 4.3 mmol) in DCM (10 mL). The reaction mixture was stirred for 1.5 h, before diluting with DCM (10 mL) and washing with saturated aqueous sodium hydrogen carbonate solution (2×20 mL). The mixture was passed through a phase separator cartridge and the organic phase concentrated in vacuo. The crude product was dissolved into DCM and purified by flash chromatography on silica (gradient elution with 10%-40% EtOAc in iso-hexane) to afford the title compound (676 mg, 101%) as a cream coloured solid. $\delta_H$ (300 MHz, DMSO-d$_6$) 11.23 (s, 1H), 4.22-4.41 (m, 2H), 3.24-3.31 (m, 1H), 2.54-2.68 (m, 2H), 1.94-2.03 (m, 1H), 1.58-1.84 (m, 4H), 1.33 (t, 3H, J 7.1 Hz), 1.12 (d, 3H, J 6.8 Hz), 0.84-0.96 (m, 4H).

Intermediate 80

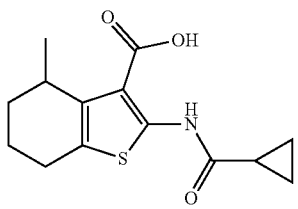

2-(Cyclopropanecarbonylamino)-4-methyl-4,5,6,7-tetrahydrobenzothiophene-3-carboxylic acid Lithium hydroxide monohydrate [1310-66-3] (236 mg, 3.15 mmol) in water (1.5 mL) was added to a solution of intermediate 79 (646 mg, 2.10 mmol) in 1,4-dioxane (7 mL). The reaction mixture was heated to 70° C. and stirred for 6.5 h, before cooling to r.t. and stirring overnight. The reaction mixture was heated to 70° C. and stirred for a further 6 h before cooling to r.t. overnight. Another portion of lithium hydroxide monohydrate [1310-66-3] (80 mg, 1.91 mmol) in water (0.5 mL) was added and the reaction mixture was heated to 70° C. for 6 h. The reaction mixture was cooled to r.t. and concentrated in vacuo before diluting with water (30 mL) and washing with DCM (2×20 mL). The aqueous phase was acidified to ~pH 5 with 2M aqueous hydrochloric acid solution. The cream solid formed was filtered off and washed with water followed by iso-hexane and was dried under vacuum to afford the title compound (454 mg, 77%) as a cream coloured solid. $\delta_H$ (400 MHz, DMSO-d$_6$) 13.12 (s, 1H), 11.60 (s, 1H), 2.51-2.65 (m, 2H), 1.88-1.95 (m, 1H), 1.66-1.82 (m, 4H), 1.58-1.63 (m, 1H), 1.12 (d, 3H, J 6.8 Hz), 0.85-0.93 (m, 4H).

Intermediate 81

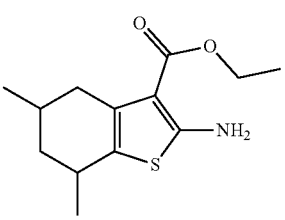 [SMILES: CCOC(=O)c1c(N)sc2c1CC(C)CC2C]

Ethyl 2-amino-5,7-dimethyl-4,5,6,7-tetrahydrobenzothiophene-3-carboxylate

Morpholine [110-91-8] (1.04 mL, 11.7 mmol) was added to a suspension of 3,5-dimethylcyclohexanone [2320-30-1] (1.12 mL, 7.76 mmol), sulfur [7704-34-9] (274 mg, 8.55 mmol) and ethyl cyanoacetate [105-56-6] (0.91 mL, 8.5 mmol) in EtOH (30 mL). The reaction was stirred at r.t. overnight. The reaction mixture was heated to 50° C. overnight followed by a further 6 h at 50° C. The reaction mixture was cooled to r.t. and stirred overnight. The mixture was concentrated in vacuo, diluted with EtOAc (20 mL) and washed with brine (2×20 mL), dried (MgSO$_4$), filtered and concentrated in vacuo. The crude product was purified by flash column chromatography on silica (gradient elution with 1%-10% EtOAc in iso-hexane) to afford the title compound (1.23 g, 63%) as a cream solid. $\delta_H$ (400 MHz, DMSO-d$_6$) 7.18 (s, 2H), 4.15 (q, 2H, J 7.1 Hz), 2.84 (dd, 1H, J 17.2, 5.0 Hz), 2.64-2.74 (m, 1H), 2.00 (ddd, 1H, J 17.4, 11.2, 3.3 Hz), 1.80-1.85 (m, 1H), 1.64-1.77 (m, 1H), 1.24 (t, 3H, J 7.1 Hz), 1.08 (d, 3H, J 6.8 Hz), 1.00 (d, 3H, J 6.5 Hz), 0.91-0.99 (m, 1H).

Intermediate 82

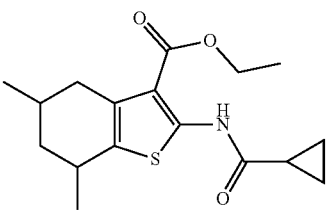 [SMILES: CCOC(=O)c1c(NC(=O)C2CC2)sc2c1CC(C)CC2C]

Ethyl 2-(cyclopropanecarbonylamino)-5,7-dimethyl-4,5,6,7-tetrahydrobenzothiophene-3-carboxylate Cyclopropanecarbonyl chloride [4023-34-1] (0.49 mL, 5.3 mmol) was added to a solution of intermediate 81 (1.23 g, 4.85 mmol) and DIPEA (1.7 mL, 9.8 mmol) in DCM (20 mL). The reaction mixture was stirred for 1.5 h, diluted with DCM (10 mL), washed with saturated aqueous sodium hydrogen carbonate solution (20 mL). The mixture was passed through a phase separator cartridge and the organic phase concentrated in vacuo to yield the crude product which was purified by flash chromatography on silica (gradient elution with 1%-10% EtOAc in iso-hexane) to afford the title compound (1.43 g, 91%) as a cream coloured solid. δ$_H$ (300 MHz, DMSO-d$_6$) 11.17 (s, 1H), 4.30 (q, 2H, J 7.1 Hz), 2.94 (dd, 1H, J 17.2, 5.0 Hz), 2.77-2.89 (m, 1H), 2.11 (ddd, 1H, J 17.1, 11.2, 3.0 Hz), 1.95-2.04 (m, 1H), 1.83-1.90 (m, 1H), 1.69-1.82 (m, 1H), 1.32 (t, 3H, J 7.1 Hz), 1.19 (d, 3H, J 6.8 Hz), 1.03 (d, 3H, J 6.6 Hz), 0.98-1.06 (m, 1H), 0.85-0.96 (m, 4H).

Intermediate 83

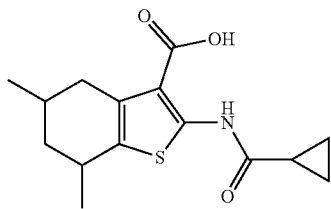 [SMILES: CC1Cc2c(sc(NC(=O)C3CC3)c2C(=O)O)C(C)C1]

2-(Cyclopropanecarbonylamino)-5,7-dimethyl-4,5,6,7-tetrahydrobenzothiophene-3-carboxylic acid Lithium hydroxide monohydrate [1310-66-3] (500 mg, 6.67 mmol) in water (5 mL) was added to a solution of intermediate 82 (1.43 g, 4.43 mmol) in 1,4-dioxane (25 mL). The reaction mixture was heated to 70° C. and stirred overnight before cooling to r.t., diluting with water (30 mL) and washing with EtOAc (2×20 mL). The aqueous phase was acidified to ~pH 5 with 2M aqueous hydrochloric acid solution. A peach coloured solid formed which was filtered off and washed with water and iso-hexane before drying in vacuo. The solid obtained was added to the EtOAc washings which were washed with the acidic aqueous phase. The acidic aqueous phase was extracted with EtOAc (20 mL) and the combined organic layers were dried (MgSO$_4$), filtered and concentrated in vacuo to a peach solid (1.40 g) which was partially dissolved in EtOAc and triturated with iso-hexane to give a cream coloured powder, which was washed with iso-hexane and dried. Trituration of the mother liquors with iso-hexane provided further compound; total title compound (1.07 g, 82%). δ$_H$ (400 MHz, DMSO-d$_6$) 13.07 (s, 1H), 11.49 (s, 1H), 2.98 (dd, 1H, J 17.3, 4.9 Hz), 2.78-2.90 (m, 1H), 2.09 (ddd, 1H, J 17.1, 11.3, 2.9 Hz), 1.90-1.99 (m, 1H), 1.83-1.89 (m, 1H), 1.69-1.82 (m, 1H), 1.18 (d, 3H, J 6.8 Hz), 0.95-1.04 (m, 1H), 1.02 (d, 3H, J 6.6 Hz), 0.85-0.93 (m, 4H).

Intermediates 84 and 85

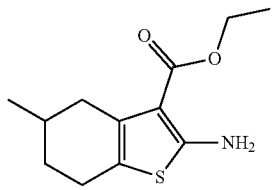

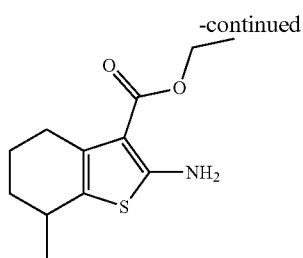

Intermediate 84

Ethyl 2-amino-5-methyl-4,5,6,7-tetrahydrobenzothiophene-3-carboxylate

Intermediate 85

Ethyl 2-amino-7-methyl-4,5,6,7-tetrahydrobenzothiophene-3-carboxylate

Morpholine [110-91-8] (1.2 mL, 14 mmol) was added to a suspension of 3-methylcyclohexanone 30 [591-24-2] (1.1 mL, 8.7 mmol), sulfur [7704-34-9] (304 mg, 9.48 mmol) and ethyl cyanoacetate [105-56-6] (1.01 mL, 9.47 mmol) in EtOH (30 mL). The reaction was stirred at r.t. for 30 minutes and was left to stir at r.t. overnight before heating at 50° C. for 5 h. The reaction mixture was cooled to r.t. and concentrated in vacuo, diluting with EtOAc (20 mL) and washing with brine (2×20 mL). The organic phase was dried (MgSO$_4$), filtered and concentrated in vacuo. The crude product was purified by flash column chromatography on silica (gradient elution with 1%-10% EtOAc in iso-hexane) to afford the title compound (1.78 g, 86%) as an off-white solid which was a 6:1 mixture of 2 compounds 5-:7-methyl isomers. Major 5-isomer intermediate 84: δ$_H$ (300 MHz, DMSO-d$_6$) 7.17 (s, 2H), 4.15 (qd, 2H, J 7.1, 0.6 Hz), 2.82 (ddd, 1H, J 17.3, 5.0, 0.7 Hz), 2.47-2.42 (m, 2H), 2.07 (ddt, 1H, J 17.2, 9.7, 2.2 Hz), 1.84-1.63 (m, 2H), 1.37-1.27 (m, 1H), 1.24 (t, 3H, J 7.1 Hz), 1.00 (d, 3H, J 6.6 Hz). Minor 7-isomer intermediate 85: δ$_H$ (300 MHz, DMSO-d$_6$) 7.19 (s, 2H), 4.14 (q, 2H, J 7.1 Hz), 2.70-2.60 (m, 2H), 1.92-1.61 (m, 3H), 1.59-1.50 (m, 1H), 1.24 (t, 3H, J 7.1 Hz), 1.10 (d, 3H, J 6.8 Hz); 1 proton is obscured.

Intermediates 86 and 87

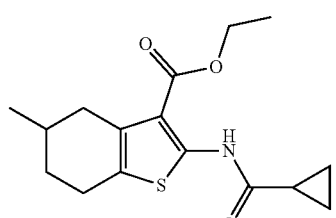

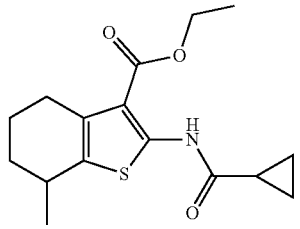

Intermediate 86

Ethyl 2-(cyclopropanecarbonylamino)-5-methyl-4,5,6,7-tetrahydrobenzothiophene-3-carboxylate

Intermediate 87

Ethyl 2-(cyclopropanecarbonylamino)-7-methyl-4,5,6,7-tetrahydrobenzothiophene-3-carboxylate Cyclopropanecarbonyl chloride [4023-34-1] (0.76 mL, 8.2 mmol) was added to a solution of a 6:1 mixture of intermediate 84 and intermediate 85 (1.78 g, 7.42 mmol) and DIPEA (2.6 mL, 15 mmol) in DCM (20 mL) and the reaction was stirred for 1.5 h. The reaction mixture was diluted with DCM (10 mL) and washed with saturated aqueous sodium hydrogen carbonate solution (20 mL). The mixture was passed through a phase separator cartridge and the organic phase concentrated in vacuo. The crude product was purified by flash column chromatography on silica (gradient elution with 1%-10% EtOAc in iso-hexane) to give the product which was recrystallized from EtOAc/iso-hexane to afford the title compound (141 mg, 0.459 mmol) as a white solid of 30:1 mixture of 5-:7-methyl isomers. The mother liquor was evaporated, re-dissolved in EtOAc, seeded with the product and allowed to crystallise overnight. The solid was washed with iso-hexane and dried under air to afford further product (0.52 g) as a white solid, ~30:1 mixture of 5-:7-methyl isomers; total 30:1 mixture of title compounds intermediates 86 and 87 (0.66 g, 29%). The mother liquors were evaporated to a cream solid (1.495 g) to give a 4:1 mixture of 5-:7-methyl isomer. Major title compound, intermediate 86: $\delta_H$ (400 MHz, DMSO-$d_6$) 11.17 (s, 1H), 4.26-4.34 (m, 2H), 2.92 (dd, 1H, J 17.2, 5.1 Hz), 2.54-2.68 (m, 2H), 2.15-2.23 (m, 1H), 1.96-2.03 (m, 1H), 1.70-1.86 (m, 2H), 1.29-1.39 (m, 1H), 1.32 (t, 3H, J 7.1 Hz), 1.03 (d, 3H, J 6.6 Hz), 0.86-0.94 (m, 4H).

Intermediates 88 and 89

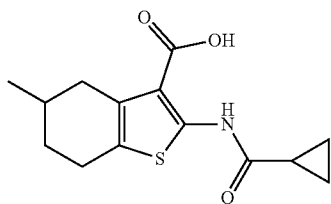

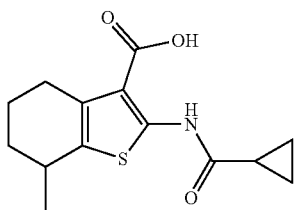

Intermediate 88

2-(Cyclopropanecarbonylamino)-5-methyl-4,5,6,7-tetrahydrobenzothiophene-3-carboxylic acid

Intermediate 89

2-(Cyclopropanecarbonylamino)-7-methyl-4,5,6,7-tetrahydrobenzothiophene-3-carboxylic acid Lithium hydroxide monohydrate [1310-66-3] (240 mg, 3.20 mmol) in water (2 mL) was added to a solution of 30:1 intermediate 86 and intermediate 87 (623 mg, 2.03 mmol) in 1,4-dioxane (12 mL). The reaction mixture was heated to 70° C. and stirred overnight. The reaction was cooled to r.t. and concentrated in vacuo to yield the crude product which was treated with water (20 mL) and EtOAc (20 mL). 2M aqueous hydrochloric acid solution was added (5 mL) and the two phases were separated. The aqueous phase was extracted with EtOAc (20 mL) and the combined organic layers were dried (Na$_2$SO$_4$), filtered and concentrated in vacuo. The solid obtained was partially dissolved in EtOAc and triturated with iso-hexane, to give a terracotta coloured powder which was washed with iso-hexane and dried under a stream of air to afford the title compound (469 mg, 82%) as a ~30:1 mixture of intermediate 88 5-Me and intermediate 89 7-Me product. Major title compound, intermediate 88: $\delta_H$ (400 MHz, DMSO-$d_6$) 13.05 (s, 1H), 11.48 (s, 1H), 2.95 (dd, 1H, J 17.3, 5.0 Hz), 2.53-2.67 (m, 2H), 2.17 (dd, 1H, J 17.1, 10.0 Hz), 1.89-1.97 (m, 1H), 1.79-1.84 (m, 1H), 1.68-1.78 (m, 1H), 1.27-1.38 (m, 1H), 1.02 (d, 3H, J 6.6 Hz), 0.84-0.93 (m, 4H).

Intermediate 90

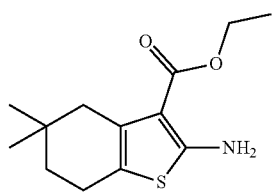 [SMILES: CCOC(=O)c1c(N)sc2c1CC(C)(C)CC2]

Ethyl 2-amino-5,5-dimethyl-6,7-dihydro-4H-benzothiophene-3-carboxylate

To a solution of 3,3-dimethylcyclohexan-1-one [2979-19-3] (500 mg, 3.96 mmoL) and ethyl cyanoacetate [105-56-6] (493 mg, 4.36 mmoL) in EtOH (15 mL) was added morpholine [110-91-8] (0.5 mL, 5.9 mmoL) followed by sulphur [7704-34-9] (140 mg, 4.4 mmoL) and the resulting suspension was stirred at r.t. under an atmosphere of nitrogen. The reaction mixture was stirred at r.t. for 20 h before heating to 50° C. for 4.5 h. The mixture was concentrated in vacuo and the residue was partitioned between EtOAc (15 mL) and water (10 mL). The layers were separated and the aqueous phase was extracted with further EtOAc (2×15 mL). The combined organic phases were washed with brine (10 mL), dried (MgSO$_4$), filtered and concentrated in vacuo. The crude material was purified by flash column chromatography on silica (gradient elution with 0 to 50% EtOAc in heptane), followed by further purification by flash column chromatography on silica (gradient elution with 0 to 100% DCM in heptane) to afford the title compound (555 mg, 55%) as an off-white solid. $\delta_H$ (500 MHz, Chloroform-d) 5.89 (s, 2H), 4.27 (q, J 7.1 Hz, 2H), 2.61-2.39 (m, 4H), 1.54 (t, 2H, partially obscured by water), 1.34 (t, J 7.1 Hz, 3H), 0.98 (s, 6H). LCMS [M+H]$^+$ 254, RT 1.51 minutes, 100% purity (Method 6).

Intermediate 91

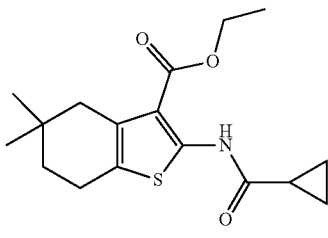 [SMILES: CCOC(=O)c1c(NC(=O)C2CC2)sc2c1CC(C)(C)CC2]

Ethyl 2-(cyclopropanecarbonylamino)-5,5-dimethyl-6,7-dihydro-4H-benzothiophene-3-carboxylate To a solution of intermediate 90 (250 mg, 0.99 mmoL) and triethylamine (0.2 mL, 1.5 mmoL) in DCM (5 mL) cooled to 0° C. was added cyclopropanecarbonyl chloride [4023-34-1] (0.12 mL, 1.28 mmoL) and the solution was stirred under an atmosphere of nitrogen. After stirring for 15 minutes the mixture was diluted with DCM (15 mL) and 1M aqueous hydrochloric acid solution (10 mL) was added. The phases were separated and the aqueous phase was extracted with further DCM (10 mL). The combined organic phases were washed with brine (10 mL), dried (MgSO$_4$), filtered and concentrated in vacuo to afford the title compound (400 mg, quantitative, 80% purity) as a light brown solid. $\delta_H$ (500 MHz, Chloroform-d) 11.46 (s, 1H), 4.34 (q, J 7.1 Hz, 2H), 2.64 (t, J 6.4 Hz, 2H), 2.55 (s, 2H), 1.69-1.61 (m, 1H), 1.59-1.50 (m, 2H, partially obscured by water peak), 1.40 (t, J 7.1 Hz, 3H), 1.17-1.10 (m, 2H), 0.98 (s, 6H), 0.95-0.88 (m, 2H). LCMS [M+H]$^+$ 322, [M+Na]$^+$344, RT 1.66 minutes, 100% purity (Method 6).

Intermediate 92

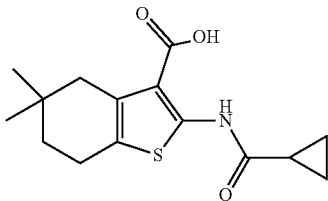 [SMILES: CC1(C)CCc2sc(NC(=O)C3CC3)c(C(=O)O)c2C1]

2-(Cyclopropanecarbonylamino)-5,5-dimethyl-6,7-dihydro-4H-benzothiophene-3-carboxylic acid To a suspension of intermediate 91 (320 mg, 1 mmoL) in 1,4-dioxane (3 mL) and water (3 mL) was added lithium hydroxide monohydrate [1310-66-3] (84 mg, 2 mmoL) and the mixture was heated to reflux. After heating for 2 h the reaction mixture was concentrated in vacuo and the residue was diluted with water (2 mL). The solution was acidified with 0.2M aqueous hydrochloric acid solution until pH 4-5 and the off-white precipitate was collected by filtration, washed with water and dried in the vacuum oven at 40° C. overnight to afford the title compound (310 mg, quantitative) as an off white solid. $\delta_H$ (250 MHz, Chloroform-d) 11.27 (s, 1H), 2.72-2.56 (m, 4H), 1.80-1.63 (m, 1H), 1.57 (t, J 6.3 Hz, 2H), 1.22-1.11 (m, 2H), 1.04-0.89 (m, 8H). LCMS [M+H]$^+$ 294, RT 1.37 minutes, 98% purity (Method 6).

Intermediate 93

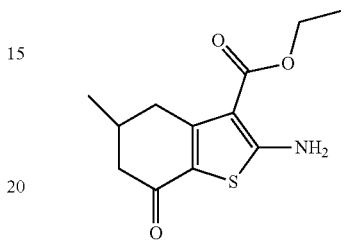

Ethyl 2-amino-5-methyl-7-oxo-5,6-dihydro-4H-benzothiophene-3-carboxylate

To a solution of 5-methylcyclohexane-1,3-dione [4341-24-6] (2.46 g, 19.5 mmol, 2.66 mL) in EtOH (10 mL) was added ethyl cyanoacetate [105-56-6] (2.42 g, 21.4 mmol), sulphur [7704-34-9] (0.69 g, 21.4 mmol) and triethylamine (2.96 g, 29.2 mmol, 4.07 mL). The reaction was stirred at r.t. for 18 h before heating at reflux for 3 days. The reaction mixture was concentrated in vacuo and the residue purified by flash column chromatography on silica (gradient elution with 0-30% EtOAc in hexane) to afford the title compound (1.28 g, 26%). $\delta_H$ (400 MHz, DMSO-d$_6$) 8.20 (s, 2H), 4.24 (q, J 7.1 Hz, 2H), 3.23 (dd, J 17.8, 3.7 Hz, 1H), 2.48-2.30 (m, 2H), 2.30-2.13 (m, 2H), 1.29 (t, J 7.1 Hz, 3H), 1.06 (d, J 5.9 Hz, 3H).

Intermediate 94

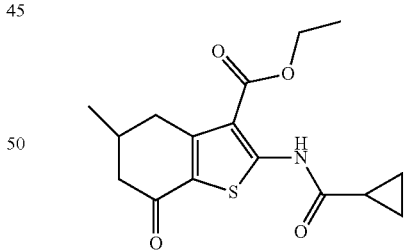

Ethyl 2-(cyclopropanecarbonylamino)-5-methyl-7-oxo-5,6-dihydro-4H-benzothiophene-3-carboxylate To a solution of intermediate 93 (1.28 g, 4.80 mmol) and triethylamine (1 mL, 7.18 mmol) in DCM (15 mL) at 0° C. was added cyclopropanecarbonyl chloride [4023-34-1] (0.6 ml, 6.61 mmol). The reaction mixture was stirred at 0° C. for 4 h, before diluting with DCM (20 mL). 1 M Aqueous hydrochloric acid (20 mL) was added and the layers were separated. The aqueous phase was extracted with further DCM (2×10 mL) and washed with water (10 mL). The organic phase was separated, dried (MgSO$_4$), filtered and concentrated in vacuo to afford the title compound (1.8 g, 99%, 85% purity) as a red/brown solid which was used in the next step without further purification. δ$_H$ (500 MHz, Chloroform-d) 11.73 (s, 1H), 4.41 (q, J 7.1 Hz, 2H), 3.41-3.28 (m, 1H), 2.63-2.57 (m, 1H), 2.54 (dd, J 17.7, 10.1 Hz, 1H), 2.41-2.32 (m, 1H), 2.27 (dd, J 16.0, 12.0 Hz, 1H), 1.70 (tq, J 8.8, 4.5 Hz, 1H), 1.43 (t, J 7.1 Hz, 3H), 1.24-1.18 (m, 2H), 1.16 (d, J 6.5 Hz, 3H), 1.06-0.96 (m, 2H).

Intermediate 95

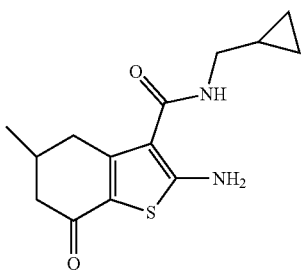 [SMILES: CC1CC(=O)c2sc(N)c(C(=O)NCC3CC3)c2C1]

2-Amino-N-(cyclopropylmethyl)-5-methyl-7-oxo-5,6-dihydro-4H-benzothiophene-3-carboxamide Intermediate 94 (85% purity, 1.8 g, 4.76 mmol) was dissolved in a solution of MeOH (10 mL) and 2M aqueous NaOH (4.5 mL) and was heated to reflux for 4 h. After cooling to r.t., the mixture was left to stand over the weekend, before addition of 4M aqueous NaOH (1.25 mL) and the mixture was heated to reflux for 4 h. The reaction mixture was allowed to cool to r.t. and the MeOH was removed in vacuo. The reaction mixture was acidified with 1 M aqueous hydrochloric acid solution and the product was extracted with EtOAc (2×20 mL). The combined organic phases were washed with water (10 mL), dried (MgSO$_4$), filtered and concentrated in vacuo to afford 2-amino-5-methyl-7-oxo-5,6-dihydro-4H-benzothiophene-3-carboxylic acid (1.4 g, 78%) as a dark brown solid which was used directly in the next step without further purification.

EDCl (640 mg, 3.34 mmol) was added to a solution of 1-cyclopropylmethanamine [2516-47-4] (0.29 mL, 3.34 mmol) and 2-amino-5-methyl-7-oxo-5,6-dihydro-4H-benzothiophene-3-carboxylic acid (500 mg, 2.22 mmol) in DCM (25 mL). The solution was stirred at r.t. for 16 h, before addition of 1-cyclopropylmethanamine [2516-47-4] (0.29 mL, 3.34 mmol) followed by EDCl (640 mg, 3.34 mmol) and stirring for a further 4 h. The reaction mixture was diluted with DCM and poured into 1 M aqueous hydrochloric acid solution (20 mL). The organic phase was dried (MgSO$_4$), filtered and concentrated in vacuo to give the crude product which was purified by flash column chromatography on silica (gradient elution with 30-80% EtOAc/Heptane) to afford the title compound (210 mg, 27%, 80% purity) as a bright yellow solid. δ$_H$ (500 MHz, Chloroform-d) 5.67 (s, 1H), 3.30-3.24 (m, 2H), 3.05 (dd, J 15.3, 3.9 Hz, 1H), 2.61 (d, J 15.4 Hz, 1H), 2.54-2.38 (m, 2H), 2.36-2.26 (m, 1H), 1.19 (d, J 6.4 Hz, 3H), 1.07 (m, 1H), 0.58 (m, 2H), 0.28 (q, J 4.9 Hz, 2H).

Intermediate 96

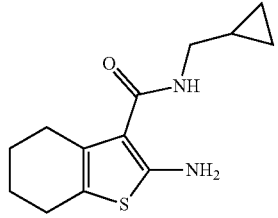 [SMILES: Nc1sc2c(c1C(=O)NCC1CC1)CCCC2]

2-Amino-N-(cyclopropylmethyl)-4,5,6,7-tetrahydrobenzothiophene-3-carboxamide

To a solution of N1-cyclopropylmethyl-2-cyanoacetamide [114153-25-2] (98%, 660 mg, 4.68 mmol) and cyclohexanone [108-94-1] (0.53 ml, 5.11 mmol) in EtOH (20 mL) was added morpholine [110-91-8] (0.61 ml, 7.05 mmol) and sulphur [7704-34-9] (165 mg, 5.15 mmol). The yellow reaction mixture was stirred over the weekend at r.t., before heating to 60° C. for 4 h and then 50° C. for 16 h. The solvent was removed in vacuo and the residue dissolved in EtOAc (30 mL) and washed with water (2×10 mL) followed by brine (10 mL). The organic phase was dried (MgSO$_4$), filtered and concentrated in vacuo. The crude residue was purified by flash column chromatography on silica (gradient elution with 30-60% EtOAc/heptane) followed by purification by flash column chromatography on silica (gradient elution with 0-3% MeOH) to afford the title compound (400 mg, 27%) as a yellow solid, the material was used without further purification in the next step. TLC (1:1 EtOAc/heptane) DP R$^f$=0.34. δ$_H$ (500 MHz, DMSO-d$_6$) 6.79 (t, J 5.6 Hz, 1H), 6.59 (s, 2H), 3.10-3.03 (m, 2H), 2.58 (t, J 5.7 Hz, 2H), 2.45 (t, J 5.8 Hz, 2H), 1.78-1.62 (m, 4H), 1.05-0.95 (m, 1H), 0.43-0.36 (m, 2H), 0.22-0.16 (m, 2H).

Intermediate 97

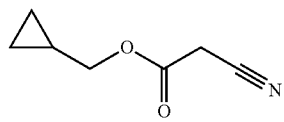

Cyclopropylmethyl 2-cyanoacetate

Cyanoacetic acid [372-09-8] (1.00 g, 12 mmol) was dissolved in cyclopropanemethanol [2516-33-8](4.20 g, 58 mmol) and hydrochloric acid (42 mg, 1.2 mmol) was added. The reaction mixture was stirred at r.t. for 16 h. The mixture was heated to 90° C. for 2 h before cooling to r.t. and concentrating in vacuo. The crude product was partitioned between water and EtOAc, the organic phase was washed with saturated sodium hydrogen carbonate and brine. The organic layer was concentrated in vacuo to afford the title compound (1.58 g, 98%) as a pale yellow oil. δ$_H$ (300 MHz, DMSO-d$_6$) 4.03 (s, 2H), 3.96 (d, J 7.3 Hz, 2H), 1.16-1.02 (m, 1H), 0.58-0.49 (m, 2H), 0.34-0.25 (m, 2H).

Intermediate 98 and 99

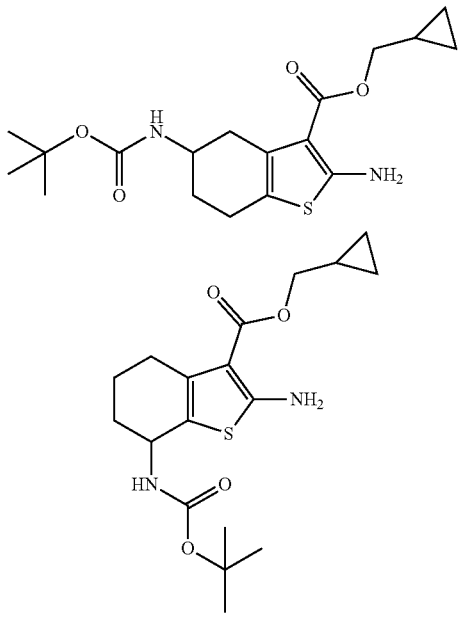

Cyclopropylmethyl 2-amino-5-(tert-butoxycarbonylamino)-4,5,6,7-tetrahydrobenzothiophene-3-carboxylate

Cyclopropylmethyl 2-amino-7-(tert-butoxycarbonylamino)-4,5,6,7-tetrahydrobenzothiophene-3-carboxylate 3-N-Boc-aminocyclohexanone [885280-38-6] (2.55 g, 11.4 mmol) was dissolved in 1,4-dioxane (20 mL). Intermediate 97 (1.58 g, 11.4 mmol), morpholine [110-91-8] (1.50 g, 17.0 mmol) and sulphur [7704-34-9] (0.40 g, 12.5 mmol) was added and the reaction mixture was stirred at r.t. for 2 h. The mixture was heated at 60° C. for ~3 h, then at r.t. overnight, followed by heating at 70° C. for a further 4 h, then at r.t. overnight. The mixture was concentrated in vacuo and the residue purified by flash column chromatography on silica (gradient elution with 5-50% EtOAc/hexane) to afford title compound 5-isomer intermediate 98 (2.34 g, 56%) and title compound 7-isomer intermediate 99 (0.73 g, 18%). Title compound intermediate 98: LCMS [M+H]$^+$ 367.2, [M+Na]$^+$389.2, RT 2.424 minutes, 88.8% purity (Method 1). Title compound intermediate 99: $\delta_H$ (400 MHz, DMSO-d$_6$) 7.38-7.05 (m, 3H), 4.44 (s, 1H), 3.97 (dd, J 7.3, 3.3 Hz, 2H), 2.58 (s, 2H), 1.96-1.74 (m, 2H), 1.69-1.57 (m, 2H), 1.40 (d, J 3.89 Hz, 9H), 1.22-1.09 (m, 1H), 0.58-0.43 (m, 2H), 0.38-0.23 (m, 2H).

Intermediate 100

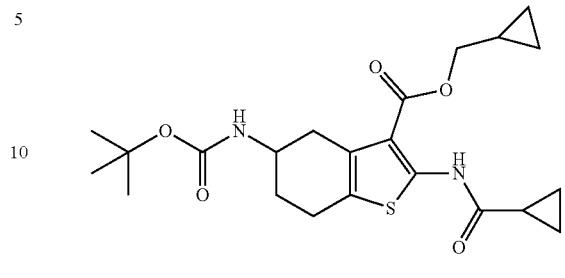

Cyclopropylmethyl 5-(tert-butoxycarbonylamino)-2-(cyclopropanecarbonylamino)-4,5,6,7-tetrahydrobenzothiophene-3-carboxylate Intermediate 98 (2.34 g, 6.37 mmol) was dissolved in DCM (50 mL) and DIPEA (1.65 g, 12.75 mmol) and cyclopropanecarbonyl chloride [4023-34-1] (0.75 g, 7.01 mmol) were added. The reaction mixture was stirred at r.t. for ~4 h. The reaction mixture was washed with water and brine, passed through a phase separation cartridge, and the organic layer was concentrated in vacuo. The residue was purified by flash column chromatography on silica (gradient elution with 5-50% EtOAc/hexane) to afford the product an off white solid which was recrystallised from EtOAc/hexane to afford the title compound (1.8 g, 65%) as white needles. LCMS [M+H]$^+$ 435.2, RT 2.968 minutes, 100.0% purity (Method 3). LCMS [M+H]$^+$ 435.2, RT 2.945 minutes, 100.0% purity (Method 2).

Intermediate 101

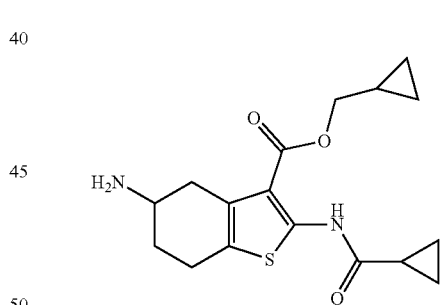

Cyclopropylmethyl 5-amino-2-(cyclopropanecarbonylamino)-4,5,6,7-tetrahydrobenzothiophene-3-carboxylate Intermediate 100 (1.80 g, 4.14 mmol) was dissolved in DCM (12 mL) and TFA (11.95 g, 104.8 mmol) was added. The reaction mixture was stirred at r.t. for 1 h before concentrating in vacuo. The residue was partitioned between 5% MeOH/DCM and saturated sodium hydrogen carbonate solution. The organic phase was washed with brine, passed through a phase separation cartridge and the organic layer was concentrated in vacuo to afford the title compound (1.40 g, 101%). LCMS [M+H]$^+$ 335.0, RT 1.402 minutes, 100.0% purity (Method 4).

Intermediates 102 and 24

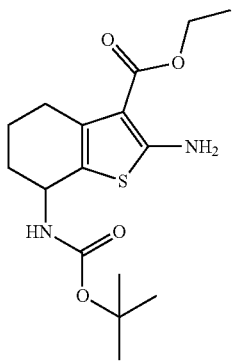

Intermediate 102

Ethyl 2-amino-7-(tert-butoxycarbonylamino)-4,5,6,7-tetrahydrobenzothiophene-3-carboxylate Intermediate 102a Ethyl 2-amino-5-(tert-butoxycarbonylamino)-4,5,6,7-tetrahydrobenzothiophene-3-carboxylate To a mixture of tert-butyl N-(3-oxocyclohexyl)carbamate [885280-38-6] (4 g, 18.7 mmol), sulphur [7704-34-9] (0.722 g, 22.5 mmol) and ethyl cyanoacetate [105-56-6] (2.75 g, 24 mmol) in EtOH (40 mL) was added triethylamine (5.22 ml, 37.5 mmol). After stirring at r.t. for 16 h the reaction mixture was concentrated in vacuo. To the residue was added water and the mixture was extracted with EtOAc. The combined organic phases were washed with brine, dried (MgSO$_4$), filtered and concentrated in vacuo and the residue was purified by flash column chromatography on silica (gradient elution with 5% to 40% EtOAc in heptane) to afford the 7-isomer title compound intermediate 102 (700 mg, 11%) and the 5-isomer title compound intermediate 102a (4.5 g, 70%) as white solids. 7-Isomer title compound intermediate 102: $\delta_H$ (500 MHz, CD$_3$OD) 4.29-4.16 (m, 2H), 3.75-3.65 (m, 1H), 3.10 (dd, J 17.0, 5.0 Hz, 1H), 2.66-2.51 (m, 2H), 2.44 (dd, J 17.1, 9.2 Hz, 1H), 2.05-1.93 (m, 1H), 1.73-1.63 (m, 1H), 1.46 (s, 9H), 1.32 (t, J 7.1 Hz, 3H). LCMS [M+H]$^+$ 341.10, [M+Na]$^+$361.10, RT 1.35 minutes, 100% purity (Method 6). 5-Isomer title compound intermediate 102a: $\delta_H$ (500 MHz, CD$_3$OD) 4.58-4.48 (m, 1H), 4.22 (q, J 7.1 Hz, 2H), 2.76-2.58 (m, 2H), 2.01-1.92 (m, 1H), 1.92-1.80 (m, 1H), 1.77-1.64 (m, 2H), 1.46 (s, 9H), 1.32 (t, J 7.1 Hz, 3H). LCMS [M+H]$^+$ 341, [M+Na]$^+$363.10, RT 1.38 minutes, 98% purity (Method 6).

Intermediate 103

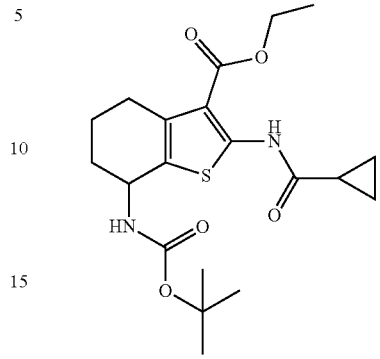

Ethyl 7-(tert-butoxycarbonylamino)-2-(cyclopropanecarbonylamino)-4,5,6,7-tetrahydrobenzothiophene-3-carboxylate To a solution of mixture of intermediate 102 (710 mg, 2.08 mmol) and DIPEA (0.72 ml, 4.17 mol) in DCM (20 mL) at 0° C. was added cyclopropanecarbonyl chloride [4023-34-1] (0.28 mL, 3.12 mmol). The reaction mixture was stirred at r.t. for 2 h before diluting with DCM (30 mL). Water (20 mL) was added and the layers were separated, extracted with DCM (2×10 mL) and washed 0.5 M aqueous hydrochloric acid solution (20 mL), saturated sodium hydrogen carbonate solution (20 mL) and brine. The organic phase was separated, dried (MgSO$_4$), filtered and concentrated in vacuo to afford the title compound (850 mg, 100%) as a pale yellow solid which was used in the next step without further purification. $\delta_H$ (500 MHz, CD$_3$OD) 4.73-4.67 (m, 1H), 4.36 (q, J 7.1 Hz, 2H), 2.85-2.71 (m, 2H), 2.06-1.89 (m, 2H), 1.86-1.80 (m, 1H), 1.79-1.68 (m, 2H), 1.47 (s, 9H), 1.38 (t, J 7.1 Hz, 3H), 1.05-1.01 (m, 2H), 1.00-0.95 (m, 2H). LCMS [M+Na]$^+$431.10, RT 1.56 minutes, 92% purity (Method 6).

Intermediate 104

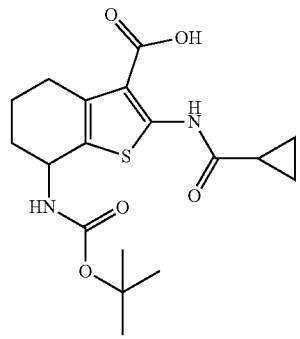 [SMILES: CC(C)(C)OC(=O)NC1CCCc2c1sc(NC(=O)C1CC1)c2C(=O)O]

7-(tert-Butoxycarbonylamino)-2-(cyclopropanecarbonylamino)-4,5,6,7-tetrahydrobenzothiophene-3-carboxylic acid Intermediate 103 (850 mg, 2.08 mmol) was dissolved in 1,4-dioxane (20 mL) and 2M lithium hydroxide monohydrate [1310-66-3] (2.6 mL, 5.2 mmol) was added. The reaction mixture was heated at 90° C. for 2 h. 1,4-Dioxane was removed in vacuo and the residue was acidified with 0.5 M aqueous hydrochloric acid solution. The resulting solid was filtered off to afford the title compound (710 mg, 90%) which was dried and utilised in the following step without further purification. $\delta_H$ (500 MHz, CD$_3$OD) 4.75-4.61 (m, 1H), 2.90-2.74 (m, 2H), 2.09-1.86 (m, 2H), 1.84-1.65 (m, 3H), 1.47 (s, 9H), 1.06-0.91 (m, 4H). LCMS [M+Na]$^+$ 403.05, RT 1.3 minutes, 95% purity (Method 6).

Intermediates 105 and 106

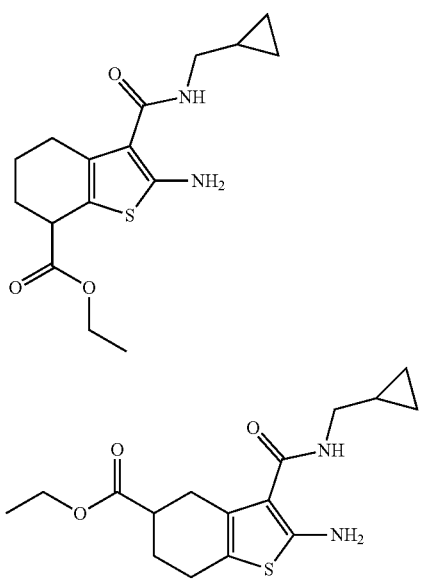 [SMILES: CCOC(=O)C1CCCc2c1sc(N)c2C(=O)NCC1CC1 ; CCOC(=O)C1CCc2sc(N)c(C(=O)NCC3CC3)c2C1]

Intermediate 105

Ethyl 2-amino-3-(cyclopropylmethylcarbamoyl)-4,5,6,7-tetrahydrobenzothiophene-7-carboxylate Intermediate 106

Ethyl 2-amino-3-(cyclopropylmethylcarbamoyl)-4,5,6,7-tetrahydrobenzothiophene-5-carboxylate To a mixture of ethyl 3-oxocyclohexanecarboxylate [33668-25-6] (1.50 g, 8.81 mmol), sulphur [7704-34-9] (367 mg, 11.4 mmol) and N1-cyclopropylmethyl-2-cyanoacetamide [114153-25-2] (1.46 g, 10.58 mmol) in EtOH (15 mL) was added triethylamine (2.45 ml, 17.63 mmol). The reaction mixture was stirred at r.t. for 5 h before heating at 60° C. for 24 h. The reaction mixture was concentrated in vacuo, water was added and the solution was extracted with EtOAc. The combined organic layers were washed with brine, dried (MgSO$_4$), filtered and concentrated in vacuo. The residue was purified by flash column chromatography on silica (gradient elution with 5% to 70% EtOAc in heptane) to afford the title compounds (653 mg, 23%) as a mixture of regioisomers (5-isomer intermediate 106 and 7-isomer intermediate 105 in a ratio of 80:20). LCMS [M+H]$^+$ 323.05, RT 1.25 minutes (Method 6). Intermediates 105 and 106 co-run by LCMS, but are both observable by $^1$H NMR.

Intermediates 107 and 108

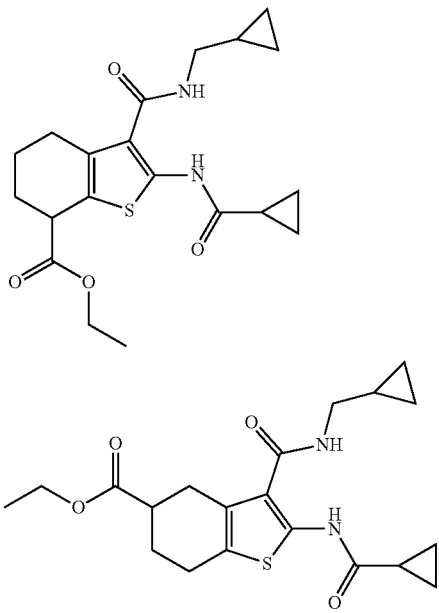 [SMILES: CCOC(=O)C1CCCc2c1sc(NC(=O)C1CC1)c2C(=O)NCC1CC1 ; CCOC(=O)C1CCc2sc(NC(=O)C3CC3)c(C(=O)NCC3CC3)c2C1]

Intermediate 107

Ethyl 2-(cyclopropanecarbonylamino)-3-(cyclopropylmethylcarbamoyl)-4,5,6,7-tetrahydrobenzothiophene-7-carboxylate Intermediate 108

Ethyl 2-(cyclopropanecarbonylamino)-3-(cyclopropylmethylcarbamoyl)-4,5,6,7-tetrahydrobenzothiophene-5-carboxylate To a solution of mixture of intermediates 105 and 106 (20:80 ratio) (653 mg, 2.02 mmol) and DIPEA (0.71 mL, 4.05 mmol) in DCM (30 mL) at 0° C. was added cyclopropanecarbonyl chloride [4023-34-1](0.28 mL, 3.08 mmol). The reaction was stirred at r.t. for 2 h before diluting with DCM (50 mL). Water (50 mL) was added and the layers were separated. The aqueous phase was extracted with DCM (2×50 mL) and washed with 0.5 M aqueous hydrochloric acid solution (50 mL), saturated sodium hydrogen carbonate solution (50 mL) and brine. The organic layer was separated, dried (MgSO$_4$), filtered and concentrated in vacuo to give a pale yellow solid as a mixture of regio-isomers which was purified by flash column chromatography on silica (gradient elution with 55 to 50% EtOAc in heptane) to afford the title compounds as a mixture of 80% 5-isomer intermediate 108, 20% 7-isomer intermediates 107 (600 mg, 76%) as a white solid. LCMS [M+H]$^+$ 391.0, RT 1.40 minutes, 100% purity (Method 6).

Intermediates 109 and 110

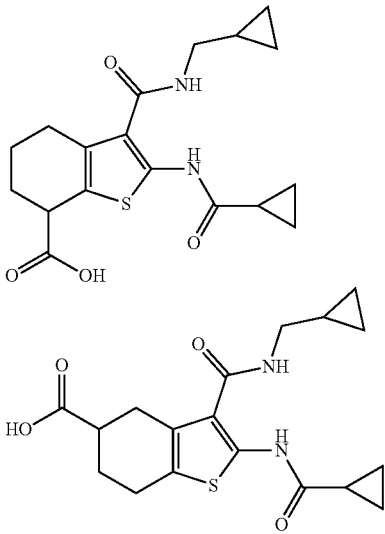

Intermediate 109

2-(Cyclopropanecarbonylamino)-3-(cyclopropylmethylcarbamoyl)-4,5,6,7-tetrahydrobenzothiophene-7-carboxylic acid Intermediate 110

2-(Cyclopropanecarbonylamino)-3-(cyclopropylmethylcarbamoyl)-4,5,6,7-tetrahydrobenzothiophene-5-carboxylic acid Intermediate 107 and intermediate 108 (20:80 ratio) (600 mg, 1.53 mmol) was dissolved in THF (10 mL) then 2M aqueous lithium hydroxide solution [1310-66-3] (2.3 mL, 4.6 mmol) was added. The reaction mixture was stirred at r.t. for 20 h and the THF was removed in vacuo. The residue was acidified with 1M aqueous hydrochloric acid solution and the resulting solid (75% 5-isomer intermediate 110 and 22% 7-isomer intermediate 109) was filtered off and dried. The mixture was separated by preparative HPLC to afford the 5-isomer title compound intermediate 110 (218 mg, 49%) and the 7-isomer title compound intermediate 109 (58.5 mg, 12%) with 92% purity containing 6% of the 5-isomer title compound intermediate 110. 5-Isomer title compound intermediate 110: LCMS [M+H]$^+$ 363.1, RT 2.78 minutes, 100% purity (Method 10). 7-Isomer title compound intermediate 109: LCMS [M+H]$^+$ 363.1, RT 2.90 minutes, 92% purity, 6% 5-regiosisomer present (Method 10).

Intermediate 111

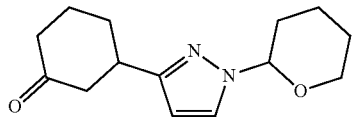 [SMILES: O=C1CCCC(c2ccn(C3CCCCO3)n2)C1]

3-(1-Tetrahydropyran-2-ylpyrazol-3-yl)cyclohexanone

Hydroxy(cyclooctadiene)rhodium(I) dimer [73468-85-6] (12 mg, 0.025 mmol) and degassed 1,4-dioxane (1.2 mL) was stirred for 15 minutes at r.t. Potassium phosphate tribasic [7778-53-2] (4 mmol, 2 mL) was added and the mixture was stirred for 15 minutes. 2-Cyclohexen-1-one [930-68-7](1.01 mmol, 100 mg) and 1-(tetrahydro-2H-pyran-2-yl)-3-pyrazole boronic acid mida ester (1.21 mmol, 383 mg) were added and the mixture was stirred at 60° C. overnight. The mixture was warmed at 70° C. overnight. The mixture was concentrated in vacuo and the crude product in water was extracted with Et$_2$O (2×3 mL) and DCM (2×3 mL). The organic phases were combined and concentrated in vacuo to yield the crude product which was purified by preparative TLC (silica plate) (elution with hexane/EtOAc 6/4). Extraction of the compound with EtOAc (100 mL) gave the title compound (22 mg, 8.7%) as a yellow oil. GCMS [M+H]$^+$ 248.96, RT 14.31 minutes.

Intermediate 112

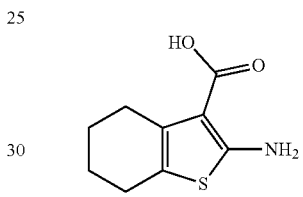

2-Amino-4,5,6,7-tetrahydrobenzothiophene-3-carboxylic acid

2M Aqueous NaOH solution (91 mL, 182 mmol) was added to a suspension of 2-amino-4,5,6,7-tetrahydro-benzo[B]thiophene-3-carboxylic acid methyl ester [108354-78-5] (13.1 g, 60.8 mmol) in EtOH (100 mL). The reaction mixture was heated to 60° C. and stirred for 4 h. The temperature was raised to 80° C. (reflux) and the reaction was stirred overnight. The reaction was left stirring at 80° C. for a further 7 h and was then cooled to r.t. and stirred overnight. The reaction mixture was concentrated in vacuo to remove the EtOH. The aqueous solution was washed with DCM (3×200 mL) and then acidified to pH 2 with concentrated hydrochloric acid. A brown solid was formed which was filtered off, washed with water, then hexane and dried to afford the title compound (7.55 g, 63%) as a dark brown solid. $\delta_H$ (400 MHz, DMSO-d$_6$) 11.8 (br. s, 1H), 7.16 (s, 2H), 2.57-2.61 (m, 2H), 2.40-2.44 (m, 2H), 1.63-1.72 (m, 4H).

Intermediate 113

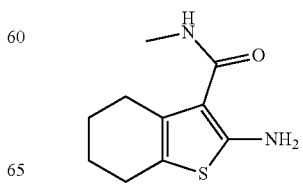

2-Amino-N-methyl-4,5,6,7-tetrahydrobenzothiophene-3-carboxamide

EDCl (5.0 g, 26 mmol) was added to a solution of intermediate 112 (4 g, 20.28 mmol), 1-hydroxybenzotriazole hydrate (3.52 g, 22.3 mmol), DIPEA (14.5 mL, 83.2 mmol) and 2M solution of methylamine in THF (31 mL, 62 mmol) in DMF (100 mL) and the reaction was stirred overnight. The reaction mixture was concentrated in vacuo and the residue was partitioned between EtOAc (100 mL) and water (100 mL) and the organic layer was separated. The organic layer was washed with brine (2×100 mL), filtered to remove an insoluble dark brown solid, dried ($Na_2SO_4$), filtered and concentrated in vacuo. The crude product was dissolved in DCM and purified by flash column chromatography on silica (gradient elution with 10%-40% EtOAc in iso-hexane). The product was recrystallised from EtOAc/iso-hexane to afford the title compound (1.32 g, 31%) as a brown solid. $\delta_H$ (300 MHz, DMSO-$d_6$) 6.67-6.73 (m, 1H), 6.64 (s, 2H), 2.68 (d, J 4.6 Hz, 3H), 2.53-2.58 (m, 2H), 2.42-2.47 (m, 2H), 1.62-1.74 (m, 4H).

Intermediate 114

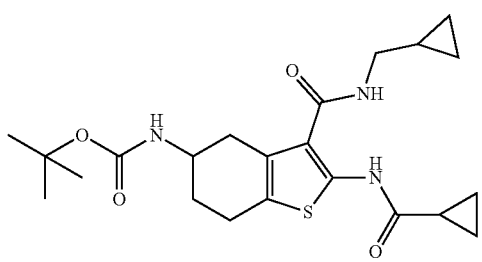 [SMILES: CC(C)(C)OC(=O)NC1CCc2sc(NC(=O)C3CC3)c(C(=O)NCC3CC3)c2C1]

tert-Butyl N-[2-(cyclopropanecarbonylamino)-3-(cyclopropylmethylcarbamoyl)-4,5,6,7-tetrahydrobenzothiophen-5-yl]carbamate To a stirred solution of intermediate 26 (12 g, 31.6 mmol) and cyclopropylmethanamine [2516-47-4](3.36 g, 47.4 mmol) in DCM (80 mL) was added triethylamine (9.57 g, 94.7 mmol) and EDCl (15.2 g, 78.9 mmol) and the reaction mixture was stirred at r.t. for 20 h. The reaction mixture was quenched with water and extracted with DCM. The organic phase was separated, washed with brine, dried ($Na_2SO_4$, filtered and concentrated in vacuo. The crude product obtained was purified by flash column chromatography on silica (elution with 10% EtOAc/n-hexane) to afford the title compound (5.5 g, 40%). $\delta_H$ (400 MHz, Chloroform-d) 12.16 (s, 1H), 5.89 (s, 1H), 4.70 (s, 1H), 4.10 (s, 1H), 3.33-3.20 (m, 2H), 3.14 (dd, J 14.6, 5.0 Hz, 1H), 2.77 (d, J 17.3 Hz, 2H), 2.62-2.57 (m, 1H), 2.04-2.02 (m, 1H), 1.90-1.84 (m, 1H), 1.73-1.60 (m, 1H), 1.48 (s, 9H), 1.46-1.36 (m, 1H), 1.04-0.96 (m, 2H), 0.90-0.89 (m, 2H), 0.61-0.57 (m, 2H), 0.28-0.23 (m, 2H).

Intermediate 115 and 116

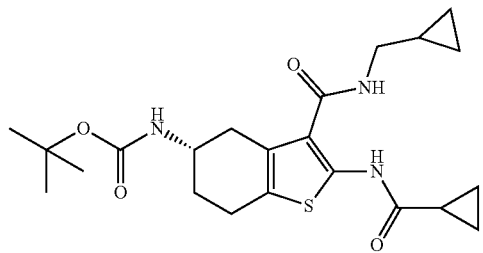

Intermediate 115 tert-Butyl N-[(5S)-2-(cyclopropanecarbonylamino)-3-(cyclopropylmethylcarbamoyl)-4,5,6,7-tetrahydrobenzothiophen-5-yl]carbamate

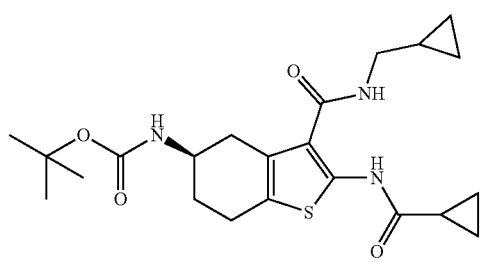

Intermediate 116 tert-Butyl N-[(5R)-2-(cyclopropanecarbonylamino)-3-(cyclopropylmethylcarbamoyl)-4,5,6,7-tetrahydrobenzothiophen-5-yl]carbamate Intermediate 114 (250 g) was separated by chiral preparative HPLC (Chiralpak AD, 50×252 mm, 30° C. 360 ml/min, $CO_2$+35% MeOH) to afford the two enantiomers Intermediate 115 (126 g) and Intermediate 116 (122 g). Intermediate 115 contained 2% impurity of tert-butyl N-[(5S)-2-(cyclopropanecarbonylamino)-3-(isobutylcarbamoyl)-4,5,6,7-tetrahydrobenzothiophen-5-yl]carbamate resulting from a 2-methylpropan-1-amine impurity in the cyclopropylmethanamine used in the preparation of Intermediate 114.

Intermediate 115 $\delta_H$ (300 MHz, DMSO-$d_6$) 11.06 (s, 1H), 7.70 (t, J 5.6 Hz, 1H), 6.94 (d, J 7.5 Hz, 1H), 3.60 (s, 1H), 3.13 (ddq, J 19.8, 13.4, 6.6, 6.0 Hz, 2H), 2.88 (dd, J 16.1, 5.1 Hz, 1H), 2.79-2.58 (m, 2H), 2.48-2.39 (m, 1H), 1.98-1.82 (m, 2H), 1.80-1.57 (m, 1H), 1.39 (s, 9H), 1.14-0.93 (m, 1H), 0.90-0.70 (m, 4H), 0.48-0.34 (m, 2H), 0.30-0.15 (m, 2H). LCMS [M+H]$^+$ 434.0, RT 2.43 minutes (Method 2). LCMS [M+H]$^+$ 434.0, RT 2.37 minutes (Method 3). Intermediate 116 LCMS [M+H]$^+$ 434.0, RT 2.44 minutes (Method 2). LCMS [M+H]$^+$ 434.0, RT 2.36 minutes (Method 3).

Intermediate 117

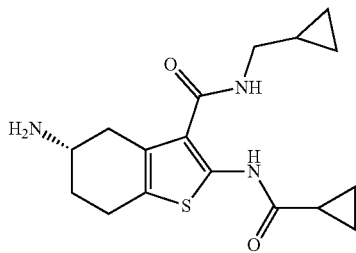 [SMILES: N[C@H]1CCc2sc(NC(=O)C3CC3)c(C(=O)NCC3CC3)c2C1]

(5S)-5-Amino-2-(cyclopropanecarbonylamino)-N-(cyclopropylmethyl)-4,5,6,7-tetrahydrobenzothiophene-3-carboxamide To a stirred solution of intermediate 115 (20 g, 43.1 mmol) in DCM (100 mL) was added TFA (67 ml, 876 mmol) dropwise over 15 minutes, keeping the temperature below 25° C. The reaction mixture was stirred at r.t. for a further 15 minutes. Toluene (120 mL) was added and the solvent was removed in vacuo. EtOAc (40 mL) was added to the residue followed by diisopropyl ether (1.4 L) leading to the precipitation of the product. The slurry was stirred at r.t. for a further 15 minutes and the precipitate was collected by filtration. The filter cake was rinsed with diisopropyl ether (180 mL) and Et$_2$O (180 mL) and dried under a flow of nitrogen for 15 minutes to yield the crude product (25.4 g) as a beige solid. The precipitate was dissolved in water (800 mL) containing TFA (4 mL) and Et$_2$O (200 mL) and EtOAc (20 mL) were added. The aqueous phase was separated and washed with Et$_2$O (100 mL). Potassium carbonate (10.2 g, 36.9 mmol) was added and the aqueous phase extracted with EtOAc (2×400 mL). The aqueous phase was saturated with sodium chloride (250 g) and then further extracted with EtOAc (400 mL). The organic extracts were combined, dried (Na$_2$SO$_4$), filtered and the solvent removed in vacuo to afford the title compound (14.8 g, 93%) as a beige solid. $\delta_H$ (500 MHz, Chloroform-d) 12.07 (s, 1H), 6.01 (t, J 5.0 Hz, 1H), 3.34-3.23 (m, 3H), 3.04 (dd, J 14.5, 4.8 Hz, 1H), 2.86-2.57 (m, 4H), 2.53 (dd, J 14.5, 8.2 Hz, 1H), 2.08-2.01 (m, 1H), 1.79-1.69 (m, 1H), 1.69-1.62 (m, 1H), 1.12-1.03 (m, 3H), 0.91-0.85 (m, 2H), 0.61-0.50 (m, 2H), 0.32-0.21 (m, 2H).

Intermediate 118

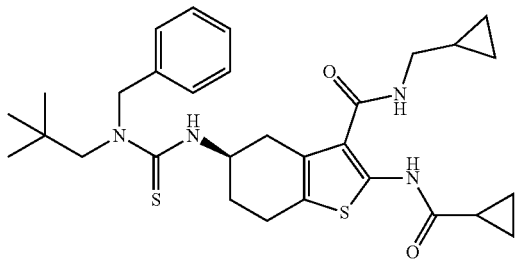 [SMILES: CC(C)(C)CN(Cc1ccccc1)C(=S)N[C@@H]1CCc2sc(NC(=O)C3CC3)c(C(=O)NCC3CC3)c2C1]

(5S)-5-[[Benzyl(2,2-dimethylpropyl)carbamothioyl]amino]-2-(cyclopropanecarbonylamino)-N-(cyclopropylmethyl)-4,5,6,7-tetrahydrobenzothiophene-3-carboxamide To a solution of intermediate 117 (400 mg, 1.20 mmol) in DCM (20 mL) was added DIPEA (234 mg, 1.80 mmol) and phenyl chlorothionocarbonate [1005-56-7] (230 mg, 1.32 mmol). The reaction mixture was stirred for 2 h. DIPEA (239 mg, 1.84 mmol) and N-benzyl-2,2-dimethyl-propan-1-amine (217 mg, 1.23 mmol) were added and the reaction was stirred for 18 h. Water (10 mL) was added to the reaction mixture and the organic layer was separated and passed through a phase separator column. The organic phase was concentrated in vacuo to yield a yellow solid which was purified by flash column chromatography on silica (gradient elution with 0-45% EtOAc/iso-hexane) to afford the title compound (539 mg, 80%) as a yellow foam. LCMS [M+H]$^+$ 553.0, RT 3.339 minutes, purity 77% (Method 1).

Intermediate 119

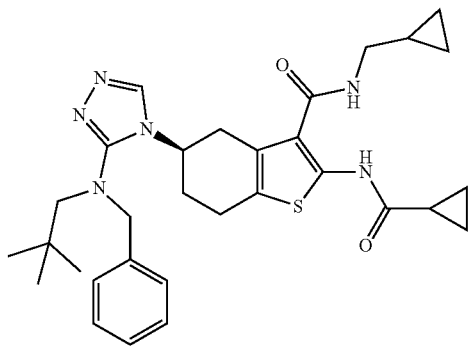 [SMILES: CC(C)(C)CN(Cc1ccccc1)c1nncn1[C@@H]1CCc2sc(NC(=O)C3CC3)c(C(=O)NCC3CC3)c2C1]

(5S)-5-[3-[Benzyl(2,2-dimethylpropyl)amino]-1,2,4-triazol-4-yl]-2-(cyclopropanecarbonylamino)-N-(cyclopropylmethyl)-4,5,6,7-tetrahydrobenzothiophene-3-carboxamide Intermediate 118 (516 mg, 0.93 mmol) was dissolved in DMF (10 mL) and formic acid hydrazide [624-84-0] (125 mg, 1.87 mmol) was added followed by mercuric chloride [7487-94-7] (507 mg, 1.87 mmol) and finally triethylamine (190 mg, 1.87 mmol). The reaction mixture was stirred for 2 minutes at r.t. and then heated at 60° C. for 3 h. The mixture was cooled and diluted with MeCN (10 mL) and then filtered through a plug of Celite. The Celite pad was washed with excess MeCN (20 mL) and the filtrate was combined and concentrated in vacuo to give a yellow oil. The crude material was purified by flash column chromatography on silica (gradient elution with 0-5% MeOH/EtOAc) to afford the title compound (150 mg, 29%) as a white solid. LCMS [M+H]$^+$ 561.0, RT 2.936 minutes (Method 1).

Intermediate 120

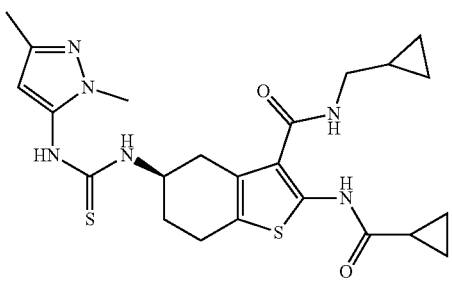 [SMILES: Cc1cc(NC(=S)N[C@@H]2CCc3sc(NC(=O)C4CC4)c(C(=O)NCC4CC4)c3C2)n(C)n1]

(5S)-2-(Cyclopropanecarbonylamino)-N-(cyclopropylmethyl)-5-[(2,5-dimethylpyrazol-3-VI)carbamothioylamino]-4,5,6,7-tetrahydrobenzothiophene-3-carboxamide To a stirred solution of intermediate 117 (33.7 g, 101 mmol) in DCM (300 mL) was added DIPEA (27 mL, 150 mmol) followed by 5-isothiocyanato-1,3-dimethyl-1H-pyrazole [205246-65-7] (23 g, 150 mmol) in DCM (50 mL) and the reaction mixture was stirred at r.t. for 17 h. The reaction mixture was concentrated in vacuo to yield the crude product as a tan solid which was stirred in DCM (100 mL) for 1 h. Et$_2$O (150 mL) was added and the resulting solid filtered, washed with Et$_2$O (100 mL×2) and dried under vacuum to afford the title compound (52 g, 100%) as an off-white solid. $\delta_H$ (300 MHz, DMSO-d$_6$) 11.09 (s, 1H), 9.11 (s, 1H), 7.95 (d, J 7.5 Hz, 1H), 7.75 (m, 1H), 5.92 (s, 1H), 4.53 (m, 1H), 3.53 (s, 3H), 3.14 (t, J 6.2 Hz, 2H), 3.05 (m, 1H), 2.79-2.56 (m, 3H), 2.09 (s, 3H), 2.05-1.80 (m, 3H), 1.11-0.95 (m, 1H), 0.93-0.74 (m, 4H), 0.50-0.36 (m, 2H), 0.32-0.16 (m, 2H).

Intermediate 121

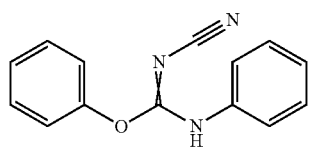 [SMILES: N#CN=C(Nc1ccccc1)Oc1ccccc1]

3-Cyano-1,2-diphenyl-isourea

To a solution of aniline [62-53-3] (500 mg, 5.37 mmol) in 2-propanol was added diphenyl N-cyanocarbonimidate [79463-77-7] (1.00 g, 6 mmol) and DIPEA (1.0 g, 8 mmol) and the reaction mixture was stirred at r.t. for 3 h. The white solid formed was filtered and washed with hexane, the solid was dried in vacuo to afford the title compound (1.0 g, 100%) as a white powder. LCMS [M+H]$^+$ 238.0, RT 1.313 minutes, 100.0% purity (Method 4).

Intermediate 122

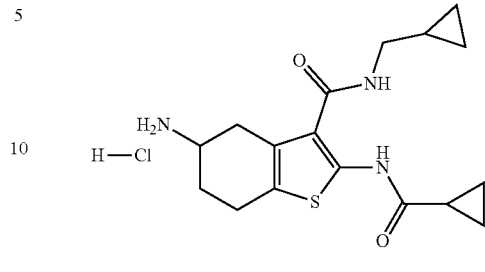

5-Amino-2-(cyclopropanecarbonylamino)-N-(cyclopropylmethyl)-4,5,6,7-tetrahydrobenzothiophene-3-carboxamide; hydrochloride To a solution of intermediate 114 (90% purity, 1.4 g, 2.91 mmol) in 1,4-dioxane (15 mL) was added 4M hydrogen chloride in 1,4-dioxane (11 mL) and the mixture was stirred for 2 h at r.t. The reaction mixture was concentrated in vacuo and the mixture was dissolved in 1,4-dioxane (10 mL). Further 4M hydrogen chloride in 1,4-dioxane (5 mL) was then added. After stirring for 3 h at r.t., the solvent was removed in vacuo to afford the title compound (1.2 g, 95%, 85% purity) as a beige solid. $\delta_H$ (500 MHz, CD$_3$OD) 3.62-3.54 (m, 1H), 3.24 (dd, J 7.0, 3.0 Hz, 2H), 3.18-3.12 (m, 1H), 2.91-2.85 (m, 2H), 2.80-2.71 (m, 1H), 2.30-2.20 (m, 1H), 2.01-1.91 (m, 1H), 1.85-1.78 (m, 1H), 1.14-1.05 (m, 1H), 1.02-0.96 (m, 2H), 0.96-0.90 (m, 2H), 0.59-0.50 (m, 2H), 0.32-0.26 (m, 2H). LCMS [M+H]$^+$ 334.1, RT 0.88 minutes, 85% purity (Method 6).

Intermediate 123

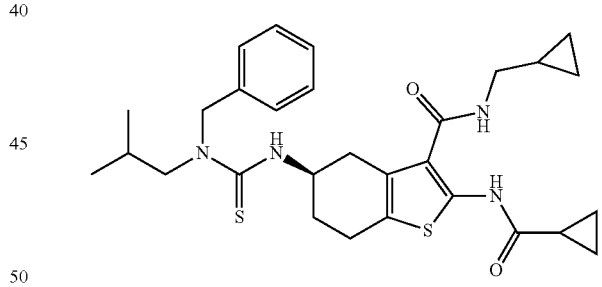

(5S)-5-[[Benzyl(isobutyl)carbamothioyl]amino]-2-(cyclopropanecarbonylamino)-N-(cyclopropylmethyl)-4,5,6,7-tetrahydrobenzothiophene-3-carboxamide To a solution of intermediate 117 (400 mg, 1.20 mmol) in DCM (20 mL) was added DIPEA (234 mg, 1.80 mmol), phenyl chlorothionocarbonate [1005-56-7] (230 mg, 1.32 mmol) and the reaction mixture was stirred for 2 h. DIPEA (238.7 mg, 1.838 mmol) and N-benzyl-2-methyl-propan-1-amine [42882-36-0] (200 mg, 1.225 mmol) were added and the reaction mixture was stirred for 18 h. Water (10 mL) was added to the reaction mixture and the organic layer was separated and passed through a phase separator column. The organic phase was concentrated in vacuo to yield the crude material as a yellow solid which was purified by flash column chromatography on silica (gradient elution with 0-100% EtOAc/iso-hexane) to afford the title compound (617 mg, 93%) as a yellow solid. LCMS [M+H]+ 539.0, RT 3.24 minutes (Method 1).

Intermediate 124

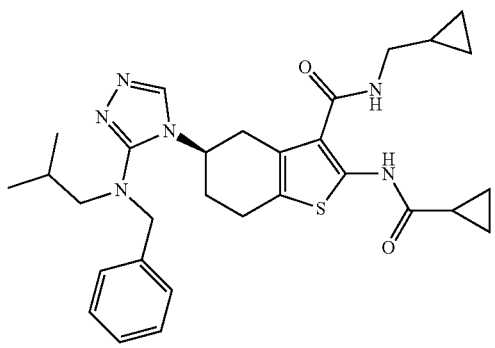 [SMILES: CC(C)CN(Cc1ccccc1)c1nncn1[C@@H]1CCc2sc(NC(=O)C3CC3)c(C(=O)NCC3CC3)c2C1]

(5S)-5-[3-[benzyl(isobutyl)amino]-1,2,4-triazol-4-yl]-2-(cyclopropanecarbonylamino)-N-(cyclopropylmethyl)-4,5,6,7-tetrahydrobenzothiophene-3-carboxamide Intermediate 123 (616 mg, 1.143 mmol) was dissolved in DMF (10 mL) and formic acid hydrazide 20 [624-84-0] (153 mg, 2.29 mmol) was added followed by mercuric chloride [7487-94-7] (621 mg, 2.29 mmol) and finally triethylamine (233 mg, 2.29 mmol). The reaction mixture was stirred for 2 minutes at r.t. and then heated at 60° C. for 4 h. The reaction mixture was cooled and diluted with MeCN (10 mL) and filtered through Celite, washing with MeCN (20 mL). The filtrate was concentrated in vacuo to yield the crude product as a yellow solid which was triturated with EtOAc and filtered. The filtrate was concentrated in vacuo to yield a yellow oil which was purified by flash column chromatography on silica (gradient elution with 0-5% MeOH/EtOAc) to afford the title compound (270 mg, 43%) as a white solid. LCMS [M+H]+ 547.0, RT 2.83 minutes (Method 1).

Intermediate 125

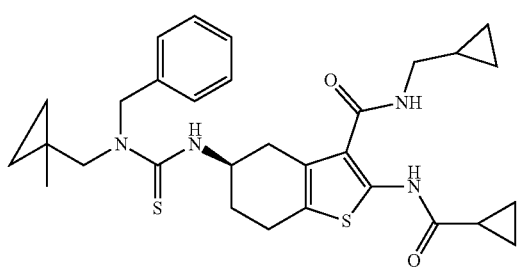 [SMILES: CC1(CN(Cc2ccccc2)C(=S)N[C@@H]2CCc3sc(NC(=O)C4CC4)c(C(=O)NCC4CC4)c3C2)CC1]

(5S)-5-[[Benzyl-[(1-methylcyclopropyl)methyl]carbamothioyl]amino]-2-(cyclopropanecarbonylamino)-N-(cyclopropylmethyl)-4,5,6,7-tetrahydrobenzothiophene-3-carboxamide Phenyl chloromethanethioate [1005-56-7] (0.46 mL, 3.3 mmol) was dissolved in DCM (15 mL) with stirring and cooled to 0° C. Intermediate 117 (1 g, 3 mmol) in DCM (15 mL) and triethylamine (1.25 mL, 9 mmol) was added dropwise and the reaction was stirred at 0° C. for 30 minutes. Benzyl[(1-methylcyclopropyl)methyl]amine (97%, 1.01 g, 5.61 mmol) in DCM (10 mL) was added and the reaction was stirred at r.t. for 2 h. The reaction was stirred for 18 h before diluting with water (40 mL) and extracted with DCM (3×30 mL). The organic phases were washed with brine, dried (Na$_2$SO$_4$), filtered and concentrated in vacuo to give a brown oil which was purified by flash column chromatography on silica (gradient elution with 0-100% EtOAc in heptane). The fractions containing the product were combined, washed with 0.5 M aqueous citric acid solution (2×25 mL) and the organic layer was dried (Na$_2$SO$_4$), filtered and concentrated in vacuo to afford the title compound (1.56 g, 94%) as a white solid. δ$_H$ (500 MHz, DMSO-d$_6$) 11.01 (s, 1H), 7.70 (t, J 5.6 Hz, 1H), 7.31 (t, J 7.4 Hz, 2H), 7.28-7.22 (m, 2H), 7.20 (d, J 7.3 Hz, 2H), 5.21-5.06 (m, 2H), 4.74-4.60 (m, 1H), 3.65-3.46 (m, 2H), 3.17 (dt, J 12.7, 6.1 Hz, 1H), 3.10 (dt, J 13.4, 6.0 Hz, 1H), 3.03 (dd, J 15.7, 5.0 Hz, 1H), 2.71-2.65 (m, 2H), 2.59 (dd, J 15.7, 9.3 Hz, 1H), 2.03-1.95 (m, 1H), 1.95-1.87 (m, 1H), 1.87-1.78 (m, 1H), 1.04-0.96 (m, 4H), 0.89-0.78 (m, 4H), 0.44-0.38 (m, 2H), 0.39-0.31 (m, 2H), 0.32-0.27 (m, 2H), 0.24-0.17 (m, 2H).

Intermediate 126

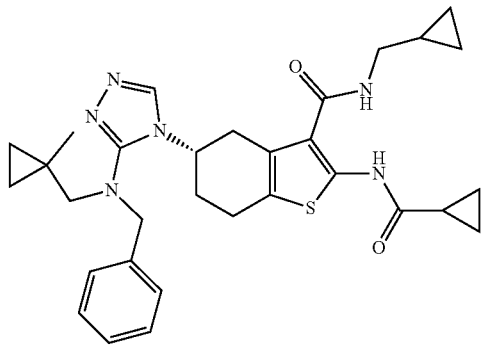

(5S)-5-[3-[Benzyl-[(1-methylcyclopropyl)methyl]amino]-1,2,4-triazol-4-yl]-2-(cyclopropanecarbonylamino)-N-(cyclopropylmethyl)-4,5,6,7-tetrahydrobenzothiophene-3-carboxamide Intermediate 125 (735 mg, 1.33 mmol) was dissolved in DMF (10 mL) and formic hydrazide [624-84-0] (240 mg, 4 mmol) was added followed by mercury dichloride [7487-94-7] (1.09 g, 4 mmol). The reaction was stirred at r.t. for 5 minutes and triethylamine (0.56 mL, 4.00 mmol) was added. The reaction was heated to 90° C. with stirring for 2 h. Further formic hydrazide [624-84-0] (200 mg) was added and the reaction heated at 90° C. for 18 h. The reaction was allowed to cool, diluted with DCM and Kieselguhr added and the mixture was filtered through a plug of Kieselguhr washing through with DCM. The filtrate was concentrated in vacuo and the residue was dissolved in EtOAc (100 mL), washed with saturated ammonium chloride solution (40 mL), water (40 mL), saturated ammonium chloride solution (40 mL) and brine. The organic phase was dried (Na$_2$SO$_4$), filtered and concentrated in vacuo. The orange residue was purified by flash column chromatography on silica (gradient elution with 0-10% MeOH in DCM) to afford the title compound (485 mg, 41% at 64% UV purity) as a yellow foam containing 31% urea starting material. LCMS [M+H]+ 559.2, RT 1.986 minutes, purity 64% (Method 12).

Intermediate 127

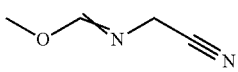

Methyl N-(cyanomethyl)methanimidate

To a stirred solution of potassium carbonate (1.74 g, 12.6 mmol) in water (2 mL), was added cyanomethanaminium chloride [6011-14-9] (2.3 g, 25.1 mmol) portionwise with stirring. The aqueous mixture was extracted with EtOAc (5×30 mL). The organic phases were combined, dried (potassium carbonate), filtered and the solvent removed in vacuo to give the free base (766 mg, 54%) as a pale yellow oil which was utilised without further purification. The oil was diluted with trimethylorthoformate [149-73-5] (2 mL) and the solution added dropwise to a refluxing solution of trimethylorthoformate [149-73-5] (18 mL) containing $Na_2SO_4$ (2.0 g) and sulfuric acid (1 drop) over 5 minutes. Stirring was continued for a further 30 minutes by which time the reaction had turned a yellow-orange colour. The mixture was concentrated in vacuo to afford the title compound (894 mg, 31%) as an orange oil. $\delta_H$ (500 MHz, DMSO-$d_6$) 7.91 (s, 1H), 4.37 (d, J 0.9 Hz, 2H), 3.65 (s, 3H) [85% pure w/w].

Intermediate 128

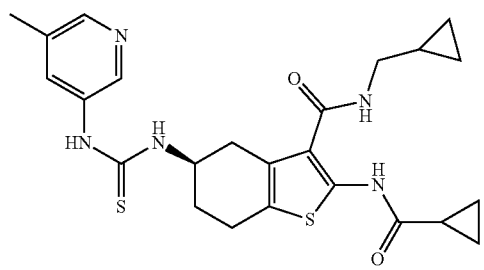

(5S)-2-(Cyclopropanecarbonylamino)-N-(cyclopropylmethyl)-5-[(5-methyl-3-pyridyl)carbamothioylamino]-4,5,6,7-tetrahydrobenzothiophene-3-carboxamide Intermediate 117 (200 mg, 0.60 mmol) was dissolved in DCM (10 mL) and DIPEA (117 mg, 0.90 mmol) was added followed by 3-isothiocyanato-5-methyl-pyridine (135 mg, 0.90 mmol). The reaction was stirred for 2 h before concentrating in vacuo to yield the crude product which was purified by flash column chromatography on silica (gradient elution with 0-100% EtOAc/iso-hexane) to afford the title compound (290 mg, 100%) as a white solid. LCMS [M+H]+ 483.9, RT 1.348 minutes, purity 100.0% (Method 4).

Intermediate 129

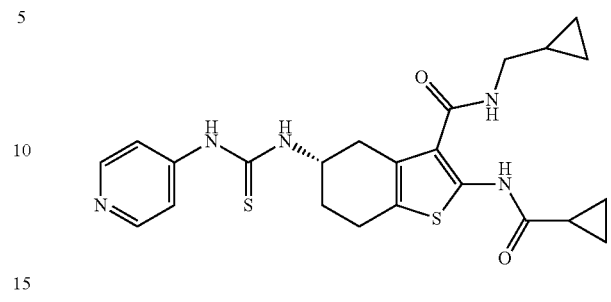

(5S)-2-(Cyclopropanecarbonylamino)-N-(cyclopropylmethyl)-5-(4-pyridylcarbamothioylamino)-4,5,6,7-tetrahydrobenzothiophene-3-carboxamide To a solution of pyridin-4-amine [90-25-5] (0.4 ml, 5.31 mmol) in THF (10 mL) was added di-1H-imidazol-1-yl-methanethione [6160-65-2] (1.14 g, 6.38 mmol) portionwise at 0° C. DCM (10 mL) was added and the mixture was warmed to r.t. and stirred for 18 h. To the reaction mixture was added intermediate 117 (1.75 g, 5.25 mmol) in DCM (10 mL) and the mixture was stirred for 18 h at r.t. The mixture was diluted with DCM (20 mL) and filtered, the filtrate was concentrated in vacuo to give the crude product which was purified by flash column chromatography on silica (gradient elution with 0% to 100% EtOAc in heptane, 0-50% MeOH in DCM) to afford the title compound (900 mg, 60%) as a brown solid. LCMS [M+H]+ 468.20/470.20, RT 1.67 minutes, purity 84% (Method 12).

Intermediate 130

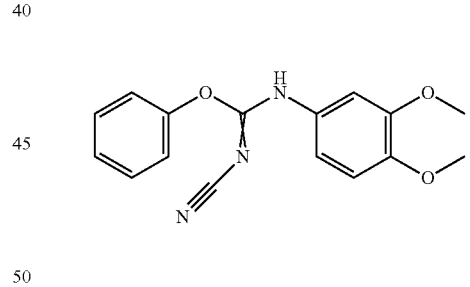

3-Cyano-1-(3,4-dimethoxyphenyl)-2-phenyl-isourea

Diphenyl N-cyanocarbonimidate [79463-77-7] (200 mg, 0.81 mmol) and 3,4-dimethoxyaniline [6315-89-5] (137 mg, 0.89 mmol) were dissolved in DCM (2 mL) and 2-propanol (2 mL) and DIPEA (159 mg, 1.22 mmol) were added and the reaction mixture was stirred at r.t. for 1 h. The mixture was concentrated in vacuo and the residue was purified by flash column chromatography on silica (gradient elution with 15-100% EtOAc/hexane) to afford the title compound (198 mg, 82%) as a white solid. $\delta_H$ (300 MHz, DMSO-$d_6$) 10.65 (s, 1H), 7.51-7.37 (m, 2H), 7.36-7.22 (m, 3H), 7.09 (d, J 1.8 Hz, 1H), 7.03-6.91 (m, 2H), 3.75 (s, 6H).

Intermediate 131

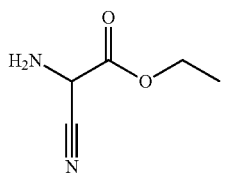

Ethyl 2-amino-2-cyano-acetate

Ethyl (2E)-cyano(hydroxyimino)ethanoate [3849-21-6] (5 g, 35.2 mmol) was suspended in water (30 mL) and the reaction mixture was stirred. Aqueous saturated sodium hydrogen carbonate solution (36 mL) was added slowly in portions to give an orange solution (pH=5). Sodium dithionite [7631-94-9] (85%, 17 g, 83.0 mmol) was added in portions over 20 minutes and the reaction was allowed to stir for an additional 30 minutes (the temperature of the solution rose to 39° C.). The reaction was extracted with DCM (4×50 mL), the organics were dried (Na$_2$SO$_4$), filtered and concentrated in vacuo to afford the title compound (2.82 g, 53% at 85% purity) as a red/brown oil which was stored in the fridge. δ$_H$ (250 MHz, Chloroform-d) 4.44 (s, 1H), 4.34 (q, J 7.1 Hz, 2H), 2.55 (s, 2H), 1.35 (t, J 7.1 Hz, 3H).

Intermediate 132

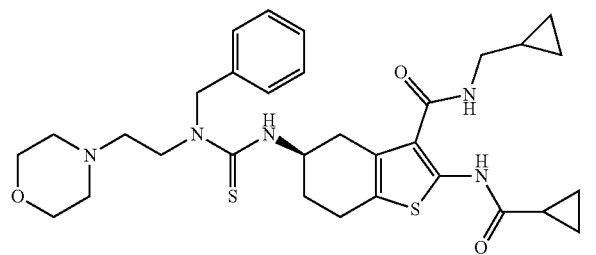

(5S)-5-[[Benzyl(2-morpholinoethyl)carbamothioyl]amino]-2-(cyclopropanecarbonylamino)-N-(cyclopropylmethyl)-4,5,6,7-tetrahydrobenzothiophene-3-carboxamide To a solution of intermediate 117 (400 mg, 1.20 mmol) in DCM (20 mL) was added DIPEA (234 mg, 1.80 mmol) and phenyl chlorothionocarbonate [1005-56-7] (230 mg, 1.32 mmol) and the solution was stirred for 2 h. DIPEA (239 mg, 1.84 mmol) and N-benzyl-2-morpholino-ethanamine [2038-05-3] (270 mg, 1.23 mmol) were added and the reaction was stirred for 18 h. Water (10 mL) was added to the reaction mixture, the organic layer was separated and passed through a phase separator column. The organic phase was concentrated in vacuo to give a yellow solid which was purified by flash column chromatography on silica (gradient elution with 0-100% EtOAc/iso-hexane) to afford the title compound (505 mg, 69%) as a yellow gum. LCMS [M+H]$^+$ 596.0, RT 2.75 minutes, 80.1% purity (Method 1).

Intermediate 133

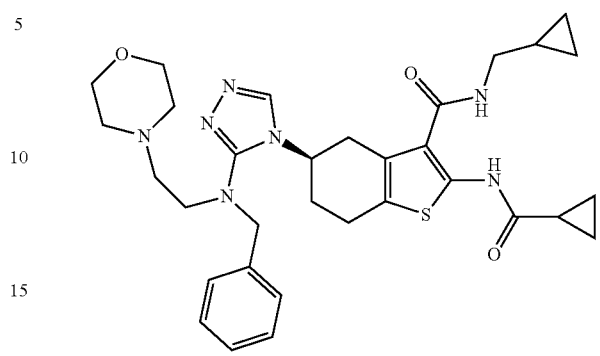

(5S)-5-[3-[Benzyl(2-morpholinoethyl)amino]-1,2,4-triazol-4-yl]-2-(cyclopropanecarbonylamino)-N-(cyclopropylmethyl)-4,5,6,7-tetrahydrobenzothiophene-3-carboxamide Intermediate 132 (758 mg, 1.27 mmol) was dissolved in DMF (10 mL) and formic acid hydrazide [624-84-0] (153 mg, 2.29 mmol) was added followed by mercuric chloride [7487-94-7] (621 mg, 2.29 mmol) and finally triethylamine (233 mg, 2.29 mmol). The mixture was stirred for 2 minutes at r.t. and then heated at 80° C. for 5 h. The mixture was cooled and diluted with MeCN (10 mL) and then filtered through a plug of Celite which was washed with excess MeCN (20 mL). The reaction mixture was concentrated in vacuo to give a yellow solid which was purified by flash column chromatography on silica (gradient elution with 10% MeOH/DCM with approx 2% aqueous ammonia]/DCM) to afford the title compound (300 mg, 39%) as a white solid. LCMS [M+H]$^+$ 604.0, RT 2.340 minutes (Method 1).

Intermediate 134

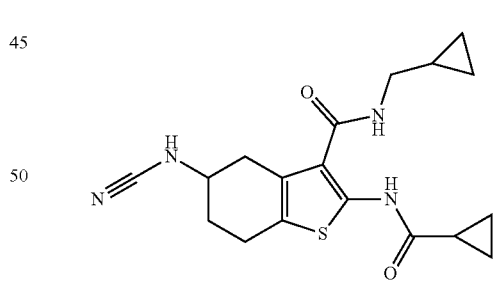

5-(Cyanoamino)-2-(cyclopropanecarbonylamino)-N-(cyclopropylmethyl)-4,5,6,7-tetrahydrobenzothiophene-3-carboxamide To a stirred solution of intermediate 122 (250 mg, 0.68 mmoL) and DIPEA (0.29 mL, 1.69 mmoL) in anhydrous DCM (3 mL) cooled to 0° C. in an ice bath, was added dropwise a solution of cyanogen bromide [506-68-3] (75 mg, 0.71 mmoL) in anhydrous DCM (2 mL) and the mixture was allowed to warm to r.t. overnight. The reaction mixture was diluted with DCM (20 mL), washed with saturated aqueous ammonium chloride solution (10 mL), saturated aqueous sodium bicarbonate solution (10 mL) and brine (10 mL), then dried (MgSO₄), filtered and concentrated in vacuo. The crude product was purified by flash column chromatography on silica (gradient elution with 0-100% of EtOAc in heptane) to afford the title compound (150 mg, 62%) as an off white solid. $\delta_H$ (250 MHz, Chloroform-d) 11.98 (s, 1H), 5.89-5.71 (m, 1H), 4.00 (d, J 5.2 Hz, 1H), 3.77-3.59 (m, 1H), 3.35-3.21 (m, 2H), 3.13 (dd, J 14.8, 4.9 Hz, 1H), 2.89-2.69 (m, 3H), 2.22-2.06 (m, 1H), 2.07-1.89 (m, 1H), 1.73-1.60 (m, 1H), 1.16-0.97 (m, 3H), 0.99-0.80 (m, 2H), 0.67-0.52 (m, 2H), 0.36-0.22 (m, 2H). LCMS [M+H]⁺ 359, RT 3.53 minutes, 96% purity (Method 5).

Intermediate 135

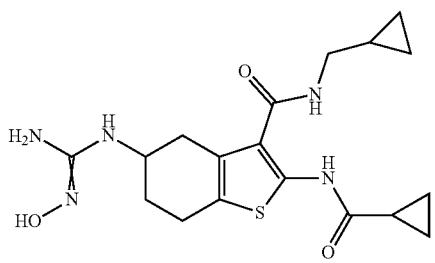

2-(cyclopropanecarbonylamino)-N-(cyclopropylmethyl)-5-[(N'-hydroxycarbamimidoyl)amino]-4,5,6,7-tetrahydrobenzothiophene-3-carboxamide To a stirred solution of intermediate 134 (140 mg, 0.39 mmoL) in EtOH (5 mL) was added hydroxylamine hydrochloride [5470-11-1] (29 mg, 0.41 mmoL) followed by potassium carbonate (108 mg, 0.78 mmoL) and the mixture was stirred at r.t. under an atmosphere of nitrogen for 18 h. Hydroxylamine hydrochloride [5470-11-1] (29 mg, 0.41 mmoL) followed by potassium carbonate (108 mg, 0.78 mmoL) were added and stirring was continued at r.t. for 1 h. The reaction mixture was filtered through a pad of celite, washed with EtOH and concentrated in vacuo. The crude material (210 mg) was purified by flash column chromatography on silica (gradient elution with 0 to 100% of EtOAc in heptane, followed by 0 to 10% of MeOH in EtOAc, followed by 10% ammonia (7N in MeOH) in EtOAc) to give the product which was further purified by preparative HPLC (low pH) to afford the title compound (2.2 mg, 1.4%) as a formate salt. The column waste was concentrated in vacuo to afford further title compound (30 mg, 13%, 66% purity). LCMS [M+H]⁺ 392, RT 2.76 minutes, 99% purity (Method 5).

Intermediate 136

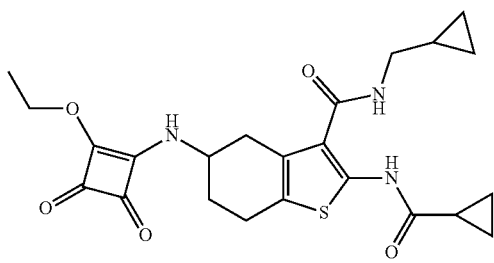

2-(Cyclopropanecarbonylamino)-N-(cyclopropylmethyl)-5-[(2-ethoxy-3,4-dioxo-cyclobuten-1-yl)amino]-4,5,6,7-tetrahydrobenzothiophene-3-carboxamide Intermediate 122 (90% purity, 100 mg, 0.24 mmol) was suspended in THF (1 mL) and DIPEA (50 µL, 0.29 mmol) was added. The solution was cooled to −78° C. and 3,4-diethoxycyclobut-3-ene-1,2-dione [5231-87-8] (42 mg, 0.25 mmol) was added. The reaction mixture was warmed to r.t. and stirred for 4 h. An additional reaction was carried out, intermediate 122 (90%, 100 mg, 0.24 mmol) was dissolved in EtOH (1 mL) and DIPEA (50 µL, 0.29 mmol) was added, the solution was stirred at r.t. for 2 h. The two reactions were combined, resulting in a clear brown solution, a further equivalent of 3,4-diethoxycyclobut-3-ene-1,2-dione [5231-87-8] (42 mg, 0.25 mmol) and DIPEA (100 µL, 0.57 mmol) were added and the solution was stirred for 1 h at r.t. The reaction mixture was concentrated in vacuo and purified by flash column chromatography on silica (gradient elution with 0-100% EtOAc/heptane) to afford the title compound (200 mg, 85%) as a 1:1 mixture of rotamers. $\delta_H$ (500 MHz, DMSO-d₆) 11.07 (d, J 7.4 Hz, 2H), 9.00 (d, J 7.8 Hz, 1H), 8.81 (d, J 8.1 Hz, 1H), 7.73 (br t, J 4.7 Hz, 2H), 4.69-4.62 (m, 4H), 4.22 (br, 1H), 3.83 (br, 1H), 3.12 (m, 4H), 2.97 (br d, J 16.5 Hz, 2H), 2.78 (br d, J 16.1 Hz, 2H), 2.70 (s, 4H), 2.04 (br, 2H), 1.95-1.88 (m, 2H), 1.84 (br, 2H), 1.41-1.30 (m, 6H), 1.07-0.97 (m, 2H), 0.89-0.79 (m, 8H), 0.44-0.37 (m, 4H), 0.24-0.18 (m, 4H).

Intermediate 137

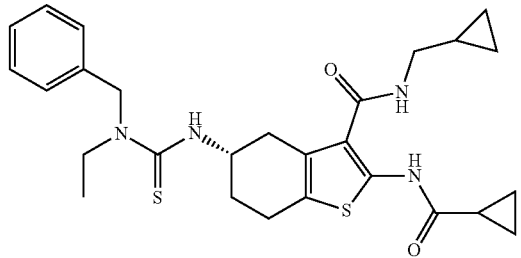

(5S)-5-[[Benzyl(ethyl)carbamothioyl]amino]-2-(cyclopropanecarbonylamino)-N-(cyclopropylmethyl)-4,5,6,7-tetrahydrobenzothiophene-3-carboxamide A solution of O-phenyl carbonochloridothioate [1005-56-7] (1.55 g, 9 mmol) in DCM (90 mL) was added over 20 minutes to an ice-cold stirred solution of intermediate 117 (3.0 g, 9 mmol) and triethylamine [121-44-8] (1.87 mL, 13.5 mmol) in DCM (180 mL). The mixture was stirred at 0° C. for 2 h and then the ice bath was removed. The reaction was quenched by adding water (100 mL), the organic phase was separated and the aqueous phase was extracted with DCM (2×100 mL). The combined organic phases were washed with brine (100 mL), dried (MgSO₄), filtered and concentrated in vacuo to afford the crude (5S)-2-(cyclopropanecarbonylamino)-N-(cyclopropylmethyl)-5-isothiocyanato-4,5,6,7-tetrahydrobenzothiophene-3-carboxamide (3.90 g, 94%, 81% purity).

A solution of N-benzylethanamine [14321-27-8] (1.36 g, 10.1 mmol) in Et₂O (70 mL) was added dropwise to a solution of crude (5S)-2-(cyclopropanecarbonylamino)-N-

(cyclopropylmethyl)-5-isothiocyanato-4,5,6,7-tetrahydrobenzothiophene-3-carboxamide (81% purity, 3.90 g, 8.41 mmol) in isopropanol (70 mL). The reaction mixture was stirred for 4 h before concentrating in vacuo and the crude material was purified by flash column chromatography on silica (gradient elution with 0-100% EtOAc in heptane) to afford the title compound (1.52 g, 59%, 84% purity). LCMS [M+H]+ 511.20/509.20, RT 2.04 minutes, 84% purity (Method 12).

Intermediate 138

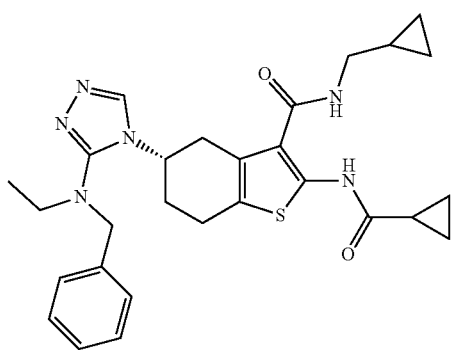

(5S)-5-[3-[Benzyl(ethyl)amino]-1,2,4-triazol-4-yl]-2-(cyclopropanecarbonylamino)-N-(cyclopropylmethyl)-4,5,6,7-tetrahydrobenzothiophene-3-carboxamide Intermediate 137 (80%, 4.20 g, 6.58 mmol) and formic hydrazide [624-84-0] (1.19 g, 19.7 mmol) were dissolved in DMF (60 mL) and mercury dichloride [7487-94-7] (5.36 mg, 19.7 mmol) was added to the reaction mixture. The reaction mixture was stirred for 5 minutes and triethylamine [121-44-8](2.74 ml, 19.7 mmol) was added. The reaction mixture was heated at 90° C. for 3 h before diluting with DCM (50 mL), filtering through a short pad of celite, and concentrating the filtrate in vacuo. The crude product was extracted with EtOAc (3×60 mL) and washed with water (60 mL). The organics were dried (MgSO$_4$), filtered, and the filtrate was concentrated in vacuo to afford the crude material which was purified by flash column chromatography on silica (gradient elution with 0-100%, 0-40% MeOH in DCM) to afford the desired product which was further purified by basic preparative HPLC to afford the title compound (1.7 g, 46%) as a yellow solid. $\delta_H$ (500 MHz, Methylene Chloride-d$_2$) 12.02 (s, 1H), 7.93 (s, 1H), 7.35-7.08 (m, 5H), 5.63-5.60 (m, 1H), 4.37-4.32 (m, 1H), 4.22 (s, 2H), 3.29-3.11 (m, 4H), 2.87 (dd, J 14.7, 5.1 Hz, 1H), 2.80-2.73 (m, 2H), 2.68 (dd, J 14.5, 9.5 Hz, 1H), 2.01-1.93 (m, 1H), 1.77-1.70 (m, 1H), 1.69-1.64 (m, 1H), 1.08 (t, J 7.1 Hz, 3H), 1.06-0.98 (m, 2H), 0.99-0.96 (m, 1H), 0.93-0.87 (m, 2H), 0.51-0.42 (m, 2H), 0.22-0.17 (m, 2H).

Intermediate 139

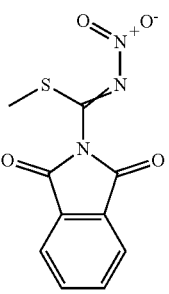

methyl N-nitro-1,3-dioxo-isoindoline-2-carboximidothioate

To a solution of 2-methyl-1-nitroisothiourea (0.5 g, 3.7 mmol) in pyridine [110-86-1] (6.5 mL) was added dropwise O-phthaloyl dichloride [88-95-9] (0.80 mL, 5.55 mmol) at 0° C. over 20 minutes. On completion of addition the reaction was stirred at 0° C. for 30 minutes and poured into cold aqueous hydrochloric acid solution (5 mL of concentrated hydrochloric acid in 20 mL of water). The reaction mixture was filtered and the pale yellow solid was collected and recrystallized from EtOH to afford the title compound (0.76 g, 70%) as white needles. $\delta_H$ (500 MHz, CD$_3$OD) 8.05-7.98 (m, 2H), 7.97-7.92 (m, 2H), 2.6 (s, 3H). LCMS [M+H]+ 265.95, RT 1.11 minutes, 90% purity (Method 6).

Intermediate 140

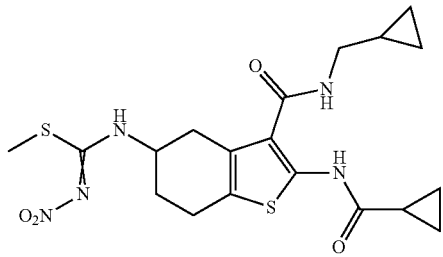

2-(cyclopropanecarbonylamino)-N-(cyclopropylmethyl)-5-[(C-methylsulfanyl-N-nitro-carbonimidoyl)amino]-4,5,6,7-tetrahydrobenzothiophene-3-carboxamide To a solution of intermediate 139 (107.5 mg, 0.40 mmol) in pyridine [88-95-9] (0.1 mL) and DCM (2 mL) was added dropwise intermediate 122 (150 mg, 0.40 mmol, free based with DIPEA) in DCM (1.5 mL) at 0° C. over 10 minutes. The reaction was warmed to r.t. and stirred for 3 h. The reaction mixture was concentrated in vacuo to give a yellow oil, which was purified by flash column chromatography on silica (gradient elution with 10% to 100% EtOAc in heptane) to afford the title compound (170 mg, 93%) as a white solid. $\delta_H$ (500 MHz, CD$_3$OD) 4.39-4.14 (m, 1H), 3.26-3.13 (m, 3H), 2.91-2.75 (m, 3H), 2.51 (s, 3H), 2.25-2.15 (m, 1H), 2.11-2.00 (m, 1H), 1.84-1. (m, 1H), 1.14-1.05 (m, 1H), 1.01-0.91 (m, 4H), 0.56-0.49 (m, 2H), 0.31-0.25 (m, 2H). LCMS [M+H]⁺ 452.1, RT 3.42 minutes, 100% purity (Method 10).

Intermediate 141

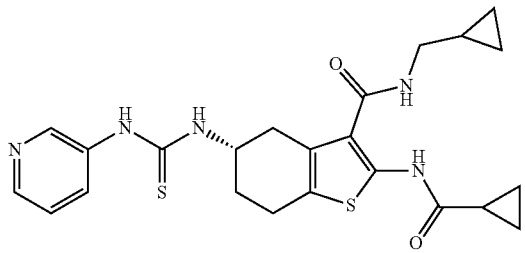 [SMILES: O=C(NCC1CC1)c1c(NC(=O)C2CC2)sc2c1C[C@@H](NC(=S)Nc1cccnc1)CC2]

(5S)-2-(Cyclopropanecarbonylamino)-N-(cyclopropylmethyl)-5-(3-pyridylcarbamothioylamino)-4,5,6,7-tetrahydrobenzothiophene-3-carboxamide Intermediate 117 (1.5 g, 4.5 mmol) was dissolved in DCM (20 mL) and DIPEA (880 mg, 6.7 mmol) was added. 3-Pyridyl isothiocyanate [17452-27-6] (940 mg, 6.7 mmol) was added and the reaction mixture was stirred at r.t. for ~1 h. The reaction was concentrated in vacuo and the residue purified by flash column chromatography on silica (gradient elution with 35-100% EtOAc/hexane to 0-5% MeOH/EtOAc) to afford the title compound (2.0 g, 95%) as a colourless gum. LCMS [M+H]⁺ 470.2, RT 1.836 minutes, 95.6% purity (Method 1).

Intermediate 142

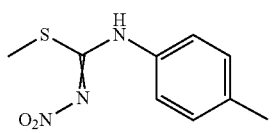

2-methyl-3-nitro-1-(p-tolyl)isothiourea

To a solution of intermediate 140 (150 mg, 0.56 mmol) in pyridine [110-86-1] (0.1 mL) and DCM (2 mL) was added dropwise 4-methylaniline [106-49-0] (60.6 mg, 0.56 mmol) in DCM (2 mL) at 0° C. over 10 minutes. The reaction mixture was allowed to warm to r.t. and stirred for 16 h. The reaction mixture was concentrated in vacuo to give a yellow oil which was purified by flash column chromatography on silica (gradient elution with 10% to 100% EtOAc in heptane) to afford the title compound (110 mg, 76%) as a white solid. δ_H (500 MHz, Chloroform-d) 11.24 (s, 1H), 7.25 (d, J 6.7 Hz, 2H), 7.18 (d, J 8.3 Hz, 2H), 2.44 (s, 3H), 2.40 (s, 3H). LCMS [M−H]⁻ 223.95, RT 1.13 minutes, 88% purity (Method 6).

Intermediate 143

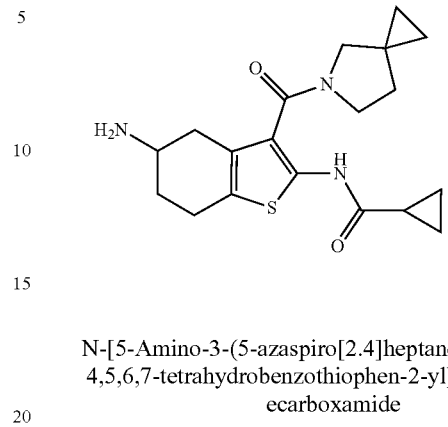

N-[5-Amino-3-(5-azaspiro[2.4]heptane-5-carbonyl)-4,5,6,7-tetrahydrobenzothiophen-2-yl]cyclopropanecarboxamide Intermediate 26 (400 mg, 1.05 mmol) was dissolved in DMF (10 mL) and triethylamine (133.6 mg, 1.31 mmol) and 5-azaspiro[2.4]heptane [185-50-2] (168.0 mg, 1.26 mmol) were added followed by EDCl (252 mg, 1.31 mmol). The mixture was stirred at r.t. for 30 minutes then 50° C. for 18 h. The reaction was cooled and further triethylamine (106 mg, 1.05 mmol) and 5-azaspiro[2.4]heptane [185-50-2] (68 mg, 0.51 mmol) and EDCl (201.5 mg, 1.05 mmol) were added. The reaction mixture was heated at 50° C. for 2 h and the solution was cooled, diluted with EtOAc (15 mL) and washed with water (3×20 mL). The organic layer was dried (Na₂SO₄), filtered and concentrated in vacuo to give a yellow oil which was purified by flash column chromatography on silica (gradient elution with 0-80% EtOAc/iso-hexane) to afford the crude material tert-butyl N-[3-(5-azaspiro[2.4]heptane-5-carbonyl)-2-(cyclopropanecarbonylamino)-4,5,6,7-tetrahydrobenzothiophen-5-yl]carbamate (364 mg, 75%) as a yellow gum. Tert-butyl N-[3-(5-azaspiro[2.4]heptane-5-carbonyl)-2-(cyclopropanecarbonylamino)-4,5,6,7-tetrahydrobenzothiophen-5-yl]carbamate was redissolved in DCM (5 mL) and cooled to 0° C. and TFA (5 mL) was added. The reaction mixture was stirred for 20 minutes at 0° C. followed by r.t. for 1 h. The reaction mixture was concentrated in vacuo, removing excess TFA with 1:1 iso-hexane/DCM. The crude residue was purified by SCX-column (eluting with 10% aqueous ammonia/MeOH) to afford the title compound (285 mg, 75%) as a yellow gum. LCMS [M+H]⁺ 360.2, RT 1.416 minutes, 100.0% purity (Method 1).

Intermediate 144

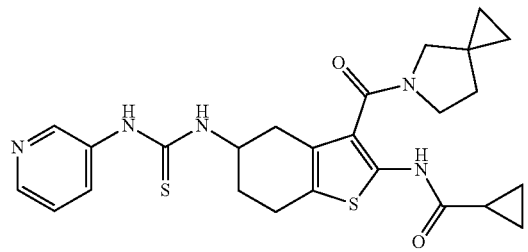 [SMILES: O=C(Nc1sc2c(c1C(=O)N1CCC3(CC3)C1)CC(NC(=S)Nc1cccnc1)CC2)C1CC1]

N-[3-(5-Azaspiro[2.4]heptane-5-carbonyl)-5-(3-pyridylcarbamothioylamino)-4,5,6,7-tetrahydrobenzothiophen-2-yl]cyclopropanecarboxamide Intermediate 143 (270 mg, 0.75 mmol) was dissolved in DCM (10 mL). DIPEA (146 mg, 1.13 mmol) was added followed by 3-isothiocyanatopyridine [17452-27-6] (153 mg, 1.13 mmol) and the reaction was stirred for 18 h. The solvent was removed in vacuo and the residue was purified by flash column chromatography on silica (gradient elution with 0-100% EtOAc/iso-hexane followed by 10% MeOH/EtOAc) to afford the title compound (359 mg, 96%) as a white solid. LCMS [M+H]+ 496.2, RT 1.800 minutes, 95.2% purity (Method 1).

Intermediates 145 and 146

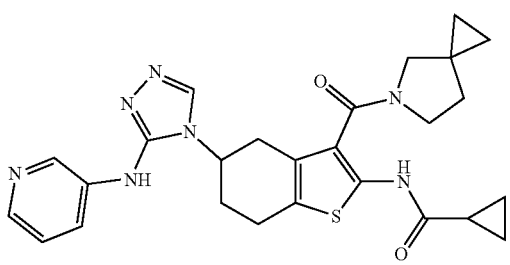

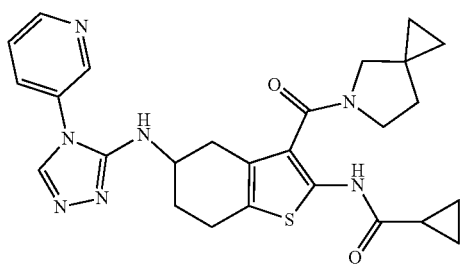

Intermediate 145

N-[3-(5-Azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide Intermediate 146

N-[3-(5-Azaspiro[2.4]heptane-5-carbonyl)-5-[[4-(3-pyridyl)-1,2,4-triazol-3-yl]amino]-4,5,6,7-tetrahydrobenzothiophen-2-yl]cyclopropanecarboxamide Intermediate 144 (359 mg, 0.72 mmol) was dissolved in DMF (10 mL) and formic acid hydrazide [624-84-0] (96.7 mg, 1.45 mmol) was added followed by mercuric chloride [7487-94-7] (393 mg, 1.45 mmol) and triethylamine (147 mg, 1.45 mmol). The reaction mixture was stirred for 2 minutes at r.t. and then heated at 60° C. for 2 h. The reaction mixture was cooled and the mixture was diluted with MeCN (10 mL) and filtered through a plug of Celite, washing with excess MeCN (20 mL). The filtrate was concentrated in vacuo to give a yellow oil which was redissolved in DCM (with 10% MeOH) and washed with water (5 mL). The organic layer was concentrated in vacuo to yield the crude material (mixture of Intermediate 145 and Intermediate 146) which was purified by flash column chromatography on silica (gradient elution with 0-15% MeOH/DCM) to afford the title compound Intermediate 145 (257 mg, 70%) as a white solid. LCMS [M+H]+ 504.2; RT 1.375 minutes, 80.1% purity; RT 1.482 minutes, 19.9% purity, (Method 2).

Intermediate 147

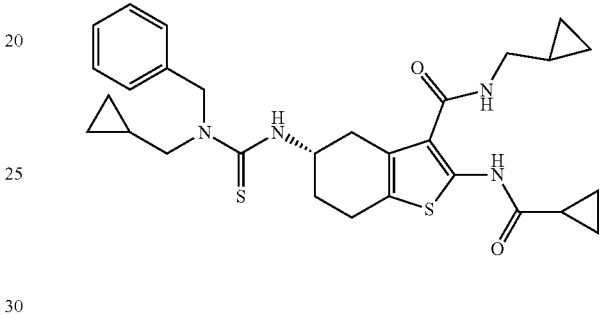

(5S)-5-[[Benzyl(cyclopropylmethyl)carbamothioyl]amino]-2-(cyclopropanecarbonylamino)-N-(cyclopropylmethyl)-4,5,6,7-tetrahydrobenzothiophene-3-carboxamide Intermediate 117 (1.96 g, 5.88 mmol) was dissolved in DCM (20 mL) and DIPEA (1.15 g, 8.90 mmol) was added and the reaction mixture was cooled to 0° C. Phenyl chlorothionocarbonate [1005-56-7] (1.13 g, 6.55 mmol) was added and the reaction mixture was stirred at 0° C. warming to r.t. over ~2 h. DIPEA (1.15 g, 8.82 mmol) and N-benzyl-1-cyclopropylmethanamine [116373-23-0] (998 mg, 5.88 mmol) was added and the reaction mixture was stirred at r.t. for 4 h. Further N-benzyl-1-cyclopropylmethanamine [116373-23-0] (99.8 mg, 0.62 mmol) was added and the reaction mixture was stirred at r.t. for 36 h. The reaction mixture was washed with water and brine, passed through a phase separation cartridge and concentrated in vacuo. The residue was purified by flash column chromatography on silica (gradient elution with 5-70% EtOAc/hexane) to afford the title compound (2.99 g, 95%) as a colourless foam. $\delta_H$ (500 MHz, DMSO-$d_6$) 11.02 (s, 1H), 7.70 (t, J 5.6 Hz, 1H), 7.31 (t, J 7.3 Hz, 2H), 7.27-7.20 (m, 3H), 7.18 (d, J 7.6 Hz, 1H), 5.16-5.02 (m, 2H), 4.72-4.58 (m, 1H), 3.60-3.45 (m, 2H), 3.21-3.06 (m, 2H), 3.01 (dd, J 15.8, 5.3 Hz, 1H), 2.70-2.64 (m, 2H), 2.58 (dd, J 15.8, 9.4 Hz, 1H), 2.03-1.95 (m, 1H), 1.91 (p, J 6.4 Hz, 1H), 1.87-1.72 (m, 1H), 1.12-0.96 (m, 2H), 0.90-0.77 (m, 4H), 0.46-0.34 (m, 4H), 0.26-0.14 (m, 4H). LCMS [M+H]+ 537.2, RT 2.097 minutes, 99% purity (Method 12). LCMS [M+H]+ 537.2, RT 2.871 minutes, 93.3% purity (Method 3).

Intermediate 148

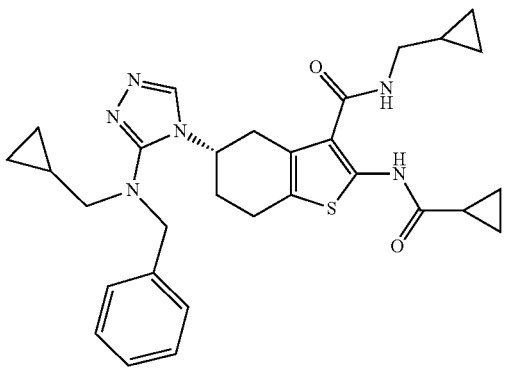 [SMILES: O=C(NCC1CC1)c1c(NC(=O)C2CC2)sc2c1C[C@@H](n1cnnc1N(Cc1ccccc1)CC1CC1)CC2]

(5S)-5-[3-[Benzyl(cyclopropylmethyl)amino]-1,2,4-triazol-4-yl]-2-(cyclopropanecarbonylamino)-N-(cyclopropylmethyl)-4,5,6,7-tetrahydrobenzothiophene-3-carboxamide Intermediate 147 (2.99 g, 5.57 mmol) was dissolved in DMF (10 mL) and formic acid hydrazide [624-84-0] (558 mg, 8.36 mmol) and mercuric chloride [7487-94-7] (1.97 g, 7.24 mmol) was added. The reaction mixture was stirred at r.t. for 5 minutes before addition of triethylamine (850 mg, 8.36 mmol). The reaction mixture was stirred at r.t. for 30 minutes and then stirred at 60° C. for ~2.5 h. Further formic acid hydrazide [624-84-0] (279 mg, 4.65 mmol) was added and the mixture was stirred at 60° C. for 4 h, then at r.t. overnight. Further formic acid hydrazide [624-84-0] (186 mg, 3.10 mmol) and mercuric chloride [7487-94-7] (379 mg, 1.40 mmol) was added and the mixture was stirred at 60° C. for 4 h before cooling, diluting with MeCN (40 mL), filtering through a pad of celite and washing with MeCN (3×10 mL). The pale yellow filtrate was concentrated in vacuo to yield a tan solid which was purified by flash column chromatography on silica (gradient elution with 50-100% EtOAc/hexane to 20% MeOH/EtOAc) to afford the title compound (2.31 g, 76%) as a pale yellow gum. LCMS [M+H] 545.2, RT 2.348 minutes, 100.0% purity (Method 2).

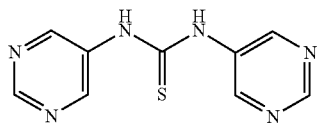 [SMILES: S=C(Nc1cncnc1)Nc1cncnc1]

1,3-Di(pyrimidin-5-yl)thiourea

To a solution of pyrimidin-5-amine [591-55-9] (500 mg, 5.26 mmol) in THF (10 mL) was added di-1H-imidazol-1-ylmethanethione [6160-65-2] (1.12 g, 6.31 mmol) portionwise at 0° C. The reaction mixture was warmed to r.t. and stirred for 18 h. The crude mixture was diluted with isopropanol (10 mL) and the solid was filtered and dried under reduced pressure to afford the title compound (0.34 g, 28%). $\delta_H$ (250 MHz, DMSO-d$_6$) 10.42 (s, 2H), 8.98 (s, 2H), 8.91 (s, 4H). LCMS [M+H]$^+$ 233.20/231.20, RT 0.50 minutes, 100% purity (Method 12).

Intermediate 150

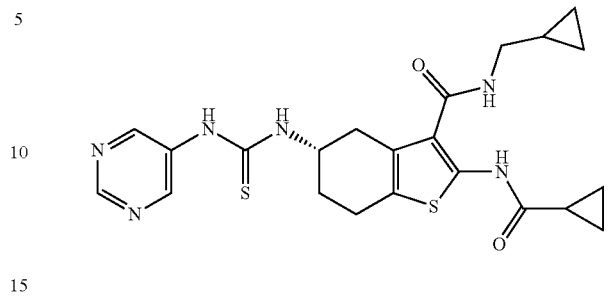

(5S)-2-(Cyclopropanecarbonylamino)-N-(cyclopropylmethyl)-5-(pyrimidin-5-ylcarbamothioylamino)-4,5,6,7-tetrahydrobenzothiophene-3-carboxamide A solution of intermediate 149 (193.5 μl, 0.9 mmol) in DCM (5 mL) was stirred at r.t. prior to the addition of intermediate 117 (300 mg, 0.9 mmol). The solution was stirred for 18 h under nitrogen and concentrated in vacuo to give a pale yellow solid which was purified by flash column chromatography on silica (gradient elution with 0% to 100% EtOAc in heptane, 0-60% MeOH in DCM) to afford the product which was further purified by preparative HPLC (basic) to afford the title compound (220 mg, 52%) as a white solid. $^1$H NMR (250 MHz, Methylene Chloride-d$_2$) δ 12.01 (s, 1H), 8.90 (s, 3H), 8.39 (s, 1H), 6.90 (d, J 6.8 Hz, 1H), 5.81-5.78 (m, 1H), 4.95-4.91 (m, 1H), 3.36-3.02 (m, 3H), 2.84-2.77 (m, 3H), 2.52-2.49 (m, 1H), 2.00-1.97 (m, 1H), 1.73-1.69 (m, 1H), 1.14-0.86 (m, 5H), 0.63-0.54 (m, 2H), 0.32-0.27 (m, 2H). LCMS [M+H]$^+$ 471.20/469.20, RT 1.73 minutes, 100% purity (Method 12).

Intermediate 151

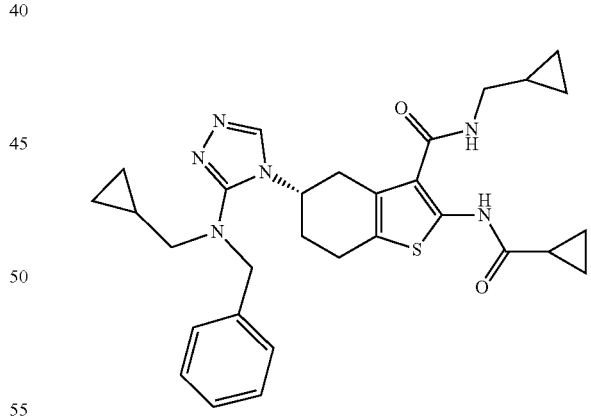

(5S)-5-[2-[Benzyl(cyclopropylmethyl)amino]imidazol-1-yl]-2-(cyclopropanecarbonylamino)-N-(cyclopropylmethyl)-4,5,6,7-tetrahydrobenzothiophene-3-carboxamide Intermediate 147 (541 mg, 1.01 mmol) was dissolved in DMF (10 mL), and 2,2-diethoxyethanamine [22483-09-6] (0.44 mL, 3.02 mmol) was added followed by mercury dichloride [7487-94-7] (821 mg, 3.02 mmol). The reaction was stirred at r.t. for 5 minutes then triethylamine (0.42 mL, 3.02 mmol) was added. The reaction was heated to 90° C. and stirred for 2 h. 4-Methylbenzene-1-sulfonic acid hydrate (PTSA hydrate) [6192-52-5] (1.15 g, 6.05 mmol) was added and the reaction was heated at 90° C. with stirring for 18 h. The reaction was allowed to cool, diluted with DCM and Kieselguhr added and the mixture was filtered through a plug of Kieselguhr washing with DCM. The filtrate was concentrated in vacuo and the residue was dissolved in EtOAc (100 mL). The organic layer was washed with water (3×20 mL), 5% aqueous lithium chloride (20 mL), dried (Na$_2$SO$_4$), filtered and concentrated in vacuo. The orange/brown residue was purified by flash column chromatography on silica (gradient elution with 0-100% EtOAc then 10% MeOH in DCM) to afford the title compound (412 mg, 69%, 92% purity) as a brown foam. LCMS [M+H]$^+$ 544.2, RT 1.824 minutes, 92% purity (Method 12).

Intermediate 152

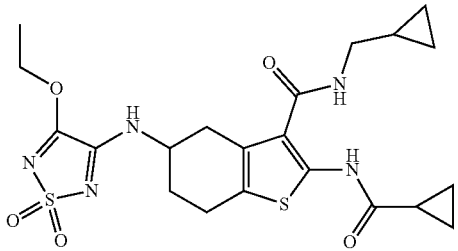 [SMILES: CCOC1=NS(=O)(=O)N=C1NC1CCc2sc(NC(=O)C3CC3)c(C(=O)NCC3CC3)c2C1]

2-(Cyclopropanecarbonylamino)-N-(cyclopropylm-ethyl)-5-[(4-ethoxy-1,1-dioxo-1,2,5-thiadiazol-3-yl)amino]-4,5,6,7-tetrahydrobenzothiophene-3-carbox-amide Intermediate 122 (50 mg, 0.13 mmol) was dissolved in EtOH (3 mL). 3,4-Diethoxy-1-{6},2,5-thiadiazole-1,1-di-one [55904-84-2] (30.7 mg, 0.14 mmol) and DIPEA (0.033 m, 0.19 mmol) were added and the reaction mixture was stirred at r.t. for 3 h. The reaction mixture was concentrated in vacuo and the crude residue, the title compound (66 mg, 85%, 86% purity) was used in the next stage without further purification. LCMS [M+H] 494.05, RT 1.27 minutes, 86% purity (Method 6).

Intermediate 153

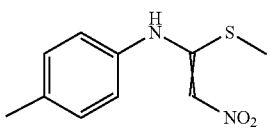

4-methyl-N-(1-methylsulfanyl-2-nitro-vinyl)aniline 1,1-Bis(methylthio)-2-nitroethylene [13623-94-4] (812 mg, 4.67 mmol) and p-toluidine [106-49-0] (500 mg, 4.67 mmol) were taken up in isopropanol (1.57 g, 26.12 mmol) and the reaction mixture was stirred at 100° C. for 2 h in the microwave before leaving to stand at r.t. overnight. The solid formed was filtered-off, washing with isopropanol (2×) and EtOAc, to afford the title compound (553 mg, 53%) as a yellow crystalline solid. δ$_H$ (500 MHz, Chloroform-d) 11.24 (s, 1H), 7.25 (d, J 6.7 Hz, 2H), 7.18 (d, J 8.3 Hz, 2H), 2.44 (s, 3H), 2.40 (s, 3H).

Intermediate 154

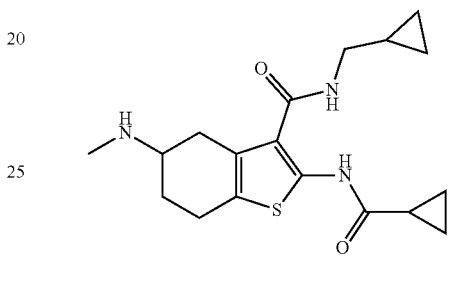

2-(Cyclopropanecarbonylamino)-N-(cyclopropylm-ethyl)-5-(methylamino)-4,5,6,7-tetrahydrobenzothi-ophene-3-carboxamide To a stirred solution of intermediate 62 (0.44 g, 1.33 mmol) in 1,2-DCE [107-06-2] (5 mL) at 30° C. was added methyl ammonium hydrochloride [593-51-1] (0.22 g, 3.32 mmol) and sodium triacetoxy borohydride [56553-60-7] (0.42 g, 1.99 mmol). The reaction mixture was stirred at r.t. for 3 h and then diluted with 1,2-DCE (10 mL), washed with water (10 mL) and washed with saturated aqueous sodium bicarbonate solution (10 mL). The organic layer was separated, dried (Na$_2$SO$_4$), filtered and concentrated in vacuo to give a pale green oil. The crude product was diluted with EtOAc (20 mL) and washed with 1M aqueous hydrochloric acid (2×10 mL). The combined acidic extracts were basified with sodium hydrogen carbonate to ~pH 7.5 and then the pH was adjusted to pH 9-10 with 2M aqueous sodium carbonate solution. The basic aqueous solution was extracted with EtOAc (2×15 mL) and the organic layers were dried (Na$_2$SO$_4$), filtered and concentrated in vacuo to give a pale yellow solid (0.13 g). The basic aqueous layer was then saturated with sodium chloride and extracted with EtOAc (3×10 mL) and 1:1 chloroform/isopropanol (2×10 mL). The combined organic extracts were dried (Na$_2$SO$_4$), filtered and concentrated in vacuo before combining with the previous batch to afford the title compound (0.14 g, 28%, 91% purity). δ$_H$ (500 MHz, DMSO-d$_6$) 11.18 (s, 1H), 7.78 (s, 1H), 3.20 (dd, J 13.4, 6.4 Hz, 1H), 3.10 (dt, J 13.3, 6.0 Hz, 1H), 2.90 (dd, J 16.2, 4.4 Hz, 1H), 2.68 (m, 2H), 2.58 (m, 1H), 2.41 (dd, J 15.7, 8.4 Hz, 1H), 2.34 (s, 3H), 2.02-1.94 (m, 1H), 1.87 (p, J 6.2 Hz, 1H), 1.56-1.46 (m, 1H), 1.09-1.00 (m, 1H), 0.82 (m, 4H), 0.46-0.39 (m, 2H), 0.23 (q, J 4.5 Hz, 2H). LCMS [M+H]$^+$ 348, RT 0.81 minutes, 91% purity (Method 11).

Intermediate 155

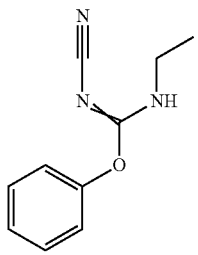

3-Cyano-1-ethyl-2-phenyl-isourea

To a solution of diphenyl N-cyanocarbonimidate [79463-77-7] (1.00 g, 4.20 mmol) in EtOH (40 mL) was added DIPEA (0.54 g, 4.20 mmol). 2.0M Ethylamine in THF (2.1 mL, 4.2 mmol) was added dropwise to the stirred solution at r.t. and the reaction was stirred at r.t. for 2 h. The reaction mixture was concentrated in vacuo and water (10 mL) was added to form a wax which was filtered and dried overnight at 40° C. The solid was cooled to r.t. to afford the title compound (0.62 g, 78%) as an off-white solid. $\delta_H$ (500 MHz, Chloroform-d) 80%+ purity, 7.40 (t, J 7.6 Hz, 2H), 7.29 (d, J 7.3 Hz, 1H), 7.09 (d, J 7.9 Hz, 2H), 6.82 (s, 1H), 3.49 (p, J 6.8 Hz, 2H), 1.30 (t, J 7.1 Hz, 3H). $^1$H NMR has broad second component that could be E/Z stereoisomer, rotational broadening or impurity. LCMS [M+H]$^+$ 190, RT 0.98 minutes, 99% purity (Method 6).

Intermediate 156

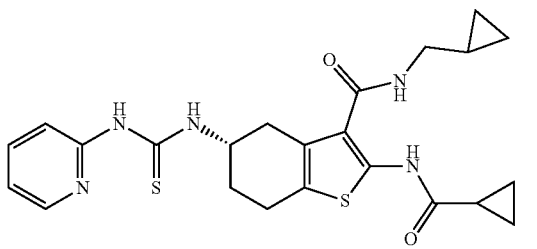 [SMILES: O=C(NCC1CC1)c1c(NC(=O)C2CC2)sc2c1C[C@@H](NC(=S)Nc1ccccn1)CC2]

(5S)-2-(Cyclopropanecarbonylamino)-N-(cyclopropylmethyl)-5-(2-pyridylcarbamothioylamino)-4,5,6,7-tetrahydrobenzothiophene-3-carboxamide Intermediate 117 (400 mg, 1.2 mmol) was dissolved in DCM (5 mL) and 2-isothiocyanatopyridine [52648-45-0] (196 mg, 1.44 mmol) in DCM (5 mL) was added and the solution was stirred for 18 h under nitrogen before stirring for a further 24 h at r.t. The reaction mixture was concentrated in vacuo to give a pale yellow solid which was washed with DCM to afford the title compound (400 mg, 71%). $\delta_H$ (500 MHz, DMSO-d$_6$) 12.01 (d, J 7.9 Hz, 1H), 11.14 (s, 1H), 10.56 (s, 1H), 8.04 (d, J 3.9 Hz, 1H), 7.79-7.72 (m, 1H), 7.69 (t, J 4.4 Hz, 1H), 7.15 (d, J 8.4 Hz, 1H), 7.01 (dd, J 7.2, 5.9 Hz, 1H), 4.73-4.62 (m, 1H), 3.19-3.07 (m, 3H), 2.88-2.70 (m, 3H), 2.17-2.05 (m, 1H), 2.03-1.81 (m, 2H), 1.09-0.94 (m, 1H), 0.90-0.76 (m, 4H), 0.46-0.36 (m, 2H), 0.27-0.16 (m, 2H).

Intermediate 157

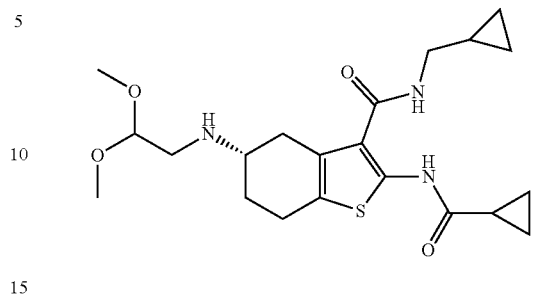

(5S)-2-(Cyclopropanecarbonylamino)-N-(cyclopropylmethyl)-5-(2,2-dimethoxyethylamino)-4,5,6,7-tetrahydrobenzothiophene-3-carboxamide To intermediate 117 (1 g, 3 mmol) in MeOH (20 mL) was added dimethoxyacetaldehyde [51673-84-8] (60% aqueous, 452 μL, 2.99 mmol) and the reaction was stirred for 18 h to give a cream coloured suspension. Sodium borohydride [16940-66-2] (113 mg, 2.99 mmol) was added in portions, and the reaction was stirred at r.t. for 15 minutes. The reaction was concentrated in vacuo and diluted with EtOAc (60 mL). The organic layer was washed with water (2×20 mL), dried (Na$_2$SO$_4$), filtered and concentrated in vacuo to give a yellow oil (1.2 g) which was purified by flash column chromatography on silica (gradient elution with 0-10% MeOH in DCM) to afford the title compound (1.07 g, 84%) as a yellow oil which solidified on standing. $\delta_H$ (500 MHz, DMSO-d$_6$) 11.20 (s, 1H), 7.66-7.57 (m, 1H), 4.40 (t, J 5.5 Hz, 1H), 3.27 (d, J 1.0 Hz, 6H), 3.24-3.15 (m, 1H), 3.15-3.05 (m, 1H), 2.87 (d, J 15.6 Hz, 1H), 2.85-2.74 (m, 1H), 2.70 (d, J 4.8 Hz, 2H), 2.69-2.64 (m, 1H), 2.63-2.53 (m, 1H), 2.42 (dd, J 15.4, 8.0 Hz, 1H), 2.01-1.93 (m, 1H), 1.93-1.84 (m, 1H), 1.59-1.39 (m, 2H), 1.10-0.99 (m, 1H), 0.88-0.77 (m, 4H), 0.47-0.39 (m, 2H), 0.27-0.21 (m, 2H).

Intermediate 158

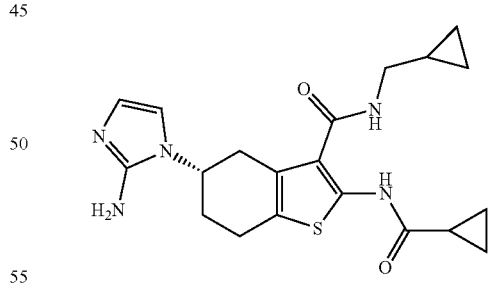

(5S)-5-(2-Aminoimidazol-1-yl)-2-(cyclopropanecarbonylamino)-N-(cyclopropylmethyl)-4,5,6,7-tetrahydrobenzothiophene-3-carboxamide Cyanamide [420-04-2] (134 mg, 3.2 mmol) was dissolved in 1,4-dioxane (10 mL) in a pressure tube and 4M hydrochloric acid in 1,4-dioxane (800 μl) was added to give a white suspension which was stirred for 5 minutes. Intermediate 157 (450 mg, 1.07 mmol) was added and the reaction was sealed and heated to 60° C., stirring for 1 h. The reaction was heated and stirred at 60° C. for a further 17 h to give a brown oily solid. The reaction mixture was diluted with MeOH and was concentrated in vacuo. The residue was diluted with DCM (30 mL) and washed with saturated aqueous sodium hydrogen carbonate solution (20 mL). The aqueous layer was further extracted with 10% MeOH in DCM (3×20 mL). The organic layers were combined, dried (Na₂SO₄), filtered and concentrated in vacuo to give the crude product (574 mg) which was purified by flash column chromatography on silica (gradient elution with 0-10% MeOH in DCM) to give the crude product (184 mg) as a yellow oil. The material was dissolved in DMSO/MeCN and purified by reverse phase preparative HPLC (basic) to give a gel which was sonicated in Et₂O to give a white solid which was collected by filtration and dried in a vacuum oven to afford the title compound (75 mg, 18%). $\delta_H$ (500 MHz, DMSO-d₆) 11.15 (s, 1H), 7.73 (s, 1H), 6.66 (d, J 1.5 Hz, 1H), 6.42 (d, J 1.5 Hz, 1H), 5.37 (s, 2H), 4.28-4.16 (m, 1H), 3.12 (qt, J 13.5, 6.2 Hz, 2H), 2.97 (dd, J 15.1, 4.0 Hz, 1H), 2.91-2.72 (m, 3H), 2.07-1.98 (m, 2H), 1.96-1.85 (m, 1H), 1.06-0.96 (m, 1H), 0.88-0.80 (m, 4H), 0.44-0.34 (m, 2H), 0.25-0.15 (m, 2H). LCMS [M+H]⁺ 400.2, RT 1.83 minutes, 100% purity (Method 10).

Intermediate 159

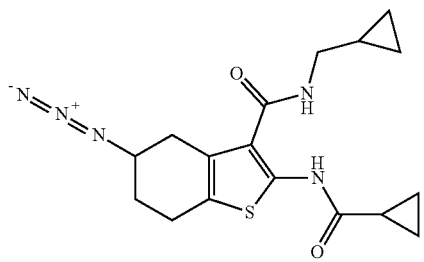

5-Azido-2-(cyclopropanecarbonylamino)-N-(cyclopropylmethyl)-4,5,6,7-tetrahydrobenzothiophene-3-carboxamide To Example 109 (1.24 g, 3.72 mmol) in MeOH (20 mL) was added potassium carbonate (1.80 g, 13.0 mmol), copper (II) sulfate pentahydrate (27.9 mg, 0.11 mmol) and 1H-imidazole-1-sulfonyl azide hydrochloride [952234-36-5] (1.07 g, 4.84 mmol). The reaction mixture was stirred at r.t. for 2 h and further 1H-imidazole-1-sulfonyl azide hydrochloride [952234-36-5] (82.3 mg, 0.39 mmol) was added and the reaction mixture was stirred for a further 30 minutes. The solvent was removed in vacuo and the solid was partitioned between water (10 mL) and EtOAc (30 mL). To this was added 2N aqueous hydrochloric acid solution (20 mL) and the organic layer was separated and the aqueous layer was further extracted with EtOAc (20 mL). The combined organic layers were dried (Na₂SO₄), filtered and the solvent removed in vacuo to give a red residue which was purified by flash column chromatography on silica (gradient elution with 0-30% EtOAc/iso-hexane) to afford the title compound (1.20 g, 90%) as a white solid. $\delta_H$ (300 MHz, DMSO-d₆) 11.08 (s, 1H), 7.75 (t, J 5.6 Hz, 1H), 4.03 (d, J 6.9 Hz, 1H), 3.26-2.92 (m, 4H), 2.72 (s, 3H), 2.10-1.76 (m, 2H), 1.12-0.98 (m, 1H), 0.89-0.81 (m, 2H), 0.83 (s, 2H), 0.50-0.37 (m, 2H), 0.29-0.18 (m, 2H).

Intermediate 160

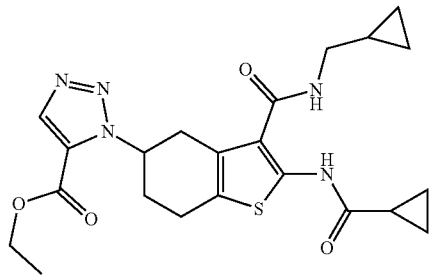

Ethyl 3-[2-(cyclopropanecarbonylamino)-3-(cyclopropylmethylcarbamoyl)-4,5,6,7-tetrahydrobenzothiophen-5-yl]triazole-4-carboxylate Intermediate 159 (49 mg, 0.14 mmol) was dissolved in toluene (2 mL) and ethyl propiolate [623-47-2] (40.1 mg, 0.41 mmol) was added. The solution was heated at 110° C. for 18 h before cooling and removing the solvent in vacuo. The residue was purified by flash column chromatography on silica (gradient elution with 0-60% EtOAc/iso-hexane) to afford the title compound (13 mg, 21%). $\delta_H$ (300 MHz, Chloroform-d) 12.06 (s, 1H), 8.21 (s, 1H), 5.82 (s, 1H), 5.57 (d, J 11.3 Hz, 1H), 4.42 (q, J 7.1 Hz, 2H), 3.62-3.48 (m, 1H), 3.39-3.16 (m, 3H), 2.98 (s, 2H), 1.77-1.54 (m, 1H), 1.59-0.93 (m, 8H), 0.98-0.86 (m, 2H), 0.58-0.46 (m, 2H), 0.24 (dt, J 5.9, 4.5 Hz, 2H).

Intermediate 161

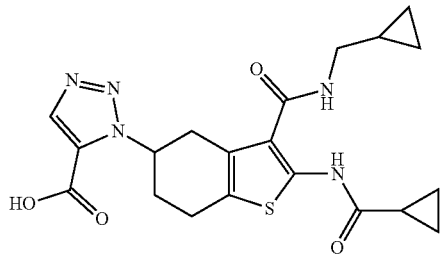

3-[2-(Cyclopropanecarbonylamino)-3-(cyclopropylmethylcarbamoyl)-4,5,6,7-tetrahydrobenzothiophen-5-yl]triazole-4-carboxylic acid Intermediate 160 (184 mg, 0.40 mmol) was dissolved in THF (1.76 g) and water (500 mg, 30 mmol).
To this was added lithium hydroxide monohydrate [1310-66-3] (50.6 mg, 1.21 mmol) and the mixture was stirred for 18 h. The reaction mixture was concentrated in vacuo and the residue was redissolved in water (5 mL) and extracted with EtOAc (10 mL). The aqueous layer was acidified to pH 1 using 2M aqueous hydrochloric acid solution (5-10 mL). A white solid crashed out and was filtered to a solid which was suspended in MeOH and the solvent removed in vacuo to afford the title compound (127 mg, 74%) as a white solid. $\delta_H$ (300 MHz, DMSO-d₆) 11.12 (s, 1H), 8.24 (s, 1H), 7.76 (t, J 5.8 Hz, 1H), 5.46 (s, 1H), 3.16 (s, 2H), 3.26-2.97 (m, 2H), 2.86 (s, 3H), 2.80-2.66 (m, 1H), 2.35 (s, 1H), 1.99-1.88 (m, 1H), 0.98 (s, 1H), 0.90-0.81 (m, 4H), 0.41-0.29 (m, 2H), 0.16 (td, J 5.4, 3.9 Hz, 2H).

Intermediate 162

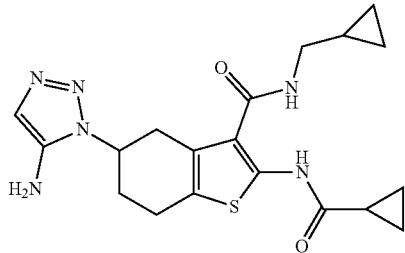

5-(5-Aminotriazol-1-yl)-2-(cyclopropanecarbonylamino)-N-(cyclopropylmethyl)-4,5,6,7-tetrahydrobenzothiophene-3-carboxamide To a solution of example 140 (81 mg, 0.16 mmol) in DCM (3 mL) at 0° C. was added TFA (3 mL, 39.7 mmol). The solution was stirred at 0° C. for 5 minutes then at r.t. for 2 h, the solvent was removed in vacuo and the excess TFA azetroped with isohexane. The residue was purified by flash column chromatography on silica (gradient elution with 0-100% MeOH/7M aqueous NH₃ in MeOH) to afford the title compound (40 mg, 61%) as a white solid. δ$_H$ (300 MHz, Methanol-d₄) 6.97 (s, 1H), 4.57 (s, 1H), 3.33-3.09 (m, 2H), 2.96 (s, 3H), 2.43 (td, J 10.7, 10.1, 6.8 Hz, 1H), 2.34 (s, 1H), 1.81 (td, J 7.7, 3.8 Hz, 1H), 1.31 (s, 2H), 1.13-0.88 (m, 4H), 0.55-0.43 (m, 2H), 0.25 (dt, J 6.2, 4.5 Hz, 2H).

Intermediate 163

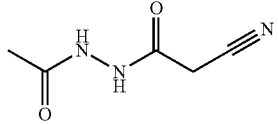

N'-acetyl-2-cyano-acetohydrazide 2-cyanoacetohydrazide [140-87-4] (2 g, 20.18 mmol) was stirred in DCE (20 mL). Acetic anhydride (1.91 mL, 20.18 mmol) and pyridine (1.63 mL, 20.18 mmol) were added to the suspension. The reaction was stirred at 60° C. for 16 hours to give a fine light brown. The reaction was allowed to cool and the DCE was removed in vacuo. The residue was suspended in diethyl ether and collected by vacuum filtration to afford the title compound (2.82 g, 89% at 90% purity) as a yellow/pale brown solid. δ$_H$ (500 MHz, DMSO-d₆) δ 10.18-10.13 (m, 1H), 9.95 (d, J 1.5 Hz, 1H), 3.73 (s, 2H), 1.86 (s, 3H).

Intermediate 164

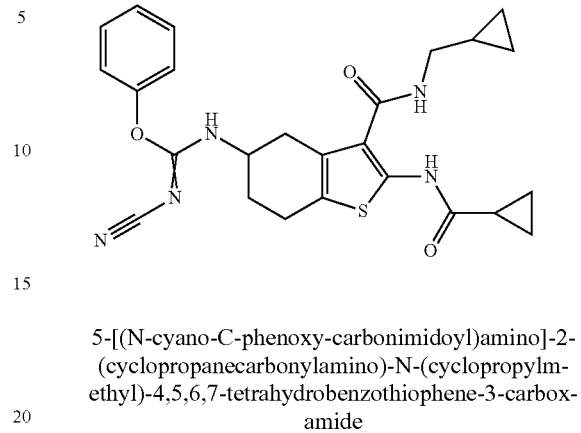

5-[(N-cyano-C-phenoxy-carbonimidoyl)amino]-2-(cyclopropanecarbonylamino)-N-(cyclopropylmethyl)-4,5,6,7-tetrahydrobenzothiophene-3-carboxamide Intermediate 122 (100 mg, 0.27 mmol) was dissolved in isopropanol (5 mL) and DIPEA (52.7 mg, 0.41 mmol) and diphenyl N-cyanocarbonimidate [79463-77-7] (79.7 mg, 0.32 mmol) were added. The reaction mixture was stirred at r.t. for ~1 h. p-Toluidine [106-49-0] (31.9 mg, 0.30 mmol) was added and the reaction mixture was stirred at r.t for ~4 h. The reaction mixture was heated at 80° C. for 30 minutes. The precipitate was filtered, washing with isopropanol and Et₂O to afford the title compound (70 mg, 0.15 mmol, 54%). LCMS [M+H]⁺ 478.2, [M+Na]⁺500.2, RT 2.174 minutes, 100.0% purity (Method 1).

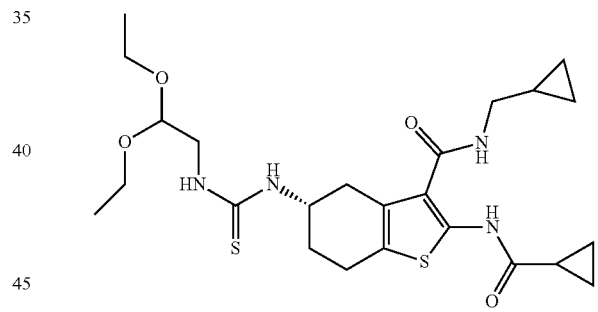

(5S)-2-(Cyclopropanecarbonylamino)-N-(cyclopropylmethyl)-5-(2,2-diethoxyethylcarbamothioylamino)-4,5,6,7-tetrahydrobenzothiophene-3-carboxamide To a stirred solution of phenyl chloromethanethioate [1005-56-7] (0.46 ml, 3.3 mmol) in DCM (30 mL), previously cooled to 0° C. was added a solution of intermediate 117 (1.0 g, 3.0 mmol) and triethylamine (1.25 ml, 9.0 mmol) in DCM (15 mL) dropwise under an atmosphere of nitrogen. The reaction mixture was stirred at r.t. for a further 3 h and a solution of 2,2-diethoxyethanamine [645-36-3] (0.87 ml, 6.0 mmol) in DCM (5 mL) was added dropwise. The reaction was stirred at r.t. for 16 hours, the mixture diluted with EtOAc (150 mL) and washed with 0.5M aqueous citric acid solution (25 mL), water (20 mL), saturated aqueous sodium hydrogen carbonate (2×20 mL) and brine (20 mL). The organic layer was dried (Na₂SO₄), filtered and the solvent removed in vacuo. The residue was purified by flash column chromatography on silica (gradient elution with EtOAc in heptane 5% to 100%) to afford the title compound (1.12 g, 70%) as a pale yellow foamy solid. δ$_H$ (500 MHz, DMSO-d$_6$) 11.12 (s, 1H), 7.74-7.59 (m, 2H), 7.28 (s, 1H), 4.56 (s, 1H), 4.50 (s, 1H), 3.64-3.57 (m, 2H), 3.56-3.43 (m, 3H), 3.20-3.07 (m, 2H), 3.02 (d, J 13.1 Hz, 1H), 2.69 (t, J 5.9 Hz, 2H), 2.55 (dd, J 16.2, 7.2 Hz, 1H), 1.98-1.87 (m, 2H), 1.87-1.75 (m, 1H), 1.15-1.09 (m, 6H), 1.07-0.99 (m, 1H), 0.87-0.81 (m, 5H), 0.45-0.39 (m, 2H), 0.25-0.20 (m, 2H). LCMS: [M−H]⁻ 507, RT=3.05 min, 96% purity (Method 16).

Intermediate 166

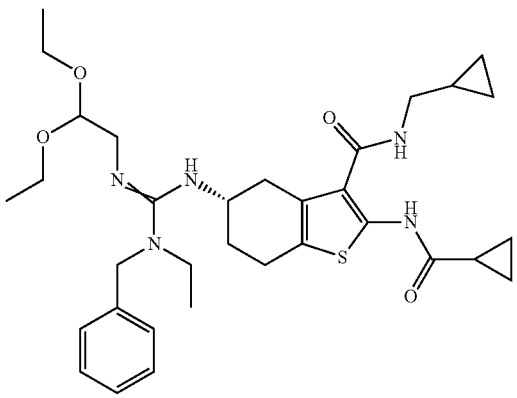

(5S)-5-[[N-benzyl-N'-(2,2-diethoxyethyl)-N-ethyl-carbamimidoyl]amino]-2-(cyclopropanecarbonylamino)-N-(cyclopropylmethyl)-4,5,6,7-tetrahydrobenzothiophene-3-carboxamide To a stirred solution of intermediate 165 (500 mg, 0.98 mmol), triethylamine (0.41 ml, 2.95 mmol) and DMAP [1122-58-3] (12 mg, 0.1 mmol) in DCM (16 mL) previously cooled to 0° C., was added a solution of methanesulfonyl chloride [124-63-0] (0.17 ml, 2.17 mmol) in DCM (2 mL) dropwise under an atmosphere of nitrogen. The reaction mixture was stirred at r.t. for a further 2 h and once the carbodiimide formation was complete, a solution of N-benzylethanamine [14321-27-8] (0.44 ml, 2.95 mmol) in DCM (2 mL) was added dropwise at r.t. and the reaction mixture was then stirred at r.t. for 3 h. A second portion of N-benzylethanamine [14321-27-8] (0.44 ml, 2.95 mmol) was added dropwise at r.t. and stirring continued at r.t. for another 16 h. The reaction mixture was heated under reflux for 48 h and the reaction mixture was left to cool to r.t., diluted with DCM (40 mL) and washed with saturated ammonium chloride solution (10 mL), 0.5M aqueous citric acid solution (10 mL), water (20 mL), 2M aqueous NaOH solution (20 mL) and brine (20 mL). The organic layer was dried (Na$_2$SO$_4$), filtered and the solvent removed in vacuo to afford the title compound (640 mg, 92%, 86% purity) as a yellow oil which was used without further purification. LCMS: [M−H]⁻ 608, RT=1.92 min, 86% purity (Method 17).

Intermediate 167

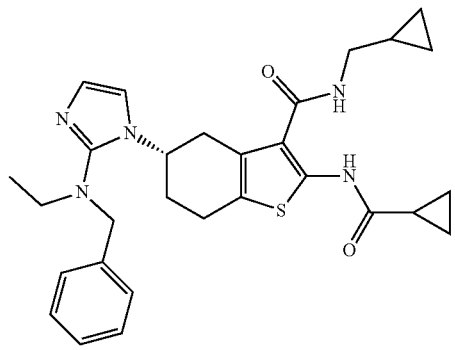

(5S)-5-[2-[Benzyl(ethyl)amino]imidazol-1-yl]-2-(cyclopropanecarbonylamino)-N-(cyclopropylmethyl)-4,5,6,7-tetrahydrobenzothiophene-3-carboxamide To a stirred solution of intermediate 166 (640 mg, 0.89 mmol) in DCM (20 mL) was added 4-methylbenzenesulfonic acid hydrate (1:1) [6192-52-5] (1.35 g, 7.14 mmol). The reaction mixture was stirred at r.t. for 2 h. The reaction mixture was diluted with DCM (20 mL) and washed with saturated aqueous sodium hydrogen carbonate solution (20 mL), water (20 mL) and brine (20 mL). The organic layer was dried (Na$_2$SO$_4$), filtered and concentrated in vacuo to give an orange oil. The residue was purified by flash column chromatography on silica (gradient elution with EtOAc in heptane 25% to 100%) to afford the title compound (238 mg, 50%) as a pale yellow foamy solid. δ$_H$ (500 MHz, DMSO-d$_6$) 11.06 (s, 1H), 7.68 (t, J 5.3 Hz, 1H), 7.25-7.17 (m, 3H), 7.15 (d, J 6.8 Hz, 2H), 6.92 (d, J 1.2 Hz, 1H), 6.79 (d, J 0.9 Hz, 1H), 4.40-4.31 (m, 1H), 4.06 (d, J 12.7 Hz, 1H), 4.02 (d, J 12.7 Hz, 1H), 3.15-3.06 (m, 2H), 3.05-2.94 (m, 2H), 2.90-2.79 (m, 1H), 2.74-2.57 (m, 3H), 1.97-1.82 (m, 2H), 1.40-1.30 (m, 1H), 0.99-0.92 (m, 1H), 0.89 (t, J 7.1 Hz, 3H), 0.87-0.80 (m, 4H), 0.38-0.26 (m, 2H), 0.20-0.10 (m, 2H). LCMS: (M+H)+518, RT=2.53 min, 98% purity (Method 10).

Intermediate 168

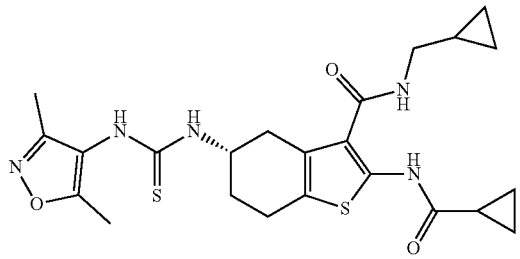

(5S)-2-(Cyclopropanecarbonylamino)-N-(cyclopropylmethyl)-5-[(3,5-dimethylisoxazol-4-yl)carbamothioylamino]-4,5,6,7-tetrahydrobenzothiophene-3-carboxamide Intermediate 117 (400 mg, 1.2 mmol) was dissolved in DCM (5 mL) and 4-isothiocyanato-3,5-dimethyl-1,2-oxazole [321309-27-7] (222 mg, 1.44 mmol) in DCM was added to the reaction mixture and the solution was stirred for 18 h under nitrogen. The reaction mixture was concentrated in vacuo to give a pale yellow solid which was purified by flash column chromatography on silica (gradient elution with 0-100% EtOAc in heptane followed by 0-20% MeOH in DCM) to afford the title compound (475 mg, 81%). $\delta_H$ (500 MHz, DMSO-$d_6$) 11.04 (s, 1H), 8.64 (s, 1H), 7.85 (s, 1H), 7.73 (t, J 5.5 Hz, 1H), 4.52 (s, 1H), 3.19-3.09 (m, 2H), 3.03 (br d, J 12.4 Hz, 1H), 2.72 (br. s., 2H), 2.64-2.61 (m, 1H), 2.22 (s, 3H), 2.07 (s, 3H), 1.94-1.89 (m, 1H), 1.87-1.78 (m, 1H), 1.06-1.01 (m, 1H), 0.89-0.77 (m, 5H), 0.45-0.40 (m, 2H), 0.25-0.20 (m, 2H). LCMS [M+H]$^+$ 488.20/486.20, RT 1.80 minutes, 99% purity (Method 12).

Intermediate 169

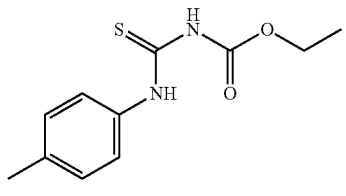 [SMILES: CCOC(=O)NC(=S)Nc1ccc(C)cc1]

Ethyl N-(p-tolylcarbamothioyl)carbamate

A solution of ethyl carbonisothiocyanatidate [16182-04-0] (0.22 mL, 1.86 mmol) in DCM (20 mL) was cooled to 0° C. before adding 4-methylaniline [106-49-0] (200 mg, 1.86 mmol). The ice bath was removed and the solution was stirred for 4 h under nitrogen and the solvent was removed in vacuo to yield a pale yellow solid which was triturated with heptane to afford the title compound (420 mg, 94%) as a white solid. LCMS [M+H]$^+$ 238.95, RT 1.16 minutes, 100% purity (Method 6).

Intermediate 170

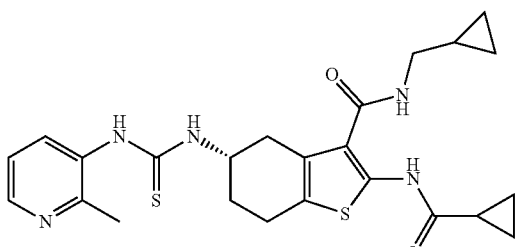

(5S)-2-(Cyclopropanecarbonylamino)-N-(cyclopropylmethyl)-5-[(2-methyl-3-pyridyl)carbamothioylamino]-4,5,6,7-tetrahydrobenzothiophene-3-carboxamide Phenyl chloromethanethioate [1005-56-7] (91 µL, 0.66 mmol) was stirred in DCM (5 mL) and cooled to 0° C. Intermediate 117 (200 mg, 0.6 mmol) in DCM (5 mL) and triethylamine (0.25 mL, 1.8 mmol) was added dropwise. The reaction was stirred for 30 minutes at r.t. and the reaction was concentrated in vacuo and the residue dissolved in 1,4-dioxane (5 mL). 2-Methylpyridin-3-amine [3430-10-2] (130 mg, 1.2 mmol) was added and the reaction stirred at 80° C. for 30 minutes followed by heating at 120° C. for 90 minutes. The reaction was diluted with EtOAc (40 mL) and washed with 0.5 M aqueous citric acid solution (20 mL) and saturated aqueous sodium hydrogen carbonate solution (20 mL), dried (Na$_2$SO$_4$), filtered and concentrated in vacuo to give a brown residue. The acidic aqueous phase was basified to pH 9 with saturated aqueous sodium hydrogen carbonate solution and was extracted with EtOAc (2×20 mL). The organic phases were combined and concentrated in vacuo. The brown residues were purified by flash column chromatography on silica (gradient elution with 0-100% EtOAc followed by 0-10% MeOH in DCM) to afford the title compound (172 mg, 54%, 91% purity) as a brown oil. LCMS [M+H]$^+$ 484.2, RT 1.668 minutes, 90.5% purity (Method 12).

Intermediate 171

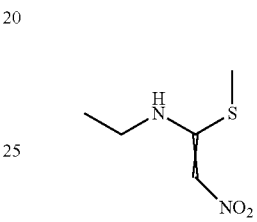

N-ethyl-1-methylsulfanyl-2-nitro-ethenamine 1,1-Bis(methylthio)-2-nitroethylene [13623-94-4] (500 mg, 2.87 mmol) was taken up in DCM (2 mL) and 2.0M ethylamine solution (1.3 g, 3.2 mmol) was added. The reaction mixture was stirred at 80° C. for 30 minutes in the microwave. The reaction mixture was concentrated in vacuo to afford the title compound (480 mg, 103%) as a brown oil which was utilised without purification. LCMS [M+H]$^+$ 163.2, [M+Na]$^+$185.2, RT 0.633 minutes, 73.7% purity (Method 1).

Intermediate 172

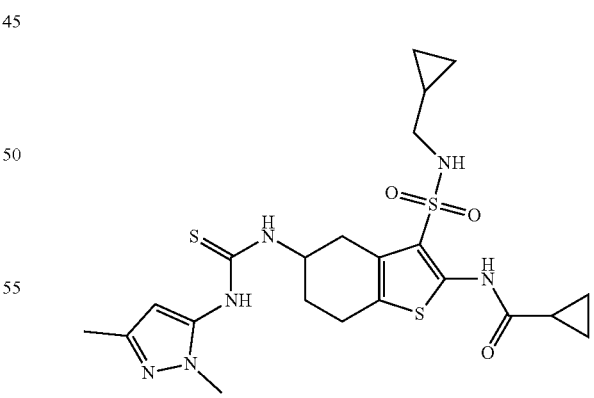

N-[3-(cyclopropylmethylsulfamoyl)-5-[(2,5-dimethylpyrazol-3-yl)carbamothioylamino]-4,5,6,7-tetrahydrobenzothiophen-2-yl]cyclopropanecarboxamide Intermediate 51 was dissolved in dichloromethane (50 mL) and N,N-diisopropylethylamine (0.45 mL, 2.6 mmol)

was added, followed by 5-isothiocyanato-1,3-dimethyl-pyrazole (260 mg, 1.6971 mmol, neat) at rt. The resulting solution was stirred at rt overnight and then diluted with DCM, washed twice with water, evaporated in vacuo and purified by flash column chromatography on silica (gradient elution with 25 g SNAP-Ultra, Isolera, eluting with 0 to 100% ethyl acetate in hexane to afford the title compound (323 mg, 0.6179 mmol, 47.87% Yield), as white solid. $^1$H NMR (300 MHz, DMSO-d$_6$) δ 10.46 (s, 1H), 9.14 (s, 1H), 7.96 (s, 2H), 5.93 (s, 1H), 4.58 (s, 1H), 3.54 (s, 3H), 3.14 (d, J=15.4 Hz, 1H), 2.71 (s, 4H), 2.62 (dd, J=16.8, 8.6 Hz, 1H), 2.10 (s, 3H), 1.92 (s, 1H), 1.83 (s, 1H), 0.97-0.75 (m, 6H), 0.49-0.27 (m, 2H), 0.09 (d, J=4.8 Hz, 2H). LCMS [M+H] 523.0, RT 1.02 minutes (Method 15).

Intermediate 173

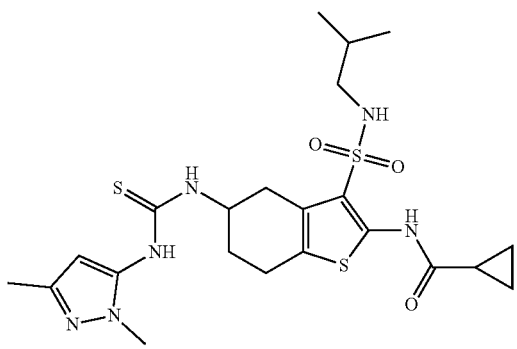 [SMILES: Cc1cc(NC(=S)NC2CCc3sc(NC(=O)C4CC4)c(S(=O)(=O)NCC(C)C)c3C2)n(C)n1]

N-[3-(isopropylmethylsulfamoyl)-5-[(2,5-dimethylpyrazol-3-yl)carbamothioylamino]-4,5,6,7-tetrahydrobenzothiophen-2-yl]cyclopropanecarboxamide Intermediate 28 (300 mg, 0.807 mmol) was dissolved in dichloromethane (50 mL) and N,N-diisopropylethylamine (0.28 mL, 1.6 mmol) was added, followed by 5-isothiocyanato-1,3-dimethyl-pyrazole (160 mg, 1.04 mmol, neat) at rt. The resulting solution was stirred at rt overnight and then diluted with DCM, washed twice with water, evaporated in vacuo and purified by flash column chromatography on silica (gradient elution with 25 g SNAP-Ultra, Isolera, eluting with 0 to 100% EtOAc in hexane to afford the title compound (200 mg, 0.381 mmol, 47.20% Yield), white solid. $^1$H NMR (300 MHz, DMSO-d$_6$) δ 10.42 (s, 1H), 9.14 (s, 1H), 7.96 (d, J=8.0 Hz, 1H), 7.82 (s, 1H), 5.93 (s, 1H), 4.57 (s, 1H), 3.53 (s, 3H), 3.13 (d, J=14.5 Hz, 2H), 2.73 (s, 3H), 2.61 (t, J=6.6 Hz, 3H), 2.10 (s, 3H), 1.64 (dt, J=13.4, 6.7 Hz, 2H), 0.91 (t, J=7.3 Hz, 4H), 0.87-0.75 (m, 6H). LCMS [M+H]$^+$ 525.2, RT 1.34 minutes (Method 15).

Intermediate 174

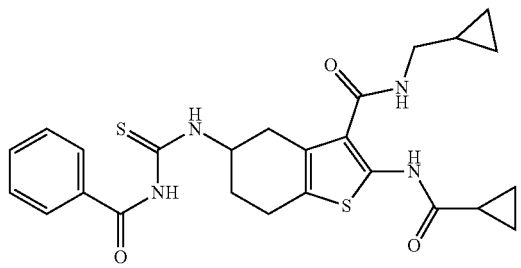 [SMILES: O=C(NC(=S)NC1CCc2sc(NC(=O)C3CC3)c(C(=O)NCC3CC3)c2C1)c1ccccc1]

5-(Benzoylcarbamothioylamino)-2-(cyclopropanecarbonylamino)-N-(cyclopropylmethyl)-4,5,6,7-tetrahydrobenzothiophene-3-carboxamide Intermediate 122 (1.02 g, 2.75 mmol) was dissolved in DCM (50 mL) and cooled to 0° C. DIPEA (0.71 mL, 4.06 mmol) was added followed by benzoyl isocyanate [4461-33-0] (0.56 mL, 4.08 mmol) and the mixture was stirred at r.t. for 20 h. The reaction mixture was washed with water and brine, passed through phase separator cartridge and the organic phase was concentrated in vacuo to afford the crude product as a golden orange solid. The residue was purified by flash column chromatography on silica (gradient elution with EtOAc/hexanes 0% 1 CV, 0-20% 11 CV, 20% 2 CV, 20-50% 6 CV, 50% 1 CV, 50-100% 5 CV, 100% 8 CV) to afford the purified material. The crude fractions were combined in vacuo and the sample was dissolved in DCM/MeOH and the material was concentrated in vacuo. To the residue was added hexane and EtOAc, the mixture was filtered and the solid washed with hexane and the trituration procedure repeated with the filtrate. The second trituration was purified by flash column chromatography on silica (gradient elution in DCM/MeOH 0% 1 CV, 0-10% 9 CV, 10% 1 CV, 10-25% 10 CV) to afford the title compound (1.12 g, 82% Yield). LCMS [M+H]$^+$ 497.0, [M+Na]$^+$519.0, RT 2.483 minutes, 100.0% purity (Method 1).

Intermediate 175

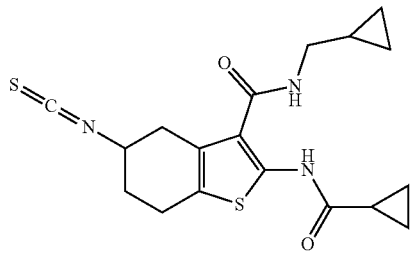 [SMILES: O=C(NCC1CC1)c1c(NC(=O)C2CC2)sc2c1CC(N=C=S)CC2]

2-(Cyclopropanecarbonylamino)-N-(cyclopropylmethyl)-5-isothiocyanato-4,5,6,7-tetrahydrobenzothiophene-3-carboxamide A solution of O-phenyl carbonochloridothioate [1005-56-7] (170 μL, 1.23 mmol) in DCM (10 mL) was added over 10 minutes to an ice-cold stirred solution of example 109 (400 mg, 1.2 mmol) and triethylamine [121-44-8] (250 μL, 1.8 mmol) in DCM (25 mL). The mixture was stirred at 0° C. for 15 minutes and then the ice bath was removed. Water (50 mL) was added and the layers were separated. The aqueous phase was extracted with DCM (2×20 mL) and the combined organic extracts were dried (MgSO$_4$), filtered and concentrated in vacuo to give the crude intermediate which was purified by flash column chromatography on silica (gradient elution with 30-60% EtOAc/heptanes) to afford the title compound (360 mg, 32%, 40% purity) as a light yellow solid. $\delta_H$ (250 MHz, DMSO-d$_6$) 10.85 (s, 1H), 4.17 (s, 1H), 2.96-2.59 (m, 3H), 2.53 (d, J 8.1 Hz, 2H), 2.18-1.78 (m, 3H), 1.72-1.68 (m, 1H), 0.81 (d, J 6.1 Hz, 1H), 0.66-0.58 (m, 4H), 0.30-0.13 (m, 2H), 0.04-0.01 (m, 2H).

Intermediate 176

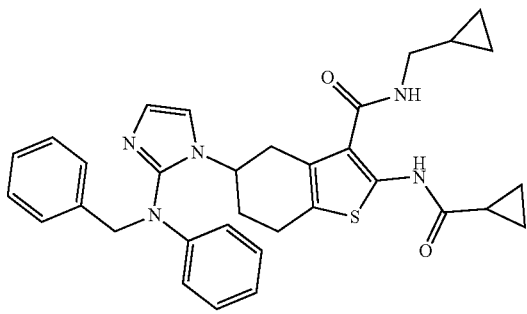 [SMILES: O=C(NCC1CC1)c1c(NC(=O)C2CC2)sc2c1CC(n1ccnc1N(Cc1ccccc1)c1ccccc1)CC2]

5-[2-(N-Benzylanilino)imidazol-1-yl]-2-(cyclopropanecarbonylamino)-N-(cyclopropylmethyl)-4,5,6,7-tetrahydrobenzothiophene-3-carboxamide Intermediate 175 (90%, 340 mg, 0.82 mmol) was dissolved in EtOH (10 mL) and 2,2-diethoxyethan-1-amine [645-36-3] (360 µL, 2.48 mmol) was added. After standing at r.t. for 16 h overnight and the solvent was removed in vacuo and the residue dissolved in EtOAc (20 mL) and washed with water (2×10 mL). The organic phase was dried (MgSO$_4$), filtered and concentrated in vacuo to afford 2-(Cyclopropanecarbonylamino)-N-(cyclopropylmethyl)-5-(2,2-diethoxyethylcarbamothioylamino)-4,5,6,7-tetrahydrobenzothiophene-3-carboxamide (364 mg, 60.6%, 69% purity) as a yellow oil. LCMS (ES+) [M+Na]$^+$531.0, RT 1.22 minutes, 69% purity (Method 11).

Methanesulfonyl chloride [124-63-0] (85 µL, 1.09 mmol) was added dropwise to a solution of 2-(Cyclopropanecarbonylamino)-N-(cyclopropylmethyl)-5-(2,2-diethoxyethylcarbamothioylamino)-4,5,6,7-tetrahydrobenzothiophene-3-carboxamide (69%, 364 mg, 0.49 mmol), triethylamine (225 µL, 1.61 mmol) and a catalytic amount of DMAP [1122-58-3] in DCM (20 mL), cooled in an ice bath. The resulting mixture was stirred for 10 minutes before removing the ice bath and stirring at r.t. for 1 h. N-Benzylaniline [103-32-2] (300 mg, 1.64 mmol) was added and stirring continued at r.t. for 16 h overnight. Further methanesulfonyl chloride [124-63-0] (113 mg, 0.99 mmol) was added prior to N-benzylaniline [103-32-2] addition (453 mg, 2.47 mmol) and further methanesulfonyl chloride [124-63-0] (85 µL, 1.09 mmol) was added, followed by N-benzylaniline [103-32-2] (200 mg, 1.09 mmol) and the reaction was stirred at r.t. for 3 days over the weekend. The reaction mixture was diluted with DCM (20 mL) and washed with saturated aqueous ammonium chloride (20 mL). The organic layer was dried (MgSO$_4$), filtered and concentrated in vacuo to afford 5-[[(E)-N-Benzyl-N'-(2,2-diethoxyethyl)-N-phenyl-carbamimidoyl]amino]-2-(cyclopropanecarbonylamino)-N-(cyclopropylmethyl)-4,5,6,7-tetrahydrobenzothiophene-3-carboxamide (970 mg, 90%, 30% purity) as a yellow oil which was used directly in the next step without purification.

5-[[(E)-N-Benzyl-N'-(2,2-diethoxyethyl)-N-phenyl-carbamimidoyl]amino]-2-(cyclopropanecarbonylamino)-N-(cyclopropylmethyl)-4,5,6,7-tetrahydrobenzothiophene-3-carboxamide (30%, 970 mg, 0.44 mmol) was dissolved in DCM (30 mL) and p-toluene sulfonic acid [6192-52-5] (675 mg, 3.55 mmol) was added. The reaction mixture was stirred at r.t. for 2 h before diluting with DCM (30 mL) and washing with water (20 mL). The organic phase was dried (MgSO$_4$), filtered and concentrated in vacuo to give the crude product which was purified by flash column chromatography on silica (gradient elution with 30-60% EtOAc/heptane) to afford the title compound (229 mg, 81%, purity 89%) as a light yellow glass. LCMS [M+H]$^+$ 566.2, RT 1.13 minutes, 89% purity (Method 11).

Intermediate 177

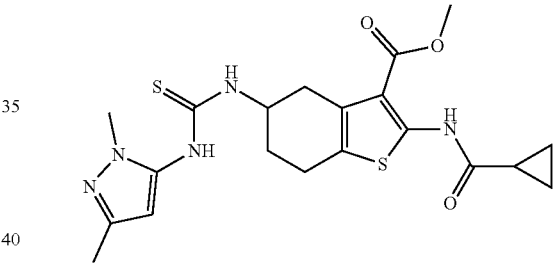

Methyl 2-(cyclopropanecarbonylamino)-5-[(2,5-dimethylpyrazol-3-yl)carbamothioylamino]-4,5,6,7-tetrahydrobenzothiophene-3-carboxylate. To a stirred solution of intermediate 184 (1.5 g, 5.1 mmol) in dichloromethane (30 mL) was added N,N-diisopropylethylamine (1.3 mL, 7.5 mmol) and 5-isothiocyanato-1,3-dimethyl-pyrazole (1 g, 6.5274 mmol). The reaction mixture was stirred at room temperature for 2 hours and then evaporated in vacuo. The resulting residue was dissolved in DCM and washed with water. Purified by chromatography (Biotage SNAP Ultra 25 g, Isolera) with a gradient of 0% to 100% ethyl acetate in iso-hexane to afford the title compound (2.12 g, 4.74 mmol, 93% Yield) as a white solid. 1H NMR (300 MHz, Chloroform-d) δ 11.42 (s, 1H), 7.17 (s, 1H), 6.10 (d, J=8.3 Hz, 1H), 5.89 (s, 1H), 4.79 (s, 1H), 3.90 (s, 3H), 3.71 (s, 3H), 3.28 (dd, J=17.1, 5.5 Hz, 1H), 2.95-2.75 (m, 1H), 2.65 (dt, J=17.2, 5.9 Hz, 2H), 2.24 (s, 3H), 2.14 (d, J=6.8 Hz, 1H), 1.99-1.83 (m, 1H), 1.69 (td, J=8.0, 4.0 Hz, 1H), 1.16 (dt, J=4.6, 3.3 Hz, 2H), 0.97 (dd, J=7.8, 3.2 Hz, 2H). LCMS [M+H]$^+$ 448.0, RT 1.39 minutes (Method 15)

Intermediate 178

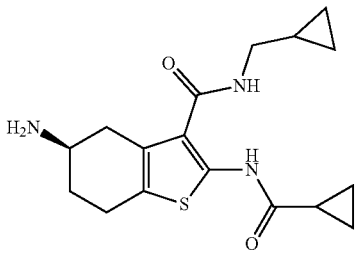 [SMILES: N[C@@H]1CCc2sc(NC(=O)C3CC3)c(C(=O)NCC3CC3)c2C1]

(5R)-5-Amino-2-(cyclopropanecarbonylamino)-N-(cyclopropylmethyl)-4,5,6,7-tetrahydrobenzothiophene-3-carboxamide To a stirred solution of intermediate 116 (5 g, 10 mmol) in DCM (25 mL) was added TFA (20 mL) dropwise over 15 minutes, maintaining the temperature below 25° C. and the reaction mixture was stirred at r.t. for a further 15 minutes. Toluene (30 mL) was added to the reaction mixture and the solvent was removed in vacuo. To the residue was added EtOAc (10 mL) followed by diisopropyl ether (350 mL) and the resulting slurry was stirred for 15 minutes. The precipitate was filtered, and the solid washed with diisopropyl ether (45 mL), Et$_2$O (45 mL) and dried under a flow of nitrogen for 15 minutes to give a beige solid as a TFA salt (6.28 g). The solid was dissolved in water (200 mL) containing TFA (1 mL) and Et$_2$O (50 mL) and EtOAc (5 mL) were added. The aqueous phase was separated and washed with Et$_2$O (25 mL). Potassium carbonate (8 g, 60 mmol) was added in portions and the aqueous phase extracted with 10% MeOH in EtOAc (100 mL×2), combined organic extracts dried (Na$_2$SO$_4$), filtered and concentrated in vacuo to afford the title compound (3.71 g, 100%) as a pale yellow solid. δ$_H$ (300 MHz, Chloroform-d) 12.19 (s, 1H), 5.97 (s, 1H), 3.31-3.15 (m, 3H), 3.10-2.94 (m, 1H), 2.88-2.65 (m, 2H), 2.44 (ddt, J 14.3, 8.4, 2.0 Hz, 1H), 2.10-1.93 (m, 1H), 1.77-1.62 (m, 2H), 1.15-1.01 (m, 3H), 0.94-0.80 (m, 2H), 0.62-0.51 (m, 2H), 0.27 (dt, J 6.0, 4.6 Hz, 2H). NH$_2$ protons not visible.

Intermediate 179

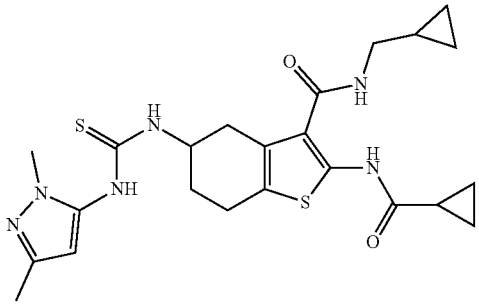 [SMILES: Cc1cc(NC(=S)NC2CCc3sc(NC(=O)C4CC4)c(C(=O)NCC4CC4)c3C2)n(C)n1]

(5S)-2-(Cyclopropanecarbonylamino)-N-(cyclopropylmethyl)-5-[(2,5-dimethylpyrazol-3-yl)carbamothioylamino]-4,5,6,7-tetrahydrobenzothiophene-3-carboxamide To a stirred solution of intermediate 178 (2.7 g, 8.1 mmol) in DCM (50 mL) was added DIPEA (2.1 mL, 12 mmol) and 5-isothiocyanato-1,3-dimethyl-1H-pyrazole [205246-65-7] (1.6 g, 10 mmol). The reaction mixture was stirred at r.t. for 17 h and concentrated in vacuo. The crude product was purified by flash column chromatography on silica (gradient elution with 0% to 100% EtOAc in iso-hexane) to afford the title compound (3.56 g, 90%) as an off-white solid. $^1$H NMR (300 MHz, DMSO-d$_6$) 11.08 (s, 1H), 9.11 (s, 1H), 7.94 (d, J 7.7 Hz, 1H), 7.74 (t, J 5.6 Hz, 1H), 5.92 (s, 1H), 4.52 (m, 1H), 3.52 (s, 3H), 3.14 (t, J 6.1 Hz, 2H), 3.09-2.96 (m, 1H), 2.78-2.56 (m, 3H), 2.09 (s, 3H), 2.03-1.82 (m, 3H), 1.01 (m, 1H), 0.92-0.75 (m, 4H), 0.50-0.36 (m, 2H), 0.30-0.17 (m, 2H).

Intermediate 180

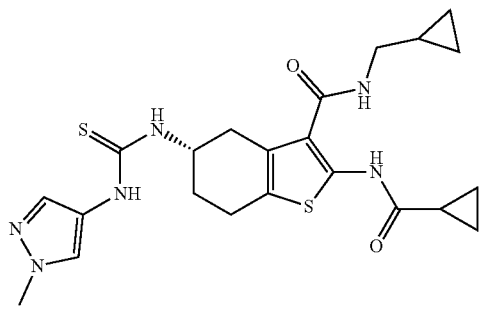 [SMILES: Cn1cc(NC(=S)N[C@H]2CCc3sc(NC(=O)C4CC4)c(C(=O)NCC4CC4)c3C2)cn1]

(5S)-2-(Cyclopropanecarbonylamino)-N-(cyclopropylmethyl)-5-[(1-methylpyrazol-4-yl)carbamothioylamino]-4,5,6,7-tetrahydrobenzothiophene-3-carboxamide Intermediate 117 (400 mg, 1.2 mmol) was dissolved in DCM (5 mL) and 4-isothiocyanato-1-methyl-1H-pyrazole [1001500-53-3] (200 mg, 1.44 mmol) in DCM (5 mL) was added to this mixture and the solution was stirred for 54 h under nitrogen. The reaction mixture was concentrated in vacuo to give a pale yellow solid and the crude product was purified by flash column chromatography on silica (gradient elution with 0-100% EtOAc in heptane, 0-40% MeOH in DCM) to afford the title compound (274 mg, 37%, 77% purity). δ$_H$ (250 MHz, Methylene Chloride-d$_2$) 12.11 (s, 1H), 7.35 (s, 2H), 7.10 (s, 1H), 6.00 (d, J 7.4 Hz, 1H), 5.87 (s, 1H), 4.82 (s, 1H), 3.85 (s, 3H), 3.35-3.19 (m, 3H), 2.84-2.80 (m, 1H), 2.69-2.63 (m, 2H), 2.11-2.07 (m, 1H), 1.98-1.94 (m, 1H), 1.74-1.60 (m, 1H), 1.08-0.97 (m, 3H), 0.94-0.83 (m, 2H), 0.60-0.50 (m, 2H), 0.31-0.19 (m, 2H). LCMS [M+H]$^+$ 473.20/471.20, RT 1.73 minutes, 77% purity (Method 12).

Intermediate 181

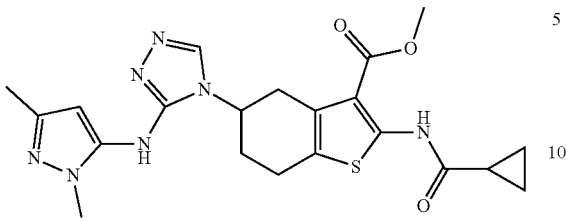

Methyl 2-(cyclopropanecarbonylamino)-5-[3-[(2,5-dimethylpyrazol-3-yl)amino]-1,2,4-triazol-4-yl]-4,5,6,7-tetrahydrobenzothiophene-3-carboxylate Intermediate 177 (2.12 g) was dissolved in N,N-dimethylformamide (40 mL) and formic acid hydrazide (853 mg, 14.2025 mmol) was added followed by mercuric chloride (3.88 mg, 0.0142 mmol) and triethylamine (2 mL, 14.3168 mmol). The resulting mixture was heated at 63° C. with a condenser for 5 h. Volatiles and DMF were then evaporated. The resulting residue was diluted with MeCN (20 mL) and filtered through a pad of celite. MeCN was added to wash through celite and resulting clear yellow solution was concentrated in vacuo to give a yellow oil. This oil was re-dissolved in MeOH/DCM, added silica to it, and dry-loaded on column for purification. The crude product was purified by flash column chromatography on silica (gradient elution with 25 g SNAP-Ultra, Isolera, MeOH/DCM, 0 to 10% in MeOH) to afford the title compound as white solid (0.882 g, 1.94 mmol, 40.9% Yield). $^1$H NMR (300 MHz, DMSO-$d_6$) δ 11.16 (s, 1H), 8.40 (s, 1H), 5.91 (s, 1H), 5.76 (s, 1H), 4.44 (s, 1H), 3.83 (s, 3H), 3.63-3.46 (m, 3H), 3.37 (m, 1H), 2.83 (s, 3H), 2.21 (dd, J=19.2, 11.0 Hz, 2H), 2.09 (d, J=4.0 Hz, 3H), 1.08-0.82 (m, 4H). LCMS [M+H]$^+$ 456.0, RT=1.51 minutes (Method 28).

Intermediate 182

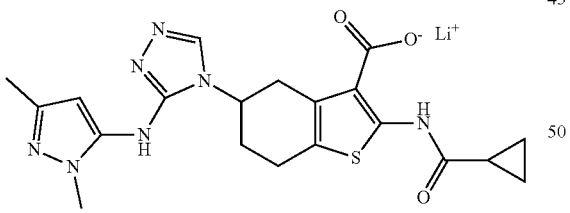

lithium; 2-(cyclopropanecarbonylamino)-5-[3-[(2,5-dimethylpyrazol-3-yl)amino]-1,2,4-triazol-4-yl]-4,5,6,7-tetrahydrobenzothiophene-3-carboxylate Intermediate 181 (453 mg, 0.9945 mmol) was suspended in THF (10 mL) and dissolved completely by adding water (1 mL) to it. Then lithium hydroxide monohydrate (66 mg, 1.57 mmol) was added and the reaction was stirred at rt for 2 days until complete. Volatiles were evaporated in vacuo until the solid was dry. Used without further purification in amide coupling reactions. $^1$H NMR (300 MHz, DMSO-$d_6$) δ 14.54 (s, 1H), 7.72 (s, 1H), 5.78 (d, J=13.3 Hz, 1H), 4.39 (s, 1H), 3.53-3.38 (m, 4H), 2.87-2.58 (m, 3H), 2.10 (dd, J=11.1, 5.6 Hz, 1H), 1.99 (d, J=12.1 Hz, 3H), 1.88-1.74 (m, 1H), 1.74-1.57 (m, 1H), 0.87-0.77 (m, 4H). LCMS [M+H] 442.0, RT=0.904 minutes (Method 15).

Intermediate 183

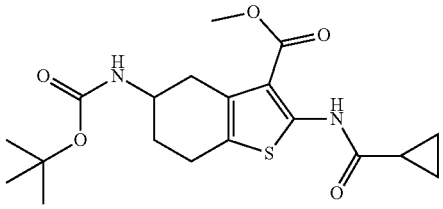

Methyl-5-(tert-butoxycarbonylamino)-2-(cyclopropanecarbonylamino)-4,5,6,7-tetrahydrobenzothiophene-3-carboxylate Intermediate 26 (3 g, 7.884 mmol) was dissolved in methanol (30 mL) and toluene (60 mL) and (trimethylsilyl)diazomethane in hexanes (4.3 mL, 8.6 mmol, 2 mol/L) was added in portions at rt. Bubbling was observed for a few minutes, then ceased. The reaction was heated at 70° C. for 3 h, then volatiles were evaporated in vacuo. The residue was dissolved in DCM and washed with water. The crude product was purified by flash column chromatography on silica (gradient elution with 100 g SNAP-Ultra, Isolera, eluting with 0 to 50% EtOAc in i-Hexane) to afford the title compound (2.117 g, 5.366 mmol, 68.06% Yield) as a yellow oil. $^1$H NMR (300 MHz, Chloroform-d) δ 11.44 (s, 1H), 4.00 (s, 1H), 3.89 (s, 3H), 3.16 (dd, J=17.1, 5.4 Hz, 1H), 2.82-2.68 (m, 2H), 2.61 (dd, J=17.2, 7.4 Hz, 1H), 2.05 (tdd, J=8.3, 5.8, 2.5 Hz, 1H), 1.75 (s, 1H), 1.69 (tt, J=7.8, 4.5 Hz, 1H), 1.60 (s, 3H), 1.48 (s, 9H), 1.21-1.10 (m, 2H), 0.97 (dt, J=8.1, 3.5 Hz, 2H). LCMS [M+H]$^+$ 395.0, RT 1.57 minutes (Method 15).

Intermediate 184

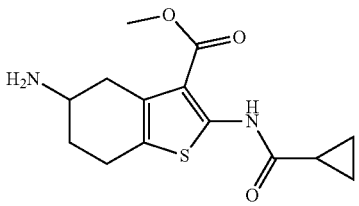 [SMILES: COC(=O)c1c(NC(=O)C2CC2)sc2c1CC(N)CC2]

Methyl 5-amino-2-(cyclopropanecarbonylamino)-4,5,6,7-tetrahydrobenzothiophene-3-carboxylate Intermediate 183 (2.170 g, 5.501 mmol) was dissolved in dichloromethane (50 mL) and trifluoroacetic acid (6 mL, 79.35 mmol) was added. The reaction was stirred at rt for 2 h, then volatiles were evaporated in vacuo and the resulting residue was dissolved in methanol, loaded on 3*10 g SCX-2 columns and eluted with 3N NH$_3$ in methanol. This purification afforded the title compound (1.5 g, 5.1 mmol, 93% Yield) of as yellow solid. $^1$H NMR (300 MHz, DMSO-$d_6$)

δ 11.13 (s, 1H), 3.84 (s, 3H), 3.04-2.88 (m, 2H), 2.75-2.54 (m, 2H), 2.38-2.20 (m, 1H), 2.04 (tt, J=7.3, 5.1 Hz, 1H), 1.86 (d, J=13.3 Hz, 3H), 1.47 (dtd, J=12.4, 9.7, 5.9 Hz, 1H), 1.00-0.76 (m, 4H). LCMS [M+H]+ 295.0, RT 0.83 minutes (Method 15).

Intermediate 185

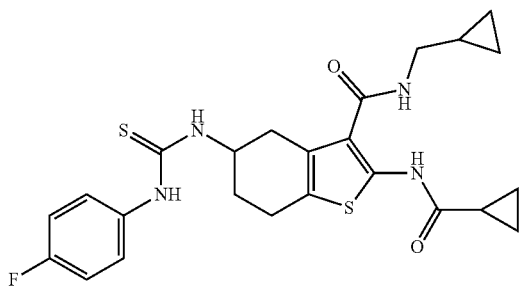 [SMILES: O=C(NCC1CC1)c1c(NC(=O)C2CC2)sc2c1CC(NC(=S)Nc1ccc(F)cc1)CC2]

2-(Cyclopropanecarbonylamino)-N-(cyclopropylmethyl)-5-[(4-fluorophenyl)carbamothioylamino]-4,5,6,7-tetrahydrobenzothiophene-3-carboxamide A solution of 1-fluoro-4-isothiocyanatobenzene [154257-75-7] (110 μl, 0.9 mmol) in DCM (5 mL) was stirred at r.t. before adding example 109 (200 mg, 0.6 mmol). The solution was stirred for 18 h under nitrogen and the reaction mixture was concentrated in vacuo to give a pale yellow solid. The crude product was purified by flash column chromatography on silica (gradient elution with 0% to 100% EtOAc in heptane) to afford the title compound (267 mg, 91%) as a white solid. δ$_H$ (250 MHz, Chloroform-d) 12.09 (s, 1H), 7.78 (s, 1H), 7.20-7.02 (m, 4H), 6.11 (d, J 7.5 Hz, 1H), 5.86 (s, 1H), 4.95 (s, 1H), 3.33-3.10 (m, 3H), 2.86-2.80 (m, 2H), 2.68-2.50 (m, 1H), 2.08-1.99 (m, 2H), 1.69-1.62 (m, 2H), 1.11-1.04 (m, 3H), 0.94-0.84 (m, 2H), 0.61-0.55 (m, 2H), 0.31-0.25 (m, 2H).

Intermediate 186

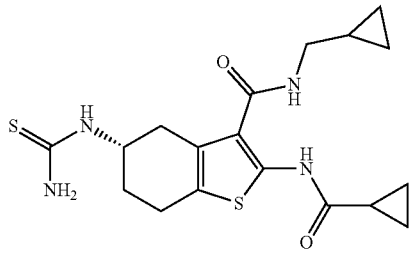 [SMILES: NC(=S)N[C@H]1CCc2sc(NC(=O)C3CC3)c(C(=O)NCC3CC3)c2C1]

(5S)-5-(Carbamothioylamino)-2-(cyclopropanecarbonylamino)-N-(cyclopropylmethyl)-4,5,6,7-tetrahydrobenzothiophene-3-carboxamide Phenyl chloromethanethioate [1005-56-7] (0.23 mL, 1.65 mmol) was dissolved in DCM (10 mL) and the reaction mixture was cooled to 0° C. Intermediate 117 (500 mg, 1.5 mmol) in DCM (10 mL) and triethylamine (0.63 mL, 4.5 mmol) was added dropwise. The reaction was stirred at r.t. for 20 minutes and the reaction mixture was split in to two, and one portion carried through to the desired reaction. To (5S)-2-cyclopropaneamido-N-(cyclopropylmethyl)-5-[(phenoxyethanethiol)amino]-4,5,6,7-tetrahydro-1-benzothiophene-3-carboxamide (352 mg, 0.75 mmol) in DCM (10 mL) was added aqueous ammonia (2 mL, 34.1 mmol) and the mixture was stirred at r.t. for 18 h. The reaction mixture was diluted with DCM (20 mL) and water (20 mL) followed by brine (50 mL) and the mixture was extracted with DCM (3×20 mL). The organic phases were washed with brine (20 mL), dried (Na$_2$SO$_4$), filtered and concentrated in vacuo to yield a yellow solid. The crude product was triturated with DCM/heptane and collected by filtration to afford the title compound (77 mg, 26%) as a white solid. LCMS [M+H]+ 393.2, RT 1.659 minutes, 100% purity (Method 12). The aqueous layer was extracted with isopropanol/chloroform (2×20 mL), and the organic phases were dried (Na$_2$SO$_4$), filtered, combined with the previous filtrate and concentrated in vacuo to afford a yellow oil (80 mg). The aqueous phase was neutralised to pH 7 using 1M aqueous hydrochloric acid and the aqueous phase was extracted with DCM (3×20 mL). The organic phases were dried (Na$_2$SO$_4$), filtered, combined with the above yellow oil and concentrated in vacuo to afford a yellow solid (300 mg). DCM and heptane were added to the crude solid, which was sonicated to give a white solid which was collected by filtration to afford the title compound (117 mg, 40%) as a white solid. LCMS [M+H]+ 393.10, RT 1.05 minutes, 95% purity (Method 11).

Intermediate 187

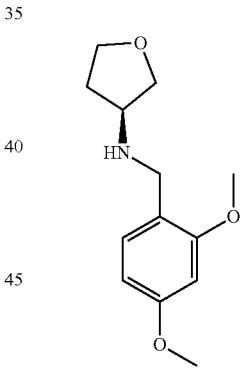

(3S)—N-[(2,4-dimethoxyphenyl)methyl]tetrahydrofuran-3-amine

To a stirred solution of (3S)-tetrahydrofuran-3-amine (75 mg, 0.86 mmol) in DCM (3 mL) was added 2,4-dimethoxybenzaldehyde (143 mg, 0.86 mmol), followed by STAB (273 mg, 1.29 mmol). The mixture was stirred at r.t. for 2 hours. Saturated sodium bicarbonate solution was added and the organic phase taken. The aqueous phase was extracted with DCM (4×3 mL) and the organic phases combined, concentrated in vacuo then purified by flash column chromatography on aminopropyl silica (gradient elution with 0-2% methanol in TBME) to afford the title compound (175 mg, 75%) as a colourless oil. δ$_H$ (250 MHz, DMSO-d$_6$) 7.17 (d, J 8.2 Hz, 1H), 6.51 (d, J 2.4 Hz, 1H), 6.46 (dd, J 8.2, 2.4 Hz, 1H), 3.76 (s, 3H), 3.74-3.58 (m, 7H), 3.58-3.53 (m, 2H), 3.42-3.37 (m, 1H), 3.26-3.16 (m, 1H), 2.00-1.83 (m, 1H), 1.70-1.56 (m, 1H). LCMS [M+H]$^+$ 238.1, RT 0.4 minutes, purity 90% (Method 14).

Intermediate 188

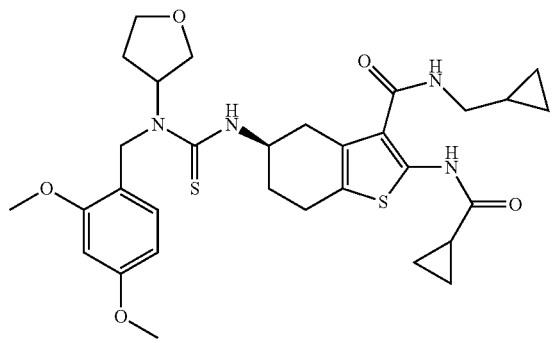 [SMILES: COc1ccc(CN(C(=S)N[C@@H]2CCc3sc(NC(=O)C4CC4)c(C(=O)NCC4CC4)c3C2)C2CCOC2)c(OC)c1]

(5S)-2-(cyclopropanecarbonylamino)-N-(cyclopropylmethyl)-5-[[(2,4-dimethoxyphenyl)methyl-[(3S)-tetrahydrofuran-3-yl]carbamothioyl]amino]-4,5,6,7-tetrahydrobenzothiophene-3-carboxamide To a stirred solution of phenyl chloromethanethioate (45.7 µL, 0.33 mmol) in DCM (5 mL), at 0° C. was added intermediate 117 (100 mg, 0.3 mmol) and triethylamine (0.13 ml, 0.9 mmol) in DCM (5 mL). The reaction was stirred at 0° C. for 30 minutes, then intermediate 187 (85.4 mg, 0.36 mmol) was added. The mixture was stirred at 0° C. for 15 minutes, then warmed to room temperature and stirred for 18 h. The reaction was concentrated in vacuo and purified by flash column chromatography on silica (gradient elution with 0-100% TBME in heptane) to afford the title compound (182 mg, 91%) as a white powder. $\delta_H$ (500 MHz, DMSO-d$_6$) 11.06 (s, 1H), 7.69-7.59 (m, 1H), 6.87 (d, J 7.3 Hz, 1H), 6.75 (d, J 8.4 Hz, 1H), 6.52 (d, J 2.3 Hz, 1H), 6.44 (dd, J 8.4, 2.3 Hz, 1H), 5.69 (s, 1H), 4.72-4.60 (m, 3H), 3.82 (td, J 8.6, 3.9 Hz, 1H), 3.77 (s, 3H), 3.73 (s, 3H), 3.69-3.62 (m, 1H), 3.54 (dd, J 9.7, 4.3 Hz, 1H), 3.49 (q, J 8.5 Hz, 1H), 3.12 (t, J 6.2 Hz, 2H), 2.99-2.89 (m, 1H), 2.67-2.58 (m, 1H), 2.57-2.53 (m, 1H), 2.15 (dtd, J 12.7, 8.6, 3.9 Hz, 1H), 1.94-1.86 (m, 2H), 1.83-1.74 (m, 1H), 1.74-1.66 (m, 1H), 1.05-0.96 (m, 1H), 0.88-0.79 (m, 4H), 0.45-0.36 (m, 2H), 0.24-0.17 (m, 2H), 1 proton under DMSO. LCMS: [M+H]$^+$ 613.2, RT 1.28 minutes, purity 92% (Method 11).

Intermediate 189

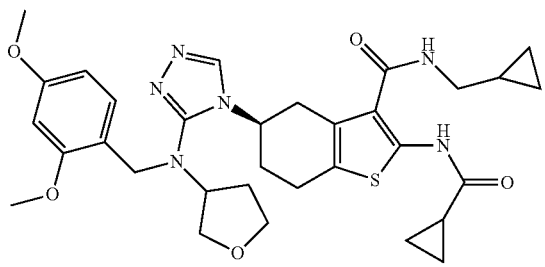 [SMILES: COc1ccc(CN(c2nncn2[C@@H]2CCc3sc(NC(=O)C4CC4)c(C(=O)NCC4CC4)c3C2)C2CCOC2)c(OC)c1]

(5S)-2-(cyclopropanecarbonylamino)-N-(cyclopropylmethyl)-5-[3-[(2,4-dimethoxyphenyl)methyl-[(3S)-tetrahydrofuran-3-yl]amino]-1,2,4-triazol-4-yl]-4,5,6,7-tetrahydrobenzothiophene-3-carboxamide To a stirred solution of intermediate 188 (75 mg, 0.11 mmol) in DMF (1 mL) was added formic hydrazide (14 mg, 0.23 mmol), followed by mercury dichloride (61 mg, 0.23 mmol). The reaction mixture was stirred at r.t. for 5 minutes, then triethylamine (47 µL, 0.34 mmol) was added and the suspension heated to 70° C. for 1 h. The suspension was cooled to r.t., diluted with DCM and kieselguhr added. The mixture was stirred for 1 minute then filtered. The filtrate was concentrated in vacuo to give a pale-yellow oil, which was purified by flash column chromatography on silica (gradient elution with 0-15% methanol in TBME) to afford the title compound (48 mg, 60%) as a white powder. LCMS [M+H]$^+$ 621.3, RT 1.14 minutes, purity 89% (Method 11).

Intermediate 190

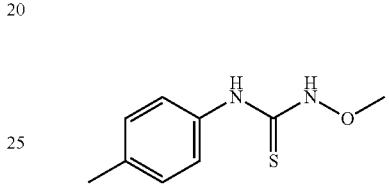

1-Methoxy-3-(p-tolyl)thiourea

A solution of 1-isothiocyanato-4-methylbenzene [622-59-3] (150 mg, 1.0 mmol) in THF (15 mL) was cooled to 0° C. prior to addition of (aminooxy)methane hydrochloride (1:1) (420 mg, 5.0 mmol) and DIPEA (1.0 mL, 6.0 mmol). The ice bath was removed and the solution was stirred for 16 hi under nitrogen. The resulting solid was filtered off and the filtrate was concentrated in vacuo to yield the crude product as a pale yellow gum which was dissolved in DCM and washed with 1 M aqueous hydrochloric acid solution, saturated sodium hydrogen carbonate solution and brine. The organic phase was dried (MgSO$_4$), filtered and concentrated in vacuo to give a pale yellow solid which was purified by flash column chromatography on silica (gradient elution with 12 to 60% EtOAc in heptane) to afford the title compound (102 mg, 51%) as a white solid. LCMS [M+H]$^+$ 196.9, RT 0.99 minutes, 99% purity (Method 6).

Intermediate 191

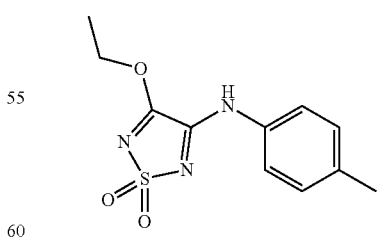

4-ethoxy-1,1-dioxo-N-(p-tolyl)-1,2,5-thiadiazol-3-amine

4-Methylaniline [106-49-0] (67.5 mg, 0.63 mmol) was dissolved in EtOH (30 ml) and 3,4-diethoxy-1-{6},2,5- thiadiazole-1,1-dione [55904-84-2] (130 mg, 0.63 mmol) was added and the reaction mixture was stirred at r.t. for 16 h. The reaction mixture was concentrated in vacuo to give the crude title compound (166 mg, 86%, 87% purity) which was utilised without further purification. LCMS [M+H]⁺ 267.95, RT 1.21 minutes, 87% purity (Method 6).

Intermediate 192

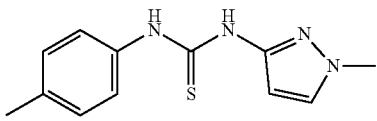

1-(1-Methylpyrazol-3-yl)-3-(p-tolyl)thiourea

A solution of 3-isothiocyanato-1-methyl-1H-pyrazole [114874-28-1] (195 mg, 1.4 mmol) in DCM (15 mL) was cooled to 0° C. before addition 4-methylaniline [106-49-0] (150 mg, 1.4 mmol). The ice bath was removed and the solution was stirred for 4 h under nitrogen. The reaction mixture was concentrated in vacuo to give the crude residue as a pale yellow solid which was triturated with Et₂O/heptane. The solid formed was collected by filtration and dried in vacuo to afford the title compound (310 mg, 90%) as a white solid. LCMS [M+H]⁺ 246.95, RT 1.09 minutes, 99% purity (Method 6).

Intermediate 193

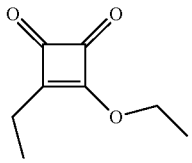

3-Ethoxy-4-ethyl-cyclobut-3-ene-1,2-dione

To a solution of diethoxycyclobut-3-ene-1,2-dione [5231-87-8] (0.2 mL, 1.35 mmol) in THF (7 mL) cooled to −78° C. and stirred under nitrogen, was added 3M ethyl magnesium bromide in Et₂O (0.47 mL, 1.42 mmol) dropwise over a period of 30 seconds and the mixture was stirred for 1 h. Trifluoroacetic anhydride [407-25-0] (0.23 mL, 1.62 mmol) was added followed by 10% aqueous ammonium chloride (1 mL) and the reaction mixture was warmed to r.t. and stirred for 1 h. The reaction mixture was partitioned between saturated sodium hydrogen carbonate solution (10 mL) and EtOAc (20 mL). The organic phase was separated and the aqueous phase was extracted with EtOAc (20 mL). The combined organic phases were washed with brine (10 mL), dried (MgSO₄), filtered and concentrated in vacuo. The pale yellow oil obtained was dissolved in DCM (5 mL), concentrated hydrochloric acid (2 drops) was added and the resulting mixture was stirred at r.t. for 15 minutes. The reaction mixture was dried (K₂CO₃), filtered and concentrated in vacuo. The crude residue was purified by flash column chromatography on silica (gradient elution with 0 to 50% of EtOAc in heptane) to afford the title compound (86 mg, 41%) as a pale yellow oil. δ$_H$ (500 MHz, Chloroform-d) 4.78 (q, J 7.1 Hz, 2H), 2.63 (q, J 7.6 Hz, 2H), 1.49 (t, J 7.1 Hz, 3H), 1.27 (t, J 7.6 Hz, 3H). LCMS [M+H]⁺ 155, RT 0.90 minutes, 97% purity (Method 11).

Intermediate 194

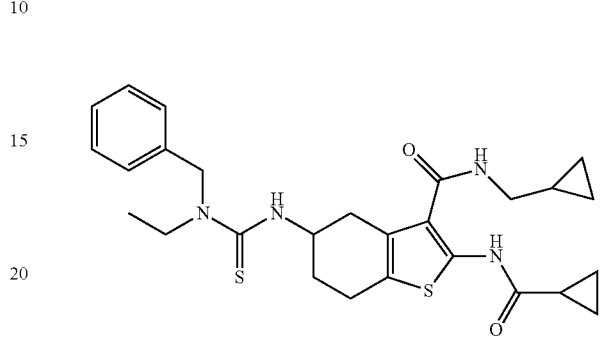

5-[[Benzyl(ethyl)carbamothioyl]amino]-2-(cyclopropanecarbonylamino)-N-(cyclopropylmethyl)-4,5,6,7-tetrahydrobenzothiophene-3-carboxamide To intermediate 122 (1.00 g, 2.70 mmol) in DCM (15 mL) was added triethylamine (0.82 g, 8.11 mmol). A solution of phenyl chloromethanethioate [1005-56-7] (513 mg, 2.97 mmol) in DCM (30 mL) was cooled to 0° C. and the amine/triethylamine solution was added dropwise at 0° C. under nitrogen. The reaction mixture was warmed to r.t. overnight. A solution of N-ethylbenzylamine [14321-27-8] (548 mg, 4.06 mmol) in DCM (5 mL) was added and the reaction was stirred at r.t. The reaction mixture was concentrated in vacuo and the residue was dissolved in EtOAc (60 mL) and washed with 1M aqueous citric acid solution (2×10 mL), saturated aqueous sodium hydrogen carbonate solution (2×10 mL) and brine (10 mL). The organic phase was dried (Na₂SO₄), filtered and the filtrate adsorbed onto silica for purification by flash column chromatography on silica (gradient elution with 200 mL of 8:2 heptane/EtOAc followed by 400 mL each of 7:3-6:4-5:5-4:6-3:7 and 2:8). Fractions were combined and concentrated in vacuo before azeotroping with EtOAc (10 mL). The residue was dried under high vacuum for 20 minutes to afford the title compound (865 mg, 62%) as an off-white foam. δ$_H$ (250 MHz, CD₃OD) 12.17 (s, 1H), 7.27-7.24 (m, 3H), 7.14-7.06 (m, 2H), 5.77 (t, J 4.7 Hz, 1H), 5.47 (d, J 7.9 Hz, 1H), 5.10-5.00 (m, 1H), 4.71-4.63 (m, 2H), 3.93 (m, 2H), 3.26 (dd, J 7.2, 5.2 Hz, 2H), 3.03 (dd, J 15.5, 4.5 Hz, 1H), 2.68 (dt, J 19.0, 5.0 Hz, 1H), 2.58 (dd, J 15.2, 3.8 Hz, 1H), 2.34-2.23 (m, 1H), 2.02-1.97 (m, 1H), 1.89-1.81 (m, 1H), 1.71-1.66 (m, 1H), 1.25 (t, J 7.1 Hz, 3H), 1.14-1.09 (m, 2H), 1.08-1.00 (m, 1H), 0.94-0.88 (m, 2H), 0.61-0.56 (m, 2H), 0.27 (q, J 5.1 Hz, 2H). LCMS [M+H]⁺ 511, [M+Na]⁺533, RT 1.33 minutes, 99% purity (Method 6).

Intermediate 195

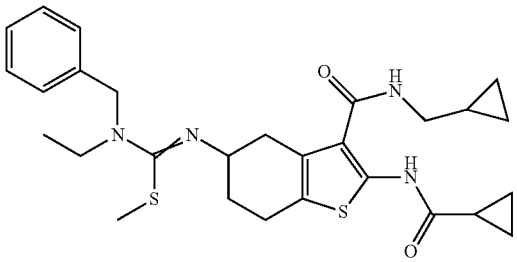 [SMILES: CCN(Cc1ccccc1)C(=NC1CCc2sc(NC(=O)C3CC3)c(C(=O)NCC3CC3)c2C1)SC]

Intermediate 195

5-[[[Benzyl(ethyl)amino]-methylsulfanyl-methylene]amino]-2-(cyclopropanecarbonylamino)-N-(cyclopropylmethyl)-4,5,6,7-tetrahydrobenzothiophene-3-carboxamide To a solution of intermediate 194 (865 mg, 1.69 mmol) in THF (18 mL) was added 1M potassium tert-butoxide in THF (5.08 mL, 5.08 mmol) dropwise at 0° C. and the reaction mixture was warmed to r.t. 5 minutes. The reaction mixture was cooled to 0° C. and iodomethane [74-88-4] (313 mg, 2.20 mmol) in THF (5 mL) was added. The reaction was then allowed to warm to r.t. and stirred for 30 minutes. The reaction mixture was diluted with EtOAc (150 mL) and washed with 1M aqueous citric acid solution (2×15 mL), saturated aqueous sodium hydrogen carbonate solution (2×15 mL) and brine (15 mL). The organic phase was dried (Na$_2$SO$_4$), filtered and concentrated in vacuo to afford the title compound (0.73 g, 75%, 92% purity) as a pale yellow foam. δ$_H$ (500 MHz, Chloroform-d) 12.20 (s, 1H), 7.31-7.20 (m, 5H), 5.97 (s, 1H), 4.60-4.45 (m, 2H), 4.06 (p, J 7.1, 6.6 Hz, 1H), 3.44-3.32 (m, 2H), 3.32-3.22 (m, 2H), 2.81-2.73 (m, 3H), 2.60-2.51 (m, 1H), 2.34 (s, 2.7H), 2.31 (s, 0.3H), 1.89-1.79 (m, 2H), 1.66 (ddd, J 12.5, 7.9, 4.6 Hz, 1H), 1.15-1.07 (m, 5H), 1.07-0.99 (m, 1H), 0.87 (dp, J 10.3, 4.9 Hz, 2H), 0.56-0.50 (m, 2H), 0.25 (q, J 4.8 Hz, 2H). Peak broadening was observed at room temperature due to E/Z or conformational isomerism. LCMS [M+H]$^+$ 525, RT 1.06 minutes, 92% purity (Method 6).

Intermediate 196

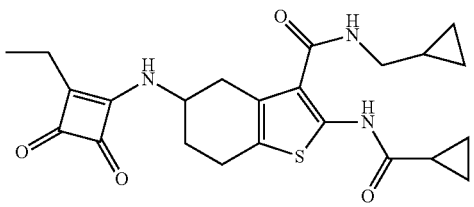 [SMILES: CCc1c(NC2CCc3sc(NC(=O)C4CC4)c(C(=O)NCC4CC4)c3C2)c(=O)c1=O]

2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide A solution of example 109 (100 mg, 0.3 mmol) and intermediate 193 (56 mg, 0.36 mmol) in EtOH was stirred at r.t. for 16 h. The reaction mixture was concentrated in vacuo and purified by preparative HPLC (low pH) to afford the title compound (86 mg, 65%) as a white solid. δ$_H$ (250 MHz, Chloroform-d) 12.09-11.87 (m, 1H), 6.54-6.41 (m, 1H-Rotamer 1), 6.30-6.18 (m, 1H-Rotamer 2), 6.02-5.84 (m, 1H), 4.86-4.66 (m, 1H-Rotamer 2), 4.04-3.91 (m, 1H-Rotamer 1), 3.38-3.10 (m, 3H), 2.95-2.76 (m, 3H), 2.76-2.63 (m, 2H-Rotamer 1), 2.63-2.44 (m, 2H-Rotamer 2), 2.24-1.93 (m, 2H), 1.73-1.59 (m, 1H-part. obs. by water peak), 1.38-1.16 (m, 3H), 1.17-1.00 (m, 3H), 0.98-0.82 (m, 2H), 0.66-0.47 (m, 2H), 0.34-0.14 (m, 2H). LCMS [M+H]$^+$ 442, RT 2.90 minutes, 100% purity (Method 10).

Intermediate 197

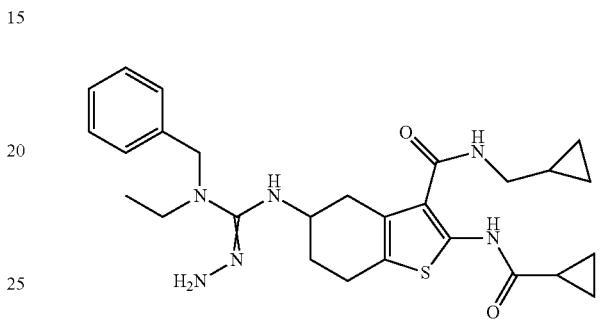

5-[(N-benzyl-N-ethyl-carbamohydrazonoyl)amino]-2-(cyclopropanecarbonylamino)-N-(cyclopropylmethyl)-4,5,6,7-tetrahydrobenzothiophene-3-carboxamide To a solution of intermediate 195 (627 mg, 1.23 mmol, 92% purity) in EtOH (10 mL) in a pressure tube was added hydrazine hydrate [10217-52-4] (1.2 mL, 23.90 mmol) and the reaction mixture was flushed with nitrogen and sealed. The mixture was warmed to 80° C. and stirred for 9 h before leaving to stand at r.t. overnight. The reaction mixture was concentrated in vacuo and the residue was dissolved in EtOAc (50 mL). The solution was washed with saturated aqueous sodium hydrogen carbonate solution (2×5 mL, water (2×10 mL) and brine (1×5 mL). The organic phase was dried (Na$_2$SO$_4$), filtered, the filtrate concentrated in vacuo to afford the title compound (455 mg, 55%, 74% purity) as a pale orange oil. LCMS [M+H]$^+$ 509, RT 1.01 minutes, 74% purity (Method 11).

Intermediate 198

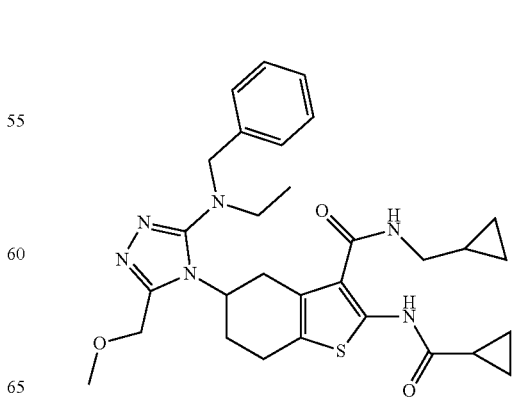

5-[3-[Benzyl(ethyl)amino]-5-(methoxymethyl)-1,2,4-triazol-4-yl]-2-(cyclopropanecarbonylamino)-N-(cyclopropylmethyl)-4,5,6,7-tetrahydrobenzothiophene-3-carboxamide To a solution of intermediate 197 (202 mg, 0.39 mmol) in DCM (8 mL) was added DIPEA (51 mg, 0.39 mmol) in DCM (0.5 mL). The reaction mixture was stirred under nitrogen and cooled to 0° C. in an ice bath. To the stirred solution at ~0° C. was added 2-methoxyacetyl chloride [38870-89-2] (43 mg, 0.39 mmol) in DCM (0.5 mL) dropwise and the reaction mixture was warmed to r.t. overnight. The reaction mixture was concentrated in vacuo and dissolved in 1,4-dioxane (5 mL). TFA [76-05-1] (0.5 mL) was added and the reaction mixture was sealed in a pressure tube under nitrogen and the mixture was heated to 80° C. overnight. The reaction mixture was mixed with a previous experiment (20 mg, 0.039 mmol starting material) and was concentrated in vacuo, redissolved in 1:1 MeCN/water and purified by preparative HPLC (acidic) to afford the title compound (45.9 mg, 20%) which was azeotroped with MeCN (3×10 mL) to give a pale brown oil. $\delta_H$ (500 MHz, CD$_3$OD) 7.27-7.15 (m, 5H), 4.61 (d, J 13.1 Hz, 1H), 4.57 (d, J 13.1 Hz, 1H), 4.57-4.51 (m, 1H), 4.25 (d, J 12.8 Hz, 1H), 4.20 (d, J 12.8 Hz, 1H), 3.31 (s, 3H), 3.28-3.12 (m, 5H), 2.82 (dd, J 16.5, 5.6 Hz, 1H), 2.79-2.71 (m, 1H), 2.46 (dd, J 15.2, 5.0 Hz, 1H), 2.32 (ddt, J 18.3, 12.1, 5.9 Hz, 1H), 1.83-1.78 (m, 1H), 1.65-1.57 (m, 1H), 1.09 (t, J 7.1 Hz, 3H), 1.04-0.90 (m, 5H), 0.44 (m, 2H), 0.23-0.15 (m, 2H). LCMS [M+H]$^+$ 563, RT 3.52 minutes, 96% purity (Method 10).

Intermediate 199

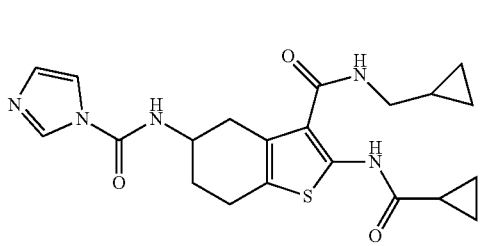

5-(Carbamothioylamino)-2-(cyclopropanecarbonylamino)-N-(cyclopropylmethyl)-4,5,6,7-tetrahydrobenzothiophene-3-carboxamide To intermediate 174 (0.11 g, 0.22 mmol) dissolved in MeOH (3.30 mL) was added potassium carbonate (70.1 mg, 0.507 mmol) and the reaction mixture was stirred for 6 h. The mixture was concentrated in vacuo to give the residue which was purified by flash column chromatography on silica (gradient elution with DCM/MeOH 0% 2 CV, 0-10% 8 CV, 10% 2 CV, 10-35% 10 CV) to afford the title compound (0.084 g, 99%) as a pale yellow oil. LCMS [M+H]$^+$ 393.2, [M+Na]$^+$ 415.0, RT 1.556 minutes, 100.0% purity (Method 1).

Intermediate 200

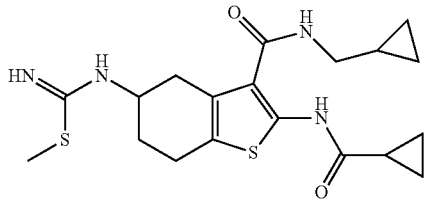 [SMILES: CSC(=N)NC1CCc2sc(NC(=O)C3CC3)c(C(=O)NCC3CC3)c2C1]

2-(Cyclopropanecarbonylamino)-N-(cyclopropylmethyl)-5-[(methylsulfanylcarbonimidoyl)amino]-4,5,6,7-tetrahydrobenzothiophene-3-carboxamide To intermediate 199 (0.32 g, 0.81 mmol) in THF (4.1 mL) was added iodomethane [74-88-4] (0.10 mL, 1.59 mmol) and the reaction mixture was heated in a microwave at 70° C. for 3 h. The reaction mixture was concentrated in vacuo to give a yellow residue which was purified by flash column chromatography on silica (DCM/MeOH 0% 2 CV, 0-10% 10 CV, 10% 4 CV) to afford the title compound (329 mg, 99%) as a pale yellow oil. LCMS [M+H]$^+$ 407.2, RT 1.609 minutes, 100.0% purity (Method 1).

Intermediate 201

N-[2-(Cyclopropanecarbonylamino)-3-(cyclopropylmethylcarbamoyl)-4,5,6,7-tetrahydrobenzothiophen-5-yl]imidazole-1-carboxamide Intermediate 122 (500 mg, 1.35 mmol) was dissolved in DCM (5 mL) and DIPEA (263 mg, 2.03 mmol) and 1,1'-carbonyldiimidazole [530-62-1] (241 mg, 1.49 mmol) were added. The reaction mixture was stirred at r.t. for 1 h, the solution of intermediate 201 was used directly without further purification. LCMS [M+H] 428.2, RT 1.283 minutes, 84.8% purity (Method 4).

Intermediate 202

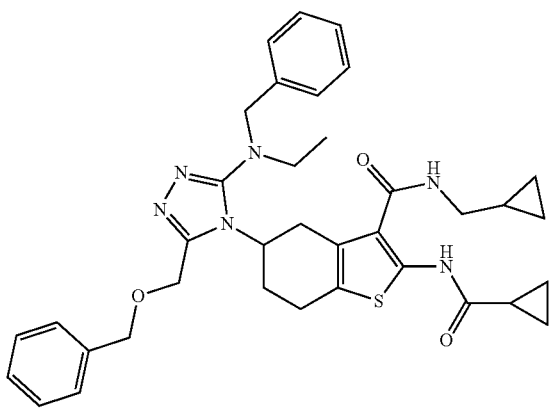 [SMILES: CCN(Cc1ccccc1)c1nnc(COCc2ccccc2)n1C1CCc2sc(NC(=O)C3CC3)c(C(=O)NCC3CC3)c2C1]

5-[3-[Benzyl(ethyl)amino]-5-(benzyloxymethyl)-1,2,4-triazol-4-yl]-2-(cyclopropanecarbonylamino)-N-(cyclopropylmethyl)-4,5,6,7-tetrahydrobenzothiophene-3-carboxamide To a solution of intermediate 197 (195 mg, 0.38 mmol) in DCM (1 mL) was added DIPEA (50 mg, 0.38 mmol) in DCM (0.5 mL) and the reaction mixture was flushed with nitrogen and cooled to 0° C. in an ice bath. To the stirred solution at 0° C. was added 2(benzyloxy)acetyl chloride [19810-31-2] (35 mg, 0.19 mmol) in DCM (0.5 mL) and the reaction mixture was warmed to r.t. overnight. The reaction mixture was concentrated in vacuo and the residue was dissolved in 1,4-dioxane (5 mL) and TFA [76-05-1] (0.5 mL) was added and the mixture transferred to a pressure tube. The reaction mixture was heated to 80° C. overnight followed by a further 8 h. The reaction mixture was combined with a small scale reaction (20 mg, 0.039 mmol) and concentrated in vacuo and the residue purified by preparative HPLC (acidic) to afford the title compound (32 mg, 13%) as a pale brown oil which was azeotroped with MeCN (3×10 mL). $\delta_H$ (500 MHz, CD$_3$OD) 7.27-7.16 (m, 10H), 4.70 (d, J 12.7 Hz, 1H), 4.65 (d, J 12.7 Hz, 1H), 4.55-4.48 (m, 1H), 4.54 (d, J 11.5 Hz, 1H), 4.50 (d, J 11.5 Hz, 1H), 4.25 (d, J 12.9 Hz, 1H), 4.19 (d, J 12.8 Hz, 1H), 3.27-3.15 (m, 3H), 3.09 (qd, J 13.8, 7.1 Hz, 2H), 2.75 (dd, J 16.6, 5.7 Hz, 1H), 2.74-2.66 (m, 1H), 2.51 (dd, J 15.2, 5.3 Hz, 1H), 2.26 (ddt, J 18.2, 12.1, 6.0 Hz, 1H), 1.84-1.79 (m, 1H), 1.54 (br. d, J 12.0 Hz, 1H), 1.09 (t, J 7.1 Hz, 3H), 1.04-0.98 (m, 2H), 0.98-0.94 (m, 2H), 0.92-0.86 (m, 1H), 0.42-0.34 (m, 2H), 0.13-0.11 (m, 2H). LCMS [M+H]$^+$ 639, RT 4.08 minutes, 96% purity (Method 10).

Intermediate 203

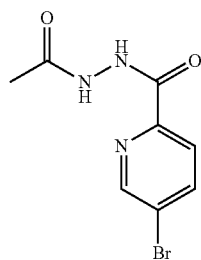

N'-acetyl-5-bromopyridine-2-carbohydrazide

Acetohydrazide (0.37 g, 4.99 mmol) was stirred in DCM (10 mL) and DIPEA (0.87 mL, 4.99 mmol). 5-bromopyridine-2-carbonyl chloride (1 g, 4.54 mmol) was added in portions and the reaction was stirred for 15 minutes. The reaction was concentrated in vacuo to afford an oil. Water (10 mL) was added and the mixture sonicated which resulted in colloid formation, DCM (30 mL) was added and an emulsion formed, more water and DCM were added which resulted in flocculation. The mixture was filtered under vacuum to remove the brown solid. The filtrate was separated and the organic DCM layer was concentrated in vacuo to give a brown residue. The aqueous layer was added to this residue and the mixture sonicated, the resulting brown solid was collected by vacuum filtration and combined with the initial brown solid to afford the title compound (683 mg, 55% at 95% purity). $\delta_H$ (250 MHz, DMSO-d$_6$) δ 10.44 (s, 1H), 9.98 (s, 1H), 8.80 (d, J 1.8 Hz, 1H), 8.28 (dd, J 8.4, 2.3 Hz, 1H), 7.95 (dd, J 8.4, 0.5 Hz, 1H), 1.91 (s, 3H).

Intermediate 204

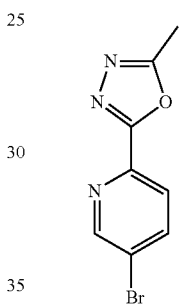

2-(5-bromo-2-pyridyl)-5-methyl-1,3,4-oxadiazole

Intermediate 203 (90%, 856 mg, 2.99 mmol) was stirred in DCM (15 mL), NEt$_3$ (2.8 mL, 20 mmol) was added followed by 4-methylbenzenesulfonyl chloride (700 mg, 3.67 mmol). The reaction was stirred for 3 hours at room temperature. The reaction was quenched with saturated aq. NaHCO$_3$ (20 mL) and extracted with DCM (2×20 mL). The organic layer was dried over sodium sulfate and concentrated in vacuo. The resulting residue was purified by flash column chromatography on silica (gradient elution with 0-100% ethyl acetate in heptane) to afford the title compound (572 mg, 80%) as a white solid. $\delta_H$ (250 MHz, DMSO-d$_6$) δ 8.91 (dd, J 2.3, 0.7 Hz, 1H), 8.31 (dd, J 8.5, 2.3 Hz, 1H), 8.09 (dd, J 8.5, 0.7 Hz, 1H), 2.61 (s, 3H).

Intermediate 205

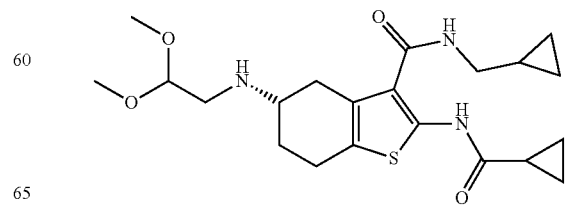

(5S)-2-(Cyclopropanecarbonylamino)-N-(cyclopropylmethyl)-5-(2,2-dimethoxyethylamino)-4,5,6,7-tetrahydrobenzothiophene-3-carboxamide To intermediate 117 (1 g, 3 mmol) in MeOH (20 mL) was added dimethoxyacetaldehyde [51673-84-8] (60% aqueous, 452 µL, 2.99 mmol) and the reaction mixture was stirred for 18 h. Sodium borohydride [16940-66-2] (113 mg, 2.99 mmol) was added in portions and the reaction mixture was stirred at r.t. for 15 minutes. The reaction was concentrated in vacuo and diluted with EtOAc (60 mL). The organic phase was washed with water (2×20 mL), dried (Na$_2$SO$_4$), filtered and concentrated in vacuo to give the crude product (1.2 g) as a yellow oil which was purified by flash column chromatography on silica (gradient elution with 0-10% MeOH in DCM) to afford the title compound (1.07 g, 84%) as a yellow oil which solidified on standing. $\delta_H$ (500 MHz, DMSO-d$_6$) 11.20 (s, 1H), 7.66-7.57 (m, 1H), 4.40 (t, J 5.5 Hz, 1H), 3.27 (d, J 1.0 Hz, 6H), 3.24-3.15 (m, 1H), 3.15-3.05 (m, 1H), 2.87 (d, J 15.6 Hz, 1H), 2.85-2.74 (m, 1H), 2.70 (d, J 4.8 Hz, 2H), 2.69-2.64 (m, 1H), 2.63-2.53 (m, 1H), 2.42 (dd, J 15.4, 8.0 Hz, 1H), 2.01-1.93 (m, 1H), 1.93-1.84 (m, 1H), 1.59-1.39 (m, 2H), 1.10-0.99 (m, 1H), 0.88-0.77 (m, 4H), 0.47-0.39 (m, 2H), 0.27-0.21 (m, 2H).

Intermediate 206

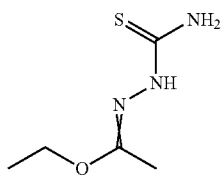

Ethyl N-carbamothioylethanehydrazonate

To a solution of ethyl acetimdate hydrochloride [2208-07-3] (6.17 g, 49.9 mmol) in DMF (100 mL) under nitrogen was added thiosemicarbazide [79-19-6] (4.55 g, 49.9 mmol) at r.t. and the reaction mixture was stirred for 20 h. The mixture was poured into ice water (500 mL) and stirred at 0° C. for 1-2 h. The solid was filtered and the precipitate washed with ice cold water (20 mL) and air dried for 60 minutes and dried in vacuo overnight to afford the title compound (4.73 g, 59%) as a white amorphous solid. $\delta_H$ (500 MHz, DMSO-d$_6$) 8.94 (s, 1H), 7.95 (s, 1H), 7.39 (s, 1H), 4.15 (q, J 7.0 Hz, 2H), 2.06 (s, 3H), 1.28 (t, J 7.0 Hz, 3H). LCMS [M+H]$^+$ 162, RT 1.06 minutes, 100% purity (Method 18).

Intermediate 207

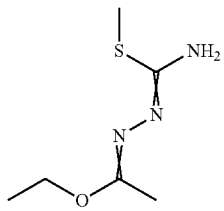

ethyl N-[amino(methylsulfanyl)methylene]ethanehydrazonate

To a suspension of intermediate 206 (1.00 g, 6.20 mmol) in DCM (5 mL) under nitrogen was added iodomethane [74-88-4] (1.76 g, 12.4 mmol) and the reaction mixture was stirred at r.t. for 4 h. The reaction mixture was concentrated in vacuo, azeotroped with DCM and the crude residue was suspended with EtOAc (40 mL) and washed with saturated aqueous sodium carbonate solution (6 mL). The organic phase was dried (Na$_2$SO$_4$), filtered and the filtrate concentrated in vacuo to give the title compound (1.09 g, 92%, 92% purity) as a pale yellow oil, mixture of isomers. 1H NMR of major isomer: $\delta_H$ (500 MHz, Chloroform-d) 4.99 (br. s, 2H), 4.13 (q, J 7.1 Hz, 2H), 2.43 (s, 3H), 2.11 (s, 3H), 1.30 (t, J 7.1 Hz, 3H). Other minor configurantional isomers also observed by 1H NMR. LCMS (ES+) [M+H]$^+$ 176, RT 1.37 minutes, 92% purity (Method 18).

Intermediate 208

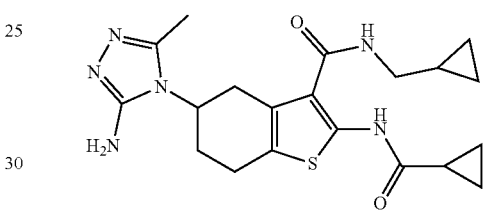

5-(3-Amino-5-methyl-1,2,4-triazol-4-yl)-2-(cyclopropanecarbonylamino)-N-(cyclopropylmethyl)-4,5,6,7-tetrahydrobenzothiophene-3-carboxamide To intermediate 122 (200 mg, 0.60 mmol) dissolved in DMF (0.5 mL) under nitrogen was added imidate intermediate 207 (946 mg, 5.40 mmol) dissolved in DMF (0.5 mL). The reaction mixture was sealed in a pressure tube and heated to 120° C. for 2 h before cooling to r.t. The suspension was filtered and washed with MeCN (0.2 mL) to afford the title compound (111 mg, 44%) as a colourless solid. $\delta_H$ (500 MHz, DMSO-d$_6$) 11.23 (s, 1H), 7.67 (t, J 5.6 Hz, 1H), 5.50 (s, 2H), 4.35-4.15 (m, 1H), 3.18-3.07 (m, 3H), 2.88-2.79 (m, 3H), 2.41-2.36 (m, 1H), 2.32 (s, 3H), 2.00 (d, J 10.5 Hz, 1H), 1.92 (p, J 6.2, 5.7 Hz, 1H), 1.01 (tq, J 7.7, 4.0, 2.7 Hz, 1H), 0.92-0.79 (m, 4H), 0.44-0.32 (m, 2H), 0.25-0.14 (m, 2H). LCMS [M+H]$^+$ 415, RT 2.18 minutes, 98% purity (Method 16).

Intermediate 209

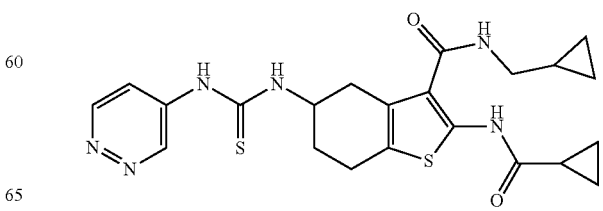

2-(Cyclopropanecarbonylamino)-N-(cyclopropylmethyl)-5-(pyridazin-4-ylcarbamothioylamino)-4,5,6,7-tetrahydrobenzothiophene-3-carboxamide A solution of pyridazin-4-amine [20744-39-2] (134 mg, 1.41 mmol) in Et$_2$O (5 mL) was added dropwise to a solution of intermediate 175 (70%, 378 mg, 0.7 mmol) in isopropanol (5 mL) and DCM (2 mL) and the reaction mixture was stirred for 18 h at r.t. The reaction mixture was concentrated in vacuo and the crude residue was purified by flash column chromatography on silica (gradient elution with 0-100% EtOAc) to afford the title compound (136 mg, 41%) as a light yellow solid. δ$_H$ (250 MHz, Chloroform-d) 12.13 (s, 1H), 7.47-7.35 (m, 2H), 7.16-7.01 (m, 2H), 5.89-5.85 (br s, 1H), 4.77 (s, 1H), 3.35-3.28 (m, 3H), 2.91-2.85 (m, 3H), 2.20-2.16 (m, 1H), 1.77-1.61 (m, 1H), 1.32-1.27 (m, 1H), 1.15-1.09 (m, 3H), 0.98-0.81 (m, 3H), 0.63-0.57 (m, 2H), 0.34-0.26 (m, 2H).

Intermediate 210

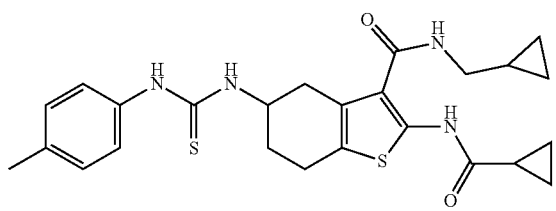 [SMILES: Cc1ccc(NC(=S)NC2CCc3sc(NC(=O)C4CC4)c(C(=O)NCC4CC4)c3C2)cc1]

2-(Cyclopropanecarbonylamino)-N-(cyclopropylmethyl)-5-(p-tolylcarbamothioylamino)-4,5,6,7-tetrahydrobenzothiophene-3-carboxamide A solution of 1-isothiocyanato-4-methylbenzene [622-59-3] (121 mg, 0.81 mmol) in DCM (20 mL) was cooled to 0° C.) before addition of intermediate 122 (300 mg, 0.81 mmol) and DIPEA (211.9 μL, 1.217 mmol). The ice bath was removed and the reaction mixture was stirred for 4 h under nitrogen. The mixture was diluted with DCM (30 mL) and washed with 1 M aqueous hydrochloric acid, saturated sodium hydrogen carbonate solution and brine. The organic phase was separated, dried (MgSO$_4$), filtered and concentrated in vacuo to give the crude product as a pale yellow solid which was purified by flash column chromatography on silica (gradient elution with 12 to 60% EtOAc in heptane) to afford the title compound (340 mg, 84%) as a white solid. LCMS [M+H]$^+$ 483.05, RT 1.23 minutes, 97% purity (Method 6).

Intermediate 211

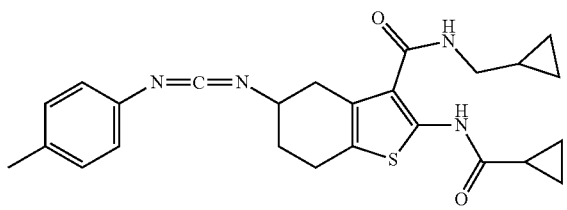 [SMILES: Cc1ccc(N=C=NC2CCc3sc(NC(=O)C4CC4)c(C(=O)NCC4CC4)c3C2)cc1]

2-Cyclopropanecarbonylamino)-N-(cyclopropylmethyl-5-(p-tolyliminomethyleneamino)-4,5,6,7-tetrahydrobenzothiophene-3-carboxamide Methanesulfonyl chloride [124-63-0] (32.3 μl, 0.41 mmol) was added over a period of 10 minutes to a solution of intermediate 210 (100 mg, 0.20 mmol), triethylamine (86.6 μl, 0.62 mmol), and DMAP [1122-58-3] (2.5 mg, catalytic amount) in DCM (4 mL) cooled in an ice bath. The reaction mixture was stirred for 15 minutes before concentrating in vacuo to give the crude product which was purified by flash column chromatography on silica (gradient elution with 5% to 50% EtOAc in heptane) to afford the title compound (75 mg, 70%, 87% purity). LCMS [M+H]$^+$ 449.2, [M+Na]+471.05 RT 1.39 minutes, 87% purity (Method 6).

Intermediate 212

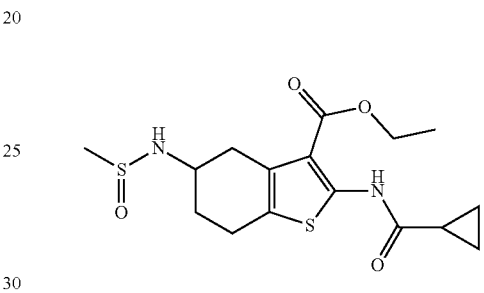

Ethyl 2-(cyclopropanecarbonylamino)-5-(methanesulfinamido)-4,5,6,7-tetrahydrobenzothiophene-3-carboxylate The following two reactions were carried out, differing in the starting amine intermediate 122 and example 109.

Reaction 1: To intermediate 122 (126 mg, 0.37 mmoL), sodium methanesulfinate [20277-69-4] (45 mg, 0.44 mmoL) and 1-ethyl-3-(3-dimethylaminopropyl)carbodiimide (84 mg, 0.44 mmoL) in DCM (5 mL) was added DIPEA (0.15 mL, 0.88 mmoL) and the resulting solution was stirred at r.t. under nitrogen. After stirring for 60 h at r.t. sodium methanesulfinate [20277-69-4] (45 mg, 0.44 mmoL), EDCl (84 mg, 0.44 mmoL) and DIPEA (0.15 mL, 0.88 mmoL) were added and stirring was continued at r.t. for further 6 h. The reaction mixture was combined with Reaction 2 for work up.

Reaction 2: To example 109 (158 mg, 0.512 mmoL), sodium methanesulfinate [20277-69-4] (63 mg, 0.62 mmoL) and EDCl (118 mg, 0.62 mmoL) in DCM (5 mL) was added DIPEA (0.21 mL, 1.23 mmoL) and the resulting solution was stirred at r.t. under nitrogen for 60 h. The reaction mixture was combined with Reaction 1 for work up. The combined reaction mixtures were diluted with DCM and washed with saturated aqueous sodium hydrogen carbonate solution (10 mL), saturated aqueous ammonium chloride (10 mL), water (10 mL) and brine (10 mL). The organic phase was dried (MgSO$_4$), filtered and concentrated in vacuo to give the crude product which was purified by flash column chromatography on silica (gradient elution with 0 to 100% of EtOAc in heptane, followed by 0 to 20% MeOH in EtOAc) to afford the title compound (183 mg, 56%) as an off-white solid. δ$_H$ (250 MHz, Chloroform-d) 11.44 (s, 1H), 4.35 (q, J 7.0 Hz, 2H), 3.90-3.71 (m, 2H), 3.34-3.16 (m, 1H), 2.85-2.68 (m, 3H), 2.69-2.47 (m, 3H), 2.20-2.00 (m, 1H), 1.95-1.78 (m, 1H), 1.74-1.59 (m, 1H), 1.40 (t, J 7.1 Hz, 3H), 1.21-1.07 (m, 2H), 1.02-0.85 (m, 2H). LCMS [M+H]⁺ 371, RT 1.20 minutes, 94% purity (Method 6).

Intermediate 213

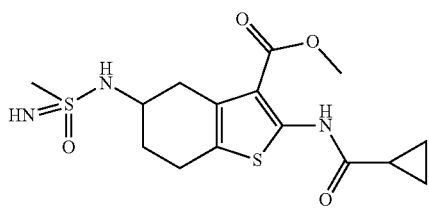 [SMILES: COC(=O)c1c(NC(=O)C2CC2)sc2c1CC(NS(C)(=N)=O)CC2]

Methyl 2-(cyclopropanecarbonylamino)-5-[(methylsulfonimidoyl)amino]-4,5,6,7-tetrahydrobenzothiophene-3-carboxylate To a solution of intermediate 212 (180 mg, 0.49 mmoL) in DCM (5 mL) was added 2,2,2-trifluoroacetamide [354-38-1] (110 mg, 0.97 mmoL), magnesium oxide [1309-48-4] (78 mg, 1.9 mmoL), rhodium diacetate dimer [15956-28-2] (5 mg, 0.012 mmoL) and iodobenzene diacetate [3240-34-4] (235 mg, 0.73 mmoL) and the resulting suspension was stirred at r.t. for 16 h under nitrogen. The reaction mixture was filtered through a pad of celite, washed with DCM and the filtrate was concentrated in vacuo to afford a mixture of ethyl 2-(cyclopropanecarbonylamino)-5-(methanesulfonamido)-4,5,6,7-tetrahydrobenzothiophene-3-carboxylate and ethyl 2-(cyclopropanecarbonylamino)-5-[[S-methyl-N-(2,2,2-trifluoroacetyl)sulfonimidoyl]amino]-4,5,6,7-tetrahydrobenzothiophene-3-carboxylate which was utilised without further purification. To this mixture dissolved in MeOH (5 mL) was added potassium carbonate (335 mg, 2.43 mmoL) and the reaction mixture was stirred at r.t. overnight. The mixture was concentrated in vacuo and the crude residue was purified by flash column chromatography on silica (gradient elution with 0 to 100% of EtOAc in heptane, followed by 0 to 10% of MeOH in EtOAc) to afford the desired title compound (44 mg, 19%) as a yellow oil. LCMS [M+H]⁺ 372.00, RT 1.00 minutes, 94% purity (Method 6).

Intermediate 214

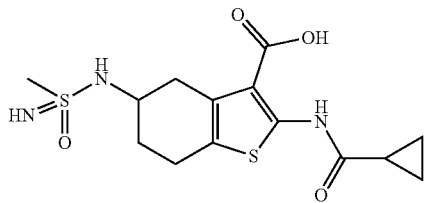 [SMILES: CS(=N)(=O)NC1CCc2sc(NC(=O)C3CC3)c(C(=O)O)c2C1]

2-(Cyclopropanecarbonylamino)-5-[(methylsulfonimidoyl)amino]-4,5,6,7-tetrahydrobenzothiophene-3-carboxylic acid To a solution of intermediate 213 (40 mg, 0.11 mmoL) in 1,4-dioxane (3 mL) and water (3 mL) was added lithium hydroxide monohydrate [1310-66-3] (9 mg, 0.22 mmoL) and the reaction mixture was stirred at r.t. for 6 h. The reaction mixture was concentrated in vacuo and the residue was diluted with water (5 mL). The aqueous solution was acidified with 0.2M aqueous hydrochloric acid solution until pH 2 and the mixture was extracted with EtOAc (3×30 mL) followed by chloroform/isopropanol (1:1, 3×20 mL). The organic phases were dried (MgSO₄), filtered and concentrated in vacuo to afford the title compound (30 mg, 54%, 69% purity) as a yellow film. LCMS [M+H]⁺ 358, RT 0.93 minutes, 69% purity (Method 6).

Intermediate 215

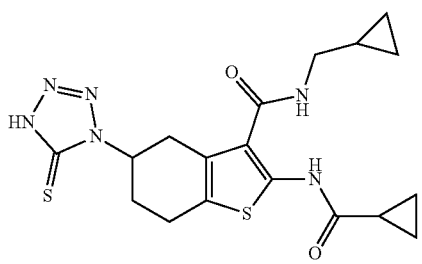 [SMILES: O=C(NCC1CC1)c1c(NC(=O)C2CC2)sc2c1CC(n1nn[nH]c1=S)CC2]

2-(Cyclopropanecarbonylamino)-N-(cyclopropylmethyl)-5-(5-thioxo-1H-tetrazol-4-yl)-4,5,6,7-tetrahydrobenzothiophene-3-carboxamide Intermediate 175 (1.13 g, 3.01 mmoL) was added to a solution of sodium azide (196 mg, 3.01 mmoL) in 2-propanol (80 mL) and water (8 mL) and the reaction mixture was heated to reflux for 1 h. The cooled suspension was filtered through Celite and concentrated in vacuo to afford the title compound (1.12 g, 49%, 55% purity) as a pale yellow solid which was utilised in the next step without purification. LCMS [M+H]⁺ 419.05, [M+Na]⁺440.95, RT 1.11 minutes, 55% purity (Method 11).

Intermediate 216

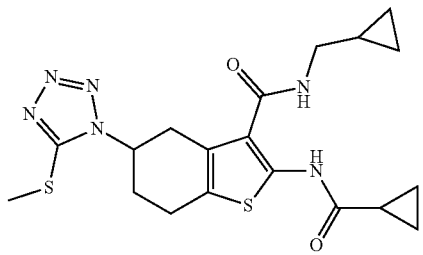 [SMILES: CSc1nnnn1C1CCc2sc(NC(=O)C3CC3)c(C(=O)NCC3CC3)c2C1]

2-(Cyclopropanecarbonylamino)-N-(cyclopropylmethyl)-5-(5-methylsufanyltetrazol-1-yl)-4,5,6,7-tetrahydrobenzothiophene-3-carboxamide To a solution of intermediate 215 (1.12 g, 2.68 mmoL) in THF (30 mL) was added 2M potassium 2-methylpropan-2-olate (4.01 mL) at r.t. The reaction mixture was stirred for 10 minutes and iodomethane [74-88-4] (0.46 mL, 3.21 mmoL) was added dropwise. The mixture was stirred for 1 h, concentrated in vacuo, diluted with 10% aqueous citric acid (300 mL) and extracted with DCM (3×50 mL). The combined organic phases were dried (Na₂SO₄), filtered and concentrated in vacuo to give the crude product which was purified by flash column chromatography on silica (gradient elution with 0-100% EtOAc in heptane followed by 0-40% MeOH in DCM) to afford the title compound (1 g, 81%, 94% purity). δ$_H$ (250 MHz, Chloroform-d) 12.01 (s, 1H), 5.74 (s, 1H), 4.59 (s, 1H), 3.49-3.13 (m, 4H), 2.99 (s, 2H), 2.89 (s, 3H), 2.65-2.25 (m, 2H), 1.75-1.64 (m, 2H), 1.21-1.11 (m, 2H), 0.99-0.91 (m, 2H), 0.59-0.51 (m, 2H), 0.31-0.13 (m, 2H).

Intermediate 217

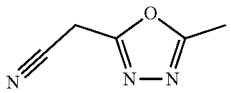

2-(5-methyl-1,3,4-oxadiazol-2-yl)acetonitrile

Intermediate 163 (90%, 2.8 g, 17.86 mmol) was stirred in toluene (75 mL). POCl₃ (4.55 g, 29.68 mmol) was added and the suspension was heated at 80° C. for 2.5 hours. The reaction was allowed to cool and the suspension was added to water (100 mL) then taken to pH7 using saturated aq. Na₂CO₃. The aqueous solution was extracted with ethyl acetate (3×100 mL), the organics were dried over sodium sulfate and concentrated in vacuo to afford the title compound (980 mg, 44%) as a red solid. δ$_H$ (500 MHz, Chloroform-d) δ 4.02 (s, 2H), 2.58 (s, 3H). 6H (500 MHz, DMSO-d₆) δ 4.57 (s, 2H), 2.51 (s, 3H).

Intermediate 218

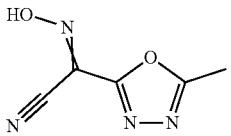

2-hydroxyimino-2-(5-methyl-1,3,4-oxadiazol-2-yl)acetonitrile

Intermediate 217 (880 mg, 7.15 mmol) was stirred in dry ethanol (10 mL) and powdered KOH (441 mg, 7.86 mmol) was added followed by ᵗbutyl nitrite (935 µl, 7.86 mmol). An exotherm was observed and the reaction was cooled in an ice bath for 10 minutes then stirred at room temperature for 18 hours. Further ᵗbutyl nitrite (250 µl, 2.1 mmol) was added and the reaction stirred for 2 hours at room temperature. The brown suspension was diluted with diethyl ether and the solid was collected by vacuum filtration to give an orange solid which was dissolved in water (50 mL) and acidified to pH1 using 1M aq. HCl. The product was extracted into EtOAc (3×50 mL), dried over sodium sulfate and concentrated in vacuo to afford the title compound as a 1:1 mixture of E/Z isomers, (912 mg, 80% at 95% purity) as a red solid. δ$_H$ (250 MHz, DMSO-d₆) δ 15.02 (s, 2H Isomer A+B), 2.61 (s, 3H Isomer A), 2.58 (s, 3H Isomer B).

Intermediate 219

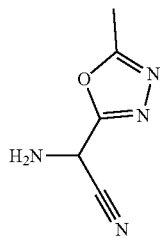

2-amino-2-(5-methyl-1,3,4-oxadiazol-2-yl)acetonitrile

Intermediate 218 (0.98 g, 6.44 mmol) was stirred in water (6 mL) and saturated NaHCO₃ (6 mL) was added slowly. The mixture was stirred until all material had dissolved. Disodium dithionite (85%, 3.17 g, 15.46 mmol) was added in portions over 15 minutes, reaction reached 29° C. The reaction was stirred for 1 hour then extracted with DCM (3×20 mL). The organics were dried over sodium sulfate and concentrated in vacuo to afford the title compound (208 mg, 16% at 68% purity) as an orange oil which solidified on standing. δ$_H$ (500 MHz, DMSO-d₆) δ 5.53 (s, 1H), 2.53 (s, 3H). δ$_H$ (500 MHz, Chloroform-d) δ 5.22 (s, 1H), 2.61 (s, 3H).

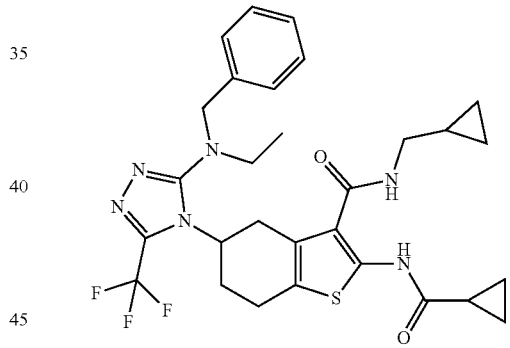

5-[3-[Benzyl(ethyl)amino]-5-(trifluoromethyl)-1,2,4-triazol-4-yl]-2-(cyclopropanecarbonylamino)-N-(cyclopropylmethyl)-4,5,6,7-tetrahydrobenzothiophene-3-carboxamide To a solution of intermediate 197 (198 mg at 57% purity-estimated 113 mg product, 0.22 mmol) in 1,4-dioxane (2 mL) in a pressure tube was added trifluoroacetic anhydride [407-25-0] (46 mg in 0.2 mL 1,4-dioxane from a 230 mg in 1 mL stock solution, 0.22 mmol) and the reaction mixture was stirred at 30° C. under nitrogen for 60 minutes. The reaction mixture was retreated with further trifluoroacetic anhydride stock solution [407-25-0] (0.2 mL, 0.22 mmol) and the reaction mixture was stirred at r.t. overnight. TFA [76-05-1] (251 mg, 2.20 mol) was added under nitrogen and the reaction mixture was warmed to 80° C. for 50 minutes. Further TFA [76-05-1] (0.1 mL) was added and the reaction mixture was warmed at 80° C. for a further 4 h. The reaction mixture was concentrated in vacuo and the crude product was purified by preparative HPLC to afford the title compound (32 mg, 25%) which was azeotroped from MeCN (3×5 mL) to give a brown oil. LCMS [M+H]$^+$ 587, RT 1.36 minutes, 100% purity (Method 11).

Intermediate 221

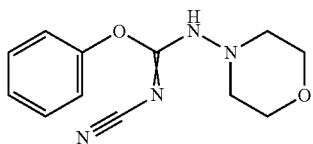 [SMILES: N#CN=C(NN1CCOCC1)Oc1ccccc1]

3-Cyano-1-morpholino-2-phenyl-isourea

Diphenyl N-cyanocarbonimidate [79463-77-7] (200 mg, 0.81 mmol, 97 mass %) and 4-aminomorpholine [4319-49-7] (100 mg, 0.98 mmol) were dissolved in DCM (2 mL) and 2-propanol (1.57 g, 26.1 mmol) and DIPEA (159 mg, 1.22 mmol) were added. The reaction mixture was stirred at r.t. for 1 h before concentrating in vacuo. The crude residue was purified by flash column chromatography on silica (gradient elution with 15-100% EtOAc/hexane) to afford the title compound (170 mg, 85%) as a white solid. $\delta_H$ (300 MHz, DMSO-d$_6$) 10.39 (s, 1H), 7.42 (t, J 7.8 Hz, 2H), 7.28 (t, J 7.4 Hz, 1H), 7.23-7.08 (m, 2H), 3.68 (s, 4H), 2.89 (s, 4H).

Intermediates 222 and 223

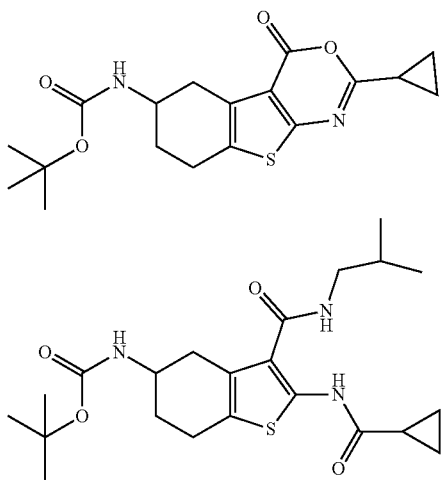

Intermediate 222 tert-Butyl N-(2-cyclopropyl-4-oxo-5,6,7,8-tetrahydrobenzothiopheno[2,3-d][1,3]oxazin-6-yl)carbamate Intermediate 223 tert-Butyl N-[2-(cyclopropanecarbonylamino)-3-(isobutylcarbamoyl)-4,5,6,7-tetrahydrobenzothiophen-5-yl]carbamate To a solution of intermediate 26 (1 g, 2.63 mmol) and isobutylamine [78-81-9] (288 mg, 3.94 mmol) in DCM (15 mL) was added EDCl (806 mg, 4.21 mmol) and the resulting solution was stirred at r.t. under an atmosphere of argon. The reaction mixture was stirred overnight and the reaction mixture was treated with 0.1N aqueous hydrochloric acid solution (15 mL). The layers were separated and the organic phase was washed with brine. The organic phase was dried (MgSO$_4$), filtered and concentrated in vacuo to give a crude residue which was purified by flash chromatography on silica (gradient elution with 100% DCM, 3 minutes; DCM/MeOH (NH$_4$OH 10%) 2%, 3 minutes; DCM/MeOH (NH$_4$OH 10%) 5%, 3 minutes; DCM/MeOH (NH$_4$OH 10%) 10%, 5 minutes) followed by preparative TLC (DCM/MeOH (NH$_4$OH 10%) 5%) to afford the title compound intermediate 222 (391 mg, 41%) and the title compound intermediate 223 (276 mg, 24%). Intermediate 222$\delta_H$ (500 MHz, CDCl$_3$) 12.15 (s, 1H), 5.94-5.70 (m, 1H), 4.67 (s, 1H), 4.10 (s, 1H), 3.28 (dd, J=7.1, 5.2 Hz, 2H), 2.87-2.70 (m, 2H), 2.68-2.54 (m, 1H), 2.06-1.94 (m, 1H), 1.91-1.79 (m, 1H), 1.72-1.61 (m, 1H), 1.46 (s, 9H), 1.18-0.98 (m, 3H), 0.99-0.72 (m, 2H), 0.67-0.47 (m, 2H), 0.36-0.14 (m, 2H). Intermediate 223 LCMS [M+H]$^+$ 436.24, [M−H]$^-$ 434.24, RT 3.09 minutes (Method 8)

Intermediate 223

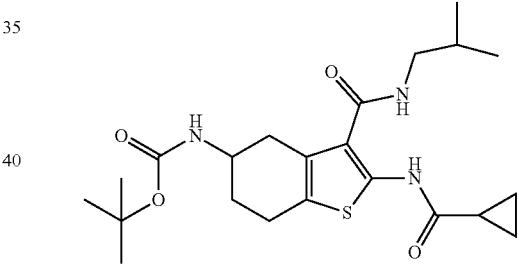

tert-Butyl N-[2-(cyclopropanecarbonylamino)-3-(isobutylcarbamoyl)-4,5,6,7-tetrahydrobenzothiophen-5-yl]carbamate Intermediate 222 (0.39 g, 1.08 mmol) was dissolved in DMF (3 mL) and isobutylamine [78-81-9] (158 mg, 2.16 mmol) was added. The reaction mixture was heated to 150° C. for 10 minutes in the microwave. The reaction mixture was poured into EtOAc and washed with water (2×). The organic phase was dried (MgSO$_4$), filtered and concentrated in vacuo to give a brown oil which was purified by flash column chromatography on silica (gradient elution with 0 to 20% DCM/MeOH-NH$_4$OH (10%)) to afford the title compound (320 mg, 68%) as a yellow oil. LCMS [M+H]$^+$ 436.24, [M−H]$^-$ 434.24, RT 3.05 minutes, 69.39% purity (Method 8).

Intermediate 224

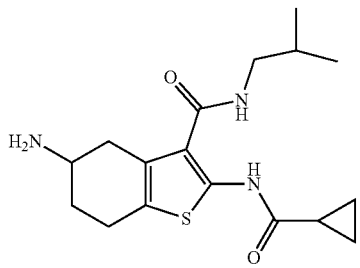 [SMILES: CC(C)CNC(=O)c1c(NC(=O)C2CC2)sc2c1CC(N)CC2]

5-Amino-2-(cyclopropanecarbonylamino)-N-isobutyl-4,5,6,7-tetrahydrobenzothiophene-3-carboxamide Intermediate 223 (276 mg, 0.634 mmol) was dissolved in EtOH (2.0 g, 43.4 mmol) and was heated at 60° C. 4N Hydrogen chloride in 1,4-dioxane (231 mg, 6.34 mmol) was added and the mixture was heated for 2 h and then left to stand at r.t. overnight. The reaction mixture was concentrated in vacuo to afford the title compound (180 mg, 85%) which was utilised as crude. LCMS [M+H]$^+$ 336.17, RT 1.53 minutes (Method 8).

Intermediate 225

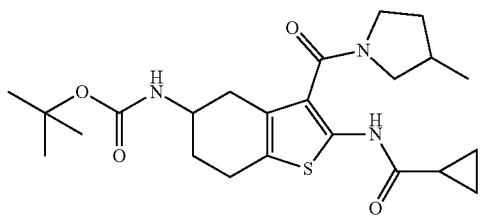 [SMILES: CC1CCN(C(=O)c2c(NC(=O)C3CC3)sc3c2CC(NC(=O)OC(C)(C)C)CC3)C1]

tert-Butyl N-[2-(cyclopropanecarbonylamino)-3-(3-methylpyrrolidine-1-carbonyl)-4,5,6,7-tetrahydrobenzothiophen-5-yl]carbamate 3-Methyl-pyrrolidine hydrochloride [120986-92-7] (0.15 g, 1.18 mmol) was suspended in DCM (10 mL) and tris-(2-aminoethyl)-amine polystyrene HL (0.40 g, 1.58 mmol, 3.95 mmol/g) was added and the reaction mixture was stirred at r.t. for ~10 minutes. Intermediate 26 (300 mg, 0.79 mmol) and EDCl (0.19 g, 0.95 mmol) was added and the reaction mixture was stirred at r.t. for 16 h. The reaction mixture was washed with water, passed through a phase separation cartridge and concentrated in vacuo to give the crude product which was purified by flash column chromatography on silica (gradient elution with 20-100% EtOAc/hexane) to afford the title compound (174 mg, 49%) as a pale yellow gum. LCMS [M+H]$^+$ 448.8, [M+Na]$^+$470.8, RT 2.283 minutes, 100.0% purity (Method 2). LCMS [M+H]$^+$ 448.8, [M+Na]$^+$470.8, RT 2.258 minutes, 100.0% purity (Method 3).

Intermediate 226

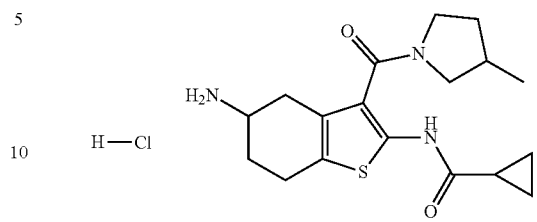

N-[5-Amino-3-(3-methylpyrrolidine-1-carbonyl)-4,5,6,7-tetrahydrobenzothiophen-2-yl]cyclopropanecarboxamide; hydrochloride Intermediate 225 (0.15 g, 0.34 mmol) was dissolved in 4M hydrogen chloride in 1,4-dioxane (10 mL, 10.5 g, 40 mmol) and the reaction mixture was stirred at r.t. for ~2 h. The reaction mixture was concentrated in vacuo to give the product which was freeze dried from water/MeCN to afford the title compound (0.13 g, 100%) as a white solid. LCMS [M+H]$^+$ 348.8, [M+Na]$^+$370.8, RT 1.223 minutes, 100% purity (Method 2). LCMS [M+H]$^+$ 348.8, [M+Na]$^+$370.5, RT 1.524 minutes, 100% purity (Method 3).

Intermediate 227

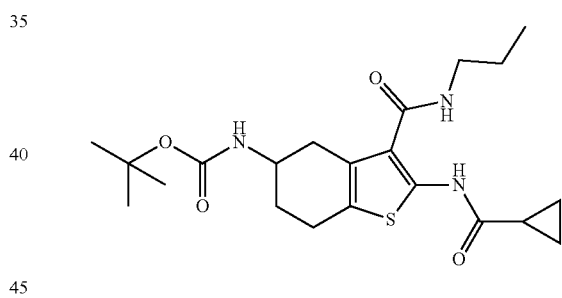

tert-Butyl N-[2-(cyclopropanecarbonylamino)-3-(propylcarbamoyl)-4,5,6,7-tetrahydrobenzothiophen-5-yl]carbamate To a solution of intermediate 26 (1 g, 2.63 mmol) and n-propylamine [107-10-8] (235 mg, 3.94 mmol) in DCM (15 mL) was added EDCl (806 mg, 4.21 mmol) and the resulting solution was stirred at r.t. under argon overnight. To the reaction mixture was added 0.1N aqueous hydrochloric acid (15 mL), the phases were separated and the organic phase was washed with brine, dried (MgSO$_4$), filtered and the organic phase was concentrated to afford the crude product which was purified by flash column chromatography on silica (gradient elution with 100% DCM 3 minutes; 2% MeOH/DCM (10% NH$_4$OH) 3 minutes; 5% MeOH/DCM (10% NH$_4$OH), 3 minutes; 10% MeOH/DCM (10% NH$_4$OH), 5 minutes) to afford the title compound (282 mg, 25%) as an off white foam. LCMS [M+H]$^+$ 422.25, RT 2.94 minutes, 88.53% purity (Method 8).

Intermediate 228

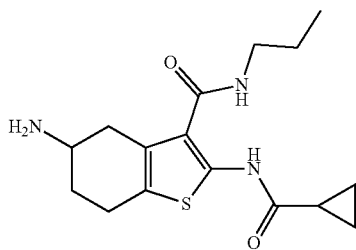 [SMILES: CCCNC(=O)c1c(NC(=O)C2CC2)sc2c1CC(N)CC2]

5-Amino-2-(cyclopropanecarbonylamino)-N-propyl-4,5,6,7-tetrahydrobenzothiophene-3-carboxamide Intermediate 227 (282 mg, 0.67 mmol) was dissolved in EtOH (2.11 g, 45.84 mmol) and heated at 60° C. 4N Hydrogen chloride in 1,4-dioxane (244 mg, 6.69 mmol) was added and mixture heated at 60° C. for 2 h before concentrating in vacuo. The crude residue was triturated in Et$_2$O to afford the title compound (215 mg, 100%) as a white powder. LCMS [M+H]$^+$ 322.18, RT 1.45 minutes (Method 8).

Intermediate 229

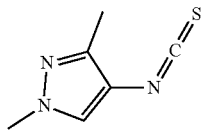

4-Isothiocyanato-1,3-dimethyl-pyrazole 1,3-Dimethyl-1H-pyrazol-4amine dihydrochloride [1692-25-7] (291.0 mg, 1.502 mmol,) was dissolved in DCM (4.5 mL) under nitrogen. 1,1'-Thiocarbonyldiimidazole (310.3 mg, 1.654 mmol) was added and the reaction was stirred at r.t. for 5.5 h. The crude reaction mixture was then concentrated in vacuo to give a yellow solid which was purified by flash column chromatography on silica (gradient elution with 0% to 100% EtOAc in isohexane) to afford the title compound (194.0 mg, 1.266 mmol, 84% Yield) as a pale yellow liquid. LCMS [M+H]$^+$ 154.2, RT 0.839 minutes (Method 15).

Intermediate 230

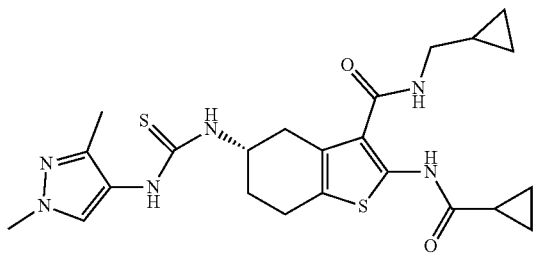 [SMILES: Cc1nn(C)cc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(1,3-dimethylpyrazol-4-ylcarbamothioylamino]-4,5,6,7-tetrahydrobenzothiophene-3-carboxamide To a stirred solution of intermediate 117 (313.5 mg, 0.9403 mmol) dissolved in DCM (3.7 mL) under nitrogen was added DIPEA (0.23 mL, 1.3 mmol) followed by a solution of intermediate 229 (194.0 mg, 1.266 mmol) in DCM (1.0 mL). The reaction was stirred at r.t. for 17.5 h before being concentrated in vacuo to give a brownish grey oil. This oil was purified by flash column chromatography on silica (gradient elution with 0% to 100% EtOAc in isohexane, 0% to 20% MeOH in EtOAc) to afford the title compound (478.3 mg, 0.9338 mmol, 95 mass %, assumed quantitative yield and that the extra 5 mass % was due to solvent) as a brownish grey oil. LCMS [M+H]$^+$ 487.0, RT 1.317 minutes, purity 98% (Method 15).

Intermediate 231

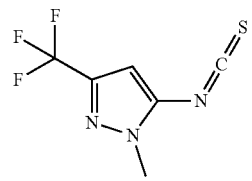

5-isothiocyanato-1-methyl-3-(trifluoromethyl)pyrazole

Hydrochloric acid in 1,4-dioxane (10.5 mL, 42.0 mmol, 4 mol/L) followed by 1,1'-thiocarbonyldiimidazole (4.38 g, 23.3 mmol) were added to a stirred solution of 1-methyl-3-(trifluoromethyl)-1H-pyrazol-5-amine [149978-43-8] (3.49 g, 21.1 mmol) in DCM (63 mL) under nitrogen. The reaction mixture was stirred at rt for 4.5 h before being left without stirring for a further 15.5 h. The reaction mixture was filtered and the pale yellow solid was washed with DCM (2×40 mL). The filtrate and washings were concentrated in vacuo to give an orange liquid which was purified by flash column chromatography on silica (gradient elution with 0% to 15% EtOAc in isohexane) to afford the title compound (3.0430 g, 14.688 mmol, 70%) as a colourless liquid. To confirm the presence of the title compound, a few drops of isobutylamine were added to the LCMS sample of the product before analysis to give the thiourea, LCMS [M+H]$^+$ 281.0, RT 1.336 minutes, purity 100% (Method 15).

Intermediate 232

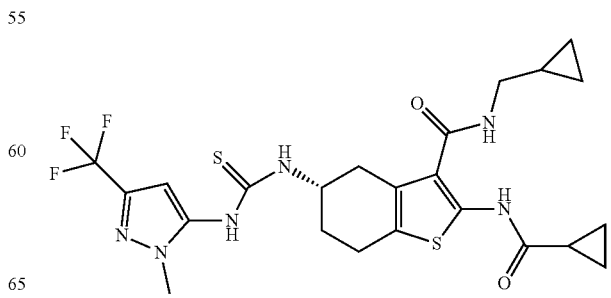

249

(5S)-2-(cyclopropanecarbonylamino)-N-(cyclopropylmethyl)-5-[[2-methyl-5-(trifluoromethyl)pyrazol-3-yl]carbamothioylamino]-4,5,6,7-tetrahydrobenzothiophene-3-carboxamide DIPEA (0.57 mL, 3.3 mmol) followed by a solution of intermediate 231 (684.5 mg, 3.304 mmol) in DCM (5.0 mL) were added to a stirred solution of intermediate 117 (1.000 g, 2.999 mmol) in DCM (10 mL) under nitrogen. The reaction mixture was stirred at rt for 4 h before being concentrated in vacuo to give a yellow oil. This oil was purified by flash column chromatography on silica (gradient elution with 0% to 100% EtOAc in isohexane) to afford impure title compound as a pale peach oil which was re-purified by flash column chromatography on silica (gradient elution with 20% to 60% EtOAc in isohexane) to give the title compound (1.191 g, 2.203 mmol, 73% Yield) as a white foam. LCMS [M+H]$^+$ 541.0, RT 1.478 minutes, purity 99% (Method 15).

Intermediate 233

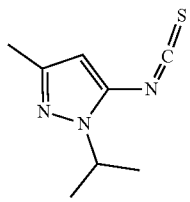

1-isopropyl-5-isothiocyanato-3-methyl-pyrazole

Hydrochloric acid in 1,4-dioxane (1.25 mL, 5.00 mmol, 4 mol/L) followed by 1,1'-thiocarbonyldiimidazole (520.1 mg, 2.773 mmol) were added to a stirred solution of 1-isopropyl-3-methyl-1H-pyrazol-5-amine [1124-16-9] (368.2 mg, 2.513 mmol) in DCM (7.5 mL) under nitrogen. The reaction mixture was stirred at rt for 19 h. The reaction mixture was filtered and the white solid was washed with DCM (2×15 mL). The filtrate and washings were concentrated in vacuo to give a golden yellow oil which was purified by flash column chromatography on silica (gradient elution with 0% to 50% EtOAc in isohexane) to afford the title compound (167.6 mg, 0.9246 mmol, 37%) as a pale yellow liquid. To confirm the presence of the title compound, a few drops of isobutylamine were added to the LCMS sample of the product before analysis to give the thiourea, LCMS [M+H]$^+$ 255.1, RT 1.256 minutes, purity 99.6% (Method 15).

Intermediate 234

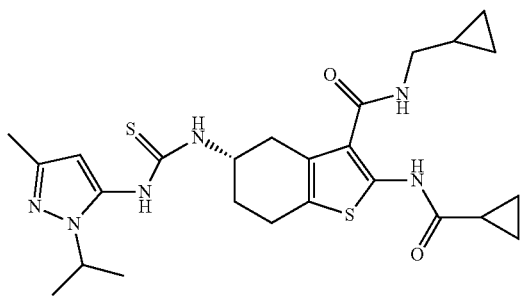 [SMILES: Cc1cc(NC(=S)N[C@H]2CCc3sc(NC(=O)C4CC4)c(C(=O)NCC4CC4)c3C2)n(C(C)C)n1]

250

(5S)-2-(cyclopropanecarbonylamino)-N-(cyclopropylmethyl)-5-[(2-isopropyl-5-methyl-pyrazol-3-yl)carbamothioylamino]-4,5,6,7-tetrahydrobenzothiophene-3-carboxamide DIPEA (0.17 mL, 0.98 mmol) followed by a solution of intermediate 233 (167.6 mg, 0.9246 mmol) in DCM (1.0 mL) were added to a stirred solution of intermediate 117 (250.0 mg, 0.7499 mmol) in DCM (2.75 mL) under nitrogen. The reaction mixture was stirred at rt for 17 h before being concentrated in vacuo to give a pale yellow oily solid which was purified by flash column chromatography on silica (gradient elution with 0% to 100% EtOAc in isohexane) to give the title compound (422.0 mg, 0.7461 mmol, 91 mass %, assumed quantitative yield and that the extra 9 mass % was due to solvent) as a white foam. LCMS [M+H]$^+$ 515.0, RT 1.432 minutes, purity 99% (Method 15).

Intermediate 235

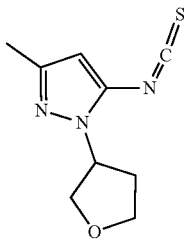

5-isothiocyanato-3-methyl-1-tetrahydrofuran-3-yl-pyrazole

Hydrochloric acid in 1,4-dioxane (1.25 mL, 5.00 mmol, 4 mol/L) followed by 1,1'-thiocarbonyldiimidazole (294.2 mg, 1.568 mmol) were added to a stirred solution of 3-methyl-1-(oxolan-3-yl)-1H-pyrazol-5-amine (250.0 mg, 1.420 mmol) in DCM (7.5 mL) under nitrogen. The reaction mixture was stirred at rt for 19 h. The reaction mixture was filtered and the white solid was washed with DCM (2×15 mL). The filtrate and washings were concentrated in vacuo to give a golden yellow oil which was purified by flash column chromatography on silica (gradient elution with 0% to 50% EtOAc in isohexane) to afford the title compound (219.0 mg, 1.046 mmol, 74%) as a pale yellow liquid. To confirm the presence of the title compound, a few drops of isobutylamine were added to the LCMS sample of the product before analysis to give the thiourea, LCMS [M+H]$^+$ 283.0, RT 1.186 minutes, purity 99% (Method 15).

Intermediate 236

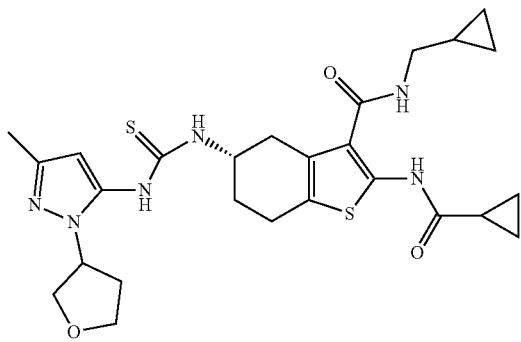 [SMILES: Cc1cc(NC(=S)N[C@H]2CCc3sc(NC(=O)C4CC4)c(C(=O)NCC4CC4)c3C2)n(C2CCOC2)n1]

(5S)-2-(cyclopropanecarbonylamino)-N-(cyclopropylmethyl)-5-[(5-methyl-2-tetrahydrofuran-3-yl-pyrazol-3-yl)carbamothioylamino]-4,5,6,7-tetrahydrobenzothiophene-3-carboxamide DIPEA (0.17 mL, 0.98 mmol) followed by a solution of intermediate 235 (219.0 mg, 1.046 mmol) in DCM (1.0 mL) were added to a stirred solution of intermediate 117 (250.0 mg, 0.7499 mmol) in DCM (2.75 mL) under nitrogen. The reaction mixture was stirred at rt for 17 h before being concentrated in vacuo to give a pale yellow oily solid which was purified by flash column chromatography on silica (gradient elution with 0% to 100% EtOAc in isohexane) to give the title compound (385.4 mg, 0.7102 mmol, 95%) as a white foam. LCMS [M+H]$^+$ 543.0, RT 1.389 minutes, purity 99% (Method 15).

Intermediate 237

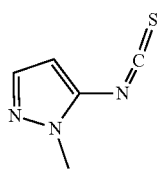

5-isothiocyanato-1-methyl-pyrazole

Hydrochloric acid in 1,4-dioxane (10.5 mL, 42.0 mmol, 4 mol/L) followed by 1,1'-thiocarbonyldiimidazole (4.361 g, 23.25 mmol) were added to a stirred solution of 1-methyl-1H-pyrazol-5-ylamine [1192-21-8] (2.110 g, 21.07 mmol) in DCM (63 mL) under nitrogen. The reaction mixture was stirred at rt for 24.5 h. The reaction mixture was filtered and the pale yellow solid was washed with DCM (2×40 mL). The filtrate and washings were concentrated in vacuo to give a yellow liquid which was purified by flash column chromatography on silica (gradient elution with 0% to 50% EtOAc in isohexane) to afford the title compound (1.7164 g, 12.332 mmol, 59%) as a yellow liquid. To confirm the presence of the title compound, a few drops of isobutylamine were added to the LCMS sample of the product before analysis to give the thiourea, LCMS [M+H]$^+$ 213.0, RT 1.021 minutes (Method 15).

Intermediate 238

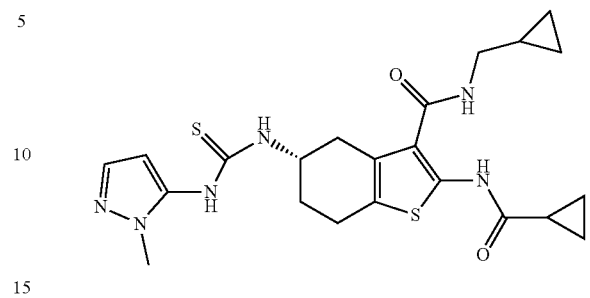

(5S)-2-(cyclopropanecarbonylamino)-N-(cyclopropylmethyl)-5-[(2-methylpyrazol-3-yl)carbamothioylamino]-4,5,6,7-tetrahydrobenzothiophene-3-carboxamide DIPEA (0.70 mL, 4.0 mmol) followed by a solution of intermediate 237 (565.4 mg, 4.062 mmol) in DCM (5.0 mL) were added to a stirred solution of intermediate 117 (1.034 g, 3.101 mmol) in DCM (10.5 mL) under nitrogen. The reaction mixture was stirred at rt for 3 h before being concentrated in vacuo to give a pale yellow solid which was purified by flash column chromatography on silica (gradient elution with 0% to 100% EtOAc in isohexane) to give the title compound (1.3368 g, 2.829 mmol, 91%) as a white foam. LCMS [M+H]$^+$ 473.0, RT 1.306 minutes, purity 100% (Method 15).

Intermediate 239

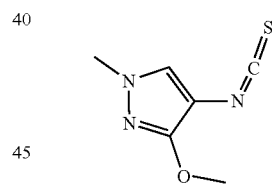

4-isothiocyanato-3-methoxy-1-methyl-pyrazole 1,1'-thiocarbonyldiimidazole (745.1 mg, 3.972 mmol) was added to a stirred solution of 3-methoxy-1-methyl-1H-pyrazol-4-amine hydrochloride [1431962-46-7] (610.5 mg, 3.545 mmol) in DCM (10.5 mL) under nitrogen. The reaction mixture was stirred at rt for 4.5 h. The reaction mixture was concentrated in vacuo to give an orange solid which was purified by flash column chromatography on silica (gradient elution with 0% to 100% EtOAc in isohexane) to afford the title compound (385.0 mg, 2.275 mmol, 64%) as a white solid. To confirm the presence of the title compound, a few drops of isobutylamine were added to the LCMS sample of the product before analysis to give the thiourea, LCMS [M+H] 243.0, RT 1.106 minutes, purity 100% (Method 15).

Intermediate 240

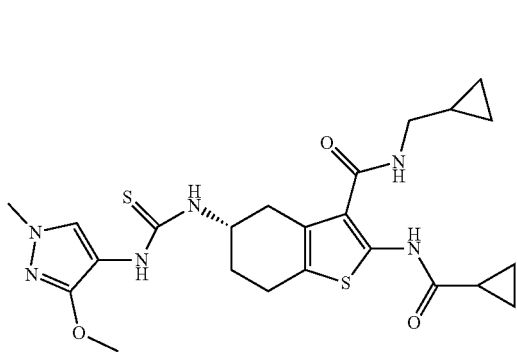 [SMILES: COc1nn(C)cc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(3-methoxy-1-methyl-pyrazol-4-yl)carbamothioylamino]-4,5,6,7-tetrahydrobenzothiophene-3-carboxamide DIPEA (0.17 mL, 0.98 mmol) followed by a solution of intermediate 239 (165.1 mg, 0.9758 mmol) in DCM (1.0 mL) were added to a stirred solution of intermediate 117 (249.3 mg, 0.7478 mmol) in DCM (2.75 mL) under nitrogen. The reaction mixture was stirred at rt for 45 min before being concentrated in vacuo to give an off white solid which was purified by flash column chromatography on silica (gradient elution with 0% to 100% EtOAc in isohexane) to give the title compound (376.0 mg, 0.7481 mmol, quantitative yield) as a white foam. LCMS [M+H]$^+$ 503.0, RT 1.361 minutes, purity 100% (Method 15).

Intermediate 241

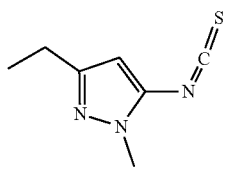

3-ethyl-5-isothiocyanato-1-methyl-pyrazole

Hydrochloric acid in 1,4-dioxane (1.25 mL, 5.00 mmol, 4 mol/L) followed by 1,1'-thiocarbonyldiimidazole (560.1 mg, 2.986 mmol) were added to a stirred solution of 3-ethyl-1-methyl-1H-pyrazol-5-amine [3524-46-7] (329.1 mg, 2.498 mmol) in DCM (7.5 mL) under nitrogen. The reaction mixture was stirred at rt for 2.5 h. The reaction mixture was concentrated in vacuo to give a golden yellow solid which was purified by flash column chromatography on silica (gradient elution with 0% to 50% EtOAc in isohexane) to afford the title compound (205.2 mg, 1.227 mmol, 49%) as a yellow liquid. To confirm the presence of the title compound, a few drops of isobutylamine were added to the LCMS sample of the product before analysis to give the thiourea, LCMS [M+H]$^+$ 241.1, RT 1.222 minutes, purity 100% (Method 15).

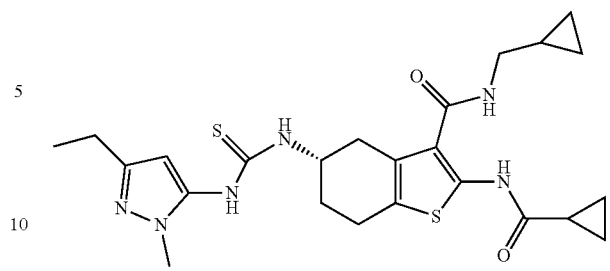

(5S)-2-(cyclopropanecarbonylamino)-N-(cyclopropylmethyl)-5-[(5-ethyl-2-methyl-pyrazol-3-yl)carbamothioylamino]-4,5,6,7-tetrahydrobenzothiophene-3-carboxamide DIPEA (0.17 mL, 0.98 mmol) followed by a solution of intermediate 241 (205.2 mg, 1.227 mmol) in DCM (1.0 mL) were added to a stirred solution of intermediate 117 (249.3 mg, 0.7478 mmol) in DCM (2.75 mL) under nitrogen. The reaction mixture was stirred at rt for 6 h before being concentrated in vacuo to give a yellow solid which was purified by flash column chromatography on silica (gradient elution with 0% to 100% EtOAc in isohexane) to give the title compound (327.6 mg, 0.6543 mmol, 88%) as a white solid. LCMS [M+H]$^+$ 501.0, RT 1.378 minutes, purity 100% (Method 15).

Intermediate 243

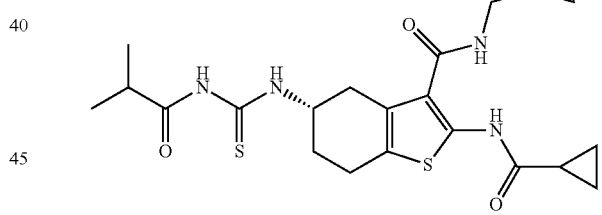

(5S)-2-(cyclopropanecarbonylamino)-N-(cyclopropylmethyl)-5-(2-methylpropanoylcarbamothioylamino)-4,5,6,7-tetrahydrobenzothiophene-3-carboxamide To a stirred solution of intermediate 117 (150 mg, 0.450 mmol) dissolved in DCM (5 mL) under nitrogen was added DIPEA (0.12 mL, 0.675 mmol) followed by 2-methylpropanecarbonyl isothiocyanate (92 mg, 0.675 mmol).

The reaction was stirred at r.t. for 65 h before being concentrated in vacuo to give a gum. This was purified by flash column chromatography on silica (gradient elution with 10% to 70% EtOAc in isohexane) to afford the title compound (144 mg, 0.311 mmol, 69%) as an off-white solid. LCMS [M+H]$^+$ 463.0, RT 2.39 minutes, purity 87% (Method 1).

Intermediate 244

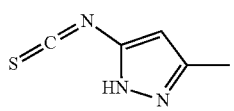

5-isothiocyanato-3-methyl-1H-pyrazole

To a solution of sodium carbonate (10.9 g, 103 mmol) and thiophosgene (4.74 g, 41.2 mmol) in water (30 ml) was added a solution of 3-methyl-1H-pyrazol-5-amine [31230-17-8] (291.0 mg, 1.502 mmol,) in DCM (15 mL). The mixture was stirred at room temperature for 2 h then added to DCM (100 mL) and water (100 mL) and the layers separated. The aqueous layer was extracted with DCM (2×25 mL). The combined organic layers were washed with brine (50 ml) and passed through a phase separation cartridge and concentrated in vacuo to give a brown gum. This was purified by flash column chromatography on silica (gradient elution with 10% to 100% EtOAc in isohexane) to afford the title compound (0.65 g, 4.70 mmol, 23% Yield) as a pale yellow liquid. LCMS [M+H]$^+$ 140.4, RT 0.58 minutes, purity 61% (Method 7).

Intermediate 245

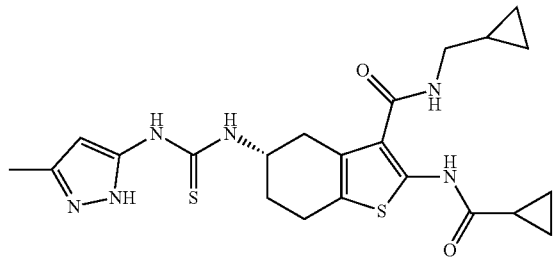 [SMILES: Cc1cc(NC(=S)N[C@H]2CCc3sc(NC(=O)C4CC4)c(C(=O)NCC4CC4)c3C2)[nH]n1]

(5S)-2-(cyclopropanecarbonylamino)-N-(cyclopropylmethyl)-5-[(3-methyl-1H-pyrazol-5-yl)carbamothioylamino]-4,5,6,7-tetrahydrobenzothiophene-3-carboxamide To a stirred solution of intermediate 117 (400 mg, 1.20 mmol) dissolved in DCM (20 mL) under nitrogen was added DIPEA (0.84 mL, 4.80 mmol) followed by intermediate 244 (250 mg, 1.80 mmol).

The reaction was stirred at r.t. for 16 h. 3-Methyl-1H-pyrazol-5-amine (200 mg, 2.10 mmol) added as a solution in acetonitrile (5 mL). The reaction was stirred at r.t. for 1 h before being concentrated in vacuo to remove the DCM. Acetonitrile (10 mL) added and the mixture was stirred at 90° C. for 16 h. The mixture was cooled to r.t. before being concentrated in vacuo to give a gum. This was purified by flash column chromatography on silica (gradient elution with 25% to 100% EtOAc in isohexane) to afford impure title compound (186 mg) as a yellow gum. This was further purified by flash column chromatography on silica (gradient elution with 30% to 80% EtOAc in isohexane) to afford the title compound (124 mg, 0.262 mmol, 22%) as a yellow gum. LCMS [M+H]$^+$ 473.0, RT 1.87 minutes, purity 80% (Method 3).

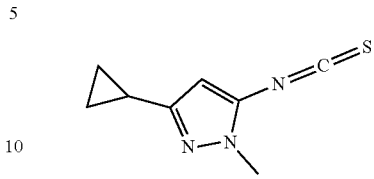

3-cyclopropyl-5-isothiocyanato-1-methyl-pyrazole

3-Cyclopropyl-1-methyl-1H-pyrazol-5-amine [118430-74-3] (2.50 g, 18.2 mmol,) was dissolved in DCM (50 mL) under nitrogen. 1,1'-Thiocarbonyldiimidazole (3.97 g, 20.0 mmol) was added and the reaction was stirred at r.t. for 64 h. The crude reaction mixture was then concentrated in vacuo to give a yellow solid which was purified by flash column chromatography on silica (gradient elution with 20% to 100% EtOAc in isohexane) to afford the title compound (135 mg, 0.753 mmol, 21% Yield) as a pale yellow liquid. LCMS [M+H]$^+$ 180.2, RT 1.02 minutes, purity 99% (Method 7).

Intermediate 247

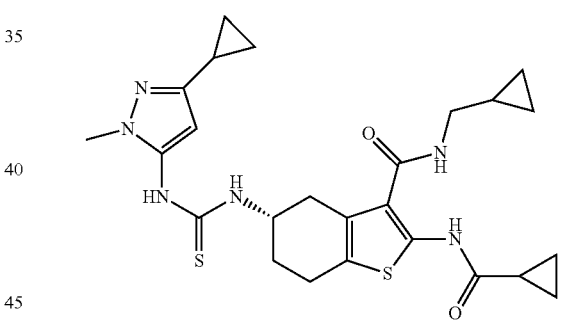

(5S)-2-(cyclopropanecarbonylamino)-N-(cyclopropylmethyl)-5-[(5-cyclopropyl-2-methyl-pyrazol-3-yl)carbamothioylamino]-4,5,6,7-tetrahydrobenzothiophene-3-carboxamide To a stirred solution of intermediate 117 (1.0 g, 3.00 mmol) dissolved in DCM (10 mL) under nitrogen was added DIPEA (0.79 mL, 4.50 mmol) followed by intermediate 246 (591 mg, 3.30 mmol).

The reaction was stirred at r.t. for 1 h before being concentrated in vacuo to give a gum. This was purified by flash column chromatography on silica (gradient elution with 30% to 100% EtOAc in isohexane) to afford the title compound (1.38 g, 2.69 mmol, 90%) as a white solid. LCMS [M+H]$^+$ 513.2, RT 1.38 minutes, purity 99% (Method 7).

Intermediate 248

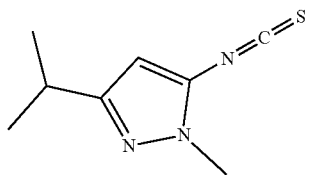

3-isopropyl-5-isothiocyanato-1-methyl-pyrazole 3-isopropyl-1-methyl-1H-pyrazol-5-amine [3702-12-3] (0.50 g, 3.59 mmol,) was dissolved in DCM (10 mL) under nitrogen. 1,1'-Thiocarbonyldiimidazole (782 mg, 3.95 mmol) was added and the reaction was stirred at r.t. for 1 h. The crude reaction mixture was then concentrated in vacuo to give a yellow solid which was purified by flash column chromatography on silica (gradient elution with 5% to 75% EtOAc in isohexane) to afford the title compound (213 mg, 1.18 mmol, 33% Yield) as a pale yellow liquid. LCMS [M+H]$^+$ 182.2, RT 1.10 minutes, purity 99% (Method 7).

Intermediate 249

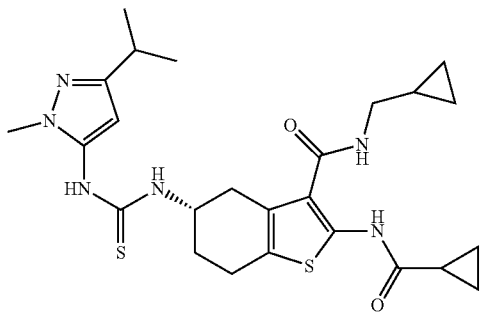 [SMILES: CC(C)c1cc(NC(=S)N[C@H]2CCc3sc(NC(=O)C4CC4)c(C(=O)NCC4CC4)c3C2)n(C)n1]

(5S)-2-(cyclopropanecarbonylamino)-N-(cyclopropylmethyl)-5-[(5-isopropyl-2-methyl-pyrazol-3-yl)carbamothioylamino]-4,5,6,7-tetrahydrobenzothiophene-3-carboxamide To a stirred solution of intermediate 117 (200 mg, 0.600 mmol) dissolved in DCM (10 mL) under nitrogen was added DIPEA (0.16 mL, 0.900 mmol) followed by intermediate 248 (163 mg, 0.900 mmol). The reaction was stirred at r.t. for 2 h before being concentrated in vacuo to give a gum. This was purified by flash column chromatography on silica (gradient elution with 30% to 100% EtOAc in isohexane) to afford the title compound (283 mg, 0.548 mmol, 91%) as a white solid. LCMS [M+H]$^+$ 515.2, RT 2.00 minutes, purity 100% (Method 1).

Intermediate 250

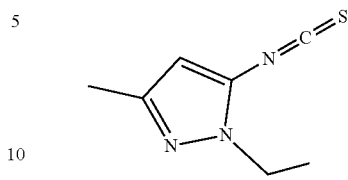

1-ethyl-5-isothiocyanato-3-methyl-pyrazole

1-Ethyl-3-methyl-1H-pyrazol-5-amine [3524-33-2] (0.50 g, 3.80 mmol,) was dissolved in DCM (10 mL) under nitrogen. 1,1'-Thiocarbonyldiimidazole (830 mg, 4.20 mmol) was added and the reaction was stirred at r.t. for 4 h. The crude reaction mixture was then concentrated in vacuo to give a yellow solid which was purified by flash column chromatography on silica (gradient elution with 30% to 100% EtOAc in isohexane) to afford the title compound (144 mg, 0.861 mmol, 23% Yield) as a pale yellow liquid. LCMS [M+H]$^+$ 168.0, RT 1.39 minutes, purity 100% (Method 7).

Intermediate 251

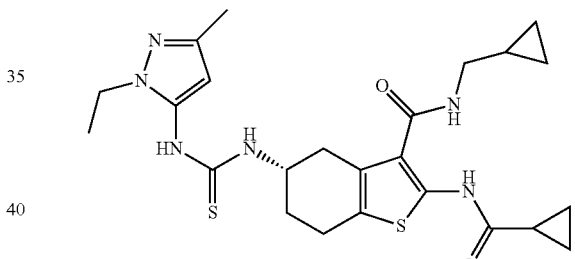

(5S)-2-(cyclopropanecarbonylamino)-N-(cyclopropylmethyl)-5-[(2-ethyl-5-methyl-pyrazol-3-yl)carbamothioylamino]-4,5,6,7-tetrahydrobenzothiophene-3-carboxamide To a stirred solution of intermediate 117 (200 mg, 0.600 mmol) dissolved in DCM (10 mL) under nitrogen was added DIPEA (0.16 mL, 0.900 mmol) followed by intermediate 250 (145 mg, 0.870 mmol).

The reaction was stirred at r.t. for 16 h before being concentrated in vacuo to give a gum. This was purified by flash column chromatography on silica (gradient elution with 30% to 100% EtOAc in isohexane) to afford the title compound (300 mg, 0.870 mmol, 100%) as a white solid. LCMS [M+H]$^+$ 501.0, RT 2.00 minutes, purity 100% (Method 3).

Intermediate 252

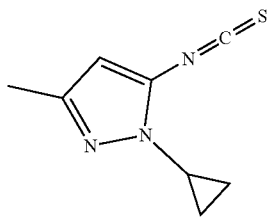

1-cyclopropyl-5-isothiocyanato-3-methyl-pyrazole 2-cyclopropyl-5-methyl-pyrazol-3-amine (352 mg, 2.57 mmol,) was dissolved in DCM (10 mL) under nitrogen. 1,1'-Thiocarbonyldiimidazole (559 mg, 2.82 mmol) was added and the reaction was stirred at r.t. for 4 h. The crude reaction mixture was then concentrated in vacuo to give a yellow solid which was purified by flash column chromatography on silica (gradient elution with 30% to 100% EtOAc in isohexane) to afford the title compound (105 mg, 0.586 mmol, 23% Yield) as a pale yellow liquid. LCMS [M+H]$^+$ 180.0, RT 1.41 minutes, purity 100% (Method 7).

Intermediate 253

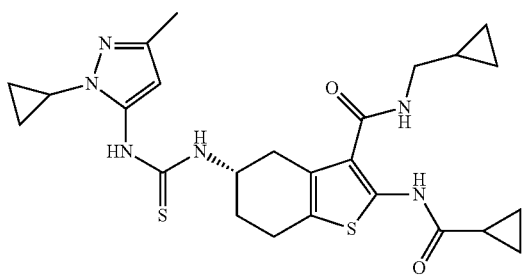 [SMILES: Cc1cc(NC(=S)N[C@H]2CCc3sc(NC(=O)C4CC4)c(C(=O)NCC4CC4)c3C2)n(C2CC2)n1]

(5S)-2-(cyclopropanecarbonylamino)-N-(cyclopropylmethyl)-5-[(2-cyclopropyl-5-methyl-pyrazol-3-yl)carbamothioylamino]-4,5,6,7-tetrahydrobenzothiophene-3-carboxamide To a stirred solution of intermediate 117 (200 mg, 0.600 mmol) dissolved in DCM (10 mL) under nitrogen was added DIPEA (0.16 mL, 0.900 mmol) followed by intermediate 252 (105 mg, 0.600 mmol). The reaction was stirred at r.t. for 16 h before being concentrated in vacuo to give a gum. This was purified by flash column chromatography on silica (gradient elution with 30% to 100% EtOAc in isohexane) to afford the title compound (282 mg, 0.550 mmol, 92%) as a white solid. LCMS [M+H]$^+$ 513.0, RT 2.03 minutes, purity 100% (Method 3).

Intermediate 254

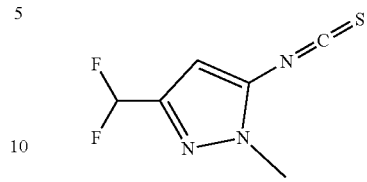

3-(difluoromethyl)-5-isothiocyanato-1-methyl-pyrazole 5-(Difluoromethyl)-2-methyl-pyrazol-3-amine (2.00 g, 13.6 mmol,) was dissolved in DCM (50 mL) under nitrogen. 1,1'-Thiocarbonyldiimidazole (2.96 mg, 15.0 mmol) was added. Hydrochloric acid in 1,4-dioxane (6.80 mL, 27.2 mmol, 4 mol/L) was added and the reaction was stirred at r.t. for 2 h. The crude reaction mixture was filtered and then concentrated in vacuo to give a yellow solid which was purified by flash column chromatography on silica (gradient elution with 5% to 50% EtOAc in isohexane) to afford the title compound (817 mg, 4.32 mmol, 32% Yield) as a pale yellow liquid. LCMS RT 0.95 minutes, purity 100% (Method 7).

Intermediate 255

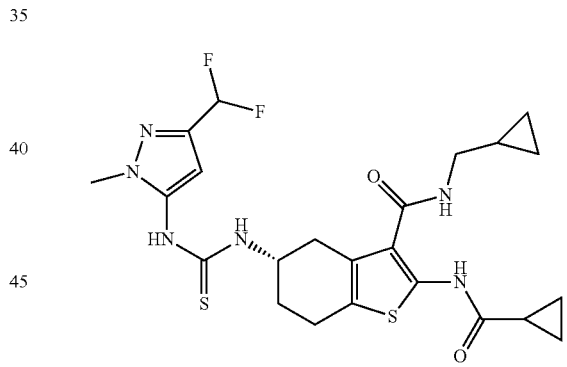

(5S)-2-(Cyclopropanecarbonylamino)-N-(cyclopropylmethyl)-5-[[5-(difluoromethyl)-2-methyl-pyrazol-3-yl]carbamothioylamino]-4,5,6,7-tetrahydrobenzothiophene-3-carboxamide To a stirred solution of intermediate 117 (1.2 g, 3.60 mmol) dissolved in DCM (10 mL) under nitrogen was added DIPEA (0.95 mL, 5.40 mmol) followed by intermediate 254 (885 mg, 4.68 mmol).

The reaction was stirred at r.t. for 40 minutes before being concentrated in vacuo to give a gum. This was purified by flash column chromatography on silica (gradient elution with 50% to 100% EtOAc in isohexane) to afford the title compound (1.75 g, 3.35 mmol, 93%) as a white solid. LCMS [M+H]$^+$ 523.2, RT 1.43 minutes, purity 99% (Method 7).

Intermediate 256

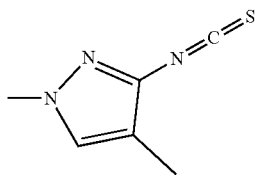

3-Isothiocyanato-1,4-dimethyl-pyrazole 1,4-Dimethyl-1H-pyrazol-3-amine [85485-61-6] (550 mg, 4.75 mmol,) was dissolved in DCM (10 mL) under nitrogen. 1,1'-Thiocarbonyldiimidazole (941 mg, 4.75 mmol) was added and the reaction was stirred at r.t. for 16 h. The crude reaction mixture was then concentrated in vacuo to give a yellow solid which was purified by flash column chromatography on silica (gradient elution with 20% to 100% EtOAc in isohexane) to afford the title compound (470 mg, 4.75 mmol, 100% Yield) as a white solid. LCMS [M+H]$^+$ 154.2, RT 0.90 minutes, purity 100% (Method 7).

Intermediate 257

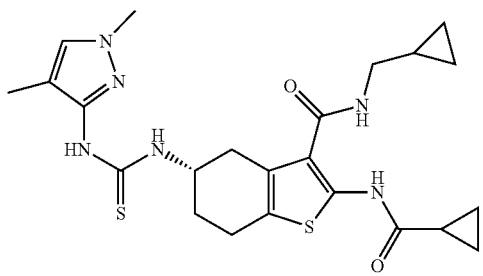 [SMILES: Cc1cn(C)nc1NC(=S)N[C@H]1CCc2sc(NC(=O)C3CC3)c(C(=O)NCC3CC3)c2C1]

(5S)-2-(Cyclopropanecarbonylamino)-N-(cyclopropylmethyl)-5-[(1,4-dimethylpyrazol-3-yl)carbamothioylamino]-4,5,6,7-tetrahydrobenzothiophene-3-carboxamide To a stirred solution of intermediate 117 (210 mg, 0.630 mmol) dissolved in DCM (10 mL) under nitrogen was added DIPEA (0.17 mL, 0.900 mmol) followed by intermediate 256 (120 mg, 0.780 mmol).

The reaction was stirred at r.t. for 2 h before being concentrated in vacuo to give a gum. This was purified by flash column chromatography on silica (gradient elution with 30% to 100% EtOAc in isohexane) to afford the title compound (301 mg, 0.619 mmol, 98%) as a white solid. LCMS [M+H]$^+$ 487.0, RT 2.19 minutes, purity 99% (Method 3).

Intermediate 22

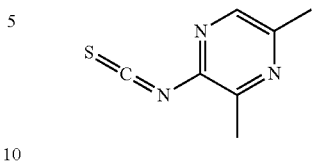

2-Isothiocyanato-3,5-dimethyl-pyrazine

To a solution of pyridine (0.51 ml, 6.20 mmol) and 3,5-dimethylpyrazin-2-amine [91678-81-8] (308 mg, 2.50 mmol) in DCM (4.5 ml) was added a solution of thiophosgene (0.21 ml, 2.70 mmol) in DCM (3 mL). The mixture was stirred at room temperature for 1 h then concentrated in vacuo to give a brown gum. This was purified by flash column chromatography on silica (gradient elution with 0% to 50% EtOAc in isohexane) to afford the title compound (303 mg, 1.83 mmol, 73% Yield) as a dark red liquid.

Intermediate 259

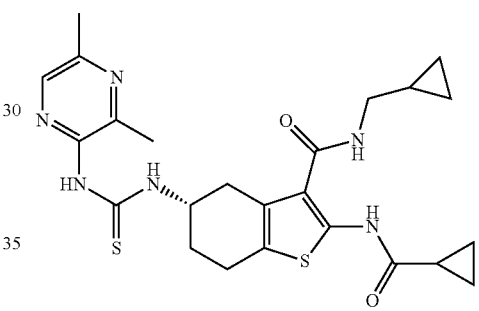

(5S)-2-(Cyclopropanecarbonylamino)-N-(cyclopropylmethyl)-5-[(3,5-dimethylpyrazin-2-yl)carbamothioylamino]-4,5,6,7-tetrahydrobenzothiophene-3-carboxamide To a stirred solution of intermediate 117 (205 mg, 0.615 mmol) dissolved in DCM (10 mL) under nitrogen was added DIPEA (0.16 mL, 0.922 mmol) followed by intermediate 258 (132 mg, 0.799 mmol).

The reaction was stirred at r.t. for 1 h before being concentrated in vacuo to give a gum. This was purified by flash column chromatography on silica (gradient elution with 30% to 100% EtOAc in isohexane) to afford the title compound (306 mg, 0.799 mmol, 100%) as a white solid. LCMS [M+H]$^+$ 499.2, RT 1.45 minutes, purity 99% (Method 7).

Intermediate 260

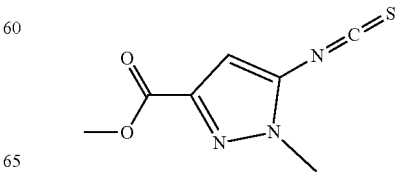

Methyl 5-isothiocyanato-1-methyl-pyrazole-3-carboxylate

Methyl 5-amino-1-methyl-pyrazole-3-carboxylate [92406-53-6] (500 mg, 3.22 mmol,) was dissolved in DCM (10 mL) under nitrogen. 1,1'-Thiocarbonyldiimidazole (702 mg, 3.55 mmol) was added and the reaction was stirred at r.t. for 16 h. The crude reaction mixture was then concentrated in vacuo to give a yellow solid which was purified by flash column chromatography on silica (gradient elution with 20% to 100% EtOAc in isohexane) to afford the title compound (177 mg, 0.900 mmol, 28% Yield) as a white solid. LCMS [M+H]$^+$ 198.0, RT 0.49 minutes, purity 91% (Method 7).

Intermediate 261

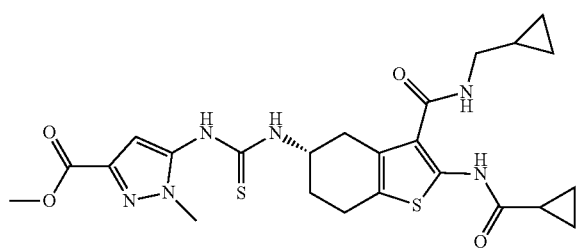 [SMILES: COC(=O)c1cc(NC(=S)N[C@H]2CCc3sc(NC(=O)C4CC4)c(C(=O)NCC4CC4)c3C2)n(C)n1]

Methyl 5-[[(5S)-2-(cyclopropanecarbonylamino)-3-(cyclopropylmethylcarbamoyl)-4,5,6,7-tetrahydrobenzothiophen-5-yl]carbamothioylamino]-1-methyl-pyrazole-3-carboxylate To a stirred solution of intermediate 117 (200 mg, 0.600 mmol) dissolved in DCM (10 mL) under nitrogen was added DIPEA (0.16 mL, 0.900 mmol) followed by intermediate 260 (177 mg, 0.900 mmol).

The reaction was stirred at r.t. for 64 h before being concentrated in vacuo to give a gum. This was purified by flash column chromatography on silica (gradient elution with 30% to 100% EtOAc in isohexane) to afford the title compound (295 mg, 0.556 mmol, 93%) as a white solid. LCMS [M+H]$^+$ 531.0, RT 1.94 minutes, purity 100% (Method 3).

Intermediate 262

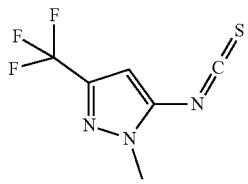

5-Isothiocyanato-1-methyl-3-(trifluoromethyl)pyrazole

1-Methyl-3-(trifluoromethyl)-1H-pyrazol-5-amine [149978-43-8] (3.49 g, 21.1 mmol,) was dissolved in DCM (63 mL) under nitrogen and hydrochloric acid in 1,4-dioxane (10.5 mL, 42.0 mmol, 4 mol/L) was added. 1,1'-Thiocarbonyldiimidazole (4.38 mg, 23.3 mmol) was added and the reaction was stirred at r.t. for 40 h. The crude reaction mixture was filtered and then concentrated in vacuo to give a yellow gum which was purified by flash column chromatography on silica (gradient elution with 0% to 50% EtOAc in isohexane) to afford the title compound (3.04 g, 14.7 mmol, 70% Yield) as a pale yellow liquid. LCMS (ES+) [M+H]$^+$ 208.0, RT 1.34 minutes, purity 97% (Method 7).

Intermediate 263

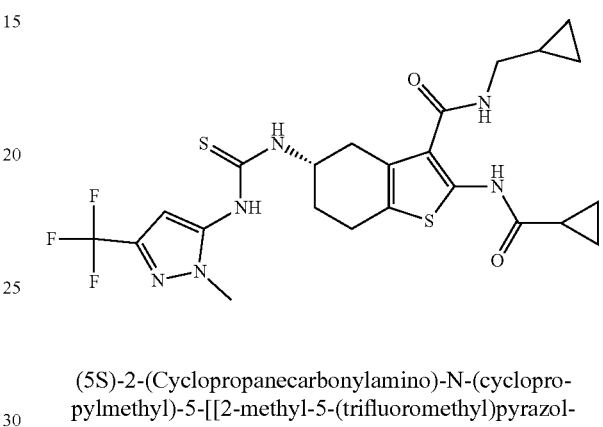

(5S)-2-(Cyclopropanecarbonylamino)-N-(cyclopropylmethyl)-5-[[2-methyl-5-(trifluoromethyl)pyrazol-3-yl]carbamothioylamino]-4,5,6,7-tetrahydrobenzothiophene-3-carboxamide To a stirred solution of intermediate 117 (1.00 g, 3.00 mmol) dissolved in DCM (15 mL) under nitrogen was added DIPEA (0.57 mL, 3.30 mmol) followed by intermediate 262 (685 mg, 3.30 mmol).

The reaction was stirred at r.t. for 4 h before being concentrated in vacuo to give a gum. This was purified by flash column chromatography on silica (gradient elution with 0% to 50% EtOAc in isohexane) to afford the title compound (1.19 g, 2.20 mmol, 73%) as a white solid. LCMS [M+H]$^+$ 541.0, RT 1.48 minutes, purity 99% (Method 7).

Intermediate 264

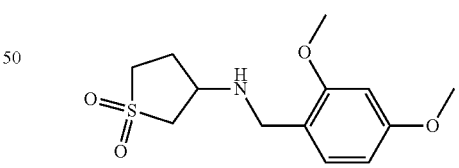

N-[(2,4-dimethoxyphenyl)methyl]-1,1-dioxo-thiolan-3-amine

To a solution of 1,1-dioxothiolan-3-amine hydrochloride (100 mg, 0.58 mmol) and TEA (0.11 mL, 0.81 mmol) in DCM (2 mL) was added 2,4-dimethoxybenzaldehyde (123 mg, 0.74 mmol), followed by STAB (235 mg, 1.11 mmol). The suspension was stirred at room temperature for 1 hour, then at 40° C. for 3 hours. 1,1-dioxothiolan-3-amine hydrochloride (20 mg, 0.12 mmol) and TEA (0.02 mL, 0.15 mmol) were added as a solution in DCM (0.5 mL), followed by STAB (92 mg, 0.44 mmol) and the mixture stirred at 40° C. for 16 hours. STAB (185 mg, 0.87 mmol) was added and the mixture stirred at 40° C. for 4 hours. The mixture was quenched with saturated sodium bicarbonate and the organic layer separated. The aqueous layer was extracted with DCM (4×5 mL) and the organic fractions combined, passed through a hydrophobic frit and concentrated in vacuo to give an oil. The oil was purified via column chromatography, using a gradient of 50-100% TBME in heptanes, followed by 0-10% methanol in TBME to give the title compound (167 mg, 84% yield). $\delta_H$ (500 MHz, d-Chloroform) 7.08 (d, J=8.1 Hz, 1H), 6.48-6.42 (m, 2H), 3.82 (s, 3H), 3.81 (s, 3H), 3.74 (d, J=2.2 Hz, 2H), 3.58-3.51 (m, 1H), 3.32-3.22 (m, 2H), 3.04-2.97 (m, 1H), 2.86 (dd, J=13.2, 6.7 Hz, 1H), 2.42-2.34 (m, 1H), 2.11-2.02 (m, 1H). LCMS [M+H]$^+$ 286, RT 1.42 (Method 18).

Intermediate 265

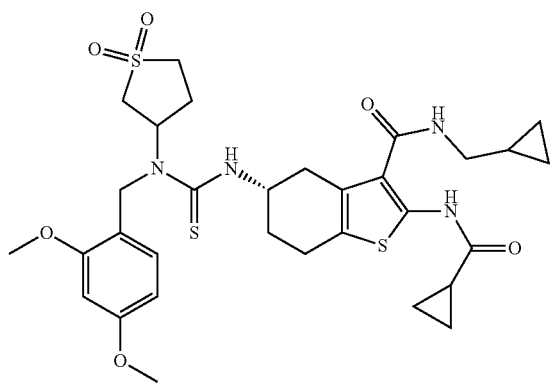 [SMILES: COc1ccc(CN(C(=S)N[C@H]2CCc3sc(NC(=O)C4CC4)c(C(=O)NCC4CC4)c3C2)C2CCS(=O)(=O)C2)c(OC)c1]

(5S)-2-(cyclopropanecarbonylamino)-N-(cyclopropylmethyl)-5-[[(2,4-dimethoxyphenyl)methyl-(1,1-dioxothiolan-3-yl)carbamothioyl]amino]-4,5,6,7-tetrahydrobenzothiophene-3-carboxamide The title compound was prepared according to general method 7, using intermediate 117 (133 mg, 0.4 mmol) and intermediate 264 (125 mg, 0.44 mmol). Purification via column chromatography, using a gradient of 0-100% TBME in heptanes, followed by 0-10% methanol in TBME gave the title compound (280 mg, 96% yield). LCMS (M+H)$^+$ 661, RT 1.2 (Method 11).

Intermediate 266

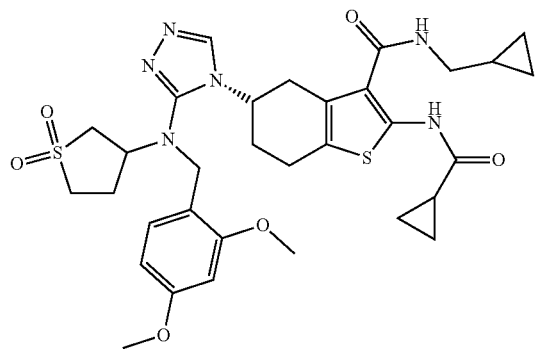

(5S)-2-(cyclopropanecarbonylamino)-N-(cyclopropylmethyl)-5-[3-[(2,4-dimethoxyphenyl)methyl-(1,1-dioxothiolan-3-yl)amino]-1,2,4-triazol-4-yl]-4,5,6,7-tetrahydrobenzothiophene-3-carboxamide The title compound was prepared according to general method 8, using intermediate 265 (280 mg, 0.38 mmol). Purification via column chromatography (KP-NH), using a gradient of 0-20% methanol in TBME gave the title compound (240 mg, 85% yield). LCMS (M+H)+ 669, RT 1.09 (Method 11).

Intermediate 267

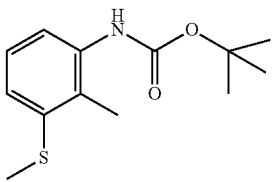 [SMILES: CSc1cccc(NC(=O)OC(C)(C)C)c1C]

(5S)-2-(cyclopropanecarbonylamino)-N-(cyclopropylmethyl)-5-[3-[(1,1-dioxothiolan-3-yl)amino]-1,2,4-triazol-4-yl]-4,5,6,7-tetrahydrobenzothiophene-3-carboxamide Intermediate 266 (240 mg, 0.32 mmol) was dissolved in DCM (5 mL) and TFA (247 µL, 3.23 mmol) was added. The reaction was stirred at room temperature overnight, then retreated with TFA (247 µL, 3.23 mmol). The reaction mixture was stirred at room temperature for 4 hours, then quenched with saturated sodium bicarbonate and the organic layer separated. The aqueous layer was extracted with DCM (3×5 mL) and the organic fractions combined, passed through a phase separator and concentrated in vacuo. The resulting oil was purified via column chromatography (KP-NH), eluting with a 0-20% gradient of methanol in TBME to give the title compound (145 mg, 85% yield). $\delta_H$ (500 MHz, DMSO-d$_6$) 11.29-11.19 (m, 1H), 8.17 (s, 1H), 7.71-7.60 (m, 1H), 6.43 (d, J=6.3 Hz, 1H), 4.48-4.37 (m, 1H), 4.29-4.19 (m, 1H), 3.58-3.49 (m, 1H), 3.22-3.13 (m, 2H), 3.12-2.98 (m, 3H), 2.92-2.79 (m, 3H), 2.49-2.44 (m, 1H), 2.27-2.08 (m, 3H), 1.96-1.87 (m, 1H), 1.07-0.96 (m, 1H), 0.92-0.79 (m, 4H), 0.43-0.33 (m, 2H), 0.25-0.14 (m, 2H). LCMS (M+H)$^+$ 519, RT 1.96 (Method 10).

Intermediate 268 tert-butyl
N-(2-methyl-3-methylsulfanyl-phenyl)carbamate

A solution of 2-methyl-3-methylsulfanyl-aniline (500 mg, 3.26 mmol) and tert-butoxycarbonyl tert-butyl carbonate (783 mg, 3.59 mmol) in THF (10 mL) was stirred under an atmosphere of nitrogen overnight at 60° C. The solution was retreated with tert-butoxycarbonyl tert-butyl carbonate (107 mg, 0.49 mmol) and stirred at 60° C. for another 3 hours. The mixture was concentrated in vacuo and purified via column chromatography, using a gradient of 0-20% TBME in heptanes to give the title compound (1 g, 98% yield) as an orange oil. $\delta_H$ (250 MHz, d-Chloroform) 7.56 (d, J=8.0 Hz, 1H), 7.17 (t, J=8.0 Hz, 1H), 6.98 (d, J=7.8 Hz, 1H), 6.26 (s, 1H), 2.44 (s, 3H), 2.27 (s, 3H), 1.55-1.48 (m, 9H).

Intermediate 269

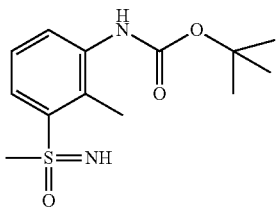 [SMILES: Cc1c(NC(=O)OC(C)(C)C)cccc1S(C)(=N)=O]

tert-butyl N-[2-methyl-3-(methylsulfonimidoyl)phenyl]carbamate

To a stirring solution of Intermediate 268 (900 mg, 2.88 mmol) in anhydrous Methanol (7 mL) was added ammonium carbamate (899 mg, 11.5 mmol) followed by (Diacetoxyiodo)benzene (2.78 g, 8.63 mmol) and the mixture was stirred at room temperature in air for 15 hours. The mixture was concentrated in vacuo, then diluted with water (10 mL) and extracted with DCM (4×10 mL). The organic fractions were combined, passed through a hydrophobic frit and concentrated in vacuo. The residue was purified via column chromatography, using a gradient of 50-100% TBME in heptanes, followed by 0-10% methanol in TBME to give the title compound (620 mg, 58%). $\delta_H$ (250 MHz, DMSO-d$_6$) 8.78 (s, 1H), 7.83 (dd, J=7.9, 1.3 Hz, 1H), 7.57-7.50 (m, 1H), 7.35 (t, J=7.9 Hz, 1H), 4.30 (s, 1H), 3.09-3.05 (m, 3H), 2.56 (s, 3H), 1.46 (s, 9H). LCMS (M+H)$^+$ 285, RT 1.55 (Method 12).

Intermediate 270

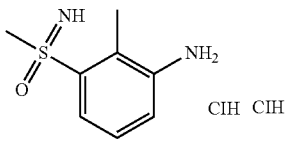

2-methyl-3-(methylsulfonimidoyl)aniline
dihydrochloride

To a stirred solution of intermediate 269 (694 mg, 1.95 mmol) in dioxane (5 ml) was added 4 M HCl in dioxane (5 mL). The mixture was stirred at 50° C. for 3 hours. The reaction mixture was concentrated in vacuo and the residue was further dried in vacuo at 40° C. for 1 hour to afford the desired product (684 mg, 25% dioxane w/w, 95% yield). $\delta_H$ (250 MHz, DMSO-d6) 7.45-7.22 (m, 3H), 3.91 (s, 3H), 2.42 (s, 3H).

Intermediate 271

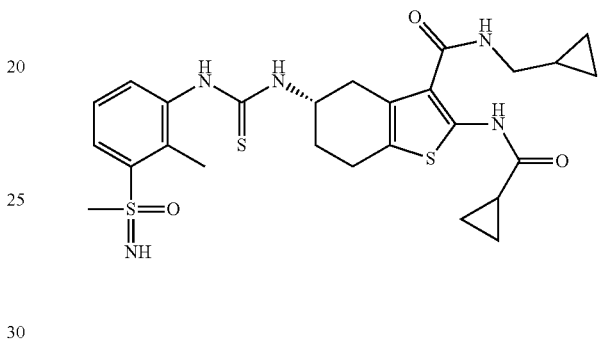

(5S)-2-(cyclopropanecarbonylamino)-N-(cyclopropylmethyl)-5-[[2-methyl-3-(methylsulfonimidoyl)phenyl]carbamothioylamino]-4,5,6,7-tetrahydrobenzothiophene-3-carboxamide To stirring solution of sodium carbonate (474 mg, 4.47 mmol) in water (4.5 mL) cooled to 0° C. in an ice bath was added DCM (9 mL), followed by thiophosgene (0.14 mL, 1.79 mmol). To the biphasic mixture was added intermediate 270 (230 mg, 0.89 mmol) and resulting mixture was stirred at room temperature for 1 hour. The layers were separated and the aqueous phase was extracted with DCM (2×10 mL). The combined organics were washed with brine (10 mL), dried (MgSO$_4$) and the concentrated in vacuo. The residue obtained was then dissolved in DCM (10 mL) and intermediate 117 (298 mg, 0.89 mmol) added, followed by triethylamine (0.62 mL, 4.47 mmol). The mixture was stirred at room temperature for 3 hours, then diluted with water (10 mL) and the organic layer separated. The aqueous layer was extracted with DCM (1×10 mL) and the organic fractions combined, passed through a hydrophobic frit and concentrated in vacuo. The residue was purified via column chromatography using a gradient of 0-20% methanol in TBME to give a powder. The powder was further purified via column chromatography, using a gradient of 0-8% methanol in DCM to give the title compound (217 mg, 39% yield). $\delta_H$ (250 MHz, DMSO-d$_6$) 11.08 (s, 1H), 9.09 (s, 1H), 7.95-7.80 (m, 2H), 7.78-7.69 (m, 1H), 7.63-7.51 (m, 1H), 7.37 (t, J=7.9 Hz, 1H), 4.57 (s, 1H), 4.31 (s, 1H), 3.15-3.10 (m, 2H), 3.11-3.03 (m, 3H), 2.81-2.64 (m, 3H), 2.53 (s, 3H), 2.14-1.80 (m, 3H), 1.09-0.96 (m, 1H), 0.89-0.79 (m, 4H), 0.48-0.38 (m, 2H), 0.27-0.18 (m, 2H). LCMS (M+H)$^+$ 560, RT 1.73 (Method 12).

Intermediate 272

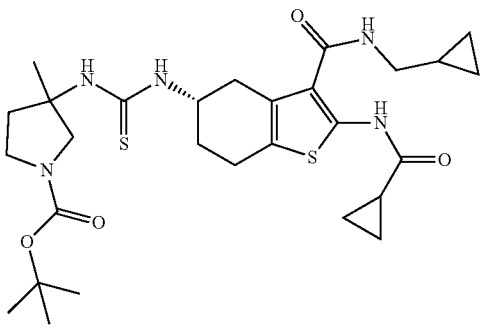 [SMILES: CC1(NC(=S)N[C@H]2CCc3sc(NC(=O)C4CC4)c(C(=O)NCC4CC4)c3C2)CCN(C(=O)OC(C)(C)C)C1]

tert-butyl 3-[[(5S)-2-(cyclopropanecarbonylamino)-3-(cyclopropylmethylcarbamoyl)-4,5,6,7-tetrahydrobenzothiophen-5-yl]carbamothioylamino]-3-methyl-pyrrolidine-1-carboxylate

The title compound was prepared according to general method 7, using intermediate 117 (46 mg, 0.14 mmol) and tert-butyl 3-amino-3-methyl-pyrrolidine-1-carboxylate (25 mg, 0.12 mmol). The reaction mixture was purified via column chromatography, using a gradient of 30-100% TBME in heptanes to give the title compound (56 mg, 70% yield). $\delta_H$ (250 MHz, d-Chloroform) 12.13 (s, 1H), 6.49-6.30 (m, 2H), 5.93-5.82 (m, 1H), 5.00-4.84 (m, 1H), 3.37-3.22 (m, 4H), 3.16-3.01 (m, 1H), 2.89-2.67 (m, 3H), 2.23-2.07 (m, 1H), 2.06-1.92 (m, 1H), 1.89-1.73 (m, 1H), 1.69-1.59 (m, 4H), 1.46-1.35 (m, 10H), 1.11-1.00 (m, 3H), 0.95-0.78 (m, 4H), 0.63-0.53 (m, 2H), 0.30-0.22 (m, 2H). LCMS (M+H)⁺ 576, RT 2.03 (Method 12).

Intermediate 273

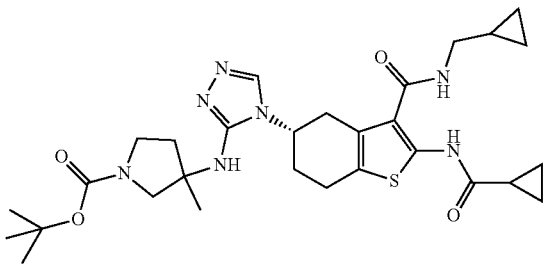 [SMILES: CC1(Nc2nncn2[C@H]2CCc3sc(NC(=O)C4CC4)c(C(=O)NCC4CC4)c3C2)CCN(C(=O)OC(C)(C)C)C1]

tert-butyl 3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-3-methyl-pyrrolidine-1-carboxylate

Intermediate 272 (720 mg, 0.9 mmol) was dissolved in DMF (25 mL) and formic hydrazide (162 mg, 2.7 mmol) was added, followed by dichloromercury (509 mg, 1.87 mmol). The reaction mixture was stirred at room temperature for 5 minutes and then DIPEA (369 ML, 2.65 mmol) was added. The reaction was stirred at 90° C. overnight. The suspension was retreated with formic hydrazide (80 mg, 1.33 mmol), stirred at 90° C. for 6 hours, before being stirred at 100° C. for 24 hours. The mixture was filtered through Celite, washing with DCM. The solution was concentrated in vacuo, then purified via column chromatography, using a gradient of 0-14% methanol in DCM to give the title compound (182 mg, 35%). $\delta_H$ (500 MHz, DMSO-d₆) 11.24 (s, 1H), 8.13 (s, 1H), 7.66 (s, 1H), 5.89-5.80 (m, 1H), 4.35-4.23 (m, 1H), 3.78-3.70 (m, 1H), 3.28-3.13 (m, 2H), 3.11-2.98 (m, 2H), 2.88-2.77 (m, 3H), 2.47-2.31 (m, 1H), 2.21-2.05 (m, 2H), 1.94-1.88 (m, 1H), 1.88-1.80 (m, 1H), 1.47-1.42 (m, 3H), 1.41-1.33 (m, 9H), 1.05-0.96 (m, 1H), 0.90-0.80 (m, 4H), 0.42-0.33 (m, 2H), 0.22-0.15 (m, 2H). LCMS (M+H)⁺ 584, RT 2.8 (Method 29).

Intermediate 274

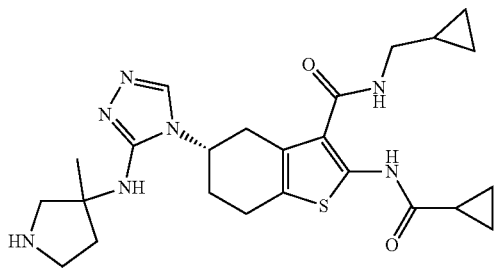 [SMILES: CC1(Nc2nncn2[C@H]2CCc3sc(NC(=O)C4CC4)c(C(=O)NCC4CC4)c3C2)CCNC1]

(5S)-2-(cyclopropanecarbonylamino)-N-(cyclopropylmethyl)-5-[3-[(3-methylpyrrolidin-3-yl)amino]-1,2,4-triazol-4-yl]-4,5,6,7-tetrahydrobenzothiophene-3-carboxamide

To a stirred solution of intermediate 273 (180 mg, 0.31 mmol) in dioxane (4 mL) was added 4 M hydrogen chloride in dioxane (2 mL, 8 mmol). The reaction mixture was then diluted with methanol (1 mL) and stirred at room temperature for 4 hours. The mixture was then concentrated under reduced pressure and purified via an SCX-2 column, washing with methanol, then eluting product with 7 M ammonia in methanol, to give the title compound (142 mg, 92% yield). $\delta_H$ (500 MHz, DMSO-d₆) 8.61 (s, 1H), 8.12 (s, 1H), 5.81-5.74 (m, 1H), 4.32-4.23 (m, 1H), 3.35-3.31 (m, 1H), 3.19-3.11 (m, 2H), 3.10-2.98 (m, 2H), 2.95-2.89 (m, 1H), 2.85-2.71 (m, 4H), 2.29-2.20 (m, 1H), 2.18-2.02 (m, 2H), 1.85-1.78 (m, 1H), 1.75-1.67 (m, 1H), 1.49-1.44 (m, 3H), 1.04-0.94 (m, 1H), 0.84-0.74 (m, 4H), 0.45-0.32 (m, 2H), 0.24-0.12 (m, 2H). LCMS (M+H)⁺ 484, RT 1.99 (Method 29).

Intermediate 275

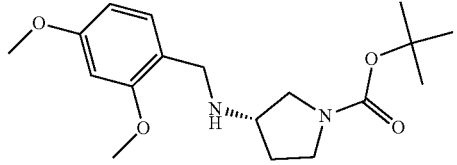 [SMILES: COc1ccc(CN[C@H]2CCN(C(=O)OC(C)(C)C)C2)c(OC)c1]

tert-butyl (3S)-3-[(2,4-dimethoxyphenyl)methylamino]pyrrolidine-1-carboxylate

To a solution of tert-butyl (3S)-3-aminopyrrolidine-1-carboxylate (1 g, 5.37 mmol) in DCM (15 mL) was added 2,4-dimethoxybenzaldehyde (892 mg, 5.37 mmol) and STAB (3.41 g, 16.1 mmol). The reaction was stirred at room temperature for 3 h. The mixture was diluted with saturated NaHCO₃ solution (10 mL) and the organic layer was separated. The aqueous layer was extracted with DCM (2×10 mL) and the combined organic layers were dried (MgSO₄). The solvent was removed in vacuo to give an oil, which was purified via column chromatography, using a gradient of 0-10% methanol in DCM, to give the title compound (638 mg, 35% yield). LCMS (M+H)⁺337, RT 1.57 (Method 12).

Intermediate 276

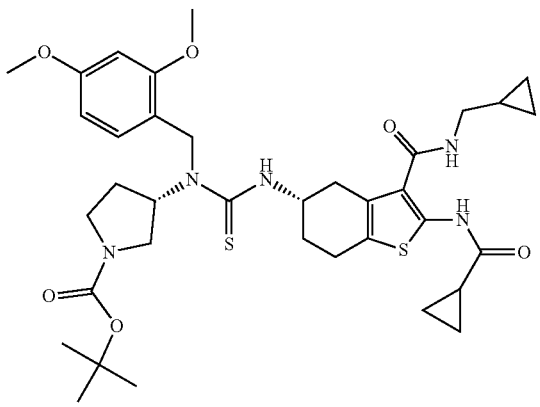 [SMILES: COc1ccc(CN(C(=S)N[C@H]2CCc3sc(NC(=O)C4CC4)c(C(=O)NCC4CC4)c3C2)[C@H]2CCN(C(=O)OC(C)(C)C)C2)c(OC)c1]

tert-butyl (3S)-3-[[(5S)-2-(cyclopropanecarbonylamino)-3-(cyclopropylmethylcarbamoyl)-4,5,6,7-tetrahydrobenzothiophen-5-yl]carbamothioyl-[(2,4-dimethoxyphenyl)methyl]amino]pyrrolidine-1-carboxylate To a solution of phenyl chloromethanethioate (183 μL, 1.32 mmol) in DCM (6 mL) at 0° C. was added a solution of intermediate 117 (400 mg, 1.2 mmol) and triethylamine (502 μL, 3.6 mmol) in DCM (10 mL) over 5 minutes. The solution was stirred at 0° C. for 30 minutes then a solution of intermediate 275 (626.9 μl, 1.92 mmol) in DCM (10 mL) was added. The reaction was stirred for 20 hours. The reaction was heated at 40° C. for 8 hours, then at room temperature for 20 hours. The reaction was diluted with DCM (10 mL), washed with water (30 mL), saturated aqueous NaHCO₃ (30 mL) and then dried (MgSO₄). The solvent was removed in vacuo to give an oil. Purification via column chromatography, using a gradient of 0-50% ethyl acetate in iso-hexane gave the title compound (700 mg, 75% yield). LCMS (M+H)⁺ 712, RT 2.16 (Method 12).

Intermediate 277

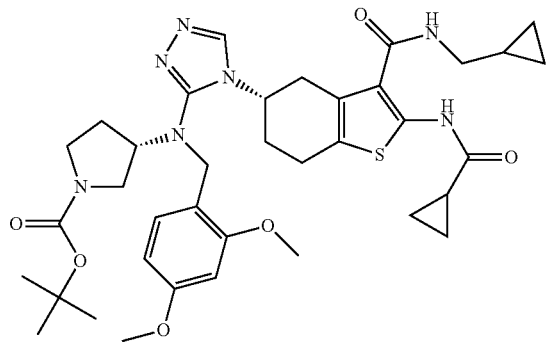 [SMILES: COc1ccc(CN(c2nncn2[C@H]2CCc3sc(NC(=O)C4CC4)c(C(=O)NCC4CC4)c3C2)[C@H]2CCN(C(=O)OC(C)(C)C)C2)c(OC)c1]

tert-butyl (3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]-[(2,4-dimethoxyphenyl)methyl]amino]pyrrolidine-1-carboxylate The title compound was prepared according to general method 8, using thiourea intermediate 276 (960 mg, 1.35 mmol). The residue was purified via column chromatography, using a gradient of 0-10% MeOH in ethyl acetate to give a yellow solid. The solid was purified via column chromatography (KP-NH), using a gradient of 0-12% methanol in TBME to give the title compound (648 mg, 67% yield). LCMS (M+H)⁺ 720, RT 1.27 (Method 11).

Intermediate 278

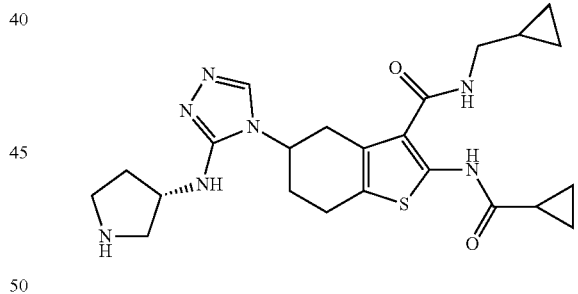

(5S)-2-(cyclopropanecarbonylamino)-N-(cyclopropylmethyl)-5-[3-[[(3S)-pyrrolidin-3-yl]amino]-1,2,4-triazol-4-yl]-4,5,6,7-tetrahydrobenzothiophene-3-carboxamide To a stirred solution of intermediate 277 (648 mg, 0.9 mmol) in DCM (10 mL) at room temperature was added TFA (0.83 mL, 10.8 mmol). The reaction mixture was stirred at room temperature for 2 hours, then was retreated with TFA (0.5 mL, 6.53 mmol) and stirred at 40° C. for 1 hour. The resulting pink suspension was concentrated in vacuo, then purified via an SCX-2 column, washing with methanol, then eluting product with 7 M ammonia in methanol, to give the title compound (444 mg, 97% yield). $\delta_H$ (500 MHz, DMSO-d₆) 8.39 (s, 1H), 8.10 (s, 1H), 6.03 (d, J=6.2 Hz, 1H), 4.27-4.19 (m, 1H), 4.12-4.05 (m, 1H), 3.16-3.03 (m, 4H), 3.00-2.93 (m, 1H), 2.86-2.73 (m, 5H), 2.18-2.11 (m, 1H), 2.11-1.98 (m, 2H), 1.88-1.81 (m, 1H), 1.74-1.66 (m, 1H), 1.04-0.95 (m, 1H), 0.84-0.77 (m, 4H), 0.43-0.34 (m, 2H), 0.24-0.14 (m, 2H). LCMS (M+H)$^+$ 470, RT 1.4 (Method 12).

Intermediate 279

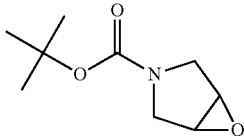

tert-butyl 6-oxa-3-azabicyclo[3.1.0]hexane-3-carboxylate

To a stirred solution of tert-butyl 2,5-dihydro-1H-pyrrole-1-carboxylate (3 g, 17.73 mmol) in DCM (45 mL), at room temperature under nitrogen was added mCPBA (7.04 g, 40.77 mmol). The mixture was stirred at room temperature overnight. 1 M aqueous NaOH (30 mL) was added and the organic layer separated. The aqueous layer was extracted with DCM (3×20 mL) and the organic fractions were combined, dried (Na$_2$SO$_4$) and concentrated in vacuo. The residue was purified via column chromatography, using a gradient of 0-30% ethyl acetate in heptanes, to give the title compound (2.17 g, 63% yield). δ$_H$ (250 MHz, d-Chloroform) 3.82 (d, J=12.9 Hz, 1H), 3.74 (d, J=12.8 Hz, 1H), 3.69-3.63 (m, 2H), 3.38-3.25 (m, 2H), 1.44 (s, 9H).

Intermediate 280

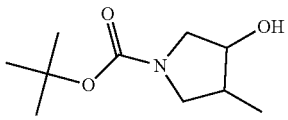

tert-butyl 3-hydroxy-4-methyl-pyrrolidine-1-carboxylate

To a stirred suspension of copper(i) iodide (4.83 g, 25.38 mmol) in diethyl ether (60 mL), at −10° C., under nitrogen was added 1.6 M methyllithium in diethyl ether (31.7 mL, 50.72 mmol). The reaction mixture was stirred between −5° C. and −10° C. for 20 minutes, then intermediate 279 (2 g, 10.1 mmol) was added as a solution in diethyl ether (20 mL). The reaction mixture was stirred at −5° C. for 1 hour, then quenched carefully with water and DCM (10 mL) added. The mixture was filtered and the aqueous layer adjusted to pH 10 using saturated ammonium chloride. The organic layer was separated and the aqueous layer extracted with DCM (3×30 mL). The organic fractions were combined, dried (Na$_2$SO$_4$) and concentrated in vacuo to give the title compound (2.03 g, 84% yield). δ$_H$ (500 MHz, d-Chloroform) 3.98-3.90 (m, 1H), 3.68-3.55 (m, 2H), 3.29-3.17 (m, 1H), 3.09-2.95 (m, 1H), 2.17-2.06 (m, 1H), 1.73 (s, 1H), 1.46 (s, 9H), 1.02 (d, J=6.9 Hz, 3H).

Intermediate 281

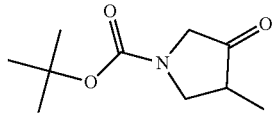

Tert-butyl 3-methyl-4-oxo-pyrrolidine-1-carboxylate

To a stirred solution of ethanedioyl dichloride (1.28 mL, 15.13 mmol) in DCM (6 mL), at −78° C. was added DMSO (2.15 mL, 30.26 mmol) as a solution in DCM (12 mL). The reaction mixture was stirred at −78° C. for 5 minutes, then intermediate 280 (2.21 g, 10.97 mmol) was added as a solution in DCM (18 mL). The mixture was stirred at this temperature for 2 hours, then DIPEA (7.03 mL, 50.43 mmol) was added. The mixture was stirred at −78° C. for 1 hour, then diluted with DCM (10 mL) and stirred at room temperature for 2 hours. The mixture was quenched with saturated sodium bicarbonate solution and extracted with DCM (3×20 mL). The organic fractions were combined, passed through a hydrophobic frit and concentrated under reduced pressure to give a yellow oil (2.9 g). The oil was purified via column chromatography, using a gradient of 0-60% TBME in heptanes to give the title compound (1.6 g, 73% yield). δ$_H$ (250 MHz, DMSO-d$_6$) 4.03-3.92 (m, 1H), 3.80 (dd, J=18.7, 1.1 Hz, 1H), 3.57 (d, J=18.7 Hz, 1H), 3.18-2.98 (m, 1H), 2.80-2.60 (m, 1H), 1.42 (s, 9H), 1.02 (d, J=7.1 Hz, 3H).

Intermediate 282

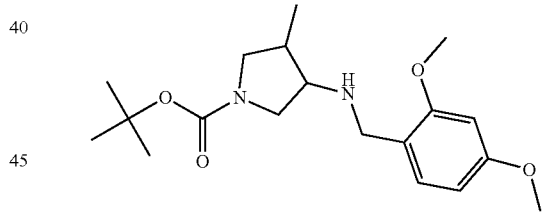

tert-butyl 3-[(2,4-dimethoxyphenyl)methylamino]-4-methyl-pyrrolidine-1-carboxylate To a solution of intermediate 281 (1.5 g, 7.53 mmol) in DCM (30 mL) was added 1-(2,4-dimethoxyphenyl)methanamine (1.26 g, 7.53 mmol). The mixture was stirred at room temperature for 10 minutes, then STAB (2.39 g, 11.29 mmol) was added. The mixture was stirred at room temperature for 3 days, then quenched with saturated sodium bicarbonate and the organic layer separated. The aqueous layer was extracted with DCM (3×5 mL) and the organic fractions combined, passed through a hydrophobic frit and purified via column chromatography (KP-NH), using a gradient of 0-100% TBME in heptanes, to give the title compound (2.16 g, 81% yield). δ$_H$ (500 MHz, DMSO-d$_6$) 7.18 (d, J=8.2 Hz, 1H), 6.52 (d, J=2.3 Hz, 1H), 6.46 (dd, J=8.2, 2.2 Hz, 1H), 3.75 (d, J=13.5 Hz, 6H), 3.57 (s, 2H), 3.31-3.20 (m, 2H), 3.10-3.00 (m, 2H), 3.01-2.94 (m, 1H), Intermediate 283

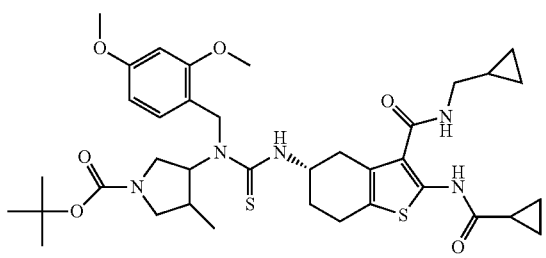 [SMILES: COc1ccc(CN(C(=S)N[C@H]2CCc3sc(NC(=O)C4CC4)c(C(=O)NCC4CC4)c3C2)C2CN(C(=O)OC(C)(C)C)CC2C)c(OC)c1]

tert-butyl 3-[[(5S)-2-(cyclopropanecarbonylamino)-
3-(cyclopropylmethylcarbamoyl)-4,5,6,7-tetrahyd-
robenzothiophen-5-yl]carbamothioyl-[(2,4-dime-
thoxyphenyl)methyl]amino]-4-methyl-pyrrolidine-1-
carboxylate The title compound was prepared according to general method 7, using intermediate 117 (1.67 g, 5 mmol) and intermediate 282 (1.93 g, 5.5 mmol). The residue was purified via column chromatography, using a gradient of 0-100% TBME in heptanes, to give the title compound (3.39 g, 72% yield). LCMS (M+H)$^+$ 726, RT 2.14 (Method 18).

Intermediate 284

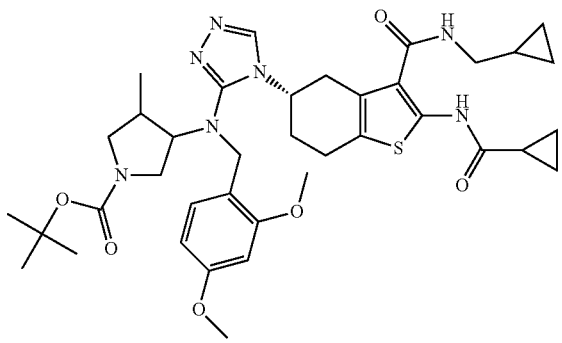 [SMILES: COc1ccc(CN(c2nncn2[C@H]2CCc3sc(NC(=O)C4CC4)c(C(=O)NCC4CC4)c3C2)C2CN(C(=O)OC(C)(C)C)CC2C)c(OC)c1]

tert-butyl 3-[[4-[(5S)-2-(cyclopropanecarbo-
nylamino)-3-(cyclopropylmethylcarbamoyl)-4,5,6,7-
tetrahydrobenzothiophen-5-yl]-1,2,4-triazol-3-yl]-
[(2,4-dimethoxyphenyl)methyl]amino]-4-methyl-
pyrrolidine-1-carboxylate The title compound was prepared according to general method 8, using intermediate 283 (3.39 g, 3.6 mmol). The residue was purified via column chromatography, using a gradient of 0-6% methanol in DCM, to give the title compound (2.59 g, 91% yield). LCMS (M+H)$^+$ 734, RT 1.28 (Method 11).

Intermediate 285

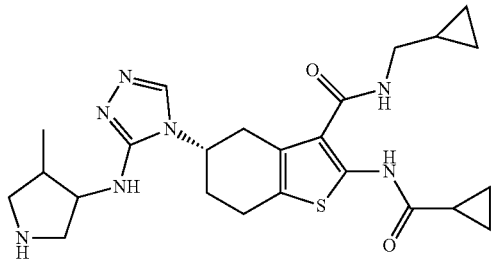 [SMILES: CC1CNCC1Nc1nncn1[C@H]1CCc2sc(NC(=O)C3CC3)c(C(=O)NCC3CC3)c2C1]

(5S)-2-(cyclopropanecarbonylamino)-N-(cyclopro-
pylmethyl)-5-[3-[(4-methylpyrrolidin-3-yl)amino]-1,
2,4-triazol-4-yl]-4,5,6,7-tetrahydrobenzothiophene-
3-carboxamide To a stirred solution of intermediate 284 (2.59 g, 3.32 mmol) in DCM (40 mL) at room temperature was added TFA (2.54 mL, 33.2 mmol). The reaction mixture was stirred overnight at room temperature. TFA (0.5 mL, 6.53 mmol) was added and the mixture stirred at room temperature for 2 hours, then at 40° C. for 2 hours. The reaction mixture was cooled to room temperature, then quenched with saturated sodium bicarbonate and filtered, to give the title compound (930 mg, 57% yield). LCMS (M+H)$^+$484, RT 0.84 (Method 11).

Intermediate 286

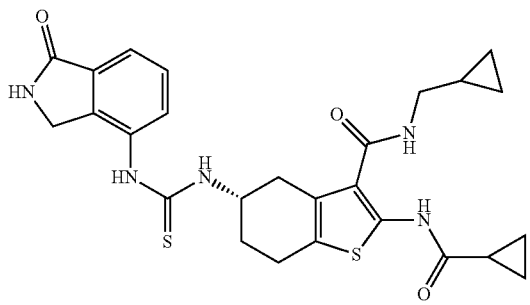 [SMILES: O=C1NCc2c(NC(=S)N[C@H]3CCc4sc(NC(=O)C5CC5)c(C(=O)NCC5CC5)c4C3)cccc21]

(5S)-2-(cyclopropanecarbonylamino)-N-(cyclopro-
pylmethyl)-5-[(1-oxoisoindolin-4-yl)carbamothioy-
lamino]-4,5,6,7-tetrahydrobenzothiophene-3-carbox-
amide To a stirred solution of di-1H-imidazol-1-ylmeth-
anethione (118 mg, 0.59 mmol) and DIPEA (188 μL, 1.08 mmol) in DCM (4 mL) was added 4-amino-2,3-dihydro-1H-isoindol-1-one (88 mg, 0.59 mmol). The reaction was stirred for 1 hour, then intermediate 117 (200 mg, 0.54 mmol) was added. The reaction mixture was stirred at room temperature for 1 hour, then concentrated in vacuo. The residue was purified via column chromatography, using 0-15% methanol in TBME to give the title compound (244 mg, 73% yield). LCMS (M+H)$^+$524, RT 1.75 (Method 12).

Intermediate 287

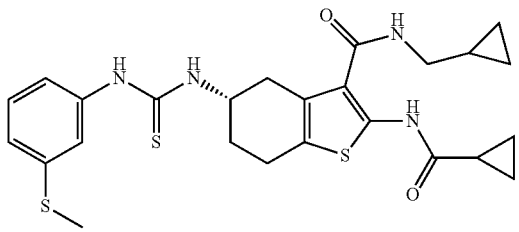 [SMILES: CSc1cccc(NC(=S)N[C@H]2CCc3sc(NC(=O)C4CC4)c(C(=O)NCC4CC4)c3C2)c1]

(5S)-2-(cyclopropanecarbonylamino)-N-(cyclopropylmethyl)-5-[(3-methylsulfanylphenyl)carbamothioylamino]-4,5,6,7-tetrahydrobenzothiophene-3-carboxamide To a stirring solution of 1-isothiocyanato-3-methylsulfanyl-benzene (113 mg, 0.62 mmol) in anhydrous DCM (2 mL) was added a solution of intermediate 117 (200 mg, 0.6 mmol) in DCM (3 mL) dropwise under an atmosphere of nitrogen and the mixture was stirred overnight at room temperature. The reaction mixture was concentrated to dryness and purified by flash column chromatography eluting with a gradient of 0 to 100% ethyl acetate in heptane to afford the title compound (300 mg, 97% yield). $\delta_H$ (500 MHz, Chloroform-d) 12.13 (s, 1H), 7.58 (s, 1H), 7.31-7.24 (m, 1H), 7.12 (d, J=8.1 Hz, 1H), 6.97 (t, J=1.8 Hz, 1H), 6.83 (dd, J=7.8, 1.5 Hz, 1H), 6.18 (d, J=7.9 Hz, 1H), 5.86 (t, J=4.9 Hz, 1H), 4.98-4.88 (m, 1H), 3.30-3.26 (m, 2H), 3.22 (dd, J=14.9, 5.0 Hz, 1H), 2.89-2.77 (m, 2H), 2.66-2.56 (m, 1H), 2.43 (s, 3H), 2.11-1.99 (m, 2H), 1.69-1.63 (m, 1H), 1.13-1.05 (m, 3H), 0.92-0.88 (m, 2H), 0.61-0.55 (m, 2H), 0.28 (q, J=4.8 Hz, 2H). LCMS [M+H]+ 515, RT 1.98 minutes (Method 12).

Intermediate 288

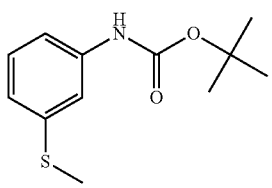 [SMILES: CSc1cccc(NC(=O)OC(C)(C)C)c1]

tert-butyl N-(3-methylsulfanylphenyl)carbamate

A solution of 3-methylsulfanylaniline (0.44 mL, 3.59 mmol) and tert-butoxycarbonyl tert-butyl carbonate (862 mg, 3.95 mmol) in THF (10 mL) was stirred under an atmosphere of nitrogen at 60° C. overnight. The mixture was concentrated to dryness and the crude was purified by flash column chromatography eluting with a 0 to 50% ethyl acetate in heptane gradient to afford the title compound (900 mg, 99% yield) as a colourless oil. $\delta_H$ (500 MHz, DMSO-d6) 9.33 (s, 1H), 7.43 (s, 1H), 7.22-7.13 (m, 2H), 6.84 (dt, J=6.7, 1.9 Hz, 1H), 2.42 (s, 3H), 1.47 (s, 9H).

Intermediate 289

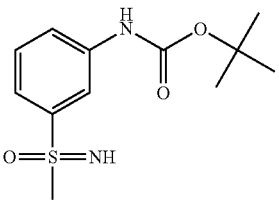 [SMILES: CC(C)(C)OC(=O)Nc1cccc(S(C)(=N)=O)c1]

tert-butyl N-[3-(methylsulfonimidoyl)phenyl]carbamate

To a stirring solution of Intermediate 288 (300 mg, 1.25 mmol) in anhydrous methanol (2.5 mL) was added ammonium carbamate (391 mg, 5.01 mmol) followed by (diacetoxyiodo)benzene (1211 mg, 3.76 mmol) and the mixture was stirred at room temperature in air for 15 hours. The mixture was concentrated to dryness and the crude was purified by flash column chromatography eluting with a 0 to 100% ethyl acetate in heptane gradient, followed by a 0 to 20% methanol in ethyl acetate gradient to afford the title compound (252 mg, 74% yield) as a white solid. $\delta_H$ (500 MHz, DMSO-d6) 9.68 (s, 1H), 8.18 (s, 1H), 7.58 (dd, J=7.9, 1.9 Hz, 1H), 7.51 (dt, J=7.7, 1.4 Hz, 1H), 7.46 (t, J=7.8 Hz, 1H), 4.11 (s, 1H), 3.01 (d, J=1.0 Hz, 3H), 1.48 (s, 9H). LCMS [M+H]+ 271, RT 1.54 minutes (Method 12).

Intermediate 290

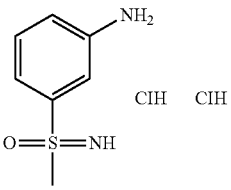

3-(methylsulfonimidoyl)aniline dihydrochloride

To a stirring solution of Intermediate 289 (285 mg, 1.05 mmol) in 1,4-Dioxane (2 mL) was added 4 M HCl in dioxane (2 mL). The reaction was stirred at room temperature for 30 minutes, then at 50° C. for 3 hours. The reaction mixture was concentrated in vacuo and the residue was further dried in vacuo at 40° C. for 2 hours to afford the title compound (280 mg, 91% purity, 98% yield) as a solid. $\delta_H$ (500 MHz, DMSO-d6) 7.44 (t, J=8.0 Hz, 1H), 7.24 (s, 1H), 7.21 (d, J=7.9 Hz, 1H), 7.05 (d, J=8.2 Hz, 1H), 3.86 (s, 3H), NH2 and NH masked by water peak.

Intermediate 291

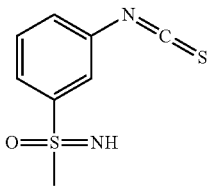

3-(methylsulfonimidoyl)phenylisothiocyanate

To a stirring solution of disodium carbonate (403 mg, 3.8 mmol) in water (3.7 mL) cooled to 0° C. in an ice bath was added DCM (7.4 mL) followed by carbonothioyl dichloride (0.12 mL, 1.52 mmol). To the biphasic mixture was Intermediate 290 (185 mg, 0.76 mmol), the ice bath was removed and the resulting mixture was stirred at room temperature for 1 hour. The layers were separated and the aqueous phase was extracted with DCM (2×10 mL). The combined organic layers were washed with brine (10 mL), dried over magnesium sulfate, filtered and the volume was reduced to about 10 mL in vacuo at 30° C. to afford the title compound as a solution in DCM. LCMS [M+H]$^+$ 213, RT 1.49 minutes (Method 12).

Intermediate 292

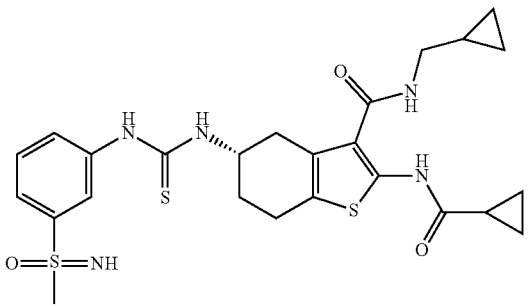

(5S)-2-(cyclopropanecarbonylamino)-N-(cyclopropylmethyl)-5-[[3-(methylsulfonimidoyl)phenyl]carbamothioylamino]-4,5,6,7-tetrahydrobenzothiophene-3-carboxamide To a stirring solution of Intermediate 291 (164 mg, 0.75 mmol) in DCM (10 mL) was added Intermediate 117 (250 mg, 0.75 mmol) portion wise under an atmosphere of nitrogen and the mixture was stirred at room temperature for 2 hours. Triethylamine (0.52 mL, 3.75 mmol) was added and stirring was continued at room temperature over the weekend. The reaction mixture was diluted with DCM (10 mL), washed with brine (10 mL), dried over magnesium sulfate, filtered and concentrated. The crude material was purified by flash column chromatography eluting with a 0 to 100% ethyl acetate in heptane gradient, followed by a 0 to 20% methanol in ethyl acetate gradient to afford the title compound (258 mg, 60% yield). δ$_H$ (500 MHz, DMSO-d6) 11.12 (s, 1H), 9.73 (s, 1H), 8.10 (s, 1H), 7.98 (s, 1H), 7.85-7.78 (m, 1H), 7.71 (t, J=5.7 Hz, 1H), 7.60 (d, J=7.7 Hz, 1H), 7.51 (t, J=7.9 Hz, 1H), 4.61 (s, 1H), 4.15 (s, 1H), 3.20-3.06 (m, 31H), 3.03 (s, 31H), 2.79-2.70 (m, 21H), 2.67 (d, J=6.9 Hz, 1H), 2.09-2.00 (m, 1H), 1.96-1.86 (m, 2H), 1.11-0.98 (m, 1H), 0.93-0.78 (m, 4H), 0.43 (q, J=5.4 Hz, 2H), 0.23 (q, J=4.7 Hz, 2H). LCMS [M+H]$^+$ 546, RT 1.74 minutes (Method 12).

Intermediate 293

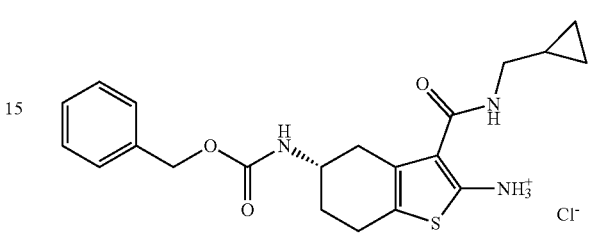

[(5S)-5-(benzyloxycarbonylamino)-3-(cyclopropylmethylcarbamoyl)-4,5,6,7-tetrahydrobenzothiophen-2-yl]ammonium chloride To a stirring solution of intermediate 564 (1400 mg, 2.80 mmol) in anhydrous 1,4-dioxane (5.6 mL) cooled to 0° C. under an atmosphere of nitrogen was added 4 M hydrogen chloride in 1,4 dioxane (14 mL, 56 mmol) and the resulting mixture was stirred for 10 minutes at this temperature, then the bath was removed and it was allowed to reach room temperature over 3 hours. The mixture was concentrated in vacuo maintaining the temperature of the bath at 30° C. to afford the title compound (1.43 g, 99% yield). LCMS [M+H]$^+$ 400, RT 1.89 minutes (Method 12).

Intermediate 294

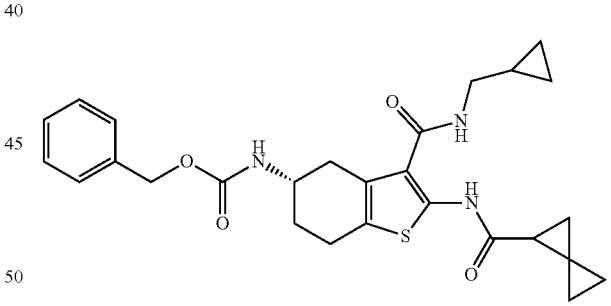

benzyl N-[(5S)-3-(cyclopropylmethylcarbamoyl)-2-(spiro[2.2]pentane-2-carbonylamino)-4,5,6,7-tetrahydrobenzothiophen-5-yl]carbamate To a stirring solution of Intermediate 293 (1220 mg, 2.8 mmol), spiro[2.2]pentane-2-carboxylic acid (314 mg, 2.8 mmol) and pyridine (1.1 mL, 14 mmol) in anhydrous DCM (56 mL) cooled to 0° C. under an atmosphere of nitrogen, was added T3P (50%, 3.3 mL, 5.6 mmol) dropwise. The resulting solution was allowed to slowly reach room temperature overnight. Water was added (20 mL), the mixture was stirred for 5 minutes, then the layers were separated and the aqueous phase was extracted further with DCM (20 mL). The combined organic layers were washed with saturated aqueous NH₄Cl solution (15 mL), brine (15 mL), dried over magnesium sulfate, filtered and concentrated in vacuo. The crude material was purified by flash column chromatography eluting with a 0 to 100% ethyl acetate in heptane gradient to afford the title compound (1.06 g, 77% yield). $\delta_H$ (500 MHz, DMSO-d6) 10.98 (s, 1H), 7.60 (t, J=5.3 Hz, 1H), 7.41 (t, J=6.1 Hz, 1H), 7.38-7.33 (m, 4H), 7.33-7.28 (m, 1H), 5.03 (s, 2H), 3.77-3.64 (m, 1H), 3.18-3.05 (m, 2H), 2.93 (d, J=15.6 Hz, 1H), 2.78-2.64 (m, 2H), 2.58-2.53 (m, 1H), 2.20 (dd, J=7.5, 4.2 Hz, 1H), 1.94 (d, J=11.4 Hz, 1H), 1.78-1.65 (m, 1H), 1.41 (dd, J=7.5, 3.7 Hz, 1H), 1.36 (t, J=3.8 Hz, 1H), 1.06-0.97 (m, 1H), 0.99-0.74 (m, 4H), 0.40 (q, J=4.7, 3.9 Hz, 2H), 0.21 (q, J=4.9 Hz, 2H). LCMS [M+H]+ 494, RT 2.08 minutes (Method 12).

Intermediate 295

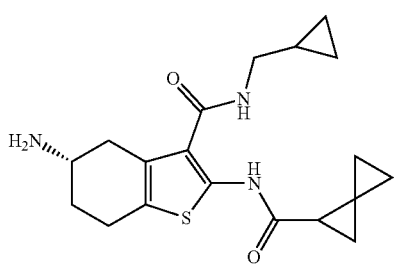

(5S)-5-amino-N-(cyclopropylmethyl)-2-(spiro[2.2]pentane-2-carbonylamino)-4,5,6,7-tetrahydrobenzothiophene-3-carboxamide To a solution of Intermediate 294 (950 mg, 1.92 mmol) in Ethanol (38 mL)/Ethyl acetate (19 mL) was added palladium (5.0%, 410 mg, 0.192 mmol) and the resulting suspension was stirred under an atmosphere of hydrogen at room temperature for 1.5 hours. The reaction mixture was filtered on a pad of celite, washed through with ethanol and ethyl acetate, then concentrated to dryness to afford the title compound (644 mg, 77% yield). LCMS [M+H]⁺ 360, RT 2.04 minutes (Method 29).

Intermediate 296

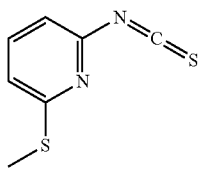

2-isothiocyanato-6-methylsulfanyl-pyridine

To stirring solution of disodium carbonate (1890 mg, 17.83 mmol) in water (5 mL) was added DCM (5 mL) followed by carbonothioyl dichloride (0.54 mL, 7.13 mmol). The biphasic mixture was cooled to 0° C. in an ice-bath and a solution of 6-methylsulfanylpyridin-2-amine (500 mg, 3.57 mmol) in DCM (5 mL) was added dropwise. The ice bath was removed and the resulting mixture was allowed to reach room temperature and stirred for 1 hour. The layers were separated and the aqueous phase was extracted with DCM (2×10 mL). The combined organic layers were washed with brine (10 mL), dried over magnesium sulfate, filtered and concentrated in vacuo to afford the title compound (334 mg, 51% yield) as an oil. $\delta_H$ (500 MHz, Chloroform-d) 7.47 (t, J=7.8 Hz, 1H), 7.08 (dd, J=8.0, 0.6 Hz, 1H), 6.77 (dd, J=7.7, 0.6 Hz, 1H), 2.55 (s, 3H).

Intermediate 297

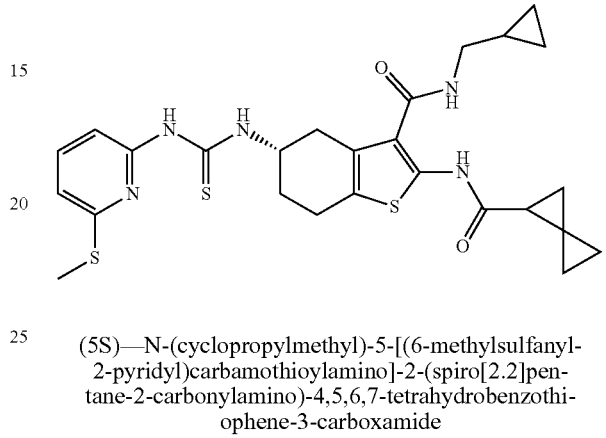

(5S)—N-(cyclopropylmethyl)-5-[(6-methylsulfanyl-2-pyridyl)carbamothioylamino]-2-(spiro[2.2]pentane-2-carbonylamino)-4,5,6,7-tetrahydrobenzothiophene-3-carboxamide To a stirring solution of Intermediate 295 (150 mg, 0.417 mmol) in DCM (5 mL) was added (dropwise) a solution of Intermediate 296 (80 mg, 0.438 mmoL) in DCM (3 mL). The mixture was stirred at room temperature for 45 minutes. Intermediate 296 (10 mg, 0.13 mmoL) in DCM (1 mL) was then added and the reaction mixture stirred at room temperature for 45 minutes. The reaction mixture was concentrated to dryness and purified by flash column chromatography eluting with a 0 to 50% ethyl acetate in heptane gradient to afford the title compound (125 mg, 50% yield). $\delta_H$ (500 MHz, DMSO-d6) 11.31 (d, J=6.1 Hz, 1H), 11.10 (s, 1H), 10.60 (s, 1H), 7.63 (t, J=8.0 Hz, 1H), 7.58 (t, J=4.6 Hz, 1H), 6.90 (dd, J=7.7, 2.5 Hz, 1H), 6.87 (d, J=8.2 Hz, 1H), 4.74-4.63 (m, 1H), 3.24-3.16 (m, 1H), 3.16-3.06 (m, 2H), 2.87-2.79 (m, 2H), 2.76 (dd, J=16.1, 6.8 Hz, 1H), 2.44-2.38 (m, 3H), 2.24-2.18 (m, 1H), 2.17-2.05 (m, 1H), 2.03-1.92 (m, 1H), 1.46-1.40 (m, 1H), 1.39-1.34 (m, 1H), 1.06-0.99 (m, 1H), 0.99-0.91 (m, 2H), 0.90-0.86 (m, 1H), 0.82-0.74 (m, 1H), 0.44-0.35 (m, 2H), 0.26-0.12 (m, 2H). LCMS [M+H]⁺ 542, RT 2.09 minutes (Method 12).

Intermediate 298

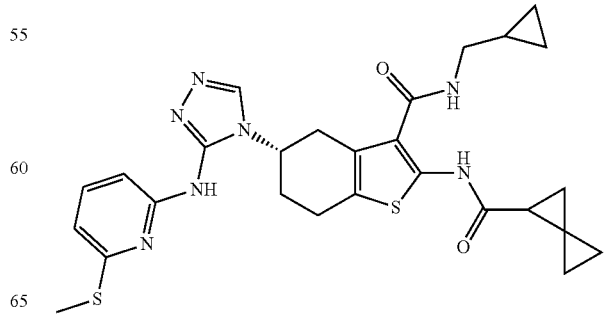

(5S)—N-(cyclopropylmethyl)-5-[3-[(6-methylsulfanyl-2-pyridyl)amino]-1,2,4-triazol-4-yl]-2-(spiro[2.2]pentane-2-carbonylamino)-4,5,6,7-tetrahydrobenzothiophene-3-carboxamide To a stirring solution of Intermediate 297 (125 mg, 0.23 mmol) in anhydrous DMF (5 mL) was added formic hydrazide (42 mg, 0.692 mmol) followed by mercury dichloride (188 mg, 0.692 mmol) and triethylamine (0.1 mL, 0.69 mmol). The resulting mixture was stirred at 90° C. for 2.5 hours. Celite was added to the stirring mixture and it was diluted with ethyl acetate (10 mL). The mixture was filtered through a pad of celite, washing through with more ethyl acetate, and the solvent was evaporated in vacuo. The crude material was purified by flash column chromatography eluting with a 0 to 10% methanol in ethyl acetate gradient to afford the title compound (80 mg, 55% yield). $\delta_H$ (500 MHz, DMSO-d6) 11.10 (s, 1H), 10.05 (s, 1H), 8.52 (d, J=4.1 Hz, 1H), 7.60 (s, 1H), 7.53 (t, J=7.9 Hz, 1H), 7.07 (t, J=7.9 Hz, 1H), 6.72 (dd, J=7.7, 1.4 Hz, 1H), 4.49-4.31 (m, 1H), 3.15-3.05 (m, 3H), 3.06-2.94 (m, 1H), 2.82-2.76 (m, 2H), 2.43-2.37 (m, 3H), 2.24-2.13 (m, 3H), 1.45-1.39 (m, 1H), 1.37 (t, J=3.8 Hz, 1H), 1.01-0.91 (m, 3H), 0.91-0.83 (m, 1H), 0.82-0.74 (m, 1H), 0.37-0.27 (m, 2H), 0.21-0.09 (m, 2H). LCMS [M+H]+ 550, RT 2.93 minutes (Method 29).

Intermediate 299

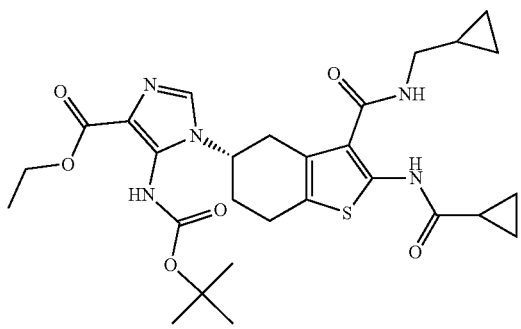

ethyl 5-(tert-butoxycarbonylamino)-1-[(5S)-2-(cyclopropanecarbonylamino)-3-(cyclopropylmethylcarbamoyl)-4,5,6,7-tetrahydrobenzothiophen-5-yl]imidazole-4-carboxylate Sodium hydride (60%, 255 mg, 6.38 mmol) was added in one portion to the stirred solution of Example 117 (1.0 g, 2.12 mmol) in dry DMF (15 mL) at room temperature. The mixture was stirred for 5 minutes, then tert-butoxycarbonyl tert-butyl carbonate (509 mg, 2.33 mmol) was added (Note: Initially a gel formed with poor stirring which was broken down after sonication and as the reaction time progressed). The mixture was diluted with dry DMF (5 mL), sonicated for 5 minutes and stirred at room temperature for 1 h. The reaction was treated with tert-butoxycarbonyl tert-butyl carbonate (100 mg, 0.46 mmol) and stirred for 1 h. The reaction was cooled to 0° C., quenched with saturated aqueous NH4Cl (5 mL), diluted with DCM (50 mL) and washed with aq. saturated NH4Cl (50 mL) followed by water (3×50 mL). The organic layers were dried over sodium sulfate, filtered and concentrated under vacuum to afford solid. The crude solid was purified by column chromatography, eluting with 0-100% Ethyl acetate in heptane to give the title compound (400 mg, 26% yield). LCMS [M+H]+ 572, RT 1.90 minutes (Method 12).

Intermediate 300

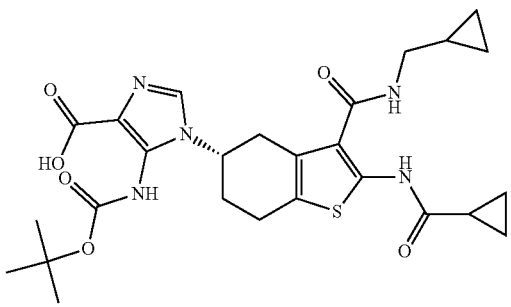

5-(tert-butoxycarbonylamino)-1-[(5S)-2-(cyclopropanecarbonylamino)-3-(cyclopropylmethylcarbamoyl)-4,5,6,7-tetrahydrobenzothiophen-5-yl]imidazole-4-carboxylic acid A solution of Intermediate 299 (78% purity, 400 mg, 0.55 mmol) in THF (4 mL) was treated with 1 M sodium hydroxide (2.7 mL, 2.7 mmol) at room temperature and stirred for 2 days. The mixture was concentrated under reduced pressure (NB water bath kept 25° C. due to concern of decarboxylation), then adjusted to pH 5 with 1 M HCl and extracted with DCM (3×10 mL), dried over sodium sulfate, concentrated under reduced pressure at 25° C. to give the title compound (267 mg, 78% yield). LCMS [M+H]+ 544, RT 1.74 minutes (Method 12).

Intermediate 301

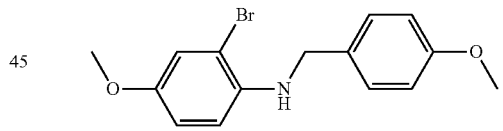

2-bromo-4-methoxy-N-[(4-methoxyphenyl)methyl]aniline

A solution of 4-methoxybenzaldehyde (60 µL, 0.49 mmol), acetic acid (30 µL, 0.52 mmol) and 4-methoxybenzaldehyde (60 µL, 0.494 mmol) in DCE (1.5 mL) was stirred for 10 min then sodium triacetoxyboranuide (210 mg, 0.99 mmol) was added and stirred at room temperature for 18 h. The reaction mixture diluted with water (10 mL) and extracted with DCM (2×10 mL). The combined organic layers were dried over sodium sulfate, filtered and evaporated to dryness to afford the crude.

This was purified by column chromatography, eluting with 0-100% ethyl acetate in heptane to give the title compound (145 mg, 84% yield). $\delta_H$ (500 MHz, Chloroform-d) 7.33-7.29 (m, 2H), 7.10 (d, J=2.8 Hz, 1H), 6.94-6.88 (m, 2H), 6.79 (dd, J=8.9, 2.9 Hz, 1H), 6.61 (d, J=8.9 Hz, 1H), 4.35 (s, 1H), 4.30 (s, 2H), 3.83 (s, 3H), 3.75 (s, 3H). LCMS [M+H]+ Doesn't ionised, RT 2.10 minutes (Method 12).

Intermediate 302

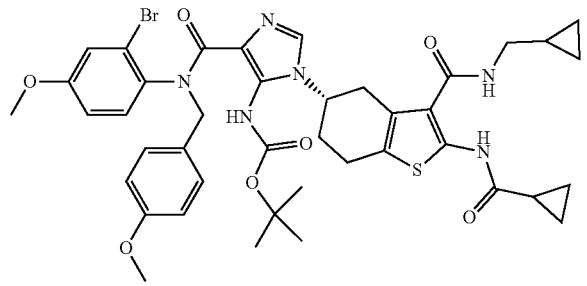 [SMILES: COc1ccc(CN(C(=O)c2ncn([C@H]3CCc4sc(NC(=O)C5CC5)c(C(=O)NCC5CC5)c4C3)c2NC(=O)OC(C)(C)C)c2ccc(OC)cc2Br)cc1]

tert-butyl N-[5-[(2-bromo-4-methoxy-phenyl)-[(4-methoxyphenyl)methyl]carbamoyl]-3-[(5S)-2-(cyclopropanecarbonylamino)-3-(cyclopropylmethyl-carbamoyl)-4,5,6,7-tetrahydrobenzothiophen-5-yl] imidazol-4-yl]carbamate T3P (50% w/w in ethyl acetate, 2.4 mL, 4.03 mmol) was added dropwise to the stirred solution of Intermediate 300 (300 mg, 0.52 mmol), Intermediate 301 (587 mg, 1.73 mmol) and pyridine (225 μL, 2.79 mmol) in dry DMF (0.2 mL) at 0° C. The mixture was then gradually warmed up to room temperature and stirred for 18 h. The reaction mixture neutralized with saturated aqueous NaHCO₃ and extracted with DCM (3×5 mL). The combined organic layers were dried over sodium sulfate, filtered and evaporated to dryness to afford the crude. This was purified by column chromatography, eluting with 0-100% ethyl acetate in heptane to give the title compound (240 mg, 54% yield). $\delta_H$ (500 MHz, Chloroform-d) 12.31-12.02 (m, 1H), 8.28-7.77 (m, 1H), 7.27-6.95 (m, 4H), 6.85-6.61 (m, 4H), 5.91-5.71 (m, 1H), 5.63 (dd, J=14.3, 5.2 Hz, 1H), 4.67-4.44 (m, 1H), 4.21-4.08 (m, 1H), 3.86-3.71 (m, 6H), 3.55-3.15 (m, 3H), 3.03-2.69 (m, 3H), 2.47-2.23 (m, 1H), 2.21-2.07 (m, 1H), 1.63-1.44 (m, 9H), 1.17-0.99 (m, 3H), 0.96-0.78 (m, 3H), 0.63-0.50 (m, 2H), 0.35-0.17 (m, 2H). LCMS [M+H]+ 847/849 (Br-isotope), RT 2.17 minutes (Method 12).

Intermediate 303

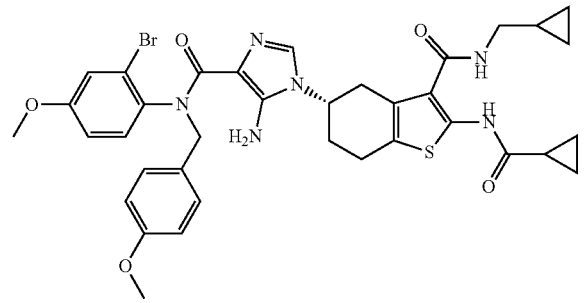

5-amino-N-(2-bromo-4-methoxy-phenyl)-1-[(5S)-2-(cyclopropanecarbonylamino)-3-(cyclopropylmethyl carbamoyl)-4,5,6,7-tetrahydrobenzothiophen-5-yl]-N-[(4-methoxyphenyl)methyl]imidazole-4-carboxamide 4 M HCl in 1,4-dioxane (708 μL, 2.83 mmol) was added to the stirred solution of Intermediate 302 (240 mg, 0.283 mmol) in DCM (0.5 mL) at room temperature and the mixture stirred for 5 h. The reaction mixture was concentrated under reduced pressure and the crude material purified by column chromatography, eluting with 0-20% methanol in DCM to give the title compound (200 mg, 94% yield). $\delta_H$ (500 MHz, DMSO-d6) 11.03 (s, 1H), 7.60-7.34 (m, 1H), 7.06-6.86 (m, 3H), 6.75-6.58 (m, 3H), 6.58-6.38 (m, 2H), 6.21-5.99 (m, 2H), 4.23-3.95 (m, 1H), 3.83-3.66 (m, 1H), 3.54 (s, 3H), 3.51 (s, 3H), 2.87 (d, J=49.9 Hz, 4H), 2.72-2.46 (m, 3H), 2.12-1.79 (m, 2H), 1.75-1.63 (m, 1H), 0.93-0.72 (m, 1H), 0.73-0.56 (m, 4H), 0.31-0.10 (m, 2H), 0.10--0.13 (m, 2H). LCMS [M+H]+ 747/749 (Br-isotope), RT 2.09 minutes (Method 12).

Intermediate 304

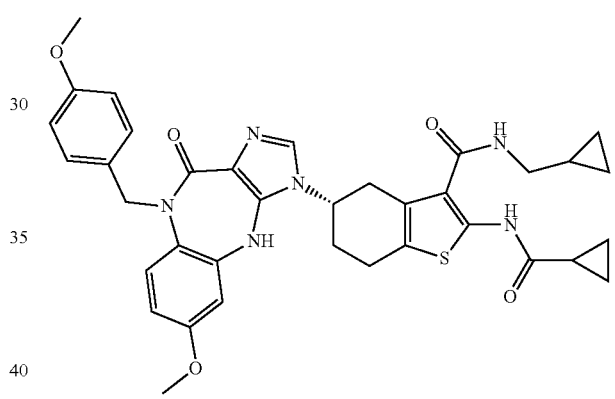

(5S)-2-(cyclopropanecarbonylamino)-N-(cyclopropylmethyl)-5-[8-methoxy-5-[(4-methoxyphenyl) methyl]-4-oxo-10H-imidazo[4,5-c][1,5]benzodiazepin-1-yl]-4,5,6,7-tetrahydrobenzothiophene-3-carboxamide Intermediate 303 (140 mg, 0.187 mmol) and sodium 2-methylpropan-2-olate (84 mg, 0.874 mmol) were suspended in dry tert-butanol (2 mL) and 1,4-Dioxane (1 mL). The mixture was de-gassed for 5 minutes, then added tBuXPhos Pd G3 (14 mg, 0.0176 mmol) was added. The mixture was heated at 90° C. in sealed tube for 24 h. The mixture was cooled to room temperature, diluted with water (20 mL) and extracted with 10% methanol in DCM (3×20 mL). The combine organic layers were diluted with brine (20 mL, pH=~14) and adjusted to pH 7 using acetic acid. The layers were separated and the organic layer dried over sodium sulfate, filtered, evaporated to dryness to afford the crude. The crude material was purified by column chromatography, eluting with 0-20% methanol in DCM to give the title compound (80 mg, 64% yield). $\delta_H$ (500 MHz, DMSO-d6) 11.24 (s, 1H), 8.20 (s, 1H), 7.72-7.63 (m, 1H), 7.51 (s, 1H), 7.20-7.13 (m, 3H), 6.84-6.76 (m, 2H), 6.68 (d, J=2.9 Hz, 1H), 6.55 (dd, J=9.0, 2.9 Hz, 1H), 5.09-4.90 (m, 2H), 4.58-4.48 (m, 1H), 3.68 (s, 3H), 3.65 (s, 3H), 3.23-3.15 (m, 1H), 3.15-3.05 (m, 1H), 3.05-2.98 (m, 1H), 2.98-2.75 (m, 3H), 2.34-2.01 (m, 2H), 1.97-1.84 (m, 1H), 1.35-1.20 (m, 4H), 0.91-0.80 (m, 1H), 0.38-0.24 (m, 2H), 0.24-0.10 (m, 2H). LCMS [M+H]+ 667, RT 1.89 minutes (Method 12).

Intermediate 305

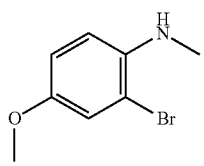

2-bromo-4-methoxy-N-methyl-aniline 1.6 M methyllithium in Et₂O (1.7 mL, 2.72 mmol) was added dropwise to the stirred solution of 2-bromo-4-methoxy-aniline (500 mg, 2.47 mmol) in dry THF (5 mL) at −78° C. The reaction mixture stirred for 1 h at −78° C., then iodomethane (185 μL, 2.97 mmol) in dry THF (3 mL) was added. The mixture was gradually warmed up to room temperature and stirred for 4 h. The reaction mixture was quenched with saturated aqueous NH₄Cl (25 mL) and extracted with ethyl acetate (3×25 mL). The combined organic layers were washed with brine (25 mL), dried over sodium sulfate, filtered and concentrated to dryness to afford the crude. The crude was purified by column chromatography, eluting with 0-100% TBME in heptane to give the title compound (416 mg, 78% yield). LCMS [M+H]+ 216/218, RT 1.75 minutes (Method 12).

Intermediate 306

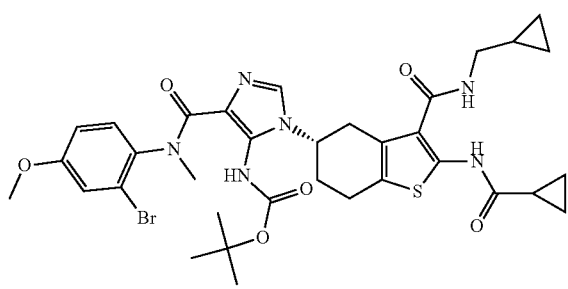

tert-butyl N-[5-[(2-bromo-4-methoxy-phenyl)-methyl-carbamoyl]-3-[(5S)-2-(cyclopropanecarbonylamino)-3-(cyclopropylmethylcarbamoyl)-4,5,6,7-tetrahydrobenzothiophen-5-yl]imidazol-4-yl]carbamate T3P (50% w/w in ethyl acetate, 800 μL, 1.34 mmol) was added dropwise to a stirred solution of Intermediate 300 (100 mg, 0.17 mmol), Intermediate 305 (160 mg, 0.74 mmol) and pyridine (75 μL, 0.931 mmol) in dry DMF (2 mL) at 0° C. The mixture was gradually warmed up to room temperature and stirred for 4 h. The reaction mixture was diluted with water (25 mL), neutralized with sat. aq. NaHCO₃ and extracted with DCM (3×25 mL). The combined organic layers were dried over sodium sulfate, filtered and evaporated to dryness to afford the crude. This was purified by column chromatography, eluting with 0-100% ethyl acetate in heptane to give the title compound (110 mg, 64% yield). LCMS [M+H]+ 741/743, RT 2.03 minutes (Method 12).

Intermediate 307

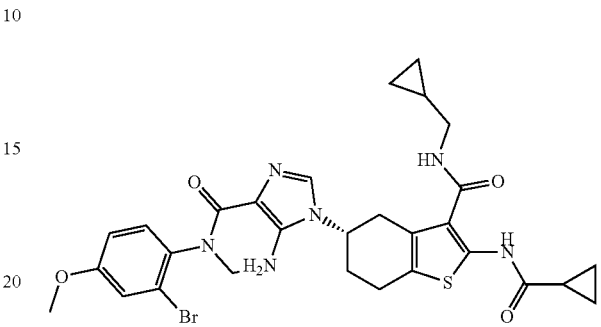

5-amino-N-(2-bromo-4-methoxy-phenyl)-1-[(5S)-2-(cyclopropanecarbonylamino)-3-(cyclopropylmethyl carbamoyl)-4,5,6,7-tetrahydrobenzothiophen-5-yl]-N-methyl-imidazole-4-carboxamide 2,2,2-Trifluoroacetic acid (0.30 mL, 4.04 mmol) was added to the stirred solution of Intermediate 306 (100 mg, 0.101 mmol) in DCM (1 mL) at room temperature. The mixture was stirred for 3 h. The reaction mixture concentrated under reduced pressure and purified by SCX chromatography, eluting with 7 M ammonia in methanol to provide a mixture of acid and the title compound. This crude material was dissolved in DCM:MeOH (9:1) (25 mL) and washed with sat. aq. NaHCO₃ (2×10 mL). The organic layer was dried over sodium sulfate, filtered and evaporated to dryness to afford the crude. This was further purified by column chromatography, eluting with 0-20% methanol in DCM to give the title compound (60 mg, 90% yield). $\delta_H$ (500 MHz, DMSO-d6) 11.23 (s, 1H), 7.66 (br s, 1H), 7.39-7.10 (m, 2H), 7.09-6.74 (m, 2H), 6.22 (s, 2H), 4.47-4.13 (m, 1H), 3.78 (s, 3H), 3.26-2.88 (m, 6H), 2.94-2.66 (m, 3H), 2.29-1.99 (m, 2H), 1.95-1.85 (m, 1H), 1.01 (s, 1H), 0.90-0.77 (m, 4H), 0.45-0.31 (m, 2H), 0.25-0.14 (m, 2H). LCMS [M+H]+ 641/643, RT 3.16 minutes (Method 10).

Intermediate 308

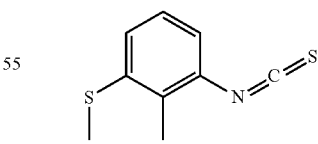

1-isothiocyanato-2-methyl-3-methylsulfanyl-benzene

To a stirring solution of sodium carbonate (881 mg, 8.16 mmol) in water (2.5 mL) previously cooled in an ice/water bath was added DCM (2.5 mL) followed by thiophosgene (0.25 mL, 3.26 mmol). The biphasic mixture was then treated with a solution of 2-methyl-3-methylsulfanyl-aniline (250 mg, 1.63 mmol) in DCM (2.5 mL) dropwise. The ice bath was removed and the resulting mixture was allowed to reach room temperature and stirred for 1 h. The layers were separated and the aqueous phase was extracted with DCM (20 mL). The combined organics were dried over magnesium sulfate, filtered and concentrated under reduced pressure. The crude material was purified by flash column chromatography eluting with a 0-10% ethyl acetate in heptane gradient to give the title compound (300 mg, 92% Yield). The material was used immediately in the next step. LCMS [no ionisation], RT 2.15 minutes (Method 12).

Intermediate 309

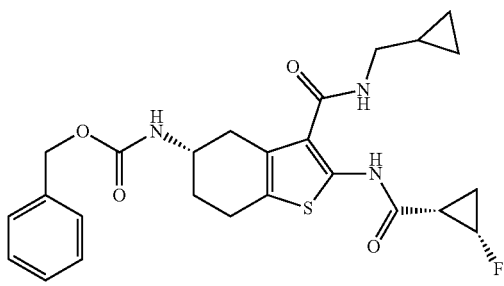

Mixture of cis isomers benzyl N-[(5S)-3-(cyclopropylmethylcarbamoyl)-2-[[(1SR,2SR)-2-fluorocyclopropanecarbonyl]amino]-4,5,6,7-tetrahydrobenzothiophen-5-yl]carbamate To a mixture of Intermediate 293 (1700 mg, 3.43 mmol), pyridine (1.11 mL, 13.73 mmol) and (1SR,2SR)-2-fluorocyclopropanecarboxylic acid (15 ⌀L, 3.43 mmol) in DCM (80 mL) was slowly added 2,4,6-Tripropyl-1,3,5,2,4,6-trioxatriphosphorinane-2,4,6-trioxide (4.09 mL, 6.86 mmol) at 0° C. The reaction mixture was slowly allowed to warm to room temperature and stirred for 3 h. The reaction mixture was diluted with DCM (40 mL) then water (50 mL) was added and layers were separated. The aqueous layer was extracted with DCM (2×10 mL) and the organic fractions combined, dried over sodium sulfate, filtered and concentrated under vacuum. The residue was purified by column chromatography using 10-80% EtOAc in heptane to give the title compound (903 mg, 54% yield). $\delta_H$ (500 MHz, DMSO-d6) 11.11 (s, 1H), 7.76-7.60 (m, 1H), 7.42 (d, J=7.0 Hz, 1H), 7.38-7.16 (m, 5H), 5.13-4.82 (m, 3H), 3.78-3.65 (m, 1H), 3.19-3.06 (m, 2H), 2.98-2.84 (m, 1H), 2.79-2.65 (m, 2H), 2.58-2.52 (m, 1H), 2.27-2.10 (m, 1H), 1.98-1.88 (m, 1H), 1.81-1.66 (m, 1H), 1.65-1.53 (m, 1H), 1.26-1.18 (m, 1H), 1.08-0.91 (m, 1H), 0.48-0.37 (m, 2H), 0.28-0.15 (m, 2H). LCMS $[M+H]^+$ 486, RT 1.91 minutes (Method 12).

Intermediate 310

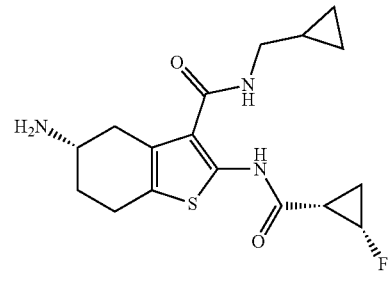

Mixture of cis isomers (5S)-5-amino-N-(cyclopropylmethyl)-2-[[(1SR,2SR)-2-fluorocyclopropanecarbonyl]amino]-4,5,6,7-tetrahydrobenzothiophene-3-carboxamide To a stirred solution of Intermediate 309 (900 mg, 1.85 mmol) in ethanol (60 mL) and ethyl acetate (10 mL) was added palladium (5%, 394 mg, 0.185 mmol). The reaction mixture was stirred under a hydrogen atmosphere for 16 h. The reaction mixture was filtered through Celite and concentrated under vacuum. The residue was purified by column chromatography using 20-100% EtOAc in heptane then 0-35% MeOH in DCM to give the title compound (503 mg, 67% yield, 87% purity). $\delta_H$ (500 MHz, DMSO-d6) 8.72 (br.s, 1H), 5.01-4.66 (m, 1H), 4.07 (br s, 1H), 3.15-2.91 (m, 5H), 2.75-2.56 (m, 2H), 2.09-2.00 (m, 1H), 1.99-1.92 (m, 1H), 1.65-1.48 (m, 2H), 1.17-0.95 (m, 2H), 0.48-0.38 (m, 2H), 0.27-0.18 (m, 2H). LCMS $[M+H]^+$ 352, RT 1.36 minutes (Method 12).

Intermediate 311

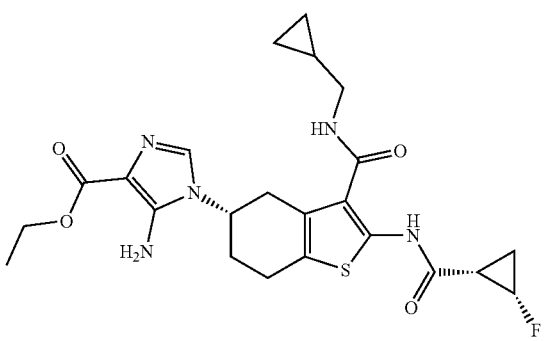

Mixture of cis isomers ethyl 5-amino-1-[(5S)-3-(cyclopropylmethylcarbamoyl)-2-[[(1SR,2SR)-2-fluorocyclopropanecarbonyl]amino]-4,5,6,7-tetrahydrobenzothiophen-5-yl]imidazole-4-carboxylate Triethylorthoformate (100 mL, 0.601 mmol) was added to a stirred solution of ethyl 2-amino-2-cyano-acetate (75% purity, 100 mg, 0.585 mmol) in acetonitrile (3 mL) and the mixture heated in a sealed tube at 90° C. for 1 h. The reaction mixture was cooled to room temperature and treated with Intermediate 310 (200 mg, 0.569 mmol). The reaction mixture was heated at 90° C. for 1 h, cooled and stirred at room temperature overnight. The reaction mixture was evaporated to dryness and the crude material was purified by column chromatography, eluting with 0-20% methanol in DCM to give the title compound (200 mg, 55% yield) as a beige solid. LCMS [M+H]⁺ 490, RT 1.63 minutes (Method 12).

Intermediate 312

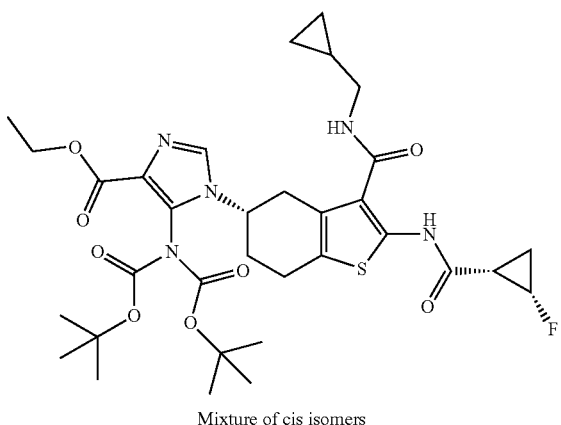 [SMILES: CCOC(=O)c1ncn([C@H]2CCc3sc(NC(=O)[C@@H]4C[C@@H]4F)c(C(=O)NCC4CC4)c3C2)c1N(C(=O)OC(C)(C)C)C(=O)OC(C)(C)C]

Mixture of cis isomers ethyl 5-[bis(tert-butoxycarbonyl)amino]-1-[(5S)-3-(cyclopropylmethylcarbamoyl)-2-[[(1SR,2SR)-2-fluorocyclopropanecarbonyl]amino]-4,5,6,7-tetrahydrobenzothiophen-5-yl]imidazole-4-carboxylate Sodium hydride (60%, 59 mg, 1.48 mmol) was added in one portion to a stirred solution of Intermediate 311 (180 mg, 0.37 mmol) in dry DMF (5 mL) at room temperature. The reaction mixture was stirred for 5 minutes, then tert-butoxycarbonyl tert-butyl carbonate (240 mg, 1.1 mmol) was added (Note: Initially a gel formed with poor stirring which broke down as reaction progressed). The mixture was stirred at room temperature for 2 h. The reaction mixture was then treated with tert-butoxycarbonyl tert-butyl carbonate (200 mg, 0.92 mmol) and stirred for 2 h. The reaction mixture was cooled to 0° C., quenched with a few drops of acetic acid, followed by saturated aqueous NH₄Cl (15 mL), and extracted with DCM (2×25 mL). The combined organic layers were dried over sodium sulfate, filtered and concentrated to dryness to afford the crude. The crude was purified by column chromatography, eluting with 0-100% ethyl acetate in heptane to give the title compound (90 mg, 30% yield). LCMS [M+H]⁺ 690, RT 1.95 minutes (Method 12).

Intermediate 313

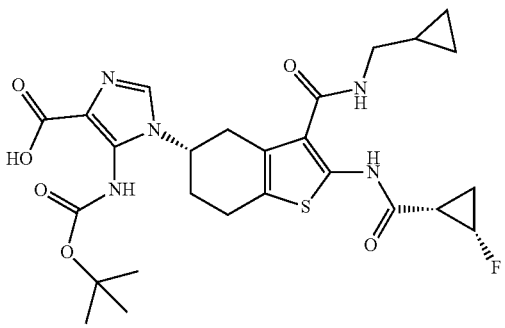

Mixture of cis isomers 5-(tert-butoxycarbonylamino)-1-[(5S)-3-(cyclopropylmethylcarbamoyl)-2-[[(1R,2SR)-2-fluorocyclopropanecarbonyl]amino]-4,5,6,7-tetrahydrobenzothiophen-5-yl]imidazole-4-carboxylic acid A solution of Intermediate 312 (90 mg, 0.13 mmol) in THF (4 mL) was treated with 1 M sodium hydroxide (0.65 mL, 0.65 mmol) and stirred at room temperature for 3 days. The mixture was concentrated under reduced pressure (Note: water bath kept 25° C. due to concern of decarboxylation), adjusted to pH 4 with 1 M HCl and extracted with DCM (3×10 mL). The combined organic layer was dried over sodium sulfate, filtered and concentrated under reduced pressure at 25° C. to give the title compound (55 mg, 75% yield). LCMS [M+H]⁺ 562, RT 1.69 minutes (Method 12).

Intermediate 314

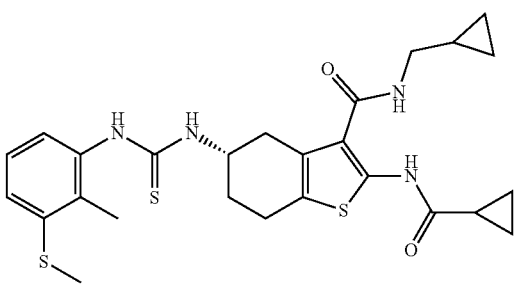 [SMILES: CSc1cccc(NC(=S)N[C@H]2CCc3sc(NC(=O)C4CC4)c(C(=O)NCC4CC4)c3C2)c1C]

(5S)-2-(cyclopropanecarbonylamino)-N-(cyclopropylmethyl)-5-[(2-methyl-3-methylsulfanyl-phenyl)carbamothioylamino]-4,5,6,7-tetrahydrobenzothiophene-3-carboxamide Intermediate 117 (250 mg, 0.75 mmol) was dissolved in DCM (5 mL) and Intermediate 308 (146 mg, 0.75 mmol) was added. The mixture was stirred at room temperature for 16 h. Concentrated under reduced pressure and purified by flash column chromatography eluting with a 30-60% ethyl acetate in heptane gradient to give the title compound (317 mg, 72% Yield). $\delta_H$ (500 MHz, Chloroform-d) 12.13 (s, 1H), 7.41 (s, 1H), 7.20 (t, J=7.9 Hz, 1H), 7.12 (d, J=7.7 Hz, 1H), 6.90 (d, J=7.7 Hz, 1H), 5.84 (t, J=4.9 Hz, 1H), 5.69 (d, J=8.1

Hz, 1H), 4.94-4.85 (m, 1H), 3.33-3.24 (m, 2H), 3.21 (dd, J=14.8, 5.0 Hz, 1H), 2.81 (dt, J=17.0, 6.4 Hz, 1H), 2.70 (dd, J=14.8, 6.2 Hz, 1H), 2.52 (dt, J=17.0, 6.2 Hz, 1H), 2.47 (s, 3H), 2.19 (s, 3H), 2.08-1.99 (m, 1H), 1.94-1.85 (m, 1H), 1.69-1.62 (m, 1H), 1.13-1.02 (m, 3H), 0.92-0.87 (m, 2H), 0.62-0.56 (m, 2H), 0.31-0.23 (m, 2H). LCMS [M+H]$^+$ 529, RT 1.97 minutes (Method 12).

Intermediate 315

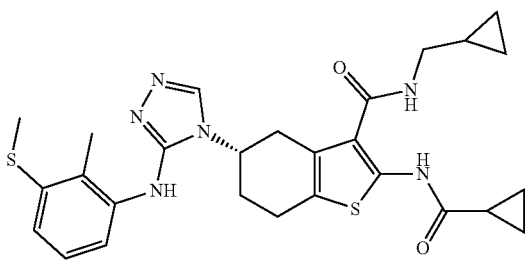 [SMILES: CSc1cccc(Nc2nncn2[C@H]2CCc3sc(NC(=O)C4CC4)c(C(=O)NCC4CC4)c3C2)c1C]

(5S)-2-(cyclopropanecarbonylamino)-N-(cyclopropylmethyl)-5-[3-(2-methyl-3-methylsulfanyl-anilino)-1,2,4-triazol-4-yl]-4,5,6,7-tetrahydrobenzothiophene-3-carboxamide Prepared according to general procedure 8 using intermediate 314 (317 mg, 0.60 mmol). Purified by flash column chromatography eluting with a 0-10% methanol in DCM gradient to give the title compound (75 mg, 21% Yield) as a white solid. $\delta_H$ (500 MHz, DMSO-d$_6$) 11.19 (s, 1H), 8.40 (s, 1H), 7.75 (s, 1H), 7.71 (t, J=5.6 Hz, 1H), 7.10 (t, J=8.0 Hz, 1H), 6.92-6.83 (m, 2H), 4.45-4.35 (m, 1H), 3.16-2.96 (m, 4H), 2.84-2.77 (m, 2H), 2.44 (s, 3H), 2.27-2.15 (m, 2H), 2.14 (s, 3H), 1.95-1.89 (m, 1H), 1.03-0.94 (m, 1H), 0.88-0.81 (m, 4H), 0.39-0.32 (m, 2H), 0.21-0.16 (m, 2H). LCMS [M+H]$^+$ 537, RT 2.83 minutes (Method 29).

Intermediate 316

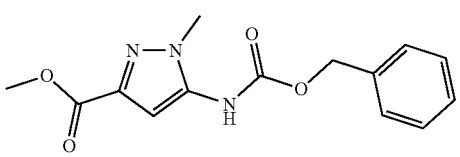 [SMILES: COC(=O)c1cc(NC(=O)OCc2ccccc2)n(C)n1]

Methyl 5-(benzyloxycarbonylamino)-1-methyl-Pyrazole-3-carboxylate

Methyl 5-amino-1-methyl-1H-pyrazole-3-carboxylate (500 mg, 3.22 mmol) was dissolved in THF (10 mL) and sodium hydrogen carbonate (298 mg, 3.54 mmol) was added followed by benzyl carbonochloridate (506 µL, 3.54 mmol). The solution was stirred at room temperature for 2 h, to give a cloudy mixture. The mixture was extracted with ethyl acetate (2×40 mL) and the combined organic extracts were washed with brine (20 mL), dried over MgSO$_4$ and filtered. Concentrated under reduced pressure and purified by flash column chromatography eluting with a 50-80% ethyl acetate in heptane gradient to give the title compound (710 mg, 66% Yield). $\delta_H$ (500 MHz, Chloroform-d) 7.34 (m, 5H), 6.91 (s, 1H), 6.69 (s, 1H), 5.19 (s, 2H), 3.87 (s, 3H), 3.76 (s, 3H). LCMS [M+H]$^+$ 290, RT 1.65 minutes (Method 12).

Intermediate 317

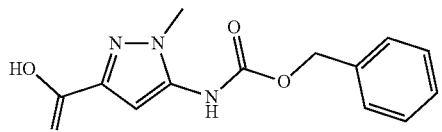

5-(benzyloxycarbonylamino)-1-methyl-pyrazole-3-carboxylic acid Intermediate 316 (816 mg, 2.45 mmol) was dissolved in 1,4-dioxane (5 mL) and 2 M aqueous lithium hydroxide (2.5 mL, 4.91 mmol) was added. The mixture was stirred at room temperature for 16 h before removing solvent under reduced pressure. The solution was acidified with conc. HCl to give a white precipitate which was collected by vacuum filtration, washing with water to afford the title compound (460 mg, 68% Yield). $\delta_H$ (500 MHz, DMSO-d$_6$) 12.56 (br s, 1H), 9.93 (s, 1H), 7.46-7.32 (m, 5H), 6.52 (s, 1H), 5.17 (s, 2H), 3.72 (s, 3H). LCMS [M+H]$^+$ 276, RT 1.51 minutes (Method 12).

Intermediate 318

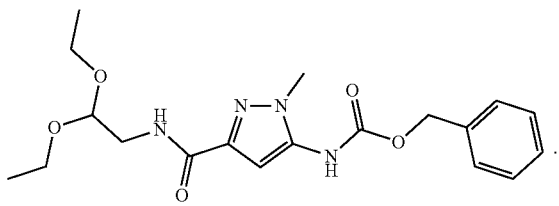 [SMILES: CCOC(CNC(=O)c1cc(NC(=O)OCc2ccccc2)n(C)n1)OCC]

Benzyl N-[5-(2,2-diethoxyethylcarbamoyl)-2-methyl-pyrazol-3-yl]carbamate

A suspension of Intermediate 317 (460 mg, 1.64 mmol) in DCM (10 mL) was treated with N-ethyl-N-isopropyl-propan-2-amine (0.63 mL, 3.60 mmol) to give a solution. HATU (685 mg, 1.80 mmol) was added and the mixture was stirred at room temperature for 10 minutes before adding 2,2-diethoxyethanamine (0.25 mL, 1.80 mmol). Stirring was continued at room temperature for 2 h before concentrating under reduced pressure. Purified by flash column chromatography eluting with a 60-80% ethyl acetate in heptane gradient to give the title compound (650 mg, 100% Yield) as a colourless oil. LCMS [M–H]$^-$ 389, RT 1.74 minutes (Method 12).

Intermediate 319

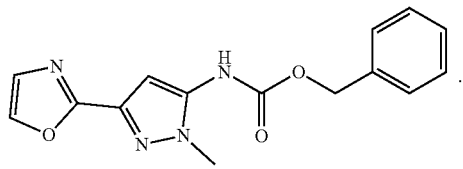 [SMILES: Cn1nc(-c2ncco2)cc1NC(=O)OCc1ccccc1]

Benzyl N-(2-methyl-5-oxazol-2-yl-pyrazol-3-yl)carbamate

Intermediate 318 (655 mg, 1.63 mmol) was dissolved in THF (10 mL) and 2 M aqueous HCl (5.0 mL, 10.0 mmol) was added. The mixture was stirred at room temperature for 16 h. The mixture was diluted with water (50 mL) and extracted with ethyl acetate (2×50 mL). The combined organic extracts were dried over MgSO$_4$, filtered and concentrated under reduced pressure. The residue was dissolved in THF (10 mL) and treated with Burgess reagent (969 mg, 4.07 mmol). The solution was stirred at room temperature for 20 h. Diluted with ethyl acetate (50 mL) then washed with water (50 mL). The aqueous was extracted further with ethyl acetate (50 mL) and the combined organic extracts were washed with brine (25 mL), dried over MgSO$_4$ and filtered. Concentrated under reduced pressure and purified by flash column chromatography eluting with a 0-10% methanol in DCM gradient to give the title compound (30 mg, 6% Yield). δ$_H$ (250 MHz, DMSO-d$_6$) 10.00 (s, 1H), 8.12 (d, J=0.8 Hz, 1H), 7.48-7.34 (m, 5H), 7.31 (d, J=0.8 Hz, 1H), 6.62 (s, 1H), 5.19 (s, 2H), 3.75 (s, 3H). LCMS [M+H]$^+$ 299, RT 1.64 minutes (Method 12).

Intermediate 320

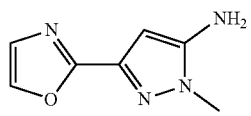

2-methyl-5-oxazol-2-yl-pyrazol-3-amine

Intermediate 319 (30 mg, 0.10 mmol) was dissolved in ethanol (2 mL) and 10% Pd/C (50% wet) (21 mg, 0.01 mmol) was added. The mixture was stirred under an atmosphere of H$_2$ at room temperature for 2 h. After this time the mixture was filtered through Celite and concentrated under reduced pressure to give the title compound (20 mg, 99% Yield). LCMS [M+H]$^+$ 165, RT 0.27 minutes (Method 12).

Intermediate 321

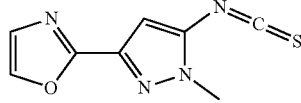

2-(5-isothiocyanato-1-methyl-pyrazol-3-yl)oxazole

To a stirring solution of sodium carbonate (53 mg, 0.487 mmol) in water (0.25 mL) cooled to 0° C. was added DCM (0.5 mL) followed by thiophosgene (15 mL, 0.195 mmol). The biphasic mixture was then treated with a solution of Intermediate 320 (16 mg, 0.0975 mmol). The ice bath was removed and the resulting mixture was allowed to reach room temperature and stirred for 1 h. The layers were separated and the aqueous phase was extracted with DCM (10 mL). The combined organics were dried over MgSO$_4$, filtered and concentrated under reduced pressure. The crude material was purified by column chromatography eluting with a 50-65% ethyl acetate in heptane gradient to give the title compound (20 mg, quantitative). LCMS [M+H]$^+$ 207, RT 1.62 minutes (Method 12).

Intermediate 322

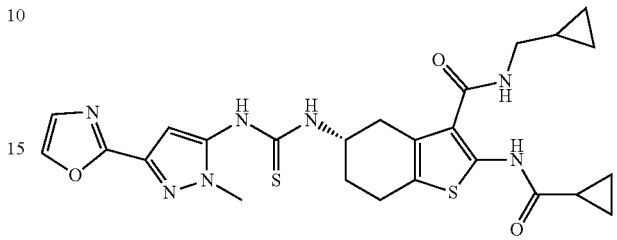

(5S)-2-(cyclopropanecarbonylamino)-N-(cyclopropylmethyl)-5-[(2-methyl-5-oxazol-2-yl-pyrazol-3-yl)carbamothioylamino]-4,5,6,7-tetrahydrobenzothiophene-3-carboxamide Intermediate 117 (32 mg, 0.097 mmol) was dissolved in DCM (2 mL) and Intermediate 321 (20 mg, 0.097 mmol) was added. The mixture was stirred at room temperature for 16 h. Concentrated under reduced pressure and purified by flash column chromatography eluting with a 5-8% methanol in DCM gradient to give the title compound (18 mg, 32% Yield). δ$_H$ (500 MHz, Chloroform-d) 12.04 (s, 1H), 7.70 (s, 1H), 7.46 (d, J=2.1 Hz, 1H), 7.21 (s, 1H), 6.66 (s, 1H), 6.30 (d, J=6.7 Hz, 1H), 5.81 (t, J=5.1 Hz, 1H), 4.90-4.82 (m, 1H), 3.83 (s, 3H), 3.31-3.21 (m, 3H), 2.91-2.80 (m, 1H), 2.77-2.63 (m, 2H), 2.16-2.07 (m, 1H), 2.07-1.98 (m, 1H), 1.70-1.63 (m, 1H), 1.12-1.03 (m, 3H), 0.94-0.88 (m, 2H), 0.62-0.54 (m, 2H), 0.29-0.24 (m, 2H). LCMS [M+H]$^+$ 540, RT 1.77 minutes (Method 12).

Intermediate 323

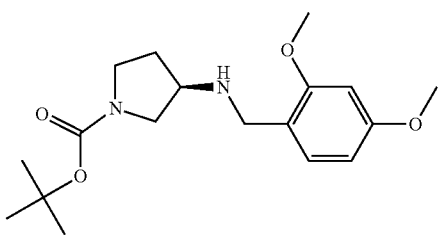 [SMILES: COc1ccc(CN[C@@H]2CCN(C(=O)OC(C)(C)C)C2)c(OC)c1]

tert-butyl (3R)-3-[(2,4-dimethoxyphenyl)methylamino]pyrrolidine-1-carboxylate

The title compound was obtained following general method 2 with tert-butyl (3R)-3-aminopyrrolidine-1-carboxylate (300 mg, 1.61 mmol), 2,4-dimethoxybenzaldehyde (267 mg, 1.61 mmol) and STAB (512 mg, 2.41 mmol). Reaction time 4 h. The residue was purified by column chromatography eluting with 0-20% MeOH in DCM to give the title compound (495 mg, 91% yield). LCMS [M+H]$^+$ 337, RT 0.91 minutes (Method 6).

Intermediate 324

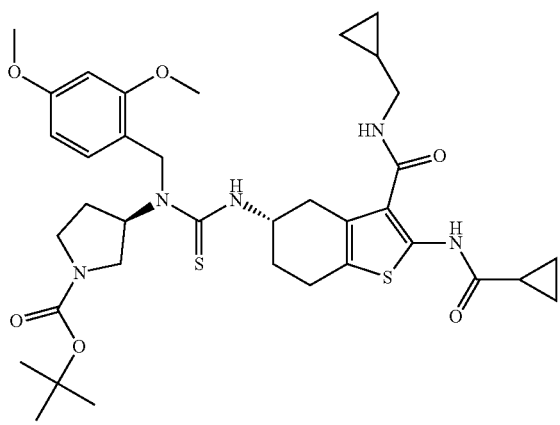 [SMILES: COc1ccc(CN(C(=S)N[C@H]2CCc3sc(NC(=O)C4CC4)c(C(=O)NCC4CC4)c3C2)[C@@H]2CCN(C(=O)OC(C)(C)C)C2)c(OC)c1]

tert-butyl (3R)-3-[[(5S)-2-(cyclopropanecarbonylamino)-3-(cyclopropylmethylcarbamoyl)-4,5,6,7-tetrahydrobenzothiophen-5-yl]carbamothioyl-[(2,4-dimethoxyphenyl)methyl]amino]pyrrolidine-1-carboxylate The title compound was obtained following general method 7 with intermediate 117 (290 mg, 0.87 mmol), triethylamine (0.364 ml, 2.60 mmol), phenyl chloromethanethioate (0.133 ml, 0.95 mmol) and intermediate 323 (497.0 mg, 1.47 mmol). Crude was purified by column chromatography eluting with 0-100% ethyl acetate in heptane to give the title compound (582 mg, 86% yield). LCMS [M+H]$^+$ 712, RT 1.4 minutes (Method 6).

Intermediate 325

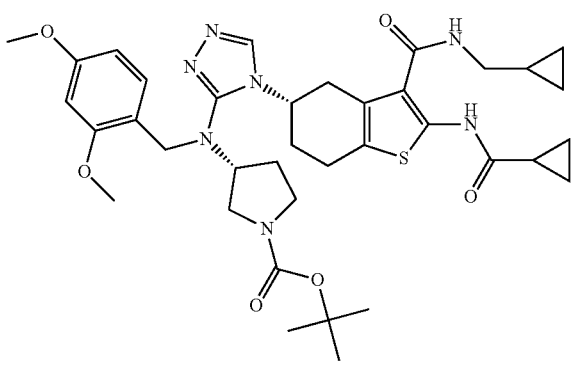 [SMILES: COc1ccc(CN(c2nncn2[C@H]2CCc3sc(NC(=O)C4CC4)c(C(=O)NCC4CC4)c3C2)[C@@H]2CCN(C(=O)OC(C)(C)C)C2)c(OC)c1]

tert-butyl (3R)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]-[(2,4-dimethoxyphenyl)methyl]amino]pyrrolidine-1-carboxylate The title compound was obtained following general method 8 with intermediate 324 (582 mg, 0.81 mmol), formic hydrazide (147.2 mg, 2.45 mmol), mercury dichloride (665.8 mg, 2.45 mmol) and triethylamine (0.34 ml, 2.45 mmol). Reaction time 2 hours. The residue was purified by column chromatography eluting with 0-20% MeOH in DCM to give the title compound (554 mg, 93% Yield). LCMS [M+H]$^+$ 720, RT 1.24 minutes (Method 11).

Intermediate 326

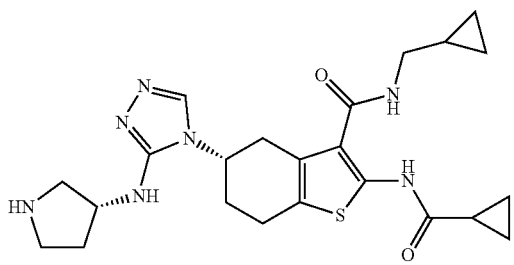 [SMILES: O=C(NCC1CC1)c1c(NC(=O)C2CC2)sc2c1C[C@@H](n1cnnc1N[C@@H]1CCNC1)CC2]

(5S)-2-(cyclopropanecarbonylamino)-N-(cyclopropylmethyl)-5-[3-[[(3R)-pyrrolidin-3-yl]amino]-1,2,4-triazol-4-yl]-4,5,6,7-tetrahydrobenzothiophene-3-carboxamide The title compound was obtained following general method 4 with intermediate 325 (554 mg, 0.53 mmol) and 4 M HCl in dioxane (3.88 ml, 15.3 mmol). Reaction time 3 h. After removing solvent crude (420 mg, bis HCl salt) material was used in the next stage without further purification. δ$_H$ (500 MHz, Methanol-d4) 8.15 (s, 1H), 4.41-4.32 (m, 1H), 4.28-4.21 (m, 1H), 3.31-3.15 (m, 4H), 3.15-3.06 (m, 1H), 3.03-2.84 (m, 5H), 2.35-2.17 (m, 3H), 1.91-1.77 (m, 2H), 1.14-1.05 (m, 1H), 1.04-0.93 (m, 4H), 0.54-0.47 (m, 2H), 0.30-0.24 (m, 2H). LCMS [M+H]$^+$ 470, RT 1.33 minutes (Method 10).

Intermediate 327

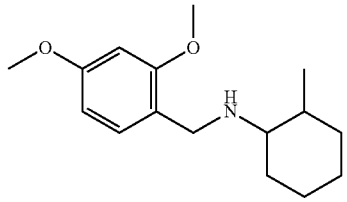 [SMILES: COc1ccc(CNC2CCCCC2C)c(OC)c1]

N-[(2,4-dimethoxyphenyl)methyl]-2-methyl-cyclohexanamine

The title compound was obtained following general method 2 with 2-methylcyclohexanamine (100 mg, 0.88 mmol), 2,4-dimethoxybenzaldehyde (147 mg, 0.88 mmol) and STAB (281 mg, 1.32 mmol). Reaction time 4 h. The residue was purified by column chromatography eluting with 0-20% MeOH in DCM to give the title compound (169 mg, 71%). LCMS [M+H]$^+$ 264, RT 0.95 minutes (Method 6).

Intermediate 328

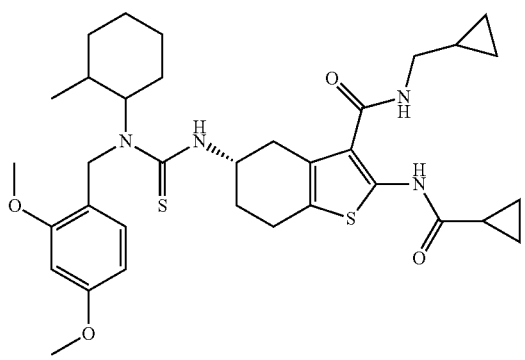 [SMILES: COc1ccc(CN(C(=S)N[C@H]2CCc3sc(NC(=O)C4CC4)c(C(=O)NCC4CC4)c3C2)C2CCCCC2C)c(OC)c1]

(5S)-2-(cyclopropanecarbonylamino)-N-(cyclopropylmethyl)-5-[[(2,4-dimethoxyphenyl)methyl-(2-methylcyclohexyl)carbamothioyl]amino]-4,5,6,7-tetrahydrobenzothiophene-3-carboxamide The title compound was obtained following general method 7 with intermediate 117 (100 mg, 0.3 mmol), triethylamine (0.125 ml, 0.9 mmol), phenyl chloromethanethioate (0.045 ml, 0.33 mmol) and intermediate 327 (134 mg, 0.51 mmol). Crude was purified by column chromatography eluting with 0-100% ethyl acetate in heptane to give the title compound (166 mg, 84% Yield). LCMS [M+H]$^+$ 639, RT 1.51 minutes (Method 6).

Intermediate 329

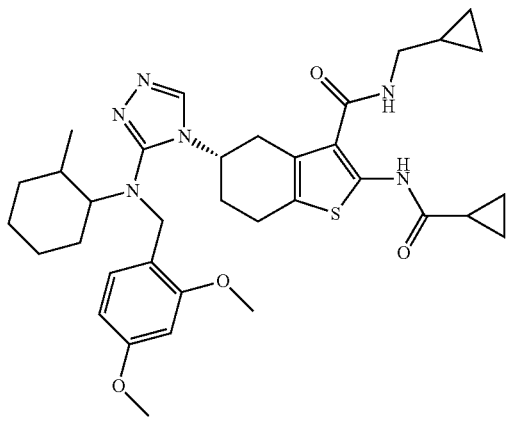 [SMILES: COc1ccc(CN(c2nncn2[C@H]2CCc3sc(NC(=O)C4CC4)c(C(=O)NCC4CC4)c3C2)C2CCCCC2C)c(OC)c1]

(5S)-2-(cyclopropanecarbonylamino)-N-(cyclopropylmethyl)-5-[3-[(2,4-dimethoxyphenyl)methyl-(2-methylcyclohexyl)amino]-1,2,4-triazol-4-yl]-4,5,6,7-tetrahydrobenzothiophene-3-carboxamide The title compound was obtained following general method 8 with intermediate 328 (166 mg, 0.25 mmol), formic hydrazide (45.8 mg, 0.76 mmol), mercury dichloride (207.3 mg, 0.76 mmol) and triethylamine (0.10 ml, 0.76 mmol). Reaction time 2 hours. The orange residue was purified by column chromatography eluting with 0-20% MeOH in DCM to give the title compound (146 mg, 85% yield). LCMS [M+H]$^+$ 647, RT 1.43 minutes (Method 11).

Intermediate 330

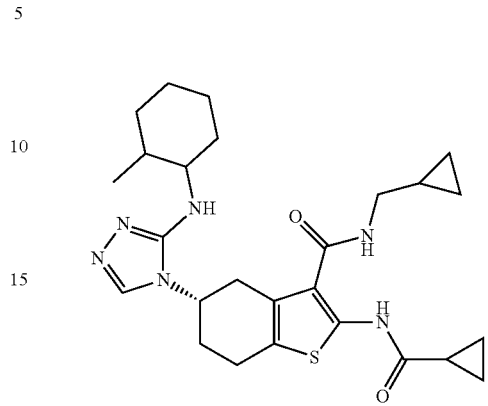

(5S)-2-(cyclopropanecarbonylamino)-N-(cyclopropylmethyl)-5-[3-[(2-methylcyclohexyl)amino]-1,2,4-triazol-4-yl]-4,5,6,7-tetrahydrobenzothiophene-3-carboxamide The title compound was obtained following general method 5 with intermediate 329 (146 mg, 0.24 mmol) and TFA (172.7 μl, 2.25 mmol). Reaction stirred for 3 h at room temperature. The crude was purified by reverse phase column chromatography eluting with 5-95% Acetonitrile (0.1% formic acid) in water (0.1% formic acid) gave the title compound (54 mg, 48% Yield) as a mixture of 4 diastereomers. δ$_H$ (500 MHz, Methanol-d4) 8.14 (s, 1H, isomer 1), 8.13 (s, 1H, isomer 2), 8.11 (s, 1H, isomer 3), 8.09 (s, 1H, isomer 4), 4.52 (m, 1H, isomers), 4.38 (m, 1H, isomers), 3.86-3.78 (m, 1H, isomer), 3.31-3.13 (m, 4H), 2.95 (m, 3H), 2.37-2.25 (m, 2H), 2.17 (m, 1H, isomer), 2.10 (m, 1H, isomer), 1.88-1.76 (m, 3H, isomers), 1.72 (m, 1H), 1.68-1.38 (m, 3H, isomers), 1.37-1.21 (m, 2H, isomers), 1.21-1.13 (m, 1H, isomer), 1.08 (m, 1H), 1.01 (m, 4H), 0.96 (m, 3H), 0.54-0.46 (m, 2H), 0.27 (m, 2H). LCMS [M+H]$^+$ 497, RT 2.25 minutes (Method 10).

Intermediate 331

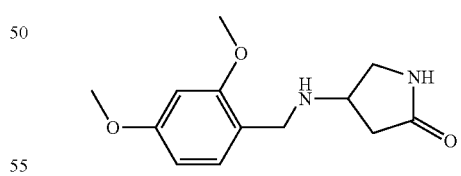

4-[(2,4-dimethoxyphenyl)methylamino]pyrrolidin-2-one

To a solution of 4-aminopyrrolidin-2-one hydrochloride (100 mg, 0.73 mmol) in DCM (10 mL) were added DIPEA (0.19 ml, 1.09 mmol) and 2,4-dimethoxybenzaldehyde (122 mg, 0.73 mmol), followed by STAB (233 mg, 1.09 mmol). The mixture was stirred at room temperature for 4 h. Then heated at 40° C. for 16 h. Reaction mixture was cooled to 0° C. and NaBH$_4$ (41.5 mg, 1.09 mmol) added and stirred at room temperature for 16 h. The mixture was quenched with saturated sodium bicarbonate and the organic layer separated. The aqueous layer was extracted with DCM (contains ~5% MeOH) (2×20 mL) and the organic fractions combined, dried over sodium sulfate and concentrated under vacuum. The residue was purified by column chromatography eluting with 0-50% MeOH in DCM to give the title compound (168 mg, 91% yield). LCMS [M+Na]*273, RT 0.61 minutes (Method 6).

Intermediate 332

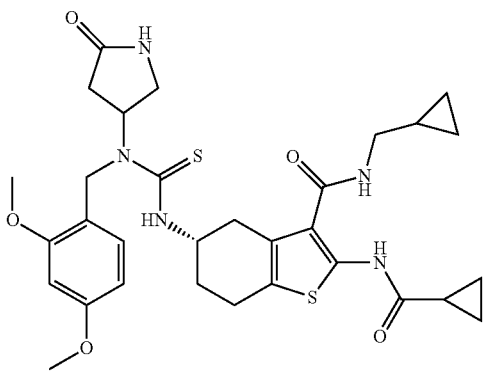 [SMILES: COc1ccc(CN(C(=S)N[C@H]2CCc3sc(NC(=O)C4CC4)c(C(=O)NCC4CC4)c3C2)C2CNC(=O)C2)c(OC)c1]

(5S)-2-(cyclopropanecarbonylamino)-N-(cyclopropylmethyl)-5-[[(2,4-dimethoxyphenyl)methyl-(5-oxopyrrolidin-3-yl)carbamothioyl]amino]-4,5,6,7-tetrahydrobenzothiophene-3-carboxamide The title compound was obtained following general method 7 with intermediate 117 (130 mg, 0.39 mmol), triethylamine (0.16 ml, 1.17 mmol), phenyl chloromethanethioate (0.059 ml, 0.42 mmol) and intermediate 331 (166 mg, 0.66 mmol). Crude was purified by column chromatography using 0-100% ethyl acetate in heptane then 0% to 10% MeOH in DCM to give the title compound (208 mg, 84%). LCMS [M+H]$^+$ 626, RT 1.11 minutes (Method 6).

Intermediate 333

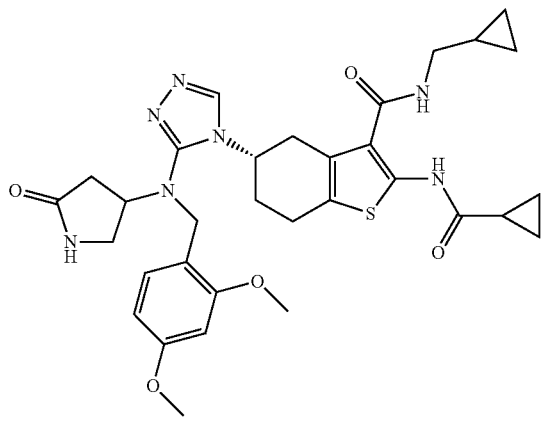 [SMILES: COc1ccc(CN(c2nncn2[C@H]2CCc3sc(NC(=O)C4CC4)c(C(=O)NCC4CC4)c3C2)C2CNC(=O)C2)c(OC)c1]

(5S)-2-(cyclopropanecarbonylamino)-N-(cyclopropylmethyl)-5-[3-[(2,4-dimethoxyphenyl)methyl-(5-oxopyrrolidin-3-yl)amino]-1,2,4-triazol-4-yl]-4,5,6,7-tetrahydrobenzothiophene-3-carboxamide The title compound was obtained following general method 8 with intermediate 332 (208 mg, 0.33 mmol), formic hydrazide (59.8 mg, 0.99 mmol), mercury dichloride (270.7 mg, 0.99 mmol) and triethylamine (0.14 ml, 0.99 mmol). Reaction time 2 hours. The residue was purified by column chromatography eluting with 0-20% MeOH in DCM to give the title compound (192 mg, 91% yield). LCMS [M+H]$^+$ 634, RT 1.03 minutes (Method 11).

Intermediate 334

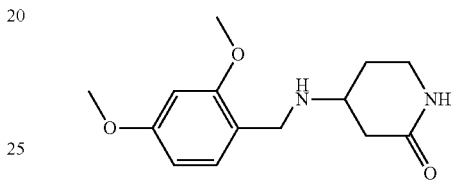

4-[(2,4-dimethoxyphenyl)methylamino]piperidin-2-one

To a solution of 4-aminopiperidin-2-one TFA (400 mg, 1.75 mmol) in EtOH (35 mL) were added DIPEA (0.458 ml, 2.63 mmol) and 2,4-dimethoxybenzaldehyde (291.3 mg, 1.75 mmol). Reaction mixture was heated at 70° C. for 6 h. Reaction mixture was cooled to 0° C. and NaBH$_4$ (94.4 mg, 2.63 mmol) was added and stirred at room temperature for 16 h. Solvent was removed water and DCM were added. The aqueous layer was extracted with DCM (2×20 mL) and the organic extracts combined, dried over sodium sulfate and concentrated under vacuum. The residue was purified by column chromatography eluting with 0-50% MeOH in DCM to give the title compound (413 mg, 89% yield). LCMS [M+Na]$^+$ 287, RT 0.71 minutes (Method 12).

Intermediate 335

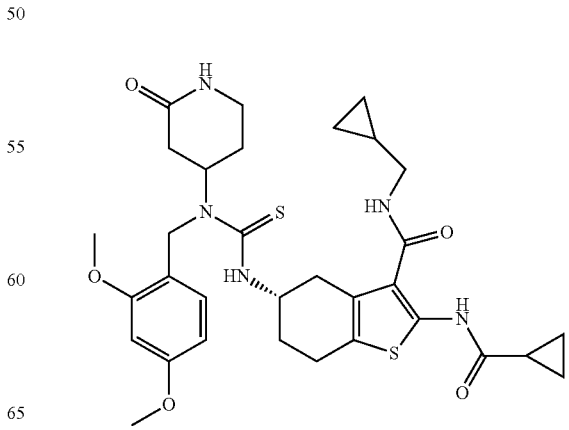

303

(5S)-2-(cyclopropanecarbonylamino)-N-(cyclopropylmethyl)-5-[[(2,4-dimethoxyphenyl)methyl-(2-oxo-4-piperidyl)carbamothioyl]amino]-4,5,6,7-tetrahydrobenzothiophene-3-carboxamide The title compound was obtained following general method 7 with intermediate 117 (300 mg, 0.9 mmol), triethylamine (0.37 ml, 2.69 mmol), phenyl chloromethanethioate (0.137 ml, 0.99 mmol) and intermediate 334 (404 mg, 1.52 mmol). Crude was purified by column chromatography eluting with 0-100% ethyl acetate in heptane then 0% to 10% MeOH in DCM to give the title compound (481 mg, 83% Yield). LCMS [M+H]⁺ 640, RT 1.85 minutes (Method 12).

Intermediate 336

(5S)-2-(cyclopropanecarbonylamino)-N-(cyclopropylmethyl)-5-[3-[(2,4-dimethoxyphenyl)methyl-(2-oxo-4-piperidyl)amino]-1,2,4-triazol-4-yl]-4,5,6,7-tetrahydrobenzothiophene-3-carboxamide The title compound was obtained following general method 8 with intermediate 335 (200 mg, 0.31 mmol), formic hydrazide (56 mg, 0.93 mmol), mercury dichloride (255 mg, 0.93 mmol) and triethylamine (0.13 ml, 0.93 mmol). Reaction time 4 hours. The residue was purified by column chromatography eluting with 0-20% MeOH in DCM to give the title compound (184 mg, 88% Yield). LCMS [M+H]⁺ 648, RT 1.74 minutes (Method 12).

Intermediate 337

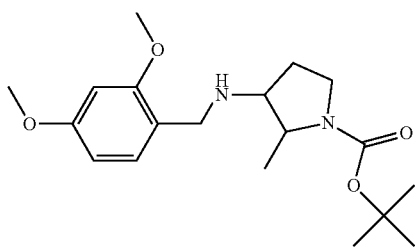 [SMILES: COc1ccc(CNC2CCN(C(=O)OC(C)(C)C)C2C)c(OC)c1]

304 tert-butyl 3-[(2,4-dimethoxyphenyl)methylamino]-2-methyl-pyrrolidine-1-carboxylate The title compound was obtained following general method 2 with tert-butyl 3-amino-2-methyl-pyrrolidine-1-carboxylate (500 mg, 2.49 mmol), 2,4-dimethoxybenzaldehyde (415 mg, 2.49 mmol) and STAB (794 mg, 3.74 mmol). Reaction time 4 h. The residue was purified by column chromatography eluting with 0-100% TBME in heptane to give the title compound (832 mg, 95% Yield). LCMS [M+H]⁺ 351, RT 1.64 minutes (Method 12).

Intermediate 338

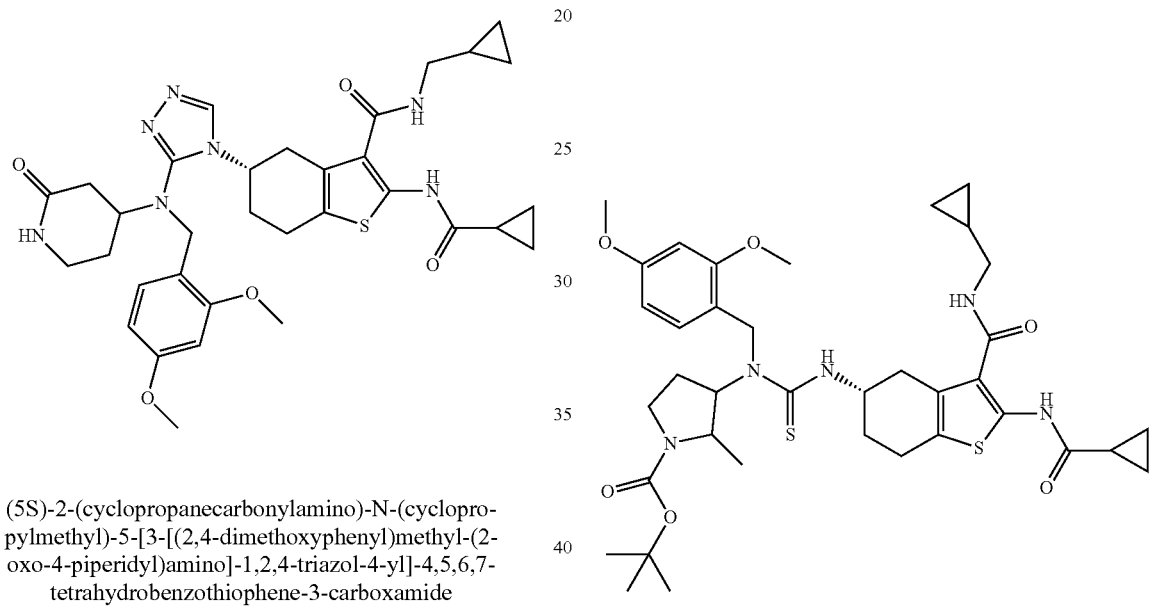

tert-butyl 3-[[(5S)-2-(cyclopropanecarbonylamino)-3-(cyclopropylmethylcarbamoyl)-4,5,6,7-tetrahydrobenzothiophen-5-yl]carbamothioyl]-[(2,4-dimethoxyphenyl)methyl]amino]-2-methyl-pyrrolidine-1-carboxylate The title compound was obtained following general method 7 with intermediate 117 (550 mg, 1.64 mmol), triethylamine (0.69 ml, 3.59 mmol), phenyl chloromethanethioate (0.251 ml, 1.81 mmol) and intermediate 337 (867.0 mg, 2.4 mmol). Crude was purified by column chromatography eluting with 0-100% ethyl acetate in heptane to give the title compound (804 mg, 67% Yield). LCMS [M+H]⁺ 726, RT 2.18 minutes (Method 6).

Intermediate 339

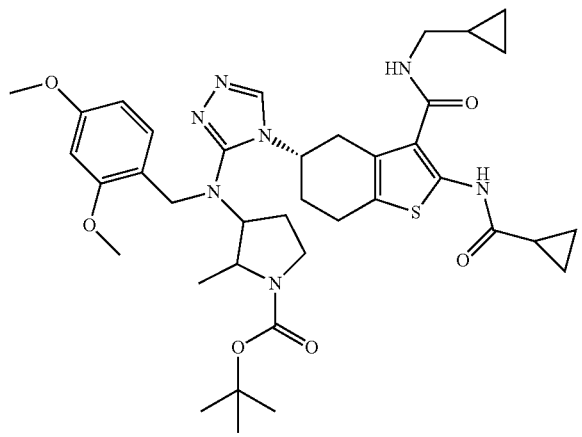

3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]-[(2,4-dimethoxyphenyl)methyl]amino]-2-methyl-pyrrolidine-1-carboxylate The title compound was obtained following general method 8 with intermediate 338 (804 mg, 1.10 mmol), formic hydrazide (199 mg, 3.32 mmol), mercury dichloride (902 mg, 3.32 mmol) and triethylamine (0.46 mL, 3.32 mmol). Reaction time 2 hours. The residue was purified by column chromatography eluting with 0-20% MeOH in DCM to give the title compound (702 mg, 84% yield). LCMS [M+H]$^+$ 734, RT 2.02 minutes (Method 12).

Intermediate 340

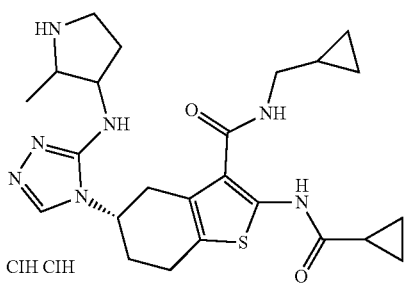

(5S)-2-(cyclopropanecarbonylamino)-N-(cyclopropylmethyl)-5-[3-[(2-methylpyrrolidin-3-yl)amino]-1,2,4-triazol-4-yl]-4,5,6,7-tetrahydrobenzothiophene-3-carboxamide dihydrochloride The title compound was obtained following general method 4 with intermediate 339 (702 mg, 0.95 mmol) and 4 M HCl in dioxane (4.78 mL, 19.13 mmol). Reaction time 16 h. After removing solvent crude (690 mg, bis HCl salt) material was used in the next stage without further purification. LCMS [M+H]$^+$ 484, RT 1.51 minutes (Method 12).

Intermediate 341

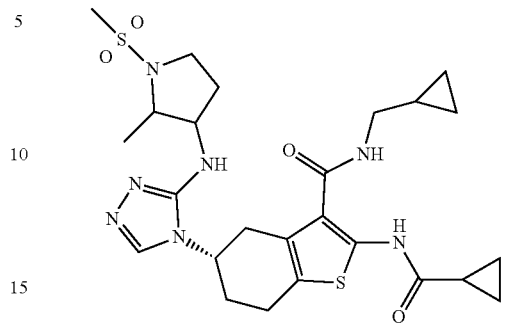

(5S)-2-(cyclopropanecarbonylamino)-N-(cyclopropylmethyl)-5-[3-[(2-methyl-1-methylsulfonyl-pyrrolidin-3-yl)amino]-1,2,4-triazol-4-yl]-4,5,6,7-tetrahydrobenzothiophene-3-carboxamide Suspension of intermediate 340 (265 mg, 0.45 mmol) was stirred in DCM (20 mL) was cooled to 0° C. then DIPEA (0.23 mL, 1.35 mmol) was added followed by methanesulfonyl methanesulfonate (70.9 mg, 0.40 mmol). Reaction stirred for 2 h at 0° C. Then warmed to room temperature. Reaction mixture was diluted with DCM (20 mL) then water (15 mL) was added and organic layer separated. The aqueous layer was extracted with DCM (2×10 mL) and the organic fractions combined, dried over sodium sulphate and concentrated under vacuum. The residue purified by column chromatography eluting with 0-100% TBME in heptane then 0 to 30% MeOH in DCM to give the title compound (137 mg, 51% Yield). LCMS [M+H]$^+$ 562, RT 2.05 minutes (Method 10).

Intermediate 342

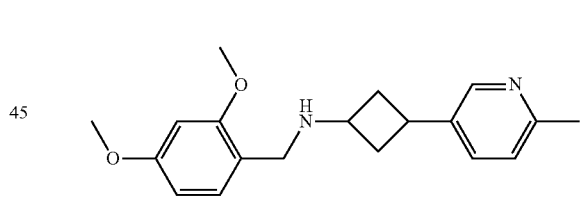

N-[(2,4-dimethoxyphenyl)methyl]-3-(6-methyl-3-pyridyl)cyclobutanamine

To a solution of 3-(6-methyl-3-pyridyl)cyclobutanone (207 mg, 1.28 mmol) in DCM (25 mL) was added (2,4-dimethoxyphenyl)methanamine (322 mg, 1.92 mmol), followed by STAB (408 mg, 1.92 mmol). The mixture was stirred at room temperature for 16 hours. The mixture was quenched with saturated sodium bicarbonate and the organic layer separated. The aqueous layer was extracted with DCM (2×30 mL) and the organic fractions combined, dried over sodium sulfate and concentrated under vacuum. The residue was purified by column chromatography eluting with 0-10% MeOH in DCM to give the title compound (318 mg, 75% Yield). 60:40 mixture of cis:trans or trans:cis isomers present. LCMS [M+H]$^+$ 313, RT 4.49 and 4.54 minutes (Method 31).

Intermediate 343

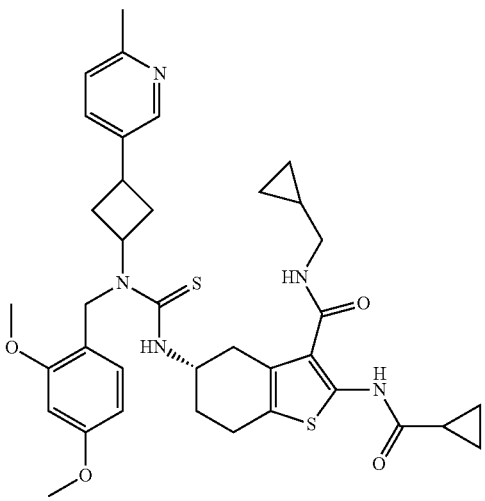

(5S)-2-(cyclopropanecarbonylamino)-N-(cyclopropylmethyl)-5-[[(2,4-dimethoxyphenyl)methyl-[3-(6-methyl-3-pyridyl)cyclobutyl]carbamothioyl]amino]-4,5,6,7-tetrahydrobenzothiophene-3-carboxamide The title compound was obtained following general method 7 with intermediate 117 (225 mg, 0.67 mmol), triethylamine (0.28 ml, 2.02 mmol), phenyl chloromethanethioate (0.10 ml, 0.74 mmol) and intermediate 342 (316.2 mg, 1.01 mmol). Crude was purified by column chromatography eluting with 0-100% ethyl acetate in heptane to give the title compound (411 mg, 83% Yield). LCMS [M+H]$^+$ 688, RT 1.89 minutes (Method 6).

Intermediate 344

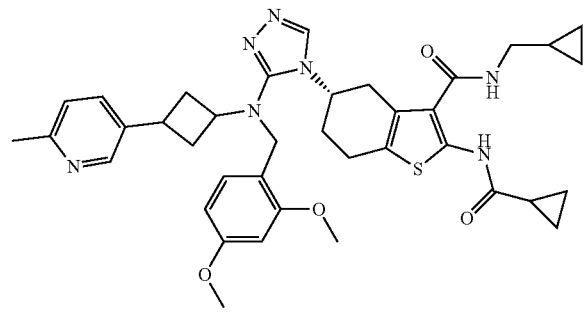

(5S)-2-(cyclopropanecarbonylamino)-N-(cyclopropylmethyl)-5-[3-[(2,4-dimethoxyphenyl)methyl-[3-(6-methyl-3-pyridyl)cyclobutyl]amino]-1,2,4-triazol-4-yl]-4,5,6,7-tetrahydrobenzothiophene-3-carboxamide The title compound was obtained following general method 8 with intermediate 343 (411 mg, 0.59 mmol), formic hydrazide (108 mg, 1.79 mmol), mercury dichloride (487 mg, 1.79 mmol) and triethylamine (0.25 mL, 1.79 mmol). Reaction time 2 hours. The residue was purified by column chromatography eluting with 0-20% MeOH in DCM to give the title compound (177 mg, 43% Yield). LCMS [M+H]$^+$ 696, RT 1.79 minutes (Method 12).

Intermediate 345

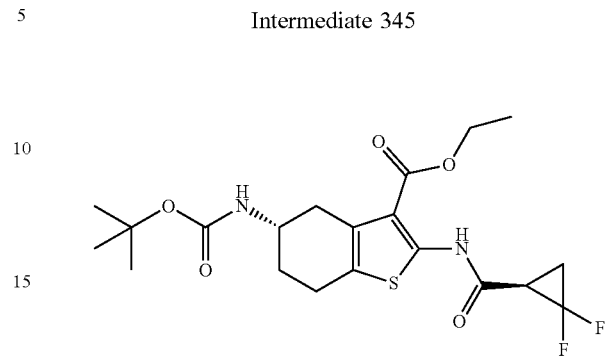

ethyl (5S)-5-(tert-butoxycarbonylamino)-2-[[(1R)-2,2-difluorocyclopropanecarbonyl]amino]-4,5,6,7-tetrahydrobenzothiophene-3-carboxylate To a stirring solution of Intermediate 567 (3000 mg, 7.96 mmol), (1R)-2,2-difluorocyclopropanecarboxylic acid (972 mg, 7.96 mmol) and pyridine (2.6 mL, 31.8 mmol) in anhydrous DCM (60 mL) at 0° C. under an atmosphere of nitrogen, was added 2,4,6-Tripropyl-1,3,5,2,4,6-trioxatriphosphorinane-2,4,6-trioxide (50%, 9.5 mL, 15.9 mmol) dropwise. The resulting solution was allowed to warm to room temperature and stirred for 18 hours. Water was added (20 mL), the mixture was stirred for 5 minutes then the layers were separated and the aqueous was extracted with more DCM (20 mL). The combined organic layers were washed with water (20 mL), brine (20 mL), dried over magnesium sulfate, filtered and concentrated in vacuo. The crude material was purified by flash column chromatography eluting with 0 to 100% of ethyl acetate in heptane gradient to afford the title compound (2.85 g, 81% Yield). $\delta_H$ (500 MHz, Chloroform-d) 11.57 (s, 1H), 4.60 (s, 1H), 4.35 (q, J=7.1 Hz, 2H), 4.06-3.82 (m, 1H), 3.18 (dd, J=17.2, 5.3 Hz, 1H), 2.80-2.69 (m, 2H), 2.60 (dd, J=17.2, 7.2 Hz, 1H), 2.56-2.49 (m, 1H), 2.28-2.19 (m, 1H), 2.07-2.00 (m, 1H), 1.87-1.75 (m, 2H), 1.46 (s, 9H), 1.39 (t, J=7.1 Hz, 3H). LCMS [M−H]$^−$ 443, RT 2.13 minutes (Method 12).

Intermediate 346

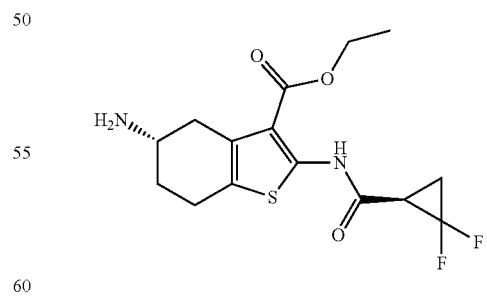

ethyl (5S)-5-amino-2-[[(1R)-2,2-difluorocyclopropanecarbonyl]amino]-4,5,6,7-tetrahydrobenzothiophene-3-carboxylate A solution of Intermediate 345 (2.85 g, 6.41 mmol) in anhydrous DCM (10 mL) was cooled to 0° C. in an ice bath and a solution of 2,2,2-trifluoroacetic acid (5.0 mL, 66.9 mmol) in anhydrous DCM (10 mL) was added dropwise. The bath was removed and the solution was stirred at room temperature for 5 hours. The mixture was partitioned between DCM (10 mL) and water (20 mL), it was then cooled to 0° C. and solid sodium hydrogen carbonate was added portion-wise until the pH of the solution was about 6-7. The layers were separated and the aqueous was extracted with more DCM (20 mL). The aqueous phase still contained product so it was basified with 2 N NaOH until pH 11-12 and extracted with DCM (10 mL), then IPA/CHCl$_3$ (1:1, 30 mL). The aqueous still contained product so 2 N HCl was added to adjust the pH to 7-8, then it was extracted with IPA/CHCl$_3$ (1:1, 3×20 mL). The combined organic extracts were then washed with brine, dried over magnesium sulphate, filtered and concentrated to afford the title compound (2.22 g, 98% Yield). δ$_H$ (500 MHz, Chloroform-d) 11.58 (s, 1H), 4.35 (q, J=7.1 Hz, 2H), 3.21-3.12 (m, 2H), 2.78 (dt, J=16.5, 4.8 Hz, 1H), 2.75-2.67 (m, 1H), 2.57-2.50 (m, 1H), 2.47 (dd, J=18.4, 9.9 Hz, 1H), 2.28-2.19 (m, 1H), 2.03-1.96 (m, 1H), 1.87-1.78 (m, 1H), 1.69-1.61 (m, 1H), 1.39 (t, J=7.1 Hz, 3H). LCMS [M+H]$^+$ 345, RT 1.49 minutes (Method 12).

Intermediate 347

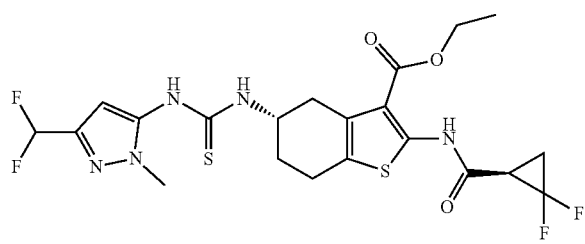 [SMILES: CCOC(=O)c1c(NC(=O)[C@H]2CC2(F)F)sc2c1C[C@@H](NC(=S)Nc1cc(C(F)F)nn1C)CC2]

ethyl (5S)-2-[[(1R)-2,2-difluorocyclopropanecarbonyl]amino]-5-[[5-(difluoromethyl)-2-methyl-pyrazol-3-yl]carbamothioylamino]-4,5,6,7-tetrahydrobenzothiophene-3-carboxylate A solution of Intermediate 346 (97%, 1.10 g, 3.10 mmol) and Intermediate 568 (797 mg, 3.10 mmol) in DCM (15 mL) were stirred at room temperature for 1 hour. Sat. aq. NH$_4$Cl solution (15 mL) was added and the biphasic mixture was stirred for 5 minutes, the layers were then separated and the aqueous was extracted further with DCM (15 mL). The combined organics were washed with brine (10 mL), dried over magnesium sulfate, filtered and concentrated. The crude material was purified by flash column chromatography eluting with 0 to 100% of ethyl acetate in heptane gradient to give the title compound (1.5 g, 91% Yield). δ$_H$ (500 MHz, DMSO-d6) 11.26 (s, 1H), 9.17 (s, 1H), 8.23 (d, J=7.3 Hz, 1H), 6.88 (t, J=54.8 Hz, 1H), 6.45 (s, 1H), 4.60-4.46 (m, 1H), 4.32 (q, J=7.1 Hz, 2H), 3.67 (s, 3H), 3.37-3.32 (m, 1H), 3.19 (dd, J=16.7, 5.1 Hz, 1H), 2.78-2.66 (m, 3H), 2.11-2.00 (m, 3H), 1.95-1.82 (m, 1H), 1.33 (t, J=7.1 Hz, 3H). LCMS [M+H]$^+$ 534, RT 2.02 minutes (Method 12).

Intermediate 348 & 349

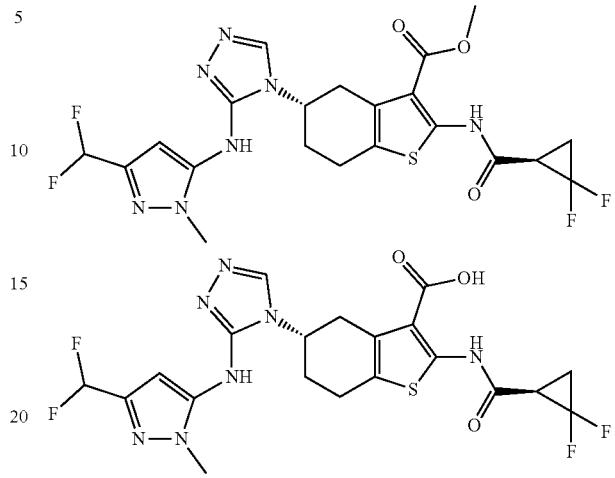

methyl (5S)-2-[[(1R)-2,2-difluorocyclopropanecarbonyl]amino]-5-[3-[[5-(difluoromethyl)-2-methyl-pyrazol-3-yl]amino]-1,2,4-triazol-4-yl]-4,5,6,7-tetrahydrobenzothiophene-3-carboxylate (348) (5S)-2-[[(1R)-2,2-difluorocyclopropanecarbonyl]amino]-5-[3-[[5-(difluoromethyl)-2-methyl-pyrazol-3-yl]amino]-1,2,4-triazol-4-yl]-4,5,6,7-tetrahydrobenzothiophene-3-carboxylic acid (349)

To a stirring solution of Intermediate 347 (1.5 g, 2.81 mmol) and N,N-diethylethanamine (1.18 mL, 8.43 mmol) in anhydrous DCM (35 mL) at 0° C. under an atmosphere of nitrogen was added methanesulfonyl chloride (239 ⌐L, 3.09 mmol). The mixture was diluted with DCM (10 mL), washed with sat. aq. NH$_4$Cl solution (10 mL) and dried over magnesium sulfate. The organic layer was concentrated to afford the intermediate carbodiimide. A solution of formic hydrazide (507 mg, 8.43 mmol) in anhydrous methanol (15 mL) was added to a solution of the above intermediate in methanol (20 mL) and the resulting mixture was stirred at room temperature under nitrogen for 1 hour. The organic solvent was reduced in vacuo and the aqueous was taken up with ethyl acetate (20 mL). The two layers were separated and the aqueous was extracted with more ethyl acetate (20 mL). The combined organic layers were then dried over magnesium sulfate, filtered and concentrated to afford a crude mixture of the title compounds.

The crude mixture obtained from the combined organic layers was purified by flash column chromatography eluting with 0 to 100% of ethyl acetate in heptane gradient to give Intermediate 348 (400 mg, 27% Yield). δ$_H$ (400 MHz, DMSO-d6) 12.06 (s, 1H), 11.24 (s, 1H), 8.25 (s, 1H), 6.78 (t, J=55.3 Hz, 1H), 6.27 (s, 1H), 4.55-4.43 (m, 1H), 3.82 (s, 3H), 3.64 (s, 31H), 3.42-3.33 (m, 2H), 2.98-2.80 (m, 3H), 2.31-2.19 (m, 1H), 2.18-2.00 (m, 3H). LCMS [M+H]$^+$ 528, RT 1.80 minutes (Method 12).

The basic aqueous from the above work up was acidified with 1 M aq. HCl to pH 3-4 and then extracted with ethyl acetate (2×20 mL) to give Intermediate 349 (340 mg, 29% yield). LCMS [M+H]$^+$ 514, RT 1.70 minutes (Method 12).

Intermediate 350

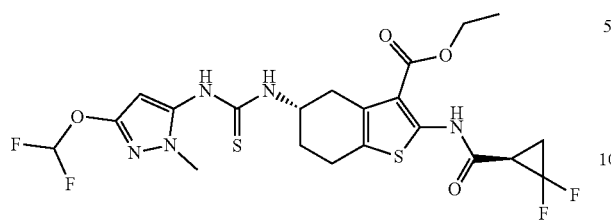

ethyl (5S)-2-[[(1R)-2,2-difluorocyclopropanecarbonyl]amino]-5-[[5-(difluoromethoxy)-2-methyl-pyrazol-3-yl]carbamothioylamino]-4,5,6,7-tetrahydrobenzothiophene-3-carboxylate To a partial suspension of Intermediate 346 (1050 mg, 3.05 mmol) in DCM (30 mL) at 0° C. was added Intermediate 644 (626 mg, 3.05 mmol) in DCM (5 mL). The reaction was allowed to warm to room temperature and then stirred for 30 minutes. The solvent was removed to give a brown oil. Purification by flash column chromatography eluting with a gradient of 0 to 60% ethyl acetate in heptane gave the title compound (1.34 g, 74% Yield). $\delta_H$ (400 MHz, DMSO-d6) 11.26 (s, 1H), 9.22 (s, 1H), 8.18 (d, J=6.6 Hz, 1H), 7.21 (t, J=73.5 Hz, 1H), 5.97 (s, 1H), 4.60-4.41 (m, 1H), 4.32 (q, J=7.1 Hz, 2H), 3.54 (s, 3H), 3.36 (dd, J=12.9, 3.4 Hz, 1H), 3.18 (dd, J=17.1, 5.2 Hz, 1H), 2.80-2.61 (m, 3H), 2.13-2.02 (m, 2H), 1.92-1.78 (m, 1H), 1.32 (t, J=7.1 Hz, 3H). LCMS [M+H]⁺ 550, RT 2.04 minutes (Method 29).

Intermediate 351

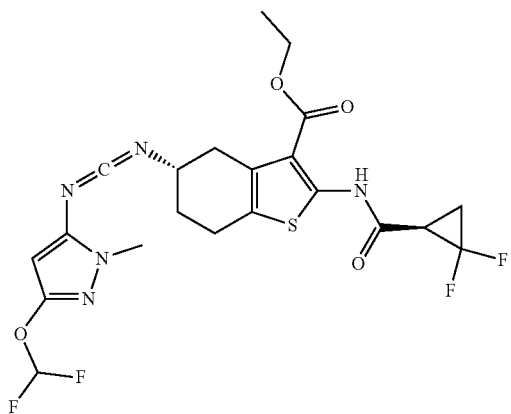

ethyl (5S)-2-[[(1R)-2,2-difluorocyclopropanecarbonyl]amino]-5-[[5-(difluoromethoxy)-2-methyl-pyrazol-3-yl]iminomethyleneamino]-4,5,6,7-tetrahydrobenzothiophene-3-carboxylate To a solution of Intermediate 350 (1092 mg, 1.99 mmol) in DCM (20 mL) at 0° C. was added triethylamine (0.83 mL, 5.96 mmol) and methanesulfonyl chloride (0.231 mL, 2.98 mmol). The reaction was stirred at 0° C. for 15 minutes. The solution was washed with sat aq. NH₄Cl solution (15 mL), dried (MgSO₄) and the solvent was removed under vacuum to give the title compound (1024 mg, quantitative). The title compound was used immediately in the formation of intermediate 352. LCMS [M+H]⁺ 516, RT 2.16 minutes (Method 29).

Intermediate 352

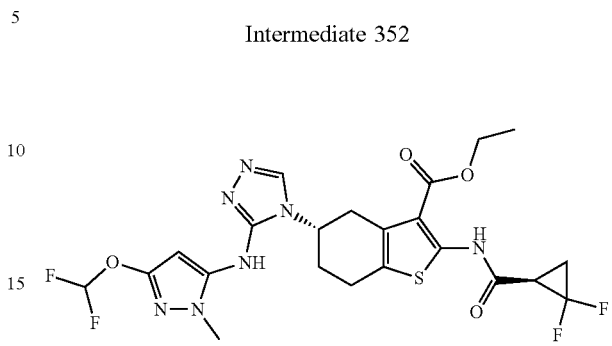

ethyl (5S)-2-[[(1R)-2,2-difluorocyclopropanecarbonyl]amino]-5-[3-[[5-(difluoromethoxy)-2-methyl-pyrazol-3-yl]amino]-1,2,4-triazol-4-yl]-4,5,6,7-tetrahydrobenzothiophene-3-carboxylate 0.5 M formic hydrazide (0.363 mg, 6.05 mmol, 12 mL of 0.5 M stock solution) in EtOH was added to the Intermediate 351 (1040 mg, 2.02 mmol). The reaction was diluted with EtOH (28 mL) and stirred for 15 minutes. To the reaction was added 1 M sodium carbonate (6.1 mL, 6.05 mmol). The reaction was heated at 40° C. for 22 hours. The reaction was filtered to remove the solid Na₂CO₃ washing with excess EtOH. The solvent was removed under reduced pressure and the resulting solid was partitioned between water (30 mL) and DCM (25 mL). A thick emulsion formed so 50% IPA/CHCl₃ (50 mL) was added. The organic layer was separated and the aqueous layer was further extracted with 50% IPA/CHCl₃ (2×20 mL). The organic layers were combined and the solvent was removed to give an orange gum. Purification by flash column chromatography eluting with a gradient of 0 to 80% ethyl acetate in heptane gave the title compound (913 mg, 68% Yield). $\delta_H$ (400 MHz, DMSO-d6) 12.02 (s, 1H), 11.27 (s, 1H), 8.23 (s, 1H), 6.97-7.40 (t, 1H, J=72 Hz), 5.71 (s, 2H), 4.54-4.39 (m, 1H), 4.30 (q, J=7.0 Hz, 2H), 3.52 (s, 3H), 3.02-2.75 (m, 4H), 2.27-2.02 (m, 4H), 1.27 (t, J=7.1 Hz, 3H). LCMS [M+H]⁺ 558, RT 2.90 minutes (Method 29).

Intermediate 353

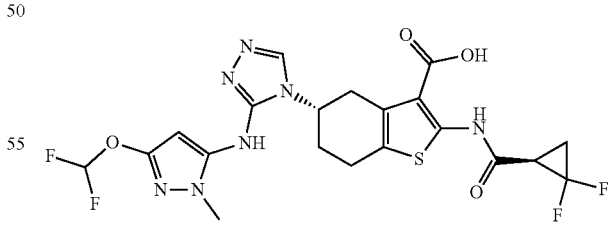

(5S)-2-[[(1R)-2,2-difluorocyclopropanecarbonyl]amino]-5-[3-[[5-(difluoromethoxy)-2-methyl-pyrazol-3-yl]amino]-1,2,4-triazol-4-yl]-4,5,6,7-tetrahydrobenzothiophene-3-carboxylic acid To a solution of Intermediate 352 (774 mg, 1.39 mmol) in methanol (4.5 mL) and THF (4.5 mL) was added lithium hydroxide hydrate (119 mg, 2.77 mmol) and then water (4.5 mL). The solution was stirred at 40° C. for 24 hours. The reaction was diluted with water (5 mL) and then concentrated under reduced pressure. The aqueous layer was extracted with EtOAc (2×10 mL) and the organic layers discarded. The aqueous layer was acidified with sat. KHSO₄ solution and extracted with EtOAc (2×15 mL). The combined organic layers were dried (MgSO₄) and the solvent was removed to give the title compound (490 mg, 67% Yield). LCMS [M+H]⁺ 530, RT 1.73 minutes (Method 12).

Intermediate 354

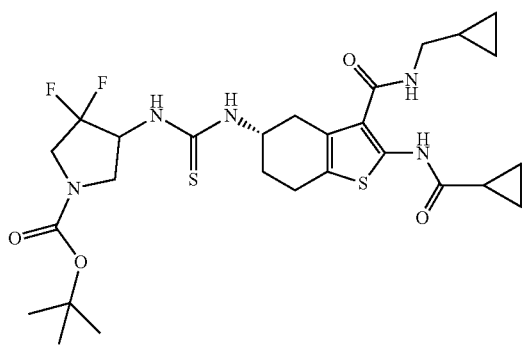

tert-butyl 4-[[(5S)-2-(cyclopropanecarbonylamino)-3-(cyclopropylmethylcarbamoyl)-4,5,6,7-tetrahydrobenzothiophen-5-yl]carbamothioylamino]-3,3-difluoro-pyrrolidine-1-carboxylate To a solution of sodium carbonate (510 mg, 4.72 mmol) in water (3 mL) at 0° C. was added DCM (4 mL) followed by thiocarbonyl dichloride (0.14 mL, 1.89 mmol). To this was added dropwise tert-butyl 4-amino-3,3-difluoro-pyrrolidine-1-carboxylate (210 mg, 0.94 mmol) in DCM (3 mL) over 1 minute. The mixture was vigorously stirred at 0° C. for 5 minutes then at room temperature for 40 minutes. The DCM layer was separated, dried (MgSO₄) and the solvent was removed to give the intermediate isothiocyanate as an oil. The oil was dissolved in DCM (5 mL) and Intermediate 117 (268 mg, 0.8 mmol) in DCM (3 mL) was added. The solution was stirred for 30 minutes. The solvent was then removed to give a residue. Purification by flash column chromatography eluting with a gradient of 0 to 60% EtOAc in heptane gave the title compound (520 mg, 84% Yield). δ_H (250 MHz, Chloroform-d) 12.01 (s, 1H), 6.87-6.60 (m, 2H), 5.73 (s, 1H), 5.57-5.25 (m, 1H), 4.98-4.79 (m, 1H), 3.78-3.57 (m, 2H), 3.37-3.17 (m, 2H), 3.11-2.94 (m, 2H), 2.81-2.64 (m, 3H), 2.58-2.38 (m, 1H), 2.00-1.82 (m, 1H), 1.69-1.60 (m, 1H), 1.55 (s, 9H), 1.12-0.73 (m, 6H), 0.64-0.47 (m, 2H), 0.32-0.13 (m, 2H). LCMS [M+H]⁺ 598, RT 2.05 minutes (Method 12).

Intermediate 355

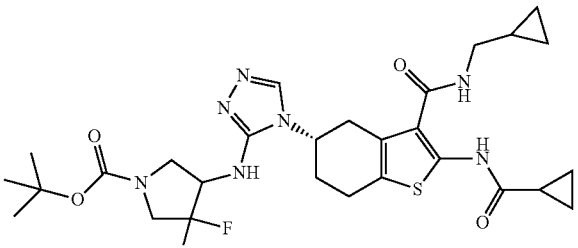

tert-butyl 4-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-3,3-difluoro-pyrrolidine-1-carboxylate To a solution of Intermediate 354 (520 mg, 0.87 mmol) in DMF (20 mL) were added formohydrazide (157 mg, 2.61 mmol) and dichloromercury (708 mg, 2.61 mmol). The reaction was stirred for 5 minutes then N,N-diethylethanamine (364 ◎L, 2.61 mmol) was added and the reaction was heated at 90° C. for 2 hours. The reaction was allowed to cool to room temperature and then was diluted with DCM (25 mL) and Kieselguhr was added. The mixture stirred for 5 minutes then filtered through a plug of Kieselguhr washing through with DCM. The filtrate was concentrated under vacuum to give an orange residue. Purification by flash column chromatography eluting with a gradient of 0 to 20% MeOH in DCM gave the title compound (350 mg, 63% Yield). LCMS [M+H]⁺ 606, RT 2.87 minutes (Method 12).

Intermediate 356

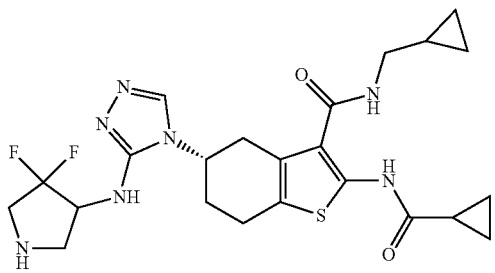 [SMILES: O=C(NCC1CC1)c1c(NC(=O)C2CC2)sc2c1C[C@@H](n1cnnc1NC1CNCC1(F)F)CC2]

(5S)-2-(cyclopropanecarbonylamino)-N-(cyclopropylmethyl)-5-[3-[(4,4-difluoropyrrolidin-3-yl)amino]-1,2,4-triazol-4-yl]-4,5,6,7-tetrahydrobenzothiophene-3-carboxamide To a solution of Intermediate 355 (297 mg, 0.45 mmol) in DCM (3 mL) was added TFA (2 mL). The solution was stirred at room temperature for 1 hour. The solvent was removed azeotroping the excess TFA with DCM/heptane (1:1, 2×20 mL) to give a brown oil. Purification by SCX column chromatography eluting with 0 to 100% 7 M NH₃ in MeOH gradient gave the title compound (230 mg, 93% Yield). δ_H (500 MHz, DMSO-d6) 11.21 (d, J=4.1 Hz, 1H), 8.15-8.04 (m, 1H), 7.72-7.57 (m, 1H), 6.26 (d, J=8.9 Hz, 1H), 4.42-4.22 (m, 2H), 3.43-3.35 (m, 1H), 3.23-2.94 (m, 5H), 2.94-2.78 (m, 3H), 2.74 (dd, J=11.6, 8.5 Hz, 1H), 2.24-2.04 (m, 2H), 1.96-1.86 (m, 1H), 1.09-0.95 (m, 1H), 0.91-0.75 (m, 4H), 0.43-0.28 (m, 2H), 0.25-0.08 (m, 2H). LCMS [M+H]$^+$ 506, RT 1.54 minutes (Method 12).

Intermediate 357

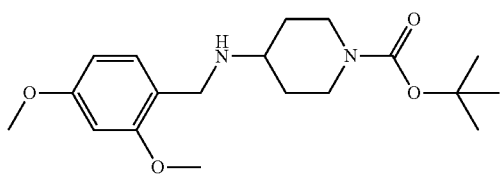 [SMILES: COc1ccc(CNC2CCN(C(=O)OC(C)(C)C)CC2)c(OC)c1]

tert-butyl 4-[(2,4-dimethoxyphenyl)methylamino]piperidine-1-carboxylate

To a solution of tert-butyl 4-aminopiperidine-1-carboxylate (300 mg, 1.5 mmol) and 2,4-dimethoxybenzaldehyde (249 mg, 1.5 mmol) in DCM (10 mL) was added sodium triacetoxyborohydride (476 mg, 2.25 mmol). The reaction was stirred at room temperature for 18 hours. Another portion of sodium triacetoxyborohydride (476 mg, 2.25 mmol) was added followed by 3 drops of AcOH. The mixture was stirred for a further 5 hours. The mixture was diluted with sat. aq. NaHCO$_3$ solution (10 mL) and the organic layer was separated. The aqueous layer was further extracted with DCM (2×10 mL) and the combined organic layers were dried (MgSO$_4$). The solvent was concentrated in vacuo to give an oil. Purification by flash column chromatography eluting with 0 to 10% 7M NH$_3$ MeOH in DCM gradient gave the title compound (379 mg, 72% Yield). $\delta_H$ (250 MHz, Chloroform-d) 7.12 (d, J=7.9 Hz, 1H), 6.48-6.38 (m, 2H), 4.07-3.92 (m, 2H), 3.80 (d, J=3.1 Hz, 6H), 3.75 (s, 2H), 2.87-2.68 (m, 2H), 2.68-2.50 (m, 1H), 1.91-1.75 (m, 2H), 1.45 (s, 9H), 1.40-1.19 (m, 2H). LCMS [M+H]$^+$ 351, RT 1.61 minutes (Method 12).

Intermediate 358

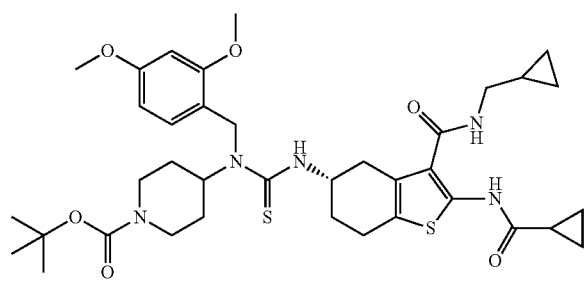 [SMILES: COc1ccc(CN(C(=S)N[C@H]2CCc3sc(NC(=O)C4CC4)c(C(=O)NCC4CC4)c3C2)C2CCN(C(=O)OC(C)(C)C)CC2)c(OC)c1]

tert-butyl 4-[[(5S)-2-(cyclopropanecarbonylamino)-3-(cyclopropylmethylcarbamoyl)-4,5,6,7-tetrahydrobenzothiophen-5-yl]carbamothioyl-[(2,4-dimethoxyphenyl)methyl]amino]piperidine-1-carboxylate A solution of intermediate 117 (200 mg, 0.6 mmol) and triethylamine (251 µl, 1.8 mmol) in DCM (8 mL) was added dropwise over 5 minutes to a solution of phenylchloromethanethioate (91.4 µl, 0.66 mmol) in DCM (8 mL) at 0° C. The solution was stirred for 30 minutes at 0° C. and then Intermediate 357 (357.34 mg, 1.02 mmol) in DCM (6 mL) was added at 0° C. The reaction was allowed to warm to room temperature and stirred for 20 hours. The reaction was diluted with DCM (10 mL), washed with water (30 mL), saturated aq. NaHCO$_3$ solution (30 mL) and then dried (MgSO$_4$). The organic layer was concentrated in vacuo to give an oil. Purification by flash column chromatography eluting with 0 to 60% EtOAc in heptane gradient gave the title compound (400 mg, 92% Yield). LCMS [M+H]$^+$ 726, RT 2.19 minutes (Method 12).

Intermediate 359

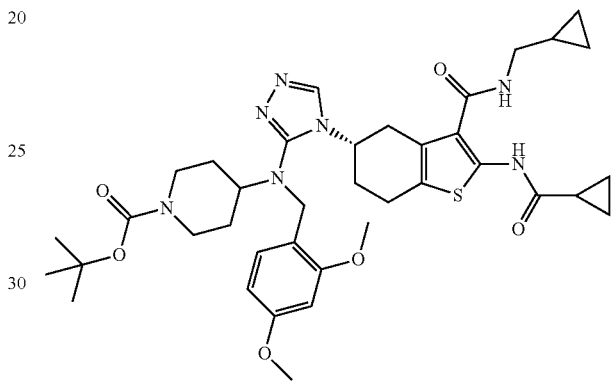

tert-butyl 4-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]-[(2,4-dimethoxyphenyl)methyl]amino]piperidine-1-carboxylate To a solution of Intermediate 358 (400 mg, 0.55 mmol) in DMF (5 mL) was added formic hydrazide (99 mg, 1.65 mmol) and mercury dichloride (449 mg, 1.65 mmol). The mixture was stirred for 5 minutes then triethylamine (230 µl, 1.65 mmol) was added. The mixture was then heated at 90° C. for 3 hours. The reaction was allowed to cool, diluted with DCM (10 mL) and ~5 g Kieselguhr was added. The mixture was stirred for 5 minutes then filtered through a plug of Kieselguhr washing the Kieselguhr with DCM (20 mL). The filtrate was concentrated under vacuum to give an orange oil. Purification by flash column chromatography eluting with 0 to 10% MeOH in DCM gradient gave the title compound (290 mg, 72% yield). $\delta_H$ (500 MHz, Chloroform-d) 12.09 (s, 1H), 7.99 (s, 1H), 6.78 (d, J=8.3 Hz, 1H), 6.29 (d, J=2.3 Hz, 1H), 6.24 (dd, J=8.2, 2.4 Hz, 1H), 5.53-5.38 (m, 1H), 4.30-4.08 (m, 4H), 3.72 (s, 3H), 3.62 (s, 3H), 3.38-3.11 (m, 3H), 2.81-2.60 (m, 4H), 2.60-2.39 (m, 2H), 2.06-1.89 (m, 2H), 1.87-1.74 (m, 1H), 1.74-1.62 (m, 1H), 1.44 (s, 9H), 1.16-1.04 (m, 2H), 1.00-0.82 (m, 3H), 0.57-0.45 (m, 2H), 0.26-0.12 (m, 2H). LCMS [M+H]$^+$ 734, RT 2.04 minutes (Method 12).

Intermediate 360

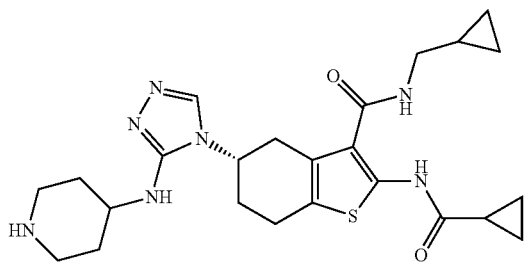 [SMILES: O=C(NCC1CC1)c1c(NC(=O)C2CC2)sc2c1C[C@@H](n1cnnc1NC1CCNCC1)CC2]

(5S)-2-(cyclopropanecarbonylamino)-N-(cyclopropylmethyl)-5-[3-(4-piperidylamino)-1,2,4-triazol-4-yl]-4,5,6,7-tetrahydrobenzothiophene-3-carboxamide To a solution of Intermediate 359 (290 mg, 0.4 mmol) in DCM (3 mL) was added TFA (0.6 mL, 7.90 mmol). The solvent was removed azeotroping the excess TFA with 1:1 DCM/heptane to give an off white residue. Purification by SCX column chromatography eluting with 0 to 100% 7 M NH$_3$ in MeOH gradient gave the title compound (165 mg, 84% Yield). δ$_H$ (500 MHz, Methanol-d4) 8.10 (s, 1H), 4.43-4.30 (m, 1H), 3.73-3.59 (m, 1H), 3.30-3.12 (m, 3H), 3.12-3.02 (m, 2H), 3.00-2.82 (m, 3H), 2.71 (td, J=12.5, 2.4 Hz, 2H), 2.32-2.22 (m, 2H), 2.10-2.00 (m, 2H), 1.86-1.77 (m, 1H), 1.56-1.42 (m, 2H), 1.12-1.03 (m, 1H), 1.03-0.91 (m, 4H), 0.53-0.45 (m, 2H), 0.32-0.22 (m, 2H). LCMS [M+H]$^+$ 484, RT 1.24 minutes (Method 10).

Intermediate 361

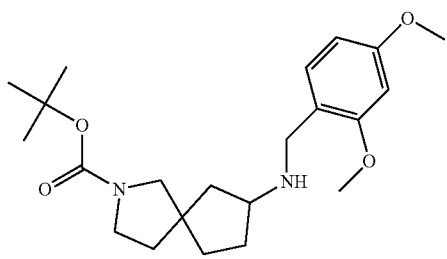 [SMILES: COc1ccc(CNC2CCC3(CCN(C(=O)OC(C)(C)C)C3)C2)c(OC)c1]

tert-butyl 7-{[(2,4-dimethoxyphenyl)methyl]amino}-2-azaspiro[4.4]nonane-2-carboxylate To a solution of tert-butyl 7-oxo-2-azaspiro[4.4]nonane-2-carboxylate (542 mg, 2.26 mmol, preparation as described in Tetrahedron Letters 2011, 52, 4204) in dichloromethane (8 mL) was introduced acetic acid (1.36 g, 22.6 mmol) and 2,4-dimethoxybenzylamine (757 mg, 4.53 mmol). After 30 minutes, sodium triacetoxyborohydride (4.80 g, 22.6 mmol) was introduced (portion-wise, approximately 1.1 g every 30 minutes). The reaction mixture was stirred at room temperature for 8 hours under an atmosphere of nitrogen then saturated aqueous potassium carbonate (20 mL) introduced. After 20 minutes, the two-phase mixture was diluted with dichloromethane (40 mL) and water (15 mL), and the two phases separated. The organic phase was washed with saturated aqueous potassium carbonate (20 mL) and brine (20 mL) then dried over sodium sulfate. Following filtration, the filtrate was concentrated in-vacuo and purified by flash column chromatography (dichloromethane containing 1% by volume of 7 M ammonia in methanol and a 0-6% gradient of methanol) to furnish the title compound (0.589 g, 48% Yield). LCMS [M+H]$^+$ 391, RT 2.10 and 2.16 mins (diastereomers) (Method 10).

Intermediate 362

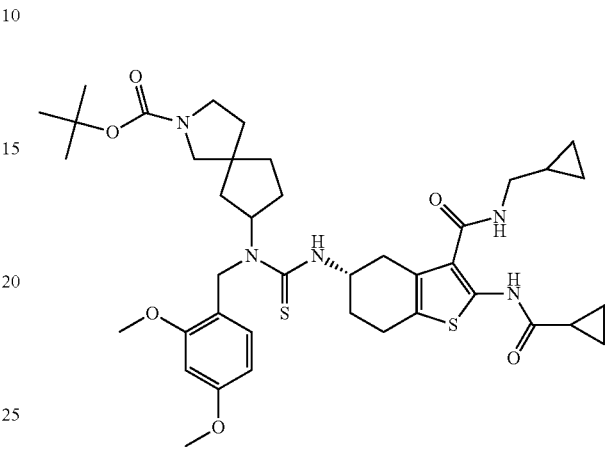

tert-butyl 8-[[(5S)-2-(cyclopropanecarbonylamino)-3-(cyclopropylmethylcarbamoyl)-4,5,6,7-tetrahydrobenzothiophen-5-yl]carbamothioyl-[(2,4-dimethoxyphenyl)methyl]amino]-2-azaspiro[4.4]nonane-2-carboxylate To a solution of O-phenyl chlorothioformate (286 mg, 1.66 mmol) in anhydrous dichloromethane (10 mL) at 0° C. was introduced a solution of Intermediate 117 (503 mg, 1.51 mmol) and triethylamine (458 mg, 4.52 mmol) in anhydrous dichloromethane (5 mL). After 40 minutes, a solution of Intermediate 361 (589 mg, 1.09 mmol) in anhydrous dichloromethane (5 mL) was introduced and the mixture warmed to room temperature for 14 hours. The reaction mixture was diluted with dichloromethane (20 mL), washed with saturated aqueous sodium bicarbonate (20 mL) and dried over sodium sulfate. Following filtration, the filtrate was concentrated in-vacuo and the residue purified by flash column chromatography (10-90% gradient of ethyl acetate in heptane) to furnish the title compound (831 mg, 64% Yield) as a mixture of diastereomers. LCMS [M+H]$^+$ 766, RT 4.85 mins (Method 10).

Intermediate 363

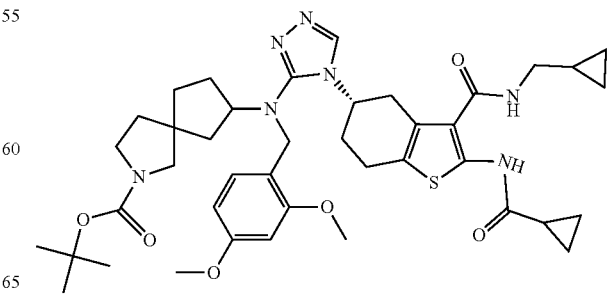

tert-butyl 8-[[4-[(5S)-2-(cyclopropanecarbo-nylamino)-3-(cyclopropylmethylcarbamoyl)-4,5,6,7-tetrahydrobenzothiophen-5-yl]-1,2,4-triazol-3-yl]-[(2,4-dimethoxyphenyl)methyl]amino]-2-azaspiro[4.4]nonane-2-carboxylate To a solution of Intermediate 362 (831 mg, 89% purity, 0.96 mmol) in anhydrous N,N-dimethylformamide (14 mL) under an atmosphere of nitrogen was introduced formyl hydrazine (195 mg, 3.25 mmol) and mercury(II) chloride (883 mg, 3.25 mmol). After 5 minutes stirring at room temperature, triethylamine (0.45 mL, 3.25 mmol) was introduced and the reaction mixture warmed to 90° C. for 2 hours. After cooling to room temperature, the resulting suspension was diluted with dichloromethane (40 mL) and kieselguhr (2 g) introduced with vigorous stirring for 30 minutes. The suspension was then filtered and the filtrate concentrated in-vacuo. The residue was dissolved in 1:1 ethyl acetate/tetrahydrofuran (40 mL), washed with water (2×5 mL) and brine (5 mL), then dried over sodium sulfate. After filtration the filtrate was concentrated in-vacuo to furnish the title compound (838 mg, 99% Yield) as a mixture of diastereomers. LCMS [M+H]$^+$ 774, RT 4.12-4.17 mins (part resolved diastereomers) (Method 10).

Intermediate 364

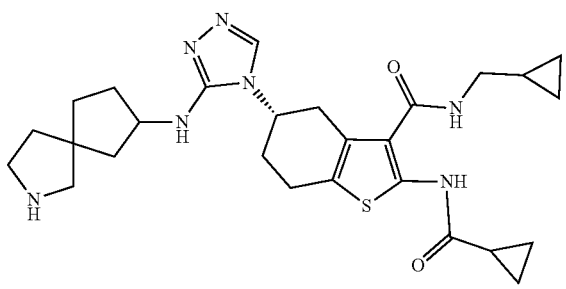 [SMILES: O=C(NCC1CC1)c1c(NC(=O)C2CC2)sc2c1C[C@@H](n1cnnc1NC1CCC3(CCNC3)C1)CC2]

(5S)-5-[3-({2-azaspiro[4.4]nonan-7-yl}amino)-4H-1,2,4-triazol-4-yl]-2-cyclopropaneamido-N-(cyclopropylmethyl)-4,5,6,7-tetrahydro-1-benzothiophene-3-carboxamide To a solution of Intermediate 363 (838 mg, 88% purity, 0.95 mmol) in 1,4-dioxane (20 mL) was introduced hydrogen chloride (2.71 mL of a 4 M solution in 1,4-dioxane, 10.83 mmol) then concentrated aqueous hydrogen chloride (1 mL). The resulting solution was stirred at room temperature for 60 minutes then re-treated with concentrated aqueous hydrogen chloride (1 mL). After 30 minutes the solution was concentrated in-vacuo to furnish an aqueous residue which was basified with saturated aqueous sodium carbonate resulting in a suspension of a black solid. Tetrahydrofuran (50 mL) was introduced to this suspension then the two-phase mixture filtered. The filtrate (two-phase) was diluted with ethyl acetate (30 mL), the organic phase separated, then washed with saturated aqueous sodium bicarbonate (2×5 mL) and brine (5 mL). The organic phase was concentrated in-vacuo to furnish the title compound (917 mg, quantitative) as a mixture of diastereoisomers, which was carried forward to the next synthetic step without purification. LCMS [M+H]$^+$ 524, RT 2.05 mins (Method 12).

Intermediate 365

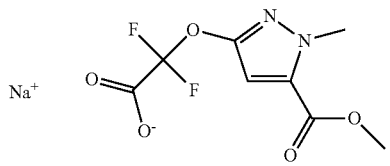 [SMILES: [Na+] ; COC(=O)c1cc(OC(F)(F)C(=O)[O-])nn1C]

Sodium 2,2-difluoro-2-{[5-(methoxycarbonyl)-1-methyl-1H-pyrazol-3-yl]oxy}acetate To a solution of methyl 3-hydroxy-1-methyl-1H-pyrazole-5-carboxylate (2.00 g, 12.81 mmol) in anhydrous 1,4-dioxane (30 mL) was introduced (dropwise addition) sodium hydride (680 mg of a 50% dispersion in mineral oil suspended in 5 mL dry 1,4-dioxane) under a stream of nitrogen. The suspension was stirred for 30 minutes at room temperature under an atmosphere of nitrogen. Sodium bromodifluoroacetate (2.77 g, 14.1 mmol) was then introduced (portion-wise over 5 minutes) and the reaction mixture warmed to 60° C. for 20 hours. After a further treatment with sodium bromodifluoroacetate (1.00 g, 5.10 mmol, portion-wise addition over 5 minutes) and warming to 80° C. for 20 hours, the reaction mixture was diluted with 1,4-dioxane (30 mL) and the suspension filtered (at room temperature). The filter cake was washed with 1,4-dioxane (30 mL) and the combined filtrates concentrated in-vacuo to furnish the title compound (3.4 g, 97% Yield). δ$_H$(500 MHz, D$_2$O) 6.70 (s, 1H), 4.06 (s, 3H), 3.94 (s, 3H); δ$_F$ (H-decoupled) −78.71.

Intermediates 366 and 367

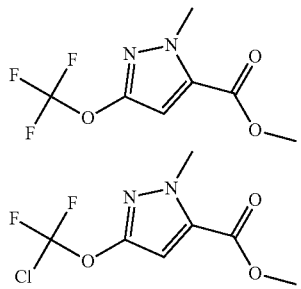

methyl 1-methyl-3-(trifluoromethoxy)-1H-pyrazole-5-carboxylate & methyl 1-methyl-3-(chlorodifluoromethoxy)-1H-pyrazole-5-carboxylate

To a solution of Intermediate 365 (1187 mg, 4.36 mmol) in 1,4-dioxane (15 mL) was introduced hydrogen chloride (1.5 mL of a 4 M solution in 1,4-dioxane, 6 mmol) and the solution immediately concentrated in-vacuo. The residue was re-dissolved in deuterochloroform (20 mL pre-dried over magnesium sulfate and filtered) then transferred to a PTFE bottle. Xenon difluoride (2.5 g, 14.99 mmol) was introduced in one portion and the bottle flushed with nitrogen and capped. The reaction mixture was subjected to sonication for 2 minutes, then stirred at room temperature for a further 20 minutes. After diluting with chloroform (50 mL), the solution was washed with a 2:1 mixture of saturated aqueous sodium bicarbonate and saturated aqueous calcium hydroxide (6 mL). The organic phase was dried over magnesium sulfate, filtered and concentrated in-vacuo to furnish a 67:33 mixture of the title compounds (1.56 g, 49% total purity LCMS-UV$_{215}$, ~78% total Yield). LCMS [M+H]$^+$ 225, RT 3.12 mins and LCMS [M+H]$^+$ 241/243, RT 3.29 mins (Method 10).

Intermediates 368 and 369

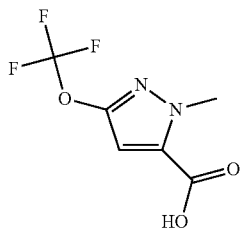 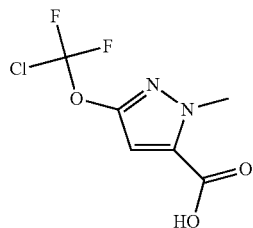

1-methyl-3-(trifluoromethoxy)-1H-pyrazole-5-carboxylic acid &

1-methyl-3-(chlorodifluoromethoxy)-1H-pyrazole-5-carboxylic acid

A mixture of Intermediates 366 and 367 (1.565 g at 33% total purity LCMS-UV$_{215}$, [18] 2.30 mmol) was dissolve in methanol (50 mL) and treated with sodium hydroxide (0.84 g, 20.95 mmol, dissolved in 25 mL of water). After 12 hours at room temperature, the pH of the reaction mixture was adjusted to 7 with 6 M aqueous hydrogen chloride and the reaction mixture concentrated in-vacuo to remove methanol. The residual aqueous solution was acidified to pH 3 (with 2 M aqueous hydrogen chloride) and extracted with ethyl acetate (3×50 mL). After saturating the aqueous phase with sodium chloride, the brine solution was extracted with 1:1 tetrahydrofuran/ethyl acetate (2×50 mL extractions). The combined organic extracts were concentrated in-vacuo, re-dissolved in ethyl acetate and dried over magnesium sulfate. Following filtration, the filtrate was concentrated in-vacuo to furnish a 71:29 mixture of the title compounds (1.113 g at 63% total purity LCMS-UV$_{215}$, quantitative). LCMS [M−H]$^−$ 209, RT 2.38 mins and LCMS [M−H]$^−$ 225/227, RT 2.61 mins (Method 10).

Intermediates 370 and 371

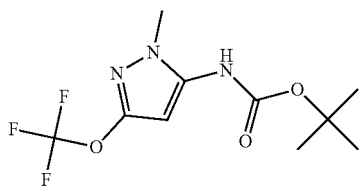

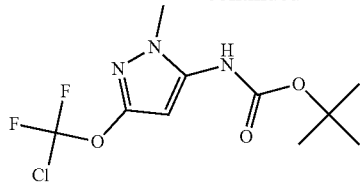

tert-butyl N-[1-methyl-3-(trifluoromethoxy)-1H-pyrazol-5-yl]carbamate (370) & tert-butyl N-[1-methyl-3-(chlorodifluoromethoxy)-1H-pyrazol-5-yl]carbamate (371)

A mixture of Intermediates 368 and 369 (1.113 g at 45% purity LCMS-UV$_{215}$, ~2.38 mmol) was dissolved in tert-butanol (25 mL) and treated with diisopropylethylamine (0.95 mL, 5.83 mmol) and diphenylphosphoryl azide (4.37 g, 15.89 mmol). The reaction mixture was warmed to 85° C. under an atmosphere of nitrogen for 5 hours. After the reaction mixture was concentrated in-vacuo, the residue was purified by flash column chromatography (5-40% gradient of ethyl acetate in heptane) to furnish a 2:1 mixture of the title compounds 370 and 371 respectively (0.552 g, 78% Yield).

Intermediate 370: δ$_H$ (400 MHz, d-chloroform) 6.41 (s, 1H), 5.96 (s, 1H), 3.67 (s, 3H), 1.51 (s, 9H); δ$_F$(H-decoupled, 376 MHz, d-chloroform) −59.2; LCMS [M+H]$^+$ 282, RT 3.26 mins (Method 10).

Intermediate 371: δ$_H$ (400 MHz, d-chloroform) 6.41 (s, 1H), 6.01 (s, 1H), 3.68 (s, 3H), 1.51 (s, 9H); δ$_F$(H-decoupled, 376 MHz, d-chloroform) −27.6; LCMS [M+H]$^+$ 298/300, RT 3.39 mins (Method 10).

Intermediates 372 & 373

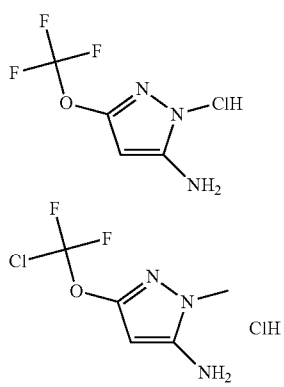

1-methyl-3-(trifluoromethoxy)-1H-pyrazol-5-amine hydrochloride (372) &

1-methyl-3-(chlorodifluoromethoxy)-1H-pyrazol-5-amine hydrochloride (373)

To solution of hydrogen chloride (5.4 mL of a 4 M solution in 1,4-dioxane) at 0° C. a solution of intermediates 370 & 371 (2:1 respectively, 0.552 g, 1.86 mmol) in 1,4-dioxane (2 mL) was added drop-wise over 5 minutes. The reaction mixture was warmed to room temperature for 4 hours, then concentrated in-vacuo to furnish a 2:1 mixture of the title compounds 372 and 373 respectively (0.318 g, 72% Yield).

Intermediates 372: δ$_H$ (500 MHz, d$_6$-dmso) 5.10 (q, J=1.0 Hz, 1H), 3.443 (s, 3H); δ$_F$ (376 MHz, d6-dmso) −57.77; LCMS [M+H]$^+$ 181, RT 0.92 mins (Method 17).

Intermediates 373: δ$_H$ (500 MHz, d$_6$-dmso) 5.12 (t, J=1.0 Hz, 1H), 3.449 (s, 3H); δ$_F$ (376 MHz, d6-dmso) −25.98; LCMS [M+H]$^+$ 198/200, RT 1.32 mins (Method 17).

Intermediate 374

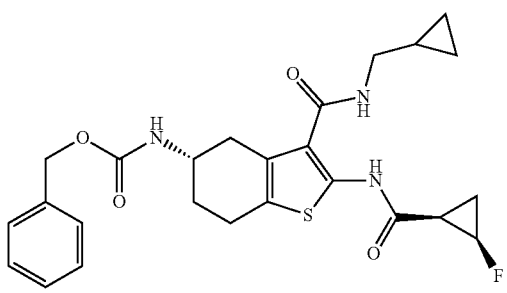 [SMILES: O=C(N[C@H]1CCc2sc(NC(=O)[C@H]3C[C@H]3F)c(C(=O)NCC3CC3)c2C1)OCc1ccccc1]

benzyl N-[(5S)-3-(cyclopropylmethylcarbamoyl)-2-[[(1R,2R)-2-fluorocyclopropanecarbonyl]amino]-4,5,6,7-tetrahydrobenzothiophen-5-yl]carbamate To a solution of Intermediate 293 (446 mg, 81% purity, 0.87 mmol) in anhydrous dichloromethane (20 mL) was introduced pyridine (406 mg, 5.11 mmol) followed by (1R,2R)-2-fluorocyclopropane-1-carboxylic acid (117 mg, 1.12 mmol). The reaction mixture was cooled to 0° C. under an atmosphere of nitrogen then T3P (1.22 mL of a 50% solution in ethyl acetate, 2.05 mmol) introduced dropwise and the reaction mixture allowed to warm to room temperature for 20 hours. Water (5 mL) was then introduced (dropwise) to the vigorously stirred reaction mixture and stirring continued for 5 minutes after which the mixture was diluted with dichloromethane (5 mL). After separation of the phases, the aqueous phase was extracted with dichloromethane (10 mL), the dichloromethane extracts combined and washed with brine (5 mL). The combined dichloromethane extract was dried over sodium sulfate, filtered and the filtrate adsorbed onto silica in-vacuo. Purification of the dry-loaded material by flash column chromatography (10-100% gradient of ethyl acetate in heptane) furnished the title compound (0.319 g, 68% Yield). LCMS [M+H]$^+$ 486; RT 3.57 mins (Method 10).

Intermediate 375

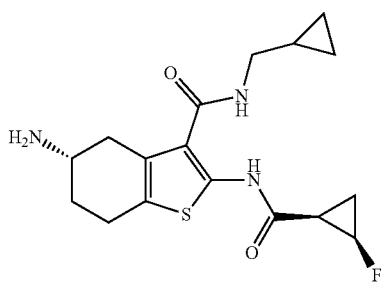 [SMILES: N[C@H]1CCc2sc(NC(=O)[C@H]3C[C@H]3F)c(C(=O)NCC3CC3)c2C1]

(5S)-5-amino-N-(cyclopropylmethyl)-2-[[(1R,2R)-2-fluorocyclopropanecarbonyl]amino]-4,5,6,7-tetrahydrobenzothiophene-3-carboxamide To a solution of Intermediate 374 (319 mg, 0.59 mmol) in 2:1 ethanol/ethyl acetate (15 mL) was introduced 10% Pd on carbon (50% wet, 419 mg) and the suspension subjected to hydrogenolysis (1 atm hydrogen) for 16 h at room temperature. The reaction mixture was then filtered and the filtrate treated with 10% Pd on carbon (50% wet, 319 mg) and subjected to hydrogenolysis (1 atm hydrogen) for 24 hours. After filtration of the reaction mixture (through a shallow bed of kieselguhr under an atmosphere of nitrogen) and washing the filter-cake with ethanol (20 mL), the filtrate was concentrated in-vacuo to furnish the title compound (169 mg, 54% Yield). LCMS [M+H]$^+$ 352, RT 1.26 mins (Method 12).

Intermediates 376 and 377

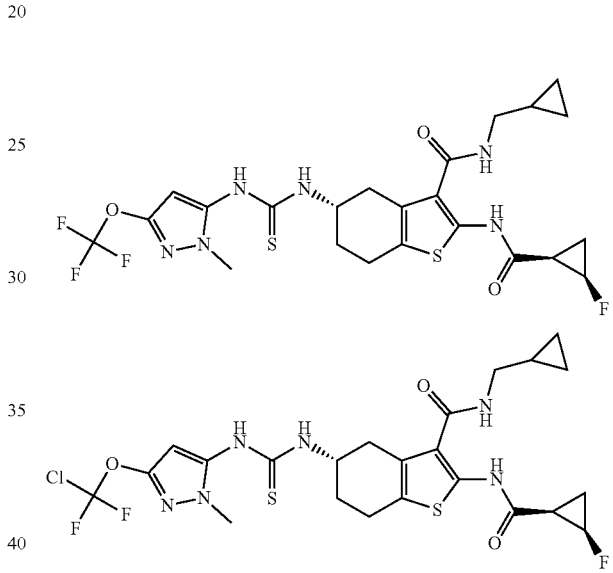

(5S)—N-(cyclopropylmethyl)-2-[[(1R,2R)-2-fluorocyclopropanecarbonyl]amino]-5-[[2-methyl-5-(trifluoromethoxy)pyrazol-3-yl]carbamothioylamino]-4,5,6,7-tetrahydrobenzothiophene-3-carboxamide (376) &

(5S)-5-[[5-[chloro(difluoro)methoxy]-2-methyl-pyrazol-3-yl]carbamothioylamino]-N-(cyclopropylmethyl)-2-[[(1R,2R)-2-fluorocyclopropanecarbonyl]amino]-4,5,6,7-tetrahydrobenzothiophene-3-carboxamide (377)

A 2:1 mixture of Intermediates 372 and 373 respectively (100 mg, 0.42 mmol) was dissolved in anhydrous dichloromethane (2.5 mL) and treated with diisopropylethylamine (0.16 mL, 0.96 mmol). After 10 minutes at room temperature, thiocarbonyldiimidazole (86 mg, 0.48 mmol) was added and the solution stirred under an atmosphere of nitrogen for 4 hours. Half the volume of this solution was introduced (dropwise addition) to a solution of Intermediate 375 (129 mg, 0.37 mmol) in dry dichloromethane (2 mL) and the reaction stirred under a nitrogen atmosphere for 2 hours. The remaining solution containing intermediates 372 and 373 was then introduced (dropwise addition) and the reaction continued for a further 12 hours at room temperature. After adsorbing the reaction mixture onto silica in-vacuo, the dry-loaded material was purified by flash column chromatography (20-100% gradient of ethyl acetate in heptane). The title compounds were isolated as a 2:1 mixture of 376 and 377 respectively (107 mg, 51% total purity LCMS-UV$_{215}$, ~23% Yield). LCMS [M+H]$^+$ 575, RT 3.49 and LCMS [M+H]$^+$ 591/593, RT 3.58 (Method 10).

Intermediates 378 and 379

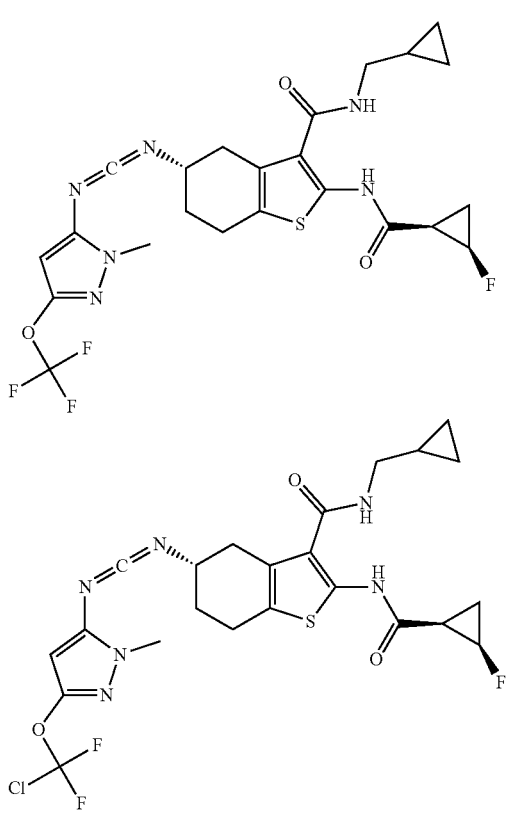

(5S)—N-(cyclopropylmethyl)-2-[[(1R,2R)-2-fluoro-cyclopropanecarbonyl]amino]-5-[[2-methyl-5-(trifluoromethoxy)pyrazol-3-yl]iminomethyleneamino]-4,5,6,7-tetrahydrobenzothiophene-3-carboxamide (378) &

(5S)-5-[[5-[chloro(difluoro)methoxy]-2-methyl-pyrazol-3-yl]iminomethyleneamino]-N-(cyclopropylmethyl)-2-[[(1R,2R)-2-fluorocyclopropanecarbonyl]amino]-4,5,6,7-tetrahydrobenzothiophene-3-carboxamide (379)

A 2:1 mixture of intermediates 376 and 377 respectively (107 mg, 51% total purity, 0.095 mmol) was dissolved in anhydrous dichloromethane (3 mL) at 0° C. and treated with triethylamine (0.15 mL, 1.11 mmol) followed by the dropwise addition of a methanesulfonyl chloride (38 mg, 0.33 mmol) solution in anhydrous dichloromethane (0.2 mL). The reaction was allowed to warm to room temperature over a period of 60 minutes, then diluted with dichloromethane (25 mL) and washed with saturated aqueous ammonium chloride (2×5 mL). The organic extract was dried over sodium sulfate, filtered and concentrated in-vacuo to furnish a 79:21 mixture of the title compounds 378 and 379 respectively (122 mg, quantitative). LCMS [M+H]$^+$ 541, RT 2.05 mins and LCMS [M+H]$^+$ 557/559, RT 2.11 mins (Method 12).

Intermediates 380 & 381

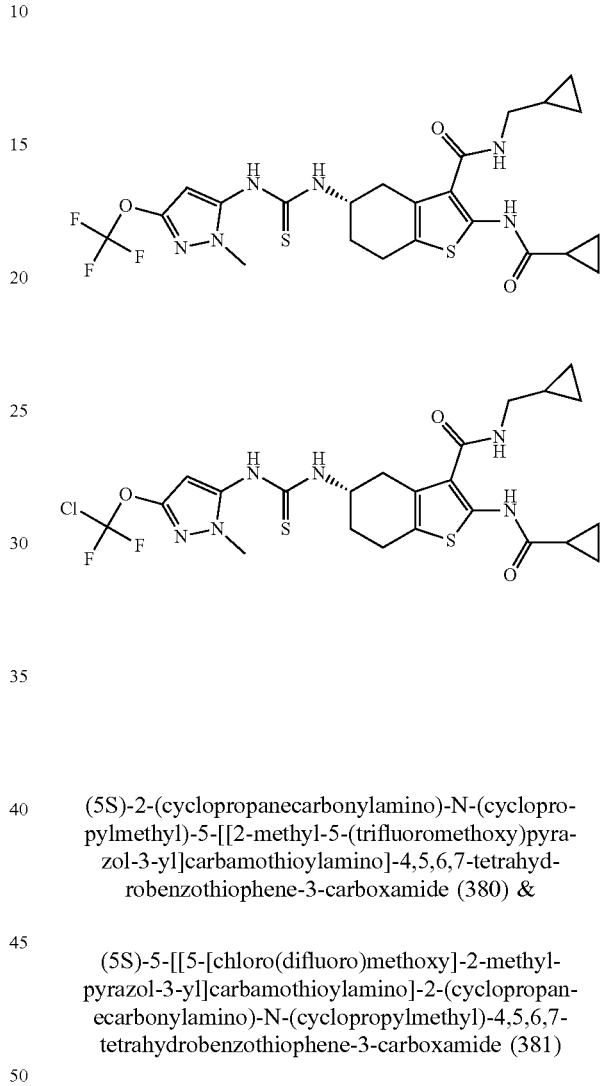

(5S)-2-(cyclopropanecarbonylamino)-N-(cyclopropylmethyl)-5-[[2-methyl-5-(trifluoromethoxy)pyrazol-3-yl]carbamothioylamino]-4,5,6,7-tetrahydrobenzothiophene-3-carboxamide (380) &

(5S)-5-[[5-[chloro(difluoro)methoxy]-2-methyl-pyrazol-3-yl]carbamothioylamino]-2-(cyclopropanecarbonylamino)-N-(cyclopropylmethyl)-4,5,6,7-tetrahydrobenzothiophene-3-carboxamide (381)

A 2:1 mixture of Intermediates 372 and 373 respectively (100 mg, 0.42 mmol) was dissolved in anhydrous dichloromethane (2.5 mL) and treated with diisopropylethylamine (0.16 mL, 0.96 mmol). After 10 minutes at room temperature, thiocarbonyldiimidazole (86 mg, 0.48 mmol) was added and the solution stirred under an atmosphere of nitrogen for 4 hours. This solution was introduced (dropwise) to a solution of intermediate 117 (122 mg, 0.37 mmol) in dry dichloromethane (2 mL) and the reaction stirred under a nitrogen atmosphere for 7 hours. After adsorbing the reaction mixture onto silica in-vacuo, the dry-loaded material was purified by flash column chromatography (10-100% gradient of ethyl acetate in heptane). The title compounds were isolated as a 2:1 mixture of 380 and 381 respectively (105 mg, 38% Yield). LCMS [M+H]$^+$ 557, RT 3.65 and LCMS [M+H]$^+$ 573/575, RT 3.74 mins (Method 32).

Intermediates 382 & 383

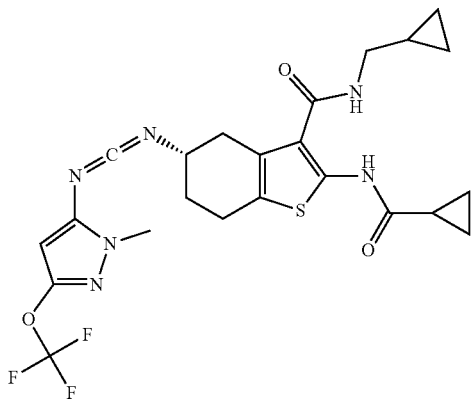

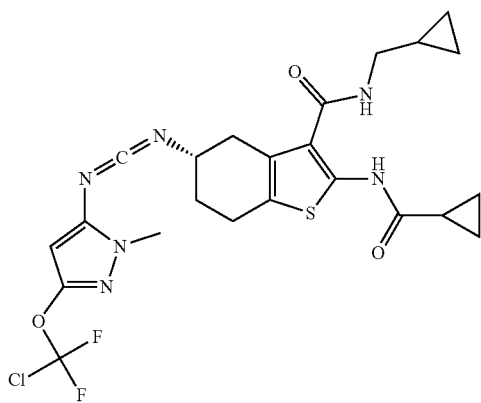

(5S)-2-(cyclopropanecarbonylamino)-N-(cyclopropylmethyl)-5-[[2-methyl-5-(trifluoromethoxy)pyrazol-3-yl]iminomethyleneamino]-4,5,6,7-tetrahydrobenzothiophene-3-carboxamide (382) &

(5S)-5-[[5-[chloro(difluoro)methoxy]-2-methylpyrazol-3-yl]iminomethyleneamino]-2-(cyclopropanecarbonylamino)-N-(cyclopropylmethyl)-4,5,6,7-tetrahydrobenzothiophene-3-carboxamide (383)

A 2:1 mixture of 380 and 381 respectively (105 mg, 0.16 mmol) was dissolved in anhydrous dichloromethane (3 mL) and cooled to 0° C. Trimethylamine (0.16 mL, 1.14 mmol) was then added followed by dropwise addition of a methanesulfonyl chloride (39 mg dissolved in 0.2 mL dry dichloromethane, 0.33 mmol). After warming to room temperature for 60 minutes, the reaction mixture was diluted with dichloromethane (25 mL) and washed with saturated aqueous ammonium chloride (2×5 mL). The organic extract was dried over sodium sulfate, filtered and concentrated in-vacuo to furnish a mixture of the title compounds (121 mg, quantitative) which was used immediately in the next synthetic step without further purification. LCMS [M+H]⁺ 523 and 539/541, RT 2.09 mins (identical retention times) (Method 12).

Intermediate 384

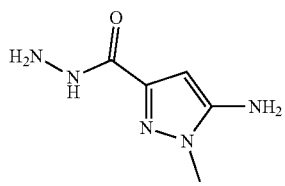

5-amino-1-methyl-1H-pyrazole-3-carbohydrazide

To a solution of methyl 5-amino-1-methylpyrrazole-2-carboxylate (1 g, 6.44 mmol) in methanol (10 mL) was introduced hydrazine hydrate (1.6 g, 32.2 mmol) and the reaction warmed to 80° C. for 16 hours. After concentration in-vacuo, the residue was dissolved in 1-butanol (5 mL) and concentrated in-vacuo (twice) to furnish the title compound (1.231 g, quantitative) which was used in the next synthetic step without purification. $\delta_H$ (500 MHz, d₄-methanol) 5.86 (1H, s), 4.83 (2H, s), 3.63 (3H, s); LCMS [M+H]⁺ 156, RT 0.40 mins (Method 18).

Intermediate 385

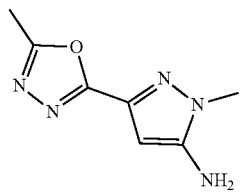

1-methyl-3-(5-methyl-1,3,4-oxadiazol-2-yl)-1H-pyrazol-5-amine

To a solution of Intermediate 384 (1.231 g, 6.44 mmol) in 1-butanol (40 mL) was introduced trimethyl orthoacetate (15.5 g, 128.9 mmol). The reaction mixture was warmed to 145° C. for 10 minutes, cooled to room temperature and DBU (981 mg, 6.44 mmol) introduced. After warming the reaction mixture to 145° C. for 70 minutes, the reaction mixture was concentrated in-vacuo. The residue was redissolved in acetonitrile (20 mL) and the pH adjusted to 1 (dropwise addition of aqueous 1 M HCl). The solution was then diluted with water (15 mL) and the acetonitrile evaporated in-vacuo. After adjusting the pH of the aqueous solution to 7 (dropwise addition of saturated aqueous sodium bicarbonate) the solution was subjected to freeze drying to furnish the crude product containing sodium chloride residues. The crude product was dissolved in water (5 mL) then applied onto a plug of reverse phase silica and eluted with a gradient of methanol (0-50%) in water. Product fractions were combined, concentrated in-vacuo and the resulting aqueous solution freeze-dried to furnish the title compound (0.384 g, 33% Yield): $\delta_H$ (500 MHz, d₆-dmso) 5.79 (s, 1H), 5.53 (s, 2H), 3.61 (s, 3H), 2.51 (s, 3H); LCMS [M+H]⁺ 180, RT 1.01 mins (Method 18).

Intermediate 386

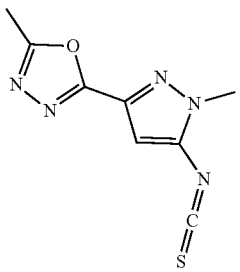

2-(5-isothiocyanato-1-methyl-1H-pyrazol-3-yl)-5-methyl-1,3,4-oxadiazole

To a vigorously stirred solution of Intermediate 385 (571 mg, 2.23 mmol) in water (8 mL) was introduced thiophosgene (256 mg, dropwise addition). After 5 minutes, the precipitated solid was collected by filtration and partially dried at the filter to furnish the (damp) title compound which was used immediately in the next synthetic step without further purification. LCMS [M+H]+ 222, RT 1.59 mins (Method 12).

Intermediate 387

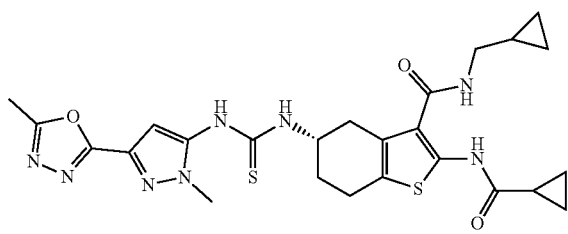 [SMILES: Cc1nnc(-c2cc(NC(=S)N[C@H]3CCc4sc(NC(=O)C5CC5)c(C(=O)NCC5CC5)c4C3)n(C)n2)o1]

(5S)-2-(cyclopropanecarbonylamino)-N-(cyclopropylmethyl)-5-[[2-methyl-5-(5-methyl-1,3,4-oxadiazol-2-yl)pyrazol-3-yl]carbamothioylamino]-4,5,6,7-tetrahydrobenzothiophene-3-carboxamide To a solution of intermediate 117 (366 mg, 1.10 mmol) in acetonitrile (5.0 mL) was introduced Intermediate 386 (243 mg [damp], <1.10 mmol, as a solution in minimum volume of acetonitrile required to solubilise). After stirring the reaction mixture for 90 minutes at room temperature, a second portion of Intermediate 386 (150 mg [damp], <0.68 mmol) was introduced and the reaction continued for 16 hours at room temperature. The reaction mixture was adsorbed onto silica in-vacuo, and the dry-loaded material purified by flash column chromatography (0-100% gradient of ethyl acetate in heptane) to furnish the title compound (281 mg, 41% Yield) ẟ$_H$ (500 MHz, d$_6$-dmso) 11.08 (s, 1H), 9.28 (s, 1H), 8.36-8.24 (m, 1H), 7.74 (t, J=5.5 Hz, 1H), 6.81 (s, 1H), 4.54 (s, 1H), 3.74 (s, 3H), 3.19-3.04 (m, 3H), 2.74 (br. s, 2H), 2.67-2.55 (m, 1H), 2.55 (s, 3H), 2.07-2.00 (m, 1H), 1.96-1.87 (m, 2H), 1.08-0.98 (m, 1H), 0.89-0.80 (m, 4H), 0.46-0.40 (m, 21H), 0.23 (q, J=4.8 Hz, 2H); LCMS [M+H]+ 555, RT 2.65 mins (Method 29).

Intermediate 388

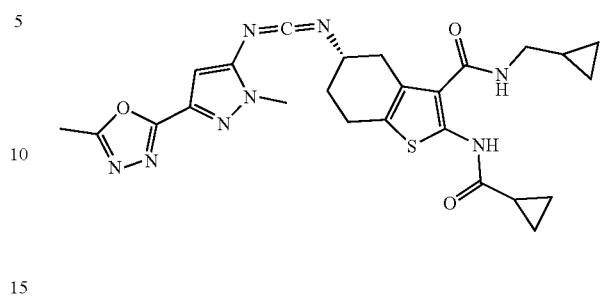

(5S)-2-(cyclopropanecarbonylamino)-N-(cyclopropylmethyl)-5-[[2-methyl-5-(5-methyl-1,3,4-oxadiazol-2-yl)pyrazol-3-yl]iminomethyleneamino]-4,5,6,7-tetrahydrobenzothiophene-3-carboxamide A solution of Intermediate 387 (256 mg, 0.41 mmol) in anhydrous dichloromethane (20 mL) under an atmosphere of nitrogen was cooled to 10° C. A solution of triethylamine (280 mg, 2.77 mmol) in anhydrous dichloromethane (1 mL) and a solution of methanesulfonyl chloride (106 mg, 0.92 mmol) in anhydrous dichloromethane (1 mL) were then added and the reaction stirred at this temperature for 30 minutes. The reaction mixture was diluted with dichloromethane (40 mL), washed with saturated aqueous ammonium chloride (5 mL) and brine (5 mL), then dried over sodium sulfate. After filtration, the filtrate was concentrated in-vacuo to furnish the crude title compound (344 mg, quantitative) which was used immediately in the next synthetic step. LCMS [M+H]+ 521, RT 1.86 mins (Method 12)

Intermediate 389

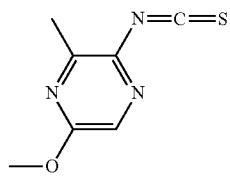

2-isothiocyanato-5-methoxy-3-methyl-pyrazine 1,1'-Thiocarbonyldiimidazole (226 mg, 1.21 mmol) and then hydrochloric acid in dioxane (0.55 mL, 2.2 mmol, 4 mol/L) were added to a solution of 5-methoxy-3-methyl-pyrazin-2-amine (153 mg, 1.10 mmol) in DCM (5.5 mL) under air. The reaction was stirred at r.t. for 4 hours, filtered and the solid washed with DCM (2×10 mL). The filtrate was concentrated in vacuo and purified by flash column chromatography on silica (gradient elution with 0% to 100% EtOAc in isohexanes) to give the title compound (127 mg, 40% Yield). A few drops of isobutylamine were added to the LCMS sample of the product before analysis LCMS [M+H]+ 255, RT 1.46 minutes [M=1-isobutyl-3-(5-methoxy-3-methyl-pyrazin-2-yl)thiourea] (Method 4).

Intermediate 390

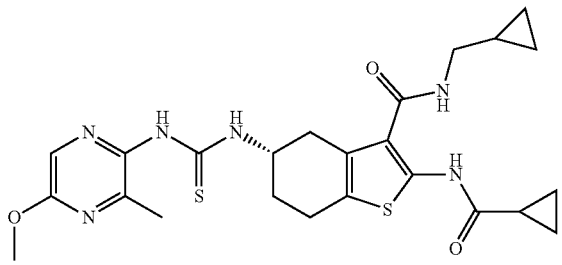 [SMILES: COc1cnc(NC(=S)N[C@H]2CCc3sc(NC(=O)C4CC4)c(C(=O)NCC4CC4)c3C2)c(C)n1]

(5S)-2-(cyclopropanecarbonylamino)-N-(cyclopropylmethyl)-5-[(5-methoxy-3-methyl-pyrazin-2-yl)carbamothioylamino]-4,5,6,7-tetrahydrobenzothiophene-3-carboxamide Intermediate 117 (200 mg, 0.600 mmol) was added to a solution of intermediate 389 (127 mg, 0.702 mmol) dissolved in DCM (3.0 mL) under air. The reaction was stirred at r.t. for 4.5 hours, concentrated in vacuo and purified by flash column chromatography on silica (gradient elution with 0% to 100% EtOAc in isohexanes then 0% to 20% MeOH in EtOAc) to give the title compound (180 mg, 58% Yield). LCMS [M+H]$^+$ 515, RT 1.56 minutes (Method 4).

Intermediate 391

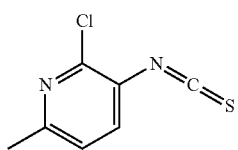

2-chloro-3-isothiocyanato-6-methyl-pyridine 1,1'-Thiocarbonyldiimidazole (426 mg, 2.27 mmol, 95 mass %) and then hydrochloric acid in dioxane (1.0 mL, 4.0 mmol, 4 mol/L) were added to a solution of 3-amino-2-chloro-6-picoline (300 mg, 2.06 mmol, 98 mass %) in DCM (10.3 mL) under air. The reaction was stirred at r.t. for 20 hours, filtered and the solid washed with DCM (2×15 mL). The filtrate was concentrated in vacuo and purified by flash column chromatography on silica (gradient elution with 0% to 100% EtOAc in isohexanes) to give the title compound (343 mg, 90% Yield). A few drops of isobutylamine were added to the LCMS sample of the product before analysis, LCMS [M+H]$^+$ 258, RT 0.82 minutes [M=1-(2-chloro-6-methyl-3-pyridyl)-3-isobutyl-thiourea] (Method 7).

Intermediate 392

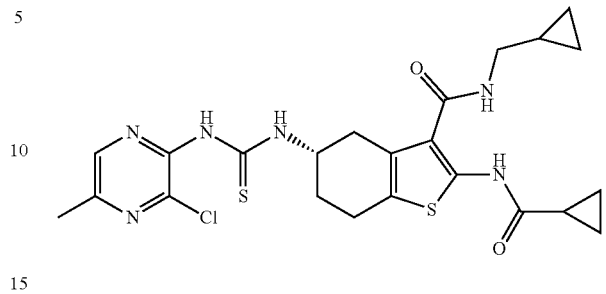

(5S)-5-[(2-chloro-6-methyl-3-pyridyl)carbamothioylamino]-2-(cyclopropanecarbonylamino)-N-(cyclopropylmethyl)-4,5,6,7-tetrahydrobenzothiophene-3-carboxamide Intermediate 117 (500 mg, 1.50 mmol) was added to a solution of intermediate 391 (332 mg, 1.80 mmol) dissolved in DCM (15 mL) under air. The reaction was stirred at r.t. for 3.5 hours, concentrated in vacuo and purified by flash column chromatography on silica (gradient elution with 40% to 100% EtOAc in isohexanes) to give the title compound (255 mg, 33% Yield). $\delta_H$ (400 MHz, DMSO-d6) 11.12 (s, 1H), 9.13 (s, 1H), 8.29 (d, J=7.6 Hz, 1H), 8.11 (d, J=8.1 Hz, 1H), 7.75 (t, J=5.7 Hz, 1H), 7.26 (d, J=8.1 Hz, 1H), 4.65-4.52 (m, 1H), 3.17-3.07 (m, 3H), 2.81-2.71 (m, 2H), 2.70-2.58 (m, 1H), 2.43 (s, 3H), 2.09-2.01 (m, 1H), 1.97-1.85 (m, 2H), 1.10-0.97 (m, 1H), 0.88-0.81 (m, 4H), 0.50-0.38 (m, 2H), 0.29-0.18 (m, 2H). Product reacts in the LCMS to generate an 5-methylthiazolo[5,4-b]pyridin-2-amine instead of the thiourea, LCMS [M+H]$^+$ 482, RT 1.47 minutes (Method 4).

Intermediate 393

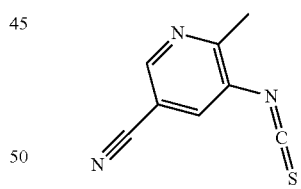

5-isothiocyanato-6-methyl-pyridine-3-carbonitrile 1,1'-Thiocarbonyldiimidazole (368 mg, 1.96 mmol, 95 mass %) and then hydrochloric acid in dioxane (0.89 mL, 3.6 mmol, 4 mol/L) were added to a solution of 5-amino-6-methylnicotinonitrile (250 mg, 1.78 mmol, 95 mass %) in DCM (8.9 mL) under air. The reaction was stirred at r.t. for 17.5 hours and then at 40° C. for a further 6.5 hours. The reaction was concentrated in vacuo and purified by flash column chromatography on silica (gradient elution with 0% to 100% EtOAc in isohexanes) to give the title compound (92 mg, 29% Yield). LCMS [M+H]$^+$ 176, RT 0.87 minutes (Method 7).

Intermediate 394

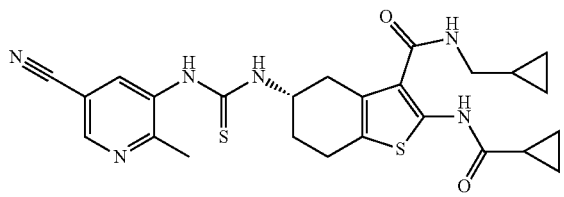 [SMILES: Cc1ncc(C#N)cc1NC(=S)N[C@H]1CCc2sc(NC(=O)C3CC3)c(C(=O)NCC3CC3)c2C1]

(5S)-5-[(5-cyano-2-methyl-3-pyridyl)carbamothioylamino]-2-(cyclopropanecarbonylamino)-N-(cyclopropylmethyl)-4,5,6,7-tetrahydrobenzothiophene-3-carboxamide Intermediate 117 (167 mg, 0.501 mmol) was added to a solution of intermediate 393 (92 mg, 0.52 mmol) dissolved in DCM (5.0 mL) under air. The reaction was stirred at r.t. for 5 hours, concentrated in vacuo and purified by flash column chromatography on silica (gradient elution with 0% to 100% EtOAc in isohexanes) to give the title compound (254 mg, 99% Yield). LCMS [M+H]$^+$ 509, RT 0.99 minutes (Method 7).

Intermediate 395

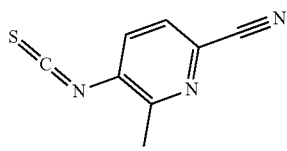

5-isothiocyanato-6-methyl-pyridine-2-carbonitrile 1,1'-Thiocarbonyldiimidazole (368 mg, 1.96 mmol, 95 mass %) and then hydrochloric acid in dioxane (0.89 mL, 3.6 mmol, 4 mol/L) were added to a solution of 5-amino-6-methylpicolinonitrile (250 mg, 1.78 mmol, 95 mass %) in DCM (8.9 mL) under air. The reaction was stirred at r.t. for 24.5 hours before being concentrated in vacuo and purified by flash column chromatography on silica (gradient elution with 0% to 100% EtOAc in isohexanes) to give the title compound (176 mg, 56% Yield). LCMS [M+H]$^+$ 176, RT 0.93 minutes (Method 7).

Intermediate 396

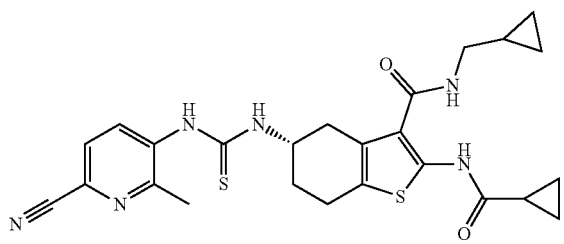 [SMILES: Cc1nc(C#N)ccc1NC(=S)N[C@H]1CCc2sc(NC(=O)C3CC3)c(C(=O)NCC3CC3)c2C1]

(5S)-5-[(6-cyano-2-methyl-3-pyridyl)carbamothioylamino]-2-(cyclopropanecarbonylamino)-N-(cyclopropylmethyl)-4,5,6,7-tetrahydrobenzothiophene-3-carboxamide Intermediate 117 (256 mg, 0.795 mmol) was added to a solution of intermediate 395 (176 mg, 1.01 mmol) dissolved in DCM (8.0 mL) under air. The reaction was stirred at r.t. for 5 hours, concentrated in vacuo and purified by flash column chromatography on silica (gradient elution with 0% to 100% EtOAc in isohexanes) to give the title compound (421 mg, quantitative yield). LCMS [M+H]$^+$ 509, RT 1.05 minutes (Method 7).

Intermediate 397

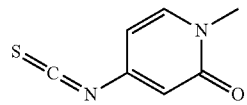

4-isothiocyanato-1-methyl-pyridin-2-one 1,1'-Thiocarbonyldiimidazole (516 mg, 2.75 mmol, 95 mass %) was added to a solution of 4-amino-1-methylpyridin-2(1H)-one (327 mg, 2.50 mmol, 95 mass %) in DCM (7.5 mL) under air. The reaction was stirred at r.t. for 24.5 hours and then at 40° C. for a further 2 hours. The reaction was cooled to r.t., concentrated in vacuo and purified by flash column chromatography on silica (gradient elution with 0% to 100% EtOAc in isohexanes) to give the title compound (210 mg, 51% Yield). A few drops of isobutylamine were added to the LCMS sample of the product before analysis, LCMS [M+H]$^+$ 240, RT 1.01 minutes [M=1-isobutyl-3-(1-methyl-2-oxo-4-pyridyl)thiourea] (Method 4).

Intermediate 398

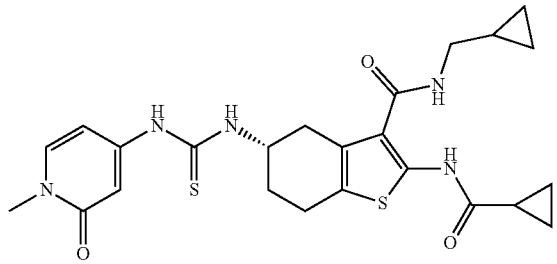 [SMILES: Cn1ccc(NC(=S)N[C@H]2CCc3sc(NC(=O)C4CC4)c(C(=O)NCC4CC4)c3C2)cc1=O]

(5S)-2-(cyclopropanecarbonylamino)-N-(cyclopropylmethyl)-5-[(1-methyl-2-oxo-4-pyridyl)carbamothioylamino]-4,5,6,7-tetrahydrobenzothiophene-3-carboxamide Intermediate 117 (278 mg, 0.834 mmol) was added to a solution of Intermediate 397 (152 mg, 0.917 mmol) dissolved in DCM (4.2 mL) under air. The reaction was stirred at r.t. for 4 hours, diluted with DCM (20 mL) and filtered and washed with further DCM. The solid was product. The filtrate was concentrated in vacuo and purified by flash column chromatography on silica (gradient elution with 50% to 100% EtOAc in isohexanes then 0% to 20% MeOH in EtOAc) to give more product. Both batches of product were combined to give the title compound (320 mg, 77% Yield). LCMS [M+H]⁺ 500, RT 1.30 minutes (Method 4).

Intermediate 399

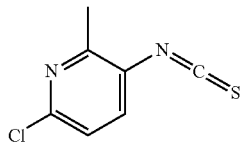

6-chloro-3-isothiocyanato-2-methyl-pyridine 1,1'-Thiocarbonyldiimidazole (516 mg, 2.75 mmol, 95 mass %) and then hydrochloric acid in dioxane (1.25 mL, 5.00 mmol, 4 mol/L) were added to a solution of 3-amino-6-chloro-2-picoline (368 mg, 2.50 mmol, 97 mass %) in DCM (7.5 mL) under air. The reaction was stirred at r.t. for 5 hours, concentrated in vacuo and purified by flash column chromatography on silica (gradient elution with 0% to 50% EtOAc in isohexanes) to give the title compound (326 mg, 71% Yield). A few drops of isobutylamine were added to the LCMS sample of the product before analysis, LCMS [M+H]⁺ 258, RT 1.24 minutes [M=1-(6-chloro-2-methyl-3-pyridyl)-3-isobutyl-thiourea] (Method 4).

Intermediate 400

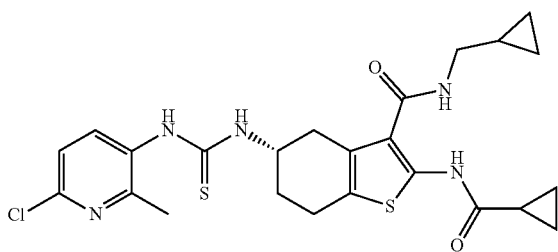 [SMILES: Cc1nc(Cl)ccc1NC(=S)N[C@H]1CCc2sc(NC(=O)C3CC3)c(C(=O)NCC3CC3)c2C1]

(5S)-5-[(6-chloro-2-methyl-3-pyridyl)carbamothioylamino]-2-(cyclopropanecarbonylamino)-N-(cyclopropylmethyl)-4,5,6,7-tetrahydrobenzothiophene-3-carboxamide Intermediate 117 (284 mg, 0.852 mmol) was added to a solution of intermediate 399 (326 mg, 1.77 mmol) dissolved in DCM (4.3 mL) under air. The reaction was stirred at r.t. for 1.5 hours, concentrated in vacuo and purified by flash column chromatography on silica (gradient elution with 0% to 100% EtOAc in isohexanes) to give the title compound (459 mg, quantitative yield). LCMS [M+H]⁺ 518, RT 1.45 minutes (Method 4).

Intermediate 401

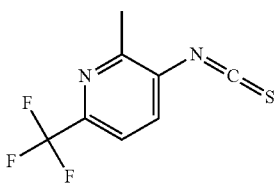

3-isothiocyanato-2-methyl-6-(trifluoromethyl)pyridine 1,1'-Thiocarbonyldiimidazole (516 mg, 2.75 mmol, 95 mass %) and then hydrochloric acid in dioxane (1.25 mL, 5.00 mmol, 4 mol/L) were added to a solution of 2-methyl-6-(trifluoromethyl)pyridin-3-amine (464 mg, 2.50 mmol, 95 mass %) in DCM (7.5 mL) under air. The reaction was stirred at r.t. for 4 hours, concentrated in vacuo and purified by flash column chromatography on silica (gradient elution with 0% to 50% EtOAc in isohexanes) to give the title compound (360 mg, 66% Yield). A few drops of isobutylamine were added to the LCMS sample of the product before analysis, LCMS [M+H]⁺ 292, RT 1.39 minutes [M=1-isobutyl-3-[2-methyl-6-(trifluoromethyl)-3-pyridyl]thiourea] (Method 4).

Intermediate 402

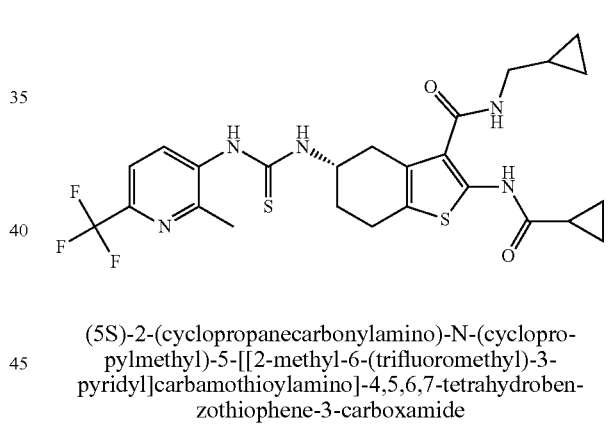

(5S)-2-(cyclopropanecarbonylamino)-N-(cyclopropylmethyl)-5-[[2-methyl-6-(trifluoromethyl)-3-pyridyl]carbamothioylamino]-4,5,6,7-tetrahydrobenzothiophene-3-carboxamide Intermediate 117 (200 mg, 0.600 mmol) was added to a solution of intermediate 401 (144 mg, 0.660 mmol) dissolved in DCM (3.0 mL) under air. The reaction was stirred at r.t. for 1.5 hours, concentrated in vacuo and purified by flash column chromatography on silica (gradient elution with 0% to 100% EtOAc in isohexanes) to give the title compound (368 mg, quantitative). LCMS [M+H]⁺ 552, RT 1.55 minutes (Method 4).

Intermediate 403

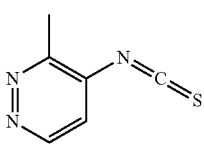

4-isothiocyanato-3-methyl-pyridazine

DIPEA (0.57 mL, 3.3 mmol) followed by 1,1'-thiocarbonyldiimidazole (516 mg, 2.75 mmol, 95 mass %) were added to a solution of 3-methylpyridazin-4-amine hydrochloride (383 mg, 2.50 mmol, 95 mass %) in DCM (7.5 mL) under air. The reaction was stirred at r.t. for 24 hours, concentrated in vacuo and purified by flash column chromatography on silica (gradient elution with 0% to 50% EtOAc in isohexanes) to give the title compound (48 mg, 13% Yield). A few drops of isobutylamine were added to the LCMS sample of the product before analysis, LCMS [M+H]$^+$ 225, RT 1.07 minutes [M=1-isobutyl-3-(3-methylpyridazin-4-yl)thiourea] (Method 4).

Intermediate 404

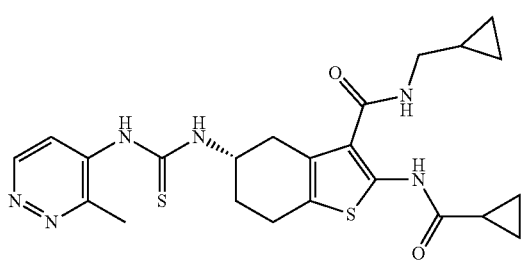 [SMILES: Cc1nnccc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(3-methylpyridazin-4-yl)carbamothioylamino]-4,5,6,7-tetrahydrobenzothiophene-3-carboxamide Intermediate 117 (105 mg, 0.315 mmol) was added to a solution of intermediate 403 (48 mg, 0.32 mmol) dissolved in DCM (1.6 mL) under air. The reaction was stirred at r.t. for 1 hour, concentrated in vacuo and purified by flash column chromatography on silica (gradient elution with 0% to 100% EtOAc in isohexanes then 0% to 20% MeOH in EtOAc) to give the title compound (152 mg, quantitative). LCMS [M+H]$^+$ 485, RT 0.92 minutes (Method 7).

Intermediate 405

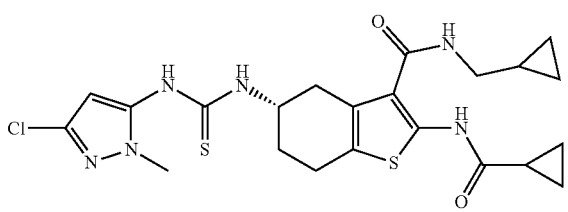 [SMILES: Cn1nc(Cl)cc1NC(=S)N[C@H]1CCc2sc(NC(=O)C3CC3)c(C(=O)NCC3CC3)c2C1]

(5S)-5-[(5-chloro-2-methyl-pyrazol-3-yl)carbamothioylamino]-2-(cyclopropanecarbonylamino)-N-(cyclopropylmethyl)-4,5,6,7-tetrahydrobenzothiophene-3-carboxamide DIPEA (0.42 mL, 2.4 mmol) followed by 1,1'-thiocarbonyldiimidazole (207 mg, 1.10 mmol, 95 mass %) were added to a solution of 3-chloro-1-methyl-1H-pyrazol-5-amine dihydrochloride (232 mg, 1.10 mmol, 97 mass %) in DCM (3.3 mL) under nitrogen. The reaction was stirred at r.t for 2.5 hours. DIPEA (0.21 mL, 1.2 mmol) followed by intermediate 117 (205 mg, 0.615 mmol) were then added and the reaction was stirred at r.t. for a further 24 hours before being concentrated in vacuo and purified by flash column chromatography on silica (gradient elution with 0% to 100% EtOAc in isohexanes) to give the title compound (258 mg, 83% Yield). LCMS [M+H]$^+$ 507, RT 1.07 minutes (Method 7).

Intermediate 406

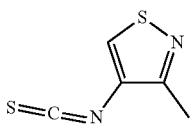

4-isothiocyanato-3-methyl-isothiazole

DIPEA (0.57 mL, 3.3 mmol) followed by 1,1'-thiocarbonyldiimidazole (516 mg, 2.75 mmol, 95 mass %) were added to a solution of 3-methylisothiazol-4-amine hydrochloride (396 mg, 2.50 mmol, 95 mass %) in DCM (7.5 mL) under air. The reaction was stirred at r.t. for 22 hours, concentrated in vacuo and purified by flash column chromatography on silica (gradient elution with 0% to 50% EtOAc in isohexanes) to give the title compound (292 mg, 75% Yield). A few drops of isobutylamine were added to the LCMS sample of the product before analysis, LCMS [M+H]$^+$ 230, RT 1.04 minutes [M=1-isobutyl-3-(3-methylisothiazol-4-yl)thiourea] (Method 4).

Intermediate 407

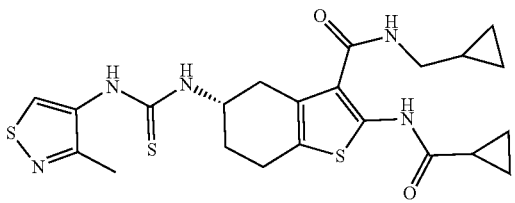 [SMILES: Cc1nscc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(3-methylisothiazol-4-yl)carbamothioylamino]-4,5,6,7-tetrahydrobenzothiophene-3-carboxamide Intermediate 117 (300 mg, 0.900 mmol) was added to a solution of intermediate 406 (155 mg, 0.990 mmol) dissolved in DCM (4.5 mL) under air. The reaction was stirred at r.t. for 3.5 hours, concentrated in vacuo and purified by flash column chromatography on silica (gradient elution with 0% to 100% EtOAc in isohexanes) to give the title compound (393 mg, 89% Yield). LCMS [M+H]$^+$ 490, RT 1.37 minutes (Method 4).

Intermediate 408

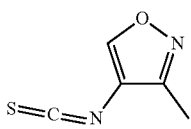

4-isothiocyanato-3-methyl-isoxazole 1,1'-Thiocarbonyldiimidazole (516 mg, 2.75 mmol, 95 mass %) and then hydrochloric acid in dioxane (1.25 mL, 5.00 mmol, 4 mol/L) were added to a solution of 3-methylisoxazol-4-amine (258 mg, 2.50 mmol, 95 mass %) in DCM (7.5 mL) under air. The reaction was stirred at r.t. for 3 hours 15 mins, concentrated in vacuo and purified by flash column chromatography on silica (gradient elution with 0% to 50% EtOAc in isohexanes) to give the title compound (250 mg, 71% Yield). A few drops of isobutylamine were added to the LCMS sample of the product before analysis, LCMS [M+H]$^+$ 214, RT 1.13 minutes [M=1-isobutyl-3-(3-methylisoxazol-4-yl)thiourea] (Method 4).

Intermediate 409

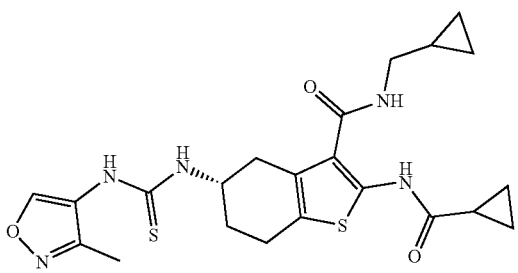 [SMILES: Cc1nocc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(3-methylisoxazol-4-yl)carbamothioylamino]-4,5,6,7-tetrahydrobenzothiophene-3-carboxamide DIPEA (0.17 mL, 0.98 mmol) followed by Intermediate 408 (112 mg, 0.799 mmol) were added to a solution of Intermediate 117 (205 mg, 0.615 mmol) in DCM (3.8 mL) under air. The reaction was stirred at r.t. for 18.5 hours, concentrated in vacuo and purified by flash column chromatography on silica (gradient elution with 0% to 100% EtOAc in isohexanes) to give the title compound (313 mg, quantitative yield). LCMS [M+H]$^+$ 474, RT 1.41 minutes (Method 4).

Intermediate 410

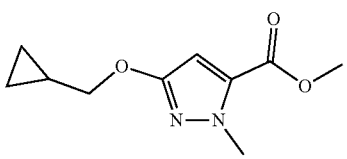

methyl 5-(cyclopropylmethoxy)-2-methyl-pyrazole-3-carboxylate

To a stirred suspension of methyl 5-hydroxy-2-methyl-pyrazole-3-carboxylate (3.00 g, 19.0 mmol) and K$_2$CO$_3$ (2.90 g, 21.0 mmol) in DMF (19 mL) at room temperature was added cyclopropylmethyl bromide (2.0 mL, 21.0 mmol) and the reaction mixture stirred at 50° C. for 16 h. The reaction mixture was diluted with water (190 mL) and the aqueous layer extracted with ethyl acetate (3×100 mL). The combined organic layers were washed with water (2×100 mL), passed through a phase separator, and concentrated in vacuo. The crude material was purified by flash chromatography using a gradient of 0-50% EtOAc in isohexanes to afford the title compound (3.14 g, 78% Yield) as a colourless oil. δ$_H$ (300 MHz, d-Chloroform) 6.18 (s, 1H), 4.02 (s, 3H), 3.94 (d, J=7.1 Hz, 2H), 3.85 (s, 3H), 1.33-1.20 (m, 1H), 0.64-0.57 (m, 2H), 0.36-0.31 (m, 2H).

Intermediate 411

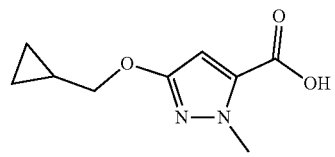

5-(cyclopropylmethoxy)-2-methyl-pyrazole-3-carboxylic acid

To a solution of intermediate 410 (3.14 g, 14.9 mmol) in MeOH (75 mL) was added NaOH (aq. 2.0 M, 15 mL) and the reaction mixture stirred at 50° C. for 1 h. The reaction mixture was concentrated in vacuo, and then acidified to pH 1 with HCl (aq. 2M). The mixture was diluted with water (200 mL) and the aqueous layer extracted with EtOAc (3×150 mL). The combined organic extracts were passed through a phase separator, and concentrated in vacuo to give the title compound (2.62 g, 89% Yield). δ$_H$ (300 MHz, d-DMSO) 13.34 (s, 1H), 6.19 (s, 1H), 3.92 (s, 3H), 3.88 (d, J=7.1 Hz, 2H), 1.27-1.13 (m, 1H), 0.57-0.51 (m, 2H), 0.32-0.27 (m, 2H).

Intermediate 412

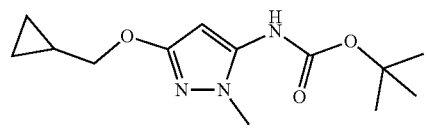 [SMILES: Cn1nc(OCC2CC2)cc1NC(=O)OC(C)(C)C]

tert-butyl N-[5-(cyclopropylmethoxy)-2-methyl-pyrazol-3-yl]carbamate

To a stirred solution of intermediate 411 (1.00 g, 5.10 mmol) and triethylamine (2.13 mL, 15.3 mmol) in THF (25 mL) at 0° C. was added diphenylphosphoryl azide (1.65 mL, 7.65 mmol). After 10 min the reaction mixture was allowed to warm to room temperature and stirred for 1 h. t-Butyl alcohol (10 mL) was added and the reaction mixture heated Intermediate 413

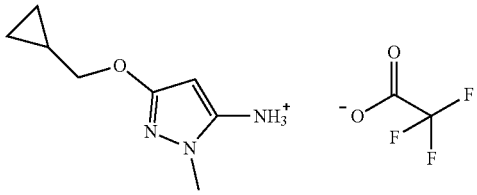

[5-(cyclopropylmethoxy)-2-methyl-pyrazol-3-yl] ammonium 2,2,2-trifluoroacetate

To a solution of intermediate 412 (1.35 g, 5.05 mmol) in CH$_2$Cl$_2$ (16 mL) was added trifluoroacetic acid (4 mL) and the reaction mixture stirred at room temperature for 16 h. The reaction mixture was concentrated in vacuo and the crude material azeotroped with toluene (3×20 mL) to give the title compound (1.60 g, quantitative) as an orange oil. $\delta_H$ (300 MHz, d-Chloroform) 5.02 (br. s, 1H), 3.96 (d, J=7.3 Hz, 2H), 3.57 (s, 3H), 1.30-1.17 (m, 1H), 0.70-0.63 (m, 2H), 0.38-0.32 (m, 2H).

Intermediate 414

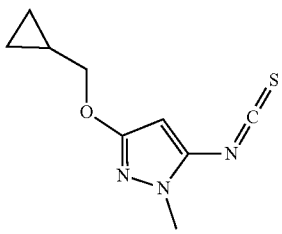

3-(cyclopropylmethoxy)-5-isothiocyanato-1-methyl-pyrazole

To a solution of intermediate 413 (1.42 mg, 5.05 mmol) and N,N-diisopropylethylamine (1.14 mL, 6.56 mmol) in CH$_2$Cl$_2$ (15 mL) was added 1,1'-thiocarbonyldiimidazole (1.04 g, 5.56 mmol) and the reaction mixture stirred at room temperature for 16 h. The reaction mixture was concentrated in vacuo and the crude material was purified by flash chromatography [EtOAc/isohexanes (0-50%)] to afford the title compound (253 mg, 24% Yield) as a yellow oil. $\delta_H$ (300 MHz, d-Chloroform) 5.64 (s, 1H), 3.92 (d, J=7.1 Hz, 2H), 3.64 (s, 3H), 1.31-1.18 (m, 1H), 0.63-0.57 (m, 2H), 0.35-0.30 (m, 2H).

Intermediate 415

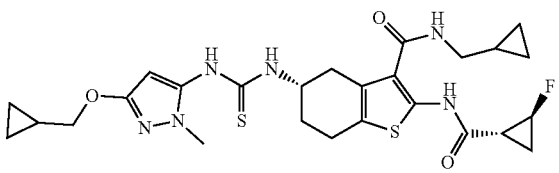 [SMILES: Cn1nc(OCC2CC2)cc1NC(=S)N[C@H]1CCc2sc(NC(=O)[C@H]3C[C@@H]3F)c(C(=O)NCC3CC3)c2C1]

(5S)-5-[[5-(cyclopropylmethoxy)-2-methyl-pyrazol-3-yl]carbamothioylamino]-N-(cyclopropylmethyl)-2-[[(1R,2S)-2-fluorocyclopropanecarbonyl]amino]-4,5,6,7-tetrahydrobenzothiophene-3-carboxamide To a vial containing intermediate 566 (100 mg, 0.285 mmol) and intermediate 414 (66 mg, 0.313 mmol) was added CH$_2$Cl$_2$ (0.28 mL) and the solution stirred at room temperature for 10 min. The reaction mixture was concentrated and the residue purified by flash chromatography [EtOAc/isohexanes (0-100%)] to afford the title compound (153 mg, 96% Yield). $\delta_H$ (400 MHz, d-DMSO) 11.08 (s, 1H), 9.17 (s, 1H), 7.99 (d, J=7.3 Hz, 1H), 7.86 (t, J=5.6 Hz, 1H), 5.60 (s, 1H), 4.90 (d, J=65.0 Hz, 1H), 4.59-4.45 (m, 1H), 3.83 (d, J=7.1 Hz, 2H), 3.45 (s, 3H), 3.20-3.10 (m, 2H), 3.02 (dd, J=16.0 and 4.4 Hz, 1H), 2.79-2.68 (m, 2H), 2.67-2.54 (m, 2H), 2.07-1.80 (m, 2H), 1.64-1.47 (m, 1H), 1.30-1.11 (m, 2H), 1.07-0.99 (m, 1H), 0.56-0.50 (m, 2H), 0.46-0.41 (m, 2H), 0.30-0.21 (m, 4H).

Intermediate 416

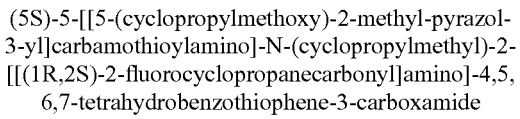

methyl 5-ethoxy-2-methyl-pyrazole-3-carboxylate

To a stirred suspension of methyl 5-hydroxy-2-methyl-pyrazole-3-carboxylate (3.00 g, 19.0 mmol) and K$_2$CO$_3$ (2.90 g, 21.0 mmol) in DMF (19 mL) at room temperature was added iodoethane (1.71 mL, 21.0 mmol) and the reaction mixture stirred at 50° C. for 16 h. The reaction mixture was diluted with water (190 mL) and the aqueous layer extracted with ethyl acetate (3×100 mL). The combined organic layers were washed with water (2×100 mL), passed through a phase separator and concentrated in vacuo. The crude material was purified by flash chromatography [EtOAc/isohexanes (0-50%)] to afford the title compound (3.33 g, 94% Yield) as a colourless oil. $\delta_H$ (300 MHz, d-Chloroform) 6.17 (s, 1H), 4.16 (q, J=7.1 Hz, 2H), 4.03 (s, 3H), 3.86 (s, 3H), 1.38 (t, J=7.1 Hz, 3H).

Intermediate 417

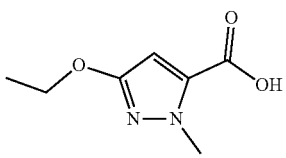

5-ethoxy-2-methyl-pyrazole-3-carboxylic acid

To a solution of intermediate 416 (3.33 g, 18.1 mmol) in MeOH (90 mL) was added NaOH (aq. 2.0 M, 18 mL) and the reaction mixture stirred at 50° C. for 1 h. The reaction mixture was concentrated in vacuo, and then acidified to pH 1 with HCl (aq. 2 M). The mixture was diluted with water (200 mL) and the aqueous layer extracted with EtOAc (3×150 mL). The combined organic extracts were passed through a phase separator, and concentrated in vacuo to give the title compound (2.91 g, 94% Yield) as a colourless crystalline solid. $\delta_H$ (300 MHz, d-DMSO) 13.36 (s, 1H), 6.19 (s, 1H), 4.09 (q, J=7.1 Hz, 2H), 3.92 (s, 3H), 1.28 (t, J=7.1 Hz, 3H).

Intermediate 418

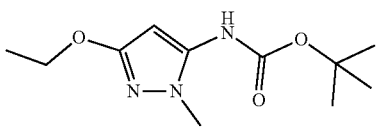 [SMILES: CCOc1cc(NC(=O)OC(C)(C)C)n(C)n1]

tert-butyl N-(5-ethoxy-2-methyl-pyrazol-3-yl)carbamate

To a stirred solution of intermediate 417 (1.00 g, 5.88 mmol) and triethylamine (2.46 mL, 17.6 mmol) in THF (29 mL) at 0° C. was added diphenylphosphoryl azide (1.90 mL, 8.81 mmol). After 10 min the reaction mixture was allowed to warm to room temperature and stirred for 1 h. t-Butyl alcohol (10 mL) was added and the reaction mixture heated to 80° C. and stirred for 16 h. The reaction mixture was concentrated in vacuo and the crude material was purified by flash chromatography [EtOAc/isohexanes (0-80%)] to afford the title compound (1.01 g, 77% Yield). $\delta_H$ (300 MHz, d-Chloroform) 6.19 (s, 1H), 5.59 (s, 1H), 4.14 (q, J=7.1 Hz, 2H), 3.58 (s, 3H), 1.50 (s, 9H), 1.36 (t, J=7.1 Hz, 3H).

Intermediate 419

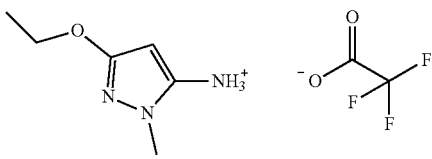

(5-ethoxy-2-methyl-pyrazol-3-yl)ammonium 2,2,2-trifluoroacetate

To a solution of intermediate 418 (1.00 g, 4.10 mmol) in CH$_2$Cl$_2$ (16 mL) was added trifluoroacetic acid (4 mL) and the reaction mixture stirred at room temperature for 16 h. The reaction mixture was concentrated in vacuo and the crude material azeotroped with toluene (3×20 mL) to give the title compound (1.51 g, quantitative yield). $\delta_H$ (300 MHz, d-DMSO) 5.08 (br. s, 1H), 4.15 (q, J=7.1 Hz, 2H), 3.44 (s, 3H), 1.30 (t, J=7.1 Hz, 3H).

Intermediate 420

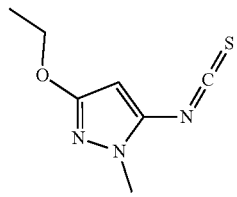

3-ethoxy-5-isothiocyanato-1-methyl-pyrazole

To a solution of intermediate 419 (1.1 g, 4.3 mmol) and N,N-diisopropylethylamine (0.97 mL, 5.6 mmol) in CH$_2$Cl$_2$ (13 mL) was added 1,1'-thiocarbonyldiimidazole (890 mg, 4.7 mmol) and the reaction mixture stirred at room temperature for 16 h. The reaction mixture was concentrated in vacuo and the crude material was purified by flash chromatography [EtOAc/isohexanes (0-50%)] to afford the title compound (199 mg, 25% Yield). $\delta_H$ (300 MHz, d-Chloroform) 5.62 (s, 1H), 4.13 (q, J=7.1 Hz, 2H), 3.65 (s, 3H), 1.36 (t, J=7.1 Hz, 3H).

Intermediate 421

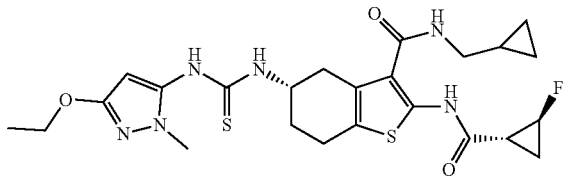 [SMILES: CCOc1cc(NC(=S)N[C@H]2CCc3sc(NC(=O)[C@H]4C[C@@H]4F)c(C(=O)NCC4CC4)c3C2)n(C)n1]

(5S)—N-(cyclopropylmethyl)-5-[(5-ethoxy-2-methyl-pyrazol-3-yl)carbamothioylamino]-2-[[(1R,2S)-2-fluorocyclopropanecarbonyl]amino]-4,5,6,7-tetrahydrobenzothiophene-3-carboxamide To a vial containing intermediate 566 (100 mg, 0.285 mmol) and intermediate 420 (86 mg, 0.470 mmol) was added CH$_2$Cl$_2$ (0.28 mL) and the solution stirred at room temperature for 10 min. The reaction mixture was concentrated in vacuo and the residue purified by flash chromatography [EtOAc/isohexanes (0-100%)] to afford the title compound (141 mg, 93% Yield) as a colourless amorphous solid. $\delta_H$ (400 MHz, d-DMSO) 11.08 (s, 1H), 9.17 (s, 1H), 7.99 (d, J=7.0 Hz, 1H), 7.87 (t, J=5.2 Hz, 1H), 5.60 (s, 1H), 4.89 (d, J=64.7 Hz, 1H), 4.59-4.46 (m, 1H), 4.05 (q, J=7.1 Hz, 2H), 3.46 (s, 3H), 3.21-2.96 (m, 3H), 2.81-2.54 (m, 3H), 2.08-1.80 (m, 2H), 1.66-1.45 (m, 2H), 1.27 (t, J=7.1 Hz, 3H), 1.08-0.79 (m, 2H), 0.47-0.39 (m, 2H), 0.26-0.21 (m, 2H).

Intermediate 422

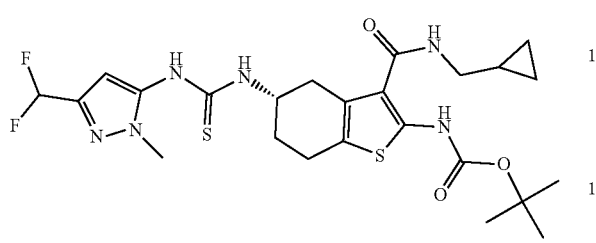

tert-butyl N-[(5S)-3-(cyclopropylmethylcarbamoyl)-5-[[5-(difluoromethyl)-2-methyl-pyrazol-3-yl]carbamothioylamino]-4,5,6,7-tetrahydrobenzothiophen-2-yl]carbamate A solution of intermediate 559 (1.0 g, 2.74 mmol) was stirred in DCM (50 mL) and cooled to 0° C. Intermediate 254 (517.63 mg, 2.74 mmol) was then added. Reaction stirred at 0° C. for 30 min then at RT for 5 h. Reaction mixture was diluted with DCM then water (30 mL) was added and organic layer separated. The aqueous layer was extracted with DCM (2×20 mL) and the organic fractions combined, dried over sodium sulfate and concentrated under vacuum. The residue was purified by column chromatography using 0-70% EtOAc in heptane to give the title compound (1480 mg, 97% Yield). LCMS [M+H]$^+$ 555, RT 2.04 minutes (Method 12).

Intermediate 423

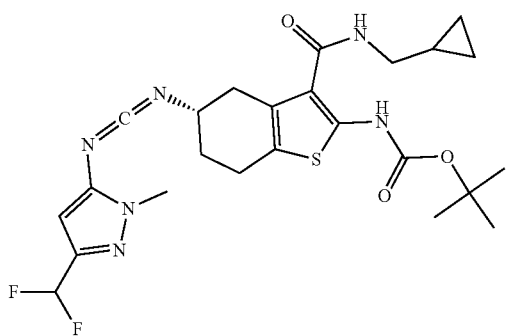 [SMILES: Cn1nc(C(F)F)cc1N=C=N[C@H]1CCc2sc(NC(=O)OC(C)(C)C)c(C(=O)NCC3CC3)c2C1]

tert-butyl N-[(5S)-3-(cyclopropylmethylcarbamoyl)-5-[[5-(difluoromethyl)-2-methyl-pyrazol-3-yl]iminomethyleneamino]-4,5,6,7-tetrahydrobenzothiophen-2-yl]carbamate To a solution of intermediate 422 (1790 mg, 3.23 mmol) in DCM (60 mL) was added triethylamine (1349 mL, 9.68 mmol). The solution was cooled to 0° C. then methanesulfonyl chloride (275 ML, 3.55 mmol) was added. Reaction stirred for 30 min at 0° C. Reaction mixture was diluted with DCM (20 mL) then sat. NH$_4$Cl solution (30 mL) was added and organic layer separated. The aqueous layer was extracted with DCM (2×25 mL) and the organic fractions combined, dried over sodium sulfate and concentrated under vacuum to give the title compound (1720 mg, 95% Yield) which was used in the next stage without further purification. LCMS [M+H]$^+$ 521, RT 2.13 minutes (Method 12).

Intermediate 424

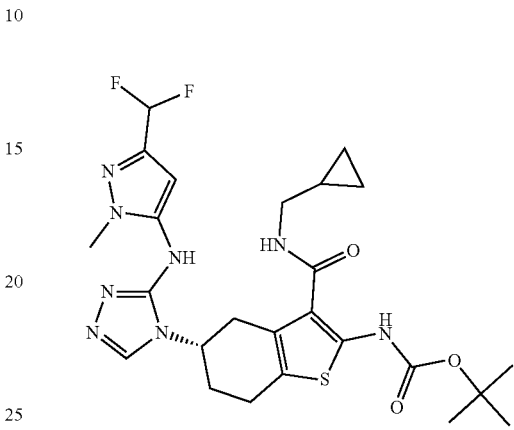

tert-butyl N-[(5S)-3-(cyclopropylmethylcarbamoyl)-5-[3-[[5-(difluoromethyl)-2-methyl-pyrazol-3-yl]amino]-1,2,4-triazol-4-yl]-4,5,6,7-tetrahydrobenzothiophen-2-yl]carbamate 1 M formic hydrazide (9.68 mL, 9.68 mmol) in MeOH was added to intermediate 423 (1680 mg, 3.23 mmol) followed by MeOH (10 mL) and stirred for 30 mins. Aqueous disodium carbonate (0.92 M, 10.52 mL, 9.68 mmol) was added and reaction heated at 50° C. with stirring for 16 hours. Reaction allowed to cool, MeOH was removed and water was added (20 mL). The mixture was extracted with DCM (2×30 mL). The solvent of the combined organic layers was dried (MgSO$_4$) before concentration to dryness. The residue was purified by column chromatography using 0 to 100% EtOAc in heptane to give the title compound (1300 mg, 71% Yield). LCMS [M+H]$^+$ 563, RT 1.91 minutes (Method 12).

Intermediate 425

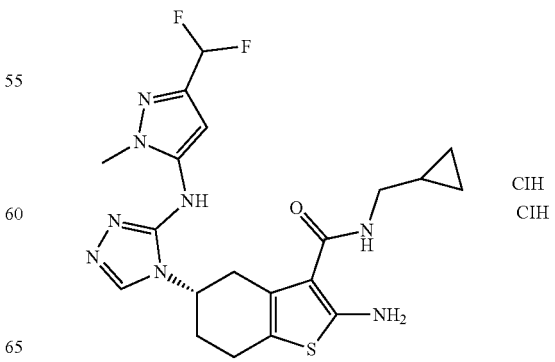

(5S)-2-amino-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide dihydrochloride Intermediate 424 (75 mg, 0.13 mmol) was dissolved in 1,4-Dioxane (1.5 mL) then 4 M 1,4-dioxane hydrochloride (0.67 mL, 2.67 mmol) was added. Reaction stirred for 5 h at room temperature. Reaction mixture was concentrated under vacuum to give the title compound (70 mg, 98% Yield) which was used in the next stage without further purification. LCMS [M+H]$^+$ 463, RT 1.57 minutes (Method 12).

Intermediate 426

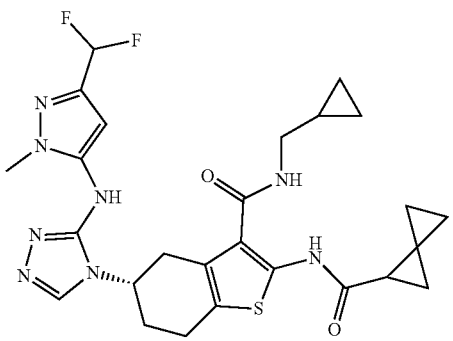 [SMILES: Cn1nc(C(F)F)cc1Nc1nncn1[C@H]1CCc2sc(NC(=O)C3CC34CC4)c(C(=O)NCC3CC3)c2C1]

(5S)—N-(cyclopropylmethyl)-5-[3-[[5-(difluoromethyl)-2-methyl-pyrazol-3-yl]amino]-1,2,4-triazol-4-yl]-2-(spiro[2.2]pentane-2-carbonylamino)-4,5,6,7-tetrahydrobenzothiophene-3-carboxamide The title compound was obtained following general method 6 with intermediate 425 (80 mg, 0.14 mmol), spiro[2.2]pentane-2-carboxylic acid (16.7 mg, 0.14 mmol), pyridine (60 µL, 0.74 mmol), T3P (178 µL, 0.29 mmol) and DCM (16 mL). Reaction duration: 16 hours. Reaction mixture was diluted with DCM (30 mL) then water (25 mL) was added and organic layer separated. The aqueous layer was extracted with DCM (2×20 mL) and the organic fractions combined, dried (Na$_2$SO$_4$) and concentrated under vacuum. Purification by HPLC (Method 4) gave the title compound (43 mg, 52% Yield). δ$_H$ (500 MHz, Methanol-d4) 8.25 (br.s, 1H), 6.61 (t, J=55.2 Hz, 1H), 6.28 (br.s, 1H), 4.61-4.47 (m, 1H), 3.72 (s, 3H), 3.38-3.32 (m, 1H), 3.26 (dd, J=12.8, 6.8 Hz, 1H), 3.21-3.13 (m, 1H), 3.13-3.04 (m, 1H), 3.02-2.83 (m, 2H), 2.44-2.29 (m, 2H), 2.20-2.09 (m, 1H), 1.55-1.47 (m, 2H), 1.12-1.03 (m, 2H), 1.03-0.84 (m, 3H), 0.51-0.43 (m, 2H), 0.27-0.20 (m, 2H). LCMS [M+H]$^+$ 557, RT 2.98 minutes (Method 10).

Intermediate 427

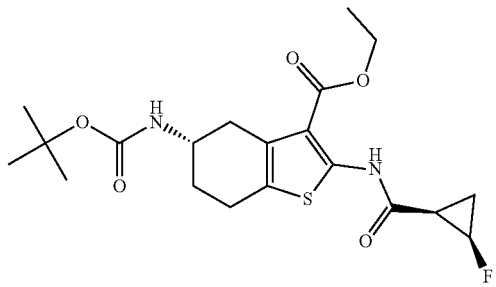 [SMILES: CCOC(=O)c1c(NC(=O)[C@H]2C[C@H]2F)sc2c1C[C@@H](NC(=O)OC(C)(C)C)CC2]

ethyl (5S)-5-(tert-butoxycarbonylamino)-2-[[(1R,2R)-2-fluorocyclopropanecarbonyl]amino]-4,5,6,7-tetrahydrobenzothiophene-3-carboxylate To a mixture of (1R,2R)-2-fluorocyclopropanecarboxylic acid (787 mg, 7.56 mmol), pyridine (2.44 mL, 30.25 mmol) and intermediate 567 (3000 mg, 7.56 mmol) in DCM (55 mL) 2,4,6-Tripropyl-1,3,5,2,4,6-trioxatriphosphorinane-2,4,6-trioxide (9.0 mL, 15.12 mmol) was slowly added at 0° C. The reaction mixture was slowly allowed to warm to r.t. and stirred for 16 h. Reaction mixture was diluted with DCM (50 mL) then water (80 mL) was added and organic layer separated. The aqueous layer was extracted with DCM (2×40 mL) and the organic fractions combined, dried over sodium sulfate and concentrated under vacuum. The residue was purified by column chromatography using 0-50% EtOAc in heptane to the title compound (2600 mg, 81% Yield). δ$_H$ (500 MHz, Chloroform-d) 11.47 (s, 1H), 4.93-4.69 (m, 1H), 4.65-4.55 (m, 1H), 4.34 (q, J=7.1 Hz, 2H), 4.06-3.89 (m, 1H), 3.17 (dd, J=17.1, 4.9 Hz, 1H), 2.78-2.69 (m, 2H), 2.60 (dd, J=16.9, 6.9 Hz, 1H), 2.04-1.99 (m, 1H), 1.96-1.86 (m, 2H), 1.85-1.76 (m, 1H), 1.46 (s, 9H), 1.38 (t, J=7.1 Hz, 3H), 1.31-1.25 (m, 1H). LCMS [M+Na]$^+$ 449, RT 2.06 minutes (Method 12).

Intermediate 428

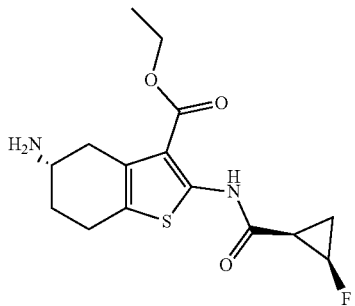 [SMILES: CCOC(=O)c1c(NC(=O)[C@H]2C[C@H]2F)sc2c1C[C@@H](N)CC2]

ethyl (5S)-5-amino-2-[[(1R,2R)-2-fluorocyclopropanecarbonyl]amino]-4,5,6,7-tetrahydrobenzothiophene-3-carboxylate Intermediate 427 (2600 mg, 6.1 mmol) was dissolved in DCM (7 mL) and 2,2,2-trifluoroacetic acid (4.5 mL, 61.0 mmol) was slowly added at 0° C. The reaction mixture was slowly allowed to warm to r.t. and stirred for 16 h. Reaction mixture was diluted with DCM (50 mL) then sat NaHCO₃ was added carefully (slowly), The aqueous layer was adjusted to pH9 and the organic layer separated. The aqueous layer was extracted with DCM (2×50 mL) and the organic fractions combined, dried over sodium sulfate and concentrated under vacuum to give the title compound (1990 mg, 99% Yield) which was used in the next stage without further purification. $\delta_H$ (500 MHz, Chloroform-d) 11.49 (s, 1H), 4.92-4.64 (m, 1H), 4.34 (q, J=7.1 Hz, 2H), 3.24-3.04 (m, 2H), 2.86-2.62 (m, 2H), 2.53-2.39 (m, 1H), 2.08-1.85 (m, 3H), 1.72-1.60 (m, 1H), 1.39 (t, J=7.1 Hz, 3H), 1.32-1.19 (m, 1H). LCMS [M+H]⁺ 327, RT 1.39 minutes (Method 12).

Intermediate 429

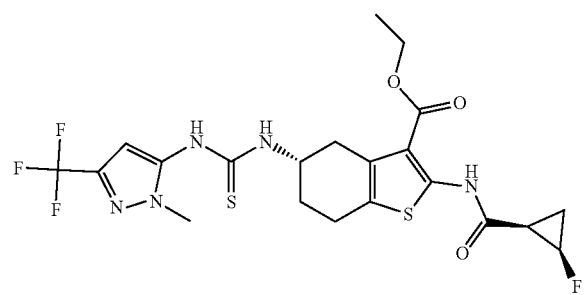 [SMILES: CCOC(=O)c1c(NC(=O)[C@H]2C[C@H]2F)sc2c1C[C@@H](NC(=S)Nc1cc(C(F)(F)F)nn1C)CC2]

ethyl (5S)-2-[[(1R,2R)-2-fluorocyclopropanecarbonyl]amino]-5-[[2-methyl-5-(trifluoromethyl)pyrazol-3-yl]carbamothioylamino]-4,5,6,7-tetrahydrobenzothiophene-3-carboxylate A solution of intermediate 428 (1000 mg, 3.06 mmol) in DCM (20 mL) was cooled to 0° C. Intermediate 262 (634.76 mg, 3.06 mmol) was added and the reaction stirred for 30 min at 0° C. then at r.t. for 5 h. Reaction mixture was diluted with DCM then water (50 mL) was added and organic layer separated. The aqueous layer was extracted with DCM (2×40 mL) and the organic fractions combined, dried over sodium sulfate and concentrated under vacuum. Resulting solid was filtered and washed with DCM to give the title compound. The DCM filtrate was purified by column chromatography using 0-80% EtOAc in heptane to give a second portion of the title compound (1560 mg, 95% Yield-combined). LCMS [M+H]⁺ 534, RT 2.03 minutes (Method 12).

Intermediate 430

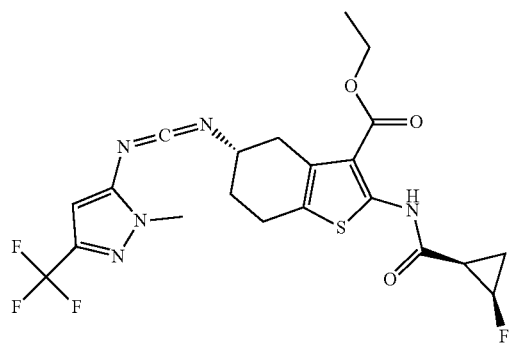 [SMILES: CCOC(=O)c1c(NC(=O)[C@H]2C[C@H]2F)sc2c1C[C@@H](N=C=Nc1cc(C(F)(F)F)nn1C)CC2]

ethyl (5S)-2-[[(1R,2R)-2-fluorocyclopropanecarbonyl]amino]-5-[[2-methyl-5-(trifluoromethyl)pyrazol-3-yl]iminomethyleneamino]-4,5,6,7-tetrahydrobenzothiophene-3-carboxylate To a solution of intermediate 429 (1560 mg, 2.92 mmol) in DCM (90 mL) was added triethylamine (1223 μL, 8.77 mmol). The solution was cooled to 0° C. then methanesulfonyl chloride (249 μL, 3.22 mmol) was added. Reaction stirred for 30 min at 0° C. then diluted with DCM (40 mL). Saturated aqueous NH₄Cl (50 mL) was added and the organic layer separated. The aqueous layer was extracted with DCM (2×40 mL) and the organic fractions combined, dried over sodium sulfate and concentrated under vacuum to give the title compound (1400 mg, 94% Yield), which was used in the next stage without further purification. LCMS [M+H]⁺ 500, RT 2.17 minutes (Method 12).

Intermediate 431

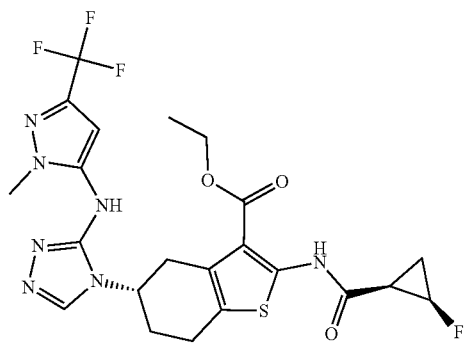 [SMILES: CCOC(=O)c1c(NC(=O)[C@H]2C[C@H]2F)sc2c1C[C@@H](n1cnnc1Nc1cc(C(F)(F)F)nn1C)CC2]

ethyl (5S)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxylate 0.5 M formic hydrazide (17 mL, 8.41 mmol) in EtOH was added to intermediate 430 (1400 mg, 2.80 mmol) followed by EtOH (35 mL) and stirred for 30 mins. Aqueous 0.92 M disodium carbonate (8.4 mL, 8.41 mmol) was added and reaction heated at 40° C. with stirring for 16 hours. Reaction allowed to cool, the remaining solid (Na₂CO₃) was filtered and washed with EtOH. The EtOH was removed under vacuum and water was added (50 mL). The mixture was extracted with DCM (2×50 mL), organic layers combined, dried (MgSO4), and concentrated to dryness. The residue was purified by column chromatography using 0-100% EtOAc in heptane to give the title compound (1500 mg, 94% Yield). $\delta_H$ (500 MHz, DMSO-d6) 12.17 (br s, 1H, major rotamer), 11.20 (s, 1H), 8.86 (br s, 1H, minor rotamer), 8.23 (br s, 1H), 6.36 (br s, 1H), 5.21-4.85 (m, 1H), 4.57-4.42 (m, 1H), 4.29 (q, J=7.0 Hz, 2H), 3.66 (br s, 3H), 3.38 (dd, J=16.8, 5.4 Hz, 1H), 3.00-2.91 (m, 1H), 2.89-2.77 (m, 2H), 2.35-2.29 (m, 1H), 2.28-2.18 (m, 1H), 2.18-2.10 (m, 1H), 1.74-1.61 (m, 1H), 1.33-1.28 (m, 1H), 1.27 (t, J=7.1 Hz, 3H). LCMS [M+H]⁺ 542, RT 1.88 minutes (Method 12).

Intermediate 432

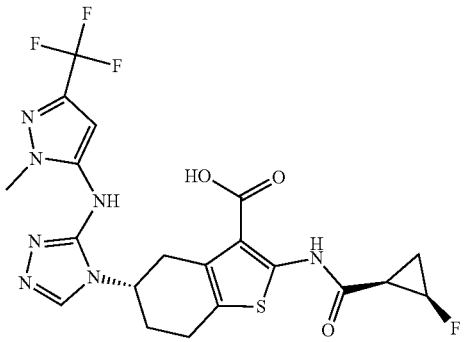 [SMILES: Cn1nc(C(F)(F)F)cc1Nc1nncn1[C@H]1CCc2sc(NC(=O)[C@H]3C[C@H]3F)c(C(=O)O)c2C1]

(5S)-2-[[(1R,2R)-2-fluorocyclopropanecarbonyl]
amino]-5-[3-[[2-methyl-5-(trifluoromethyl)pyrazol-
3-yl]amino]-1,2,4-triazol-4-yl]-4,5,6,7-tetrahydrobenzothiophene-3-carboxylic acid To a stirred solution of intermediate 431 (100 mg, 0.18 mmol) in mixture of THF (0.5 mL) and Methanol (0.5 mL) was added lithium hydroxide hydrate (15 mg, 0.351 mmol) in water (0.5 mL) at 0° C. and the mixture was stirred at 40° C. under nitrogen for 5 h. Reaction mixture was diluted with water and the organic solvents removed under vacuum. The resulting aqueous mixture was washed with EtOAc (2×20 mL). The aqueous layer was acidified to pH=4 with sat KHSO₄, and then extracted with EtOAc (2×30 mL). The organics were then separated, dried (MgSO₄), and concentrated under reduced pressure to give the title compound (90 mg, 88% Yield) which was used in the next stage without further purification. $\delta_H$ (500 MHz, DMSO-d6) 13.17 (br s, 1H, major rotamer), 12.17 (s, 1H, major rotamer), 11.51 (br s, 1H), 8.86 (s, 1H, minor rotamer), 8.47 (s, 1H, minor rotamer), 8.24 (s, 1H, major rotamer), 7.31 (s, 1H, minor rotamer), 6.61 (s, 1H, minor rotamer), 6.36 (s, 1H, major rotamer), 5.13-4.89 (m, 1H), 4.55-4.42 (m, 1H), 3.76 and 3.64 (2×s, 3H, rotamers), 3.47-3.38 (m, 1H), 2.94-2.74 (m, 3H), 2.34-2.20 (m, 2H), 2.19-2.08 (m, 1H), 1.72-1.59 (m, 1H), 1.33-1.21 (m, 1H). LCMS [M+H]⁺ 514, RT 1.73 minutes (Method 12).

Intermediate 433

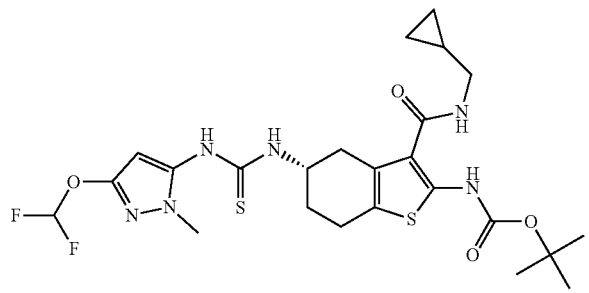 [SMILES: Cn1nc(OC(F)F)cc1NC(=S)N[C@H]1CCc2sc(NC(=O)OC(C)(C)C)c(C(=O)NCC3CC3)c2C1]

tert-butyl N-[(5S)-3-(cyclopropylmethylcarbamoyl)-
5-[[5-(difluoromethoxy)-2-methyl-pyrazol-3-yl]carbamothioylamino]-4,5,6,7-tetrahydrobenzothiophen-2-yl]carbamate To a solution of intermediate 559 (600 mg, 1.64 mmol) in DCM (20 mL) at 0° C., Intermediate 644 (336.85 mg, 1.64 mmol) was added. Reaction was stirred for 30 min at 0° C. then at r.t. for 3 h. The reaction mixture was diluted with DCM then water (30 mL) was added and organic layer separated. The aqueous layer was extracted with DCM (2×20 mL) and the organic fractions combined, dried over sodium sulfate and concentrated under vacuum. The residue was purified by column chromatography using 0-80% EtOAc in heptane to give the title compound (903 mg, 96% Yield). LCMS [M+H]⁺ 571, RT 2.12 minutes (Method 12).

Intermediate 434

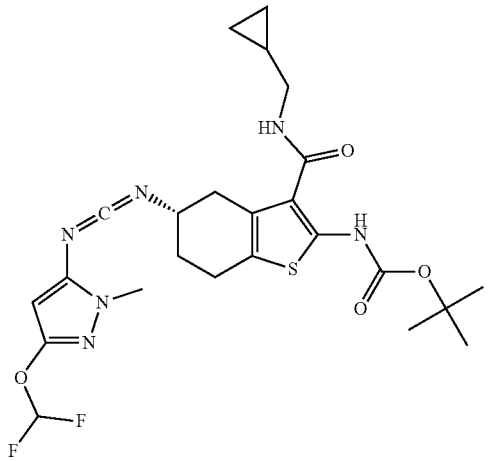 [SMILES: Cn1nc(OC(F)F)cc1N=C=N[C@H]1CCc2sc(NC(=O)OC(C)(C)C)c(C(=O)NCC3CC3)c2C1]

tert-butyl N-[(5S)-3-(cyclopropylmethylcarbamoyl)-
5-[[5-(difluoromethoxy)-2-methyl-pyrazol-3-yl]iminomethyleneamino]-4,5,6,7-tetrahydrobenzothiophen-2-yl]carbamate To a solution of intermediate 433 (903 mg, 1.58 mmol) in DCM (10 mL) was added triethylamine (662 μL, 4.75 mmol). The solution was cooled to 0° C. then methanesulfonyl chloride (135 μL, 1.74 mmol) was added and the reaction stirred for 30 min at 0° C. The reaction mixture was diluted with DCM (10 mL) then saturated aqueous NH₄Cl (20 mL) was added and organic layer separated. The aqueous layer was extracted with DCM (2×20 mL) and the organic fractions combined, dried over sodium sulfate and concentrated under vacuum to give the title compound (840 mg, 93% Yield) which was used in the next stage without further purification. LCMS [M+H]⁺ 537, RT 2.22 minutes (Method 12).

Intermediate 435

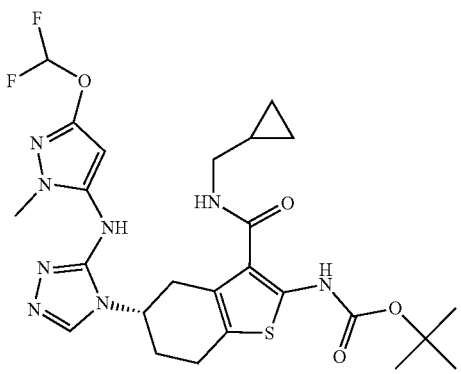 [SMILES: Cn1nc(OC(F)F)cc1Nc1nncn1[C@H]1CCc2sc(NC(=O)OC(C)(C)C)c(C(=O)NCC3CC3)c2C1]

tert-butyl N-[(5S)-3-(cyclopropylmethylcarbamoyl)-5-[3-[[5-(difluoromethoxy)-2-methyl-pyrazol-3-yl]amino]-1,2,4-triazol-4-yl]-4,5,6,7-tetrahydrobenzothiophen-2-yl]carbamate 1 M formic hydrazide (4.4 mL, 4.41 mmol) in MeOH was added to intermediate 434 (840 mg, 1.47 mmol) followed by MeOH (10 mL). The reaction mixture was stirred for 30 mins then aqueous 0.92 M disodium carbonate (4.4 mL, 4.41 mmol) was added and reaction heated to 50° C. with stirring for 6 hours. Reaction allowed to cool, MeOH was removed and water was added (20 mL). The aqueous layer was extracted with DCM (2×30 mL) and the organic fractions combined, dried over sodium sulfate and concentrated under vacuum. The residue was purified by column chromatography using 0-100% EtOAc in heptane to give the title compound (585 mg, 67% Yield). $\delta_H$ (500 MHz, DMSO-d6) 12.04 (s, 1H, major rotamer), 10.39 (s, 1H), 8.73 (s, 1H, minor rotamer), 8.40 and 8.19 (2×s, 1H, isomers), 7.48 (s, 1H), 7.35-6.93 (m, 1H), 5.90 and 5.65 (2×s, 1H, isomers), 4.53-4.29 (m, 1H), 3.57 and 3.48 (2×s, 3H, isomers), 3.22-2.96 (m, 4H), 2.92-2.74 (m, 2H), 2.28-2.13 (m, 2H), 1.47 (s, 9H), 1.04-0.93 (m, 1H), 0.39-0.31 (m, 2H), 0.22-0.14 (m, 2H). LCMS [M+H]⁺ 579, RT 1.96 minutes (Method 12).

Intermediate 436

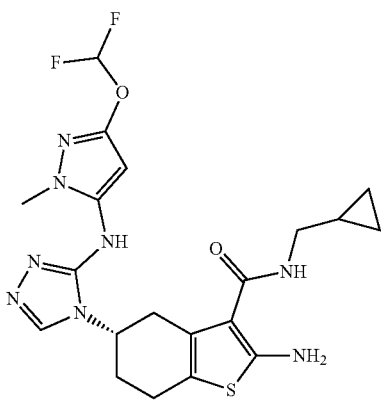

(5S)-2-amino-N-(cyclopropylmethyl)-5-[3-[[5-(difluoromethoxy)-2-methyl-pyrazol-3-yl]amino]-1,2,4-triazol-4-yl]-4,5,6,7-tetrahydrobenzothiophene-3-carboxamide dihydrochloride Intermediate 435 (40 mg, 0.07 mmol) was dissolved in 1,4-Dioxane (1 mL) then 4 M 1,4-dioxane hydrochloride (0.35 mL, 1.38 mmol) was added. Reaction was stirred for 16 h at room temperature. Reaction mixture was concentrated under vacuum to give the title compound (38 mg, 99% Yield) which was used in the next stage without further purification. LCMS [M+H]⁺ 479, RT 1.63 minutes (Method 12).

Intermediate 437

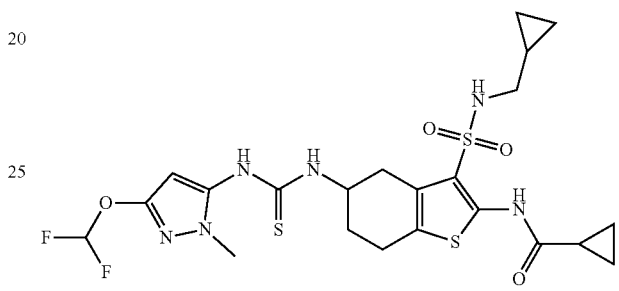

N-[3-(cyclopropylmethylsulfamoyl)-5-[[5-(difluoromethoxy)-2-methyl-pyrazol-3-yl]carbamothioylamino]-4,5,6,7-tetrahydrobenzothiophen-2-yl]cyclopropanecarboxamide A solution of intermediate 528 (210 mg, 0.57 mmol) in DCM (17.5 mL) was cooled to 0° C. Intermediate 644 (116 mg, 0.57 mmol) was added and the reaction stirred for 30 min at 0° C. followed by 5 h at room temperature. Reaction mixture was diluted with DCM then water (30 mL) was added and organic layer separated. The aqueous layer was extracted with DCM (2×20 mL) and the organic fractions combined, dried over sodium sulfate and concentrated under vacuum. The residue was purified by column chromatography using 0-80% EtOAc in heptane to give the title compound (230 mg, 69% Yield). LCMS [M+H]⁺ 575, RT 1.93 minutes (Method 12).

Intermediate 438

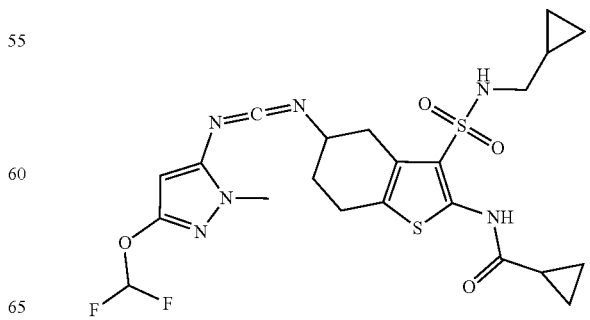

N-[3-(cyclopropylmethylsulfamoyl)-5-[[5-(difluoromethoxy)-2-methyl-pyrazol-3-yl]iminomethyleneamino]-4,5,6,7-tetrahydrobenzothiophen-2-yl] cyclopropanecarboxamide To a solution of intermediate 437 (230 mg, 0.4 mmol) in DCM (15 mL) was added triethylamine (167 ⌷L, 1.2 mmol). The solution was cooled to 0° C. then methanesulfonyl chloride (34 mL, 0.44 mmol) was added. Reaction was stirred for 30 min at 0° C. then diluted with DCM (15 mL). Saturated aqueous NH$_4$Cl (20 mL) was added and the organic layer separated. The aqueous layer was extracted with DCM (2×15 mL), the organic fractions combined, dried over sodium sulfate and concentrated under vacuum to give the title compound (215 mg, 99% Yield) which was used in the next stage without further purification. LCMS [M+H]$^+$ 541, RT 2.00 minutes (Method 12).

Intermediate 439

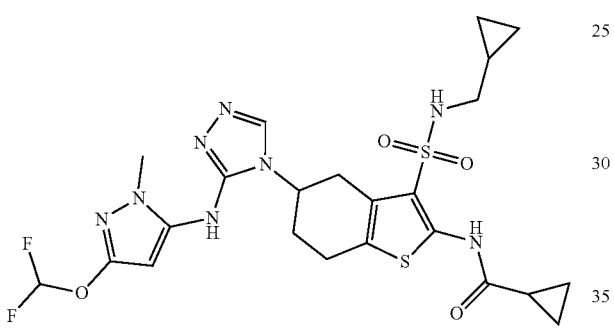

N-[3-(cyclopropylmethylsulfamoyl)-5-[3-[[5-(difluoromethoxy)-2-methyl-pyrazol-3-yl]amino]-1,2,4-triazol-4-yl]-4,5,6,7-tetrahydrobenzothiophen-2-yl] cyclopropanecarboxamide 1 M formic hydrazide (1.19 mL, 1.19 mmol) in MeOH was added to intermediate 438 (215 mg, 0.4 mmol) followed by MeOH (5 mL). The reaction was stirred for 30 mins then aqueous 0.92 M disodium carbonate (1.3 mL, 1.19 mmol) was added and reaction heated to 50° C. with stirring for 16 hours. Reaction allowed to cool, MeOH was removed and water was added (15 mL). The mixture was extracted with DCM (2×15 mL). The solvent of the combined organic layers was dried (MgSO$_4$) before concentration to dryness. The residue was purified by column chromatography using 0-100% EtOAc in heptane to give the title compound (136 mg, 56% Yield). δ$_H$ (500 MHz, DMSO-d6) 11.97 (s, 1H, major rotamer), 10.40 (s, 1H), 8.70 (s, 1H, minor rotamer), 8.37 and 8.17 (2×s, 1H), 7.96-7.77 (m, 1H), 7.28-6.83 (m, 1H), 5.88 and 5.60 (2×s, 1H), 4.48-4.30 (m, 1H), 3.51 and 3.44 (2×s, 31H), 3.33-3.29 (m, 1H), 2.83-2.73 (m, 3H), 2.69-2.61 (m, 21H), 2.25-2.06 (m, 21H), 1.93-1.81 (m, 1H), 0.96-0.77 (m, 4H), 0.74-0.59 (m, 1H), 0.36-0.23 (m, 21H), 0.06--0.14 (m, 21H). LCMS [M+H]$^+$ 583, RT 3.03 minutes (Method 10).

Intermediate 440

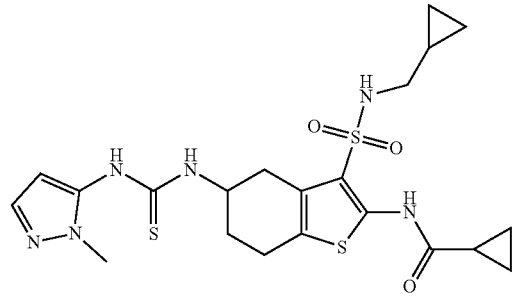 [SMILES: Cn1nccc1NC(=S)NC1CCc2sc(NC(=O)C3CC3)c(S(=O)(=O)NCC3CC3)c2C1]

N-[3-(cyclopropylmethylsulfamoyl)-5-[(2-methylpyrazol-3-yl)carbamothioylamino]-4,5,6,7-tetrahydrobenzothiophen-2-yl]cyclopropanecarboxamide A solution of intermediate 528 (500 mg, 1.35 mmol) and was stirred in DCM (30 mL) was cooled to 0° C. then followed by Intermediate 237 (188 mg, 1.35 mmol) was added. Reaction stirred for 30 min at 0° C. then room temperature for 5 h. During the reaction white precipitate was formed, it was filtered and washed with DCM/Ether mixture, and dried to give the title compound (620 mg, 90% Yield). LCMS [M+H]$^+$ 509, RT 1.80 minutes (Method 12).

Intermediate 441

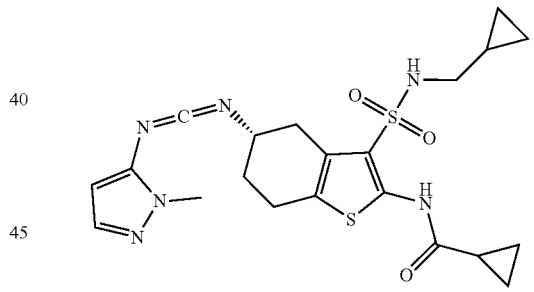

N-[(5S)-3-(cyclopropylmethylsulfamoyl)-5-[(2-methylpyrazol-3-yl)iminomethyleneamino]-4,5,6,7-tetrahydrobenzothiophen-2-yl]cyclopropanecarboxamide To a solution of intermediate 440 (576 mg, 1.13 mmol) in DCM (25 mL) was added triethylamine (473 ⌷L, 3.4 mmol). The solution was cooled to 0° C. then methanesulfonyl chloride (96 ⌷L, 1.25 mmol) was added. Reaction stirred for 30 min at 0° C. Reaction mixture was diluted with DCM (10 mL) then saturated aqueous NH$_4$Cl (15 mL) was added and organic layer separated. The aqueous layer was extracted with DCM (2×10 mL), the organic fractions combined, dried over sodium sulfate and concentrated under vacuum to give the title compound (535 mg, 87% Yield) which was used in the next stage without further purification. LCMS [M+H]$^+$ 475, RT 1.89 minutes (Method 12).

Intermediate 442

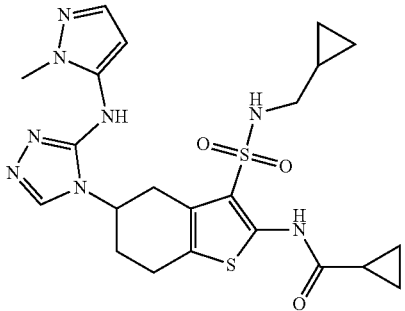 [SMILES: Cn1nccc1Nc1nncn1C1CCc2sc(NC(=O)C3CC3)c(S(=O)(=O)NCC3CC3)c2C1]

N-[3-(cyclopropylmethylsulfamoyl)-5-[3-[(2-methylpyrazol-3-yl)amino]-1,2,4-triazol-4-yl]-4,5,6,7-tetrahydrobenzothiophen-2-yl]cyclopropanecarboxamide 1 M formic hydrazide (2.98 mL, 2.98 mmol) in MeOH was added to intermediate 441 (535 mg, 0.99 mmol) followed by MeOH (5 mL). The reaction was stirred for 30 mins, then aqueous 0.92 M disodium carbonate (3.23 mL, 2.98 mmol) was added and reaction heated to 50° C. with stirring for 16 hours. Reaction allowed to cool, MeOH was removed and water was added (30 mL). The mixture was extracted with DCM (2×25 mL). The solvent of the combined organic layers was dried (MgSO₄) and concentration to dryness. The residue was purified first by column chromatography using 50-100% EtOAc in heptane then 0-20% MeOH in DCM followed by HPLC (method 4) to the afford the title compound (314 mg, 60% Yield). δ$_H$ (500 MHz, DMSO-d6) 11.82 (s, 1H, minor rotamer), 10.47 (s, 1H), 8.52 (s, 1H, major rotamer), 8.38 (s, 1H, major rotamer), 8.17 (s, 1H, minor rotamer), 8.05-7.89 (m, 1H), 7.30 (s, 1H, major rotamer), 7.19 (s, 1H, minor rotamer), 6.14 (s, 1H, major rotamer), 5.91 (s, 1H, minor rotamer), 4.59-4.40 (m, 1H), 3.65 (s, 3H, major rotamer), 3.56 (s, 3H, minor rotamer), 2.91-2.79 (m, 3H), 2.75-2.65 (m, 2H), 2.33-2.10 (m, 2H), 2.00-1.89 (m, 1H), 1.05-0.86 (m, 4H), 0.81-0.68 (m, 1H), 0.42-0.26 (m, 2H), 0.14-0.06 (m, 2H). LCMS [M+H]⁺ 517, RT 2.37 minutes (Method 10).

Intermediate 443

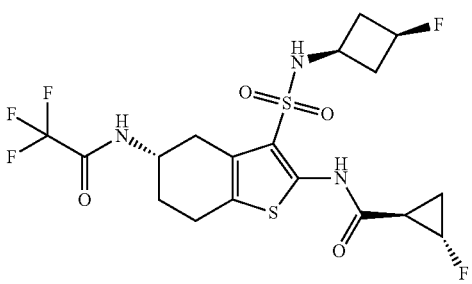 [SMILES: O=C(Nc1sc2c(c1S(=O)(=O)N[C@H]1C[C@@H](F)C1)C[C@@H](NC(=O)C(F)(F)F)CC2)[C@H]1C[C@@H]1F]

(1R,2S)-2-fluoro-N-[(5S)-3-[cis-(3-fluorocyclobutyl)sulfamoyl]-5-[(2,2,2-trifluoroacetyl)amino]-4,5,6,7-tetrahydrobenzothiophen-2-yl]cyclopropanecarboxamide To a stirring solution of Cis-3-fluorocyclobutanamine hydrochloride (159 mg, 1.27 mmol) and triethylamine (350 μL, 2.51 mmol) in anhydrous DCM (10 mL) was added portion-wise intermediate 474 (380 mg, 0.847 mmol). The solution was stirred at room temperature under an atmosphere of nitrogen for 1 h. The reaction mixture evaporated to dryness, dissolved in ethyl acetate (100 mL), washed with water (20 mL), sat. aq. NH₄CL (20 mL), brine (20 mL), dried over magnesium sulfate, filtered, and evaporated to dryness to afford crude. This was absorbed on silica and purified by column chromatography eluted with 0-100% ethyl acetate in heptane to give the title compound (368 mg, 87% Yield) as an off white solid. δ$_H$ (400 MHz, DMSO-d6) 10.49 (br s, 1H), 9.58 (d, J=8.0 Hz, 1H), 8.21 (d, J=7.4 Hz, 1H), 5.09-4.84 (m, 1H), 4.84-4.57 (m, 1H), 4.18-3.91 (m, 1H), 3.28-3.17 (m, 1H), 3.10 (dd, J=16.5, 5.3 Hz, 1H), 2.84-2.72 (m, 2H), 2.68-2.54 (m, 2H), 2.49-2.36 (m, 2H), 2.14-1.88 (m, 3H), 1.88-1.73 (m, 1H), 1.70-1.51 (m, 1H), 1.41-1.21 (m, 1H). LCMS [M+H]⁺ 502, RT 1.92 minutes (Method 12).

Intermediate 444

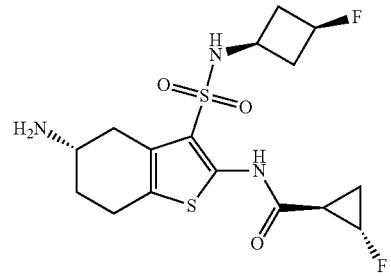 [SMILES: N[C@H]1CCc2sc(NC(=O)[C@H]3C[C@@H]3F)c(S(=O)(=O)N[C@H]3C[C@@H](F)C3)c2C1]

(1R,2S)—N-[(5S)-5-amino-3-[cis-(3-fluorocyclobutyl)sulfamoyl]-4,5,6,7-tetrahydrobenzothiophen-2-yl]-2-fluoro-cyclopropanecarboxamide Dipotassium carbonate (400 mg, 2.90 mmol) was added to the stirred solution of intermediate 443 (363 mg, 0.724 mmol) in methanol (20 mL) and water (3 mL) at room temperature and the mixture was stirred at 40° C. for 40 h. The reaction mixture evaporated to dryness, diluted with water (10 mL) and the aqueous layer adjusted to pH 10 with 1 M HCl and extracted with 10% methanol in DCM (3×30 mL). The combined organic layers were dried over sodium sulfate, filtered and concentrated to dryness to give the title compound (305 mg, 90% Yield) which was used in the next stage without further purification. LCMS [M+H]⁺ 406, RT 0.86 minutes (Method 11).

Intermediate 445

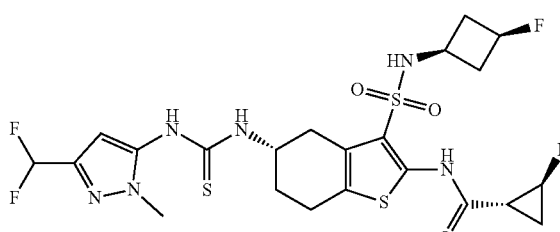

(1R,2S)—N-[(5)-5-[[5-(difluoromethyl)-2-methyl-pyrazol-3-yl]carbamothioylamino]-3-[cis-(3-fluoro-cyclobutyl)sulfamoyl]-4,5,6,7-tetrahydrobenzothi-ophen-2-yl]-2-fluoro-cyclopropanecarboxamide A solution of intermediate 444 (150.0 mg, 0.32 mmol) in DCM (5 mL) was cooled to 0° C. Intermediate 568 (82.8 mg, 0.32 mmol) was then added and the reaction stirred for 30 min at 0° C. then at r.t. for 5 h. Reaction mixture was diluted with DCM then water (30 mL) was added and organic layer separated. The aqueous layer was extracted with DCM (2×10 mL) and the organic fractions combined, dried over sodium sulfate and concentrated under vacuum. The resulting residue was purified by column chromatography using 0-70% EtOAc in heptane to give the title compound (171 mg, 86% Yield). LCMS [M+H]+ 595, RT 1.91 minutes (Method 12).

Intermediate 446

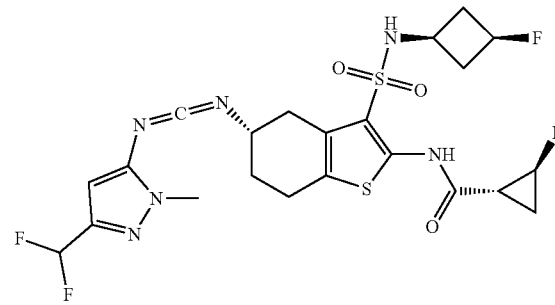

(1R,2S)—N-[(5S)-5-[[5-(difluoromethyl)-2-methyl-pyrazol-3-yl]iminomethyleneamino]-3-[cis-(3-fluo-rocyclobutyl)sulfamoyl]-4,5,6,7-tetrahydrobenzothi-ophen-2-yl]-2-fluoro-cyclopropanecarboxamide To a solution of intermediate 445 (170 mg, 0.27 mmol) in DCM (10 mL) was added triethylamine (115 μL, 0.82 mmol). The solution was cooled to 0° C. then methanesulfonyl chloride (23 μL, 0.3 mmol) was added. Reaction stirred for 30 min at 0° C. then diluted with DCM (15 mL) and saturated aqueous NH₄Cl (20 mL). The organic layer was separated and the aqueous layer extracted with DCM (2×15 mL). Organic layers combined, dried over sodium sulfate and concentrated under vacuum to give the title compound (151 mg, 84% Yield) which was used in the next stage without further purification. LCMS [M+H]+ 561, RT 2.00 minutes (Method 12).

Intermediate 447

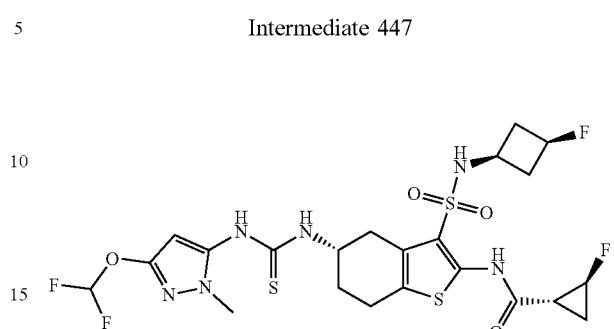

(1R,2S)—N-[(5S)-5-[[5-(difluoromethoxy)-2-methyl-pyrazol-3-yl]carbamothioylamino]-3-[cis-(3-fluorocyclobutyl)sulfamoyl]-4,5,6,7-tetrahydroben-zothiophen-2-yl]-2-fluoro-cyclopropanecarboxamide A solution of intermediate 444 (150 mg, 0.32 mmol) in DCM (5 mL) was cooled to 0° C. Intermediate 644 (66 mg, 0.32 mmol) was added and the reaction stirred for at 0° C. for 30 min and at r.t. for 5 h. Reaction mixture was diluted with DCM then water (20 mL) was added and organic layer separated. The aqueous layer was extracted with DCM (2×10 mL), organic fractions combined, dried over sodium sulfate and concentrated under vacuum. The resulting residue was purified by column chromatography using 0-60% EtOAc in heptane to give the title compound (150 mg, 75% Yield). LCMS [M+H]+ 611, RT 1.94 minutes (Method 12).

Intermediate 448

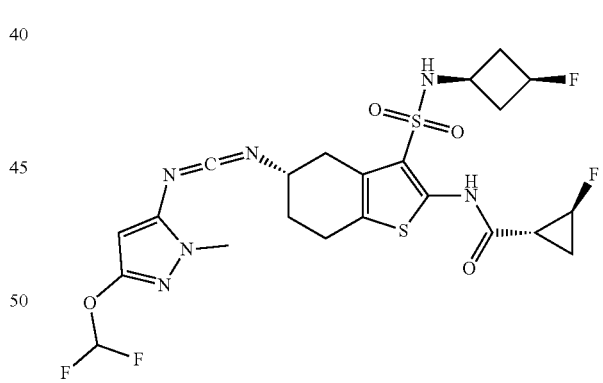

(1R,2S)—N-[(5)-5-[[5-(difluoromethoxy)-2-methyl-pyrazol-3-yl]iminomethyleneamino]-3-[cis-(3-fluo-rocyclobutyl)sulfamoyl]-4,5,6,7-tetrahydrobenzothi-ophen-2-yl]-2-fluoro-cyclopropanecarboxamide To a solution of intermediate 447 (150 mg, 0.25 mmol) in DCM (10 mL) was added triethylamine (103 μL, 0.74 mmol). The solution was cooled to 0° C. and methanesulfonyl chloride (21 μL, 0.27 mmol) added. Reaction was stirred for 30 min at 0° C. the diluted with DCM (15 mL) and saturated aqueous NH₄Cl (20 mL). The organic layer was separated and the aqueous layer extracted with DCM (2×15 mL). Organic fractions were combined, dried over sodium sulfate and concentrated under vacuum to give the title compound (140 mg, 86% Yield) which was used in the next stage without further purification. LCMS [M+H]+ 577, RT 2.01 minutes (Method 12).

Intermediate 449

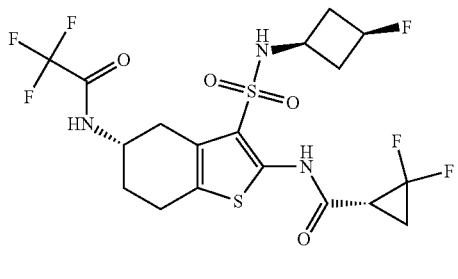 [SMILES: O=C(Nc1sc2c(c1S(=O)(=O)N[C@H]1C[C@@H](F)C1)C[C@@H](NC(=O)C(F)(F)F)CC2)[C@H]1CC1(F)F]

2,2-difluoro-N-[(5S)-3-[cis-(3-fluorocyclobutyl)sulfamoyl]-5-[(2,2,2-trifluoroacetyl)amino]-4,5,6,7-tetrahydrobenzothiophen-2-yl]cyclopropanecarboxamide To a stirring solution of Cis 3-fluorocyclobutanamine hydrochloride (274 mg, 2.18 mmol) and triethylamine (609 μL, 4.37 mmol) in anhydrous DCM (15 mL) was added portion-wise intermediate 481 (680 mg, 1.46 mmol) and the resulting yellow solution was stirred at room temperature under an atmosphere of nitrogen for 1 h. The reaction mixture was diluted with DCM (50 mL), washed with water (30 mL), brine (20 mL), dried over magnesium sulfate, filtered, and evaporated to dryness. The resulting residue was purified by column chromatography eluting with 0-60% ethyl acetate in heptane to give the title compound (690 mg, 91% Yield). δ$_H$ (500 MHz, DMSO-d6) 10.51 (s, 1H), 9.57 (d, J=8.1 Hz, 1H), 8.22 (d, J=6.2 Hz, 1H), 4.82-4.56 (m, 1H), 4.18-3.96 (m, 1H), 3.29-3.16 (m, 2H), 3.10 (dd, J=16.5, 5.2 Hz, 1H), 2.86-2.65 (m, 2H), 2.62-2.54 (m, 1H), 2.47-2.36 (m, 2H), 2.15-1.88 (m, 5H), 1.87-1.72 (m, 1H). LCMS [M+H]+ 519, RT 1.92 minutes (Method 12).

Intermediate 450

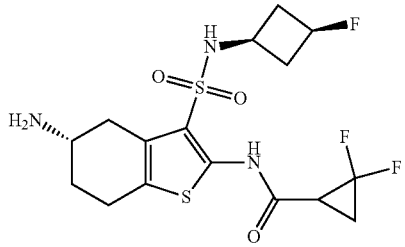 [SMILES: N[C@H]1CCc2sc(NC(=O)C3CC3(F)F)c(S(=O)(=O)N[C@H]3C[C@@H](F)C3)c2C1]

N-[(5S)-5-amino-3-[cis-(3-fluorocyclobutyl)sulfamoyl]-4,5,6,7-tetrahydrobenzothiophen-2-yl]-2,2-difluoro-cyclopropanecarboxamide Dipotassium carbonate (734 mg, 5.31 mmol) was added to the stirred solution of intermediate 449 (690 mg, 1.33 mmol) in a mixture of methanol (30 mL) and water (4 mL). The mixture was then heated at 40° C. for 20 h. The reaction mixture evaporated to dryness, diluted with water (20 mL) and the aqueous layer adjusted to pH 10 with 1 M HCl. The aqueous layer was then extracted with 10% methanol in DCM (3×30 mL) and the combined organic layers, dried over sodium sulfate, filtered and concentrated to dryness to the afford the title compound (550 mg, 92% Yield). The product was used in the next stage without further purification. LCMS [M+H]+ 424, RT 1.51 minutes (Method 12).

Intermediate 451

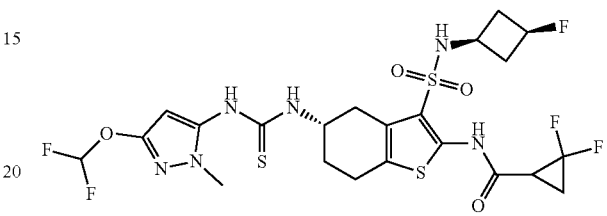

N-[(5S)-5-[[5-(difluoromethoxy)-2-methyl-pyrazol-3-yl]carbamothioylamino]-3-[cis-(3-fluorocyclobutyl)sulfamoyl]-4,5,6,7-tetrahydrobenzothiophen-2-yl]-2,2-difluoro-cyclopropanecarboxamide A solution of intermediate 450 (285 mg, 0.67 mmol) in DCM (10 mL) was cooled to 0° C. Intermediate 644 (138 mg, 0.67 mmol) was then added and the reaction stirred for 30 min at 0° C. and at r.t. for 5 h. Reaction mixture was diluted with DCM and water (20 mL). The organic layer was separated and the aqueous layer extracted with DCM (2×20 mL). The organic fractions were combined, dried over sodium sulfate and concentrated under vacuum. The resulting residue was purified by column chromatography using 0-60% EtOAc in heptane to give the title compound (420 mg, 92% Yield). LCMS [M+H]+ 629, RT 1.94 minutes (Method 12).

Intermediate 452

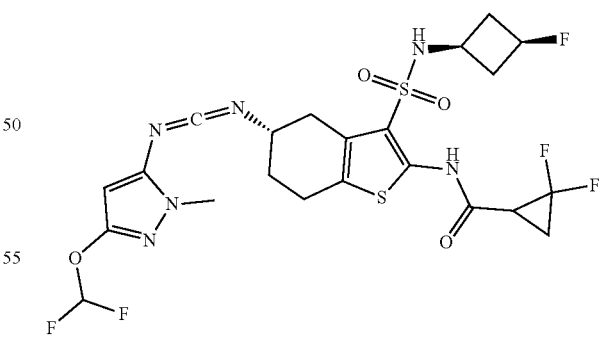

N-[(5S)-5-[[5-(difluoromethoxy)-2-methyl-pyrazol-3-yl]iminomethyleneamino]-3-[cis-(3-fluorocyclobutyl)sulfamoyl]-4,5,6,7-tetrahydrobenzothiophen-2-yl]-2,2-difluoro-cyclopropanecarboxamide To a solution of intermediate 452 (420 mg, 0.67 mmol) in DCM (15 mL) was added triethylamine (279 μL, 2 mmol).

The solution was cooled to 0° C. then methanesulfonyl chloride (57 μL, 0.73 mmol) was added. Reaction stirred for 30 min at 0° C. then diluted with DCM (15 mL) and saturated aqueous NH₄Cl (20 mL). The organic layer was separated and the aqueous layer extracted with DCM (2×15 mL). Organic fractions combined, dried over sodium sulfate and concentrated under vacuum to give the title compound (390 mg, 73% Yield) which was used in the next stage without further purification. LCMS [M+H]⁺ 595, RT 2.02 minutes (Method 12).

Intermediate 453

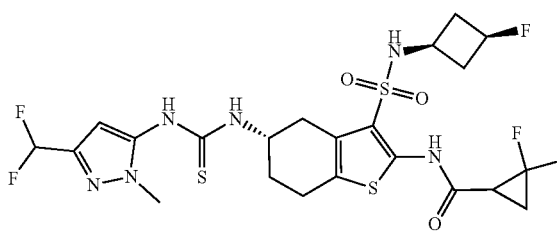

N-[(5S)-5-[[5-(difluoromethyl)-2-methyl-pyrazol-3-yl]carbamothioylamino]-3-[cis-(3-fluorocyclobutyl)sulfamoyl]-4,5,6,7-tetrahydrobenzothiophen-2-yl]-2,2-difluoro-cyclopropanecarboxamide A solution of intermediate 450 (275 mg, 0.65 mmol) in DCM (10 mL) was cooled to 0° C. Intermediate 568 (167 mg, 0.65 mmol) was added and the reaction stirred at 0° C. for 30 min then at r.t. for 5 h. Reaction mixture was diluted with DCM and water (30 mL). The organic layer separated and the aqueous layer extracted with DCM (2×10 mL). Organic fractions combined, dried over sodium sulfate and concentrated under vacuum. The resulting residue was purified by column chromatography using 0-60% EtOAc in heptane to give the title compound (380 mg, 89% Yield). LCMS [M+H]⁺ 613, RT 1.93 minutes (Method 12).

Intermediate 454

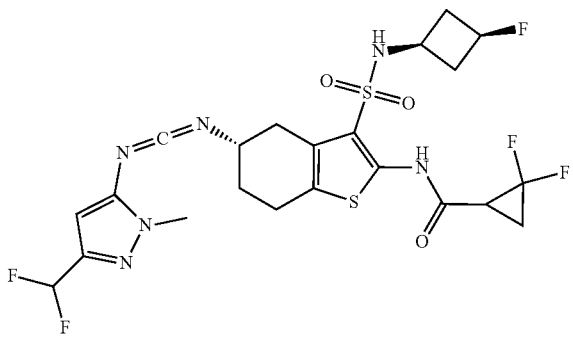 [SMILES: Cn1nc(C(F)F)cc1N=C=N[C@H]1CCc2sc(NC(=O)C3CC3(F)F)c(S(=O)(=O)N[C@H]3C[C@@H](F)C3)c2C1]

N-[(5S)-5-[[5-(difluoromethyl)-2-methyl-pyrazol-3-yl]iminomethyleneamino]-3-[cis-(3-fluorocyclobutyl)sulfamoyl]-4,5,6,7-tetrahydrobenzothiophen-2-yl]-2,2-difluoro-cyclopropanecarboxamide To a solution of intermediate 453 (380 mg, 0.62 mmol) in DCM (15 mL) was added triethylamine (259 μL, 1.86 mmol). The solution was cooled to 0° C. then methanesulfonyl chloride (53 μL, 0.68 mmol) was added. Reaction stirred for 30 min at 0° C. then diluted with DCM (15 mL) and saturated aqueous NH₄Cl (20 mL). The organic layer was separated and the aqueous layer extracted with DCM (2×15 mL). Organic fractions combined, dried over sodium sulfate and concentrated under vacuum to give the title compound (350 mg, 74% Yield) which was used in the next stage without further purification. LCMS [M+H]⁺ 579, RT 2.00 minutes (Method 12).

Intermediate 455

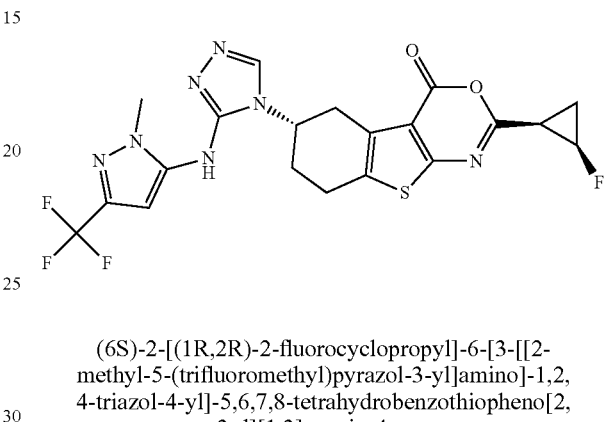

(6S)-2-[(1R,2R)-2-fluorocyclopropyl]-6-[3-[[2-methyl-5-(trifluoromethyl)pyrazol-3-yl]amino]-1,2,4-triazol-4-yl]-5,6,7,8-tetrahydrobenzothiopheno[2,3-d][1,3]oxazin-4-one A mixture of intermediate 432 (950 mg, 1.85 mmol) and pyridine (596 μL, 7.40 mmol) in DCM (150 mL), T3P (50%, 3304 μL, 5.55 mmol) was slowly added at 0° C. The reaction mixture was slowly allowed to warm to r.t. and stirred for 72 h. Reaction mixture was diluted with DCM (100 mL) then water (100 mL) was added and organic layer separated. The aqueous layer was extracted with DCM (2×50 mL) and the organic fractions combined, dried (Na₂SO₄), and concentrated under reduced pressure to give the title compound (12.3 g, 2.33 mmol, quantitative) with residual pyridine and T3P as minor impurities. LCMS [M+H]⁺ 496, RT 1.81 minutes (Method 12).

Intermediate 456

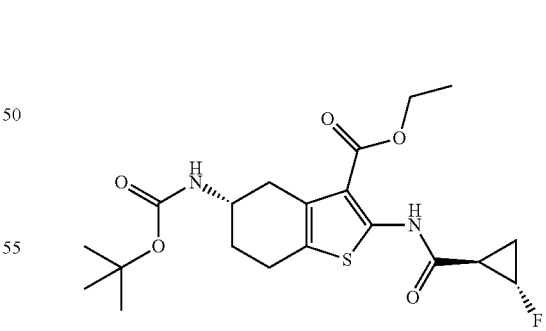

Ethyl (5S)-5-(tert-butoxycarbonylamino)-2-[[(1R,2S)-2-fluorocyclopropanecarbonyl]amino]-4,5,6,7-tetrahydrobenzothiophene-3-carboxylate T3P (50% in EtOAc, 15 mL, 25.2 mmol) was added drop wise to a stirred solution of intermediate 567 (5.00 g, 12.6 mmol), (1R,2S)-2-fluorocyclopropanecarboxylic acid (1.312 g, 12.6 mmol) and pyridine (4.06 mL, 50.4 mmol) in dry DCM (100 mL) at 0° C. The reaction mixture was allowed to warm up to room temperature and stirred for 16 hours. The reaction mixture was diluted with water (50 mL) and extracted with DCM (2×50 mL). The combined organic layers were dried over sodium sulfate, filtered, evaporated to dryness. The resulting residue was purified by column chromatography, eluting with 0-100% EtOAc in heptane to give the title compound (4.40 g, 82% Yield). $\delta_H$ (500 MHz, Chloroform-d) 11.55 (s, 1H), 5.07-4.76 (m, 1H), 4.73-4.48 (m, 1H), 4.35 (q, J=7.1 Hz, 2H), 3.98 (br s, 1H), 3.17 (dd, J=17.1, 5.1 Hz, 1H), 2.80-2.68 (m, 2H), 2.60 (dd, J=17.2, 7.3 Hz, 1H), 2.20-2.09 (m, 1H), 2.08-1.97 (m, 1H), 1.87-1.71 (m, 1H), 1.56-1.48 (m, 2H), 1.46 (s, 9H), 1.39 (t, J=7.1 Hz, 3H). LCMS [M+Na]*449, RT 2.13 minutes (Method 12).

Intermediate 457

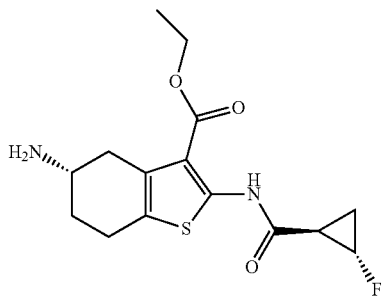 [SMILES: CCOC(=O)c1c(NC(=O)[C@H]2C[C@@H]2F)sc2c1C[C@@H](N)CC2]

Ethyl (5S)-5-amino-2-[[(1R,2S)-2-fluorocyclopropanecarbonyl]amino]-4,5,6,7-tetrahydrobenzothiophene-3-carboxylate 2,2,2-Trifluoroacetic acid (8 mL, 0.108 mol) was added drop wise to a stirred solution of intermediate 456 (4.40 g, 10.3 mmol) in dry DCM (10 mL) at room temperature. The reaction mixture was stirred for 4 h and left to stand at room temperature overnight. The reaction mixture was evaporated to dryness, dissolved in DCM (200 mL) and washed with sat. aqueous NaHCO₃ (50 mL) and brine (25 mL). The combined organic layers were dried over sodium sulfate, filtered, evaporated to dryness to give the title compound (2.84 g, 84% Yield). $\delta_H$ (500 MHz, Chloroform-d) 11.58 (s, 1H), 5.03-4.80 (m, 1H), 4.38 (q, J=7.1 Hz, 2H), 3.26-3.14 (m, 2H), 2.84-2.66 (m, 2H), 2.58-2.44 (m, 1H), 2.24-2.10 (m, 1H), 2.09-1.97 (m, 1H), 1.79 (s, 2H), 1.74-1.62 (m, 1H), 1.61-1.47 (m, 2H), 1.42 (t, J=7.1 Hz, 3H). LCMS [M+H]⁺ 327, RT 1.45 minutes (Method 12).

Intermediate 458

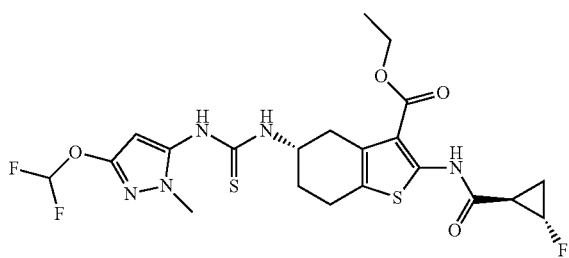 [SMILES: CCOC(=O)c1c(NC(=O)[C@H]2C[C@@H]2F)sc2c1C[C@@H](NC(=S)Nc1cc(OC(F)F)nn1C)CC2]

Ethyl (5S)-5-[[5-(difluoromethoxy)-2-methyl-pyrazol-3-yl]carbamothioylamino]-2-[[(1R,2S)-2-fluoro cyclopropanecarbonyl]amino]-4,5,6,7-tetrahydrobenzothiophene-3-carboxylate A solution of intermediate 644 (1.02 g, 4.72 mmol) in dry DCM (10 mL) was added to a stirred solution of intermediate 457 (1.40 g, 4.29 mmol) in dry DCM (10 mL) at room temperature and stirred for 18 hours. The reaction mixture was washed with saturated aqueous NH₄Cl (25 mL). The combined organic layers were dried over sodium sulfate, filtered and evaporated to afford light brown oil. The crude material was purified by column chromatography, eluting with 0-100% EtOAc in heptane to give the title compound (2.01 g, 88% Yield). $\delta_H$ (500 MHz, Chloroform-d) 11.53 (s, 1H), 7.45 (br s, 1H), 6.80 (t, J=72.8 Hz, 1H), 6.13 (d, J=7.3 Hz, 1H), 5.78 (s, 1H), 5.03-4.84 (m, 1H), 4.77 (br s, 1H), 4.44-4.32 (m, 2H), 3.69 (s, 3H), 3.31 (dd, J=17.3, 5.3 Hz, 1H), 2.89-2.77 (m, 1H), 2.76-2.62 (m, 2H), 2.23-2.09 (m, 2H), 2.02-1.90 (m, 1H), 1.60-1.54 (m, 1H), 1.54-1.48 (m, 1H), 1.41 (t, J=7.1 Hz, 3H). LCMS [M+H]⁺ 532, RT 2.04 minutes (Method 12).

Intermediate 459

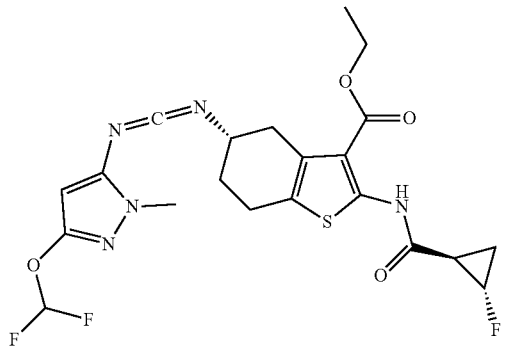 [SMILES: CCOC(=O)c1c(NC(=O)[C@H]2C[C@@H]2F)sc2c1C[C@@H](N=C=Nc1cc(OC(F)F)nn1C)CC2]

Ethyl (5S)-5-[[5-(difluoromethoxy)-2-methyl-pyrazol-3-yl]iminomethyleneamino]-2-[[(1R,2S)-2-fluoro cyclopropanecarbonyl]amino]-4,5,6,7-tetrahydrobenzothiophene-3-carboxylate Methanesulfonyl chloride (33 μL, 0.426 mmol) was added to a stirred solution of intermediate 458 (200 mg, 0.376 mmol) and triethylamine (160 μL, 1.15 mmol) in dry DCM (4 mL) at ~5° C. The reaction mixture was stirred for 30 min. The reaction mixture was diluted with DCM (25 mL) and washed with saturated aqueous NH₄Cl (50 mL). The combined organic layers were dried over sodium sulfate, filtered, evaporated to dryness to give the title compound (187 mg, 97% Yield). LCMS [M+H]⁺ 498, RT 2.17 minutes (Method 12).

Intermediate 460

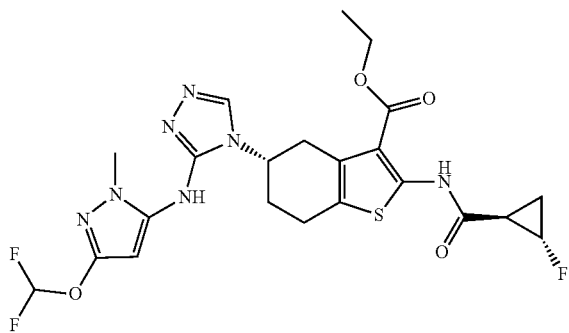 [SMILES: CCOC(=O)c1c(NC(=O)[C@H]2C[C@@H]2F)sc2c1C[C@@H](n1cnnc1Nc1cc(OC(F)F)nn1C)CC2]

Ethyl (5S)-5-[3-[[5-(difluoromethoxy)-2-methyl-pyrazol-3-yl]amino]-1,2,4-triazol-4-yl]-2-[[(1R,2S)-2-fluoro cyclopropanecarbonyl]amino]-4,5,6,7-tetrahydrobenzothiophene-3-carboxylate A solution of formic hydrazide (70 mg, 1.17 mmol) in ethanol (3 mL) was added to the intermediate 459 (193 mg, 0.388 mmol). The reaction mixture was stirred at room temperature for 30 min then aqueous 0.92 M disodium carbonate (1.2 mL, 1.17 mmol) was added and the reaction heated at 45° C. overnight. The reaction mixture cooled to room temperature, filtered and the resulting filtrate was evaporated to dryness, diluted with saturated aqueous NH$_4$Cl (25 mL) and extracted with DCM (20 mL×3). The combined organic layers were dried over sodium sulfate, filtered, evaporated to dryness. The residue was then purified by column chromatography, eluting with 0-100% EtOAc in heptane to give the title compound (100 mg, 48% Yield). δ$_H$ (400 MHz, Chloroform-d) 11.57 (s, 1H), 9.19 (s, 1H), 7.50 (br s, 1H), 6.83 (t, J=73.9 Hz, 1H), 5.39 (s, 1H), 5.07-4.79 (m, 1H), 4.77-4.50 (m, 1H), 4.39 (q, J=7.1 Hz, 2H), 3.66 (s, 3H), 3.50-3.41 (m, 1H), 3.01 (dd, J=17.4, 7.4 Hz, 1H), 2.94-2.83 (m, 1H), 2.83-2.67 (m, 1H), 2.36-2.25 (m, 1H), 2.25-2.11 (m, 2H), 1.68-1.48 (m, 2H), 1.40 (t, J=7.1 Hz, 3H). LCMS [M+H]⁺ 540, RT 1.87 minutes (Method 12).

Intermediate 461

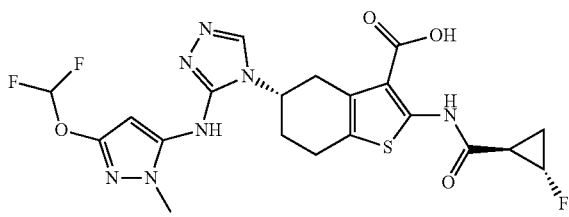 [SMILES: Cn1nc(OC(F)F)cc1Nc1nncn1[C@H]1CCc2sc(NC(=O)[C@H]3C[C@@H]3F)c(C(=O)O)c2C1]

(5S)-5-[3-[[5-(difluoromethoxy)-2-methyl-pyrazol-3-yl]amino]-1,2,4-triazol-4-yl]-2-[[1R,2S)-2-fluoro-cyclopropanecarbonyl]amino]-4,5,6,7-tetrahydrobenzothiophene-3-carboxylic acid To a stirred solution of intermediate 460 (1.10 g, 2.04 mmol) in mixture of methanol (7 mL) and THF (7 mL) then added drop wise solution of lithium hydroxide hydrate (175 mg, 4.08 mmol) in water (7 mL) at room temperature. The reaction mixture was heated at 40° C. for 30 h and stirred at room temperature overnight. The reaction mixture was diluted with water (30 mL) and removed THF and methanol under vacuum. The resulting aqueous layers were washed with EtOAc (2×50 mL). The aqueous layer was acidified to pH=2-3 with saturated aqueous KHSO$_4$ and extracted with EtOAc (3×100 mL). The combined organic layers were dried over magnesium sulfate, filtered, evaporated to dryness to give the title compound (870 mg, 83% Yield). δ$_H$ (500 MHz, DMSO-d6) 12.03 (br s, 1H), 8.25 (br s, 1H), 7.16 (t, J=74.2 Hz, 1H), 5.79 (br s, J=94.9 Hz, 1H), 5.05-4.86 (m, 1H), 4.46 (s, 1H), 3.52 (s, 3H), 3.45-3.42 (m, 1H), 2.94-2.70 (m, 4H), 2.31-2.19 (m, 1H), 2.18-2.10 (m, 1H), 1.65-1.55 (m, 1H), 1.37-1.25 (m, 1H). 15% trans F-cyclopropyl due to epimerization. LCMS [M+H]⁺ 512, RT 1.72 minutes (Method 12).

Intermediate 462

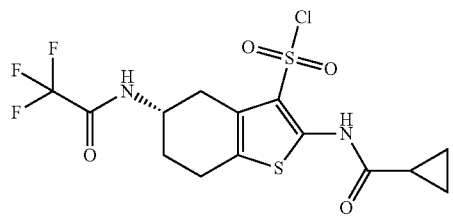 [SMILES: O=C(Nc1sc2c(c1S(=O)(=O)Cl)C[C@@H](NC(=O)C(F)(F)F)CC2)C1CC1]

(5S)-2-(cyclopropanecarbonylamino)-5-[(2,2,2-trifluoroacetyl)amino]-4,5,6,7-tetrahydrobenzothiophene-3-sulfonyl chloride A cold solution of sulfurochloridic acid (0.20 mL, 3.01 mmol) in dry acetonitrile (1 mL) was added drop wise to a stirred solution of intermediate 585 (200 mg, 0.602 mmol) at 0-5° C. The ice bath was removed and stirred at room temperature for 15 min, then heated at 40° C. for 18 h. The reaction mixture was cooled to room temperature then poured onto ice water. The resulting solid was collected by filtration and washed with water followed by heptane and dried in vacuo at 40° C. to give the title compound (190 mg, 64% Yield). δ$_H$ (500 MHz, DMSO-d6) 11.38 (s, 1H), 9.51 (d, J=7.9 Hz, 1H), 3.97 (s, 1H), 3.12 (dd, J=16.7, 5.1 Hz, 1H), 2.70 (br s, 2H), 2.65-2.55 (m, 1H), 2.01-1.88 (m, 1H), 1.83-1.69 (m, 1H), 1.69-1.53 (m, 1H), 0.97-0.74 (m, 4H). LCMS [M+H]⁺ 431/433, RT 1.98 minutes (Method 12).

Intermediate 463

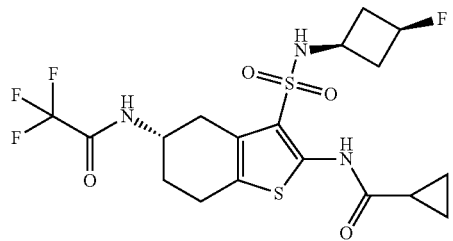 [SMILES: O=C(Nc1sc2c(c1S(=O)(=O)N[C@H]1C[C@@H](F)C1)C[C@@H](NC(=O)C(F)(F)F)CC2)C1CC1]

N-[(5S)-3-[cis-(3-fluorocyclobutyl)sulfamoyl]-5-[(2,2,2-trifluoroacetyl)amino]-4,5,6,7-tetrahydrobenzothiophen-2-yl]cyclopropanecarboxamide To a stirred solution of cis-3-fluorocyclobutan-1-amine hydrochloride (39 mg, 0.311 mmol) and triethylamine (86 μL, 0.617 mmol) in anhydrous DCM (2 mL) was added portion wise intermediate 462 (100 mg, 0.204 mmol) and the resulting yellow solution was stirred at room temperature under an atmosphere of nitrogen for 2 h. The reaction mixture was diluted with DCM (10 mL) and washed with water (5 mL). The combined organic layers were dried over sodium sulfate, filtered, evaporated to dryness. This crude residue was purified by column chromatography, eluting with 0-20% methanol in DCM to give the title compound (110 mg, 98% Yield). LCMS [M+H]$^+$ 484, RT 1.88 minutes (Method 12).

Intermediate 464

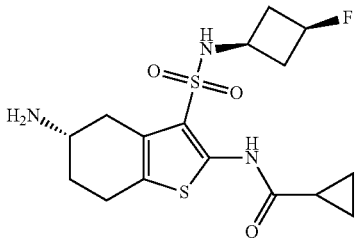 [SMILES: N[C@H]1CCc2sc(NC(=O)C3CC3)c(S(=O)(=O)N[C@H]3C[C@@H](F)C3)c2C1]

N-[(5S)-5-amino-3-{[(cis)-3-fluorocyclobutyl]sulfamoyl}-4,5,6,7-tetrahydro-1-benzothiophen-2-yl]cyclopropanecarboxamide Dipotassium carbonate (86 mg, 0.62 mmol) was added to a stirred solution of intermediate 463 (110 mg, 0.20 mmol) in methanol (6.1 mL) and water (1.2 mL) at room temperature and the mixture was stirred at 40° C. for 20 h. The reaction mixture was evaporated to dryness and the residue was partitioned between EtOAc (10 mL) and brine (5 mL), aqueous layer was further extracted with 10% methanol in DCM (2×5 mL). The combined organic layers were dried over sodium sulfate, filtered and evaporated to dryness to give the title compound (80 mg, 94% Yield). LCMS [M+H]$^+$ 388, RT 1.53 minutes (Method 12).

Intermediate 465

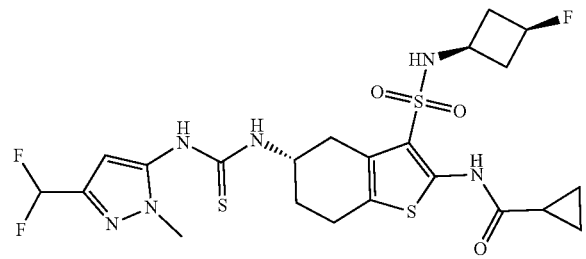 [SMILES: Cn1nc(C(F)F)cc1NC(=S)N[C@H]1CCc2sc(NC(=O)C3CC3)c(S(=O)(=O)N[C@H]3C[C@@H](F)C3)c2C1]

N-[(5S)-5-({[3-(difluoromethyl)-1-methyl-1H-pyrazol-5-yl]carbamothioyl}amino)-3-{[(cis)-3-fluorocyclobutyl]sulfamoyl}-4,5,6,7-tetrahydro-1-benzothiophen-2-yl]cyclopropanecarboxamide To a stirred solution of intermediate 464 (80 mg, 0.188 mmol) in anhydrous DCM (2 mL) was added dropwise solution of intermediate 254 (39 mg, 0.206 mmol) in DCM (1 mL) at room temperature and stirred for 1.5 h. The reaction mixture was evaporated to dryness and purified by column chromatography, eluting with 0-100% EtOAc in heptane. The resulting mixture was further purified by HPLC (Method 1) to give the title compound (84 mg, 78% Yield). LCMS [M+H]$^+$ 577, RT 1.89 minutes (Method 12).

Intermediate 466

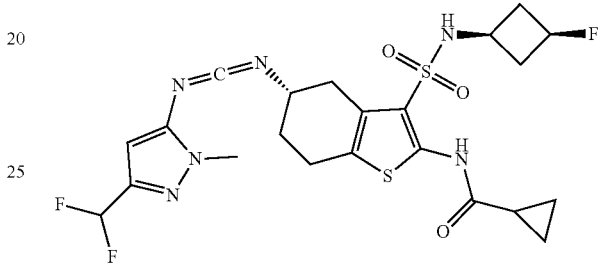

N-[(5S)-5-[({[3-(difluoromethyl)-1-methyl-1H-pyrazol-5-yl]imino}methylidene)amino]-3-{[(cis-3-fluorocyclobutyl]sulfamoyl}-4,5,6,7-tetrahydro-1-benzothiophen-2-yl]cyclopropanecarboxamide Methanesulfonyl chloride (16 μL, 0.207 mmol) was added to a stirred solution of intermediate 465 (80 mg, 0.139 mmol) and N,N-diethylethanamine (60 μL, 0.430 mmol) in dry DCM (2.4623 mL) at 0-5° C. and stirred for 30 min. The reaction mixture was diluted with DCM (20 mL) and washed with saturated aqueous NH$_4$Cl (10 mL), followed by brine (10 mL). The combined organic layers were dried over sodium sulfate, filtered, evaporated to dryness to give the title compound (85 mg, 68% Yield; 60% purity). LCMS [M+H]$^+$ 543, RT 1.98 minutes (Method 12).

Intermediate 467

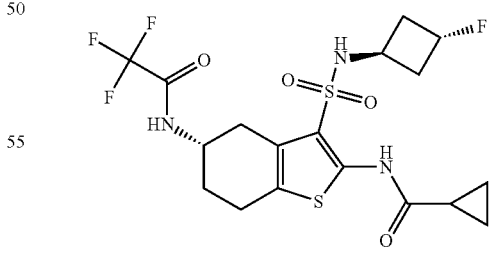

N-[(5S)-3-{[(trans)-3-fluorocyclobutyl]sulfamoyl}-5-(2,2,2-trifluoroacetamido)-4,5,6,7-tetrahydro-1-benzothiophen-2-yl]cyclopropanecarboxamide To a stirred solution of (trans)-3-fluorocyclobutan-1-amine hydrochloride (39 mg, 0.311 mmol) and triethylamine (86 mL, 0.617 mmol) in anhydrous DCM (2 mL) was added portion wise Intermediate 462 (100 mg, 0.204 mmol) and the resulting solution stirred at room temperature for 2 h. The reaction mixture was diluted with DCM (10 mL) and washed with water (5 mL). The combined organic layers were dried over sodium sulfate, filtered, evaporated to dryness. The crude residue was purified by column chromatography, eluting with 0-20% methanol in DCM to give the title compound (100 mg, 84% Yield). LCMS [M+H]+ 484, RT 1.87 minutes (Method 12).

Intermediate 468

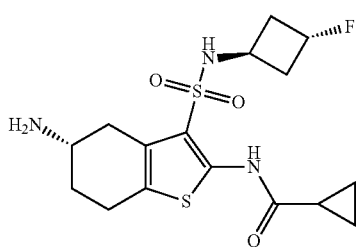 [SMILES: N[C@H]1CCc2sc(NC(=O)C3CC3)c(S(=O)(=O)N[C@H]3C[C@H](F)C3)c2C1]

N-[(5S)-5-amino-3-{[(trans)-3-fluorocyclobutyl]sulfamoyl}-4,5,6,7-tetrahydro-1-benzothiophen-2-yl]cyclopropanecarboxamide Dipotassium carbonate (74 mg, 0.536 mmol) was added to a stirred solution of intermediate 467 (100 mg, 0.172 mmol) in methanol (5.9 mL) and water (1.2 mL) at room temperature and the mixture was stirred at 40° C. for 20 h. The reaction mixture was evaporated to dryness and the residue was partitioned between EtOAc (10 mL) and brine (5 mL). The aqueous layer was further extracted with 10% methanol in DCM (2×5 mL). The combined organic layers were dried over sodium sulfate, filtered and evaporated to dryness to give the title compound (65 mg, 90% Yield). LCMS [M+H]+ 388, RT 1.54 minutes (Method 12).

Intermediate 469

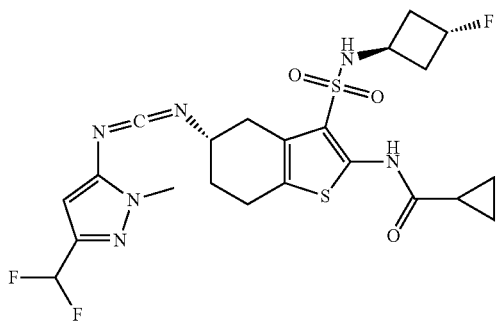 [SMILES: Cn1nc(C(F)F)cc1N=C=N[C@H]1CCc2sc(NC(=O)C3CC3)c(S(=O)(=O)N[C@H]3C[C@H](F)C3)c2C1]

N-[(5S)-5-[[5-(difluoromethyl)-2-methyl-pyrazol-3-yl]iminomethyleneamino]-3-[trans-(3-fluorocyclobutyl)sulfamoyl]-4,5,6,7-tetrahydrobenzothiophen-2-yl]cyclopropanecarboxamide To a stirring solution of intermediate 468 (65 mg, 0.154 mmol) in DCM (2 mL) was added dropwise a solution of intermediate 254 (32 mg, 0.169 mmol) in DCM (1 mL) and stirred for 1.5 h. The reaction mixture was concentrated to dryness and purified by HPLC (Method 1) to give the corresponding thio-urea* as an off white solid (59 mg). The solid was dissolved in dry DCM (2 mL), N,N-diethylethanamine (44 ꙮL, 0.317 mmol) was added and cooled to 0-5° C. The mixture was then treated with methanesulfonyl chloride (9.0 ꙮL, 0.116 mmol). The reaction mixture was stirred for 30 min, additional methanesulfonyl chloride (3 ꙮL) was added and the reaction stirred at room temperature for 30 min. The reaction mixture was diluted with DCM (20 mL) and washed with saturated aqueous NH4Cl (10 mL) followed by brine (10 mL). The combined organic layers were dried over sodium sulfate, filtered, and evaporated to dryness to give the title compound (55 mg, 86% Yield). LCMS [M+H]+ 543, RT 1.96 minutes (Method 12).

* Thio-urea=N-[(5S)-5-[[5-(difluoromethyl)-2-methyl-pyrazol-3-yl]carbamothioylamino]-3-[trans-(3-fluorocyclobutyl)sulfamoyl]-4,5,6,7-tetrahydrobenzothiophen-2-yl]cyclopropanecarboxamide Intermediate 470

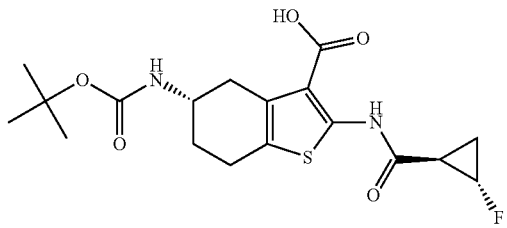 [SMILES: CC(C)(C)OC(=O)N[C@H]1CCc2sc(NC(=O)[C@H]3C[C@@H]3F)c(C(=O)O)c2C1]

(5S)-5-(tert-butoxycarbonylamino)-2-[[(1R,2S)-2-fluorocyclopropanecarbonyl]amino]-4,5,6,7-tetrahydrobenzothiophene-3-carboxylic acid To a stirred suspension of intermediate 456 (1.00 g, 2.34 mmol) in a mixture of MeOH (5 mL) and THF (5 mL) was added lithium hydroxide hydrate (206 mg, 4.79 mmol). The mixture was cooled (~0° C.) and then water (5 mL) was added drop wise. After 5 minutes, the cooling bath was removed and the reaction was heated to 40° C. for 17 hours. The cooled reaction mixture had the volatiles concentrated in vacuo at about 20° C.; water (20 mL) was added and then 10% citric acid (~15 mL). EtOAc (10 mL) was added to dissolve the solid. The organic layer was separated and the aqueous layer was re-extracted with EtOAc (1×10 mL plus 2×5 mL). The organic layers were combined and washed with a 1:1 mixture of water and brine (10 mL) followed by brine (5 mL), dried over magnesium sulphate, filtered and concentrated in vacuo. The product was purified by adding EtOAc (0.5 mL) and heptane (9.5 mL); the mixture was sonicated then rotated in a water bath at 40° C. More EtOAc (0.5 mL) and heptane (5 mL) were then added. The mixture was filtered and any lumps were broken up. The filter cake was then washed with heptane (2×5 mL and 10 mL) then dried to give the title compound (769 mg, 82% yield). $\delta_H$ (400 MHz, DMSO-d6) 13.15 (s, 1H), 11.49 (s, 1H), 6.91 (d, J=7.3 Hz, 1H), 5.08-4.77 (m, 1H), 3.65-3.52 (m, 1H), 3.11-2.98 (m, 1H), 2.78-2.60 (m, 3H), 2.47-2.41 (m, 1H), 1.95-1.81 (m, 1H), 1.68-1.49 (m, 2H), 1.39 (s, 9H), 1.34-1.21 (m, 1H). LCMS [M−H]− 397, RT 3.28 minutes (Method 10).

Intermediate 471

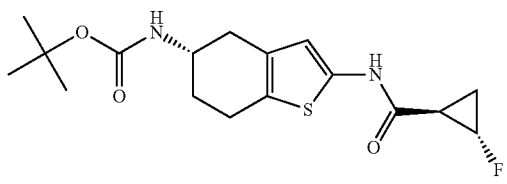 [SMILES: CC(C)(C)OC(=O)N[C@H]1CCc2sc(NC(=O)[C@H]3C[C@@H]3F)cc2C1]

tert-butyl N-[(5S)-2-[[(1R,2S)-2-fluorocyclopropan-ecarbonyl]amino]-4,5,6,7-tetrahydrobenzothiophen-5-yl]carbamate A stirred solution of intermediate 470 (301 mg, 0.755 mmol) in N,N-dimethylacetamide (2.5 ml) was heated to 170° C. for 7.5 hours. The reaction mixture allowed to cool to room temperature and the volatiles concentrated under high vacuo at 50° C. The crude residue was purified by column chromatography, eluting with 0-60% ethyl acetate in heptane to give the title compound (221 mg, 78% Yield). $\delta_H$ (500 MHz, Chloroform-d) 8.42 (s, 1H), 6.28 (s, 1H), 4.98-4.76 (m, 1H), 4.73-4.56 (m, 1H), 4.02-3.85 (m, 1H), 2.86 (dd, J=15.8, 4.9 Hz, 1H), 2.78-2.70 (m, 2H), 2.36 (dd, J=15.9, 7.6 Hz, 1H), 2.07-1.96 (m, 2H), 1.86-1.73 (m, 1H), 1.52-1.39 (m, 11H). LCMS [M+H]$^+$ 355, RT 3.22 minutes (Method 10).

Intermediate 472

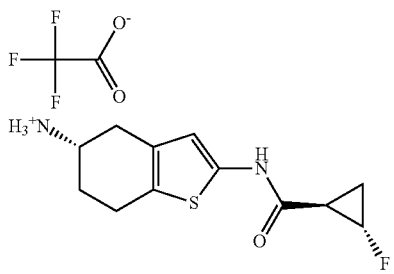

[(5S)-2-[[(1R,2S)-2-fluorocyclopropanecarbonyl]amino]-4,5,6,7-tetrahydrobenzothiophen-5-yl]ammonium 2,2,2-trifluoroacetate To a stirred solution of intermediate 471 (2.74 g, 7.34 mmol) in DCM (15 ml) was added 2,2,2-trifluoroacetic acid (3 mL, 40.4 mmol) dropwise over 2 minutes. After stirring for 6 hours, more TFA (3 ml) was added. After a further 2.5 days of stirring, the volatiles were concentrated in vacuo and the residue was azeotroped twice with DCM prior to further concentration under vacuum to give the title compound (2.28 g, 80% Yield). $\delta_H$ (400 MHz, DMSO-d6) 11.37 (s, 1H), 7.99 (s, 3H), 6.38 (s, 1H), 5.02-4.73 (m, 1H), 3.50-3.33 (m, 1H), 2.87 (dd, J=15.8, 5.1 Hz, 1H), 2.79-2.64 (m, 2H), 2.48-2.42 (m, 1H), 2.24 (ddd, J=17.9, 10.6, 6.7 Hz, 1H), 2.15-2.04 (m, 1H), 1.84-1.69 (m, 1H), 1.60-1.44 (m, 1H), 1.30-1.18 (m, 1H). LCMS [M+H]$^+$ 255, RT 2.08 minutes (Method 30).

Intermediate 473

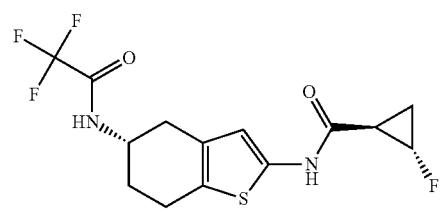 [SMILES: O=C(Nc1cc2c(s1)CC[C@H](NC(=O)C(F)(F)F)C2)[C@H]1C[C@@H]1F]

(1R,2S)-2-fluoro-N-[(5S)-5-[(2,2,2-trifluoroacetyl)amino]-4,5,6,7-tetrahydrobenzothiophen-2-yl]cyclopropanecarboxamide To an stirred solution of intermediate 472 (2.28 g, 5.88 mmol) in dry MeOH (40 mL) at 0° C. was added triethylamine (2.0 mL, 14.3 mmol) and ethyl 2,2,2-trifluoroacetate (1.5 mL, 12.6 mmol). After a further 5 minutes, the external cooling was removed and the reaction was stirred for at least 18 h. More triethylamine (1 mL) and ethyl trifluoroacetate (1 mL) were added and the reaction was heated to 40° C. After heating for 3 hours, more triethylamine (1 mL) and ethyl trifluoroacetate (1 mL) were added; after a further 1 h, more triethylamine (1 mL) and ethyl trifluoroacetate (1 mL) were added; after a further 2 h, more triethylamine (2 mL) and ethyl trifluoroacetate (1.5 mL) were added, the reaction was cooled and stirred for a least 18 hours. The solvent was then concentrated in vacuo; EtOAc (30 mL) was added and the organic phase was washed with water (60 mL), brine (30 mL), dried over magnesium sulphate, filtered and concentrated in vacuo. The crude solid was purified by column chromatography, eluting with 0-60% ethyl acetate in heptane to give the title compound (1.50 g, 71% yield). $\delta_H$ (400 MHz, DMSO-d6) 11.29 (s, 1H), 9.47 (d, J=7.4 Hz, 1H), 6.33 (s, 1H), 5.02-4.74 (m, 1H), 4.09-3.90 (m, 1H), 2.84-2.64 (m, 3H), 2.54-2.51 (m, 1H), 2.29-2.15 (m, 1H), 2.02-1.90 (m, 1H), 1.87-1.70 (m, 1H), 1.60-1.43 (m, 1H), 1.30-1.13 (m, 1H). LCMS [M+H]$^+$ 351, RT 2.82 minutes (Method 30).

Intermediate 474

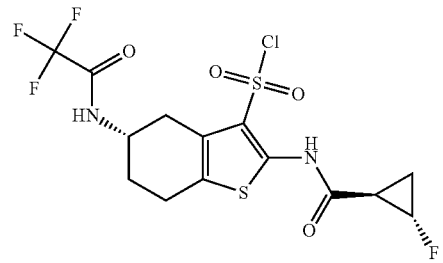 [SMILES: O=C(Nc1sc2c(c1S(=O)(=O)Cl)C[C@@H](NC(=O)C(F)(F)F)CC2)[C@H]1C[C@@H]1F]

(5S)-2-[[(1R,2S)-2-fluorocyclopropanecarbonyl]amino]-5-[(2,2,2-trifluoroacetyl)amino]-4,5,6,7-tetrahydrobenzothiophene-3-sulfonyl chloride To a solution of intermediate 473 (1.50 g, 4.20 mmol) in dry acetonitrile (20 mL) at (+4° C.) a solution of chlorosulphonic acid (1.5 mL, 22.6 mmol) in acetonitrile (5 mL) was added dropwise over 5 minutes. After 15 min at room temperature, the reaction was heated to 40° C. for 17 hours. The cooled reaction mixture was poured into cold water and stirred for 10 minutes. The precipitated solid was filtered, washed with cold water (2×15 mL), heptane (2×15 mL) and dried to give the title compound (1.47 g, 77% Yield). $\delta_H$ (400 MHz, Chloroform-d) 10.19 (s, 1H), 6.30 (d, J=7.5 Hz, 1H), 5.02-4.79 (m, 1H), 4.44-4.31 (m, 1H), 3.33 (dd, J=16.7, 5.4 Hz, 1H), 2.91-2.69 (m, 3H), 2.26-2.08 (m, 2H), 1.98-1.87 (m, 1H), 1.72-1.59 (m, 1H), 1.61-1.48 (m, 1H).

Intermediate 475

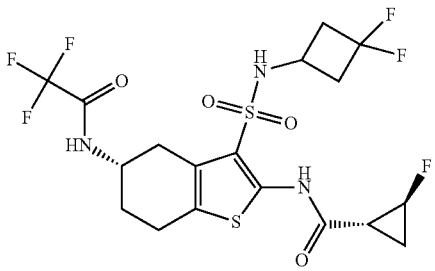 [SMILES: O=C(Nc1sc2c(c1S(=O)(=O)NC1CC(F)(F)C1)C[C@@H](NC(=O)C(F)(F)F)CC2)[C@H]1C[C@@H]1F]

(1R,2S)—N-[(5S)-3-[(3,3-difluorocyclobutyl)sulfamoyl]-5-[(2,2,2-trifluoroacetyl)amino]-4,5,6,7-tetrahydrobenzothiophen-2-yl]-2-fluoro-cyclopropanecarboxamide To a stirring solution of (3,3-difluorocyclobutyl)ammonium chloride (182 mg, 1.27 mmol) and triethylamine (0.35 mL, 2.54 mmol) in anhydrous DCM (10 mL) was added portion-wise intermediate 474 (380 mg, 0.847 mmol) and the resulting yellow solution was stirred at room temperature under an atmosphere of nitrogen for 1 h. The reaction mixture was evaporated to dryness, dissolved in EtOAc (100 mL) and washed with water (20 mL), saturated aqueous NH₄Cl (20 mL) and brine (20 mL). The combined organic layers were dried over magnesium sulfate, filtered, and evaporated to dryness to afford crude material. This was absorbed on silica and purified by column chromatography, eluting with 0-100% EtOAc in heptane to give the title compound (390 mg, 89% Yield). $\delta_H$ (400 MHz, Methanol-d4) 5.02-4.77 (m, 1H), 4.58 (br s, 1H), 4.27-4.14 (m, 1H), 3.76-3.63 (m, 1H), 3.22 (dd, J=17.0, 5.7 Hz, 1H), 2.92-2.81 (m, 3H), 2.78-2.57 (m, 2H), 2.57-2.33 (m, 3H), 2.17-2.06 (m, 1H), 1.97-1.82 (m, 1H), 1.68-1.51 (m, 1H), 1.46-1.35 (m, 1H). Comment: 2H exchanged with solvent. LCMS [M+H]⁺ 520, RT 1.95 minutes (Method 12).

Intermediate 476

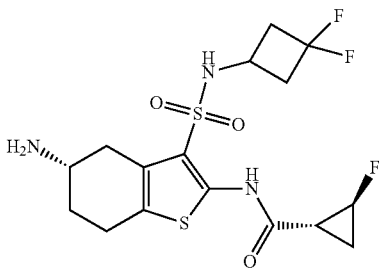 [SMILES: N[C@H]1CCc2sc(NC(=O)[C@H]3C[C@@H]3F)c(S(=O)(=O)NC3CC(F)(F)C3)c2C1]

(1R,2S)—N-[(5S)-5-amino-3-[(3,3-difluorocyclobutyl)sulfamoyl]-4,5,6,7-tetrahydrobenzothiophen-2-yl]-2-fluoro-cyclopropanecarboxamide A solution of dipotassium carbonate (380 mg, 2.75 mmol) in water (2.9 mL) was added to a stirred solution of intermediate 475 (380 mg, 0.732 mmol) in methanol (20 mL) at room temperature and the mixture was stirred at 40° C. for 24 h. The reaction mixture was evaporated to dryness, diluted with water (15 mL) and neutralised to pH 10 with 1 N HCl then extracted with 10% methanol in DCM (3×30 mL). The combined organic layers were dried over sodium sulfate, filtered and evaporated to dryness to give the title compound (290 mg, 80% Yield; 87% purity). $\delta_H$ (500 MHz, DMSO-d6) 4.98-4.76 (m, 1H), 3.64-3.55 (m, 1H), 3.12-3.04 (m, 1H), 3.04-2.95 (m, 1H), 2.79-2.51 (m, 4H), 2.48-2.40 (m, 3H), 2.35-2.27 (m, 1H), 1.95-1.86 (m, 1H), 1.59-1.44 (m, 2H), 1.28-1.16 (m, 1H). Comment: 4H exchanged with solvent. LCMS [M+H]⁺ 424, RT 0.58 minutes (Method 14).

Intermediate 477

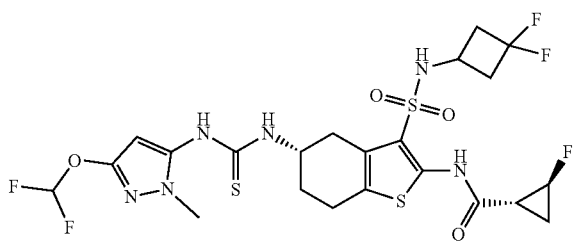 [SMILES: Cn1nc(OC(F)F)cc1NC(=S)N[C@H]1CCc2sc(NC(=O)[C@H]3C[C@@H]3F)c(S(=O)(=O)NC3CC(F)(F)C3)c2C1]

(1R,2S)—N-[(5S)-3-[(3,3-difluorocyclobutyl)sulfamoyl]-5-[[5-(difluoromethoxy)-2-methyl-pyrazol-3-yl]carbamothioylamino]-4,5,6,7-tetrahydrobenzothiophen-2-yl]-2-fluoro-cyclopropanecarboxamide A solution of intermediate 644 (70 mg, 0.324 mmol) in dry DCM (10 mL) was added to a stirred solution of intermediate 476 (145 mg, 0.291 mmol) in dry DCM (10 mL) at room temperature and stirred for 4 h. The reaction mixture was left to stand over the weekend, evaporated to dryness to afford crude material. This was purified by column chromatography, eluting with 0-100% EtOAc in heptane to give the title compound (145 mg, 76% Yield). $\delta_H$ (500 MHz, DMSO-d6) 10.45 (br s, 1H), 9.23 (s, 1H), 8.32 (br s, J=13.9 Hz, 1H), 8.21 (d, J=7.7 Hz, 1H), 7.21 (t, J=73.5 Hz, 1H), 5.95 (s, 1H), 5.07-4.85 (m, 1H), 4.65-4.45 (m, 1H), 3.71-3.60 (m, 1H), 3.54 (s, 3H), 3.18-3.08 (m, 1H), 2.84-2.63 (m, 5H), 2.63-2.55 (m, 1H), 2.48-2.38 (m, 2H), 2.10-2.01 (m, 1H), 1.88-1.73 (m, 1H), 1.66-1.53 (m, 1H), 1.35-1.25 (m, 1H). LCMS [M+H]⁺ 629, RT 1.96 minutes (Method 12).

Intermediate 478

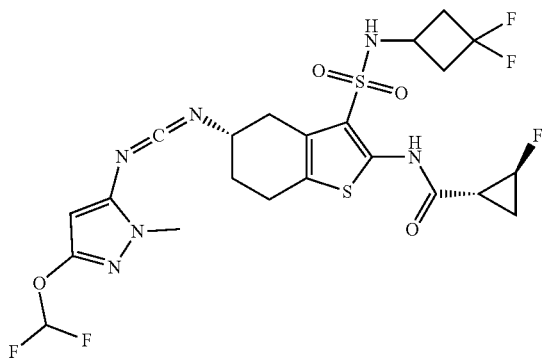 [SMILES: Cn1nc(OC(F)F)cc1N=C=N[C@H]1CCc2sc(NC(=O)[C@H]3C[C@@H]3F)c(S(=O)(=O)NC3CC(F)(F)C3)c2C1]

(1R,2S)—N-[(5S)-3-[(3,3-difluorocyclobutyl)sulfamoyl]-5-[[5-(difluoromethoxy)-2-methyl-pyrazol-3-yl]iminomethyleneamino]-4,5,6,7-tetrahydrobenzothiophen-2-yl]-2-fluoro-cyclopropanecarboxamide Methanesulfonyl chloride (17 ᴑL, 0.220 mmol) was added to a stirred solution of intermediate 477 (125 mg, 0.199 mmol) and triethylamine (85 ᴑL, 0.607 mmol) in dry DCM (2 mL) at ~5° C. (ice bath) and stirred for 30 min. The reaction mixture was further treated with methanesulfonyl chloride (3 ᴑL) and stirred for 30 min. The reaction mixture was diluted with DCM (5 mL) and washed with saturated aqueous NH₄Cl (10 mL). The combined organic layers were dried over sodium sulfate, filtered, evaporated to dryness to give the title compound (118 mg, quantitative). LCMS [M+H]⁺ 595, RT 2.04 minutes (Method 12).

Intermediate 479

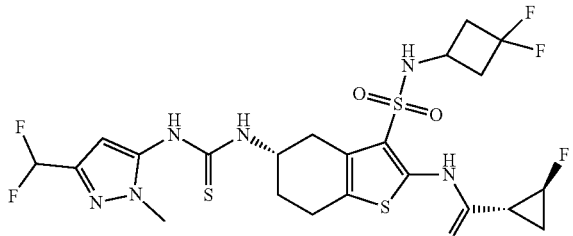

(1R,2S)—N-[(5S)-3-[(3,3-difluorocyclobutyl)sulfamoyl]-5-[[5-(difluoromethyl)-2-methyl-pyrazol-3-yl]carbamothioylamino]-4,5,6,7-tetrahydrobenzothiophen-2-yl]-2-fluoro-cyclopropanecarboxamide A solution of intermediate 568 (83 mg, 0.324 mmol) in DCM (3 mL) was added to a stirred solution of intermediate 476 (85%, 145 mg, 0.291 mmol) in DCM (3 mL) at room temperature. The mixture was stirred at room temperature over the weekend. The mixture was evaporated to dryness to afford a residue that was purified by column chromatography, eluting with 0-100% EtOAc in heptane to give a mixture of the product and imidazole. The mixture was dissolved in DCM (10 mL) and saturated aqueous NH₄Cl (10 mL) added. The bi-phasic solution was stirred for 10 min. The organic layer was separated, dried over sodium sulfate, filtered, and evaporated to dryness. The resulting residue was purified by column chromatography, eluting with 0-100% EtOAc in heptane to give the title compound (149 mg, 79% Yield). $\delta_H$ (500 MHz, DMSO-d6) 10.46 (br s, 1H), 9.18 (s, 1H), 8.32 (br s, J=17.7 Hz, 1H), 8.27 (d, J=7.7 Hz, 1H), 6.88 (t, J=54.8 Hz, 1H), 6.44 (s, 1H), 5.07-4.82 (m, 1H), 4.66-4.43 (m, 1H), 3.66 (s, 3H), 3.66-3.60 (m, 1H), 3.20-3.06 (m, 1H), 2.84-2.64 (m, 5H), 2.62-2.56 (m, 1H), 2.49-2.37 (m, 2H), 2.11-2.01 (m, 1H), 1.88-1.73 (m, 1H), 1.66-1.52 (m, 1H), 1.36-1.23 (m, 1H). LCMS [M+H]⁺ 613, RT 1.95 minutes (Method 12).

Intermediate 480

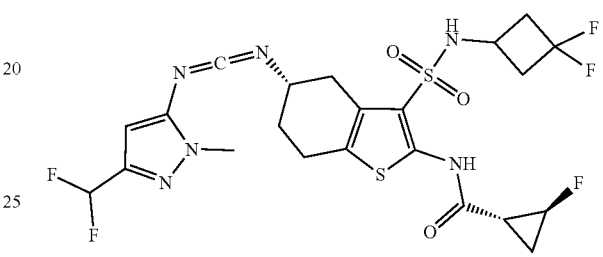

(1R,2S)—N-[(5)-3-[(3,3-difluorocyclobutyl)sulfamoyl]-5-[[5-(difluoromethyl)-2-methyl-pyrazol-3-yl]iminomethyleneamino]-4,5,6,7-tetrahydrobenzothiophen-2-yl]-2-fluoro-cyclopropanecarboxamide Methanesulfonyl chloride (20 ML, 0.258 mmol) was added to a stirred solution of intermediate 479 (95%, 149 mg, 0.231 mmol) and triethylamine (98 ᴑL, 0.705 mmol) in dry DCM (2 mL) at ~5° C. and stirred for 30 min. The reaction mixture was diluted with DCM (10 mL) and washed with saturated aqueous NH₄Cl (10 mL). The combined organic layer was dried over sodium sulfate, filtered, evaporated to dryness to give the title compound (150 mg, 86% Yield). LCMS [M+H]⁺ 579, RT 2.03 minutes (Method 12).

Intermediate 481

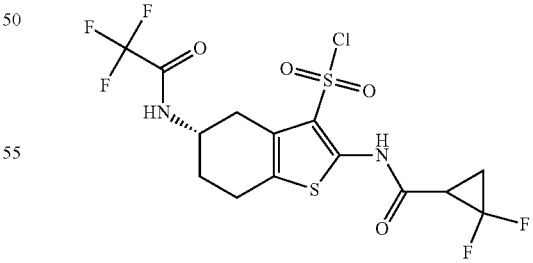

(5S)-2-[(2,2-difluorocyclopropanecarbonyl)amino]-5-[(2,2,2-trifluoroacetyl)amino]-4,5,6,7-tetrahydrobenzothiophene-3-sulfonyl chloride To a partial suspension of intermediate 539 (1.98 g, 5.38 mmol) in acetonitrile (25 mL) at −5° C., a solution of sulfurochloridic acid (1.8 mL, 27.1 mmol) in acetonitrile (5 mL) was added drop-wise. After 10 minutes, the external cooling was removed and the reaction was stirred at ambient temperature for 16 hours. The reaction was cooled to 0.5° C. and a second portion of sulfurochloridic acid (1 mL) was added drop wise and the reaction was stirred at ambient temperature for 6 hours. The reaction mixture was added drop wise to a mixture of cold water (200 mL) and EtOAc (100 mL) over 2 minutes. The organic layer was separated and kept cold. The aqueous layer was extracted with EtOAc (3×50 mL) and the cold organic layers combined and washed with a 1:1 mixture of water and brine (100 mL), followed by brine (50 mL), then dried over magnesium sulphate, filtered and concentrated in vacuo. The crude residue was purified by column chromatography, eluting with 0-50% EtOAc in heptane to give the title compound (1.75 g, 66% yield). LCMS [M+H]$^+$ 465/467, RT 3.66 minutes (Method 10).

Intermediate 482

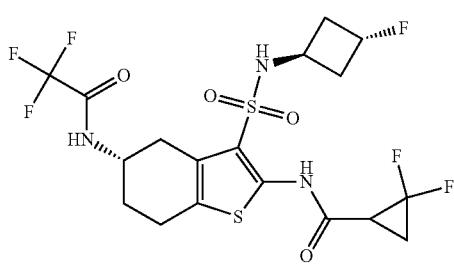 [SMILES: O=C(Nc1sc2c(c1S(=O)(=O)N[C@H]1C[C@H](F)C1)C[C@@H](NC(=O)C(F)(F)F)CC2)C1CC1(F)F]

2,2-difluoro-N-[(5S)-3-{[(trans)-3-fluorocyclobutyl]sulfamoyl}-5-(2,2,2-trifluoroacetamido)-4,5,6,7-tetrahydro-1-benzothiophen-2-yl]cyclopropane-1-carboxamide To a stirring solution of (trans)-3-fluorocyclobutan-1-amine hydrochloride (274 mg, 2.18 mmol) and triethylamine (0.61 mL, 4.37 mmol) in anhydrous DCM (15 mL) was added portion-wise intermediate 481 (680 mg, 1.46 mmol) and the resulting solution was stirred at room temperature for 1 h. The reaction mixture was evaporated to dryness, dissolved in EtOAc (100 mL), washed with water (20 mL), saturated aqueous NH$_4$Cl (20 mL) and brine (20 mL). The organic layer was dried over magnesium sulfate, filtered and evaporated to dryness. The crude residue was purified by column chromatography, eluting with 0-100% EtOAc in heptane to give the title compound (700 mg, 93% Yield). LCMS [M+H]$^+$ 520, RT 1.92 minutes (Method 12).

Intermediate 483

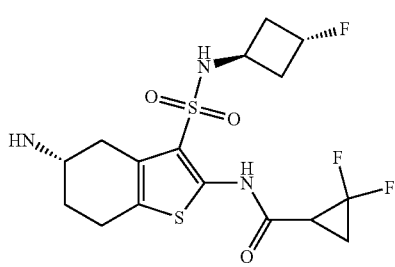 [SMILES: N[C@H]1CCc2sc(NC(=O)C3CC3(F)F)c(S(=O)(=O)N[C@H]3C[C@H](F)C3)c2C1]

N-[(5S)-5-amino-3-{[(trans)-3-fluorocyclobutyl]sulfamoyl}-4,5,6,7-tetrahydro-1-benzothiophen-2-yl]-2,2-difluorocyclopropane-1-carboxamide A solution of dipotassium carbonate (745 mg, 5.39 mmol) in water (4 mL) was added to a stirred solution of intermediate 482 (700 mg, 1.35 mmol) in methanol (30 mL) at room temperature and the mixture was stirred at 40° C. for 19 h. The reaction mixture was evaporated to dryness, diluted with water (15 mL), neutralised to pH 10 with 1 N HCl and extracted with 10% methanol in DCM (3×30 mL). The combined organic layers were dried over sodium sulfate, filtered and evaporated to dryness to give the title compound (520 mg, 84% Yield). LCMS [M+H]$^+$ 424, RT 1.5 minutes (Method 12).

Intermediate 484

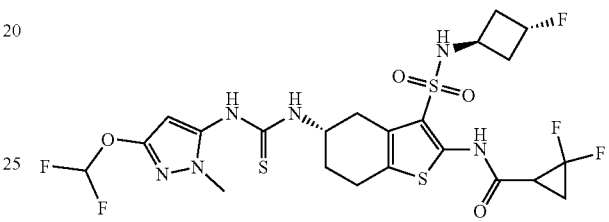

N-[(5S)-5-({[3-(difluoromethoxy)-1-methyl-1H-pyrazol-5-yl]carbamothioyl}amino)-3-{[(trans)-3-fluorocyclobutyl]sulfamoyl}-4,5,6,7-tetrahydro-1-benzothiophen-2-yl]-2,2-difluorocyclopropane-1-carboxamide A solution of intermediate 644 (126 mg, 0.614 mmol) in DCM (5 mL) was added to a stirred solution of intermediate 483 (90%, 260 mg, 0.553 mmol) in DCM (5 mL) at room temperature and stirred for 1 hour. The reaction mixture was evaporated to dryness. The crude residue was purified by column chromatography, eluting with 0-100% EtOAc in heptane to give the title compound (380 mg, 98% Yield). LCMS [M+H]$^+$ 629, RT 1.95 minutes (Method 12).

Intermediate 485

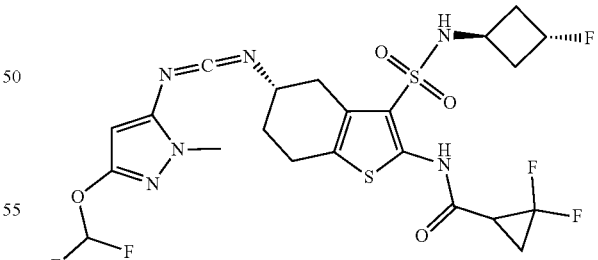

N-[(5S)-5-[({[3-(difluoromethoxy)-1-methyl-1H-pyrazol-5-yl]imino}methylidene)amino]-3-{[(trans)-3-fluorocyclobutyl]sulfamoyl}-4,5,6,7-tetrahydro-1-benzothiophen-2-yl]-2,2-difluorocyclopropane-1-carboxamide Methanesulfonyl chloride (47 μL, 0.601 mmol) was added to a stirred solution of intermediate 484 (90%, 380 mg, 0.544 mmol) and triethylamine (231 μL, 1.66 mmol) in DCM (15 mL) at ~5° C. and stirred for 30 min. The reaction mixture was diluted with DCM (25 mL) and washed with saturated aqueous NH₄Cl (25 mL). The organic layer was dried over sodium sulfate, filtered, evaporated to dryness to give the title compound (423 mg, 92% Yield). LCMS [M+H]⁺ 595, RT 2.01 minutes (Method 12).

Intermediate 486

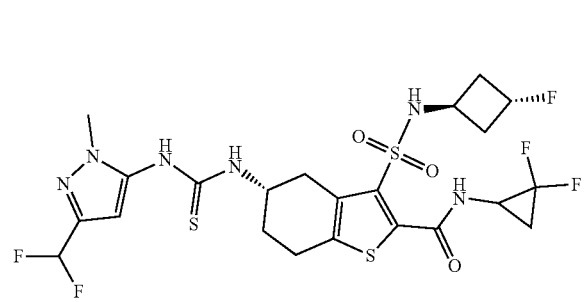 [SMILES: Cn1nc(C(F)F)cc1NC(=S)N[C@H]1CCc2sc(C(=O)NC3CC3(F)F)c(S(=O)(=O)N[C@H]3C[C@H](F)C3)c2C1]

3-[(5S)-2-[(2,2-difluorocyclopropyl)amino]-3-{[(trans)-3-fluorocyclobutyl]sulfamoyl}-4,5,6,7-tetra-hydro-1-benzothiophen-5-yl]-1-[3-(difluoromethyl)-1-methyl-H-pyrazol-5-yl]thiourea A solution of intermediate 568 (158 mg, 0.615 mmol) in DCM (3 mL) was added to a stirred solution of intermediate 483 (90%, 260 mg, 0.553 mmol) in DCM (3 mL) at room temperature and stirred for 1 hour. The reaction mixture was diluted with DCM (25 mL) and washed with saturated aqueous NH₄Cl (25 mL). The organic layer was dried over sodium sulfate, filtered and evaporated to dryness. The crude residue was purified by column chromatography, eluting with 0-100% EtOAc in heptane to give the title compound (380 mg, quantitative). LCMS [M+H]⁺ 613, RT 1.93 minutes (Method 12)

Intermediate 487

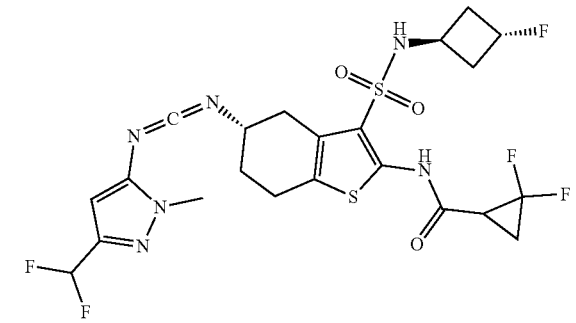 [SMILES: Cn1nc(C(F)F)cc1N=C=N[C@H]1CCc2sc(NC(=O)C3CC3(F)F)c(S(=O)(=O)N[C@H]3C[C@H](F)C3)c2C1]

N-[(5S)-5-[({[3-(difluoromethyl)-1-methyl-1H-pyrazol-5-yl]imino}methylidene)amino]-3-{[(trans)-3-fluorocyclobutyl]sulfamoyl}-4,5,6,7-tetrahydro-1-benzothiophen-2-yl]-2,2-difluorocyclopropane-1-carboxamide Methanesulfonyl chloride (48 μL, 0.617 mmol) was added to a stirred solution of intermediate 486 (380 mg, 0.558 mmol) and triethylamine (237 μL, 1.70 mmol) in DCM (15 mL) at ~5° C. and mixture was stirred for 30 min. The reaction mixture was diluted with DCM (25 mL) and washed with saturated aqueous NH₄Cl (25 mL). The organic layer was dried over sodium sulfate, filtered, evaporated to dryness to give the title compound (322 mg, quantitative). LCMS [M+H]⁺ 579, RT 2.00 minutes (Method 12).

Intermediate 488

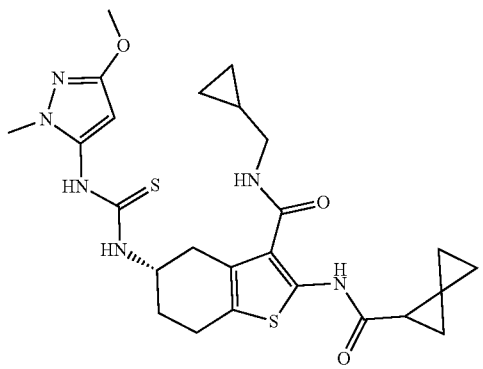 [SMILES: COc1cc(NC(=S)N[C@H]2CCc3sc(NC(=O)C4CC45CC5)c(C(=O)NCC4CC4)c3C2)n(C)n1]

(5S)—N-(cyclopropylmethyl)-5-[(5-methoxy-2-methyl-pyrazol-3-yl)carbamothioylamino]-2-(spiro[2.2]pentane-2-carbonylamino)-4,5,6,7-tetrahydrobenzothiophene-3-carboxamide To a stirring solution of intermediate 295 (220 mg, 0.61 mmol) in anhydrous DCM (3 mL) was added a solution of intermediate 525 (218 mg, 0.92 mmol) in DCM (3 mL) dropwise under an atmosphere of nitrogen and the mixture was stirred at room temperature for 2 hours. The reaction mixture was diluted with DCM (10 mL), washed with sat. aq. NH₄Cl solution (10 mL), sat. aq. NaHCO₃ solution (10 mL), water (10 mL), brine (10 mL), dried over magnesium sulfate, filtered and concentrated. The crude material was purified by flash column chromatography with a 0 to 100% ethyl acetate in heptane gradient to afford the title compound (270 mg, 77% yield). LCMS [M+H]⁺ 529, RT 1.89 minutes (Method 12)

Intermediate 489

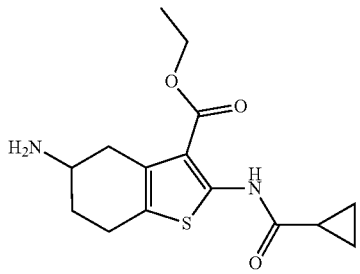 [SMILES: CCOC(=O)c1c(NC(=O)C2CC2)sc2c1CC(N)CC2]

Ethyl 5-amino-2-(cyclopropanecarbonylamino)-4,5,6,7-tetrahydrobenzothiophene-3-carboxylate 2,2,2-Trifluoroacetic acid (10 mL, 0.135 mol) was added drop wise to a stirred solution of intermediate (3.30 g, 8.08 mmol) in DCM (10 mL) at room temperature and stirred for 1 h. The reaction mixture was evaporated to dryness and residue dissolved in DCM (100 mL). The organic layer was washed with saturated aqueous NaHCO$_3$ (2×25 mL), followed by brine (25 mL), dried over sodium sulfate, filtered, evaporated to dryness to give the title compound (2.50 g, 97% Yield). LCMS [M+H]$^+$ 309, RT 1.55 minutes (Method 12).

Intermediate 490

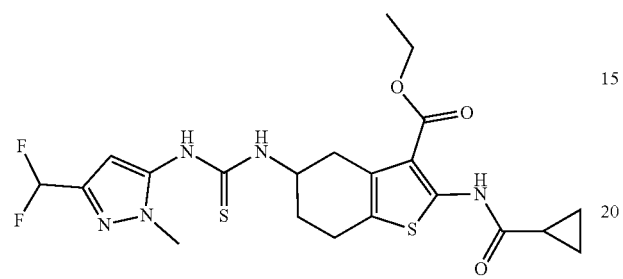

Ethyl 2-(cyclopropanecarbonylamino)-5-[[5-(difluoromethyl)-2-methyl-pyrazol-3-yl]carbamothioylamino]-4,5,6,7-tetrahydrobenzothiophene-3-carboxylate To a stirred solution of intermediate 489 (2.58 g, 8.11 mmol) in anhydrous DCM (2 mL) was added dropwise solution of intermediate 254 (1.68 g, 8.89 mmol) in DCM (1 mL) at room temperature and mixture was stirred for 2 h. A second portion of intermediate 254 (0.5 g, 2.64 mmol) was added and stirred for 2 h. The reaction mixture was diluted with DCM (50 mL), washed with water (50 mL), dried over sodium sulfate, filtered, and concentrated to dryness. The crude residue was purified by column chromatography, eluting with 0-100% ethyl acetate in heptane to give the title compound (2.95 g, 68% Yield). δ$_H$ (500 MHz, Chloroform-d) 11.43 (s, 1H), 7.45 (s, 1H), 6.60 (t, J=55.0 Hz, 1H), 6.36 (s, 1H), 6.17 (br s, 1H), 4.78 (br s, 1H), 4.45-4.29 (m, 2H), 3.81 (s, 3H), 3.29 (dd, J=17.0, 5.0 Hz, 1H), 2.91-2.79 (m, 1H), 2.79-2.62 (m, 2H), 2.20-2.11 (m, 1H), 2.03-1.92 (m, 1H), 1.73-1.65 (m, 1H), 1.41 (t, J=7.1 Hz, 3H), 1.18-1.13 (m, 2H), 1.01-0.94 (m, 2H). LCMS [M+H]$^+$ 498, RT 1.9 minutes (Method 12).

Intermediate 491

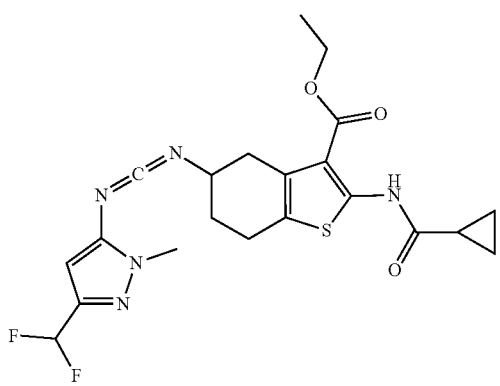 [SMILES: CCOC(=O)c1c(NC(=O)C2CC2)sc2c1CC(N=C=Nc1cc(C(F)F)nn1C)CC2]

Ethyl 2-(cyclopropanecarbonylamino)-5-[[5-(difluoromethyl)-2-methyl-pyrazol-3-yl]iminomethyleneamino]-4,5,6,7-tetrahydrobenzothiophene-3-carboxylate Methanesulfonyl chloride (0.47 mL, 6.01 mmol) was added to a stirred suspension of intermediate 490 (2.60 g, 5.23 mmol) and triethylamine (2.2 mL, 15.7 mmol) in dry DCM (50 mL) at ~5° C. and mixture was stirred for 30 min. The reaction mixture was diluted with DCM (50 mL), washed with water (50 mL), saturated aqueous NH$_4$Cl (50 mL) and brine (50 mL). The organic layer was dried over sodium sulfate, filtered, concentrated to dryness to give the title compound (2.40 g, 95% Yield). LCMS [M+H]$^+$ 464, RT 2.15 minutes (Method 12).

Intermediate 492

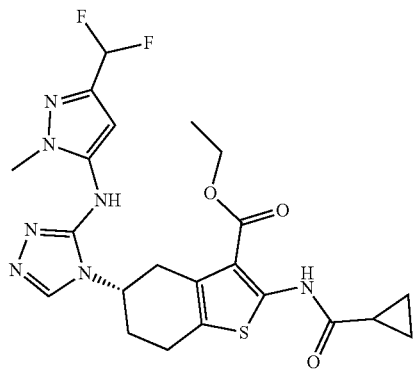 [SMILES: CCOC(=O)c1c(NC(=O)C2CC2)sc2c1C[C@@H](n1cnnc1Nc1cc(C(F)F)nn1C)CC2]

ethyl (5S)-2-(cyclopropanecarbonylamino)-5-[3-[[5-(difluoromethyl)-2-methyl-pyrazol-3-yl]amino]-1,2,4-triazol-4-yl]-4,5,6,7-tetrahydrobenzothiophene-3-carboxylate Formic hydrazide (0.90 g, 14.9 mmol) was added to a stirred solution of intermediate 491 (2.40 g, 4.97 mmol) in ethanol (50 mL) and stirred at room temperature for 30 min. Aqueous 2 M disodium carbonate (10 mL, 19.9 mmol) was added and the reaction mixture heated at 45° C. for 16 h. The reaction mixture was cooled to room temperature and the inorganic solid removed by filtration. The filtrate was concentrated to dryness, diluted with water (50 mL), neutralized to pH 7, and extracted with 10% methanol in DCM (2×50 mL), followed by (1:1) IPA:CHCL$_3$ (2×50 mL). The combined organic layers were washed with brine (50 mL), dried over sodium sulfate, filtered, conc. to dryness to afford crude material. The crude material was dissolved in DCM (20 mL) and triturated with diethyl ether (100 mL) to afford precipitation which was filtered off and washed with TBME (2×10 mL) to afford crude material. The crude material was purified twice by column chromatography, eluting with 0-20% methanol in DCM to afford racemic mixture (1.70 g, 68% Yield). This was purified by chiral SFC to afford title compound (850 mg, 49%). LCMS [M+H]$^+$ 506, RT 1.82 minutes (Method 12). Chiral LC* RT 10.54 minutes (Peak 1).

* Chiral analysis was carried out using CHIRALPAK IG 4.6×250 mm, 5 μm column, 2.4 mL/min, 200 Bar, eluting with a gradient of 60/40 CO$_2$/MEOH+ 0.5% Isopropylamine, using a 30 minutes run time on SFC Berger.

Intermediate 493

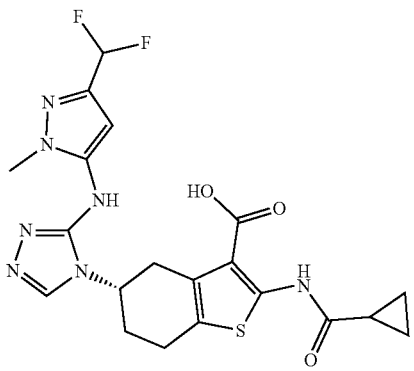 [SMILES: Cn1nc(C(F)F)cc1Nc1nncn1[C@H]1CCc2sc(NC(=O)C3CC3)c(C(=O)O)c2C1]

(5S)-2-(cyclopropanecarbonylamino)-5-[3-[[5-(difluoromethyl)-2-methyl-pyrazol-3-yl]amino]-1,2,4-triazol-4-yl]-4,5,6,7-tetrahydrobenzothiophene-3-carboxylic acid 1 M aqueous sodium hydroxide (6.7 mL, 6.73 mmol) was added to a stirred solution of intermediate 492 (850 mg, 1.68 mmol) in THF (7 mL) and mixture was stirred at room temperature over the weekend. The reaction mixture evaporated to dryness, acidified to pH ~5 using 1 M aqueous HCl to afford white precipitated. This was filtered off, washed with water (2 mL), and dried in a vacuum oven to give the title compound (590 mg, 73% yield). $\delta_H$ (500 MHz, DMSO-d6) 12.54 (br s, 1H), 12.06 (s, 1H), 8.60-8.05 (m, 1H), 7.05-6.56 (m, 1H), 6.50-6.10 (m, 1H), 4.48 (s, 1H), 3.77-3.58 (m, 5H), 2.91-2.76 (m, 3H), 2.33-2.05 (m, 2H), 1.89-1.79 (m, 1H), 0.95-0.81 (m, 4H). LCMS [M+H]$^+$ 478, RT 1.65 minutes (Method 12).

Intermediate 494

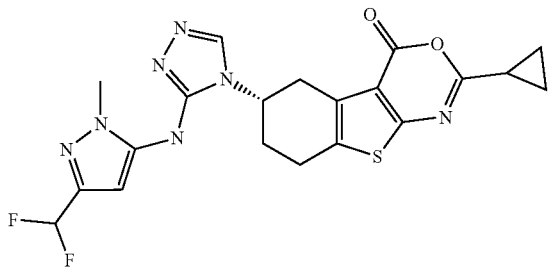 [SMILES: Cn1nc(C(F)F)cc1Nc1nncn1[C@H]1CCc2sc3nc(C4CC4)oc(=O)c3c2C1]

(6S)-2-cyclopropyl-6-[3-[[5-(difluoromethyl)-2-methyl-pyrazol-3-yl]amino]-1,2,4-triazol-4-yl]-5,6,7,8-tetrahydrobenzothiopheno[2,3-d][1,3]oxazin-4-one 3-(ethyliminomethyleneamino)-N,N-dimethyl-propan-1-amine hydrochloride (270 mg, 1.41 mmol) was added to a stirred suspension of intermediate 493 (560 mg, 1.17 mmol) in acetonitrile (15 mL) and the mixture heated at 50° C. for 5 h. The reaction mixture was stirred at room temperature over the weekend and then treated with 3-(ethyliminomethyleneamino)-N,N-dimethyl-propan-1-amine hydrochloride (50 mg, 0.261 mmol) and heated at 50° C. for 7 h. The reaction mixture was cooled to room temperature, evaporated to dryness, dissolved in 10% methanol in DCM (50 mL) and washed with water (20 mL) followed by brine (20 mL). The combined organic layers were dried over sodium sulfate, filtered, evaporated to dryness and purified by column chromatography, eluting with 0-100% ethyl acetate in heptane followed by 60% methanol in ethyl acetate to give the title compound (289 mg, 54% Yield). LCMS [M+H]$^+$ 460, RT 1.75 minutes (Method 12)

Intermediate 495

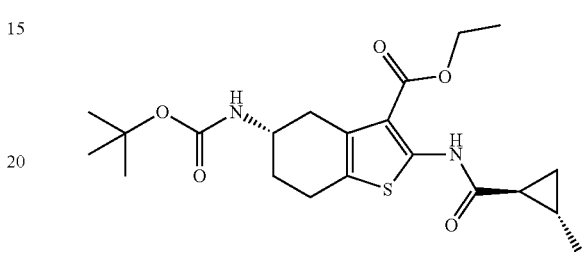

Ethyl (5S)-5-(tert-butoxycarbonylamino)-2-[[(1S,2S)-2-methylcyclopropanecarbonyl]amino]-4,5,6,7-tetrahydrobenzothiophene-3-carboxylate To a mixture of intermediate 567 (3.00 g, 7.96 mmol), (1S,2S)-2-methylcyclopropanecarboxylic acid (0.80 g, 7.96 mmol) and pyridine (2.6 mL, 31.8 mmol) in anhydrous dichloromethane (60 mL) at 0° C. was introduced 2,4,6-tripropyl-1,3,5,2,4,6-trioxatriphosphorinane-2,4,6-trioxide (50% solution in ethyl acetate, 9.5 mL, 15.9 mmol, drop-wise). After 16 hours at room temperature, water (20 mL) was introduced and the bi-phasic mixture stirred vigorously for 15 minutes. The phases were separated and the aqueous phase extracted with dichloromethane (20 mL). The organic extracts were combined, washed with brine (20 mL) and dried over sodium sulfate. Following filtration, the filtrate was adsorbed onto silica in-vacuo and the dry-loaded material purified by flash column chromatography (7-60% gradient of ethyl acetate in heptane) to furnish the title compound (2.24 g, 66% Yield). $\delta_H$ (500 MHz, d-chloroform) 11.40 (s, 1H), 4.61 (s, 1H), 4.34 (q, J=7.1 Hz, 2H), 3.98 (s, 1H), 3.16 (dd, J=17.1, 5.2 Hz, 1H), 2.72 (d, J=5.8 Hz, 2H), 2.60 (dd, J=17.2, 7.1 Hz, 1H), 2.02 (ddd, J=9.5, 7.1, 4.4 Hz, 1H), 1.87-1.74 (m, 1H), 1.54-1.49 (m, 1H), 1.46 (s, 9H), 1.41-1.35 (m, 4H), 1.32 (dt, J=8.7, 4.3 Hz, 1H), 1.15 (d, J=6.0 Hz, 3H), 0.76 (ddd, J=7.8, 6.6, 4.1 Hz, 1H); LCMS [M–H]$^-$ 421, RT 2.19 minutes (Method 12)

Intermediate 496

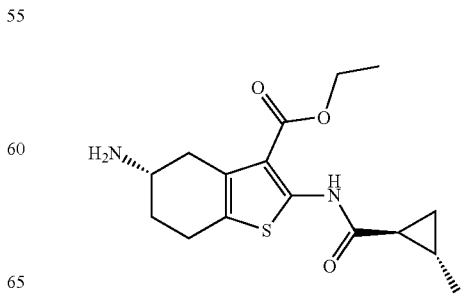

Ethyl (5S)-5-amino-2-[[(1S,2S)-2-methylcyclopropanecarbonyl]amino]-4,5,6,7-tetrahydrobenzothiophene-3-carboxylate To a solution of intermediate 495 (2.21 g, 5.23 mmol) in dichloromethane (20 mL) at 0° C. was introduced trifluoroacetic acid (5.00 mL, 7.75 mmol, dropwise). The reaction mixture was warmed to room temperature, and kept at this temperature for 2 hours. After concentrating the reaction mixture in-vacuo, the residue was re-dissolved in dichloromethane (100 mL) and water (20 mL) introduced. The aqueous phase was adjusted to pH 8 by addition of 2 M aqueous sodium carbonate solution and the phases separated. The aqueous phase was extracted with additional dichloromethane (100 mL) and the organic extracts combined, washed with brine (20 mL) and dried over sodium sulfate. After filtration, the filtrate was concentrated in-vacuo to furnish the title compound (1.93 g, quantitative). δ$_H$ (500 MHz, d-chloroform) 11.37 (s, 1H), 4.40-4.25 (m, 2H), 3.79 (s, 2H), 3.39-3.28 (m, 2H), 2.83-2.69 (m, 2H), 2.65 (dd, J=16.7, 8.5 Hz, 1H), 2.17-2.10 (m, 1H), 1.89-1.76 (m, 1H), 1.55-1.46 (m, 1H), 1.37 (t, J=7.1 Hz, 3H), 1.38-1.35 (m, 1H), 1.34-1.31 (m, 1H), 1.15 (d, J=6.0 Hz, 3H), 0.79-0.75 (m, 1H); LCMS [M+H]$^+$ 323, RT 1.55 minutes (Method 12).

Intermediate 497

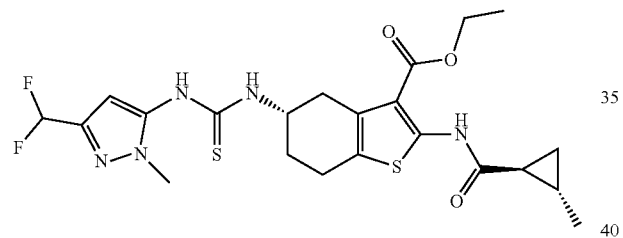

ethyl (5S)-5-[[5-(difluoromethyl)-2-methyl-pyrazol-3-yl]carbamothioylamino]-2-[[(1S,2S)-2-methylcyclopropanecarbonyl]amino]-4,5,6,7-tetrahydrobenzothiophene-3-carboxylate A mixture of intermediate 496 (1.93 g, ≤5.23 mmol) and intermediate 568 (1.54 g, 5.98 mmol) was dissolved in anhydrous dichloromethane (15 mL) at room temperature. After 60 minutes, the reaction mixture was diluted with dichloromethane (50 mL), washed with saturated aqueous ammonium chloride (20 mL) and the organic phase dried over sodium sulfate. Following filtration, the filtrate was concentrated in-vacuo and the residue purified by flash column chromatography (0-100% gradient of ethyl acetate in heptane) to furnish the title compound (2.47 g, 81% Yield). δ$_H$ (500 MHz, d-chloroform) 11.36 (s, 1H), 7.68 (s, 1H), 6.58 (t, J=55.0 Hz, 1H), 6.34 (s, 1H), 6.24 (s, 1H), 4.76 (s, 1H), 4.34 (qq, J=10.8, 7.1 Hz, 2H), 3.78 (s, 3H), 3.29-3.20 (m, 1H), 2.79 (dt, J=16.5, 6.3 Hz, 1H), 2.67 (ddt, J=23.2, 12.4, 6.4 Hz, 2H), 2.14-2.06 (m, 1H), 1.99 (dt, J=13.2, 7.0 Hz, 1H), 1.53-1.43 (m, 1H), 1.41-1.34 (m, 4H), 1.29 (dd, J=8.8, 4.4 Hz, 1H), 1.16 (d, J=6.0 Hz, 3H), 0.79 (ddd, J=7.8, 6.7, 4.2 Hz, 1H); LCMS [M+H]$^+$ 512, RT 2.07 minutes (Method 12).

Intermediate 498

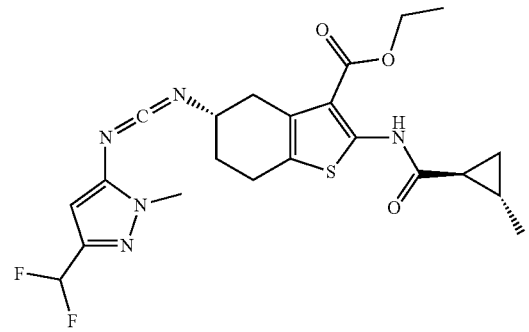 [SMILES: CCOC(=O)c1c(NC(=O)[C@H]2C[C@@H]2C)sc2c1C[C@@H](N=C=Nc1cc(C(F)F)nn1C)CC2]

ethyl (5S)-5-[({[3-(difluoromethyl)-1-methyl-1H-pyrazol-5-yl]imino}methylidene)amino]-2-[(1S,2S)-2-methylcyclopropaneamido]-4,5,6,7-tetrahydro-1-benzothiophene-3-carboxylate To a solution of intermediate 497 (2.47 g, 4.83 mmol) in dichloromethane (50 mL) at +5° C. was introduced triethylamine (4.03 mL, 28.97 mmol) followed by methanesulfonyl chloride (0.995 g, 8.69 mmol, dropwise). After warming to room temperature, the reaction was held at this temperature for 1 h then diluted with dichloromethane (50 mL) and washed with saturated aqueous ammonium chloride (2×20 mL). The organic extract was dried over sodium sulfate, filtered through a shallow bed of kieselguhr and the filter cake washed with dichloromethane (20 mL). The filtrate was concentrated in-vacuo to furnish the title compound (2.762 g, quantitative). LCMS [M+H]$^+$ 478, RT 2.19 mins (Method 12).

Intermediate 499

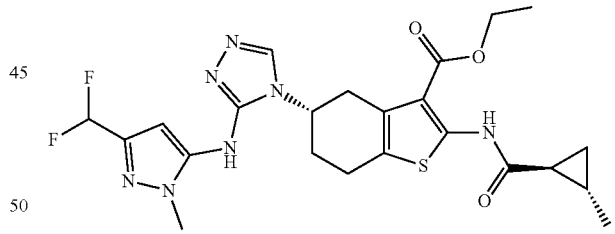

Ethyl (5S)-5-[3-[[5-(difluoromethyl)-2-methyl-pyrazol-3-yl]amino]-1,2,4-triazol-4-yl]-2-[[(1S,2S)-2-methylcyclopropanecarbonyl]amino]-4,5,6,7-tetrahydrobenzothiophene-3-carboxylate A solution of formic hydrazide (0.872 g, 14.51 mmol) in ethanol (80 mL) was introduced to Intermediate 498 (2.31 g, 4.84 mmol) at room temperature. After 1 h, sodium carbonate (16.50 mL of a 1 M aqueous solution, 16.50 mmol) was introduced and the reaction mixture warmed to 40° C. for 20 hours. The reaction mixture was cooled to room temperature and filtered, washing with ethanol (50 mL). After concentrating the filtrate in-vacuo, the residue was suspended in dichloromethane (100 mL) and washed with water (50 mL).

The aqueous phase was extracted with dichloromethane (50 mL) and chloroform-isopropanol (1:1, 50 mL), then all the organic extracts combined and dried over magnesium sulfate. Following filtration, the filtrate was concentrated in-vacuo and the residue purified by flash column chromatography (25-100% gradient of ethyl acetate in heptane) to furnish the title compound (1.695 g, 64% Yield). δ$_H$ (500 MHz, d-chloroform) 11.40 (s, 1H), 9.41 (s, 1H), 7.43 (s, 1H), 6.57 (t, J=55.4 Hz, 1H), 5.95 (s, 1H), 4.61 (s, 1H), 4.35 (q, J=7.1 Hz, 2H), 3.75 (s, 3H), 3.44 (dd, J=17.2, 5.1 Hz, 1H), 2.99 (dd, J=17.3, 7.5 Hz, 1H), 2.90-2.80 (m, 1H), 2.77-2.67 (m, 1H), 2.32-2.22 (m, 1H), 2.21-2.13 (m, 1H), 1.58-1.47 (m, 1H), 1.42-1.29 (m, 5H), 1.16 (d, J=6.0 Hz, 3H), 0.79 (ddd, J=7.7, 6.7, 4.1 Hz, 1H); LCMS [M+H]$^+$ 520, RT 1.90 minutes (Method 12)

Intermediate 500

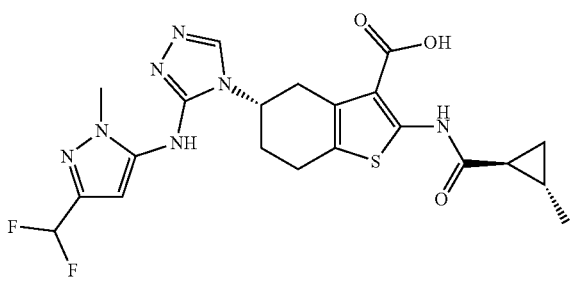 [SMILES: C[C@H]1C[C@@H]1C(=O)Nc1sc2c(c1C(=O)O)C[C@@H](n1cnnc1Nc1cc(C(F)F)nn1C)CC2]

(5S)-5-[3-[[5-(difluoromethyl)-2-methyl-pyrazol-3-yl]amino]-1,2,4-triazol-4-yl]-2-[[(1S,2S)-2-methyl-cyclopropanecarbonyl]amino]-4,5,6,7-tetrahydrobenzothiophene-3-carboxylic acid To a solution of intermediate 499 (1.680 g, 3.23 mmol) in a mixture of tetrahydrofuran and methanol (1:1, 20 mL) at room temperature was introduced lithium hydroxide hydrate (0.298 g, 7.09 mmol dissolved in 10 mL water). The reaction mixture was warmed to 45° C. for 18 hours. After diluting with water (20 mL) the reaction mixture was concentrated in-vacuo to remove the organic solvents and water (10 mL) added to the residual aqueous solution. After acidification of the aqueous solution with saturated aqueous potassium hydrogen sulfate, the solution was extracted with ethyl acetate (3×100 mL). The combined organic extracts were dried over sodium sulfate, filtered through a shallow bed of kieselguhr and the filtrate concentrated in-vacuo to furnish the title compound (1.009 g, 1.95 mmol, 60% Yield) as a colourless solid. LCMS [M+H]$^+$ 492, RT 1.73 minutes (Method 12).

Intermediate 501

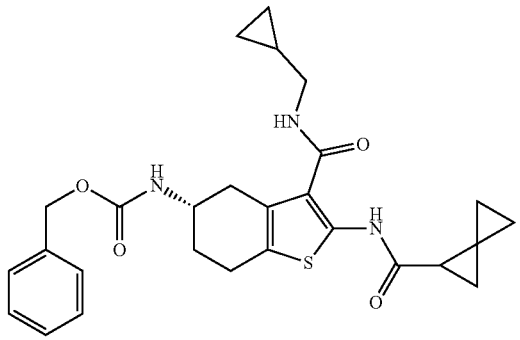 [SMILES: O=C(N[C@H]1CCc2sc(NC(=O)C3CC34CC4)c(C(=O)NCC3CC3)c2C1)OCc1ccccc1]

Benzyl N-[(5S)-3-(cyclopropylmethylcarbamoyl)-2-(spiro[2.2]pentane-2-carbonylamino)-4,5,6,7-tetra-hydrobenzothiophen-5-yl]carbamate To a mixture of intermediate 293 (1.2 g, 2.80 mmol), spiro[2.2]pentane-2-carboxylic acid (314 mg, 2.80 mmol) and pyridine (1.1 mL, 14 mmol) in anhydrous DCM (55.967 mL) cooled to 0° C. under an atmosphere of nitrogen, was added T3P (50%, 3.3 mL, 5.60 mmol) dropwise. The resulting solution was allowed to slowly reach room temperature overnight. Water was added (20 mL), the mixture was stirred for 5 minutes then the layers were separated and the aqueous phase was further extracted with DCM (20 mL). The combined organic layers were washed with saturated aqueous NH$_4$Cl solution (15 mL), followed by brine (15 mL), dried over magnesium sulfate, filtered and concentrated in vacuo. The crude material was purified by flash column chromatography with a 0 to 100% ethyl acetate in heptane gradient to afford the title compound (1.06 g, 77% yield). δH (500 MHz, DMSO-d6) 10.98 (s, 1H), 7.60 (t, J=5.3 Hz, 1H), 7.41 (t, J=6.1 Hz, 1H), 7.38-7.33 (m, 4H), 7.33-7.28 (m, 1H), 5.03 (s, 2H), 3.77-3.64 (m, 1H), 3.18-3.05 (m, 2H), 2.93 (d, J=15.6 Hz, 1H), 2.78-2.64 (m, 2H), 2.58-2.53 (m, 1H), 2.20 (dd, J=7.5, 4.2 Hz, 1H), 1.94 (d, J=11.4 Hz, 1H), 1.78-1.65 (m, 1H), 1.41 (dd, J=7.5, 3.7 Hz, 1H), 1.36 (t, J=3.8 Hz, 1H), 1.06-0.97 (m, 1H), 0.99-0.74 (m, 4H), 0.40 (q, J=4.7, 3.9 Hz, 2H), 0.21 (q, J=4.9 Hz, 2H). LCMS [M+H]$^+$ 494, RT 2.08 minutes (Method 12).

Intermediate 502

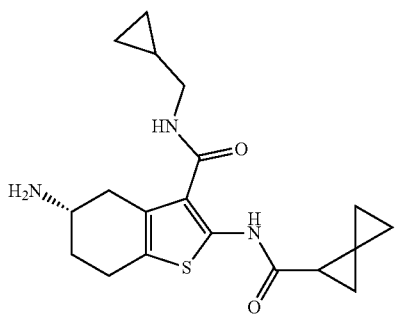 [SMILES: N[C@H]1CCc2sc(NC(=O)C3CC34CC4)c(C(=O)NCC3CC3)c2C1]

(5S)-5-amino-N-(cyclopropylmethyl)-2-(spiro[2.2]pentane-2-carbonylamino)-4,5,6,7-tetrahydrobenzothiophene-3-carboxamide To a solution of intermediate 501 (950 mg, 1.92 mmol) in ethanol (38 mL)/ethyl acetate (19 mL) was added palladium (5.0%, 410 mg, 0.19 mmol) and the resulting suspension was stirred under an atmosphere of hydrogen at room temperature for 1.5 hours. The reaction mixture was filtered on a pad of celite, washed through with ethanol and ethyl acetate, then concentrated to dryness to afford the title compound (644 mg, 77% yield). LCMS [M+H]$^+$ 360, RT 2.04 minutes (Method 29).

Intermediate 503

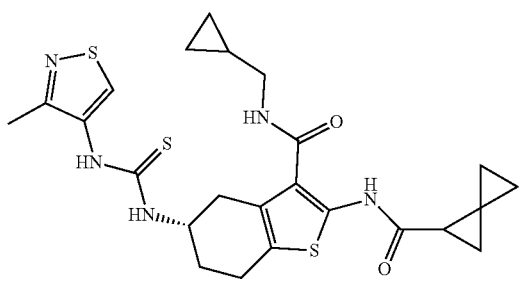 [SMILES: Cc1nscc1NC(=S)N[C@H]1CCc2sc(NC(=O)C3CC34CC4)c(C(=O)NCC3CC3)c2C1]

(5S)—N-(cyclopropylmethyl)-5-[(3-methylisothiazol-4-yl)carbamothioylamino]-2-(spiro[2.2]pentane-2-carbonylamino)-4,5,6,7-tetrahydrobenzothiophene-3-carboxamide To a solution of intermediate 502 (150 mg, 0.42 mmol) in DCM (6 mL) a solution of intermediate 406 (68 mg, 0.44 mmol) in DCM (4 mL) was added dropwise, and the mixture was stirred at room temperature for 1 hour. The reaction mixture was concentrated to dryness and purified by flash column chromatography with a 0 to 100% ethyl acetate in heptane gradient to afford the title compound (220 mg, 90% yield). δ$_H$ (500 MHz, DMSO-d6) 11.03 (s, 1H), 9.15 (s, 1H), 9.09 (s, 1H), 8.08 (s, 1H), 7.63 (t, J=4.7 Hz, 1H), 4.58 (s, 1H), 3.20-3.06 (m, 3H), 2.74 (s, 2H), 2.70-2.61 (m, 1H), 2.31 (s, 3H), 2.22 (dd, J=7.5, 4.3 Hz, 1H), 2.06-1.97 (m, 1H), 1.96-1.86 (m, 1H), 1.42 (dd, J=7.5, 3.7 Hz, 1H), 1.37 (t, J=3.9 Hz, 1H), 1.06-0.98 (m, 1H), 0.98-0.91 (m, 2H), 0.91-0.84 (m, 1H), 0.83-0.74 (m, 1H), 0.45-0.40 (m, 2H), 0.23 (q, J=4.8 Hz, 2H). LCMS [M+H]$^+$ 516, RT 3.06 minutes (Method 29).

Intermediate 504

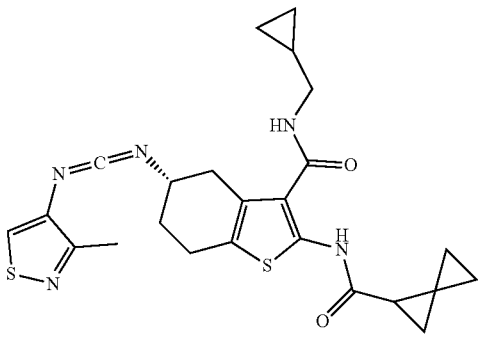 [SMILES: Cc1nscc1N=C=N[C@H]1CCc2sc(NC(=O)C3CC34CC4)c(C(=O)NCC3CC3)c2C1]

(5S)—N-(cyclopropylmethyl)-5-[(3-methylisothiazol-4-yl)iminomethyleneamino]-2-(spiro[2.2]pentane-2-carbonylamino)-4,5,6,7-tetrahydrobenzothiophene-3-carboxamide To a mixture of intermediate 503 (220 mg, 0.43 mmol) and triethylamine (0.18 mL, 1.28 mmol) in DCM (5 mL) at 0° C., methanesulfonyl chloride (36 μL, 0.47 mmol) was added. The mixture was stirred for 1.5 hours, then further triethylamine (0.18 mL, 1.28 mmoL) followed by methanesulfonyl chloride (36 μL, 0.47 mmol) were added and stirring was continued for further 45 minutes. The mixture was diluted with DCM (10 mL), washed with saturated aqueous NH$_4$Cl (10 mL), dried over magnesium sulfate, filtered and concentrated to afford the title compound (185 mg, 74% yield). LCMS [M+H]$^+$ 482, RT 3.35 minutes (Method 29).

Intermediate 505

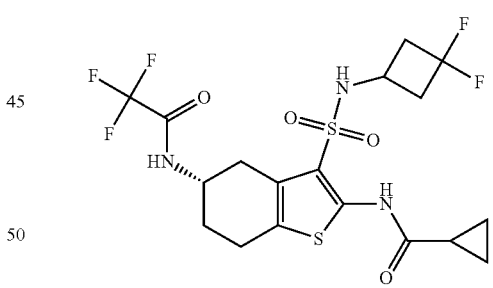

N-[(5S)-3-[(3,3-difluorocyclobutyl)sulfamoyl]-5-[(2,2,2-trifluoroacetyl)amino]-4,5,6,7-tetrahydrobenzothiophen-2-yl]cyclopropanecarboxamide To a mixture of (3,3-difluorocyclobutyl)ammonium chloride (50 mg, 0.35 mmol) and triethylamine (0.097 mL, 0.7 mmol) in DCM (2 mL) intermediate 462 (100 mg, 0.23 mmol) was added and the resulting solution stirred at room temperature for 15 minutes. The solvent was removed in vacuo and the residue was partitioned between ethyl acetate (10 mL) and saturated aqueous NaHCO$_3$ (10 mL). The layers were separated and the aqueous phase was extracted with more ethyl acetate (10 mL). The combined organics were washed with saturated aqueous NH₄Cl (5 mL), brine (5 mL), dried over magnesium sulfate, filtered and concentrated. The crude material was purified by flash column chromatography with a 0 to 100% ethyl acetate in heptane gradient to afford the title compound (91 mg, 78% yield). LCMS [M+H]⁺ 502, RT 1.91 minutes (Method 12).

Intermediate 506

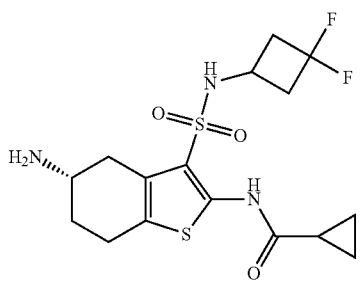 [SMILES: N[C@H]1CCc2sc(NC(=O)C3CC3)c(S(=O)(=O)NC3CC(F)(F)C3)c2C1]

N-[(5S)-5-amino-3-[(3,3-difluorocyclobutyl)sulfamoyl]-4,5,6,7-tetrahydrobenzothiophen-2-yl]cyclopropanecarboxamide To a suspension of intermediate 505 (90 mg, 0.18 mmol) in methanol (7.5 mL) and water (1.5 mL) was added potassium carbonate (74 mg, 0.54 mmoL) and the mixture was stirred at 40° C. for 20 hours. Further potassium carbonate (74 mg, 0.54 mmoL) was added and stirring was continued at 40° C. for a total of 48 hours. The solvent was removed in vacuo and the residue was partitioned between ethyl acetate (10 mL) and brine (5 mL). The layers were separated and the organic phase was dried over magnesium sulfate, filtered and concentrated to dryness to afford the title compound (83 mg, quantitative). LCMS [M+H]⁺ 406, RT 1.59 minutes (Method 12)

Intermediate 507

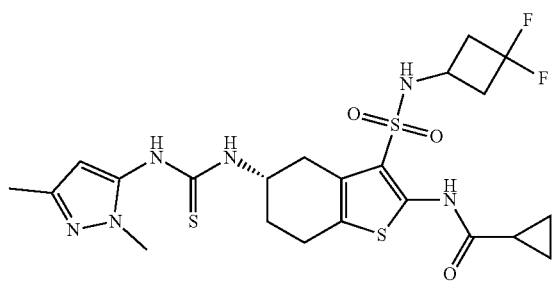 [SMILES: Cc1cc(NC(=S)N[C@H]2CCc3sc(NC(=O)C4CC4)c(S(=O)(=O)NC4CC(F)(F)C4)c3C2)n(C)n1]

N-[(5S)-3-[(3,3-difluorocyclobutyl)sulfamoyl]-5-[(2,5-dimethylpyrazol-3-yl)carbamothioylamino]-4,5,6,7-tetrahydrobenzothiophen-2-yl]cyclopropanecarboxamide To a solution of intermediate 506 (83 mg, 0.21 mmol) in DCM (3 mL) a solution of 5-isothiocyanato-1,3-dimethylpyrazole (33 mg, 0.22 mmol) in DCM (2 mL) was added dropwise and the mixture was stirred at room temperature for 30 minutes. The reaction mixture was concentrated to dryness and purified by flash column chromatography with a 0 to 100% ethyl acetate in heptane gradient to afford the title compound (95 mg, 83% yield). $\delta_H$ (500 MHz, DMSO-d6) 10.35 (s, 1H), 9.12 (s, 1H), 8.34 (d, J=8.0 Hz, 1H), 7.95 (d, J=7.7 Hz, 1H), 5.92 (s, 1H), 4.65-4.47 (m, 1H), 3.68-3.57 (m, 1H), 3.53 (s, 3H), 3.11 (dd, J=16.6, 4.7 Hz, 1H), 2.85-2.66 (m, 4H), 2.57 (dd, J=16.7, 8.1 Hz, 1H), 2.47-2.38 (m, 2H), 2.10 (s, 3H), 2.06-2.00 (m, 1H), 1.97-1.90 (m, 1H), 1.88-1.76 (m, 1H), 0.97-0.84 (m, 4H). LCMS [M+H]⁺ 559, RT 1.84 minutes (Method 12).

Intermediate 508

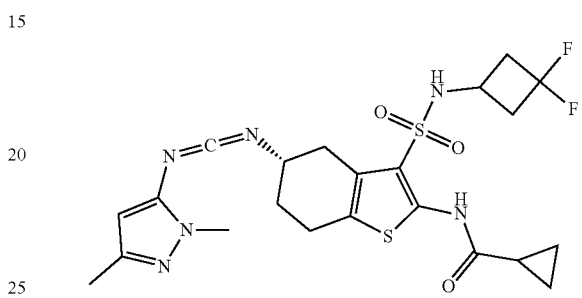

N-[(5S)-3-[(3,3-difluorocyclobutyl)sulfamoyl]-5-[(2,5-dimethylpyrazol-3-yl)iminomethyleneamino]-4,5,6,7-tetrahydrobenzothiophen-2-yl]cyclopropanecarboxamide To a mixture of intermediate 507 (90 mg, 0.16 mmol) and triethylamine (0.07 mL, 0.48 mmol) in DCM (2 mL) at 0° C., methanesulfonyl chloride (14 ℳL, 0.18 mmol) was added. The mixture was stirred for 1 hour, then further methanesulfonyl chloride (14 ℳL, 0.18 mmol) followed by triethylamine (0.067 mL, 0.48 mmol) were added (3 times at 30 minutes interval) and the reaction was stirred for a total of 3.5 hours. The mixture was diluted with DCM (10 mL), washed with saturated aqueous NH₄Cl solution (10 mL), dried over magnesium sulfate, filtered and concentrated to afford the title compound (100 mg, 79% yield). LCMS [M+H]⁺ 525, RT 1.91 minutes (Method 12).

Intermediate 509

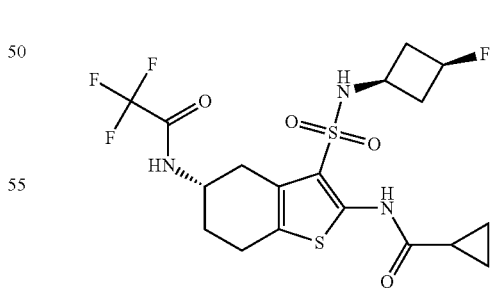

N-[(5S)-3-{[(cis)-3-fluorocyclobutyl]sulfamoyl}-5-(2,2,2-trifluoroacetamido)-4,5,6,7-tetrahydro-1-benzothiophen-2-yl]cyclopropanecarboxamide To a mixture of cis-(3-fluorocyclobutyl)ammonium chloride (52 mg, 0.42 mmol) and triethylamine (0.12 mL, 0.84 mmol) in DCM (2.8 mL) intermediate 462 (120 mg, 0.28 mmol) was added and the reaction mixture stirred at room temperature for 1 hour. The solvent was removed in vacuo and the residue was purified by flash column chromatography with a 0 to 100% ethyl acetate in heptane gradient to afford the title compound (110 mg, 82% yield). LCMS [M+H]$^+$ 484, RT 1.89 minutes (Method 12).

Intermediate 510

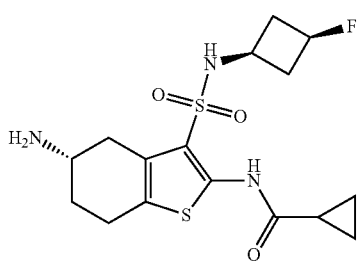 [SMILES: N[C@H]1CCc2sc(NC(=O)C3CC3)c(S(=O)(=O)N[C@H]3C[C@@H](F)C3)c2C1]

N-[(5S)-5-amino-3-{[(cis)-3-fluorocyclobutyl]sulfamoyl}-4,5,6,7-tetrahydro-1-benzothiophen-2-yl]cyclopropanecarboxamide To a suspension of intermediate 509 (110 mg, 0.23 mmol) in a mixture of methanol (9.5 mL) and water (1.9 mL) dipotassium carbonate (189 mg, 1.37 mmol) was added. The mixture was stirred at 40° C. for 15 hours. The solvent was removed in vacuo and the residue was partitioned between ethyl acetate (10 mL) and brine (5 mL). The layers were separated and the organic phase was dried over magnesium sulfate, filtered and concentrated to dryness to afford the title compound (100 mg, quantitative). LCMS [M+H]$^+$ 388, RT 1.52 minutes (Method 12)

Intermediate 511

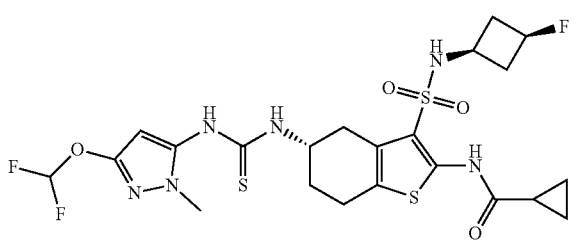 [SMILES: Cn1nc(OC(F)F)cc1NC(=S)N[C@H]1CCc2sc(NC(=O)C3CC3)c(S(=O)(=O)N[C@H]3C[C@@H](F)C3)c2C1]

N-[(5S)-5-({[3-(difluoromethoxy)-1-methyl-1H-pyrazol-5-yl]carbamothioyl}amino)-3-{[(cis)-3-fluorocyclobutyl]sulfamoyl}-4,5,6,7-tetrahydro-1-benzothiophen-2-yl]cyclopropanecarboxamide To a solution of intermediate 510 (100 mg, 0.26 mmol) in DCM (6 mL) a solution of intermediate 644 (56 mg, 0.271 mmol) in DCM (3 mL) was added dropwise. The mixture was stirred at room temperature for 15 hours then concentrated to dryness and purified by flash column chromatography (0 to 100% ethyl acetate in heptane gradient) to afford the title compound (130 mg, 83% yield). $\delta_H$ (500 MHz, DMSO-d6) 10.39 (s, 1H), 9.24 (s, 1H), 8.37-8.07 (m, 2H), 7.21 (t, J=73.5 Hz, 1H), 5.96 (s, 1H), 4.71 (dp, J=56.4, 6.8 Hz, 1H), 4.62-4.50 (m, 1H), 3.54 (s, 3H), 3.25-3.18 (m, 1H), 3.18-3.10 (m, 1H), 2.77-2.70 (m, 2H), 2.62-2.56 (m, 1H), 2.47-2.38 (m, 2H), 2.09-1.88 (m, 4H), 1.87-1.74 (m, 1H), 0.97-0.87 (m, 4H). LCMS [M+H]$^+$ 593, RT 1.89 minutes (Method 12).

Intermediate 512

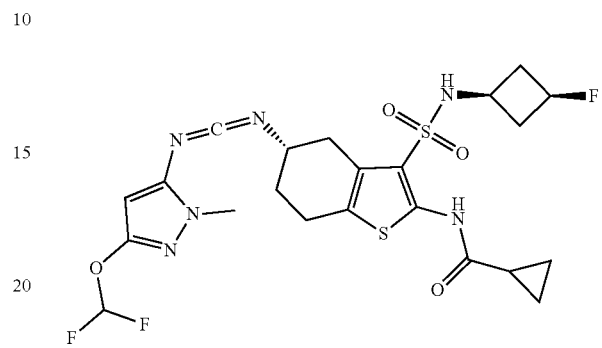

N-[(5S)-5-[({[3-(difluoromethoxy)-1-methyl-1H-pyrazol-5-yl]imino}methylidene)amino]-3-{[(cis)-3-fluorocyclobutyl]sulfamoyl}-4,5,6,7-tetrahydro-1-benzothiophen-2-yl]cyclopropanecarboxamide To a mixture of intermediate 511 (130 mg, 0.22 mmol) and triethylamine (0.09 mL, 0.66 mmol) in DCM (5 mL) at 0° C., methanesulfonyl chloride (19 μL, 0.24 mmol) was added. The reaction mixture was stirred for 10 minutes. Triethylamine (0.09 mL, 0.66 mmoL) followed by methanesulfonyl chloride (19 μL, 0.24 mmoL) were added and the mixture was stirred for 10 minutes. The mixture was diluted with DCM (10 mL), washed with saturated aqueous NH$_4$Cl (10 mL), dried over magnesium sulfate, filtered and concentrated to afford the title compound (140 mg, 89% yield). LCMS [M+H]$^+$ 559, RT 1.97 minutes (Method 12)

Intermediate 513

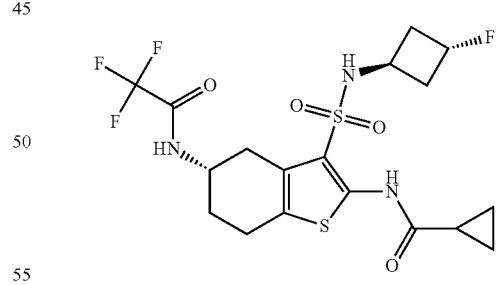

N-[(5S)-3-{[(trans)-3-fluorocyclobutyl]sulfamoyl}-5-(2,2,2-trifluoroacetamido)-4,5,6,7-tetrahydro-1-benzothiophen-2-yl]cyclopropanecarboxamide To a mixture of trans-(3-fluorocyclobutyl)ammonium chloride (52 mg, 0.42 mmol) and triethylamine (0.12 mL, 0.84 mmol) in DCM (2.8 mL), intermediate 462 (120 mg, 0.28 mmol) was added and the solution stirred at room temperature for 30 minutes. The solvent was removed in vacuo and the residue was purified by flash column chromatography (0 to 100% ethyl acetate in heptane gradient) to afford the title compound (113 mg, 84% yield). LCMS [M+H]+ 484, RT 1.89 minutes (Method 12).

Intermediate 514

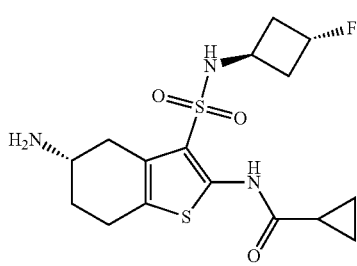 [SMILES: N[C@H]1CCc2sc(NC(=O)C3CC3)c(S(=O)(=O)N[C@H]3C[C@H](F)C3)c2C1]

N-[(5S)-5-amino-3-{[(trans)-3-fluorocyclobutyl]sulfamoyl}-4,5,6,7-tetrahydro-1-benzothiophen-2-yl]cyclopropanecarboxamide To a suspension of intermediate 513 (110 mg, 0.228 mmol) in a mixture of methanol (9.5 mL) and water (1.9 mL), dipotassium carbonate (189 mg, 1.37 mmol) was added. The mixture was stirred at 40° C. for 15 hours. The solvent was removed in vacuo and the residue was partitioned between ethyl acetate (10 mL) and brine (5 mL). The layers were separated and the organic phase was dried over magnesium sulfate, filtered and concentrated to dryness to afford the title compound (115 mg, quantitative). LCMS [M+H]+ 388, RT 1.54 minutes (Method 12).

Intermediate 515

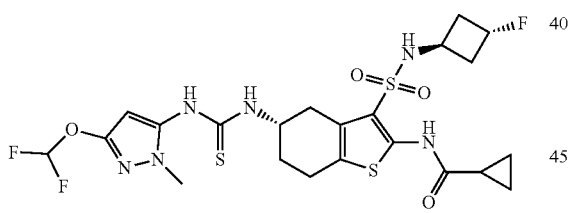

N-[(5S)-5-({[3-(difluoromethoxy)-1-methyl-1H-pyrazol-5-yl]carbamothioyl}amino)-3-{[(trans)-3-fluorocyclobutyl]sulfamoyl}-4,5,6,7-tetrahydro-1-benzothiophen-2-yl]cyclopropanecarboxamide To a suspension of intermediate 514 (115 mg, 0.30 mmol) in DCM (6 mL) a solution of intermediate 644 (64 mg, 0.31 mmol) in DCM (4 mL) was added dropwise and the mixture stirred at room temperature for 15 hours. THF (3 mL) followed by triethylamine (82 μL, 0.59 mmoL) were added and the reaction mixture stirred for 4 hours, then concentrated to dryness. The crude residue was purified by flash column chromatography (0 to 100% ethyl acetate in heptane gradient) to afford the title compound (120 mg, 67% yield). $\delta_H$ (500 MHz, DMSO-d6) 10.38 (s, 1H), 9.24 (s, 1H), 8.34-8.12 (m, 2H), 7.21 (t, J=73.5 Hz, 1H), 5.96 (s, 1H), 5.27-5.02 (m, 1H), 4.62-4.50 (m, 1H), 3.92-3.81 (m, 1H), 3.54 (s, 3H), 3.17-3.07 (m, 1H), 2.78-2.69 (m, 2H), 2.59 (dd, J=16.6, 8.5 Hz, 1H), 2.40-2.10 (m, 4H), 2.08-2.00 (m, 1H), 1.96-1.89 (m, 1H), 1.88-1.77 (m, 1H), 0.97-0.85 (m, 4H). LCMS [M+H]+ 593, RT 1.9 minutes (Method 12)

Intermediate 516

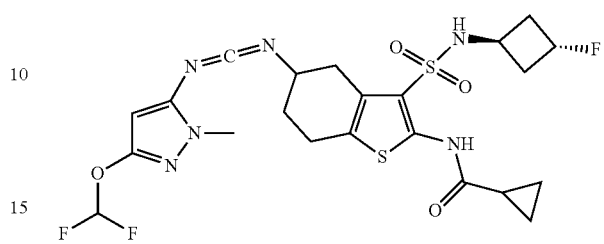

N-[(5S)-5-[({[3-(difluoromethoxy)-1-methyl-1H-pyrazol-5-yl]imino}methylidene)amino]-3-{[(trans)-3-fluorocyclobutyl]sulfamoyl}-4,5,6,7-tetrahydro-1-benzothiophen-2-yl]cyclopropanecarboxamide To a mixture of intermediate 515 (120 mg, 0.2 mmol) and triethylamine (0.08 mL, 0.61 mmol) in DCM (5 mL) at 0° C., methanesulfonyl chloride (17 μL, 0.22 mmol) was added. The mixture was stirred for 30 minutes, then it was diluted with DCM (10 mL), washed with saturated aqueous NH4Cl (10 mL), dried over magnesium sulfate, filtered and concentrated to afford the title compound (88 mg, 70% yield). LCMS [M+H]+ 559, RT 1.98 minutes (Method 12).

Intermediate 517

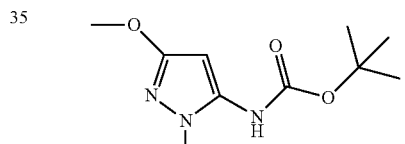

tert-butyl N-(5-methoxy-2-methyl-pyrazol-3-yl)carbamate

To a solution of 5-methoxy-2-methyl-pyrazole-3-carboxylic acid (1.0 g, 6.40 mmol) in tert-butanol (50 mL) was introduced diisopropylethylamine (1.14 mL, 6.53 mmol) and diphenylphosphoryl azide (4.14 mL, 19.21 mmol). The reaction was warmed to 85° C. for 5 hours. After concentrating in-vacuo, the residue was purified by flash column chromatography (0-100% ethyl acetate gradient in heptane) to furnish the title compound (1.05 g, 68% Yield). $\delta_H$ (500 MHz, d6-dmso) 9.28 (s, 1H), 5.51 (s, 1H), 3.69 (s, 3H), 3.47 (s, 3H), 1.45 (s, 9H); LCMS [M+H]+ 228, RT 1.37 minutes (Method 18).

Intermediate 518

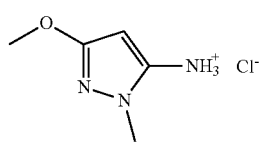

(5-methoxy-2-methyl-pyrazol-3-yl)ammonium chloride

To a solution of intermediate 517 (1270 mg, 5.59 mmol) in anhydrous 1,4-Dioxane (11 mL) was added 4 M HCl in dioxane (14 mL, 55.9 mmol) and the resulting solution stirred at room temperature for 16 hours. 4 M HCl in dioxane (3 mL, 12 mmol) was added and stirring was continued at room temperature for 3 hours. The reaction mixture was concentrated to dryness to afford the title compound (930 mg, quantitative). $\delta_H$ (500 MHz, DMSO-d6) 5.14 (s, 1H), 3.87 (s, 3H), 3.48 (s, 3H). Note: 3 exchangeable protons missing.

Intermediate 519

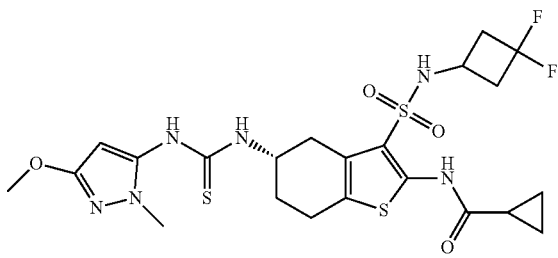 [SMILES: COc1cc(NC(=S)N[C@H]2CCc3sc(NC(=O)C4CC4)c(S(=O)(=O)NC4CC(F)(F)C4)c3C2)n(C)n1]

N-[(5S)-3-[(3,3-difluorocyclobutyl)sulfamoyl]-5-[(5-methoxy-2-methyl-pyrazol-3-yl)carbamothioylamino]-4,5,6,7-tetrahydrobenzothiophen-2-yl]cyclopropanecarboxamide To a solution of di(imidazol-1-yl)methanethione (90%, 64 mg, 0.32 mmol) and N-ethyl-N-isopropyl-propan-2-amine (0.11 mL, 0.64 mmol) in DCM (1.2 mL), intermediate 518 (50 mg, 0.31 mmol) was added portion-wise. The solution was stirred at room temperature for 36 hours, then added dropwise to a stirring solution of intermediate 506 (83 mg, 0.21 mmol) in anhydrous DCM (2 mL). The reaction mixture was stirred at room temperature for 2 hours, then concentrated to dryness and the crude material was purified by flash column chromatography (0 to 100% ethyl acetate in heptane gradient) to afford the title compound (92 mg, 77% yield). LCMS [M+H]⁺ 575, RT 1.91 minutes (Method 12).

Intermediate 520

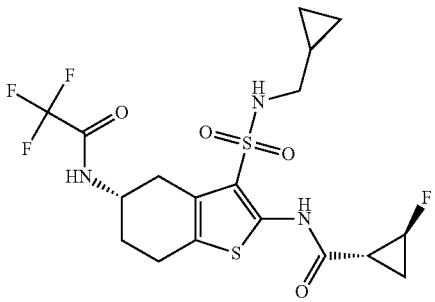 [SMILES: O=C(Nc1sc2c(c1S(=O)(=O)NCC1CC1)C[C@@H](NC(=O)C(F)(F)F)CC2)[C@H]1C[C@@H]1F]

(1R,2S)—N-[(5S)-3-(cyclopropylmethylsulfamoyl)-5-[(2,2,2-trifluoroacetyl)amino]-4,5,6,7-tetrahydrobenzothiophen-2-yl]-2-fluoro-cyclopropanecarboxamide To a mixture of cyclopropylmethanamine (90 mg, 1.27 mmol) and triethylamine (350 μL, 2.51 mmol) in DCM (10 mL), intermediate 474 (380 mg, 0.85 mmol) was added portion-wise. The solution was stirred at room temperature for 1 hour. The reaction mixture was then evaporated to dryness. The residue was dissolved in ethyl acetate (100 mL), washed with water (20 mL), saturated aqueous NH₄Cl (20 mL), brine (20 mL), dried over magnesium sulfate, filtered, and evaporated to dryness. The crude material was purified by flash column chromatography (0 to 100% ethyl acetate in heptane gradient) to afford the title compound (377 mg, 92% yield). LCMS [M+H]⁺ 484, RT 1.94 minutes (Method 12).

Intermediate 521

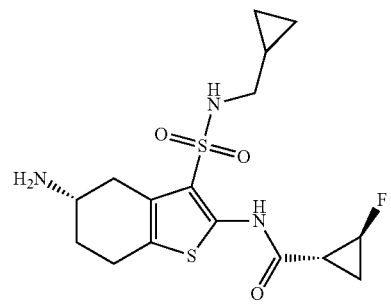 [SMILES: N[C@H]1CCc2sc(NC(=O)[C@H]3C[C@@H]3F)c(S(=O)(=O)NCC3CC3)c2C1]

(1R,2S)—N-[(5S)-5-amino-3-(cyclopropylmethylsulfamoyl)-4,5,6,7-tetrahydrobenzothiophen-2-yl]-2-fluoro-cyclopropanecarboxamide A solution of dipotassium carbonate (398 mg, 2.88 mmol) in water (3 mL) was added to a stirring solution of intermediate 520 (370 mg, 0.77 mmol) in methanol (20 mL). The mixture was heated at 40° C. for 24 hours. The reaction mixture was then evaporated to dryness, diluted with water (15 mL) and extracted with 10% methanol in DCM (3×30 mL). The combined organic layers were dried over sodium sulfate, filtered and concentrated to dryness to afford the title compound (270 mg, 74% yield). $\delta_H$ (500 MHz, DMSO-d6) 4.99-4.77 (m, 1H), 3.10-3.06 (m, 1H), 3.05-2.99 (m, 1H), 2.73-2.55 (m, 4H), 2.47-2.25 (m, 2H), 1.97-1.84 (m, 1H), 1.61-1.39 (m, 2H), 1.30-1.11 (m, 1H), 0.88-0.71 (m, 1H), 0.42-0.28 (m, 2H), 0.14--0.00 (m, 2H).

Intermediate 522

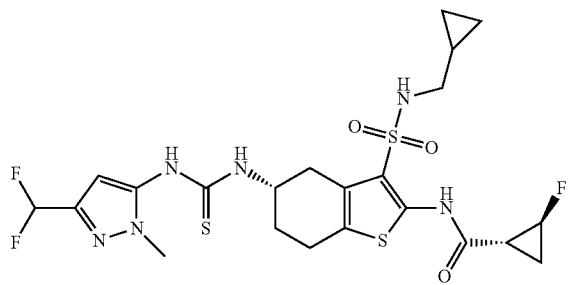 [SMILES: Cn1nc(C(F)F)cc1NC(=S)N[C@H]1CCc2sc(NC(=O)[C@H]3C[C@@H]3F)c(S(=O)(=O)NCC3CC3)c2C1]

(1R,2S)—N-[(5S)-3-(cyclopropylmethylsulfamoyl)-5-[[5-(difluoromethyl)-2-methyl-pyrazol-3-yl]carbamothioylamino]-4,5,6,7-tetrahydrobenzothiophen-2-yl]-2-fluoro-cyclopropanecarboxamide To a solution of intermediate 521 (90 mg, 0.23 mmol) in DCM (3 mL), intermediate 568 (90 mg, 0.35 mmol) was added and the mixture stirred at room temperature for 18 hours. The reaction mixture was concentrated to dryness and the crude material purified by flash column chromatography (0 to 100% ethyl acetate in heptane gradient) to afford the title compound (132 mg, 94% yield). LCMS [M+H]$^+$ 577, RT 1.94 minutes (Method 12)

Intermediate 523

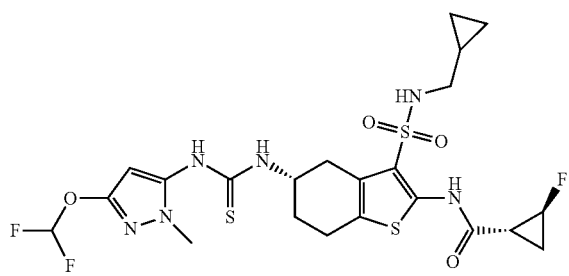 [SMILES: Cn1nc(OC(F)F)cc1NC(=S)N[C@H]1CCc2sc(NC(=O)[C@H]3C[C@@H]3F)c(S(=O)(=O)NCC3CC3)c2C1]

(1R,2S)—N-[(5S)-3-(cyclopropylmethylsulfamoyl)-5-[[5-(difluoromethoxy)-2-methyl-pyrazol-3-yl]carbamothioylamino]-4,5,6,7-tetrahydrobenzothiophen-2-yl]-2-fluoro-cyclopropanecarboxamide To a solution of intermediate 521 (90 mg, 0.23 mmol) in DCM (2 mL) a solution of intermediate 644 (71 mg, 0.35 mmol) in DCM (1 mL) was added dropwise. The mixture was stirred at room temperature for 18 hours, then concentrated to dryness and the crude material purified by flash column chromatography (0 to 100% ethyl acetate in heptane gradient) to afford the title compound (137 mg, 93% yield). LCMS [M+H]$^+$ 593, RT 1.96 minutes (Method 12).

Intermediate 524

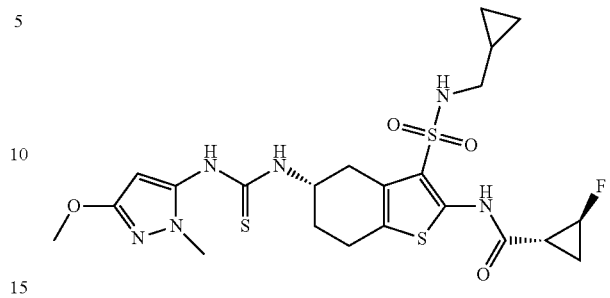

(1R,2S)—N-[(5S)-3-(cyclopropylmethylsulfamoyl)-5-[(5-methoxy-2-methyl-pyrazol-3-yl)carbamothioylamino]-4,5,6,7-tetrahydrobenzothiophen-2-yl]-2-fluoro-cyclopropanecarboxamide To a mixture of di(imidazol-1-yl)methanethione (75 mg, 0.38 mmol) and N-ethyl-N-isopropyl-propan-2-amine (0.13 mL, 0.76 mmol) in DCM (3 mL), intermediate 518 (60 mg, 0.36 mmol) was added portion-wise. The solution was stirred at room temperature overnight. This solution was then added dropwise to a solution of intermediate 521 (90 mg, 0.23 mmol) in DCM (3 mL). The reaction mixture was stirred at room temperature for 18 hours, then partitioned between DCM (5 mL) and saturated aqueous NH$_4$Cl (5 mL). The aqueous phase was extracted with DCM (5 mL) and the combined organic layers washed with brine (5 mL), dried over magnesium sulfate, filtered and concentrated to dryness. The crude material was purified by flash column chromatography (0 to 100% ethyl acetate in heptane gradient) to afford the title compound (100 mg, 73% yield). LCMS [M+H]$^+$ 557, RT 1.88 minutes (Method 12).

Intermediate 525

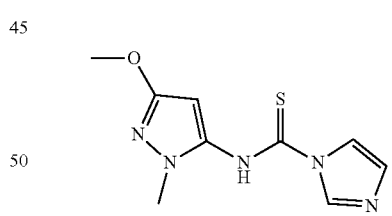

N-(5-methoxy-2-methyl-pyrazol-3-yl)imidazole-1-carbothioamide

To a mixture of di(imidazol-1-yl)methanethione (90%, 890 mg, 4.49 mmol) and N-ethyl-N-isopropyl-propan-2-amine (1.6 mL, 8.98 mmol) in DCM (20 mL), (5-methoxy-2-methyl-pyrazol-3-yl)ammonium chloride (700 mg, 4.28 mmol) was added portion-wise and the resulting solution stirred at room temperature for 18 hours. The reaction mixture was used directly in the next step (1015 mg, quantitative). LCMS [M+H]$^+$ 238, RT 1.69 minutes (Method 12).

Intermediate 526

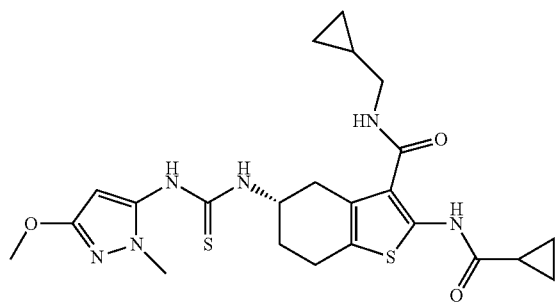 [SMILES: COc1cc(NC(=S)N[C@H]2CCc3sc(NC(=O)C4CC4)c(C(=O)NCC4CC4)c3C2)n(C)n1]

(5S)-2-(cyclopropanecarbonylamino)-N-(cyclopropylmethyl)-5-[(5-methoxy-2-methyl-pyrazol-3-yl)carbamothioylamino]-4,5,6,7-tetrahydrobenzothiophene-3-carboxamide To a solution of intermediate 117 (940 mg, 2.82 mmol) in DCM (10 mL) a solution of intermediate 525 (1003 mg, 4.23 mmol) in DCM (20 mL) was added dropwise. The mixture was stirred at room temperature for 18 hours. The reaction mixture was diluted with DCM (30 mL) and washed with saturated aqueous NH$_4$Cl (30 mL), saturated aqueous NaHCO$_3$ (30 mL), water (30 mL), brine (30 mL), and then dried over magnesium sulfate. The solvent was then concentrated under reduced pressure and the residue purified by flash column chromatography (0 to 100% of ethyl acetate in heptane gradient) to afford the title compound (1398 mg, 93% Yield). $\delta_H$ (400 MHz, DMSO-d6) 11.09 (s, 1H), 9.16 (s, 1H), 8.00 (d, J=7.5 Hz, 1H), 7.79-7.59 (m, 1H), 5.61 (s, 1H), 4.63-4.41 (m, 1H), 3.72 (s, 3H), 3.46 (s, 3H), 3.21-3.00 (m, 3H), 2.82-2.59 (m, 3H), 2.07-0.98 (m, 1H), 1.95-1.83 (m, 2H), 1.09-0.98 (m, 1H), 0.93-0.80 (m, 4H), 0.51-0.40 (m, 2H), 0.29-0.16 (m, 2H). LCMS [M+H]$^+$ 503, RT 1.80 minutes (Method 12).

Intermediate 527

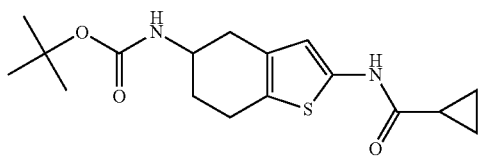 [SMILES: CC(C)(C)OC(=O)NC1CCc2sc(NC(=O)C3CC3)cc2C1]

tert-butyl N-[2-(cyclopropanecarbonylamino)-4,5,6,7-tetrahydrobenzothiophen-5-yl]carbamate A solution of intermediate 26 (27.60 g, 72.54 mmol, 1.0 eq.) in N,N-dimethylacetamide (240 mL) was heated at 170° C. for 2 hours. The reaction mixture was left to cool down to ambient temperature and the solution diluted with ethyl acetate (1 L). The organic phase was washed with water (500 mL) and brine (500 mL), dried over anhydrous sodium sulfate, filtered and the solvent removed in vacuo. The residue was purified by column chromatography using a gradient of ethyl acetate in heptane (5% to 80%) to afford the title compound (14.2 g, 58% yield). $\delta_H$ (250 MHz, Chloroform-d) 8.30 (s, 1H), 6.26 (s, 1H), 4.66 (d, J=7.7 Hz, 1H), 3.96 (s, 1H), 2.85 (dd, J=15.8, 5.0 Hz, 1H), 2.74 (t, J=6.1 Hz, 2H), 2.36 (dd, J=15.9, 7.3 Hz, 1H), 2.09-1.95 (m, 1H), 1.88-1.73 (m, 1H), 1.59-1.49 (m, 1H), 1.45 (s, 9H), 1.16-1.02 (m, 2H), 0.89-0.79 (m, 2H). LCMS [M+H]$^+$ 337, RT 2.77 minutes (Method 12)

Intermediate 528

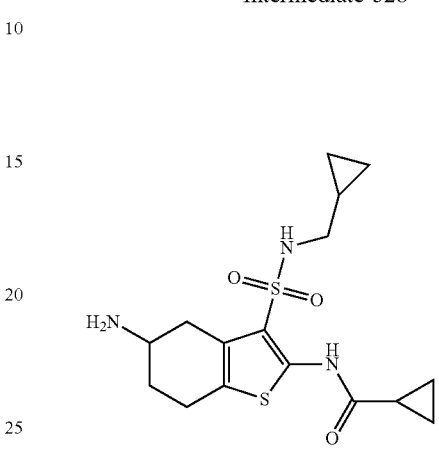

N-[5-amino-3-(cyclopropylmethylsulfamoyl)-4,5,6,7-tetrahydrobenzothiophen-2-yl]cyclopropanecarboxamide To a suspension of intermediate 527 (11.13 g, 33.08 mmol) in acetonitrile (176 mL) at 7° C., sulfurochloridic acid (11 mL, 165.49 mmol) was added drop wise over 10 minutes. After 20 minutes at room temperature the reaction was heated to 70° C. for 3 hours. Once at room temperature the mixture was added to an externally cooled (2° C.) mixture of 1-cyclopropylmethanamine (60 mL, 691.78 mmol) and triethylamine (25 mL, 176.89 mmol) in CHCl$_3$ over 20 minutes (not exceeding 9° C.). The reaction was slowly warmed to room temperature over 18 hours. The volatiles were then concentrated under vacuo. EtOAc (0.75 L) and saturated aqueous Na$_2$CO$_3$ (0.5 L) were added followed by water (0.75 L). The organic layer was separated and the aqueous layer was extracted with EtOAc (3×0.25 L). The organic layers were then combined and washed with a 1:1 mixture of saturated Na$_2$CO$_3$ (2×0.5 L), water (2×0.5 L) and saturated Na$_2$CO$_3$ (0.5 L). The organic layer was separated and the combined second aqueous washings were filtered through wool. The aqueous filtrate was extracted with EtOAc (2×0.25 L). The organic layers were combined and washed with a mixture of water (300 ml) and brine (0.25 L), dried over magnesiumsulphate, filtered and concentrated in vacuo. The crude solid was adsorbed onto silica gel and purified by flash column chromatography eluting with 0 to 10% of 7 M NH$_3$ in methanol in DCM gradient to give the title compound as a white solid (4.49 g, 32% yield). $\delta_H$ (500 MHz, DMSO-d6) 3.04-2.95 (m, 2H), 2.74-2.64 (m, 3H), 2.64-2.54 (m, 1H), 2.33-2.23 (m, 1H), 1.90-1.81 (m, 2H), 1.54-1.43 (m, 1H), 0.93-0.82 (m, 4H), 0.84-0.70 (m, 1H), 0.39-0.30 (m, 2H), 0.11-0.03 (m, 2H). LCMS [M+H]$^+$ 370, RT 1.62 minutes (Method 10).

Intermediate 529

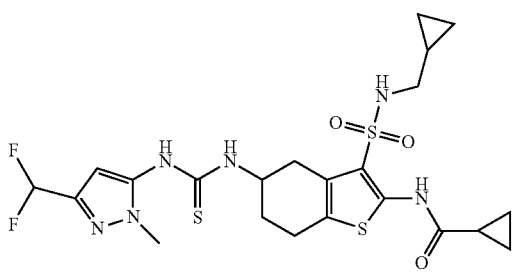 [SMILES: Cn1nc(C(F)F)cc1NC(=S)NC1CCc2sc(NC(=O)C3CC3)c(S(=O)(=O)NCC3CC3)c2C1]

N-[3-(cyclopropylmethylsulfamoyl)-5-[[5-(difluoromethyl)-2-methyl-pyrazol-3-yl]carbamothioylamino]-4,5,6,7-tetrahydrobenzothiophen-2-yl]cyclopropanecarboxamide To a solution of intermediate 528 (85%, 950 mg, 2.19 mmol) in DCM (12 mL), a solution of intermediate 254 (92%, 0.54 g, 2.62 mmol) in DCM (5 mL) was added. The solution was stirred at room temperature for 10 minutes. The solvent was removed and the residue purified by flash column chromatography (0 to 50% of EtOAc in heptane gradient) to give the title compound (1127 mg, 85% Yield). $\delta_H$ (250 MHz, Chloroform-d) 10.48 (s, 1H), 7.67 (s, 1H), 6.69 (d, J=55.0 Hz, 1H), 6.36 (s, 1H), 6.18 (d, J=7.7 Hz, 1H), 5.22 (t, J=5.9 Hz, 1H), 4.86-4.62 (m, 1H), 3.80 (s, 3H), 3.33 (dd, J=16.1, 5.3 Hz, 1H), 2.98-2.65 (m, 4H), 2.65-2.34 (m, 1H), 2.14 (s, 1H), 2.00-1.62 (m, 2H), 1.73-1.59 (m, 1H), 1.14 (p, J=4.1, 3.5 Hz, 2H), 1.04-0.78 (m, 3H), 0.61-0.37 (m, 2H), 0.21--0.00 (m, 2H). LCMS [M+H]$^+$ 559, RT 1.92 minutes (Method 12).

Intermediate 530

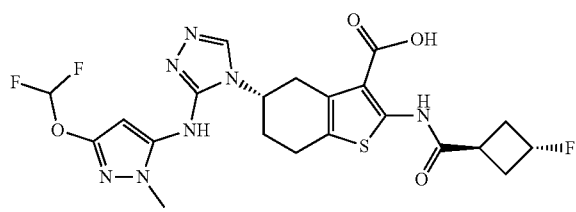 [SMILES: Cn1nc(OC(F)F)cc1Nc1nncn1[C@H]1CCc2sc(NC(=O)[C@H]3C[C@H](F)C3)c(C(=O)O)c2C1]

(5S)-5-[3-[[5-(difluoromethoxy)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxylic acid To a stirred solution of intermediate 667 (1.20 g, 0.22 mmol) in THF (9 mL) at r.t. was added 1 N sodium hydroxide in water (4 mL). After 48 hours the reaction mixture was diluted with DCM (30 mL) and water (30 mL), the phases separated and the organics discarded. The aqueous was re-extracted with DCM (8×15 mL, containing 3 mL of IPA). The aqueous phase was acidified with 0.5 N HCl (5 mL) resulting in a beige precipitate which was filtered and washed with Et$_2$O (5 mL). The aqueous phase was extracted with chloroform containing (30 mL then 2×15 mL, containing a 3 mL of IPA) and the combined organics dried (phase separator) and concentrated in vacuo. This was combined with the precipitate and further purified via trituration with Et$_2$O (25 mL) to give the title compound (430 mg, 42% Yield). $\delta_H$ (400 MHz, DMSO-d6) 13.28 (s, 1H), 12.04 (s, 1H), 11.72-10.93 (m, 0.5H), 8.75 (s, 0.5H), 8.49-8.11 (m, 1H), 7.47-6.99 (m, 1H), 5.99-5.61 (m, 1H), 5.23 (dp, J=56.6, 6.3 Hz, 1H), 4.43 (s, 1H), 3.60-3.45 (m, 3H), 3.45-3.35 (m, 3H), 2.91-2.75 (m, 3H), 2.64-2.52 (m, 3H), 2.31-2.18 (m, 1H), 2.18-2.06 (m, 1H).

Intermediate 531

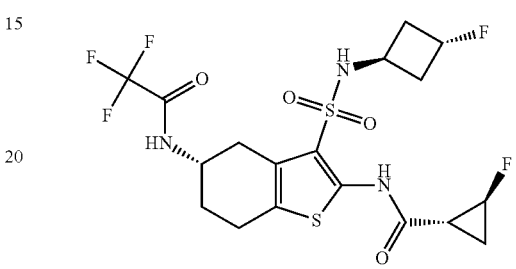

(1R,2S)-2-fluoro-N-[(5S)-3-[trans-(3-fluorocyclobutyl)sulfamoyl]-5-[(2,2,2-trifluoroacetyl)amino]-4,5,6,7-tetrahydrobenzothiophen-2-yl]cyclopropanecarboxamide To a mixture of trans-3-fluorocyclobutanamine hydrochloride (159 mg, 1.27 mmol) and triethylamine (350 μL, 2.51 mmol) in DCM (10 mL), intermediate 474 (380 mg, 0.847 mmol) was added portion-wise. The solution was stirred at room temperature for 1 hour. The reaction mixture evaporated to dryness, dissolved in ethyl acetate (100 mL), washed with water (20 mL), saturated aqueous NH$_4$Cl (20 mL), brine (20 mL), dried over magnesium sulfate, filtered, and evaporated to dryness. The residue was absorbed on silica and purified by flash column chromatography (0 to 100% of EtOAc in heptane gradient) to give the title compound (376 mg, 89% yield): $\delta_H$ (400 MHz, DMSO-d6) 10.47 (br s, 1H), 9.56 (d, J=8.0 Hz, 1H), 8.22 (br s, 1H), 5.26-5.06 (m, 1H), 5.06-4.83 (m, 1H), 4.16-3.99 (m, 1H), 3.99-3.81 (m, 1H), 3.09 (dd, J=16.7, 5.3 Hz, 1H), 2.75 (d, J=13.4 Hz, 2H), 2.62-2.56 (m, 1H), 2.43-2.04 (m, 5H), 2.04-1.92 (m, 1H), 1.87-1.71 (m, 1H), 1.70-1.52 (m, 1H), 1.38-1.22 (m, 1H). LCMS [M+H]$^+$ 502, RT 1.92 minutes (Method 12).

Intermediate 532

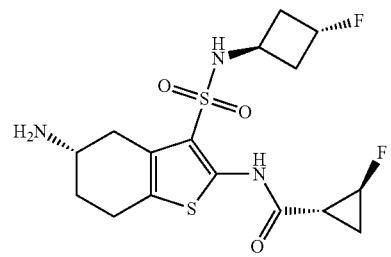 [SMILES: N[C@H]1CCc2sc(NC(=O)[C@H]3C[C@@H]3F)c(S(=O)(=O)N[C@H]3C[C@H](F)C3)c2C1]

(1R,2S)—N-[(5S)-5-amino-3-[trans-(3-fluorocyclobutyl)sulfamoyl]-4,5,6,7-tetrahydrobenzothiophen-2-yl]-2-fluoro-cyclopropanecarboxamide Potassium carbonate (411 mg, 2.98 mmol) was added to a solution of intermediate 531 (373 mg, 0.744 mmol) in a mixture of methanol (20 mL) and water (3 mL). The mixture was stirred at 40° C. for 20 hours. The reaction mixture was evaporated to dryness, diluted with water (10 mL) and the aqueous layer adjusted to pH ~10 with 1 M HCl before being extracted with 10% methanol in DCM (3×30 mL). The combined organic layers were dried over sodium sulfate, filtered and concentrated to dryness to give the title compound (310 mg, 86% yield). $\delta_H$ (500 MHz, Chloroform-d) 10.51 (s, 1H), 5.21-5.03 (m, 1H), 5.01-4.76 (m, 1H), 4.06-3.93 (m, 1H), 3.28-3.17 (m, 1H), 3.10-3.01 (m, 1H), 2.84-2.67 (m, 2H), 2.58-2.41 (m, 2H), 2.39-2.17 (m, 3H), 2.15-2.06 (m, 1H), 2.06-1.97 (m, 1H), 1.73-1.40 (m, 6H). LCMS [M+H]$^+$ 406, RT 0.86 minutes (Method 11).

Intermediate 533

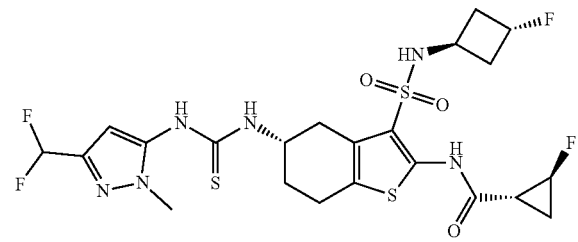 [SMILES: Cn1nc(C(F)F)cc1NC(=S)N[C@H]1CCc2sc(NC(=O)[C@H]3C[C@@H]3F)c(S(=O)(=O)N[C@H]3C[C@H](F)C3)c2C1]

(1R,2S)—N-[(5S)-5-[[5-(difluoromethyl)-2-methyl-pyrazol-3-yl]carbamothioylamino]-3-[trans-(3-fluorocyclobutyl)sulfamoyl]-4,5,6,7-tetrahydrobenzothiophen-2-yl]-2-fluoro-cyclopropanecarboxamide To a solution of intermediate 532 (165 mg, 0.393 mmol) in DCM (6 mL), intermediate 568 (101 mg, 0.393 mmol) was added. The solution was stirred for 20 minutes. The solvent was removed and the residue purified by flash column chromatography (0 to 60% of EtOAc in heptane gradient) to give the title compound (195 mg, 83% yield). LCMS [M+H]$^+$ 595, RT 1.92 minutes (Method 12).

Intermediate 534

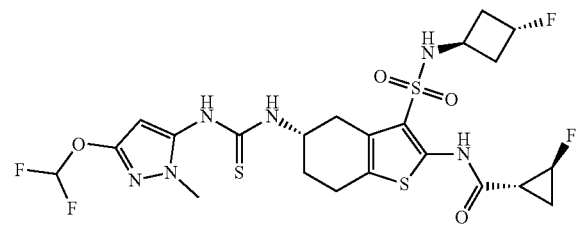 [SMILES: Cn1nc(OC(F)F)cc1NC(=S)N[C@H]1CCc2sc(NC(=O)[C@H]3C[C@@H]3F)c(S(=O)(=O)N[C@H]3C[C@H](F)C3)c2C1]

(1R,2S)—N-[(5S)-5-[[5-(difluoromethoxy)-2-methyl-pyrazol-3-yl]carbamothioylamino]-3-[trans-(3-fluorocyclobutyl)sulfamoyl]-4,5,6,7-tetrahydrobenzothiophen-2-yl]-2-fluoro-cyclopropanecarboxamide To a solution of intermediate 532 (157 mg, 0.387 mmol) in DCM (4 mL), a solution of intermediate 644 (79 mg, 0.387 mmol) in DCM (2 mL) was added. The mixture was stirred for 15 minutes, then the solvent was removed and the residue purified by flash column chromatography (0 to 60% of EtOAc in heptane gradient) to give the title compound (217 mg, 85% yield): LCMS [M+H]$^+$ 611, RT 1.93 minutes (Method 12).

Intermediate 535

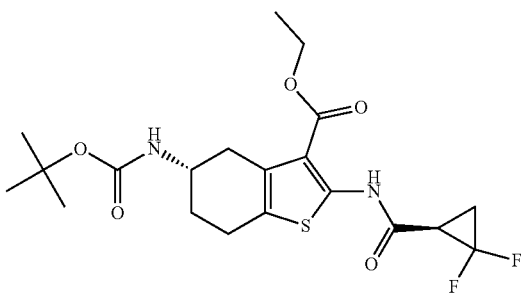 [SMILES: CCOC(=O)c1c(NC(=O)[C@H]2CC2(F)F)sc2c1C[C@@H](NC(=O)OC(C)(C)C)CC2]

ethyl (5S)-5-(tert-butoxycarbonylamino)-2-[[(1R)-2,2-difluorocyclopropanecarbonyl]amino]-4,5,6,7-tetrahydrobenzothiophene-3-carboxylate To an externally cooled (−2.1° C.) mixture of intermediate 567 (10.08 g, 26.7 mmol) and (1R)-2,2-difluorocyclopropanecarboxylic acid (3.26 g, 26.7 mmol) in DCM (200 mL), pyridine (8.6 mL, 0.106 mol) was added. Then, 2,4,6-tripropyl-1,3,5,2,4,6-trioxatriphosphorinane-2,4,6-trioxide (50%, 33 mL, 55.4 mmol) was added drop wise over a period of 8 minutes. The reaction was allowed to slowly warm and stirred for at least 18 hours. Water (70 mL) was added and the two-phased mixture was stirred for about 10 minutes. The organic layer was separated and the aqueous layer was extracted with DCM (4×35 mL). The organic layers were combined, washed with water (70 mL), brine (70 mL), dried over magnesium sulphate, filtered and concentrated in vacuo. The crude solid was adsorbed onto silica gel and then partially purified by flash column chromatography (0 to 100% of EtOAc in heptane gradient) to give the impure product. This was further purified by sonication in a solution of 17% EtOAc in heptane followed by cooling in an ice bath before filtering off. The solid was washed with heptane (2×100 mL) and dried to give the title compound (6.75 g, 57% yield). $\delta_H$(400 MHz, Chloroform-d) 11.59 (s, 1H), 4.71-4.53 (m, 1H), 4.37 (q, J=7.1 Hz, 2H), 4.08-3.90 (m, 1H), 3.20 (dd, J=17.1, 5.1 Hz, 1H), 2.77 (t, J=5.9 Hz, 2H), 2.69-2.49 (m, 2H), 2.34-2.19 (m, 1H), 2.12-1.99 (m, 1H), 1.93-1.74 (m, 2H), 1.49 (s, 9H), 1.41 (t, J=7.1 Hz, 3H). LCMS [M+H-tBu]$^+$389, RT 4.12 minutes (Method 10).

Intermediate 536

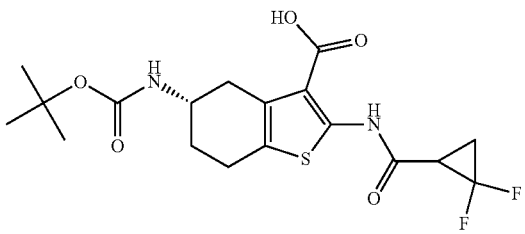 [SMILES: CC(C)(C)OC(=O)N[C@H]1CCc2sc(NC(=O)C3CC3(F)F)c(C(=O)O)c2C1]

(5S)-5-(tert-butoxycarbonylamino)-2-[(2,2-difluoro-cyclopropanecarbonyl)amino]-4,5,6,7-tetrahydrobenzothiophene-3-carboxylic acid To an externally cooled suspension of intermediate 535 (6.54 g, 14.7 mmol) in a mixture of THF (45 mL) and MeOH (45 mL), lithium hydroxide hydrate (1.25 g, 29.1 mmol) was added. When the solids had almost dissolved, water (45 mL) was poured slowly over 1 minute whereupon a thick precipitate was produced. The reaction mixture was then heated to 40° C. for 16.5 hours. The cooled reaction mixture had the light volatiles removed at 20° C.; water (50 mL) and 10% citric acid (100 mL) were then added. The mixture was extracted with EtOAc (75 mL). The organic layer was separated and the aqueous was extracted with EtOAc (3×50 mL). The organic layers were combined and washed with a 1:1 mixture of water and brine (50 mL), followed by brine (25 mL), dried over magnesium sulphate, filtered and concentrated in vacuo. The isolated solid was sonicated in a mixture of EtOAc (5 mL) and heptane (100 mL); the solid was filtered off, washed with heptane (2×50 mL) and dried. The isolated product was further purified by being sonicated in 10% EtOAc in heptane (100 mL), filtered off, washed with heptane (2×50 mL) and dried to afford the title compound (4.34 g, 68% Yield). $\delta_H$ (400 MHz, DMSO-d6) 13.11 (s, 1H), 11.49 (s, 1H), 6.92 (d, J=7.3 Hz, 1H), 3.65-3.53 (m, 1H), 3.05 (dd, J=16.8, 4.3 Hz, 1H), 2.77-2.59 (m, 2H), 2.56-2.51 (m, 1H), 2.48-2.42 (m, 1H), 2.10-1.99 (m, 2H), 1.95-1.85 (m, 1H), 1.68-1.56 (m, 1H), 1.39 (s, 9H). LCMS [M–H]⁻ 415, RT 3.35 minutes (Method 10).

Intermediate 537

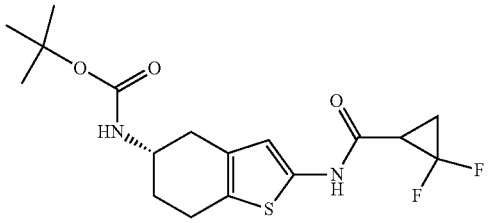 [SMILES: CC(C)(C)OC(=O)N[C@H]1CCc2sc(NC(=O)C3CC3(F)F)cc2C1]

tert-butyl N-[(5S)-2-[(2,2-difluorocyclopropanecarbonyl)amino]-4,5,6,7-tetrahydrobenzothiophen-5-yl]carbamate A solution of intermediate 536 (4.34 g, 10.4 mmol) in DMA (35 mL) was heated to 170° C. for 6 hours. The cooled reaction mixture had the volatiles concentrated in vacuo. The crude residue was adsorbed onto silica gel and purified by flash column chromatography (0 to 50% of EtOAc in heptane gradient) to give the title compound (2.51 g, 67% yield). $\delta_H$ (500 MHz, Chloroform-d) 8.85 (s, 1H), 6.37-6.15 (m, 1H), 4.83-4.52 (m, 1H), 3.91 (s, 1H), 2.87-2.78 (m, 1H), 2.72 (s, 2H), 2.53-2.42 (m, 1H), 2.38-2.29 (m, 1H), 2.26-2.15 (m, 1H), 2.06-1.96 (m, 1H), 1.83-1.69 (m, 2H), 1.46 (s, 9H).

LCMS [M+H]⁺ 373, RT 3.31 minutes (Method 10).

Intermediate 538

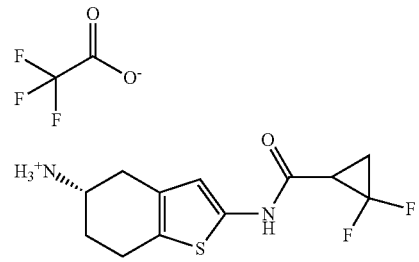

[(5S)-2-[(2,2-difluorocyclopropanecarbonyl)amino]-4,5,6,7-tetrahydrobenzothiophen-5-yl]ammonium 2,2,2-trifluoroacetate To a suspension of intermediate 537 (2.51 g, 6.74 mmol) in dry DCM (20 mL), 2,2,2-trifluoroacetic acid (5.0 mL, 67.3 mmol) was added portion-wise at room temperature. The reaction was stirred for 18 hours before the volatiles were concentrated in vacuo, azeotroped twice with DCM and heptane. The residue was concentrated under vacuo to afford the title compound (2.60 g, 100% yield). $\delta_H$ (500 MHz, DMSO-d6) 11.45 (s, 1H), 8.00 (s, 3H), 6.42 (s, 1H), 3.50-3.38 (m, 1H), 2.88 (dd, J=15.9, 5.1 Hz, 1H), 2.81-2.66 (m, 3H), 2.49-2.45 (m, 1H), 2.14-2.07 (m, 1H), 2.07-1.93 (m, 2H), 1.83-1.72 (m, 1H). LCMS [M+H]⁺ 273, RT 1.07 minutes (Method 10).

Intermediate 539

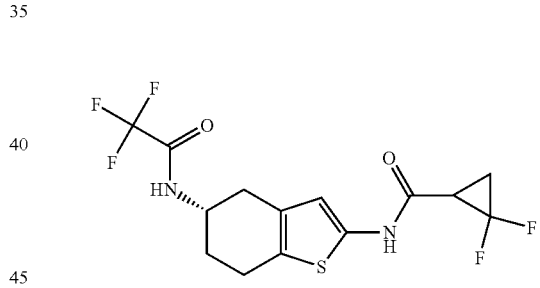

2,2-difluoro-N-[(5S)-5-[(2,2,2-trifluoroacetyl)amino]-4,5,6,7-tetrahydrobenzothiophen-2-yl]cyclopropanecarboxamide To an externally cooled (0° C.) suspension of intermediate 538 (2.60 g, 6.73 mmol) in MeOH (35 mL), triethylamine (3.8 mL, 27.3 mmol) was added drop wise over 5 minutes. After stirring for a further 5 minutes, ethyl 2,2,2-trifluoroacetate (3.2 mL, 26.9 mmol) was added drop wise over 5 minutes. After a further 5 minutes, the external cooling was removed and the reaction was stirred at ambient temperature for 17 hours. The volatiles were concentrated in vacuo; EtOAc (50 mL) was added and the organic phase was washed with a 1:1 mixture of water and brine (25 mL), brine (12.5 mL), dried over magnesium sulphate, filtered and concentrated in vacuo. The crude solid was adsorbed onto silica gel and purified by flash column chromatography (0 to 60% of EtOAc in heptane gradient) to give the title compound (2.19 g, 88% yield). $\delta_H$ (400 MHz, DMSO-d6) 11.33 (s, 1H), 9.47 (s, 1H), 6.42-6.33 (m, 1H), 4.10-3.92 (m, 1H), 2.86-2.68 (m, 4H), 2.55-2.45 (m, 1H), 2.08-1.90 (m, 3H), 1.87-1.72 (m, 1H). LCMS [M+H]+ 369, RT 2.95 minutes (Method 10).

Intermediate 540

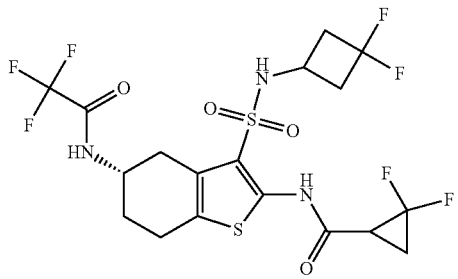 [SMILES: O=C(Nc1sc2c(c1S(=O)(=O)NC1CC(F)(F)C1)C[C@@H](NC(=O)C(F)(F)F)CC2)C1CC1(F)F]

N-[(5S)-3-[(3,3-difluorocyclobutyl)sulfamoyl]-5-[(2,2,2-trifluoroacetyl)amino]-4,5,6,7-tetrahydrobenzothiophen-2-yl]-2,2-difluoro-cyclopropanecarboxamide To a solution of intermediate 481 (42 mg, 0.0900 mmol) in DCM (3 mL) triethylamine (0.038 mL, 0.270 mmol) was added followed by 3,3-difluorocyclobutan-1-amine hydrochloride (19 mg, 0.135 mmol). The solution was stirred at room temperature for 20 minutes. Saturated aqueous NH4Cl solution (5 mL) was added to the reaction. The organic layer was separated and dried (MgSO4). The solvent was removed to give a solid. Purification by flash column chromatography eluting with 0 to 40% of EtOAc in heptane gradient gave the title compound as a white solid (33 mg, 100% pure. 68% yield): LCMS [M+H]+ 538, RT 1.96 minutes (Method 12).

Intermediate 541

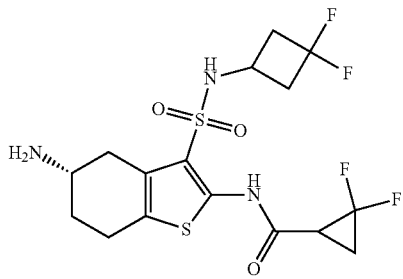 [SMILES: N[C@H]1CCc2sc(NC(=O)C3CC3(F)F)c(S(=O)(=O)NC3CC(F)(F)C3)c2C1]

N-[(5S)-5-amino-3-[(3,3-difluorocyclobutyl)sulfamoyl]-4,5,6,7-tetrahydrobenzothiophen-2-yl]-2,2-difluoro-cyclopropanecarboxamide To a solution of intermediate 540 (354 mg, 0.659 mmol) in methanol (23 mL), potassium carbonate (341 mg, 2.47 mmol) was added followed by water (2.3 mL). The mixture was vigorously stirred at 40° C. for 22 hours. Saturated aqueous NH4Cl (5 mL) was added and the organic layer separated and dried (MgSO4). The solvent was removed and the residue purified by flash column chromatography (0 to 40% of EtOAc in heptane gradient) to give the title compound (274 mg, 94% yield). LCMS [M+H]+ 442, RT 1.57 minutes (Method 12).

Intermediate 542

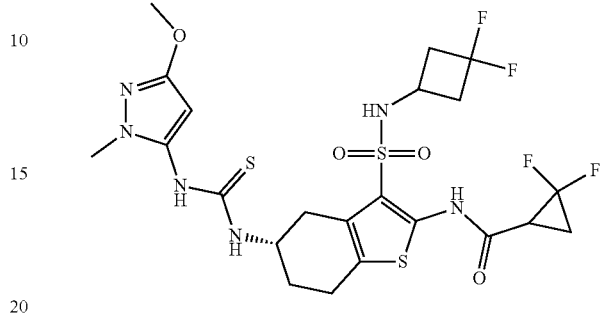

N-[(5S)-3-[(3,3-difluorocyclobutyl)sulfamoyl]-5-[(5-methoxy-2-methyl-pyrazol-3-yl)carbamothioylamino]-4,5,6,7-tetrahydrobenzothiophen-2-yl]-2,2-difluoro-cyclopropanecarboxamide To a stirred solution of intermediate 541 (290 mg, 0.657 mmol) in DCM (10 mL), a solution of intermediate 525 (234 mg, 0.985 mmol) in DCM (15 mL) was added. The reaction was stirred for 72 hours. The reaction mixture was partitioned between DCM (5 mL) and saturated aqueous NH4Cl (5 mL). The aqueous was extracted with DCM (5 mL) and the combined organics were washed with brine (5 mL), dried over magnesium sulfate and concentrated to dryness. Purification by flash column chromatography (0 to 80% of EtOAc in heptane gradient) gave the title compound (356 mg, 80% yield). LCMS [M+H]+ 611, RT 1.90 minutes (Method 12).

Intermediate 543

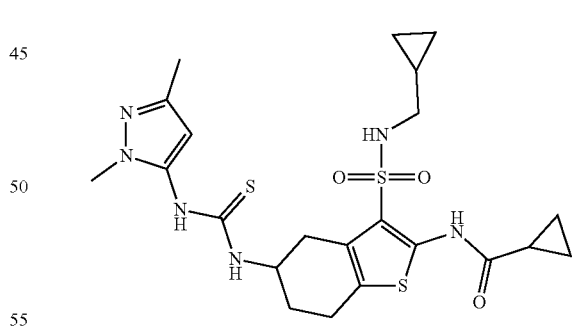

N-[3-(cyclopropylmethylsulfamoyl)-5-[(2,5-dimethylpyrazol-3-yl)carbamothioylamino]-4,5,6,7-tetrahydrobenzothiophen-2-yl]cyclopropanecarboxamide To a solution of intermediate 528 (1450 mg, 3.92 mmol) in DCM (20 mL) was added 5-isothiocyanato-1,3-dimethyl-pyrazole (80%, 901.77 mg, 4.71 mmol) in DCM (10 mL). The reaction was stirred for 15 minutes. The reaction was retreated with 5-isothiocyanato-1,3-dimethyl-pyrazole (80%, 91 mg, 0.47 mmol). The reaction was stirred for another 10 minutes. The solvent was removed and the residue purified by flash column chromatography (0 to 75% of EtOAc in heptane gradient) to give the title compound (1847 mg, 85% yield). $\delta_H$ (250 MHz, Chloroform-d) 10.50 (s, 1H), 7.34 (s, 1H), 6.07 (d, J=8.3 Hz, 1H), 5.90 (s, 1H), 4.94 (t, J=5.8 Hz, 1H), 4.82-4.56 (m, 1H), 3.70 (s, 3H), 3.30 (dd, J=16.4, 4.8 Hz, 1H), 2.96-2.66 (m, 4H), 2.65-2.45 (m, 1H), 2.29-2.13 (m, 4H), 1.96-1.77 (m, 1H), 1.69-1.60 (m, 1H), 1.20-1.05 (m, 2H), 1.05-0.79 (m, 3H), 0.58-0.44 (m, 2H), 0.23-0.08 (m, 2H). LCMS [M+H]$^+$ 523, RT 1.85 minutes (Method 12).

Intermediate 544

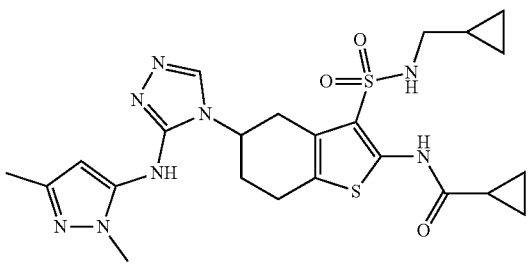 [SMILES: Cc1cc(Nc2nncn2C2CCc3sc(NC(=O)C4CC4)c(S(=O)(=O)NCC4CC4)c3C2)n(C)n1]

N-[3-(cyclopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide To s solution of intermediate 543 (996 mg, 1.91 mmol) in DCM (12 mL), triethylamine (796 µl, 5.72 mmol) was added. The solution was cooled to −20° C. and methanesulfonyl chloride (166.3 µl, 2.13 mmol) was added. The −20° C. bath was replaced with an ice bath and the reaction was stirred for 5 minutes. Another portion of methanesulfonyl chloride (193 µl, 2.48 mmol) was added at −20° C. then allowed to stir at 0° C. for 15 minutes. Saturated aqueous NH$_4$Cl (10 mL) was added to the solution and the DCM layer was separated and dried (MgSO$_4$). The solvent was removed at 30° C. to give the carbodiimide intermediate. 1 M Formic hydrazide in anhydrous MeOH (10 mL) was added to the carbodiimide. The reaction was stirred for 20 minutes. 10% wt. aqueous Na$_2$CO$_3$ aqueous solution (6.06 mL, 0.01 mol) was added to the solution followed by MeOH (5 mL). The reaction was heated at 50° C. for 4 hours and at room temperature for 18 hours. The majority of the MeOH was removed and water (10 mL) was added. the mixture was extracted with 15% MeOH/DCM (3×15 mL). The solvent of the combined organic layers was removed to give an orange oil. Purification by flash column chromatography (0 to 10% of MeOH in DCM gradient) gave the title compound (370 mg, 36% yield). $\delta_H$ (500 MHz, DMSO-d6) 11.74 and 8.42 (2×s, 1H, rotamers), 10.47 (s, 1H), 8.38 and 8.15 (2×s, 1H, rotamers), 8.03-7.92 (m, 1H), 5.93 and 5.72 (2×s, 1H, rotamers), 4.57-4.40 (m, 1H), 3.57 and 3.48 (2×s, 3H, rotamers), 2.94-2.78 (m, 3H), 2.79-2.64 (m, 2H), 2.34-2.14 (m, 2H), 2.07 (2×s, 3H, rotamers), 1.98-1.89 (m, 1H), 1.00-0.84 (m, 4H), 0.82-0.65 (m, 1H), 0.43-0.29 (m, 2H), 0.16--0.00 (m, 2H). LCMS [M+H]$^+$ 531, RT 2.33 minutes (Method 10).

Intermediate 545

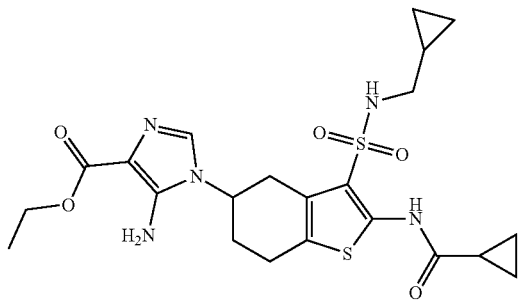 [SMILES: CCOC(=O)c1ncn(C2CCc3sc(NC(=O)C4CC4)c(S(=O)(=O)NCC4CC4)c3C2)c1N]

ethyl 5-amino-1-[2-(cyclopropanecarbonylamino)-3-(cyclopropylmethylsulfamoyl)-4,5,6,7-tetrahydrobenzothiophen-5-yl]imidazole-4-carboxylate To a solution of ethyl 2-amino-2-cyano-acetate (27 mg, 0.13 mmol) in acetonitrile (1 mL) was added triethylorthoformate (0.02 mL, 0.13 mmol). The mixture was sealed and heated at 90° C. for 1 hour. The solution was cooled and intermediate 528 (50 mg, 0.13 mmol) was added followed by acetonitrile (1 mL). The reaction was stirred for 19 hours. The precipitate was filtered and washed with ice cold acetonitrile (2 mL) to give the title compound (55 mg, 78% yield). $\delta_H$ (500 MHz, DMSO-d6) 10.46 (s, 1H), 7.97 (s, 1H), 7.28 (s, 1H), 6.08 (s, 2H), 4.48-4.34 (m, 1H), 4.25-4.10 (m, 2H), 3.27-3.16 (m, 2H), 2.90-2.75 (m, 3H), 2.75-2.68 (m, 2H), 2.26-2.13 (m, 1H), 2.13-2.02 (m, 1H), 1.97-1.83 (m, 1H), 1.24 (t, J=7.1 Hz, 3H), 0.98-0.82 (m, 4H), 0.80-0.71 (m, 1H), 0.44-0.31 (m, 2H), 0.13--0.01 (m, 2H). LCMS [M+H]$^+$ 508, RT 2.35 minutes (Method 10).

Intermediate 546

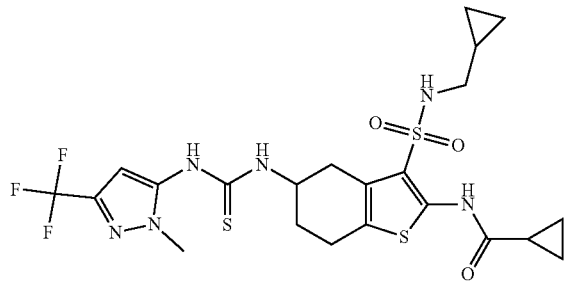 [SMILES: Cn1nc(C(F)(F)F)cc1NC(=S)NC1CCc2sc(NC(=O)C3CC3)c(S(=O)(=O)NCC3CC3)c2C1]

N-[3-(cyclopropylmethylsulfamoyl)-5-[[2-methyl-5-(trifluoromethyl)pyrazol-3-yl]carbamothioylamino]-4,5,6,7-tetrahydrobenzothiophen-2-yl]cyclopropanecarboxamide To a solution of intermediate 528 (1450 mg, 3.92 mmol) in DCM (20 mL), a solution of intermediate 262 (89%, 1.1 g, 4.71 mmol) in DCM (10 mL) was added. The reaction was stirred for 5 minutes. The solvent was removed to give a brown oil. Purification by flash column chromatography (0 to 60% of EtOAc in heptane gradient) gave the title compound (2.16 g, 86% yield). $\delta_H$ (500 MHz, Chloroform-d)

10.48 (s, 1H), 7.58 (s, 1H), 6.43 (s, 1H), 6.18 (s, 1H), 5.10-4.97 (m, 1H), 4.90-4.68 (m, 1H), 3.84 (s, 3H), 3.35-3.22 (m, 1H), 2.89-2.81 (m, 21H), 2.81-2.69 (m, 2H), 2.68-2.55 (m, 1H), 2.22-2.10 (m, 1H), 1.99-1.86 (m, 1H), 1.69-1.60 (m, 1H), 1.16-1.08 (m, 2H), 1.02-0.81 (m, 3H), 0.55-0.40 (m, 2H), 0.15-0.07 (m, 21H). LCMS [M+H]⁺ 577, RT 1.99 minutes (Method 12).

Intermediate 547

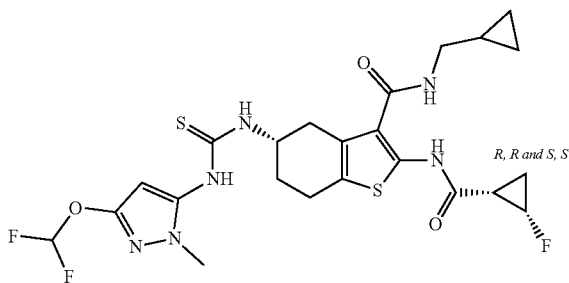 [SMILES: Cn1nc(OC(F)F)cc1NC(=S)N[C@H]1CCc2sc(NC(=O)[C@@H]3C[C@@H]3F)c(C(=O)NCC3CC3)c2C1]

(5S)—N-(cyclopropylmethyl)-5-[[5-(difluoromethoxy)-2-methyl-pyrazol-3-yl]carbamothioylamino]-2-[[(1SR,2SR)-2-fluorocyclopropanecarbonyl]amino]-4,5,6,7-tetrahydrobenzothiophene-3-carboxamide A solution of intermediate 310 (143 mg, 0.35 mmol) in DCM (4 mL) was cooled to 0° C. Intermediate 644 (73.4 mg, 0.36 mmol) was then added. The reaction mixture was stirred for 30 min at 0° C. then at room temperature for 5 h. DCM was added followed by water (30 mL). The aqueous layer was extracted with DCM (2×20 mL) and the organic fractions combined, dried (Na₂SO₄) and concentrated under vacuum. The residue was purified by column chromatography eluting with a gradient of 0-80% EtOAc in to afford the title compound (180 mg, 85% Yield). LCMS [M+H]⁺ 557, RT 1.82 minutes (Method 12).

Intermediate 548

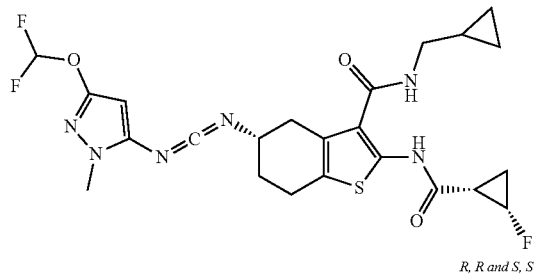 [SMILES: Cn1nc(OC(F)F)cc1N=C=N[C@H]1CCc2sc(NC(=O)[C@@H]3C[C@@H]3F)c(C(=O)NCC3CC3)c2C1]

(5S)—N-(cyclopropylmethyl)-5-[[5-(difluoromethoxy)-2-methyl-pyrazol-3-yl]iminomethyleneamino]-2-[[(1SR,2SR)-2-fluorocyclopropanecarbonyl]amino]-4,5,6,7-tetrahydrobenzothiophene-3-carboxamide To a solution of intermediate 547 (180 mg, 0.32 mmol) in DCM (10 mL) triethylamine (135 μL, 0.97 mmol) was added. The solution was cooled to 0° C. and methanesulfonyl chloride (28 μL, 0.36 mmol) was added. The reaction mixture was stirred for 30 min at 0° C. DCM (10 mL) was added followed by saturated aqueous ammonium chloride (15 mL). The aqueous layer was extracted with DCM (2×20 mL) and the organic fractions combined, dried (Na₂SO₄) and concentrated under vacuum to give the title compound (165 mg, 91% Yield). LCMS [M+H]⁺ 523.0, RT 1.93 minutes (Method 12).

Intermediate 549

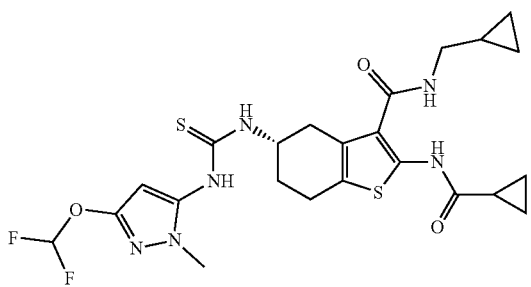 [SMILES: Cn1nc(OC(F)F)cc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[[5-(difluoromethoxy)-2-methyl-pyrazol-3-yl]carbamothioylamino]-4,5,6,7-tetrahydrobenzothiophene-3-carboxamide A solution of the intermediate 117 (40.0 mg, 0.12 mmol) in DCM (4 mL) was cooled to 0° C. Intermediate 644 (24.6 mg, 0.12 mmol) then was added. The reaction mixture was stirred for 30 min at 0° C. then RT for 5 h. DCM was added followed by water (30 mL). The aqueous layer was extracted with DCM (2×20 mL) and the organic fractions combined, dried over (Na₂SO₄) and concentrated under vacuum. The residue was purified by column chromatography eluting with 0-100% EtOAc in heptane to afford product the title compound (41 mg, 63% Yield). LCMS [M+H]⁺ 539, RT 1.89 minutes (Method 12).

Intermediate 550

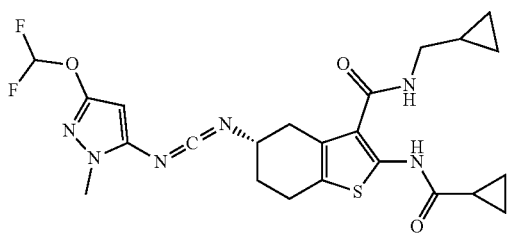 [SMILES: Cn1nc(OC(F)F)cc1N=C=N[C@H]1CCc2sc(NC(=O)C3CC3)c(C(=O)NCC3CC3)c2C1]

(5S)-2-(cyclopropanecarbonylamino)-N-(cyclopropylmethyl)-5-[[5-(difluoromethoxy)-2-methyl-pyrazol-3-yl]iminomethyleneamino]-4,5,6,7-tetrahydrobenzothiophene-3-carboxamide To a solution of intermediate 549 (41 mg, 0.08 mmol) in DCM (2 mL) triethylamine (32 μL, 0.23 mmol) was added. The solution was cooled to 0° C. then methanesulfonyl chloride (6 μL, 0.08 mmol) was added. The reaction mixture was stirred for 30 min at 0° C. DCM (10 mL) was then added followed by a saturated aqueous ammonium chloride solution (10 mL). The aqueous layer was extracted with DCM (2×15 ml) and the organic fractions combined, dried over (Na₂SO₄) and concentrated under vacuum to give the title compound (38 mg, 98% Yield). LCMS [M+H]⁺ 505, RT 1.99 minutes (Method 12).

Intermediate 551

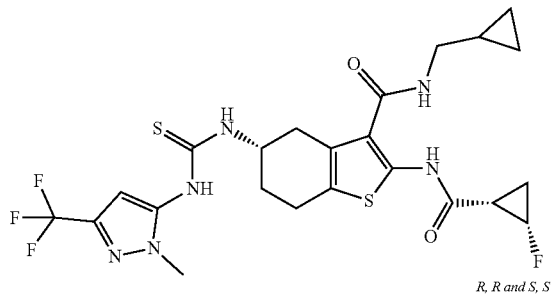 [SMILES: Cn1nc(C(F)(F)F)cc1NC(=S)N[C@H]1CCc2sc(NC(=O)[C@@H]3C[C@@H]3F)c(C(=O)NCC3CC3)c2C1]

R, R and S, S (5S)—N-(cyclopropylmethyl)-2-[[(1RS,2RS)-2-fluorocyclopropanecarbonyl]amino]-5-[[2-methyl-5-(trifluoromethyl)pyrazol-3-yl]carbamothioylamino]-4,5,6,7-tetrahydrobenzothiophene-3-carboxamide A solution of intermediate 310 (143 mg, 0.35 mmol) in DCM (4 mL) was cooled to 0° C. Intermediate 262 (73.3 mg, 0.35 mmol) was then added. Reaction mixture was stirred for 30 min at 0° C. then room temperature for 5 h. Reaction mixture was diluted with DCM then water (30 mL) was added and organic layer separated. The aqueous layer was extracted with DCM (2×20 mL) and the organic fractions combined, dried (Na₂SO₄) and concentrated under vacuum. The residue was purified by column chromatography eluting with 0-100% EtOAc in heptane to afford the title compound (163 mg, 81% Yield). LCMS [M+H]⁺ 559, RT 1.90 minutes (Method 12).

Intermediate 552

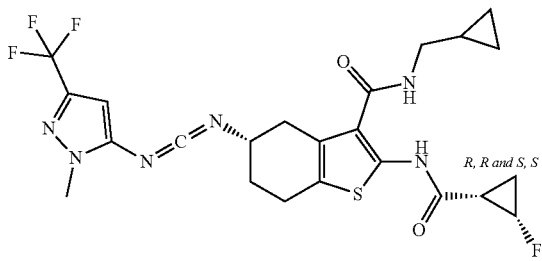 [SMILES: Cn1nc(C(F)(F)F)cc1N=C=N[C@H]1CCc2sc(NC(=O)[C@@H]3C[C@@H]3F)c(C(=O)NCC3CC3)c2C1]

R, R and S, S (5S)—N-(cyclopropylmethyl)-2-[[(1SR,2SR)-2-fluorocyclopropanecarbonyl]amino]-5-[[2-methyl-5-(trifluoromethyl)pyrazol-3-yl]iminomethyleneamino]-4,5,6,7-tetrahydrobenzothiophene-3-carboxamide To a solution of intermediate 551 (163 mg, 0.29 mmol) in DCM (10 mL), triethylamine (122 μL, 0.88 mmol) was added. The solution was cooled to 0° C. and methanesulfonyl chloride (25 μL, 0.32 mmol) added. The reaction mixture was stirred for 30 min at 0° C. then diluted with DCM (10 mL) and saturated ammonium chloride solution (15 mL). The aqueous layer was extracted with DCM (2×20 mL) and the organic fractions combined, dried (Na₂SO₄) and concentrated under vacuum to give the title compound (150 mg, 92% Yield). LCMS [M+H]⁺ 525, RT 1.99 minutes (Method 12).

Intermediate 553

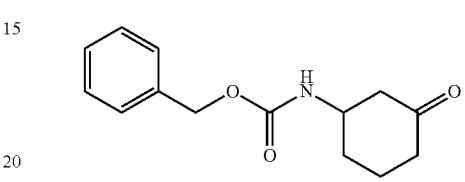

Benzyl N-(3-oxocyclohexyl)carbamate

To a solution of benzyl carbamate (80 g, 530 mmol) and 2-cyclohexen-1-one (50 g, 510 mmol) in DCM (50 mL) was added bismuth(III) nitrate pentahydrate (25 g, 51 mmol) portion-wise over 15 min. The mixture was stirred for 16 h at ambient temperature. The reaction mixture was diluted with DCM (400 ml), filtered through celite and then washed with saturated aqueous sodium bicarbonate solution (twice), water, and then brine, and dried over MgSO₄. The solvent was removed in vacuo to give a yellow/orange gum that solidified. This was triturated with ether and stirred for 1 h. The slurry was filtered, washing with ether (×3) to give the title compound (62 g, 48% Yield). $\delta_H$ (300 MHz, DMSO-d6) 7.49 (d, J=7.6 Hz, 1H), 7.42-7.27 (m, 5H), 5.01 (s, 2H), 3.76-3.62 (m, 1H), 2.48-2.11 (m, 4H), 1.97-1.85 (m, 2H), 1.66-1.46 (m, 2H). LCMS [M+H]⁺ 248, RT 0.84 minutes (Method 7).

Intermediate 554

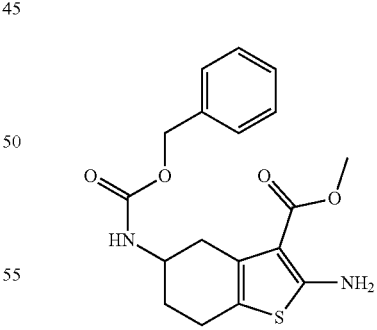

Methyl 2-amino-5-(benzyloxycarbonylamino)-4,5,6,7-tetrahydrobenzothiophene-3-carboxylate To a solution of methyl cyanoacetate (25.0 g, 250 mmol), intermediate 553 (61.8 g, 250 mmol) and morpholine (32.6 g, 375 mmol) in 1,4-dioxane (200 mL) was added sulfur (8.81 g, 275 mmol). The mixture was stirred for 30 min at ambient temperature then at 70° C. for 16 h. The reaction mixture was allowed to cool and the solvent removed in vacuo. The residue was stirred in diethyl ether (750 mL) for 4 h and the crude product filtered off. This was recrystallised from methanol/water to give the title compound (40.7 g, 45% Yield). LCMS [M+H]+ 361, RT 1.10 minutes (Method 7).

Intermediate 555

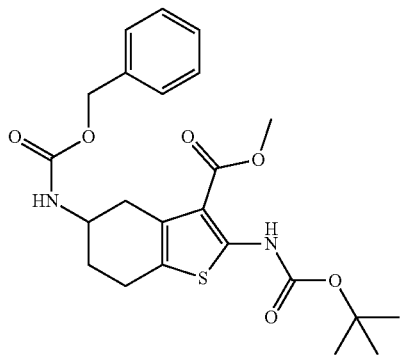 [SMILES: COC(=O)c1c(NC(=O)OC(C)(C)C)sc2c1CC(NC(=O)OCc1ccccc1)CC2]

Methyl 5-(benzyloxycarbonylamino)-2-(tert-butoxycarbonylamino)-4,5,6,7-tetrahydrobenzothiophene-3-carboxylate To a solution of intermediate 554 (25.0 g, 69.4 mmol), N,N-diisopropylethylamine (13.5 g, 104 mmol) and 4-dimethylaminopyridine (0.437 g, 3.47 mmol) in DCM (500 mL) was added di-tert-butyl dicarbonate (15.9 g, 72.8 mmol). The mixture was stirred 2 h at reflux. The reaction mixture was allowed to cool, and then washed with water and then brine. The organic phase was passed through a phase separator cartridge and the solvent removed in vacuo. The crude product was purified by flash chromatography eluting with 8-40% EtOAc in iso-hexane to afford the title compound (13.8 g, 43%) as a colourless gum. $\delta_H$ (300 MHz, DMSO-d6) 10.16 (s, 1H), 7.44-7.27 (m, 6H), 5.03 (s, 2H), 3.78 (s, 3H), 3.70 (s, 1H), 3.02 (dd, J=16.8, 5.4 Hz, 1H), 2.77-2.57 (m, 2H), 2.55-2.43 (m, 1H), 1.97-1.87 (m, 1H), 1.72-1.57 (m, 1H), 1.48 (s, 9H). LCMS [M−H]− 459, RT 1.60 minutes (Method 7).

Intermediate 556

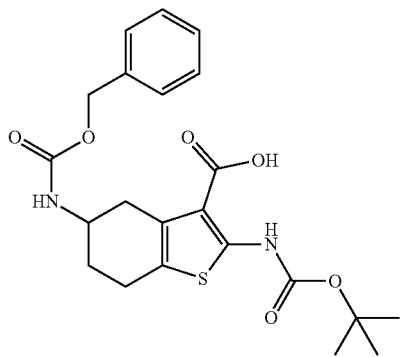 [SMILES: CC(C)(C)OC(=O)Nc1sc2c(c1C(=O)O)CC(NC(=O)OCc1ccccc1)CC2]

5-(Benzyloxycarbonylamino)-2-(tert-butoxycarbonylamino)-4,5,6,7-tetrahydrobenzothiophene-3-carboxylic acid To a solution of intermediate 555 (13.8 g, 29.9 mmol) in 1,4-dioxane (200 mL) was added a solution of lithium hydroxide monohydrate (3.84 g, 89.7 mmol) in water (100 mL). The mixture was heated at 50° C. for 12 h. The reaction mixture was allowed to cool and the solvent removed in vacuo. The residue was portioned between EtOAc and water. The aqueous phase was further extracted with EtOAc (×2). Combined organic extracts were washed with water and then brine, dried (MgSO4) and the solvent removed in vacuo to give the title compound (12.2 g, 91%). LCMS [M+H]+ 447, RT 0.89 minutes (Method 7).

Intermediate 557 (SN161465/003)

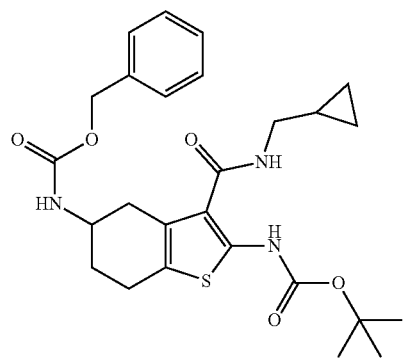 [SMILES: CC(C)(C)OC(=O)Nc1sc2c(c1C(=O)NCC1CC1)CC(NC(=O)OCc1ccccc1)CC2]

tert-Butyl N-[5-(benzyloxycarbonylamino)-3-(cyclopropylmethylcarbamoyl)-4,5,6,7-tetrahydrobenzothiophen-2-yl]carbamate To a solution of intermediate 556 (12.2 g, 27.3 mmol), N,N-diisopropylethylamine (7.42 g, 57.4 mmol) and cyclopropylmethylamine (3.17 g, 43.7 mmol) in DMF (10 mL) at 0° C. was added HATU (20.8 g, 54.7 mmol). The mixture was stirred for 3 h and then the solvent was removed in vacuo. The residue was portioned between EtOAc and water. The aqueous phase was further extracted with EtOAc (×2). Combined organic extracts were washed with water and then brine, dried (MgSO4) and the solvent removed in vacuo to give a brown gum. The crude product was purified by flash chromatography eluting with 5-35% EtOAc in iso-hexane to afford the title compound (10.2 g, 75%) as a colourless solid. LCMS [M+H]+ 500, RT 2.94 minutes (Method 3).

Intermediate 558

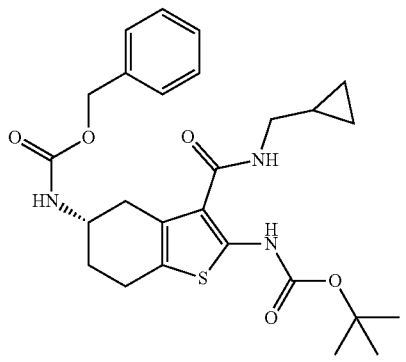

tert-Butyl N-[(5S)-5-(benzyloxycarbonylamino)-3-(cyclopropylmethylcarbamoyl)-4,5,6,7-tetrahydrobenzothiophen-2-yl]carbamate The title compound was obtained by chiral separation of intermediate 557 (16.9 g, 33.9 mmol) to give the title compound. Peak 1 (9.24 g, 55% Yield). $\delta_H$ (400 MHz, DMSO-d6) 10.23 (s, 1H), 7.53-7.41 (m, 2H), 7.40-7.28 (m, 5H), 5.04 (s, 2H), 3.76-3.66 (m, 1H), 3.17-3.05 (m, 2H), 2.94 (dd, J=16.0, 5.2 Hz, 1H), 2.79-2.63 (m, 2H), 2.62-2.53 (m, 1H), 1.98-1.89 (m, 1H), 1.78-1.65 (m, 1H), 1.46 (s, 9H), 1.06-0.95 (m, 1H), 0.45-0.36 (m, 2H), 0.26-0.17 (m, 2H). LCMS [M+H]$^+$ 500, RT 3.00 minutes (Method 3). Chiral LC* RT 3.29 minutes,

* Chiral analysis was performed using a Chiralpak IC, eluted using an isocratic 50% IPA in heptane (+0.1% DEA) method, flow rate of 1.5 mL/min, 100 bar and an 8 minute run time on an Agilent Infinity II 1290.

Intermediate 559

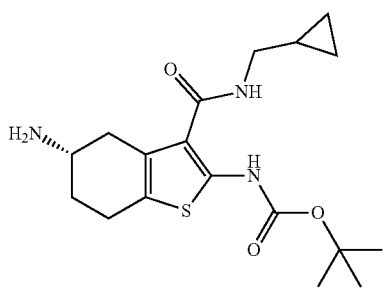 [SMILES: CC(C)(C)OC(=O)Nc1sc2c(c1C(=O)NCC1CC1)C[C@@H](N)CC2]

tert-Butyl N-[(5S)-5-amino-3-(cyclopropylmethylcarbamoyl)-4,5,6,7-tetrahydrobenzothiophen-2-yl]carbamate To a solution of intermediate 558 (4.0 g, 8.00 mmol) in EtOAc (75 mL) was added 10% palladium on carbon (0.80 g). Stirred under an atmosphere of hydrogen for 5 days. The reaction mixture was filtered through celite, washing with methanol and the solvent removed in vacuo to give the title compound (2.44 g, 83% Yield) as a green/yellow sticky solid. $\delta_H$ (300 MHz, DMSO-d6) 7.77 (s, 1H), 3.72-3.37 (m, 3H), 3.18-2.98 (m, 3H), 2.89 (dd, J=15.9, 5.0 Hz, 1H), 2.75-2.54 (m, 2H), 2.48-2.38 (m, 1H), 1.96-1.85 (m, 1H), 1.59-1.50 (m, 1H), 1.46 (s, 9H), 1.08-0.96 (m, 1H), 0.46-0.38 (m, 2H), 0.27-0.19 (m, 2H). LCMS [M+H]$^+$ 366, RT 1.88 minutes (Method 3).

Intermediate 560

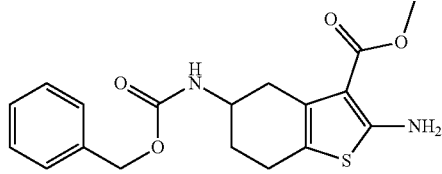 [SMILES: COC(=O)c1c(N)sc2c1CC(NC(=O)OCc1ccccc1)CC2]

methyl(5S)-2-amino-5-(benzyloxycarbonylamino)-4,5,6,7-tetrahydrobenzothiophene-3-carboxylate, hydrochloride The title compound was prepared from benzyl N-(3-oxocyclohexyl)carbamate, methyl cyanoacetate and sulphur, using a method analogous to that used to prepare intermediate 567. The title compound was isolated after salt formation in iso-propanol as an off-white solid (89.5 g, 25% Yield). LCMS [M+H]$^+$ 361, RT 1.90 minutes (Method 12).

Intermediate 561

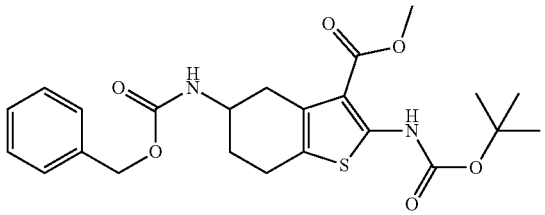 [SMILES: COC(=O)c1c(NC(=O)OC(C)(C)C)sc2c1CC(NC(=O)OCc1ccccc1)CC2]

methyl(5S)-5-(benzyloxycarbonylamino)-2-(tert-butoxycarbonylamino)-4,5,6,7-tetrahydrobenzothiophene-3-carboxylate A solution of intermediate 560 (31.2 g, 76.9 mmol), in DCM (450 mL) was treated with triethylamine (53 mL, 308 mmol) and 4-dimethylaminopyridine (1.9 g 15 mmol). Tert-butoxycarbonyl-tert-butyl-carbonate (36.9 g, 169.2 mmol) was added portionwise and the resulting mixture was stirred at reflux for 4 days during which further charges of tert-butoxycarbonyl-tert-butyl-carbonate (total of 25 g 114.5 mmol) were added. The reaction mixture was washed with water and brine and concentrated in vacuo. The crude residue was purified by chromatography on a pad of silica gel eluting with a gradient of EtOAc in hexane (5 to 20%) and by trituration with hexane to yield the title compound as a cream-coloured solid (24.6 g, 70% Yield). LCMS [M+Na]$^+$ 483, RT 2.23 minutes (Method 12).

Intermediate 562

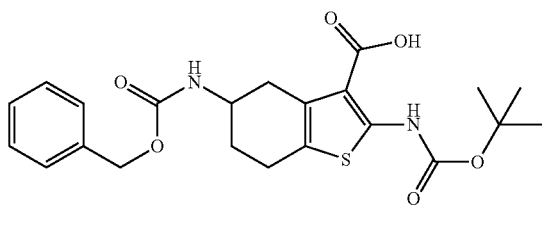 [SMILES: CC(C)(C)OC(=O)Nc1sc2c(c1C(=O)O)CC(NC(=O)OCc1ccccc1)CC2]

5-(benzyloxycarbonylamino)-2-(tert-butoxycarbonylamino)-4,5,6,7-tetrahydrobenzothiophene-3-carboxylic acid A solution of intermediate 561 (24.5 g, 53 mmol) in 1,4-dioxane (250 mL) was treated with lithium hydroxide (3.97 g, 159.3 mmol in 125 mL water). The resulting mixture was treated with methanol until a single phase solution was achieved and was heated to 40° C. for 1 day, after which time the reaction mixture was concentrated in vacuo and suspended in 1,4-dioxane (250 mL) and water (100 mL) and treated with citric acid (10% aqueous solution, approximately 250 mL added) until the mixture reached pH4. The mixture was filtered and solid washed with water and dried in vacuo to give the title compound as a cream-coloured solid (22 g, 76% Yield). LCMS [M−H]⁻ 445, RT 2.08 minutes (Method 12).

Intermediate 563

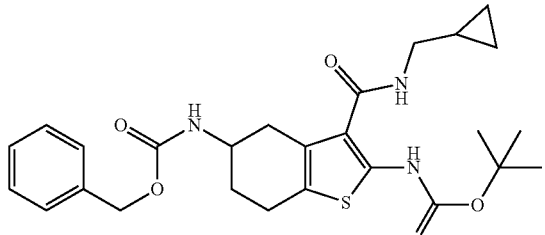

tert-butylN-[5-(benzyloxycarbonylamino)-3-(cyclopropylmethylcarbamoyl)-4,5,6,7-tetrahydrobenzothiophen-2-yl]carbamate A solution of intermediate 562 (34.5 g, 77.3 mmol) in DMF (345 mL) was treated with DIPEA (15 g, 116 mmol) and cyclopropylmethylamine (6.2 g, 85 mmol), followed by HATU (38.2 g, 100.4 mmol) and the resulting stirred for 15 minutes and then poured into ice-water. After 18 h the resulting solid was removed and taken up in tert-butyl-methyl ether, the resulting solution was washed with water and brine and filtered through a phase-separation cartridge, washing with EtOAc. The resulting solution was concentrated in vacuo and the residue recrystallised from a mixture of heptane and EtOAc to give the title compound as a pale yellow solid (22.3 g, 58% Yield). LCMS [M+H]⁺ 499, RT 4.45 minutes (Method 10).

Intermediate 564

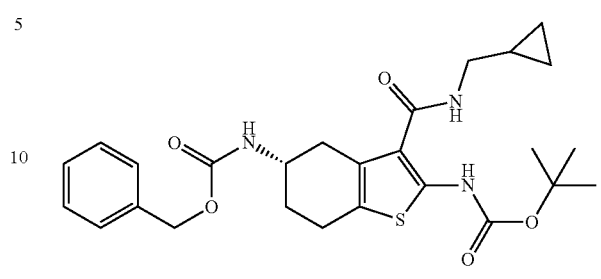

tert-butylN-[(5S)-5-(benzyloxycarbonylamino)-3-(cyclopropylmethylcarbamoyl)-4,5,6,7-tetrahydrobenzothiophen-2-yl]carbamate The title compound was prepared by chiral SFC separation of racemic intermediate 563 (30 g), using a 50×229-10 μm GS-NO2 column, eluted with 20% MeOH in $CO_2$ at a flow rate of 360 ml/min to give the title compound as a brown solid (13 g). LCMS [M+H]⁺ 500, RT 1.56 minutes (Method system 3, pH10 short). $[\alpha]_D^{20}$ 50.8 (c 2.0, $CH_3OH$).

Example 565

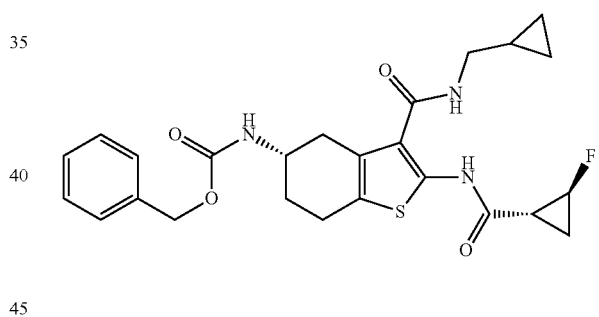

Benzyl N-[(5S)-3-(cyclopropylmethylcarbamoyl)-2-[[(1R,2S)-2-fluorocyclopropanecarbonyl]amino]-4,5,6,7-tetrahydrobenzothiophen-5-yl]carbamate (1R,2S)-2-fluorocyclopropanecarboxylic acid (457 mg, 4.39 mmol) followed by 2,4,6-tripropyl-1,3,5,2,4,6-trioxatriphosphorinane-2,4,6-trioxide (5.17 mL, 8.77 mmol, 50 mass % in EtOAc) were added to a solution of Intermediate 293 (2.36 g, 4.39 mmol, 81 mass %) and pyridine (1.79 mL, 21.9 mmol) in DCM (21.3 mL) cooled to 0° C. and under nitrogen. The reaction was stirred for 17 hours whilst allowing the ice bath to melt. Water was added and the reaction stirred for a further 10 mins before the layers were separated. The aq. layer was extracted with DCM (2×20 mL). The combing organic layers were washed with sat. aq. $NH_4Cl$, passed through a phase separator, concentrated in vacuo and purified by flash column chromatography on silica (gradient elution with 0% to 100% EtOAc in isohexanes) to give the title compound (2.15 g, quantitative yield). LCMS [M+H]⁺ 486, RT 1.34 minutes (Method 3).

Intermediate 566

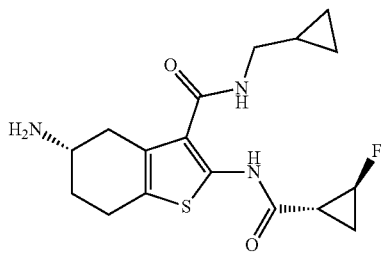 [SMILES: N[C@H]1CCc2sc(NC(=O)[C@H]3C[C@@H]3F)c(C(=O)NCC3CC3)c2C1]

(5S)-5-amino-N-(cyclopropylmethyl)-2-[[(1R,2S)-2-fluorocyclopropanecarbonyl]amino]-4,5,6,7-tetrahydrobenzothiophene-3-carboxamide A solution of intermediate 565 (2.1 g, 4.3 mmol) in EtOAc (50 mL) and EtOH (20 mL) was degassed (three cycles of vacuum and $N_2$), treated with Palladium on carbon (Alfa Aesar 10% Pc/C type 487, 600 mg) and stirred under an atmosphere of $H_2$ (1 atm) for four days. The mixture was filtered and concentrated in vacuo to afford the title compound as a greenish solid (1.2 g, 76% Yield). LCMS [M+H]$^+$ 352, RT 0.77 minutes (Method 7).

Intermediate 567

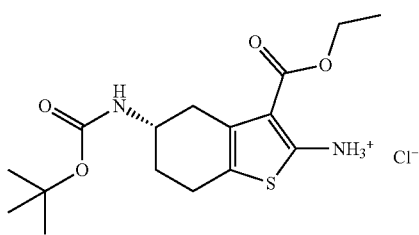 [SMILES: CCOC(=O)c1c([NH3+])sc2c1C[C@@H](NC(=O)OC(C)(C)C)CC2 ; [Cl-]]

[(5S)-5-(tert-butoxycarbonylamino)-3-ethoxycarbonyl-4,5,6,7-tetrahydrobenzothiophen-2-yl]ammonium chloride The title compound was prepared by a method analogous to that used to prepare intermediate 102a. A solution of tert-butyl N-[(1S)-3-oxocyclohexyl]carbamate (100 g, 70% w/w, 328 mmol) in ethanol (600 mL) was treated with elemental sulphur (18 g, 561 mmol) followed by ethyl cyanoacetate (65 mL, 609 mmol). The resulting suspension was treated with triethylamine (30 mL, 215 mmol, added over minutes whilst maintaining internal temperature below 20° C.) and stirred at 20° C. for 18 h then filtered and the filtrate concentrated to dryness. The residue was taken up in EtOAc (750 mL) and treated with HCl (110 mL, 5.5 M in iso-propanol, added slowly whilst maintaining the internal temperature below 30° C.) and the resulting suspension stirred at 20° C. for 18 h. The title compound was obtained as a solid (89 g, 72% Yield) after filtration and washing with EtOAc (250 mL). LCMS [M+H]$^+$ 341, RT 1.13 minutes (Method 7).

Note: tert-butyl N-[(1S)-3-oxocyclohexyl]carbamate (also called: (S)-3-Boc-aminocyclohexanone) may be purchased commercially from a number of suppliers including J&W Pharmlab Ltd of Levittown, PA, USA (CAS [1803033-61-5])

Intermediate 568

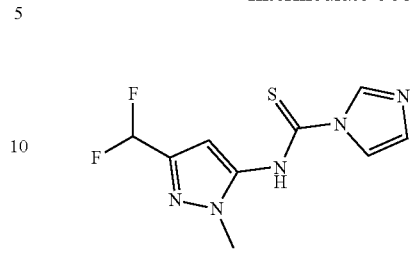

N-[5-(difluoromethyl)-2-methyl-pyrazol-3-yl]imidazole-1-carbothioamide

A suspension of thiocarbonyl diimidazole (107.3 g, 572 mmol) in DCM (275 mL) was cooled to −10° C. and treated with a solution of 5-(Difluoromethyl)-2-methyl-pyrazol-3-amine (42.0 g, 285 mmol) in DCM (210 mL) whilst maintaining internal temperature between −8° C. and −10° C. The resulting mixture was stirred at −10° C. for 18 h and filtered and the solid washed with DCM (300 mL) to provide the title compound as a pale solid (71.4 g, 49% Yield). LCMS ion observed results from solvolysis by MeOH to give $C_7H_9F_2N_3OS$ [M+H]$^+$ 222, RT 0.34 minutes (Method 7).

Intermediate 569

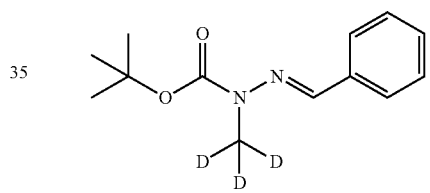

tert-Butyl N-[(E)-benzylideneamino]-N-(trideuteriomethyl)carbamate

A solution of tert-Butyl N-[(E)-benzylideneamino]carbamate (68 g, 308 mmol) in THF (680 mL) was treated with t-BuOK (41.6 g, 370.5 mmol) followed by $CD_3I$ (53.7 g, 370.5 mmol, added dropwise). The resulting mixture was stirred at 25° C. for 12 h after which time the mixture was diluted with water (500 mL) and extracted with EtOAc (three portions of 500 mL). The crude organic extracts were dried over $Na_2SO_4$ and concentrated in vacuo to afford the title compound as a yellow solid (68 g, 93% Yield). $\delta_H$ (400 MHz, CDCl3) 7.68-7.74 (m, 2H), 7.65 (s, 1H), 7.29-7.44 (m, 3H), 1.59 (s, 9H).

Intermediate 570

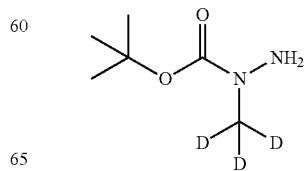

tert-Butyl N-amino-N-(trideuteriomethyl)carbamate

A suspension of intermediate 569 (68 g, 286.5 mmol) and Palladium on carbon (6.8 g) in MeOH (680 mL) was degassed in vacuo and purged with $H_2$ three times and then stirred un an atmosphere of $H_2$ (50 psi) at 50° C. for 12 h. The reaction mixture was filtered and concentrated in vacuo to yield the title product as a yellow oil (40 g, 93% Yield). $\delta_H$ (400 MHz, DMSO-d6) 4.48 (s, 2H), 1.40 (s, 9H).

Intermediate 571

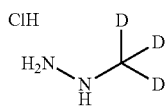

Trideuteriomethylhydrazine hydrochloride

A solution of intermediate 570 (40 g, 268.1 mmol) in EtOAc (40 mL) was treated with HCl (4 N in EtOAc, 200 mL, 800 mmol) and stirred at 25 C for 12 h, after which time the reaction mixture was concentrated in vacuo to give the title compound as a yellow solid (20 g, 47% Yield). $\delta_H$ (400 MHz, DMSO-d6) 7.84 (br s, 3H).

Intermediate 572

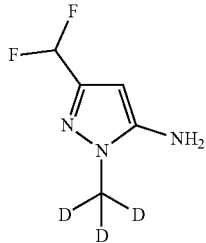 [SMILES: [2H]C([2H])([2H])n1nc(C(F)F)cc1N]

5-(Difluoromethyl)-2-(trideuteriomethyl)pyrazol-3-amine

A solution of 4,4-difluoro-3-oxo-butanenitrile (22.5 g, 189.3 mmol) in EtOH (105 mL) was treated with intermediate 571 (20 g, 126.2 mmol) followed by $Et_3N$ (51.1 g, 504.8 mmol) and heated to 80 C with stirring for 2 h. The resulting mixture was concentrated in vacuo and the residue diluted with water (100 mL) and extracted with EtOAc (three portions of 100 mL). The combined organic extracts were dried over $Na_2SO_4$, filtered and concentrated in vacuo. The residue was purified by flash column chromatography on silica eluting with EtOAc to yield the title compound as a yellow oil (5.50 g, 28% Yield). $\delta_H$ (400 MHz, DMSO-d6) 6.48-6.90 (t, J=54.8 Hz, 1H), 5.43 (br d, J=16 Hz, 3H).

Intermediate 573

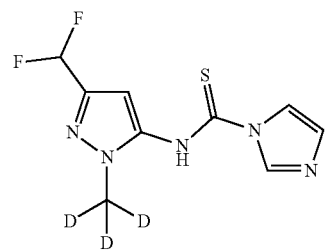 [SMILES: [2H]C([2H])([2H])n1nc(C(F)F)cc1NC(=S)n1ccnc1]

N-[5-(difluoromethyl)-2-(trideuteriomethyl)pyrazol-3-yl]imidazole-1-carbothioamide The title compound was prepared by a method analogous to that used to prepare intermediate 572 using intermediate 571. The title compound was obtained as a solid (3.61 g, 74% Yield). $\delta_H$ (400 MHz, $D_2O$) 8.51 (s, 1H), 7.83 (s, 1H), 6.96 (s, 1H), 6.72 (t, 1H), 6.62 (s, 1H).

Intermediate 574

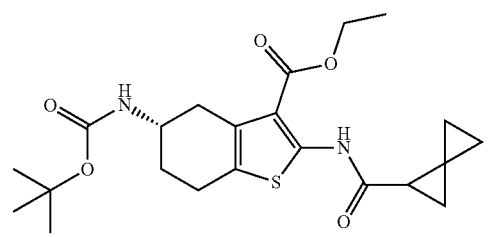 [SMILES: CCOC(=O)c1c(NC(=O)C2CC23CC3)sc2c1C[C@@H](NC(=O)OC(C)(C)C)CC2]

Ethyl (5S)-5-(tert-butoxycarbonylamino)-2-(spiro[2.2]pentane-2-carbonylamino)-4,5,6,7-tetrahydrobenzothiophene-3-carboxylate Synthesised using general procedure general method 6, using intermediate 567 (7.0 g, 19.0 mmol), spiro[2.2]pentane-1-carboxylic acid (2.20 g, 20.0 mmol) and comparable stoichiometries of reagents. The product was purified by flash chromatography eluting with 30-80% EtOAc in isohexane to afford the title compound (5.59 g, 69%). LCMS [M+H]+ 435, RT 2.80 minutes (Method 3).

Intermediate 575

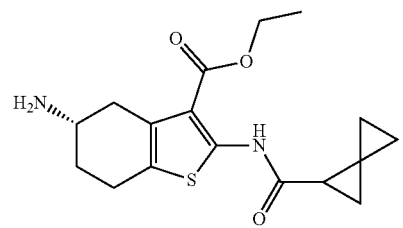 [SMILES: CCOC(=O)c1c(NC(=O)C2CC23CC3)sc2c1C[C@@H](N)CC2]

Ethyl (5S)-5-amino-2-(spiro[2.2]pentane-2-carbonylamino)-4,5,6,7-tetrahydrobenzothiophene-3-carboxylate Synthesised in the same manner as Intermediate 117, using intermediate 574 (5.59 g, 12.9 mmol) and comparable stoichiometries of reagents to afford the title compound (4.30 g, 12.9 mmol). $\delta_H$(300 MHz, DMSO-d6) 11.04 (s, 1H), 4.30 (q, J=7.1 Hz, 2H), 3.06-2.91 (m, 2H), 2.75-2.55 (m, 2H), 2.38-2.22 (m, 2H), 1.92-1.81 (m, 1H), 1.55-1.39 (m, 3H), 1.32 (t, J=7.1 Hz, 3H), 1.03-0.79 (m, 4H). LCMS [M+H]$^+$ 335, RT 1.10 minutes (Method 3).

Intermediate 576

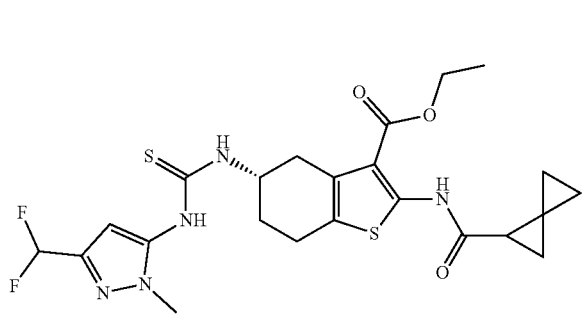 [SMILES: CCOC(=O)c1c(NC(=O)C2CC23CC3)sc2c1C[C@@H](NC(=S)Nc1cc(C(F)F)nn1C)CC2]

Ethyl (5S)-5-[[5-(difluoromethyl)-2-methyl-pyrazol-3-yl]carbamothioylamino]-2-(spiro[2.2]pentane-2-carbonylamino)-4,5,6,7-tetrahydrobenzothiophene-3-carboxylate The title compound was obtained following the procedure used to make intermediate 168 with amine intermediate 575 (4.30 g, 12.9 mmol), intermediate 568 (3.64 g, 14.1 mmol) and DCM (150 mL). Purification by column chromatography with a gradient of 30-80% EtOAc in iso-hexane gave the title compound (6.65 g, 99% Yield). $\delta_H$ (300 MHz, DMSO-d6) 11.05 (s, 1H), 9.18 (s, 1H), 8.24 (s, 1H), 6.89 (t, J=54.7 Hz, 1H), 6.46 (s, 1H), 4.52 (s, 1H), 4.31 (q, J=7.1 Hz, 2H), 3.67 (s, 3H), 3.24-3.12 (m, 1H), 2.78-2.63 (m, 3H), 2.35-2.26 (m, 1H), 2.08-1.79 (m, 2H), 1.55-1.48 (m, 1H), 1.47-1.41 (m, 1H), 1.32 (t, J=7.1 Hz, 3H), 1.04-0.79 (m, 4H). LCMS [M+H]$^+$ 524, RT 2.15 minutes (Method 25).

Intermediate 577

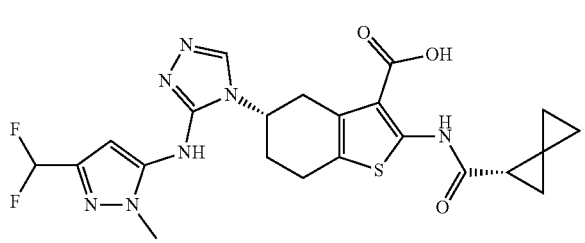 [SMILES: Cn1nc(C(F)F)cc1Nc1nncn1[C@H]1CCc2sc(NC(=O)[C@H]3CC34CC4)c(C(=O)O)c2C1]

(5S)-5-[3-[[5-(Difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxylic acid To a solution of Example 417 (1.47 g, 2.77 mmol) in dioxane (15 mL) was added a solution of lithium hydroxide monohydrate (377 mg, 8.85 mmol) in water (15 mL). The reaction was stirred for 3 days at ambient temperature. The solvent was removed in vacuo to give a pale brown gum, this was dissolved in water. Washed with DCM then the aqueous phase was acidified with 2 M HCl and extracted with EtOAc (×3). Combined organic extracts were washed with brine, passed through a phase separator cartridge and evaporated to leave the title compound (1.3 g, 93%) as an off-white solid. Used directly in the next step without purification. LCMS [M+H]$^+$ 504, RT 1.05 minutes (Method 25).

Intermediate 578

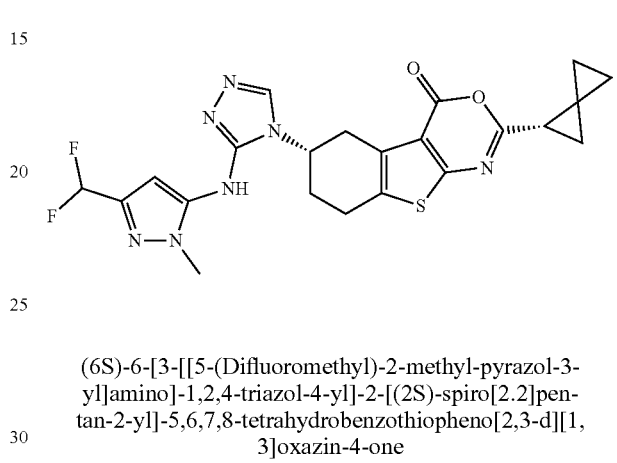

(6S)-6-[3-[[5-(Difluoromethyl)-2-methyl-pyrazol-3-yl]amino]-1,2,4-triazol-4-yl]-2-[(2S)-spiro[2.2]pentan-2-yl]-5,6,7,8-tetrahydrobenzothiopheno[2,3-d][1,3]oxazin-4-one To a solution of Intermediate 577 (1.30 g, 2.58 mmol) in DCM (100 mL) was added 1-(3-dimethylaminopropyl)-3-ethylcarbodiimide hydrochloride (536 mg, 2.71 mmol). The reaction was stirred for 2.5 h at ambient temperature. The reaction mixture was diluted with DCM and washed with water and then brine, passed through a phase separator cartridge and evaporated to leave a gum. The crude product was purified by flash chromatography eluting with a gradient of 40-100% EtOAc in iso-hexane to afford the title compound (600 mg, 48%) as an off-white solid. LCMS [M+H]$^+$ 486, RT 1.18 minutes (Method 7).

Intermediate 579

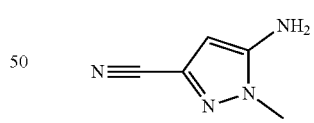

5-Amino-1-methyl-pyrazole-3-carbonitrile

1-Methyl-5-nitro-1H-pyrazole-3-carbonitrile (1000 mg, 6.25 mmol) was dissolved in tetrahydrofuran (15 mL) and methanol (15 mL). Ammonium chloride (4.68 g, 87.4 mmol) added. Cooled to 0° C. Zinc (5840 mg, 87.4 mmol) as filings added portion-wise. Ice bath removed after 60 mins. Stirred at room temperature for a further 1 h. Filtered through celite washing with MeOH (10 mL×2). Evaporated to leave a pale yellow solid. Used directly in the next step without purification. $\delta_H$ (300 MHz, DMSO-d6) 5.81 (s, 1H), 5.71 (s, 2H), 3.60 (s, 3H).

Intermediate 580

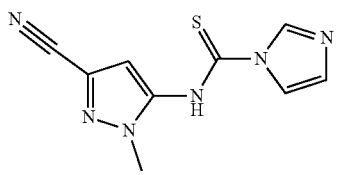 [SMILES: Cn1nc(C#N)cc1NC(=S)n1ccnc1]

N-(5-Cyano-2-methyl-pyrazol-3-yl)imidazole-1-carbothioamide 1,1'-Thiocarbonyldiimidazole (653 mg, 3.30 mmol) was added to a stirred solution of intermediate 579 (403 mg, 3.30 mmol) in DCM (20 mL) at −10° C. and the reaction stirred for 90 min at −10° C. The mixture was filtered and the solvent was removed in vacuo to give the crude product as a beige foam. Used directly in the next step without purification.

Intermediate 581

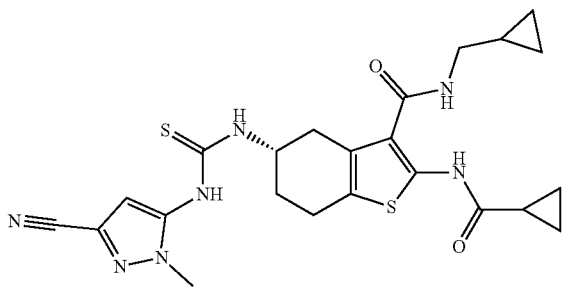 [SMILES: Cn1nc(C#N)cc1NC(=S)N[C@H]1CCc2sc(NC(=O)C3CC3)c(C(=O)NCC3CC3)c2C1]

(5S)-5-[(5-Cyano-2-methyl-pyrazol-3-yl)carbamothioylamino]-2-(cyclopropanecarbonylamino)-N-(cyclopropylmethyl)-4,5,6,7-tetrahydrobenzothiophene-3-carboxamide Intermediate 117 (1100 mg, 3.30 mmol) was added to a stirred solution of intermediate 580 (766 mg, 3.30 mmol) in DCM (10 mL) and the reaction stirred for 90 min at ambient temperature. The solvent was removed in vacuo to give the crude product as a beige foam. Used directly in the next step without purification.

Intermediate 582

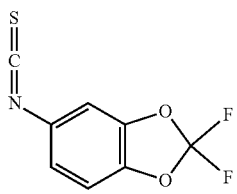 [SMILES: FC1(F)Oc2ccc(N=C=S)cc2O1]

2,2-Difluoro-5-isothiocyanato-1,3-benzodioxole 2,2-Difluoro-5-aminobenzodioxole (1.0 g, 5.70 mmol) was dissolved in DCM (20 mL) and 4 N HCl in dioxane (2.8 mL, 11.0 mmol) was added. 1,1'-Thiocarbonyldiimidazole (1100 mg, 5.70 mmol) was added. The reaction was stirred at ambient temperature for 2 h, filtered and concentrated in vacuo to afford the crude title compound, which was carried through to the next stage without purification.

Intermediate 583

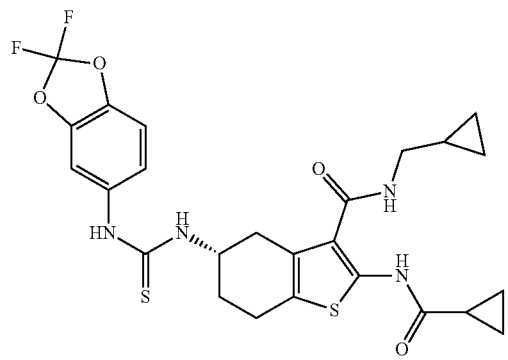 [SMILES: O=C(NCC1CC1)c1c(NC(=O)C2CC2)sc2c1C[C@@H](NC(=S)Nc1ccc3c(c1)OC(F)(F)O3)CC2]

(5S)-2-(Cyclopropanecarbonylamino)-N-(cyclopropylmethyl)-5-[(2,2-difluoro-1,3-benzodioxol-5-yl)carbamothioylamino]-4,5,6,7-tetrahydrobenzothiophene-3-carboxamide Intermediate 117 (300 mg, 0.900 mmol) was added to a stirred solution of intermediate 582 (232 mg, 1.08 mmol) in DCM (20 mL) and the reaction stirred for 40 min at ambient temperature. The solvent was removed in vacuo. The crude product was purified by flash chromatography eluting with 5-100% EtOAc in iso-hexane to afford the title compound (455 mg, 92%) as a colourless powder. $\delta_H$(300 MHz, DMSO-d6) 11.11 (s, 1H), 9.54 (s, 1H), 7.91 (s, 1H), 7.91-7.66 (m, 2H), 7.34 (d, J=8.6 Hz, 1H), 7.09 (dd, J=8.6, 2.1 Hz, 1H), 4.57 (s, 1H), 3.24-3.00 (m, 3H), 2.78-2.58 (m, 3H), 2.10-1.81 (m, 3H), 1.10-0.97 (m, 1H), 0.91-0.78 (m, 4H), 0.48-0.38 (m, 2H), 0.27-0.19 (m, 2H). LCMS [M+H]+ 549, RT 1.06 minutes (Method 7).

Intermediate 584

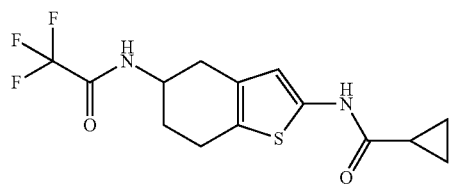 [SMILES: O=C(Nc1cc2c(s1)CCC(NC(=O)C(F)(F)F)C2)C1CC1]

N-[5-[(2,2,2-trifluoroacetyl)amino]-4,5,6,7-tetrahydrobenzothiophen-2-yl]cyclopropanecarboxamide A solution of the trifluoroacetamide salt of intermediate 29 (83.0 g, 237 mmol) in methanol (1500 mL) was stirred at 20° C. and treated with DIPEA (87 mL, 498 mmol) followed by ethyl trifluoacetate (56.6 mL, 474 mmol). After 16 h the reaction mixture was cooled to 0° C. and poured into ice-water (3 L). The resulting solid was collected by filtration, washed with water (4 portions of 300 mL) and cyclohexane (300 mL). The solid was further dried by azeotrope with toluene and drying in vacuo to yield the title compound as a beige solid (76 g, 95% Yield). $\delta_H$ (250 MHz, DMSO-d6) 11.12 (s, 1H), 9.46 (d, J=7.5 Hz, 1H), 6.30 (s, 1H), 4.13-3.88 (m, 1H), 2.84-2.61 (m, 3H), 2.56-2.41 (m, 1H), 2.04-1.89 (m, 1H), 1.89-1.62 (m, 2H), 0.8 (d, J=6.1 Hz, 4H). LCMS [M+H]+ 333 RT 1.66 minutes (Method 12).

Intermediate 585

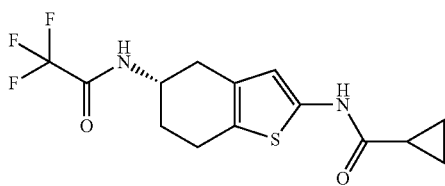 [SMILES: O=C(Nc1cc2c(s1)CC[C@H](NC(=O)C(F)(F)F)C2)C1CC1]

N-[(5S)-5-[(2,2,2-trifluoroacetyl)amino]-4,5,6,7-tetrahydrobenzothiophen-2-yl]cyclopropanecarboxamide Purification of intermediate 584 by chiral-SFC using a 50×250 mm, 20 μm ChiralPak IG column, eluting with 25% EtOH in CO$_2$, yielded the title compound (the second peak eluted form the column) as a beige solid (2.196 g, 44% Yield). LCMS [M+H]+ 333 RT 0.91 minutes (Method 7). $[\alpha]_D^{20}$ 28.4 (c 1.0, CH$_3$OH)

Intermediate 586

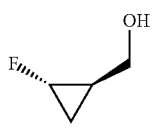

[(1R,2S)-2-fluorocyclopropyl]methanol

To a stirred solution of (1R,2S)-2-fluorocyclopropanecarboxylic acid (5 g, 48.0 mmol) in anhydrous THF (25 mL) under a N$_2$ atmosphere and cooled in an ice bath was added 2 M lithium aluminum hydride in THF (31 mL, 62 mmol) dropwise. Initial effervescence subsided and a white precipitate was observed during the addition. The reaction was warmed to ambient temperature over 90 min and was stirred at this temperature overnight, during which time the precipitate went back into solution. The reaction was cooled with an ice bath prior to dropwise addition of water (3 mL) then 2 M sodium hydroxide (3 mL). THF (30 mL) was added to the resulting thick precipitate and stirring continued for 25 min. The mixture was filtered, washed with THF (3×25 mL) and the filtrate concentrated under reduced pressure to afford the title compound (5 g, 67% Yield) as a colourless oil (~42% THF w/w/present). $\delta_H$ (300 MHz, d-Chloroform) 4.46 (ddt, J=64.1, 6.3, 2.2 Hz, 1H), 3.55-3.36 (m, 2H), 1.56 (ddqd, J=19.9, 11.0, 6.9, 1.9 Hz, 1H), 1.08 (dddd, J=21.0, 10.9, 7.0, 2.6 Hz, 1H), 0.61 (dq, J=10.3, 6.7 Hz, 1H).

Intermediate 587

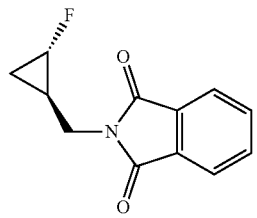 [SMILES: O=C1c2ccccc2C(=O)N1C[C@H]1C[C@@H]1F]

2-[[(1R,2S)-2-fluorocyclopropyl]methyl]isoindoline-1,3-dione

Intermediate 586 (5 g, 32 mmol), phthalimide (5.74 g, 38 mmol) and triphenylphosphine (12.8 g, 48 mmol) were suspended in anhydrous THF (25 mL) and stirred under N$_2$ at 0° C. prior to dropwise addition of diethyl azodicarboxylate (6.3 mL, 40 mmol). Upon completion of addition, the suspension went into solution. The reaction was warmed to ambient temperature and stirred for 23 h. The reaction was concentrated under reduced pressure to remove volatiles and diluted with EtOAc (75 mL). The solution was washed with sat aqueous NaHCO$_3$ (50 mL) followed by aqueous 2 M HCl (50 mL) and then brine (25 mL). The organic phase was dried (Na$_2$SO$_4$) and concentrated in vacuo. White needles had crystallised overnight. Upon breaking these up for filtration, a further crystalline solid crashed out. Combined solids were filtered, washing with diethyl ether. The residue & filtrate both contained product. These were combined, and purified by column chromatography eluting with 0-100% EtOAc in iso-hexanes to give the title compound (4.83 g, 68% Yield). $\delta_H$ (300 MHz, d-DMSO) 8.00-7.73 (m, 4H), 4.71 (dddd, J=64.3, 6.2, 2.6, 1.9 Hz, 1H), 3.56-3.36 (m, 2H), 1.72-1.43 (m, 1H), 1.06 (dddd, J=21.9, 11.0, 7.0, 2.7 Hz, 1H), 0.72 (dq, J=10.8, 6.7 Hz, 1H).

Intermediate 588

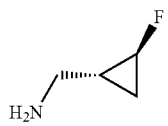

[(1R,2S)-2-fluorocyclopropyl]methanamine

A suspension of intermediate 587 (4.3 g, 20 mmol) in ethanol (20 mL) was treated with 24% hydrazine hydrate (4.5 mL, 22 mmol). The reaction was sealed and heated to 60° C. with stirring for 3 hours. A second aliquot of 24% hydrazine hydrate (1 mL, 4.9 mmol) was added and heating increased to 80° C. for a further 90 min. The reaction was filtered to remove colourless precipitate (washing with DCM). A solution of the crude product was obtained by distillation (120 mBar to 10 mBar at 40° C.). 4 M HCl in dioxane (2.5 mL) was added to the solution which was subsequently concentrated in vacuo. The resulting colourless powder was dissolved in DMSO (10 mL) and purified via column chromatography (KP-NH) eluting with a 0-100% gradient of MeOH in DCM to give the title compound as a 6% w/v solution in DMSO (10.5 g, 36% Yield). δ$_H$ (300 MHz, Chloroform-d) 4.38 (ddt, J=64.2, 6.2, 2.1 Hz, 1H), 2.55-2.49 (m, 2H), 1.52-1.26 (m, 1H), 1.10-0.92 (m, 1H), 0.50 (dq, J=10.0, 6.7 Hz, 1H).

Intermediate 589

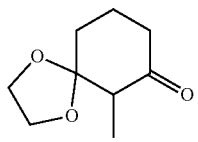

6-methyl-1,4-dioxaspiro[4.5]decan-7-one ethylene glycol (43 mL, 769 mmol), 2-methyl-1,3-cyclohexanedione (25 g, 192 mmol) and PTSA (100 mg, 0.58 mmol) were suspended in toluene (350 mL) in a 1 L round bottom flask equipped with Dean-Stark condenser, and the mixture refluxed (set temp 130° C.) overnight with stirring. The mixture was cooled and concentrated in vacuo. The crude product was redissolved in DCM (250 mL) and treated with silica (40 g) and 3 M aqueous sulfuric acid (6.0 mL). The resulting slurry was stirred vigorously overnight at ambient temperature. The reaction was filtered and washed with saturated aqueous NaHCO$_3$ solution (2×250 mL). The organic layer was dried over Na$_2$SO$_4$ and the solvent removed in vacuo. The crude product was purified using column chromatography (eluting with a 0-60% gradient of Et$_2$O in isohexane) to afford the title compound (12.5 g, 38.2% Yield). δ$_H$ (300 MHz, Chloroform-d) 4.02-3.86 (m, 4H), 2.73 (qd, J=6.7, 1.1 Hz, 1H), 2.49-2.37 (m, 1H), 2.33-2.17 (m, 1H), 2.02-1.92 (m, 1H), 1.92-1.64 (m, 3H), 1.04 (d, J=6.7 Hz, 3H).

Intermediate 590

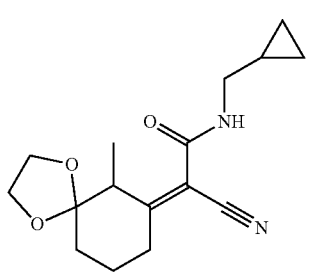 [SMILES: CC1/C(=C(/C#N)C(=O)NCC2CC2)CCCC12OCCO2]

(2Z)-2-cyano-N-(cyclopropylmethyl)-2-(6-methyl-1,4-dioxaspiro[4.5]decan-7-ylidene)acetamide To a stirred solution of intermediate 589 (10.2 g, 74.0 mmol) and 6-methyl-1,4-dioxaspiro[4.5]decan-7-one (12000 mg, 70.5 mmol) in anhydrous THF (200 mL) at r.t. were added pyridine (10.7 g, 133.95 mmol) and titanium (IV) isopropoxide (62.0 g, 211.50 mmol). The reaction was stirred at ambient temperature overnight. The reaction was stirred vigorously as it was quenched by dropwise addition of water (200 mL). The organic layer was decanted, passing through a phase separator cartridge and the TiO$_2$ residues slurried with DCM (2×150 mL), also passing through phase separator cartridge. The combined organic layers were concentrated in vacuo. The crude product was purified by column chromatography (eluting with a 0-80% gradient of EtOAc in isohexane) to afford the title compound (10.95 g, 40% Yield). δ$_H$ (300 MHz, Chloroform-d) 6.48-6.09 (m, 1H), 4.02-3.88 (m, 4H), 3.23-3.11 (m, 2H), 2.89-2.74 (m, 1H), 2.52-2.35 (m, 1H), 2.00-1.79 (m, 2H), 1.75-1.51 (m, 2H), 1.21 (d, J=7.1 Hz, 3H), 1.10-0.88 (m, 1H), 0.62-0.47 (m, 2H), 0.23 (dt, J=5.8, 4.6 Hz, 2H).

Intermediate 591

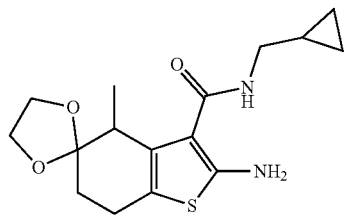 [SMILES: CC1c2c(sc(N)c2C(=O)NCC2CC2)CCC12OCCO2]

2'-amino-N-(cyclopropylmethyl)-4'-methyl-spiro[1,3-dioxolane-2,5'-6,7-dihydro-4H-benzothiophene]-3'-carboxamide To a solution of intermediate 590 (10.95 g, 37.7 mmol) in ethanol (200 mL) was added morpholine (6.70 mL, 75.4 mmol) and sulfur (1.81 g 56.6 mmol). The reaction was heated to 100° C. with stirring for 5.5 h. The volatiles were removed in vacuo to afford the crude title compound (24 g), which was used in the next stage without purification.

Intermediate 592

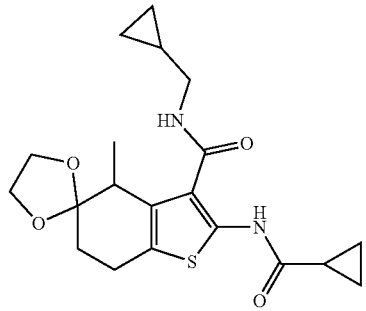 [SMILES: CC1c2c(sc(NC(=O)C3CC3)c2C(=O)NCC2CC2)CCC12OCCO2]

2'-(cyclopropanecarbonylamino)-N-(cyclopropylmethyl)-4'-methyl-spiro[1,3-dioxolane-2,5'-6,7-dihydro-4H-benzothiophene]-3'-carboxamide Crude intermediate 591 (24 g) was dissolved in DCM (300.0 mL) and DIPEA (26.0 mL, 148.9 mmol) was added. The solution was cooled in an ice bath with stirring prior to dropwise addition of cyclopropanecarbonyl chloride (7.58 mL, 81.89 mmol). Upon completion of addition the ice bath was removed and stirring continued for 30 min. The reaction was diluted with water (200 mL) and partitioned. The organic layer was passed through a phase separator and concentrated in vacuo. The crude product was purified by column chromatography (eluting with a 0-100% gradient of EtOAc in isohexane) to afford the title compound (8.8 g, 30% Yield). $\delta_H$ (300 MHz, DMSO-$d_6$) 10.68 (s, 1H), 8.09 (t, J=5.7 Hz, 1H), 3.98-3.86 (m, 4H), 3.22-3.00 (m, 3H), 2.80-2.57 (m, 2H), 2.01-1.86 (m, 2H), 1.69 (dt, J=12.9, 4.4 Hz, 1H), 1.10-0.97 (m, 4H), 0.88-0.76 (m, 4H), 0.67-0.56 (m, 1H), 0.46-0.35 (m, 2H), 0.26-0.18 (m, 2H).

Intermediate 593

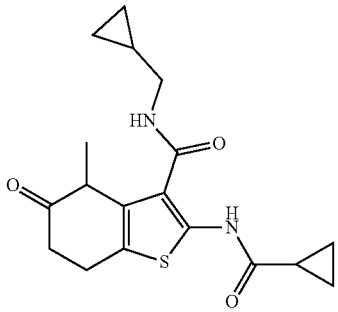 [SMILES: CC1C(=O)CCc2sc(NC(=O)C3CC3)c(C(=O)NCC3CC3)c21]

2-(cyclopropanecarbonylamino)-N-(cyclopropylmethyl)-4-methyl-5-oxo-6,7-dihydro-4H-benzothiophene-3-carboxamide To a solution of intermediate 592 (10.0 g, 25.6 mmol) in THF (200 mL) was degassed using a stream of $N_2$ for 10 min prior to addition of 1 M HCl (25 mL). The solution was degassed for 2 more minutes and then stirred at 70° C. under $N_2$ until complete. The reaction mixture was basified with solid NaHCO$_3$ until effervescence ceased and then diluted with EtOAc until 2 layers formed. The top layer was partitioned and dried over Na$_2$SO$_4$, then concentrated in vacuo to afford the title compound (9.31 g, 89% Yield). LCMS [M+H]$^+$ 347, RT 1.11 minutes (Method 33).

Intermediate 594

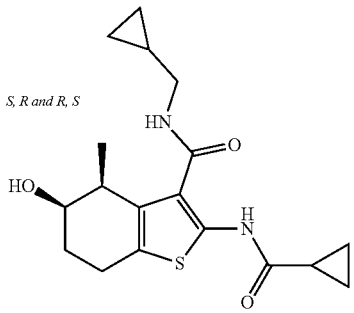 [SMILES: C[C@H]1c2c(sc(NC(=O)C3CC3)c2C(=O)NCC2CC2)CC[C@H]1O]

(4SR,5RS)-2-(cyclopropanecarbonylamino)-N-(cyclopropylmethyl)-5-hydroxy-4-methyl-4,5,6,7-tetrahydrobenzothiophene-3-carboxamide To an ice-cold stirred solution intermediate 593 (9.1 g, 26 mmol) in MeOH (200 mL) and DCM (40.00 mL) was added NaBH$_4$ (1500 mg, 39 mmol) portion-wise over 30 min. The reaction mixture was stirred at this temperature for 2.5 h. The reaction mixture was quenched by addition aqueous AcOH (1 mL AcOH in 25 mL H$_2$O) and concentrated in vacuo. The resulting slurry was diluted with DCM (150 mL), MeOH (10 mL) and water (50 mL). The organic layer was partitioned and the aqueous layer extracted with DCM/MeOH (150 mL). The organic layer was concentrated and then purified by column chromatography (eluting with a 0-100% gradient of EtOAc in isohexane followed by 0-20% MeOH in EtOAc) to afford the title compound (4.5 g, 49% Yield). $\delta_H$ (400 MHz, Chloroform-d) 12.21 (s, 1H), 6.24-6.11 (m, 1H), 4.18 (ddd, J=11.6, 5.2, 3.9 Hz, 1H), 3.41-3.19 (m, 2H), 3.18-3.09 (m, 1H), 2.84-2.78 (m, 2H), 2.03-1.85 (m, 2H), 1.69-1.63 (m, 2H), 1.26 (d, J=6.9 Hz, 3H), 1.17-1.00 (m, 3H), 0.89 (dt, J=7.8, 3.5 Hz, 2H), 0.65-0.57 (m, 2H), 0.28 (dt, J=5.7, 4.5 Hz, 2H).

Intermediate 595

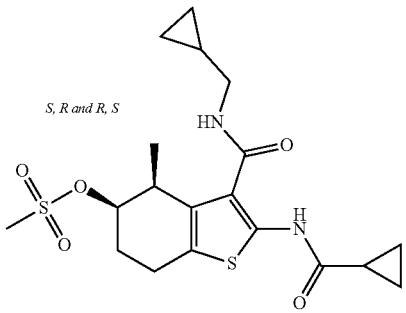 [SMILES: C[C@H]1c2c(sc(NC(=O)C3CC3)c2C(=O)NCC2CC2)CC[C@H]1OS(C)(=O)=O]

[(4SR,5RS)-2-(cyclopropanecarbonylamino)-3-(cyclopropylmethylcarbamoyl)-4-methyl-4,5,6,7-tetrahydrobenzothiophen-5-yl]methanesulfonate Intermediate 594 (4.5 g, 13 mmol) was dissolved in DCM (200 mL). TEA (2.7 mL, 19 mmol) was added and the mixture cooled with an ice bath. Methanesulfonyl chloride (1.1 mL, 14 mmol) was added dropwise and the reaction sealed and stirred at this temp for 150 min. Additional methanesulfonyl chloride (0.4 mL) was added at ambient temperature and reaction stirred at this temp overnight. The reaction mixture was concentrated in vacuo and triturated in Et$_2$O (100 mL) with sonication. The resulting solids were filtered and washed with ether, air drying under suction to afford the title compound (4.52 g, 82% Yield). $\delta_H$ (300 MHz, Chloroform-d) 11.98 (s, 1H), 6.01 (m, 1H), 5.13 (ddd, J=12.0, 5.3, 3.8 Hz, 1H), 3.51-3.17 (m, 3H), 3.10 (s, 3H), 2.92-2.82 (m, 2H), 2.31-2.05 (m, 2H), 1.70-1.57 (m, 1H), 1.33 (d, J=6.9 Hz, 3H), 1.13-1.05 (m, 3H), 0.90 (dt, J=8.0, 3.4 Hz, 2H), 0.66-0.51 (m, 2H), 0.29 (dt, J=5.9, 4.6 Hz, 2H).

Intermediate 596

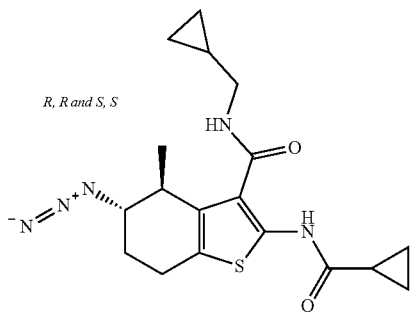

(4SR,5SR)-5-azido-2-(cyclopropanecarbonylamino)-N-(cyclopropylmethyl)-4-methyl-4,5,6,7-tetrahydrobenzothiophene-3-carboxamide Intermediate 595 (2.5 g, 5.9 mmol) was dissolved in DMF (30.0 mL) and NaN₃ (0.96 g, 15 mmol) added. The reaction was sealed and stirred at 75° C. for 2.5 h. Additional NaN₃ (250 mg) was added and stirring resumed at 75° C. for 4 h. The reaction was cooled and diluted with water (50 mL) and extracted with EtOAc (3×50 mL). The combined organic extracts were dried over Na₂SO₄ and concentrated in vacuo. The resulting beige powder was purified using column chromatography eluting with a 0-40% gradient of EtOAc in isohexane to afford after dry down the title compound (572 mg, 26% Yield). δ$_H$ (300 MHz, Chloroform-d) 11.72 (s, 1H), 6.16-5.71 (m, 1H), 3.77 (ddd, J=6.3, 3.8, 2.8 Hz, 1H), 3.48-3.16 (m, 2H), 3.00-2.64 (m, 3H), 2.19-1.95 (m, 2H), 1.72-1.55 (m, 1H), 1.31 (d, J=7.0 Hz, 3H), 1.17-0.99 (m, 3H), 0.89 (dt, J=8.0, 3.4 Hz, 2H), 0.68-0.52 (m, 2H), 0.28 (dt, J=5.9, 4.6 Hz, 2H).

Intermediate 597

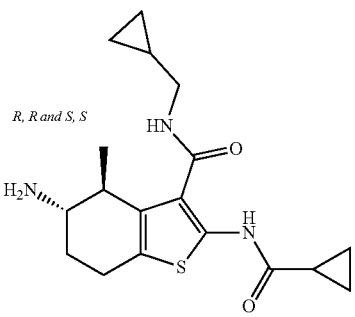 [SMILES: C[C@H]1c2c(sc(NC(=O)C3CC3)c2C(=O)NCC2CC2)CC[C@@H]1N]

(4SR,5SR)-5-amino-2-(cyclopropanecarbonylamino)-N-(cyclopropylmethyl)-4-methyl-4,5,6,7-tetrahydrobenzothiophene-3-carboxamide Intermediate 596 (0.57 g, 1.53 mmol) was dissolved in EtOH (2 mL) and the solution degassed with 2 cycles of vacuum/N₂ prior to addition of 10% w/w Pd on carbon (50 mg). The solution was degassed with a further cycle of vacuum/N₂ before regassing with 3 cycles of vacuum/H₂. The reaction was stirred under balloon pressure H₂ at ambient temperature for 3 h. The reaction mixture was degassed and filtered through celite, washing with EtOAc (50 mL). The solvents were removed in vacuo to afford a beige solid, which was dissolved in MeOH (12 mL) and absorbed on an SCX2 cartridge. The absorbed crude was washed with MeOH (40 mL) and the product eluted with 4 M NH₃ in MeOH (60 mL). Solvents were removed in vacuo to afford the title compound (498 mg, 94% Yield). δ$_H$ (300 MHz, Chloroform-d) 11.94 (s, 1H), 6.26 (t, J=4.8 Hz, 1H), 3.41-3.13 (m, 2H), 3.07 (dt, J=5.7, 2.9 Hz, 1H), 2.86-2.60 (m, 3H), 2.09-1.94 (m, 1H), 1.82-1.58 (m, 4H), 1.27 (d, J=6.9 Hz, 3H), 1.21-0.98 (m, 3H), 0.87 (dt, J=8.0, 3.4 Hz, 2H), 0.63-0.50 (m, 2H), 0.27 (dt, J=5.9, 4.5 Hz, 2H).

Intermediate 598

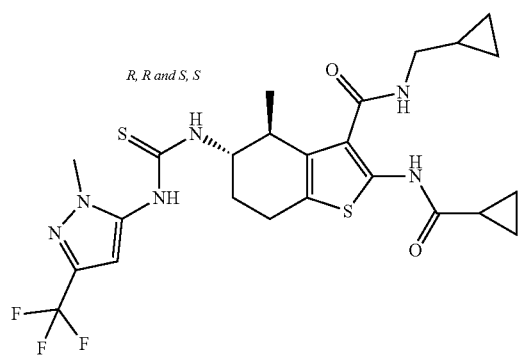 [SMILES: C[C@H]1c2c(sc(NC(=O)C3CC3)c2C(=O)NCC2CC2)CC[C@@H]1NC(=S)Nc1cc(C(F)(F)F)nn1C]

(4SR,5SR)-2-(cyclopropanecarbonylamino)-N-(cyclopropylmethyl)-4-methyl-5-[[2-methyl-5-(trifluoromethyl)pyrazol-3-yl]carbamothioylamino]-4,5,6,7-tetrahydrobenzothiophene-3-carboxamide Synthesised in the same manner as intermediate 168, using intermediate 597 (75 mg, 0.22 mmol) and intermediate 262 (49 mg, 0.24 mmol). The product was purified by column chromatography eluting with a 0-100% gradient of EtOAc in isohexane to afford the title compound (105 mg, 88% Yield). δ$_H$ (300 MHz, Chloroform-d) 12.59 (s, 1H), 8.41 (s, 1H), 7.24 (s, 1H), 6.54 (s, 1H), 6.25 (s, 1H), 4.69-4.55 (m, 1H), 3.77 (s, 3H), 3.49-3.32 (m, 2H), 3.17 (ddd, J=13.7, 7.2, 4.3 Hz, 1H), 2.84-2.45 (m, 2H), 2.28-2.07 (m, 2H), 1.75-1.64 (m, 1H), 1.37 (d, J=7.0 Hz, 3H), 1.17-0.80 (m, 5H), 0.68-0.59 (m, 2H), 0.35-0.24 (m, 2H).

Intermediate 599

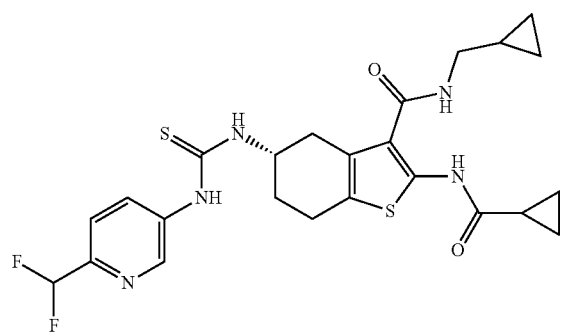 [SMILES: O=C(NCC1CC1)c1c(NC(=O)C2CC2)sc2c1C[C@@H](NC(=S)Nc1ccc(C(F)F)nc1)CC2]

(5S)-2-(cyclopropanecarbonylamino)-N-(cyclopropylmethyl)-5-[[6-(difluoromethyl)-3-pyridyl]carbamothioylamino]-4,5,6,7-tetrahydrobenzothiophene-3-carboxamide A solution of 2-(difluoromethyl)-5-isothiocyanato-pyridine (200 mg, 1.07 mmol) in DCM (2 mL) was added dropwise to a solution of intermediate 117 (286 mg, 0.86 mmol) in DCM (10 mL). The reaction was stirred at ambient temperature for 20 min and then concentrated in vacuo. The crude product was purified by column chromatography eluting with a 0-100% gradient of EtOAc in isohexane. Product-containing fractions were combined and concentrated to afford the title compound (403 mg, 72.2% Yield). $\delta_H$ (300 MHz, Chloroform-d) 12.01 (s, 1H), 8.91 (s, 1H), 8.52 (dd, J=8.5, 2.5 Hz, 1H), 8.42 (d, J=2.5 Hz, 1H), 7.56 (d, J=8.5 Hz, 1H), 7.06 (d, J=7.0 Hz, 1H), 6.57 (t, J=55.6 Hz, 1H), 5.74 (t, J=5.2 Hz, 1H), 5.10-4.87 (m, 1H), 3.38-3.17 (m, 2H), 3.06 (dd, J=15.4, 4.5 Hz, 1H), 2.92-2.49 (m, 4H), 1.87 (dq, J=13.7, 6.1, 3.7 Hz, 1H), 1.77-1.60 (m, 2H), 1.11-0.78 (m, 4H), 0.67-0.51 (m, 2H), 0.27 (dt, J=5.9, 4.6 Hz, 2H).

Intermediate 600

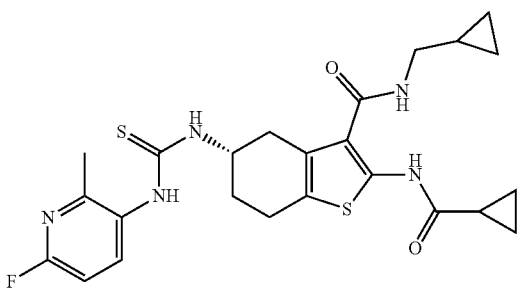 [SMILES: Cc1nc(F)ccc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(6-fluoro-2-methyl-3-pyridyl)carbamothioylamino]-4,5,6,7-tetrahydrobenzothiophene-3-carboxamide A solution of 6-fluoro-3-isothiocyanato-2-methyl-pyridine (200 mg, 1.19 mmol) in DCM (2 mL) was added dropwise to a solution of Intermediate 117 (285 mg, 0.86 mmol) in DCM (10 mL). The reaction was stirred at ambient temperature for 20 min and then concentrated in vacuo. The crude product was purified by column chromatography eluting with a 0-100% gradient of EtOAc in isohexane. Product-containing fractions were combined and concentrated to afford the title compound (469 mg, 78% Yield). $\delta_H$ (300 MHz, Chloroform-d) 11.99 (s, 1H), 7.98 (s, 1H), 7.94-7.82 (m, 1H), 6.76 (dd, J=8.6, 3.5 Hz, 1H), 6.70 (d, J=7.1 Hz, 1H), 5.78 (t, J=5.2 Hz, 1H), 5.06-4.81 (m, 1H), 3.36-3.15 (m, 2H), 3.10 (dd, J=15.2, 4.7 Hz, 1H), 2.83-2.61 (m, 3H), 2.49-2.40 (m, 1H), 2.37 (s, 3H), 1.98-1.84 (m, 1H), 1.65 (tt, J=7.6, 4.7 Hz, 1H), 1.09-0.80 (m, 5H), 0.64-0.52 (m, 2H), 0.26 (dt, J=5.9, 4.6 Hz, 2H).

Intermediate 601

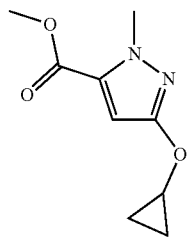

methyl 5-(cyclopropoxy)-2-methyl-pyrazole-3-carboxylate

Cyclopropanol (413 mg, 6.40 mmol) and methyl 5-hydroxy-2-methyl-pyrazole-3-carboxylate (1.0 g, 6.40 mmol) were suspended in anhydrous toluene (10.0 mL) prior to addition of triphenylphosphine (1.69 g, 6.40 mmol) and then di-tert-butylazodicarboxylate (1.47 g, 6.40 mmol). The reaction was heated to 110° C. with stirring in a sealed vessel for 4.5 h, cooled & diluted with EtOAc (10 mL) and washed with water (10 mL). The organic layer was dried over $Na_2SO_4$ and concentrated in vacuo. The crude product was purified by column chromatography eluting with a 0-100% gradient of EtOAc in isohexane. Product-containing fractions were combined and concentrated to afford the title compound (730 mg, 58% Yield). $\delta_H$ (300 MHz, Chloroform-d) 6.31 (s, 1H), 4.04 (s, 3H), 3.91 (tt, J=6.0, 3.0 Hz, 1H), 3.86 (s, 3H), 0.82-0.66 (m, 4H).

Intermediate 602

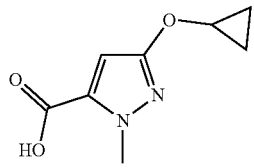

5-(cyclopropoxy)-2-methyl-pyrazole-3-carboxylic acid

Intermediate 601 (730 mg, 3.7 mmol) was dissolved in MeOH (15 mL) and 2 M aqueous NaOH (3.7 mL). The reaction was stirred at 50° C. for 1.25 h. The reaction mixture was concentrated to remove MeOH, acidified to pH~1 with 2 N HCl and extracted with EtOAc (4×15 mL) The organic extracts were dried over $Na_2SO_4$ and concentrated in vacuo and concentrated to afford the title compound (730 mg, 97% Yield) as a colourless powder. $\delta_H$ (300 MHz, DMSO-d6) 13.20 (s, 1H), 6.31 (s, 1H), 3.98-3.91 (m, 4H), 0.76-0.56 (m, 4H).

Intermediate 603

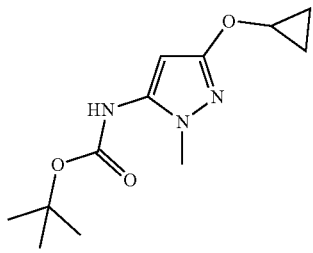 [SMILES: Cn1nc(OC2CC2)cc1NC(=O)OC(C)(C)C]

tert-butyl N-[5-(cyclopropoxy)-2-methyl-pyrazol-3-yl]carbamate

Intermediate 602 (730 mg, 4.0 mmol) was dissolved in THF (10 mL) and TEA (1.68 mL, 12.0 mmol) was added and the solution cooled in an ice bath. DPPA (1.65 g, 6.01 mmol) was added dropwise and the reaction stirred at this temp for 0.25 h, then allowed to warm to ambient temperature for 1 h. Tert-butanol (10 mL, 110 mmol) was added and the reaction heated to 85° C. for 6 h. The reaction mixture was concentrated in vacuo and the crude product purified by column chromatography eluting with a 0-100% gradient of EtOAc in isohexane. Product-containing fractions were combined and concentrated to afford the title compound (670 mg, 66% Yield). $\delta_H$ (300 MHz, Chloroform-d) 6.24 (s, 1H), 5.73 (s, 1H), 3.90 (tt, J=6.0, 3.0 Hz, 1H), 3.60 (s, 3H), 1.50 (s, 9H), 0.81-0.64 (m, 4H).

Intermediate 604

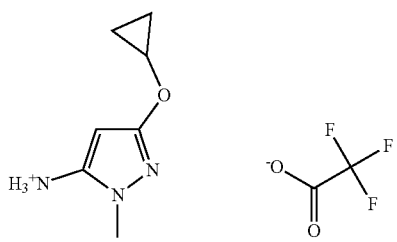

[5-(cyclopropoxy)-2-methyl-pyrazol-3-yl]ammonium 2,2,2-trifluoroacetate

Intermediate 603 (530 mg, 2.1 mmol) was dissolved in 20% TFA/DCM (10 mL) and stirred at ambient temperature for 2 h The reaction mixture was concentrated in vacuo and then azeotroped with toluene and concentrated in vacuo to afford the title compound as a brown oil. Yield not recorded. $\delta_H$(300 MHz, Methanol-d4) 4.15-4.07 (m, 1H), 3.53 (s, 3H), 0.88-0.81 (m, 4H).

Intermediate 605

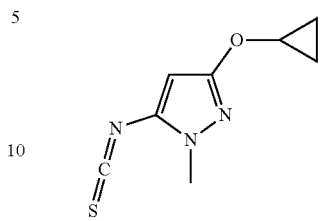

3-(cyclopropoxy)-5-isothiocyanato-1-methyl-pyrazole

DIPEA (600 mg, 4.6 mmol) was added to a solution of intermediate 604 (560 mg, 2.1 mmol) and 1,1'-thiocarbonyldiimidazole (470 mg, 2.5 mmol) in DCM (10 mL) under N₂ and the reaction stirred for 90 min. The crude product was used directly in the next stage without any purification.

Intermediate 606

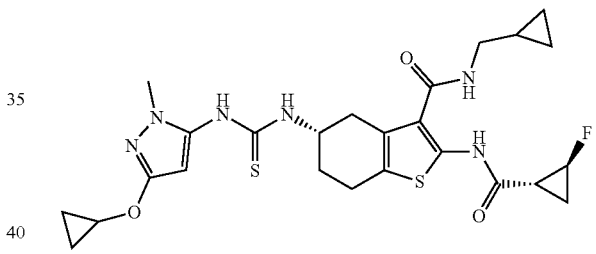

(5S)-5-[[5-(cyclopropoxy)-2-methyl-pyrazol-3-yl]carbamothioylamino]-N-(cyclopropylmethyl)-2-[[(1R,2S)-2-fluorocyclopropanecarbonyl]amino]-4,5,6,7-tetrahydrobenzothiophene-3-carboxamide To a stirred solution of intermediate 566 (100 mg, 0.2732 mmol) in DCM (0.2 mL) was added a solution of intermediate 605 (58.7 mg, 0.30 mmol) in DCM (10 mL). The reaction mixture was stirred at room temperature for 45 min. The reaction was concentrated in vacuo and the crude product was purified by column chromatography eluting with a 0-100% gradient of EtOAc in isohexane followed by 0-20% MeOH in EtOAc. Product-containing fractions were combined and concentrated to the title compound (90 mg, 60% Yield). $\delta_H$ (300 MHz, Chloroform-d) 12.24 (s, 1H), 7.86 (s, 1H), 6.68-6.48 (m, 1H), 5.90 (t, J=5.3 Hz, 1H), 5.05-4.69 (m, 2H), 3.98-3.82 (m, 1H), 3.75-3.55 (m, 4H), 3.39-3.15 (m, 3H), 3.02-2.60 (m, 3H), 2.23-2.02 (m, 3H), 1.63-0.82 (m, 3H), 0.80-0.68 (m, 4H), 0.65-0.54 (m, 2H), 0.34-0.23 (m, 2H).

Intermediate 607

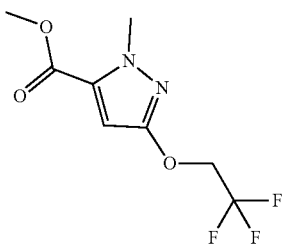 [SMILES: COC(=O)c1cc(OCC(F)(F)F)nn1C]

methyl 2-methyl-5-(2,2,2-trifluoroethoxy)pyrazole-3-carboxylate methyl 5-hydroxy-2-methyl-pyrazole-3-carboxylate (2.7 g, 17.0 mmol) and 2-iodo-1,1,1-trifluoroethane (2.1 mL, 21 mmol) were dissolved in anhydrous DMF (20 mL). The reaction was cooled in an ice bath prior to addition of sodium hydride (1.20 g, 29 mmol, 60 mass % in mineral oil) portion-wise over 10 min. Upon completion of addition, the reaction was sealed and heated to 100° C. with stirring for 2 h. The reaction was diluted with water (20 mL) and extracted with EtOAc (3×20 mL). The organic layer was dried over Na$_2$SO$_4$ and concentrated in vacuo. The crude product was purified by column chromatography eluting with a 0-50% gradient of EtOAc in isohexane. Product-containing fractions were combined and concentrated to afford the title compound (660 mg, 16% Yield). δ$_H$ (300 MHz, Chloroform-d) 6.25 (s, 1H), 4.55 (q, J=8.4 Hz, 2H), 4.03 (s, 3H), 3.87 (s, 3H).

Intermediate 608

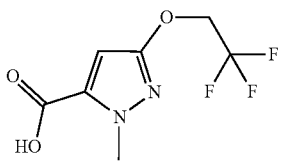

2-methyl-5-(2,2,2-trifluoroethoxy)pyrazole-3-carboxylic acid

Intermediate 607 (660 mg, 2.77 mmol) was dissolved in MeOH (13 mL) and 2 M aqueous sodium hydroxide (3.4 mL). The reaction was stirred at 50° C. for 1.25 h. The reaction mixture was acidified to pH 1 with 2 M HCl and concentrated to remove most of the MeOH. The resulting aqueous was extracted with EtOAc (3×20 mL) and the combined organic extracts dried over Na$_2$SO$_4$ and concentrated in vacuo to afford the title compound (559 mg, 81% Yield). δ$_H$ (300 MHz, DMSO-d6) 13.52 (s, 1H), 6.38 (s, 1H), 4.79 (q, J=9.0 Hz, 2H), 3.94 (s, 3H).

Intermediate 609

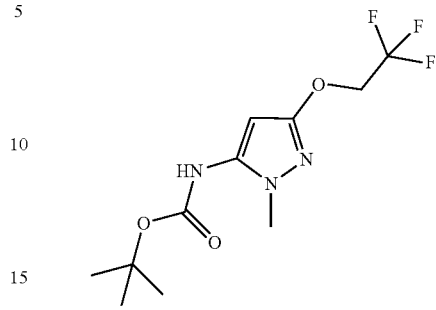

tert-butyl N-[2-methyl-5-(2,2,2-trifluoroethoxy)pyrazol-3-yl]carbamate

Intermediate 608 (559 mg, 2.49 mmol) was dissolved in THF (10.0 mL) and TEA (1.0 mL, 7.49 mmol) was added and the solution cooled in an ice bath. DPPA (0.81 mL, 3.74 mmol) was added dropwise and the reaction stirred at this temperature for 0.25 h, then allowed to warm to ambient temperature for 1. Tert-butanol (10 mL) was added and the reaction heated to 85° C. for 3 h. The reaction mixture was concentrated in vacuo and purified by column chromatography eluting with a 0-100% gradient of EtOAc in isohexane. Product-containing fractions were combined and concentrated to afford the title compound (530 mg, 72% Yield). δ$_H$ (300 MHz, Chloroform-d) 6.27 (s, 1H), 5.66 (s, 1H), 4.51 (q, J=8.4 Hz, 2H), 3.58 (s, 3H), 1.50 (s, 9H).

Intermediate 610

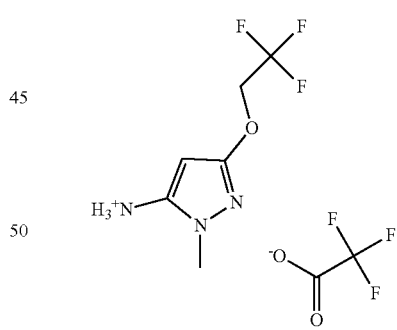

[2-methyl-5-(2,2,2-trifluoroethoxy)pyrazol-3-yl] ammonium 2,2,2-trifluoroacetate Intermediate 609 (530 mg, 1.8 mmol) was dissolved in TFA/DCM (10 mL) and stirred at ambient temperature for 2 h. The reaction mixture was concentrated in vacuo and then azeotroped with toluene and concentrated in vacuo to afford the title compound as a brown oil. Yield not recorded. δ$_H$ (300 MHz, Methanol-d4) 4.68 (q, J=8.4 Hz, 2H), 3.51 (s, 3H).

Intermediate 611

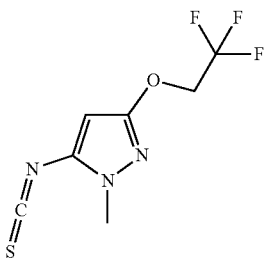

5-isothiocyanato-1-methyl-3-(2,2,2-trifluoroethoxy)pyrazole

DIPEA (510 mg, 4.0 mmol) was added to a solution of intermediate 610 (560 mg, 1.8 mmol) and 1,1'-thiocarbonyldiimidazole (410 mg, 2.2 mmol) in DCM (10 mL) under $N_2$. The reaction was stirred for 90 min. The crude product was used directly in the next stage without any purification.

Intermediate 612

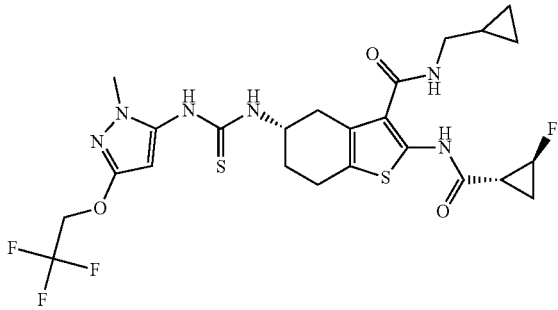 [SMILES: Cn1nc(OCC(F)(F)F)cc1NC(=S)N[C@H]1CCc2sc(NC(=O)[C@H]3C[C@@H]3F)c(C(=O)NCC3CC3)c2C1]

(5S)—N-(cyclopropylmethyl)-2-[[(1R,2S)-2-fluoro-cyclopropanecarbonyl]amino]-5-[[2-methyl-5-(2,2,2-trifluoroethoxy)pyrazol-3-yl]carbamothioylamino]-4,5,6,7-tetrahydrobenzothiophene-3-carboxamide To a stirred solution of intermediate 566 (100 mg, 0.27 mmol) in DCM (0.2 mL) was added a solution of intermediate 611 (71 mg, 0.30 mmol) in DCM (10 mL). The reaction mixture was stirred at room temperature for 45 min. The reaction was concentrated in vacuo and the crude product was purified by column chromatography eluting with a 0-100% gradient of EtOAc in isohexane followed by 0-20% MeOH in EtOAc. Product-containing fractions were combined and concentrated to the title compound (93 mg, 57.8% Yield). $\delta_H$ (300 MHz, Chloroform-d) 12.33-12.10 (m, 1H), 7.78-7.51 (m, 1H), 6.48 (d, J=7.9 Hz, 1H), 5.96-5.80 (m, 1H), 5.00-4.67 (m, 2H), 4.62-4.42 (m, 2H), 3.73-3.53 (m, 4H), 3.33-3.16 (m, 3H), 2.95-2.59 (m, 3H), 2.33-2.00 (m, 3H), 1.60-0.72 (m, 3H), 0.70-0.47 (m, 2H), 0.34-0.15 (m, 2H).

Intermediate 613

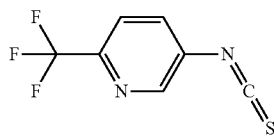 [SMILES: FC(F)(F)c1ccc(N=C=S)cn1]

5-isothiocyanato-2-(trifluoromethyl)pyridine

5-Amino-2-(trifluoromethyl)pyridine (0.2 g) was dissolved in a solution of 1,1'-thiocarbonyldiimidazole (284 mg, 1.59 mmol) in DCM (2 mL) and 4 N HCl in dioxane (0.35 mL) was added. The reaction was stirred at ambient temperature for 2.5 h, filtered and concentrated in vacuo to afford the crude title compound, which was carried through to the next stage without purification.

Intermediate 614

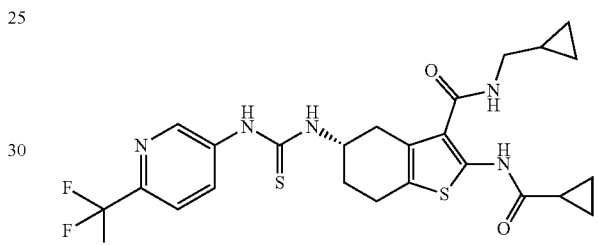

(5S)-2-(cyclopropanecarbonylamino)-N-(cyclopropylmethyl)-5-[[6-(trifluoromethyl)-3-pyridyl]carbamothioylamino]-4,5,6,7-tetrahydrobenzothiophene-3-carboxamide Intermediate 613 (0.165 mmol) was dissolved in DCM (2 mL) and added to a solution of intermediate 117 (50 mg, 0.15 mmol) in DCM (0.5 mL). The reaction was stirred at ambient temperature for 45 min and then absorbed directly silica and purified by column chromatography eluting with a 0-100% gradient of EtOAc in isohexane, followed by 0-20% MeOH in EtOAc. Product-containing fractions were combined and concentrated to afford the title compound (78 mg, 97%). $\delta_H$ (300 MHz, Chloroform-d) 12.02 (s, 1H), 8.99 (s, 1H), 8.78-8.65 (m, 1H), 8.41 (d, J=2.5 Hz, 1H), 7.62 (d, J=8.6 Hz, 1H), 7.06 (d, J=6.9 Hz, 1H), 5.71 (t, J=5.2 Hz, 1H), 5.00 (s, 1H), 3.40-3.15 (m, 2H), 3.15-2.91 (m, 1H), 2.89-2.57 (m, 4H), 1.88 (q, J=11.7, 11.2 Hz, 1H), 1.76-1.64 (m, 1H), 1.11-0.87 (m, 5H), 0.67-0.55 (m, 2H), 0.34-0.20 (m, 2H).

Intermediate 615

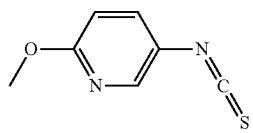

5-isothiocyanato-2-methoxy-pyridine

The title compound was prepared according to the same procedure described for intermediate 613 using 5-amino-2-methoxypyridine (0.2 g), 1,1'-thiocarbonyldiimidazole (284 mg, 1.59 mmol) in DCM (2 mL) and 4 N HCl in dioxane (0.35 mL). The crude product was carried through to the next stage without purification.

Intermediate 616

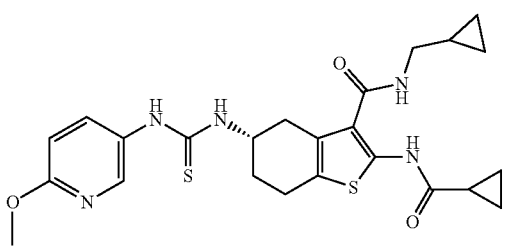 [SMILES: COc1ccc(NC(=S)N[C@H]2CCc3sc(NC(=O)C4CC4)c(C(=O)NCC4CC4)c3C2)cn1]

(5S)-2-(cyclopropanecarbonylamino)-N-(cyclopropylmethyl)-5-[(6-methoxy-3-pyridyl)carbamothioylamino]-4,5,6,7-tetrahydrobenzothiophene-3-carboxamide Intermediate 117 (50 mg, 0.15 mmol) and Intermediate 615 (0.15 mmol) were combined in DCM (2.5 mL) using to the same procedure described for intermediate 614. The crude product was purified by column chromatography eluting with a 0-100% gradient of EtOAc in isohexane, followed by 0-20% MeOH in EtOAc to afford, after dry down, the title compound (80 mg, 100%). $\delta_H$ (300 MHz, Chloroform-d) 12.10 (s, 1H), 8.02 (d, J=2.7 Hz, 1H), 7.55-7.47 (m, 1H), 7.44 (dd, J=8.8, 2.7 Hz, 1H), 6.77 (d, J=8.7 Hz, 1H), 6.00-5.75 (m, 2H), 5.04-4.75 (m, 1H), 3.93 (s, 3H), 3.28 (dd, J=7.2, 5.2 Hz, 3H), 2.93-2.52 (m, 3H), 2.08-2.01 (m, 2H), 1.65 (td, J=7.9, 4.0 Hz, 1H), 1.13-1.02 (m, 3H), 0.91 (dt, J=8.0, 3.4 Hz, 2H), 0.66-0.53 (m, 2H), 0.36-0.16 (m, 2H).

Intermediate 617

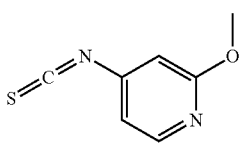

4-isothiocyanato-2-methoxy-pyridine

The title compound was prepared according to the same procedure described for intermediate 613 using 4-amino-2-methoxypyridine (0.2 g), 1,1'-thiocarbonyldiimidazole (1.59 mmol, 284 mg) in DCM (2 mL) and 4 N HCl in dioxane (0.35 mL). The crude product was carried through to the next stage without purification.

Intermediate 618

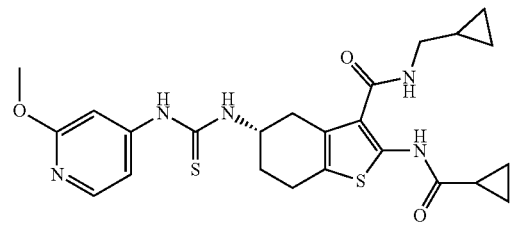 [SMILES: COc1cc(NC(=S)N[C@H]2CCc3sc(NC(=O)C4CC4)c(C(=O)NCC4CC4)c3C2)ccn1]

(5S)-2-(cyclopropanecarbonylamino)-N-(cyclopropylmethyl)-5-[(2-methoxy-4-pyridyl)carbamothioylamino]-4,5,6,7-tetrahydrobenzothiophene-3-carboxamide Intermediate 117 (50 mg, 0.15 mmol) and intermediate 617 (0.15 mmol) were combined in DCM (2.5 mL) according to the same procedure described for intermediate 614. The crude product was purified by column chromatography eluting with a 0-100% gradient of EtOAc in isohexane, followed by 0-20% MeOH in EtOAc to afford, after dry down, the title compound (11 mg, 15% Yield). $\delta_H$ (300 MHz, Chloroform-d) 12.09 (s, 1H), 8.04 (d, J=5.5 Hz, 1H), 6.73 (s, 3H), 5.86-5.76 (m, 1H), 5.05-4.89 (m, 1H), 3.90 (s, 3H), 3.36-3.23 (m, 2H), 3.23-3.07 (m, 1H), 2.97-2.64 (m, 4H), 2.37-2.11 (m, 1H), 1.67 (tt, J=8.1, 4.3 Hz, 1H), 1.15-1.00 (m, 3H), 0.97-0.81 (m, 3H), 0.67-0.53 (m, 2H), 0.35-0.21 (m, 2H).

Intermediate 619

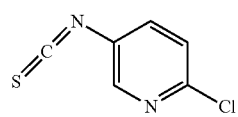

2-chloro-5-isothiocyanato-pyridine

The title compound was prepared according to the same procedure described for intermediate 613 using 5-amino-2-chloropyridine (0.2 g), 1,1'-thiocarbonyldiimidazole (1.59 mmol, 284 mg) in DCM (2 mL) and 4 N HCl in dioxane (0.35 mL). The crude product was carried through to the next stage without purification.

Intermediate 620

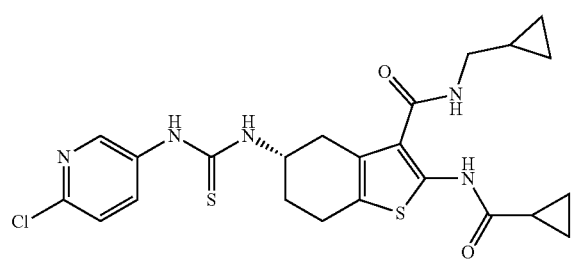 [SMILES: O=C(NCC1CC1)c1c(NC(=O)C2CC2)sc2c1C[C@@H](NC(=S)Nc1ccc(Cl)nc1)CC2]

(5S)-5-[(6-chloro-3-pyridyl)carbamothioylamino]-2-(cyclopropanecarbonylamino)-N-(cyclopropylmethyl)-4,5,6,7-tetrahydrobenzothiophene-3-carboxamide Intermediate 117 (50 mg, 0.15 mmol) and intermediate 619 (0.15 mmol) were combined in DCM (2.5 mL) according to the same procedure described for intermediate 614. The crude product was purified by column chromatography eluting with a 0-100% gradient of EtOAc in isohexane, followed by 0-20% MeOH in EtOAc to afford, after dry down, the title compound (62 mg, 82%). $\delta_H$ 300 MHz, Chloroform-d) 12.01 (s, 1H), 8.52 (s, 1H), 8.22-8.15 (m, 2H), 7.28 (dd, J=8.6, 1.0 Hz, 1H), 6.86 (d, J=7.2 Hz, 1H), 5.75 (t, J=5.2 Hz, 1H), 4.98 (s, 1H), 3.36-3.16 (m, 2H), 3.15-3.00 (m, 1H), 2.87-2.64 (m, 3H), 2.59-2.42 (m, 1H), 1.99-1.83 (m, 1H), 1.72-1.61 (m, 1H), 1.14-0.83 (m, 5H), 0.67-0.54 (m, 2H), 0.27 (dt, J=5.9, 4.6 Hz, 2H).

Intermediate 621

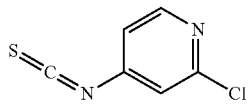

2-chloro-4-isothiocyanato-pyridine

The title compound was prepared according to the same procedure described for intermediate 613 using 4-amino-2-chloropyridine (0.2 g), 1,1'-thiocarbonyldiimidazole (1.59 mmol, 284 mg) in DCM (2 mL) and 4 N HCl in dioxane (0.35 mL). The crude product was carried through to the next stage without purification.

Intermediate 622

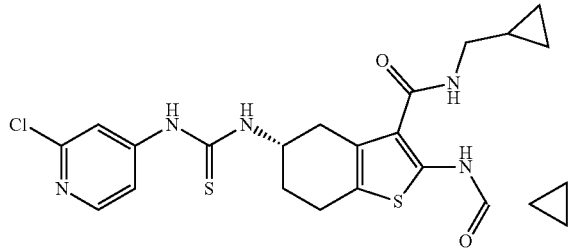

(5S)-5-[(2-chloro-4-pyridyl)carbamothioylamino]-2-(cyclopropanecarbonylamino)-N-(cyclopropylmethyl)-4,5,6,7-tetrahydrobenzothiophene-3-carboxamide Intermediate 117 (50 mg, 0.15 mmol) and intermediate 621 (0.15 mmol) were combined in DCM (2.5 mL) according to the same procedure described for intermediate 614. The crude product was purified by column chromatography eluting with a 0-100% gradient of EtOAc in isohexane, followed by 0-20% MeOH in EtOAc to afford, after dry down, the title compound (59 mg, 78%). $\delta_H$ (300 MHz, Chloroform-d) 12.08 (s, 1H), 9.04 (s, 1H), 8.21-8.06 (m, 1H), 7.75-7.66 (m, 1H), 7.51 (dd, J=5.7, 2.1 Hz, 1H), 7.11 (d, J=7.0 Hz, 1H), 5.69 (t, J=5.2 Hz, 1H), 5.06-4.82 (m, 1H), 3.45-3.14 (m, 2H), 3.14-2.96 (m, 1H), 2.86-2.56 (m, 4H), 1.96-1.78 (m, 1H), 1.79-1.66 (m, 1H), 1.13-0.80 (m, 5H), 0.69-0.55 (m, 2H), 0.28 (dt, J=5.9, 4.6 Hz, 2H).

Intermediate 623

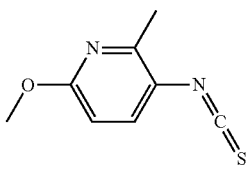

3-isothiocyanato-6-methoxy-2-methyl-pyridine

The title compound was prepared according to the same procedure described for intermediate 613 using 3-amino-6-methoxy-2-picoline (0.2 g), 1,1'-thiocarbonyldiimidazole (1.59 mmol, 284 mg) in DCM (2 mL) and 4N HCl in dioxane (0.35 mL). The crude product was carried through to the next stage without purification.

Intermediate 624

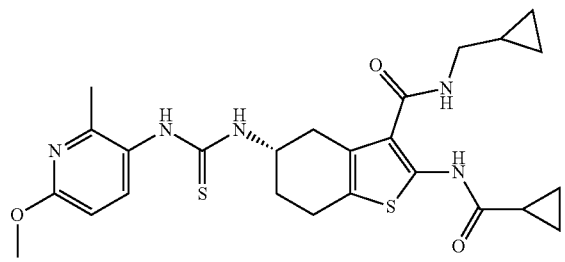 [SMILES: COc1ccc(NC(=S)N[C@H]2CCc3sc(NC(=O)C4CC4)c(C(=O)NCC4CC4)c3C2)c(C)n1]

(5S)-2-(cyclopropanecarbonylamino)-N-(cyclopropylmethyl)-5-[(6-methoxy-2-methyl-3-pyridyl)carbamothioylamino]-4,5,6,7-tetrahydrobenzothiophene-3-carboxamide Intermediate 117 (50 mg, 0.15 mmol) and intermediate 623 (0.15 mmol) were combined in DCM (2.5 mL) according to the same procedure described for intermediate 614. The crude product was purified by column chromatography eluting with a 0-100% gradient of EtOAc in isohexane, followed by 0-20% MeOH in EtOAc to afford, after dry down, the title compound (47 mg, 61% Yield). $\delta_H$ (300 MHz, Chloroform-d) 12.10 (s, 1H), 7.34-7.27 (m, 2H), 6.59 (d, J=8.5 Hz, 1H), 5.83 (t, J=5.2 Hz, 1H), 5.59 (d, J=8.0 Hz, 1H), 4.95-4.79 (m, 1H), 3.92 (s, 3H), 3.32-3.19 (m, 3H), 2.91-2.50 (m, 3H), 2.36 (s, 3H), 2.11-1.85 (m, 2H), 1.71-1.60 (m, 1H), 1.13-0.99 (m, 3H), 0.90 (dt, J=8.0, 3.5 Hz, 2H), 0.64-0.54 (m, 2H), 0.27 (dt, J=5.9, 4.6 Hz, 2H).

453

Intermediate 625

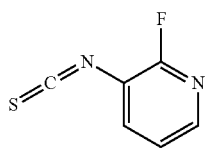

2-fluoro-3-isothiocyanato-pyridine

The title compound was prepared according to the same procedure described for intermediate 613 using 3-amino-2-fluoropyridine (0.2 g), 1,1'-thiocarbonyldiimidazole (1.59 mmol, 284 mg) in DCM (2 mL) and 4 N HCl in dioxane (0.35 mL). The crude product was carried through to the next stage without purification.

Intermediate 626

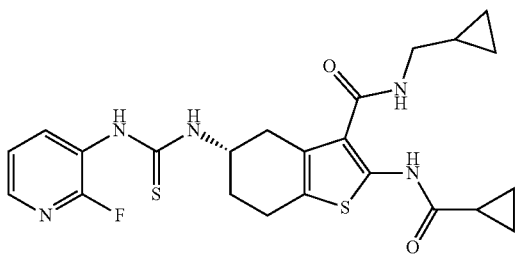 [SMILES: O=C(NCC1CC1)c1c(NC(=O)C2CC2)sc2c1C[C@@H](NC(=S)Nc1cccnc1F)CC2]

(5S)-2-(cyclopropanecarbonylamino)-N-(cyclopropylmethyl)-5-[(2-fluoro-3-pyridyl)carbamothioylamino]-4,5,6,7-tetrahydrobenzothiophene-3-carboxamide Intermediate 117 (50 mg, 0.15 mmol) and intermediate 625 (0.15 mmol) were combined in DCM (2.5 mL) according to the same procedure described for intermediate 614. The crude product was purified by column chromatography eluting with a 0-100% gradient of EtOAc in isohexane, followed by 0-20% MeOH in EtOAc to afford, after dry down, the title compound (25 mg, 34% Yield). $\delta_H$ (300 MHz, Chloroform-d) 12.00 (s, 1H), 8.83 (t, J=9.4 Hz, 1H), 8.50-8.32 (m, 1H), 7.89 (d, J=4.9 Hz, 1H), 7.24-7.13 (m, 2H), 5.73 (t, J=5.2 Hz, 1H), 5.10-4.85 (m, 1H), 3.38-3.15 (m, 2H), 3.16-3.00 (m, 1H), 2.93-2.66 (m, 3H), 2.63-2.49 (m, 1H), 2.00-1.83 (m, 1H), 1.81-1.48 (m, 1H), 1.13-0.98 (m, 3H), 0.98-0.77 (m, 2H), 0.67-0.56 (m, 2H), 0.37-0.23 (m, 2H).

Intermediate 627

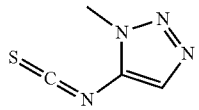

5-isothiocyanato-1-methyl-triazole

The title compound was prepared according to the same procedure described for intermediate 613 using 5-amino-1-methyl-1,2,3-triazole (240 mg, 2.32 mmol), 1,1'-thiocarbonyldiimidazole (479 mg, 2.56 mmol), 4 M HCl in 1,4-dioxane (1.2 mL) in DCM (7 mL). The crude product was purified by column chromatography eluting with a 0-100% gradient of EtOAc in isohexane. Product-containing fractions were combined and concentrated to afford the title compound (72 mg, 22% Yield). $\delta_H$ (300 MHz, Chloroform-d) 7.65 (s, 1H), 3.99 (s, 3H).

Intermediate 628

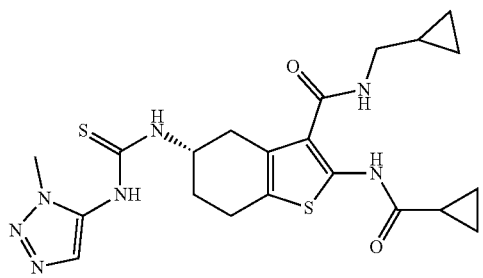 [SMILES: Cn1nncc1NC(=S)N[C@H]1CCc2sc(NC(=O)C3CC3)c(C(=O)NCC3CC3)c2C1]

(5S)-2-(cyclopropanecarbonylamino)-N-(cyclopropylmethyl)-5-[(3-methyltriazol-4-yl)carbamothioylamino]-4,5,6,7-tetrahydrobenzothiophene-3-carboxamide Intermediate 117 (100 mg, 0.30 mmol) was added to a stirred solution of intermediate 627 (72 mg, 0.51 mmol) in DCM (12 mL) and the reaction stirred for 45 min at ambient temperature. The solvent was removed in vacuo and the crude product purified by column chromatography eluting with a 0-100% gradient of EtOAc in isohexane followed by 0-20% MeOH in EtOAc to afford, after dry down, the title compound (213 mg, 87% Yield) as a beige foam. $\delta_H$ (300 MHz, Chloroform-d) 12.08 (s, 1H), 8.60 (s, 1H), 7.69 (s, 1H), 7.30 (d, J=7.5 Hz, 1H), 5.87 (t, J=5.3 Hz, 1H), 5.03-4.84 (m, 1H), 3.86 (s, 3H), 3.36-3.18 (m, 2H), 3.12 (dd, J=15.3, 4.7 Hz, 1H), 2.84 (dd, J=15.5, 4.0 Hz, 1H), 2.79-2.59 (m, 2H), 2.45-2.30 (m, 1H), 2.01-1.88 (m, 1H), 1.77-1.61 (m, 2H), 1.13-0.87 (m, 4H), 0.64-0.53 (m, 2H), 0.27 (dt, J=6.1, 4.6 Hz, 2H).

Intermediate 629

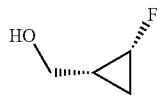

[(1R,2R)-2-fluorocyclopropyl]methanol

To a stirred suspension of (1R,2R)-2-fluorocyclopropanecarboxylic acid (5.00 g, 48 mmol) in THF (25 mL) in an ice-bath under N₂ was added lithium aluminum hydride (32 mL, 64 mmol) dropwise over 15-20 min. [Note: Effervescence observed upon immediate addition and a white precipitate formed after 8 mL of the reagent were added]. Reaction mixture slowly warmed to r.t. o/n. The reaction mixture was then cooled in an ice-bath and water (3 mL) was added followed by 2 M aqueous sodium hydroxide (3 mL). Diethyl ether (30 mL) was then added and the reaction mixture stirred for 1 h at room temperature [Note: quench was exothermic and formed a thick white copious precipitate which at times was not stirring]. The reaction mixture was filtered and washed with diethyl ether (100 mL). The solution was then concentrated under reduced pressure to remove most of the solvent. The residual solution was dried (MgSO$_4$) and concentrated in vacuo to give the title compound in THF (56% wt) (9 g, 92% Yield). $\delta_H$ (300 MHz, d-Chloroform) 4.73 (dtd, J=65.1, 5.9, 2.7 Hz, 1H), 3.94 (ddd, J=11.7, 5.9, 1.4 Hz, 1H), 3.64 (ddd, J=11.7, 8.7, 1.1 Hz, 1H), 1.59 (ddd, J=7.6, 4.8, 2.7 Hz, 1H), 1.33-1.16 (m, 1H), 0.94-0.68 (m, 2H).

Intermediate 630

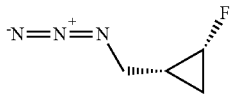

(1R,2R)-1-(azidomethyl)-2-fluoro-cyclopropane

To a stirred solution of intermediate 629 (8.0 g, 39 mmol) in DCM (30 mL, 468 mmol) in an ice-bath were added triethylamine (8 mL, 57.4 mmol) and methansulfonyl chloride (3.6 mL, 46 mmol). The ice-bath was removed and the reaction mixture allowed to stir at room temperature. A second portion of DCM (10 mL) was added. After 1 hour the reaction mixture was diluted with aqueous 0.2 N HCl (50 mL) and the aqueous phase extracted with DCM (2×10 mL). The organics were combined dried and concentrated in vacuo. The residue was then dissolved in anhydrous DMF (20 mL, 259 mmol) at room temperature. Sodium azide (3.0 g, 46 mmol) was added and the reaction mixture stirred at room temperature for 48 hours. The reaction mixture was diluted with diethyl ether (50 mL) and washed with brine (200 mL). The aqueous layer was extracted with diethyl ether (50 mL) and the combined organics dried and concentrated in vacuo. DMF (10 mL) was then added along with sodium azide (1 g, 15 mmol). The reaction mixture was stirred a r.t. for 72 hours. Diethyl ether (50 mL) was added and the solution washed with brine (200 mL). The aqueous layer was extracted with diethyl ether (50 mL) and the combined organics dried and concentrated in vacuo to give the title compound (6.3 g, 84% Yield). $\delta_H$ (300 MHz, d-Chloroform) 4.74 (dtd, J=64.6, 5.9, 2.7 Hz, 1H), 3.36 (td, J=13.7, 13.2, 7.5 Hz, 2H), 1.21 (t, J=7.0 Hz, 1H), 1.02-0.68 (m, 2H).

Intermediate 631

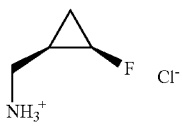

[(1R,2R)-2-fluorocyclopropyl]methylammonium chloride

To a solution of intermediate 630 (6.33 g, 33 mmol) in methanol (10 mL) was added a slurry of palladium on carbon (200 mg) in MeOH (4 mL). The reaction mixture was subjected to vacuum and backfilled with H$_2$ (twice). The reaction mixture was then stirred at room temperature overnight. A second portion of palladium on carbon (50 mg) was added and the reaction mixture stirred under an atmosphere of H$_2$ for 1 hour. The reaction mixture was then filtered through a pre-packed cartridge of celite (1 g) eluting with MeOH. A solution of 1 M HCl in diethyl ether (50 mL) was then added and the resulting solution concentrated in vacuo to give the title compound (3.95 g, 92% Yield). $\delta_H$ (400 MHz, d-MeOH) 4.84 (dtd, J=64.8, 5.9, 2.7 Hz, 1H), 3.14 (dd, J=13.4, 7.3 Hz, 1H), 3.04 (dd, J=13.4, 8.2 Hz, 1H), 1.30-1.16 (m, 1H), 1.02 (dddd, J=12.5, 9.8, 7.4, 5.9 Hz, 1H), 0.88 (dtd, J=23.4, 7.3, 2.7 Hz, 1H).

Intermediate 632

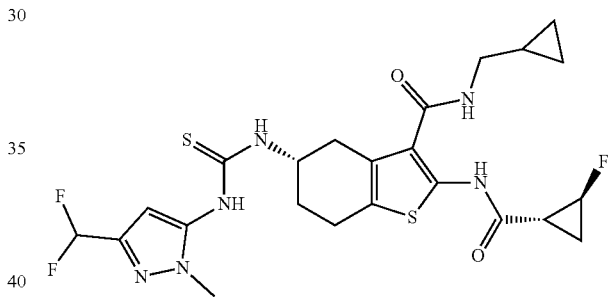

(5S)—N-(cyclopropylmethyl)-5-[[5-(difluoromethyl)-2-methyl-pyrazol-3-yl]carbamothioylamino]-2-[[(1R,2S)-2-fluorocyclopropanecarbonyl]amino]-4,5,6,7-tetrahydrobenzothiophene-3-carboxamide To a stirred solution of intermediate 566 (500 mg, 1.42 mmol) in DCM (10 mL) was added intermediate 568 (410 mg, 1.59 mmol) and the reaction mixture heated to 45° C. for 45 min. Purification by column chromatography with a gradient of 0-80% EtOAc in iso-hexane gave the title compound (785 mg, 79% Yield). $\delta_H$ (300 MHz, DMSO-d6) 11.25-10.81 (m, 1H), 9.17 (s, 1H), 8.24 (d, J=7.5 Hz, 1H), 7.96-7.57 (m, 1H), 6.88 (t, J=54.8 Hz, 1H), 6.45 (s, 1H), 4.89 (d, J=64.9 Hz, 1H), 4.52 (s, 1H), 3.74-3.57 (m, 3H), 3.14 (s, 2H), 3.11-2.98 (m, 1H), 2.73 (s, 2H), 2.67-2.54 (m, 1H), 2.01 (s, 1H), 1.97-1.79 (m, 1H), 1.63-1.43 (m, 1H), 1.31-1.21 (m, 1H), 1.11-0.95 (m, 1H), 0.89-0.76 (m, 1H), 0.49-0.34 (m, 2H), 0.29-0.17 (m, 2H). LCMS [M+H]$^+$ 541, RT 1.24 minutes (Method 3).

Intermediate 633

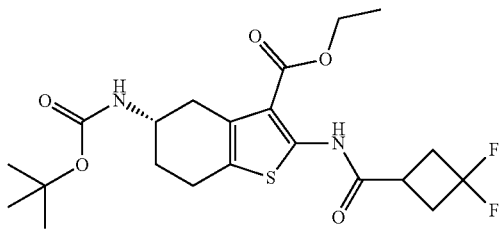 [SMILES: CCOC(=O)c1c(NC(=O)C2CC(F)(F)C2)sc2c1C[C@@H](NC(=O)OC(C)(C)C)CC2]

ethyl (5S)-5-(tert-butoxycarbonylamino)-2-[(3,3-difluorocyclobutanecarbonyl)amino]-4,5,6,7-tetrahydrobenzothiophene-3-carboxylate To a stirred suspension of intermediate 567 (5.00 g, 13.28 mmol) in DCM (250 mL) cooled with an ice-bath were added pyridine (5.4 mL, 66 mmol) and 3,3-difluorocyclobutanecarboxylic acid (1.85 g, 13.3 mmol). 2,4,6-Tripropyl-1,3,5,2,4,6-trioxatriphosphorinane-2,4,6-trioxide (50 mass % solution in EtOAc) (15 mL, 15 mmol) was then added via a dropping funnel over a period of 10 min and the reaction mixture allowed to warm to room temperature After a total of 18 h, the reaction mixture was diluted with $H_2O$ (20 mL) and stirred for 5 min then diluted with brine (50 mL) and the phases separated. The aqueous was extracted with DCM (2×20 mL) and the combined organics were dried (phase separator) and concentrated in vacuo. Purification via column chromatography with a gradient of 0-30% EtOAc in iso-hexane gave the title compound as an off-white solid (4.53 g, 74% Yield). $δ_H$ (400 MHz, DMSO-d6) 11.01 (s, 1H), 6.93 (d, J=7.8 Hz, 1H), 4.28 (q, J=7.0 Hz, 2H), 3.60 (s, 1H), 3.38 (td, J=8.5, 3.1 Hz, 1H), 3.04 (dd, J=17.1, 5.4 Hz, 1H), 2.92-2.73 (m, 4H), 2.73-2.61 (m, 2H), 2.46 (d, J=13.0 Hz, 1H), 1.92 (d, J=12.4 Hz, 1H), 1.66-1.51 (m, 1H), 1.40 (s, 9H), 1.31 (t, J=7.1 Hz, 3H). LCMS [M+H]$^+$ 459, RT 1.50 minutes (Method 3).

Intermediate 634

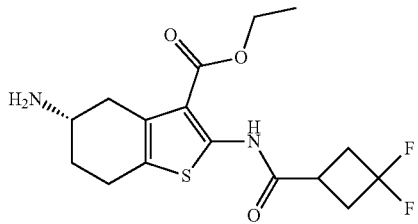 [SMILES: CCOC(=O)c1c(NC(=O)C2CC(F)(F)C2)sc2c1C[C@@H](N)CC2]

ethyl (5S)-5-amino-2-[(3,3-difluorocyclobutanecarbonyl)amino]-4,5,6,7-tetrahydrobenzothiophene-3-carboxylate To a stirred semi-solution intermediate 633 (4.53 g, 9.89 mmol) in anhydrous DCM (30 mL) under nitrogen at r.t. was added trifluoroacetic acid (10 mL). After 1 hr, the reaction mixture was concentrated in vacuo, diluted DCM (100 mL), saturated aq. $NaHCO_3$ (50 mL) and the phases separated. The aqueous was extracted with DCM (3×20 mL), the combined organics dried (phase separator) and concentrated in vacuo. Purification via a SCX-2 cartridge eluting with 7 N NH3 in MeOH gave the title compound (3.84 g, 100% Yield). $δ_H$ (300 MHz, DMSO-d6) 4.29 (q, J=7.1 Hz, 2H), 3.44-3.20 (m, 4H), 3.10-2.96 (m, 2H), 2.93-2.73 (m, 4H), 2.71-2.54 (m, 2H), 2.32 (dt, J=13.9, 6.9 Hz, 1H), 1.99-1.81 (m, 1H), 1.60-1.39 (m, 1H), 1.32 (t, J=7.1 Hz, 3H). LCMS [M+H]$^+$ 359, RT 1.03 minutes (Method 3)

Intermediate 635

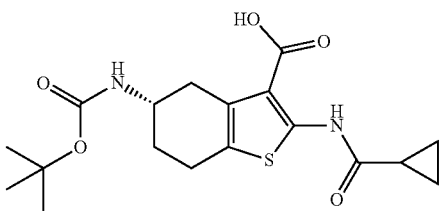 [SMILES: CC(C)(C)OC(=O)N[C@H]1CCc2sc(NC(=O)C3CC3)c(C(=O)O)c2C1]

(5S)-5-(tert-butoxycarbonylamino)-2-(cyclopropanecarbonylamino)-4,5,6,7-tetrahydrobenzothiophene-3-carboxylic acid Intermediate 26 was separated by chiral SFC (using an IG column 250×50 mm, 20 om, eluting with isocratic 25% MeOH in supercritical $CO_2$, 30° C., 360 mL/min, run time of 15 min) to give the title compound. Chiral SFC* RT=3.36 minutes.

* Chiral analysis was preformed using SFC, Lux Cellulose-4 150×4.6 mm, 3 mm, eluting with isocratic 100% MeOH with 0.1% DEA in supercritical $CO_2$, 1.5 mL/min, 8 min run time, 30° C., 100 bar.

Intermediate 636

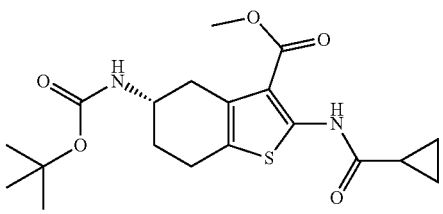 [SMILES: COC(=O)c1c(NC(=O)C2CC2)sc2c1C[C@@H](NC(=O)OC(C)(C)C)CC2]

methyl (5S)-5-(tert-butoxycarbonylamino)-2-(cyclopropanecarbonylamino)-4,5,6,7-tetrahydrobenzothiophene-3-carboxylate Intermediate 635 (2.5 g, 6.6 mmol) was dissolved in MeOH (30 mL) and toluene (60 mL). 2 M (trimethylsilyl)diazomethane in hexanes (5.3 mL, 11 mmol) was added in portions to the stirred solution at ambient temperature and the reaction stirred for 15 min. 2 M (trimethylsilyl)diazomethane in hexanes (1.0 mL, 11 mmol) was added and the reaction stirred for a further 10 min. AcOH was added until effervescence ceased and the volatiles evaporated to afford a brown solid, which was recrystallised from IPA to afford the title compound (2.10 g, 81% Yield). $δ_H$ (300 MHz, Chloroform-d) 11.41 (s, 1H), 4.71-4.50 (m, 1H), 4.07-3.91 (m, 1H), 3.87 (s, 3H), 3.14 (dd, J=17.2, 5.4 Hz, 1H), 2.78-2.68 (m, 2H), 2.59 (dd, J=17.2, 7.3 Hz, 1H), 2.10-1.96

(m, 1H), 1.86-1.72 (m, 1H), 1.67 (tt, J=7.9, 4.6 Hz, 1H), 1.17-1.10 (m, 2H), 0.94 (dt, J=8.0, 3.4 Hz, 2H)

Intermediate 637

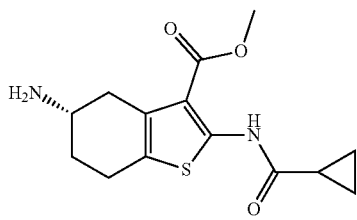 [SMILES: COC(=O)c1c(NC(=O)C2CC2)sc2c1C[C@@H](N)CC2]

methyl (5S)-5-amino-2-(cyclopropanecarbonylamino)-4,5,6,7-tetrahydrobenzothiophene-3-carboxylate Intermediate 636 (2.1 g, 5.32 mmol) was dissolved in DCM (30 mL) and trifluoroacetic acid (6 mL, 79 mmol) was added. The reaction was stirred at ambient temperature for 45 min. The reaction mixture was concentrated in vacuo and taken back up in MeOH (5 mL). Upon dissolution in MeOH, the product crashed out of solution. The solvent was removed under vacuum and the resulting residue suspended in EtOAc (40 mL). The solution was stirred vigorously during addition of saturated aqueous $K_2CO_3$ (15 mL). After 15 min, the organic phase was separated. The aqueous layer was extracted with EtOAc (20 mL) and the combined organic extracts dried ($Na_2SO_4$). The solvent was then removed in vacuo to afford the title compound (2.5 g, quantitative). $\delta_H$ (400 MHz, DMSO-d6) 11.12 (s, 1H), 3.83 (s, 3H), 3.03-2.91 (m, 2H), 2.73-2.52 (m, 2H), 2.35-2.23 (m, 1H), 2.03 (tt, J=7.5, 4.9 Hz, 1H), 1.91-1.81 (m, 3H), 1.53-1.37 (m, 1H), 0.96-0.82 (m, 4H).

Intermediate 638

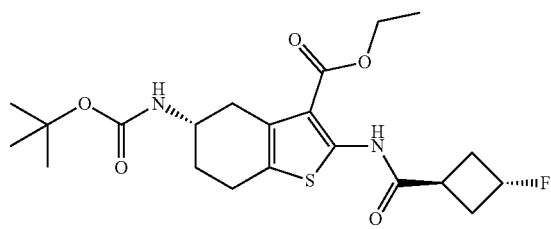 [SMILES: CCOC(=O)c1c(NC(=O)[C@H]2C[C@H](F)C2)sc2c1C[C@@H](NC(=O)OC(C)(C)C)CC2]

ethyl (5S)-5-(tert-butoxycarbonylamino)-2-[trans-(3-fluorocyclobutanecarbonyl)amino]-4,5,6,7-tetrahydrobenzothiophene-3-carboxylate Trans-3-fluorocyclobutane-1-carboxylic acid (1.67 g, 13.4 mmol, 95 mass %) followed by 2,4,6-tripropyl-1,3,5,2,4,6-trioxatriphosphorinane-2,4,6-trioxide (15.8 mL, 26.8 mmol, 50 mass % as a solution in EtOAc) were added to a solution of intermediate 567 (5.05 g, 13.4 mmol, 97 mass %) in DCM (100 mL) cooled to 0° C. and under nitrogen. The reaction was stirred for 20 hours, during this time the ice bath was allowed to melt and the reaction warm to room temperature. Added water (100 mL) and stirred the reaction for a further 10 mins. The layers were separated and the aq. layer was extracted with DCM (2×20 mL). The combined organic layers were washed with sat. aq. $NH_4Cl$ (100 mL) and this aq. Layer was extracted with DCM (2×20 mL). The combined organic layers were passed through a phase separation cartridge, concentrated in vacuo and purified by flash column chromatography on silica (gradient elution with 0% to 100% EtOAc in isohexanes) to give the title compound (5.14 g, 87% Yield). LCMS [M+H]$^+$ 441, RT 1.46 minutes (Method 33).

Intermediate 639

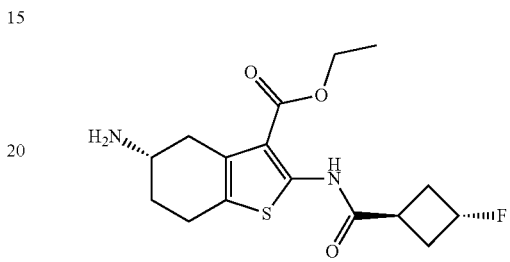

ethyl (5S)-5-amino-2-[trans-(3-fluorocyclobutanecarbonyl)amino]-4,5,6,7-tetrahydrobenzothiophene-3-carboxylate Trifluoroacetic acid (9.1 mL, 120 mmol) was added slowly to a solution of intermediate 638 (5.14 g, 11.7 mmol) in DCM (29 mL) under nitrogen. The reaction was stirred at r.t. for 2 hours 15 mins and then concentrated in vacuo. The material was re-dissolved in DCM (75 mL) and washed with sat. aq. $NaHCO_3$ (2×25 mL). The combined aq. layers were extracted with DCM (2×25 mL). The combined organic layers were passed through a phase separation cartridge, concentrated in vacuo to give the title compound which was used without further purification (3.48 g, 87% Yield). LCMS [M+H]$^+$ 341, RT 0.95 minutes (Method 33).

Intermediate 640

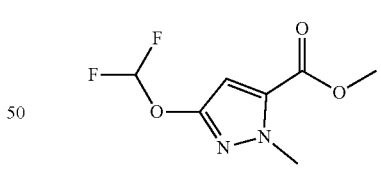

methyl 5-(difluoromethoxy)-2-methyl-pyrazole-3-carboxylate

Methyl 3-hydroxy-1-methylpyrazole-5-carboxylate (10 g, 60.8 mmol) was dissolved in DMF (200 mL). sodium chlorodifluoroacetate (23.2 g, 152 mmol) was added followed by potassium carbonate (25.2 g, 182 mmol). The reaction mixture was heated to 80° C. with stirring under $N_2$ overnight. The reaction was cooled & poured into water (200 mL). The mixture was then extracted with EtOAc (3×200 mL) and the combined organic extracts dried ($Na_2SO_4$) and concentrated under reduced pressure. The residue was purified by column chromatography eluting with a gradient of 0-25% EtOAc in iso-hexanes to give the title compound (6.41 g, 51% Yield). $\delta_H$ (300 MHz, Chloroform-d) 6.76 (t, J=73.1 Hz, 1H), 6.41 (s, 1H), 4.08 (s, 3H), 3.88 (s, 3H).

Intermediate 641

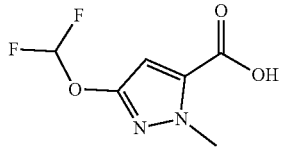

5-(difluoromethoxy)-2-methyl-pyrazole-3-carboxylic acid

Intermediate 640 (6.4 g, 31 mmol) was diluted in methanol (130 mL) and 2 M aqueous sodium hydroxide (31 mL, 62 mmol). The reaction was stirred at 50° C. for 1.25 h. The reaction mixture was cooled to room temperature and acidified to pH 1 with 2 M HCl (30 mL). The reaction mixture was concentrated under vacuum to remove most of the MeOH. The resulting aqueous solution was extracted with EtOAc (3×60 mL) and the combined organic extracts dried (Na$_2$SO$_4$) and concentrated in vacuo to afford the title compound (5.87 g, 98% Yield). $\delta_H$ (300 MHz, DMSO-d6) 13.70 (s, 1H), 7.26 (t, J=73.2 Hz, 1H), 6.51 (s, 1H), 3.99 (s, 3H).

Intermediate 642

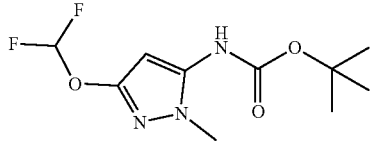 [SMILES: Cn1nc(OC(F)F)cc1NC(=O)OC(C)(C)C]

tert-butyl N-[5-(difluoromethoxy)-2-methyl-pyrazol-3-yl]carbamate

Intermediate 641 (6.00 g, 31.2 mmol) was dissolved in tert-butyl alcohol (100 mL, 1100 mmol) and triethylamine (13.1 mL, 93.7 mmol) was added. The reaction mixture was cooled using an ice bath and diphenylphosphoryl azide (10.1 mL, 46.8 mmol) added dropwise. The reaction mixture was stirred at 0° C. for 30 minutes. The ice bath was then removed and the reaction mixture heated to 85° C. for 3 h. The reaction was cooled to room temperature and poured into water (150 mL). The mixture was extracted with EtOAc (3×150 mL) and the combined organic extracts dried (Na$_2$SO$_4$) and concentrated in vacuo. The resulting residue was purified by column chromatography eluting with a gradient of 0-40% EtOAc in iso-hexanes to give the title compound (6.1 g, 74% Yield). $\delta_H$ (300 MHz, Chloroform-d) 6.75 (t, J=73.5 Hz, 1H), 6.37 (s, 1H), 5.82 (s, 1H), 3.63 (s, 3H), 1.50 (s, 9H).

Intermediate 643

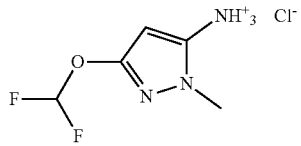

[5-(difluoromethoxy)-2-methyl-pyrazol-3-yl]ammonium chloride

Intermediate 642 (3.0 g, 11.4 mmol) was suspended in 1,4-dioxane (25 mL) and hydrochloric acid (4.0 mol/L) in dioxane (5.7 mL, 23 mmol) was added. The suspension was stirred for 45 min. Methanol (5 mL) was added and the reaction mixture stirred for 5 h at room temperature. The reaction mixture was then stored at −21° C. for 2 days. Reaction mixture was defrosted and a second portion of hydrochloric acid (4.0 mol/L) in dioxane (5 mL, 20 mmol) was added and stirred reaction mixture heated to 45° C. for 90 min. The reaction mixture was then cooled to room temperature and concentrated in vacuo. The resulting oil was stirred vigorously with diethyl ether (25 mL) for 15 min. The ether layer was then decanted and the residual oil concentrated under reduced pressure to give the title compound (2.55 g, quantitative). $\delta_H$ (300 MHz, DMSO-d6) 8.00 (s, 3H), 7.13 (t, J=73.9 Hz, 1H), 5.09 (s, 1H), 3.44 (s, 3H).

Intermediate 644

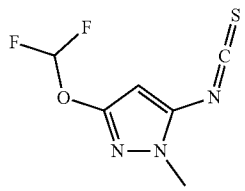

3-(difluoromethoxy)-5-isothiocyanato-1-methyl-pyrazole

A solution of Intermediate 643 (2.5 g, 15 mmol) in water (25 mL) was added dropwise to a vigorously stirred mixture of sodium carbonate (8.1 g, 77 mmol), DCM (50 mL), water (25 mL) and thiophosgene (3.5 g, 31 mmol) at 0° C. After the addition was complete, the reaction was stirred at this temperature for 10 min, the ice bath was then removed and the reaction mixture was stirred at room temperature for 45 min. The reaction mixture was partitioned with phase separator cartridge. The aqueous layer was then extracted with DCM (30 mL). The combined organic extracts were concentrated under reduced pressure and purified by column chromatography eluting with a gradient of 0-40% ethyl acetate in iso-hexanes to afford the title compound (1.37 g, 44% Yield). $\delta_H$ (300 MHz, Chloroform-d) 6.76 (t, J=73.0 Hz, 1H), 5.87 (s, 1H), 3.70 (s, 3H).

Intermediate 645

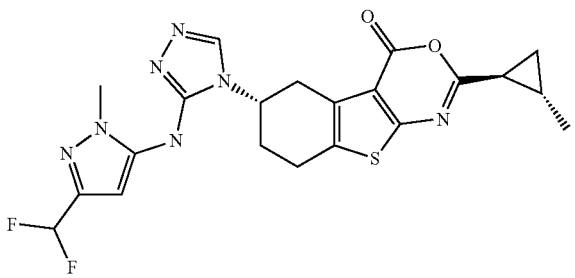 [SMILES: C[C@H]1C[C@@H]1c1nc2sc3c(c2c(=O)o1)C[C@@H](n1cnnc1Nc1cc(C(F)F)nn1C)CC3]

(6S)-6-[3-[[5-(difluoromethyl)-2-methyl-pyrazol-3-yl]amino]-1,2,4-triazol-4-yl]-2-[(1S,2S)-2-methylcyclopropyl]-5,6,7,8-tetrahydrobenzothiopheno[2,3-d][1,3]oxazin-4-one Intermediate 500 (950 mg, 1.9 mmol) was suspended in DMF (38 mL) and heated to 55° C. with stirring prior to addition of EDC (450 mg, 2.3 mmol). The reaction was heated at this temperature for 40 min. The reaction mixture was concentrated in vacuo and the residue purified by column chromatography eluting with a 0-100% gradient of EtOAc in isohexane to give the title compound (770 mg, 82% Yield). $\delta_H$ (300 MHz, d-Chloroform) 7.93-7.83 (m, 1H), 6.56 (t, J=55.2 Hz, 1H), 6.21 (s, 1H), 5.20-4.85 (m, 1H), 3.80 (s, 3H), 3.65 (dd, J=15.8, 6.4 Hz, 1H), 3.23-3.02 (m, 2H), 2.94-2.80 (m, 1H), 2.47-2.18 (m, 3H), 1.73-1.57 (m, 2H), 1.53-1.41 (m, 1H), 1.24-1.17 (m, 3H), 1.03-0.91 (m, 1H).

Intermediate 646

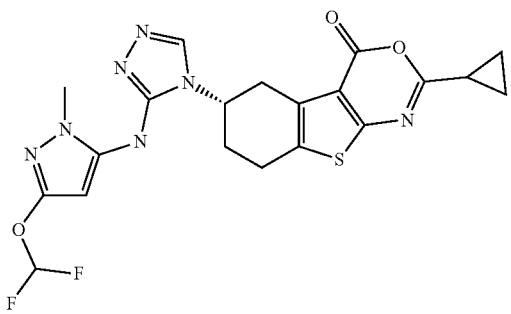 [SMILES: Cn1nc(OC(F)F)cc1Nc1nncn1[C@H]1CCc2sc3nc(C4CC4)oc(=O)c3c2C1]

(6S)-2-cyclopropyl-6-[3-[[5-(difluoromethoxy)-2-methyl-pyrazol-3-yl]amino]-1,2,4-triazol-4-yl]-5,6,7,8-tetrahydrobenzothiopheno[2,3-d][1,3]oxazin-4-one Intermediate 660 (10.5 g, 2.13 mmol) was suspended in MeCN (42 mL) and heated to 55° C. with stirring prior to addition of EDC (499 mg, 2.55 mmol). The reaction was heated at this temperature for 40 min. The reaction mixture was concentrated in vacuo and the residue purified by column chromatography eluting with a 0-100% gradient of EtOAc in isohexane to give the title compound (650 mg, 64% Yield). $\delta_H$ (300 MHz, d-Chloroform) 7.54 (s, 1H), 6.79 (t, J=73.9 Hz, 1H), 5.42 (s, 1H), 4.78-4.57 (m, 1H), 3.66-3.54 (m, 4H), 3.15-2.83 (m, 3H), 2.38-2.24 (m, 2H), 2.01-1.91 (m, 1H), 1.33-1.06 (m, 4H).

Intermediate 647

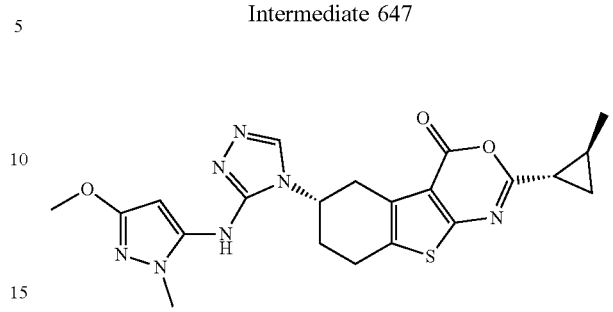

(6S)-6-[3-[(5-methoxy-2-methyl-pyrazol-3-yl)amino]-1,2,4-triazol-4-yl]-2-[(1S,2S)-2-methylcyclopropyl]-5,6,7,8-tetrahydrobenzothiopheno[2,3-d][1,3]oxazin-4-one EDC (20 mg, 0.11 mmol) was added to an opaque white solution of intermediate 663 (50 mg, 0.11 mmol) in DMF (1.6 mL) under an atmosphere of $N_2$ at 50° C. The reaction mixture was stirred at 50° C. for 1.5 h then stirred at room temperature overnight. EtOAc (50 mL) was added followed by water (40 mL). The aqueous layer was extracted with EtOAc (2×20 mL). The combined organic layers were then washed with Brine (30 mL), dried and concentrated in vacuo. The resulting residue was purified by column chromatography eluting with a gradient of 0-100% EtOAc in Hexanes followed by 0-20% MeOH in EtOAc to give the title compound (32 mg, 66% Yield). LCMS [M+H]⁺ 454, RT 1.07 minutes (Method 33).

Intermediate 648

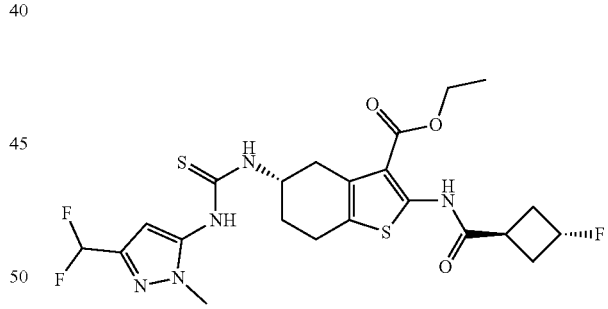

ethyl (5S)-5-[[5-(difluoromethyl)-2-methyl-pyrazol-3-yl]carbamothioylamino]-2-[trans-(3-fluorocyclobutanecarbonyl)amino]-4,5,6,7-tetrahydrobenzothiophene-3-carboxylate Intermediate 568 (756 mg, 2.94 mmol) was added to a solution of intermediate 639 (1.00 g, 2.94 mmol) dissolved in DCM (14.7 mL) under air. The reaction was stirred at r.t. for 4 hours, concentrated in vacuo and purified by flash column chromatography on silica (gradient elution with 0% to 100% EtOAc in isohexanes) to give the title compound (1.38 g, 84% Yield). LCMS [M+H]⁺ 530, RT 1.35 minutes (Method 33).

Intermediate 649

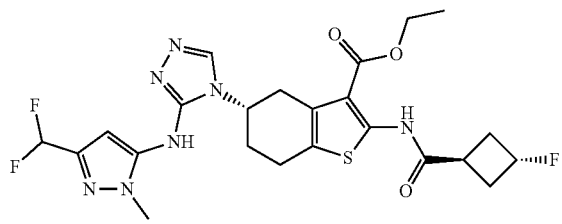 [SMILES: CCOC(=O)c1c(NC(=O)[C@H]2C[C@H](F)C2)sc2c1C[C@@H](n1cnnc1Nc1cc(C(F)F)nn1C)CC2]

ethyl (5S)-5-[3-[[5-(difluoromethyl)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxylate A solution of methanesulfonyl chloride (0.32 mL, 4.1 mmol) in DCM (1.9 mL) was added dropwise to a solution of intermediate 648 (1.96 g, 3.69 mmol) and triethylamine (1.6 mL, 11 mmol) in DCM (35 mL) at 0° C. and under nitrogen. The reaction was stirred at 0° C. for 1 hour. The reaction was diluted with DCM (15 mL) and washed with sat. aq. NH₄Cl (50 mL). The layers were separated and the aq. layer extracted with DCM (2×20 mL). The combined organic layers were passed through a phase separation cartridge and concentrated in vacuo. This material was dissolved in DMF (19 mL) and formic acid hydrazide (244 mg, 4.06 mmol) was added. The reaction was stirred at r.t. for 2.5 hours. Water (9 mL) followed by sodium carbonate (1.17 g, 11.1 mmol) were added and the reaction was stirred for 9 h at 45° C. The reaction was cooled to r.t., water (75 mL) and EtOAc (50 mL) were added and the layers separated. The aq. layer was extracted with EtOAc (2×20 mL). The combined organic layers were washed with water (3×30 mL), then brine (30 mL), passed through a phase separation cartridge, concentrated in vacuo and purified by flash column chromatography on silica (gradient elution with 0% to 100% EtOAc in isohexanes) followed by further flash column chromatography on silica (gradient elution with 0% to 10% MeOH in DCM) to give the title compound (1.41 g, 71% Yield). LCMS [M+H]⁺ 538, RT 2.02 minutes (Method 3).

Intermediate 650

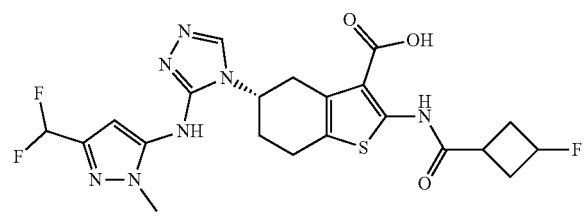 [SMILES: Cn1nc(C(F)F)cc1Nc1nncn1[C@H]1CCc2sc(NC(=O)C3CC(F)C3)c(C(=O)O)c2C1]

(5S)-5-[3-[[5-(difluoromethyl)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxylic acid Sodium hydroxide (5.2 mL, 10 mmol, 2 M aq. solution) was added to a solution of intermediate 649 (1.41 g, 2.62 mmol) in THF (26 mL). The reaction was stirred at r.t. for 22 hours then at 45° C. for 2 hours. The reaction was cooled to r.t. and partially concentrated in vacuo to remove the organic solvent. Added DCM (30 mL) and water (30 mL) and separated the layers. The aq. layer was extracted with DCM (2×30 mL) followed by 5% MeOH in DCM (6×30 mL). 5% MeOH in EtOAc (100 mL) was added to the aq. layer, which was then acidified to pH 4-5 with 2 M aq. HCl (7 mL) and separated the layers. The aq. layer was extracted with 5% MeOH in EtOAc (2×50 mL), the combined 5% MeOH in EtOAc layers were washed with brine (70 mL), passed through a phase separation cartridge and concentrated in vacuo to give a solid which was triturated with Et₂O to give the title compound which was used without further purification (445 mg, 33% Yield). δ_F (282 MHz, Methanol-d4) −113.32--−113.81 (m), −164.29--−164.78 (m), −166.68--−167.12 (m). LCMS [M+H]⁺ 510, RT 0.84 minutes (Method 33).

Intermediate 651

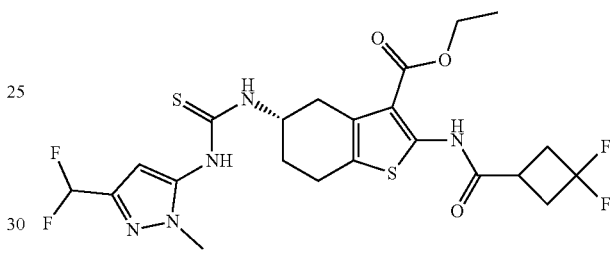

ethyl (5S)-2-[(3,3-difluorocyclobutanecarbonyl)amino]-5-[[5-(difluoromethyl)-2-methyl-pyrazol-3-yl]carbamothioylamino]-4,5,6,7-tetrahydrobenzothiophene-3-carboxylate To a stirred solution of intermediate 634 (1.51 g, 4.21 mmol) in DCM (30 mL) at room temperature intermediate 568 (1.15 g, 4.47 mmol) was added. The reaction mixture was heated to 40° C. for 40 min. The reaction was concentrated in vacuo and purified by column chromatography eluting with 0-80% EtOAc in iso-hexane to give the title compound (2.29 g, 99% Yield). LCMS [M+H]⁺ 548, RT 1.17 minutes (Method 7).

Intermediate 652

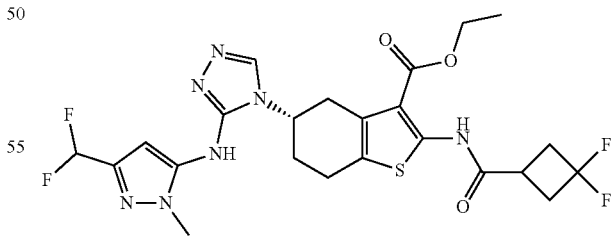

ethyl (5S)-2-[(3,3-difluorocyclobutanecarbonyl)amino]-5-[3-[[5-(difluoromethyl)-2-methyl-pyrazol-3-yl]amino]-1,2,4-triazol-4-yl]-4,5,6,7-tetrahydrobenzothiophene-3-carboxylate Synthesised in the same manner as intermediate Example 229, using intermediate 651 (2.29 g, 4.18 mmol) and com-

Intermediate 653 parable stoichiometries of reagents. Purification by column chromatography eluting with 0-80% EtOAc in iso-hexane gave the title compound (1.41 g, 55% Yield). LCMS [M+H]+ 556, RT 2.10 minutes (Method 3).

Intermediate 653

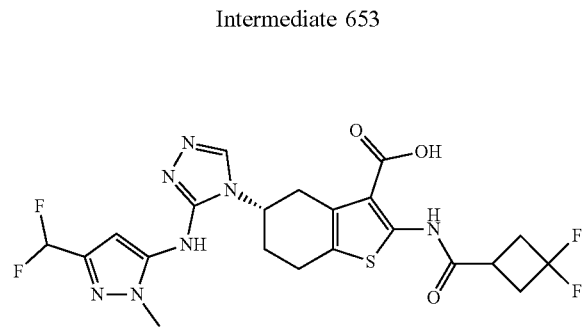

(5S)-2-[(3,3-difluorocyclobutanecarbonyl)amino]-5-[3-[[5-(difluoromethyl)-2-methyl-pyrazol-3-yl]amino]-1,2,4-triazol-4-yl]-4,5,6,7-tetrahydrobenzothiophene-3-carboxylic acid To a stirred solution of intermediate 652 (1.18 g, 1.91 mmol) in a mixture of 1,4-dioxane (20 mL) and water (20 mL) at r.t. was added lithium hydroxide monohydrate (160 mg, 3.76 mmol). The reaction mixture was stirred at r.t. for 36 hours then diluted with DCM (50 mL) and water (30 mL). Saturated aq. NaHCO$_3$ (20 mL) was added and a precipitate formed which did not re-dissolve upon addition of water (20-30 mL). The phases were separated and the organics discarded. The aqueous phase acidified with 2 M HCl (20 mL) and extracted with a mixture of EtOAc (100 mL) and MeOH (10 mL). The aqueous layer was re-extracted with EtOAC (3×100 mL). The combined organics were dried and concentrated in vacuo to give the title compound (693 mg, 1.10 mmol, 58% Yield). LCMS [M+H]+ 528, RT 0.71 minutes (Method 7).

Intermediate 654

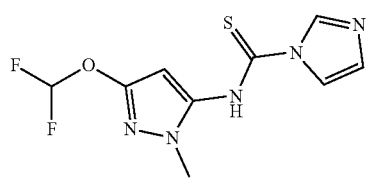 [SMILES: Cn1nc(OC(F)F)cc1NC(=S)n1ccnc1]

N-[5-(difluoromethoxy)-2-methyl-pyrazol-3-yl]imidazole-1-carbothioamide

To a stirred suspension of 5-(difluoromethoxy)-2-methyl-pyrazol-3-amine hydrochloride (1.00 g, 5.01 mmol) in DCM (15 mL) at room temperature were added DIPEA (1.3 mL, 7.5 mmol) and 1,1'-thiocarbonyldiimidazole (1.05 g, 5.60 mmol). The reaction mixture was used directly in the next step. LCMS [M−H]− 272, RT 1.42 minutes (Method 7).

Intermediate 655

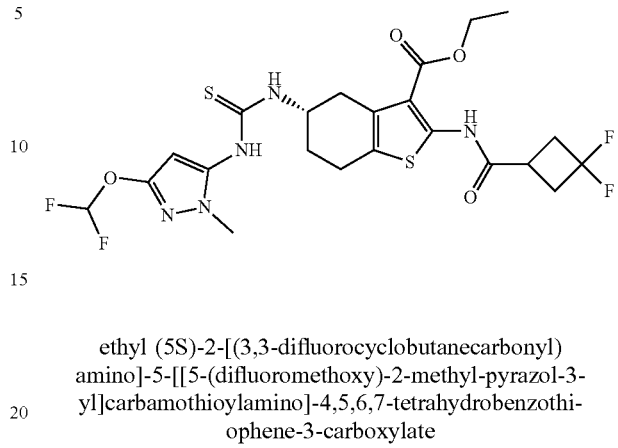

ethyl (5S)-2-[(3,3-difluorocyclobutanecarbonyl)amino]-5-[[5-(difluoromethoxy)-2-methyl-pyrazol-3-yl]carbamothioylamino]-4,5,6,7-tetrahydrobenzothiophene-3-carboxylate To a stirred solution of 0.3 N intermediate 654 in DCM (16.3 mL g, 5.00 mmol) at room temperature was added intermediate 634 (1.68 g, 4.69 mmol). After 2 hr, the reaction mixture was concentrated in vacuo and purified by column chromatography eluting with 0-80% EtOAc in iso-hexane to give the title compound (1.63 g, 56% Yield). LCMS [M+H]+ 564, RT 1.19 minutes (Method 7).

Intermediate 656

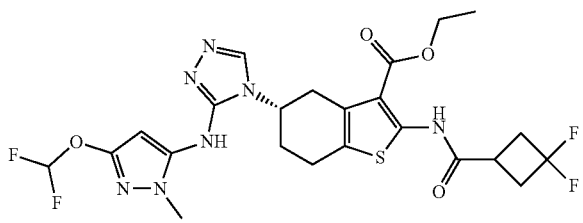 [SMILES: CCOC(=O)c1c(NC(=O)C2CC(F)(F)C2)sc2c1C[C@@H](n1cnnc1Nc1cc(OC(F)F)nn1C)CC2]

ethyl (5S)-2-[(3,3-difluorocyclobutanecarbonyl)amino]-5-[3-[[5-(difluoromethoxy)-2-methyl-pyrazol-3-yl]amino]-1,2,4-triazol-4-yl]-4,5,6,7-tetrahydrobenzothiophene-3-carboxylate Synthesised in the same manner as Example 229, using intermediate 655 (1.63 g, 2.89 mmol) and comparable stoichiometries of reagents. Purification by column chromatography eluting with 0-80% EtOAc in iso-hexane gave the title compound (826 mg, 45% Yield). δ$_H$ (300 MHz, MeOD-d4) 8.22 (s, 1H), 6.89 (t, J=73.8 Hz, 1H), 5.74 (s, 1H), 4.54 (tt, J=9.7, 5.2 Hz, 1H), 4.36 (q, J=7.1 Hz, 2H), 4.28-4.02 (m, 1H), 3.62 (d, J=6.5 Hz, 3H), 3.55 (dt, J=16.7, 3.7 Hz, 1H), 3.29-3.19 (m, 1H), 3.10-2.95 (m, 1H), 2.98-2.79 (m, 5H), 2.40-2.21 (m, 2H), 1.34 (t, J=7.1 Hz, 3H). LCMS [M+H]+ 572, RT 2.17 minutes (Method 3).

Intermediate 657

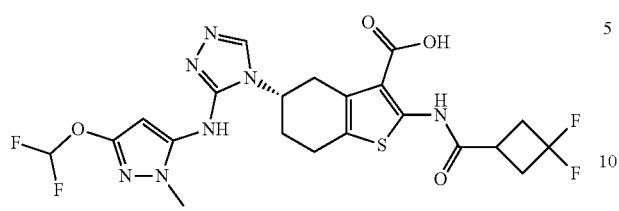

(5S)-2-[(3,3-difluorocyclobutanecarbonyl)amino]-5-[3-[[5-(difluoromethoxy)-2-methyl-pyrazol-3-yl]amino]-1,2,4-triazol-4-yl]-4,5,6,7-tetrahydrobenzothiophene-3-carboxylic acid To a stirred solution of intermediate 656 (825 mg, 1.44 mmol) in 1,4-dioxane (12 mL) and water (12 mL) at r.t. was added lithium hydroxide monohydrate (130 mg, 3.05 mmol). The reaction mixture was stirred at r.t. overnight then diluted with DCM (50 mL) and water (30 mL). Saturated aq. NaHCO$_3$ (30 mL) was added and a precipitate formed. The phases were separated, the aqueous phase was re-extracted with DCM (20 mL) and the organics discarded. The aqueous phase was acidified with 2 M HCl (20 mL) and extracted with a mixture of EtOAc (90 mL) and MeOH (10 mL). The aqueous layer was re-extracted with EtOAc (3×50 mL). The combined organics were dried (phase separator) and concentrated in vacuo to give the title compound (389 mg, 45% Yield). LCMS [M+H]$^+$ 544, RT 0.69 minutes (Method 7).

Intermediate 658

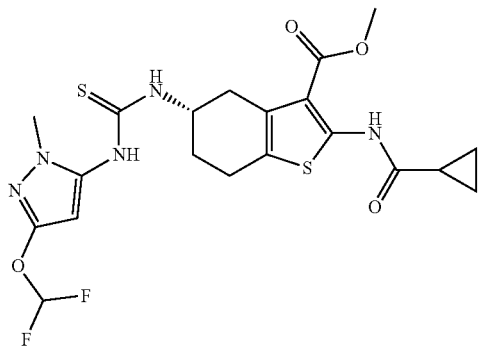 [SMILES: COC(=O)c1c(NC(=O)C2CC2)sc2c1C[C@@H](NC(=S)Nc1cc(OC(F)F)nn1C)CC2]

methyl (5S)-2-(cyclopropanecarbonylamino)-5-[[5-(difluoromethoxy)-2-methyl-pyrazol-3-yl]carbamothioylamino]-4,5,6,7-tetrahydrobenzothiophene-3-carboxylate To a stirred solution of intermediate 636 (2.0 g, 6.8 mmol) in DCM (20 mL) was added a solution of Intermediate 644 (1.4 g, 6.8 mmol) in DCM (20 mL). The reaction mixture was stirred at room temperature for 10 minutes. The reaction mixture was concentrated under reduced pressure and purified by column chromatography eluting with a gradient of 0-100% ethyl acetate in iso-hexanes to give the title compound (2.54 g, 75% Yield). δ$_H$ (300 MHz, Chloroform-d) 11.40 (s, 1H), 7.55 (s, 1H), 6.78 (t, J=72.9 Hz, 1H), 6.29 (d, J=8.0 Hz, 1H), 5.81 (s, 1H), 4.87-4.65 (m, 1H), 3.88 (s, 3H), 3.67 (s, 3H), 3.24 (dd, J=17.1, 5.4 Hz, 1H), 2.91-2.58 (m, 3H), 2.18-1.91 (m, 1H), 1.67 (tt, J=8.2, 4.5 Hz, 1H), 1.12 (dt, J=4.6, 3.3 Hz, 2H), 0.97 (dt, J=8.0, 3.4 Hz, 2H).

Intermediate 659

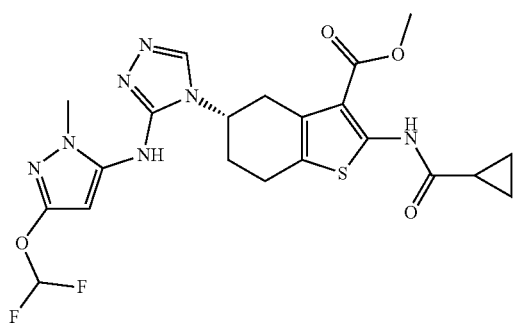 [SMILES: COC(=O)c1c(NC(=O)C2CC2)sc2c1C[C@@H](n1cnnc1Nc1cc(OC(F)F)nn1C)CC2]

methyl (5S)-2-(cyclopropanecarbonylamino)-5-[3-[[5-(difluoromethoxy)-2-methyl-pyrazol-3-yl]amino]-1,2,4-triazol-4-yl]-4,5,6,7-tetrahydrobenzothiophene-3-carboxylate Synthesised in the same manner as Example 229, using intermediate 658 (2.5 g, 5.0 mmol) and comparable stoichiometries of reagents. The product was purified by column chromatography (eluting with a 0-100% gradient of EtOAc in isohexane) to afford the title compound (1.5 g, 59% Yield) as a pale brown oil. δ$_H$ (300 MHz, Chloroform-d) 11.42 (s, 1H), 7.50 (s, 1H), 6.79 (t, J=73.9 Hz, 1H), 5.45 (s, 1H), 4.74-4.58 (m, 1H), 3.88 (s, 3H), 3.64 (s, 3H), 3.43 (dd, J=17.2, 5.7 Hz, 1H), 3.01-2.66 (m, 2H), 2.32-2.14 (m, 2H), 1.69 (tt, J=7.8, 4.5 Hz, 1H), 1.15 (dt, J=4.4, 3.3 Hz, 2H), 1.03-0.90 (m, 2H).

Intermediate 660

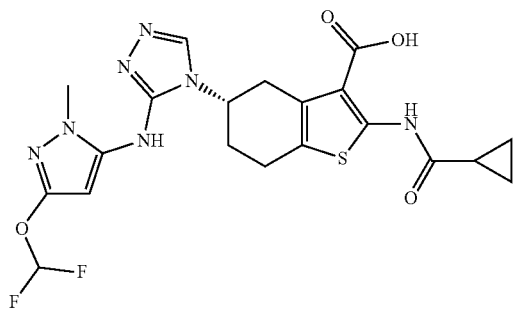 [SMILES: Cn1nc(OC(F)F)cc1Nc1nncn1[C@H]1CCc2sc(NC(=O)C3CC3)c(C(=O)O)c2C1]

(5S)-2-(cyclopropanecarbonylamino)-5-[3-[[5-(difluoromethoxy)-2-methyl-pyrazol-3-yl]amino]-1,2,4-triazol-4-yl]-4,5,6,7-tetrahydrobenzothiophene-3-carboxylic acid Intermediate 659 (1.51 g, 2.98 mmol) was dissolved in THF (25 mL) and 2 M aqueous sodium hydroxide (5.95 mL, 11.9 mmol) added. Reaction heated to 50° C. with stirring for 6 h. The volatiles were removed in vacuo and the aqueous solution acidified to pH5 with 2 M HCl. A thick purple precipitate formed, which was diluted with water and filtered, washing with diethyl ether. The residue was dried in vacuum pistol (3 mBar, 50° C.) overnight to afford the title compound (1.05 g, 71% Yield). $\delta_H$ (400 MHz, DMSO-d6) 13.24 (s, 1H), 12.04 (s, 1H), 11.43 (s, 1H), 8.84-8.39 (m, 1H), 8.21 (s, 1H), 7.42-6.94 (m, 1H), 5.99-5.60 (m, 1H), 4.53-4.32 (m, 1H), 3.63-3.34 (m, 31H), 2.94-2.73 (m, 3H), 2.30-2.06 (m, 21H), 1.99 (tt, J=7.7, 5.2 Hz, 1H), 0.97-0.85 (m, 4H). LCMS [M+H]⁺ 494, RT 0.96 minutes (Method 26).

Intermediate 661

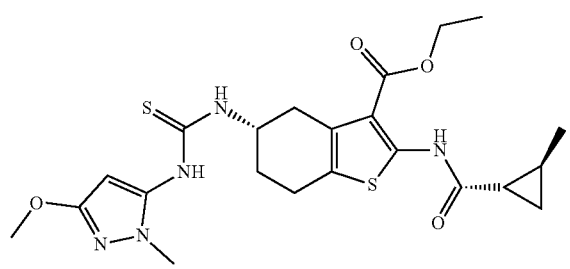

ethyl (5S)-5-[[(5-methoxy-2-methyl-pyrazol-3-yl)carbamothioylamino]-2-[[(1S,2S)-2-methylcyclopropanecarbonyl]amino]-4,5,6,7-tetrahydrobenzothiophene-3-carboxylate 1,1'-Thiocarbonyldiimidazole (1.70 mg, 9.07 mmol, 95 mass %) followed by DIPEA (1.45 mL, 8.34 mmol) were added to a solution of intermediate 518 (2.58 mg, 7.56 mmol, 48 mass % in 1,4-dioxane) in DCM (34 mL) under air. The reaction was stirred at room temperature for 19 hours. A solution of intermediate 496 (2.55 g, 7.58 mmol, 96 mass %) in DCM (19 mL) was added to the reaction and stirring continued for a further 3.5 hours at room temperature. The reaction was concentrated in vacuo and purified by flash column chromatography on silica (gradient elution with 0% to 100% EtOAc in isohexanes) to give the title compound (2.14 g, 57% Yield). LCMS [M+H]⁺ 492, RT 1.32 minutes (Method 33).

Intermediate 662

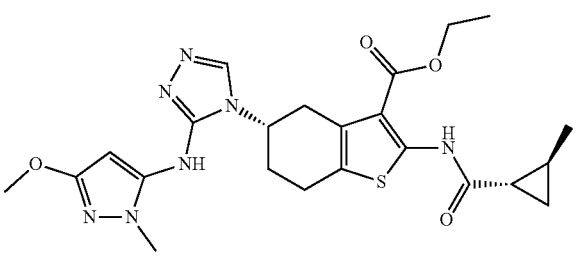

ethyl (5S)-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxylate A solution of methanesulfonyl chloride (0.37 mL, 4.8 mmol) in DCM (3.5 mL) was added dropwise to a solution of intermediate 661 (2.14 g, 4.35 mmol) and triethylamine (1.8 mL, 13 mmol) in DCM (40 mL) at 0° C. and under nitrogen. The reaction was stirred at 0° C. for 45 mins. The reaction was diluted with DCM (10 mL) and washed with sat. aq. NH₄Cl (50 mL). The layers were separated, and the aq. layer extracted with DCM (2×20 mL). The combined organic layers were passed through a phase separation cartridge and concentrated in vacuo. This material was dissolved in DMF (22 mL) and formic acid hydrazide (288 mg, 4.79 mmol) was added. The reaction was stirred at r.t. for 1.5 hours. Water (11 mL) followed by sodium carbonate (1.38 g, 13.1 mmol) were added and the reaction was stirred for 12 h at 45° C. The reaction was cooled to r.t., water (100 mL) and EtOAc (75 mL) were added and the layers separated. The aq. layer was extracted with EtOAc (2×20 mL). The combined organic layers were washed with water (50 mL), then brine (50 mL), passed through a phase separation cartridge, concentrated in vacuo and purified by flash column chromatography on silica (gradient elution with 0% to 100% EtOAc in isohexanes then 0% to 20% MeOH in EtOAc) followed by further flash column chromatography on silica (gradient elution with 0% to 10% MeOH in DCM) to give the title compound (800 mg, 37% Yield). LCMS [M+H]⁺ 500, RT 1.92 minutes (Method 3).

Intermediate 663

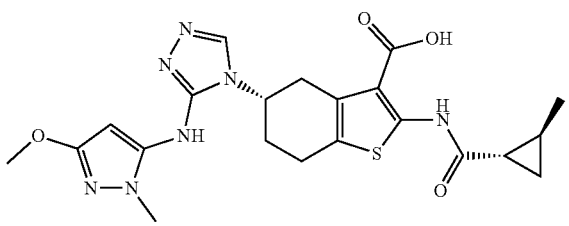

(5S)-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxylic acid Lithium hydroxide monohydrate (135 mg, 3.16 mmol, 98.5 mass %) in water (4.7 mL) was added to a solution of intermediate 662 (790 mg, 1.58 mmol) in THF (4.7 mL) and MeOH (4.7 mL). The reaction was stirred at 45° C. for 2 hours then cooled to room temperature Added water (20 mL) and partially concentrated in vacuo to remove the organic solvent. Added EtOAc (50 mL) and water (30 mL) and separated the layers. 5% MeOH in EtOAc (50 mL) was added to the aq. layer, which was then acidified to pH2-3 with 2 M aq. HCl (3.0 mL). The aq. layer was extracted with 5% MeOH in EtOAc (2×50 mL), then 10% MeOH in DCM (6×50 mL), the combined organic layers were washed with brine (90 mL) and concentrated in vacuo to give the title compound which was used without further purification (732 mg, 98% Yield). LCMS [M+H]⁺ 472, RT 0.79 minutes (Method 33).

Intermediate 664

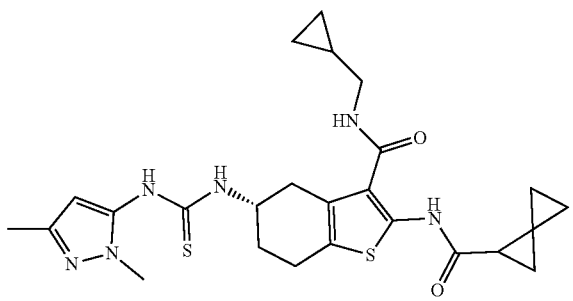

(5S)—N-(cyclopropylmethyl)-5-[(2,5-dimethylpyrazol-3-yl)carbamothioylamino]-2-(spiro[2.2]pentane-2-carbonylamino)-4,5,6,7-tetrahydrobenzothiophene-3-carboxamide To a stirring solution of intermediate 295 (150 mg, 0.42 mmol) in anhydrous DCM (6 mL) was added a solution of 5-isothiocyanato-1,3-dimethyl-1H-pyrazole (67 mg, 0.44 mmol) in DCM (4 mL) dropwise under an atmosphere of nitrogen and the mixture was stirred at room temperature for 30 minutes. The reaction mixture was concentrated to dryness and purified by flash column chromatography with a 0 to 100% ethyl acetate in heptane gradient to afford the title compound (209 mg, 84% yield) as a yellow solid. $\delta_H$ (500 MHz, DMSO-d6) 11.01 (s, 1H), 9.09 (s, 1H), 7.98-7.85 (m, 1H), 7.62 (t, J=5.3 Hz, 1H), 5.92 (s, 1H), 4.53 (s, 1H), 3.52 (s, 3H), 3.13 (t, J=5.5 Hz, 2H), 3.07 (dd, J=15.9, 3.5 Hz, 1H), 2.72 (s, 2H), 2.68-2.59 (m, 1H), 2.22 (dd, J=7.5, 4.3 Hz, 1H), 2.09 (s, 3H), 2.05-1.97 (m, 1H), 1.94-1.83 (m, 1H), 1.42 (dd, J=7.4, 3.6 Hz, 1H), 1.37 (t, J=4.0 Hz, 1H), 1.07-0.98 (m, 1H), 0.98-0.91 (m, 2H), 0.91-0.86 (m, 1H), 0.83-0.75 (m, 1H), 0.45-0.39 (m, 2H), 0.23 (q, J=4.8 Hz, 2H). LCMS [M+H]$^+$ 513, RT 2.94 minutes (Method 29).

Intermediate 665

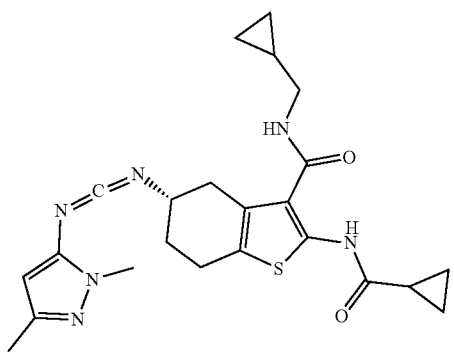

(5S)—N-(cyclopropylmethyl)-5-[(2,5-dimethylpyrazol-3-yl)iminomethyleneamino]-2-(spiro[2.2]pentane-2-carbonylamino)-4,5,6,7-tetrahydrobenzothiophene-3-carboxamide To a stirring solution of intermediate 644 (209 mg, 0.41 mmol) and triethylamine (0.17 mL, 1.22 mmol) in anhydrous DCM (5 mL) cooled to 0° C. under an atmosphere of nitrogen was added methanesulfonyl chloride (35 μL, 0.45 mmol) and stirring was continued for 1.5 hours. Triethylamine (0.18 mL, 1.28 mmol) followed by methanesulfonyl chloride (36 μL, 0.47 mmol) were added twice at 45 minutes intervals and after a total of 4.5 hours the mixture was diluted with DCM (10 mL), washed with sat. aq. NH$_4$Cl solution (10 mL), dried over magnesium sulfate, filtered and concentrated to afford the title compound (200 mg, 75% yield) as a yellow foam. LCMS [M+H]$^+$ 479, RT 3.14 minutes (Method 29).

Intermediate 666

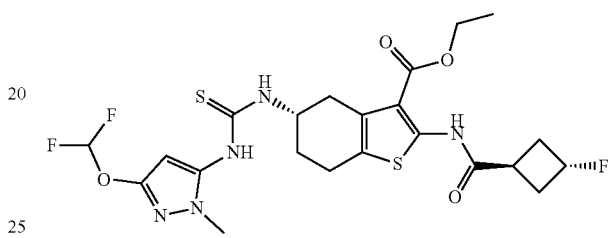

ethyl (5S)-5-[[5-(difluoromethoxy)-2-methyl-pyrazol-3-yl]carbamothioylamino]-2-[(3-fluorocyclobutanecarbonyl)amino]-4,5,6,7-tetrahydrobenzothiophene-3-carboxylate To a stirred solution of 639 (1.43 g, 4.20 mmol) in DCM (25 mL) was added 654 (3.25 g, 3.57 mmol, 30% purity) in DCM (15 mL). The reaction mixture was heated to 40° C. for 20 min then stirred at room temperature for 2.5 hr. The reaction was concentrated in vacuo and purified by column chromatography eluting with 0-80% EtOAc in iso-hexanes to give the title compound (1.94 g, 83% Yield). LCMS [M+H]$^+$ 546, RT 1.19 minutes (Method 7).

Intermediate 667

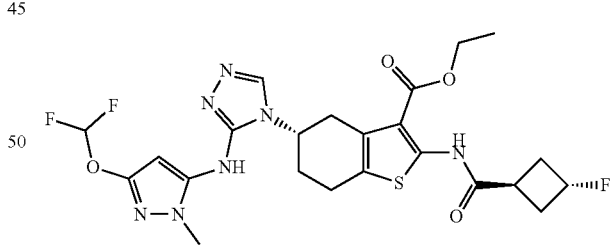

ethyl (5S)-5-[3-[[5-(difluoromethoxy)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxylate Synthesised in the same manner as Example 229, intermediate 666 (1.94 g, 3.55 mmol) and comparable stoichiometries of reagents. Purification by column chromatography eluting with 0-80% EtOAc in iso-hexane gave the title compound (1.20 g, 55% Yield). LCMS [M+H]$^+$ 554, RT 2.08 minutes (Method 2).

Intermediate 668

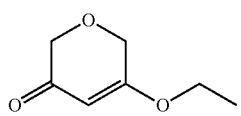

3-ethoxy-2H-pyran-5-one

2H-Pyran-3,5(4H,6H)-dione (1.36 g, 11.6 mmol) was dissolved in EtOH (50 mL) and conc. sulfuric acid (1.5 mL) added. The reaction was stirred at ambient temperature overnight. The reaction was concentrated to remove the EtOH and basified (pH ~8) with saturated aqueous NaHCO$_3$ solution. The resulting brown solution was extracted with EtOAc (3×50 mL). The combined organic extracts were dried over Na$_2$SO$_4$ and concentrated in vacuo. The resulting crude oil was purified by column chromatography eluting with a 0-100% gradient of EtOAc in isohexane. Product-containing fractions were combined and concentrated to afford the title compound (331 mg, 20% Yield). $\delta_H$ (300 MHz, Chloroform-d) 5.46 (s, 1H), 4.25 (s, 2H), 4.08 (d, J=0.8 Hz, 2H), 3.99 (q, J=7.0 Hz, 2H), 1.39 (t, J=7.0 Hz, 3H).

Intermediate 669

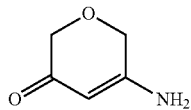

3-amino-2H-pyran-5-one

Intermediate 668 (331 mg, 2.33 mmol) was dissolved in EtOH (25 mL) and the solution cooled to −78° C. Ammonia gas was bubbled through the solution for 5 min. The cooling was removed, and the reaction allowed to warm to ambient temperature with stirring under a positive pressure of N$_2$ gas. The reaction was stirred overnight and then concentrated in vacuo and the crude product purified by column chromatography eluting with a 0-20% gradient of MeOH in DCM. Product-containing fractions were combined and concentrated to afford the title compound (223 mg, 85% Yield). $\delta_H$ (300 MHz, DMSO-d6) 7.00 (s, 2H), 5.01 (s, 1H), 4.18 (s, 2H), 3.80 (s, 2H).

Intermediate 670

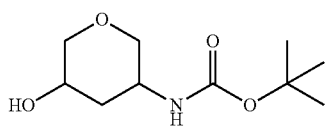

tert-butyl N-(5-hydroxytetrahydropyran-3-yl)carbamate

A solution of intermediate 669 (1.50 g, 13 mmol) in EtOH (100 mL) was treated with nickel aluminide (1.10 g, 6.6 mmol, 50% slurry in water). The reaction was sealed in a stainless-steel pressure vessel and evacuated then placed under 4 bar H$_2$ and heated to 60° C. with stirring for 3 days. The reaction was cooled and degassed and the slurry filtered through a pad of celite, washing with EtOH (20 mL). The ethanolic solution was concentrated in vacuo to afford a brown oily solid, which was dissolved in a mixture of TEA (5.5 mL, 40 mmol), DCM (2.5 mL) and di-tert-butyl dicarbonate (1 mol/L) in THF (9.9 mL, 20 mmol). The reaction stirred overnight at ambient temperature. The reaction was filtered to removed undissolved solids and concentrated in vacuo. The crude product was purified by column chromatography eluting with a 30-100% gradient of EtOAc in isohexane. Product-containing fractions were combined and concentrated to afford the title compound (741 mg, 26% Yield). $\delta_H$(300 MHz, Chloroform-d) 5.71-4.51 (m, 1H), 4.03-3.82 (m, 2H), 3.82-3.55 (m, 3H), 3.54-3.26 (m, 2H), 1.99-1.68 (m, 2H), 1.44 (s, 9H).

Intermediate 671

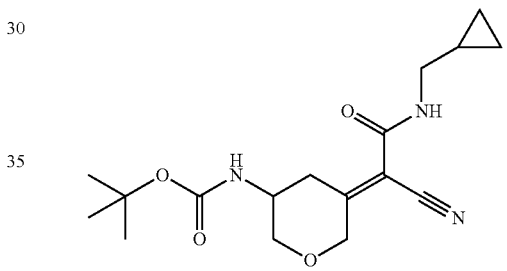

tert-butyl N-[(5E)-5-[1-cyano-2-(cyclopropylmethyl-amino)-2-oxo-ethylidene]tetrahydropyran-3-yl]carbamate Intermediate 670 (350 mg, 1.61 mmol) was dissolved in DCM (4 mL) and the solution cooled in an ice bath under a N$_2$ atmosphere prior to addition of Dess-Martin Periodinane (1.02 g, 2.42 mmol). The reaction was stirred for 1 h at 0° C. The reaction was quenched by addition of saturated aqueous Na$_2$S$_2$O$_7$ solution (1.5 mL) with vigorous stirring. Saturated aqueous NaHCO$_3$ (10 mL) was added followed by portions of solid NaHCO$_3$ until pH~8 was achieved. The organic layer was partitioned, and the aqueous layer extracted with DCM (10 mL). The combined organic extracts were dried over Na$_2$SO$_4$ and the solvents removed in vacuo. The resulting crude ketone was dissolved in in THF (10 mL) and 2-cyano-N-(cyclopropylmethyl)acetamide (510 mg, 3.7 mmol), pyridine (530 mg, 6.6 mmol) and titanium (IV) isopropoxide (3.0 g, 10 mmol) were added and the reaction stirred at ambient temperature overnight. The reaction was diluted with DCM (10 mL) and quenched with water (7 mL) with vigorous stirring. The organic layer was partitioned and the aqueous extracted with DCM (2×10 mL). The combined organic extracts were passed through a plug of celite and the solvents removed in vacuo. The crude product was purified by column chromatography eluting

Intermediate 672

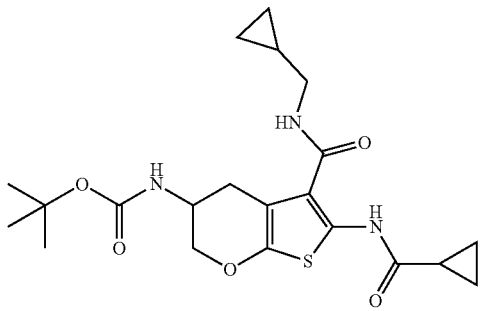

tert-butyl N-[6-amino-5-(cyclopropylmethylcarbamoyl)-3,4-dihydro-2H-thieno[2,3-b]pyran-3-yl]carbamate To a solution of Intermediate 671 (700 mg, 2.09 mmol) in EtOH (7.5 mL) were added morpholine (0.37 mL, 4.17 mmol) and sulfur (100 mg, 3.13 mmol). The vessel was sealed and heated to 70° C. for 1 h in a microwave reactor with stirring. The crude product mixture was filtered and concentrated to give a residue, which was dissolved in a mixture of DCM (30 mL) and DIPEA (0.43 mL, 2.45 mmol). The solution was stirred prior to dropwise addition of cyclopropanecarbonyl chloride (125 ⌀L, 1.35 mmol) and the reaction allowed to stir overnight at ambient temperature. The reaction was washed with water (10 mL) and passed through a phase separator cartridge prior to removal of volatiles in vacuo. The crude product was purified by column chromatography eluting with a 0-60% gradient of EtOAc in isohexane. Product-containing fractions were combined and concentrated to afford the title compound (317 mg, 50% Yield). $\delta_H$ (400 MHz, Chloroform-d) 12.15 (s, 1H), 5.79-5.68 (m, 1H), 5.10-4.93 (m, 1H), 4.35-4.14 (m, 2H), 3.33-3.20 (m, 2H), 3.04 (dd, J=14.9, 5.6 Hz, 1H), 2.79-2.67 (m, 1H), 1.69-1.59 (m, 1H), 1.45 (s, 9H), 1.18-0.97 (m, 3H), 0.96-0.82 (m, 2H), 0.64-0.54 (m, 2H), 0.32-0.20 (m, 2H).

Intermediate 673

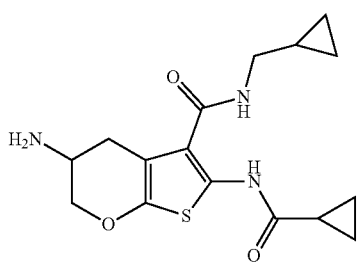

3-amino-6-(cyclopropanecarbonylamino)-N-(cyclopropylmethyl)-3,4-dihydro-2H-thieno[2,3-b]pyran-5-carboxamide Intermediate 672 (300 mg, 0.69 mmol) was dissolved in DCM (5 mL) and TFA (1 mL) was added. The reaction was stirred at ambient temperature for 2 h. The reaction was concentrated in vacuo and the crude product dissolved in MeOH (3 mL) and absorbed on to an SCX2 cartridge. The absorbed product was washed with MeOH (20 mL) and then eluted using 4 M NH₃ in MeOH (30 mL). The methanolic ammonia was removed in vacuo to afford the title compound (175 mg, 75% Yield). $\delta_H$ (400 MHz, Chloroform-d) 12.08 (s, 1H), 5.90 (s, 1H), 4.14 (dd, J=10.5, 2.5 Hz, 1H), 3.94 (dd, J=10.4, 6.6 Hz, 1H), 3.51-3.44 (m, 1H), 3.25 (dd, J=7.1, 5.3 Hz, 2H), 3.05 (dd, J=14.6, 5.6 Hz, 1H), 2.59 (dd, J=15.3, 5.4 Hz, 1H), 2.53-1.81 (m, 2H), 1.63 (tt, J=8.0, 4.6 Hz, 1H), 1.15-0.99 (m, 3H), 0.88 (dq, J=7.3, 4.1 Hz, 2H), 0.63-0.48 (m, 2H), 0.29-0.20 (m, 2H).

Intermediate 674

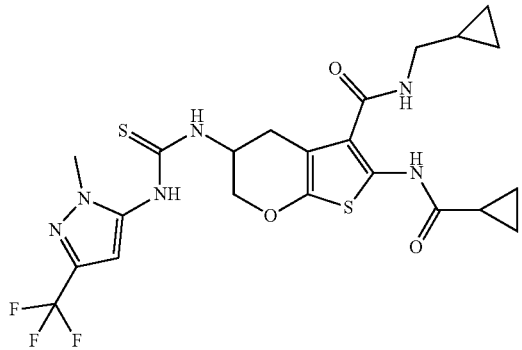

6-(cyclopropanecarbonylamino)-N-(cyclopropylmethyl)-3-[[2-methyl-5-(trifluoromethyl)pyrazol-3-yl]carbamothioylamino]-3,4-dihydro-2H-thieno[2,3-b]pyran-5-carboxamide To a stirred solution of intermediate 673 (175 mg, 0.52 mmol) in DCM (3.5 mL) was added a solution of intermediate 262 (113 mg, 0.559 mmol) in DCM (1.5 mL). The reaction mixture was stirred at room temperature for 10 min. The reaction mixture was dry loaded onto silica and purified by column chromatography with a gradient of 0-100% EtOAc in isohexane. Product-containing fractions were combined and concentrated to afford the title compound (215 mg, 75.9% Yield). $\delta_H$ (400 MHz, Chloroform-d) 11.97 (s, 1H), 8.56 (s, 1H), 7.95 (d, J=7.3 Hz, 1H), 6.49 (s, 1H), 5.84 (t, J=5.2 Hz, 1H), 5.24-5.10 (m, 1H), 4.49-4.37 (m, 1H), 4.16-4.11 (m, 1H), 3.81 (s, 3H), 3.25 (dddd, J=43.4, 13.7, 7.2, 5.1 Hz, 2H), 3.08-2.96 (m, 2H), 1.58-1.48 (m, 1H), 1.16-0.80 (m, 5H), 0.67-0.53 (m, 2H), 0.36-0.18 (m, 2H).

EXAMPLES

Example 1

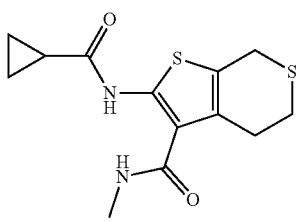

2-(Cyclopropanecarbonylamino)-N-methyl-5,7-di-hydro-4H-thieno[2,3-c]thiopyran-3-carboxamide To ethyl 2-amino-5,7-dihydro-4H-thieno[2,3-c]thiopyran-3-carboxylate [173281-01-1] (237 mg, 0.97 mmol) dissolved in DCM (10 mL) was added DIPEA (0.436 mL, 2.5 mmol) and cyclopropanecarbonyl chloride (0.093 mmol, 1 mmol) and the reaction mixture was stirred at r.t. over the weekend. To the reaction mixture was added water (5 mL) and the mixture was stirred rapidly for 10 minutes before filtering through a phase separation cartridge and concentrating in vacuo to yield crude ethyl 2-(cyclopropanecarbonylamino)-5,7-dihydro-4H-thieno[2,3-c]thiopyran-3-carboxylate which was carried through to the ester hydrolysis step.

To the crude product ethyl 2-(cyclopropanecarbonylamino)-5,7-dihydro-4H-thieno[2,3-c]thiopyran-3-carboxylate (140 mg, 0.45 mmol) was added lithium hydroxide monohydrate (64 mg, 1.52 mmol), 1,4-dioxane (5 mL) and water (0.5 mL) and the mixture was heated at 70° C. for 3 h under nitrogen. Further lithium hydroxide (62 mg, 1.47 mmol) in water (1 mL) was added and the reaction mixture was heated at 70° C. overnight under nitrogen. The reaction was acidified with 2M aqueous hydrochloric acid and the reaction mixture was concentrated in vacuo to afford 2-(cyclopropanecarbonylamino)-5,7-dihydro-4H-thieno[2,3-c]thiopyran-3-carboxylic acid.

To 2-(cyclopropanecarbonylamino)-5,7-dihydro-4H-thieno[2,3-c]thiopyran-3-carboxylic acid was added DCM (14 mL), EDCl (235 mg, 1.19 mmol) dissolved in DCM (6 mL) and 2.0M methylamine in THF (0.9 mL). To the reaction was added methylamine (0.9 mL), DIPEA (0.32 mmol, 1.81 mmol) and DMF (4 mL) and the reaction mixture was left to stir at r.t. under nitrogen overnight. The reaction mixture was concentrated in vacuo and the crude residue was purified by flash column chromatography on silica (gradient elution with 20% EtOAc/isohexane to 100% EtOAc/isohexane followed by 100% DCM to 20% MeOH/DCM) to afford the product (37 mg) which was purified by preparative HPLC to afford the title compound (22 mg, 7.6%) as a white solid. $\delta_H$ (300 MHz, DMSO-$d_6$) 11.02 (s, 1H), 7.68 (d, J 4.9 Hz, 1H), 3.65 (s, 2H), 2.77 (s, 4H), 2.69 (d, J 4.6 Hz, 3H), 1.87 (q, J 7.2, 6.4 Hz, 1H), 0.94-0.66 (m, 4H).

Example 2

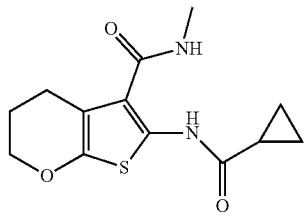

6-(Cyclopropanecarbonylamino)-N-methyl-3,4-di-hydro-2H-thieno[2,3-b]pyran-5-carboxamide To intermediate 3 (206 mg, 0.77 mmol) in DCM (20 mL) was added 1-hydroxybenzotriazole hydrate (182 mg, 1.19 mmol) followed by 2M methylamine in THF (0.75 mL, 1.5 mmol), followed by EDCl (199 mg, 1.01 mmol). The reaction mixture was stirred at r.t. under nitrogen for 3 h before partitioning between water (30 mL) and DCM (30 mL). The aqueous layer was separated and the organic phase was washed with brine (30 mL). The organic layer was separated, filtered through a phase separation cartridge and concentrated in vacuo to yield a pale brown solid which was purified by flash column chromatography on silica (gradient elution with 20% EtOAc/isohexane to 100% EtOAc) to afford the title compound (153 mg, 71%) as a white solid. $\delta_H$ (300 MHz, DMSO-$d_6$) 11.40 (s, 1H), 7.49-7.29 (m, 1H), 4.14 (t, J 5.0 Hz, 2H), 2.76 (d, J 4.6 Hz, 3H), 2.62 (t, J 6.4 Hz, 2H), 2.04-1.76 (m, 3H), 0.92-0.76 (m, 4H). LCMS (ES+) [M+H]$^+$ 250.8, RT 1.563 minutes, 94.2% purity (Method 3).

Example 3

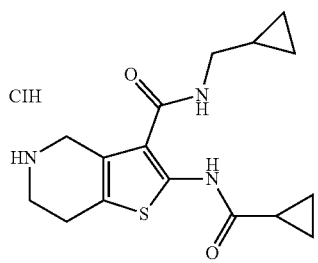

2-(Cyclopropanecarbonylamino)-N-(cyclopropylmethyl)-4,5,6,7-tetrahydrothieno[3,2-c]pyridine-3-carboxamide; hydrochloride Intermediate 8 (0.87 g, 2.08 mmol) was dissolved in 4 N hydrochloric acid solution in 1,4-dioxane (20 mL) and the reaction was stirred at r.t. for 16 h. Further 4 N hydrochloric acid solution in 1,4-dioxane (6 mL) was added and the reaction was stirred at r.t. for 4 h. The reaction mixture was concentrated in vacuo to afford the title compound (820 mg, 111%) as an off white solid. $\delta_H$ (400 MHz, DMSO-$d_6$) 10.73 (s, 1H), 9.07 (s, 2H), 7.87 (t, J 5.6 Hz, 1H), 3.96 (q, J 6.4, 4.3 Hz, 2H), 3.13 (d, J 6.4 Hz, 2H), 2.90 (dd, J 6.9, 5.6 Hz, 2H), 2.70 (t, J 6.0 Hz, 2H), 1.81-1.71 (m, 1H), 0.91-0.73 (m, 1H), 0.73-0.55 (m, 4H), 0.26-0.16 (m, 2H), 0.08--0.08 (m, 2H). LCMS (ES+) [M+H]⁺ 320.8, RT 1.008 minutes (method 6140, pH 3 Method 2). LCMS (ES+) [M+H] 320.8, RT 1.372 minutes (Method 3).

Example 4

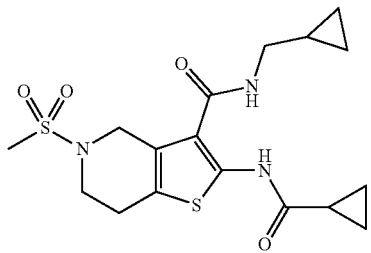 [SMILES: CS(=O)(=O)N1CCc2sc(NC(=O)C3CC3)c(C(=O)NCC3CC3)c2C1]

2-(Cyclopropanecarbonylamino)-N-(cyclopropylmethyl)-5-methylsulfonyl-6,7-dihydro-4H-thieno[3,2-c]pyridine-3-carboxamide Example 3 (56 mg, 0.16 mmol) was dissolved in DCM (6.6 mg, 78.0 mmol) and DIPEA (51.1 mg, 0.39 mmol) and methanesulfonyl chloride [124-63-0] (23.5 mg, 0.20 mmol) was added and the reaction mixture was stirred at r.t. for 16 h. The reaction mixture was washed with water, passed through a phase separation cartridge and the filtrate evaporated in vacuo. The crude reaction mixture was purified by flash column chromatography on silica (gradient elution 30-100% EtOAc/hexane) to afford the title compound (48 mg, 77%) as a white solid. LCMS (ES+) [M+H]⁺ 398.6, RT 1.779 minutes (Method 3). LCMS (ES+) [M+H]⁺ 398.7, RT 1.848 minutes (Method 2).

Example 5

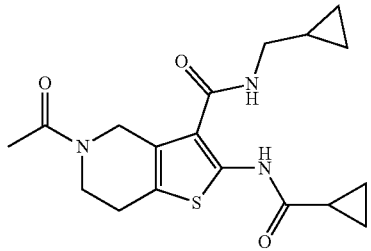 [SMILES: CC(=O)N1CCc2sc(NC(=O)C3CC3)c(C(=O)NCC3CC3)c2C1]

5-Acetyl-2-(cyclopropanecarbonylamino)-N-(cyclopropylmethyl)-6,7-dihydro-4H-thieno[3,2-c]pyridine-3-carboxamide Example 3 (56 mg, 0.16 mmol) was dissolved in DCM (5 mL) and DIPEA (51 mg, 0.39 mmol) and acetyl chloride (16 mg, 0.20 mmol) was added and the reaction mixture was stirred at r.t. for 16 h. The reaction mixture was washed with water, passed through a phase separation cartridge and the filtrate was concentrated in vacuo to give the crude product which was purified by flash column chromatography on silica (gradient elution with 30-100% EtOAc/hexane) to afford the title compound (37 mg, 65%) as a white solid. $\delta_H$ (400 MHz, DMSO-d₆) 11.07-10.83 (m, 1H), 7.97-7.75 (m, 1H), 4.57 (d, J 2.0 Hz, 2H), 3.78-3.62 (m, 2H), 3.16 (q, J 5.5 Hz, 2H), 2.81-2.70 (m, 1H), 2.70-2.61 (m, 1H), 2.14-2.02 (m, 3H), 2.00-1.86 (m, 1H), 1.14-1.00 (m, 1H), 0.94-0.77 (m, 4H), 0.52-0.36 (m, 2H), 0.28-0.18 (m, 2H). LCMS (ES+) [M+H]⁺ 362.8, RT 1.406 minutes (Method 3). LCMS [M−H]⁻ 360.0, RT 1.661 minutes (Method 2).

Example 6

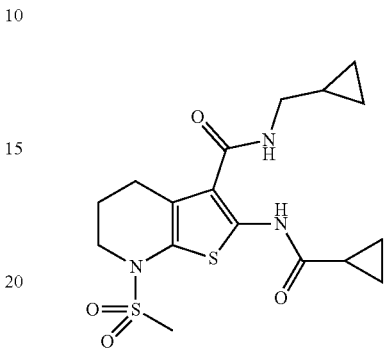

2-(Cyclopropanecarbonylamino)-N-(cyclopropylmethyl)-7-methylsulfonyl-5,6-dihydro-4H-thieno[2,3-b]pyridine-3-carboxamide Intermediate 12 (75 mg, 0.21 mmol) was dissolved in DCM (5 mL) and DIPEA (68 mg, 0.53 mmol) and methanesulfonyl chloride [124-63-0] (32 mg, 0.27 mmol) were added and the reaction mixture was stirred at r.t. for 16 h. The reaction mixture was washed with water, passed through a phase separation cartridge and the filtrate was concentrated in vacuo. The crude residue was purified by flash column chromatography on silica (gradient elution 30-100% EtOAc/hexane) to afford the title compound (58 mg, 69%) as a white solid. $\delta_H$ (400 MHz, DMSO-d₆) 10.91 (s, 1H), 7.58 (t, J 5.7 Hz, 1H), 3.49-3.39 (m, 2H), 2.98-2.86 (m, 2H), 2.81 (s, 3H), 2.48 (t, J 6.4 Hz, 2H), 1.76-1.64 (m, 3H), 0.88-0.77 (m, 1H), 0.69-0.55 (m, 4H), 0.28-0.18 (m, 2H), 0.07--0.04 (m, 2H). LCMS (ES+) [M+H]⁺ 398.6, RT 1.956 minutes (Method 3). LCMS (ES+) [M+H]⁺ 398.6, RT 1.991 minutes (Method 2).

Example 7

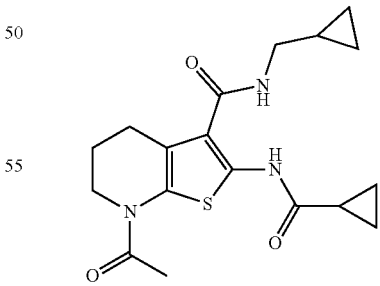

7-Acetyl-2-(cyclopropanecarbonylamino)-N-(cyclopropylmethyl)-5,6-dihydro-4H-thieno[2,3-b]pyridine-3-carboxamide Intermediate 12 (75 mg, 0.21 mmol) was dissolved in DCM (5 mL) and DIPEA (68 mg, 0.53 mmol) and acetyl chloride (22 mg, 0.27 mmol) were added. The reaction mixture was stirred at r.t. for 16 h. The mixture was washed with water, passed through a phase separation cartridge and the filtrate concentrated in vacuo to yield the crude product which was purified by flash column chromatography on silica (gradient elution 30-100% EtOAc/hexane) to afford the title compound (60 mg, 79%) as a white solid. δ$_H$ (400 MHz, DMSO-d$_6$) 10.71 (s, 1H), 7.46 (t, J 5.7 Hz, 1H), 3.58-3.50 (m, 2H), 2.91 (t, J 6.2 Hz, 2H), 2.49 (t, J 6.2 Hz, 2H), 1.99 (s, 3H), 1.71 (s, 2H), 1.65-1.57 (m, 1H), 0.87-0.72 (m, 1H), 0.63-0.54 (m, 4H), 0.25-0.15 (m, 2H), 0.05--0.07 (m, 2H). LCMS (ES+) [M+H]$^+$ 362.8, RT 1.744 minutes (Method 3). LCMS (ES+) [M+H]$^+$ 362.8, RT 1.797 minutes (Method 2).

Example 8

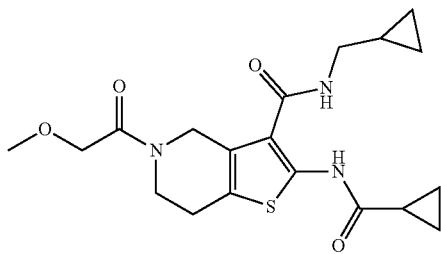 [SMILES: COCC(=O)N1CCc2sc(NC(=O)C3CC3)c(C(=O)NCC3CC3)c2C1]

2-(Cyclopropanecarbonylamino)-N-(cyclopropylmethyl)-5-(2-methoxyacetyl)-6,7-dihydro-4H-thieno[3,2-c]pyridine-3-carboxamide To example 3 (36 mg, 0.10 mmol) and N,N-(diisopropyl) aminomethylpolystyrene (40 mg, 3.53 mmol/g, 0.30 mmol) in DCM (0.8 mL) was added methoxyacetyl chloride (14 mg, 0.13 mmol) and the reaction mixture was stirred at r.t. overnight. To the reaction mixture was added methoxyacetyl chloride (11 mg, 0.10 mmol) and was stirred for 4 h at r.t. prior to addition of further methoxyacetyl chloride (11 mg, 0.10 mmol) and the mixture was stirred overnight. To the sample was added N,N-(diisopropyl)aminomethylpolystyrene (40 mg, 3.53 mmol/g, 0.30 mmol) and the mixture was stirred at r.t. for 2 h then MP-trisamine (55 mg, 0.21 mmol) was added and the mixture was stirred for 1 h at r.t. The reaction mixture was filtered, washed with MeCN and concentrated in vacuo to give the crude product which was purified by reverse phase HPLC (basic) to afford the title compound (0.011 g, 27%). LCMS [M+H]$^+$ 391.2, RT 3.77 minutes (Method 8).

Example 9

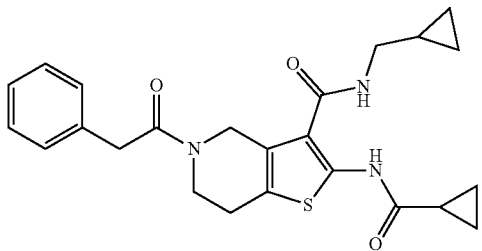 [SMILES: O=C(NCC1CC1)c1c(NC(=O)C2CC2)sc2c1CN(C(=O)Cc1ccccc1)CC2]

2-(Cyclopropanecarbonylamino)-N-(cyclopropylmethyl)-5-(2-phenylacetyl)-6,7-dihydro-4H-thieno[3,2-c]pyridine-3-carboxamide To example 3 (36 mg, 0.10 mmol) and N,N-(diisopropyl) aminomethylpolystyrene (40 mg, 3.53 mmol/g, 0.30 mmol) in DCM (0.8 mL) was added phenylacetyl chloride (20 mg, 0.13 mmol) and the reaction mixture was stirred at r.t. overnight. To the reaction mixture was added further phenylacetyl chloride (16 mg, 0.10 mmol) and the mixture was stirred overnight. To the sample was added N,N-(diisopropyl)aminomethylpolystyrene (40 mg, 3.53 mmol/g, 0.30 mmol) and the mixture was stirred at r.t. for 2 h then MP-trisamine (55 mg, 0.21 mmol) was added and the mixture was stirred for 1 h at r.t. The reaction mixture was filtered, washed with MeCN and concentrated in vacuo to give the crude product which was purified by reverse phase HPLC (basic) to afford the title compound (0.0087 g, 20%). LCMS [M+H]$^+$ 437.2, RT 4.48 minutes (Method 8).

Example 10

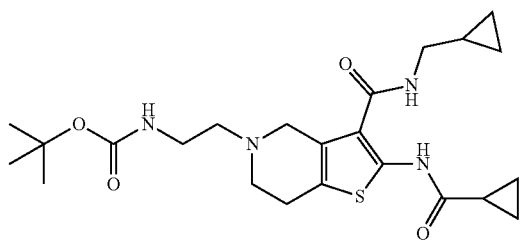 [SMILES: CC(C)(C)OC(=O)NCCN1CCc2sc(NC(=O)C3CC3)c(C(=O)NCC3CC3)c2C1]

Tert-butyl N-[2-[2-(cyclopropanecarbonylamino)-3-(cyclopropylmethylcarbamoyl)-6,7-dihydro-4H-thieno[3,2-c]pyridin-5-yl]ethyl]carbamate To example 3 (36 mg, 0.10 mmol) in THF (1 mL) and EtOH (0.5 mL) was added MP-carbonate (75 mg, 0.25 mmol, 3.36 mmol/g). The mixture was stirred for 1 h at r.t., filtered and rinsed with EtOH (2×200 μL). To the filtrate was added N-Boc-2-aminoacetaldehyde [89711-08-0] (20 mg, 0.13 mmol), MP-cyanoborohydride (100 mg, 0.25 mmol, 2.49 mmol/g) and acetic acid (0.1 mL, 2 mmol). The reaction mixture was stirred at r.t. overnight. The reaction mixture was filtered, rinsed with EtOH and the filtrate concentrated in vacuo reaction mixture. To the reaction mixture was added DCM (1 mL) and a portion of the reaction mixture containing the product (20 mg, 0.043 mmol) was removed and purified by reverse phase HPLC (basic) to afford the title compound (4.4 mg, 9.5%). LCMS [M+H]$^+$ 463.1, RT 4.67 minutes, 95.55% purity (Method 9).

Example 11

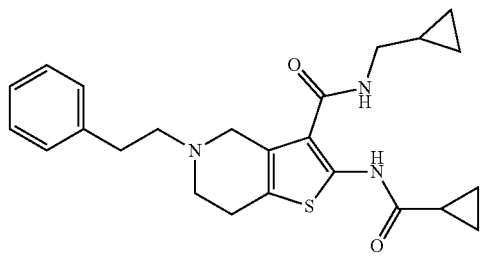 [SMILES: O=C(NCC1CC1)c1c(NC(=O)C2CC2)sc2c1CN(CCc1ccccc1)CC2]

2-(Cyclopropanecarbonylamino)-N-(cyclopropylmethyl)-5-(2-phenylethyl)-6,7-dihydro-4H-thieno[3,2-c]pyridine-3-carboxamide To example 3 (36 mg, 0.10 mmol) in THF (1 mL) and EtOH (0.5 mL) was added MP-carbonate (75 mg, 0.25 mmol, 3.36 mmol/g). The mixture was stirred for 1 h at r.t., filtered and rinsed with EtOH (2×200 µL). To the filtrate was added phenylacetaldehyde [122-78-1] (14 mg, 0.12 mmol), MP-cyanoborohydride (100 mg, 0.25 mmol, 2.49 mmol/g) and acetic acid (0.1 mL, 2 mmol). The reaction mixture was stirred at r.t. overnight. The reaction mixture was filtered, rinsed with EtOH and the filtrate concentrated in vacuo reaction to give the product which was purified by reverse phase HPLC (basic) to afford the title compound (4.1 mg, 10%). LCMS [M+H]+ 424.19, RT 5.10 minutes, 95.60% purity (Method 9).

Example 12

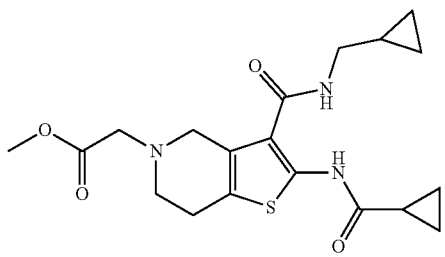 [SMILES: COC(=O)CN1CCc2sc(NC(=O)C3CC3)c(C(=O)NCC3CC3)c2C1]

Methyl 2-[2-(cyclopropanecarbonylamino)-3-(cyclopropylmethylcarbamoyl)-6,7-dihydro-4H-thieno[3,2-c]pyridin-5-yl]acetate To example 3 (36 mg, 0.100 mmol) in THF (1 mL) and EtOH (0.5 mL) was added MP-carbonate (75 mg, 0.25 mmol, 3.36 mmol/g). The mixture was stirred for 1 h at r.t., filtered and rinsed with EtOH (2×200 µL). To the filtrate was added methyl glyoxylate (11 mg, 0.12 mmol), MP-cyanoborohydride (100 mg, 0.25 mmol, 2.49 mmol/g) and acetic acid (0.1 mL, 2 mmol). The reaction mixture was stirred at r.t. overnight. The reaction mixture was filtered, rinsed with EtOH and the filtrate concentrated in vacuo. Reaction mixture was purified by reverse phase HPLC (basic) to afford the title compound (0.0048 g, 12%). LCMS [M+H]+ 376.205, RT 2.93 minutes, 100% purity (Method 20).

Example 13 and Example 14

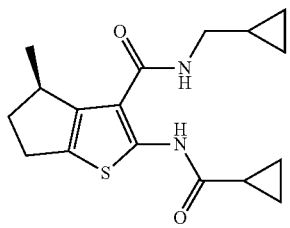

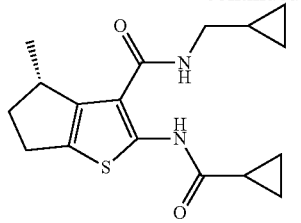

Example 13

(4R)-2-(Cyclopropanecarbonylamino)-N-(cyclopropylmethyl)-4-methyl-5,6-dihydro-4H-cyclopenta[b]thiophene-3-carboxamide

Example 14

(4S)-2-(Cyclopropanecarbonylamino)-N-(cyclopropylmethyl)-4-methyl-5,6-dihydro-4H-cyclopenta[b]thiophene-3-carboxamide The 2 enantiomers of intermediate 15 were separated by chiral preparative chromatography (Chiralpak IC, 200 mL/min 1:1 hexane:iPrOH) to afford two isomers isomer A, example 13 and Isomer B, example 14. The absolute stereochemistry of the two isomers was arbitrarily assigned. Isomer A, example 13 was repurified by flash column chromatography on silica (gradient elution with 20-80% EtOAc/hexane) and was freeze-dried from MeCN/water to afford isomer A, example 13 (6.5 mg, 20%) as a white solid. $\delta_H$ (400 MHz, DMSO-$d_6$) 11.44 (s, 1H), 7.19 (t, J 5.9 Hz, 1H), 3.33 (t, J 7.3 Hz, 1H), 3.14-3.08 (m, 1H), 2.73 (ddd, J 13.6, 7.0, 5.1 Hz, 1H), 2.68-2.53 (m, 1H), 2.53-2.41 (m, 1H), 2.39-2.29 (m, 1H), 1.77-1.67 (m, 1H), 1.67-1.56 (m, 1H), 0.88-0.73 (m, 4H), 0.68-0.54 (m, 4H), 0.24-0.08 (m, 2H), 0.06--0.08 (m, 2H). Isomer B, example 14 (11 mg, 34%). $\delta_H$ (400 MHz, DMSO-$d_6$) 11.44 (s, 1H), 7.19 (t, J 5.9 Hz, 1H), 3.33 (t, J 7.5 Hz, 1H), 3.15-3.08 (m, 1H), 2.79-2.67 (m, 1H), 2.68-2.54 (m, 1H), 2.53-2.40 (m, 1H), 2.39-2.29 (m, 1H), 1.77-1.66 (m, 1H), 1.66-1.56 (m, 1H), 0.89-0.77 (m, 4H), 0.67-0.54 (m, 4H), 0.22-0.13 (m, 2H), 0.00 (dd, J 4.5, 2.2 Hz, 2H).

Example 15

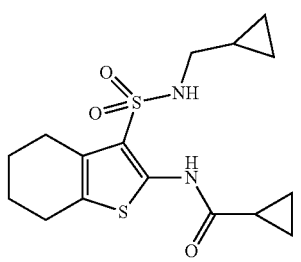 [SMILES: O=C(Nc1sc2c(c1S(=O)(=O)NCC1CC1)CCCC2)C1CC1]

N-[3-(Cyclopropylmethylsulfamoyl)-4,5,6,7-tetrahydrobenzothiophen-2-yl]cyclopropanecarboxamide To a suspension of intermediate 17 (500 mg, 2.26 mmol) in DCM (7 mL) cooled in an ice-bath was added chlorosulfonic acid (1.33 g, 11.30 mmol) dropwise over 1 minute. The solids dissolved and the reaction was stirred in the ice-bath for 2.5 h followed by 18 hours at r.t. The crude reaction was divided in half and to this mixture was slowly added cyclopropylmethylamine (803 mg, 11.30 mmol) dropwise. After 10 minutes the reaction was poured into EtOAc, washed with 0.5M aqueous hydrochloric acid solution (2×) and saturated sodium bicarbonate solution (2×). The organic phase was separated, dried ($MgSO_4$), filtered and concentrated in vacuo to yield crude product as a brown gum which was purified by flash column chromatography on silica (gradient elution with 0-25% EtOAc/heptane) to afford the title compound (65 mg, 16%) as a white solid. $\delta_H$ (500 MHz, DMSO-$d_6$) 10.45 (s, 1H), 7.84 (t, J 5.9 Hz, 1H), 2.75-2.63 (m, 4H), 2.58 (d, J 5.5 Hz, 2H), 1.89 (ddd, J 12.4, 7.7, 4.7 Hz, 1H), 1.72 (m, 4H), 0.94-0.83 (m, 4H), 0.80-0.70 (m, 1H), 0.41-0.29 (m, 2H), 0.13-0.01 (m, 2H).

Example 16

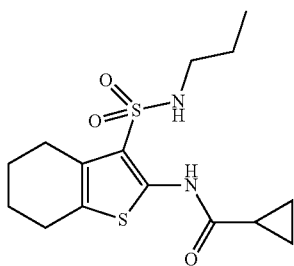 [SMILES: CCCNS(=O)(=O)c1c(NC(=O)C2CC2)sc2c1CCCC2]

N-[3-(Propylsulfamoyl)-4,5,6,7-tetrahydrobenzothiophen-2-yl]cyclopropanecarboxamide To a suspension of intermediate 17 (2.1 g, 9.49 mmol) in DCM (30 mL) cooled in an ice-bath was added chlorosulfonic acid (3.35 g, 28.5 mmol) dropwise over 1 minute. The solids dissolved and the reaction was stirred in an ice-bath for 2.5 h followed by 18 h at r.t. The reaction mixture containing 2-(cyclopropanecarbonylamino)-4,5,6,7-tetrahydrobenzothiophene-3-sulfonyl chloride was divided and utilised crude. To a rapidly stirred solution of 2-(cyclopropanecarbonylamino)-4,5,6,7-tetrahydrobenzothiophene-3-sulfonyl chloride (430 mg, 1.35 mmol) in DCM (4 mL) at r.t. was slowly added n-propylamine (642 mg, 10.8 mmol) over 1 minute. After 10 minutes the reaction was poured into EtOAc and washed with 0.5M aqueous hydrochloric acid solution (2×) followed by saturated sodium bicarbonate solution (2×). The mixture was dried ($MgSO_4$), filtered and concentrated in vacuo to yield the crude material as brown gum which was purified by flash column chromatography on silica (gradient elution with 0-20% EtOAc/heptane) to afford the title compound (60 mg, 13%) as colourless foam. $\delta_H$ (500 MHz, DMSO-$d_6$) 10.43 (s, 1H), 7.68 (d, J 5.2 Hz, 1H), 2.74 (q, J 6.7 Hz, 2H), 2.64 (t, J 4.8 Hz, 2H), 2.59 (d, J 5.6 Hz, 2H), 1.89 (ddd, J 12.4, 7.8, 4.7 Hz, 1H), 1.72 (m, 4H), 1.38 (h, J 7.3 Hz, 2H), 0.94-0.85 (m, 4H), 0.79 (t, J 7.4 Hz, 3H).

Example 17

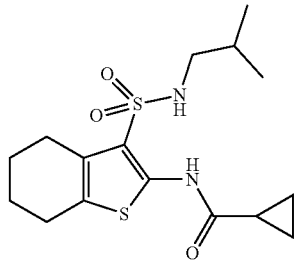 [SMILES: CC(C)CNS(=O)(=O)c1c(NC(=O)C2CC2)sc2c1CCCC2]

N-[3-(Isobutylsulfamoyl)-4,5,6,7-tetrahydrobenzothiophen-2-yl]cyclopropanecarboxamide To a suspension of intermediate 17 (2.1 g, 9.49 mmol) in DCM (30 mL) cooled in an ice-bath was added chlorosulfonic acid (3.35 g, 28.5 mmol) dropwise over 1 minute. The solids dissolved and the reaction was stirred in an ice-bath for 2.5 h followed by 18 h at r.t. The reaction mixture containing 2-(cyclopropanecarbonylamino)-4,5,6,7-tetrahydrobenzothiophene-3-sulfonyl chloride was divided and utilised crude. To a rapidly stirred solution of 2-(cyclopropanecarbonylamino)-4,5,6,7-tetrahydrobenzothiophene-3-sulfonyl chloride (430 mg, 1.35 mmol) in DCM (4 mL) at r.t. was slowly added 2-methylpropan-1-amine [78-81-9] (787 mg, 10.8 mmol) over 1 minute. After 10 minutes the reaction was poured into DCM (20 mL) and was washed with water (20 mL) followed by 1M aqueous hydrochloric acid solution (2×15 mL) and saturated sodium bicarbonate solution (2×15 mL). The mixture was dried ($MgSO_4$), filtered and the solvent removed in vacuo to yield the crude material as a brown gum which was purified by flash column chromatography on silica (gradient elution with 0-20% EtOAc/heptane) to afford the title compound (85 mg, 18%) as a white solid. $\delta_H$ (500 MHz, DMSO-$d_6$) 10.42 (s, 1H), 7.71 (t, J 6.0 Hz, 1H), 2.65 (t, J 5.0 Hz, 2H), 2.59 (t, J 6.4 Hz, 4H), 1.92-1.85 (m, 1H), 1.75-1.68 (m, 4H), 1.62 (dq, J 13.4, 6.7 Hz, 1H), 0.94-0.86 (m, 4H), 0.80 (d, J 6.7 Hz, 6H).

Example 18

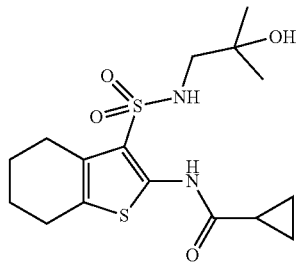 [SMILES: CC(C)(O)CNS(=O)(=O)c1c(NC(=O)C2CC2)sc2c1CCCC2]

N-[3-[(2-Hydroxy-2-methyl-propyl)sulfamoyl]-4,5,6,7-tetrahydrobenzothiophen-2-yl]cyclopropanecarboxamide To a suspension of intermediate 17 (1.2 g, 5.42 mmol) in MeCN (24 mL) cooled in an ice-bath was added chlorosulfonic acid (1.60 g, 13.6 mmol) dropwise over 1 minute. The solids dissolved to a brown solution and the reaction was stirred at r.t. for 10 minutes followed by 2 h at 60° C. The reaction was split into 6 equal portions and utilised crude in subsequent reactions. To a rapidly stirred solution of 2-(cyclopropanecarbonylamino)-4,5,6,7-tetrahydrobenzothiophene-3-sulfonyl chloride (289 mg, 0.90 mmol) in MeCN (4 mL) at r.t. was slowly added 1-amino-2-methylpropan-2-ol (509 mg, 5.42 mmol) over 1 minute. After 10 minutes the reaction was poured into EtOAc, washed with water and 0.5M aqueous hydrochloric acid solution (2×) and dried (MgSO$_4$). The mixture was filtered and the solvent was removed in vacuo to yield the crude product as a pale brown solid which was purified by flash column chromatography on silica (gradient elution with 0-60% EtOAc/heptane) to afford the title compound (162 mg, 48%) as a white solid. $\delta_H$ (500 MHz, DMSO-d$_6$) 10.41 (s, 1H), 7.51 (t, J 6.0 Hz, 1H), 4.46 (s, 1H), 2.69 (d, J 6.0 Hz, 2H), 2.65 (t, J 5.7 Hz, 2H), 2.58 (d, J 5.6 Hz, 2H), 1.88 (td, J 7.7, 3.9 Hz, 1H), 1.77-1.66 (m, 4H), 1.04 (s, 6H), 0.95-0.84 (m, 4H).

Example 19

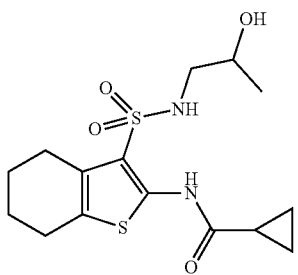 [SMILES: CC(O)CNS(=O)(=O)c1c(NC(=O)C2CC2)sc2c1CCCC2]

N-[3-(2-Hydroxypropylsulfamoyl)-4,5,6,7-tetrahydrobenzothiophen-2-yl]cyclopropanecarboxamide The method for example 18 was utilised substituting 1-amino-2-propanol (416 mg, 5.42 mmol) for 1-amino-2-methylpropan-2-ol to afford the title compound (173 mg, 53%) as a white solid. $\delta_H$ (500 MHz, DMSO-d$_6$) 10.42 (s, 1H), 7.64 (s, 1H), 4.71 (d, J 4.7 Hz, 1H), 3.60 (dt, J 10.8, 6.1 Hz, 1H), 2.78-2.66 (m, 2H), 2.66-2.62 (m, 2H), 2.59 (d, J 5.7 Hz, 2H), 1.88 (ddd, J 12.4, 7.7, 4.7 Hz, 1H), 1.78-1.66 (m, 4H), 1.00 (d, J 6.2 Hz, 3H), 0.96-0.85 (m, 4H).

Example 20

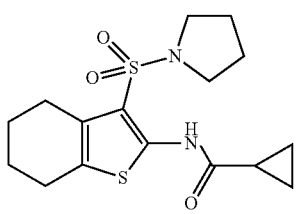 [SMILES: O=C(Nc1sc2c(c1S(=O)(=O)N1CCCC1)CCCC2)C1CC1]

N-(3-Pyrrolidin-1-ylsulfonyl-4,5,6,7-tetrahydrobenzothiophen-2-yl)cyclopropanecarboxamide Chlorosulfonic acid (25 μL, 0.37 mmol) was added dropwise to a suspension of intermediate 17 (33 mg, 0.15 mmol) in MeCN (1 mL) at 0° C. The reaction mixture was stirred at r.t. for 0.5 h and then heated at 60° C. in a sealed vial for 1.5 h. The resulting solution was cooled to r.t. and pyrrolidine (43 mg, 0.60 mmol) was added dropwise. The reaction mixture was stirred at r.t. overnight and the mixture was concentrated in vacuo. The residue was diluted with DCM (2 mL) and washed with water (2 mL). The organic phase was separated and the aqueous layer washed with further DCM (2×2 mL). The organic layers were combined and the mixture concentrated in vacuo to yield the crude product which was purified by reverse phase HPLC (basic) to afford the title compound (0.015 g, 28%). LCMS (ES+) [M+H]$^+$ 355.1137, RT 5.5 minutes (Method 20).

Example 21

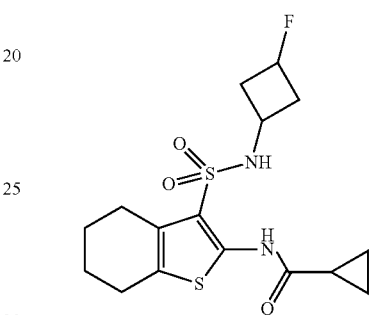

N-[3-[(3-Fluorocyclobutyl)sulfamoyl]-4,5,6,7-tetrahydrobenzothiophen-2-yl]cyclopropanecarboxamide The method for example 20 was utilised substituting 3-fluorocyclobutanamine (56 mg, 0.63 mmol) for pyrrolidine to afford the title compound (0.0081 g, 15%). LCMS (ES+) [M+H]+ 373.1049, RT 5.15 minutes (Method 20)

Example 22

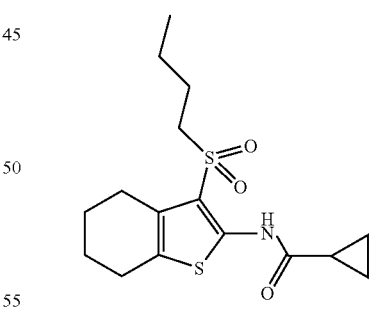

N-(3-Butylsulfonyl-4,5,6,7-tetrahydrobenzothiophen-2-yl)cyclopropanecarboxamide

To a solution of intermediate 23 (32 mg, 0.12 mmoL) and triethylamine (0.024 mL, 0.18 mmoL) in DCM (5 mL) cooled to 0° C., was added cyclopropanecarbonyl chloride (0.014 mL, 0.15 mmoL) and the solution was stirred under an atmosphere of nitrogen. The reaction mixture was stirred for 1 h prior to addition of DMAP (catalytic amount) and stirring was continued at r.t. for 1 h. Triethylamine (0.024 mL, 0.18 mmoL) and cyclopropanecarbonyl chloride (0.028 mL, 0.3 mmoL) were added and the reaction mixture was heated to 40° C. The reaction mixture was stirred over the weekend at r.t., diluted with DCM (15 mL) and saturated ammonium chloride solution (10 mL). The layers were separated and the aqueous phase was extracted with DCM (10 mL). The combined organic phases were washed with brine (10 mL), dried (MgSO$_4$), filtered and concentrated in vacuo to yield the crude product which was purified by reverse phase HPLC (basic) to afford the title compound (19 mg, 45%). δ$_H$ (250 MHz, Chloroform-d) 10.68 (s, 1H), 3.16-3.02 (m, 2H), 2.78-2.57 (m, 4H), 1.90-1.76 (m, 4H), 1.77-1.68 (m, 2H), 1.68-1.55 (m, 1H), 1.53-1.33 (m, 2H), 1.19-1.08 (m, 2H), 1.02-0.88 (m, 5H).

Example 23

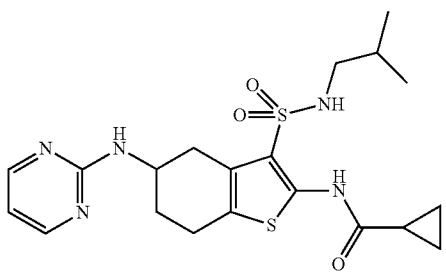 [SMILES: CC(C)CNS(=O)(=O)c1c(NC(=O)C2CC2)sc2c1CC(Nc1ncccn1)CC2]

N-[3-(Isobutylsulfamoyl)-5-(pyrimidin-2-ylamino)-4,5,6,7-tetrahydrobenzothiophen-2-yl]cyclopropanecarboxamide To intermediate 28 (194 mg, 0.52 mmol) and 2-bromopyrimidine (144 mg, 0.91 mmol) in DMSO (2 mL) was added DIPEA (0.4 mL, 2 mmol). The reaction mixture was stirred at 80° C. for 4.5 h and then at r.t. overnight. The reaction mixture was heated to 80° C. for 6.5 h and then at r.t. over the weekend. To the reaction mixture was added EtOAc (100 mL) and the mixture was washed with saturated ammonium chloride solution (3×50 mL) and dried (MgSO$_4$). The mixture was filtered, concentrated in vacuo to yield a brown oil which was purified by flash column chromatography on silica (gradient elution with DCM/MeOH/NH$_4$OH 99.5/0.5/0.05 to 90/10/1) and preparative chromatography (elution with a mixture of 95/5/0.5 DCM/MeOH/NH$_4$OH) to afford the title compound (10 mg, 4%) as a yellow solid. LCMS (ES+) [M+H]$^+$ 448.17, RT 2.59 minutes 84.25% purity (Method 9).

Example 24

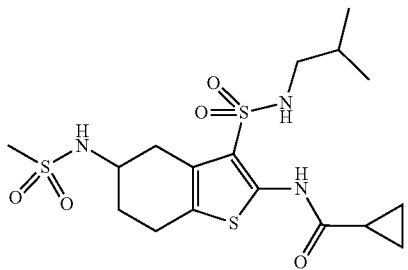 [SMILES: CC(C)CNS(=O)(=O)c1c(NC(=O)C2CC2)sc2c1CC(NS(C)(=O)=O)CC2]

N-[3-(Isobutylsulfamoyl)-5-(methanesulfonamido)-4,5,6,7-tetrahydrobenzothiophen-2-yl]cyclopropanecarboxamide Chlorosulfonic acid (143 μl, 2.14 mmol) was added dropwise to a suspension of intermediate 30 (270 mg, 0.85 mmol) in MeCN (21 mL) at 0° C. The resulting solution was stirred at r.t. for 0.5 h and was then heated at 50° C. in sealed tube for 3 h. The crude sulphonyl chloride was split into three and used for sulfonamide formation. To a solution of 2-cyclopropaneamido-5-methanesulfonamido-4,5,6,7-tetrahydro-1-benzothiophene-3-sulfonyl chloride (116 mg, 0.28 mmol) in MeCN (6 mL) was added 2-methylpropan-1-amine (0.22 ml, 2.24 mmol) dropwise and reaction mixture was stirred at r.t. for 2 h. The solvent was removed in vacuo and the reaction mixture was diluted with DCM (100 mL) and washed with water, 1M aqueous hydrochloric acid, saturated sodium hydrogen carbonate solution and brine. The organic phases were dried (MgSO$_4$), filtered and concentrated in vacuo to yield the crude product which was purified by preparative HPLC (low pH) to afford the title compound (43.5 mg, 34%) as an off white solid. δ$_H$ (500 MHz, CD$_3$OD) 3.76-3.69 (m, 1H), 3.20 (dd, J 16.7, 5.3 Hz, 1H), 3.00 (s, 3H), 2.86-2.75 (m, 2H), 2.74-2.63 (m, 3H), 2.18-2.11 (m, 1H), 1.92-1.82 (m, 1H), 1.82-1.76 (m, 1H), 1.74-1.65 (m, 1H), 1.04-0.96 (m, 4H), 0.90-0.85 (m, 6H).

Example 25

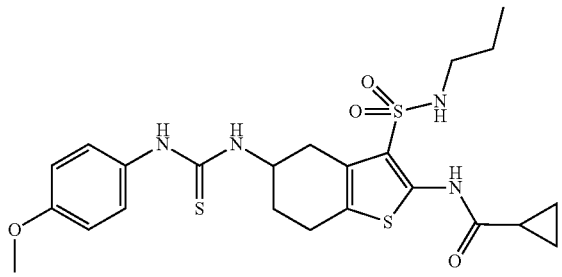

N-[5-[(4-Methoxyphenyl)carbamothioylamino]-3-(propylsulfamoyl)-4,5,6,7-tetrahydrobenzothiophen-2-yl]cyclopropanecarboxamide 1-Isothiocyanato-4-methoxy-benzene (31 mg, 0.19 mmol) was added to a solution of intermediate 31 (45 mg, 0.13 mmol) dissolved in DCM (1 mL). The reaction was stirred at r.t. for 5 h and the reaction mixture was concentrated in vacuo to yield the crude product which was purified by reverse phase HPLC (basic) to afford the title compound (15 mg, 23%) as an off white powder. 1H NMR (400 MHz, DMSO-d$_6$) δ 10.43 (s, 1H), 9.26 (s, 1H), 7.77 (s, 1H), 7.58 (s, 1H), 7.28 (d, J=8.5 Hz, 2H), 6.96-6.81 (m, 2H), 4.61 (s, 1H), 3.73 (s, 3H), 3.12 (dd, J=16.9, 5.2 Hz, 1H), 2.74 (q, J=7.3 Hz, 4H), 2.58 (dd, J=16.8, 8.3 Hz, 1H), 2.03 (d, J=13.1 Hz, 1H), 1.95-1.74 (m, 2H), 1.39 (h, J=7.3 Hz, 2H), 0.99-0.84 (m, 4H), 0.80 (t, J=7.4 Hz, 3H). LCMS [M+H]$^+$ 523.15, RT 2.52 minutes, 100.0% purity (Method 7). LCMS [M+H]$^+$ 523.14, RT 2.62 minutes, 98.15% purity (Method 9).

Example 26

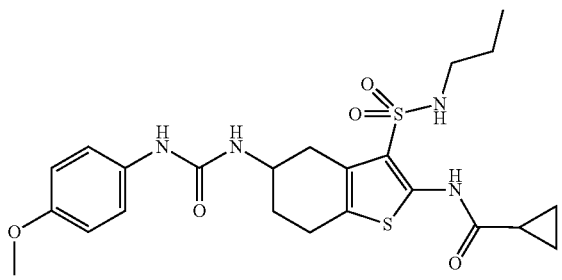 [SMILES: CCCNS(=O)(=O)c1c(NC(=O)C2CC2)sc2c1CC(NC(=S)Nc1ccc(OC)cc1)CC2]

N-[5-[(4-Methoxyphenyl)carbamoylamino]-3-(propylsulfamoyl)-4,5,6,7-tetrahydrobenzothiophen-2-yl]cyclopropanecarboxamide Chlorosulfonic acid (69.0 μl, 1.03 mmol) was added dropwise to a suspension of intermediate 38 (160 mg, 0.41 mmol) in MeCN (15 mL) at 0° C. The resulting solution was stirred at r.t. for 0.5 h then heated at 50° C. in sealed tube for 3 h. The crude sulphonyl chloride was split into two and utilised for sulfonamide formation. To a solution of 2-(cyclopropanecarbonylamino)-5-[(4-methoxyphenyl)carbamoylamino]-4,5,6,7-tetrahydrobenzothiophene-3-sulfonyl chloride (100 mg, 0.20 mmol) in MeCN (6 ml) was added dropwise propan-1-amine (0.13 ml, 1.6 mmol) and the reaction mixture was stirred at r.t. for 2 h. The mixture was concentrated in vacuo and diluted with DCM (50 mL). The mixture was washed with water, 1M aqueous hydrochloric acid solution, saturated sodium hydrogen carbonate solution and brine. The organic phase was dried (MgSO$_4$), filtered and concentrated in vacuo to yield the crude product which was purified by preparative HPLC (low pH) to afford the title compound (35 mg, 33%) as an off white solid. $\delta_H$ (500 MHz, CD$_3$OD) 7.25-7.20 (m, 2H), 6.86-6.81 (m, 2H), 4.15-4.06 (m, 1H), 3.75 (s, 3H), 3.10 (dd, J 16.7, 4.9 Hz, 1H), 2.89-2.77 (m, 4H), 2.71-2.61 (m, 1H), 2.10-2.04 (m, 1H), 1.92-1.83 (m, 1H), 1.82-1.75 (m, 1H), 1.46 (m, 2H), 1.05-0.95 (m, 4H), 0.86 (t, J 7.4 Hz, 3H). LCMS (ES+) [M+H]$^+$ 507.3, RT 3.40 minutes (Method 10).

Example 27

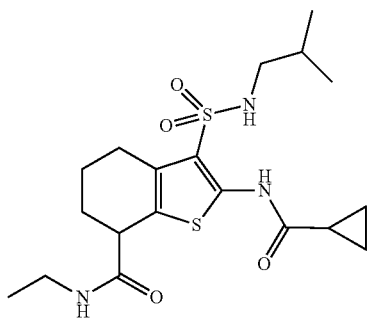 [SMILES: CCNC(=O)C1CCCc2c1sc(NC(=O)C1CC1)c2S(=O)(=O)NCC(C)C]

2-(Cyclopropanecarbonylamino)-N-ethyl-3-(isobutylsulfamoyl)-4,5,6,7-tetrahydrobenzothiophene-7-carboxamide Intermediate 46 (75 mg, 0.26 mmol) was suspended in MeCN (1 mL) and sulfurochloridic acid (0.05 mL, 0.77 mmol) was added, the solution was heated at 80° C. in a sealed tube for 6 h. After cooling to r.t. further sulfurochloridic acid (0.05 mL, 0.77 mmol) was added and the mixture was heated to 80° C. for 16 h and then cooled to r.t. 2-Methylpropan-1-amine (0.41 mL, 4.13 mmol) was added and the mixture stirred for 10 minutes. The reaction mixture was diluted with EtOAc (5 mL) and washed with 1M aqueous hydrochloric acid solution (2×10 mL) followed by saturated aqueous sodium hydrogen carbonate solution (10 mL). The organic phase was dried (MgSO$_4$), filtered and concentrated in vacuo to yield the crude product which was purified by flash column chromatography on silica (gradient elution with 40-80% EtOAc/heptane) to afford the crude product (30 mg), a yellow oil which was purified by preparative HPLC (basic) to afford the title compound (4.8 mg, 4.4%) as a white solid. $\delta_H$ (500 MHz, CD$_3$OD) 3.63-3.57 (m, 1H), 3.29-3.18 (m, 2H), 2.86-2.79 (m, 1H), 2.75-2.63 (m, 3H), 2.09-1.95 (m, 3H), 1.82-1.66 (m, 3H), 1.15 (t, J 7.3 Hz, 3H), 1.03-0.95 (m, 4H), 0.89 (d, J 1.5 Hz, 3H), 0.88 (d, J 1.5 Hz, 3H). LCMS (ES+) [M+H]$^+$ 428.3, RT 3.1 minutes (Method 10).

Example 28

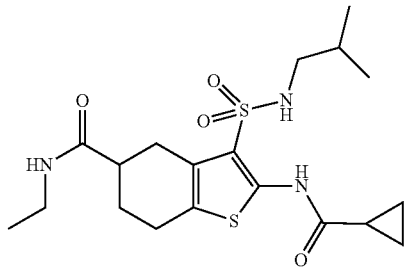 [SMILES: CCNC(=O)C1CCc2sc(NC(=O)C3CC3)c(S(=O)(=O)NCC(C)C)c2C1]

2-(Cyclopropanecarbonylamino)-N-ethyl-3-(isobutylsulfamoyl)-4,5,6,7-tetrahydrobenzothiophene-5-carboxamide Intermediate 45 (100 mg, 0.22 mmol, 64% purity) was suspended in MeCN (1 mL) and sulfurochloridic acid (0.04 mL, 0.66 mmol) was added. The solution was heated at 80° C. in a sealed tube for 6 h and after cooling to r.t., further sulfurochloridic acid (0.04 mL, 0.66 mmol) was added and the mixture heated to 80° C. for 16 h and then cooled to r.t. 2-Methylpropan-1-amine (0.35 mL, 3.5 mmol) was added and the mixture stirred for 10 minutes. The reaction mixture was diluted with EtOAc (5 mL) and washed with 1M aqueous hydrochloric acid solution (2×10 mL) followed by saturated sodium hydrogen carbonate solution (10 mL). The organic layer was dried (MgSO$_4$), filtered and concentrated in vacuo to yield the crude product which was purified by flash column chromatography on silica (gradient elution with 40-80% EtOAc/heptane) to afford the product (20 mg) as a yellow oil which was purified by preparative HPLC (basic) to afford the title compound (1.8 mg, 1.8%) as a white solid. $\delta_H$ (500 MHz, CD$_3$OD) 3.27-3.20 (m, 2H), 3.05 (dd, J 16.5, 5.0 Hz, 1H), 2.86-2.65 (m, 5H), 2.59-2.50 (m, 1H), 2.11-2.04 (m, 1H), 1.90-1.75 (m, 2H), 1.74-1.64 (m, 1H), 1.14 (t, J 7.3 Hz, 3H), 1.04-0.95 (m, 4H), 0.88 (d, J 1.2 Hz, 3H), 0.87 (d, J 1.2 Hz, 3H). LCMS (ES+) [M+H]$^+$ 428.3, RT 3.19 minutes (Method 10).

Example 29

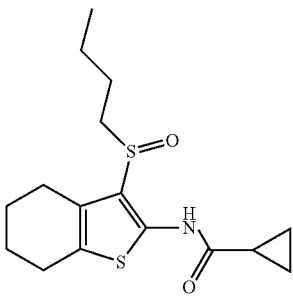 [SMILES: CCCCS(=O)c1c(NC(=O)C2CC2)sc2c1CCCC2]

N-(3-Butylsulfinyl-4,5,6,7-tetrahydrobenzothiophen-2-yl)cyclopropanecarboxamide

To a solution of intermediate 49 (20 mg, 0.078 mmoL) and triethylamine (0.04 mL, 0.29 mmol) in DCM (4 mL) cooled to 0° C. was added cyclopropanecarbonyl chloride (0.016 mL, 0.18 mmol) and the solution was allowed to warm to r.t., then heated to 40° C. under nitrogen. The reaction mixture was diluted with DCM (15 mL) and saturated ammonium chloride solution (10 mL) was added. The phases were separated and the aqueous layer was extracted with further DCM (10 mL). The combined organic phases were washed with brine (10 mL), dried (MgSO$_4$), filtered and concentrated in vacuo. The crude product was purified by preparative HPLC (low pH) to afford the title compound (3.1 mg, 12%) as a thin film. $\delta_H$ (250 MHz, Chloroform-d) 11.23 (s, 1H), 3.12-2.82 (m, 2H), 2.75-2.60 (m, 2H), 2.58-2.41 (m, 1H), 2.26-2.06 (m, 1H), 1.95-1.67 (m, 6H), 1.66-1.42 (m, 3H, part. obs. by water signal), 1.18-1.04 (m, 2H), 0.96 (t, J 7.3 Hz, 3H), 0.92-0.84 (m, 2H). LCMS (ES+) [M+H]$^+$ 326, RT 3.91 minutes (Method 10).

Example 30

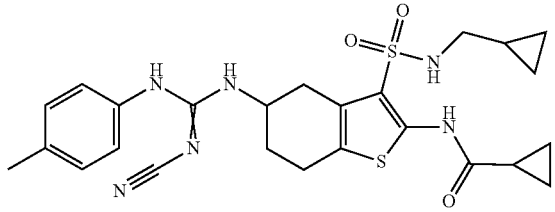 [SMILES: Cc1ccc(NC(=NC#N)NC2CCc3sc(NC(=O)C4CC4)c(S(=O)(=O)NCC4CC4)c3C2)cc1]

N-[5-[[N'-Cyano-N-(p-tolyl)carbamimidoyl]amino]-3-(cyclopropylmethylsulfamoyl)-4,5,6,7-tetrahydrobenzothiophen-2-yl]cyclopropanecarboxamide Intermediate 50 (90 mg, 0.35 mmol) was dissolved in 2-propanol (2 mL). Intermediate 51 (119 mg, 0.32 mmol) was added and the reaction mixture was heated in the microwave at 120° C. for 2 h. The reaction mixture was concentrated in vacuo and the crude product was purified by preparative HPLC (acidic) to afford the title compound (12 mg, 6.4%) as a white solid. $\delta_H$ (500 MHz, CD$_3$OD) 7.21 (d, J 8.2 Hz, 2H), 7.16-7.10 (m, 2H), 4.26-4.13 (m, 1H), 3.22-3.16 (m, 1H), 2.85-2.69 (m, 4H), 2.63 (dd, J 16.6, 8.8 Hz, 1H), 2.34 (s, 3H), 2.13-2.04 (m, 1H), 1.90-1.75 (m, 2H), 1.04-0.95 (m, 4H), 0.88-0.78 (m, 1H), 0.48-0.39 (m, 2H), 0.09 (m, 2H). LCMS (ES+) [M+H]$^+$ 527.3, RT 3.59 minutes (Method 10).

Example 31

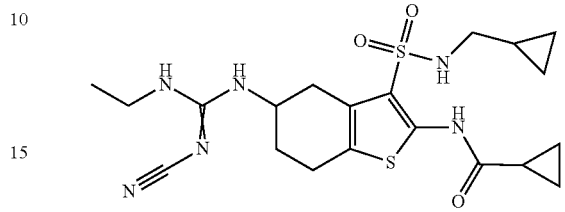

N-[5-[[N'-Cyano-N-ethyl-carbamimidoyl]amino]-3-(cyclopropylmethylsulfamoyl)-4,5,6,7-tetrahydrobenzothiophen-2-yl]cyclopropanecarboxamide Intermediate 52 (80 mg, 0.15 mmol) was dissolved in DCM (4 mL) and 2 M ethyl amine in THF (3.8 mL, 7.78 mmol) was added and the reaction mixture was stirred at r.t for 16 h. The reaction mixture was concentrated in vacuo and the crude product was purified by preparative HPLC (acidic) to afford the title compound (15 mg, 21%) as a white solid. $\delta_H$ (500 MHz, CD$_3$OD) 4.13-3.98 (m, 1H), 3.30-3.20 (m, 3H), 2.84-2.73 (m, 4H), 2.68-2.58 (m, 1H), 2.15-2.06 (m, 1H), 1.91-1.75 (m, 2H), 1.18 (t, J 7.2 Hz, 3H), 1.05-0.95 (m, 4H), 0.88-0.80 (m, 1H), 0.50-0.40 (m, 2H), 0.15-0.05 (m, 2H). LCMS (ES+) [M+H]$^+$ 465.3, RT 3.09 minutes (Method 10).

Example 32

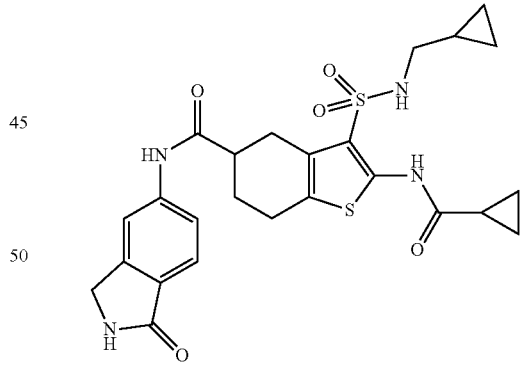

2-(Cyclopropanecarbonylamino)-3-(cyclopropylmethylsulfamoyl)-N-(1-oxoisoindolin-5-yl)-4,5,6,7-tetrahydrobenzothiophene-5-carboxamide To intermediate 55 (40 mg, 0.10 mmol), COMU (53 mg, 0.12 mmol) and DCM (1 mL) was added 5-aminoisoindolin-1-one [222036-66-0] (14.8 mg, 0.10 mmol) and DIPEA (17.4 µL, 0.10 mmol). The reaction mixture was stirred at r.t. overnight. To the mixture was added DCM (2 mL) and water (4 mL) and the mixture was filtered through a phase separator cartridge and the aqueous phase was further extracted with DCM (2×2 mL). The organic phases were combined and concentrated in vacuo. The crude product was purified by reverse phase HPLC to afford the title compound (9 mg, 20%). LCMS (ES+) [M+H]+ 529.15, RT 4.5 minutes (Method 20).

Example 33

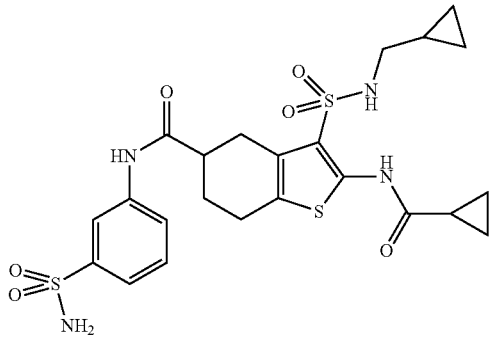 [SMILES: NS(=O)(=O)c1cccc(NC(=O)C2CCc3sc(NC(=O)C4CC4)c(S(=O)(=O)NCC4CC4)c3C2)c1]

2-(Cyclopropanecarbonylamino)-3-(cyclopropylmethylsulfamoyl)-N-(3-sulfamoylphenyl)-4,5,6,7-tetrahydrobenzothiophene-5-carboxamide The method for example 32 was utilised substituting 3-aminobenzenesulfonamide [98-18-0] (17.2 mg, 0.10 mmol) for 5-aminoisoindolin-1-one [222036-66-0] to afford the title compound (17.2 mg, 0.10 mmol). LCMS (ES+) [M+H]+ 553.12, RT 4.68 minutes (Method 20).

Example 34

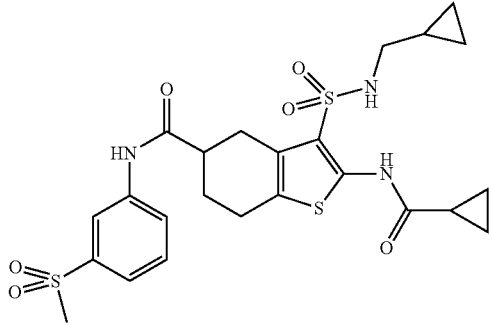 [SMILES: CS(=O)(=O)c1cccc(NC(=O)C2CCc3sc(NC(=O)C4CC4)c(S(=O)(=O)NCC4CC4)c3C2)c1]

2-(Cyclopropanecarbonylamino)-3-(cyclopropylmethylsulfamoyl)-N-(3-methylsulfonylphenyl)-4,5,6,7-tetrahydrobenzothiophene-5-carboxamide The method for example 32 was utilised substituting 3-(methylsulfonyl)aniline hydrochloride [80213-28-1] (21.9 mg, 0.10 mmol) for 5-aminoisoindolin-1-one [222036-66-0] and adding additional DIPEA (17.4 µL, 0.100 mmol) to afford the title compound (0.028 g, 51%). LCMS (ES+) [M+H]+ 552.131, RT 4.88 minutes (Method 20).

Example 35

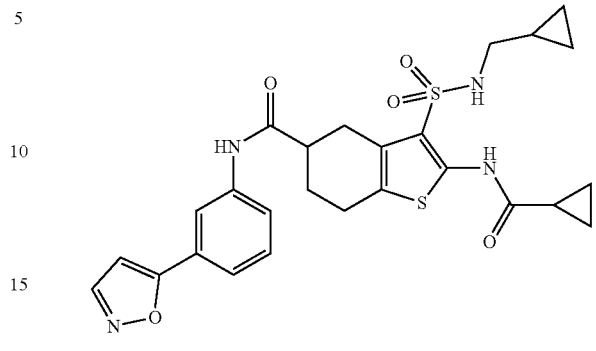

2-(Cyclopropanecarbonylamino)-3-(cyclopropylmethylsulfamoyl)-N-(3-isoxazol-5-ylphenyl)-4,5,6,7-tetrahydrobenzothiophene-5-carboxamide The method for example 32 was utilised substituting 3-isoxazol-5-ylaniline [832740-15-5] (16.0 mg, 0.10 mmol) for 5-aminoisoindolin-1-one [222036-66-0] to afford the title compound (0.024 g, 43%). LCMS (ES+) [M+H]+ 541.1534, RT 5.22 minutes (Method 20).

Example 36

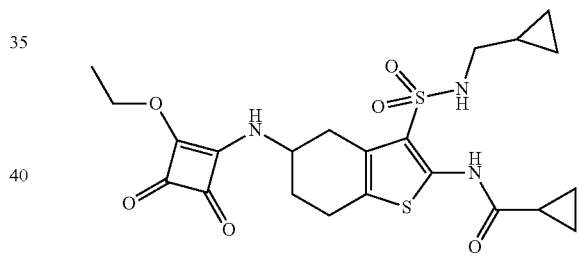

N-[3-(Cyclopropylmethylsulfamoyl)-5-[(2-ethoxy-3,4-dioxo-cyclobuten-1-yl)amino]-4,5,6,7-tetrahydrobenzothiophen-2-yl]cyclopropanecarboxamide Intermediate 51 (100 mg, 0.27 mmol) was dissolved in EtOH (0.5 mL) and DIPEA (50 µL, 0.29 mmol) was added, followed by 3,4-diethoxycyclobut-3-ene-1,2-dione [5231-87-8] (70 mg, 0.41 mmol) and the solution was stirred at r.t. for 2 h. The reaction mixture was concentrated in vacuo and purified by flash column chromatography on silica (gradient elution with 0-100% EtOAc/heptane) to afford the impure product which was purified by preparative HPLC (acidic) to afford the title compound (10 mg, 7.4%) as a 1:1 rotameric mixture. $\delta_H$ (500 MHz, DMSO-$d_6$) 10.44 (s, 1H), 9.03 (d, J 7.8 Hz, 0.5H), 8.84 (d, J 8.5 Hz, 0.5H), 7.92 (br. s, 1H), 4.72-4.61 (m, 2H), 4.32-4.21 (m, 0.5H), 3.90-3.78 (m, 0.5H), 3.23-3.09 (m, 1H), 2.80 (br d, J 16.1 Hz, 1H), 2.70 (br. s, 3H), 2.62-2.54 (m, 1H), 2.11-2.01 (m, 1H), 1.96-1.87 (m, 1H), 1.86-1.74 (m, 1H), 1.43-1.32 (m, 3H), 0.96-0.84 (m, 4H), 0.81-0.69 (m, 1H), 0.42-0.30 (m, 2H), 0.11-0.02 (m, 2H). LCMS (ES+) [M+H]+ 494.2, RT 3.21 minutes (Method 10).

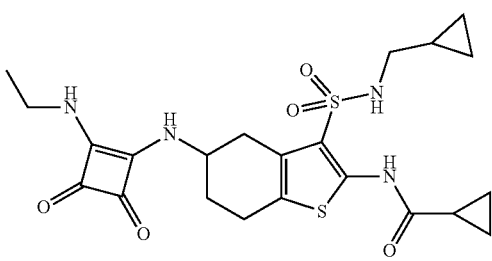 [SMILES: CCNc1c(NC2CCc3sc(NC(=O)C4CC4)c(S(=O)(=O)NCC4CC4)c3C2)c(=O)c1=O]

N-[3-(Cyclopropylmethylsulfamoyl)-5-[[2-(ethyl-amino)-3,4-dioxo-cyclobuten-1-yl]amino]-4,5,6,7-tetrahydrobenzothiophen-2-yl]cyclopropanecarbox-amide Example 36 (95%, 50 mg, 0.10 mmol) was dissolved in EtOH (1 mL) and 2M ethanamine in THF (50 µL, 0.10 mmol) was added and the reaction mixture was left to stand for 2 h at r.t. The white precipitate was filtered and washed with EtOH to afford the title compound (27 mg, 62%) as a white solid. 1H NMR (500 MHz, DMSO-d6) δ 10.45 (s, 1H), 7.93 (s, 1H), 7.51 (br. s, 1H), 7.33 (br. s, 1H), 4.35 (br s, 1H), 3.58-3.47 (m, 2H), 3.12 (dd, J 16.7, 4.8 Hz, 1H), 2.79-2.65 (m, 5H), 2.07-1.98 (m, 1H), 1.96-1.81 (m, 2H), 1.16 (t, J 7.2 Hz, 3H), 0.96-0.85 (m, 4H), 0.82-0.71 (m, 1H), 0.39-0.32 (m, 2H), 0.12-0.02 (m, 2H). LCMS (ES+) [M+H]+ 493.1, RT 2.80 minutes (Method 10).

Example 38

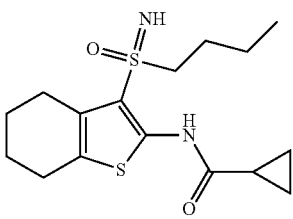 [SMILES: CCCCS(=N)(=O)c1c(NC(=O)C2CC2)sc2c1CCCC2]

N-[3-(Butylsulfonimidoyl)-4,5,6,7-tetrahydrobenzo-thiophen-2-yl]cyclopropanecarboxamide To a solution of example 29 (560 mg, 1.72 mmoL) in DCM (17 mL) was added 2,2,2-trifluoroacetamide [354-38-1] (389 mg, 3.44 mmoL), magnesium oxide [1309-48-4] (277 mg, 6.88 mmoL), rhodium diacetate dimer [15956-28-2] (19 mg, 0.043 mmoL) and iodobenzene diacetate [3240-34-4] (831 mg, 2.58 mmoL) and the resulting suspension was stirred at r.t. under nitrogen for 16 h. The reaction mixture was filtered through a pad of celite and concentrated in vacuo to give the crude material (1.4 g) which was purified by flash column chromatography on silica (gradient elution with 0 to 100% of DCM in heptane) to afford the protected sulfoximine (158 mg, 21%) as a light yellow oil. To a stirred solution of the protected suloximine (153 mg) in MeOH (10 mL) was added potassium carbonate (1.2 g, 8.6 mmoL) and the reaction mixture was stirred at r.t. for 30 minutes. The reaction mixture was concentrated in vacuo and the crude material was purified by flash column chromatography on silica (gradient elution with 0 to 100% of EtOAc in heptane) followed by purification by preparative HPLC (low pH) to afford the title compound (70 mg, 12%) as a colourless gum. δ$_H$ (250 MHz, Chloroform-d) 11.87 (br. s, 1H), 3.28-3.06 (m, 2H), 3.00 (br. s, 1H), 2.81-2.70 (m, 2H), 2.68-2.57 (m, 2H), 1.88-1.53 (m, 7H), 1.51-1.27 (m, 2H), 1.18-1.05 (m, 2H), 1.00-0.79 (m, 5H). LCMS (ES+) [M+H]+ 341, RT 3.55 minutes (Method 10).

Example 39

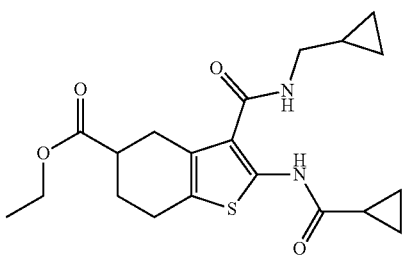 [SMILES: CCOC(=O)C1CCc2sc(NC(=O)C3CC3)c(C(=O)NCC3CC3)c2C1]

Ethyl 2-(cyclopropanecarbonylamino)-3-(cyclopro-pylmethylcarbamoyl)-4,5,6,7-tetrahydrobenzothi-ophene-5-carboxylate Intermediate 43 (5.3 g, 15.7 mmol) was dissolved in DCM (100 mL) and 1-cyclopropylmethanamine (2.7 mL, 31.42 mmol) and EDCl (4.5 g, 23.56 mmol) was added and the reaction mixture was stirred at r.t. for 16 h. The reaction mixture was diluted with DCM (100 mL) then washed with water, 1M aqueous hydrochloric acid solution and saturated sodium hydrogen carbonate solution. The organic phase was washed with brine, dried (MgSO$_4$), filtered and concentrated in vacuo to give the crude residue which was purified by flash column chromatography on silica (gradient elution with 5% to 50% EtOAc in heptane) to afford the title compound (3.11 g, 51%) as a white solid. δ$_H$ (500 MHz, DMSO-d$_6$) 11.03 (s, 1H), 7.74 (t, J 5.6 Hz, 1H), 4.10 (q, J 7.1 Hz, 2H), 3.25-3.16 (m, 1H), 3.13-3.05 (m, 1H), 2.90-2.76 (m, 2H), 2.75-2.64 (m, 3H), 2.18-2.08 (m, 1H), 1.94-1.87 (m, 1H), 1.82-1.70 (m, 1H), 1.20 (t, J 7.1 Hz, 3H), 1.09-0.97 (m, 1H), 0.87-0.80 (m, 4H), 0.45-0.39 (m, 2H), 0.26-0.20 (m, 2H). LCMS (ES+) [M+H]+ 391.05, [M+Na]+ 413.10, RT 1.41 minutes, 100% purity (Method 6). LCMS (ES+) [M+H]+ 391.1, RT 3.73 minutes, purity 97.5%, 1.2% 7-regioisomer present (Method 10).

Example 40

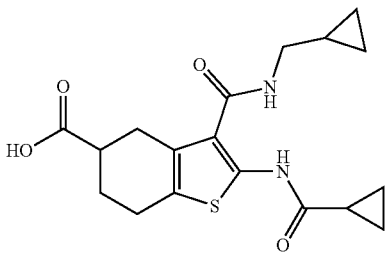 [SMILES: O=C(NCC1CC1)c1c(NC(=O)C2CC2)sc2c1CC(C(=O)O)CC2]

2-(Cyclopropanecarbonylamino)-3-(cyclopropylmethylcarbamoyl)-4,5,6,7-tetrahydrobenzothiophene-5-carboxylic acid Example 39 (3.5 g, 8.96 mmol) was dissolved in THF (35 mL) and 2M lithium hydroxide monohydrate solution was added (13.44 mL). The reaction mixture was stirred at r.t. for 48 h before concentrating in vacuo and the crude residue was dissolved in water (5 mL) and sonicated for 2 minutes. The resulting solution was acidified with 1M aqueous hydrochloric acid solution and the resulting solid was filtered off, washed with water and dried in vacuo to afford the title compound (3.2 g, 90%). $\delta_H$ (500 MHz, DMSO-d$_6$) 12.29 (s, 1H), 11.07 (s, 1H), 7.72 (s, 1H), 3.21-3.06 (m, 2H), 2.89-2.76 (m, 2H), 2.72-2.56 (m, 3H), 2.16-2.06 (m, 1H), 1.94-1.86 (m, 1H), 1.80-1.69 (m, 1H), 1.09-0.98 (m, 1H), 0.88-0.79 (m, 4H), 0.46-0.38 (m, 2H), 0.26-0.19 (m, 2H). LCMS (ES+) [M+H]$^+$ 363.10, RT 1.18 minutes, 98% purity (Method 6).

Example 41

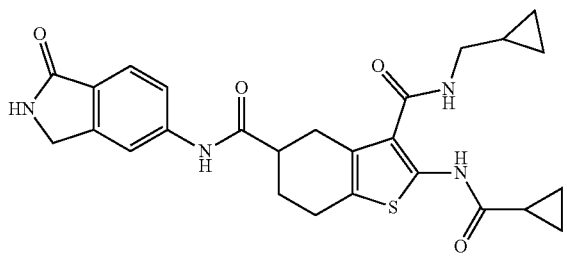 [SMILES: O=C1NCc2cc(NC(=O)C3CCc4sc(NC(=O)C5CC5)c(C(=O)NCC5CC5)c4C3)ccc21]

2-(Cyclopropanecarbonylamino)-N3-(cyclopropylmethyl)-N5-(1-oxoisoindolin-5-yl)-4,5,6,7-tetrahydrobenzothiophene-3,5-dicarboxamide To the reaction vessel was added example 40 (47.1 mg, 0.13 mmol), 5-aminoisoindolin-1-one [222036-66-0] (19.3 mg, 0.13 mmol), COMU (69 mg, 0.16 mmol), DCM (1.3 mL) and DIPEA (17 mg, 0.13 mmol). The reaction mixture was shaken at r.t. for 3 nights. To the dry reaction mixture was added DCM (2 mL) and water (2 mL) and the mixture was filtered through a phase separator and washed with DCM (2×2 mL). The combined organic phases were concentrated in vacuo and purified by preparative HPLC (basic) to afford the title compound (0.0041 g, 6.3%). LCMS (ES+) [M+H]$^+$ 493.1893, RT 4.28 minutes (Method 20).

Example 42

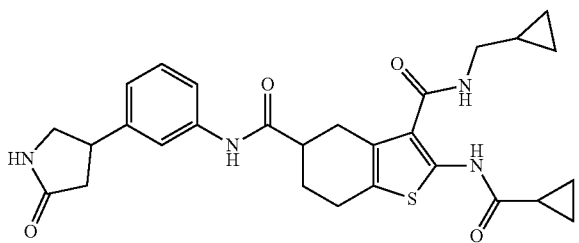 [SMILES: O=C1CC(c2cccc(NC(=O)C3CCc4sc(NC(=O)C5CC5)c(C(=O)NCC5CC5)c4C3)c2)CN1]

2-(Cyclopropanecarbonylamino)-N3-(cyclopropylmethyl)-N5-[3-(5-oxopyrrolidin-3-yl)phenyl]-4,5,6,7-tetrahydrobenzothiophene-3,5-dicarboxamide The method for example 41 was utilised substituting 4-(3-aminophenyl)-2-pyrrolidinone (23 mg, 0.130 mmol) for 5-aminoisoindolin-1-one to afford the title compound (0.027 g, 39%). LCMS (ES+) [M+H]$^+$ 521.2209, RT 4.42 minutes (Method 20).

Example 43

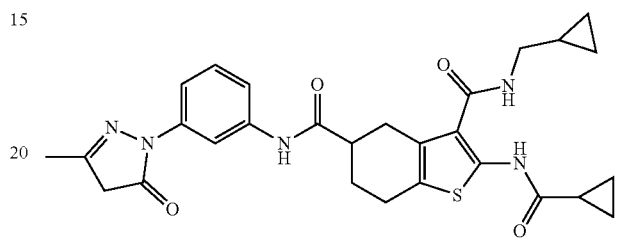

2-(Cyclopropanecarbonylamino)-N3-(cyclopropylmethyl)-N5-[3-(3-methyl-5-oxo-4H-pyrazol-1-yl)phenyl]-4,5,6,7-tetrahydrobenzothiophene-3,5-dicarboxamide The method for example 41 was utilised substituting 2-(3-aminophenyl)-5-methyl-2,4-dihydro-pyrazol-3-one hydrochloride [292151-88-3] (29 mg, 0.13 mmol) for 5-aminoisoindolin-1-one and adding an additional equivalent of DIPEA (17 mg, 0.13 mmol) to afford the title compound (0.018 g, 26%). LCMS (ES+) [M+H]$^+$ 534.2139, RT 4.69 minutes (Method 20).

Example 44

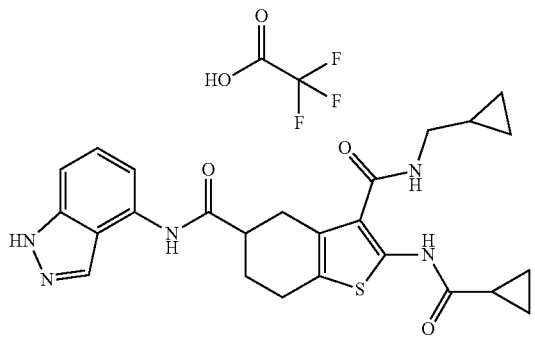

2-(Cyclopropanecarbonylamino)-N3-(cyclopropylmethyl)-N5-(1H-indazol-4-yl)-4,5,6,7-tetrahydrobenzothiophene-3,5-dicarboxamide; 2,2,2-trifluoroacetic acid To the reaction vessel was added example 40 (54 mg, 0.15 mmol), COMU (67 mg, 0.15 mmol), DCM (0.8 mL) and DIPEA (58 mg, 0.45 mmol). The reaction mixture was stirred for 5 minutes prior to addition of tert-butyl 4-aminoindazole-1-carboxylate (35 mg, 0.15 mmol) and the reaction was stirred at r.t. overnight before heating to 40° C. for a further night. To the reaction mixture was added water (1 mL) and the mixture was filtered through a phase separation cartridge and the aqueous phase was washed with further DCM (1 mL). The organic phases were combined and to this mixture was added TFA (0.5 mL, 6 mmol) and the mixture was shaken for 2 h at r.t. before concentrating in vacuo to yield the crude product which was purified by preparative HPLC (acidic) to afford the title compound (12.4 mg, 14%). LCMS (ES+) [M+H]$^+$ 478.17, RT 3.98 minutes (Method 13).

Example 45

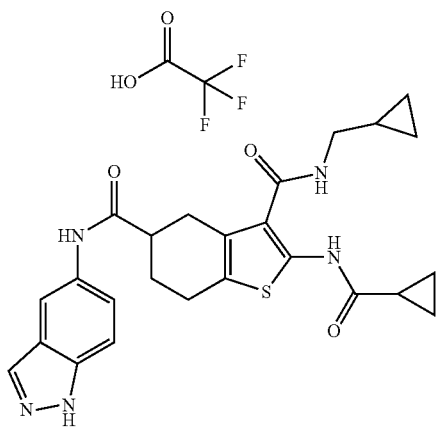

2-(Cyclopropanecarbonylamino)-N3-(cyclopropylmethyl)-N5-(1H-indazol-5-yl)-4,5,6,7-tetrahydrobenzothiophene-3,5-dicarboxamide; 2,2,2-trifluoroacetic acid To a reaction vessel cooled in an ice bath was added example 40 (55 mg, 0.15 mmol), 5-aminoindazole [19335-11-6] (21 mg, 0.15 mmol), TBTU [125700-67-6] (49 mg, 0.15 mmol), DMF (0.8 mL) and DIPEA (78 µL, 0.45 mmol). The reaction mixture was stirred and allowed to warm to r.t. for 1 h. The reaction mixture was purified by preparative HPLC (basic) followed by preparative HPLC (acidic) to afford the title compound (28 mg, 31%) as a white solid. LCMS (ES+) [M+H]$^+$ 478.20, RT 2.36 minutes (Method 8).

Example 46

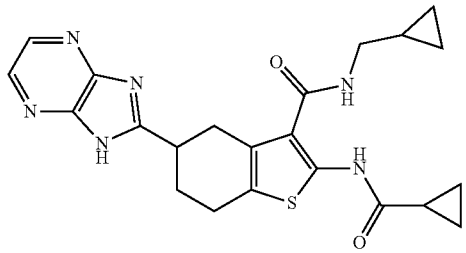 [SMILES: O=C(NCC1CC1)c1c(NC(=O)C2CC2)sc2c1CC(c1nc3nccnc3[nH]1)CC2]

2-(Cyclopropanecarbonylamino)-N-(cyclopropylmethyl)-5-(1H-imidazo[4,5-b]pyrazin-2-yl)-4,5,6,7-tetrahydrobenzothiophene-3-carboxamide To example 40 (0.080 mmol, 30 mg) and pyrazine-2,3-diamine [13134-31-1] (9.5 mg, 0.086 mmol) was added pyridine (0.6 mL) and triphenyl phosphite (31 mg, 0.10 mmol). The reaction mixture was heated at 220° C. in the microwave for 1 h. The solvent was removed in vacuo and the crude product was purified by reverse phase HPLC (basic) to afford the title compound (0.0092 g, 26%). LCMS (ES+) [M+H]$^+$ 437.1735, RT 4.18 minutes (Method 20).

Example 47

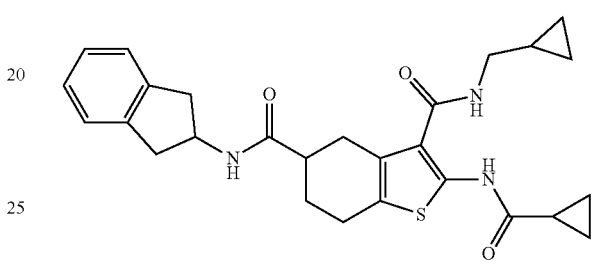

2-(Cyclopropanecarbonylamino)-N3-(cyclopropylmethyl)-N5-indan-2-yl-4,5,6,7-tetrahydrobenzothiophene-3,5-dicarboxamide To example 40 (36 mg, 0.10 mmol), COMU (53 mg, 0.12 mmol) and DCM (1 mL) was added 2-aminoindanhydrochloride [2338-18-3] (17 mg, 0.10 mmol) and a solution of DIPEA (26 mg, 0.20 mmol) in DCM (300 µL). The reaction mixture was stirred overnight at r.t. and to the reaction mixture was added DCM (2 mL) and water (4 mL) and the mixture was filtered through a phase separation cartridge. The aqueous phase was extracted with further DCM (2×2 mL) and the organic phases were concentrated in vacuo and purified by reverse phase HPLC (basic) to afford the title compound (0.025 mg, 53%). LCMS (ES+) [M+H]$^+$ 478.2157, RT 5.28 minutes, 89% Purity (Method 20).

Example 48

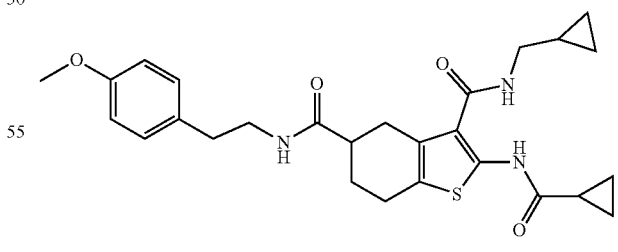

2-(Cyclopropanecarbonylamino)-N3-(cyclopropylmethyl)-N5-[2-(4-methoxyphenyl)ethyl]-4,5,6,7-tetrahydrobenzothiophene-3,5-dicarboxamide The method for example 47 was utilised substituting 2-(4-methoxyphenyl)ethylamine [55-81-2] (15 mg, 0.10 mmol) for 2-aminoindanhydrochloride and adding DIPEA (13 mg, 0.10 mmol) rather than DIPEA (26 mg, 0.20 mmol) to afford the title compound (0.028 g, 55%). LCMS (ES+) [M+H]+ 496.2283, RT 5.14 minutes, Purity 98% (Method 20).

Example 49

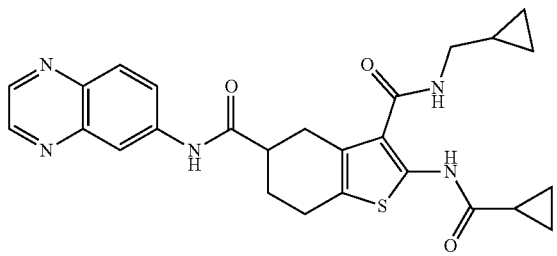 [SMILES: O=C(NCC1CC1)c1c(NC(=O)C2CC2)sc2c1CC(C(=O)Nc1ccc3nccnc3c1)CC2]

2-(Cyclopropanecarbonylamino)-N3-(cyclopropylmethyl)-N5-quinoxalin-6-yl-4,5,6,7-tetrahydrobenzothiophene-3,5-dicarboxamide To the reaction vessel was added example 40 (36 mg, 0.10 mmol), 6-aminoquinoxaline [6298-37-9](15 mg, 0.10 mmol), COMU (53 mg, 0.12 mmol), DCM (1.3 mL) and DIPEA (17 µL, 0.10 mmol). The reaction mixture was stirred at r.t. overnight. To the reaction mixture was added water (1.2 mL) and the mixture was filtered through a phase separator. The aqueous phase was further extracted with DCM (2×400 µL), the organic phases were combined and concentrated in vacuo to yield the crude product which was purified by preparative HPLC (basic) to afford the title compound (0.0092 g, 19%). LCMS (ES+) [M+H]+ 490.1892, RT 4.72 minutes (Method 20).

Example 50

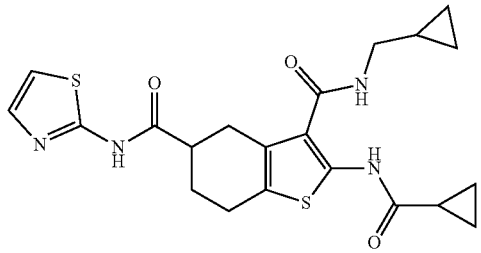 [SMILES: O=C(NCC1CC1)c1c(NC(=O)C2CC2)sc2c1CC(C(=O)Nc1nccs1)CC2]

2-(Cyclopropanecarbonylamino)-N3-(cyclopropylmethyl)-N5-thiazol-2-yl-4,5,6,7-tetrahydrobenzothiophene-3,5-dicarboxamide The method for example 49 was utilised substituting 2-aminothiazole [96-50-4] (10 mg, 0.10 mmol) for 6-aminoquinoxaline [6298-37-9] to afford the title compound (0.0032 g, 7.2%). LCMS (ES+) [M+H]+ 445.1337, RT 4.84 minutes, Purity 93.51% (Method 20).

Example 51

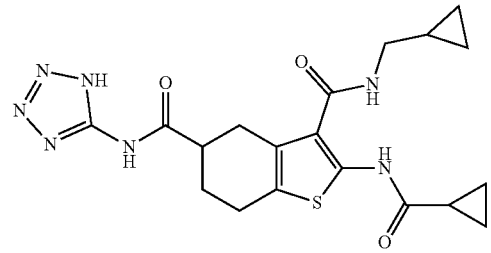 [SMILES: O=C(NCC1CC1)c1c(NC(=O)C2CC2)sc2c1CC(C(=O)Nc1nnn[nH]1)CC2]

2-(Cyclopropanecarbonylamino)-N3-(cyclopropylmethyl)-N5-(1H-tetrazol-5-yl)-4,5,6,7-tetrahydrobenzothiophene-3,5-dicarboxamide The method for example 49 was utilised substituting 5-amino-1H-tetrazole [4418-61-5] (8.5 mg, 0.10 mmol) for 6-aminoquinoxaline [6298-37-9] to afford the title compound (0.0019 g, 4.5%). LCMS (ES+) [M+H]+ 430.1638, RT 4.18 minutes, purity 81.79% (Method 20).

Example 52

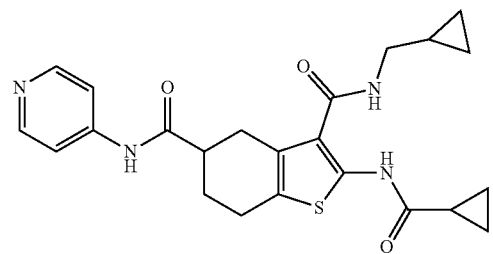 [SMILES: O=C(NCC1CC1)c1c(NC(=O)C2CC2)sc2c1CC(C(=O)Nc1ccncc1)CC2]

2-(Cyclopropanecarbonylamino)-N3-(cyclopropylmethyl)-N5-(4-pyridyl)-4,5,6,7-tetrahydrobenzothiophene-3,5-dicarboxamide The method for example 49 was utilised substituting 4-aminopyridine [504-24-5] (9.5 mg, 0.10 mmol) for 6-aminoquinoxaline [6298-37-9] to afford the title compound (0.0075 g, 17%). LCMS (ES+) [M+H]+ 439.1781, RT 3.56 minutes, purity 96.16% (Method 20).

Example 53

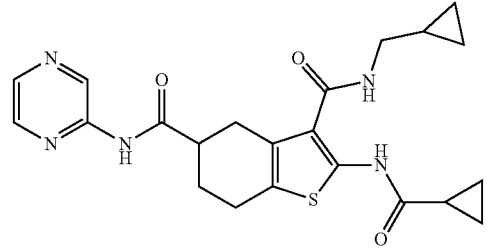

2-(Cyclopropanecarbonylamino)-N3-(cyclopropylmethyl)-N5-pyrazin-2-yl-4,5,6,7-tetrahydrobenzothiophene-3,5-dicarboxamide The method for example 49 was utilised substituting 2-aminopyrazine [5049-61-6] (9.5 mg, 0.10 mmol) for 6-aminoquinoxaline [6298-37-9] to afford the title compound (0.0018 g, 4.1%). LCMS (ES+) [M+H]+ 439.1781, RT 3.56 minutes, Purity 96.16% (Method 20).

Example 54

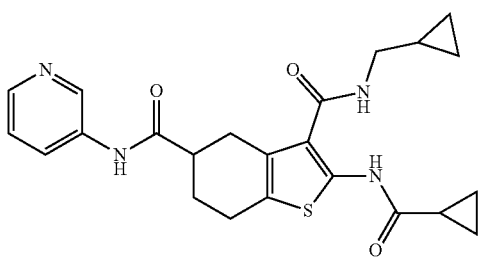

2-(Cyclopropanecarbonylamino)-N3-(cyclopropylmethyl)-N5-(3-pyridyl)-4,5,6,7-tetrahydrobenzothiophene-3,5-dicarboxamide The method for example 49 was utilised substituting 3-aminopyridine [462-08-8] (9.4 mg, 0.10 mmol) for 6-aminoquinoxaline [6298-37-9] to afford the title compound (0.011 g, 24%). LCMS (ES+) [M+H]+ 439.1788, RT 3.89 minutes, purity 91.94% (Method 20).

Example 55

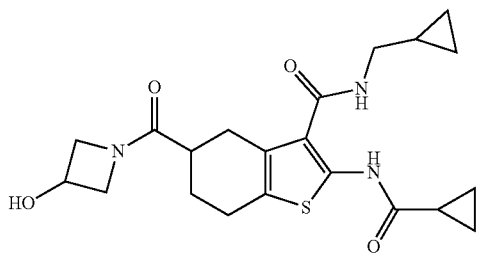 [SMILES: O=C(NCC1CC1)c1c(NC(=O)C2CC2)sc2c1CC(C(=O)N1CC(O)C1)CC2]

2-(Cyclopropanecarbonylamino)-N-(cyclopropylmethyl)-5-(3-hydroxyazetidine-1-carbonyl)-4,5,6,7-tetrahydrobenzothiophene-3-carboxamide The method for example 49 was utilised substituting 3-hydroxyazetidine hydrochloride [18621-18-6] (11 mg, 0.10 mmol) for 6-aminoquinoxaline [6298-37-9] and adding an additional equivalent of DIPEA (13 mg, 0.10 mmol). The reaction mixture afforded the title compound (0.028 g, 66%). LCMS (ES+) [M+H] 418.1791, RT 3.97 minutes, purity 98.93% (Method 20).

Example 56

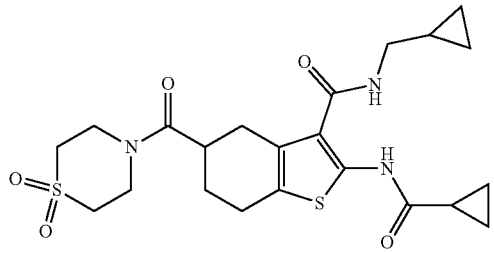 [SMILES: O=C(NCC1CC1)c1c(NC(=O)C2CC2)sc2c1CC(C(=O)N1CCS(=O)(=O)CC1)CC2]

2-(Cyclopropanecarbonylamino)-N-(cyclopropylmethyl)-5-(1,1-dioxo-1,4-thiazinane-4-carbonyl)-4,5,6,7-tetrahydrobenzothiophene-3-carboxamide The method for example 49 was utilised substituting thiomorpholine 1,1-dioxide [39093-93-1] (14 mg, 0.10 mmol) for 6-aminoquinoxaline [6298-37-9] to afford the title compound (0.026 g, 55%). LCMS (ES+) [M+H]+ 430.1638, RT 4.18 minutes, purity 81.79% (Method 20).

Example 57

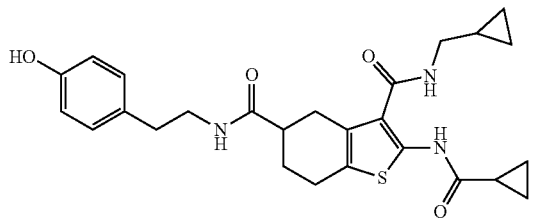 [SMILES: O=C(NCC1CC1)c1c(NC(=O)C2CC2)sc2c1CC(C(=O)NCCc1ccc(O)cc1)CC2]

2-(Cyclopropanecarbonylamino)-N3-(cyclopropylmethyl)-N5-[2-(4-hydroxyphenyl)ethyl]-4,5,6,7-tetrahydrobenzothiophene-3,5-dicarboxamide To example 40 (36 mg, 0.10 mmol), COMU (53 mg, 0.12 mmol) and DCM (1 mL) was added tyramine [51-67-2] (14 mg, 0.10 mmol) and a solution of DIPEA (13 mg, 0.10 mmol) in DCM (300 μL). The reaction mixture was stirred at r.t. overnight and to the mixture was added DCM (2 mL) and water (4 mL) and the mixture was filtered through a phase separation cartridge. The aqueous phase was further extracted with DCM (2×2 mL). The organic phases were combined and concentrated in vacuo to yield the crude product which was purified by reverse phase HPLC (basic) to afford the title compound (0.017 g, 34%). LCMS (ES+) [M+H] 481.2, RT 4.14 minutes, purity 93.89% (Method 20).

Example 58

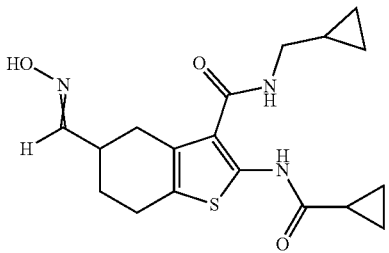 [SMILES: O=C(NCC1CC1)c1c(NC(=O)C2CC2)sc2c1CC(C=NO)CC2]

2-(cyclopropanecarbonylamino)-N-(cyclopropylmethyl)-5-(hydroxyiminomethyl)-4,5,6,7-tetrahydrobenzothiophene-3-carboxamide Intermediate 59 (1.46 g, 4.21 mmol) was dissolved in EtOH (30 mL) and hydroxylamine (1.11 g, 33.7 mmol) was added to the reaction mixture. The reaction mixture was stirred at r.t. for 16 h and then diluted with 1N aqueous hydrochloric acid solution and extracted with DCM (20 mL). The organic phase was dried (MgSO$_4$), filtered and the filtrate was concentrated in vacuo to give the crude product (1.2 g) as a yellow solid. The oxime was purified by flash column chromatography on silica (gradient elution with 0-100% EtOAc in heptane) to afford the title compound (1.0 g, 68%) as a white solid. $\delta_H$ (500 MHz, DMSO-d$_6$) 11.15 (s, 1H), 10.54 (s, 1H), 7.68 (t, J 5.6 Hz, 1H), 7.38 (d, J 5.2 Hz, 1H), 3.16-3.11 (m, 2H), 2.79 (dd, J 15.9, 4.5 Hz, 1H), 2.68-2.63 (m, 3H), 2.59-2.57 (m, 1H), 2.06-1.95 (m, 1H), 1.94-1.84 (m, 1H), 1.72-1.59 (m, 1H), 1.05-1.03 (m, 1H), 0.90-0.78 (m, 4H), 0.46-0.36 (m, 2H), 0.26-0.21 (m, 2H). LCMS (ES+) [M+H]$^+$ 362.18, RT 2.87 minutes, 100.0% purity (Method 10).

Example 59

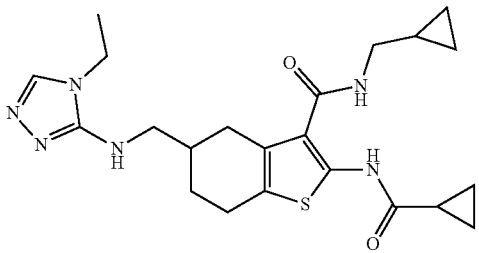 [SMILES: CCn1cnnc1NCC1CCc2sc(NC(=O)C3CC3)c(C(=O)NCC3CC3)c2C1]

2-(Cyclopropanecarbonylamino)-N-(cyclopropylmethyl)-5-[[(4-ethyl-1,2,4-triazol-3-yl)amino]methyl]-4,5,6,7-tetrahydrobenzothiophene-3-carboxamide Intermediate 61 (300 mg, 0.72 mmol) and formic hydrazide [624-84-0] (129 mg, 2.15 mmol) were dissolved in DMF (3 mL). Mercury dichloride [7487-94-7] (584 mg, 2.15 mmol) was added to the reaction mixture and the mixture stirred for 5 minutes. Triethylamine (0.3 mL, 2.15 mmol) was added to the reaction mixture which was heated at 90° C. for 2 h. The mixture was diluted with DCM (20 mL), filtered, and the filtrate was concentrated in vacuo to yield crude material which was extracted with EtOAc (3×20 mL) and washed with water (20 mL). The organics phase was separated, dried (MgSO$_4$) filtered and the filtrate was concentrated in vacuo to afford the crude product which was purified by flash column chromatography on silica (gradient elution with 0-100% EtOAc followed by 0-50% MeOH in DCM) to afford the product which was further purified by preparative HPLC to afford the title compound (21 mg, 6.4%). $\delta_H$ (500 MHz, DMSO-d$_6$) 11.20 (s, 1H), 7.94 (s, 1H), 7.61 (s, 1H), 6.05 (t, J 5.5 Hz, 1H), 3.77 (q, J 7.2 Hz, 2H), 3.22-3.16 (m, 3H), 3.11-3.08 (m, 1H), 2.76-2.72 (m, 2H), 2.65-2.55 (m, 1H), 2.45-2.32 (m, 1H), 2.10-2.06 (s, 1H), 2.03-1.95 (m, 1H), 1.92-1.88 (m, 1H), 1.48-1.42 (m, 1H), 1.23 (t, J 7.2 Hz, 3H), 1.04-1.00 (m, 1H), 0.87-0.78 (m, 4H), 0.45-0.34 (m, 2H), 0.24-0.20 (m, 2H). LCMS: RT 6.79 minutes, MH+ 443.3 (Method 19).

Example 60

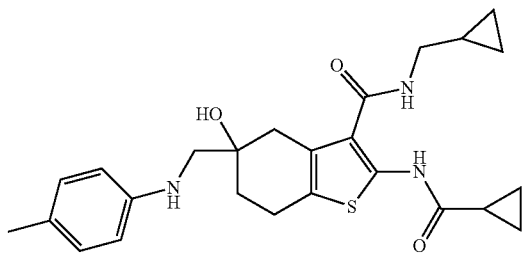 [SMILES: Cc1ccc(NCC2(O)CCc3sc(NC(=O)C4CC4)c(C(=O)NCC4CC4)c3C2)cc1]

2-(Cyclopropanecarbonylamino)-N-(cyclopropylmethyl)-5-hydroxy-5-[(4-methylanilino)methyl]-6,7-dihydro-4H-benzothiophene-3-carboxamide To intermediate 63 (400 mg, 1.15 mmol) was added p-toluidine [106-49-0] (150 mg, 1.40 mmol) in EtOH (1.16 mL). The reaction mixture was heated to 70° C. overnight before concentrating in vacuo to yield the crude product which was purified by flash column chromatography on silica (gradient elution with DCM/MeOH [NH$_4$OH 10%] 5% to 10%) to afford the title compound (272 mg, 46%). $^1$H NMR (400 MHz, Chloroform-d) δ 12.15 (s, 1H), 6.99 (d, J=7.9 Hz, 2H), 6.60 (d, J=7.9 Hz, 2H), 5.81 (s, 1H), 3.92 (s, 1H), 3.35-3.12 (m, 4H), 2.83 (m, 4H), 2.23 (s, 3H), 2.16 (d, J=1.1 Hz, 1H), 2.04 (dt, J=12.1, 6.0 Hz, 1H), 1.91 (dt, J=13.6, 7.4 Hz, 1H), 1.66 (tt, J=8.3, 4.7 Hz, 1H), 1.11 (t, J=3.4 Hz, 2H), 0.98 (dd, J=9.5, 5.2 Hz, 1H), 0.93-0.85 (m, 2H), 0.55-0.47 (m, 2H), 0.21 (d, J=4.8 Hz, 2H). LCMS (ES+) [M+H]$^+$ 454.22, RT 2.72 minutes, purity 91.65% (Method 9).

Example 61

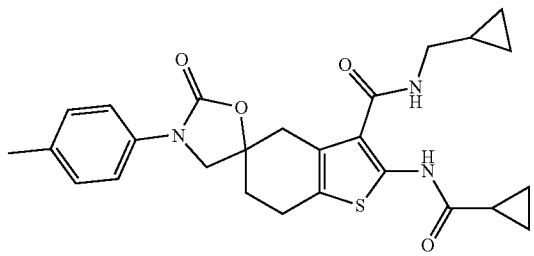 [SMILES: Cc1ccc(N2CC3(CCc4sc(NC(=O)C5CC5)c(C(=O)NCC5CC5)c4C3)OC2=O)cc1]

2-(Cyclopropanecarbonylamino)-N-(cyclopropylmethyl)-2'-oxo-3'-(p-tolyl)spiro[6,7-dihydro-4H-benzothiophene-5,5'-oxazolidine]-3-carboxamide To example 60 (75 mg, 0.17 mmol) in MeCN was added 1,8-diazabicyclo[5.4.0]undec-7-ene [6674-22-2] (67 mg, 0.43 mmol) and 1,1'-carbonyldiimidazole [530-62-1] (40.2 mg, 0.248 mmol) and the reaction mixture was heated at 80° C. overnight. Further 1,1'-carbonyldiimidazole [530-62-1] (20 mg, 0.123 mmol) was added and the reaction was heated at 80° C. before leaving to cool for 2 nights. The reaction mixture was concentrated in vacuo and purified by preparative TLC to afford the title compound (18 mg, 23%). LCMS (ES+) [M+H]$^+$ 480.15, RT 2.98 minutes, purity 93.32% (Method 8).

Example 62

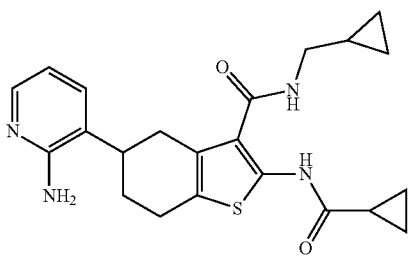 [SMILES: Nc1ncccc1C1CCc2sc(NC(=O)C3CC3)c(C(=O)NCC3CC3)c2C1]

5-(2-Amino-3-pyridyl)-2-(cyclopropanecarbonylamino)-N-(cyclopropylmethyl)-4,5,6,7-tetrahydrobenzothiophene-3-carboxamide A sealed tube was charged with intermediate 64 (146 mg, 0.26 mmol), {2-[(tert-butoxycarbonyl)amino]pyridin-3-yl}boronic acid [863753-35-9] (94 mg, 0.39 mmol) and cesium carbonate (130 mg, 0.40 mmol) and was placed under vacuum for 10 minutes. The tube was back-filled with nitrogen and the solids suspended in 1,4-dioxane (1.05 mL). The mixture was degassed with nitrogen for 5 minutes before sealing and heating at 110° C. for 16 h. The reaction mixture was cooled to r.t. and partitioned between EtOAc (20 mL) and saturated aqueous sodium hydrogen carbonate solution (10 mL). The organic phase was separated and the aqueous phase extracted with EtOAc (2×20 mL). The combined organic phases were washed with brine (20 mL), dried (MgSO$_4$), filtered and concentrated in vacuo to afford the crude product (127 mg) as a dark orange semi-solid. The crude product was purified by flash column chromatography on silica (gradient elution with 0 to 100% EtOAc in heptane) to afford the product (14 mg) as a red gum which was further purified by preparative HPLC (low pH) to afford the title compound (2.2 mg, 2%) as a white powder. δ$_H$ (500 MHz, DMSO-d$_6$) 11.20 (s, 1H), 7.81 (dd, J 4.9, 1.7 Hz, 1H), 7.63 (dd, J 7.4, 1.4 Hz, 1H), 7.33 (dd, J 7.4, 1.4 Hz, 1H), 6.55 (dd, J 7.4, 4.9 Hz, 1H), 5.75 (s, 2H), 3.19-3.13 (m, 1H), 3.12-3.06 (m, 1H), 2.98-2.86 (m, 2H), 2.86-2.78 (m, 1H), 2.76-2.64 (m, 2H), 2.03-1.94 (m, 1H), 1.94-1.86 (m, 1H), 1.87-1.77 (m, 1H), 1.04-0.95 (m, 1H), 0.92-0.77 (m, 4H), 0.40-0.34 (m, 2H), 0.22-0.16 (m, 2H). LCMS ES+[M+H]$^+$ 411.2, RT 2.00 minutes, purity 100% (Method 10).

Example 63

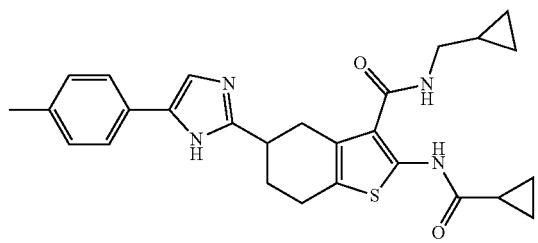 [SMILES: Cc1ccc(-c2cnc(C3CCc4sc(NC(=O)C5CC5)c(C(=O)NCC5CC5)c4C3)[nH]2)cc1]

2-(Cyclopropanecarbonylamino)-N-(cyclopropylmethyl)-5-[5-(p-tolyl)-1H-imidazol-2-yl]-4,5,6,7-tetrahydrobenzothiophene-3-carboxamide Intermediate 65 (100 mg, 0.2 mmol) was suspended in toluene (2 mL) and ammonium acetate (0.31 g, 4.04 mmol) and acetic acid (0.24 ml, 4.04 mmol) were added. The reaction mixture was heated at 120° C. for 1.5 h. The reaction mixture was diluted with EtOAc and washed with water followed by brine. The organic phase was separated, dried (Na$_2$SO$_4$), filtered and concentrated in vacuo to yield the crude product which was purified by preparative HPLC (basic) to afford the product which was further purified by re-crystallisation with IPA/water (2×) to afford the title compound (16 mg, 17%) as a tautomeric mixture (20:80). δ$_H$ (500 MHz, DMSO-d$_6$) 12.03 (s, 0.2H-isomer 1), 11.83 (s, 0.8H-isomer 2), 11.15 (s, 1H), 7.72 (s, 1H), 7.65 (d, J 8.0 Hz, 1.6H-isomer 2), 7.51 (d, J 7.6 Hz, 0.4H-isomer 1), 7.46 (d, J 1.7 Hz, 0.8H-isomer 2), 7.20 (d, J 8.2 Hz, 0.4H-isomer 1), 7.17 (s, 0.2H-isomer 1), 7.13 (d, J 8.0 Hz, 1.6H-isomer 2), 3.22-2.94 (m, 5H), 2.81-2.77 (m, 2H), 2.32-2.27 (m, 4H), 1.95-1.90 (m, 2H), 1.06-1.03 (m, 1H), 0.90-0.79 (m, 4H), 0.43-0.39 (m, 2H), 0.23 (s, 2H) as mixture of tautomers (20:80). LCMS (ES+) [M+H]$^+$ 475.05, RT 3.48 minutes, purity 100% (Method 5).

Example 64 and 65

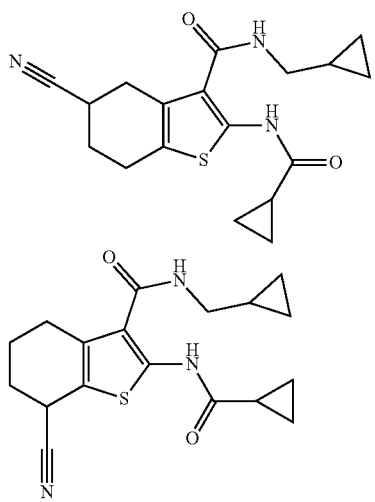

Example 64

5-Cyano-2-(cyclopropanecarbonylamino)-N-(cyclopropylmethyl)-4,5,6,7-tetrahydrobenzothiophene-3-carboxamide

Example 65

7-Cyano-2-(cyclopropanecarbonylamino)-N-(cyclopropylmethyl)-4,5,6,7-tetrahydrobenzothiophene-3-carboxamide To 3-oxocyclohexane-1-carbonitrile [17983-30-1] (63 mg, 0.49 mmol) and 2-cyano-N-(cyclopropylmethyl)acetamide [114153-25-2] (79 mg, 0.55 mmol) in THF (1 mL) was added ammonium acetate (52 mg, 0.675 mmol) and acetic acid (30 µL). The reaction mixture was stirred at 70° C. for 3 h. To the reaction mixture was added sulphur [7704-34-9] (26 mg, 0.81 mmol), EtOH (3 mL) and triethylamine (210 µL, 1.49 mmol) and the mixture was warmed at 65° C. overnight and the mixture was concentrated in vacuo. To the residue was added EtOAc (5 mL) and 10% potassium bisulfate (2 mL), the organic layer was separated and washed with saturated sodium hydrogen carbonate solution followed by brine. The organic phase was separated, dried ($Na_2SO_4$), filtered and concentrated in vacuo to yield a crude brown oil. To the residue was added DCM (2.5 mL) and DIPEA (130 µL, 0.75 mmol) and the mixture was cooled to 0° C. in an ice-bath and a solution of cyclopropanecarbonyl chloride [4023-34-1] (75 mg, 0.70 mmol) in DCM (0.5 mL) was added. The reaction mixture was stirred at r.t. for 4 h before addition of saturated sodium hydrogen carbonate solution. The organic phase was separated with a phase separation cartridge and the aqueous was further extracted with DCM (2 mL). The combined organic layers were concentrated in vacuo to yield the crude products which were purified by preparative HPLC (basic), to afford title compound example 64 (15 mg, 9%). LCMS [M+H]+ 344.10, RT 4.11 minutes, (Method 13). Preparative HPLC purification (acidic) of impure fractions from the initial purification (basic) afforded title compound example 65 (1.4 mg, 0.8%). LCMS [M+H]+ 344.10, [M+Na]+366.13, RT 4.60 minutes, 100.0% purity (Method 21). LCMS [M+H]+ 344.10, [M+Na]+366.08, [M−H]− 342.06, RT 4.30 minutes, 97.08% purity (Method 13).

Examples 66 and 67

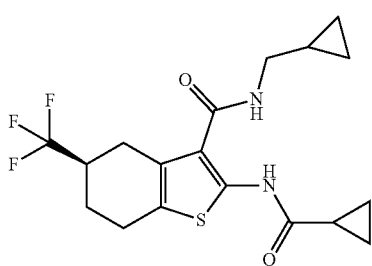

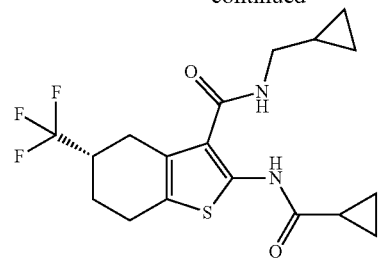

Example 66

(5R)-2-(Cyclopropanecarbonylamino)-N-(cyclopropylmethyl)-5-(trifluoromethyl)-4,5,6,7-tetrahydrobenzothiophene-3-carboxamide

Example 67

(5S)-2-(Cyclopropanecarbonylamino)-N-(cyclopropylmethyl)-5-(trifluoromethyl)-4,5,6,7-tetrahydrobenzothiophene-3-carboxamide Intermediate 70 (23 mg) was purified by chiral separation on preparative HPLC (solvent $CO_2$+20% EtOH) to afford the two separated title chiral compounds as title compound example 66 (7.5 mg, 33%) and title compound example 67 (8.2 mg, 36%). Example 66 LCMS [M−H]− 385.0, RT 2.683 minutes (Method 2). Example 67 LCMS (ES+) [M+H]+ 387.8, RT 2.671 minutes (Method 2).

Example 68

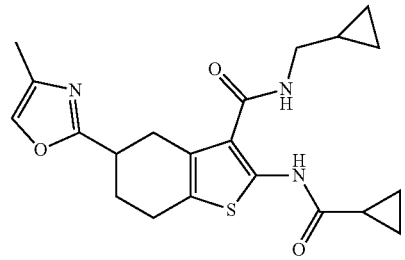 [SMILES: Cc1coc(C2CCc3sc(NC(=O)C4CC4)c(C(=O)NCC4CC4)c3C2)n1]

2-(Cyclopropanecarbonylamino)-N-(cyclopropylmethyl)-5-(4-methyloxazol-2-yl)-4,5,6,7-tetrahydrobenzothiophene-3-carboxamide Intermediate 71 (80 mg, 0.19 mmol) was dissolved in acetic acid (3 mL) and acetic acid ammoniate (1:1) (59 mg, 0.76 mmol) was added and the reaction mixture was stirred at 100° C. for 24 h. The acetic acid was removed in vacuo and EtOAc (50 mL) and water (50 mL) were added. The organic phases were separated and dried ($MgSO_4$), filtered and concentrated in vacuo to yield the crude product which was purified by preparative HPLC (low pH) to afford the title compound (20 mg, 26%) as an off-white solid. $\delta_H$ (500 MHz, $CD_3OD$) 7.56 (s, 1H), 3.29-3.19 (m, 3H), 3.16-3.09 (m, 1H), 3.08-2.98 (m, 1H), 2.88-2.76 (m, 2H), 2.40-2.31 (m, 1H), 2.15 (s, 3H), 2.10-1.99 (m, 1H), 1.84-1.76 (m, 1H), 1.17-1.07 (m, 1H), 1.02-0.97 (m, 2H), 0.96-0.91 (m, 2H), 0.55-0.49 (m, 2H), 0.31-0.26 (m, 2H). LCMS (ES+) [M+H]⁺ 400.2, RT 3.52 minutes, purity 100% (Method 10). Peak was split (51.23% and 48.77%).

Example 69

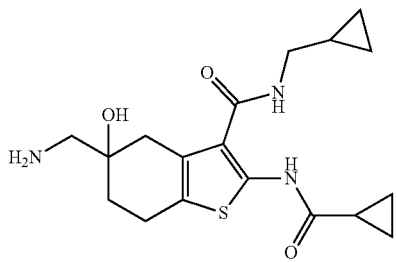 [SMILES: NCC1(O)CCc2sc(NC(=O)C3CC3)c(C(=O)NCC3CC3)c2C1]

5-(Aminomethyl)-2-(cyclopropanecarbonylamino)-N-(cyclopropylmethyl)-5-hydroxy-6,7-dihydro-4H-benzothiophene-3-carboxamide Intermediate 63 (450 mg, 1.30 mmol) and ammonia (1.43 g, 13.0 mmol) were heated at 70° C. overnight. The reaction mixture was concentrated in vacuo and the residue was purified by flash column chromatography on silica (gradient elution with DCM/MeOH (NH₄OH 10%) 5% to 10%) to afford the title compound (292 mg, 62%) as a white solid. LCMS (ES+) [M+H]⁺ 364.18, RT 1.69 minutes (Method 8).

Example 70

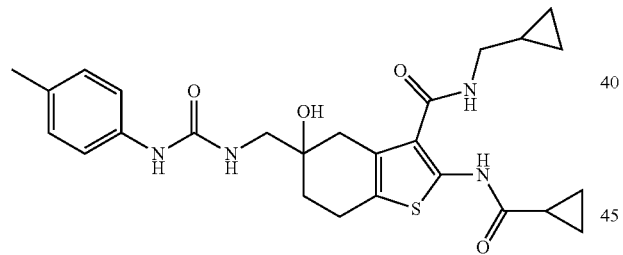

2-(Cyclopropanecarbonylamino)-N-(cyclopropylmethyl)-5-hydroxy-5-[(p-tolylcarbamoylamino)methyl]-6,7-dihydro-4H-benzothiophene-3-carboxamide To example 69 (292 mg, 0.80 mmol) in DCM (0.80 mL) was added triethylamine (123 mg, 1.21 mmol). The mixture was cooled to 0° C. and p-tolyl isocyanate [622-58-2] (162 mg, 1.21 mmol) was added dropwise. The reaction was allowed to warm to r.t. and was stirred overnight before concentrating in vacuo. To the crude material was added EtOH (10 mL) and the mixture was heated in the microwave at 150° C. for 20 minutes. The reaction mixture was concentrated in vacuo and purified by flash column chromatography on silica (gradient elution with DCM/0-10% MeOH [NH₄OH 10%] to afford the title compound (0.0043 g, 0.87%). LCMS (ES+) [M+H]⁺ 497.2, RT 2.36 minutes, purity 87.07% (Method 9).

Example 71

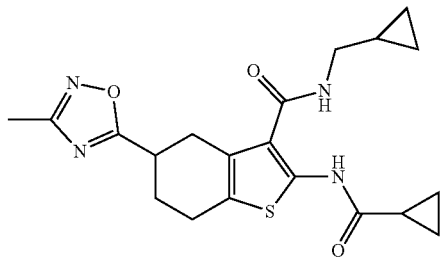 [SMILES: Cc1noc(C2CCc3sc(NC(=O)C4CC4)c(C(=O)NCC4CC4)c3C2)n1]

2-(Cyclopropanecarbonylamino)-N-(cyclopropylmethyl)-5-(3-methyl-1,2,4-oxadiazol-5-yl)-4,5,6,7-tetrahydrobenzothiophene-3-carboxamide To a solution of example 40 (30 mg, 0.083 mmoL) and N-hydroxyacetamidine [22059-22-9] (9 mg, 0.12 mmoL) in anhydrous DCM (2 mL) was added EDCl (25 mg, 0.13 mmoL) and the resulting solution was stirred at r.t. Further N-hydroxyacetamidine [22059-22-9] (9 mg, 0.12 mmoL) and EDCl (25 mg, 0.13 mmoL) were added and stirring was continued for a further 24 h. The solvent was removed in vacuo and the residue was taken up in toluene and heated to 100° C. for 5 h. The reaction mixture was diluted with EtOAc (10 mL) and water (10 mL). The layers were separated and the aqueous layer was extracted with further EtOAc (10 mL). The combined organics were washed with brine (10 mL), dried (MgSO₄), filtered and concentrated in vacuo to yield the crude product which was purified by flash column chromatography on silica (gradient elution with EtOAc/heptane 0 to 100%) to afford the title compound (11 mg, 33%) as a white solid. δ$_H$ (250 MHz, Chloroform-d) 12.07 (s, 1H), 5.96-5.79 (m, 1H), 3.53-3.17 (m, 4H), 3.17-2.97 (m, 1H), 2.93-2.79 (m, 2H), 2.51-2.36 (m, 4H), 2.23-1.97 (m, 1H), 1.75-1.53 (m, 1H), 1.20-1.01 (m, 3H), 0.98-0.81 (m, 2H), 0.63-0.49 (m, 2H), 0.36-0.18 (m, 2H). LCMS (ES+) [M+H]⁺ 401, RT 3.36 minutes (Method 10).

Example 72

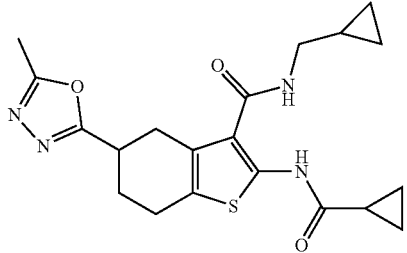 [SMILES: Cc1nnc(C2CCc3sc(NC(=O)C4CC4)c(C(=O)NCC4CC4)c3C2)o1]

2-(Cyclopropanecarbonylamino)-N-(cyclopropylmethyl)-5-(5-methyl-1,3,4-oxadiazol-2-yl)-4,5,6,7-tetrahydrobenzothiophene-3-carboxamide Intermediate 72 (95 mg, 0.25 mmol) was dissolved in acetic acid (2 mL) and 1,1,1-triethoxyethane [78-39-7] (0.23 ml, 1.26 mmol) was added. The reaction mixture was stirred at 120° C. for 3 h before concentrating in vacuo. The crude product was purified by preparative HPLC (low pH) to afford the title compound (74 mg, 73%) as a white solid. δ$_H$ (500 MHz, CD$_3$OD) 3.42-3.34 (m, 1H), 3.29-3.15 (m, 3H), 3.11-3.03 (m, 1H), 2.90-2.80 (m, 2H), 2.53 (s, 3H), 2.45-2.37 (m, 1H), 2.14-2.02 (m, 1H), 1.84-1.76 (m, 1H), 1.16-1.06 (m, 1H), 1.02-0.96 (m, 2H), 0.96-0.91 (m, 2H), 0.58-0.48 (m, 2H), 0.33-0.24 (m, 2H). LCMS (ES+) [M+H]$^+$ 401.2, RT 2.93 minutes, purity 99% (Method 10), peak split (50.19% and 48.91%).

Example 73

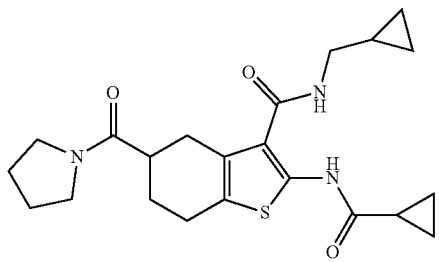 [SMILES: O=C(NCC1CC1)c1c(NC(=O)C2CC2)sc2c1CC(C(=O)N1CCCC1)CC2]

2-(Cyclopropanecarbonylamino)-N-(cyclopropylmethyl)-5-(pyrrolidine-1-carbonyl)-4,5,6,7-tetrahydrobenzothiophene-3-carboxamide Example 40 (50 mg, 0.13 mmol) was dissolved in DCM (4 mL) and EDCl (40 mg, 0.20 mmol) was added and the reaction mixture was stirred for 1 h. Pyrrolidine [123-75-1] (0.023 mL, 0.28 mmol) was added and the reaction mixture was stirred at r.t. for 16 h. The mixture was diluted with DCM (20 mL) and washed with water, 1M aqueous hydrochloric acid solution and saturated sodium hydrogen carbonate solution. The organic layer was washed with brine, dried (MgSO$_4$), filtered and concentrated in vacuo. The crude residue was purified by preparative HPLC (acidic) to afford the title compound (22 mg, 38%) as a white solid. δ$_H$ (500 MHz, CD$_3$OD) 3.60 (t, J 6.8 Hz, 2H), 3.49-3.43 (m, 2H), 3.30-3.25 (m, 1H), 3.21-3.15 (m, 1H), 2.94-2.75 (m, 5H), 2.13-2.06 (m, 1H), 2.04-1.97 (m, 2H), 1.94-1.84 (m, 3H), 1.82-1.75 (m, 1H), 1.14-1.05 (m, 1H), 1.02-0.90 (m, 4H), 0.55-0.49 (m, 2H), 0.30-0.25 (m, 2H). LCMS (ES+) [M+H]$^+$ 416.2, RT 3.10 minutes, purity 100% (Method 10).

Example 74

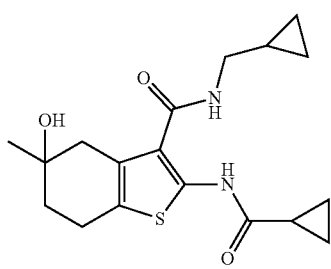 [SMILES: CC1(O)CCc2sc(NC(=O)C3CC3)c(C(=O)NCC3CC3)c2C1]

2-(Cyclopropanecarbonylamino)-N-(cyclopropylmethyl)-5-hydroxy-5-methyl-6,7-dihydro-4H-benzothiophene-3-carboxamide Intermediate 63 (50 mg, 0.14 mmol) in THF (0.30 mL) was cooled to 0° C. and lithium triethylborohydride [22560-16-3] (0.11 mL, 0.19 mmol) was added dropwise. After stirring for 5 minutes the reaction was allowed to warm to r.t. and stirred over the weekend. Further lithium triethylborohydride [22560-16-3] (0.11 mL, 0.19 mmol) was added dropwise at 0° C. and the reaction mixture was allowed to warm to r.t. and stirred for 2 h. The reaction mixture was quenched with water at 0° C. and was extracted with DCM. The organic phase was separated, dried (MgSO$_4$), filtered and concentrated in vacuo to yield the crude product which was purified by TLC prep (eluted with DCM/MeOH (NH$_4$OH 10%) 5%) to afford the title compound (20 mg, 40%). LCMS (ES+) [M+H]$^+$ 249.20, RT 2.16 minutes, purity 98.83% (Method 8).

Example 75

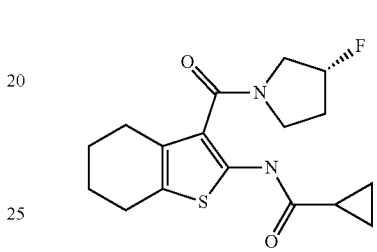

N-[3-[(3R)-3-Fluoropyrrolidine-1-carbonyl]-4,5,6,7-tetrahydrobenzothiophen-2-yl]cyclopropanecarboxamide To (R)-(−)-3-fluoropyrrolidine hydrochloride [136725-55-8] (13 mg, 0.10 mmol) was added MP-carbonate (90 mg, 0.30 mmol) in DCM (1.5 mL) and the reaction mixture was stirred at r.t. for 3 h. The mixture was filtered and rinsed with DCM (2×1 mL) and concentrated in vacuo. To the amine was added intermediate 73 (25 mg, 0.10 mmol) and DMF (1 mL). The mixture was heated in the microwave at 120° C. for 30 minutes. Further (R)-(−)-3-fluoropyrrolidine hydrochloride [136725-55-8](13 mg, 0.10 mmol) and MP-carbonate (90 mg, 0.303 mmol) was added and the reaction mixture was heated in the microwave at 140° C. and the reaction mixture was concentrated in vacuo. The crude product was purified by preparative HPLC (basic) to afford the title compound (0.0071 g, 21%). LCMS [M+H]$^+$ 337.2, RT 4.1 minutes, 88.18% purity (Method 9).

Example 76

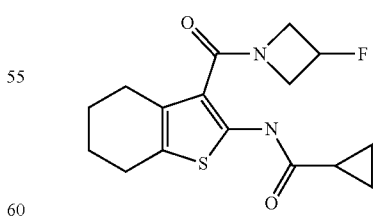

N-[3-(3-Fluoroazetidine-1-carbonyl)-4,5,6,7-tetrahydrobenzothiophen-2-yl]cyclopropanecarboxamide The method for example 75 was utilised substituting 3-fluorocyclobutanamine [1234616-60-4] (9.5 mg, 0.11 mmol) for (R)-(-)-3-fluoropyrrolidine hydrochloride [136725-55-8] to afford the title compound (0.0073 g, 21%). LCMS [M+H]⁺ 337.2, RT 4.8 minutes, 99.23% purity (Method 9).

Example 77

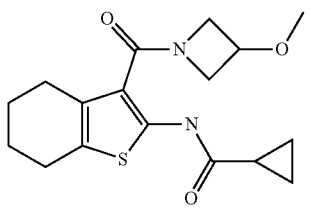 [SMILES: COC1CN(C(=O)c2c(NC(=O)C3CC3)sc3c2CCCC3)C1]

To 3-methoxyazetidine hydrochloride [148644-09-1] (28 mg, 0.23 mmol) was added MP-carbonate (130 mg, 0.44 mmol) and DCM (1.5 mL) and the mixture was stirred at r.t. for 3 h. The mixture was filtered and washed with DCM (500 mL), COMU (80 mg, 0.18 mmol) and intermediate 16 (40 mg, 0.151 mmol) were added and the reaction mixture was stirred at r.t. overnight. Water (2 mL) was added and the mixture was filtered through a phase separation cartridge. The aqueous phase was further extracted with DCM (2×2 mL) and the organic phase was concentrated in vacuo to yield the crude product which was purified by reverse phase preparative HPLC (basic) to afford the title compound (0.0074 g, 15%). LCMS [M+H]⁺ 335.1425, RT 4.06 minutes, 94.53% purity (Method 20).

Example 78

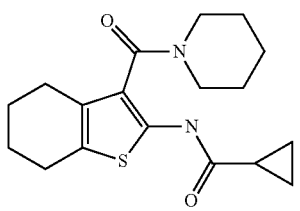 [SMILES: O=C(Nc1sc2c(c1C(=O)N1CCCCC1)CCCC2)C1CC1]

N-[3-(Piperidine-1-carbonyl)-4,5,6,7-tetrahydrobenzothiophen-2-yl]cyclopropanecarboxamide To intermediate 16 (100 mg, 0.38 mmol) was added DCM (3 mL) and piperidine [110-89-4] (48 mg, 0.57 mmol). A solution of EDCl (0.089 g, 0.45 mmol) in DCM (2 mL) was added and the reaction mixture was stirred at r.t. overnight. The reaction mixture was washed with water and passed through a phase separation cartridge, washing with DCM (5 mL) and the mixture was concentrated to yield the crude product which was purified by flash column chromatography on silica (gradient elution with 20-100% EtOAc/hexane) to afford the product which was freeze-dried from MeCN/water, to afford the title compound (37 mg, 30%). δ$_H$ (400 MHz, DMSO-d₆) 10.47 (s, 1H), 3.38 (s, 3H), 2.51 (t, J 6.1 Hz, 2H), 2.25 (s, 2H), 1.97-1.82 (m, 1H), 1.73-1.55 (m, 5H), 1.56-1.39 (m, 4H), 1.39-1.19 (m, 2H), 0.79-0.63 (m, 4H). LCMS (ES+) [M+H]⁺ 333.8, RT 2.183 minutes (Method 2). LCMS (ES+) [M+H]⁺ 333.8, RT 2.171 minutes (Method 3).

Example 79

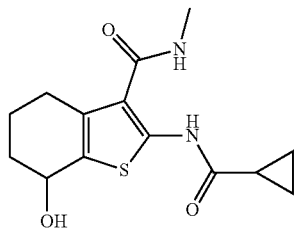 [SMILES: CNC(=O)c1c(NC(=O)C2CC2)sc2c1CCCC2O]

2-(Cyclopropanecarbonylamino)-7-hydroxy-N-methyl-4,5,6,7-tetrahydrobenzothiophene-3-carboxamide To a solution of intermediate 77 in MeOH (3 mL) was added sodium borohydride (26 mg, 0.68 mmol) portionwise over a 40 minute period. Further sodium borohydride (5 eq.) and a further six batches of sodium borohydride (3 eq.) were added every 30 minutes. The reaction mixture was added to EtOAc/water, washed with water (3×), dried (MgSO₄), filtered and the solvent was removed to give the crude product (22 mg) as a white solid which was purified by flash column chromatography on silica (gradient elution with 30-90% EtOAc in hexane) to afford the title compound (11 mg, 27%). δ$_H$ (400 MHz, DMSO-d₆) 11.44 (s, 1H), 7.55-7.35 (m, 1H), 5.28 (d, J 6.3 Hz, 1H), 4.67-4.51 (m, 1H), 2.78 (d, J 4.6 Hz, 3H), 2.59 (dt, J 17.4, 5.4 Hz, 1H), 1.98-1.78 (m, 3H), 1.72-1.51 (m, 2H), 0.93-0.77 (m, 4H). LCMS [M−H]⁻ 293.0, RT 1.276 minutes, 89.4% purity (030114-6140-10072, pH3 registration Method 2). LCMS (ES+) [M+Na] 317.6, RT 1.254 minutes, 91.0% purity (Method 3).

Example 80

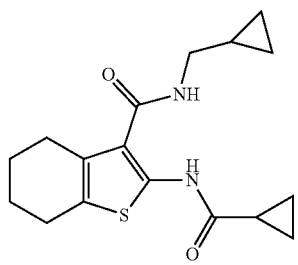 [SMILES: O=C(NCC1CC1)c1c(NC(=O)C2CC2)sc2c1CCCC2]

2-(Cyclopropanecarbonylamino)-N-(cyclopropylmethyl)-4-methyl-4,5,6,7-tetrahydrobenzothiophene-3-carboxamide To a solution of intermediate 80 (181 mg, 0.65 mmol) in DCM (4 mL) was added cyclopropylmethylamine [2516-47-4] (92 mg, 1.30 mmol) followed by EDCl (186 mg, 0.97 mmol). The reaction was stirred at r.t. for 45 minutes before leaving for 3 days at r.t. The reaction was poured into EtOAc, washed with saturated sodium hydrogen carbonate solution (2×), 0.1M aqueous hydrochloric acid solution and dried (MgSO₄). The mixture was filtered and concentrated in vacuo to yield a brown oil/gum which was purified by flash column chromatography on silica (gradient elution with 0-20% EtOAc in heptane) to afford the title compound (43 mg, 20%). δ$_H$ (500 MHz, DMSO-d$_6$) 10.64 (s, 1H), 8.04 (s, 1H), 3.24-3.10 (m, 2H), 3.04 (dt, J 13.0, 6.2 Hz, 1H), 2.62-2.54 (m, 2H), 1.97-1.87 (m, 1H), 1.87-1.64 (m, 3H), 1.58-1.42 (m, 1H), 1.05 (d, J 6.9 Hz, 4H), 0.81 (d, J 4.9 Hz, 4H), 0.47-0.37 (m, 2H), 0.31-0.14 (m, 2H).

Example 81

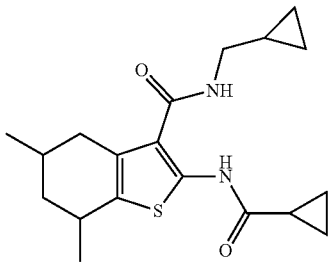 [SMILES: CC1Cc2c(sc(NC(=O)C3CC3)c2C(=O)NCC2CC2)C(C)C1]

2-(Cyclopropanecarbonylamino)-N-(cyclopropylmethyl)-5,7-dimethyl-4,5,6,7-tetrahydrobenzothiophene-3-carboxamide A mixture of intermediate 83 (103 mg, 0.35 mmol), EDCl (67 mg, 0.35 mmol) and cyclopropylmethylamine [2516-47-4] (37 mg, 0.52 mmol) in DCM (5 mL) were stirred overnight. Water (5 mL) was added to the reaction mixture and the mixture was passed through a phase separator cartridge and the organic phase concentrated in vacuo onto silica. The reaction mixture was purified by flash column chromatography on silica (gradient elution with 5%-40% EtOAc in iso-hexane) to afford the title compound (31 mg, 26%) as a white solid which was freeze-dried overnight from MeCN/water. δ$_H$ (400 MHz, DMSO-d$_6$) 11.12 (s, 1H), 7.65 (s, 1H), 3.15-3.23 (m, 1H), 3.05-3.12 (m, 1H), 2.80-2.90 (m, 1H), 2.60-2.68 (m, 1H), 2.20-2.31 (m, 1H), 1.84-1.93 (m, 2H), 1.70-1.82 (m, 1H), 1.18 (d, J 6.7 Hz, 3H), 0.97-1.07 (m, 2H), 1.03 (d, J 6.4 Hz, 3H), 0.78-0.89 (m, 4H), 0.40-0.45 (m, 2H), 0.21-0.25 (m, 2H).

Examples 82 and 83

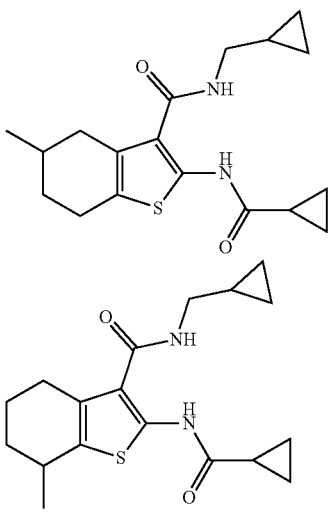

Example 82

2-(Cyclopropanecarbonylamino)-N-(cyclopropylmethyl)-5-methyl-4,5,6,7-tetrahydrobenzothiophene-3-carboxamide Example 83

2-(cyclopropanecarbonylamino)-N-(cyclopropylmethyl)-7-methyl-4,5,6,7-tetrahydrobenzothiophene-3-carboxamide The method for example 81 was utilised substituting a ~25:1 mixture of intermediates 88 5-isomer and 89 7-isomer (98 mg, 0.350 mmol) for intermediate 83 to afford the title compounds (34 mg, 0.10 mmol) as a ~60:1 mixture of example 82, 5-isomer: example 83, 7-isomer. Example 82: δ$_H$ (400 MHz, DMSO-d$_6$) 11.19 (s, 1H), 7.57-7.63 (m, 1H), 3.15-3.22 (m, 1H), 3.07-3.13 (m, 1H), 2.56-2.73 (m, 3H), 2.28 (m, 3H), 1.70-1.92 (m, 3H), 1.30-1.41 (m, 1H), 1.00-1.10 (m, 1H), 1.03 (d, J 6.6 Hz, 3H), 0.79-0.88 (m, 4H), 0.40-0.45 (m, 2H), 0.21-0.25 (m, 2H).). LCMS [M+H]$^+$ 333.8, RT 2.72 minutes, (Method 2), LCMS [M+H]$^+$ 333.8, RT 2.70 minutes, (Method 3).

Example 84

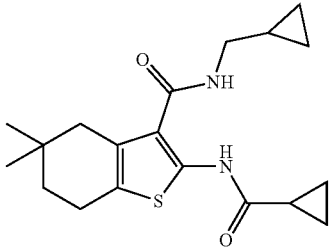 [SMILES: CC1(C)CCc2sc(NC(=O)C3CC3)c(C(=O)NCC3CC3)c2C1]

2-(Cyclopropanecarbonylamino)-N-(cyclopropylmethyl)-5,5-dimethyl-6,7-dihydro-4H-benzothiophene-3-carboxamide To a solution of intermediate 92 (150 mg, 0.51 mmoL) and cyclopropylmethanamine [2516-47-4] (0.067 mL, 0.77 mmoL) in DCM (5 mL) was added EDCl (157 mg, 0.82 mmoL) and the resulting solution was stirred at r.t. under an atmosphere of nitrogen. After stirring for 20 h the mixture was diluted with DCM (15 mL) and 1M aqueous hydrochloric acid solution (10 mL). The layers were separated and the aqueous phase was further extracted with DCM (10 mL). The combined organics were washed with brine (10 mL), dried (MgSO$_4$), filtered and concentrated in vacuo. The crude material was purified by flash column chromatography on silica (elution with 100% DCM followed by a gradient of EtOAc 0 to 50% in DCM) to afford the title compound (60 mg, 34%) as a white solid. δ$_H$ (250 MHz, Chloroform-d) 12.16 (s, 1H), 5.97 (s, 1H), 3.37-3.24 (m, 2H), 2.68 (t, J 6.5 Hz, 2H), 2.46 (s, 2H), 1.74-1.56 (m, 3H), 1.17-1.05 (m, 3H), 1.02 (s, 6H), 0.95-0.82 (m, 2H), 0.67-0.52 (m, 2H), 0.34-0.23 (m, 2H). LCMS [M+H]$^+$ 347, RT 4.22 minutes, 98% purity (Method 10).

Example 85

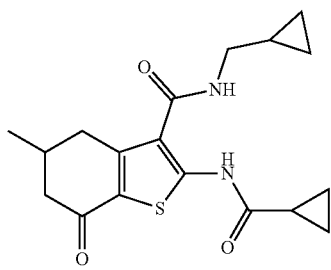 [SMILES: CC1CC(=O)c2sc(NC(=O)C3CC3)c(C(=O)NCC3CC3)c2C1]

2-(Cyclopropanecarbonylamino)-N-(cyclopropylmethyl)-5-methyl-7-oxo-5,6-dihydro-4H-benzothiophene-3-carboxamide To a solution of intermediate 95 (290 mg, 0.99 mmol) and triethylamine (0.2 mL, 1.44 mmol) in DCM (5 mL) at 0° C. was added cyclopropanecarbonyl chloride [4023-34-1] (0.12 ml, 1.32 mmol). The reaction mixture was stirred at 0° C. for 2 h. Further cyclopropanecarbonyl chloride [4023-34-1] (0.12 ml, 1.32 mmol) was added and the reaction was stirred for 1 h at r.t. The reaction mixture was diluted with DCM (20 mL) and 1 M aqueous hydrochloric acid solution (20 mL) was added. The organic layer was separated and the remaining aqueous phase extracted with further DCM (2×10 mL) and washed with water (10 mL). The combined organic phases were dried (MgSO$_4$), filtered and concentrated in vacuo and purified by flash column chromatography on silica (gradient elution with 30-60% EtOAc/heptane) to afford the title compound (90 mg, 34%) as an orange solid. δ$_H$ (500 MHz, Chloroform-d) 12.31 (s, 1H), 5.90 (s, 1H), 3.37-3.30 (m, 2H), 3.10 (dd, J 15.3, 4.3 Hz, 1H), 2.64 (dd, J 16.3, 2.9 Hz, 1H), 2.57 (dd, J 15.3, 9.8 Hz, 1H), 2.51-2.41 (m, 1H), 2.32 (dd, J 16.2, 11.9 Hz, 1H), 1.74-1.67 (m, 1H), 1.21 (d, J 6.5 Hz, 3H), 1.19-1.15 (m, 2H), 1.14-1.06 (m, 1H), 0.99-0.94 (m, 2H), 0.65-0.58 (m, 2H), 0.34-0.29 (m, 2H).

Example 86

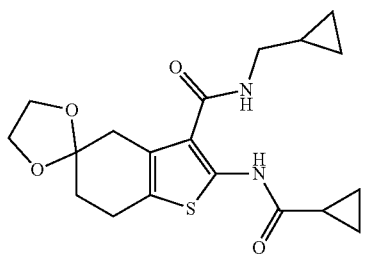 [SMILES: O=C(NCC1CC1)c1c(NC(=O)C2CC2)sc2c1CC1(CC2)OCCO1]

2'-(Cyclopropanecarbonylamino)-N-(cyclopropylmethyl)spiro[1,3-dioxolane-2,5'-6,7-dihydro-4H-benzothiophene]-3'-carboxamide Intermediate 34 (540 mg, 1.67 mmol) was dissolved in DMF (10 mL) and triethylamine (425 mg, 4.17 mmol) and cyclopropanemethylamine hydrochloride [7252-53-1] (290 mg, 2.67 mmol) were added prior to addition of EDCl (512 mg, 2.67 mmol) and the reaction mixture was stirred at r.t. for 72 h. The mixture was diluted with EtOAc (15 mL) and washed with water (3×15 mL). The organic phase was separated, dried (Na$_2$SO$_4$), filtered and the concentrated in vacuo to give a yellow oil which was purified by flash column chromatography on silica (gradient elution with 0-50% EtOAc/iso-hexane) to afford the title compound (420 mg, 67%) as a yellow gum. LCMS (ES+) [M+H]$^+$ 377.0, RT 1.367 minutes, purity 98.0% (Method 4).

Example 87

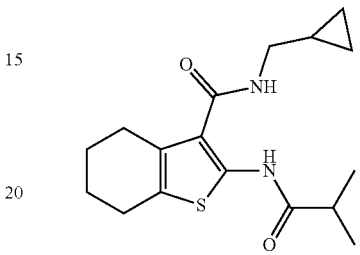

N-(Cyclopropylmethyl)-2-(2-methylpropanoylamino)-4,5,6,7-tetrahydrobenzothiophene-3-carboxamide To a solution of intermediate 96 (60 mg, 0.24 mmol) and triethylamine (50 μL, 0.36 mmol) in DCM (2 mL) at 0° C. was added 2-methylpropanoyl chloride [79-30-1] (38 μl, 0.36 mmol). The reaction mixture was stirred at 0° C. for 15 minutes then at r.t. for 45 minutes. 1 M aqueous hydrochloric acid solution (2 mL) was added and the mixture was stirred vigorously. The organic phase was isolated, dried (MgSO$_4$) and filtered before concentrating in vacuo. Purification by flash column chromatography on silica (gradient elution with 15-30% EtOAc/heptanes) afforded the title compound (37 mg, 47%) as a yellow solid. δ$_H$ (500 MHz, Chloroform-d) 12.17 (s, 1H), 6.03 (s, 1H), 3.28 (dd, J 7.1, 5.2 Hz, 2H), 2.73 (t, J 5.7 Hz, 2H), 2.71-2.67 (m, 2H), 2.64 (p, J 6.9 Hz, 1H), 1.91-1.81 (m, 4H), 1.27 (d, J 7.0 Hz, 6H), 1.10-1.01 (m, 1H), 0.60-0.55 (m, 2H), 0.29-0.25 (m, 2H). LCMS [M+H]$^+$ 321.1, RT 3.91 minutes, 97% purity (Method 10).

Example 88

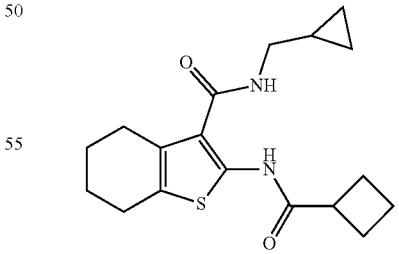

2-(Cyclobutanecarbonylamino)-N-(cyclopropylmethyl)-4,5,6,7-tetrahydrobenzothiophene-3-carboxamide To a solution of intermediate 96 (100 mg, 0.4 mmol) and triethylamine (85 μL, 0.61 mmol) in DCM (5 mL) at 0° C.

was added cyclobutanecarbonyl chloride [5006-22-4] (50 µL, 0.49 mmol). The reaction was stirred at 0° C. for 15 minutes and then at r.t. for 45 minutes. 1 M aqueous hydrochloric acid solution (2 mL) was added and the mixture was stirred vigorously. The organic layer was isolated and dried (MgSO$_4$) and filtered before concentrating in vacuo. The residue was purified by flash column chromatography on silica (gradient elution with 15-30% EtOAc/heptanes) to afford the title compound (70 mg, 52%) as an off white solid. δ$_H$ (500 MHz, Chloroform-d) 11.99 (s, 1H), 6.03 (s, 1H), 3.29-3.19 (m, 3H), 2.71 (t, J 5.6 Hz, 2H), 2.67 (t, J 5.5 Hz, 2H), 2.42-2.32 (m, 2H), 2.30-2.20 (m, 2H), 2.05-1.88 (m, 2H), 1.88-1.78 (m, 4H), 1.08-0.99 (m, 1H), 0.55 (dt, J 7.8, 5.2 Hz, 2H), 0.25 (q, J 4.8 Hz, 2H). LCMS [M+H]$^+$ 333.1, RT 4.04 minutes, 98% purity (Method 10).

Example 89

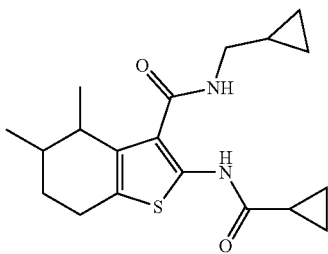 [SMILES: CC1CCc2sc(NC(=O)C3CC3)c(C(=O)NCC3CC3)c2C1C]

2-(Cyclopropanecarbonylamino)-N-(cyclopropylmethyl)-4,5-dimethyl-4,5,6,7-tetrahydrobenzothiophene-3-carboxamide 2-(Cyclopropanecarbonylamino)-4,5-dimethyl-4,5,6,7-tetrahydrobenzothiophene-3-carboxylic acid To a solution of 2,3-dimethylcyclohexanone (MFCD11223163) (2.43 g, 19.2 mmol) in EtOH (10 mL) was added ethyl cyanoacetate [105-56-6] (2.25 mL, 21.1 mmol), sulphur [7704-34-9] (0.68 g, 21.1 mmol) and diethylamine (2.97 mL, 28.8 mmol). The reaction was stirred at r.t. for 18 h followed by heating at 50° C. for 7 h. The reaction was left to cool to r.t. overnight and the mixture was concentrated in vacuo. The crude product was purified by flash column chromatography on silica (gradient elution with heptane/EtOAc 100:0 to 0:100) to afford ethyl 2-amino-4,5-dimethyl-4,5,6,7-tetrahydrobenzothiophene-3-carboxylate (1.29 g, 26%) which was used in the following step.

To a solution of ethyl 2-amino-4,5-dimethyl-4,5,6,7-tetrahydrobenzothiophene-3-carboxylate (1.29 g, 5.09 mmol) and DIPEA (1.68 mL, 10.17 mol) in DCM (24 mL) was added cyclopropanecarbonyl chloride [4023-34-1] (0.51 mL, 5.60 mmol). The reaction mixture was stirred at r.t. for 1.5 h before diluting with DCM (15 mL) and washing with saturated aqueous sodium hydrogen carbonate solution (2×30 mL). The combined organic phases were dried (brine and MgSO$_4$), filtered and the organic phase was concentrated in vacuo. The crude product was purified by flash column chromatography on silica (gradient elution with heptane/EtOAc 100:0 to 60:40) to afford ethyl 2-(cyclopropanecarbonylamino)-4,5-dimethyl-4,5,6,7-tetrahydrobenzothiophene-3-carboxylate (1.47 g, 90%).

1M Aqueous NaOH solution (2 mL) was added to a solution of ethyl 2-(cyclopropanecarbonylamino)-4,5-dimethyl-4,5,6,7-tetrahydrobenzothiophene-3-carboxylate (1.47 g, 4.57 mmol) in an 8:1 mixture of THF:water (9 mL). The reaction mixture was stirred at r.t. for 12.5 h. A further portion of 1M aqueous NaOH solution (2 mL) was added and stirring was continued for a further 6 h. The reaction mixture was concentrated in vacuo, diluted with water (30 mL) and washed with DCM (2×20 mL). The aqueous layer was acidified to pH 5 with 2M aqueous hydrochloric acid solution and the solid was filtered off and washed with water and heptane to afford 2-(cyclopropanecarbonylamino)-4,5-dimethyl-4,5,6,7-tetrahydrobenzothiophene-3-carboxylic acid which was utilised in the following step. LCMS [M+H]$^+$ 294.0, RT 3.749 minutes, 98.9% purity.

To a solution of 2-(cyclopropanecarbonylamino)-4,5-dimethyl-4,5,6,7-tetrahydrobenzothiophene-3-carboxylic acid (200 mg, 0.68 mmol) in DCM (4 mL) was added cyclopropylmethylamine [2516-47-4](97.0 mg, 1.36 mmol) followed by EDCl (196 mg, 1.02 mmol). The reaction was stirred at r.t. for 3 h before heating at 80° C. in a microwave for 2 h and leaving overnight at r.t. The reaction was poured into EtOAc, washed with saturated sodium hydrogen carbonate solution (2×), 0.1M aqueous hydrochloric acid solution (1×) and dried (MgSO$_4$). The mixture was filtered and the solvent was removed in vacuo to yield a brown oil/gum which was purified by flash column chromatography on silica (gradient elution with 0-20% EtOAc in heptane) to afford the title compound (46 mg, 19%) as a white solid. δ$_H$ (500 MHz, Chloroform-d) 12.28 (s, 1H), 6.26 (s, 1H), 3.40 (ddd, J 13.0, 7.2, 5.5 Hz, 1H), 3.27 (ddd, J 13.7, 7.2, 4.7 Hz, 1H), 2.84 (p, J 6.8 Hz, 1H), 2.80-2.64 (m, 2H), 2.13-2.02 (m, 1H), 1.72-1.62 (m, 3H), 1.18-1.04 (m, 8H), 0.90 (dq, J 7.1, 3.5 Hz, 2H), 0.61 (dt, J 7.9, 4.7 Hz, 2H), 0.31 (q, J 4.6 Hz, 2H).

Example 90 and 91

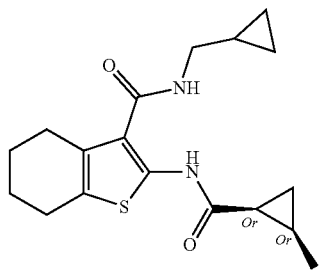

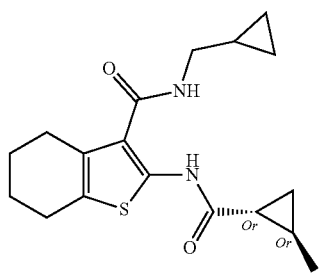

Example 90

N-(cyclopropylmethyl)-2-[(2-methylcyclopropan-ecarbonyl)amino]-4,5,6,7-tetrahydrobenzothiophene-3-carboxamide—Diastereomer 1

Example 91

N-(cyclopropylmethyl)-2-[(2-methylcyclopropan-ecarbonyl)amino]-4,5,6,7-tetrahydrobenzothiophene-3-carboxamide—Diastereomer 2

To a solution of intermediate 96 (250 mg, 0.65 mmol, 65% purity) and triethylamine (140 µL, 1 mmol) in DCM (8 mL) at 0° C. was added 2-methylcyclopropane-1-carbonyl chloride [60733-34-8](120 µl, 1.01 mol, assumed density 1.00). The reaction mixture was stirred at 0° C. for 15 minutes then at r.t. for 45 minutes. 1 M aqueous hydrochloric acid solution (2 mL) was added and the mixture was stirred vigorously. The organic layer was separated, dried (MgSO$_4$) and filtered before concentrating in vacuo. Purification by flash column chromatography on silica (gradient elution with 0-30% EtOAc/heptane) gave a white solid (210 mg), consisting of a roughly 8:2 mixture of diastereomers by LCMS. Purification by basic prep-HPLC gave the mixture of diastereomers (140 mg, 63%) as a white solid. All four diastereomers were separated by chiral HPLC including the title compounds 90 and 91 as white solids. Diastereomer 1 (35 mg, 16%) and Diastereomer 2 (4.5 mg, 2.1%). 1H NMR studies were unable to characterise the respective diastereomers. Diastereomer 1: $\delta_H$ (500 MHz, DMSO-d$_6$) 11.22 (br s, 1H), 7.56 (br s, 1H), 3.14 (t, J 6.2 Hz, 2H), 2.68-2.61 (m, 3H), 2.61-2.56 (m, 2H), 1.80-1.67 (m, 4H), 1.67-1.60 (m, 1H), 1.31-1.21 (m, 1H), 1.06-0.99 (m, 4H), 0.73-0.66 (m, 1H), 0.46-0.39 (m, 2H), 0.23 (q, J 4.9, 4.4 Hz, 2H). LCMS [M+H]$^+$ 333.2, RT 4.11 minutes, 100% purity, (Method 10). 98% ee by UV (Method 23). Diastereomer 2: $\delta_H$ (500 MHz, Chloroform-d) 12.18 (s, 1H), 6.02 (s, 1H), 3.29 (dd, J 7.1, 5.3 Hz, 2H), 2.73 (t, J 5.7 Hz, 2H), 2.68 (t, J 5.9 Hz, 2H), 1.93-1.79 (m, 4H), 1.76-1.69 (m, 1H), 1.36-1.27 (m, 1H), 1.18 (d, J 6.2 Hz, 3H), 1.11-0.99 (m, 3H), 0.62-0.54 (m, 2H), 0.31-0.22 (m, 2H). Chiral SFCMS [M+H]$^+$ 333.2, RT 17.74 minutes, 100% purity, 100% ee by UV (Method 23).

Example 92

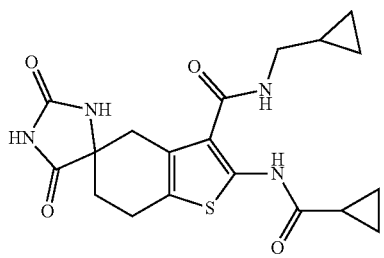 [SMILES: O=C1NC(=O)C2(CCc3sc(NC(=O)C4CC4)c(C(=O)NCC4CC4)c3C2)N1]

2-(Cyclopropanecarbonylamino)-N-(cyclopropylmethyl)-2',5'-dioxo-spiro[6,7-dihydro-4H-benzothiophene-5,4'-imidazolidine]-3-carboxamide Intermediate 62 (420 mg, 1.26 mmol) was dissolved in EtOH (2.5 mL) and water (2.5 mL). Potassium cyanide [151-50-8] (123 mg, 1.90 mmol) was added followed by ammonium carbonate (850 mg, 8.84 mmol), the reaction mixture was stirred at 65° C. for 1 h before cooling to r.t. overnight. The reaction mixture was concentrated in vacuo, water was added and the mixture was filtered to afford a solid. The filtrate was extracted with n-butanol, and the organic phase was washed with brine, dried (MgSO$_4$), filtered and concentrated in vacuo. The residue was triturated with Et$_2$O, filtered and dried in an oven at 40° C. to afford the title compound (410 mg, 81%). $^1$H NMR (400 MHz, DMSO-d$_6$) δ 10.77 (s, 2H), 8.11 (s, 1H), 2.89 (td, J=14.6, 13.7, 8.1 Hz, 3H), 2.50 (s, 1H), 2.30 (s, 3H), 1.66 (q, J=13.2, 11.5 Hz, 3H), 0.94-0.33 (m, 5H), 0.20 (d, J=7.9 Hz, 2H), −0.00 (d, J=4.9 Hz, 2H). LCMS [M+H]$^+$ 403.19, RT 1.77 minutes (Method 8).

Example 93

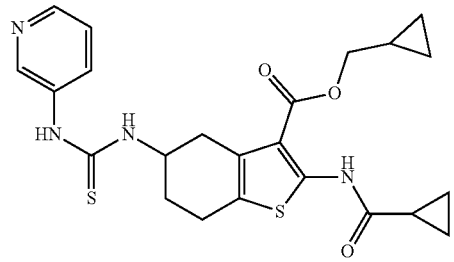 [SMILES: O=C(OCC1CC1)c1c(NC(=O)C2CC2)sc2c1CC(NC(=S)Nc1cccnc1)CC2]

Cyclopropylmethyl 2-(cyclopropanecarbonylamino)-5-(3-pyridylcarbamothioylamino)-4,5,6,7-tetrahydrobenzothiophene-3-carboxylate Intermediate 101 (500 mg, 1.5 mmol) was dissolved in DCM (20 mL) and DIPEA (290 mg, 2.2 mmol), and 3-pyridyl isothiocyanate [17452-27-6] (310 mg, 2.2 mmol) was added. The reaction mixture was stirred at r.t. for ~2 h before washing with water and brine and filtering through a phase separation cartridge. The organic phase was concentrated in vacuo to yield the crude product which was purified by flash column chromatography on silica (gradient elution with 50-100% EtOAc/hexane to 0-5% MeOH/EtOAc) to afford the title compound (0.59 g, 83%) as a colourless gum which crystallised on standing. $\delta_H$ (400 MHz, DMSO-d$_6$) 11.17 (s, 1H), 9.52 (s, 1H), 8.59 (d, J 2.6 Hz, 1H), 8.28 (dd, J 4.8, 1.5 Hz, 1H), 8.15-7.93 (m, 2H), 7.34 (dd, J 8.3, 4.7 Hz, 1H), 4.59 (s, 1H), 4.14 (d, J 7.3 Hz, 2H), 3.28-3.17 (m, 1H), 2.78-2.69 (m, 3H), 2.12-1.97 (m, 2H), 1.95-1.82 (m, 1H), 1.32-1.16 (m, 1H), 1.00-0.83 (m, 4H), 0.64-0.53 (m, 2H), 0.45-0.33 (m, 2H).

Example 94

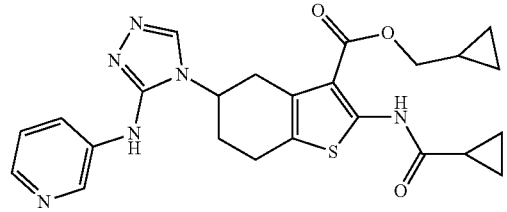 [SMILES: O=C(OCC1CC1)c1c(NC(=O)C2CC2)sc2c1CC(n1cnnc1Nc1cccnc1)CC2]

Cyclopropylmethyl 2-(cyclopropanecarbonylamino)-5-[3-(3-pyridylamino)-1,2,4-triazol-4-yl]-4,5,6,7-tetrahydrobenzothiophene-3-carboxylate Example 93 (576 mg, 1.22 mmol) was dissolved in DMF (10 mL) and formic acid hydrazide [624-84-0](123 mg, 1.84 mmol) and mercuric chloride [7487-94-7] (366 mg, 1.35 mmol) were added. The reaction mixture was stirred at r.t. for 5 minutes and triethylamine (187 mg, 1.84 mmol) was added. The reaction mixture was stirred at r.t. for 5 minutes before heating to 60° C. for ~3 h. The reaction mixture was cooled to r.t., diluted with MeCN (20 mL) and filtered through a pad of celite, washing with MeCN (3×10 mL). The pale yellow filtrate was concentrated in vacuo to yield a tan solid which was dissolved in 5% MeOH/DCM, washed with water (2×) and brine, passed through a phase separation cartridge and the organic phase was concentrated in vacuo to afford a tan solid which was purified by flash column chromatography on silica (gradient elution with 2-15% MeOH/DCM) followed by a second purification by flash column chromatography on silica (gradient elution with 1-6% MeOH/DCM) to afford the title compound (216 mg, 37%). $\delta_H$ (400 MHz, DMSO-d$_6$) 11.17 (s, 1H), 8.84 (s, 1H), 8.76 (d, J 2.6 Hz, 1H), 8.45 (s, 1H), 8.16-8.03 (m, 2H), 7.38-7.23 (m, 1H), 4.64-4.46 (m, 1H), 4.17-4.01 (m, 2H), 3.43 (dd, J 16.5, 5.2 Hz, 1H), 2.93-2.82 (m, 3H), 2.37-2.12 (m, 2H), 2.08-1.96 (m, 1H), 1.21-1.06 (m, 1H), 1.03-0.83 (m, 4H), 0.49-0.35 (m, 2H), 0.32-0.19 (m, 2H).

Examples 95 and 96

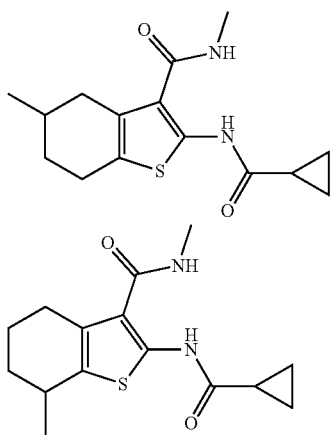

Example 95

2-(Cyclopropanecarbonylamino)-N,5-dimethyl-4,5,6,7-tetrahydrobenzothiophene-3-carboxamide Example 96

2-(Cyclopropanecarbonylamino)-N,7-dimethyl-4,5,6,7-tetrahydrobenzothiophene-3-carboxamide 2M Methylamine in THF (0.40 mL, 0.80 mmol) was added to a solution of EDCl (67 mg, 0.35 mmol) and a 3:1 mixture of intermediate 88 and intermediate 89 (151 mg, 0.54 mmol) in DCM (5 mL) and the reaction was left to stir overnight. Water (5 mL) was added, and the mixture was passed through a phase separator cartridge, the organic phase was concentrated in vacuo to yield the crude product which was purified by flash column chromatography on silica (gradient elution with 5%-40% EtOAc in iso-hexane) to afford the product which was freeze-dried from MeCN/water overnight to afford the title compound isomers 95 and 96 (31 mg) as a white solid in the ratio 9.5:1. The material was submitted for purification by preparative HPLC to afford a 9:1 mixture of title compound example 95 and title compound example 96 (3.2 mg, 2%) as a white solid. Major isomer title compound example 96: $\delta_H$ (400 MHz, DMSO-d$_6$) 11.32 (s, 1H), 7.51 (s, 1H), 2.80 (m, 1H), 2.75 (d, 3H, J=4.4 Hz), 2.59 (m, 2H), 1.77-1.93 (m, 3H), 1.50-1.65 (m, 1H), 1.28-1.36 (m, 1H), 1.18 (d, 3H, J=6.7 Hz), 0.81 (m, 4H).

Example 97

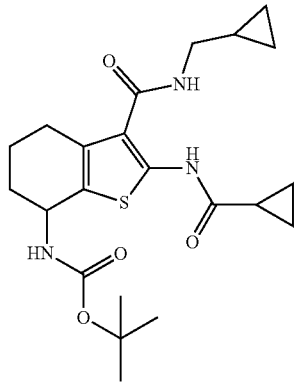 [SMILES: CC(C)(C)OC(=O)NC1CCCc2c1sc(NC(=O)C1CC1)c2C(=O)NCC1CC1]

tert-Butyl N-[2-(cyclopropanecarbonylamino)-3-(cyclopropylmethylcarbamoyl)-4,5,6,7-tetrahydrobenzothiophen-7-yl]carbamate To intermediate 104 (700 mg, 1.84 mmol) dissolved in DCM (50 mL) was added 1-cyclopropylmethanamine [2516-47-4] (0.63 mL, 7.36 mmol) and EDCl (600 mg, 3.12 mmol). The reaction mixture was stirred at r.t. for 16 h before diluting with DCM (50 mL) and washing with water, 0.5M aqueous hydrochloric acid solution and saturated sodium hydrogen carbonate solution. The organic layer was separated and washed with brine, dried (MgSO$_4$), filtered and concentrated in vacuo. The crude residue was purified by flash column chromatography on silica to afford the title compound (319 mg, 40%) as a white solid. 25 mg was purified by preparative HPLC (basic) to afford the pure compound (5 mg) for analysis. $\delta_H$ (500 MHz, CD$_3$OD) 4.79-4.67 (m, 1H), 3.24 (d, J 6.9 Hz, 2H), 2.76-2.64 (m, 2H), 2.08-1.91 (m, 2H), 1.78 (m, 3H), 1.47 (s, 9H), 1.10 (m, 1H), 1.01-0.91 (m, 4H), 0.56-0.51 (m, 2H), 0.31-0.26 (m, 2H). LCMS [M+H]$^+$ 434.2, RT 3.87 minutes, 96% purity (Method 10).

Examples 98 and 99

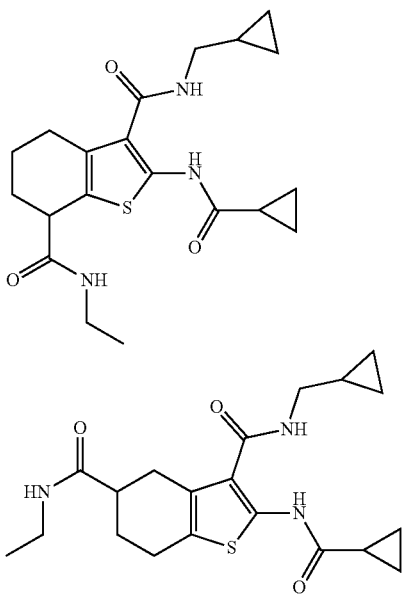

2-(Cyclopropanecarbonylamino)-N3-(cyclopropylmethyl)-N7-ethyl-4,5,6,7-tetrahydrobenzothiophene-3,7-dicarboxamide A mixture of intermediates 109 and 110 (30 mg, 0.083 mmol) (6% intermediate 110) was dissolved in DCM (3 mL) then EDCl (24 mg, 0.12 mmol) was added and the reaction mixture was stirred for 20 minutes. 2M Ethyl amine in THF (0.083 mL, 0.16 mmol) was added and the reaction mixture was stirred at r.t. for 16 h. The reaction mixture was diluted with DCM (20 mL) and washed with water, 1M aqueous hydrochloric acid solution and saturated sodium hydrogen carbonate solution. The organic layer was washed with brine, dried (MgSO$_4$), filtered and concentrated in vacuo. The residue was purified by preparative HPLC (acidic) to afford the title compound (16 mg, 50%) as a white solid which contained 91% of the 7-isomer title compound example 98 and 9% of the 5-isomer title compound example 99. $\delta_H$ (500 MHz, CD$_3$OD) 3.62 (t, J 6.3 Hz, 1H, 7-isomer), 3.29-3.16 (m, 4H), 2.87-2.66 (m, 2H, 7-isomer, 4H, 5-isomer), 2.60-2.47 (m, 1H, 5-isomer), 2.12-1.95 (m, 3H, 7-isomer, 1H, 5-isomer), 1.93-1.87 (m, 1H, 5-isomer), 1.85-1.67 (m, 2H, 7-isomer, 1H, 5-isomer), 1.22-1.05 (m, 4H), 1.03-0.89 (m, 4H), 0.59-0.49 (m, 2H), 0.32-0.25 (m, 2H). 9% 5-regio isomer present. LCMS [M+H]$^+$ 390.2, RT 2.82 minutes, 90% 7-isomer, 9% 5-isomer (Method 10).

Examples 100 and 101

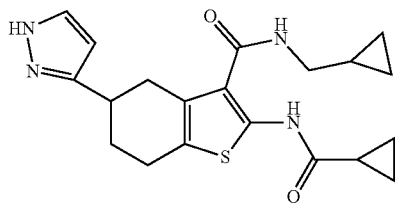

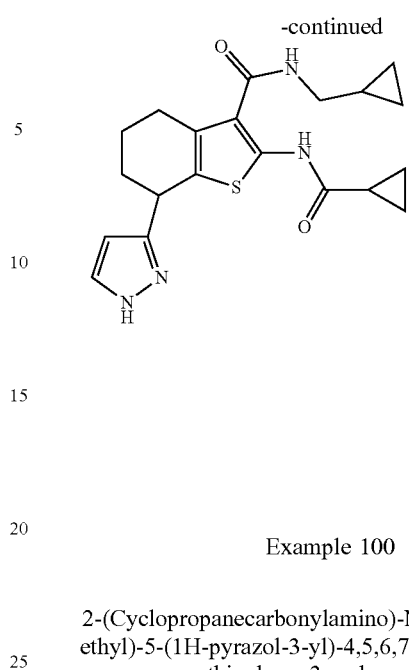

Example 100

2-(Cyclopropanecarbonylamino)-N-(cyclopropylmethyl)-5-(1H-pyrazol-3-yl)-4,5,6,7-tetrahydrobenzothiophene-3-carboxamide

Example 101

2-(Cyclopropanecarbonylamino)-N-(cyclopropylmethyl)-7-(1H-pyrazol-3-yl)-4,5,6,7-tetrahydrobenzothiophene-3-carboxamide To intermediate 111 (22 mg, 0.089 mmol) and 2-cyano-N-(cyclopropylmethyl)acetamide [114153-25-2] (15 mg, 0.0977 mmol) in THF (0.6 mL) was added ammonium acetate (7 mg, 0.0908 mmol) and acetic acid (5.4 mg, 0.089 mmol). The reaction mixture was stirred at 60° C. overnight. To the reaction mixture was added sulphur [7704-34-9] (8 mg, 0.250 mmol), EtOH (1.8 mL) and triethylamine (30 mg, 0.294 mmol) and the mixture was warmed at 65° C. for 2 h. The reaction mixture was concentrated in vacuo and EtOAc (5 mL) and 5% potassium bisulfate (2 mL) was added.

The organic layer was separated and washed with saturated sodium hydrogen carbonate solution and brine. The organic layer was dried (Na$_2$SO$_4$), filtered and concentrated in vacuo to yield a brown oil. To this oil was added DCM (0.8 mL), DIPEA (17 mg, 0.132 mmol) and cyclopropanecarbonyl chloride [4023-34-1] (11 mg, 0.1031 mmol). The reaction mixture was stirred at r.t. overnight. To the reaction mixture was added saturated sodium hydrogen carbonate solution (2 mL) and the mixture was filtered through a phase separation cartridge. The aqueous layer was further extracted with DCM (2 mL) and the combined organic phases were concentrated in vacuo. To this was added DCM (2 mL) and TFA (1 mL) and the reaction mixture was stirred at r.t. for 2 h and then concentrated in vacuo. Purification was carried out by reverse phase HPLC (basic) to afford the title compounds examples 100 and 101 (2.1 mg, 6.2%) in the ratio of 8/2 respectively. LCMS [M+H]$^+$ 385.06, RT 3.87 minutes, 82.13%; [M+H]$^+$ 385.00, RT 3.63 minutes, 17.87% (Method 13). LCMS [M+H]$^+$ 385.15, [M+Na]$^+$407.08, RT 3.87 minutes, 84.06%; [M+H]$^+$ 385.15, RT 3.95 minutes, 15.94% (Method 21).

Example 102

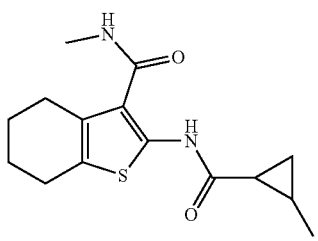 [SMILES: CNC(=O)c1c(NC(=O)C2CC2C)sc2c1CCCC2]

N-Methyl-2-[(2-methylcyclopropanecarbonyl)amino]-4,5,6,7-tetrahydrobenzothiophene-3-carboxamide 2-Methyl-cyclopropanecarbonyl chloride [52194-65-7] (0.06 mL, 0.5 mmol) was added to a solution of intermediate 113 (100 mg, 0.48 mmol) and DIPEA (0.21 mL, 1.2 mmol) in DCM (5 mL) and the reaction was left to stir overnight. The reaction mixture was diluted with DCM (20 mL) and washed with brine (20 mL), passed through a phase separator cartridge and concentrated in vacuo. The crude product was purified by flash column chromatography on silica (gradient elution with 10%-50% EtOAc in iso-hexane) to give the product which was freeze dried from MeCN/water overnight. This afforded the title compound (93 mg, 67%) as an off-white solid as a 6:1 mixture of cyclopropyl diastereomers. $\delta_H$ (400 MHz, DMSO-$d_6$) 11.41 (s, 0.14H) and 11.35 (s, 0.86H), 7.40-7.49 (m, 1H), 2.78 (d, 3H, J 4.6 Hz), 2.58-2.64 (m, 4H), 1.89-1.94 (0.14H), 1.70-1.76 (m, 4H), 1.63-1.68 (m, 0.86H), 1.22-1.36 (m, 1H), 1.10 (d, 3H, J 6.0 Hz), 0.98-1.06 (m, 1H), 0.78-0.82 (m, 0.14H), 0.68-0.74 (m, 0.86H).

Example 103

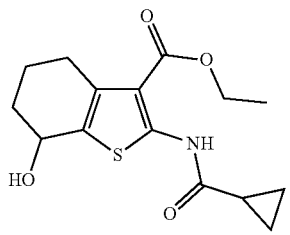 [SMILES: CCOC(=O)c1c(NC(=O)C2CC2)sc2c1CCCC2O]

Ethyl 2-(cyclopropanecarbonylamino)-7-hydroxy-4,5,6,7-tetrahydrobenzothiophene-3-carboxylate To ethyl 2-(cyclopropanecarbonylamino)-7-oxo-5,6-dihydro-4H-benzothiophene-3-carboxylate intermediate 74 (102 mg, 0.33 mmol) dissolved in 1,4-dioxane (2 mL) and MeOH (0.5 mL) and heated to 40° C. was added sodium borohydride [16940-66-2] (28 mg, 0.75 mmol) portionwise over a period of approximately 15 minutes. The reaction mixture was stirred at 40° C. under nitrogen for 30 minutes. The reaction mixture was poured into water and the white precipitate formed was filtered off under reduced pressure and washed with water to afford the title compound (89 mg, 87%) as a white solid. $\delta_H$ (300 MHz, DMSO-$d_6$) 11.24 (s, 1H), 5.34 (br. s, 1H), 4.57 (s, 1H), 4.29 (q, J 7.1 Hz, 2H), 2.73-2.61 (m, 2H), 2.06-1.93 (m, 1H), 1.94-1.76 (m, 2H), 1.72-1.50 (m, 2H), 1.31 (t, J 7.1 Hz, 3H), 1.00-0.77 (m, 4H).

Example 104

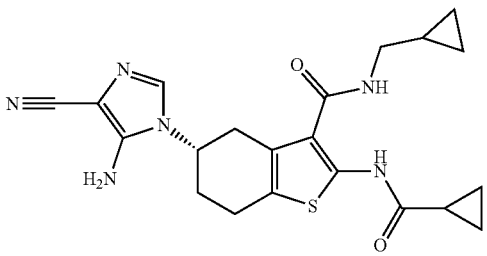 [SMILES: N#Cc1ncn([C@H]2CCc3sc(NC(=O)C4CC4)c(C(=O)NCC4CC4)c3C2)c1N]

(5S)-5-(5-Amino-4-cyano-imidazol-1-yl)-2-(cyclopropanecarbonylamino)-N-(cyclopropylmethyl)-4,5,6,7-tetrahydrobenzothiophene-3-carboxamide To aminopropanedinitrile 4-methylbenzenesulfonate (1:1) [5098-14-6] (0.15 g, 0.6 mmol) stirring in MeCN (2 mL) was added triethylamine (84 μL, 0.6 mmol) and triethylorthoformate [122-51-0] (100 μL, 0.6 mmol). The reaction was sealed and heated to 90° C. for 1 h. Intermediate 117 (0.2 g, 0.6 mmol) was added followed by further MeCN (3 mL). The suspension was sonicated and stirred for 15 minutes, the reaction was heated to 60° C. for 45 minutes before concentrating in vacuo. The residue was dissolved in DCM (50 mL) and washed with water (50 mL). An emulsion was obtained and the mixture was diluted with DCM, water and brine. The organic phase was collected and the aqueous phase extracted with further DCM (2×50 mL). Aqueous layer was adjusted to pH 8 using 1M aqueous sodium hydroxide solution and was extracted with EtOAc (2×50 mL). The organics were dried ($Na_2SO_4$), filtered and concentrated in vacuo to give the crude product as a light brown solid (280 mg) which was purified by flash column chromatography on silica (gradient elution with 0-10% MeOH in DCM) to afford the title compound as a solid which was triturated with EtOAc and heptane (1:1) to afford the purified title compound (65 mg, 26%) as a cream coloured solid. $\delta_H$ (500 MHz, DMSO-$d_6$) 11.22 (s, 1H), 7.68 (t, J 5.7 Hz, 1H), 7.34 (s, 1H), 6.24 (s, 2H), 4.35-4.23 (m, 1H), 3.20-3.08 (m, 2H), 3.08-3.01 (m, 1H), 2.99-2.89 (m, 1H), 2.89-2.74 (m, 2H), 2.21-2.05 (m, 2H), 1.96-1.87 (m, 1H), 1.07-0.97 (m, 1H), 0.90-0.79 (m, 4H), 0.44-0.32 (m, 2H), 0.26-0.12 (m, 2H). LCMS (ES+) [M+H]$^+$ 425.1, RT 2.59 minutes, purity 97% (Method 10).

Example 105

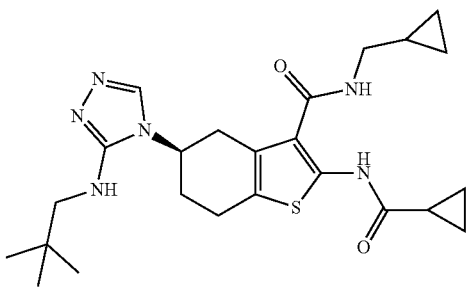 [SMILES: CC(C)(C)CNc1nncn1[C@@H]1CCc2sc(NC(=O)C3CC3)c(C(=O)NCC3CC3)c2C1]

(5S)-2-(Cyclopropanecarbonylamino)-N-(cyclopropylmethyl)-5-[3-(2,2-dimethylpropylamino)-1,2,4-triazol-4-yl]-4,5,6,7-tetrahydrobenzothiophene-3-carboxamide Intermediate 119 (150 mg, 0.268 mmol) was dissolved in EtOH (10 mL) and formic acid [64-18-6] (10 mL). The reaction mixture was stirred under nitrogen and a slurry of 10% palladium on carbon (100 mg, 0.94 mmol) was added and the reaction was heated at 80° C. for 3 h. The reaction mixture was cooled and further 10% palladium on carbon (50 mg) was added. The mixture was then heated at 80° C. for a further 3 h before cooling and filtering through Celite. The solvent was removed in vacuo to give a pink gum which was purified by flash column chromatography on silica (gradient elution with 0-5% EtOAc/iso-hexane) to give the desired product as an impure solid which was repurified by flash column chromatography on silica (gradient elution with 0-3% EtOAc/iso-hexane) to afford the title compound (65 mg, 51%) as a white solid. $\delta_H$ (400 MHz, DMSO-$d_6$) 11.23 (s, 1H), 8.04 (s, 1H), 7.69 (t, J 5.7 Hz, 1H), 5.85 (t, J 6.4 Hz, 1H), 4.36 (p, J 5.0 Hz, 1H), 3.23-3.02 (m, 5H), 2.83 (s, 3H), 2.14 (s, 2H), 1.97-1.89 (m, 1H), 1.12-0.92 (m, 1H), 0.90 (s, 11H), 0.43-0.33 (m, 2H), 0.20 (ddd, J 5.6, 4.7, 3.6 Hz, 2H). LCMS (ES+) [M+H]$^+$ 471.2, RT 2.11 minutes, 100.0% purity (Method 3).

Example 106, 107 and 108

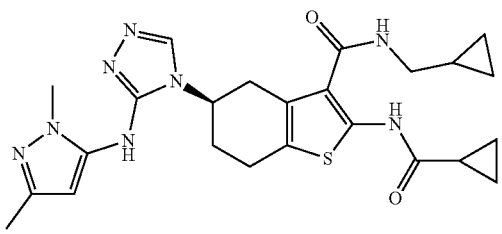

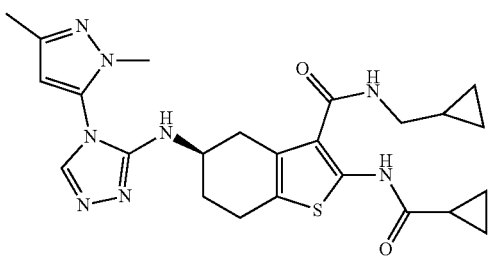

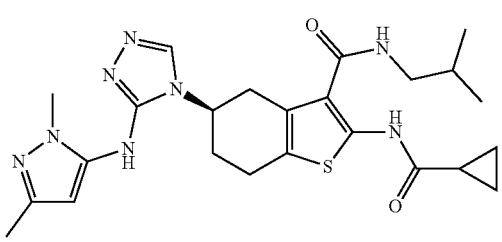

Example 106

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide Example 107

(5S)-2-(Cyclopropanecarbonylamino)-N-(cyclopropylmethyl)-5-[[4-(2,5-dimethylpyrazol-3-yl)-1,2,4-triazol-3-yl]amino]-4,5,6,7-tetrahydrobenzothiophene-3-carboxamide Example 108

(5S)-2-(Cyclopropanecarbonylamino)-5-[3-[(2,5-dimethylpyrazol-3-yl)amino]-1,2,4-triazol-4-yl]-N-isobutyl-4,5,6,7-tetrahydrobenzothiophene-3-carboxamide Intermediate 120 (3.50 g, 7.19 mmol) was dissolved in DMF (94 g, 1.29 mol). Formic acid hydrazide [624-84-0] (0.62 g, 9.35 mmol) was added followed by mercuric chloride [7487-94-7] (2.54 g, 9.35 mmol). The reaction mixture was stirred at r.t. for ~10 minutes and triethylamine (0.81 g, 7.91 mmol) was added and the mixture was stirred at 80° C. for ~2.5 h. Further formyl hydrazine [624-84-0] (0.22 g, 3.60 mmol) and mercuric chloride [7487-94-7] (1.75 g, 3.60 mmol) were added and the reaction mixture was stirred at 80° C. for ~1 h. The mixture was cooled to r.t. and left to stand over the weekend. Further triethylamine (0.81 g, 7.96 mmol) was added and the mixture was heated at 80° C. for ~1 h. The reaction mixture was cooled to r.t. and diluted with MeCN (100 mL), filtered through a pad of celite and washed with MeCN (2×50 mL). The filtrate was concentrated in vacuo to yield the crude product as an orange/brown gum which was dissolved in 5% MeOH/DCM, washed with water and brine, passed through a phase separation cartridge and the organic phase concentrated in vacuo to yield an orange/brown solid (~5.5 g) which was purified by flash column chromatography on silica (gradient elution with 2-15% MeOH/DCM) to afford title compound 106 (contaminated with title compound 108) and title compound 107. Title compound 108 was present as a result of a 2-methylpropan-1-amine impurity in the cyclopropylmethanamine used in the preparation of intermediate 114) Title compound 106 was further purified by reverse phase chromatography on C18 silica to afford the title compound 106 (1.57 g, 44.1% as a 2:1 mixture of rotamers) as a white solid. Reverse phase fractions containing title compound 108 were further purified by preparative HPLC to afford title compound example 108 (15 mg, 0.030 mmol, 0.42%) as a ~2:1 mixture of rotamers. LCMS (ES+) [M+H]$^+$ 497.36, RT 1.91 minutes, purity 97.80% (Method 24). LCMS (ES+) [M+H]$^+$ 497.36, RT 1.94 minutes, purity 97.52% (Method 25).

Title compound example 106: $\delta_H$ (500 MHz, DMSO-$d_6$) 11.22 (s, 1H), 8.42 (s, 1H), 8.33 (s, 1H), 7.74 (s, 1H), 5.89 (s, 1H), 4.45-4.40 (m, 1H), 3.55 (s, 3H), 3.19-3.05 (m, 3H), 2.99-2.94 (m, 1H), 2.86-2.80 (m, 2H), 2.25-2.17 (m, 2H), 2.06 (s, 3H), 1.93-1.90 (m, 1H), 1.04-0.98 (m, 1H), 0.86-0.82 (m, 4H), 0.40-0.36 (m, 2H), 0.22-0.17 (m, 2H), mixture of rotamers (2:1). LCMS (ES+) [M+H]$^+$ 495.2, RT 1.68 minutes, 100.0% purity (Method 3). LCMS (ES+) [M+H]$^+$ 495.2, RT 1.63 minutes, 100.0% purity (Method 2).

Title compound example 107: $\delta_H$ (500 MHz, DMSO-$d_6$) 11.00 (br s, 1H), 8.15 (s, 1H), 7.70 (s, 1H), 6.27 (s, 1H), 6.16

(d, J 7.2 Hz, 1H), 3.87-3.84 (m, 1H), 3.49 (s, 3H), 3.13-3.08 (m, 3H), 2.75-2.68 (m, 2H), 2.62-2.55 (m, 1H), 2.18 (s, 3H), 2.08-2.05 (m, 1H), 1.89-1.82 (m, 2H), 1.04-0.98 (m, 1H), 0.88-0.79 (m, 4H), 0.41-0.37 (m, 2H), 0.24-0.19 (m, 2H).

Example 109

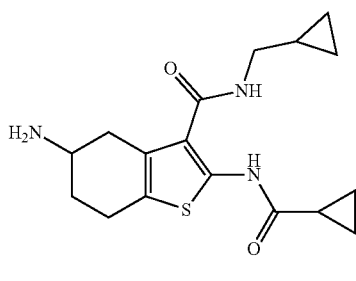 [SMILES: NC1CCc2sc(NC(=O)C3CC3)c(C(=O)NCC3CC3)c2C1]

5-Amino-2-(cyclopropanecarbonylamino)-N-(cyclopropylmethyl)-4,5,6,7-tetrahydrobenzothiophene-3-carboxamide To a stirred solution of intermediate 114 (10 g, 23.1 mmol) in 1,4-dioxane (120 mL), 4M hydrogen chloride in 1,4-dioxane (120 mL) was added at 0° C. The reaction mixture was stirred at r.t. for 16 h. The reaction mixture was concentrated in vacuo and the crude product obtained was washed with sodium hydrogen carbonate solution and extracted with 10% MeOH:DCM. The organic layer was dried (Na$_2$SO$_4$), filtered and concentrated in vacuo to afford the title compound (6.5 g, 84%) which was triturated using n-pentane. δ$_H$ (400 MHz, DMSO-d$_6$) 3.12-3.09 (m, 4H), 3.07 (s, 1H), 2.97-2.88 (m, 1H), 2.70-2.60 (d, J 16.1 Hz, 2H), 2.49-2.38 (m, 2H), 1.92-1.86 (m, 2H), 1.57-1.51 (m, 1H), 1.26-1.13 (m, 1H), 1.04-0.99 (m, 1H), 0.80-0.79 (m, 4H), 0.46-0.41 (m, 2H), 0.23-0.21 (q, J 4.8 Hz, 2H).

Example 110

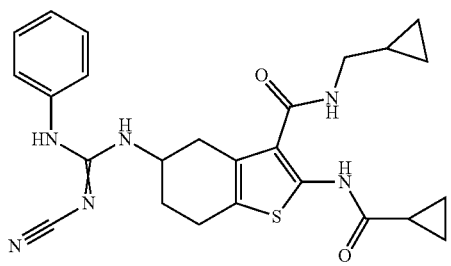 [SMILES: N#CN=C(Nc1ccccc1)NC1CCc2sc(NC(=O)C3CC3)c(C(=O)NCC3CC3)c2C1]

5-[[N'-Cyano-N-phenyl-carbamimidoyl]amino]-2-(cyclopropanecarbonylamino)-N-(cyclopropylmethyl)-4,5,6,7-tetrahydrobenzothiophene-3-carboxamide Intermediate 122 (50 mg, 0.14 mmol) was dissolved in DCM (4 mL) and DIPEA (26 mg, 0.20 mmol) and intermediate 121 (64 mg, 0.270 mmol calculated not actual) was added. The reaction mixture was stirred at 100° C. in the microwave for 1 h. The mixture was purified by flash column chromatography on silica (gradient elution was 15-100% EtOAc/hexane) to afford the title compound (52 mg) as a tan solid which was purified by preparative HPLC to afford the title compound (2.9 mg, 4.5%) as a white solid. LCMS (ES+) [M+H]$^+$ 477.8, RT 2.197 minutes, purity 100.0% (Method 3).

Example 111

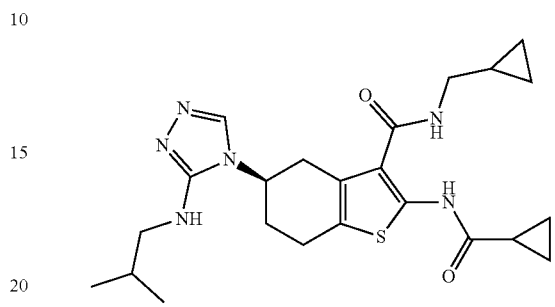

(5S)-2-(Cyclopropanecarbonylamino)-N-(cyclopropylmethyl)-5-[3-(isobutylamino)-1,2,4-triazol-4-yl]-4,5,6,7-tetrahydrobenzothiophene-3-carboxamide Intermediate 124 (266 mg, 0.49 mmol) was dissolved in EtOH (10 mL) and formic acid [64-18-6] (10 mL). To the reaction mixture stirred under a nitrogen atmosphere was added a slurry of 10% palladium on carbon (200 mg, 1.88 mmol) and the reaction was heated at 80° C. for 5 h. The reaction mixture was cooled and further 10% Palladium on carbon (200 mg, 1.88 mmol) in EtOH (1.5 mL) was added. The reaction mixture was stirred under nitrogen and heated at 80° C. for a further 3 h. The mixture was cooled and stirred for 18 h at r.t. Further 10% Palladium on carbon (100 mg, 0.94 mmol) was added and the mixture was stirred under nitrogen and heated at 80° C. for a further 2 h. The reaction mixture was filtered through Celite washing with EtOH (2×10 mL). The solvent was removed in vacuo to give a pale yellow solid which was purified by flash column chromatography on silica (gradient elution with 0-3% MeOH/DCM) to afford the title compound (70 mg, 32%) as a white solid. δ$_H$ (400 MHz, DMSO-d$_6$) 11.23 (s, 1H), 8.05 (s, 1H), 7.69 (t, J 5.7 Hz, 1H), 6.06 (t, J 5.7 Hz, 1H), 4.25 (dq, J 10.0, 4.9 Hz, 1H), 3.23-2.79 (m, 6H), 2.83 (s, 2H), 2.14 (td, J 9.9, 6.0 Hz, 2H), 1.92 (pd, J 6.7, 5.7, 3.4 Hz, 2H), 1.07-0.95 (m, 1H), 0.88 (dd, J 12.1, 5.3 Hz, 10H), 0.43-0.34 (m, 2H), 0.24-0.16 (m, 2H).

Example 112

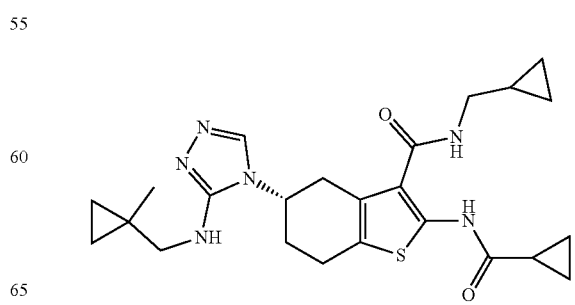

(5S)-2-(Cyclopropanecarbonylamino)-N-(cyclopropylmethyl)-5-[3-[(1-methylcyclopropyl)methylamino]-1,2,4-triazol-4-yl]-4,5,6,7-tetrahydrobenzothiophene-3-carboxamide Intermediate 126 (64% purity, 485 mg, 0.56 mmol) was dissolved in EtOH (20 mL) and formic acid [64-18-6] (20 mL). 10% Palladium on carbon (50% wet) (5%, 1.18 g, 0.56 mmol) was added and the reaction was heated at 90° C. for 2.5 h. The reaction was heated at 90° C. for a further 16 h before filtering and washing with EtOH (50 mL). The filtrate was concentrated in vacuo and the oily residue (500 mg) was dissolved in formic acid (20 mL) and 10% palladium on carbon (50% wet) (5%, 1.18 g) added. The reaction was heated at 100° C. for 2 h. The reaction was allowed to cool and filtered, washing with EtOH:formic acid (1:1, 40 mL). The filtrate was concentrated in vacuo to yield the crude product as an oil. EtOAc (80 mL) was added and the organic layer was washed with saturated aqueous sodium hydrogen carbonate (2×20 mL) and brine. The organic phase was dried (Na$_2$SO$_4$), filtered and concentrated in vacuo to yield the crude product which was purified by flash column chromatography on silica (gradient elution with 0-10% MeOH in DCM) to afford the crude title compound which was purified by preparative HPLC to afford the title compound (28 mg, 11%) as a white solid. δ$_H$ (500 MHz, DMSO-d$_6$) 11.23 (s, 1H), 8.04 (s, 1H), 7.68 (s, 1H), 5.96 (t, J 5.9 Hz, 1H), 4.32 (tt, J 10.2, 5.1 Hz, 1H), 3.16 (td, J 12.5, 11.6, 5.9 Hz, 3H), 3.12-3.02 (m, 2H), 2.90-2.75 (m, 3H), 2.19-2.06 (m, 2H), 1.96-1.88 (m, 1H), 1.07 (s, 3H), 1.05-0.96 (m, 1H), 0.88-0.81 (m, 4H), 0.50-0.43 (m, 2H), 0.41-0.33 (m, 2H), 0.25-0.21 (m, 2H), 0.21-0.16 (m, 2H).

Example 113

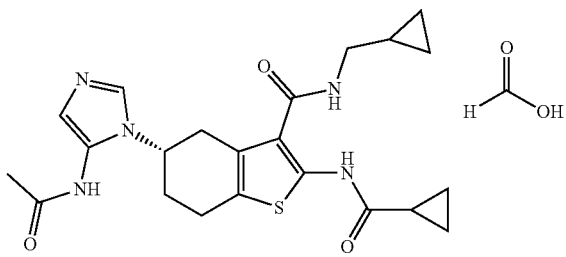 [SMILES: CC(=O)Nc1cncn1[C@H]1CCc2sc(NC(=O)C3CC3)c(C(=O)NCC3CC3)c2C1 ; O=CO]

(5S)-5-(5-Acetamidoimidazol-1-yl)-2-(cyclopropanecarbonylamino)-N-(cyclopropylmethyl)-4,5,6,7-tetrahydrobenzothiophene-3-carboxamide To a stirred solution of intermediate 127 (85%, 42 mg, 0.36 mmol) in anhydrous DCM (2 mL) was added intermediate 117 (100 mg, 0.30 mmol). The reaction mixture was heated in a microwave (up to 100 W) at 50° C. for 1 h. The reaction mixture was left to cool to r.t. and a solution of acetic anhydride (0.071 ml, 0.75 mmol) in DCM (0.5 mL) was added dropwise and the reaction mixture was stirred at r.t. for 2 h. The reaction mixture was diluted with DCM (5 mL) and washed with water (2 mL), 1M aqueous sodium hydrogen carbonate (2 mL) and brine (2 mL). The organic layer was dried (Na$_2$SO$_4$), filtered and the solvent was removed in vacuo to yield the crude product which was purified by preparative HPLC (low pH) to afford the title compound (22 mg, 16%) as a clear glass. δ$_H$ (500 MHz, DMSO-d$_6$) 11.16 (s, 1H), 9.53 (s, 1H), 8.16 (s, 1H, formate), 7.78-7.67 (m, 1H), 7.63 (s, 1H), 6.76 (s, 1H), 4.27-4.13 (m, 1H), 3.17-3.06 (m, 2H), 3.02 (d, J 7.5 Hz, 2H), 2.85-2.73 (m, 2H), 2.21-2.09 (m, 2H), 2.02 (s, 3H), 1.96-1.87 (m, 1H), 1.06-0.94 (m, 1H), 0.88-0.79 (m, 4H), 0.43-0.33 (m, 2H), 0.23-0.15 (m, 2H). LCMS [M–H]$^-$ 442, RT 1.61 minutes, purity 100% (Method 10).

Example 114

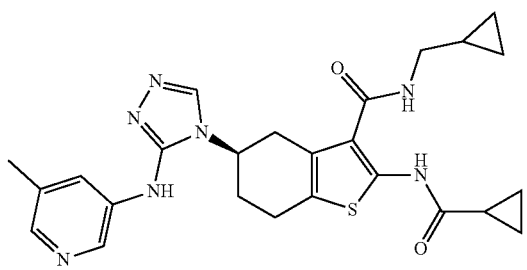 [SMILES: Cc1cncc(Nc2nncn2[C@@H]2CCc3sc(NC(=O)C4CC4)c(C(=O)NCC4CC4)c3C2)c1]

(5S)-2-(cyclopropanecarbonylamino)-N-(cyclopropylmethyl)-5-[3-[(5-methyl-3-pyridyl)amino]-1,2,4-triazol-4-yl]-4,5,6,7-tetrahydrobenzothiophene-3-carboxamide Intermediate 128 (290 mg, 0.60 mmol) was dissolved in DMF (10 mL) and formic acid hydrazide [624-84-0] (80 mg, 1.20 mmol) was added followed by mercuric chloride [7487-94-7] (326 mg, 1.20 mmol) and triethylamine (122 mg, 1.20 mmol). The mixture was stirred for 2 minutes at r.t. and then heated at 60° C. for 2 hrs. The reaction mixture was cooled and diluted with MeCN (10 mL) and then filtered through a plug of Celite, washing with MeCN (20 mL). The filtrate was concentrated in vacuo to yield a yellow oil which was dissolved in 10% MeOH/DCM and washed with water (2×5 mL). The organic phase was dried (Na$_2$SO$_4$), filtered and concentrated in vacuo to yield the crude product which was purified by flash column chromatography on silica (gradient elution with 0-20% MeOH/DCM) to afford the title compound (158 mg, 53%) as a white solid. δ$_H$ (400 MHz, DMSO-d$_6$) 11.26 (s, 1H), 8.77 (s, 1H), 8.54 (d, J 2.5 Hz, 1H), 8.41 (s, 1H), 7.96 (d, J 6.6 Hz, 2H), 7.68 (s, 1H), 4.53 (s, 1H), 3.21-3.01 (m, 3H), 2.92 (d, J 28.9 Hz, 3H), 2.28 (s, 6H), 1.04-0.75 (m, 5H), 0.34-0.27 (m, 2H), 0.16 (t, J 4.6 Hz, 2H).

Example 115

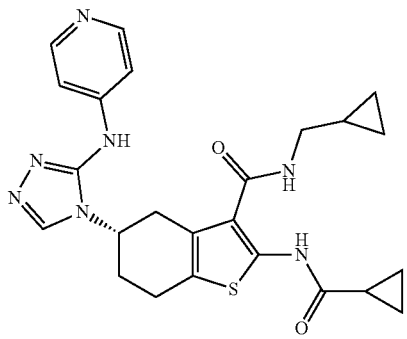 [SMILES: O=C(NCC1CC1)c1c(NC(=O)C2CC2)sc2c1C[C@@H](n1cnnc1Nc1ccncc1)CC2]

(5S)-2-(Cyclopropanecarbonylamino)-N-(cyclopropylmethyl)-5-[3-(4-pyridylamino)-1,2,4-triazo-4-yl]-4,5,6,7-tetrahydrobenzothiophene-3-carboxamide Intermediate 129 (80%, 150 mg, 0.26 mmol) and formic hydrazide [624-84-0] (46 mg, 0.77 mmol) were dissolved in DMF (3 mL). Mercury dichloride [7487-94-7] (208 mg, 0.77 mmol) was added to the reaction mixture. The mixture was stirred for 5 minutes and triethylamine (0.11 ml, 0.77 mmol) was added. The reaction mixture was heated at 60° C. for 1 h. The reaction mixture was stirred for 1 h at 90° C. and the reaction mixture was diluted with DCM (20 mL), filtered, and the filtrate concentrated in vacuo. The crude product was extracted with EtOAc (3×20 mL), washed with water (20 mL) and the organic phases were dried ($MgSO_4$), filtered, and the filtrate was evaporated to afford the crude product. The crude material was purified by flash column chromatography on silica (gradient elution with EtOAc then 0-50% MeOH in DCM). The relevant fractions were concentrated in vacuo to give the crude desired product which was further purified by preparative HPLC (acidic) to afford the title compound (21 mg, 17%) as a partial formate salt, white solid. $\delta_H$ (500 MHz, $CD_3OD$) 8.52 (s, 1H), 8.31 (d, J 5.7 Hz, 2H), 8.26 (s, 1H), 7.50 (s, 2H), 4.61-4.56 (m, 1H), 3.27-3.18 (m, 2H), 3.12 (dd, J 13.8, 7.0 Hz, 1H), 3.05 (dd, J 15.4, 9.8 Hz, 1H), 3.01-2.85 (m, 2H), 2.42-2.26 (m, 2H), 1.80 (tt, J 8.1, 4.6 Hz, 1H), 1.06-0.85 (m, 5H), 0.47-0.35 (m, 2H), 0.23-0.14 (m, 2H). LCMS (ES+) [M+H]⁺ 478.14, RT 1.66 minutes (Method 10). Chiral analysis 100% ee.

Example 116

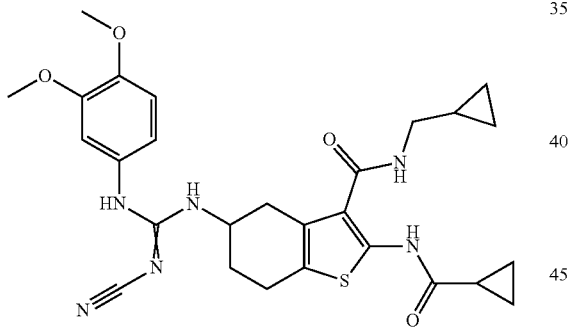

5-[[N'-Cyano-N-(3,4-dimethoxyphenyl)carbamimidoyl]amino]-2-(cyclopropanecarbonylamino)-N-(cyclopropylmethyl)-4,5,6,7-tetrahydrobenzothiophene-3-carboxamide Intermediate 122 (50 mg, 0.14 mmol) was dissolved in DCM (4 mL) and DIPEA (26 mg, 0.20 mmol) and intermediate 130 (60 mg, 0.20 mmol) was added. The reaction mixture was stirred at 100° C. in the microwave for 3 h before leaving at r.t. overnight. The mixture was concentrated in vacuo and the residue was purified by flash column chromatography on silica (gradient elution with 15-100% EtOAc/hexane). The residue was freeze dried from MeCN/water to afford the product as a tan solid which was purified by preparative HPLC and freeze dried from MeCN/water to afford the title compound (10 mg, 14%) as a white solid. $\delta_H$ (300 MHz, DMSO-$d_6$) 10.83 (s, 1H), 8.65 (s, 1H), 7.59-7.41 (m, 1H), 6.78-6.56 (m, 3H), 6.52 (dd, J 8.7, 2.4 Hz, 1H), 3.79 (br. s, 1H), 3.50 (d, J 4.3 Hz, 6H), 2.91 (t, J 6.4 Hz, 2H), 2.80-2.63 (m, 1H), 2.58-2.44 (m, 2H), 2.43-2.31 (m, 1H), 1.82-1.44 (m, 3H), 0.79 (s, 1H), 0.59 (s, 4H), 0.27-0.14 (m, 2H), 0.04--0.06 (m, 2H).

Example 117

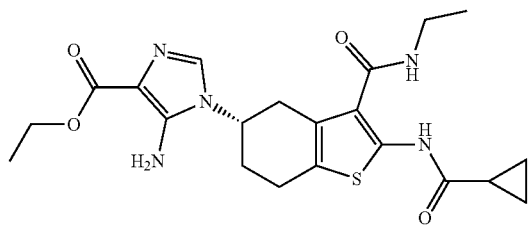 [SMILES: CCNC(=O)c1c(NC(=O)C2CC2)sc2c1C[C@@H](n1cnc(C(=O)OCC)c1N)CC2]

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate To intermediate 131 (85% purity, 23 mg, 0.15 mmol) in MeCN (2 mL) was added triethylorthoformate [122-51-0] (25 µL, 0.15 mmol) in a pressure tube. The reaction was sealed and stirred and heated at 90° C. for 1 h. The reaction was allowed to cool to r.t. and intermediate 117 (50 mg, 0.15 mmol) was added and the reaction was stirred at r.t. for 18 h. The reaction mixture was concentrated in vacuo and the residue was purified by flash column chromatography on silica (gradient elution with 0-10% MeOH in DCM) to afford the title compound (10 mg, 13% at 94% purity) as a grey solid. $\delta_H$ (500 MHz, DMSO-$d_6$) 11.21 (s, 1H), 7.70 (t, J 5.6 Hz, 1H), 7.28 (s, 1H), 6.09 (s, 2H), 4.39-4.24 (m, 1H), 4.17 (q, J 7.1 Hz, 2H), 3.22-3.02 (m, 3H), 3.02-2.92 (m, 1H), 2.91-2.74 (m, 2H), 2.25-2.05 (m, 2H), 2.00-1.83 (m, 1H), 1.24 (t, J 7.1 Hz, 3H), 1.08-0.93 (m, 1H), 0.93-0.75 (m, 4H), 0.44-0.31 (m, 2H), 0.20 (q, J 5.0 Hz, 2H).

Example 118

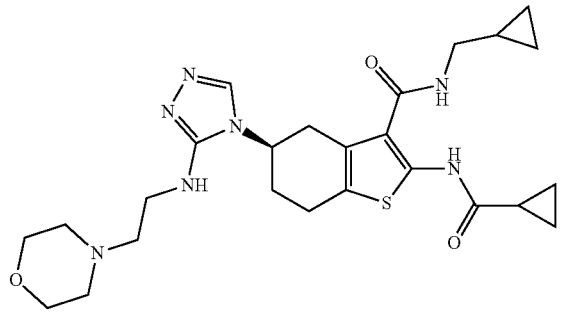 [SMILES: O=C(NCC1CC1)c1c(NC(=O)C2CC2)sc2c1C[C@H](n1cnnc1NCCN1CCOCC1)CC2]

(5S)-2-(Cyclopropanecarbonylamino)-N-(cyclopropylmethyl)-5-[3-(2-morpholinoethylamino)-1,2,4-triazol-4-yl]-4,5,6,7-tetrahydrobenzothiophene-3-carboxamide To a solution of intermediate 133 (300 mg, 0.50 mmol) in EtOH (10 mL) was added formic acid [64-18-6] (10 mL, 100 mass %). The reaction mixture was placed under a nitrogen atmosphere and a slurry of 10% palladium on carbon (200 mg, 0.19 mmol) in EtOH (2 mL) was added and the solution was stirred for 5 h at 80° C. Further 10% palladium on carbon (200 mg, 0.19 mmol) was added and the reaction heated for a further 2 h at 80° C. then 72 h at r.t. The reaction mixture was cooled and further 10% palladium on carbon (150 mg, 0.14 mmol) was added. The reaction was evacuated and under a nitrogen atmosphere was heated at 80° C. for 4 h. The reaction was cooled, filtered through Celite and washed with excess EtOH (2×10 mL). The solvent was removed in vacuo to give a yellow gum which was purified by flash column chromatography on silica (gradient elution with 0-100% [10% v/v MeOH/DCM with 2% v/v aqueous ammonia]/DCM) to give the product which was freeze dried from MeCN/water to afford the title compound (92 mg, 36%) as a white solid. δ$_H$ (400 MHz, DMSO-d$_6$) 11.21 (s, 1H), 8.07 (s, 1H), 7.69 (t, J 5.7 Hz, 1H), 5.97 (t, J 5.7 Hz, 1H), 4.22 (dt, J 10.0, 5.0 Hz, 1H), 3.60-3.53 (m, 5H), 3.38-3.27 (m, 4H), 3.22-2.98 (m, 3H), 2.94-2.76 (m, 3H), 2.45-2.36 (m, 3H), 2.12 (s, 2H), 1.92 (q, J 6.8, 6.3 Hz, 1H), 1.06-0.98 (m, 1H), 0.92-0.83 (m, 4H), 0.39 (dt, J 8.1, 2.9 Hz, 2H), 0.25-0.16 (m, 2H).

Example 119

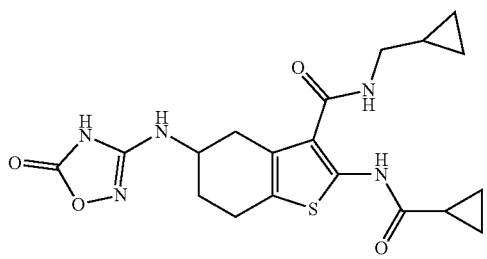 [SMILES: O=C(NCC1CC1)c1c(NC(=O)C2CC2)sc2c1CC(Nc1noc(=O)[nH]1)CC2]

2-(Cyclopropanecarbonylamino)-N-(cyclopropylmethyl)-5-[(5-oxo-4H-1,2,4-oxadiazol-3-yl)amino]-4,5,6,7-tetrahydrobenzothiophene-3-carboxamide To a stirred solution of intermediate 135 (30 mg, 0.077 mmoL) in THF (3 mL) was added CDI (15 mg, 0.092 mmoL) and the mixture was stirred at r.t. under an atmosphere of nitrogen for 20 h. The reaction mixture was concentrated in vacuo and the residue was purified by preparative HPLC (low pH) to afford the title compound (1 mg, 3%, 82% purity). δ$_H$ (250 MHz, CD$_3$OD) 3.69-3.53 (m, 1H), 3.17-3.02 (m, 3H, part. obs. by MeOD peak), 2.77-2.65 (m, 2H), 2.66-2.47 (m, 1H), 2.13-1.97 (m, 1H), 1.94-1.76 (m, 1H), 1.77-1.62 (m, 1H), 1.08-0.92 (m, 1H), 0.97-0.73 (m, 4H), 0.51-0.32 (m, 2H), 0.24-0.11 (m, 2H). LCMS [M+H]$^+$ 418, RT 2.61 minutes, 82% purity (Method 10).

Example 120

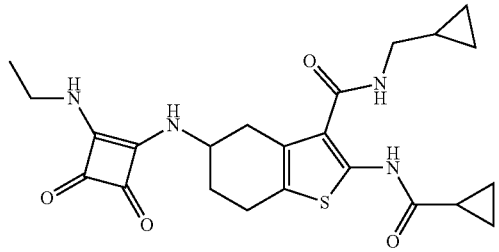 [SMILES: CCNc1c(NC2CCc3sc(NC(=O)C4CC4)c(C(=O)NCC4CC4)c3C2)c(=O)c1=O]

2-(Cyclopropanecarbonylamino)-N-(cyclopropylmethyl)-5-[[2-(ethylamino)-3,4-dioxo-cyclobuten-1-yl]amino]-4,5,6,7-tetrahydrobenzothiophene-3-carboxamide Intermediate 136 (95% purity, 50 mg, 0.1 mmol) was suspended in EtOH (4 mL) and 2M ethanamine in THF (60 µL) was added. The reaction mixture was warmed to ~50° C. until the solids dissolved and the solution was left to stand for 16 h at r.t. The precipitate was filtered and washed with EtOH to afford the title compound (25 mg, 50%) as a white solid. δ$_H$ (500 MHz, CD$_3$OD) 4.49 (br, 1H), 3.68-3.61 (m, 2H), 3.28-3.14 (m, 3H), 2.85 (br t, J 5.8 Hz, 2H), 2.78 (dd, J 15.9, 6.5 Hz, 1H), 2.20-2.10 (m, 1H), 2.10-2.00 (m, 1H), 1.84-1.76 (m, 1H), 1.25 (t, J 7.2 Hz, 3H), 1.14-1.05 (m, 1H), 1.02-0.89 (m, 4H), 0.55-0.49 (m, 2H), 0.31-0.24 (m, 2H). LCMS[M+H]$^+$ 457.3, RT 2.57 minutes, 95% purity (Method 10).

Example 121

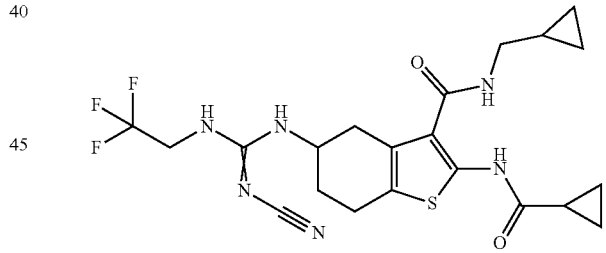

5-[[N'-cyano-N-(2,2,2-trifluoroethyl)carbamimidoyl]amino]-2-(cyclopropanecarbonylamino)-N-(cyclopropylmethyl)-4,5,6,7-tetrahydrobenzothiophene-3-carboxamide To diphenyl N-cyanocarbonimidate [79463-77-7] (40 mg, 0.17 mmol) was added 2,2,2-trifluoroethylamine [753-90-2] (18 mg, 0.19 mmol) and 1:1 DCM/isopropanol (1 mL). To this was added DIPEA (44 mg, 0.34 mmol) and the reaction was stirred at r.t. overnight. To the mixture was added intermediate 122 (40 mg, 0.11 mmol) and the mixture was stirred at 100° C. for 5 h. The reaction mixture was concentrated in vacuo, solubilised in 7:3 MeCN/water (700 µL) and the solvent was removed in vacuo, followed by solubilisation in DMF (700 µL) and MeCN/water (200 µL). The compound was purified by reverse phase HPLC (basic)

followed by reverse phase HPLC (acidic) to afford the title compound (5.1 mg, 9.8%). LCMS [M+H]$^+$ 483.1762, RT 4.69 minutes, 87.03% purity (Method 20).

Example 122

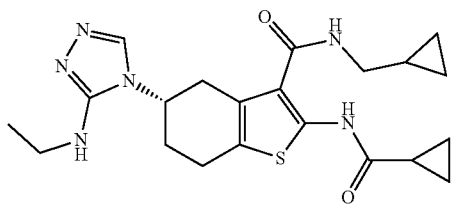 [SMILES: CCNc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-(ethylamino)-1,2,4-triazol-4-yl]-4,5,6,7-tetrahydrobenzothiophene-3-carboxamide Intermediate 138 (92%, 1.71 g, 3.03 mmol) was dissolved in EtOH (70 mL) and formic acid [64-18-6] (70 mL). Palladium on carbon (3.22 g, 30.3 mmol) was added to the reaction mixture and the mixture was refluxed for 2 h at 90° C. Further palladium on carbon (2 g) was added to the reaction mixture and the mixture was refluxed for 3 h at 90° C. The crude reaction mixture was filtered through a short pad of celite and washed with EtOH. The solvent was removed under reduced pressure to give the crude solid which was dissolved in EtOAc and neutralised with sodium hydrogen carbonate to pH 7. The organic phase was separated, dried (MgSO$_4$), filtered, and the filtrate was concentrated in vacuo to give the product which was purified by flash column chromatography on silica (gradient elution with 0-25% MeOH in DCM) to afford the title compound (407 mg, 32%). $\delta_H$ (500 MHz, Methylene Chloride-d$_2$) 11.97 (s, 1H), 7.76 (s, 1H), 5.82 (s, 1H), 4.15-4.10 (m, 1H), 3.89 (t, J 5.5 Hz, 1H), 3.50-3.37 (m, 2H), 3.32-3.26 (m, 2H), 3.22-3.15 (m, 1H), 2.91-2.81 (m, 3H), 2.34-2.15 (m, 2H), 1.68-1.58 (m, 1H), 1.28 (t, J 7.2 Hz, 3H), 1.08-1.01 (m, 3H), 0.96-0.83 (m, 2H), 0.57-0.44 (m, 2H), 0.28-0.22 (m, 2H). LCMS [M+H]$^+$ 429.20, RT 1.81 minutes, 96% purity (Method 10).

Example 123

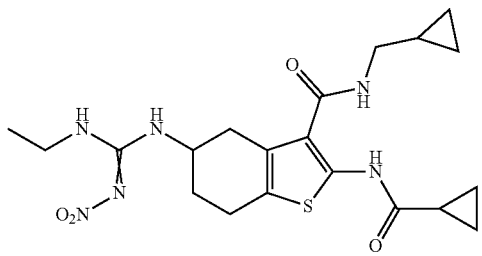 [SMILES: CCNC(=N[N+](=O)[O-])NC1CCc2sc(NC(=O)C3CC3)c(C(=O)NCC3CC3)c2C1]

2-(cyclopropanecarbonylamino)-N-(cyclopropylmethyl)-5-[(N-ethyl-N'-nitro-carbamimidoyl)amino]-4,5,6,7-tetrahydrobenzothiophene-3-carboxamide A mixture of intermediate 140 (60 mg, 0.13 mmol) and 2M ethanamine in THF (99.6 μL, 0.19 mmol) in MeOH (1.5 mL) was stirred and heated at 70° C. for 1 h in a microwave. The reaction mixture was concentrated in vacuo and the residue was purified by acidic HPLC to afford the title compound (45 mg, 76%) as a white solid. $\delta_H$ (500 MHz, CD$_3$OD) 4.31-3.91 (m, 1H), 3.36 (q, J 7.2 Hz, 2H), 3.27-3.12 (m, 3H), 2.92-2.79 (m, 2H), 2.78-2.63 (m, 1H), 2.20-2.10 (m, 1H), 2.01-1.90 (m, 1H), 1.84-1.76 (m, 1H), 1.31-1.18 (m, 3H), 1.14-1.05 (m, 1H), 1.01-0.90 (m, 4H), 0.56-0.49 (m, 2H), 0.32-0.24 (m, 2H). LCMS [M+H]$^+$ 449.2, RT 2.96 minutes, 100% purity (Method 10).

Example 124

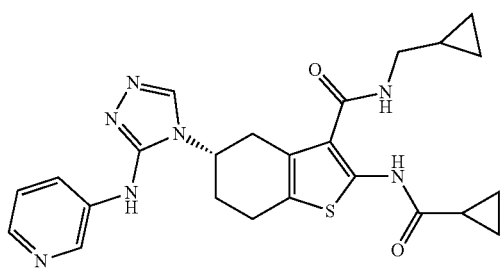

(5S)-2-(Cyclopropanecarbonylamino)-N-(cyclopropylmethyl)-5-[3-(3-pyridylamino)-1,2,4-triazol-4-yl]-4,5,6,7-tetrahydrobenzothiophene-3-carboxamide Intermediate 141 (2.00 g, 4.26 mmol) was dissolved in DMF (25 mL). Formic acid hydrazide [624-84-0] (313 mg, 4.68 mmol) and mercuric chloride [7487-94-7] (1.27 g, 4.68 mmol) was added. The reaction mixture was stirred at r.t. for 5 minutes. Triethylamine (476 mg, 4.68 mmol) was added and the reaction mixture was stirred at r.t. for ~30 minutes before heating to 60° C. for ~2.5 h. Further triethylamine (216 mg, 2.14 mmol) and formic acid hydrazide [624-84-0] (83 mg, 1.38 mmol) was added and the reaction mixture was stirred at 60° C. for a further ~1 h. The reaction mixture was cooled, diluted with MeCN (20 mL), filtered through a pad of celite and washed with MeCN (3×10 mL). The pale yellow filtrate was concentrated in vacuo to give a tan solid which was dissolved in 5% MeOH/DCM and washed with water (2×) and brine. The mixture was passed through a phase separation cartridge and concentrated in vacuo to give a tan solid which was purified by flash column chromatography on silica (gradient elution with 5-15% MeOH/DCM) followed by further purification by flash column chromatography on silica (gradient elution with 2-15% MeOH/DCM) to afford the title compound (736 mg, 36%) which was freeze-dried from MeCN/water to yield a white powder. $\delta_H$ (300 MHz, DMSO-d$_6$) 11.26 (s, 1H), 8.85 (s, 1H), 8.76 (dd, J 2.7, 0.7 Hz, 1H), 8.42 (s, 1H), 8.17-8.05 (m, 2H), 7.70 (t, J 5.7 Hz, 1H), 7.35-7.24 (m, 1H), 4.62-4.44 (m, 1H), 3.22-2.99 (m, 3H), 2.99-2.80 (m, 3H), 2.35-2.13 (m, 2H), 2.01-1.85 (m, 1H), 1.03-0.90 (m, 1H), 0.90-0.80 (m, 4H), 0.35-0.22 (m, 2H), 0.20-0.08 (m, 2H). LCMS [M+H]$^+$ 478.2, RT 1.385 minutes, 97.5% purity (Method 2). LCMS [M+H]$^+$ 478.2, RT 1.644 minutes, 96.9% purity (Method 3).

Example 125

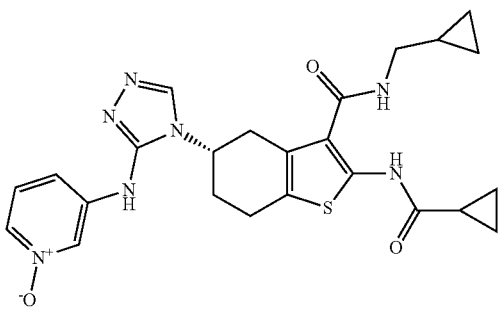

(5S)-2-(Cyclopropanecarbonylamino)-N-(cyclopropylmethyl)-5-[3-[(1-oxidopyridin-1-ium-3-yl)amino]-1,2,4-triazol-4-yl]-4,5,6,7-tetrahydrobenzothiophene-3-carboxamide Example 124 (72 mg, 0.15 mmol) was dissolved in DCM (5 mL) with a few drops of MeOH. m-CPBA [937-14-4] (37 mg, 0.17 mmol) was added and the reaction mixture was stirred at r.t. for ~2 h. Further mCPBA [937-14-4] (17 mg, 0.075 mmol) and the reaction was stirred at r.t. for ~16 h. The reaction mixture was washed with saturated sodium hydrogen carbonate solution and brine before passing through a phase separation cartridge. The filtrate was concentrated in vacuo and the residue was purified by flash column chromatography on silica (gradient elution with 5-25% MeOH/DCM) to afford the title compound (21 mg, 28%) which was freeze-dried from MeCN/water to give a white solid. $\delta_H$ (300 MHz, DMSO-d$_6$) 11.27 (s, 1H), 9.09 (s, 1H), 8.77 (t, J 1.9 Hz, 1H), 8.46 (s, 1H), 7.80 (ddd, J 6.2, 1.7, 0.9 Hz, 1H), 7.67 (t, J 5.6 Hz, 1H), 7.49 (ddd, J 8.6, 2.1, 0.9 Hz, 1H), 7.30 (dd, J 8.6, 6.2 Hz, 1H), 4.51 (br. s, 1H), 3.21-2.77 (m, 6H), 2.36-2.10 (m, 2H), 2.01-1.82 (m, 1H), 1.03-0.72 (m, 5H), 0.36-0.23 (m, 2H), 0.22-0.08 (m, 2H).

Example 126

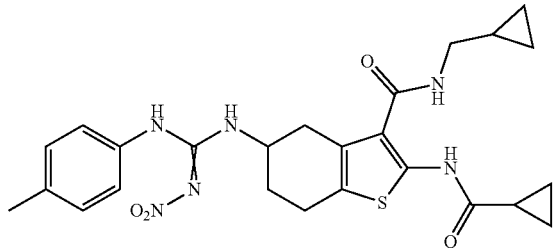 [SMILES: Cc1ccc(NC(=N[N+](=O)[O-])NC2CCc3sc(NC(=O)C4CC4)c(C(=O)NCC4CC4)c3C2)cc1]

2-(cyclopropanecarbonylamino)-N-(cyclopropylmethyl)-5-[[N'-nitro-N-(p-tolyl)carbamimidoyl]amino]-4,5,6,7-tetrahydrobenzothiophene-3-carboxamide A mixture of intermediate 122 (60 mg, 0.16 mmol), intermediate 142 (44 mg, 0.19 mmol) and DIPEA (42.3 µl, 0.24 mmol) in isopropanol (3 mL) was stirred and heated at 80° C. for 3 h in a microwave. The reaction mixture was concentrated in vacuo and the residue was purified by acidic HPLC to afford the title compound (25 mg, 30%) as a white solid. $\delta_H$ (500 MHz, CD$_3$OD) 7.24 (d, J 7.9 Hz, 2H), 7.17 (d, J 8.3 Hz, 2H), 4.33-4.17 (m, 1H), 3.27-3.19 (m, 2H), 3.17-3.08 (m, 1H), 2.93-2.57 (m, 3H), 2.35 (s, 3H), 2.21-2.04 (m, 1H), 1.99-1.86 (m, 1H), 1.84-1.75 (m, 1H), 1.14-1.04 (m, 1H), 1.00-0.91 (m, 4H), 0.56-0.48 (m, 2H), 0.31-0.24 (m, 2H). LCMS [M+H]$^+$ 511.2, RT 3.6 minutes, 98% purity (Method 10).

Example 127

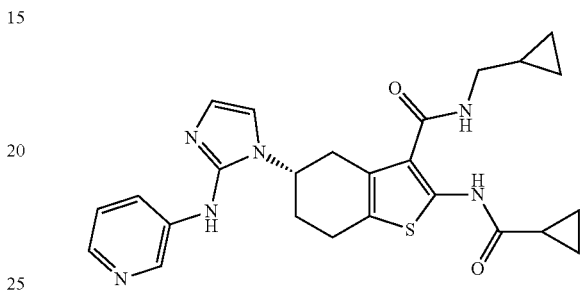

(5S)-2-(Cyclopropanecarbonylamino)-N-(cyclopropylmethyl)-5-[2-(3-pyridylamino)imidazol-1-yl]-4,5,6,7-tetrahydrobenzothiophene-3-carboxamide To a stirred solution of intermediate 141 (222 mg, 0.47 mmol) and 2,2-diethoxyethanamine [645-36-3] (0.21 ml, 1.42 mmol) in DMF (4.5 mL) was added mercury dichloride [7487-94-7] (385 mg, 1.42 mmol). The reaction mixture was stirred at ambient temperature for 5 minutes then triethylamine (0.197 ml, 1.42 mmol) was added. The reaction mixture was heated at 90° C. for 1 h. 4-Methylbenzenesulfonic acid hydrate (1:1) [6192-52-5] (539 mg, 2.84 mmol) was added and heated continued at 90° C. for a further 2.5 h. The reaction mixture was diluted with DCM (40 mL), filtered through a pad of celite, and the filtrate concentrated in vacuo. The residue was diluted with water (20 mL) and extracted with EtOAc (3×20 mL). The organic extracts were combined, washed with water (10 mL) and brine (10 mL), dried (Na$_2$SO$_4$), filtered and the reaction mixture concentrated in vacuo. The residue was purified by flash column chromatography on silica (gradient elution with 1% to 10% MeOH/DCM) to afford the title compound (71.5 mg, 31%) as an off-white solid. $\delta_H$ (500 MHz, DMSO-d$_6$) 11.18 (s, 1H), 8.59 (d, J 2.6 Hz, 1H), 8.48 (s, 1H), 7.99 (dd, J 4.6, 1.4 Hz, 1H), 7.90 (ddd, J 8.4, 2.7, 1.4 Hz, 1H), 7.70 (t, J=5.5 Hz, 1H), 7.20 (dd, J=8.4, 4.6 Hz, 1H), 7.03 (d, J=1.5 Hz, 1H), 6.76 (d, J 1.4 Hz, 1H), 4.57-4.47 (m, 1H), 3.16-2.99 (m, 3H), 2.99-2.90 (m, 1H), 2.89-2.79 (m, 2H), 2.24-2.14 (m, 1H), 2.13-2.05 (m, 1H), 1.96-1.87 (m, 1H), 1.00-0.91 (m, 1H), 0.90-0.82 (m, 4H), 0.37-0.26 (m, 2H), 0.20-0.11 (m, 2H). LCMS: M+H$^+$ 477, RT=1.73 min (97%) (Method 10).

Examples 128 and Example 129

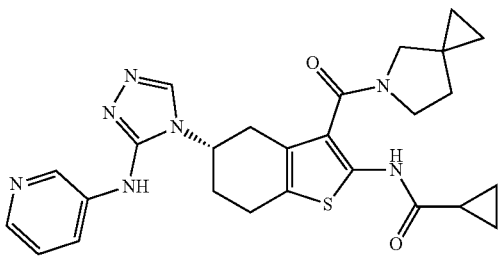

Example 128

N-[(5S)-3-(5-azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide

Example 129

N-[(5R)-3-(5-Azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide Intermediate 145 (208 mg, 73% purity, 0.41 mmol) was purified by Waters XBridge Prep C18 5 uM column to give 100% pure racemic material which was then purified by chiral chromatography (Lux Cellulose-4 21.2×250 mm 5 μm column, flow rate 7.5 mL/min, see SN134028 Chiral analysis file) to afford the two isomers, uncertain of specific stereochemistry. The title compound example 128 (26 mg, 12.5%) was afforded as a white solid and the title compound 129 (26 mg, 12.5%) was afforded as a white solid. Title compound example 128: $\delta_H$ (300 MHz, DMSO-$d_6$) 10.85 (s, 1H), 8.84 (s, 1H), 8.79-8.71 (m, 1H), 8.43 (s, 1H), 8.16-8.05 (m, 2H), 7.35-7.24 (m, 1H), 4.59 (d, J 8.0 Hz, 1H), 3.58 (s, 1H), 3.31 (s, 3H), 2.85 (s, 2H), 2.79-2.59 (m, 1H), 2.27 (s, 2H), 2.16 (s, 1H), 2.00 (s, 1H), 1.75 (s, 2H), 0.83 (d, J=5.0 Hz, 4H), 0.54 (s, 4H). LCMS [M+H]+ 504.2, RT 1.388 minutes (Method 2). LCMS [M+H]+ 504.2, RT 1.609 minutes, (Method 3).

Title compound example 129: $\delta_H$ (300 MHz, DMSO-$d_6$) 10.85 (s, 1H), 8.85 (s, 1H), 8.78-8.70 (m, 1H), 8.43 (s, 1H), 8.15-7.99 (m, 2H), 7.36-7.22 (m, 1H), 4.67-4.51 (m, 1H), 3.76-3.32 (m, 3H), 3.08-2.60 (m, 5H), 2.31-2.05 (m, 2H), 2.05-1.86 (m, 1H), 1.75 (s, 2H), 0.89-0.69 (m, 4H), 0.54 (s, 4H). LCMS [M+H]+ 504.2, RT 1.389 minutes (Method 2). LCMS [M+H]+ 504.2, RT 1.581 minutes, (Method 3).

Example 130

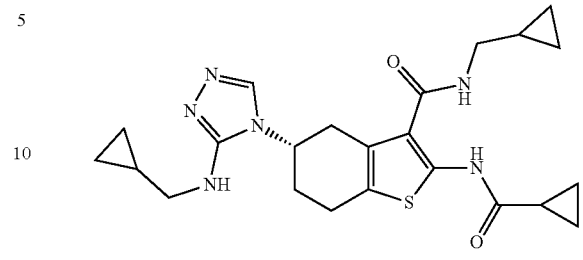

(5S)-2-(Cyclopropanecarbonylamino)-N-(cyclopropylmethyl)-5-[3-(cyclopropylmethylamino)-1,2,4-triazol-4-yl]-4,5,6,7-tetrahydrobenzothiophene-3-carboxamide Intermediate 148 (2.31 g, 4.24 mmol) was dissolved in EtOH (30 mL) and formic acid [64-18-6] (30 mL) was added. The reaction mixture was degassed (2×) and 10% Pd/C (1.2 g, 1.13 mmol) was added. The reaction mixture was stirred at 80° C. for ~2 h. Further 10% Pd/C (1.2 g, 1.13 mmol) was added and the reaction mixture was stirred at 80° C. for ~5 h. Further 10% Pd/C (1.0 g, 0.94 mmol) was added and the mixture was stirred at 80° C. for ~1 h followed by r.t. overnight. Further 10% Pd/C (1.0 g, 0.94 mmol) was added and the mixture was stirred at 80° C. for ~1 h. The mixture was cooled, filtered through a pad of celite, washed with EtOH (4×) and the filtrate was concentrated in vacuo.

The residue was purified by flash column chromatography on silica (gradient elution with 2-15% MeOH/DCM) to afford the crude material which was further purified by flash column chromatography on silica (gradient elution with 0-10% MeOH/DCM) and freeze dried to afford the title compound (720 mg, 37%) as a white solid. $\delta_H$ (300 MHz, DMSO-$d_6$) 11.22 (s, 1H), 8.06 (s, 1H), 7.69 (t, J=5.4 Hz, 1H), 6.09 (t, J=5.7 Hz, 1H), 4.36-4.16 (m, 1H), 3.23-3.00 (m, 5H), 3.00-2.69 (m, 3H), 2.17-2.03 (m, 2H), 2.03-1.77 (m, 1H), 1.20-0.94 (m, 2H), 0.94-0.77 (m, 4H), 0.53-0.31 (m, 4H), 0.28-0.15 (m, 4H).

Example 131

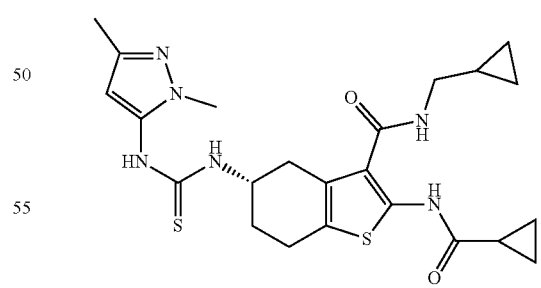

(5S)-2-(Cyclopropanecarbonylamino)-N-(cyclopropylmethyl)-5-[(2,5-dimethylpyrazol-3-yl)carbamothioylamino]-4,5,6,7-tetrahydrobenzothiophene-3-carboxamide Intermediate 117 (2.5 g, 7.5 mmol) was dissolved in DCM (20 mL) and DIPEA (1.50 g, 11 mmol). 5-Isothiocyanato- 1,3-dimethyl-1H-pyrazole [2052446-65-7] (1.50 g, 9.0 mmol) was added and the reaction mixture was stirred at r.t. for 18 h. The mixture was concentrated in vacuo and the residue was purified by flash column chromatography on silica (gradient elution with 50-100% EtOAc/hexane) to afford the title compound (3.54 g, 97%) as a white solid which was freeze dried from MeCN/water. $\delta_H$ (400 MHz, DMSO-$d_6$) 11.09 (s, 1H), 9.11 (s, 1H), 7.95 (d, J 7.8 Hz, 1H), 7.74 (t, J 5.7 Hz, 1H), 5.93 (s, 1H), 4.53 (s, 1H), 3.53 (s, 3H), 3.35 (s, 6H), 3.15 (t, J 6.2 Hz, 2H), 3.05 (dd, J 16.1, 5.1 Hz, 1H), 2.79-2.69 (m, 2H), 2.63 (dd, J 15.9, 7.7 Hz, 1H), 2.10 (s, 3H), 2.06-1.96 (m, 1H), 1.96-1.82 (m, 2H), 1.12-0.95 (m, 1H), 0.92-0.73 (m, 4H), 0.54-0.36 (m, 2H), 0.28-0.16 (m, 2H). LCMS (ES+) [M+H]− 485.0, RT 1.973 minutes, 97.4% purity (Method 2).

Example 132

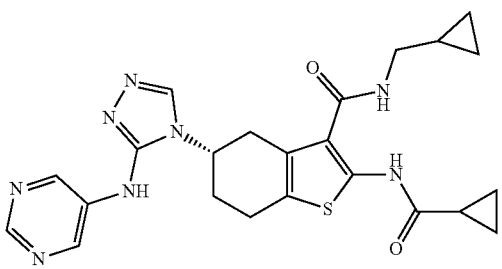 [SMILES: O=C(NCC1CC1)c1c(NC(=O)C2CC2)sc2c1C[C@@H](n1cnnc1Nc1cncnc1)CC2]

(5S)-2-(Cyclopropanecarbonylamino)-N-(cyclopropylmethyl)-5-[3-(pyrimidin-5-ylamino)-1,2,4-triazol-4-yl]-4,5,6,7-tetrahydrobenzothiophene-3-carboxamide Intermediate 150 (141 mg, 0.3 mmol) and formic hydrazide [624-84-0] (54 mg, 0.9 mmol) were dissolved in DMF (3 mL) and mercury dichloride [7487-94-7] (244 mg, 0.9 mmol) was added. The reaction mixture was stirred for 5 minutes and triethylamine (0.12 ml, 0.9 mmol) was added. The reaction mixture was heated at 90° C. for 3 h before diluting with DCM (20 mL) and the reaction mixture was filtered and concentrated in vacuo. The crude residue was extracted with EtOAc (3×20 mL), washed with water (20 mL) and the organic layer was separated and dried (MgSO$_4$), filtered, and the filtrate was concentrated in vacuo to afford the crude product which was purified by flash column chromatography on silica (gradient elution with 0-100% EtOAc then 0-50% MeOH in DCM) to yield the product which was further purified by preparative HPLC to afford the title compound (14 mg, 9.8%) as a white solid. LCMS [M+H]$^+$ 479.16, RT 2.22 minutes, 100.0% purity (Method 10).

Example 133

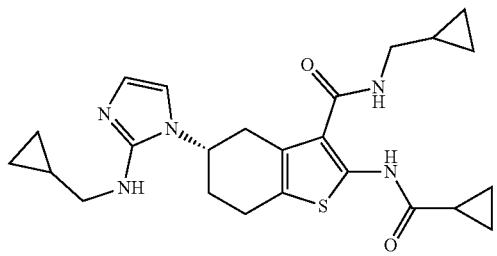

(5S)-2-(Cyclopropanecarbonylamino)-N-(cyclopropylmethyl)-5-[2-(cyclopropylmethylamino)imidazol-1-yl]-4,5,6,7-tetrahydrobenzothiophene-3-carboxamide Intermediate 151 (92%, 412 mg, 0.7 mmol) was dissolved in EtOH (20 mL) and formic acid [624-84-0] (20 mL). 10% Pd/C (50% wet) (5%, 0.74 g, 0.35 mmol) was added and the reaction was heated at 90° C. for 2.5 h. The reaction was heated at 90° C. for a further 18 h before filtering through glass filter paper to remove Pd/C and washed with EtOH (50 mL). The filtrate was concentrated in vacuo and the residue (400 mg) was dissolved in formic acid [624-84-0] (20 mL) and 10% Pd/C (50% wet) (5%, 0.74 g, 0.35 mmol) added. The reaction was heated at 100° C. for 2 h before addition of further 10% Pd/C (50% wet) (740 mg) and the reaction was heated at 110° C. for 75 minutes. The reaction was allowed to cool and filtered through glass filter paper washing though with formic acid [624-84-0] (30 mL). The filtrate was concentrated in vacuo to give an oil, EtOAc (80 mL) was added and the organic layer washed with saturated aqueous sodium hydrogen carbonate solution (2×20 mL), brine, dried (Na$_2$SO$_4$), filtered and concentrated in vacuo to give an oil which was purified by flash column chromatography on silica (gradient elution with 0-10% MeOH in DCM) to give the product (25 mg) as a yellow oil. The product was dissolved in EtOH (0.5 mL) and precipitated by addition of water (a few drops) to give a white solid which was collected by filtration, washing with water. The solid and filtrate were combined in MeCN and concentrated in vacuo. The residue (an oil) was dissolved in MeCN (0.5 mL) and drops of water added until a white precipitate formed, Et$_2$O was added and the mixture concentrated in vacuo. The solid was dried under vacuum at 50° C. to afford the title compound (20 mg, 6%) as a white solid. $\delta_H$ (500 MHz, DMSO-$d_6$) 11.16 (s, 1H), 7.70 (s, 1H), 6.70 (d, J 1.5 Hz, 1H), 6.46 (d, J 1.2 Hz, 1H), 5.71 (s, 1H), 4.34-4.21 (m, 1H), 3.12 (dh, J 19.8, 6.3 Hz, 2H), 3.03 (t, J=6.2 Hz, 2H), 3.01-2.92 (m, 1H), 2.91-2.71 (m, 3H), 2.13-1.99 (m, 2H), 1.97-1.85 (m, 1H), 1.14-1.04 (m, 1H), 1.05-0.95 (m, 1H), 0.92-0.77 (m, 4H), 0.43-0.34 (m, 4H), 0.26-0.10 (m, 4H). LCMS [M+H]$^+$ 454.1, RT 2.21 minutes, 95% purity (Method 10).

Example 134

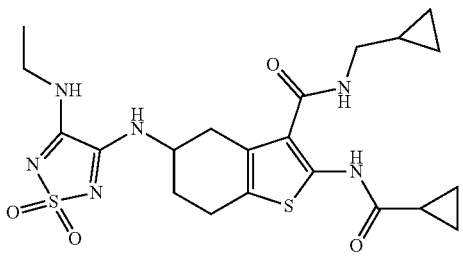 [SMILES: CCNC1=NS(=O)(=O)N=C1NC1CCc2sc(NC(=O)C3CC3)c(C(=O)NCC3CC3)c2C1]

2-(Cyclopropanecarbonylamino)-N-(cyclopropylmethyl)-5-[[4-(ethylamino)-1,1-dioxo-1,2,5-thiadiazol-3-yl]amino]-4,5,6,7-tetrahydrobenzothiophene-3-carboxamide Intermediate 152 (67 mg, 0.13 mmol) was dissolved in EtOH (4 ml). 2M Ethyl amine in THF (2.7 mL, 5.4 mmol) was added and the reaction mixture was stirred at r.t for 3 h. The reaction mixture was concentrated in vacuo and the crude product was purified by preparative HPLC (acidic) to afford the title compound (35 mg, 52%) as a white solid. $\delta_H$ (500 MHz, CD$_3$OD) 4.29-4.22 (m, 1H), 3.44 (q, J 7.3 Hz, 2H), 3.29-3.23 (m, 2H), 3.22-3.17 (m, 1H), 2.88-2.80 (m, 2H), 2.81-2.73 (m, 1H), 2.20-2.10 (m, 2H), 1.85-1.77 (m, 1H), 1.28 (t, J 7.3 Hz, 3H), 1.15-1.05 (m, 1H), 1.02-0.90 (m, 4H), 0.59-0.49 (m, 2H), 0.32-0.22 (m, 2H). LCMS [M+H]$^+$ 493.4, RT 2.71 minutes, 100% purity (Method 10).

Example 135

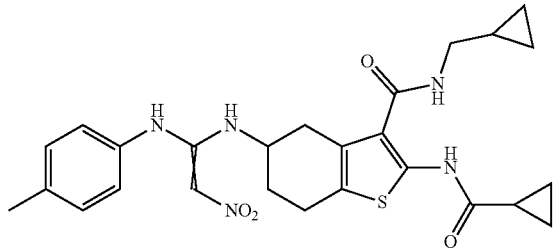 [SMILES: Cc1ccc(NC(=C[N+](=O)[O-])NC2CCc3sc(NC(=O)C4CC4)c(C(=O)NCC4CC4)c3C2)cc1]

2-(cyclopropanecarbonylamino)-N-(cyclopropylmethyl)-5-[[1-(4-methylanilino)-2-nitro-vinyl]amino]-4,5,6,7-tetrahydrobenzothiophene-3-carboxamide Intermediate 122 (50 mg, 0.14 mmol) was dissolved in DCM (4 mL) and DIPEA (53 mg, 0.41 mmol). Intermediate 153 (36 mg, 0.16 mmol), silver nitrate [7761-88-8] (25 mg, 0.15 mmol) and 2-propanol (785 mg, 13.1 mmol) was added. The reaction mixture was stirred at r.t. for ~1.5 h followed by 100° C. in the microwave for 30 minutes. The reaction mixture was concentrated in vacuo and the residue purified by flash column chromatography on silica (gradient elution with 15-100% EtOAc/hexane) to afford the title compound (7.7 mg, 11%) as a yellow solid. $\delta_H$ (400 MHz, DMSO-d$_6$) 11.14 (s, 1H), 10.41 (br.s, 1H), 9.54-9.07 (m, 1H), 7.77 (t, J 5.6 Hz, 1H), 7.27 (d, J 8.0 Hz, 2H), 7.15 (d, J 8.1 Hz, 2H), 6.03 (br.s, 1H), 4.18 (br.s, 1H), 3.26-3.04 (m, 3H), 2.95-2.69 (m, 3H), 2.34 (s, 3H), 2.23-2.11 (m, 1H), 1.96-1.85 (m, 2H), 0.89-0.82 (m, 5H), 0.54-0.31 (m, 2H), 0.31-0.10 (m, 2H).

Example 136

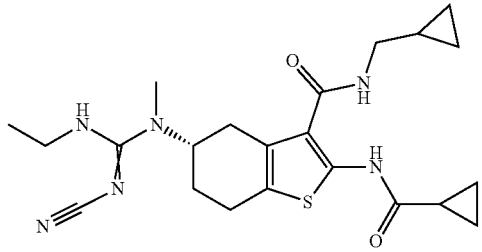 [SMILES: CCNC(=NC#N)N(C)[C@H]1CCc2sc(NC(=O)C3CC3)c(C(=O)NCC3CC3)c2C1]

(5S)-5-[(N'-cyano-N-ethyl-carbamimidoyl)-methylamino]-2-(cyclopropanecarbonylamino)-N-(cyclopropylmethyl)-4,5,6,7-tetrahydrobenzothiophene-3-carboxamide To a solution of intermediate 154 (439 mg, 1.26 mmol) in DMF (6.0 mL) in a pressure tube was added intermediate 155 (239 mg, 1.26 mmol) and DIPEA (490 mg, 3.79 mmol). The reaction mixture was heated to 140° C. for 4 h and then left to stand at r.t. overnight. The reaction mixture was concentrated in vacuo and the residue was dissolved in EtOAc (50 mL) then washed with water (2×20 mL), saturated aqueous sodium hydrogen carbonate solution (2×20 mL) and brine (20 mL). The organic layer was separated, dried (Na$_2$SO$_4$), filtered and the filtrate concentrated in vacuo to give a brown foam (0.638 g). The product was pooled with smaller batches (42 mg), (55 mg) and (127 mg) and evaporated to yield a single batch (0.87 g) which was purified by preparative HPLC (basic) to afford the racemic title compound (373 mg). The product was purified by chiral preparative HPLC to afford the title compound (103 mg, 18%). $\delta_H$ (500 MHz, Chloroform-d) 11.95 (s, 1H), 6.08 (t, J 5.1 Hz, 1H), 4.95 (t, J 4.2 Hz, 1H), 4.49 (tt, J 10.3, 4.8 Hz, 1H), 3.64-3.51 (m, 2H), 3.36-3.20 (m, 2H), 3.06 (dd, J 14.4, 5.1 Hz, 1H), 2.94 (s, 3H), 2.88-2.81 (m, 2H), 2.74-2.64 (m, 1H), 2.04-1.90 (m, 2H), 1.65 (tt, J 8.0, 4.6 Hz, 1H), 1.27 (t, J 7.2 Hz, 3H), 1.13-1.04 (m, 3H), 0.93-0.85 (m, 2H), 0.58-0.52 (m, 2H), 0.31-0.23 (m, 2H). LCMS [M+H]$^+$ 443, RT 2.85 minutes, 100% purity (Method 10).

Example 137

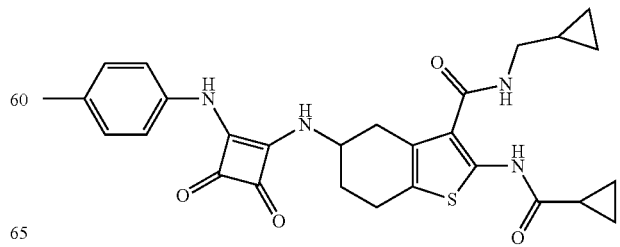

2-(Cyclopropanecarbonylamino)-N-(cyclopropylmethyl)-5-[[2-(4-methylanilino)-3,4-dioxo-cyclobuten-1-yl]amino]-4,5,6,7-tetrahydrobenzothiophene-3-carboxamide Intermediate 136 (95%, 50 mg, 0.1 mmol) was suspended in EtOH (1 mL) and 4-methylaniline [106-49-0] (50 mg, 0.47 mmol) was added. The mixture was heated to 160° C. in the microwave for 2 h. The solvent was removed in vacuo and the residue purified by preparative HPLC (basic) to afford the title compound (16.4 mg, 29%) as a white solid. $\delta_H$ (500 MHz, DMSO-d$_6$) 11.14 (br. s, 1H), 9.55 (br. s, 1H), 7.86-7.66 (m, 2H), 7.32 (d, J 8.0 Hz, 2H), 7.13 (d, J 8.3 Hz, 2H), 4.41 (br. s, 1H), 3.18-3.07 (m, 3H), 2.76 (br. s, 3H), 2.25 (s, 3H), 2.12-2.02 (m, 1H), 2.01-1.86 (m, 2H), 1.08-0.98 (m, 1H), 0.84 (s, 4H), 0.45-0.35 (m, 2H), 0.25-0.17 (m, 2H). LCMS [M+H]$^+$ 519.3, RT 3.32 minutes, 95% purity (Method 10).

Example 138

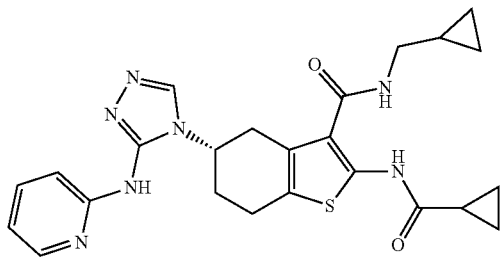 [SMILES: O=C(NCC1CC1)c1c(NC(=O)C2CC2)sc2c1C[C@@H](n1cnnc1Nc1ccccn1)CC2]

(5S)-2-(Cyclopropanecarbonylamino)-N-(cyclopropylmethyl)-5-[3-(2-pyridylamino)-1,2,4-triazo-4-yl]-4,5,6,7-tetrahydrobenzothiophene-3-carboxamide To a stirred solution of intermediate 156 (92 mg, 0.20 mmol) and formic hydrazide [624-84-0] (35 mg, 0.59 mmol) in DMF (2.0 mL) was added mercury dichloride [7487-94-7] (159 mg, 0.59 mmol). The reaction mixture was stirred at r.t. for 5 minutes and triethylamine (0.082 ml, 0.59 mmol) was added. The reaction mixture was heated at 90° C. for 1 h before diluting with DCM (40 mL), filtering over a pad of celite and concentrating the filtrate in vacuo. The residue was diluted with water (20 mL) and extracted with EtOAc (3×20 mL). The organic extracts were combined, washed with water (10 mL) and brine (10 mL), dried (Na$_2$SO$_4$), filtered and the solvent removed in vacuo. The residue was purified by flash column chromatography on silica (gradient elution with 1-10% MeOH in DCM) followed by preparative HPLC (acidic) to afford the title compound (34 mg, 36%) as an off white solid. $\delta_H$ (500 MHz, DMSO-d$_6$) 11.19 (s, 1H), 9.34 (s, 1H), 8.52 (s, 1H), 8.11 (d, J 3.7 Hz, 1H), 7.73 (s, 1H), 7.65 (t, J 7.5 Hz, 1H), 7.40 (d, J 8.2 Hz, 1H), 6.84 (dd, J 6.0, 5.4 Hz, 1H), 4.42 (s, 1H), 3.17-3.03 (m, 3H), 3.01-2.93 (m, 1H), 2.79 (s, 2H), 2.18 (s, 2H), 1.95-1.86 (m, 1H), 1.02-0.91 (m, 1H), 0.89-0.78 (m, 4H), 0.39-0.29 (m, 2H), 0.20-0.13 (m, 2H). LCMS [M+H]$^+$ 478, RT 2.05 minutes, purity 100% (Method 10).

Example 139

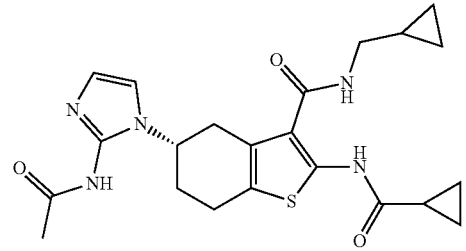 [SMILES: CC(=O)Nc1nccn1[C@H]1CCc2sc(NC(=O)C3CC3)c(C(=O)NCC3CC3)c2C1]

(5S)-5-(2-Acetamidoimidazol-1-yl)-2-(cyclopropanecarbonylamino)-N-(cyclopropylmethyl)-4,5,6,7-tetrahydrobenzothiophene-3-carboxamide Intermediate 158 (30 mg, 0.08 mmol) was dissolved in DCM (3 mL), triethylamine (12.6 µl, 0.09 mmol) was added followed by a solution of 1.41 M acetyl chloride in DCM (53 µL, 1 eq). The reaction was stirred at r.t. for 5 minutes. Further 1.41 M acetyl chloride in DCM (5 µL) was added and the reaction was stirred for 15 minutes. The reaction was quenched with saturated aqueous sodium hydrogen carbonate solution (2 mL), separated and extracted with DCM (2×2 mL). The organic layers were washed with brine (1 mL), dried (Na$_2$SO$_4$), filtered and concentrated in vacuo to yield a clear oil (30 mg) which was purified by silica flash column chromatography (gradient elution with 0-10% MeOH in DCM) followed by silica flash column chromatography (gradient elution 0-3% MeOH in DCM) to give the product. To the product was added Et$_2$O and the mixture was sonicated to give a white solid. The Et$_2$O was removed and the material dried in a vacuum oven to afford the title compound (14 mg, 42%) as a white solid. $\delta_H$ (500 MHz, DMSO-d$_6$) 11.09 (s, 1H), 9.87 (s, 1H), 7.73 (t, J 5.5 Hz, 1H), 7.20 (s, 1H), 6.84 (s, 1H), 4.25-4.09 (m, 1H), 3.11 (t, J 6.0 Hz, 2H), 3.04-2.89 (m, 2H), 2.85-2.72 (m, 2H), 2.18-1.84 (m, 6H), 1.04-0.95 (m, 1H), 0.91-0.75 (m, 4H), 0.38 (d, J 8.0 Hz, 2H), 0.19 (d, J 4.3 Hz, 2H). LCMS [M+H]$^+$ 442.1, RT 1.81 minutes, 100% purity (Method 10).

Example 140

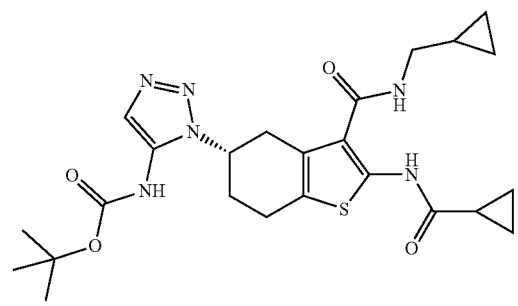 [SMILES: CC(C)(C)OC(=O)Nc1cnnn1[C@H]1CCc2sc(NC(=O)C3CC3)c(C(=O)NCC3CC3)c2C1]

tert-Butyl N-[3-[2-(cyclopropanecarbonylamino)-3-(cyclopropylmethylcarbamoyl)-4,5,6,7-tetrahydrobenzothiophen-5-yl]triazol-4-yl]carbamate Intermediate 161 (40 mg, 0.093 mmol) was suspended in toluene (2 mL) and triethylamine (28 mg, 0.28 mmol, tert-butyl alcohol (15 mg, 0.21 mmol) and diphenylphosphoryl azide [26386-88-9] (77 mg, 0.28 mmol) were added and the mixture was heated at 90° C. for 3 h. The solution was allowed to cool and the solvent removed in vacuo to give the residue which was purified by flash column chromatography on silica (gradient elution with 0-80% EtOAc/iso-hexane) to afford the title compound (26 mg, 56%) as a colourless gum. LCMS (ES+) [M+H]+ 501.2, RT 2.237 minutes, 100.0% purity (Method 2). LCMS (ES+) [M+H]+ 501.2, RT 2.247 minutes, 95.9% purity (Method 3).

Example 141

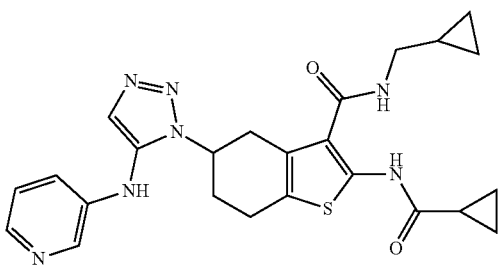 [SMILES: O=C(NCC1CC1)c1c(NC(=O)C2CC2)sc2c1CC(n1nncc1Nc1cccnc1)CC2]

2-(Cyclopropanecarbonylamino)-N-(cyclopropylmethyl)-5-[5-(3-pyridylamino)triazo-1-yl]-4,5,6,7-tetrahydrobenzothiophene-3-carboxamide To a microwave vial was added 2-(dicyclohexylphosphino)-2',4',6'-triisopropylbiphenyl XPhos (1 mg, 0.0021 mmol) and tBuXPhos (0.01 equiv., 0.00015 mmol). A solution of intermediate 162 (6 mg, 0.015 mmol) in tert-butyl alcohol (1.56 g, 20.9 mmol) was added, followed by 3-bromopyridine [626-55-1] (3.08 mg, 0.019 mmol) and potassium tert-butoxide (3.60 mg, 0.031 mmol). The reaction was heated at 85° C. for 3 h. The reaction mixture was cooled and left to stand overnight. The solvent was removed in vacuo and the residue partitioned between water (3 mL) and DCM (5 mL). The organic layer was separated, dried (Na$_2$SO$_4$), filtered and the solvent removed to give a residue which was purified by flash column chromatography on silica (gradient elution with 0-10% MeOH/DCM) to afford the title compound (3.8 mg, 53%) which was freeze-dried to give an off white solid. δ$_H$ (300 MHz, CD$_3$OD) 8.24 (d, J 2.8 Hz, 1H), 8.12-7.97 (m, 1H), 7.65 (s, 1H), 7.45-7.21 (m, 2H), 4.76 (s, 1H), 3.36 (s, 1H), 3.33-3.06 (m, 1H), 2.96 (d, J 7.1 Hz, 2H), 2.66-2.47 (m, 1H), 2.37 (d, J 12.7 Hz, 1H), 1.81 (tt, J 7.7, 4.7 Hz, 1H), 1.30 (s, 2H), 1.10-0.86 (m, 4H), 0.51-0.38 (m, 2H), 0.28-0.16 (m, 2H). LCMS (ES+) [M+Na]+500.167, RT 1.593 minutes, 100.0% purity (Method 2). LCMS (ES+) [M+H]+ 478.196, RT 1.829 minutes (Method 3).

Example 142

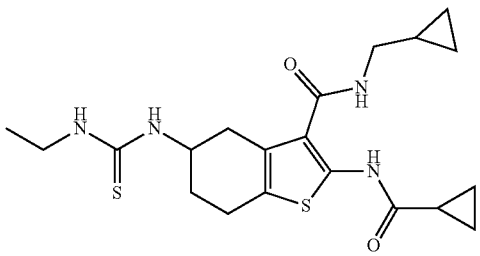 [SMILES: CCNC(=S)NC1CCc2sc(NC(=O)C3CC3)c(C(=O)NCC3CC3)c2C1]

2-(Cyclopropanecarbonylamino)-N-(cyclopropylmethyl)-5-(ethylcarbamothioylamino)-4,5,6,7-tetrahydrobenzothiophene-3-carboxamide Intermediate 122 (50 mg, 0.14 mmol) was dissolved in DCM (5 mL) and DIPEA (26 mg, 0.20 mmol) and ethyl isothiocyanate [542-85-8] (18 mg, 0.21 mmol) were added. The reaction mixture was stirred at r.t. for 16 h. The reaction mixture was directly purified by flash column chromatography on silica (gradient elution with 30-90% EtOAc/hexane) followed by further flash column chromatography on silica (gradient elution with 35-80% EtOAc/hexane). The product was freeze-dried from MeCN/water to afford the title compound (6.5 mg, 11%) as a white solid. δ$_H$ (400 MHz, DMSO-d$_6$) 11.12 (s, 1H), 7.68 (t, J 5.7 Hz, 1H), 7.51-7.16 (m, 2H), 4.42 (s, 1H), 3.45-3.34 (m, 2H), 3.22-3.06 (m, 2H), 3.01 (dd, J 16.1, 5.1 Hz, 1H), 2.75-2.64 (m, 2H), 2.61-2.52 (m, 1H), 2.02-1.87 (m, 2H), 1.86-1.73 (m, 1H), 1.06 (t, J 7.2 Hz, 4H), 0.90-0.76 (m, 4H), 0.47-0.37 (m, 2H), 0.28-0.18 (m, 2H).

Example 143

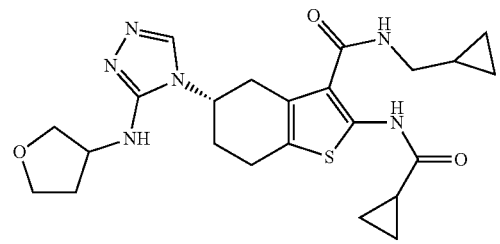 [SMILES: O=C(NCC1CC1)c1c(NC(=O)C2CC2)sc2c1C[C@@H](n1cnnc1NC1CCOC1)CC2]

(5S)-2-(cyclopropanecarbonylamino)-N-(cyclopropylmethyl)-5-[3-[[(3S)-tetrahydrofuran-3-yl]amino]-1,2,4-triazol-4-yl]-4,5,6,7-tetrahydrobenzothiophene-3-carboxamide Intermediate 189 (47.5 mg, 0.07 mmol) was dissolved in DCM (2 mL) and TFA (52 µL, 0.68 mmol) was added. The reaction was stirred at r.t. for 18 h, then 2M sodium carbonate solution was added and the organic phase taken. The aqueous phase was extracted with DCM (4×3 mL) and the organic phases combined, passed through a phase separator and concentrated in vacuo. The residue was suspended in 1:1 DMSO:MeOH (1 mL), filtered and purified via low pH, reverse-phase HPLC to afford a white powder. The powder was dissolved in 1:1 water:MeCN and freeze-dried to afford a white powder, which was subsequently triturated with heptane, then dissolved in acetonitrile and filtered under vacuum. The filtrate was concentrated in vacuo to afford the formic acid salt of the title compound (8.3 mg, 23%) as a colourless glass. δ$_H$ (500 MHz, DMSO-d$_6$) 11.22 (s, 1H), 8.12 (s, 1H), 7.67 (s, 1H), 6.15 (d, J 5.9 Hz, 1H), 4.31-4.23 (m, 1H), 4.23-4.16 (m, 1H), 3.86 (dd, J 9.0, 6.0 Hz, 1H), 3.84-3.78 (m, 1H), 3.77-3.66 (m, 2H), 3.59-3.55 (m, 1H), 3.21-3.13 (m, 1H), 3.11-3.00 (m, 2H), 2.88-2.77 (m, 3H), 2.20-2.06 (m, 3H), 1.94-1.82 (m, 2H), 1.05-0.96 (m, 1H), 0.89-0.81 (m, 4H), 0.41-0.35 (m, 2H), 0.21-0.17 (m, 2H).

LCMS: [M+H]+ 471.1, RT 1.73 minutes, purity 97% (Method 10).

Example 144

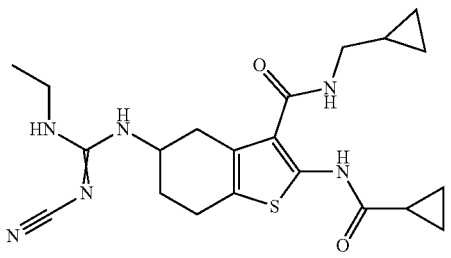 [SMILES: CCNC(=NC#N)NC1CCc2sc(NC(=O)C3CC3)c(C(=O)NCC3CC3)c2C1]

5-[[N'-Cyano-N-ethyl-carbamimidoyl]amino]-2-(cyclopropanecarbonylamino)-N-(cyclopropylmethyl)-4,5,6,7-tetrahydrobenzothiophene-3-carboxamide Intermediate 164 (35 mg, 0.073 mmol) was dissolved in DCM (3 mL) and MeOH (60 mL) and 2.0 M ethylamine in THF (1.62 g, 4.0 mmol, 2.0 mol/L) was added. The reaction mixture was stirred at r.t. for ~5 h before concentrating onto silica. The crude product was purified by flash column chromatography on silica (gradient elution with 35-100% EtOAc/hexane to 20% MeOH/EtOAc) before freeze drying from MeCN/water to afford the title compound (19 mg, 60.5%) as a white solid. $\delta_H$ (400 MHz, DMSO-$d_6$) 11.08 (s, 1H), 7.73 (s, 1H), 6.98 (t, J 5.6 Hz, 1H), 6.74 (d, J 8.1 Hz, 1H), 3.86 (s, 1H), 3.25-3.06 (m, 4H), 2.94 (dd, J 16.0, 5.0 Hz, 1H), 2.80-2.65 (m, 2H), 2.60 (dd, J 15.8, 9.5 Hz, 1H), 2.02-1.65 (m, 3H), 1.10-0.97 (m, 4H), 0.91-0.73 (m, 4H), 0.55-0.31 (m, 2H), 0.31-0.11 (m, 2H).

Examples 145 and 146

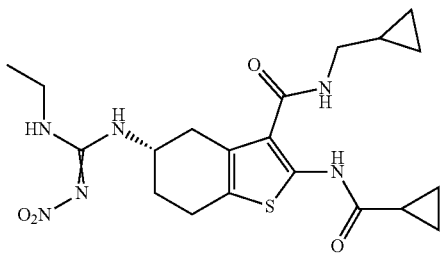

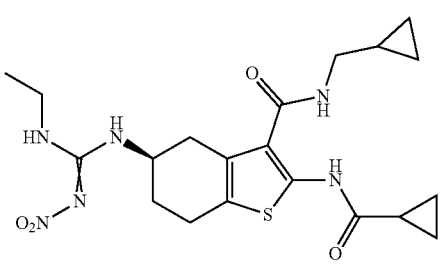

Example 145

(5S)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide

Example 146

(5R)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide To a solution of intermediate 140 (224 mg, 0.50 mmol) in MeOH (6 mL) in a pressure tube was added 2M ethylamine in THF (0.37 mL, 0.75 mmol). The reaction mixture was flushed with nitrogen and warmed to 70° C. with stirring for 60 minutes before leaving to cool to r.t. overnight. The reaction mixture was concentrated in vacuo and re-suspended in MeOH (3 mL). The mixture was transferred to a pressure tube and warmed to 80° C. and then cooling to r.t. The reaction mixture was diluted with ~0.5 mL MeOH and filtered under vacuum and washed with further MeOH (0.5 mL) to afford a colourless solid (0.15 g) which was chirally separated (85% heptane:15% ethanol, Chiral OD-H, 25 cm, 18 ml/min) and freeze dried from 1:1 MeCN/water to afford title compound example 145 and title compound example 146. Each compound was repurified by flash column chromatography on silica (gradient elution with 1:1 heptane/EtOAc (10 mL)-1:3 heptane/EtOAc (20 mL)-neat EtOAc (100 mL)) to afford title compound example 145 and title compound example 146 as colourless solids which were repurified by flash column chromatography on silica [gradient elution with 1:1 heptane/EtOAc (10 mL)-1:3 heptane/EtOAc (20 mL)-neat EtOAc (100 mL)] to afford the title compound example 145 (24 mg, 11%) and title compound example 146 (18 mg, 8%) as colourless solids. Title compound example 145: $\delta_H$ (500 MHz, DMSO-$d_6$) 11.09 (s, 1H), 9.18 (s, 1H), 7.73 (s, 1H), 3.96 (s, 1H), 3.29-3.23 (m, 2H), 3.18 (dt, J 11.5, 6.0 Hz, 1H), 3.10 (dt, J 13.2, 6.1 Hz, 1H), 3.00 (d, J 13.7 Hz, 1H), 2.75 (s, 2H), 2.69-2.62 (m, 1H), 2.01 (d, J 8.8 Hz, 1H), 1.96-1.80 (m, 2H), 1.11 (t, J 7.0 Hz, 3H), 1.03 (dt, J 12.2, 5.5 Hz, 1H), 0.91-0.75 (m, 4H), 0.45-0.36 (m, 2H), 0.22 (q, J 4.8 Hz, 2H). LCMS [M+H]⁺ 449, RT 2.90 minutes, 99% purity (Method 10). Title compound example 146: $\delta_H$ (500 MHz, DMSO-$d_6$) 11.09 (s, 1H), 9.16 (s, 1H), 7.73 (s, 1H), 3.96 (s, 1H), 3.29-3.23 (m, 2H), 3.22-3.14 (m, 1H), 3.14-3.06 (m, 1H), 3.00 (d, J 14.0 Hz, 1H), 2.75 (s, 2H), 2.67 (d, J 10.7 Hz, 1H), 2.00 (s, 1H), 1.96-1.80 (m, 2H), 1.11 (t, J 7.0 Hz, 3H), 1.02 (td, J 12.5, 6.5 Hz, 1H), 0.85 (d, J 7.8 Hz, 4H), 0.46-0.36 (m, 2H), 0.22 (q, J 4.8 Hz, 2H). LCMS [M+H]⁺ 449, RT 2.90 minutes, 100% purity (Method 10).

Example 147

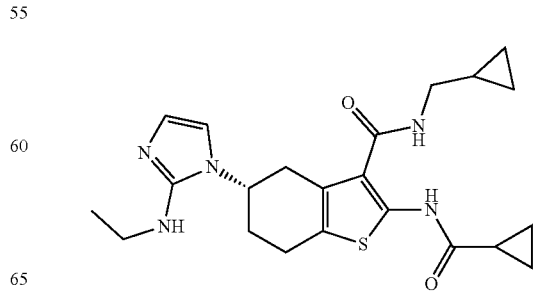

(5S)-2-(Cyclopropanecarbonylamino)-N-(cyclopropylmethyl)-5-[2-(ethylamino)imidazol-1-yl]-4,5,6,7-tetrahydrobenzothiophene-3-carboxamide To a stirred solution of intermediate 167 (235 mg, 0.45 mmol) in a mixture of formic acid [64-18-6](88% purity, 12 mL) and EtOH (12 mL) was added 10% palladium on charcoal (50% wet, 483 mg). The reaction mixture was heated at 90° C. for 5 h. A second aliquot of 10% palladium on charcoal (50% wet, 483 mg) was added and heating at 90° C. was continued for a further 16 h. The reaction mixture was cooled to r.t. and filtered through a pad of celite. The filter cake was extracted with EtOH (20 mL) and formic acid [64-18-6] (20 mL). The filtrate and extracts were combined and the solvent removed in vacuo. The residue was dissolved in EtOAc (50 mL), washed with saturated aqueous sodium hydrogen carbonate (2×10 mL) and brine (10 mL), dried (Na$_2$SO$_4$), filtered and the solvent removed in vacuo. The residue was purified by flash column chromatography on silica (gradient elution with MeOH in DCM 1% to 10%) to afford the title compound (94 mg, 47%) as an off-white solid. δ$_H$ (500 MHz, DMSO-d$_6$) 11.16 (s, 1H), 7.70 (s, 1H), 6.72 (d, J 1.3 Hz, 1H), 6.49 (d, J 1.3 Hz, 1H), 5.67 (s, 1H), 4.23 (dq, J 9.4, 5.0 Hz, 1H), 3.22-3.06 (m, 4H), 2.96 (dd, J 15.3, 4.8 Hz, 1H), 2.87-2.75 (m, 3H), 2.09-1.99 (m, 2H), 1.91 (p, J 6.2 Hz, 1H), 1.12 (t, J 7.1 Hz, 3H), 1.05-0.95 (m, 1H), 0.87-0.82 (m, 4H), 0.41-0.34 (m, 2H), 0.22-0.15 (m, 2H). LCMS: M+H$^+$ 428, RT=1.95 min (97%) (Method 10).

Example 148

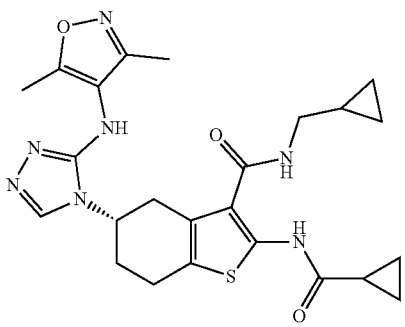 [SMILES: Cc1noc(C)c1Nc1nncn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[3-[(3,5-dimethylisoxazol-4-yl)amino]-1,2,4-triazol-4-yl]-4,5,6,7-tetrahydrobenzothiophene-3-carboxamide Intermediate 168 (250 mg, 0.51 mmol), formic hydrazide [624-84-0] (92 mg, 1.54 mmol) were dissolved in DMF (3 mL). Mercury dichloride [7487-94-7] (418 mg, 1.54 mmol) was added to the reaction mixture. The mixture was stirred for 5 minutes and triethylamine [121-44-8] (0.21 mL, 1.54 mmol) was added to this mixture and the reaction mixture was heated at 90° C. for 1 h. The reaction mixture was diluted with DCM (20 mL), filtered, and the filtrate was concentrated in vacuo. The crude material was extracted with EtOAc (3×20 mL) and washed with water (20 mL). The organic layers were dried (MgSO$_4$), filtered and the filtrate was concentrated to afford the desired product. The crude product was purified by flash column chromatography on silica (gradient elution with 0-100% EtOAc then 0-50% MeOH in DCM) to afford the desired product which was further purified by preparative HPLC (acidic) to afford the title compound (37 mg, 15%). δ$_H$ (500 MHz, DMSO-d$_6$) 11.26 (s, 1H), 8.23 (s, 1H), 7.74 (s, 1H), 7.73-7.70 (m, 1H), 4.38 (d, J 15.5 Hz, 1H), 3.22-3.16 (m, 2H), 3.09-3.05 (m, 1H), 3.01-2.91 (m, 1H), 2.90-2.85 (m, 2H), 2.26 (s, 3H), 2.25-2.20 (m, 2H), 2.06 (s, 3H), 1.95-1.91 (m, 1H), 1.03-0.98 (m, 1H), 0.91-0.77 (m, 4H), 0.42-0.32 (m, 2H), 0.22-0.18 (m, 2H). LCMS [M+H]$^+$ 496.22, RT 2.17 minutes, 99% purity (Method 10).

Example 149

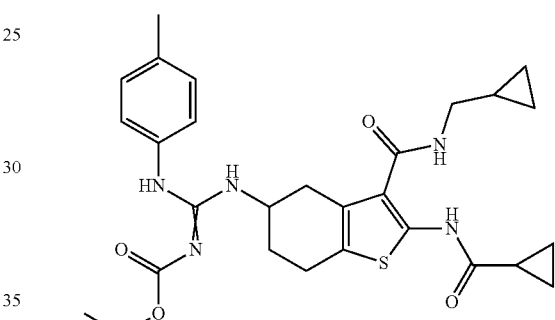

ethyl N-[[[2-(cyclopropanecarbonylamino)-3-(cyclopropylmethylcarbamoyl)-4,5,6,7-tetrahydrobenzothiophen-5-yl]amino]-(4-methylanilino)methylene]carbamate A stirred solution of intermediate 169 (35 mg, 0.14 mmol), intermediate 122 (60 mg, 0.16 mmol) and DIPEA (0.057 mL, 0.32 mmol) in DCM (4 mL) was cooled to 0° C. EDCl [1892-57-5] (37 mg, 0.19 mmol) was added and the solution was stirred at r.t. overnight. The reaction mixture was washed with water (20 mL), brine, dried (Na$_2$SO$_4$), filtered and concentrated in vacuo. The crude residue was purified by acidic preparative HPLC to afford the title compound (50 mg, 57%) as a white solid. δ$_H$ (500 MHz, CD$_3$OD) 7.21 (d, J 8.1 Hz, 2H), 7.12 (d, J 8.1 Hz, 2H), 4.36-4.21 (m, 1H), 4.11 (q, J 7.1 Hz, 2H), 3.29-3.19 (m, 2H), 3.15-3. (m, 1H), 2.90-2.81 (m, 1H), 2.80-2.71 (m, 1H), 2.69-2.55 (m, 1H), 2.34 (s, 3H), 2.17-2.05 (m, 1H), 1.97-1.83 (m, 1H), 1.83-1.75 (m, 1H), 1.25 (t, J 7.1 Hz, 3H), 1.13-1.05 (m, 1H), 1.01-0.91 (m, 4H), 0.58-0.47 (m, 2H), 0.33-0.23 (m, 2H). 2.5% w/w HCOOH, 0.4% w/w DMSO and 0.3% w/w. LCMS [M+H] 538.2, RT 2.58 minutes, 100% purity (Method 10).

Example 150

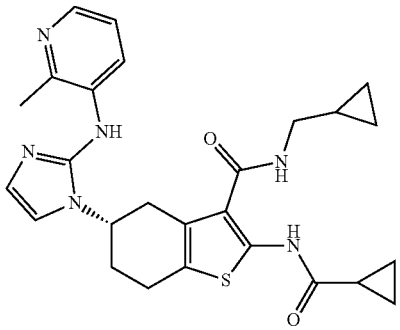 [SMILES: Cc1ncccc1Nc1nccn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[2-[(2-methyl-3-pyridyl)amino]imidazol-1-yl]-4,5,6,7-tetrahydrobenzothiophene-3-carboxamide Intermediate 170 (225 mg, 0.47 mmol) was dissolved in DMF (4.5 mL) and 2,2-diethoxyethanamine [645-36-3] (0.2 mL, 1.4 mmol) was added followed by mercury dichloride [7487-94-7] (380 mg, 1.4 mmol). The reaction was stirred at r.t. for 5 minutes and triethylamine (0.19 mL, 1.4 mmol) was added. The reaction mixture was heated to 90° C. and stirred for 1 h. p-Toluene sulfonic acid (531 mg, 2.79 mmol) was added and the reaction heated at 90° C. for 18 h. The reaction mixture was allowed to cool and filtered through kieselguhr washing with DCM. The filtrate was concentrated in vacuo and the residue was dissolved in EtOAc (60 mL). The organics were washed with water (3×20 mL), dried ($Na_2SO_4$), filtered and concentrated in vacuo. The aqueous layer was basified to pH 9 using 1M aqueous NaOH and extracted with DCM (2×20 mL). The organic phases were dried ($Na_2SO_4$), filtered and concentrated in vacuo to afford a yellow liquid which was purified by flash column chromatography on silica (gradient elution with 0-10% MeOH in DCM) to give a yellow solid which was further purified by preparative HPLC (acidic) and again by flash column chromatography on silica (gradient elution with 0-10% MeOH in DCM) to afford the title compound (35 mg, 15%) as a yellow solid. $\delta_H$ (500 MHz, DMSO-$d_6$) 11.10 (s, 1H), 7.97-7.91 (m, 1H), 7.73 (t, J 5.7 Hz, 1H), 7.55 (s, 1H), 7.26-7.17 (m, 1H), 7.12 (d, J 1.4 Hz, 1H), 7.03 (dd, J 8.1, 4.7 Hz, 1H), 6.81 (d, J 1.3 Hz, 1H), 4.55-4.40 (m, 1H), 3.20-3.02 (m, 2H), 3.03-2.92 (m, 2H), 2.85-2.73 (m, 2H), 2.37 (s, 3H), 2.21-2.01 (m, 2H), 1.96-1.84 (m, 1H), 1.02-0.90 (m, 1H), 0.91-0.76 (m, 4H), 0.40-0.28 (m, 2H), 0.23-0.10 (m, 2H). LCSM [M+H]$^+$ 491.3, RT 1.69 minutes, 97% purity (Method 10).

Example 151

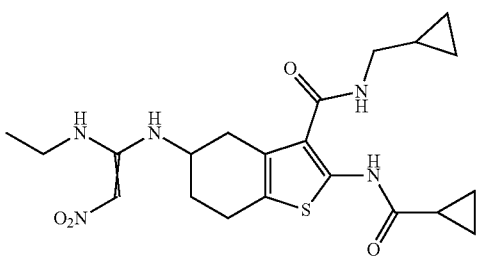 [SMILES: CCNC(=C[N+](=O)[O-])NC1CCc2sc(NC(=O)C3CC3)c(C(=O)NCC3CC3)c2C1]

2-(cyclopropanecarbonylamino)-N-(cyclopropylmethyl)-5-[[1-(ethylamino)-2-nitro-vinyl]amino]-4,5,6,7-tetrahydrobenzothiophene-3-carboxamide Intermediate 122 (50 mg, 0.14 mmol) was dissolved in DCM (4 mL) and DIPEA (53 mg, 0.41 mmol). Intermediate 171 (33 mg, 0.20 mmol), silver nitrate [7761-88-8] (25 mg, 0.15 mmol) and isopropanol (1 mL, 785 mg, 13.06 mmol) were added and the reaction mixture was stirred at 100° C. in the microwave for 60 minutes. Further silver nitrate [7761-88-8] (23 mg, 0.14 mmol) was added and the reaction mixture was stirred at r.t. for ~16 h. Further intermediate 171 (33 mg, 0.20 mmol) in DCM (1 mL) was added and the reaction mixture was stirred at r.t. for ~16 h. Further silver nitrate [7761-88-8] (23 mg, 0.14 mmol) was added and the reaction mixture was stirred at r.t. for 6 days. The reaction mixture was concentrated in vacuo and partitioned between DCM and water. The mixture was passed through a phase separation cartridge and was concentrated in vacuo to give a residue which was purified by flash column chromatography on silica (gradient elution with 15-100% EtOAc/hexane to 0-20% MeOH/EtOAc). The material was freeze dried from MeCN/water to afford the title compound (8.3 mg, 14%) as a yellow solid. LCMS [M+H]$^+$ 448.2, [M+Na]$^+$ 470.0, RT 1.725 minutes, 100.0% purity (Method 2).

Example 152

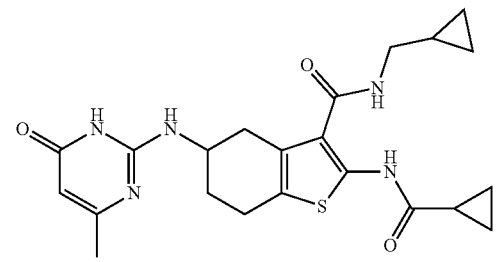 [SMILES: Cc1cc(=O)[nH]c(NC2CCc3sc(NC(=O)C4CC4)c(C(=O)NCC4CC4)c3C2)n1]

2-(Cyclopropanecarbonylamino)-N-(cyclopropylmethyl)-5-[(4-methyl-6-oxo-1H-pyrimidin-2-yl)amino]-4,5,6,7-tetrahydrobenzothiophene-3-carboxamide A mixture of intermediate 122 (40 mg, 0.1 mmoL), 6-methyl-2-(methylsulfanyl)-3,4-dihydropyrimidin-4-one [6328-58-1] (20 mg, 0.13 mmoL) and DIPEA (0.038 mL, 0.22 mmoL) in tert-butanol (2 mL) was heated to 120° C. in a microwave reactor. The reaction mixture was heated at 140° C. for 1 h, followed by 160° C. for 7 h. Further 6-methyl-2-(methylsulfanyl)-3,4-dihydropyrimidin-4-one [6328-58-1] (20 mg, 0.13 mmoL) was added and stirring was continued at 160° C. in the microwave reactor for 16 h. The reaction mixture was concentrated in vacuo and purified by preparative HPLC (acidic) to afford the title compound (2.5 mg, 5%) as a white solid. $\delta_H$ (250 MHz, $CD_3OD$) 5.61 (s, 1H), 4.44-4.31 (m, 1H), 3.27-3.10 (m, 3H), 2.84 (t, J 6.0 Hz, 2H), 2.75-2.60 (m, 1H), 2.15 (s, 3H), 2.13-2.05 (m, 1H), 2.05-1.92 (m, 1H), 1.86-1.70 (m, 1H), 1.16- (m, 1H), 1.03-0.89 (m, 4H), 0.59-0.42 (m, 2H), 0.32-0.21 (m, 2H). LCMS [M+H]$^+$ 442, RT 2.23 minutes, 100% purity (Method 10).

Example 153

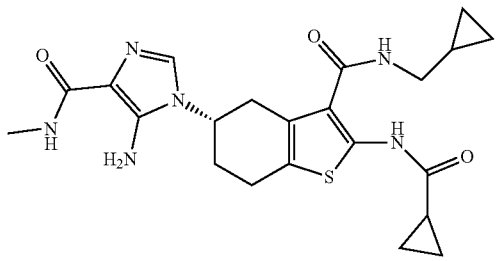 [SMILES: CNC(=O)c1ncn([C@H]2CCc3sc(NC(=O)C4CC4)c(C(=O)NCC4CC4)c3C2)c1N]

5-amino-1-[(5S)-2-cyclopropaneamido-3-[(cyclopropylmethyl)carbamoyl]-4,5,6,7-tetrahydro-1-benzothiophen-5-yl]-N-methyl-1H-imidazole-4-carboxamide Intermediate 48 (92%, 37 mg, 0.3 mmol) was stirred in dry MeCN (3 mL) in a 20 mL pressure tube. Triethylorthoformate (50 µl, 0.3 mmol) was added, the reaction was sealed and heated to 90° C. for 1 hour to give a yellow solution. The reaction was allowed to cool to room temperature and intermediate 117 (100 mg, 0.3 mmol) was added. The solution was stirred for 17 hours to give a light brown suspension. The solid was collected by vacuum filtration and purified by flash column chromatography on silica (gradient elution with 0-100% ethyl acetate in heptane followed by 0-10% MeOH in ethyl acetate) followed by purification by preparative HPLC (H$_2$O, MeCN, formic acid) and then trituration with MeCN then EtOH afford the title compound (40 mg, 29% at 98% UV purity) as a white solid. δ$_H$ (500 MHz, DMSO-d$_6$) δ 11.20 (s, 1H), 7.71 (t, J 5.5 Hz, 1H), 7.34 (q, J 4.7 Hz, 1H), 7.24 (s, 1H), 5.81 (s, 2H), 4.33-4.24 (m, 1H), 3.19-3.04 (m, 3H), 3.01-2.93 (m, 1H), 2.90-2.75 (m, 2H), 2.69 (d, J 4.8 Hz, 3H), 2.24-2.10 (m, 2H), 1.97-1.88 (m, 1H), 1.07-0.96 (m, 1H), 0.91-0.79 (m, 4H), 0.44-0.32 (m, 2H), 0.26-0.15 (m, 2H). LCMS [M+H]$^+$ 457.3, RT 2.21 minutes, 98% purity (Method 10).

Example 154

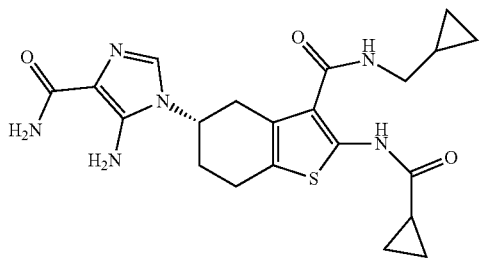 [SMILES: NC(=O)c1ncn([C@H]2CCc3sc(NC(=O)C4CC4)c(C(=O)NCC4CC4)c3C2)c1N]

5-amino-1-[(5S)-2-cyclopropaneamido-3-[(cyclopropylmethyl)carbamoyl]-4,5,6,7-tetrahydro-1-benzothiophen-5-yl]-1H-imidazole-4-carboxamide 2-amino-2-cyanoacetamide (30 mg, 0.3 mmol) was stirred in dry MeCN (3 mL) in a 20 mL pressure tube. Triethylorthoformate (50 µl, 0.3 mmol) was added, the reaction was sealed and heated at 90° C. for 1 hour with stirring. The reaction was allowed to cool to room temperature, intermediate 117 (100 mg, 0.3 mmol) was added and the reaction mixture was stirred at room temperature for 17 hours. The reaction solution was concentrated in vacuo and purified by flash column chromatography on silica (gradient elution using 0-100% ethyl acetate in heptane followed by 0-10% MeOH in ethyl acetate). The material obtained was purified further by preparative HPLC (H$_2$O, MeCN, formic acid) then by flash column chromatography on silica (gradient elution using 0-10% MeOH in DCM). Further purification by reverse phase column chromatography (gradient elution with 10-100% MeCN in water) afforded the title compound (10 mg, 7.5%) as a white solid. δ$_H$ (500 MHz, DMSO-d$_6$) δ 11.21 (s, 1H), 7.71 (s, 1H), 7.23 (s, 1H), 6.75 (s, 1H), 6.61 (s, 1H), 5.87 (s, 2H), 4.37-4.15 (m, 1H), 3.21-3.03 (m, 3H), 3.03-2.92 (m, 1H), 2.90-2.75 (m, 2H), 2.22-2.08 (m, 2H), 1.97-1.87 (m, 1H), 1.07-0.95 (m, 1H), 0.92-0.75 (m, 4H), 0.44-0.34 (m, 2H), 0.26-0.14 (m, 2H). LCMS [M+H]$^+$ 443.3, RT 2.16 minutes, 99% purity (Method 10)

Example 155

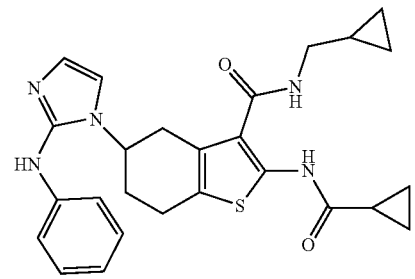 [SMILES: O=C(NCC1CC1)c1c(NC(=O)C2CC2)sc2c1CC(n1ccnc1Nc1ccccc1)CC2]

5-(2-Anilinoimidazol-1-yl)-2-(cyclopropanecarbonylamino)-N-(cyclopropylmethyl)-4,5,6,7-tetrahydrobenzothiophene-3-carboxamide Intermediate 176 (89%, 120 mg, 0.19 mmol) was dissolved in EtOH (5 mL) and a drop of concentrated sulphuric acid was added, followed by 20% Pd(OH)$_2$/C (30 mg, 0.21 mmol). The reaction mixture was stirred at 60° C. under ~7 bar hydrogen for 24 h in a pressure vessel. Additional 20% Pd(OH)$_2$/C (30 mg, 0.21 mmol) was added and the reaction was returned to 60° C. under ~7 bar hydrogen for a further 24 h. The reaction mixture was filtered through a pad of Celite and concentrated in vacuo to give the crude residue which was purified by flash column chromatography on silica (gradient elution with 0-10% MeOH/DCM) followed by preparative HPLC (basic) to afford the title compound (9.5 mg, 10%). δ$_H$ (500 MHz, DMSO-d$_6$) 11.16 (s, 1H), 8.17 (s, 1H), 7.70 (t, J 5.8H 1H), 7.30 (d, J 7.9 Hz, 2H), 7.20-7.12 (m, 2H), 7.01 (d, J 1.5 Hz, 1H), 6.80-6.69 (m, 2H), 4.49 (br. s, 1H), 3.16-3.03 (m, 2H), 3.03-2.90 (m, 2H), 2.87-2.78 (m, 2H), 2.21-2.10 (m, 1H), 2.10-2.03 (m, 1H), 1.96-1.88 (m, 1H), 1.00-0.90 (m, 1H), 0.89-0.80 (m, 4H), 0.35-0.30 (m, 2H), 0.18-0.14 (m, 2H). LCMS (ES+) [M+H]$^+$ 476.1, RT 2.17 minutes, 95% purity (Method 10).

Example 156

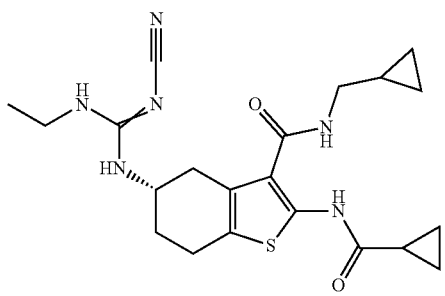 [SMILES: CCNC(=NC#N)N[C@H]1CCc2sc(NC(=O)C3CC3)c(C(=O)NCC3CC3)c2C1]

(5S)-5-[[N'-cyano-N-ethyl-carbamimidoyl]amino]-2-(cyclopropanecarbonylamino)-N-(cyclopropylmethyl)-4,5,6,7-tetrahydrobenzothiophene-3-carboxamide Diphenyl cyanocarbonimidate [79463-77-7] (210 mg, 0.88 mmol) was added to a solution of intermediate 117 (265 mg, 0.79 mmol) in isopropanol (10 mL). The reaction mixture was stirred at r.t. for 1 h. DIPEA (140 μL, 0.8 mmol) was added and the reaction was stirred at r.t. for 1 h. 2M Ethanamine (1 mL) was added, and then solution was stirred at r.t. for 3 days. The solution was heated in the microwave at 100° C. for 2 h. The reaction mixture was concentrated in vacuo and the residue purified by flash column chromatography on silica (EtOAc), followed by further purification by flash column chromatography on silica (gradient elution with 0-5% MeOH/DCM) to afford the title compound (200 mg, 95% purity) as a light yellow foam which was further purified by acid prep-HPLC and freeze dried from 1:1 MeCN/H$_2$O to afford the title compound (120 mg, 35%) as a fluffy white solid. δ$_H$ (500 MHz, DMSO-d$_6$) 11.07 (s, 1H), 7.75-7.67 (m, 1H), 7.01-6.94 (m, 1H), 6.73 (d, J 8.1 Hz, 1H), 3.84 (br. s, 1H), 3.23-3.07 (m, 4H), 2.93 (dd, J 16.0, 4.1 Hz, 1H), 2.75-2.68 (m, 2H), 2.59 (dd, J 15.7, 9.4 Hz, 1H), 1.98-1.87 (m, 2H), 1.86-1.76 (m, 1H), 1.06 (t, J 7.1 Hz, 3H), 1.04-0.98 (m, 1H), 0.88-0.78 (m, 4H), 0.45-0.39 (m, 2H), 0.25-0.20 (m, 2H). LCMS (ES+) [M+H]$^+$ 429.1, RT 2.82 minutes, 99% purity (Method 10).

Example 157

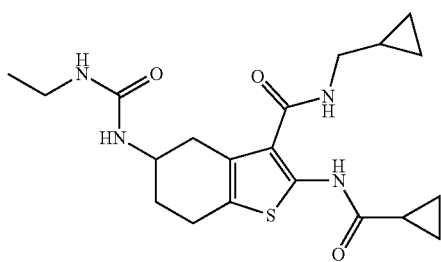

2-(Cyclopropanecarbonylamino)-N-(cyclopropylmethyl)-5-(ethylcarbamoylamino)-4,5,6,7-tetrahydrobenzothiophene-3-carboxamide Intermediate 122 (50 mg, 0.14 mmol) was dissolved in DCM (5 mL) and DIPEA (26 mg, 0.20 mmol). Ethyl isocyanate [109-90-0] (15 mg, 0.20 mmol) was added and the reaction mixture was stirred at r.t. for ~16 h. The crude residue was pre-adsorbed onto silica from DCM/MeOH and the material was purified by flash column chromatography on silica (gradient elution with 30-100% EtOAc/hexane to 0-20% MeOH/EtOAc) to give the product which was freeze-dried from MeCN/water to afford the title compound (14 mg, 25%) as a white solid. δ$_H$ (400 MHz, DMSO-d$_6$) 11.13 (s, 1H), 7.66 (t, J 5.6 Hz, 1H), 5.87 (d, J 7.7 Hz, 1H), 5.74 (t, J 5.6 Hz, 1H), 3.91-3.75 (m, 1H), 3.14 (td, J 7.0, 2.6 Hz, 2H), 3.01 (qd, J 7.1, 5.5 Hz, 2H), 2.91 (dd, J 16.1, 5.1 Hz, 1H), 2.77-2.61 (m, 2H), 2.47-2.40 (m, 1H), 2.01-1.77 (m, 2H), 1.77-1.57 (m, 1H), 1.11-1.00 (m, 1H), 0.98 (t, J 7.2 Hz, 3H), 0.90-0.78 (m, 4H), 0.51-0.31 (m, 2H), 0.27-0.15 (m, 2H).

Example 158

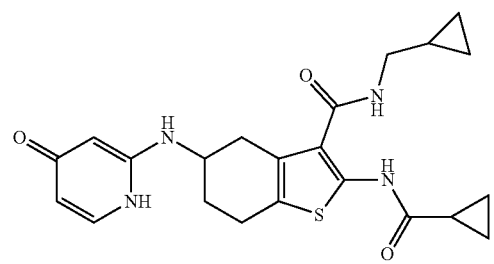

2-(Cyclopropanecarbonylamino)-N-(cyclopropylmethyl)-5-[(4-oxo-1H-pyridin-2-yl)amino]-4,5,6,7-tetrahydrobenzothiophene-3-carboxamide Intermediate 122 (46 mg, 0.12 mmol) and 2-chloro-4-hydroxypyridine [17368-12-6] (23 mg, 0.17 mmol) were dissolved in tert-butyl alcohol (0.4 mL) and DIPEA (60 μL, 0.35 mmol) was added. The reaction was sealed and heated in microwave at 160° C. for 36 h. The reaction mixture was concentrated in vacuo to give the crude residue as a red oil which was purified by flash column chromatography on silica (gradient elution with 0-20% MeOH/DCM) to give the crude product. The crude material was repurified by flash column chromatography on silica (gradient elution with 0-30% MeOH/DCM) to afford the product which was repurified by preparative HPLC to afford the title compound (2 mg, 3.8%) as an off white solid. LCMS [M+H]$^+$ 427.21, RT 1.26 minutes, 98.53% (Method 24). LCMS [M+H]$^+$ 427.21, RT 1.19 minutes, 98.94% (Method 25).

Example 159

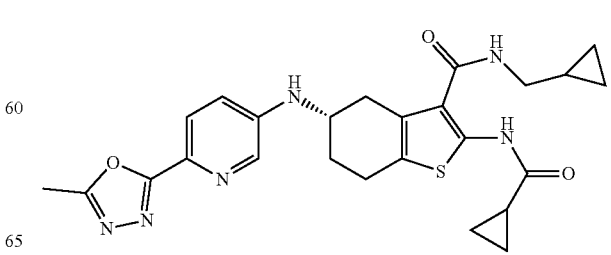

(5S)-2-(cyclopropanecarbonylamino)-N-(cyclopropylmethyl)-5-[[6-(5-methyl-1,3,4-oxadiazol-2-yl)-3-pyridyl]amino]-4,5,6,7-tetrahydrobenzothiophene-3-carboxamide Dry dioxane (3 mL) and dry $^t$BuOH (1.5 mL) were added to intermediate 117 (100 mg, 0.3 mmol), intermediate 204 (101 mg, 0.42 mmol), NaO$^t$Bu (86 mg, 0.9 mmol) and $^t$BuXPhos Pd G3 (36 mg, 0.04 mmol). The reaction mixture was sonicated for 1 minute and stirred at room temperature for 2 hours to give a light brown suspension. The reaction was quenched with saturated aq. NH$_4$Cl (20 mL) and extracted with DCM (2×20 mL). The organics were dried over sodium sulfate and concentrated in vacuo followed by purification by flash chromatography on silica (elution gradient using 0-100% ethyl acetate in heptane followed by 0-10% MeOH in ethyl acetate) then further purification by preparative HPLC (H$_2$O, MeCN, formic acid) to afford the title compound (42 mg, 28%) as an off white solid. $\delta_H$ (500 MHz, DMSO-d$_6$) δ 11.05 (s, 1H), 8.15 (d, J 2.7 Hz, 1H), 7.83 (s, 1H), 7.75 (s, 1H), 7.15 (dd, J 8.8, 2.8 Hz, 1H), 6.73 (d, J 7.7 Hz, 1H), 3.86-3.74 (m, 1H), 3.17-3.04 (m, 3H), 2.84-2.73 (m, 2H), 2.61-2.55 (m, 1H), 2.54 (s, 3H), 2.12-2.04 (m, 1H), 1.95-1.88 (m, 1H), 1.81-1.71 (m, 1H), 1.05-0.94 (m, 1H), 0.88-0.79 (m, 4H), 0.40-0.31 (m, 2H), 0.24-0.12 (m, 2H). LCMS [M+H]$^+$ 493.3, RT 3.00 minutes, 100% purity (Method 10)

Example 160

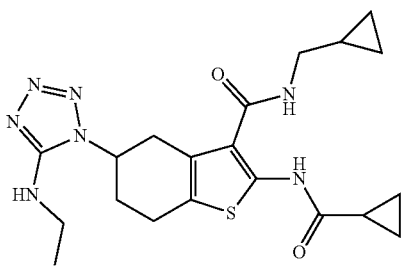

2-(Cyclopropanecarbonylamino)-N-(cyclopropylmethyl)-5-[5-(ethylamino)tetrazol-1-yl]-4,5,6,7-tetrahydrobenzothiophene-3-carboxamide Example 142 (150 mg, 0.36 mmol) was added to a stirred solution of mercury dichloride [7487-94-7](290 mg, 1.08 mmol) and triethylamine (0.14 ml, 1.08 mmol) in DMF (4 mL). The reaction mixture was stirred for 5 minutes and sodium azide [26628-22-8] (70 mg, 1.06 mmol) was slowly added to the reaction mixture with continued stirring for 1 h at r.t. The reaction mixture was quenched with sodium hydrogen carbonate solution (10 mL) and the aqueous layer was extracted with EtOAc (3×20 mL). The organic phases were dried (MgSO$_4$), filtered and the filtrate concentrated in vacuo to yield the crude residue which was purified by preparative HPLC (acidic) to afford the title compound (22 mg, 14%) as a white solid. $^1$H NMR (500 MHz, Chloroform-d) δ 11.95 (s, 1H), 5.76 (s, 1H), 4.28-4.23 (m, 2H), 3.60-3.55 (m, 2H), 3.38-3.27 (m, 2H), 3.27-3.18 (m, 1H), 3.18-3.13 (m, 1H), 2.99-2.93 (m, 2H), 2.51-2.38 (m, 1H), 2.34-2.29 (m, 1H), 1.69-1.61 (m, 1H), 1.33 (t, J 7.2 Hz, 3H), 1.14-1.08 (m, 2H), 1.06-1.02 (m, 1H), 0.96-0.89 (m, 2H), 0.58-0.51 (m, 2H), 0.28-0.21 (m, 2H). LCMS [M+H]$^+$ 430.13, RT 2.87 minutes, 99% purity (Method 10).

Example 161

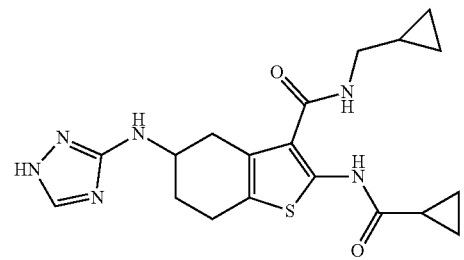

2-(Cyclopropanecarbonylamino)-N-(cyclopropylmethyl)-5-(1H-1,2,4-triazol-3-ylamino)-4,5,6,7-tetrahydrobenzothiophene-3-carboxamide To a mixture of intermediate 62 (70 mg, 0.21 mmol) and 1H-1,2,4-triazol-3-amine [61-82-5] (17.7 mg, 0.21 mmol) in acetic acid (3 mL) was gradually added sodium triacetoxyborohydride [56553-60-7](67 mg, 0.31 mmol) whilst cooling in ice. The reaction mixture was stirred at r.t. for 16 h and the reaction mixture was diluted with DCM and washed with saturated sodium bicarbonate. The organic phase was dried (MgSO$_4$), filtered and concentrated in vacuo to give the crude residue which was purified by preparative HPLC (acidic) to afford the title compound (8 mg, 9%) as white solid. $\delta_H$ (500 MHz, CD$_3$OD) 7.64 (s, 1H), 3.94-3.84 (m, 1H), 3.27-3.16 (m, 3H), 2.89-2.79 (m, 2H), 2.65 (dd, J 15.7, 8.4 Hz, 1H), 2.23-2.13 (m, 1H), 1.95-1.84 (m, 1H), 1.83-1.74 (m, 1H), 1.12-1.03 (m, 1H), 1.01-0.91 (m, 4H), 0.53-0.47 (m, 2H), 0.28-0.22 (m, 2H). LCMS [M+H]$^+$ 401.2, RT 1.87 minutes, 98% purity (Method 10).

Example 162

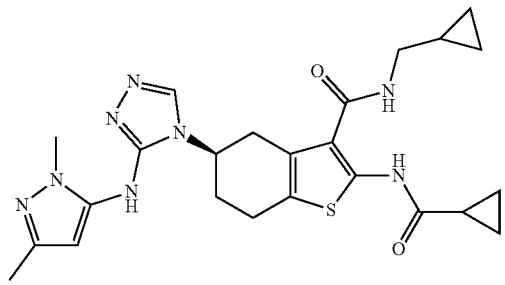

(5R)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide To a stirred solution of intermediate 179 (3.4 g, 7.0 mmol) in DMF (35 mL) was added formic acid hydrazide [624-84-0] (1.4 g, 21 mmol) followed by mercuric chloride [7487-94-7] (3.8 g, 14 mmol). The mixture was stirred for 10 minutes at r.t. before the addition of triethylamine (2.9 mL, 21 mmol). The reaction mixture was stirred at 80° C. for 4 h and the reaction mixture was cooled to r.t. The mixture was diluted with MeCN (35 mL), filtered through a pad of celite and washed with MeCN (35 mL×3). The filtrate was diluted with DCM (70 mL), washed with water (70 mL×2), brine (70 mL), dried ($Na_2SO_4$), filtered and concentrated in vacuo. To the resulting residue was added water (70 mL) and the precipitated solid filtered, washed with water (70 mL×3) and dried in vacuo to give crude product (5.9 g) as a beige solid. The solid was dissolved in DCM (20 mL), passed through a phase separator and purified by flash column chromatography on silica (gradient elution with 0% to 15% MeOH in DCM) to afford the product (960 mg) as a yellow foam which was further purified by reverse phase chromatography on silica (gradient elution with 0 to 100% MeCN [containing 0.1% ammonia] in water [containing 0.1% ammonia]) to give the product fractions which were diluted with DCM. The aqueous phase was separated, extracted with 10% MeOH in DCM (2×) and the combined organic phases were passed through a phase separator and concentrated in vacuo to afford the product (625 mg) as a pale green solid. The crude product was dissolved in MeOH (20 mL) and the resulting pale green solution was treated with QuadraSil methylthiourea (1 g). The mixture was heated at 40° C. for 4 h and a few drops of water were added followed by further QuadraSil methylthiourea (0.5 g). The mixture was heated at 40° C. for 3 h before cooling to r.t. The cooled solution was filtered through celite, washed with MeOH (20 mL×3) and the filtrate concentrated in vacuo to give the product which was further purified by flash column chromatography on silica (gradient elution with 0% to 15% MeOH in DCM) to afford the title compound (566 mg, 16%) as a white solid. $\delta_H$ (300 MHz, DMSO-$d_6$) 11.74 (s, 0.3H), 11.22 (m, 1H), 8.43 (s, 0.7H), 8.34 (s, 0.7H), 8.12 (s, 0.3H), 7.72 (t, J 6.1 Hz, 1H), 5.89 (s, 0.7H), 5.70 (s, 0.3H), 4.53-4.30 (m, 1H), 3.51 (m, 3H), 3.25-3.05 (m, 3H), 3.05-2.90 (m, 1H), 2.83 (m, 2H), 2.33-2.13 (m, 2H), 2.06 (m, 3H), 1.93 (p, J 6.3 Hz, 1H), 1.09-0.92 (m, 1H), 0.90-0.77 (m, 4H), 0.36 (ddd, J 8.0, 4.0, 1.7 Hz, 2H), 0.24-0.13 (m, 2H), compound partially rotameric. LCMS (ES+) [M+H]$^+$ 495.0, RT 1.643 minutes, 100.0% purity (Method 3).

Example 163

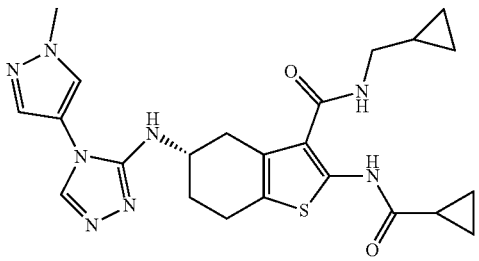

(5S)-2-(Cyclopropanecarbonylamino)-N-(cyclopropylmethyl)-5-[[4-(1-methylpyrazol-4-yl)-1,2,4-triazol-3-yl]amino]-4,5,6,7-tetrahydrobenzothiophene-3-carboxamide Intermediate 180 (77%, 274 mg, 0.45 mmol) and formic hydrazide [624-84-0] (80 mg, 1.34 mmol) were dissolved in DMF (3 mL). Mercury dichloride [7487-94-7] (364 mg, 1.34 mmol) was added and the reaction mixture was stirred for 5 minutes. Triethylamine (0.19 ml, 1.34 mmol) was added to the reaction mixture, which was stirred for 1 h at 90° C. The reaction mixture was diluted with DCM (20 mL), filtered, and the filtrate was concentrated in vacuo and the crude product was extracted with EtOAc (3×20 mL) and washed with water (20 mL). The organic phases were dried (MgSO$_4$), filtered and concentrated in vacuo to afford the product which was purified by flash column chromatography on silica (gradient elution with 0-100% EtOAc in DCM followed by 0-50% MeOH in DCM). The product was further purified twice by preparative HPLC to afford the title compound (50 mg, 23%) as a white solid. $\delta_H$ (500 MHz, DMSO-$d_6$) 11.01 (s, 1H), 8.08 (s, 1H), 8.07 (s, 1H), 7.70 (s, 1H), 7.65 (s, 1H), 5.71 (d, J 7.0 Hz, 1H), 3.87 (s, 3H), 3.83-3.80 (m, 1H), 3.15-2.99 (m, 3H), 2.75-2.68 (m, 2H), 2.61 (dd, J 16.0, 9.3 Hz, 1H), 2.21-2.02 (m, 1H), 1.97-1.63 (m, 2H), 1.03-0.96 (m, 1H), 0.90-0.73 (m, 4H), 0.47-0.30 (m, 2H), 0.22-0.19 (m, 2H). LCMS [M+H]$^+$ 481.24, RT 4.08 minutes, 98% purity (Method 22).

Example 164

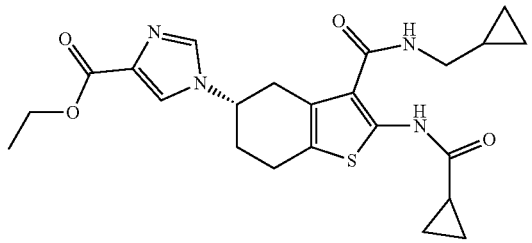

ethyl 1-[(5S)-2-cyclopropaneamido-3-[(cyclopropylmethyl)carbamoyl]-4,5,6,7-tetrahydro-1-benzothiophen-5-yl]-1H-imidazole-4-carboxylate Intermediate 117 (100 mg, 0.3 mmol) and intermediate 24 (50 mg, 0.3 mmol) were heated in "BuOH (1 mL) in a sealed tube with stirring at 70° C. for 1.5 hours then at 120° C. for 17 hours with stirring. Reaction was allowed to cool to room temperature and purified by SCX column (2 g, washed with MeOH and eluted with 3M NH$_3$ in MeOH). The brown residue obtained was purified further by preparative HPLC (H$_2$O, MeCN, NH$_4$OH) to afford the title compound (5 mg, 3% at 85% purity) as a yellow solid. $\delta_H$ (500 MHz, Methanol-d4) δ 7.95 (s, 1H), 7.87 (s, 1H), 4.68-4.59 (m, 1H), 4.32 (q, J 7.1 Hz, 2H), 3.29-3.22 (m, 2H), 3.21-3.10 (m, 2H), 3.01-2.80 (m, 2H), 2.38-2.22 (m, 2H), 1.85-1.73 (m, 1H), 1.35 (t, J 7.1 Hz, 3H), 1.13-1.03 (m, 1H), 1.03-0.96 (m, 2H), 0.96-0.88 (m, 2H), 0.53-0.43 (m, 2H), 0.27-0.21 (m, 2H). LCMS [M+H]$^+$ 457.2, RT 2.83 minutes, 93% purity (Method 10).

Example 165

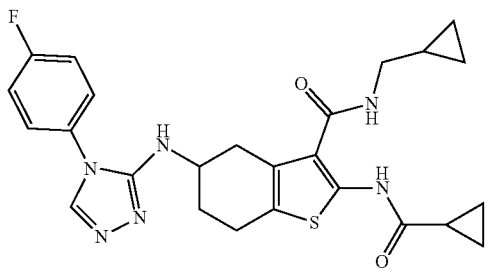

2-(Cyclopropanecarbonylamino)-N-(cyclopropylmethyl)-5-[[4-(4-fluorophenyl)-1,2,4-triazol-3-yl]amino]-4,5,6,7-tetrahydrobenzothiophene-3-carboxamide Intermediate 185 (167 mg, 0.34 mmol) and formic hydrazide [624-84-0] (62 mg, 1.03 mmol) were dissolved in DMF (3 mL). Mercury dichloride [7487-94-7] (280 mg, 1.03 mmol) was added to the reaction mixture which was stirred for 5 minutes. Triethylamine (0.12 ml, 0.87 mmol) was added to this mixture which was heated at 90° C. for 1 h. The reaction mixture was diluted with DCM (20 mL), filtered, and the filtrate was concentrated in vacuo to give the crude residue which was extracted with EtOAc (3×20 mL) and washed with water (20 mL). The organic phases were dried (MgSO$_4$), filtered and the filtrate was concentrated in vacuo to afford the product which was purified by preparative HPLC (basic) to afford the title compound (0.018 g, 11%) as a white solid. δ$_H$ (500 MHz, Methylene Chloride-d$_2$) 12.06 (s, 1H), 7.83 (s, 1H), 7.35-7.30 (m, 2H), 7.27-7.18 (m, 2H), 5.98 (s, 1H), 4.29-4.24 (m, 1H), 3.96 (d, J 7.4 Hz, 1H), 3.29 (dd, J 14.7, 4.7 Hz, 1H), 3.24 (dd, J 7.0, 5.5 Hz, 2H), 2.88-2.2.70 (m, 3H), 2.19-2.13 (m, 1H), 2.04-1.93 (m, 1H), 1.67-1.62 (m, 1H), 1.09-0.98 (m, 3H), 0.93-0.85 (m, 2H), 0.57-0.47 (m, 2H), 0.28-0.20 (m, 2H). LCMS [M+H]$^+$ 495, RT 2.39 minutes, 100% purity (Method 10).

Example 166

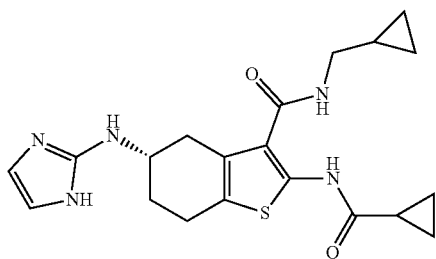

(5S)-2-(Cyclopropanecarbonylamino)-N-(cyclopropylmethyl)-5-(1H-imidazol-2-ylamino)-4,5,6,7-tetrahydrobenzothiophene-3-carboxamide Intermediate 186 (194 mg, 0.49 mmol) was stirred in DMF (4.5 mL) and 2,2-diethoxyethanamine [645-36-3] (0.22 mL, 1.48 mmol) was added followed by mercury dichloride [7487-94-7] (403 mg, 1.48 mmol). The reaction mixture was stirred at r.t. for 5 minutes and triethylamine (0.21 mL, 1.48 mmol) was added. The reaction was heated at 90° C. whilst stirring for 2 h. 4-Methylbenzene-1-sulfonic acid hydrate (PTSA hydrate) [6192-52-5] (564 mg, 2.97 mmol) was added and the reaction mixture was stirred at 90° C. for 20 h. The mixture was diluted with DCM (10 mL) and filtered through kieselguhr washing with DCM. The filtrate was concentrated in vacuo and the orange residue was dissolved in EtOAc (100 mL), washed with water (3×20 mL) and 5% aqueous lithium chloride (20 mL). The organic phases were dried (Na$_2$SO$_4$), filtered and concentrated in vacuo to give an orange oil. The aqueous layer was basified to pH 9 using 1M aqueous NaOH solution and was extracted with EtOAc (100 mL). The organic phases were washed with water (2×20 mL), 5% aqueous lithium chloride solution (20 mL), dried (Na$_2$SO$_4$), filtered and combined with the initial extracted material. The combined organic phases were concentrated in vacuo to afford the crude product which was purified by flash column chromatography on silica (gradient elution with 0-10% MeOH in DCM) to afford a brown solid (50 mg) which was further purified by preparative HPLC (basic) to afford the title compound (14.4 mg, 6%) as a white solid. δ$_H$ (500 MHz, DMSO-d$_6$) 11.09 (s, 1H), 10.18 (s, 1H), 7.66 (s, 1H), 6.47 (s, 2H), 5.55 (d, J 7.7 Hz, 1H), 3.79-3.70 (m, 1H), 3.11 (hept, J 6.7, 6.0 Hz, 2H), 3.03 (dd, J 15.9, 4.4 Hz, 1H), 2.76-2.66 (m, 2H), 2.59-2.53 (m, 1H), 2.12-2.00 (m, 1H), 1.90 (p, J 6.3 Hz, 1H), 1.82-1.62 (m, 1H), 1.09-0.92 (m, 1H), 0.89-0.76 (m, 4H), 0.44-0.32 (m, 2H), 0.20 (q, J 5.2 Hz, 2H).

Example 167

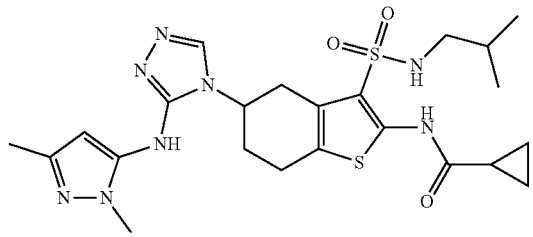

N-[3-(isopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide Intermediate 173 (200 mg, 0.3812 mmol) was dissolved in N,N-dimethylformamide (4 mL) and formic acid hydrazide (70 mg, 0.165 mmol) was added followed by mercuric chloride (156 mg mg, 0.571 mmol) and after 15 min, triethylamine (0.160 mL, 1.15 mmol). Heated at 65° C. with a condenser overnight. Volatiles and DMF were evaporated in vacuo. The residue was diluted with MeCN (20 mL) and filtered through a pad of celite. MeCN was added to wash through celite and resulting clear yellow solution was concentrated in vacuo to give a yellow oil. This oil was re-dissolved in MeOH/DCM, added silica to it, and dry-loaded on column for purification (no aqueous wash). The crude product was purified by flash column chromatography on silica (gradient elution with 25 g SNAP-Ultra, Isolera, MeOH/DCM, 0 to 10% in MeOH) to afford the title compound as white solid. (60 mg, 0.112 mmol, 29.55% Yield).

1H NMR (300 MHz, Methanol-d₄) δ 8.26 (s, 1H), 5.93 (s, 2H), 4.55 (s, 1H), 3.66 (s, 1H), 3.58-3.46 (m, 1H), 2.95 (d, J=12.5 Hz, 2H), 2.71 (d, J=6.9 Hz, 1H), 2.35 (d, J=5.0 Hz, 1H), 2.21 (s, 1H), 1.91-1.64 (m, 1H), 1.34-1.14 (m, 1H), 1.29-1.38 (m, 10H), 1.19-0.97 (m, 3H), 0.89 (dd, J=6.7, 1.0 Hz, 6H). LCMS [M+H]⁺ 533.0, RT 1.82 minutes (Method 26). LCMS [M+H]⁺ 533.0, RT 1.84 minutes, (Method 27).

Example 168

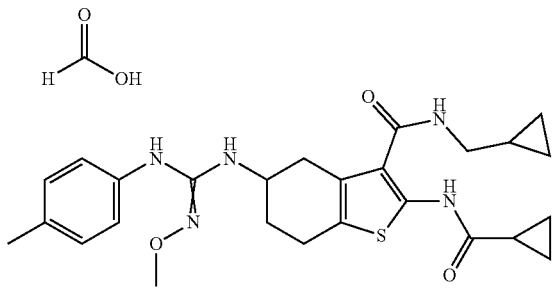

2-(Cyclopropanecarbonylamino)-N-(cyclopropylmethyl)-5-[[N'-methoxy-N-(p-tolyl)carbamimidoyl]amino]-4,5,6,7-tetrahydrobenzothiophene-3-carboxamide A stirred solution of intermediate 190 (30 mg, 0.15 mmol), intermediate 122 (57 mg, 0.15 mmol) and DIPEA (0.053 ml, 0.30 mmol) in DCM (4 mL) was cooled to 0° C. EDCl [1892-57-5] (35 mg, 0.18 mmol) was added and the solution was stirred at r.t. overnight. The reaction mixture was washed with water (20 mL), brine and dried (Na₂SO₄). The mixture was filtered and concentrated in vacuo and the crude product was purified by preparative HPLC (acidic) to afford the title compound (40 mg, 53%) as a white solid. δ_H (500 MHz, CD₃OD) 8.37 (s, 1H), 7.13 (d, J 8.3 Hz, 2H), 7.08 (d, J 8.3 Hz, 2H), 3.87-3.77 (m, 1H), 3.70 (s, 3H), 3.28-3.18 (m, 2H), 3.05 (dd, J 15.5, 5.0 Hz, 1H), 2.83-2.73 (m, 2H), 2.71-2.64 (m, 1H), 2.30 (s, 3H), 2.15-2.06 (m, 1H), 1.93-1.84 (m, 1H), 1.83-1.75 (m, 1H), 1.14-1.04 (m, 1H), 1.00-0.90 (m, 4H), 0.57-0.50 (m, 2H), 0.31-0 (m, 2H). 5.1% w/w HCOOH present (Formate salt with stoichiometry of 0.6). LCMS [M+H]⁺ 496.2, RT 2.36 minutes, 100% purity (Method 10).

Example 169

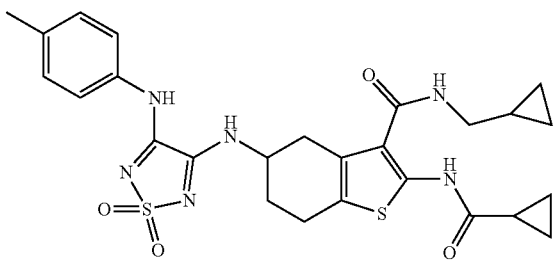

2-(Cyclopropanecarbonylamino)-N-(cyclopropylmethyl)-5-[[4-(4-methylanilino)-1,1-dioxo-1,2,5-thiadiazol-3-yl]amino]-4,5,6,7-tetrahydrobenzothiophene-3-carboxamide Intermediate 191 (84 mg, 0.31 mmol) was dissolved in EtOH (4 mL). Intermediate 122 (116 mg, 0.31 mmol) was added and the reaction mixture was stirred at 80° C. in the microwave for 30 minutes. The reaction mixture was concentrated in vacuo and the resulting crude residue was purified by preparative HPLC (acidic) to afford the title compound (70 mg, 40%) as a white solid. δ_H (500 MHz, CD₃OD) 7.60 (d, J 8.4 Hz, 2H), 7.23 (d, J 8.3 Hz, 2H), 4.37-4.28 (m, 1H), 3.34-3.33 (m, 1H), 3.28-3.24 (m, 1H), 3.24-3.18 (m, 1H), 2.92-2.79 (m, 3H), 2.34 (s, 3H), 2.24-2.16 (m, 2H), 1.86-1.77 (m, 1H), 1.15-1.06 (m, 1H), 1.01-0.92 (m, 4H), 0.58-0.50 (m, 2H), 0.31-0.24 (m, 2H). LCMS [M+H]⁺ 555.2, RT 3.38 minutes, 100% purity (Method 10).

Example 170

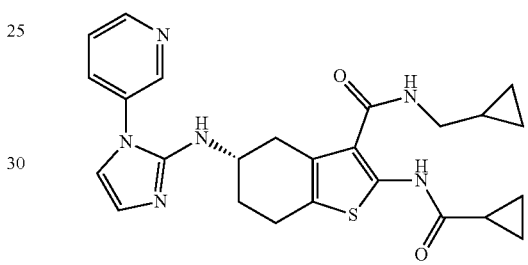

(5S)-2-(Cyclopropanecarbonylamino)-N-(cyclopropylmethyl)-5-[[1-(3-pyridyl)imidazol-2-yl]amino]-4,5,6,7-tetrahydrobenzothiophene-3-carboxamide To a stirred solution of intermediate 141 (222 mg, 0.47 mmol) and 2,2-diethoxyethanamine [645-36-3] (0.21 ml, 1.42 mmol) in DMF (4.5 mL) was added mercury dichloride [7487-94-7] (385 mg, 1.42 mmol). The reaction mixture was stirred at r.t. for 5 minutes and triethylamine (0.20 ml, 1.42 mmol) was added and the reaction mixture was heated at 90° C. for 1 h. 4-Methylbenzenesulfonic acid hydrate (1:1) [6192-52-5] (539 mg, 2.84 mmol) was added and heating continued at 90° C. for a further 2.5 h. The reaction mixture was diluted with DCM (40 mL), filtered over a pad of Celite, and the filtrate concentrated in vacuo. The crude residue was diluted with water (20 mL) and extracted with EtOAc (3×20 mL). The organic phases were combined, washed with water (10 mL) and brine (10 mL), dried (Na₂SO₄), filtered and concentrated in vacuo. The residue was purified by flash column chromatography on silica (gradient elution with 1% to 10% MeOH in DCM) to afford the title compound (19 mg, 8.3%) as a beige solid. δ_H (500 MHz, DMSO-d₆) 11.04 (s, 1H), 8.70 (d, J 2.2 Hz, 1H), 8.55 (dd, J 4.7, 1.4 Hz, 1H), 7.89 (ddd, J 8.2, 2.6, 1.5 Hz, 1H), 7.66 (t, J 5.5 Hz, 1H), 7.53 (ddd, J 8.2, 4.8, 0.6 Hz, 1H), 6.98 (d, J 1.6 Hz, 1H), 6.67 (d, J 1.6 Hz, 1H), 5.68 (d, J 6.4 Hz, 1H), 3.91-3.81 (m, 1H), 3.16-3.03 (m, 3H), 2.74-2.66 (m, 2H), 2.57 (dd, J 16.0, 9.3 Hz, 1H), 2.16-2.09 (m, 1H), 1.93-1.86 (m, 1H), 1.81-1.69 (m, 1H), 1.01 (s, 1H), 0.86-0.80 (m, 4H), 0.42-0.37 (m, 2H), 0.22-0.17 (m, 2H). LCMS [M+H]⁺ 477, RT 1.83 minutes, 97% purity (Method 10).

Example 171

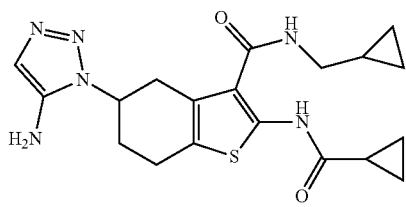

5-(5-Aminotriazol-1-yl)-2-(cyclopropanecarbonylamino)-N-(cyclopropylmethyl)-4,5,6,7-tetrahydrobenzothiophene-3-carboxamide To a solution of example 140 (81 mg, 0.16 mmol) in DCM (3 mL) at 0° C. was added TFA [76-05-1] (3 mL, 40 mmol). The solution was stirred at 0° C. for 5 minutes and then r.t. for 2 h. The solvent was removed and the excess TFA azetroped with isohexane. The residue was purified by flash column chromatography on silica (gradient elution with 0-100% MeOH/7M aqueous $NH_3$ in MeOH) to afford the title compound (40 mg, 61%) as a white solid. $\delta_H$ (300 MHz, $CD_3OD$) 6.97 (s, 1H), 4.57 (s, 1H), 3.33-3.09 (m, 2H), 2.96 (s, 3H), 2.43 (td, J 10.7, 10.1, 6.8 Hz, 1H), 2.34 (s, 1H), 1.81 (td, J 7.7, 3.8 Hz, 1H), 1.31 (s, 2H), 1.13-0.88 (m, 4H), 0.55-0.43 (m, 2H), 0.25 (dt, J 6.2, 4.5 Hz, 2H).

Example 172

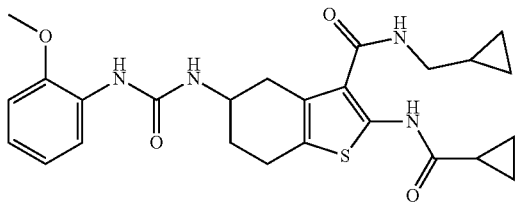 [SMILES: COc1ccccc1NC(=O)NC1CCc2sc(NC(=O)C3CC3)c(C(=O)NCC3CC3)c2C1]

2-(Cyclopropanecarbonylamino)-N-(cyclopropylmethyl)-5-[(2-methoxyphenyl)carbamoylamino]-4,5,6,7-tetrahydrobenzothiophene-3-carboxamide Intermediate 122 (50 mg, 0.14 mmol) was dissolved in DCM (5 mL) and DIPEA (26 mg, 0.20 mmol). 2-Methoxyphenyl isocyanate [700-87-8] (31 mg, 0.20 mmol) was added and the reaction mixture was stirred at r.t. for 16 h. The precipitate was filtered off, washing with DCM (2×), to afford the title compound (17 mg, 26%) as a white solid. $\delta_H$ (400 MHz, DMSO-$d_6$) 11.17 (s, 1H), 8.10 (dd, J 7.5, 2.2 Hz, 1H), 7.94 (s, 1H), 7.68 (t, J 5.7 Hz, 1H), 7.01 (d, J 7.5 Hz, 1H), 6.95 (dd, J 7.5, 2.0 Hz, 1H), 6.88-6.75 (m, 2H), 4.03-3.88 (m, 1H), 3.82 (s, 3H), 3.14 (qt, J 13.3, 6.2 Hz, 2H), 3.00 (dd, J 16.1, 5.1 Hz, 1H), 2.78-2.69 (m, 2H), 2.58-2.52 (m, 1H), 2.01-1.85 (m, 2H), 1.85-1.68 (m, 1H), 1.15-0.97 (m, 1H), 0.95-0.82 (m, 4H), 0.47-0.33 (m, 2H), 0.28-0.14 (m, 2H). LCMS (ES+) [M+H]$^+$ 483.8, RT 2.429 minutes, 99.2% purity (Method 2). LCMS (ES+) [M+H]$^+$ 483.8, RT 2.408 minutes, 99.2% purity (Method 3).

Example 173

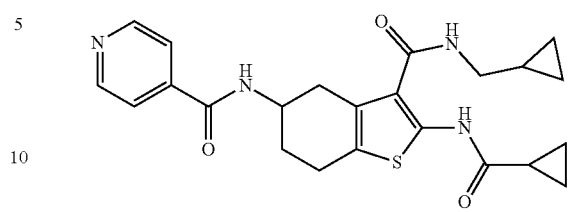

N-[2-(Cyclopropanecarbonylamino)-3-(cyclopropylmethylcarbamoyl)-4,5,6,7-tetrahydrobenzothiophen-5-yl]pyridine-4-carboxamide To intermediate 122 (18 mg, 0.050 mmol) in DCM (0.8 mL) was added DIPEA (26 μL, 0.075 mmol). DIPEA (26 μL, 0.075 mmol), isonicotinic acid [55-22-1] (8 mg, 0.065 mmol) and COMU [1075198-30-9] (27 mg, 0.060 mmol) were added and the reaction mixture was stirred at 30° C. After 1 h, water (1 mL) was added and the reaction mixture was passed through a phase separator. To the filtrate was added DCM (1 mL) and the reaction mixture was concentrated to give the crude residue which was purified by reverse phase HPLC (basic) to afford the title compound (6.8 mg, 32%). LCMS [M+H]$^+$ 439.30, RT 2.20 minutes, 96.63% purity (Method 9). LCMS [M+H]$^+$ 439.26, RT 1.56 minutes, 100% purity (Method 8).

Example 174

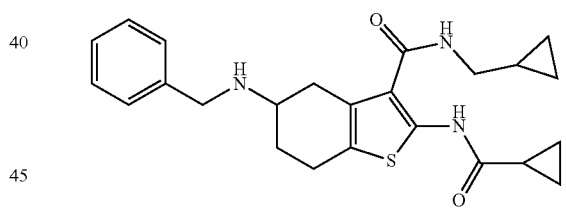

5-(Benzylamino)-2-(cyclopropanecarbonylamino)-N-(cyclopropylmethyl)-4,5,6,7-tetrahydrobenzothiophene-3-carboxamide To intermediate 122 (37 mg, 0.10 mmol) in THF (1 mL) and EtOH (0.5 mL) was added MP-carbonate (75 mg, 0.25 mmol, 3.36 mmol/g). The mixture was shaken for 1 h, filtered and rinsed with EtOH (2×200 μL). To the filtrate was added benzaldehyde [100-52-7] (13 mg, 0.12 mmol), MP-cyanoborohydride (100 mg, 0.25 mmol, 2.49 mmol/g) and acetic acid (0.1 mL, 2 mmol). The reaction mixture was shaken at r.t. for 3 h, filtered and rinsed with EtOH. The filtrate was concentrated in vacuo to give the crude residue which was purified by preparative HPLC (basic) to afford the title compound (9.6 mg, 23%). LCMS [M+H]$^+$ 423.2, RT 3.73 minutes, 95.9% purity (Method 8).

Example 175

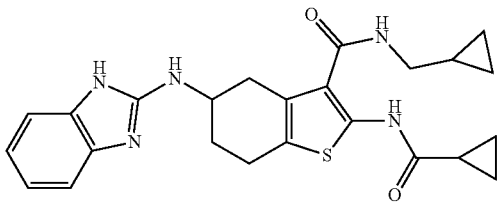 [SMILES: O=C(NCC1CC1)c1c(NC(=O)C2CC2)sc2c1CC(Nc1nc3ccccc3[nH]1)CC2]

5-(1H-Benzimidazol-2-ylamino)-2-(cyclopropanecarbonylamino)-N-(cyclopropylmethyl)-4,5,6,7-tetrahydrobenzothiophene-3-carboxamide A solution of intermediate 62 (60 mg, 0.18 mmol) and 1H-1,3-benzodiazol-2-amine (25 mg, 0.19 mmol) in THF (1 mL) was treated with titanium(IV) isopropoxide [546-68-9] (95 μL, 0.32 mmol). The reaction mixture was stirred at r.t. for 3.5 h prior to addition of sodium triacetoxyborohydride [56553-60-7] (80 mg, 0.38 mmol) and the reaction mixture was then stirred at r.t. for 16 h. The reaction mixture was quenched with sodium hydrogen carbonate solution (2 mL) and diluted with EtOAc (5 mL). A solid precipitate formed which was filtered off and extracted with EtOAc (2×5 mL). The combined organic phases were dried (MgSO$_4$), filtered and concentrated in vacuo and the residue purified by preparative HPLC (acidic) followed by preparative HPLC (basic) to afford the title compound (24 mg, 29%) as a white solid. δ$_H$ (500 MHz, DMSO-d$_6$) 11.10 (s, 1H), 10.64 (br s, 1H), 7.70 (t, J 5.6 Hz, 1H), 7.16-7.09 (m, 2H), 6.86 (dd, J 5.6, 3.2 Hz, 2H), 6.70 (br d, J 5.9 Hz, 1H), 4.06-3.95 (m, 1H), 3.18-3.08 (m, 3H), 2.82-2.73 (m, 2H), 2.71-2.61 (m, 1H), 2.17-2.05 (m, 1H), 1.99-1.79 (m, 2H), 1.06-0.94 (m, 1H), 0.91-0.79 (m, 4H), 0.41-0.30 (m, 2H), 0.24-0.13 (m, 2H). LCMS [M+H]$^+$ 450.2, RT 2.04 minutes, 99% purity (Method 10).

Example 176

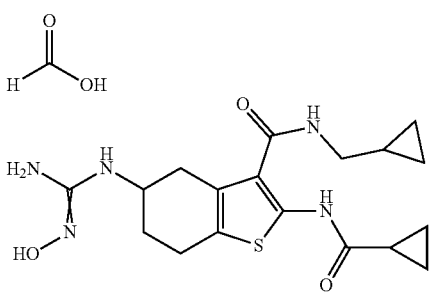

2-(Cyclopropanecarbonylamino)-N-(cyclopropylmethyl)-5-[[N'-hydroxycarbamimidoyl]amino]-4,5,6,7-tetrahydrobenzothiophene-3-carboxamide To a stirred solution of intermediate 134 (140 mg, 0.39 mmol) in EtOH (5 mL) was added hydroxylamine hydrochloride [5470-11-1] (29 mg, 0.41 mmoL) followed by potassium carbonate (108 mg, 0.78 mmoL) and the reaction mixture was stirred at r.t. under nitrogen. After stirring for 18 h further hydroxylamine hydrochloride [5470-11-1] (29 mg, 0.41 mmoL) and potassium carbonate (108 mg, 0.78 mmoL) were added and the reaction mixture was stirred at r.t. for 1 h. The reaction mixture was filtered through a pad of celite, washed with EtOH and concentrated in vacuo to give the crude residue (210 mg) which was purified by flash column chromatography on silica (gradient elution with 0 to 100% of EtOAc in heptane, followed by 0 to 10% MeOH in EtOAc, followed by 10% NH$_3$ (7N in MeOH) in EtOAc). The product was further purified by preparative HPLC (low pH×2) to afford the title compound (2.2 mg, 1.4%) as a white formate salt. δ$_H$ (500 MHz, CD$_3$OD) 8.55 (s, 1H), 3.90-3.80 (m, 1H), 3.30-3.17 (m, 2H), 3.10 (dd, J 15.7, 5.1 Hz, 1H), 2.88-2.81 (m, 2H), 2.74-2.64 (m, 1H), 2.17-2.06 (m, 1H), 2.01-1.87 (m, 1H), 1.86-1.75 (m, 1H), 1.14-1.04 (m, 1H), 1.03-0.86 (m, 4H), 0.60-0.47 (m, 2H), 0.32-0.23 (m, 2H). LCMS [M+H]$^+$ 392, RT 2.76 minutes, 99% purity (Method 5).

Example 177

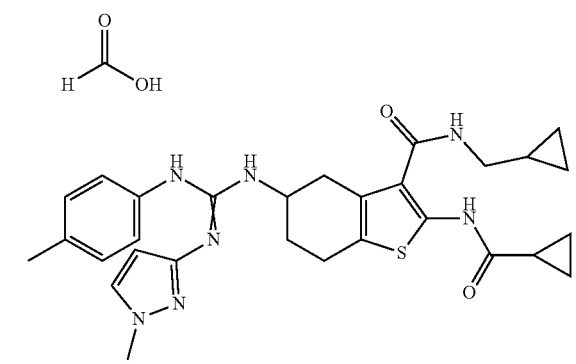

2-(Cyclopropanecarbonylamino)-N-(cyclopropylmethyl)-5-[[N'-(1-methylpyrazol-3-yl)-N-(p-tolyl)carbamimidoyl]amino]-4,5,6,7-tetrahydrobenzothiophene-3-carboxamide; formic acid A stirred solution of intermediate 192 (36 mg, 0.14 mmol), intermediate 122 (60 mg, 0.16 mmol), and DIPEA (0.057 ml, 0.32 mmol) in DCM (4 mL) was cooled to 0° C. EDCl (37 mg, 0.19 mmol) was added and the solution was stirred at r.t. overnight. The reaction mixture was washed with water (20 mL), followed by brine and dried (Na$_2$SO$_4$). The mixture was filtered and concentrated in vacuo to give the crude residue which was purified by preparative HPLC (acidic) to afford the title compound (55 mg, 57%) as a white solid (formate salt). δ$_H$ (500 MHz, CD$_3$OD) 8.48 (s, 1H), 7.49 (d, J 2.2 Hz, 1H), 7.33 (d, J 8.1 Hz, 2H), 7.23 (d, J 8.3 Hz, 2H), 5.95 (s, 1H), 4.45-4.30 (m, 1H), 3.70 (s, 3H), 3.29-3.18 (m, 3H), 3.00-2.84 (m, 3H), 2.40 (s, 3H), 2.25-2.13 (m, 2H), 1.85-1.78 (m, 1H), 1.14-1.04 (m, 1H), 1.01-0.92 (m, 4H), 0.55-0.48 (m, 2H), 0.32-0.24 (m, 2H). LCMS [M+H]$^+$ 546.3, RT 2.56 minutes, 99% purity (Method 10).

Example 178

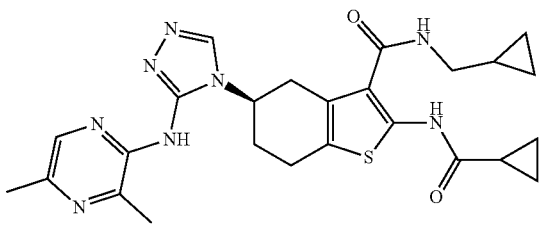 [SMILES: Cc1cnc(Nc2nncn2[C@@H]2CCc3sc(NC(=O)C4CC4)c(C(=O)NCC4CC4)c3C2)c(C)n1]

(5S)-2-(Cyclopropanecarbonylamino)-N-(cyclopropylmethyl)-5-[3-[(3,5-dimethylpyrazin-2-yl)amino]-1,2,4-triazol-4-yl]-4,5,6,7-tetrahydrobenzothiophene-3-carboxamide To a stirred solution of intermediate 259 (290 mg, 0.582 mmol) in DMF (10 mL) under nitrogen was added formic acid hydrazide [624-84-0] (116 mg, 1.75 mmol) and mercuric chloride [7487-94-7] (237 mg, 0.872 mmol). The reaction mixture was stirred at r.t. for 15 min before the addition of triethylamine (0.24 mL, 1.75 mmol) and the mixture was stirred at 85° C. for 16 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 2% to 20% MeOH in DCM) to afford impure title compound as a white solid. This was dissolved in MeOH (10 mL) and QuadraSil® MTU (130 mg) was added and the suspension was stirred at 40° C. for 1 h before being filtered and washed with MeOH (2×10 mL). The filtrate was concentrated in vacuo to give a gum. This was further purified by flash column chromatography on silica (gradient elution with 4% to 20% MeOH in EtOAc) product containing fractions were freeze dried to afford the title compound (169 mg, 0.334 mmol, 57%) as a white solid. LCMS (ES+) [M+H]+ 507.0, RT 1.73 minutes, purity 99% (Method 3). LCMS (ES+) [M+H]+ 507.0, RT 1.71 minutes, purity 99% (Method 2). 1H NMR (300 MHz, DMSO-d6) (contained 2 tautomers in an approximate ratio of 0.6:0.4) δ 12.88 (s, 0.4H), 11.22 (s, 0.4H), 11.10 (s, 0.6H), 8.73 (s, 0.6H), 8.64 (s, 0.6H), 8.29 (s, 0.4H), 7.85-7.66 (m, 2H), 4.70-4.46 (m, 0.4H), 4.19-3.94 (m, 0.6H), 3.29-2.57 (m, 6H), 2.44 (s, 1.8H), 2.40 (s, 1.2H), 2.36-2.04 (m, 5H), 2.01-1.83 (m, 1H), 1.10-0.93 (m, 1H), 0.91-0.77 (m, 4H), 0.47-0.29 (m, 2H), 0.26-0.13 (m, 2H).

Example 179

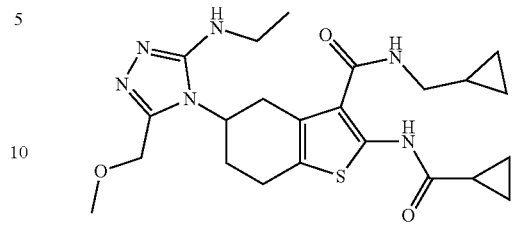

2-(Cyclopropanecarbonylamino)-N-(cyclopropylmethyl)-5-[3-(ethylamino)-5-(methoxymethyl)-1,2,4-triazol-4-yl]-4,5,6,7-tetrahydrobenzothiophene-3-carboxamide To a solution of intermediate 198 (46 mg, 0.082 mmol) in 88% formic acid [64-18-6] (6 mL) was added 10% Pd on carbon (50% wet type) (30 mg) under nitrogen. The reaction mixture was warmed to 80° C. and stirred for 60 minutes. The reaction was filtered through Celite and washed with formic acid [64-18-6] (2 mL). The filtrate was concentrated in vacuo to give the crude product as a colourless oil which was purified by preparative HPLC (basic) to afford the title compound (21 mg, 51%) which was freeze dried from 1:1 MeCN/water overnight. $\delta_H$ (500 MHz, Chloroform-d) 12.07 (s, 1H), 5.88 (t, J 5.0 Hz, 1H), 4.56 (d, J 13.0 Hz, 1H), 4.52 (d, J 13.0 Hz, 1H), 4.40-4.33 (m, 1H), 4.01 (s, 1H), 3.51-3.42 (m, 2H), 3.35 (s, 3H), 3.32-3.18 (m, 3H), 3.01 (dd, J 14.6, 5.5 Hz, 1H), 2.94-2.83 (m, 2H), 2.39 (tdd, J 12.3, 9.8, 7.2 Hz, 1H), 2.24-2.18 (m, 1H), 1.66 (tt, J 8.0, 4.6 Hz, 1H), 1.27 (t, J 7.2 Hz, 3H), 1.10 (p, J 3.7, 3.3 Hz, 2H), 1.06-0.99 (m, 1H), 0.95-0.87 (m, 2H), 0.57-0.46 (m, 2H), 0.23 (q, J 4.7 Hz, 2H). LCMS (ES+) [M+H]+ 473, RT 2.05 minutes, 97% purity (Method 10).

Example 180

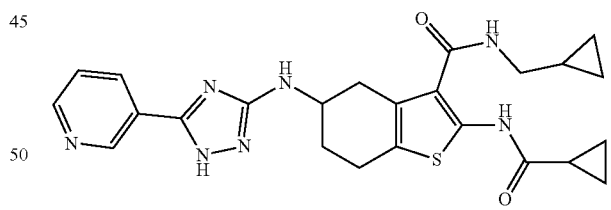

2-(Cyclopropanecarbonylamino)-N-(cyclopropylmethyl)-5-[[5-(3-pyridyl)-1H-1,2,4-triazol-3-yl]amino]-4,5,6,7-tetrahydrobenzothiophene-3-carboxamide To intermediate 200 (120 mg, 0.29 mmol) in DCM (2.5 mL) and 2-propanol (2.5 mL) was added nicotinic acid hydrazide [553-53-7] (133 mg, 0.94 mmol), triethylamine (0.06 mL, 0.4 mmol) and silver nitrate [7761-88-8] (59 mg, 0.35 mmol). The reaction mixture was heated in a microwave at 130° C. for 9 h before filtering through a phase separator cartridge. The aqueous phase was washed with DCM/MeOH, concentrated in vacuo to give the crude residue as a yellow oil which was purified by flash column chromatography on silica (gradient elution with 0-20% MeOH/DCM) to give the product which was purified by preparative HPLC to afford the title compound (11 mg, 8%) as a white solid. $\delta_H$ (300 MHz, DMSO-$d_6$) 12.41 (br. s, 1H), 11.05 (br. s, 1H), 9.06 (dd, J 2.2, 0.9 Hz, 1H), 8.54 (dd, J 4.8, 1.7 Hz, 1H), 8.19 (dt, J 7.9, 1.9 Hz, 1H), 7.77 (br. s, 1H), 7.50-7.37 (m, 1H), 6.88 (br. s, 1H), 3.89-3.68 (m, 1H), 3.18-3.02 (m, 3H), 2.85-2.69 (m, 2H), 2.61 (dd, J 16.1, 8.7 Hz, 1H), 2.14-2.01 (m, 1H), 1.96-1.72 (m, 2H), 1.07-0.90 (m, 1H), 0.89-0.78 (m, 4H), 0.42-0.28 (m, 2H), 0.22-0.13 (m, 2H).

Example 181

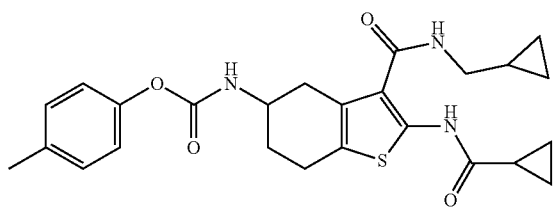 [SMILES: Cc1ccc(OC(=O)NC2CCc3sc(NC(=O)C4CC4)c(C(=O)NCC4CC4)c3C2)cc1]

p-Tolyl N-[2-(cyclopropanecarbonylamino)-3-(cyclopropylmethylcarbamoyl)-4,5,6,7-tetrahydrobenzothiophen-5-yl]carbamate To a solution of the reaction mixture of intermediate 201 in DCM (5 mL) was added p-cresol [106-44-5] (38 mg, 0.35 mmol) and the mixture was stirred at 100° C. for 60 minutes in the microwave. The reaction mixture was purified directly by flash column chromatography on silica (gradient elution with 20-100% EtOAc/hexane) and the product was freeze-dried from MeCN/water to afford the title compound (35 mg, 63%) as a white solid. $\delta_H$ (400 MHz, DMSO-$d_6$) 11.06 (s, 1H), 7.87 (d, J 7.4 Hz, 1H), 7.74 (t, J 5.6 Hz, 1H), 7.23-7.12 (m, 2H), 7.03-6.95 (m, 2H), 3.74 (br s, 1H), 3.24-3.07 (m, 2H), 2.97 (dd, J 15.9, 5.2 Hz, 1H), 2.86-2.55 (m, 3H), 2.29 (s, 3H), 2.08-1.96 (m, 1H), 1.95-1.87 (m, 1H), 1.86-1.70 (m, 1H), 1.09-0.98 (m, 1H), 0.93-0.77 (m, 4H), 0.51-0.36 (m, 2H), 0.30-0.17 (m, 2H).

Example 182

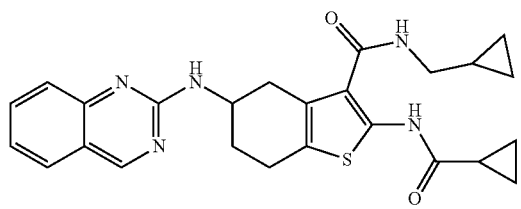 [SMILES: O=C(NCC1CC1)c1c(NC(=O)C2CC2)sc2c1CC(Nc1ncc3ccccc3n1)CC2]

2-(Cyclopropanecarbonylamino)-N-(cyclopropylmethyl)-5-(quinazolin-2-ylamino)-4,5,6,7-tetrahydrobenzothiophene-3-carboxamide Intermediate 122 (50 mg, 0.13 mmol) was dissolved in butanol (2 mL). 2-Chloroquinazoline [6141-13-5] (33 mg, 0.20 mmol) and DIPEA (0.035 ml, 0.2 mmol) were added and the reaction mixture was stirred at 100° C. in the microwave for 2 h. The reaction mixture was concentrated in vacuo and the crude residue was purified by preparative HPLC (acidic) to afford the title compound (18 mg, 28%) as an off white solid. $\delta_H$ (500 MHz, CD$_3$OD) 9.05 (s, 1H), 7.81-7.74 (m, 1H), 7.74-7.67 (m, 1H), 7.55 (d, J 8.4 Hz, 1H), 7.30-7.23 (m, 1H), 4.46-4.36 (m, 1H), 3.29-3.22 (m, 2H), 3.21-3.14 (m, 1H), 2.95-2.84 (m, 2H), 2.78-2.70 (m, 1H), 2.30-2.20 (m, 1H), 2.06-1.95 (m, 1H), 1.84-1.75 (m, 1H), 1.08-0.91 (m, 5H), 0.46-0.34 (m, 2H), 0.26-0.15 (m, 2H). LCMS (ES+) [M+H]$^+$ 462.3, RT 3.01 minutes, 96% purity (Method 10).

Example 183

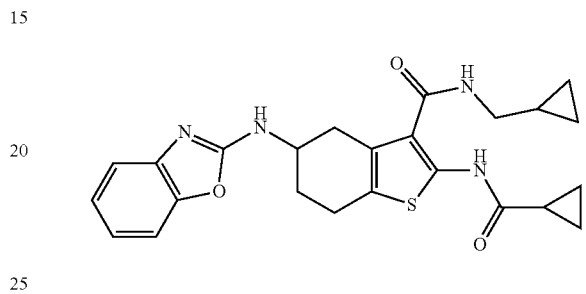

5-(1,3-Benzoxazol-2-ylamino)-2-(cyclopropanecarbonylamino)-N-(cyclopropylmethyl)-4,5,6,7-tetrahydrobenzothiophene-3-carboxamide Intermediate 122 (90%, 50 mg, 0.12 mmol) was suspended in MeCN (1 mL) and DIPEA (45 μL, 0.26 mmol) and 2-chloro-1,3-benzoxazole [615-18-9] (16 μL, 0.14 mmol) were added. The reaction mixture was heated to 100° C. in the microwave for 30 minutes followed by heating at 120° C. in the microwave for 30 minutes. The reaction mixture was concentrated in vacuo to give the crude residue which was purified by preparative HPLC to afford the title compound (26 mg, 48%) as a white solid. $\delta_H$ (500 MHz, DMSO-$d_6$) 11.07 (s, 1H), 8.06 (d, J 6.8 Hz, 1H), 7.78-7.68 (m, 1H), 7.33 (d, J 7.8 Hz, 1H), 7.24 (d, J 7.2 Hz, 1H), 7.11 (td, J 7.7, 1.0 Hz, 1H), 6.97 (td, J 7.8, 1.2 Hz, 1H), 3.97 (br. s, 1H), 3.20-3.02 (m, 3H), 2.86-2.66 (m, 3H), 2.19-2.10 (m, 1H), 1.97-1.83 (m, 2H), 1.06-0.93 (m, 1H), 0.84 (m, 4H), 0.42-0.32 (m, 2H), 0.23-0.13 (m, 2H). LCMS (ES+) [M+H]$^+$ 451.3, RT 3.45 minutes, 100% purity (Method 10).

Example 184

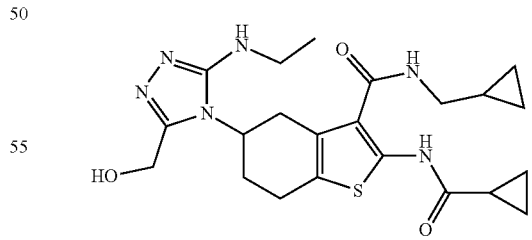

2-(Cyclopropanecarbonylamino)-N-(cyclopropylmethyl)-5-[3-(ethylamino)-5-(hydroxymethyl)-1,2,4-triazol-4-yl]-4,5,6,7-tetrahydrobenzothiophene-3-carboxamide To a solution of intermediate 202 (32 mg, 0.050 mmol) in 88% formic acid [64-18-6] (4 mL) was added 10% Pd on carbon (50% wet type, 53 mg, 0.050 mmol). The reaction mixture was heated to 80° C. under nitrogen for 60 minutes. The reaction mixture was filtered through a glass fibre filter paper and washed with formic acid [64-18-6] (1 mL). The filtrate was concentrated in vacuo and the crude residue dried under vacuum to give a colourless oil. The crude product was dissolved in THF (3 mL) and 1M lithium hydroxide solution (0.1 mL, ~2 equiv) was added. The reaction mixture was stirred at r.t. for 60 minutes. The pH was adjusted to pH7 by dropwise addition of 1M aqueous hydrochloric acid solution and the mixture was then concentrated in vacuo. The residue was partitioned between EtOAc (10 mL) and saturated aqueous sodium hydrogen carbonate solution (3 mL). The organic phase was separated and washed with brine (3 mL), dried (Na$_2$SO$_4$), filtered and concentrated in vacuo to give the crude product which was purified by preparative HPLC to afford the title compound (13 mg, 55%) as a colourless solid. δ$_H$ (500 MHz, Chloroform-d) 12.14 (s, 1H), 6.46-6.32 (m, 1H), 4.72 (d, J 13.9 Hz, 1H), 4.65 (d, J 13.9 Hz, 1H), 4.52-4.42 (m, 1H), 4.42-4.19 (m, 1H), 3.47-3.39 (m, 3H), 3.31-3.26 (m, 1H), 3.26-3.15 (m, 2H), 2.94-2.87 (m, 2H), 2.53-2.42 (m, 1H), 2.29-2.20 (m, 1H), 1.68 (tt, J 8.0, 4.6 Hz, 1H), 1.26 (t, J 7.2 Hz, 3H), 1.11 (dt, J 6.7, 3.3 Hz, 2H), 1.09-1.01 (m, 1H), 0.92 (dq, J 7.3, 4.0 Hz, 2H), 0.50-0.44 (m, 2H), 0.21 (q, J 4.7 Hz, 2H). LCMS (ES+) [M+H]$^+$ 459, RT 1.77 minutes, 100% purity (Method 10).

Example 185

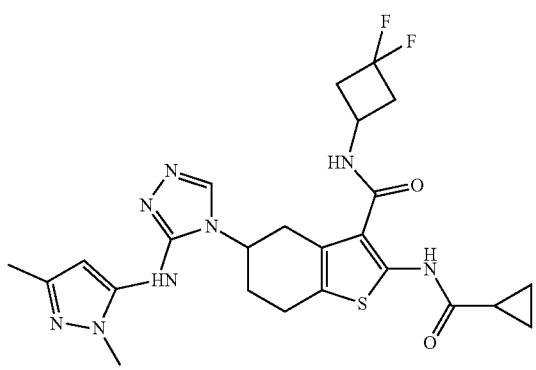 [SMILES: Cc1cc(Nc2nncn2C2CCc3sc(NC(=O)C4CC4)c(C(=O)NC4CC(F)(F)C4)c3C2)n(C)n1]

2-(cyclopropanecarbonylamino)-N-(3,3-difluorocyclobutyl)-5-[3-[(2,5-dimethylpyrazol-3-yl)amino]-1,2,4-triazol-4-yl]-4,5,6,7-tetrahydrobenzothiophene-3-carboxamide Intermediate 182 (50 mg, 0.1118 mmol) was dissolved in N,N-dimethylformamide (3 ml) and triethylamine (0.070 mL, 0.51 mmol) and 3,3-difluorocyclobutanamine hydrochloride (65 mg, 0.45277 mmol) was added, followed by 1-(3-dimethylaminopropyl)-3-ethylcarbodiimide hydrochloride (50 mg, 0.2608 mmol). The reaction mixture was heated at 70° C. for 2 h, then volatiles were evaporated in vacuo and crude product was purified by flash column chromatography on silica (gradient elution with 10 g SNAP-Ultra, Isolera, eluting with 0 to 100% EtOAc in i-Hexane followed by 0 to 20% MeOH in DCM) to afford the title compound as white solid (6 mg, 0.01131 mmol, 10.12% Yield). $^1$H NMR (300 MHz, DMSO-d$_6$) δ 10.98 (s, 1H), 8.43 (s, 1H), 8.33 (s, 2H), 5.89 (s, 1H), 4.41 (br s, 1H), 4.22 (br s, 1H), 3.52 (d, J=18.7 Hz, 3H), 3.11 (d, J=15.6 Hz, 1H), 3.00-2.59 (m, 8H), 2.27-2.12 (m, 2H), 2.07 (d, J=9.0 Hz, 2H), 1.93 (d, J=6.4 Hz, 1H), 0.91-0.74 (m, 4H). LCMS [M+H]$^+$ 531.0, RT 1.60 minutes (Method 27), LCMS [M–H]$^+$ 528.8, RT 1.57 minutes (Method 26), Example 186

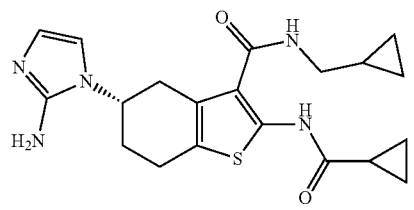 [SMILES: Nc1nccn1[C@H]1CCc2sc(NC(=O)C3CC3)c(C(=O)NCC3CC3)c2C1]

(5S)-5-(2-Aminoimidazol-1-yl)-2-(cyclopropanecarbonylamino)-N-(cyclopropylmethyl)-4,5,6,7-tetrahydrobenzothiophene-3-carboxamide Cyanamide [420-04-2] (134 mg, 3.2 mmol) was dissolved in 1,4-dioxane (10 mL) and 4M hydrogen chloride in 1,4-dioxane (800 μl) was added and the reaction mixture was stirred for 5 minutes. Intermediate 205 (450 mg, 1.07 mmol) was added and the reaction was sealed and heated to 60° C. for 18 h. The reaction mixture was diluted with MeOH and concentrated in vacuo. The crude residue was diluted with DCM (30 mL) and saturated aqueous sodium hydrogen carbonate solution (20 mL) was added. The mixture was extracted with 10% MeOH in DCM (3×20 mL), the organic phases were combined, dried (Na$_2$SO$_4$), filtered and concentrated in vacuo to give a yellow oil (574 mg). The crude product was purified by flash column chromatography on silica (gradient elution with 0-10% MeOH in DCM) to give impure product (184 mg) which was purified by preparative HPLC (basic) to give the desired product which was sonicated in Et$_2$O to afford the title compound (75 mg, 18%) as a white solid which was collected by filtration and dried in vacuo. δ$_H$ (500 MHz, DMSO-d$_6$) 11.15 (s, 1H), 7.73 (s, 1H), 6.66 (d, J 1.5 Hz, 1H), 6.42 (d, J 1.5 Hz, 1H), 5.37 (s, 2H), 4.28-4.16 (m, 1H), 3.12 (qt, J 13.5, 6.2 Hz, 2H), 2.97 (dd, J 15.1, 4.0 Hz, 1H), 2.91-2.72 (m, 3H), 2.07-1.98 (m, 2H), 1.96-1.85 (m, 1H), 1.06-0.96 (m, 1H), 0.88-0.80 (m, 4H), 0.44-0.34 (m, 2H), 0.25-0.15 (m, 2H). LCMS (ES+) [M+H]$^+$ 400.2, RT 1.83 minutes, 100% purity (Method 10).

Example 187

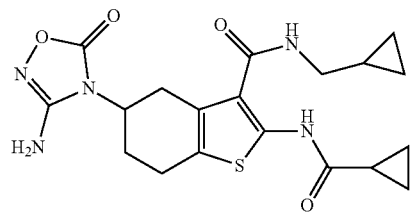 [SMILES: Nc1noc(=O)n1C1CCc2sc(NC(=O)C3CC3)c(C(=O)NCC3CC3)c2C1]

5-(3-Amino-5-oxo-1,2,4-oxadiazol-4-yl)-2-(cyclopropanecarbonylamino)-N-(cyclopropylmethyl)-4,5,6,7-tetrahydrobenzothiophene-3-carboxamide To a stirred solution of example 176 (30 mg, 0.077 mmoL) in THF (3 mL) was added 1,1'-carbonyldiimidazole [530-62-1] (15 mg, 0.092 mmoL) and the reaction mixture was stirred at r.t. under nitrogen for 20 h. The mixture was concentrated in vacuo and the residue was purified by preparative HPLC (acidic) to afford the title compound (4 mg, 12%) as a white solid. $\delta_H$ (250 MHz, Chloroform-d) 11.98 (s, 1H), 5.90-5.67 (m, 1H), 4.72 (s, 2H), 4.14-3.96 (m, 1H), 3.52-3.31 (m, 1H), 3.36-3.11 (m, 2H), 2.94-2.74 (m, 3H), 2.77-2.56 (m, 1H), 2.18-2.02 (m, 1H), 1.76-1.59 (m, 1H, part. obs. by water peak), 1.15-0.85 (m, 5H), 0.70-0.48 (m, 2H), 0.33-0.19 (m, 2H). LCMS (ES+) [M+H]$^+$ 418, RT 2.74 minutes, 99% purity (Method 10).

Example 188

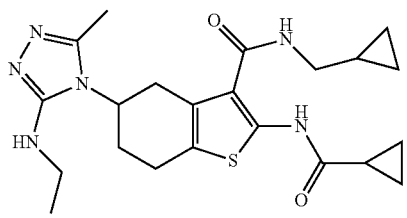 [SMILES: CCNc1nnc(C)n1C1CCc2sc(NC(=O)C3CC3)c(C(=O)NCC3CC3)c2C1]

2-(Cyclopropanecarbonylamino)-N-(cyclopropylmethyl)-5-[3-(ethylamino)-5-methyl-1,2,4-triazol-4-yl]-4,5,6,7-tetrahydrobenzothiophene-3-carboxamide To a solution of intermediate 208 (70 mg, 0.17 mmol) in DCM (6 mL) was added acetic acid (0.7 mL of a 290 mg acetic acid/10 mL DCM stock solution) and acetaldehyde [75-07-0] (0.7 mL of a 106 mg/10 mL DCM stock solution). The reaction mixture was stirred for 10 minutes prior to the addition of sodium triacetoxyborohydride [56553-60-7] (72 mg, 0.34 mmol) in 3 equal portions over 10 minute intervals. The reaction mixture was stirred at r.t. under nitrogen for 4 h. The reaction mixture was retreated with further acetaldehyde [75-07-0] (0.7 mL of a 106 mg/10 mL DCM stock solution) and after 15 minutes stirring further sodium triacetoxyborohydride [56553-60-7] (72 mg, 0.34 mmol) was added portionwise over 15 minutes and the reaction mixture was stirred for 4 h. The reaction mixture was retreated with further acetaldehyde [75-07-0] (0.7 mL of a 106 mg/10 mL DCM stock solution) and sodium triacetoxyborohydride [56553-60-7] (72 mg, 0.34 mmol) was added in three portions over 15 minutes and the reaction mixture was stirred at r.t. overnight. The reaction mixture was retreated with further acetaldehyde [75-07-0] (0.7 mL of a 106 mg/10 mL DCM stock solution) and after 15 minutes stirring further sodium triacetoxyborohydride [56553-60-7] (72 mg, 0.34 mmol) was added in three portions over 15 minutes and then stirred at r.t. for 4 h before being retreated with further acetaldehyde [75-07-0] (0.7 mL of a 106 mg/10 mL DCM stock solution) and after 15 minutes stirring further sodium triacetoxyborohydride [56553-60-7] (72 mg, 0.34 mmol) was added in three portions over 15 minutes. The reaction mixture was cooled to 4° C. overnight, concentrated in vacuo, combined with another reaction (10 mg, 0.024 mmol starting material) and dissolved in MeOH (10 mL). The pH was adjusted to pH13 with aqueous 1M sodium hydroxide solution and the mixture was stirred at r.t. for 15 minutes before concentrating in vacuo to remove the MeOH and adjusting to pH7 with 1M aqueous hydrochloric acid solution. To the solution was added saturated sodium bicarbonate solution (3 mL) and the aqueous phase was extracted with EtOAc (3×15 mL). The combined organic phases were washed with water (10 mL) and brine (10 mL, separated and dried (Na$_2$SO$_4$), filtered and concentrated in vacuo to give a colourless oil which was combined with a another reaction (10 mg, 0.024 mmol starting material). The crude product was purified by preparative HPLC (basic) to afford the title compound (13.4 mg, 18%). $\delta_H$ (500 MHz, DMSO-d$_6$) 11.19 (s, 1H), 7.67 (s, 1H), 5.69 (t, J 5.2 Hz, 1H), 4.29-4.15 (m, 1H), 3.14 (dtd, J 22.9, 13.7, 6.7 Hz, 5H), 2.93-2.75 (m, 3H), 2.43-2.34 (m, 1H), 2.32 (s, 3H), 2.00 (d, J 11.1 Hz, 1H), 1.89 (s, 1H), 1.13 (t, J 7.1 Hz, 3H), 1.05-0.94 (m, 1H), 0.91-0.74 (m, 4H), 0.43-0.34 (m, 2H), 0.23-0.15 (m, 2H). LCMS (ES+) [M+H]$^+$ 443, RT 1.90 minutes, 99% purity (Method 10).

Examples 189 and 190

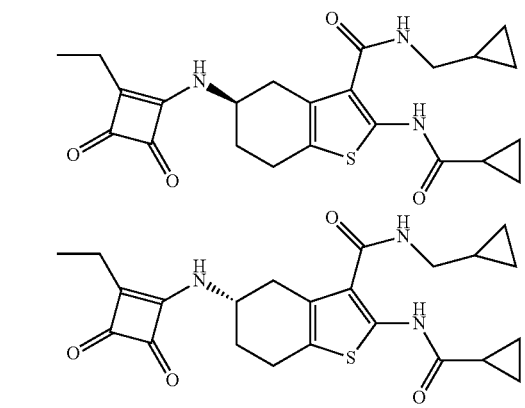

Example 189

(5R)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide

Example 190

(5S)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide Intermediate 196 (79 mg, 0.18 mmol) was purified by chiral HPLC (Column—Chiralcel OD-H 25 cm at 15 mL/min, eluent—35% IPA: 65% CO$_2$) and the 2 enantiomers were isolated in high purity: first eluting enantiomer (Example 189) (30 mg, 38%), second eluting enantiomer (Example 190) (30 mg, 38%).

Example 189: $\delta_H$ (250 MHz, Chloroform-d) 12.14-11.73 (m, 1H), 6.30-6.16 (m, 1H-Rotamer 1), 6.04-5.92 (m, 1H-Rotamer 2), 5.91-5.79 (m, 1H), 4.84-4.56 (m, 1H-Rotamer 2), 4.06-3.90 (m, 1H-Rotamer 1), 3.39-3.10 (m, 3H), 2.93-2.75 (m, 3H), 2.75-2.64 (m, 2H-Rotamer 1), 2.63-2.43 (m, 2H-Rotamer 2), 2.19-2.00 (m, 2H), 1.73-1.59 (m, 1H, part. obs. by water peak), 1.39-1.19 (m, 3H), 1.16-1.01 (m, 3H), 0.98-0.82 (m, 2H), 0.70-0.47 (m, 2H), 0.33-0.17 (m, 2H). LCMS [M+H]+ 442, RT 2.89 minutes, 98% purity (Method 10).

Example 190: $\delta_H$ (250 MHz, Chloroform-d) 12.18-11.77 (m, 1H), 6.44-6.31 (m, 1H-Rotamer 1), 6.25-6.06 (m, 1H-Rotamer 2), 6.03-5.82 (m, 1H), 4.85-4.67 (m, 1H-Rotamer 2), 4.09-3.84 (m, 1H-Rotamer 1), 3.37-3.12 (m, 3H), 2.96-2.76 (m, 3H), 2.75-2.64 (m, 2H, Rotamer 1), 2.62-2.46 (m, 2H-Rotamer 2), 2.21-1.98 (m, 2H), 1.73-1.56 (m, 1H, part. obs. by water peak), 1.40-1.17 (m, 3H), 1.08 (m, 3H), 0.97-0.84 (m, 2H), 0.64-0.48 (m, 2H), 0.34-0.15 (m, 2H). LCMS [M+H]+ 442, RT 2.89 minutes, 94% purity (Method 10).

Example 191

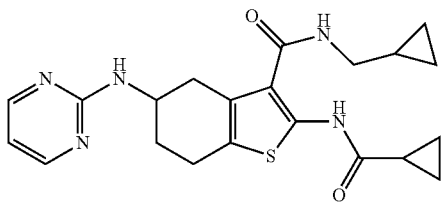 [SMILES: O=C(NCC1CC1)c1c(NC(=O)C2CC2)sc2c1CC(Nc1ncccn1)CC2]

2-(Cyclopropanecarbonylamino)-N-(cyclopropylmethyl)-5-(pyrimidin-2-ylamino)-4,5,6,7-tetrahydrobenzothiophene-3-carboxamide Intermediate 122 (50 mg, 0.14 mmol) and 2-chloropyrimidine [1722-12-9] (30 mg, 0.26 mmol) were dissolved in MeCN (1 mL) and DIPEA (85 μL, 0.49 mmol) was added. The reaction mixture was heated at 150° C. for 1 h in the microwave. The solvent was removed in vacuo and the crude material was purified by preparative HPLC (basic) to afford the title compound (10 mg, 17%) as a light brown solid. $\delta_H$ (500 MHz, CD$_3$OD) 8.28 (d, J 4.8 Hz, 2H), 6.61 (t, J 4.9 Hz, 1H), 4.28-4.17 (m, 1H), 3.26 (dd, J 13.8, 7.0 Hz, 1H), 3.23-3.15 (m, 2H), 2.84 (t, J 5.9 Hz, 2H), 2.72-2.64 (m, 1H), 2.21-2.14 (m, 1H), 1.97-1.87 (m, 1H), 1.82-1.75 (m, 1H), 1.12-1.03 (m, 1H), 1.01-0.96 (m, 2H), 0.96-0.91 (m, 2H), 0.52-0.45 (m, 2H), 0.28-0.21 (m, 2H). LCMS (ES+) [M+H]+ 412.2, RT 2.87 minutes, 95% purity (Method 10).

Example 192

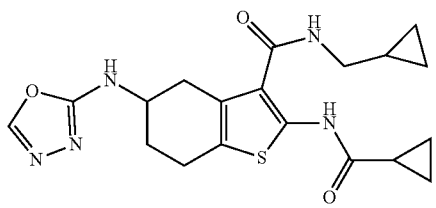 [SMILES: O=C(NCC1CC1)c1c(NC(=O)C2CC2)sc2c1CC(Nc1nnco1)CC2]

2-(Cyclopropanecarbonylamino)-N-(cyclopropylmethyl)-5-(1,3,4-oxadiazol-2-ylamino)-4,5,6,7-tetrahydrobenzothiophene-3-carboxamide Intermediate 209 (136 mg, 0.29 mmol) and formic hydrazide [624-84-0] (52 mg, 0.87 mmol) were dissolved in DMF (3 mL). Mercury dichloride [7487-94-7] (235 mg, 0.87 mmol) was added and the mixture was stirred for 5 minutes. Triethylamine (0.12 ml, 0.87 mmol) was added and the reaction mixture was heated at 90° C. for 1 h. The mixture was quenched with saturated sodium hydrogen carbonate solution (10 mL) and the aqueous layer was extracted with EtOAc (3×20 mL), dried (MgSO$_4$), filtered and concentrated in vacuo to give the crude product which was purified by preparative HPLC (basic) to afford the title compound (2 mg, 1.7%). $\delta_H$ (500 MHz, Methylene Chloride-d$_2$) 11.97 (s, 1H), 7.80 (s, 1H), 5.80 (s, 1H), 4.93 (d, J 6.8 Hz, 1H), 4.13-4.09 (m, 1H), 3.25-3.15 (m, 3H), 2.80-2.69 (m, 3H), 2.11-2.06 (m, 1H), 2.04-1.93 (m, 1H), 1.62-1.54 (m, 1H), 1.02-0.91 (m, 3H), 0.85-0.78 (m, 2H), 0.50-0.42 (m, 2H), 0.21-0.12 (m, 2H). LCMS (ES+) [M+H]+ 402.11, RT 2.48 minutes, 97% purity (Method 10).

Example 193

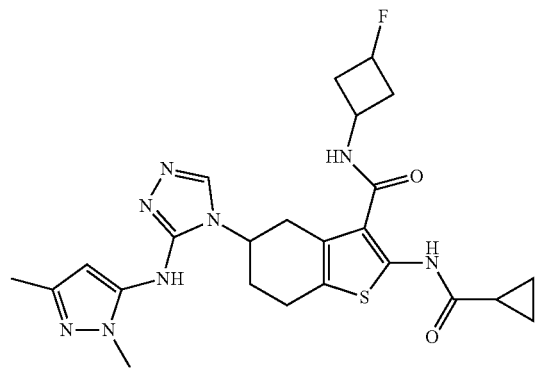 [SMILES: Cc1cc(Nc2nncn2C2CCc3sc(NC(=O)C4CC4)c(C(=O)NC4CC(F)C4)c3C2)n(C)n1]

2-(cyclopropanecarbonylamino)-5-[3-[(2,5-dimethylpyrazol-3-yl)amino]-1,2,4-triazol-4-yl]-N-(3-fluorocyclobutyl)-4,5,6,7-tetrahydrobenzothiophene-3-carboxamide Intermediate 182 (50 mg, 0.1133 mmol) was dissolved in N,N-dimethylformamide (3 mL) and triethylamine (0.15 mL, 1.1 mmol) and 3-fluorocyclobutanamine;hydrochloride (57 mg, 0.45393 mmol) were added, followed by 1-(3-dimethylaminopropyl)-3-ethylcarbodiimide hydrochloride (50 mg, 0.2608 mmol). The reaction mixture was heated up at 70° C. for 2 h, then volatiles were evaporated in vacuo and crude product was purified by flash column chromatography on silica (gradient elution with 10 g SNAP-Ultra, Isolera, eluting with 0 to 100% EtOAc in i-Hexane followed by 0 to 20% MeOH in DCM) to afford the title compound as white solid (13 mg, 0.02536 mmol, 22.39% Yield). $^1$H NMR (300 MHz, DMSO-d$_6$) δ 10.99 (s, 1H), 8.43 (s, 1H), 8.38-8.26 (m, 1H), 8.09 (s, 1H), 5.89 (s, 1H), 5.29-4.74 (m, 1H), 4.41 (s, 2H), 3.93 (d, J=8.2 Hz, 1H), 3.55 (s, 2H), 3.49 (s, 1H), 3.11 (s, 1H), 3.02-2.60 (m, 2H), 2.55 (s, 1H), 2.17 (s, 4H), 2.07 (d, J=8.7 Hz, 2H), 1.93 (s, 2H), 0.84 (d, J=5.7 Hz, 4H).

LCMS [M−H]⁺ 510.8, RT 1.45 minutes (Method 26), LCMS [M+H]⁺ 513.0, RT 1.48 minutes (Method 27).

Example 194

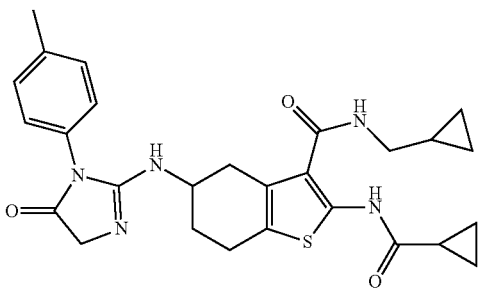 [SMILES: Cc1ccc(N2C(=O)CN=C2NC2CCc3sc(NC(=O)C4CC4)c(C(=O)NCC4CC4)c3C2)cc1]

2-(Cyclopropanecarbonylamino)-N-(cyclopropylmethyl)-5-[[5-oxo-1-(p-tolyl)-4H-imidazol-2-yl]amino]-4,5,6,7-tetrahydrobenzothiophene-3-carboxamide Intermediate 211 (75 mg, 0.16 mmol) in MeCN (3 mL) was added to a stirred solution of methyl glycinate hydrochloride (1:1) [5680-79-5] (21 mg, 0.16 mmol) and triethylamine (0.035 mL, 0.25 mmol) in MeCN (1 mL). The reaction mixture was stirred at r.t. for 16 h and the mixture was concentrated in vacuo to give the crude product which was purified by preparative HPLC (basic) to afford the title compound (15 mg, 18%) as a white solid. $\delta_H$ (500 MHz, Chloroform-d) 12.08 (s, 1H), 7.30 (d, J 8.1 Hz, 2H), 7.09 (d, J 8.1 Hz, 2H), 5.97-5.82 (m, 1H), 4.35 (s, 1H), 4.21 (s, 2H), 4.15-4.01 (m, 1H), 3.35-3.14 (m, 3H), 2.87-2.77 (m, 1H), 2.76-2.60 (m, 2H), 2.40 (s, 3H), 2.13-2.02 (m, 1H), 1.99-1.89 (m, 1H), 1.68-1.65 (m, 1H), 1.15-1.01 (m, 3H), 0.94-0.87 (m, 2H), 0.61-0.51 (m, 2H), 0.31-0.22 (m, 2H). LCMS (ES+) [M+H]⁺ 506.3, RT 2.18 minutes, 100% purity (Method 10).

Example 195

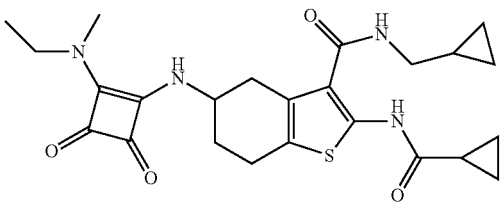 [SMILES: CCN(C)c1c(NC2CCc3sc(NC(=O)C4CC4)c(C(=O)NCC4CC4)c3C2)c(=O)c1=O]

2-(Cyclopropanecarbonylamino)-N-(cyclopropylmethyl)-5-[[2-[ethyl(methyl)amino]-3,4-dioxo-cyclobuten-1-yl]amino]-4,5,6,7-tetrahydrobenzothiophene-3-carboxamide Intermediate 136 (93%, 50 mg, 0.1 mmol) was suspended in EtOH (3 mL) and ethyl(methyl)amine [624-78-2] (20 μL, 0.23 mmol) was added. The reaction mixture was stirred for 16 h at r.t. before adding further ethyl(methyl)amine [624-78-2] (20 μL, 0.23 mmol) and stirring at r.t. for 4 h. The precipitate was filtered and washed with EtOH to afford the title compound (42.9 mg, 57%) as a white solid. $\delta_H$ (500 MHz, DMSO-d₆) 11.04 (s, 1H), 7.76 (t, J 5.6 Hz, 1H), 7.61 (d, J 8.2 Hz, 1H), 4.48-4.36 (m, 1H), 3.57 (s, 2H), 3.19 (s, 3H), 3.13 (t, J 6.2 Hz, 2H), 2.97 (dd, J 15.4, 4.8 Hz, 1H), 2.82-2.65 (m, 3H), 2.11-2.01 (m, 1H), 1.95-1.79 (m, 2H), 1.15 (t, J 7.1 Hz, 3H), 1.07-0.97 (m, 1H), 0.90-0.76 (m, 4H), 0.45-0.37 (m, 2H), 0.24-0.17 (m, 2H). LCMS (ES+) [M+H]⁺ 471.1, RT 2.66 minutes, 96% purity (Method 10).

Example 196

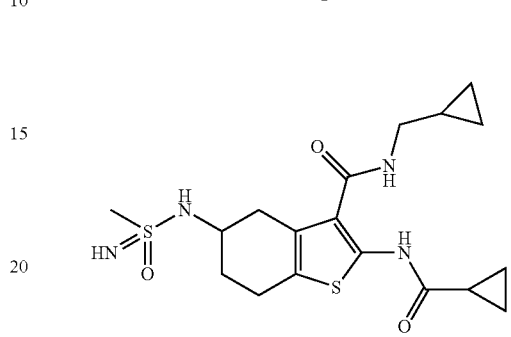

2-(Cyclopropanecarbonylamino)-N-(cyclopropylmethyl)-5-[(methylsulfonimidoyl)amino]-4,5,6,7-tetrahydrobenzothiophene-3-carboxamide To a suspension of intermediate 214 (32 mg, 0.09 mmoL) and cyclopropylmethanamine [2516-47-4](0.012 mL, 0.13 mmoL) in DCM (3 mL) was added EDCl (28 mg, 0.14 mmoL) and the reaction mixture was stirred at r.t. under nitrogen for 20 h. Cyclopropylmethanamine [2516-47-4] (0.047 mL, 0.54 mmoL) was added and stirring was continued at 40° C. before diluting with chloroform/isopropanol (2:1, 15 mL) and saturated aqueous ammonium chloride (10 mL). The phases were separated and the aqueous phase was extracted with further chloroform/isopropanol (2:1, 10 mL). The combined organic phases were washed with brine (10 mL), dried (MgSO₄), filtered and concentrated in vacuo to give the crude product which was purified by preparative HPLC (acidic) to afford the title compound (2.5 mg, 7%) as a thin film. $\delta_H$ (250 MHz, Chloroform-d) 12.18-11.93 (m, 1H), 5.93-5.79 (m, 1H), 3.95-3.81 (m, 1H), 3.36-3.22 (m, 2H), 3.25-3.03 (m, 4H), 2.92-2.77 (m, 2H), 2.79-2.65 (m, 1H), 2.61-2.33 (2H, obscured by water peak), 2.19-2.03 (m, 1H), 2.02-1.83 (m, 1H), 1.74-1.58 (m, 1H), 1.18-1.00 (m, 3H), 0.99-0.82 (m, 2H), 0.69-0.47 (m, 2H), 0.35-0.21 (m, 2H). LCMS (ES+) [M+H]⁺ 411, RT 1.92 minutes, 97% purity (Method 10).

Example 197

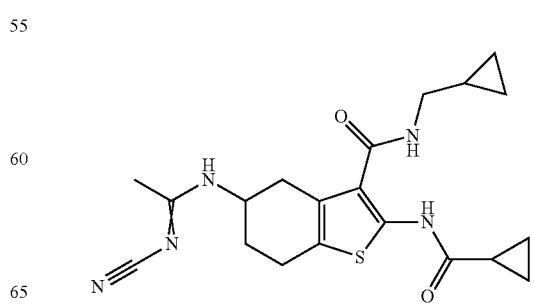

5-[[N-Cyano-C-methyl-carbonimidoyl]amino]-2-(cyclopropanecarbonylamino)-N-(cyclopropylmethyl)-4,5,6,7-tetrahydrobenzothiophene-3-carboxamide Intermediate 122 (50 mg, 0.13 mmol) was dissolved in EtOH (3 ml) and ethyl (1Z)-N-cyanoethanimidoate [1558-82-3] (20 mg, 0.17 mmol) and DIPEA (0.035 ml, 0.2 mmol) was added. The reaction mixture was stirred at 100° C. in the microwave for 4 h. The mixture was concentrated in vacuo to give the crude product which was purified by preparative HPLC (acidic) to afford the title compound (20 mg, 37%) as a white solid. $\delta_H$ (500 MHz, CD$_3$OD) 4.27-4.15 (m, 1H), 3.27-3.19 (m, 2H), 3.12 (dd, J 15.9, 5.1 Hz, 1H), 2.85-2.73 (m, 2H), 2.67-2.57 (m, 1H), 2.29 (s, 3H), 2.13-2.04 (m, 1H), 1.99-1.89 (m, 1H), 1.84-1.76 (m, 1H), 1.15-1.05 (m, 1H), 1.01-0.90 (m, 4H), 0.59-0.50 (m, 2H), 0.33-0.24 (m, 2H). LCMS (ES+) [M+H]$^+$ 400.3, RT 2.75 minutes, 100% (Method 10).

Example 198

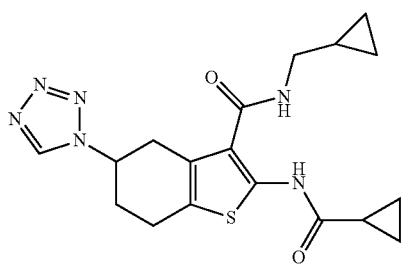 [SMILES: O=C(NCC1CC1)c1c(NC(=O)C2CC2)sc2c1CC(n1cnnn1)CC2]

2-(Cyclopropanecarbonylamino)-N-(cyclopropylmethyl)-5-(tetrazol-1-yl)-4,5,6,7-tetrahydrobenzothiophene-3-carboxamide Intermediate 216 (100 mg, 0.23 mmol) was dissolved in 1,4-dioxane (2 mL) and water (2 mL). Potassium hydrogen sulfate sulfate sulfodioxidanide (5:1:1:2) (255 mg, 0.42 mmol) was added portionwise over 5 minutes. The reaction mixture was stirred for 2 h at r.t. and the mixture was concentrated in vacuo. The crude residue was dissolved in EtOAc (2×30 mL) and washed with water and brine, dried (MgSO$_4$), filtered and concentrated in vacuo to afford a mixture of the crude sulfoxide intermediate 2-(cyclopropanecarbonylamino)-N-(cyclopropylmethyl)-5-(5-methylsulfinyltetrazol-1-yl)-4,5,6,7-tetrahydrobenzothiophene-3-carboxamide (43%) and Intermediate 216 (27%). The crude material was dissolved in dimethylacetamide [127-19-5] (1 mL) and cyclopropanamine [765-30-0] (36 mg, 0.62 mmol) was added to the mixture which was heated at 140° C. for 8 h. The crude material was purified by preparative HPLC to afford the title compound (6 mg, 13%). $\delta_H$ (500 MHz, Methylene Chloride-d$_2$) 11.95 (s, 1H), 8.64 (s, 1H), 5.73 (s, 1H), 5.08-4.98 (m, 1H), 3.44 (dd, J=15.0, 5.2 Hz, 1H), 3.30-3.17 (m, 3H), 3.04-2.92 (m, 1H), 2.86 (dt, J=17.0, 5.0 Hz, 1H), 2.53-2.39 (m, 2H), 1.70-1.65 (m, 1H), 1.07-1.00 (m, 3H), 0.93-0.87 (m, 2H), 0.55-0.48 (m, 2H), 0.26-0.20 (m, 2H).

Example 199

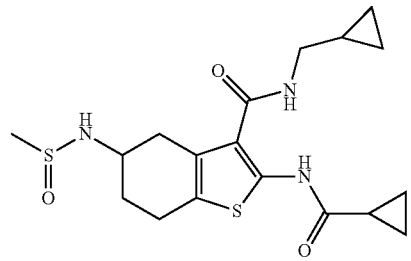 [SMILES: CS(=O)NC1CCc2sc(NC(=O)C3CC3)c(C(=O)NCC3CC3)c2C1]

2-(Cyclopropanecarbonylamino)-N-(cyclopropylmethyl)-5-(methanesulfinamido)-4,5,6,7-tetrahydrobenzothiophene-3-carboxamide To intermediate 122 (150 mg, 0.41 mmoL), sodium methanesulfinate [20277-69-4] (50 mg, 0.49 mmoL) and EDCl (93 mg, 0.49 mmoL) in DCM (5 mL) was added DIPEA (0.17 mL, 0.97 mmoL) and the reaction mixture was stirred at r.t. under nitrogen for 18 h. Sodium methanesulfinate [20277-69-4] (50 mg, 0.49 mmoL), EDCl (93 mg, 0.49 mmoL) and DIPEA (0.17 mL, 0.97 mmoL) were again added and stirring continued at r.t. for a further 5 h. The reaction mixture was diluted with DCM (10 mL) and washed with saturated aqueous sodium hydrogen carbonate (10 mL), saturated aqueous ammonium chloride (10 mL), water (10 mL), brine (10 mL), dried (MgSO$_4$), filtered and concentrated in vacuo. The crude product was purified by flash column chromatography on silica (gradient elution with 0 to 100% EtOAc in heptane, followed by 0 to 20% MeOH in EtOAc) to afford the title compound (125 mg, 78%) as an off-white solid, a mixture of two diastereomers. $\delta_H$ (250 MHz, Chloroform-d) 12.18-11.85 (m, 1H), 6.24-5.81 (m, 1H), 4.04-3.77 (m, 2H), 3.33-3.22 (m, 2H), 3.22-3.05 (m, 1H), 2.98-2.69 (m, 3H), 2.70-2.61 (m, 3H), 2.21-2.03 (m, 1H), 2.03-1.83 (m, 1H), 1.75-1.57 (m, 1H, partially obs. by water), 1.17-0.99 (m, 3H), 0.96-0.82 (m, 2H), 0.64-0.51 (m, 2H), 0.32-0.22 (m, 2H). LCMS (ES+) [M+H]$^+$ 396, RT 1.12 minutes, 96% purity (Method 6). LCMS (ES+) [M+H]$^+$ 396, RT 2.49 minutes, 95% purity (Method 10).

Example 200

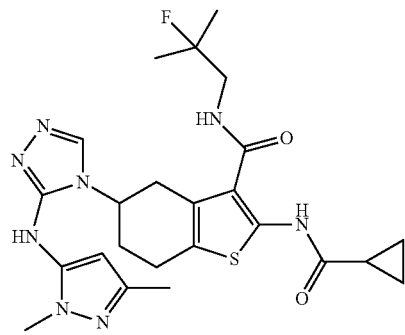 [SMILES: Cc1cc(Nc2nncn2C2CCc3sc(NC(=O)C4CC4)c(C(=O)NCC(C)(C)F)c3C2)n(C)n1]

2-(cyclopropanecarbonylamino)-5-[3-[(2,5-dimeth-ylpyrazol-3-yl)amino]-1,2,4-triazol-4-yl]-N-(2-fluoro-2-methyl-propyl)-4,5,6,7-tetrahydrobenzothiophene-3-carboxamide Intermediate 182 (50 mg, 0.1133 mmol) was dissolved in N,N-dimethylformamide (3 mL) and triethylamine (0.2 mL) and 2-fluoro-2-methylpropane-1-amine hydrochloride (70 mg, 0.5486 mmol) was added, followed by 1-(3-dimethyl-aminopropyl)-3-ethylcarbodiimide hydrochloride (60 mg, 0.313 mmol). Stirred at 70° C. for 2 h, then cooled down to rt. DMF was evaporated in vacuo, the resulting residue was dissolved in EtOAc and extracted with brine 4 times. The crude product was purified by flash column chromatography on silica (gradient elution with 10 g SNAP-Ultra, Isolera, eluting with 0 to 20% MeOH in DCM to afford the title compound as a white solid (2 mg, 0.003887 mmol, 3.4% Yield). 1H NMR (400 MHz, DMSO-$d_6$) δ 11.07 (s, 1H), 8.43 (s, 1H), 8.32 (s, 1H), 7.85 (s, 1H), 5.88 (s, 1H), 4.42 (s, 2H), 3.54 (s, 3H), 3.48 (s, 1H), 2.08 (s, 3H), 2.05 (s, 2H), 1.33 (d, J=5.0 Hz, 5H), 1.30-1.23 (m, 4H), 0.85 (s, 6H) (mixture of rotamers). LCMS [M+H]$^+$ 515.0, RT 1.53 minutes (Method 27), [M+H]$^+$ 515.0, RT 1.51 minutes (Method 26).

Example 201

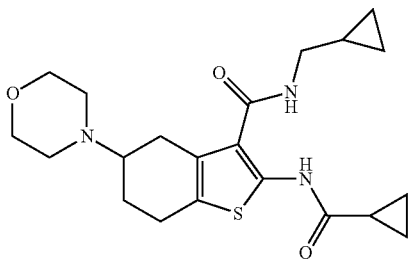 [SMILES: O=C(NCC1CC1)c1c(NC(=O)C2CC2)sc2c1CC(N1CCOCC1)CC2]

2-(Cyclopropanecarbonylamino)-N-(cyclopropylm-ethyl)-5-morpholino-4,5,6,7-tetrahydrobenzothi-ophene-3-carboxamide To a solution of intermediate 62 (50 mg, 0.15 mmoL) and morpholine [110-91-8] (0.02 mL, 0.23 mmoL) in 1,2-dichloroethane [107-06-2] (3 mL) was added acetic acid [64-19-7] (0.009 mL, 0.15 mmoL) followed by sodium triacetoxyborohydride [56553-60-7] (48 mg, 0.23 mmoL) and the mixture was stirred at r.t. under nitrogen for 21 h. Further morpholine [110-91-8] (0.02 mL, 0.23 mmoL) and sodium triacetoxyborohydride [56553-60-7] (48 mg, 0.23 mmoL) were added and stirring was continued at r.t. for 6 h. The reaction mixture was partitioned between DCM (10 mL) and saturated sodium hydrogen carbonate solution (10 mL). The phases were separated and the aqueous phase was extracted with DCM (15 mL). The combined organic phases were washed with water (10 mL), brine (10 mL) and dried (MgSO$_4$), filtered and concentrated in vacuo to give the crude product which was purified by flash column chromatography on silica (gradient elution with 0 to 100% EtOAc in heptane followed by a gradient 0 to 20% MeOH in EtOAc) to give the product which was purified by preparative HPLC (basic) to afford the title compound (23 mg, 38%). δ$_H$ (250 MHz, CD$_3$OD) 3.74 (t, J 4.7 Hz, 4H), 3.42-3.28 (m, 1H, partially obscured by MeOD signal), 3.15 (dd, J 13.7, 7.0 Hz, 1H), 2.98-2.82 (m, 1H), 2.85-2.60 (m, 8H), 2.30-2.12 (m, 1H), 1.87-1.59 (m, 2H), 1.18-1.02 (m, 1H), 1.02-0.85 (m, 4H), 0.63-0.46 (m, 2H), 0.37-0.21 (m, 2H). LCMS (ES+) [M+H]$^+$ 404, RT 1.53 minutes, 98% purity (Method 10).

Example 202

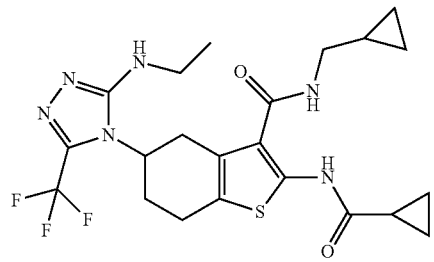 [SMILES: CCNc1nnc(C(F)(F)F)n1C1CCc2sc(NC(=O)C3CC3)c(C(=O)NCC3CC3)c2C1]

2-(Cyclopropanecarbonylamino)-N-(cyclopropylm-ethyl)-5-[3-(ethylamino)-5-(trifluoromethyl)-1,2,4-triazol-4-yl]-4,5,6,7-tetrahydrobenzothiophene-3-carboxamide To a solution of intermediate 220 (31 mg, 0.053 mmol) in 88% formic acid [64-18-6] (6 mL) was added 10% Pd on carbon (50% wet type, 30 mg, 0.028 mmol) under nitrogen. The reaction mixture was warmed to 80° C. and stirred for 120 minutes. The reaction mixture was treated with additional 10% Pd/C (50% wet type, 30 mg, 0.028 mmol) and was heated at 80° C. for 60 minutes. The reaction mixture was filtered through Celite and the filtrate was concentrated in vacuo to give the crude product as a colourless glass which was purified by preparative HPLC (basic) to afford the title compound (18 mg, 70%) as a colourless solid. δ$_H$ (500 MHz, Chloroform-d) 12.04 (s, 1H), 5.82 (t, J 4.9 Hz, 1H), 4.49 (s, 1H), 4.16 (s, 1H), 3.52 (p, J 6.9 Hz, 2H), 3.34-3.18 (m, 3H), 3.07 (dd, J 14.8, 5.8 Hz, 1H), 2.97-2.87 (m, 2H), 2.45-2.32 (m, 1H), 2.30-2.21 (m, 1H), 1.68 (ddd, J 12.5, 7.9, 4.6 Hz, 1H), 1.29 (t, J 7.2 Hz, 3H), 1.14-1.09 (m, 2H), 1.05 (ddd, J 12.7, 8.7, 5.1 Hz, 1H), 0.96-0.90 (m, 2H), 0.56-0.51 (m, 2H), 0.24 (q, J 4.6 Hz, 2H). LCMS (ES+) [M+H]$^+$ 497, RT 3.19 minutes, 100% purity (Method 10).

Example 203

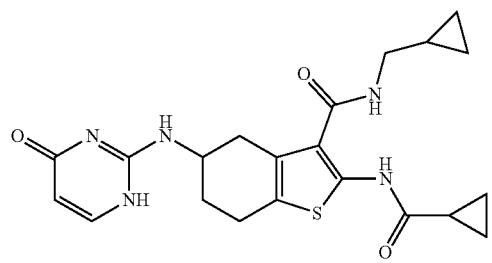

2-(Cyclopropanecarbonylamino)-N-(cyclopropylm-ethyl)-5-[(4-oxo-1H-pyrimidin-2-yl)amino]-4,5,6,7-tetrahydrobenzothiophene-3-carboxamide Intermediate 122 (156 mg, 0.42 mmol) and 2-methylth-iopyrimidin-4-ol [124700-70-5] (72 mg, 0.51 mmol) was

Example 204 dissolved in tert-butyl alcohol (1.5 mL) and DIPEA (0.18 mL, 1.03 mmol) was added. The reaction was heated in the microwave at 160° C. for 16 h before concentrating in vacuo. The crude product was purified by flash column chromatography on silica (gradient elution with 0-20% MeOH in DCM) to afford the title compound (63 mg, 35%) as an off white solid. $\delta_H$ (400 MHz, DMSO-$d_6$) 11.12 (s, 1H), 10.42 (s, 1H), 7.71 (t, J 5.7 Hz, 1H), 7.60 (d, J 6.5 Hz, 1H), 6.71-6.44 (m, 1H), 5.54 (d, J 6.5 Hz, 1H), 4.31-4.03 (m, 1H), 3.14 (t, J 6.2 Hz, 2H), 3.05 (d d, J 16.3, 5.1 Hz, 1H), 2.79-2.69 (m, 2H), 2.61 (dd, J 16.2, 7.2 Hz, 1H), 2.09-1.74 (m, 3H), 1.12-0.96 (m, 1H), 0.95-0.72 (m, 4H), 0.51-0.32 (m, 2H), 0.30-0.14 (m, 2H). LCMS [M−H]⁻ 426.0, RT 1.530 minutes, 94.8% purity (Method 2). LCMS [M−H]⁻ 426.0, RT 1.598 minutes, 96.9% purity (Method 3).

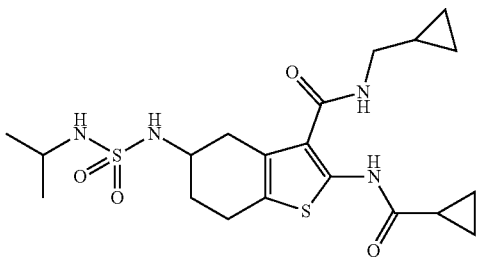

2-(Cyclopropanecarbonylamino)-N-(cyclopropylmethyl)-5-(isopropylsulfamoylamino)-4,5,6,7-tetrahydrobenzothiophene-3-carboxamide Intermediate 122 (50 mg, 0.14 mmol) was dissolved in DCM (5 mL) and DIPEA (26 mg, 0.20 mmol) and isopropylsulfamoyl chloride [26118-67-2] (32 mg, 0.20 mmol) was added. The reaction mixture was stirred at r.t. for 3 days. Further isopropylsulfamoyl chloride [26118-67-2] was added (32 mg, 0.20 mmol) and the reaction mixture was stirred at r.t. for 4 days. The reaction mixture was directly purified by flash column chromatography on silica (gradient elution with 35-100% EtOAc/hexane) to give the product which was freeze-dried from MeCN/water to afford the title compound (9 mg, 15%) as a white solid. LCMS [M−H]⁻ 453.0, RT 2.084 minutes, 100.0% purity (Method 3). LCMS [M−H]⁻ 453.0, RT 2.156 minutes, 100.0% purity (Method 2).

Example 205

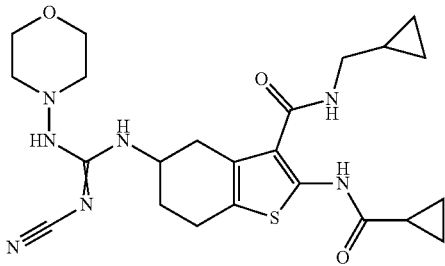

5-[[N'-Cyano-N-morpholino-carbamimidoyl]amino]-2-(cyclopropanecarbonylamino)-N-(cyclopropylmethyl)-4,5,6,7-tetrahydrobenzothiophene-3-carboxamide Intermediate 122 (100 mg, 0.27 mmol) was dissolved in DCM (4 mL) and DIPEA (88 mg, 0.68 mmol) and intermediate 221 (100 mg, 0.41 mmol) was added. The reaction mixture was stirred at 130° C. in the microwave for 4 h. The reaction mixture was concentrated in vacuo and the crude residue was purified by flash column chromatography on silica (gradient elution with 30-100% EtOAc/hexane to 20% MeOH/EtOAc) to give the product which was freeze dried from MeCN/water to afford the product which was purified by preparative HPLC to afford the title compound (5.5 mg, 4.2%) as a white solid. $\delta_H$ (400 MHz, DMSO-$d_6$) 11.01 (s, 1H), 8.72 (s, 1H), 7.75 (t, J 5.6 Hz, 1H), 7.00 (d, J 8.3 Hz, 1H), 3.93 (br. s, 1H), 3.65 (br. d, J 61.3 Hz, 4H), 3.19-3.06 (m, 2H), 2.97-2.61 (m, 8H), 2.05-1.68 (m, 3H), 1.10-0.96 (m, 1H), 0.92-0.76 (m, 4H), 0.48-0.36 (m, 2H), 0.30-0.17 (m, 2H). LCMS (ES+) [M+H]⁺ 486.20, RT 1.890 minutes, purity 100.0% (Method 2).

Example 206

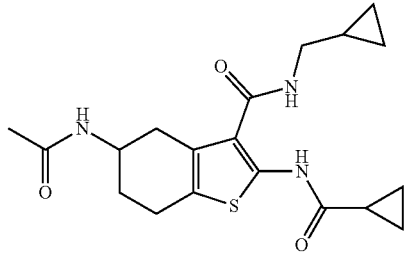

5-Acetamido-2-(cyclopropanecarbonylamino)-N-(cyclopropylmethyl)-4,5,6,7-tetrahydrobenzothiophene-3-carboxamide Intermediate 122 (50 mg, 0.14 mmol) was dissolved in DCM (5 mL) and DIPEA (44 mg, 0.34 mmol) and acetyl chloride [75-36-5] (14 mg, 0.18 mmol) were added. The reaction mixture was stirred at r.t. for 4 h. The reaction mixture was washed with water and passed through a phase separation cartridge and concentrated in vacuo. The crude residue was purified by flash column chromatography on silica (gradient elution with 30-100% EtOAc/hexane to 20% MeOH/EtOAc) to give the product which was freeze-dried from MeCN/water to afford the title compound (16 mg, 32%) as a white solid. $\delta_H$ (400 MHz, DMSO-$d_6$) 10.85 (s, 1H), 7.67 (d, J 7.4 Hz, 1H), 7.47 (s, 1H), 3.80-3.59 (m, 1H), 2.96-2.82 (m, 2H), 2.67 (d, J 16.9 Hz, 1H), 2.54-2.36 (m, 2H), 1.76-1.62 (m, 2H), 1.59 (s, 3H), 1.46 (br. s, 1H), 0.93 (d, J 6.7 Hz, 1H), 0.85-0.71 (m, 1H), 0.68-0.48 (m, 4H), 0.29-0.13 (m, 2H), 0.09--0.08 (m, 2H). LCMS [M−H]⁻ 374.0, [M+H]⁺ 376.8, RT 1.693 minutes, 94.4% purity (Method 2). LCMS (ES+) [M+H]⁺ 376.8, [M+Na]⁺398.6, RT 1.621 minutes, 94.1% purity (Method 3).

Example 207

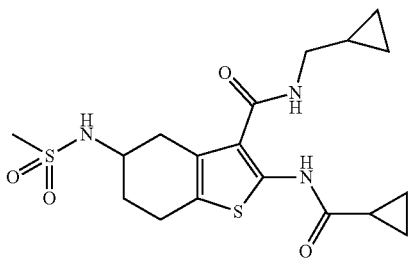

2-(Cyclopropanecarbonylamino)-N-(cyclopropylmethyl)-5-(methanesulfonamido)-4,5,6,7-tetrahydrobenzothiophene-3-carboxamide Intermediate 122 (50 mg, 0.14 mmol) was dissolved in DCM (5 mL) and DIPEA (44 mg, 0.34 mmol) and methanesulfonyl chloride [124-63-0] (20 mg, 0.18 mmol) were added. The reaction mixture was stirred at r.t. for 4 h. The reaction mixture was washed with water, passed through a phase separation cartridge and concentrated in vacuo to give the crude residue which was purified by flash column chromatography on silica (gradient elution with 30-100% EtOAc/hexane). The product was freeze dried from MeCN/water to afford the title compound (21 mg, 38%) as a white solid. $\delta_H$ (400 MHz, DMSO-$d_6$) 10.78 (s, 1H), 7.49 (s, 1H), 6.95 (d, J 6.7 Hz, 1H), 3.31 (s, 1H), 2.96-2.85 (m, 2H), 2.73 (s, 4H), 2.53-2.45 (m, 2H), 2.37 (dd, J 16.1, 8.6 Hz, 1H), 1.82-1.74 (m, 1H), 1.67 (s, 1H), 1.55-1.42 (m, 1H), 0.82-0.72 (m, 1H), 0.68-0.50 (m, 4H), 0.24-0.09 (m, 2H), 0.06--0.10 (m, 2H). LCMS [M+H]$^+$ 412.8, [M−H]$^−$ 410.0, RT 1.812 minutes, 100.0% purity (Method 2). LCMS (ES+) [M+H]$^+$ 412.7, [M+Na]$^+$434.6, RT 1.735 minutes, 100.0% purity (Method 3).

Example 208

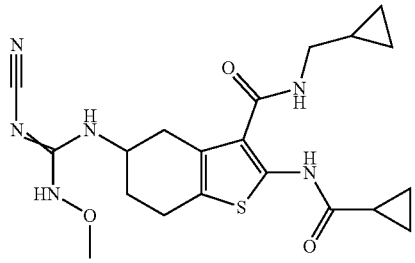

5-[[N'-Cyano-N-methoxy-carbamimidoyl]amino]-2-(cyclopropanecarbonylamino)-N-(cyclopropylmethyl)-4,5,6,7-tetrahydrobenzothiophene-3-carboxamide To diphenyl N-cyanocarbonimidate [76463-77-7] (40 mg, 0.17 mmol) was added O-methylhydroxylamine [67-62-9] (15 mg, 0.18 mmol) and 1:1 DCM/isopropanol (1 mL) followed by DIPEA (44 mg, 0.34 mmol). The reaction mixture was stirred at r.t. overnight. To the reaction mixture was added intermediate 122 (40 mg, 0.11 mmol) and the reaction mixture was stirred at 100° C. for 5 h. The reaction mixture was concentrated in vacuo and purified by preparative HPLC (basic) to afford the title compound (4.1 mg, 8.8%). LCMS [M+H]$^+$ 431.1855, RT 4.41 minutes, 90.56% purity (Method 20).

Example 209

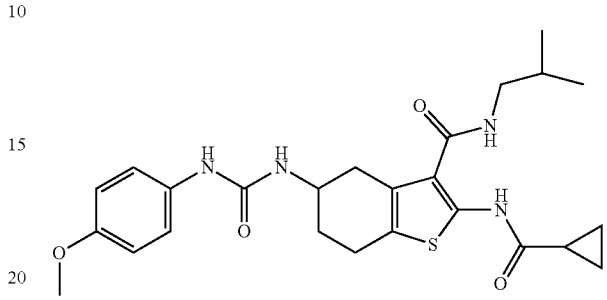

2-(Cyclopropanecarbonylamino)-N-isobutyl-5-[(4-methoxyphenyl)carbamoylamino]-4,5,6,7-tetrahydrobenzothiophene-3-carboxamide To intermediate 224 (70 mg, 0.21 mmol) dissolved in DCM (1 mL) was added triethylamine (89 mg, 0.87 mmol) and 1-isocyanato-4-methoxy-benzene [5416-93-3] (48 mg, 0.32 mmol) and the reaction mixture was stirred at r.t. for 3 days. Et$_2$O (1 mL) was added and the precipitate filtered, washed with Et$_2$O (3×), isopropanol (2×) and then Et$_2$O (3×) to afford the title compound (32 mg, 32%) as a beige solid. LCMS [M+H]$^+$ 485.27, [M−H]$^−$ 483.19, RT 2.30 minutes, 97.81% purity (Method 8).

Example 210

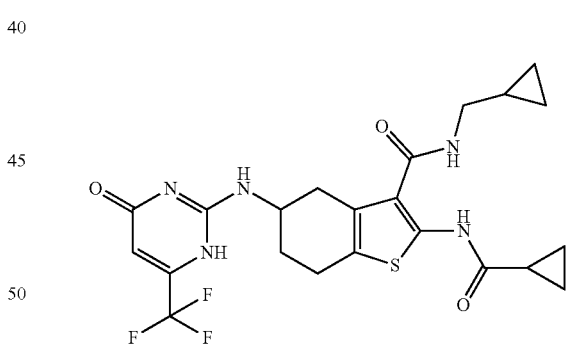

2-(Cyclopropanecarbonylamino)-N-(cyclopropylmethyl)-5-[[4-oxo-6-(trifluoromethyl)-1H-pyrimidin-2-yl]amino]-4,5,6,7-tetrahydrobenzothiophene-3-carboxamide To intermediate 122 (144 mg, 0.39 mmol) and 4-hydroxy-2-(methylthio)-6-(trifluoromethyl)pyrimidine [16097-62-4] (109 mg, 0.50 mmol) dissolved in tert-butyl alcohol (1.5 mL) was added DIPEA (0.18 mL, 1.03 mmol). The reaction mixture was heated in the microwave at 160° C. for 60 h, concentrated in vacuo and purified by preparative HPLC to afford the title compound (17 mg, 8.7%) as a white solid. LCMS (ES+) [M+H]$^+$ 496.0, [M+Na]$^+$518.0, RT 2.293

Example 211

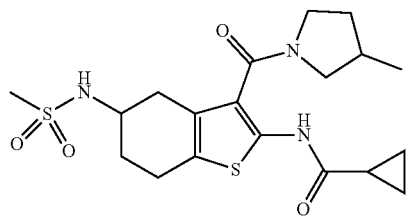

N-[5-(Methanesulfonamido)-3-(3-methylpyrrolidine-1-carbonyl)-4,5,6,7-tetrahydrobenzothiophen-2-yl]cyclopropanecarboxamide Intermediate 226 (129 mg, 0.34 mmol) was dissolved in DCM (5 mL) and DIPEA (109 mg, 0.84 mmol) and methanesulfonyl chloride [124-63-0] (50 mg, 0.44 mmol) added. The reaction was stirred at r.t. for ~16 h, was washed with water and passed through a phase separation cartridge and the organic phase was concentrated in vacuo. The crude residue was purified by flash column chromatography on silica (gradient elution with 40-100% EtOAc/hexane) to give the product which was freeze-dried from MeCN/water to afford the title compound (78 mg, 55%) as a white solid. $\delta_H$ (400 MHz, DMSO-$d_6$) 10.61 (s, 1H), 7.07 (s, 1H), 3.70-3.28 (m, 3H), 3.24 (s, 5H), 2.72-2.49 (m, 3H), 2.15 (s, 2H), 2.04-1.77 (m, 3H), 1.63 (br. s, 1H), 1.50-1.30 (m, 1H), 1.07-0.79 (m, 3H), 0.79-0.64 (m, 4H). LCMS (ES+) [M+H]+ 426.8, RT 1.649 minutes, 100.0% purity (Method 3). LCMS (ES+) [M+H]+ 426.8, RT 1.706 minutes, 100.0% purity (Method 2).

Example 212

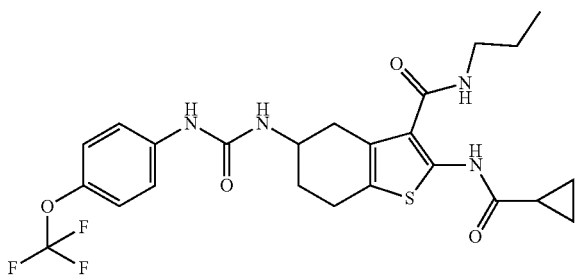

2-(Cyclopropanecarbonylamino)-N-propyl-5-[[4-(trifluoromethoxy)phenyl]carbamoylamino]-4,5,6,7-tetrahydrobenzothiophene-3-carboxamide Intermediate 228 (170 mg, 0.53 mmol) was dissolved in DCM (3 mL) and cooled to 0° C. and triethylamine (216 mg, 2.12 mmol) and 1-isocyanato-4-(trifluoromethoxy)benzene was added dropwise. The reaction mixture was warmed to r.t. and stirred overnight. The reaction mixture was concentrated in vacuo, Et$_2$O added and the precipitate filtered. The crude precipitate was purified by preparative HPLC (acidic) to afford the title compound (31 mg, 11%). $\delta_H$ (400 MHz, DMSO-$d_6$) δ 11.13 (s, 1H), 8.57 (s, 1H), 7.61 (t, J=5.7 Hz, 1H), 7.53-7.39 (m, 2H), 7.21 (d, J=8.6 Hz, 2H), 6.33 (d, J=7.6 Hz, 1H), 3.97 (t, J=7.8 Hz, 1H), 3.21 (ddd, J=12.4, 6.9, 5.1 Hz, 2H), 2.97 (dd, J=16.1, 5.1 Hz, 1H), 2.72 (t, J=6.4 Hz, 2H), 2.61-2.51 (m, 1H), 1.92 (dtd, J=12.5, 6.8, 4.0 Hz, 2H), 1.85-1.69 (m, 1H), 1.52 (h, J=7.3 Hz, 2H), 0.98-0.76 (m, 7H).
LCMS [M+H]+ 525.18, [M−H]− 523.18, RT 2.76 minutes, 97.76% purity (Method 9).

Example 213

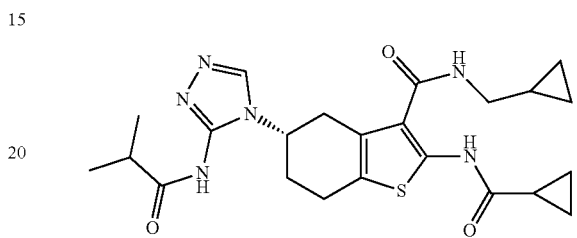

(5S)-2-(cyclopropanecarbonylamino)-N-(cyclopropylmethyl)-5-[3-(2-methylpropanoylamino)-1,2,4-triazol-4-yl]-4,5,6,7-tetrahydrobenzothiophene-3-carboxamide To a stirred solution of intermediate 243 (128 mg, 0.277 mmol) in DMF (7 mL) under nitrogen was added formic acid hydrazide [624-84-0] (46 mg, 0.692 mmol) and mercuric chloride [7487-94-7] (98 mg, 0.360 mmol). The reaction mixture was stirred at r.t. for 5 min before the addition of triethylamine (0.058 mL, 0.415 mmol) and the mixture was stirred at 80° C. for 17 h. The mixture was cooled to r.t. and diluted with MeCN (5 mL), filtered through a pad of celite and washed with MeCN (15 mL). The filtrate was concentrated in vacuo to yield the crude product as an tan solid. This solid was purified by flash column chromatography on silica (gradient elution with 50% to 100% EtOAc in isohexanes and then 0% to 20% EtOAc in DCM) to afford impure title compound as an off-white solid (14 mg). This solid was further purified by reverse phase chromatography on C18 silica (5% to 100% MeCN (w/0.1% NH3) in water (w/0.1% NH3)) and the product containing fractions were freeze dried to afford the title compound (3.0 mg, 0.006 mmol, 2%) as a white solid. LCMS (ES+) [M+H]+ 471.2, RT 1.60 minutes, purity 100% (Method 3). LCMS (ES+) [M+H]+ 471.2, RT 1.63 minutes, purity 100% (Method 2).

Example 214

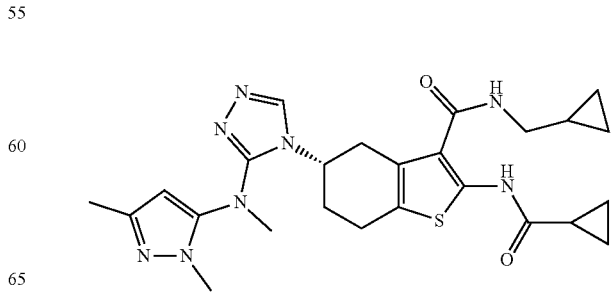

(5S)-2-(cyclopropanecarbonylamino)-N-(cyclopropylmethyl)-5-[3-[(2,5-dimethylpyrazol-3-yl)-methylamino]-1,2,4-triazol-4-yl]-4,5,6,7-tetrahydrobenzothiophene-3-carboxamide To a stirred solution of example 106 (70 mg, 0.142 mmol) dissolved in acetonitrile (5 mL) was added cesium carbonate (69 mg, 0.212 mmol) followed by iodomethane (11 μl, 0.170 mmol). The reaction was stirred at r.t. for 17 h before being concentrated in vacuo to give a gum. This gum was dissolved in DCM (50 mL), washed with water (30 mL) and the layers separated. The Aq layer was extracted with DCM (2×25 mL). The combined organic layers were passed through a phase separation cartridge and concentrated in vacuo to give a tan gum. This was purified by flash column chromatography on silica (gradient elution with 1% to 20% MeOH in DCM) to afford the title compound RF3 (15 mg, 0.029 mmol, 21%) as a white solid. LCMS [M+H]$^+$ 509.2, RT 1.67 minutes, purity 95.6% (Method 3). LCMS [M+H]$^+$ 509.2, RT 1.60 minutes, purity 95.1% (Method 3). 1H NMR (400 MHz, Methanol-d4) δ 8.43 (s, 1H), 5.85 (s, 1H), 3.92-3.78 (m, 1H), 3.67 (s, 3H), 3.33 (s, 3H), 3.26 (dd, J=13.8, 7.0 Hz, 1H), 3.18 (dd, J=13.8, 7.0 Hz, 1H), 3.05-2.96 (m, 1H), 2.92 (dd, J=15.6, 5.6 Hz, 1H), 2.85-2.76 (m, 1H), 2.72-2.60 (m, 1H), 2.20-2.01 (m, 5H), 1.86-1.77 (m, 1H), 1.15-1.03 (m, 1H), 1.03-0.89 (m, 4H), 0.55-0.48 (m, 2H), 0.31-0.24 (m, 2H).

Example 215

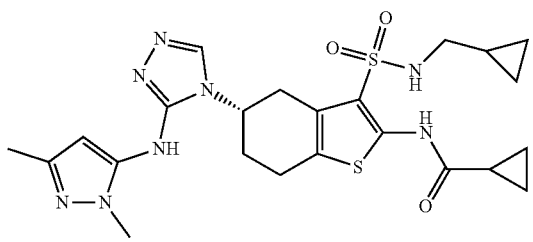

N-[(5S)-3-(cyclopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide Intermediate 172 (323 mg, 0.6179 mmol) was dissolved in N,N-dimethylformamide (10 mL) and formic acid hydrazide (111 mg, 1.8482 mmol) was added followed by mercuric chloride (337 mg, 1.235 mmol) and after 15 min triethylamine (0.26 mL, 1.9 mmol) was added. The reaction mixture was heated at 65° C. with a condenser o/n. Volatiles and DMF were then evaporated. The resulting residue was diluted with MeCN (20 mL) and filtered through a pad of celite. MeCN was added to wash through celite and resulting clear yellow solution was concentrated in vacuo to give a yellow oil. This oil was re-dissolved in MeOH/DCM, silica added, and dry-loaded on column for purification. The crude product was purified by flash column chromatography on silica (gradient elution with 25 g SNAP-Ultra, Isolera, MeOH/DCM, 0 to 10% in MeOH) to afford racemic title compound as white solid (140 mg, 0.2638 mmol, 42.69% Yield). This material was chiraly separated into its enantiomers to afford 13 mgs (4.00% yield) of the title compound. Conditions for separation: Lux Cellulose-2 21.2×250 mm 5 μm column, flow rate 10 mL/min, 100% MeOH isocratic, (R)-enantiomer: 4.105 min, (S)-enantiomer: 3.860 min.

$^1$H NMR (600 MHz, DMSO-d$_6$) δ 10.40 (s, 1H), 8.37 (s, 1H), 8.30 (s, 1H), 7.91 (d, J=18.4 Hz, 1H), 5.86 (s, 1H), 4.39 (d, J=30.0 Hz, 1H), 3.49 (s, 2H), 3.41 (s, 1H), 2.76 (s, 3H), 2.63 (s, 2H), 2.01 (s, 2H), 2.00-2.20 (m, 3H), 1.97 (s, 1H), 1.87 (s, 1H), 0.90-0.77 (m, 4H), 0.69 (s, 1H), 0.28 (t, J=9.0 Hz, 2H), 0.02 (m, 2H). LCMS [M+H]$^+$ 531.0, RT 1.75 minutes (Method 27), LCMS [M+H]$^+$ 531.0, RT 1.79 minutes (Method 26).

Example 216

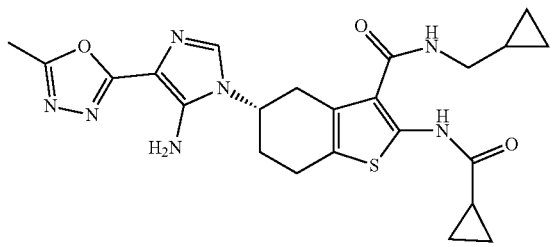

(5S)-5-[5-amino-4-(5-methyl-1,3,4-oxadiazol-2-yl)imidazol-1-yl]-2-(cyclopropanecarbonylamino)-N-(cyclopropylmethyl)-4,5,6,7-tetrahydrobenzothiophene-3-carboxamide Intermediate 219 (68%, 61 mg, 0.3 mmol) was dissolved in dry MeCN (4 mL) in a 20 mL pressure tube. Triethylorthoformate (50 μl, 0.3 mmol) was added, the reaction was sealed and heated to 90° C. for 1 hour. The reaction was allowed to cool to room temperature and intermediate 117 (100 mg, 0.3 mmol) was added. The suspension was stirred for 3 days at room temperature. The pale brown suspension was concentrated in vacuo and the solid purified by flash chromatography on silica (gradient elution using 0-10% MeOH in DCM) followed by trituration with ethyl acetate:heptane (1:1) to afford the title compound (20.5 mg, 14%) as a pink solid. δ$_H$ (500 MHz, DMSO-d$_6$) δ 11.21 (s, 1H), 7.72 (t, J 5.7 Hz, 1H), 7.44 (s, 1H), 5.96 (s, 2H), 4.45-4.35 (m, 1H), 3.20-3.05 (m, 3H), 3.05-2.96 (m, 1H), 2.93-2.76 (m, 2H), 2.55-2.44 (m, 3H, obscured by DMSO, observed in HSQC), 2.27-2.12 (m, 2H), 1.97-1.88 (m, 1H), 1.07-0.95 (m, 1H), 0.91-0.80 (m, 4H), 0.43-0.33 (m, 2H), 0.26-0.14 (m, 2H). LCMS [M+H]$^+$ 482.2, RT 2.49 minutes, 98% purity (Method 10).

Example 217

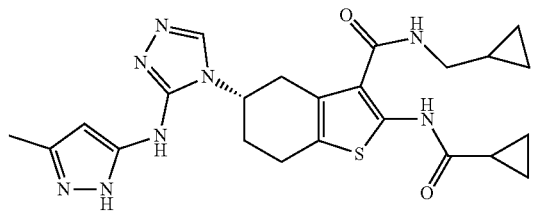

(5S)-2-(cyclopropanecarbonylamino)-N-(cyclopropylmethyl)-5-[3-[(3-methyl-1H-pyrazol-5-yl)amino]-1,2,4-triazol-4-yl]-4,5,6,7-tetrahydrobenzothiophene-3-carboxamide To a stirred solution of intermediate 245 (105 mg, 0.222 mmol) in DMF (5 mL) under nitrogen was added formic acid hydrazide [624-84-0] (22 mg, 0.333 mmol) and mercuric chloride [7487-94-7] (78 mg, 0.289 mmol). The reaction mixture was stirred at r.t. for 5 min before the addition of triethylamine (0.046 mL, 0.333 mmol) and the mixture was stirred at 80° C. for 2 h. The mixture was cooled to r.t. and diluted with MeCN (5 mL), filtered through a pad of celite and washed with MeCN (15 mL). The filtrate was concentrated in vacuo to yield the crude product as a tan solid. This solid was purified by flash column chromatography on silica (gradient elution with 90% to 100% EtOAc in isohexanes and then 0% to 20% MeOH in EtOAc) to afford impure title compound as an off-white solid (23 mg). This solid was further purified by reverse phase chromatography on C18 silica (5% to 100% MeCN (w/0.1% NH3) in water (w/0.1% NH3)) and the product containing fractions were freeze dried to afford the title compound (9.0 mg, 0.019 mmol, 8.4%) as a white solid. LCMS (ES+) [M+H]$^+$ 481.0, RT 1.53 minutes, purity 100% (Method 3). LCMS (ES+) [M+H]$^+$ 481.0, RT 1.50 minutes, purity 100% (Method 2). 1H NMR (400 MHz, DMSO-d6) δ 11.72 (s, 1H), 11.24 (s, 1H), 8.93 (s, 1H), 8.27 (s, 1H), 7.89-7.50 (m, 1H), 6.21 (s, 1H), 4.68-4.28 (m, 1H), 3.20-3.03 (m, 3H), 3.00-2.75 (m, 3H), 2.23-2.09 (m, 5H), 1.99-1.88 (m, 1H), 1.04-0.95 (m, 1H), 0.91-0.81 (m, 4H), 0.40-0.31 (m, 2H), 0.21-0.15 (m, 2H).

Example 218

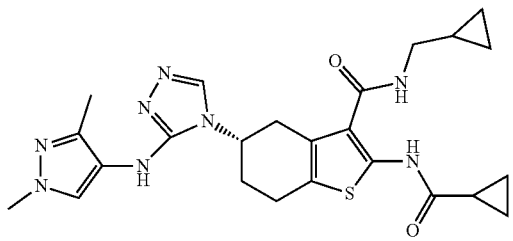 [SMILES: Cc1nn(C)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(1,3-dimethylpyrazol-4-yl)amino]-1,2,4-triazol-4-yl]-4,5,6,7-tetrahydrobenzothiophene-3-carboxamide To a stirred solution of intermediate 230 (478.3 mg, 0.9338 mmol, 95 mass %) in DMF (6.6 mL) under nitrogen was added formic acid hydrazide [624-84-0] (170.1 mg, 2.832 mmol) and mercuric chloride [7487-94-7] (770.5 mg, 2.824 mmol). The reaction mixture was stirred at r.t. for 5 min before the addition of triethylamine (0.40 mL, 2.9 mmol) and the mixture was stirred at 60° C. for 19.5 h. The mixture was cooled to r.t. and diluted with MeCN (20 mL), filtered through a pad of celite and washed with MeCN (25 mL). The filtrate was concentrated in vacuo to yield the crude product as an orange oil which was dissolved in 5% MeOH in DCM (50 mL), washed with water (30 mL) and the layers separated. The aqueous layer was extracted with 5% MeOH in DCM (2×25 mL). The combined organic layers were passed through a phase separation cartridge and concentrated in vacuo to give an orange oil. This oil was purified by flash column chromatography on silica (gradient elution with 0% to 20% MeOH in DCM) to afford impure title compound as a white residue (116.0 mg). This residue was dissolved in MeOH (4 mL), QuadraSil® MTU (120 mg) was added and the suspension was stirred at r.t. for 4.5 h before being filtered and washed with MeOH (2×5 mL). The filtrate was concentrated in vacuo to give a white solid which was further purified by reverse phase chromatography on C18 silica (5% to 100% MeCN (w/0.1% NH3) in water (w/0.1% NH3)) and the product containing fractions were freeze dried to afford the title compound (51.5 mg, 0.104 mmol, 11%) as a white solid. LCMS (ES+) [M+H]$^+$ 494.8, RT 1.91 minutes, purity 97% (Method 24). LCMS (ES+) [M+H]$^+$ 494.8, RT 1.97 minutes, purity 97% (Method 25). 1H NMR (400 MHz, DMSO-d$_6$) δ 11.25 (s, 1H), 8.21 (s, 1H), 7.80 (s, 1H), 7.72 (t, J=5.9 Hz, 1H), 7.64 (s, 1H), 4.53-4.41 (m, 1H), 3.72 (s, 3H), 3.21-3.04 (m, 3H), 3.00-2.78 (m, 3H), 2.26-2.13 (m, 2H), 2.08 (s, 3H), 1.98-1.88 (m, 1H), 1.06-0.94 (m, 1H), 0.92-0.77 (m, 4H), 0.43-0.30 (m, 2H), 0.22-0.15 (m, 2H).

Example 219

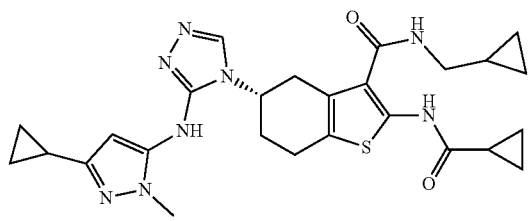 [SMILES: Cn1nc(C2CC2)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide To a stirred solution of intermediate 247 (1.38 g, 2.69 mmol) in DMF (20 mL) under nitrogen was added formic acid hydrazide [624-84-0] (539 mg, 8.07 mmol) and mercuric chloride [7487-94-7] (1.1 g, 4.04 mmol). The reaction mixture was stirred at r.t. for 15 min before the addition of triethylamine (1.13 mL, 8.07 mmol) and the mixture was stirred at 60° C. for 16 h. The mixture was cooled to r.t. and diluted with MeCN (20 mL), filtered through a pad of celite and washed with MeCN (30 mL). The filtrate was concentrated in vacuo to yield the crude product as a yellow gum which was dissolved in DCM (100 mL), washed with water (50 mL) and the layers separated. The Aq layer was extracted with DCM (2×25 mL). The combined organic layers were washed with brine (50 ml) and passed through a phase separation cartridge and concentrated in vacuo to give a yellow gum. This was purified by flash column chromatography on silica (gradient elution with 2% to 20% MeOH in DCM) to afford impure title compound as an off-white solid. This solid was dissolved in MeOH (50 mL) and QuadraSil® MTU (2.0 g) was added and the suspension was stirred at r.t. for 2 h before being filtered and washed with MeOH (2×15 mL). The filtrate was concentrated in vacuo to give a colourless gum. This was further purified by flash column chromatography on silica (gradient elution with 5% to 25% MeOH in EtOAc) product containing fractions were freeze dried to afford the title compound (673 mg, 1.29 mmol, 48%) as a white solid. LCMS (ES+) [M+H]⁺ 521.0, RT 1.71 minutes, purity 100% (Method 3). LCMS (ES+) [M+H]⁺ 521.0, RT 1.68 minutes, purity 100% (Method 2). 1H NMR (300 MHz, DMSO-d6) (contained 2 tautomers in an approximate ratio of 0.7:0.3) δ 11.71 (s, 0.3H), 11.25 (s, 0.7H), 11.20 (s, 0.3H), 8.43 (s, 0.7H), 8.35 (s, 0.7H), 8.12 (s, 0.3H), 7.87-7.59 (m, 1H), 5.80 (s, 0.7H), 5.60 (s, 0.3H), 4.55-4.26 (m, 1H), 3.55 (s, 2H), 3.47 (s, 1H), 3.22-2.74 (m, 6H), 2.29-2.10 (m, 2H), 2.01-1.86 (m, 1H), 1.83-1.63 (m, 0.7H), 1.08-0.93 (m, 0.3H), 0.91-0.72 (m, 6H), 0.62-0.54 (m, 2H), 0.42-0.33 (m, 2H), 0.23-0.15 (m, 2H).

Example 220

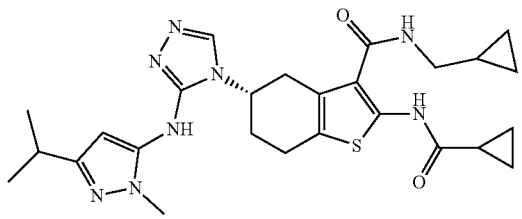 [SMILES: CC(C)c1cc(Nc2nncn2[C@H]2CCc3sc(NC(=O)C4CC4)c(C(=O)NCC4CC4)c3C2)n(C)n1]

(5S)-2-(cyclopropanecarbonylamino)-N-(cyclopropylmethyl)-5-[3-[(5-isopropyl-2-methyl-pyrazol-3-yl)amino]-1,2,4-triazol-4-yl]-4,5,6,7-tetrahydrobenzothiophene-3-carboxamide To a stirred solution of intermediate 249 (282 mg, 0.548 mmol) in DMF (10 mL) under nitrogen was added formic acid hydrazide [624-84-0] (110 mg, 1.64 mmol) and mercuric chloride [7487-94-7] (446 mg, 1.64 mmol). The reaction mixture was stirred at r.t. for 15 min before the addition of triethylamine (0.23 mL, 1.64 mmol) and the mixture was stirred at 60° C. for 16 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 1% to 20% MeOH in DCM) to afford impure title compound as a pale yellow gum. This was purified again by flash column chromatography on silica (gradient elution with 5% to 25% MeOH in EtOAc) to give a white solid. This solid was dissolved in MeOH (10 mL) and QuadraSil® MTU (130 mg) was added and the suspension was stirred at r.t. for 2 h before being filtered and washed with MeOH (2×10 mL). The filtrate was concentrated in vacuo to give a colourless gum. This was further purified by flash column chromatography on silica (gradient elution with 5% to 25% MeOH in EtOAc) product containing fractions were freeze dried to afford the title compound (98 mg, 0.188 mmol, 34%) as a white solid. LCMS (ES+) [M+H]⁺ 523.0, RT 1.80 minutes, purity 100% (Method 3). LCMS (ES+) [M+H]⁺ 523.0, RT 1.75 minutes, purity 100% (Method 2). 1H NMR (300 MHz, DMSO-d6) (contained 2 tautomers in an approximate ratio of 0.7:0.3) δ 11.74 (s, 0.3H), 11.37-11.07 (m, 1H), 8.43 (s, 0.7H), 8.36 (s, 0.7H), 8.12 (s, 0.3H), 7.84-7.62 (m, 1H), 5.93 (s, 0.7H), 5.79 (s, 0.3H), 4.47-4.31 (m, 1H), 3.58 (s, 2H), 3.50 (s, 1H), 3.22-2.66 (m, 7H), 2.30-2.11 (m, 2H), 1.99-1.85 (m, 1H), 1.16 (d, J=6.9 Hz, 6H), 0.90-0.78 (m, 4H), 0.42-0.31 (m, 2H), 0.23-0.15 (m, 2H).

Example 221

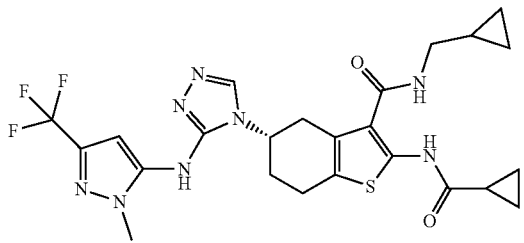 [SMILES: Cn1nc(C(F)(F)F)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide To a stirred solution of intermediate 232 (1.040 g, 1.924 mmol) in DMF (13.5 mL) under nitrogen was added formic acid hydrazide [624-84-0] (347.1 mg, 5.779 mmol) and mercuric chloride [7487-94-7] (630.2 mg, 2.310 mmol). The reaction mixture was stirred at r.t. for 5 min before the addition of triethylamine (0.80 mL, 5.7 mmol) and the mixture was stirred at 80° C. for 21.5 h. The mixture was cooled to r.t. and diluted with MeCN (60 mL), filtered through a pad of celite and washed with MeCN (30 mL). The filtrate was concentrated in vacuo to yield the crude product as an orange oil which was dissolved in 5% MeOH in DCM (100 mL), washed with water (100 mL) and the layers separated. The aqueous layer was extracted with 5% MeOH in DCM (2×50 mL). The combined organic layers were passed through a phase separation cartridge and concentrated in vacuo to give an orange oil. This oil was purified by flash column chromatography on silica (gradient elution with 0% to 15% MeOH in DCM) to afford impure title compound as an orange oil (1.443 g). This residue was dissolved in MeOH (13.5 mL), QuadraSil® MTU (2.00 g) was added and the suspension was stirred at 40° C. for 4 h before being filtered and washed with MeOH (2×10 mL). The filtrate was concentrated in vacuo to give an orange oil which was further purified by preparative SFC (Waters Prep 100, Column—Viridis BEH 2-ethylpyridine (2-EP), 5-15% MeOH+0.1% NH4OH in CO₂) and the product containing fractions were freeze dried to afford the title compound (505.8 mg, 0.9220 mmol, 48%) as a white solid. LCMS (ES+) [M+H]⁺ 549.0, RT 2.101 minutes, purity 99.7% (Method 2). LCMS (ES+) [M+H]⁺ 549.0, RT 2.020 minutes, purity 99.7% (Method 3). 1H NMR (300 MHz, DMSO-d6) (contained 2 tautomers in an approximate ratio of 0.8:0.2) δ 12.19 (s, 0.8H), 11.21 (s, 1H), 8.90 (s, 0.2H), 8.42 (s, 0.2H), 8.24 (s, 0.8H), 7.75 (s, 1H), 6.60 (s, 0.2H), 6.36 (s, 0.8H), 4.62-4.32 (m, 1H), 3.86-3.49 (m, 3H), 3.25-2.76 (m, 6H), 2.32-2.12 (m, 2H), 2.01-1.84 (m, 1H), 1.08-0.93 (m, 1H), 0.92-0.76 (m, 4H), 0.43-0.30 (m, 2H), 0.22-0.10 (m, 2H).

Example 222

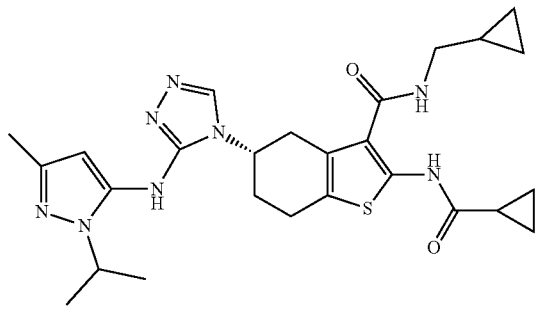 [SMILES: Cc1cc(Nc2nncn2[C@H]2CCc3sc(NC(=O)C4CC4)c(C(=O)NCC4CC4)c3C2)n(C(C)C)n1]

(5S)-2-(cyclopropanecarbonylamino)-N-(cyclopropylmethyl)-5-[3-[(2-isopropyl-5-methyl-pyrazol-3-yl)amino]-1,2,4-triazol-4-yl]-4,5,6,7-tetrahydrobenzothiophene-3-carboxamide To a stirred solution of intermediate 234 (385.9 mg, 0.7498 mmol) in DMF (5.3 mL) under nitrogen was added formic acid hydrazide [624-84-0] (136.1 mg, 2.266 mmol) and mercuric chloride [7487-94-7] (615.2 mg, 2.255 mmol). The reaction mixture was stirred at r.t. for 5 min before the addition of triethylamine (0.31 mL, 2.2 mmol) and the mixture was stirred at 80° C. for 5 h and then at 60° C. for a further 17 h. The mixture was cooled to r.t. and diluted with MeCN (20 mL), filtered through a pad of celite and washed with MeCN (25 mL). The filtrate was concentrated in vacuo to yield the crude product as an orange oil that solidified upon standing which was dissolved in 5% MeOH in DCM (50 mL), washed with water (30 mL) and the layers separated. The aqueous layer was extracted with 5% MeOH in DCM (2×25 mL). The combined organic layers were passed through a phase separation cartridge and concentrated in vacuo to give an orange oil. This oil was purified by flash column chromatography on silica (gradient elution with 0% to 20% MeOH in DCM) to afford impure title compound as a pale yellow glass (196.0 mg). The impure product was dissolved in a mixture of MeOH (3 mL) and MeCN (1.0 mL), QuadraSil® MTU (200 mg) was added and the suspension was stirred at 40° C. for 2 h before being filtered and washed with MeOH (2×5 mL). The filtrate was concentrated in vacuo to give a pale yellow oil which was further purified by flash column chromatography on silica (gradient elution with 0% to 20% MeOH in EtOAc) and the product containing fractions were concentrated then the material was freeze dried to afford the title compound (96.4 mg, 0.184 mmol, 25%) as a white solid. LCMS (ES+) [M+H]$^+$ 523.0, RT 1.675 minutes, purity 96.6% (Method 2). LCMS (ES+) [M+H]$^+$ 523.0, RT 1.742 minutes, purity 96.1% (Method 3). 1H NMR (400 MHz, DMSO-d6) (contained 2 tautomers in an approximate ratio of 0.6:0.4) δ 11.71 (s, 0.4H), 11.23 (s, 0.6H), 11.20 (s, 0.4H), 8.33 (s, 0.6H), 8.27 (s, 0.6H), 8.10 (s, 0.4H), 7.74 (s, 1H), 5.84 (s, 0.6H), 5.69 (s, 0.4H), 4.71-4.62 (m, 0.4H), 4.48-4.30 (m, 1.6H), 3.24-3.05 (m, 3H), 3.04-2.90 (m, 1H), 2.87-2.78 (m, 2H), 2.27-2.14 (m, 2H), 2.11 (s, 1.8H), 2.07 (s, 1.2H), 1.99-1.87 (m, 1H), 1.29 (d, J=6.6 Hz, 3.6H), 1.25 (d, J=6.7 Hz, 1.2H), 1.22 (d, J=6.6 Hz, 1.2H), 1.07-0.94 (m, 1H), 0.93-0.79 (m, 4H), 0.41-0.32 (m, 2H), 0.23-0.13 (m, 2H).

Example 223

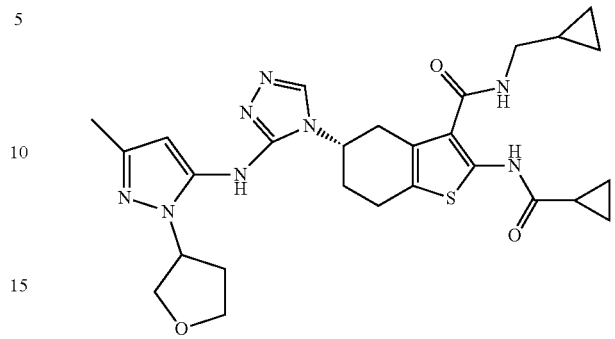

(5S)-2-(cyclopropanecarbonylamino)-N-(cyclopropylmethyl)-5-[3-[(5-methyl-2-tetrahydrofuran-3-yl-pyrazol-3-yl)amino]-1,2,4-triazol-4-yl]-4,5,6,7-tetrahydrobenzothiophene-3-carboxamide To a stirred solution of intermediate 236 (385.4 mg, 0.7102 mmol) in DMF (5.0 ml-) under nitrogen was added formic acid hydrazide [624-84-0] (130.1 mg, 2.166 mmol) and mercuric chloride [7487-94-7] (595.1 mg, 2.181 mmol). The reaction mixture was stirred at r.t. for 5 min before the addition of triethylamine (0.30 mL, 2.1 mmol) and the mixture was stirred at 80° C. for 5 h and then at 60° C. for a further 18 h. The mixture was cooled to r.t. and diluted with MeCN (20 mL), filtered through a pad of celite and washed with MeCN (25 mL). The filtrate was concentrated in vacuo to yield the crude product as an orange oil that solidified upon standing which was dissolved in 5% MeOH in DCM (50 mL), washed with water (30 mL) and the layers separated. The Aq layer was extracted with 5% MeOH in DCM (2×25 mL). The combined organic layers were passed through a phase separation cartridge and concentrated in vacuo to give an orange oil. This oil was purified by flash column chromatography on silica (gradient elution with 0% to 20% MeOH in DCM) to afford impure title compound as a pale yellow glass (190.6 mg). The impure product was dissolved in a mixture of MeOH (3 mL) and MeCN (1.0 mL), QuadraSil® MTU (200 mg) was added and the suspension was stirred at 40° C. for 2 h before being filtered and washed with MeOH (2×5 mL). The filtrate was concentrated in vacuo to give a very pale yellow solid which was further purified by flash column chromatography on silica (gradient elution with 0% to 20% MeOH in EtOAc) and the product containing fractions were concentrated then the material was freeze dried to afford the title compound (104.0 mg, 0.1889 mmol, 27%) as a white solid. LCMS (ES+) [M+H]+ 551.0, RT 1.613 minutes, purity 98.2% (Method 2). LCMS (ES+) [M+H]+ 551.0, RT 1.646 minutes, purity 96.6% (Method 3). 1H NMR (400 MHz, DMSO-d6) (contained 2 tautomers in an approximate ratio of 0.5:0.5) δ 11.79 (s, 0.5H), 11.24 (s, 0.5H), 11.20 (d, J=5.9 Hz, 0.5H), 8.40 (s, 0.5H), 8.35 (s, 0.5H), 8.13 (d, J=2.0 Hz, 0.5H), 7.80-7.67 (m, 1H), 5.91 (d, J=1.5 Hz, 0.5H), 5.74 (s, 0.5H), 5.16-5.02 (m, 0.5H), 4.94-4.82 (m, 0.5H), 4.49-4.33 (m, 1H), 4.04-3.83 (m, 2H), 3.81-3.61 (m, 2H), 3.23-3.05 (m, 3H), 3.04-2.77 (m, 3H), 2.33-2.13 (m, 4H), 2.12 (s, 1.5H), 2.08 (s, 1.5H), 2.00-1.85 (m, 1H), 1.07-0.95 (m, 1H), 0.93-0.76 (m, 4H), 0.43-0.31 (m, 2H), 0.26-0.14 (m, 2H).

Example 224

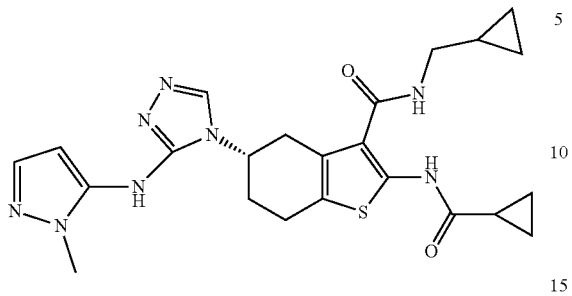

(5S)-2-(cyclopropanecarbonylamino)-N-(cyclopropylmethyl)-5-[3-[(2-methylpyrazol-3-yl)amino]-1,2,4-triazol-4-yl]-4,5,6,7-tetrahydrobenzothiophene-3-carboxamide To a stirred solution of intermediate 238 (1.3368 g, 2.829 mmol) in DMF (20 mL) under nitrogen was added formic acid hydrazide [624-84-0] (550.4 mg, 9.164 mmol) and mercuric chloride [7487-94-7](1.201 g, 4.402 mmol). The reaction mixture was stirred at r.t. for 20 min before the addition of triethylamine (1.2 mL, 8.6 mmol) and the mixture was stirred at 80° C. for 4 h. The mixture was cooled to r.t. and diluted with MeCN (50 mL), filtered through a pad of celite and washed with MeCN (40 mL). The filtrate was concentrated in vacuo to yield the crude product as a grey oil. This grey oil was purified by flash column chromatography on silica (dry loaded, gradient elution with 0% to 20% MeOH in DCM) to afford impure title compound as a pale yellow oil (1.8369 g). This oil was dissolved in 5% MeOH in DCM (150 mL), washed with water (125 mL) and the layers separated. The Aq layer was extracted with 5% MeOH in DCM (2×50 mL). The combined organic layers were passed through a phase separation cartridge and concentrated in vacuo to give a pale yellow oil (1.0345 g) that solidified upon standing. The impure product was dissolved in MeOH (20 mL), QuadraSil® MTU (2.0 g) was added and the suspension was stirred at 40° C. for 3.5 h before being filtered and washed with MeOH (2×10 mL). The filtrate was concentrated in vacuo to give a colourless oil which was further purified by flash column chromatography on silica (gradient elution with 0% to 20% MeOH in EtOAc) and the product containing fractions were concentrated then the material was freeze dried to afford the title compound (801.0 mg, 1.667 mmol, 59%) as a white solid. LCMS (ES+) [M+H]+ 481.0, RT 1.473 minutes, purity 99% (Method 2). LCMS (ES+) [M+H]+ 481.0, RT 1.495 minutes, purity 99% (Method 3). 1H NMR (300 MHz, DMSO-d6) (contained 2 tautomers in an approximate ratio of 0.6:0.4) δ 11.83 (s, 0.4H), 11.25 (s, 0.6H), 11.21 (s, 0.4H), 8.51 (s, 0.6H), 8.36 (s, 0.6H), 8.15 (s, 0.4H), 7.83-7.63 (m, 1H), 7.30 (d, J=1.9 Hz, 0.6H), 7.19 (d, J=2.0 Hz, 0.4H), 6.11 (d, J=1.9 Hz, 0.6H), 5.91 (d, J=2.0 Hz, 0.4H), 4.53-4.34 (m, 1H), 3.65 (s, 1.8H), 3.57 (s, 1.2H), 3.25-2.77 (m, 6H), 2.27-2.11 (m, 2H), 1.99-1.88 (m, 1H), 1.08-0.94 (m, 1H), 0.92-0.78 (m, 4H), 0.43-0.31 (m, 2H), 0.25-0.10 (m, 2H).

Example 225

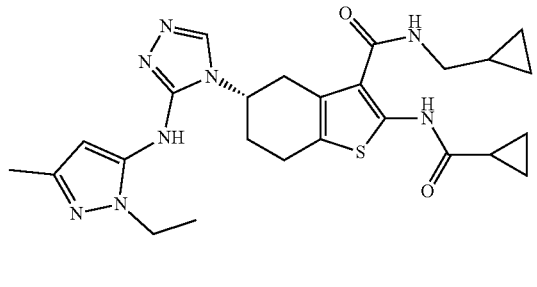 [SMILES: CCn1nc(C)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(2-ethyl-5-methyl-pyrazol-3-yl)amino]-1,2,4-triazol-4-yl]-4,5,6,7-tetrahydrobenzothiophene-3-carboxamide To a stirred solution of intermediate 251 (303 mg, 0.605 mmol) in DMF (10 mL) under nitrogen was added formic acid hydrazide [624-84-0] (121 mg, 1.82 mmol) and mercuric chloride [7487-94-7] (493 mg, 1.82 mmol). The reaction mixture was stirred at r.t. for 15 min before the addition of triethylamine (0.25 mL, 1.82 mmol) and the mixture was stirred at 60° C. for 4 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 1% to 20% MeOH in DCM) to afford impure title compound as a pale yellow gum. This was dissolved in MeOH (10 mL) and QuadraSil® MTU (130 mg) was added and the suspension was stirred at 50° C. for 2 h before being filtered and washed with MeOH (2×10 mL). The filtrate was concentrated in vacuo to give a colourless gum. This was further purified by flash column chromatography on silica (gradient elution with 5% to 25% MeOH in EtOAc) product containing fractions were freeze dried to afford the title compound (83 mg, 0.163 mmol, 27%) as a white solid. LCMS (ES+) [M+H]+ 509.0, RT 1.63 minutes, purity 100% (Method 3). LCMS (ES+) [M+H]+ 509.0, RT 1.60 minutes, purity 100% (Method 2). 1H NMR (300 MHz, DMSO-d6) (contained 2 tautomers in an approximate ratio of 0.6:0.4) δ 11.73 (s, 0.4H), 11.36-11.08 (m, 1H), 8.43-8.25 (m, 1.2H), 8.11 (s, 0.4H), 7.86-7.62 (m, 1H), 5.87 (s, 0.6H), 5.70 (s, 0.4H), 4.51-4.23 (m, 1H), 3.90 (q, J=7.2 Hz, 2H), 3.24-2.76 (m, 5.6H), 2.32-2.14 (m, 2H), 2.10 (s, 2H), 2.06 (s, 1H), 2.00-1.87 (m, 1H), 1.29-1.13 (m, 3H), 1.07-0.94 (m, 0.3H), 0.93-0.79 (m, 4H), 0.42-0.30 (m, 2H), 0.24-0.15 (m, 2H).

Example 226

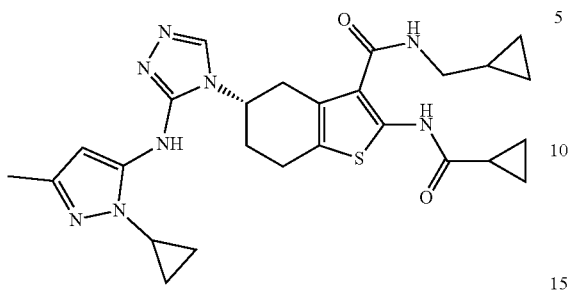

(5S)-2-(cyclopropanecarbonylamino)-N-(cyclopropylmethyl)-5-[3-[(2-cyclopropyl-5-methyl-pyrazol-3-yl)amino]-1,2,4-triazol-4-yl]-4,5,6,7-tetrahydrobenzothiophene-3-carboxamide To a stirred solution of intermediate 253 (292 mg, 0.570 mmol) in DMF (10 mL) under nitrogen was added formic acid hydrazide [624-84-0] (114 mg, 1.71 mmol) and mercuric chloride [7487-94-7] (464 mg, 1.71 mmol). The reaction mixture was stirred at r.t. for 15 min before the addition of triethylamine (0.24 mL, 1.71 mmol) and the mixture was stirred at 60° C. for 4 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 1% to 20% MeOH in DCM) to afford impure title compound as a pale yellow gum. This was dissolved in MeOH (10 mL) and QuadraSil® MTU (130 mg) was added and the suspension was stirred at 50° C. for 2 h before being filtered and washed with MeOH (2×10 mL). The filtrate was concentrated in vacuo to give a gum. This was further purified by flash column chromatography on silica (gradient elution with 5% to 25% MeOH in EtOAc) product containing fractions were freeze dried to afford the title compound (46 mg, 0.088 mmol, 16%) as a white solid. LCMS (ES+) [M+H]$^+$ 521.0, RT 1.65 minutes, purity 100% (Method 3). LCMS (ES+) [M+H]$^+$ 521.0, RT 1.61 minutes, purity 100% (Method 2). 1H NMR (300 MHz, DMSO-d6) (contained 2 tautomers in an approximate ratio of 0.7:0.3) δ 11.75 (s, 0.3H), 11.34-11.04 (m, 1H), 8.45 (s, 0.7H), 8.35 (s, 0.7H), 8.13 (s, 0.3H), 7.84-7.62 (m, 1H), 5.89 (s, 0.7H), 5.69 (s, 0.3H), 4.60-4.29 (m, 1H), 3.25-2.76 (m, 6H), 2.30-2.15 (m, 2H), 2.06 (s, 2H), 2.03 (s, 1H), 1.99-1.83 (m, 1H), 1.07-0.69 (m, 8H), 0.42-0.33 (m, 2H), 0.25-0.15 (m, 2H).

Example 227

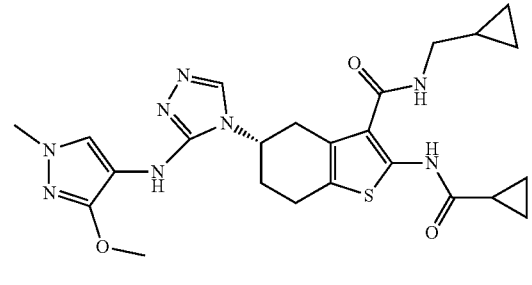 [SMILES: COc1nn(C)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(3-methoxy-1-methy-pyrazol-4-yl)amino]-1,2,4-triazol-4-yl]-4,5,6,7-tetrahydrobenzothiophene-3-carboxamide To a stirred solution of intermediate 240 (376.0 mg, 0.7481 mmol) in DMF (5.2 mL) under nitrogen was added formic acid hydrazide [624-84-0] (134.0 mg, 2.231 mmol) and mercuric chloride [7487-94-7] (640.5 mg, 2.347 mmol). The reaction mixture was stirred at r.t. for 5 min before the addition of triethylamine (0.31 mL, 2.2 mmol) and the mixture was stirred at 80° C. for 2.5 h. The mixture was cooled to r.t. and diluted with MeCN (20 mL), filtered through a pad of celite and washed with MeCN (25 mL). The filtrate was concentrated in vacuo to yield the crude product as a yellow oil that solidified upon standing which was dissolved in 5% MeOH in DCM (50 mL), washed with water (30 mL) and the layers separated. The Aq layer was extracted with 5% MeOH in DCM (2×25 mL). The combined organic layers were passed through a phase separation cartridge and concentrated in vacuo to give a yellow oil. This oil was purified by flash column chromatography on silica (gradient elution with 0% to 20% MeOH in DCM) to afford impure title compound as a colourless oil (59.5 mg). The impure product was dissolved in MeOH (4 mL), QuadraSil® MTU (250 mg) was added and the suspension was stirred at 40° C. for 0.5 h before being filtered and washed with MeOH (2×5 mL). The filtrate was concentrated in vacuo to give a colourless oil which was further purified by flash column chromatography on silica (gradient elution with 0% to 20% MeOH in EtOAc) and the product containing fractions were concentrated then the material was freeze dried to afford the title compound (27.7 mg, 0.0542 mmol, 7%) as a white solid. LCMS (ES+) [M+H]$^+$ 511.0, RT 1.404 minutes, purity 100% (Method 2). LCMS (ES+) [M+H]$^+$ 511.0, RT 1.541 minutes, purity 100% (Method 3). 1H NMR (400 MHz, DMSO-d6) δ 11.23 (s, 1H), 8.20 (s, 1H), 7.80 (s, 1H), 7.78 (s, 1H), 7.72 (t, J=5.7 Hz, 1H), 4.56-4.40 (m, 1H), 3.80 (s, 3H), 3.66 (s, 3H), 3.21-3.02 (m, 3H), 2.98-2.74 (m, 3H), 2.27-2.03 (m, 2H), 2.03-1.82 (m, 1H), 1.08-0.94 (m, 1H), 0.93-0.77 (m, 4H), 0.46-0.29 (m, 2H), 0.26-0.11 (m, 2H).

Example 228

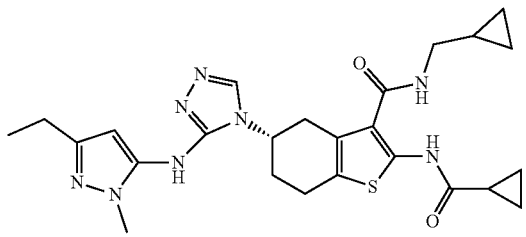 [SMILES: CCc1cc(Nc2nncn2[C@H]2CCc3sc(NC(=O)C4CC4)c(C(=O)NCC4CC4)c3C2)n(C)n1]

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide To a stirred solution of intermediate 243 (327.6 mg, 0.6543 mmol) in DMF (4.6 mL) under nitrogen was added formic acid hydrazide [624-84-0] (140.1 mg, 2.333 mmol) and mercuric chloride [7487-94-7] (562.3 mg, 2.061 mmol). The reaction mixture was stirred at r.t. for 5 min before the addition of triethylamine (0.27 mL, 1.9 mmol) and the mixture was stirred at 80° C. for 4 h. The mixture was cooled to r.t. and diluted with MeCN (20 mL), filtered through a pad of celite and washed with MeCN (25 mL). The filtrate was concentrated in vacuo to yield the crude product a yellow oil which was dissolved in 5% MeOH in DCM (50 mL), washed with water (30 mL) and the layers separated. The Aq layer was extracted with 5% MeOH in DCM (2×25 mL). The combined organic layers were passed through a phase separation cartridge and concentrated in vacuo to give a yellow oil. This oil was purified by flash column chromatography on silica (gradient elution with 0% to 20% MeOH in DCM) to afford impure title compound as a grey oil (229.8 mg). The impure product was dissolved in MeOH (4 mL), QuadraSil® MTU (500 mg) was added and the suspension was stirred at 40° C. for 0.5 h before being filtered and washed with MeOH (2×5 mL). The filtrate was concentrated in vacuo to give a grey oil which was further purified by flash column chromatography on silica (gradient elution with 0% to 20% MeOH in EtOAc) and the product containing fractions were concentrated then the material was freeze dried to afford the title compound (157.3 mg, 0.3093 mmol, 47%) as a white solid. LCMS (ES+) [M+H]$^+$ 509.0, RT 1.644 minutes, purity 99% (Method 2). LCMS (ES+) [M+H]$^+$ 509.0, RT 1.680 minutes, purity 99% (Method 3). 1H NMR (300 MHz, DMSO-d6) (contained 2 tautomers in an approximate ratio of 0.7:0.3) 6 11.75 (s, 0.3H), 11.25 (s, 0.7H), 11.20 (s, 0.3H), 8.44 (s, 0.7H), 8.35 (s, 0.7H), 8.12 (s, 0.3H), 7.81-7.65 (m, 1H), 5.93 (s, 0.7H), 5.76 (s, 0.3H), 4.53-4.33 (m, 1H), 3.57 (s, 2.1H), 3.50 (s, 0.9H), 3.32 (s, 3H), 3.24-2.75 (m, 6H), 2.48-2.37 (m, 2H), 2.31-2.10 (m, 2H), 1.98-1.85 (m, 1H), 1.20-1.08 (m, 3H), 1.07-0.93 (m, 1H), 0.93-0.77 (m, 4H), 0.43-0.31 (m, 2H), 0.23-0.14 (m, 2H).

Example 229

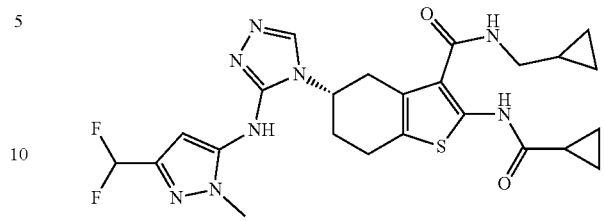

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide To a stirred solution of intermediate 255 (1.08 g, 2.07 mmol) in DCM (15 mL) at 0° C. under nitrogen was added triethylamine (0.865 mL, 6.19 mmol) and methanesulfonyl chloride [124-63-0] (0.17 ml, 2.19 mmol). The reaction mixture was stirred at 0° C. for 1 h then transferred to a separating funnel, diluting with DCM (80 ml), washed with saturated NH4Cl solution (50 ml) and brine (50 ml). The organic layer was passed through a phase separation cartridge and concentrated in vacuo to give a yellow gum. This was dissolved in DMF (10 ml) under nitrogen and formic acid hydrazide [624-84-0](372 mg, 6.19 mmol) added. The reaction mixture was stirred at r.t. for 30 min. Sodium carbonate (481 mg, 4.54 mmol) was added and the mixture stirred at 45° C. under nitrogen for 16 h then allowed to cool to room temperature. Sodium carbonate (240 mg, 2.27 mmol) as a solution in water (2 ml) was added and the mixture stirred at 55° C. under nitrogen for 5 h. The mixture was cooled to r.t. and concentrated in vacuo. The residue was dissolved in 5% MeOH/DCM (100 mL), washed with water (50 mL) and the layers separated. The Aq layer was extracted with DCM (2×25 mL). The combined organic layers were washed with brine (50 ml) and passed through a phase separation cartridge and concentrated in vacuo to give a brown gum. This was purified by flash column chromatography on silica (gradient elution with 1% to 10% MeOH in DCM) to afford impure title compound as an off-white solid. This was further purified by flash column chromatography on silica (gradient elution with 60% to 100% EtOAc in isohexane) product containing fractions were freeze dried to afford the title compound (613 mg, 1.16 mmol, 56%) as a white solid. LCMS (ES+) [M+H]$^+$ 531.0, RT 1.92 minutes, purity 99% (Method 3). LCMS (ES+) [M+H]$^+$ 531.0, RT 1.86 minutes, purity 99% (Method 2). 1H NMR (300 MHz, DMSO-d6) (contained 2 tautomers in an approximate ratio of 0.6:0.4) 6 12.08 (s, 0.6H), 11.32-11.12 (m, 1H), 8.75 (s, 0.4H), 8.41 (s, 0.4H), 8.20 (s, 0.6H), 7.84-7.65 (m, 1H), 7.07-6.50 (m, 1H), 6.41 (s, 0.4H), 6.20 (s, 0.6H), 4.47 (dt, J=9.9, 5.0 Hz, 0.6H), 3.71 (s, 1H), 3.61 (s, 2H), 3.24-2.75 (m, 4H), 2.33-2.12 (m, 3H), 2.02-1.86 (m, 1H), 1.08-0.94 (m, 1H), 0.92-0.78 (m, 5H), 0.35 (dq, J=7.7, 3.5, 2.7 Hz, 2H), 0.24-0.11 (m, 2H).

Example 230

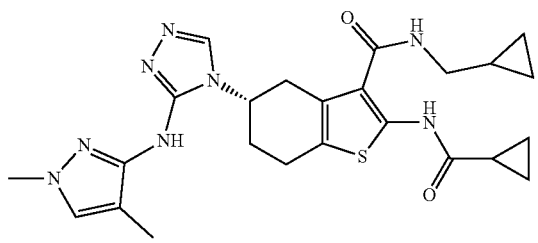 [SMILES: Cc1cn(C)nc1Nc1nncn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[3-[(1,4-dimethylpyrazol-3-yl)amino]-1,2,4-triazol-4-yl]-4,5,6,7-tetrahydrobenzothiophene-3-carboxamide To a stirred solution of intermediate 257 (288 mg, 0.592 mmol) in DMF (10 mL) under nitrogen was added formic acid hydrazide [624-84-0] (119 mg, 1.78 mmol) and mercuric chloride [7487-94-7] (241 mg, 0.888 mmol). The reaction mixture was stirred at r.t. for 15 min before the addition of triethylamine (0.25 mL, 1.78 mmol) and the mixture was stirred at 60° C. for 16 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 2% to 20% MeOH in DCM) to afford impure title compound as a white solid. This was dissolved in MeOH (10 mL) and QuadraSil® MTU (130 mg) was added and the suspension was stirred at 40° C. for 1 h before being filtered and washed with MeOH (2×10 mL). The filtrate was concentrated in vacuo to give a gum. This was further purified by flash column chromatography on silica (gradient elution with 4% to 20% MeOH in EtOAc) product containing fractions were freeze dried to afford the title compound (46 mg, 0.093 mmol, 16%) as a white solid. LCMS (ES+) [M+H]+ 495.0, RT 1.63 minutes, purity 100% (Method 3). LCMS (ES+) [M+H]+ 495.0, RT 1.52 minutes, purity 100% (Method 2). 1H NMR (300 MHz, DMSO-d6) δ 11.17 (s, 1H), 8.31 (s, 1H), 8.17 (s, 1H), 7.76 (t, J=5.6 Hz, 1H), 7.31 (s, 1H), 4.38-4.20 (m, 1H), 3.63 (s, 3H), 3.21-2.70 (m, 6H), 2.22-2.10 (m, 2H), 2.00-1.85 (m, 1H), 1.79 (s, 3H), 1.08-0.96 (m, 1H), 0.90-0.80 (m, 4H), 0.43-0.34 (m, 2H), 0.26-0.15 (m, 2H).

Example 231

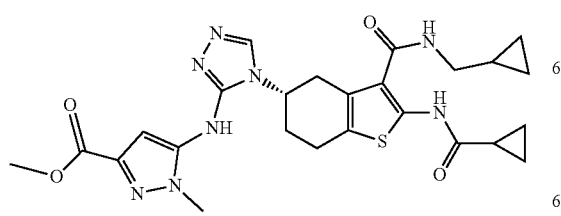

Methyl 5-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylate To a stirred solution of intermediate 261 (261 mg, 0.492 mmol) in DMF (10 mL) under nitrogen was added formic acid hydrazide [624-84-0] (98 mg, 1.48 mmol) and mercuric chloride [7487-94-7] (200 mg, 0.738 mmol). The reaction mixture was stirred at r.t. for 15 min before the addition of triethylamine (0.21 mL, 1.48 mmol) and the mixture was stirred at 80° C. for 16 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 2% to 20% MeOH in DCM) to afford impure title compound as a yellow gum. This was dissolved in MeOH (10 mL) and QuadraSil® MTU (130 mg) was added and the suspension was stirred at 40° C. for 1 h before being filtered and washed with MeOH (2×10 mL). The filtrate was concentrated in vacuo to give a gum. This was further purified by flash column chromatography on silica (gradient elution with 4% to 20% MeOH in EtOAc) product containing fractions were freeze dried to afford the title compound (134 mg, 0.248 mmol, 50%) as a white solid. LCMS (ES+) [M+H]+ 539.0, RT 1.63 minutes, purity 100% (Method 3). LCMS (ES+) [M+H]+ 539.0, RT 1.71 minutes, purity 100% (Method 2). 1H NMR (300 MHz, DMSO-d6) (contained 2 tautomers in an approximate ratio of 0.7:0.3) δ 12.14 (s, 0.7H), 11.38-11.09 (m, 1H), 8.78 (s, 0.3H), 8.41 (s, 0.3H), 8.20 (s, 0.7H), 7.85-7.64 (m, 1H), 6.67 (s, 0.3H), 6.48 (s, 0.7H), 4.60-4.30 (m, 1H), 3.83-3.73 (m, 3.9H), 3.66 (s, 2.1H), 3.24-2.77 (m, 6H), 2.32-2.12 (m, 2H), 2.00-1.86 (m, 1H), 1.08-0.94 (m, 1H), 0.93-0.79 (m, 4H), 0.42-0.30 (m, 2H), 0.23-0.14 (m, 2H).

Example 232

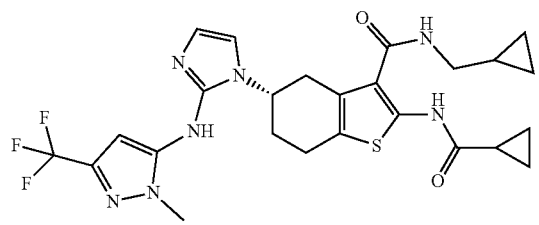 [SMILES: Cn1nc(C(F)(F)F)cc1Nc1nccn1[C@H]1CCc2sc(NC(=O)C3CC3)c(C(=O)NCC3CC3)c2C1]

(5S)-2-(Cyclopropanecarbonylamino)-N-(cyclopropylmethyl)-5-[2-[[2-methyl-5-(trifluoromethyl)pyrazol-3-yl]amino]imidazol-1-yl]-4,5,6,7-tetrahydrobenzothiophene-3-carboxamide To a stirred solution of intermediate 263 (148 mg, 0.274 mmol) in DMF (10 mL) under nitrogen was added aminoacetaldehyde diethyl acetal [645-36-3] (109 mg, 0.821 mmol) and mercuric chloride [7487-94-7] (112 mg, 0.411 mmol). The reaction mixture was stirred at r.t. for 15 min before the addition of triethylamine (0.11 mL, 0.821 mmol) and the mixture was stirred at 90° C. for 16 h. p-Toluenesulfonic acid monohydrate (319 mg, 1.64 mmol) was added and the mixture was stirred at 90° C. for 7 h. An additional amount of p-toluenesulfonic acid monohydrate (160 mg, 0.820 mmol) was added and the mixture was stirred at 90° C. for a further 16 h. The mixture was cooled to r.t. and diluted with MeCN (10 mL), filtered through a pad of celite and washed with MeCN (15 mL). The filtrate was concentrated in vacuo to yield the crude product as a yellow gum which was dissolved in DCM (50 mL), washed with water (30 mL) and the layers separated. The Aq layer was extracted with DCM (2×15 mL). The combined organic layers were washed with brine (30 ml) and passed through a phase separation cartridge and concentrated in vacuo to give a yellow gum. This was purified by flash column chromatography on silica (gradient elution with 2% to 20% MeOH in DCM) to afford impure title compound as a yellow gum. This was dissolved in MeOH (10 mL) and QuadraSil® MTU (130 mg) was added and the suspension was stirred at 40° C. for 1 h before being filtered and washed with MeOH (2×10 mL). The filtrate was concentrated in vacuo to give a gum. This was further purified by flash column chromatography on silica (gradient elution with 4% to 20% MeOH in EtOAc) product containing fractions were freeze dried to afford the title compound (22 mg, 0.040 mmol, 15%) as a white solid. LCMS (ES+) [M+H]$^+$ 548.0, RT 2.25 minutes, purity 100% (Method 3). LCMS (ES+) [M+H]$^+$ 548.0, RT 1.84 minutes, purity 100% (Method 2). 1H NMR (300 MHz, DMSO-d6)) (contained 2 tautomers in an approximate ratio of 0.7:0.3) δ 11.25-11.10 (m, 1H), 10.37 (s, 0.7H), 8.52 (s, 0.3H), 7.83-7.67 (m, 1H), 7.05 (s, 0.3H), 6.83 (s, 0.7H), 6.75-6.60 (m, 1H), 6.39 (s, 0.3H), 6.19 (s, 0.7H), 4.71-4.37 (m, 1H), 3.71 (s, 0.9H), 3.60 (s, 2.1H), 3.22-2.76 (m, 6H), 2.24-2.03 (m, 2H), 1.99-1.87 (m, 1H), 1.08-0.92 (m, 1H), 0.92-0.81 (m, 4H), 0.43-0.30 (m, 2H), 0.24-0.13 (m, 2H).

Example 233

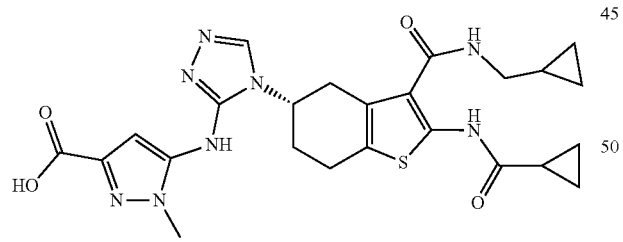

5-[[4-[(5S)-2-(Cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylic acid To a stirred solution of example 231 (88 mg, 0.163 mmol) in 1,4-dioxane (10 mL) was added a solution of lithium hydroxide monohydrate [1310-66-3] (21 mg, 0.490 mmol) in water (2 mL). The reaction mixture was stirred at r.t. for 5 h and then concentrated in vacuo. The residue was dissolved in DCM (50 mL) and water (50 mL) and the layers separated. The Aq layer was washed with DCM (2×15 mL). The Aq layer was acidified to pH 1 by addition of 0.5M HCl (aq) and then extracted with EtOAc (4×30 mL). The combined organic layers were washed with brine (30 ml) and passed through a phase separation cartridge and concentrated in vacuo to give a white solid. This was purified by flash column chromatography on silica (gradient elution with 5% to 25% MeOH in DCM) to afford impure title compound as a white solid. This solid was further purified by reverse phase chromatography on C18 silica (5% to 100% MeCN (w/0.1% NH3) in water (w/0.1% NH3)) and the product containing fractions were freeze dried to afford the title compound (20 mg, 0.038 mmol, 23%) as a white solid. LCMS (ES+) [M+H]$^+$ 525.0, RT 1.18 minutes, purity 100% (Method 3). LCMS (ES+) [M+H]$^+$ 525.0, RT 1.50 minutes, purity 100% (Method 2). 1H NMR (300 MHz, DMSO-d6) (contained 2 tautomers in an approximate ratio of 0.7:0.3) δ 12.25 (brs, 1H), 12.09 (s, 0.7H), 11.23 (s, 1H), 8.72 (s, 0.3H), 8.40 (s, 0.3H), 8.19 (s, 0.7H), 7.90-7.57 (m, 1H), 6.58 (s, 0.3H), 6.42 (s, 0.7H), 4.62-4.25 (m, 1H), 3.74 (s, 0.9H), 3.65 (s, 2.1H), 3.25-2.77 (m, 6H), 2.31-2.11 (m, 2H), 1.99-1.86 (m, 1H), 1.10-0.94 (m, 1H), 0.93-0.80 (m, 4H), 0.42-0.31 (m, 2H), 0.25-0.13 (m, 2H).

Example 234

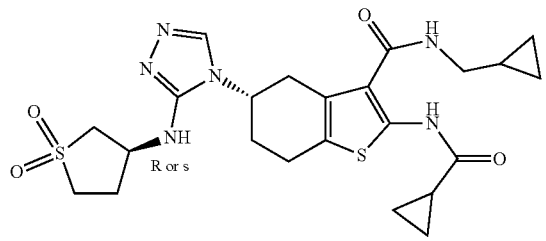 [SMILES: O=C(NCC1CC1)c1c(NC(=O)C2CC2)sc2c1C[C@@H](n1cnnc1N[C@H]1CCS(=O)(=O)C1)CC2]

(5S)-2-(cyclopropanecarbonylamino)-N-(cyclopropylmethyl)-5-[3-[[(3S*)-1,1-dioxothiolan-3-yl]amino]-1,2,4-triazol-4-yl]-4,5,6,7-tetrahydrobenzothiophene-3-carboxamide [*or R]

Intermediate 267 (140 mg, 0.27 mmol) was purified via chiral chromatography (Ethanol with Cellulose-4 25 cm column at 6 mL/min) to give the title compound (21 mg, 15% yield). δ$_H$ (500 MHz, DMSO-d$_6$) 11.28 (s, 1H), 8.17 (s, 1H), 7.74 (s, 1H), 6.45 (d, J=6.3 Hz, 1H), 4.47-4.37 (m, 1H), 4.27-4.19 (m, 1H), 3.54 (dd, J=13.4, 7.5 Hz, 1H), 3.35-3.29 (m, 1H), 3.21-3.13 (m, 2H), 3.12-2.99 (m, 3H), 2.91-2.86 (m, 1H), 2.86-2.79 (m, 2H), 2.48-2.44 (m, 1H), 2.28-2.07 (m, 3H), 1.95-1.87 (m, 1H), 1.07-0.96 (m, 1H), 0.90-0.78 (m, 4H), 0.43-0.32 (m, 2H), 0.24-0.14 (m, 2H). LCMS (M+H)$^+$ 519, RT 2.53 (Method 10). Chiral LC **RT=36.89 min

** Chiral analysis was carried out using a Cellulose-4 (4.6×250 mm 5 μm) column, flow rate 0.2 mL/min eluting with ethanol, using a 60 min run time on a Waters 2795.

Example 235

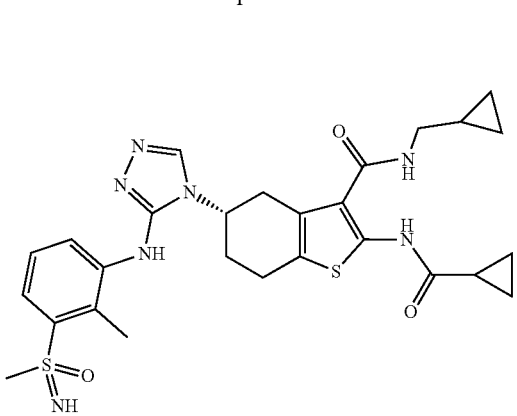

(5S)-2-cyclopropaneamido-N-(cyclopropylmethyl)-5-[3-({3-[imino(methyl)oxo-lambda6-sulfanyl]-2-methylphenyl}amino)-4H-1,2,4-triazol-4-yl]-4,5,6,7-tetrahydro-1-benzothiophene-3-carboxamide The title compound was prepared according to general method 8, using intermediate 271 (195 mg, 0.35 mmol). The residue was purified via column chromatography (KP-NH), eluting with a gradient of 0-8% methanol in DCM to give a pale-yellow solid (95 mg). The solid was dissolved in DMSO:MeCN (1:1, 2 mL) and purified via HPLC (Method 4) to give the title compound (43.5 mg, 22% yield). $\delta_H$ (500 MHz, DMSO-$d_6$) 11.19 (s, 1H), 8.49-8.43 (m, 1H), 8.14 (s, 1H), 7.87 (s, 1H), 7.75-7.69 (m, 1H), 7.69-7.64 (m, 1H), 7.36-7.25 (m, 2H), 4.49-4.41 (m, 1H), 4.28 (s, 1H), 3.18-2.99 (m, 7H), 2.85-2.78 (m, 2H), 2.58 (s, 3H), 2.27-2.14 (m, 2H), 1.95-1.89 (m, 1H), 1.02-0.94 (m, 1H), 0.88-0.81 (m, 4H), 0.38-0.33 (m, 2H), 0.21-0.15 (m, 2H). LCMS (M+H)$^+$ 568, RT 1.98 (Method 10).

Examples 236 & 237

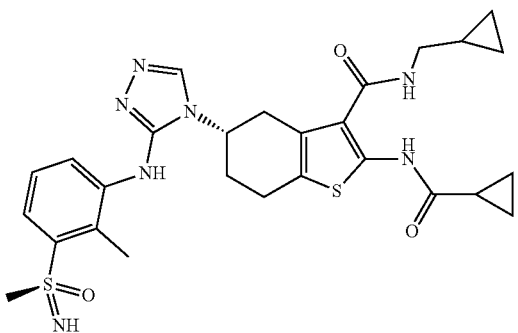

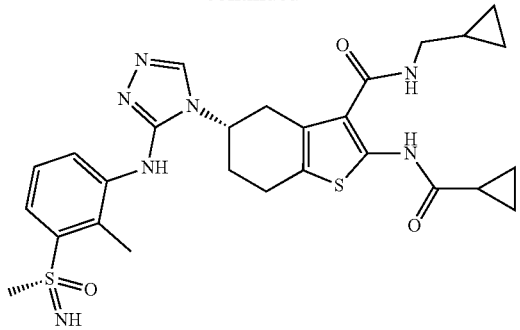 [SMILES: Cc1c(Nc2nncn2[C@H]2CCc3sc(NC(=O)C4CC4)c(C(=O)NCC4CC4)c3C2)cccc1S(C)(=N)=O]

(5S)-2-(cyclopropanecarbonylamino)-N-(cyclopropylmethyl)-5-[3-[2-methyl-3-[(S)-methylsulfonimidoyl]anilino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[2-methyl-3-[(R)-methylsulfonimidoyl]anilino]-1,2,4-triazol-4-yl]-4,5,6,7-tetrahydrobenzothiophene-3-carboxamide Example 235 (39 mg, 0.07 mmol) was purified via chiral chromatography, to give the title compounds examples:

Peak 1 (3.5 mg). $\delta_H$ (500 MHz, DMSO-$d_6$) 11.18 (s, 1H), 8.47 (s, 1H), 7.87 (s, 1H), 7.72 (t, J=5.7 Hz, 1H), 7.66 (dd, J=7.5, 1.5 Hz, 1H), 7.35-7.23 (m, 2H), 4.49-4.37 (m, 1H), 4.28 (s, 1H), 3.19-2.98 (m, 7H), 2.85-2.78 (m, 2H), 2.58 (s, 3H), 2.28-2.15 (m, 2H), 1.96-1.88 (m, 1H), 1.03-0.93 (m, 1H), 0.89-0.80 (m, 4H), 0.40-0.32 (m, 2H), 0.23-0.15 (m, 2H). LCMS (M+H)$^+$ 568, RT 2.01 (Method 10). Chiral SFC* RT=28.28 min.

Peak 2 (4.5 mg). $\delta_H$ (500 MHz, DMSO-$d_6$) 11.19 (s, 1H), 8.47 (s, 1H), 7.87 (s, 1H), 7.72 (t, J=5.6 Hz, 1H), 7.66 (dd, J=7.7, 1.3 Hz, 1H), 7.36-7.25 (m, 2H), 4.49-4.41 (m, 1H), 4.28 (s, 1H), 3.19-2.98 (m, 7H), 2.86-2.78 (m, 2H), 2.58 (s, 3H), 2.29-2.13 (m, 2H), 1.96-1.88 (m, 1H), 1.03-0.94 (m, 1H), 0.89-0.82 (m, 4H), 0.39-0.32 (m, 2H), 0.20-0.16 (m, 2H). LCMS (M+H)$^+$ 568, RT 2.01 (Method 10). Chiral SFC* RT=33.04 min.

* Chiral analysis was carried out using a Chiralcel OJ-H 4.6×250 mm, 5 μm column, flow rate 4 mL/min eluting with 25% Ethanol+0.2% DEA (diethylamine): 75% CO2, using a 50 min run time on a WatersThar Resolution-3100.

Example 238

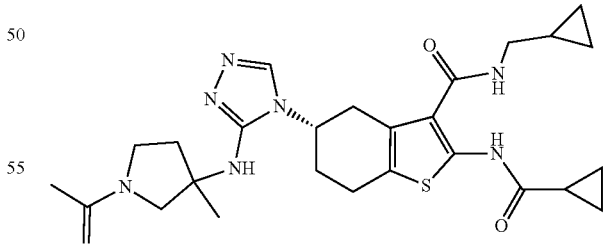

(5S)-5-{3-[(1-acetyl-3-methylpyrrolidin-3-yl)amino]-4H-1,2,4-triazol-4-yl}-2-cyclopropaneamido-N-(cyclopropylmethyl)-4,5,6,7-tetrahydro-1-benzothiophene-3-carboxamide To a stirred solution of intermediate 274 (37 mg, 0.07 mmol) in DCM (1 mL) was added acetyl chloride (6 μL, 0.08 mmol) and DIPEA (26 μL, 0.15 mmol). The reaction mixture was stirred at room temperature for 2 hours, then retreated with DIPEA (26 μL, 0.15 mmol) and acetyl chloride (6 μL, 0.08 mmol) before being left to stand as a solution overnight. The solution was purified via column chromatography, using a gradient of 0--15% methanol in DCM. Product was eluted using 0-15% methanol in DCM to give an off-white powder. The powder was dissolved in DCM (3 mL) and 0.5 M HCl (1 mL) added. The organic layer was separated and the aqueous extracted with DCM (3×3 mL) and 1:1 IPA:CHCl$_3$ (3×3 mL). The aqueous layer was then adjusted to pH 7 using saturated sodium bicarbonate and extracted with DCM (3×3 mL). The organic fractions were combined, passed through a hydrophobic frit and concentrated in vacuo. The residue was purified via reverse-phase column chromatography, using a gradient of 10-30% acetonitrile in water (+0.1% formic acid) to give the title compound (19 mg, 49% yield). $\delta_H$ (500 MHz, DMSO-d$_6$) 11.25-11.18 (m, 1H), 8.17-8.11 (m, 1H), 7.66 (s, 1H), 5.92-5.83 (m, 1H), 4.34-4.25 (m, 1H), 3.97-3.77 (m, 1H), 3.53-3.44 (m, 2H), 3.39-3.37 (m, 1H), 3.27-3.22 (in, 1H), 3.22-3.14 (m, 1H), 3.10-2.98 (m, 2H), 2.89-2.77 (m, 3H), 2.21-2.05 (m, 2H), 1.96-1.79 (m, 5H), 1.48-1.43 (m, 3H), 1.05-0.95 (m, 1H), 0.89-0.81 (m, 4H), 0.41-0.32 (m, 2H), 0.23-0.14 (in, 2H). LCMS (M+H)$^+$ 526, RT 1.97 & 2.01 (two diastereomers), (Method 10).

Example 239

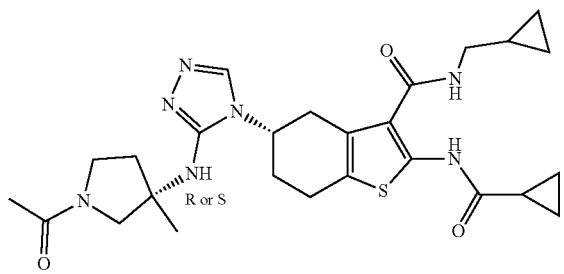

(5S)-5-[3-[[(3*)-1-acetyl-3-methyl-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R]

Example 238 (15 mg, 0.03 mmol) was separated via SFC (90:10 CO$_2$: Ethanol+0.2% DEA using a Chiralcel OJ-H 25 cm column at 15 mL/min) to give the title compound (4.7 mg, 31%). $\delta_H$ (500 MHz, d-Chloroform) 11.94-11.78 (m, 1H), 7.88-7.79 (m, 1H), 6.29-5.81 (m, 1H), 4.53-4.38 (m, 1H), 4.32-4.18 (m, 1H), 4.13-3.62 (m, 1H), 3.57-3.13 (m, 6H), 2.91-2.73 (m, 3H), 2.44-1.84 (m, 6H), 1.75-1.54 (m, 4H), 1.12-1.00 (m, 3H), 0.95-0.87 (m, 3H), 0.56-0.47 (m, 2H), 0.28-0.20 (m, 2H). LCMS (M+H)$^+$ 526, RT 1.89 (Method 10). Chiral SFC** RT=11.77 min.

** Chiral analysis was carried out using a Cellulose-3 (4.6×250 mm 5 μm) column, flow rate 4 mL/min eluting with 70:30 CO$_2$:Ethanol+0.2% DEA, using a 20 minute run time on a WatersThar Resolution-3100.

Example 240

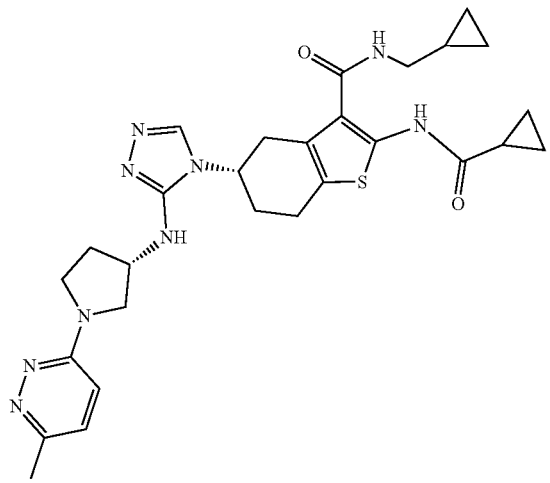 [SMILES: Cc1ccc(N2CC[C@H](Nc3nncn3[C@H]3CCc4sc(NC(=O)C5CC5)c(C(=O)NCC5CC5)c4C3)C2)nn1]

(5S)-2-cyclopropaneamido-N-(cyclopropylmethyl)-5-(3-{[(3S)-1-(6-methylpyridazin-3-yl)pyrrolidin-3-yl]amino}-4H-1,2,4-triazol-4-yl)-4,5,6,7-tetrahydro-1-benzothiophene-3-carboxamide Intermediate 278 (25 mg, 0.05 mmol), cesium carbonate (34 mg, 0.11 mmol) and 3-fluoro-6-methyl-pyridazine (7 mg, 0.06 mmol) were suspended in DMSO (0.5 mL). The mixture was stirred at 100° C. for 5 hours, then diluted with methanol (0.5 mL) and purified HPLC (Method 2) to give a brown solid (4 mg). The solid was then purified via HPLC, using a gradient of 5-95% acetonitrile in water with 0.1 20% formic acid to give the title compound (2.9 mg, 10% yield). $\delta_H$ (500 MHz, MeOD-d$_4$) 8.31 (s, 1H), 8.17 (s, 1H), 7.31 (d, J=9.3 Hz, 1H), 6.95 (d, J=9.3 Hz, 1H), 4.49-4.43 (m, 1H), 4.43-4.35 (m, 1H), 3.89 (dd, J=10.9, 6.0 Hz, 1H), 3.72-3.65 (m, 1H), 3.65-3.59 (m, 1H), 3.55 (dd, J=10.9, 4.1 Hz, 1H), 3.25-3.15 (m, 2H), 3.14-3.09 (m, 1H), 3.00-2.84 (m, 3H), 2.47 (s, 3H), 2.45-2.38 (m, 1H), 2.31-2.24 (m, 2H), 2.24-2.18 (m, 1H), 1.83-1.76 (m, 1H), 1.06-0.96 (m, 3H), 0.96-0.91 (m, 2H), 0.45-0.39 (m, 2H), 0.22-0.17 (m, 2H). LCMS (M+H)$^+$ 562, RT 1.45 (Method 10).

Example 241

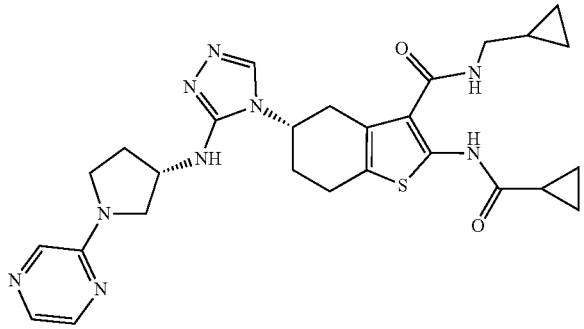 [SMILES: O=C(NCC1CC1)c1c(NC(=O)C2CC2)sc2c1C[C@@H](n1cnnc1N[C@H]1CCN(c3cnccn3)C1)CC2]

(5S)-2-(cyclopropanecarbonylamino)-N-(cyclopropylmethyl)-5-[3-[[(3S)-1-pyrazin-2-ylpyrrolidin-3-yl]amino]-1,2,4-triazol-4-yl]-4,5,6,7-tetrahydrobenzothiophene-3-carboxamide To a stirred solution of intermediate 278 (92% purity, 45 mg, 0.088 mmol) and cesium carbonate (58 mg, 0.18 mmol) in DMSO (1 mL) was added 2-fluoropyrazine (10 mg, 0.11 mmol). The mixture was stirred at 100° C. for 4 hours, then purified by HPLC (Method 4) to give the title compound (19 mg, 38% yield). $\delta_H$ (500 MHz, DMSO-$d_6$) 11.21 (s, 1H), 8.14 (s, 1H), 8.01 (dd, J=2.7, 1.5 Hz, 1H), 7.93 (d, J=1.4 Hz, 1H), 7.74 (d, J=2.7 Hz, 1H), 7.64 (s, 1H), 6.24 (d, J=5.9 Hz, 1H), 4.39-4.31 (m, 1H), 4.30-4.22 (m, 1H), 3.78 (dd, J=11.0, 6.2 Hz, 1H), 3.61-3.49 (m, 2H), 3.45 (dd, J=11.0, 4.0 Hz, 1H), 3.16-3.09 (m, 1H), 3.07-3.00 (m, 2H), 2.87-2.77 (m, 3H), 2.32-2.23 (m, 1H), 2.22-2.07 (m, 3H), 1.95-1.86 (m, 1H), 0.98-0.91 (m, 1H), 0.88-0.80 (m, 4H), 0.34-0.28 (m, 2H), 0.18-0.12 (m, 2H). LCMS: (M+H)$^+$ 548, RT 1.89 (Method 10).

Examples 242 and 243

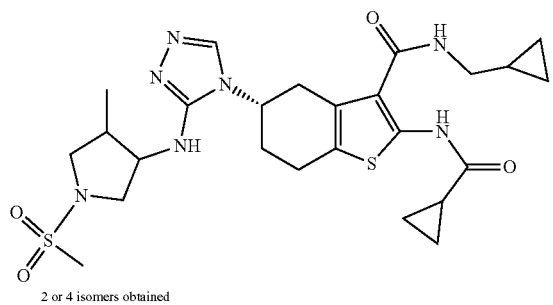

2 or 4 isomers obtained (5S)-2-(cyclopropanecarbonylamino)-N-(cyclopropylmethyl)-5-[3-[(4-methyl-1-methylsulfonyl-pyrrolidin-3-yl)amino]-1,2,4-triazol-4-yl]-4,5,6,7-tetrahydrobenzothiophene-3-carboxamide *Absolute stereochemistry of the (4-methyl-1-methylsulfonyl-pyrrolidin-3-yl)amino group in the separated isomers is unknown To a stirred solution of intermediate 285 (300 mg, 0.61 mmol) and DIPEA (0.32 mL, 1.84 mmol) in DCM (6 mL), at 0° C. was added methanesulfonyl chloride (0.04 mL, 0.55 mmol). The mixture was stirred at room temperature for 1 hour. Methanesulfonyl chloride (4.2 µL, 0.05 mmol) was added and the mixture was stirred at room temperature for 30 minutes. The mixture was concentrated in vacuo and purified via column chromatography (KP-NH) using a gradient of 0-30% methanol in TBME to give an off-white powder (114 mg). The powder was separated by SFC (Methanol with Lux Cellulose-4 25 cm column at 5 mL/min), to give the following 2 diastereoisomers (2 out of 4):

Peak 1 (1.9 mg). $\delta_H$ (500 MHz, DMSO-$d_6$) 11.31-11.13 (m, 1H), 8.14 (s, 1H), 7.67 (s, 1H), 6.18 (d, J=6.2 Hz, 1H), 4.31-4.21 (m, 1H), 3.85-3.78 (m, 1H), 3.70 (dd, J=10.2, 6.9 Hz, 1H), 3.56-3.50 (m, 1H), 3.18-3.14 (m, 2H), 3.11-3.03 (m, 3H), 2.94-2.88 (m, 4H), 2.87-2.77 (m, 3H), 2.36-2.30 (m, 1H), 2.23-2.08 (m, 2H), 1.99-1.84 (m, 1H), 1.07-1.03 (m, 3H), 1.03-0.96 (m, 1H), 0.89-0.79 (m, 4H), 0.42-0.36 (m, 2H), 0.22-0.17 (m, 2H). LCMS (M+H)$^+$ 562, RT 2.06 (Method 10). Chiral SFC** RT=19.22 min.

Peak 4 (22 mg). $\delta_H$ (500 MHz, DMSO-$d_6$) 11.26 (s, 1H), 8.12 (s, 1H), 7.66 (s, 1H), 6.02 (d, J=7.6 Hz, 1H), 4.42-4.34 (m, 1H), 4.33-4.27 (m, 1H), 3.58 (dd, J=10.3, 6.6 Hz, 1H), 3.45 (dd, J=9.9, 7.1 Hz, 1H), 3.23 (dd, J=10.4, 5.2 Hz, 1H), 3.19-3.13 (m, 1H), 3.13-3.01 (m, 3H), 2.93-2.76 (m, 6H), 2.59-2.53 (m, 1H), 2.19-2.07 (m, 2H), 1.96-1.87 (m, 1H), 1.06-0.97 (m, 1H), 0.94-0.89 (m, 3H), 0.88-0.81 (m, 4H), 0.43-0.34 (m, 2H), 0.23-0.16 (m, 2H). LCMS (M+H)$^+$ 562, RT 2.06 (Method 10). Chiral SFC* RT=25.05 min

** Chiral analysis was carried out using a Lux Cellulose-4 4.6×250 mm, 5 µm column, flowrate 0.3 mL/min eluting with methanol, using a 40 min run time on a Waters 2795.

Example 244

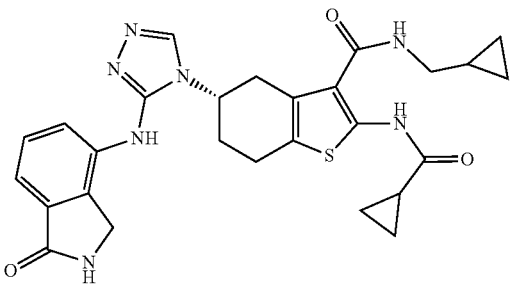 [SMILES: O=C1NCc2c(Nc3nncn3[C@H]3CCc4sc(NC(=O)C5CC5)c(C(=O)NCC5CC5)c4C3)cccc21]

(5S)-2-cyclopropaneamido-N-(cyclopropylmethyl)-5-{3-[(1-oxo-2,3-dihydro-1H-isoindol-4-yl)amino]-4H-1,2,4-triazol-4-yl}-4,5,6,7-tetrahydro-1-benzothiophene-3-carboxamide The title compound was prepared according to general method 8, using of intermediate 286 (130 mg, 0.25 mmol). The resulting residue was dissolved in 2:1 MeOH:DMSO (3 mL). The solution was purified by HPLC (Method 4) to give the title compound (36 mg, 26% yield). $\delta_H$ (500 MHz, DMSO-$d_6$) 11.22 (s, 1H), 8.50-8.47 (m, 2H), 8.31 (s, 1H), 7.69 (s, 1H), 7.46 (d, J=7.5 Hz, 1H), 7.37 (t, J=7.7 Hz, 1H), 7.25 (d, J=6.8 Hz, 1H), 4.57-4.44 (m, 1H), 4.21 (s, 2H), 3.15-2.96 (m, 4H), 2.86-2.79 (m, 2H), 2.28-2.14 (m, 2H), 1.94-1.86 (m, 1H), 0.98-0.90 (m, 1H), 0.88-0.81 (m, 4H), 0.35-0.27 (m, 2H), 0.18-0.13 (m, 2H). LCMS (M+H)$^+$ 532, RT 2.12 (Method 10).

Example 245

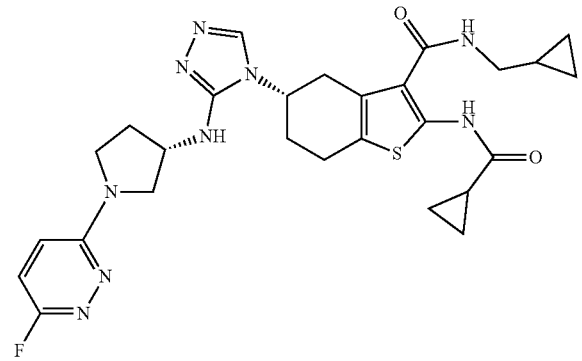 [SMILES: O=C(NCC1CC1)c1c(NC(=O)C2CC2)sc2c1C[C@@H](n1cnnc1N[C@H]1CCN(c3ccc(F)nn3)C1)CC2]

(5S)-2-(cyclopropanecarbonylamino)-N-(cyclopropylmethyl)-5-[3-[[(3S)-1-(6-fluoropyridazin-3-yl)pyrrolidin-3-yl]amino]-1,2,4-triazol-4-yl]-4,5,6,7-tetrahydrobenzothiophene-3-carboxamide To a stirred solution of intermediate 278 (50 mg, 0.1 mmol) in DMSO (1 mL) was added dipotassium carbonate (41 mg, 0.29 mmol) and 3,6-difluoropyridazine (14 mg, 0.12 mmol). The mixture was stirred at room temperature for 1 hour, then left to stand overnight. The mixture was diluted with water (1 mL) and extracted with DCM (3×3 mL). The organic fractions were combined, passed through a hydrophobic frit and purified via column chromatography (KP-NH), using a gradient of 0-25% methanol in TBME to give an off-white powder. The powder was triturated using DCM and the filtrate taken to give the title compound (20.5 mg, 35% yield). δ$_H$ (500 MHz, DMSO-d6) 11.21 (s, 1H), 8.14 (s, 1H), 7.64 (t, J=5.5 Hz, 1H), 7.34 (dd, J=9.6, 2.1 Hz, 1H), 7.14 (dd, J=9.6, 6.8 Hz, 1H), 6.24 (d, J=5.9 Hz, 1H), 4.41-4.32 (m, 1H), 4.31-4.22 (m, 1H), 3.79 (dd, J=11.0, 6.2 Hz, 1H), 3.62-3.49 (m, 2H), 3.46 (dd, J=10.9, 4.0 Hz, 1H), 3.17-3.09 (m, 1H), 3.07-3.00 (m, 2H), 2.87-2.78 (m, 3H), 2.33-2.24 (m, 1H), 2.22-2.08 (m, 3H), 1.95-1.87 (m, 1H), 0.99-0.90 (m, 1H), 0.88-0.81 (m, 4H), 0.34-0.28 (m, 2H), 0.17-0.11 (m, 2H). LCMS (M+H)$^+$ 566, RT 2.61 (Method 10).

Example 246

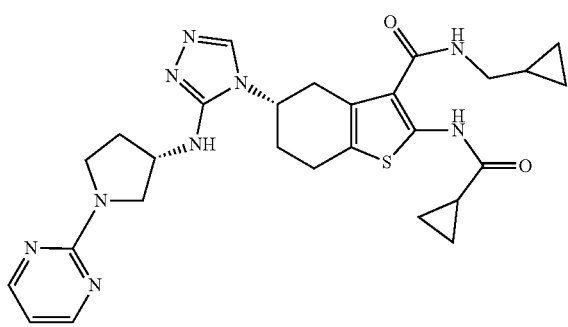 [SMILES: O=C(NCC1CC1)c1c(NC(=O)C2CC2)sc2c1C[C@@H](n1cnnc1N[C@H]1CCN(c3ncccn3)C1)CC2]

(5S)-2-(cyclopropanecarbonylamino)-N-(cyclopropylmethyl)-5-[3-[[(3S)-1-pyrimidin-2-ylpyrrolidin-3-yl]amino]-1,2,4-triazol-4-yl]-4,5,6,7-tetrahydro-1-benzothiophene-3-carboxamide To a stirred solution of intermediate 278 (30 mg, 0.06 mmol) and DIPEA (31 µL, 0.18 mmol) in DMF (0.5 mL) was added 2-chloropyrimidine (9 mg, 0.08 mmol). The mixture was stirred at 120° C. for 2 hours and then concentrated in vacuo. The residue was purified via column chromatography (KP-NH), using a gradient of 0-20% methanol in TBME to give the title compound (21.5 mg, 65% yield). δ$_H$ (500 MHz, DMSO-d6) 11.22 (s, 1H), 8.31 (d, J=4.7 Hz, 2H), 8.13 (s, 1H), 7.64 (t, J=5.4 Hz, 1H), 6.57 (t, J=4.7 Hz, 1H), 6.22 (d, J=5.8 Hz, 1H), 4.34-4.23 (m, 2H), 3.81 (dd, J=11.6, 6.2 Hz, 1H), 3.65-3.54 (m, 2H), 3.51 (dd, J=11.6, 4.1 Hz, 1H), 3.17-3.10 (m, 1H), 3.07-3.01 (m, 2H), 2.86-2.78 (m, 3H), 2.29-2.20 (m, 1H), 2.20-2.03 (m, 3H), 1.95-1.87 (m, 1H), 1.00-0.91 (m, 1H), 0.89-0.80 (m, 4H), 0.37-0.28 (m, 2H), 0.21-0.10 (m, 2H). LCMS (M+H)$^+$ 548, RT 1.86 (Method 10).

Example 247

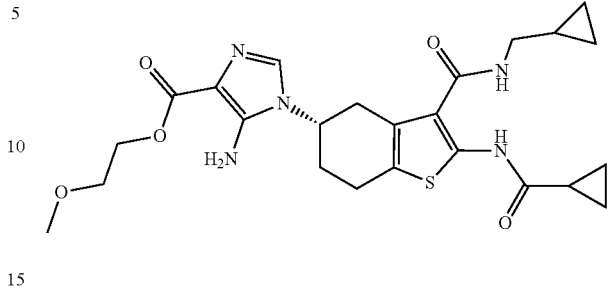

2-methoxyethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate To a pressure tube containing 2-methoxyethanol (0.5 mL, 6.37 mmol) was added sodium hydride (17 mg, 0.42 mmol) and the resulting mixture was stirred under a flow of nitrogen for 5 minutes. Example 117 (20 mg, 0.04 mmol) was added and stirring was continued until it was in solution. The pressure tube was then sealed and heated to 50° C. for 4 hours. The reaction mixture was then diluted with ethyl acetate (10 mL) and quenched with sat. aq. NH$_4$Cl solution (5 mL) and water (5 mL). The layers were separated and the aqueous phase was extracted further with ethyl acetate (10 mL). The combined organic layers were washed with brine (10 mL), dried over magnesium sulfate, filtered and concentrated. The residual solid was purified by reverse phase column chromatography (Method 4) to afford the title compound (12 mg, 25% yield). δ$_H$ (500 MHz, DMSO-d6) 11.21 (s, 1H), 7.70 (s, 1H), 7.28 (s, 1H), 6.10 (s, 2H), 4.38-4.27 (m, 1H), 4.27-4.22 (m, 2H), 3.61-3.55 (m, 2H), 3.28 (s, 3H), 3.19-3.03 (m, 3H), 3.01-2.92 (m, 1H), 2.91-2.75 (m, 2H), 2.23-2.14 (m, 1H), 2.12 (s, 1H), 1.96-1.86 (m, 1H), 1.06-0.95 (m, 1H), 0.92-0.78 (m, 4H), 0.42-0.35 (m, 2H), 0.23-0.17 (m, 2H). LCMS [M+H]$^+$ 502, RT 2.05 minutes (Method 10).

Example 248

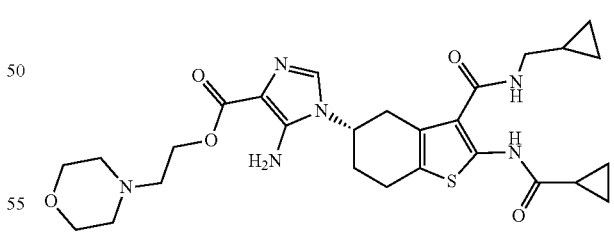

2-morpholin-4-ylethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate To a stirring mixture of 2-morpholinoethanol (500 µL, 4.13 mmol) and THF (300 µL) in a vial was added sodium (15 mg, 0.64 mmol) and the resulting mixture was stirred under a flow of nitrogen until completely in solution (1 hour at room temperature and 1 hour at 40° C.). Example 117 (30 mg, 0.06 mmol) was added, the vial was sealed and the mixture was heated to 50° C. for 2 hours. The reaction mixture was diluted with ethyl acetate (10 mL) and washed with water (10 mL). The layers were separated and the aqueous phase was extracted with ethyl acetate (10 mL). The combined organic layers were dried over magnesium sulfate, filtered and concentrated in vacuo. The residual solid was purified by reverse phase column chromatography (Method 4) to afford the title compound (13 mg, 36% yield). $\delta_H$ (500 MHz, DMSO-d6) 11.21 (s, 1H), 7.71 (s, 1H), 7.29 (s, 1H), 6.20 (s, 2H), 4.36-4.28 (m, 1H), 4.22 (t, J=5.8 Hz, 2H), 3.59-3.55 (m, 4H), 3.18-3.08 (m, 2H), 3.08-3.03 (m, 1H), 2.99-2.90 (m, 1H), 2.90-2.76 (m, 2H), 2.59 (t, J=5.9 Hz, 2H), 2.46-2.38 (m, 4H), 2.23-2.16 (m, 1H), 2.16-2.08 (m, 1H), 1.95-1.89 (m, 1H), 1.06-0.97 (m, 1H), 0.89-0.81 (m, 4H), 0.41-0.35 (m, 2H), 0.22-0.16 (m, 2H). LCMS [M+H]$^+$ 557, RT 1.66 minutes (Method 10).

Example 249

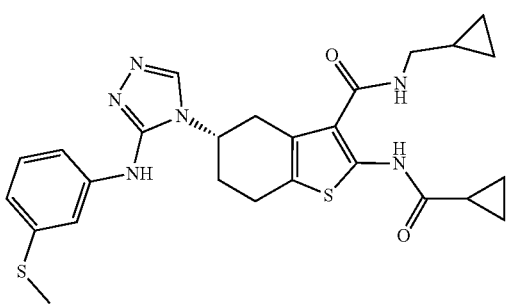 [SMILES: CSc1cccc(Nc2nncn2[C@H]2CCc3sc(NC(=O)C4CC4)c(C(=O)NCC4CC4)c3C2)c1]

(5S)-2-(cyclopropanecarbonylamino)-N-(cyclopropylmethyl)-5-[3-(3-methylsulfanylanilino)-1,2,4-triazol-4-yl]-4,5,6,7-tetrahydrobenzothiophene-3-carboxamide To a solution of intermediate 287 (275 mg, 0.53 mmol) in anhydrous DMF (5 mL) was added formic hydrazide (96 mg, 1.6 mmol) followed by mercury dichloride (435 mg, 1.60 mmol) and triethylamine (0.22 mL, 1.6 mmol). The resulting mixture was stirred at 90° C. for 2.5 hours. Celite was added to the stirring mixture and it was diluted with ethyl acetate (10 mL). The mixture was then filtered through a pad of celite, washing through with more ethyl acetate, and the solvent was evaporated in vacuo. The crude material was purified by flash column chromatography eluting with a 0 to 10% methanol in DCM gradient to afford the title compound (115 mg, 42% yield). $\delta_H$ (500 MHz, DMSO-d6) 11.25 (s, 1H), 8.61 (s, 1H), 8.38 (s, 1H), 7.67 (t, J=5.4 Hz, 1H), 7.57 (t, J=1.9 Hz, 1H), 7.37-7.32 (m, 1H), 7.19 (t, J=8.0 Hz, 1H), 6.76 (dd, J=7.8, 0.9 Hz, 1H), 4.56-4.46 (m, 1H), 3.17-3.02 (m, 3H), 2.98-2.82 (m, 3H), 2.45 (s, 3H), 2.31-2.13 (m, 2H), 1.96-1.88 (m, 1H), 1.00-0.90 (m, 1H), 0.90-0.82 (m, 4H), 0.35-0.27 (m, 2H), 0.18-0.10 (m, 2H). LCMS [M+H]$^+$ 523, RT 2.93 minutes (Method 10).

Example 250

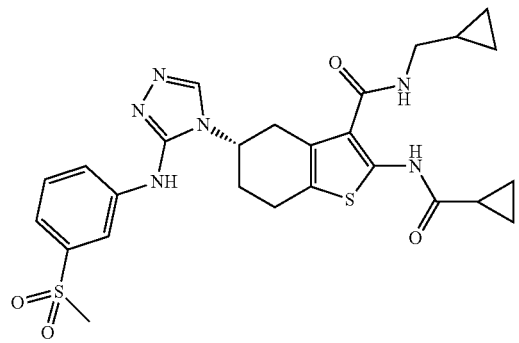 [SMILES: CS(=O)(=O)c1cccc(Nc2nncn2[C@H]2CCc3sc(NC(=O)C4CC4)c(C(=O)NCC4CC4)c3C2)c1]

(5S)-2-(cyclopropanecarbonylamino)-N-(cyclopropylmethyl)-5-[3-(3-methylsulfonylanilino)-1,2,4-triazol-4-yl]-4,5,6,7-tetrahydrobenzothiophene-3-carboxamide To a stirring solution of Example 249 (21 mg, 0.04 mmol) in anhydrous DCM (1 mL) was added 3-chlorobenzenecarboperoxoic acid (10 mg, 0.046 mmol) and the resulting solution was stirred at room temperature for 1.5 hours. Another portion of 3-chlorobenzenecarboperoxoic acid (18 mg, 0.08 mmol) was added and stirring was continued at room temperature for 2 hours. The reaction mixture was concentrated in vacuo and the residue was purified by reverse phase column chromatography (Method 4) to afford the title compound (2.3 mg, 10% yield). $\delta_H$ (500 MHz, Methanol-d4) 8.42 (s, 1H), 8.04 (t, J=1.8 Hz, 1H), 7.73-7.68 (m, 1H), 7.57-7.48 (m, 2H), 4.65-4.57 (m, 1H), 3.29-3.21 (m, 2H), 3.13 (s, 4H), 3.10-3.03 (m, 1H), 3.03-2.88 (m, 2H), 2.39-2.33 (m, 2H), 1.84-1.77 (m, 1H), 1.05-0.97 (m, 3H), 0.97-0.91 (m, 2H), 0.43-0.38 (m, 2H), 0.22-0.17 (m, 2H). LCMS [M+H]$^+$ 555, RT 2.58 minutes (Method 10).

Example 251

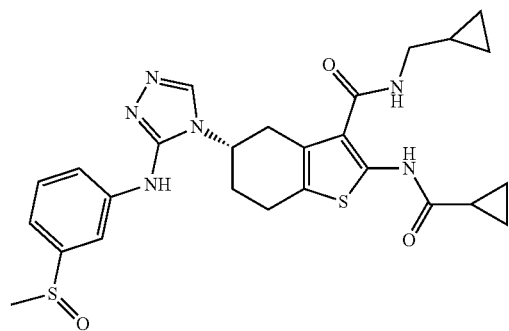 [SMILES: CS(=O)c1cccc(Nc2nncn2[C@H]2CCc3sc(NC(=O)C4CC4)c(C(=O)NCC4CC4)c3C2)c1]

(5S)-2-(cyclopropanecarbonylamino)-N-(cyclopropylmethyl)-5-[3-(3-methylsulfinylanilino)-1,2,4-triazol-4-yl]-4,5,6,7-tetrahydrobenzothiophene-3-carboxamide To a solution of Example 249 (88 mg, 0.168 mmol) in anhydrous DCM (4 mL) was added 3-chlorobenzenecarboperoxoic acid (38 mg, 0.168 mmol) and the resulting solution was stirred at room temperature for 45 minutes. The reaction mixture was diluted with DCM (10 mL) and washed with sat. aq. NaHCO$_3$ solution (10 mL). The aqueous layer was extracted further with DCM (10 mL), the combined organic layers were washed with brine (10 mL), dried over magnesium sulphate, filtered and concentrated. The crude material was purified by flash column chromatography with a 0 to 10% methanol in DCM gradient to afford the title compound (65 mg, 68% yield). δ$_H$ (500 MHz, DMSO-d6) 11.25 (d, J=4.1 Hz, 1H), 8.98 (s, 1H), 8.42 (s, 1H), 7.93 (t, J=1.7 Hz, 1H), 7.83-7.75 (m, 1H), 7.67 (t, J=5.3 Hz, 1H), 7.44 (t, J=7.9 Hz, 1H), 7.11 (d, J=7.6 Hz, 1H), 4.60-4.48 (m, 1H), 3.18-3.10 (m, 2H), 3.09-3.01 (m, 1H), 2.99-2.90 (m, 1H), 2.90-2.83 (m, 2H), 2.71 (s, 3H), 2.32-2.24 (m, 1H), 2.23-2.16 (m, 1H), 1.95-1.88 (m, 1H), 0.99-0.91 (m, 1H), 0.90-0.81 (m, 4H), 0.29 (d, J=7.8 Hz, 2H), 0.18-0.09 (m, 2H). LCMS [M+H]$^+$ 539, RT 2.29 minutes (Method 10).

Example 252

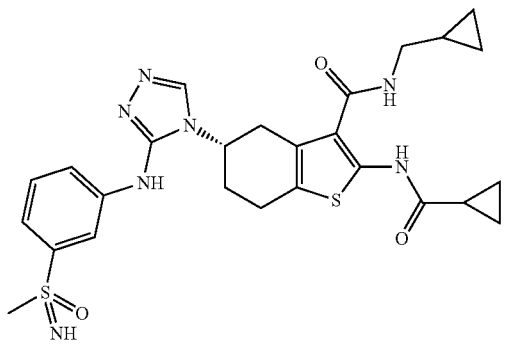 [SMILES: CS(=N)(=O)c1cccc(Nc2nncn2[C@H]2CCc3sc(NC(=O)C4CC4)c(C(=O)NCC4CC4)c3C2)c1]

(5S)-2-(cyclopropanecarbonylamino)-N-(cyclopropylmethyl)-5-[3-[3-(methylsulfonimidoyl)anilino]-1,2,4-triazol-4-yl]-4,5,6,7-tetrahydrobenzothiophene-3-carboxamide To a solution of Intermediate 292 (255 mg, 0.46 mmol) in anhydrous DMF (4.3 mL) was added formic hydrazide (82 mg, 1.37 mmol) followed by mercury dichloride (371 mg, 1.37 mmol) and triethylamine (0.19 mL, 1.37 mmol) and the resulting mixture was stirred at 90° C. overnight. Celite was added to the stirring mixture and it was diluted with ethyl acetate (10 mL). The mixture was then filtered through a pad of celite, washing through with more ethyl acetate, and the solvent was evaporated in vacuo. The crude material was purified by reverse phase column chromatography (Method 4) to afford the title compound (formic acid salt) (55 mg, 20% yield). δ$_H$ (250 MHz, DMSO-d6) 11.25 (s, 1H), 9.03 (s, 1H), 8.43 (s, 1H), 8.20-8.11 (m, 2H), 8.00-7.93 (m, 1H), 7.69 (t, J=5.8 Hz, 1H), 7.54-7.38 (m, 2H), 4.63-4.46 (m, 1H), 4.10 (s, 1H), 3.16-3.05 (m, 3H), 3.02 (s, 3H), 3.00-2.93 (m, 1H), 2.92-2.82 (m, 2H), 2.35-2.14 (m, 2H), 2.00-1.84 (m, 1H), 1.03-0.89 (m, 1H), 0.89-0.80 (m, 4H), 0.36-0.26 (m, 2H), 0.19-0.10 (m, 2H). LCMS [M+H]$^+$ 554, RT 2.15 minutes (Method 10).

Examples 253 & 254

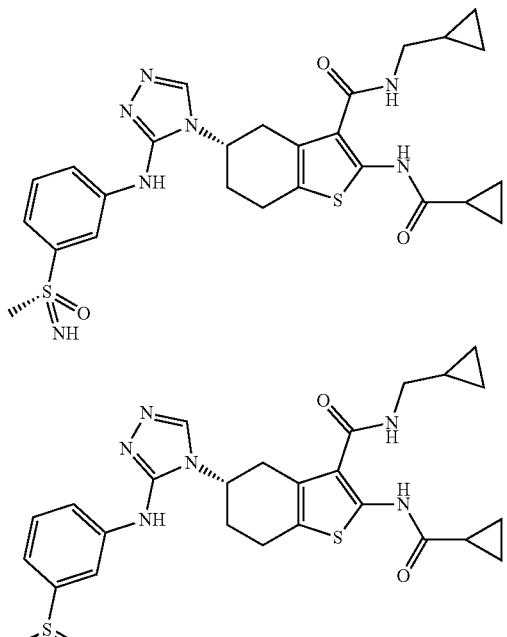

(5S)-2-(cyclopropanecarbonylamino)-N-(cyclopropylmethyl)-5-[3-[3-[(S)-methylsulfonimidoyl]anilino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[3-[(R)-methylsulfonimidoyl]anilino]-1,2,4-triazol-4-yl]-4,5,6,7-tetrahydrobenzothiophene-3-carboxamide The title compounds were obtained by separating the two diastereoisomers of Example 252 (45 mg) by chiral chromatography (Ethanol+0.2% DEA with Amylose-2 25 cm at 7 mL/min). Each sample after separation was dissolved in DCM (5 mL), washed with saturated aqueous NH$_4$Cl (2×5 mL), water (5 mL), then brine (5 mL). The organic layer was filtered through a phase separator and concentrated under reduced pressure. The residue was dissolved in acetonitrile:water (1:1) and freeze dried to afford the final compounds:

Isomer 1 (Peak 1, 11.5 mg). δ$_H$ (500 MHz, DMSO-d6) 11.25 (s, 1H), 9.03 (s, 1H), 8.43 (s, 1H), 8.16 (t, J=1.9 Hz, 1H), 8.02-7.92 (m, 1H), 7.69 (t, J=5.7 Hz, 1H), 7.49 (t, J=7.9 Hz, 1H), 7.45-7.37 (m, 1H), 4.62-4.46 (m, 1H), 4.09 (br s, 1H), 3.18-3.10 (m, 2H), 3.10-3.04 (m, 1H), 3.03 (s, 3H), 3.00-2.91 (m, 1H), 2.91-2.82 (m, 2H), 2.33-2.23 (m, 1H), 2.23-2.15 (m, 1H), 1.98-1.87 (m, 1H), 1.01-0.93 (m, 1H), 0.92-0.82 (m, 4H), 0.38-0.26 (m, 2H), 0.21-0.10 (m, 2H). LCMS [M+H]$^+$ 554, RT 2.15 minutes (Method 10). Chiral LC* RT=9.99 minutes.

Isomer 2 (Peak 2, 14 mg). δ$_H$ (500 MHz, DMSO-d6) 11.24 (s, 1H), 9.05 (s, 1H), 8.44 (s, 1H), 8.16 (t, J=2.0 Hz, 1H), 8.00-7.93 (m, 1H), 7.69 (t, J=5.7 Hz, 1H), 7.53-7.46 (m, 1H), 7.46-7.37 (m, 1H), 4.61-4.50 (m, 1H), 3.18-3.11 (m, 2H), 3.10-3.06 (m, 1H), 3.04 (s, 3H), 3.00-2.92 (m, 1H), 2.91-2.82 (m, 2H), 2.32-2.23 (m, 1H), 2.23-2.15 (m, 1H), 1.96-1.89 (m, 1H), 1.00-0.91 (m, 1H), 0.89-0.81 (m, 4H), 0.35-0.26 (m, 2H), 0.20-0.09 (m, 2H), NH proton missing. LCMS [M+H]⁺ 554, RT 2.17 minutes (Method 10). Chiral LC* RT=15.70 minutes.

* Chiral analysis using Amylose-2 (4.6×250 mm 5 μm) column, flow rate 0.5 mL/min, eluting with Ethanol+0.2% DEA, 30 minutes run time on a Waters 2795.

Example 255

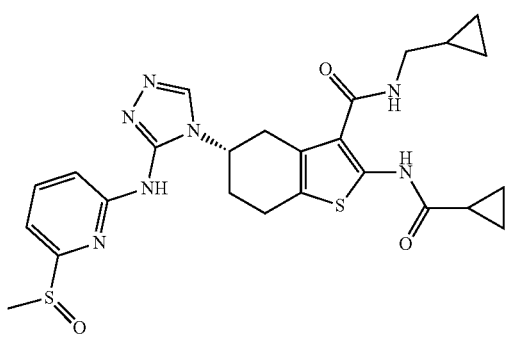 [SMILES: CS(=O)c1cccc(Nc2nncn2[C@H]2CCc3sc(NC(=O)C4CC4)c(C(=O)NCC4CC4)c3C2)n1]

(5S)—N-(cyclopropylmethyl)-5-[3-[(6-methylsulfinyl-2-pyridyl)amino]-1,2,4-triazo-4-yl]-2-(spiro[2.2]pentane-2-carbonylamino)-4,5,6,7-tetrahydrobenzothiophene-3-carboxamide To a solution of Intermediate 298 (76 mg, 0.138 mmol) in anhydrous DCM (4 mL) was added 3-chlorobenzenecarboperoxoic acid (40 mg, 0.180 mmol) and the resulting solution was stirred at room temperature for 1 hour. The reaction mixture was diluted with DCM (10 mL) and washed with saturated aqueous NaHCO₃ solution (10 mL). The aqueous phase was further extracted with DCM (10 mL), the combined organic layers were washed with brine (10 mL), dried over magnesium sulphate, filtered and concentrated. The crude material was purified by flash column chromatography eluting with a 0 to 10% methanol in DCM gradient, followed by reverse phase column chromatography (Method 4). The sample was freeze dried to afford the title compound as a white solid (5.7 mg, 7% yield). δ_H (500 MHz, DMSO-d6) 11.11 (s, 1H), 9.81-9.70 (m, 1H), 8.60-8.51 (m, 1H), 7.97-7.88 (m, 1H), 7.60 (s, 1H), 7.56-7.50 (m, 1H), 7.40-7.27 (m, 1H), 4.52-4.36 (m, 1H), 3.16-3.04 (m, 3H), 3.04-2.95 (m, 1H), 2.86-2.73 (m, 2H), 2.72-2.69 (m, 3H), 2.29-2.10 (m, 3H), 1.48-1.39 (m, 1H), 1.39-1.32 (m, 1H), 1.02-0.91 (m, 3H), 0.90-0.84 (m, 1H), 0.83-0.74 (m, 1H), 0.36-0.28 (m, 2H), 0.19-0.11 (m, 2H). LCMS [M+H]⁺ 566, RT 2.39 minutes (Method 10).

Example 256

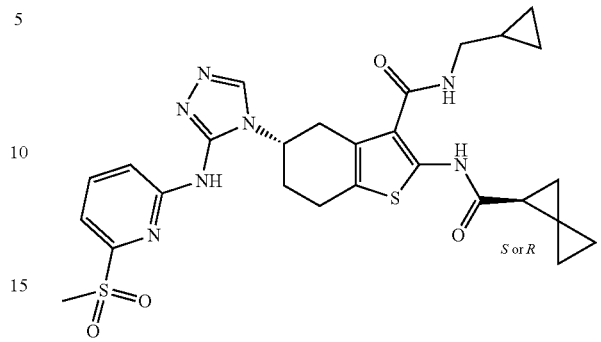

(5S)—N-(cyclopropylmethyl)-5-[3-[(6-methylsulfonyl-2-pyridyl)amino]-1,2,4-triazol-4-yl]-2-[[(2S*)-spiro[2.2]pentane-2-carbonyl]amino]-4,5,6,7-tetrahydrobenzothiophene-3-carboxamide [* or R]

Prepared as described for Example 255. After purification by flash column chromatography, the title compound was obtained by separating the two diastereoisomers by chiral chromatography (70:30 Heptane: Ethanol with Chiralcel OD-H 25 cm column at 18 mL/min):

Peak 1 (12.3 mg). δ_H (500 MHz, DMSO-d6) 11.13 (s, 1H), 9.99 (s, 1H), 8.58 (s, 1H), 8.02-7.94 (m, 1H), 7.77 (d, J=8.4 Hz, 1H), 7.58 (s, 1H), 7.48 (d, J=7.3 Hz, 1H), 4.56-4.45 (m, 1H), 3.17 (s, 3H), 3.15-3.04 (m, 3H), 3.04-2.94 (m, 1H), 2.89-2.72 (m, 2H), 2.28-2.12 (m, 3H), 1.46-1.39 (m, 1H), 1.39-1.33 (m, 1H), 1.01-0.90 (m, 3H), 0.90-0.84 (m, 1H), 0.78 (s, 1H), 0.36-0.28 (m, 2H), 0.19-0.11 (m, 2H). LCMS [M+H]⁺ 582, RT 2.78 minutes (Method 10). Chiral LC** RT=14.02

** Chiral analysis using Chiralcel OD-H (4.6×250 mm 5 μm) column, flow rate 1 mL/min, eluting with 70:30 Heptane:Ethanol, 40 minutes run time on a Waters 2795.

Example 257

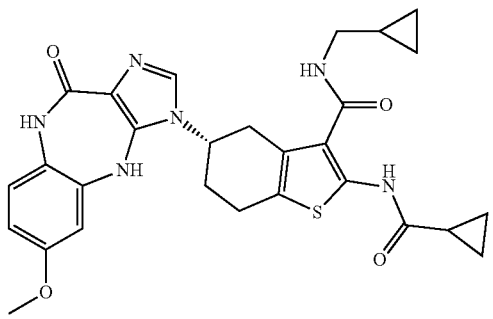 [SMILES: COc1ccc2c(c1)Nc1c(ncn1[C@H]1CCc3sc(NC(=O)C4CC4)c(C(=O)NCC4CC4)c3C1)C(=O)N2]

(5S)-2-(cyclopropanecarbonylamino)-N-(cyclopropylmethyl)-5-(8-methoxy-4-oxo-5,10-dihydroimidazo[4,5-c][1,5]benzodiazepin-1-yl)-4,5,6,7-tetrahydrobenzothiophene-3-carboxamide 2,2,2-Trifluoroacetic acid (133 mL, 1.79 mmol) was added to the stirred solution of Intermediate 304 (60 mg, 0.09 mmol) in DCM (0.7 mL) and the mixture stirred at room temperature for 24 h. The reaction mixture was evaporated to dryness and purified by column chromatography, eluting with 0-20% methanol in DCM to afford the title compound (30 mg, 61% yield). $\delta_H$ (500 MHz, DMSO-d6) 11.08 (s, 1H), 8.64 (br s, 1H), 7.91 (br s, 1H), 7.53 (t, J=5.6 Hz, 1H), 7.47 (br s, 1H), 6.67 (d, J=8.7 Hz, 1H), 6.47 (d, J=2.7 Hz, 1H), 6.34 (dd, J=8.7, 2.7 Hz, 1H), 4.41-4.31 (m, 1H), 3.50 (s, 3H), 3.04-2.85 (m, 3H), 2.82-2.65 (m, 3H), 2.15-1.99 (m, 2H), 1.82-1.73 (m, 1H), 0.87-0.78 (m, 1H), 0.74-0.66 (m, 4H), 0.23-0.11 (m, 2H), 0.05-−0.05 (m, 2H). LCMS [M+H]$^+$ 547, RT 2.38 minutes (Method 10).

Example 258

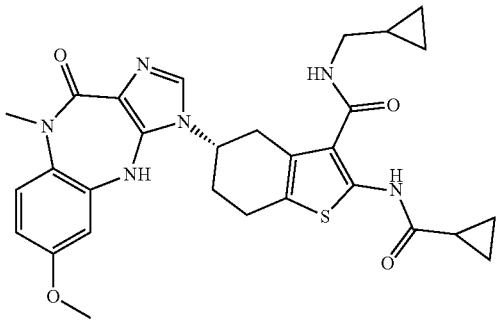 [SMILES: COc1ccc2c(c1)Nc1c(ncn1[C@H]1CCc3sc(NC(=O)C4CC4)c(C(=O)NCC4CC4)c3C1)C(=O)N2C]

(5S)-2-(cyclopropanecarbonylamino)-N-(cyclopropylmethyl)-5-(8-methoxy-5-methyl-4-oxo-10H-imidazo[4,5-c][1,5]benzodiazepin-1-yl)-4,5,6,7-tetrahydrobenzothiophene-3-carboxamide Intermediate 307 (42 mg, 0.066 mmol) and sodium 2-methylpropan-2-olate (29 mg, 0.306 mmol) were suspended in dry tert-butanol (0.84 mL) and dioxane (0.4 mL) and de-gassed for 5 minutes. tBuXPhos Pd G3 (5.2 mg, 6.55 μmol) was added and the mixture heated at 90° C. in a sealed tube for 11 h. The mixture was cooled to room temperature, diluted with water (5 mL), neutralized with 1 M HCl and extracted with IPA:CHCl$_3$ (1:1, 3×5 mL). The combined organic layers were dried over sodium sulfate, filtered and evaporated to dryness to afford the crude. This was dissolved in DMSO and purified by HPLC (Method 2) to give the title compound (5.0 mg, 14% yield). $\delta_H$ (500 MHz, DMSO-d6) 11.25 (s, 1H), 8.20 (s, 1H), 7.75-7.59 (m, 1H), 7.47 (s, 1H), 7.11 (d, J=8.9 Hz, 1H), 6.72 (d, J=2.9 Hz, 1H), 6.65 (dd, J=8.9, 2.9 Hz, 1H), 4.59-4.45 (m, 1H), 3.70 (s, 3H), 3.18 (s, 3H), 3.17-3.12 (m, 1H), 3.11-3.00 (m, 2H), 2.98-2.91 (m, 1H), 2.91-2.79 (m, 2H), 2.30-2.14 (m, 2H), 1.99-1.86 (m, 1H), 1.03-0.92 (m, 1H), 0.92-0.76 (m, 4H), 0.38-0.24 (m, 2H), 0.21-0.08 (m, J=4.9 Hz, 2H). LCMS [M+H]$^+$ 561, RT 2.50 minutes (Method 10).

Example 259

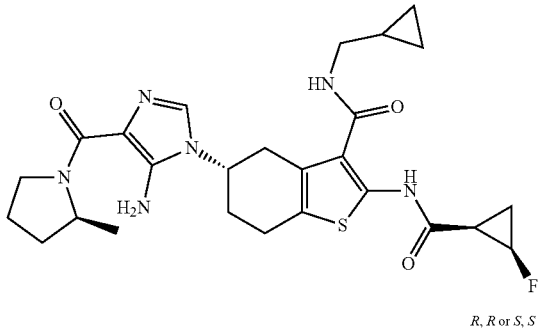 [SMILES: C[C@H]1CCCN1C(=O)c1ncn([C@H]2CCc3sc(NC(=O)[C@H]4C[C@H]4F)c(C(=O)NCC4CC4)c3C2)c1N]

R, R or S, S (5S)-5-[5-amino-4-[(2S)-2-methylpyrrolidine-1-carbonyl]imidazol-1-yl]-N-(cyclopropylmethyl)-2-[[(1R*,2R*)-2-fluorocyclopropanecarbonyl]amino]-4,5,6,7-tetrahydrobenzothiophene-3-carboxamide [* or 1S,2S]

HATU (45 mg, 0.12 mmol) was added to a stirred solution of Intermediate 313 (55 mg, 0.1 mmol), (2{S})-2-methylpyrrolidine (20 mg, 0.235 mmol) and DIPEA (50 μL, 0.29 mmol) in dry DMF (0.6 mL) at room temperature. The reaction mixture was stirred for 30 minutes then diluted with water (5 mL) and extracted with DCM (3×5 mL). The combined organic layers were dried over sodium sulfate, filtered and evaporated to dryness to afford crude material. The crude material was treated with 4 M HCl in 1,4-dioxane (374 μL, 1.49 mmol) and stirred for 2 h. The reaction mixture was diluted with saturated aqueous NaHCO$_3$ (5 mL) and the aq. layer extracted with DCM (3×5 mL). The combined organic layers were dried over sodium sulfate, filtered, evaporated to dryness and purified by HPLC (Method 2) to give the title compound (40 mg, 77% yield). This was purified by chiral SFC (Chiralpak ID 5 μm 250×20 mm, CO$_2$/MeOH+0.5% isopropylamine 65/35, 50 mL/min, 40° C., 100 bar) to give the title compound. Peak 1 (3.2 mg). $\delta_H$ (500 MHz, Methanol-d4) 7.25 (s, 1H), 5.01-4.92 (m, 1H), 4.48-4.33 (m, 1H), 3.75 (br s, 2H), 3.32-3.25 (m, 2H), 3.22-3.14 (m, 1H), 3.13-3.04 (m, 1H), 3.04-2.94 (m, 1H), 2.94-2.83 (m, 1H), 2.40-2.27 (m, 2H), 2.12-1.98 (m, 3H), 1.96-1.84 (m, 1H), 1.82-1.71 (m, 1H), 1.71-1.49 (m, 1H), 1.40-1.30 (m, 3H), 1.30-1.20 (m, 4H), 1.15-1.04 (m, 1H), 0.56-0.45 (m, 2H), 0.32-0.21 (m, 2H). LCMS [M+H]$^+$ 529, RT 2.55 minutes (Method 10). Chiral SFC** RT=13.15 minutes.

** Chiral analysis was carried out using CHIRALPAK ID (4.6×250 mm 5 μm) column, 2.4 mL/min, 100 Bar, 65/35 CO$_2$/MEOH+0.5% isopropylamine, using a 30 minutes run time.

Example 260

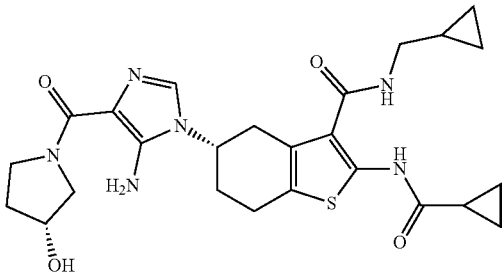 [SMILES: Nc1c(C(=O)N2CC[C@@H](O)C2)ncn1[C@H]1CCc2sc(NC(=O)C3CC3)c(C(=O)NCC3CC3)c2C1]

(5S)-5-[5-amino-4-[(3R)-3-hydroxypyrrolidine-1-carbonyl]imidazol-1-yl]-2-(cyclopropanecarbonylamino)-N-(cyclopropylmethyl)-4,5,6,7-tetrahydrobenzothiophene-3-carboxamide HATU (25 mg, 0.07 mmol) was added to a stirred solution of Intermediate 300 (30 mg, 0.06 mmol), (3R)-pyrrolidin-3-ol (10 ᴍL, 0.124 mmol) and DIPEA (30 ᴍL, 0.17 mmol) in dry DMF (0.6 mL) at room temperature. The reaction mixture was stirred for 2 h, diluted with water (5 mL) and extracted with DCM (3×5 mL). The combined organic layers were dried over sodium sulfate, filtered and evaporated to dryness to afford the crude. The crude material was purified by column chromatography, eluted with 0-20% methanol in DCM to afford crude material. This was treated with 4 M HCl in 1,4-dioxane (222 ᴍL, 0.889 mmol) and stirred for 3 h. The mixture was diluted with saturated aqueous NaHCO$_3$ (5 mL) and extracted with DCM (3×5 mL). The combined organic layers were dried over sodium sulfate, filtered, evaporated to dryness and purified by HPLC (Method 1) to give the title compound (8.0 mg, 28% yield). δ$_H$ (500 MHz, DMSO-d6) 11.20 (s, 1H), 7.71 (br s, 1H), 7.24 (s, 1H), 6.14 (s, 2H), 4.84 (d, J=3.3 Hz, 1H), 4.35-4.27 (m, 1H), 4.27-4.01 (m, 1H), 4.01-3.74 (m, 2H), 3.64-3.43 (m, 2H), 3.19-3.03 (m, 3H), 3.03-2.89 (m, 1H), 2.89-2.74 (m, 2H), 2.24-2.07 (m, 2H), 1.96-1.89 (m, 1H), 1.89-1.65 (m, 2H), 1.06-0.95 (m, 1H), 0.94-0.74 (m, 4H), 0.43-0.33 (m, 2H), 0.25-0.14 (m, 2H). LCMS [M+H]$^+$ 513, RT 2.00 minutes (Method 10).

Example 261

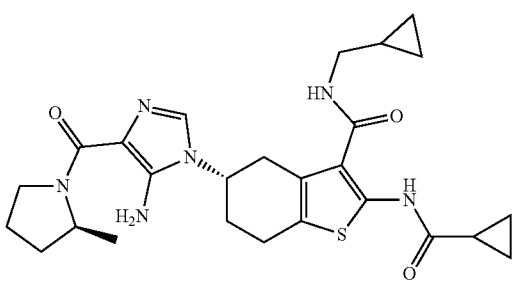 [SMILES: C[C@H]1CCCN1C(=O)c1ncn([C@H]2CCc3sc(NC(=O)C4CC4)c(C(=O)NCC4CC4)c3C2)c1N]

(5S)-5-[5-amino-4-[(2S)-2-methylpyrrolidine-1-carbonyl]imidazol-1-yl]-2-(cyclopropanecarbonylamino)-N-(cyclopropylmethyl)-4,5,6,7-tetrahydrobenzothiophene-3-carboxamide HATU (24 mg, 0.06 mmol) was added to a stirred solution of Intermediate 300 (30 mg, 0.05 mmol), (2{S})-2-methylpyrrolidine (10 mg, 0.117 mmol) and DIPEA (27 ᴍL, 0.15 mmol) in dry DMF (0.6 mL) at room temperature. The reaction mixture was stirred for 30 min. The reaction mixture was diluted with water (5 mL) and extracted with DCM (3×5 mL). The combined organic layers were dried over sodium sulfate, filtered and evaporated to dryness to afford the crude. The crude material was treated with 4 M HCl in 1,4-dioxane (200 ᴍL, 0.800 mmol) and stirred for 2 h. The reaction mixture was diluted with saturated aqueous NaHCO$_3$ (5 mL) and extracted with DCM (3×5 mL). The combined organic layers were dried over sodium sulfate, filtered, evaporated to dryness and purified by column chromatography, eluting with 20% methanol in DCM, followed by HPLC (Method 1) to give the title compound (18 mg, 67% yield). δ$_H$ (500 MHz, DMSO-d6) 11.20 (s, 1H), 7.71 (t, J=5.3 Hz, 1H), 7.24 (s, 1H), 6.17 (s, 2H), 4.37-4.28 (m, 1H), 4.18 (br s, 1H), 3.96 (br s, 1H), 3.61-3.35 (m, 1H), 3.17-3.10 (m, 2H), 3.09-3.02 (m, 1H), 3.02-2.91 (m, 1H), 2.91-2.71 (m, 2H), 2.23-2.06 (m, 2H), 1.98-1.83 (m, 3H), 1.83-1.72 (m, 1H), 1.70-1.37 (m, 1H), 1.15 (d, J=6.3 Hz, 3H), 1.08-0.95 (m, 1H), 0.91-0.79 (m, 4H), 0.43-0.34 (m, 2H), 0.26-0.14 (m, 2H). LCMS [M+H]$^+$ 511, RT 2.71 minutes (Method 10).

Example 262

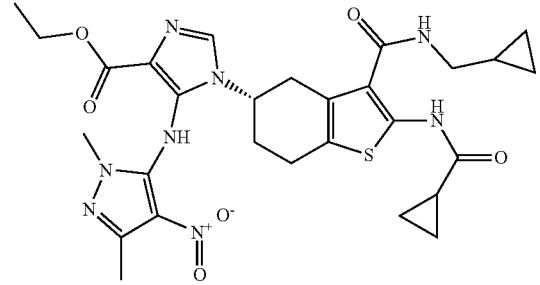

Ethyl 1-[(5S)-2-(cyclopropanecarbonylamino)-3-(cyclopropylmethylcarbamoyl)-4,5,6,7-tetrahydrobenzothiophen-5-yl]-5-[(2,5-dimethyl-4-nitropyrazol-3-yl)amino]imidazole-4-carboxylate 5-chloro-1,3-dimethyl-4-nitro-1H-pyrazole (179 mg, 1.02 mmol), Example 117 (400 mg, 0.85 mmol) and cesium carbonate (1.38 g, 4.24 mmol) were suspended in dry DMF (7 mL) at room temperature. The reaction mixture was heated at 100° C. for 5 h, then cooled to room temperature. The cesium carbonate was filtered, washing with ethyl acetate. The filtrate was diluted with water and neutralized with saturated aqueous NH$_4$Cl then extracted with ethyl acetate (3×25 mL). The combined organic layers were washed with brine (25 mL), dried over sodium sulfate, filtered, concentrated under reduced pressure and purified by HPLC (Method 3) to give the title compound (120 mg, 22% yield). δ$_H$ (500 MHz, Chloroform-d) 11.96 (br s, 1H), 8.48 (s, 1H), 7.63 (s, 1H), 5.64 (s, 1H), 4.75-4.64 (m, 1H), 4.24 (q, J=7.1 Hz, 2H), 3.38-3.22 (m, 3H), 3.19 (s, 3H), 3.11-2.77 (m, 3H), 2.49 (s, 3H), 2.44-2.22 (m, 2H), 1.71-1.63 (m, 1H), 1.22-1.17 (m, 3H), 1.15-1.08 (m, 2H), 1.07-0.96 (m, 1H), 0.95-0.90 (m, 2H), 0.60-0.45 (m, 2H), 0.30-0.19 (m, 2H). LCMS [M+H]$^+$ 611, RT 3.15 minutes (Method 10).

Example 263

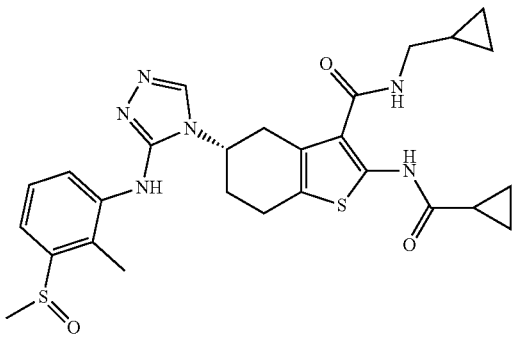 [SMILES: Cc1c(Nc2nncn2[C@H]2CCc3sc(NC(=O)C4CC4)c(C(=O)NCC4CC4)c3C2)cccc1S(C)=O]

(5S)-2-(cyclopropanecarbonylamino)-N-(cyclopropylmethyl)-5-[3-(2-methyl-3-methylsulfinyl-anilino)-1,2,4-triazol-4-yl]-4,5,6,7-tetrahydrobenzothiophene-3-carboxamide To a solution of Intermediate 315 (33 mg, 0.061 mmol) in anhydrous DCM (2 mL) was added 3-chlorobenzenecarboperoxoic acid (14 mg, 0.061 mmol) and the resulting solution was stirred at room temperature for 30 minutes. Concentrated under reduced pressure and purified by flash column chromatography eluting with a 0-20% methanol in DCM gradient, followed by reverse phase HPLC (Method 4) to give the title compound (14 mg, 40% Yield). $\delta_H$ (500 MHz, DMSO-$d_6$) 11.27-11.09 (m, 1H), 8.51-8.43 (m, 1H), 7.88-7.83 (m, 1H), 7.81-7.66 (m, 1H), 7.43 (d, J=7.8 Hz, 1H), 7.37 (t, J=7.8 Hz, 1H), 7.27-7.20 (m, 1H), 4.49-4.38 (m, 1H), 3.20-2.94 (m, 4H), 2.87-2.76 (m, 2H), 2.66-2.65 (m, 3H), 2.26-2.14 (m, 5H), 1.95-1.88 (m, 1H), 1.02-0.92 (m, 1H), 0.89-0.79 (m, 4H), 0.39-0.30 (m, 2H), 0.24-0.13 (m, 2H). LCMS [M+H]⁺ 553, RT 2.07 minutes (Method 10).

Example 264

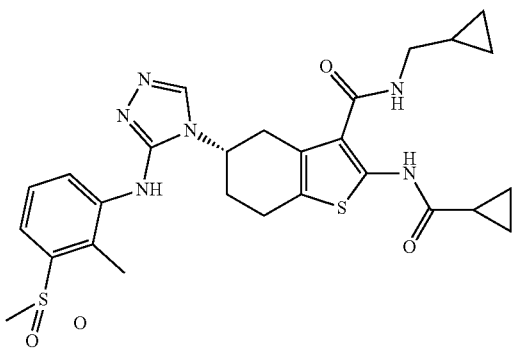

(5S)-2-(cyclopropanecarbonylamino)-N-(cyclopropylmethyl)-5-[3-(2-methyl-3-methylsulfonyl-anilino)-1,2,4-triazol-4-yl]-4,5,6,7-tetrahydrobenzothiophene-3-carboxamide To a solution of Example 263 (33 mg, 0.061 mmol) in anhydrous DCM (2 mL) was added 3-chlorobenzenecarboperoxoic acid (41 mg, 0.18 mmol) and the resulting solution was stirred at room temperature for 2 h. Further 3-chlorobenzenecarboperoxoic acid (41 mg, 0.18 mmol) was added and the mixture was stirred at room temperature for a further 20 mins. Concentrated under reduced pressure and first purified by flash column chromatography eluting with a 0-10% methanol in DCM gradient, then by HPLC (Method 4), and finally by HPLC (Method 2) to give the title compound (1.5 mg, 4.2% Yield). $\delta_H$ (500 MHz, Methanol-$d_4$) 8.42 (s, 1H), 7.84 (dd, J=6.8, 2.4 Hz, 1H), 7.48-7.38 (m, 2H), 4.58 (s, 1H), 3.32-3.25 (m, 2H), 3.23-3.16 (m, 4H), 3.12 (dd, J=15.6, 9.6 Hz, 1H), 3.02-2.89 (m, 2H), 2.61 (s, 3H), 2.42-2.34 (m, 2H), 1.87-1.79 (m, 1H), 1.13-1.04 (m, 1H), 1.04-0.99 (m, 2H), 0.99-0.93 (m, 2H), 0.53-0.47 (m, 2H), 0.29-0.24 (m, 2H). LCMS [M+H]⁺ 569, RT 2.36 minutes (Method 10).

Example 265

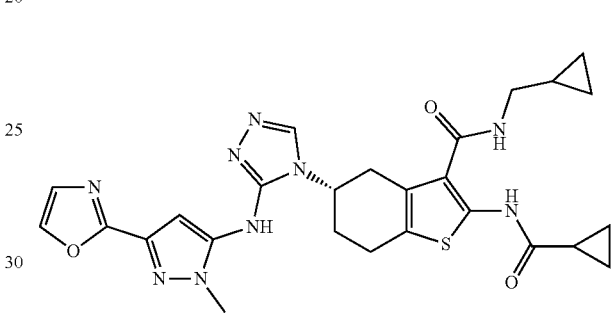

(5S)-2-(cyclopropanecarbonylamino)-N-(cyclopropylmethyl)-5-[3-[(2-methyl-5-oxazol-2-yl-pyrazol-3-yl)amino]-1,2,4-triazol-4-yl]-4,5,6,7-tetrahydrobenzothiophene-3-carboxamide Methanesulfonyl chloride (7.7 μL, 0.10 mmol) was added to a stirred suspension of Intermediate 322 (18 mg, 0.033 mmol) and triethylamine (42 μL, 0.30 mmol) in DCM (1 mL) at 0° C. and stirred at this temperature for 20 minutes. Further methanesulfonyl chloride (7.7 μL, 0.10 mmol) and triethylamine (42 μL, 0.30 mmol) were added and the mixture was stirred at 0° C. for 30 minutes. Further methanesulfonyl chloride (7.7 μL, 0.10 mmol) and triethylamine (42 μL, 0.30 mmol) were added and the mixture was stirred at 0° C. for 15 minutes. The reaction mixture was diluted with DCM (10 mL) and washed with sat. aq. NH₄Cl (2×10 mL), brine (10 mL), dried over MgSO₄, filtered and concentrated under reduced pressure to afford intermediate carbodiimide. To this was added a solution of formic hydrazide (8.0 mg, 0.13 mmol) in dry methanol (1 mL) and the reaction mixture was stirred at room temperature for 30 minutes. Sodium carbonate (14 mg, 0.13 mmol) was added and the mixture was stirred and heated to 50° C. for 18 h. The reaction mixture was cooled to room temperature, concentrated under reduced pressure, diluted with water (10 mL) and extracted with DCM:methanol (9:1, 3×10 mL). The combined organic layers were dried over MgSO₄, filtered, concentrated under reduced pressure and purified by flash column chromatography eluting with a 4-10% methanol in DCM gradient, followed by HPLC (Method 2). The residue was then dissolved in methanol and passed through an SCX-2 cartridge (eluting with methanol followed by 3.5 M ammonia in methanol). The fractions containing the product were concentrated under reduced pressure and purified by flash column chromatography eluting with a 2-8% methanol in DCM gradient to give the title compound (3.4 mg, 18% Yield). δ$_H$ (500 MHz, DMSO-d$_6$) 12.15 (s, 1H, R1), 11.31-11.16 (m, 1H), 8.77 (s, 1H, R2), 8.41 (s, 1H, R2), 8.19 (s, 1H, R1), 8.12 (s, 1H, R2), 8.08 (s, 1H, R1), 7.73 (s, 1H), 7.31 (s, 1H, R2), 7.28 (s, 1H, R1), 6.66 (s, 1H, R2), 6.49 (s, 1H, R1), 4.55-4.41 (m, 1H), 3.80-3.72 (m, 3H, R2), 3.70-3.62 (m, 3H, R1), 3.22-3.05 (m, 3H), 3.04-2.91 (m, 1H), 2.91-2.78 (m, 2H), 2.30-2.15 (m, 2H), 1.96-1.89 (m, 1H), 1.04-0.96 (m, 1H), 0.89-0.79 (m, 4H), 0.38-0.32 (m, 2H), 0.21-0.15 (m, 2H). 1 Contains 2:1 rotamers (R1 and R2). LCMS [M+H]$^+$ 548, RT 2.45 minutes (Method 10).

Example 266

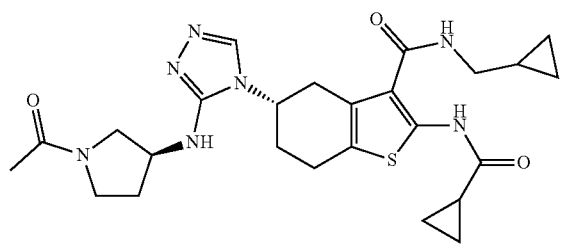 [SMILES: CC(=O)N1CC[C@H](Nc2nncn2[C@H]2CCc3sc(NC(=O)C4CC4)c(C(=O)NCC4CC4)c3C2)C1]

(5S)-5-[3-[[(3S)-1-acetylpyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide Suspension of intermediate 278 (50 mg, 0.092 mmol) was stirred in DCM (5 mL) and cooled to 0° C. DIPEA (48.1 μL, 0.27 mmol) followed by acetic anhydride (7.8 μL, 0.083 mmol) were then added. Reaction stirred for 1 h at 0° C. then warmed to room temperature. Reaction mixture was diluted with DCM then water (15 mL) was added and organic layer separated. The aqueous layer was extracted with DCM (2×10 mL) and the organic extracts combined, dried over sodium sulphate and concentrated under vacuum. The residue was purified by revers phase column chromatography eluting with 5-95% acetonitrile (0.2% ammonium hydroxide) in water (0.2% ammonium hydroxide) to give the title compound (15 mg, 32% Yield). δ$_H$ (500 MHz, Methanol-d4) 8.18 (s, 1H, rotamer), 8.17 (s, 1H, rotamer), 4.46-4.28 (m, 2H), 3.93 (dd, J=11.0, 6.0 Hz, 1H, rotamer), 3.77 (dd, J=12.5, 6.2 Hz, 1H, rotamer), 3.72-3.43 (m, 3H), 3.31-3.15 (m, 3H), 3.05-2.84 (m, 3H), 2.41-2.32 (m, 1H, rotamer), 2.32-2.24 (m, 2H and 1H rotamer), 2.19-2.08 (m, 1H), 2.07 (s, 3H, rotamer), 2.06 (s, 3H, rotamer), 1.13-1.05 (m, 1H), 1.84-1.79 (m, 1H), 1.03-0.93 (m, 4H), 0.53-0.48 (m, 2H), 0.29-0.24 (m, 2H). LCMS [M+H]$^+$ 512, RT 1.68 minutes (Method 10).

Example 267

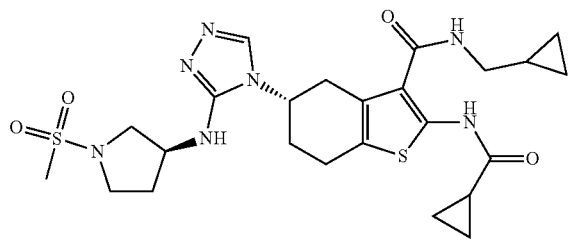 [SMILES: CS(=O)(=O)N1CC[C@H](Nc2nncn2[C@H]2CCc3sc(NC(=O)C4CC4)c(C(=O)NCC4CC4)c3C2)C1]

(5S)-2-(cyclopropanecarbonylamino)-N-(cyclopropylmethyl)-5-[3-[[(3S)-1-methylsulfonylpyrrolidin-3-yl]amino]-1,2,4-triazol-4-yl]-4,5,6,7-tetrahydrobenzothiophene-3-carboxamide Suspension of intermediate 278 (50 mg, 0.092 mmol) was stirred in DCM (5 mL) was cooled to 0° C. DIPEA (48.1 μL, 0.27 mmol) followed by methanesulfonyl methanesulfonate (14.4 mg, 0.083 mmol) were then added. Reaction stirred for 1 h at 0° C. Then warm to room temperature. Reaction mixture was diluted with DCM (20 mL) then water (15 mL) was added and organic layer separated. The aqueous layer was extracted with DCM (2×10 mL) and the organic extracts combined, dried over sodium sulphate and concentrated under vacuum. The residue was purified by reverse phase column chromatography eluting with 5-95% Acetonitrile (0.2% ammonium hydroxide) in water (0.2% ammonium hydroxide) to give the title compound (16 mg, 31% Yield). δ$_H$ (500 MHz, Methanol-d4) 8.18 (s, 1H), 4.45-4.37 (m, 1H), 4.36-4.30 (m, 1H), 3.68 (dd, J=10.6, 6.0 Hz, 1H), 3.59-3.52 (m, 1H), 3.45-3.39 (m, 1H), 3.37-3.34 (m, 1H), 3.31-3.17 (m, 3H), 3.03-2.86 (m, 6H), 2.42-2.33 (m, 1H), 2.33-2.25 (m, 2H), 2.16-2.07 (m, 1H), 1.87-1.78 (m, 1H), 1.15-1.06 (m, 1H), 1.04-0.93 (m, 4H), 0.55-0.48 (m, 2H), 0.30-0.23 (m, 2H). LCMS [M+H]$^+$ 548, RT 1.90 minutes (Method 10).

Example 268

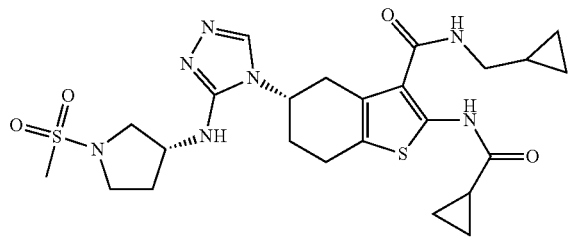 [SMILES: CS(=O)(=O)N1CC[C@@H](Nc2nncn2[C@H]2CCc3sc(NC(=O)C4CC4)c(C(=O)NCC4CC4)c3C2)C1]

(5S)-2-(cyclopropanecarbonylamino)-N-(cyclopropylmethyl)-5-[3-[[(3R)-1-methylsulfonylpyrrolidin-3-yl]amino]-1,2,4-triazol-4-yl]-4,5,6,7-tetrahydrobenzothiophene-3-carboxamide Suspension of intermediate 326 (50 mg, 0.092 mmol) was stirred in DCM (5 mL) was cooled to 0° C. then DIPEA (48.101, 0.27 mmol) followed by methanesulfonyl methanesulfonate (14.4 mg, 0.083 mmol) were added. Reaction stirred for 2 h at 0° C., then warmed to room temperature. Reaction mixture was diluted with DCM (20 mL) then water (15 mL) was added and organic layer separated. The aqueous layer was extracted with DCM (2×10 mL) and the organic fractions combined, dried over sodium sulphate and concentrated under vacuum. The residue was purified by HPLC (Method 4) to give the title compound (12 mg, 23% Yield). $\delta_H$ (500 MHz, Methanol-d4) 8.21 (s, 1H), 4.45-4.37 (m, 1H), 4.36-4.30 (m, 1H), 3.67 (dd, J=10.6, 5.9 Hz, 1H), 3.59-3.52 (m, 1H), 3.45-3.39 (m, 1H), 3.36 (dd, J=10.6, 4.2 Hz, 1H), 3.32-3.17 (m, 3H), 3.07-2.84 (m, 6H), 2.42-2.33 (m, 1H), 2.33-2.25 (m, 2H), 2.17-2.06 (m, 1H), 1.87-1.77 (m, 1H), 1.14-1.04 (m, 1H), 1.04-0.91 (m, 4H), 0.56-0.46 (m, 2H), 0.34-0.22 (m, 2H). LCMS [M+H]$^+$ 548, RT 1.90 minutes (Method 10).

Example 269

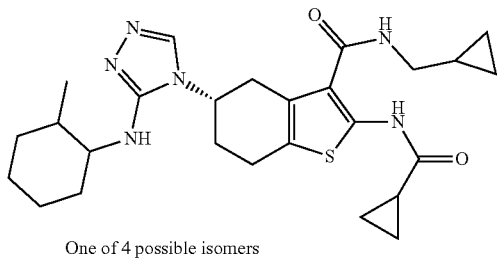 [SMILES: CC1CCCCC1Nc1nncn1[C@H]1CCc2sc(NC(=O)C3CC3)c(C(=O)NCC3CC3)c2C1]

One of 4 possible isomers (5S)-2-(cyclopropanecarbonylamino)-N-(cyclopropylmethyl)-5-[3-[(2-methylcyclohexyl)amino]-1,2,4-triazol-4-yl]-4,5,6,7-tetrahydrobenzothiophene-3-carboxamide Absolute stereochemistry of the 2-methylcyclohexanamine group is unknown Intermediate 330 (49.0 mg, 0.099 mmol) was separated by chiral SFC (using 28% Methanol: 72% $CO_2$ with Chiralpak IC 25 cm column at 15 mL/min) to give the title compound as one of 4 possible diastereoisomers (Peak 3, 12.9 mg, 19.6% Yield). $\delta_H$ (500 MHz, Methanol-d4) 8.10 (s, 1H), 4.54-4.49 (m, 1H), 3.89-3.81 (m, 1H), 3.31-3.27 (m, 1H), 3.24 (dd, J=15.5, 4.9 Hz, 1H), 3.18 (dd, J=13.8, 7.0 Hz, 1H), 3.05-2.93 (m, 2H), 2.92-2.83 (m, 1H), 2.33-2.22 (m, 2H), 2.22-2.10 (m, 1H), 1.87-1.73 (m, 2H), 1.71-1.54 (m, 5H), 1.51-1.37 (m, 2H), 1.15-1.05 (m, 1H), 1.04-0.99 (m, 2H), 0.99-0.92 (m, 5H), 0.53-0.48 (m, 2H), 0.29-0.25 (m, 2H). LCMS [M+H]$^+$ 497, RT 2.92 minutes (Method 10). Chiral SFC** RT=34.91 minutes.
** Chiral analysis using Chiralpak IC 4.6×250 mm, 5 µm column, flow rate 4 mL/min, eluting with 72:28 $CO_2$:Methanol, 50 minutes run time on a WatersThar Resolution-3100 MS.

Example 270

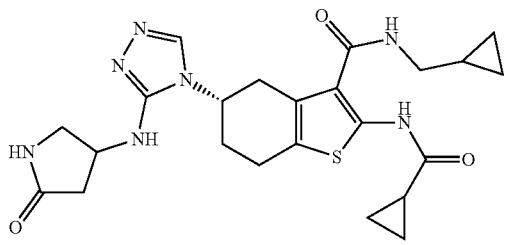 [SMILES: O=C1CC(Nc2nncn2[C@H]2CCc3sc(NC(=O)C4CC4)c(C(=O)NCC4CC4)c3C2)CN1]

(5S)-2-(cyclopropanecarbonylamino)-N-(cyclopropylmethyl)-5-[3-[(5-oxopyrrolidin-3-yl)amino]-1,2,4-triazol-4-yl]-4,5,6,7-tetrahydrobenzothiophene-3-carboxamide The title compound was obtained following general method 5 with intermediate 333 (192 mg, 0.30 mmol) and TFA (231.8 µl, 3.0 mmol). Purification by HPLC (Method 4) gave the title compound (78 mg, 47% Yield). $\delta_H$ (500 MHz, Methanol-d4) 8.20 (s, 1H), 4.54-4.45 (m, 1H), 4.44-4.36 (m, 1H), 3.86-3.79 (m, 1H), 3.40-3.34 (m, 1H), 3.30-3.14 (m, 3H), 3.05-2.79 (m, 4H), 2.46-2.35 (m, 1H), 2.34-2.20 (m, 2H), 1.87-1.79 (m, 1H), 1.13-1.05 (m, 1H), 1.04-0.99 (m, 2H), 0.99-0.92 (m, 2H), 0.54-0.48 (m, 2H), 0.30-0.23 (m, 2H). LCMS [M+H]$^+$ 484, RT 1.64 minutes (Method 10).

Example 271

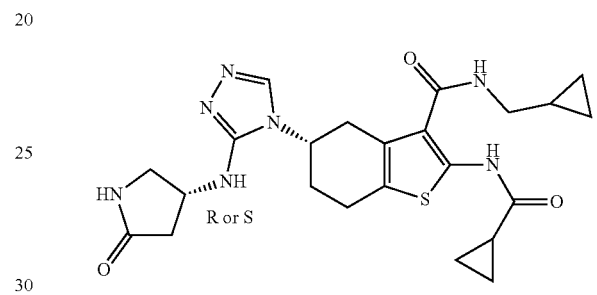

R or S (5S)-2-(cyclopropanecarbonylamino)-N-(cyclopropylmethyl)-5-[3-[[(3R*)-5-oxopyrrolidin-3-yl]amino]-1,2,4-triazol-4-yl]-4,5,6,7-tetrahydrobenzothiophene-3-carboxamide (*or S)

Example 270 (65 mg, 0.134 mmol) was separated by chiral chromatography (60:40 Ethanol: Methanol with a Cellulose-4 25 cm column at 8 mL/min) to give the title compound (18.3 mg, 28% Yield). $\delta_H$ (500 MHz, Methanol-d4) 8.18 (s, 1H), 4.54-4.46 (m, 1H), 4.43-4.32 (m, 1H), 3.83 (dd, J=10.7, 6.8 Hz, 1H), 3.36 (dd, J=10.7, 3.7 Hz, 1H), 3.31-3.14 (m, 3H), 3.06-2.87 (m, 3H), 2.83 (dd, J=17.3, 8.1 Hz, 1H), 2.40 (dd, J=17.3, 4.5 Hz, 1H), 2.33-2.23 (m, 2H), 1.86-1.78 (m, 1H), 1.14-1.04 (m, 1H), 1.04-0.99 (m, 2H), 0.99-0.92 (m, 2H), 0.55-0.47 (m, 2H), 0.29-0.23 (m, 2H). LCMS [M+H]$^+$ 484, RT 1.63 minutes (Method 10). Chiral LC** RT=6.03 minutes.
** Chiral analysis using Cellulose-4 (4.6×250 mm 5 µm) column, flow rate 1 mL/min, eluting with 60:40 Ethanol:Methanol, 10 minutes run time on a Waters 2795.

Example 272

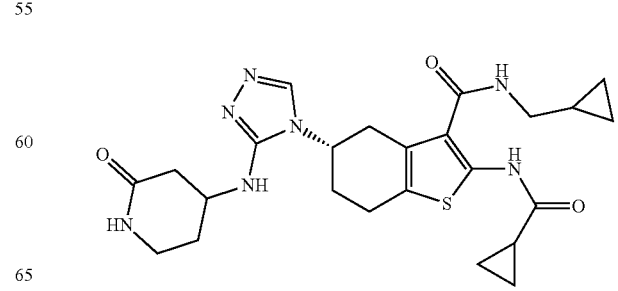

(5S)-2-(cyclopropanecarbonylamino)-N-(cyclopropylmethyl)-5-[3-[(2-oxo-4-piperidyl)amino]-1,2,4-triazol-4-yl]-4,5,6,7-tetrahydrobenzothiophene-3-carboxamide The title compound was obtained following general method 5 with intermediate 336 (184 mg, 0.27 mmol) and TFA (210.8 µl, 3.0 mmol). Purification by HPLC (Method 4) gave the title compound (52 mg, 38% Yield). $\delta_H$ (500 MHz, Methanol-d4) 8.20 (s, 1H), 4.48-4.36 (m, 1H), 4.13-3.99 (m, 1H), 3.43-3.35 (m, 2H), 3.31-3.15 (m, 3H), 3.07-2.86 (m, 3H), 2.80 (dd, J=17.5, 4.6 Hz, 1H), 2.47-2.35 (m, 1H), 2.33-2.20 (m, 3H), 1.90-1.77 (m, 2H), 1.14-1.06 (m, 1H), 1.03-0.99 (m, 2H), 0.98-0.94 (m, 2H), 0.55-0.48 (m, 2H), 0.30-0.24 (m, 2H). LCMS [M+H]$^+$ 498, RT 1.60 minutes (Method 10).

Example 273

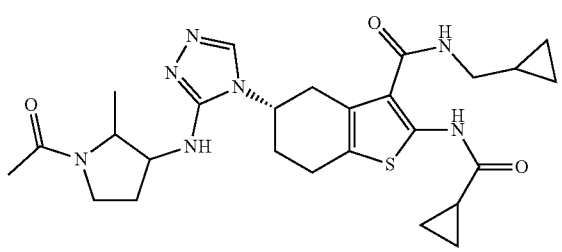 [SMILES: CC(=O)N1CCC(Nc2nncn2[C@H]2CCc3sc(NC(=O)C4CC4)c(C(=O)NCC4CC4)c3C2)C1C]

(5S)-5-[3-[(1-acetyl-2-methyl-pyrrolidin-3-yl)amino]-1,2,4-triazol-4-yl]-2-(cyclopropanecarbonylamino)-N-(cyclopropylmethyl)-4,5,6,7-tetrahydrobenzothiophene-3-carboxamide Suspension of intermediate 340 (265 mg, 0.452 mmol) was stirred in DCM (20 mL) was cooled to 0° C. DIPEA (236.3 µL, 1.35 mmol) followed by acetic anhydride (38.4 µL, 0.407 mmol) were then added. Reaction stirred for 1 h at 0° C. then warmed to room temperature. Reaction mixture was diluted with DCM then water (25 mL) was added and the organic layer separated. The aqueous layer was extracted with DCM (2×20 mL) and the organic extracts combined, dried over sodium sulphate and concentrated under vacuum. The residue was purified by column chromatography eluting with 0 to 30% MeOH in DCM to give the title compound (169 mg, 68% Yield). $\delta_H$ (500 MHz, Methanol-d4) 8.23-8.06 (m, 1H), 4.58-4.46 (m, 1H), 4.42 (dt, J=9.2, 4.3 Hz, 1H), 4.27-4.08 (m, 1H), 3.98 (dd, J=28.0, 3.6 Hz, 1H), 3.76-3.60 (m, 2H), 3.57-3.41 (m, 1H), 3.29-3.12 (m, 3H), 3.05-2.80 (m, 3H), 2.28 (tt, J=14.1, 5.9 Hz, 3H), 2.21-2.07 (m, 2H), 2.07-1.99 (m, 2H), 1.81 (td, J=7.7, 4.3 Hz, 1H), 1.39-1.25 (m, 5H), 1.08-0.92 (m, 7H), 0.53-0.44 (m, 2H), 0.28-0.20 (m, 2H). LCMS [M+H]$^+$ 526, RT 1.76 minutes (Method 10).

Example 274

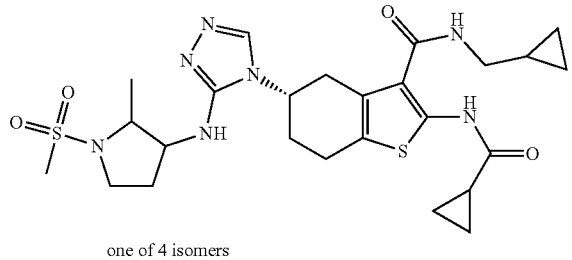 [SMILES: CC1C(Nc2nncn2[C@H]2CCc3sc(NC(=O)C4CC4)c(C(=O)NCC4CC4)c3C2)CCN1S(C)(=O)=O]

one of 4 isomers

(5S)-2-(cyclopropanecarbonylamino)-N-(cyclopropylmethyl)-5-[3-[(2-methyl-1-methylsulfonyl-pyrrolidin-3-yl)amino]-1,2,4-triazol-4-yl]-4,5,6,7-tetrahydrobenzothiophene-3-carboxamide *Absolute stereochemistry of the 2-methyl-1-methylsulfonyl-pyrrolidin-3-amine group is unknown Intermediate 341 (135 mg, 0.24 mmol) was separated by SFC (Chiralcel OJ-H 25 cm column, with 10% Methanol+ 0.2% DEA:90% CO$_2$ at 15 mL/min) to give the title compound as a single isomer (8.5 mg, 6% Yield). $\delta_H$ (500 MHz, Methanol-d4) 8.18 (s, 1H), 4.49-4.35 (m, 1H), 4.26-4.14 (m, 2H), 3.53-3.45 (m, 1H), 3.30-3.24 (m, 2H), 3.20 (dd, J=15.4, 5.1 Hz, 1H), 3.14 (dd, J=13.8, 7.0 Hz, 1H), 3.03-2.98 (m, 1H), 2.97 (s, 3H), 2.96-2.85 (m, 2H), 2.36-2.24 (m, 3H), 2.21-2.08 (m, 1H), 1.84-1.76 (m, 1H), 1.10-1.02 (m, 4H), 1.02-0.98 (m, 2H), 0.97-0.89 (m, 2H), 0.56-0.41 (m, 2H), 0.28-0.21 (m, 2H). LCMS [M+H]$^+$ 562, RT 2.09 minutes (Method 10). Chiral SFC** RT=10.36 minutes.

** Chiral analysis using Chiralpak AS-H 4.6×250 mm, 5 µm column, flow rate 4 mL/min, eluting with 30% Methanol: 70% CO$_2$, 30 minutes run time on a WatersThar Resolution-3100 MS.

Example 275

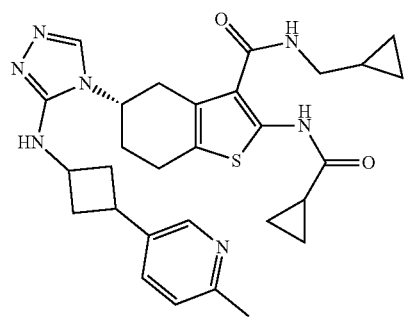 [SMILES: Cc1ccc(C2CC(Nc3nncn3[C@H]3CCc4sc(NC(=O)C5CC5)c(C(=O)NCC5CC5)c4C3)C2)cn1]

(5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamide The title compound was obtained following general method 5 with intermediate 344 (160 mg, 0.23 mmol) and TFA (175.9 µl, 2.29 mmol). Purification by HPLC (Method 4) gave the title compound (91 mg, 72% Yield). $\delta_H$ (500 MHz, Methanol-d4) 8.35 (d, J=2.3 Hz, 1H, isomer), 8.31 (d, J=2.2 Hz, 1H, isomer), 8.17 (s, 1H, isomer), 8.15 (s, 1H, isomer), 7.83 (dd, J=8.1, 2.3 Hz, 1H, isomer), 7.71 (dd, J=8.1, 2.3 Hz, 1H, isomer), 7.33 (d, J=8.1 Hz, 1H, isomer), 7.28 (d, J=8.1 Hz, 1H, isomer), 4.50-4.40 (m, 1H, isomer), 4.40-4.30 (m, 1H), 4.27-4.17 (m, 1H, isomer), 3.74-3.66 (m, 1H, isomer), 3.30-3.20 (m, 2H, 1H, isomer), 3.20-3.12 (m, 1H), 3.05-2.86 (m, 4H), 2.65-2.54 (m, 2H), 2.53 (s, 3H, isomer), 2.50 (s, 3H, isomer), 2.37-2.22 (m, 2H), 2.18-2.07 (m, 1H), 1.86-1.76 (m, 1H), 1.13-1.03 (m, 1H), 1.02-0.91 (m, 4H), 0.52-0.43 (m, 2H), 0.31-0.18 (m, 2H). LCMS [M+H]⁺ 546, RT 1.38 minutes (Method 10).

Example 276 and 277

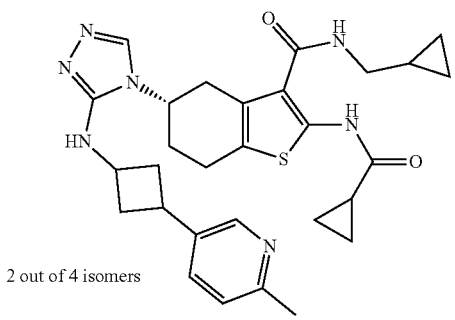 [SMILES: Cc1ccc(C2CC(Nc3nncn3[C@H]3CCc4sc(NC(=O)C5CC5)c(C(=O)NCC5CC5)c4C3)C2)cn1]

(5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamid * Absolute stereochemistry of the 3-(6-methyl-3-pyridyl)cyclobutanamine group in both isolated isomers is unknown Example 275 (49.0 mg, 0.089 mmol) was separated by chiral liquid chromatography (eluting with 85:15 Heptane:Ethanol using Chiralcel OD-H 25 cm column at 18 mL/min) to give two out of four possible diastereoisomers.

Isomer 1 (Peak 1, 7.5 mg, 15% Yield). δ$_H$ 500 MHz, Methanol-d4) 8.29 (d, J=2.2 Hz, 1H), 8.12 (s, 1H), 7.67 (dd, J=8.0, 2.3 Hz, 1H), 7.24 (d, J=8.0 Hz, 1H), 4.43-4.30 (m, 1H), 4.27-4.14 (m, 1H), 3.29-3.20 (m, 3H), 3.15 (dd, J=13.8, 7.0 Hz, 1H), 3.03-2.84 (m, 5H), 2.48 (s, 3H), 2.34-2.24 (m, 2H), 2.18-2.05 (m, 2H), 1.85-1.75 (m, 1H), 1.10-1.03 (m, 1H), 1.04-0.98 (m, 2H), 0.97-0.92 (m, 2H), 0.51-0.43 (m, 2H), 0.27-0.19 (m, 2H). LCMS [M+H]⁺ 546, RT 1.37 minutes (Method 10). Chiral LC** RT=26.23 minutes.

Isomer 2 (peak 2, 8.7 mg, 18% Yield). δ$_H$ (500 MHz, Methanol-d4) 8.32 (d, J=2.3 Hz, 1H), 8.14 (s, 1H), 7.78 (dd, J=8.1, 2.3 Hz, 1H), 7.29 (d, J=8.1 Hz, 1H), 4.46-4.39 (m, 1H), 4.38-4.32 (m, 1H), 3.73-3.62 (m, 1H), 3.30-3.23 (m, 2H), 3.16 (dd, J=13.8, 7.0 Hz, 1H), 3.04-2.94 (m, 2H), 2.93-2.86 (m, 1H), 2.65-2.52 (m, 4H), 2.51 (s, 3H), 2.35-2.25 (m, 2H), 1.87-1.76 (m, 1H), 1.11-1.05 (m, 1H), 1.02-0.97 (m, 2H), 0.97-0.93 (m, 2H), 0.53-0.45 (m, 2H), 0.31-0.21 (m, 2H). LCMS [M+H]⁺ 546, RT 1.40 minutes (Method 10). Chiral LC** RT=31.22 minutes.
** Chiral analysis using Chiralcel OD-H (4.6×250 mm 5 μm) column, flow rate 1 mL/min, eluting with 85:15 Heptane:Ethanol, 120 minutes run time on a Waters 2795

Example 278

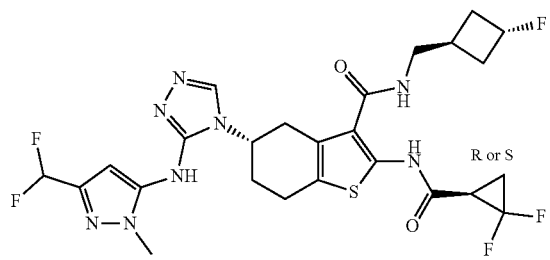 [SMILES: Cn1nc(C(F)F)cc1Nc1nncn1[C@H]1CCc2sc(NC(=O)[C@H]3CC3(F)F)c(C(=O)NC[C@H]3C[C@H](F)C3)c2C1]

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [*or S]

To a suspension of Intermediate 349 (75 mg, 0.146 mmol) and trans-(3-fluorocyclobutyl)methanamine hydrochloride (61 mg, 0.438 mmol) in DCM (3 mL) was added DIPEA (0.077 mL, 0.438 mmol) and 1-[bis(dimethylamino)methylidene]-1H-[1,2,3]triazolo[4,5-b]pyridin-1-ium 3-oxide hexafluorophosphate (83 mg, 0.219 mmol). The solution was stirred at room temperature for 1 hour. The DCM was removed and the mixture was dissolved in CH₃CN (2 mL) and heated at 40° C. for 2 hours. The solvent was removed to give a brown gum. Purification by flash column chromatography eluting with 0 to 100% of ethyl acetate in heptane gradient gave the racemic compound (60 mg, 86% pure, 59% Yield). This racemate was separated using SFC conditions (Chiralpak IG 5 μm 250×30 mm, CO₂/(MeOH+0.5% IPA) 70/30, 70 g/min, 40° C., 100 bar) to give the title compound (13.8 mg, 25% yield). δ$_H$ (500 MHz, Methanol-d4) 8.22 (2×s, 2H), 6.62 (t, J=55.2 Hz, 1H), 6.27 (s, 1H), 5.15 (p, J=6.0 Hz, 0.5H), 5.03 (q, J=5.9 Hz, 0.5H), 4.60-4.47 (m, 1H), 3.73 (s, 3H), 3.51-3.41 (m, 1H), 3.38-3.32 (m, 1H), 3.26 (m, 1H), 3.07-2.87 (m, 3H), 2.87-2.77 (m, 1H), 2.64-2.53 (m, 1H), 2.34 (tt, J=12.3, 5.5 Hz, 2H), 2.30-2.16 (m, 4H), 2.10 (dt, J=13.6, 6.9 Hz, 1H), 1.98-1.88 (m, 1H). LCMS [M+H]⁺ 599, RT 2.89 minutes (Method 10). Chiral SFC** RT=5.47 minutes.
** Chiralpak IG (250 mm×4.6 5 μm) column, 70/30% CO₂ (MeOH+0.5% osopropylamine), 2.4 mL/min, 100 Bar, 40° C., SFC BERGER.

Example 279

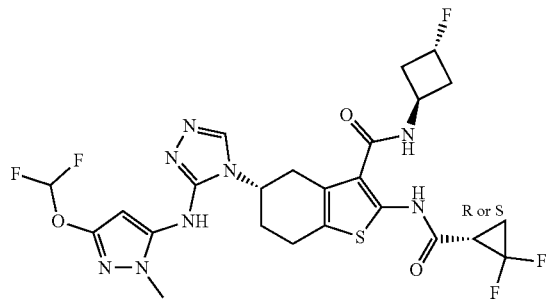 [SMILES: Cn1nc(OC(F)F)cc1Nc1nncn1[C@H]1CCc2sc(NC(=O)[C@@H]3CC3(F)F)c(C(=O)N[C@H]3C[C@H](F)C3)c2C1]

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-(trans-3-fluorocyclobutyl)-4,5,6,7-tetrahydrobenzothiophene-3-carboxamide (* or S)

To a suspension of Intermediate 353 (42 mg, 0.079 mmol) and trans-3-fluorocyclobutanamine hydrochloride (30 mg, 0.238 mmol) in DCM (3 mL) was added DIPEA (0.042 mL, 0.238 mmol) and 1-[bis(dimethylamino)methylidene]-1H-[1,2,3]triazolo[4,5-b]pyridin-1-ium 3-oxide hexafluorophosphate (45 mg, 0.119 mmol). The solution was stirred at room temperature for 1 hour. The DCM was removed and the mixture was suspended in acetonitrile (3 mL) and heated at 75° C. for 2 hours. The solvent was removed to give a brown oil. Purification by HPLC (Method 4) gave the racemic product as a white solid (26 mg, 53% yield). The racemic compound was separated by chiral SFC to give the title compound (6 mg, 24% Yield). $\delta_H$ (400 MHz, Methanol-d4) 8.29 (s, 1H), 6.89 (t, J=73.7 Hz, 1H), 5.77 (s, 1H), 5.17 (dtt, J=56.5, 6.5, 3.4 Hz, 1H), 4.62 (dd, J=8.3, 6.1 Hz, 1H), 4.53 (s, 1H), 3.60 (s, 3H), 3.27 (s, 1H), 2.97 (ddd, J=32.4, 16.1, 7.7 Hz, 3H), 2.88-2.74 (m, 1H), 2.70-2.51 (m, 2H), 2.50-2.24 (m, 4H), 2.15-2.03 (m, 1H), 1.97-1.82 (m, 1H). LCMS [M+H]+ 601, RT 1.53 minutes (Method 26). Chiral SFC** RT=2.92 minutes.

** Using chiral SFC Method 1 with Chiral Analysis Method, using a Chiral Art Cellulose SJ column and eluting with a 25 to 40% MeOH (+0.1% NH4OH) gradient Example 280

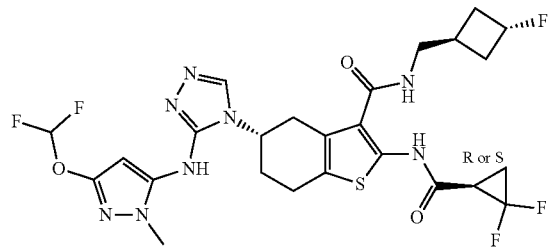 [SMILES: Cn1nc(OC(F)F)cc1Nc1nncn1[C@H]1CCc2sc(NC(=O)[C@H]3CC3(F)F)c(C(=O)NC[C@H]3C[C@H](F)C3)c2C1]

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [* or S]

To a suspension of Intermediate 353 (41 mg, 0.0774 mmol) and trans-(3-fluorocyclobutyl)methanamine hydrochloride (32 mg, 0.232 mmol) in DCM (3 mL) were added DIPEA (0.041 mL, 0.232 mmol) and 1-[bis(dimethylamino)methylidene]-1H-[1,2,3]triazolo[4,5-b]pyridin-1-ium 3-oxide hexafluorophosphate (44 mg, 0.116 mmol). The solution was stirred at room temperature for 1 hour. The DCM was removed and the mixture was suspended in acetonitrile (3 mL) and heated at 75° C. for 2 hours. The solvent was removed to give a brown oil. Purification by flash column chromatography eluting with 0 to 100% of ethyl acetate in heptane gradient then 10% MeOH in EtOAc gradient gave the racemic compound as a white solid (20 mg, 95% pure, 48% Yield). The racemic compound was separated by chiral SFC to give the title compound (4 mg, 20% Yield). $\delta_H$ (400 MHz, Methanol-d4) 8.32 (s, 1H), 6.88 (t, J=73.8 Hz, 1H), 5.79 (s, 1H), 5.09 (dp, J=55.8, 6.1 Hz, 1H), 4.52 (s, 1H), 3.60 (s, 3H), 3.51-3.33 (m, 2H), 3.26 (s, 1H), 3.11-2.86 (m, 3H), 2.81 (q, J=10.8 Hz, 1H), 2.57 (ddq, J=12.7, 8.4, 4.3 Hz, 1H), 2.43-2.25 (m, 3H), 2.25-2.12 (m, 3H), 2.12-2.02 (m, 1H), 1.96-1.81 (m, 1H). LCMS [M+H]+ 615, RT 1.63 minutes (Method 26). Chiral SFC** RT=4.58 minutes.

** Using chiral SFC Method 1 with a Chiral Art Cellulose SJ column.

Example 281

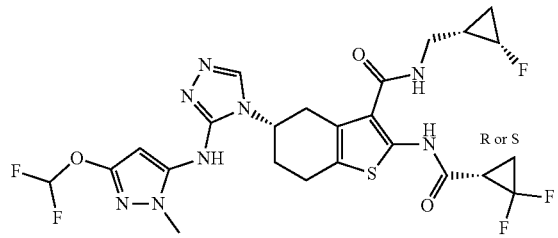 [SMILES: Cn1nc(OC(F)F)cc1Nc1nncn1[C@H]1CCc2sc(NC(=O)[C@@H]3CC3(F)F)c(C(=O)NC[C@@H]3C[C@@H]3F)c2C1]

(5S)-2-[[(1S*)-2,2-difluorocyclopropanecarbonyl]amino]-5-[3-[[5-(difluoromethoxy)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R]

To a suspension of Intermediate 353 (95 mg, 0.179 mmol) and [(1S,2S)-2-fluorocyclopropyl]methanamine hydrochloride (68 mg, 0.538 mmol) in DCM (3 mL) were added DIPEA (0.094 mL, 0.538 mmol) and 1-[bis(dimethylamino)methylidene]-1H-[1,2,3]triazolo[4,5-b]pyridin-1-ium 3-oxide hexafluorophosphate (102 mg, 0.269 mmol). The solution was stirred at room temperature for 1 hour. The DCM was removed and the mixture was dissolved in CH3CN (3 mL) and heated at 50° C. for 2 hours. The solvent was removed to give a brown gum. Purification by flash column chromatography eluting with 0 to 100% of ethyl acetate in heptane gradient then 0-5% MeOH in EtOAc gradient gave the racemic compound (70 mg, 63% yield). The racemic compound was separated using the SFC conditions (Chiralpak IC, 5 μm 250×30 mm, CO2/(MeOH+0.5% isopropylamine) 70/30, 70 g/min, 40° C., 100 bar) to give the title compound (32 mg, 47% Yield. $\delta_H$ (500 MHz, Methanol-d4) 8.18 (s, 1H), 6.89 (t, J=73.9 Hz, 1H), 5.74 (s, 1H), 4.76 (td, J=6.0, 2.6 Hz) and 4.63 (td, J=6.0, 2.6 Hz, 1H in total), 4.54 (dt, J=8.9, 4.2 Hz, 1H), 3.65 (dd, J=13.8, 6.3 Hz, 1H), 3.61 (s, 3H), 3.42-3.36 (m, 1H), 3.10-2.86 (m, 3H), 2.86-2.74 (m, 1H), 2.41-2.30 (m, 2H), 2.15-2.03 (m, 1H), 1.97-1.80 (m, 1H), 1.25 (dd, J=18.7, 6.8 Hz, 2H), 0.90-0.69 (m, 2H). LCMS [M+H]+ 601, RT 2.78 minutes (Method 10). Chiral SFC* RT=18.0 minutes.

* CHIRALPAK IC (250×4.6 mm 5 μm) column, 70/30% CO2/(MeOH+0.5% isopropylamine) 2.4 mL/min, 100 Bar 40° C., SFC Berger.

Example 282 and 283

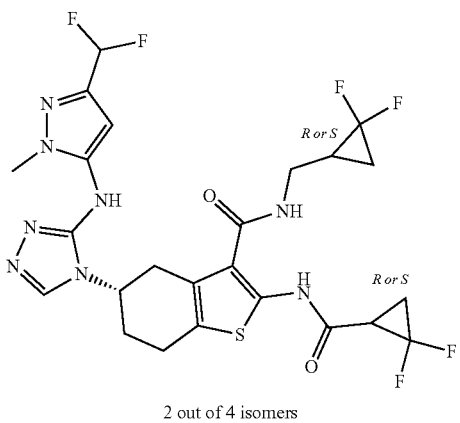 [SMILES: Cn1nc(C(F)F)cc1Nc1nncn1[C@H]1CCc2sc(NC(=O)C3CC3(F)F)c(C(=O)NCC3CC3(F)F)c2C1]

2 out of 4 isomers (5S)-2-[(2,2-difluorocyclopropanecarbonyl)amino]-N-[(2,2-difluorocyclopropyl)methyl]-5-[3-[[5-(difluoromethyl)-2-methyl-pyrazol-3-yl]amino]-1,2,4-triazol-4-yl]-4,5,6,7-tetrahydrobenzothiophene-3-carboxamide * Note absolute stereochemistry at either difluorocyclopropane moiety is unknown To a suspension of (2,2-difluorocyclopropyl)methanamine hydrochloride (84 mg, 0.584 mmol) and Intermediate 349 (100 mg, 0.195 mmol) in DCM (3 mL) were added N-ethyl-N-isopropyl-propan-2-amine (0.10 mL, 0.584 mmol) and 1-[bis(dimethylamino)methylidene]-1H-[1,2,3]triazolo[4,5-b]pyridin-1-ium 3-oxide hexafluorophosphate (111 mg, 0.292 mmol). The solution was stirred at room temperature for 50 minutes. The DCM was removed and the mixture was dissolved in CH₃CN (2 mL) and heated at 40° C. for 2 hours. The reaction was stirred for a further 18 hours at room temperature. Purification by reverse phase column chromatography eluting with a gradient of 10-50% CH₃CN/H₂O to 100% CH₃CN [containing 0.1% formic acid] gave the title compound as a mixture of isomers (56 mg, 47% yield). The mixture was separated using the SFC conditions (Chiralpak IB and IC, 5 μm 250×30 mm, CO₂/MeOH+0.5% isopropylamine 85/15 or 70/30, Flowrate: 70 g/min, 40° C., 100 bar) to give 2 out of 4 possible isomers.

Isomer 1 (5.4 mg, 10% Yield). $\delta_H$ (500 MHz, Methanol-d4) 8.09 (s, 1H), 6.62 (t, J=55.1 Hz, 1H), 6.30 (s, 1H), 4.63-4.49 (m, 1H), 3.73 (s, 3H), 3.56-3.40 (m, 2H), 3.12-2.77 (m, 4H), 2.40-2.27 (m, 2H), 2.17-2.06 (m, 1H), 2.06-1.94 (m, 1H), 1.94-1.82 (m, 1H), 1.55-1.41 (m, 1H). LCMS [M+H]⁺ 603, RT 2.82 minutes (Method 10). Chiral SFC** RT=7.83 minutes.

Isomer 2 (6 mg, 11% Yield). $\delta_H$ (500 MHz, Methanol-d4) 8.19 (s, 1H), 6.62 (t, J=55.1 Hz, 1H), 6.29 (s, 1H), 4.62-4.50 (m, 1H), 3.73 (s, 3H), 3.69-3.51 (m, 2H), 3.40-3.35 (m, 2H), 3.11-2.74 (m, 4H), 2.39-2.30 (m, 2H), 2.13-1.93 (m, 2H), 1.93-1.78 (m, 1H), 1.48 (tdd, J=12.1, 7.8, 4.5 Hz, 1H). LCMS [M+H]⁺ 603, RT 2.82 minutes (Method 10). Chiral SFC** RT=6.81 minutes.

** Chiralpak IG (250 mm×4.6) 5 μm, 70/30% CO₂ (MeOH+0.5% isopropylamine) 2.4 mL/min, 100 Bar, 40° C., SFC BERGER.

Example 284

(5S)-2-[[(1S*)-2,2-difluorocyclopropanecarbonyl]amino]-5-[3-[[5-(difluoromethyl)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R]

To a suspension of Intermediate 349 (99 mg, 0.193 mmol) and [(1S,2S)-2-fluorocyclopropyl]methanamine hydrochloride (73 mg, 0.578 mmol) in DCM (3 mL) were added DIPEA (0.10 mL, 0.578 mmol) and 1-[bis(dimethylamino)methylidene]-1H-[1,2,3]triazolo[4,5-b]pyridin-1-ium 3-oxide hexafluorophosphate (110 mg, 0.289 mmol). The solution was stirred at room temperature for 1 hour. The DCM was removed and the mixture was dissolved in CH₃CN (3 mL) and heated at 50° C. for 2 hours. The solvent was removed to give a brown gum. Purification by flash column chromatography eluting with 0 to 5% MeOH in EtOAc gradient gave the racemic compound (65 mg, 55% yield). The racemic compound was separated using SFC conditions (Chiralpak IC, 5 μm 250×30 mm, CO₂/(MeOH+0.5% isopropylamine) 70/30, 70 g/min, 40° C., 100 bar) to give the title compound (27.4 mg, 40% Yield). $\delta_H$ (500 MHz, Methanol-d4) 8.19 (s, 1H), 6.62 (t, J=55.2 Hz, 1H), 6.29 (s, 1H), 4.76 (td, J=5.9, 2.6 Hz) and 4.63 (td, J=6.0, 2.6 Hz, 1H in total), 4.60-4.49 (m, 1H), 3.73 (s, 3H), 3.66 (dd, J=13.0, 6.9 Hz, 1H), 3.44-3.35 (m, 2H), 3.29-3.26 (m, 1H), 3.12-3.02 (m, 1H), 3.01-2.86 (m, 2H), 2.84-2.72 (m, 1H), 2.41-2.28 (m, 2H), 2.12-2.00 (m, 1H), 1.92-1.82 (m, 1H), 0.87-0.67 (m, 2H). LCMS [M+H]⁺ 585, RT 2.67 minutes (Method 10). Chiral SFC** RT=12.9 minutes.

** Analytical chiral analysis: CHIRALPAK IC (250 mm×4.6) 5 μm, 70/30% CO₂/(MeOH+0.5% isopropylamine) 2.4 mL/min, 100 Bar, 40° C., SFC Berger

Example 285

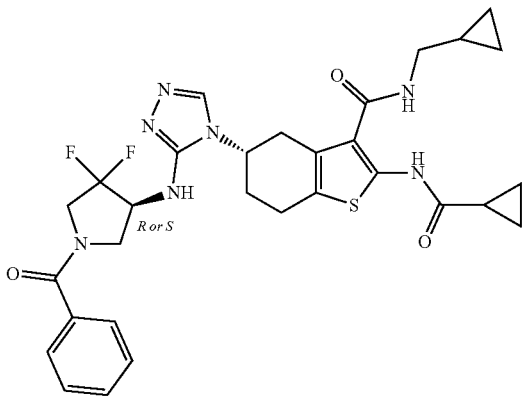 [SMILES: O=C(NCC1CC1)c1c(NC(=O)C2CC2)sc2c1C[C@@H](n1cnnc1N[C@H]1CN(C(=O)c3ccccc3)CC1(F)F)CC2]

(5S)-5-[3-[[(3S*)-1-benzoyl-4,4-difluoro-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R]

To a solution of Intermediate 356 (69 mg, 0.14 mmol) in DCM (2 mL) and DMF (0.2 mL) was added DIPEA (0.07 mL, 0.41 mmol) and benzoyl chloride (0.01 mL, 0.12 mmol). The solution was stirred at room temperature for 20 minutes. The solvent was removed to give a pale brown oil. Purification by flash column chromatography eluting with 0 to 10% MeOH in DCM gradient gave the racemic compound (58 mg, 70% Yield). The two diastereoisomers were separated by reverse phase chiral chromatography (Waters Xbridge column 100×19 mm, 5 µm, 5-95% CH$_3$CN with 0.2% NH$_4$OH in water over 27.5 minutes) to give the title compound (15.4 mg, 30% Yield). $\delta_H$ (500 MHz, Chloroform-d) 11.89 (s, 1H), 7.81 (s, 1H), 7.51-7.32 (m, 5H), 5.97-5.60 (2×m, 1H, rotamers), 5.04-4.48 (m, 2H, rotamers), 4.35-3.79 (m, 4H, rotamers), 3.77-3.46 (m, 1H), 3.39-3.09 (m, 3H), 2.95-2.76 (m, 3H), 2.35-2.11 (m, 2H), 1.65 (tt, J=8.0, 4.6 Hz, 1H), 1.14-1.06 (m, 2H), 1.06-0.93 (m, 1H), 0.94-0.76 (m, 2H), 0.58-0.42 (m, 2H), 0.22 (d, J=4.8 Hz, 2H). LCMS [M+H]$^+$ 610, RT 2.61 minutes (Method 10).

Example 286

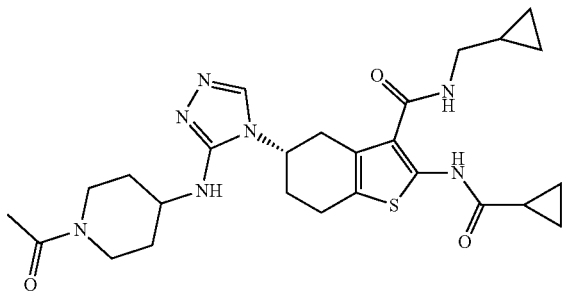 [SMILES: CC(=O)N1CCC(Nc2nncn2[C@H]2CCc3sc(NC(=O)C4CC4)c(C(=O)NCC4CC4)c3C2)CC1]

(5S)-5-[3-[(1-acetyl-4-piperidyl)amino]-1,2,4-triazol-4-yl]-2-(cyclopropanecarbonylamino)-N-(cyclopropylmethyl)-4,5,6,7-tetrahydrobenzothiophene-3-carboxamide To a solution of Intermediate 360 (41 mg, 0.08 mmol) in DCM (3 mL) and DMF (0.2 mL) was added DIPEA (0.04 mL, 0.25 mmol) and acetic anhydride (0.01 mL, 0.08 mmol). The reaction was stirred for 30 minutes. The DCM was removed to give an oil. Purification by flash column chromatography eluting with 0 to 10% 7 M NH$_3$ in MeOH in DCM gradient gave the title compound (41 mg, 89% Yield). $\delta_H$ (500 MHz, Methanol-d4) 8.12 (s, 1H), 4.51-4.43 (m, 1H), 4.40-4.28 (m, 1H), 4.00-3.88 (m, 1H), 3.83-3.76 (m, 1H), 3.30-3.13 (m, 4H), 3.03-2.92 (m, 2H), 2.92-2.78 (m, 2H), 2.32-2.23 (m, 2H), 2.22-2.15 (m, 1H), 2.15-2.06 (m, 4H), 1.87-1.75 (m, 1H), 1.55-1.36 (m, 2H), 1.13-1.03 (m, 1H), 1.03-0.90 (m, 4H), 0.54-0.43 (m, 2H), 0.31-0.20 (m, 2H). LCMS [M+H]$^+$ 526, RT 2.35 minutes (Method 32).

Example 287

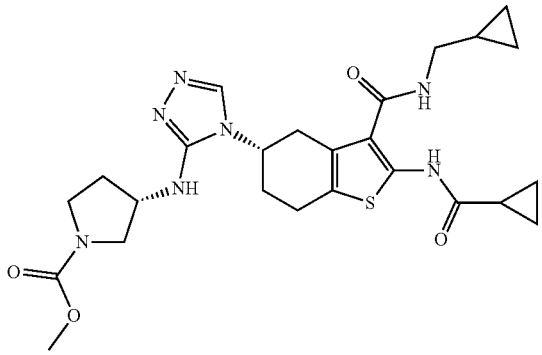 [SMILES: COC(=O)N1CC[C@H](Nc2nncn2[C@H]2CCc3sc(NC(=O)C4CC4)c(C(=O)NCC4CC4)c3C2)C1]

Methyl (3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]pyrrolidine-1-carboxylate To a solution of Intermediate 278 (62 mg, 0.07 mmol) in DCM (5 mL) was added DIPEA (35 µl, 0.2 mmol) and dimethyl dicarbonate (5.66 µl, 0.05 mmol). The mixture was stirred for 18 hours. The reaction mixture was wet loaded directly onto a column and purified by flash column chromatography eluting with 0 to 10% 7 M NH$_3$ in MeOH in DCM gradient to give the title compound as a gum (40 mg). LCMS showed it to be a mixture of two products. Further purification by HPLC (Method 4) gave the title compound (2.6 mg, 7% Yield). $\delta_H$ (500 MHz, Methanol-d4) 8.16 (s, 1H), 4.44-4.34 (m, 1H), 4.34-4.24 (m, 1H), 3.77-3.70 (m, 1H), 3.68 (s, 3H), 3.59-3.45 (m, 2H), 3.43-3.36 (m, 1H), 3.28-3.14 (m, 3H), 2.99-2.84 (m, 3H), 2.31-2.22 (m, 3H), 2.10-1.98 (m, 1H), 1.81 (ddd, J=12.6, 7.9, 4.6 Hz, 1H), 1.07 (ddd, J=12.5, 7.6, 4.9 Hz, 1H), 0.97 (ddt, J=23.8, 5.9, 3.8 Hz, 4H), 0.54-0.42 (m, 2H), 0.25 (q, J=4.6 Hz, 2H). LCMS [M+H]$^+$ 528, RT 2.56 minutes (Method 32).

Example 288

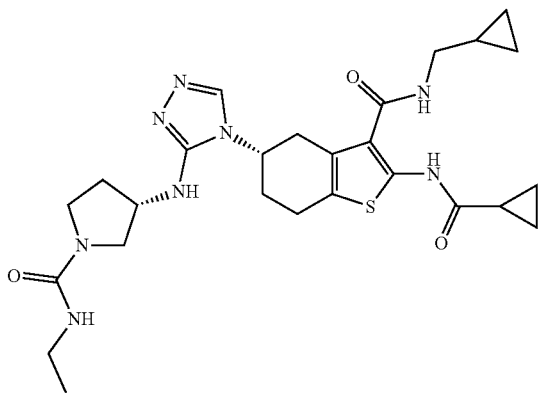 [SMILES: CCNC(=O)N1CC[C@H](Nc2nncn2[C@H]2CCc3sc(NC(=O)C4CC4)c(C(=O)NCC4CC4)c3C2)C1]

(3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-N-ethyl-pyrrolidine-1-carboxamide To a solution of Intermediate 278 (30 mg, 0.06 mmol) in DCM (3 mL) was added triethylamine (19 mg, 0.19 mmol). The solution was cooled to 0° C. then isocyanatomethane (3.96 μl, 0.06 mmol) was added. The reaction was stirred at 0° C. for 5 minutes then at room temperature for 1 hour. The solvent was removed to give a brown solid. Purification by flash column chromatography eluting with 0 to 20% 7 M NH₃ in MeOH in DCM gradient gave the title compound (25 mg, 68% Yield). $\delta_H$ (500 MHz, Methanol-d4) 8.15 (s, 1H), 6.14 (t, J=5.5 Hz, 1H), 4.43-4.35 (m, 1H), 4.35-4.22 (m, 1H), 3.75-3.65 (m, 1H), 3.54-3.38 (m, 2H), 3.27-3.21 (m, 2H), 3.21-3.11 (m, 4H), 3.03-2.83 (m, 3H), 2.32-2.21 (m, 3H), 2.10-2.02 (m, 1H), 1.86-1.76 (m, 1H), 1.14-1.03 (m, 4H), 1.03-0.90 (m, 4H), 0.55-0.43 (m, 2H), 0.28-0.18 (m, 2H). LCMS [M+H]⁺ 541, RT 2.37 minutes (Method 32).

Examples 289, 290 & 291

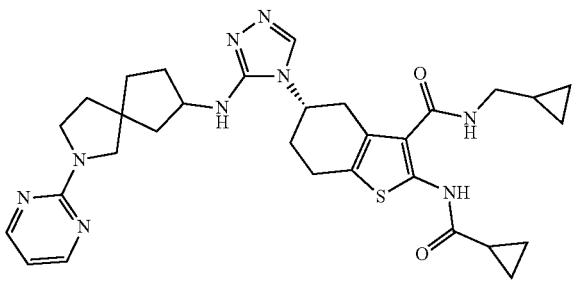

3 out of 4 isomers (5S)-2-cyclopropaneamido-N-(cyclopropylmethyl)-5-(3-{[2-(pyrimidin-2-yl)-2-azaspiro[4.4]nonan-7-yl]amino}-4H-1,2,4-triazol-4-yl)-4,5,6,7-tetrahydro-1-benzothiophene-3-carboxamide To a solution of Intermediate 364 (200 mg, 0.38 mmol) in N,N-dimethylformamide (5 mL) was introduced diisopropylethylamine (148 mg, 1.14 mmol) and 2-chloropyrimidine (58 mg, 0.49 mmol, pre-dissolved in N,N-dimethylformamide [1 mL]). The resulting solution was warmed to 110° C. for 2 hours, concentrated in-vacuo and the residue suspended in a mixture of acetonitrile/water/DMSO (95:5:5 ratio, 3 mL). The insoluble solid was removed by filtration and the filtrate was purified by low pH achiral preparative-LC chromatography (Method 3) to furnish the title compound (100 mg at 93% purity LCMS-UV₂₁₅, 0.155 mmol) as a mixture of four diastereomers. Diastereomer separation by chiral chromatography (Cellulose 4 [25 cm column] with 100% methanol followed by a Chiralcel-OD [25 cm column] using 1:1 methanol/ethanol) furnished all four diastereomers (three are reported below):

Example 289—Peak 2 from initial separation on the cellulose column (5.5 mg, 2% Yield). $\delta_H$ [500 MHz, d₄-Methanol] 8.27 (d, J=4.8 Hz, 2H), 8.11 (s, 1H), 6.56 (t, J=4.8 Hz, 1H), 4.43-4.35 (m, 1H), 4.20 (p, J=6.9 Hz, 1H), 3.64-3.54 (m, 2H), 3.51 (d, J=10.8 Hz, 1H), 3.47 (d, J=10.8 Hz, 1H), 3.30-3.26 (m, 1H), 3.23 (dd, J=15.1, 4.9 Hz, 1H), 3.15 (dd, J=13.8, 7.0 Hz, 1H), 2.97 (dt, J=17.5, 9.1 Hz, 2H), 2.87 (td, J=16.4, 5.1 Hz, 1H), 2.31-2.23 (m, 3H), 2.20 (dd, J=13.3, 7.3 Hz, 1H), 2.01-1.92 (m, 2H), 1.85-1.77 (m, 2H), 1.76-1.67 (m, 3H), 1.11-1.04 (m, 1H), 1.01-0.97 (m, 2H), 0.97-0.93 (m, 2H), 0.51-0.46 (m, 2H), 0.24 (q, J=4.7 Hz, 2H). LCMS [M+H]⁺ 602, RT 1.94 mins (Method 10). Chiral LC* RT=34.12 minutes.

Example 290—Peak 1 from initial separation on the cellulose column and peak 2 on the Chiralcel-OD column (7.1 mg, 3% Yield). $\delta_H$ [500, d₄-Methanol] 8.29 (d, J=4.8 Hz, 2H), 8.10 (s, 1H), 6.57 (t, J=4.8 Hz, 1H), 4.43-4.30 (m, 1H), 4.18 (p, J=7.2 Hz, 1H), 3.56 (tt, J=11.1, 5.5 Hz, 2H), 3.48 (d, J=10.7 Hz, 1H), 3.43 (d, J=10.7 Hz, 1H), 3.27 (dd, J=13.8, 7.1 Hz, 1H), 3.21 (dd, J=15.3, 5.0 Hz, 1H), 3.15 (dd, J=13.8, 6.9 Hz, 1H), 2.95 (dt, J=15.3, 7.8 Hz, 2H), 2.87 (d, J=16.2 Hz, 1H), 2.30-2.20 (m, 4H), 2.00 (tq, J=9.6, 5.2 Hz, 2H), 1.87-1.70 (m, 4H), 1.65 (dd, J=13.2, 7.4 Hz, 1H), 1.06 (dt, J=12.0, 6.2 Hz, 1H), 1.01-0.90 (m, 4H), 0.47 (q, J=5.2 Hz, 2H), 0.23 (q, J=4.8 Hz, 2H); LCMS [M+H]⁺ 602, RT 1.94 mins (Method 10) Chiral LC** RT=6.46 minutes.

Example 291 Peak 1 from initial separation on the cellulose column and peak 1 on the Chiralcel-OD column (1.1 mg, 0.5% Yield). $\delta_H$ [500 MHz, d₄-Methanol] 8.29 (d, J=4.8 Hz, 2H), 8.10 (s, 1H), 6.58 (t, J=4.8 Hz, 1H), 4.43-4.32 (m, 1H), 4.19 (p, J=7.2 Hz, 1H), 3.58 (tq, J=8.7, 4.1 Hz, 2H), 3.48 (d, J=10.8 Hz, 1H), 3.44 (d, J=10.7 Hz, 1H), 3.28 (d, J=7.1 Hz, 1H), 3.23 (dd, J=15.1, 5.1 Hz, 1H), 3.16 (dd, J=13.8, 7.0 Hz, 1H), 2.99-2.93 (m, 2H), 2.88 (dt, J=16.2, 4.5 Hz, 1H), 2.31-2.22 (m, 4H), 2.07-1.95 (m, 2H), 1.87-1.70 (m, 4H), 1.66 (dd, J=13.3, 7.4 Hz, 1H), 1.11-1.06 (m, 1H), 1.02-0.97 (m, 2H), 0.95 (dt, J=7.9, 3.0 Hz, 2H), 0.52-0.46 (m, 2H), 0.28-0.23 (m, 2H); LCMS [M+H]⁺ 602, RT 1.97 mins (Method 10). Chiral LC** RT=5.02 minutes.

* Chiral analysis using Cellulose 4-4.6×250 mm, 5 μm column, flow rate 0.3 mL/min eluting with methanol, 50 minute run time on a Waters 2795
** Chiral analysis using Chiralcel OD −4.6×250 mm, 5 μm column, flow rate 1 mL/min eluting with 1:1 ethanol/methanol, 15 minute run time on a Waters 2795

Examples 292 and 293

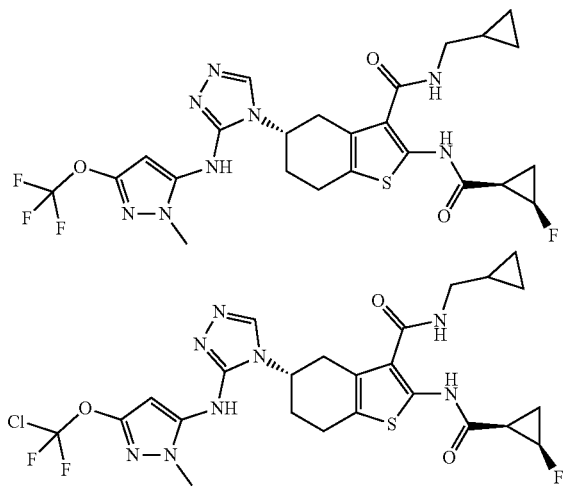

(5S)—N-(cyclopropylmethyl)-2-[[(1R,2R)-2-fluoro-cyclopropanecarbonyl]amino]-5-[3-[[2-methyl-5-(trifluoromethoxy)pyrazol-3-yl]amino]-1,2,4-triazol-4-yl]-4,5,6,7-tetrahydrobenzothiophene-3-carboxamide (292) &

(5S)-5-[3-[[5-[chloro(difluoro)methoxy]-2-methyl-pyrazol-3-yl]amino]-1,2,4-triazol-4-yl]-N-(cyclopropylmethyl)-2-[[(1R,2R)-2-fluorocyclopropanecarbonyl]amino]-4,5,6,7-tetrahydrobenzothiophene-3-carboxamide (293)

A solution of formic hydrazide (33 mg, 0.56 mmol) in ethanol (3 mL) was introduced in one portion to a 2:1 mixture of intermediates 378 and 379 respectively (122 mg, 0.14 mmol). The resulting solution was stirred at room temperature for 60 minutes then at 30° C. for 60 minutes. After cooling to room temperature, 1 M aqueous sodium carbonate (0.60 mL, 0.6 mmol) was introduced in one portion and the reaction mixture stirred at 40° C. for 15 hours. The reaction mixture was cooled to room temperature and filtered, washing the filter-cake with ethanol (4 mL). Following concentration of the combined filtrates in-vacuo, the residue was dissolved in dichloromethane (20 mL) and washed with water (10 mL). The aqueous phase was extracted with 1:1 chloroform/isopropanol (10 mL). All the organic extracts were combined, dried over sodium sulfate and filtered through a shallow bed of kieselguhr. Following concentration of the filtrate in-vacuo, the residue was purified by HPLC (Method 3) to give the title compounds:

Example 292 (4.9 mg, 6% Yield). $\delta_H$ (500 MHz, d-chloroform) 12.11 (s, 1H), 9.92-8.40 (m, 1H), 7.47 (s, 1H), 5.78 (t, J=5.2 Hz, 1H), 5.52 (s, 1H), 4.79 (dtd, J=64.8, 6.0, 4.3 Hz, 1H), 4.63 (td, J=10.5, 10.0, 5.5 Hz, 1H), 3.65 (s, 3H), 3.40 (dd, J=14.7, 5.1 Hz, 1H), 3.33-3.21 (m, 2H), 3.00-2.78 (m, 3H), 2.35 (ddd, J=18.4, 9.1, 5.7 Hz, 1H), 2.29-2.20 (m, 1H), 1.97-1.86 (m, 2H), 1.30-1.20 (m, 1H), 1.02 (dtd, J=10.3, 7.6, 3.7 Hz, 1H), 0.56-0.49 (m, 2H), 0.23 (q, J=4.8 Hz, 2H); LCMS[M+H]$^+$ 583, RT 2.90 mins (Method 10).

Example 293 (0.5 mg, 0.5% Yield). $\delta_H$ (500 MHz, d-chloroform) 12.15 (s, 1H), 9.04 (s, 1H), 7.41 (s, 1H), 5.80-5.69 (m, 1H), 5.52 (s, 1H), 4.89-4.72 (m, 1H), 4.66 (s, 1H), 3.67 (s, 3H), 3.44 (d, J=13.1 Hz, 1H), 3.34-3.22 (m, 2H), 3.01-2.79 (m, 3H), 2.44-2.31 (m, 1H), 2.29-2.20 (m, 1H), 1.96 (td, J=7.2, 3.9 Hz, 1H), 1.93-1.87 (m, 1H), 1.31-1.21 (m, 1H), 1.08-0.97 (m, 1H), 0.56-0.49 (m, 2H), 0.24 (q, J=5.1 Hz, 2H); LCMS [M+H]$^+$ 599/601, RT 2.99 mins (Method 10).

Examples 294 and 295

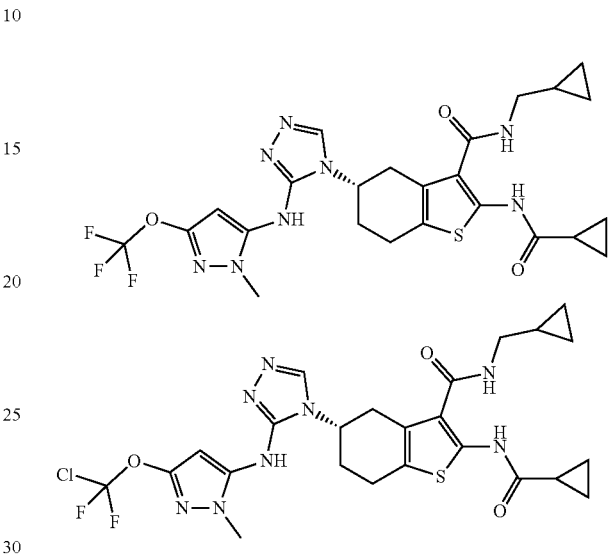

(5S)-2-(cyclopropanecarbonylamino)-N-(cyclopropylmethyl)-5-[3-[[2-methyl-5-(trifluoromethoxy)pyrazol-3-yl]amino]-1,2,4-triazol-4-yl]-4,5,6,7-tetrahydrobenzothiophene-3-carboxamide (294) &

(5S)-5-[3-[[5-[chloro(difluoro)methoxy]-2-methyl-pyrazol-3-yl]amino]-1,2,4-triazol-4-yl]-2-(cyclopropanecarbonylamino)-N-(cyclopropylmethyl)-4,5,6,7-tetrahydrobenzothiophene-3-carboxamide (295)

A solution of formic hydrazide (35 mg, 0.57 mmol) in ethanol (3 mL) was introduced in one portion to a mixture of Intermediates 382 and 383 (121 mg, 0.18 mmol). The resulting solution was stirred at room temperature for 90 minutes. 1 M aqueous sodium carbonate (0.57 mL, 0.57 mmol) was introduced in one portion and the reaction mixture stirred at 40° C. for 16 hours. The reaction mixture was concentrated in-vacuo, then the residue was diluted with water (10 mL) and the precipitated solid collected by filtration and washed with water (3 mL). Purification of the solid by HPLC eluting with 5-95% acetonitrile (with 0.1% formic acid) in water (with 0.1% formic acid) gave the title compounds:

Example 294 (9.7 mg, 9% Yield). $\delta_H$ (500 MHz, d-chloroform) 11.98 (s, 1H), 7.47 (s, 1H), 5.79 (t, J=5.2 Hz, 1H), 5.55 (s, 1H), 4.66-4.56 (m, 1H), 3.64 (s, 3H), 3.37 (dd, J=14.6, 4.8 Hz, 1H), 3.33-3.21 (m, 2H), 2.96-2.87 (m, 2H), 2.82 (dt, J=16.8, 5.1 Hz, 1H), 2.34 (m, 1H), 2.28-2.19 (m, 1H), 1.67 (td, J=7.9, 4.0 Hz, 1H), 1.10 (h, J=4.6 Hz, 2H), 1.03 (dddd, J=15.1, 12.3, 7.5, 4.9 Hz, 1H), 0.92 (dt, J=7.8, 3.7 Hz, 2H), 0.56-0.49 (m, 2H), 0.23 (q, J=4.7 Hz, 2H); $\delta_F$ (376 MHz, d-chloroform, H-decoupled) −58.93; LCMS [M+H]$^+$ 565, RT 3.06 mins (Method 10).

Example 295 (3.2 mg, 3% Yield). $\delta_H$ (500 MHz, d-chloroform) 12.03 (s, 1H), 9.17 (s, 1H), 7.43 (s, 1H), 5.75 (t, J=5.2 Hz, 1H), 5.55 (s, 1H), 4.65 (d, J=6.3 Hz, 1H), 3.67 (s, 3H), 3.41 (dd, J=14.7, 4.8 Hz, 1H), 3.34-3.21 (m, 2H), 2.95-2.89 (m, 2H), 2.82 (dt, J=16.9, 5.4 Hz, 1H), 2.40-2.33 (m, 1H), 2.28-2.19 (m, 1H), 1.68 (ddd, J=12.5, 8.0, 4.6 Hz, 1H), 1.12 (ddd, J=7.0, 4.3, 3.0 Hz, 2H), 1.03 (tt, J=7.9, 5.1 Hz, 1H), 0.96-0.89 (m, 2H), 0.57-0.48 (m, 2H), 0.24 (q, J=4.7 Hz, 2H); $\delta_F$ (376 MHz, d-chloroform, H-decoupled) −27.10; LCMS [M+H]$^+$ 581/583, RT 3.16 mins (Method 10).

Example 296

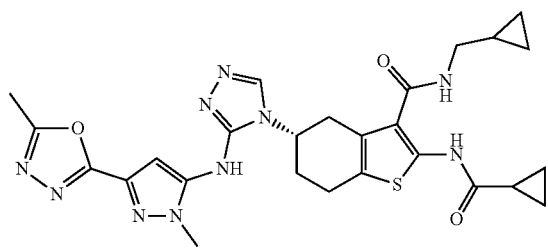 [SMILES: Cc1nnc(-c2cc(Nc3nncn3[C@H]3CCc4sc(NC(=O)C5CC5)c(C(=O)NCC5CC5)c4C3)n(C)n2)o1]

(5S)-2-cyclopropaneamido-N-(cyclopropylmethyl)-5-(3-{[1-methyl-3-(5-methyl-1,3,4-oxadiazol-2-yl)-1H-pyrazol-5-yl]amino}-4H-1,2,4-triazol-4-yl)-4,5,6,7-tetrahydro-1-benzothiophene-3-carboxamide To a solution of Intermediate 388 (240 mg, 0.41 mmol) in methanol (16 mL) was introduced formic hydrazide (111 mg, 1.84 mmol). After 40 minutes at room temperature, 1 M aqueous sodium carbonate (1.5 mL, 1.5 mmol) was introduced and the solution stirred at 50° C. for 4 hours. The reaction mixture was concentrated in-vacuo and the residue suspended in water (8 mL) and extracted with a mixture of tetrahydrofuran and ethyl acetate (1:1, 3×20 mL). The combined organic extracts were washed with brine (10 mL) and dried over sodium sulfate. After filtration, the filtrate was adsorbed onto silica in-vacuo and the dry-loaded material partially purified by flash column chromatography (dichloromethane containing 0-5% methanol and 0-3% 7 M ammonia in methanol). The product from flash column chromatography was further purified by HPLC (Method 2) to furnish the title compound (35 mg, 15% Yield) $\delta_H$ (500 MHz, d4-methanol) 8.15 (s, 1H), 6.60 (s, 1H), 4.62-4.53 (m, 1H), 3.80 (s, 3H), 3.37-3.32 (m, 1H), 3.27 (dd, J=13.8, 7.0 Hz, 1H), 3.18 (dd, J=13.8, 7.0 Hz, 1H), 3.07 (dd, J=15.4, 9.2 Hz, 1H), 2.98 (dt, J=16.0, 8.0 Hz, 1H), 2.90 (dt, J=17.1, 4.6 Hz, 1H), 2.60 (s, 3H), 2.39-2.31 (m, 2H), 1.81 (ddd, J=12.6, 7.9, 4.7 Hz, 1H), 1.12-1.02 (m, 1H), 1.02-0.97 (m, 2H), 0.94 (ddt, J=7.5, 4.7, 2.2 Hz, 2H), 0.52-0.43 (m, 2H), 0.28-0.21 (m, 2H); LCMS [M+H]$^+$ 563, RT 2.41 mins (Method 10).

Example 297

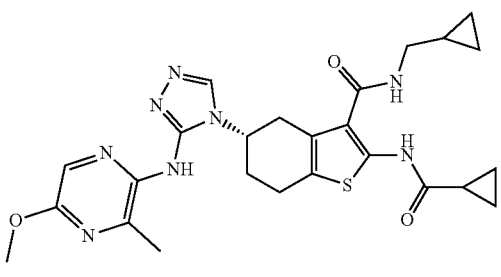 [SMILES: COc1cnc(Nc2nncn2[C@H]2CCc3sc(NC(=O)C4CC4)c(C(=O)NCC4CC4)c3C2)c(C)n1]

(5S)-2-(cyclopropanecarbonylamino)-N-(cyclopropylmethyl)-5-[3-[(5-methoxy-3-methyl-pyrazin-2-yl)amino]-1,2,4-triazol-4-yl]-4,5,6,7-tetrahydrobenzothiophene-3-carboxamide To a stirred solution of intermediate 390 (180 mg, 0.349 mmol) in DMF (3.5 mL) under nitrogen was added formic acid hydrazide (63 mg, 1.1 mmol) and mercuric chloride (114 mg, 0.419 mmol). The reaction mixture was stirred at room temperature for 15 min before the addition of triethylamine (0.15 mL, 1.1 mmol) and the mixture was stirred at 60° C. for 3 hours. Additional mercuric chloride (114 mg, 0.419 mmol) was added and the reaction stirred for a further 16 hours at 60° C. The mixture was cooled to r.t. and diluted with MeCN (15 mL), filtered through a pad of celite and washed with MeCN (20 mL). The filtrate was concentrated in vacuo to yield the crude product which was dissolved in 5% MeOH in DCM (50 mL), washed with water (30 mL) and the layers separated. The aqueous layer was extracted with 5% MeOH in DCM (2×25 mL). The combined organic layers were passed through a phase separation cartridge and concentrated in vacuo to give crude product which was purified by reverse phase HPLC to afford the title compound (27 mg, 15% Yield). $\delta_H$ (400 MHz, d-Chloroform) 12.13 (s, 1H), 7.69 (s, 1H), 7.56 (s, 1H), 5.95-5.86 (m, 1H), 4.90-4.77 (m, 1H), 3.94 (s, 3H), 3.56 (dd, J=14.9, 5.5 Hz, 1H), 3.33-3.25 (m, 2H), 3.06-2.91 (m, 2H), 2.86 (dt, J=16.8, 5.2 Hz, 1H), 2.57 (s, 3H), 2.49-2.38 (m, 1H), 2.35-2.25 (m, 1H), 1.71 (tt, J=8.2, 4.5 Hz, 1H), 1.18-1.12 (m, 2H), 1.11-0.99 (m, 1H), 0.98-0.91 (m, 2H), 0.56-0.48 (m, 2H), 0.28-0.20 (m, 2H). LCMS [M+H]$^+$ 523, RT 1.93 minutes (Method 26).

Example 298

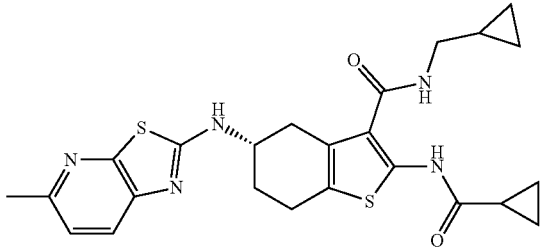 [SMILES: Cc1ccc2nc(N[C@H]3CCc4sc(NC(=O)C5CC5)c(C(=O)NCC5CC5)c4C3)sc2n1]

(5S)-2-(cyclopropanecarbonylamino)-N-(cyclopropylmethyl)-5-[(5-methylthiazolo[5,4-b]pyridin-2-yl)amino]-4,5,6,7-tetrahydrobenzothiophene-3-carboxamide Methanesulfonyl chloride (0.042 mL, 0.54 mmol) was added dropwise to a solution of intermediate 392 (255 mg, 0.493 mmol) and triethylamine (0.21 mL, 1.5 mmol) in DCM (4.9 mL) at 0° C. and under nitrogen. The reaction was stirred with warming to room temperature for 0.5 hours. The reaction was diluted with DCM (20 mL) and washed with sat. aqueous NH₄Cl (20 mL). The layers were separated and the aqueous layer extracted with DCM (2×20 mL). The combined organic layers were passed through a phase separation cartridge and concentrated in vacuo. This material was dissolved in DMF (2.5 mL) and formic acid hydrazide (33 mg, 0.54 mmol) was added. The reaction was stirred at room temperature for 2 hours. Water (20 mL) and DCM (20 mL) were added and the layers separated. The aqueous layer was extracted with DCM (2×20 mL). The combined organic layers were passed through a phase separation cartridge and concentrated in vacuo to give crude product which was purified by flash column chromatography on silica (gradient elution with 0% to 100% EtOAc in isohexanes then 0% to 20% MeOH in EtOAc) to afford the title compound (78 mg, 33% Yield). $\delta_H$ (300 MHz, DMSO-d6) 11.11 (s, 1H), 8.32 (d, J=6.9 Hz, 1H), 7.73 (t, J=5.6 Hz, 1H), 7.57 (d, J=8.1 Hz, 1H), 7.10 (d, J=8.4 Hz, 1H), 4.28-4.10 (m, 1H), 3.25-3.05 (m, 3H), 2.87-2.62 (m, 3H), 2.45 (s, 3H), 2.20-2.06 (m, 1H), 2.01-1.81 (m, 2H), 1.08-0.93 (m, 1H), 0.92-0.75 (m, 4H), 0.42-0.31 (m, 2H), 0.24-0.12 (m, 2H). LCMS [M+H]⁺ 482, RT 2.19 minutes (Method 26).

Example 299

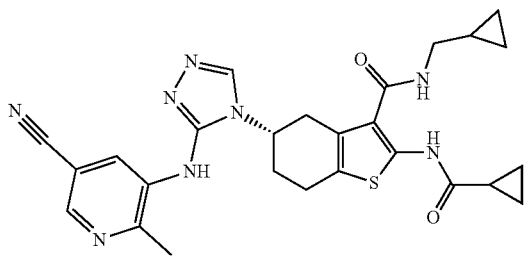 [SMILES: Cc1ncc(C#N)cc1Nc1nncn1[C@H]1CCc2sc(NC(=O)C3CC3)c(C(=O)NCC3CC3)c2C1]

(5S)-5-[3-[(5-cyano-2-methyl-3-pyridyl)amino]-1,2,4-triazo-4-yl]-2-(cyclopropanecarbonylamino)-N-(cyclopropylmethyl)-4,5,6,7-tetrahydrobenzothiophene-3-carboxamide A solution of methanesulfonyl chloride (0.043 mL, 0.55 mmol) in DCM (1.0 mL) was added dropwise to a solution of intermediate 394 (254 mg, 0.498 mmol) and triethylamine (0.21 mL, 1.5 mmol) in DCM (4.0 mL) at 0° C. The reaction was stirred at 0° C. for 1.5 hours. The reaction was diluted with DCM (20 mL) and washed with sat. aqueous NH₄Cl (20 mL). The layers were separated and the aq. layer extracted with DCM (2×20 mL). The combined organic layers were passed through a phase separation cartridge and concentrated in vacuo. This material was dissolved in DMF (2.5 mL) and formic acid hydrazide (45 mg, 0.75 mmol) was added. The reaction was stirred at room temperature for 1.5 hours. Water (1.2 mL) followed by sodium carbonate (158 mg, 1.49 mmol) were added and the reaction was stirred for 16 h at 45° C. Water (10 mL) and DCM (10 mL) were then added and the layers separated. The organic layer was concentrated in vacuo and re-dissolved in 5% MeOH in DCM (50 mL). The initial aqueous layer and additional water (20 mL) were added and the layers separated. The aqueous layer was extracted with 5% MeOH in DCM (2×25 mL). The combined organic layers were passed through a phase separation cartridge and concentrated in vacuo to give crude product which was purified using HPLC (Method 5) to give the title compound (155 mg, 60% Yield). $\delta_H$ (300 MHz, DMSO-d6) 11.25 (s, 1H), 8.57 (s, 1H), 8.46 (d, J=1.9 Hz, 1H), 8.19 (s, 1H), 8.07 (d, J=1.9 Hz, 1H), 7.70 (t, J=5.8 Hz, 1H), 4.62-4.45 (m, 1H), 3.21-2.94 (m, 4H), 2.91-2.78 (m, 2H), 2.55 (s, 3H), 2.35-2.13 (m, 2H), 2.00-1.86 (m, 1H), 1.05-0.91 (m, 1H), 0.91-0.76 (m, 4H), 0.39-0.26 (m, 2H), 0.22-0.10 (m, 2H). LCMS [M+H]⁺ 517, RT 1.69 minutes (Method 26).

Example 300

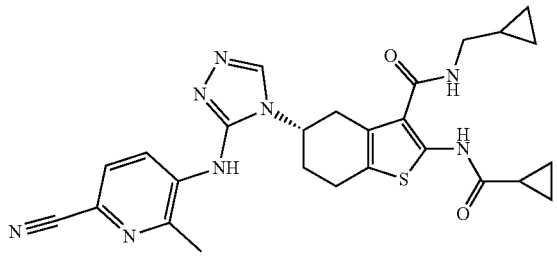 [SMILES: Cc1nc(C#N)ccc1Nc1nncn1[C@H]1CCc2sc(NC(=O)C3CC3)c(C(=O)NCC3CC3)c2C1]

(5S)-5-[3-[(6-cyano-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide A solution of methanesulfonyl chloride (0.068 mL, 0.88 mmol) in DCM (1.0 mL) was added dropwise to a solution of intermediate 396 (421 mg, 0.795 mmol) and triethylamine (0.33 mL, 2.4 mmol) in DCM (7 mL) at 0° C. The reaction was stirred at 0° C. for 1 hours. The reaction was diluted with DCM (20 mL) and washed with sat. aqueous NH₄Cl (20 mL). The layers were separated and the aqueous layer extracted with DCM (2×20 mL). The combined organic layers were passed through a phase separation cartridge and concentrated in vacuo. This material was dissolved in DMF (4.0 mL) and formic acid hydrazide (72 mg, 1.2 mmol) was added. The reaction was stirred at room temperature for 1.5 hours. Water (2 mL) followed by sodium carbonate (253 mg, 2.39 mmol) were added and the reaction was stirred for 16 h at 45° C. Water (10 mL) and DCM (10 mL) were then added and the layers separated. The organic layer was concentrated in vacuo and re-dissolved in 5% MeOH in DCM (50 mL). The initial aqueous layer and additional water (20 mL) were added and the layers separated. The aqueous layer was extracted with 5% MeOH in DCM (2×25 mL). The combined organic layers were passed through a phase separation cartridge and concentrated in vacuo to give crude product which was purified using HPLC (method 5) to give the title compound (181 mg, 44% Yield). $\delta_H$ (300 MHz, DMSO-d6) 11.18 (s, 1H), 8.65 (s, 1H), 8.38 (s, 1H), 7.72 (d, J=8.4 Hz, 2H), 7.60 (d, J=8.5 Hz, 1H), 4.59-4.40 (m, 1H), 3.18-2.92 (m, 4H), 2.89-2.76 (m, 2H), 2.51 (obs. s, 3H), 2.34-2.09 (m, 2H), 2.00-1.81 (m, 1H), 1.00-0.89 (m, 1H), 0.89-0.77 (m, 4H), 0.40-0.25 (m, 2H), 0.21-0.10 (m, 2H). LCMS [M+H]$^+$ 517, RT 1.75 minutes (Method 26).

Example 301

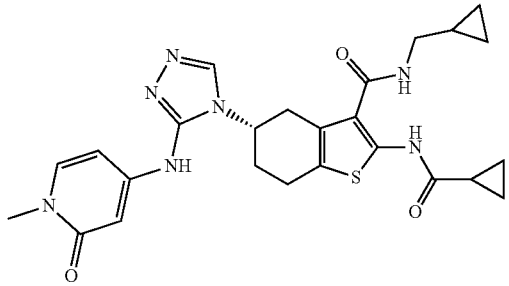 [SMILES: Cn1ccc(Nc2nncn2[C@H]2CCc3sc(NC(=O)C4CC4)c(C(=O)NCC4CC4)c3C2)cc1=O]

(5S)-2-(cyclopropanecarbonylamino)-N-(cyclopropylmethyl)-5-[3-[(1-methyl-2-oxo-4-pyridyl)amino]-1,2,4-triazol-4-yl]-4,5,6,7-tetrahydrobenzothiophene-3-carboxamide A solution of methanesulfonyl chloride (0.055 mL, 0.71 mmol) in DCM (1.0 mL) was added dropwise to a solution of intermediate 398 (320 mg, 0.641 mmol) and triethylamine (0.27 mL, 1.9 mmol) in DCM (5.2 mL) at 0° C. and under nitrogen. The reaction was stirred at 0° C. for 45 mins. The reaction was diluted with DCM (20 mL) and washed with sat. aqueous NH$_4$Cl (20 mL). The layers were separated and the aqueous layer extracted with 5% MeOH in DCM (2×20 mL). The combined organic layers were passed through a phase separation cartridge and concentrated in vacuo. To this material was added MeOH (3.2 mL), MeCN (3.2 mL) and formic acid hydrazide (42 mg, 0.71 mmol). The reaction was stirred at room temperature for 1 hour 45 mins. Water (1.6 mL) was added and the reaction stirred for a further 30 mins at room temperature before adding DCM (1.6 mL) and then stirring at room temperature for another 1 hour 15 mins. Added more formic acid hydrazide (116 mg, 1.92 mmol) and stirred for a further 16.5 hours at room temperature before adding sodium carbonate (204 mg, 1.92 mmol) and stirring for 4 h at 45° C. Water (20 mL) and 5% MeOH in DCM (50 mL) were added and the layers separated. The aqueous layer was extracted with 5% MeOH in DCM (2×25 mL). The combined organic layers were passed through a phase separation cartridge and concentrated in vacuo to give crude product which was purified by flash column chromatography on silica (gradient elution with 0% to 20% MeOH in DCM) to give the title compound (76 mg, 23% Yield). $\delta_H$ (300 MHz, DMSO-d6) 11.26 (s, 1H), 8.92 (s, 1H), 8.50 (s, 1H), 7.69 (t, J=5.7 Hz, 1H), 7.52 (d, J=7.5 Hz, 1H), 6.56 (d, J=2.4 Hz, 1H), 6.29 (dd, J=7.5, 2.5 Hz, 1H), 4.57-4.42 (m, 1H), 3.32 (s, 4H), 3.22-2.75 (m, 6H), 2.33-2.11 (m, 2H), 2.00-1.87 (m, 1H), 1.06-0.91 (m, 1H), 0.91-0.74 (m, 4H), 0.41-0.28 (m, 2H), 0.23-0.09 (m, 2H). LCMS [M+H]$^+$ 508, RT 1.51 minutes (Method 26).

Example 302

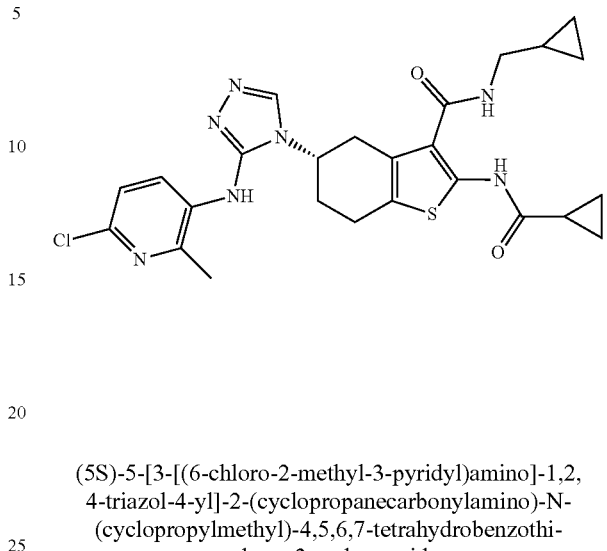

(5S)-5-[3-[(6-chloro-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide A solution of methanesulfonyl chloride (0.073 mL, 0.94 mmol) in DCM (1.0 mL) was added dropwise to a solution of intermediate 400 (459 mg, 0.851 mmol) and triethylamine (0.35 mL, 2.5 mmol) in DCM (7.5 mL) at 0° C. and under nitrogen. The reaction was stirred at 0° C. for 45 mins. Additional methanesulfonyl chloride (0.023 mL, 0.30 mmol) was added and the reaction stirred for a further 15 mins at 0° C. before adding formic acid hydrazide (153 mg, 2.55 mmol). The reaction was stirred at room temperature for a further 6 hours and then at 40° C. for another 1.5 hours. The reaction was diluted with 5% MeOH in DCM (50 mL) and washed with sat. aq. NH$_4$Cl (20 mL). The layers were separated and the aqueous layer extracted with 5% MeOH in DCM (2×25 mL). The combined organic layers were passed through a phase separation cartridge and concentrated in vacuo. To this material was added MeOH (4.3 mL), water (2.1 mL), MeCN (4.3 mL), formic acid hydrazide (153 mg, 2.55 mmol) and sodium carbonate (361 mg, 3.40 mmol). The reaction was stirred for 15 h at 45° C. Water (20 mL) and 5% MeOH in DCM (50 mL) were added and the layers separated. The aqueous layer was extracted with 5% MeOH in DCM (2×25 mL). The combined organic layers were passed through a phase separation cartridge and concentrated in vacuo to give crude product which was purified by flash column chromatography on silica (gradient elution with 0% to 20% MeOH in DCM) followed by further flash column chromatography on silica (gradient elution with 0% to 20% MeOH in EtOAc) to give the title compound (114 mg, 25% Yield). $\delta_H$ (300 MHz, DMSO-d6) 11.22 (s, 1H), 8.48 (s, 1H), 7.98 (s, 1H), 7.82-7.63 (m, 2H), 7.25 (d, J=8.5 Hz, 1H), 4.60-4.38 (m, 1H), 3.21-2.91 (m, 4H), 2.91-2.77 (m, 2H), 2.40 (s, 3H), 2.30-2.13 (m, 2H), 1.99-1.85 (m, 1H), 1.03-0.91 (m, 1H), 0.91-0.77 (m, 4H), 0.39-0.28 (m, 2H), 0.22-0.12 (m, 2H). LCMS [M+H]$^+$ 526, RT 1.95 minutes (Method 26).

Example 303

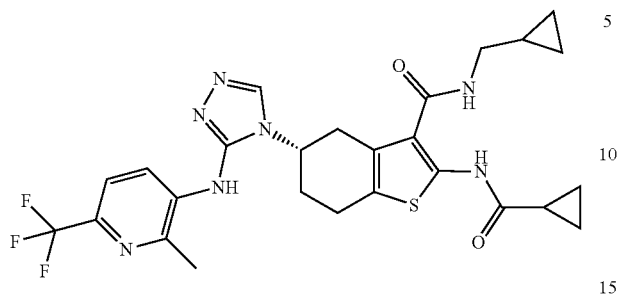

(5S)-2-(cyclopropanecarbonylamino)-N-(cyclopropylmethyl)-5-[3-[[2-methyl-6-(trifluoromethyl)-3-pyridyl]amino]-1,2,4-triazol-4-yl]-4,5,6,7-tetrahydrobenzothiophene-3-carboxamide A solution of methanesulfonyl chloride (0.048 mL, 0.62 mmol) in DCM (1.0 mL) was added dropwise to a solution of intermediate 402 (348 mg, 0.568 mmol, 90 mass %) and triethylamine (0.24 mL, 1.7 mmol) in DCM (4.7 mL) at 0° C. The reaction was stirred at 0° C. for 45 mins. Additional methanesulfonyl chloride (0.009 mL, 0.1 mmol) in DCM (0.5 mL) was added dropwise and the reaction stirred for a further 20 mins at 0° C. before adding formic acid hydrazide (102 mg, 1.70 mmol). The reaction was stirred at room temperature for a further 5.5 hours. The reaction was diluted with 5% MeOH in DCM (50 mL) and washed with sat. aqueous NH$_4$Cl (20 mL). The layers were separated and the aqueous layer extracted with 5% MeOH in DCM (2×25 mL). The combined organic layers were passed through a phase separation cartridge and concentrated in vacuo. To this material was added MeOH (3.0 mL), water (1.5 mL), MeCN (3 mL) and sodium carbonate (255 mg, 2.41 mmol). The reaction was stirred for 16 h at 45° C. The reaction was cooled to room temperature then water (20 mL) and 5% MeOH in DCM (50 mL) were added and the layers separated. The aqueous layer was extracted with 5% MeOH in DCM (2×25 mL). The combined organic layers were passed through a phase separation cartridge and concentrated in vacuo to give crude product which was purified by flash column chromatography on silica (gradient elution with 0% to 20% MeOH in DCM) followed by further flash column chromatography on silica (gradient elution with 0% to 20% MeOH in EtOAc) to give the title compound (97 mg, 31% Yield). $\delta_H$ (300 MHz, DMSO-d6) 11.19 (s, 1H), 8.61 (s, 1H), 8.22 (s, 1H), 7.78-7.67 (m, 2H), 7.60 (d, J=8.5 Hz, 1H), 4.64-4.42 (m, 1H), 3.19-2.91 (m, 4H), 2.91-2.77 (m, 2H), 2.53 (s, 3H), 2.35-2.10 (m, 2H), 1.98-1.82 (m, 1H), 1.01-0.89 (m, 1H), 0.91-0.78 (m, 4H), 0.37-0.24 (m, 2H), 0.22-0.10 (m, 21H). LCMS [M+H]$^+$ 560, RT 2.20 minutes (Method 26).

Example 304

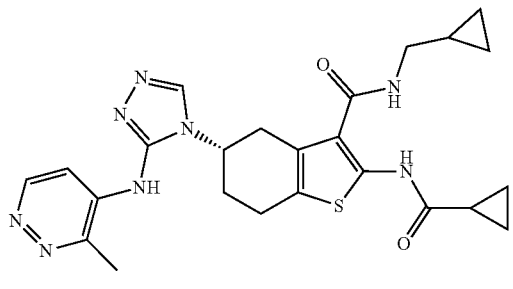 [SMILES: Cc1nnccc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(3-methylpyridazin-4-yl)amino]-1,2,4-triazol-4-yl]-4,5,6,7-tetrahydrobenzothiophene-3-carboxamide Methanesulfonyl chloride (0.027 mL, 0.35 mmol) was added dropwise to a solution of intermediate 404 (152 mg, 0.314 mmol) and triethylamine (0.13 mL, 0.93 mmol) in DCM (3.2 mL) at 0° C. and under nitrogen. The reaction was stirred at 0° C. for 15 mins and then at room temperature for a further 1.5 hours. Formic acid hydrazide (57 mg, 0.94 mmol) was added as a solution in DMF (1.0 mL). The reaction was stirred at room temperature for 1 hour before additional formic acid hydrazide (57 mg, 0.94 mmol) was added and the reaction stirred at room temperature for a further 2 hours. The reaction was diluted with DCM (20 mL) and washed with water (20 mL). The layers were separated and the aqueous layer extracted with DCM (2×20 mL). The combined organic layers were washed with sat. aqueous NH$_4$Cl (20 mL), then brine (20 mL), passed through a phase separation cartridge and concentrated in vacuo. To this material was added DMF (0.5 mL) and sodium carbonate (73 mg, 0.69 mmol). The reaction was stirred for 15.5 h at 45° C. The reaction was cooled to room temperature then filtered, the filter was washed with DCM (20 mL). The filtrate was collected and washed with water (2×20 mL), then brine (20 mL), passed through a phase separation cartridge and concentrated in vacuo to give crude product. The combined water washings were also concentrated in vacuo to give further crude product. The combined crude product was purified by flash column chromatography on silica (gradient elution with 0% to 20% MeOH in DCM) followed by further flash column chromatography on silica (gradient elution with 0% to 40% MeOH in EtOAc) to give the title compound (15 mg, 10% Yield). $\delta_H$ (300 MHz, DMSO-d6) 12.95 (s, 1H), 11.21 (s, 1H), 8.30 (s, 1H), 8.12 (d, J=7.5 Hz, 1H), 7.97 (d, J=7.4 Hz, 1H), 7.72 (t, J=5.6 Hz, 1H), 4.65-4.53 (m, 1H), 3.21-2.94 (m, 4H), 2.86-2.77 (m, 2H), 2.29 (s, 3H), 2.23-2.15 (m, 2H), 1.97-1.89 (m, 1H), 1.02-0.92 (m, 1H), 0.90-0.75 (m, 4H), 0.35-0.29 (m, 2H), 0.18-0.12 (m, 2H). LCMS [M+H]$^+$ 493, RT 1.68 minutes (Method 26).

Example 305

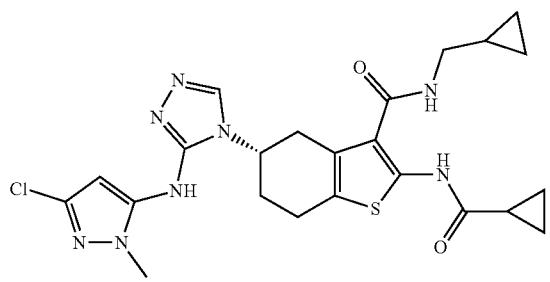 [SMILES: Cn1nc(Cl)cc1Nc1nncn1[C@H]1CCc2sc(NC(=O)C3CC3)c(C(=O)NCC3CC3)c2C1]

(5S)-5-[3-[(5-chloro-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide To a stirred solution of intermediate 405 (258 mg, 0.509 mmol) in DMF (3.6 mL) under nitrogen was added formic acid hydrazide (92 mg, 1.5 mmol) and mercuric chloride (190 mg, 0.697 mmol). The reaction mixture was stirred at r.t. for 5 min before the addition of triethylamine (0.21 mL, 1.5 mmol) and the mixture was stirred at 80° C. for 18 hours. The mixture was cooled to r.t. and diluted with MeCN (20 mL), filtered through a pad of celite and washed with MeCN (25 mL). The filtrate was concentrated in vacuo to yield the crude product which was dissolved in 5% MeOH in DCM (50 mL), washed with water (30 mL) and the layers separated. The aqueous layer was extracted with 5% MeOH in DCM (2×25 mL). The combined organic layers were passed through a phase separation cartridge and concentrated in vacuo to give crude product which was purified by flash column chromatography on silica (gradient elution with 0% to 10% MeOH in DCM). The product containing fractions were concentrated in vacuo and dissolved in MeOH (4 mL), QuadraSil® MTU (500 mg) was added and the suspension was stirred at 40° C. for 2.5 h before being filtered and washed with MeOH (2×5 mL). The filtrate was concentrated in vacuo and was further purified by flash column chromatography on silica (gradient elution with 0% to 20% MeOH in EtOAc) to give the title compound (103 mg, 39% Yield). $\delta_H$ (300 MHz, DMSO-d6) (contained 2 tautomers in an approximate ratio of 0.7:0.3) 12.07 (s, 0.7H), 11.29-11.15 (m, 1H), 8.79 (s, 0.3H), 8.41 (s, 0.3H), 8.21 (s, 0.7H), 7.82-7.66 (m, 1H), 6.21 (s, 0.3H), 5.96 (s, 0.7H), 4.53-4.34 (m, 1H), 3.63 (s, 0.9H), 3.53 (s, 2.1H), 3.23-3.04 (m, 3H), 3.03-2.76 (m, 3H), 2.33-2.12 (m, 2H), 1.99-1.87 (m, 1H), 1.08-0.94 (m, 1H), 0.92-0.78 (m, 4H), 0.41-0.32 (m, 2H), 0.23-0.15 (m, 2H). LCMS [M+H]$^+$ 515, RT 1.80 minutes (Method 26).

Example 306

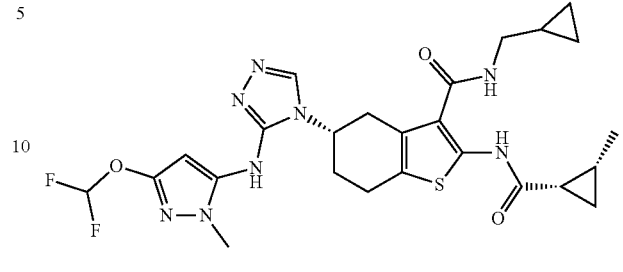

(5S)—N-(cyclopropylmethyl)-5-[3-[[5-(difluoromethoxy)-2-methyl-pyrazol-3-yl]amino]-1,2,4-triazol-4-yl]-2-[[(1S,2R)-2-methylcyclopropanecarbonyl]amino]-4,5,6,7-tetrahydrobenzothiophene-3-carboxamide (1S,2R)-2-methylcyclopropane-1-carboxylic acid (13 mg, 0.13 mmol) as a solution in DCM (0.6 mL) followed by 2,4,6-tripropyl-1,3,5,2,4,6-trioxatriphosphorinane-2,4,6-trioxide (0.14 mL, 0.24 mmol, 50 mass % solution in EtOAc) were added to a solution of Intermediate 436 (72 mg, 0.12 mmol) and pyridine (0.047 mL, 0.58 mmol) in DCM (2.3 mL) at 0° C. The reaction was stirred for 17 hours allowing the ice bath to melt and the reaction to warm to room temperature. Water (10 mL) was added and the reaction stirred for a further 5 mins. The layers were separated, and the aq. layer was extracted with DCM (2×10 mL). The combined organic layers were washed with sat. aq. NH$_4$Cl (15 mL), passed through a phase separation cartridge, concentrated in vacuo and purified by flash column chromatography on silica (gradient elution with 0% to 100% EtOAc in isohexanes then 0% to 20% MeOH in EtOAc) to give the title compound (34 mg, 54% Yield). $\delta_H$ (400 MHz, DMSO-d6) (contained 2 tautomers in an approximate ratio of 0.7:0.3) 12.05 (s, 0.7H), 11.26 (s, 1H), 8.76 (s, 0.3H), 8.41 (s, 0.3H), 8.21 (s, 0.7H), 7.68 (s, 1H), 7.21 (t, J=74.2 Hz, 0.3H), 7.15 (t, J=74.2 Hz, 0.7H), 5.92 (s, 0.3H), 5.67 (s, 0.7H), 4.45 (s, 1H), 3.58 (s, 0.9H), 3.50 (s, 2.1H), 3.23-3.04 (m, 3H), 3.04-2.92 (m, 1H), 2.92-2.76 (m, 2H), 2.29-2.13 (m, 2H), 1.94 (td, J=8.2, 5.3 Hz, 1H), 1.39-1.26 (m, 1H), 1.09 (d, J=6.2 Hz, 3H), 1.05-0.96 (m, 2H), 0.85-0.77 (m, 1H), 0.43-0.29 (m, 2H), 0.23-0.12 (m, 2H). LCMS [M+H]$^+$ 561, RT 1.76 minutes (Method 25).

Example 307

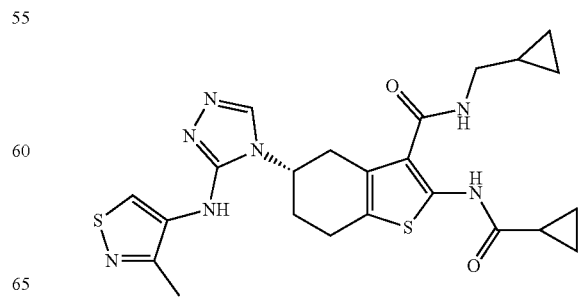

(5S)-2-(cyclopropanecarbonylamino)-N-(cyclopropylmethyl)-5-[3-[(3-methylisothiazol-4-yl)amino]-1,2,4-triazol-4-yl]-4,5,6,7-tetrahydrobenzothiophene-3-carboxamide A solution of methanesulfonyl chloride (0.076 mL, 0.98 mmol) in DCM (1 mL) was added dropwise to a solution of intermediate 407 (393 mg, 0.803 mmol) and triethylamine (0.37 mL, 2.6 mmol) in DCM (8 mL) at 0° C. and under nitrogen. The reaction was stirred at 0° C. for 1 hour 10 mins. Additional methanesulfonyl chloride (0.014 mL, 0.18 mmol) as a solution in DCM (1 mL) was added and the reaction stirred at 0° C. for a further 10 mins. The reaction was diluted with DCM (20 mL) and washed with sat. aq. NH$_4$Cl (20 mL). The layers were separated and the aqeuous layer extracted with 5% MeOH in DCM (2×20 mL). The combined organic layers were passed through a phase separation cartridge and concentrated in vacuo. To this material was added MeOH (4.5 mL), MeCN (4.5 mL) and formic acid hydrazide (81 mg, 1.3 mmol). The reaction was stirred at room temperature for 3 hours, DMF (2.2 mL) was added and the reaction stirred for a further 1.5 hours at room temperature. Water (2.2 mL) followed by sodium carbonate (284 mg, 2.68 mmol) were added and the reaction was stirred for 16 h at 45° C. The reaction was concentrated in vacuo and re-dissolved in 5% MeOH in DCM (50 mL). Water (20 mL) was added and the layers separated. The Aq layer was extracted with 5% MeOH in DCM (2×25 mL). The combined organic layers were passed through a phase separation cartridge and concentrated in vacuo to give the crude product which was purified by flash column chromatography on silica (gradient elution with 0% to 20% MeOH in DCM) followed by further flash column chromatography on silica (gradient elution with 0% to 40% MeOH in EtOAc) and then HPLC (Method 5) to give the title compound (32 mg, 8% Yield). δH (300 MHz, DMSO-d6) 11.25 (s, 1H), 8.84 (s, 1H), 8.39 (s, 1H), 8.27 (s, 1H), 7.73 (t, J=5.7 Hz, 1H), 4.64-4.50 (m, 1H), 3.23-2.91 (m, 4H), 2.91-2.78 (m, 2H), 2.40 (s, 31H), 2.31-2.14 (m, 21H), 1.94 (p, J=6.4 Hz, 1H), 1.06-0.92 (m, 1H), 0.91-0.78 (m, 4H), 0.42-0.27 (m, 2H), 0.23-0.10 (m, 2H). LCMS [M+H]$^+$ 498, RT 1.79 minutes (Method 26).

Example 308

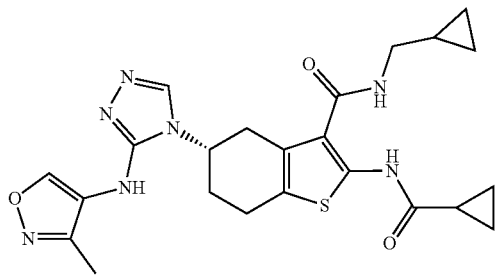 [SMILES: Cc1nscc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(3-methylisoxazol-4-yl)amino]-1,2,4-triazol-4-yl]-4,5,6,7-tetrahydrobenzothiophene-3-carboxamide To a stirred solution of intermediate 409 (313 mg, 0.614 mmol, 93 mass %) in DMF (4.3 mL) under nitrogen was added formic acid hydrazide [624-84-0] (111 mg, 1.84 mmol) and mercuric chloride [7487-94-7] (201 mg, 0.734 mmol). The reaction mixture was stirred at r.t. for 5 min before the addition of triethylamine (0.26 mL, 1.9 mmol) and the mixture was stirred at 80° C. for 4.5 hours. The mixture was cooled to r.t. and diluted with MeCN (20 mL), filtered through a pad of celite and washed with MeCN (25 mL). The filtrate was concentrated in vacuo to yield the crude product which was dissolved in 5% MeOH in DCM (50 mL), washed with water (30 mL) and the layers separated. The aq. layer was extracted with 5% MeOH in DCM (2×25 mL). The combined organic layers were passed through a phase separation cartridge and concentrated in vacuo. The crude product was dissolved in MeOH (6 mL) and MeCN (3 mL), QuadraSil® MTU (600 mg) was added and the suspension was stirred at 40° C. for 4.5 h before being filtered and washed with MeOH (2×5 mL). The filtrate was concentrated in vacuo and was purified by flash column chromatography on silica (gradient elution with 0% to 20% MeOH in DCM) followed by flash column chromatography on silica (gradient elution with 0% to 20% MeOH in EtOAc) and then by SFC to give the title compound (83 mg, 28% Yield). δ$_H$ (300 MHz, DMSO-d6) 11.26 (s, 1H), 9.02 (s, 1H), 8.35 (s, 1H), 8.16 (s, 1H), 7.72 (t, J=5.7 Hz, 1H), 4.62-4.48 (m, 1H), 3.21-3.03 (m, J=6.3 Hz, 3H), 3.03-2.79 (m, 3H), 2.28 (s, 3H), 2.26-2.13 (m, 2H), 1.99-1.88 (m, 1H), 1.06-0.95 (m, 1H), 0.92-0.80 (m, 4H), 0.40-0.29 (m, 2H), 0.23-0.13 (m, 2H). LCMS [M+H]$^+$ 482, RT 1.64 minutes (Method 26).

Example 309

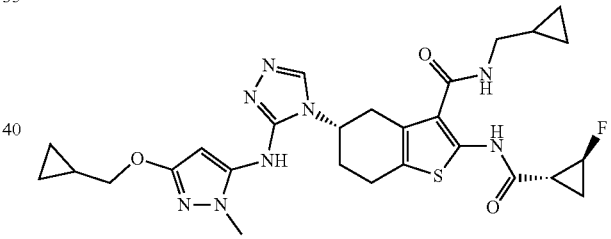

(5S)-5-[3-[[5-(cyclopropylmethoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide To a stirred solution intermediate 415 (160 mg, 0.285 mmol) and triethylamine (87 mg, 0.86 mmol) in CH$_2$Cl$_2$ (2.9 mL) at 0° C. was added methanesulfonyl chloride (36 mg, 0.32 mmol). After 10 min the reaction mixture was diluted with CH$_2$Cl$_2$ (5 mL) and washed with sat. aq. ammonium chloride (10 mL). The aqueous layer was extracted with CH$_2$Cl$_2$ (2×5 mL). The combined organic extracts were passed through a phase separator, and concentrated in vacuo. The crude material was dissolved in DMF (1.4 mL), formic acid hydrazide (19 mg, 0.31 mmol) was added, and the reaction mixture was stirred at room temperature for 1 h. To the reaction mixture was added water (0.71 mL) and Na$_2$CO$_3$ (91 mg, 0.86 mmol), and the solution stirred at 45° C. for 16 h. The reaction mixture was diluted with water (20 mL) and extracted with ethyl acetate (3×20 mL). The combined organic extracts were washed with water (2×60 mL), passed through a phase separator, and concentrated in vacuo. The crude material was purified by flash chromatography [methanol/CH₂Cl₂ (0-10%)] followed by HPLC to afford the title compound (33 mg, 29% Yield). δ$_H$ (400 MHz, d-DMSO) 11.82 (s, 0.5H), 11.22 (s, 0.5H), 11.18 (s, 0.5H), 8.54 (s, 0.5H), 8.37 (s, 0.5H), 8.15 (s, 0.5H), 7.89 (t, J=5.8 Hz, 0.5H), 7.86 (t, J=5.8 Hz, 0.5H), 5.54 (s, 0.5H), 5.36 (s, 0.5H), 4.90 (d, J=65.1 Hz, 1H), 4.48-4.36 (m, 1H), 3.84-3.80 (m, 2H), 3.48 (s, 1.5H), 3.42 (s, 1.5H), 3.19-3.06 (m, 3H), 2.98-2.79 (m, 3H), 2.66-2.56 (m, 1H), 2.28-2.12 (m, 2H), 1.60-1.50 (m, 1H), 1.30-1.14 (m, 2H), 1.05-0.95 (m, 1H), 0.55-0.50 (m, 2H), 0.39-0.35 (m, 2H), 0.30-0.25 (m, 2H), 0.21-0.17 (m, 2H). LCMS (M+H)⁺ 569, RT 1.74 (Method 25).

Example 310

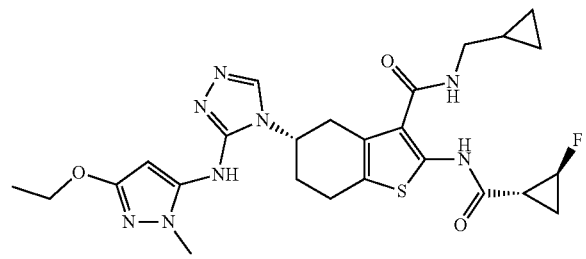 [SMILES: CCOc1cc(Nc2nncn2[C@H]2CCc3sc(NC(=O)[C@H]4C[C@@H]4F)c(C(=O)NCC4CC4)c3C2)n(C)n1]

(5S)—N-(cyclopropylmethyl)-5-[3-[(5-ethoxy-2-methyl-pyrazol-3-yl)amino]-1,2,4-triazol-4-yl]-2-[[(1R,2S)-2-fluorocyclopropanecarbonyl]amino]-4,5,6,7-tetrahydrobenzothiophene-3-carboxamide To a stirred solution of intermediate 421 (141 mg, 0.264 mmol) and triethylamine (0.11 mmol, 0.80 mmol) in CH₂Cl₂ (2.8 mL) at 0° C. was added methanesulfonyl chloride (33 mg, 0.29 mmol). After 10 min the reaction mixture was diluted with CH₂Cl₂ (5 mL) and washed with sat. aq. ammonium chloride (10 mL). The aqueous layer was extracted with CH₂Cl₂ (2×5 mL) and the combined organic extracts passed through a phase separator, and concentrated in vacuo. The crude material was dissolved in DMF (1.4 mL), formic acid hydrazide (17 mg, 0.29 mmol) was added, and the reaction mixture was stirred at room temperature for 1 h 15 min. To the reaction mixture was added water (0.7 mL) and Na₂CO₃ (84 mg, 0.79 mmol), and the solution stirred at 45° C. for 16 h. The reaction mixture was diluted with water (20 mL) and extracted with EtOAc (3×20 mL). The combined organic extracts were washed with water (2×60 mL), passed through a phase separator, and concentrated in vacuo. The crude material was purified by flash chromatography (0-10% methanol in CH₂Cl₂) followed by HPLC to afford the title compound (21 mg, 15% Yield). δ$_H$ (400 MHz, d-DMSO) 11.82 (s, 0.5H), 11.20 (br. s, 1H), 8.54 (s, 0.5H), 8.37 (s, 0.5H), 8.15 (s, 0.5H), 7.88 (br. s, 1H), 5.54 (s, 0.5H), 5.37 (s, 0.5H), 4.89 (d, J=65.2 Hz, 0.5H), 4.46-4.35 (m, 1H), 4.07-4.00 (m, 2H), 3.49 (s, 1.5H), 3.42 (s, 1.5H), 3.18-3.06 (m, 3H), 2.97-2.78 (m, 3H), 2.68-2.53 (m, 1H), 2.27-2.12 (m, 2H), 1.62-1.47 (m, 1H), 1.30-1.20 (m, 4H), 1.05-0.96 (m, 1H), 0.41-0.34 (m, 2H), 0.22-0.16 (m, 2H). LCMS (M-H)⁻ 541, RT 1.59 (Method 25)

Example 311

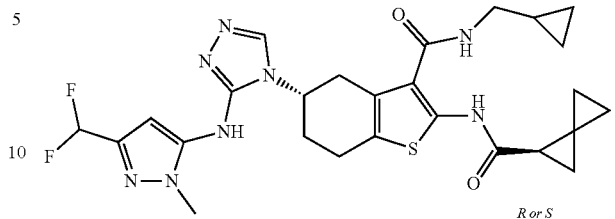

(5S)—N-(cyclopropylmethyl)-5-[3-[[5-(difluoromethyl)-2-methyl-pyrazol-3-yl]amino]-1,2,4-triazol-4-yl]-2-[[(2R*)-spiro[2.2]pentane-2-carbonyl]amino]-4,5,6,7-tetrahydrobenzothiophene-3-carboxamide [* or S]

Intermediate 426 (35.0 mg, 0.062 mmol) was separated by chiral SFC (eluting with CO₂:ethanol 75:25+0.5% isopropylamine, using Chiralcel OD-H 25 cm column at 50 mL/min) to give the title compound:

Peak 2 (7.6 mg, 21% Yield). δ$_H$ (500 MHz, Methanol-d4) 8.18 (s, 1H), 6.61 (t, J=55.2 Hz, 1H), 6.27 (s, 1H), 4.61-4.49 (m, 1H), 3.72 (s, 3H), 3.39-3.33 (m, 1H), 3.28-3.24 (m, 1H), 3.20-3.12 (m, 1H), 3.12-3.05 (m, 1H), 3.02-2.85 (m, 2H), 2.41-2.30 (m, 2H), 2.21-2.11 (m, 1H), 1.56-1.45 (m, 2H), 1.11-1.04 (m, 2H), 1.03-0.88 (m, 3H), 0.54-0.41 (m, 2H), 0.30-0.19 (m, 2H. LCMS [M+H]⁺ 557, RT 2.97 minutes (Method 10). Chiral SFC** RT=14.41 minutes.

** Chiral analysis using CHIRALPAK AD (4.6×250 mm 5 μm) column, flow rate 2.4 mL/min, eluting 75:25% CO₂:(EtOH+0.5% isopropylamine), 20 minutes run time on an SFC Berger.

Example 312

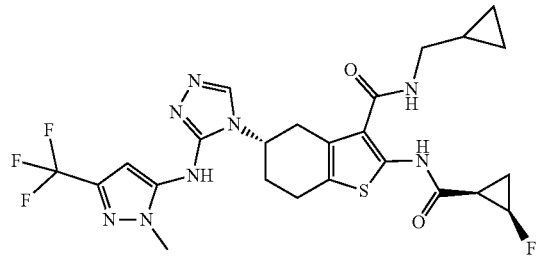 [SMILES: Cn1nc(C(F)(F)F)cc1Nc1nncn1[C@H]1CCc2sc(NC(=O)[C@H]3C[C@H]3F)c(C(=O)NCC3CC3)c2C1]

(5S)—N-(cyclopropylmethyl)-2-[[(1R,2R)-2-fluoro-cyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide A mixture of intermediate 432 (90 mg, 0.15 mmol), pyridine (37 μL, 0.46 mmol) and cyclopropylmethanamine (16.5 mg, 0.23 mmol) in DCM (6 mL) at 0° C., 2,4,6-Tripropyl-1,3,5,2,4,6-trioxatriphosphorinane-2,4,6-trioxide (184 μL, 0.31 mmol) was slowly added. The reaction mixture was slowly allowed to warm to room temperature and stirred for 16 h. Reaction mixture was diluted with DCM (20 mL) and water (15 mL). The aqueous layer was extracted with DCM (2×10 mL) and the organic fractions combined, dried over sodium sulfate and concentrated under vacuum. Resulting mixture was dissolved in DMF (3 mL) and cyclopropylmethanamine (16 mg, 0.231 mmol) added. The reaction mixture was heated at 100° C. for 2 h before the solvent was removed under vacuum. The residue was purified by HPLC (Method 4) to give the title compound (35 mg, 39.6% Yield). $\delta_H$ (500 MHz, Methanol-d4) 8.34 and 7.93 (2×s, 1H, rotamers), 6.49 and 6.22 (2×s, 1H, rotamers), 5.00-4.75 (m, 1H), 4.64-4.47 (m, 1H), 3.75 (s, 3H), 3.40-3.32 (m, 1H), 3.29-3.22 (m, 1H), 3.22-3.13 (m, 1H), 3.12-2.80 (m, 3H), 2.42-2.28 (m, 2H), 2.09-1.98 (m, 1H), 1.81-1.66 (m, 1H), 1.31-1.20 (m, 1H), 1.13-1.00 (m, 1H), 0.51-0.41 (m, 2H), 0.27-0.20 (m, 2H). LCMS [M+H]$^+$ 567, RT 2.86 minutes (Method 10).

Example 313

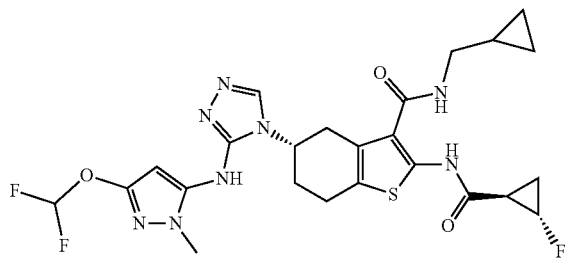 [SMILES: Cn1nc(OC(F)F)cc1Nc1nncn1[C@H]1CCc2sc(NC(=O)[C@H]3C[C@@H]3F)c(C(=O)NCC3CC3)c2C1]

(5S)—N-(cyclopropylmethyl)-5-[3-[[5-(difluoromethoxy)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide The title compound was obtained following general method 6 with intermediate 436 (20 mg, 0.04 mmol), (1R,2S)-2-fluorocyclopropanecarboxylic acid (3.7 mg, 0.04 mmol), pyridine (15 µL, 0.18 mmol), T3P (43 µL, 0.07 mmol) and DCM (3 mL). Reaction duration: 16 hours. Reaction mixture was diluted with DCM (20 mL) then water (15 mL) was added and organic layer separated. The aqueous layer was extracted with DCM (2×10 mL) and the organic fractions combined, dried (Na$_2$SO$_4$) and concentrated under vacuum. Purification by HPLC (Method 4) gave the title compound (9 mg, 43% Yield). $\delta_H$ (500 MHz, Methanol-d4) 8.31 (br s, 1H), 6.88 (t, J=73.9 Hz, 1H), 5.77 (br s, 1H), 4.92-4.75 (m, 1H), 4.55-4.49 (m, 1H), 3.60 (s, 3H), 3.29-3.24 (m, 2H), 3.21-3.15 (m, 1H), 3.09-2.81 (m, 3H), 2.44-2.25 (m, 3H), 1.66-1.47 (m, 1H), 1.42-1.27 (m, 1H), 1.15-0.98 (m, 1H), 0.57-0.41 (m, 2H), 0.31-0.18 (m, 2H). LCMS [M+H]$^+$ 565, RT 2.81 minutes (Method 10).

Example 314

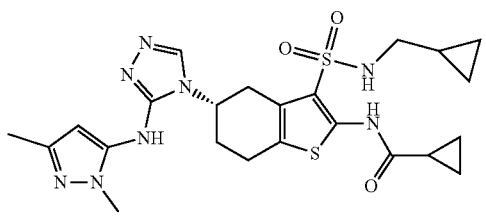 [SMILES: Cc1cc(Nc2nncn2[C@H]2CCc3sc(NC(=O)C4CC4)c(S(=O)(=O)NCC4CC4)c3C2)n(C)n1]

N-[(5S)-3-(cyclopropylmethylsulfamoyl)-5-[3-[(2,5-dimethylpyrazol-3-yl)amino]-1,2,4-triazol-4-yl]-4,5,6,7-tetrahydro-1-benzothiophen-2-yl]cyclopropanecarboxamide Intermediate 544 (915.0 mg, 1.72 mmol) was separated by SFC (eluting with CO$_2$/EtOH+0.5% isopropylamine 60/40 using Chiralpak AD 5 µm 250×20 mm column at 50 mL/min) to give the title compound. (314 mg, 34% Yield). $\delta_H$ (500 MHz, DMSO-d6) 11.73 (s, 1H, minor rotamer), 10.47 (s, 1H), 8.44 (s, 1H, major rotamer), 8.37 (s, 1H, major rotamer), 8.15 (s, 1H, minor rotamer), 7.98 (s, 1H), 5.93 (s, 1H, major rotamer), 5.71 (s, 1H, minor rotamer), 4.55-4.39 (m, 1H), 3.56 (s, 3H, major rotamer), 3.48 (s, 3H, minor rotamer), 3.39-3.33 (m, 1H), 2.89-2.79 (m, 3H), 2.71 (d, J=6.9 Hz, 2H), 2.31-2.12 (m, 2H), 2.08 (s, 3H, major isomer), 2.05 (s, 3H, minor rotamer), 2.00-1.87 (m, 1H), 0.97-0.86 (m, 4H), 0.83-0.70 (m, 1H), 0.41-0.32 (m, 2H), 0.12-0.03 (m, 2H). LCMS [M+H]$^+$ 531, RT 2.32 minutes (Method 10). Chiral SFC* RT=3.0 minutes.

* Chiral analysis using CHIRALPAK AD (4.6×250 mm 5 µm) column, flow rate 2.4 mL/min, eluting with 60/40% CO$_2$/(EtOH+0.5% isopropylamine), 10 minutes run time.

Example 315

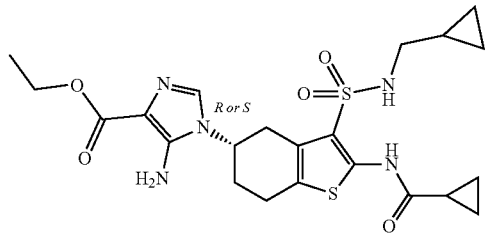 [SMILES: CCOC(=O)c1ncn([C@H]2CCc3sc(NC(=O)C4CC4)c(S(=O)(=O)NCC4CC4)c3C2)c1N]

ethyl 5-amino-1-[(5S*)-2-(cyclopropanecarbonylamino)-3-(cyclopropylmethylsulfamoyl)-4,5,6,7-tetrahydrobenzothiophen-5-yl]imidazole-4-carboxylate (* or R)

Intermediate 545 (55 mg, 0.10 mmol) was separated by SFC (eluting with CO$_2$/EtOH+0.5% isopropylamine 70/30 using Chiralpak AD 5 µm 250×20 mm column at 50 mL/min) to give the title compound (4.6 mg, 8% Yield). $\delta_H$ (500 MHz, Methanol-d4) 7.25 (s, 1H), 4.51-4.42 (m, 1H), 4.29 (q, J=7.1 Hz, 2H), 3.44 (dd, J=16.3, 5.5 Hz, 1H), 3.00 (dd, J=17.2, 9.2 Hz, 1H), 2.97-2.89 (m, 1H), 2.85-2.73 (m, 3H), 2.34-2.23 (m, 2H), 1.85-1.75 (m, 1H), 1.35 (t, J=7.1 Hz, 3H), 1.06-0.97 (m, 4H), 0.88-0.79 (m, 1H), 0.51-0.41 (m, 2H), 0.16-0.07 (m, 2H). LCMS [M+H]$^+$ 508, RT 2.43 minutes (Method 10). Chiral SFC** RT=3.09 minutes.

** Chiral analysis using CHIRALPAK AD (4.6×250 mm 5 µm) column, flow rate 2.4 mL/min, eluting with 60/40% CO$_2$/(EtOH+0.5% isopropylamine), 10 minutes run time on a SFC Berger.

Example 316

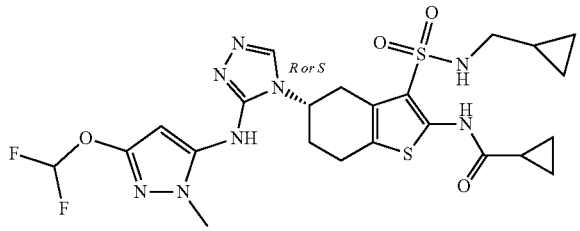 [SMILES: Cn1nc(OC(F)F)cc1Nc1nncn1[C@H]1CCc2sc(NC(=O)C3CC3)c(S(=O)(=O)NCC3CC3)c2C1]

N-[(5S*)-3-(cyclopropylmethylsulfamoyl)-5-[3-[[5-(difluoromethoxy)-2-methyl-pyrazol-3-yl]amino]-1,2,4-triazol-4-yl]-4,5,6,7-tetrahydrobenzothiophen-2-yl]cyclopropanecarboxamide (* or R)

Intermediate 439 (127 mg, 0.21 mmol) was separated by SFC (eluting with CO$_2$/IPOH+0.5% isopropylamine 70/30 using Chiralpak IA 5 µm 250×20 mm at 50 mL/min) to give the title compound (36 mg, 27% Yield). δ$_H$ (500 MHz, DMSO-d6) 12.03 (s, 1H, major rotamer), 10.46 (s, 1H), 8.75 (s, 1H, minor rotamer), 8.24 (s, 1H), 7.96 (s, 1H), 7.40-6.81 (m, 1H), 5.93 and 5.67 (2×s, 1H), 4.47 (s, 1H), 3.50 (s, 3H), 3.42-3.34 (m, 1H), 2.92-2.79 (m, 3H), 2.75-2.66 (m, 2H), 2.36-2.21 (m, 1H), 2.20-2.12 (m, 1H), 1.97-1.89 (m, 1H), 1.00-0.86 (m, 4H), 0.81-0.68 (m, 1H), 0.43-0.27 (m, 2H), 0.11--0.01 (m, 2H). LCMS [M+H]$^+$ 583, RT 3.03 minutes (Method 10). Chiral SFC** RT=6.6 minutes.

** Chiral analysis using CHIRALPAK IA (4.6×250 mm 5 µm) column, flow rate 2.4 mL/min, eluting with 70/30% CO$_2$/(IPOH+0.5% isopropylamine), 25 minutes run time on a SFC Agilent.

Example 317

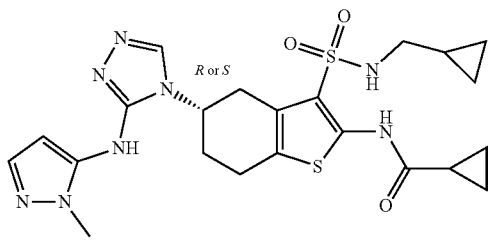 [SMILES: Cn1nccc1Nc1nncn1[C@H]1CCc2sc(NC(=O)C3CC3)c(S(=O)(=O)NCC3CC3)c2C1]

N-[(5S*)-3-(cyclopropylmethylsulfamoyl)-5-[3-[(2-methylpyrazol-3-yl)amino]-1,2,4-triazol-4-yl]-4,5,6,7-tetrahydrobenzothiophen-2-yl]cyclopropanecarboxamide (* or R)

Intermediate 442 (314 mg, 0.60 mmol) was separated by SFC (eluting with CO$_2$/(isopropanol+0.5% isopropylamine) 70/30 using Chiralpak IA 5 µm 250×21 mm at 50 mL/min) to give the title compound (73 mg, 23% Yield). δ$_H$ (500 MHz, DMSO-d6) 11.81 (s, 1H, minor rotamer), 10.47 (s, 1H), 8.51 (s, 1H, major rotamer), 8.38 and 8.18 (2×s, 1H), 8.04-7.88 (m, 1H), 7.30 and 7.19 (2×d, J=1.9 Hz, 1H), 6.14 and 5.91 (2×d, J=1.9 Hz, 1H), 4.56-4.41 (m, 1H), 3.66 and 3.57 (2×s, 3H), 3.41-3.33 (m, 1H), 2.91-2.79 (m, 3H), 2.75-2.67 (m, 2H), 2.32-2.11 (m, 2H), 2.02-1.91 (m, 1H), 0.99-0.87 (m, 4H), 0.82-0.70 (m, 1H), 0.42-0.31 (m, 2H), 0.14--0.02 (m, 2H). LCMS [M+H]$^+$ 517, RT 2.36 minutes (Method 10). Chiral SFC** RT=14.6 minutes.

** Chiral analysis using CHIRALPAK IA (4.6×250 mm 5 µm) column, flow rate 2.4 mL/min, eluting with 70/30% CO$_2$/(IPA+0.5% isopropylamine), 22 minutes run time on a SFC Berger.

Example 318

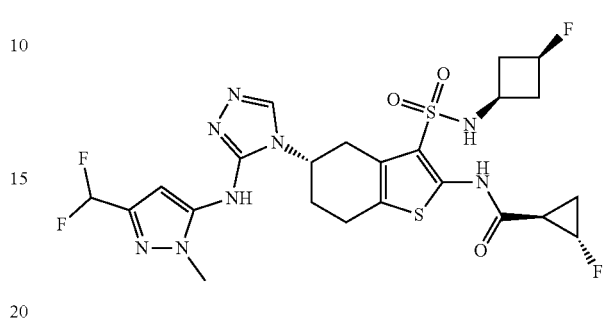

(1R,2S)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluorocyclopropanecarboxamide 1 M formic hydrazide (0.81 mL, 0.81 mmol) in MeOH was added to intermediate 446 (152 mg, 0.27 mmol) followed by MeOH (5 mL). The reaction was stirred for 30 mins then aqueous 1 M sodium carbonate (0.81 mL, 0.81 mmol) was added and reaction heated to 50° C. with stirring for 16 hours. Reaction allowed to cool, MeOH removed and water added (15 mL). The mixture was extracted with DCM (2×15 mL), organics combined, dried (MgSO$_4$) and concentration under reduced pressure. The residue was purified by HPLC (Method 4) to give the title compound (82 mg, 49% Yield). δ$_H$ (500 MHz, Methanol-d4) 8.31 (br s, 1H), 6.62 (t, J=55.2 Hz, 1H), 6.37 (br s, 1H), 4.96-4.78 (m, 1H), 4.76-4.61 (m, 1H), 4.60-4.51 (m, 1H), 3.73 (s, 3H), 3.58-3.45 (m, 1H), 3.36-3.32 (m, 1H), 3.01-2.81 (m, 3H), 2.64-2.49 (m, 2H), 2.45-2.26 (m, 3H), 2.12-1.95 (m, 2H), 1.65-1.52 (m, 1H), 1.44-1.34 (m, 1H). LCMS [M+H]$^+$ 603, RT 2.90 minutes (Method 10).

Example 319

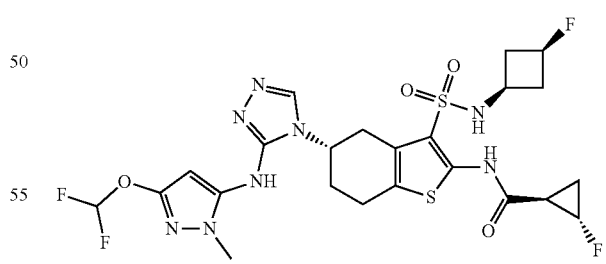

(1R,2S)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluorocyclopropanecarboxamide 1 M formic hydrazide (0.62 mL, 0.62 mmol) in MeOH was added to intermediate 448 (140 mg, 0.21 mmol) followed by MeOH (5 mL). The reaction mixture was stirred for 30 mins then aqueous 1 M sodium carbonate (0.62 mL, 0.62 mmol) was added and reaction heated to 50° C. with stirring for 6 hours. Reaction allowed to cool, MeOH was removed and water was added (15 mL). The mixture was extracted with DCM (2×15 mL), organics combined, dried (MgSO$_4$) and concentrated under reduced pressure. The residue was purified HPLC (Method 4) to give the title compound (52 mg, 41% Yield). δ$_H$ (500 MHz, Methanol-d4) 8.26 (br s, 1H), 6.88 (t, J=73.0 Hz, 1H), 5.79 (br s, 1H), 4.98-4.78 (m, 1H), 4.77-4.60 (m, 1H), 4.60-4.47 (m, 1H), 3.61 (s, 3H), 3.55-3.44 (m, 1H), 3.35-3.32 (m, 1H), 3.00-2.82 (m, 3H), 2.64-2.51 (m, 2H), 2.44-2.27 (m, 3H), 2.12-1.92 (m, 2H), 1.65-1.52 (m, 1H), 1.44-1.34 (m, 1H. LCMS [M+H]$^+$ 619, RT 3.01 minutes (Method 10).

Example 320

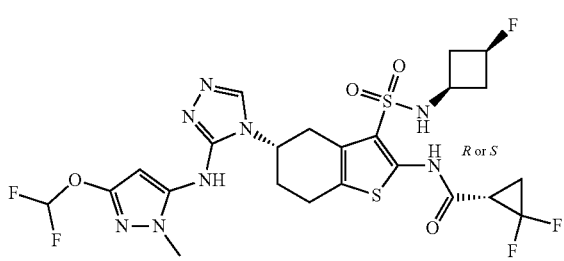 [SMILES: Cn1nc(OC(F)F)cc1Nc1nncn1[C@H]1CCc2sc(NC(=O)[C@@H]3CC3(F)F)c(S(=O)(=O)N[C@H]3C[C@@H](F)C3)c2C1]

(1S*)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R]

1 M formic hydrazide (1.97 mL, 1.97 mmol) in MeOH was added to intermediate 452 (390 mg, 0.66 mmol) followed by MeOH (10 mL). The reaction mixture was stirred for 30 mins then aqueous 1 M sodium carbonate (1.97 mL, 1.97 mmol) was added and reaction heated to 50° C. with stirring for 16 hours. Reaction allowed to cool, MeOH was removed and water was added (15 mL). The mixture was extracted with DCM (2×15 mL), organics combined, dried (MgSO$_4$) and concentrated under reduced pressure. The residue was purified first by column chromatography using 0-100% EtOAc in heptane then by HPLC (Method 4) to give the title compound as a mixture of diastereoisomers (96 mg, 23% Yield). The mixture was separated by chiral SFC to give the title compound as a single isomer (8 mg, 8% Yield). δ$_H$ (400 MHz, DMSO-d6) 11.92 (s, 1H), 10.48 (s, 1H), 8.68-7.96 (m, 2H), 7.46-6.83 (m, 1H), 6.06-5.57 (m, 1H), 5.11 (d, J=56.9 Hz, 1H), 4.49 (s, 1H), 3.90 (s, 1H), 3.64-3.46 (m, 3H), 3.35 (dd, J=16.4, 5.4 Hz, 1H), 3.24 (q, J=11.3, 10.7 Hz, 1H), 2.94-2.84 (m, 3H), 2.39-2.13 (m, 6H), 2.06 (q, J=9.2 Hz, 2H). LCMS [M+H]$^+$ 637, RT 1.71 minutes (Method 26). Chiral SFC** RT=4.75 min.
** Using chiral SFC Method 1

Example 321

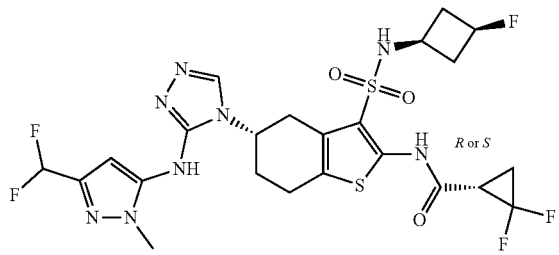 [SMILES: Cn1nc(C(F)F)cc1Nc1nncn1[C@H]1CCc2sc(NC(=O)[C@@H]3CC3(F)F)c(S(=O)(=O)N[C@H]3C[C@@H](F)C3)c2C1]

(1S*)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R]

1 M formic hydrazide (1.81 mL, 1.81 mmol) in MeOH was added to intermediate 454 (350 mg, 0.6 mmol) followed by MeOH (10 mL). The reaction was stirred for 30 mins then aqueous 1 M sodium carbonate (1.81 mL, 1.81 mmol) was added and reaction heated to 50° C. with stirring for 16 hours.

Reaction allowed to cool, MeOH was removed and water was added (15 mL). The mixture was extracted with DCM (2×15 mL), organics combined, dried (MgSO$_4$) and concentrated under reduced pressure. The residue was purified first by column chromatography using 0-100% EtOAc in heptane the by HPLC (Method 4) to the title as a mixture of isomers (93 mg, 24% Yield). The mixture was separated by chiral SFC to give the title compound (14 mg, 15% Yield). δH (400 MHz, MeOH-d4) 8.19 (s, 1H), 6.62 (t, J=55.2 Hz, 1H), 6.22 (d, J=51.9 Hz, 1H), 4.80-4.52 (m, 2H), 3.73 (s, 3H), 3.53 (dd, J=16.3, 5.3 Hz, 1H), 3.38-3.24 (m, 1H), 3.02-2.85 (m, 4H), 2.57 (dp, J=17.5, 6.3 Hz, 2H), 2.44-2.31 (m, 2H), 2.19-1.89 (m, 4H). LCMS [M+H]$^+$ 621, RT 1.65 minutes (Method 26). Chiral SFC** RT=4.52 minutes.
** Using chiral SFC Method 1

Example 322

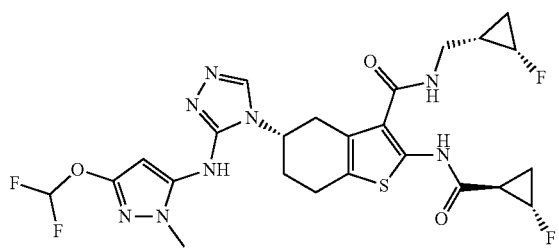 [SMILES: Cn1nc(OC(F)F)cc1Nc1nncn1[C@H]1CCc2sc(NC(=O)[C@H]3C[C@@H]3F)c(C(=O)NC[C@@H]3C[C@@H]3F)c2C1]

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1S,2S)-2-fluorocyclopropyl]methyl]-4,5,6,7-tetrahydro-1-benzothiophene-3-carboxamide HATU (149 mg, 0.391 mmol) to a mixture of intermediate 461 (100 mg, 0.196 mmol), [(1S,2S)-2-fluorocyclopropyl]

methanamine hydrochloride (73 mg, 0.577 mmol) and N-ethyl-N-isopropyl-propan-2-amine (137 µL, 0.782 mmol) in DMF (2 mL) at room temperature. The reaction mixture was stirred for 1 h at room temperature and heated at 70° C. for 1 h. The mixture was allowed cool to room temperature and stirred overnight. The reaction mixture was diluted with saturated aqueous NH₄Cl (5 mL) and extracted with DCM (3×5 mL). The combined organic layers were dried over sodium sulfate, filtered and evaporated to dryness to afford crude material. The crude material was purified by HPLC (Method 4) to give the title compound (10 mg, 8.8% Yield). δ_H (500 MHz, Methanol-d4) 8.19 (s, 1H), 6.89 (t, J=73.8 Hz, 1H), 5.75 (s, 1H), 4.92-4.76 (m, 1H), 4.75-4.60 (m, 1H), 4.58-4.48 (m, 1H), 3.68-3.62 (m, 1H), 3.60 (s, 3H), 3.39 (dd, J=14.1, 8.0 Hz, 1H), 3.28 (d, J=5.1 Hz, 1H), 3.09-2.98 (m, 1H), 2.98-2.83 (m, 2H), 2.40-2.28 (m, 3H), 1.60-1.47 (m, 1H), 1.41-1.31 (m, 1H), 1.31-1.15 (m, 1H), 0.87-0.68 (m, 2H). Comment: 3H exchanged with solvent. LCMS [M+H]⁺ 583, RT 2.72 minutes (Method 10).

Example 323

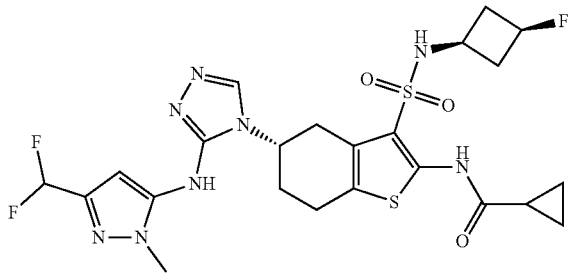 [SMILES: Cn1nc(C(F)F)cc1Nc1nncn1[C@H]1CCc2sc(NC(=O)C3CC3)c(S(=O)(=O)N[C@H]3C[C@@H](F)C3)c2C1]

N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]cyclopropanecarboxamide A solution of formic hydrazide (28 mg, 0.466 mmol) in methanol (2 mL) was added to intermediate 466 (85 mg, 0.094 mmol) and stirred at room temperature for 30 min then 0.92 M aqueous sodium carbonate (0.46 mL, 0.463 mmol) was added and the mixture was heated at 50° C. for 20 h. The reaction mixture was allowed to cooled to room temperature, evaporated to dryness, diluted with water (20 mL) and extracted with DCM:MeOH (9:1, 3×20 mL). The combined organic layers were dried over sodium sulfate, filtered, evaporated to dryness to afford crude material. The crude material was purified by HPLC (Method 2) to give the title compound (22 mg, 40% Yield). δ_H (500 MHz, DMSO-d6) 12.08 (br s, 1H), 10.43 (s, 1H), 8.89-8.07 (m, 2H), 6.75 (t, J=55.2 Hz, 1H), 6.54-6.12 (m, 1H), 4.85-4.60 (m, 1H), 4.59-4.38 (m, 1H), 3.80-3.54 (m, 3H), 3.40-3.34 (m, 1H), 3.22 (d, J=7.2 Hz, 1H), 2.94-2.84 (m, 2H), 2.81 (dd, J=16.3, 10.5 Hz, 1H), 2.48-2.39 (m, 2H), 2.35-2.12 (m, 2H), 2.06-1.95 (m, 2H), 1.95-1.90 (m, 1H), 0.98-0.86 (m, 4H). 28% of imidazole tautomer and minor amount of impurity from DMSO-d6. LCMS [M+H]⁺ 585, RT 2.84 minutes (Method 10).

Example 324

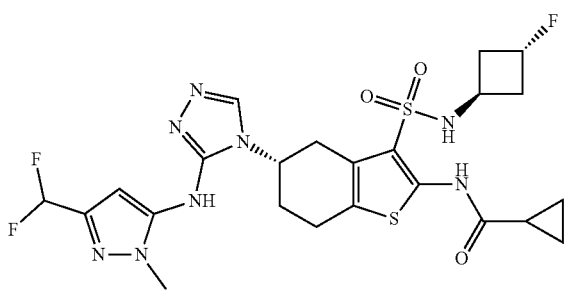 [SMILES: Cn1nc(C(F)F)cc1Nc1nncn1[C@H]1CCc2sc(NC(=O)C3CC3)c(S(=O)(=O)N[C@H]3C[C@H](F)C3)c2C1]

N-[(5S)-5-[3-[[5-(difluoromethyl)-2-methyl-pyrazol-3-yl]amino]-1,2,4-triazol-4-yl]-3-[trans-(3-fluorocyclobutyl)sulfamoyl]-4,5,6,7-tetrahydrobenzothiophen-2-yl]cyclopropanecarboxamide A solution of formic hydrazide (21 mg, 0.353 mmol) in dry methanol (2 mL) was added to the Intermediate 469 (55 mg, 0.0882 mmol). The reaction mixture was stirred at room temperature for 30 min then 1 M sodium carbonate (353 µL, 0.353 mmol) was added and the mixture heated at 50° C. for 20 h. The reaction mixture was allowed cooled to room temperature, evaporated to dryness, diluted with water (20 mL) and extracted with DCM:MeOH (9:1, 3×20 mL). The combined organic layers were dried over sodium sulfate, filtered, evaporated to dryness to afford crude material. This was purified by HPLC (Method 2) to give the title compound (18 mg, 35% Yield). δ_H (500 MHz, DMSO-d6) 12.05 (br s, 1H), 10.41 (s, 1H), 9.00-7.87 (m, 2H), 7.07-6.58 (m, 1H), 6.58-6.01 (m, 1H), 5.26-5.00 (m, 1H), 4.51 (br s, 1H), 3.94-3.84 (m, 1H), 3.64 (br s, 3H), 3.43-3.35 (m, 1H), 2.93-2.84 (m, 2H), 2.84-2.76 (m, 1H), 2.39-2.25 (m, 3H), 2.25-2.11 (m, 3H), 2.02-1.92 (m, 1H), 0.98-0.85 (m, 4H). LCMS [M+H]⁺ 585, RT 2.85 minutes (Method 10).

Example 325

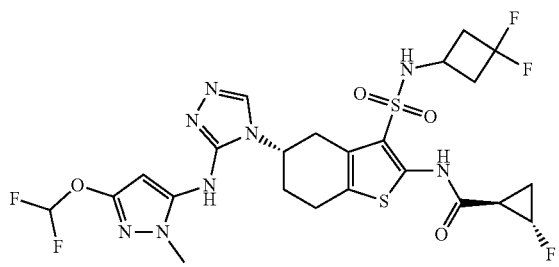 [SMILES: Cn1nc(OC(F)F)cc1Nc1nncn1[C@H]1CCc2sc(NC(=O)[C@H]3C[C@@H]3F)c(S(=O)(=O)NC3CC(F)(F)C3)c2C1]

(1R,2S)—N-[(5)-3-[(3,3-difluorocyclobutyl)sulfamoyl]-5-[3-[[5-(difluoromethoxy)-2-methylpyrazol-3-yl]amino]-1,2,4-triazol-4-yl]-4,5,6,7-tetrahydro-1-benzothiophen-2-yl]-2-fluorocyclopropane-1-carboxamide A solution of formic hydrazide (30 mg, 0.494 mmol) in methanol (2 mL) was added to intermediate 478 (83%, 118 mg, 0.165 mmol) at room temperature and stirred for 30 min. The reaction mixture was diluted with methanol (3 mL)

then 0.92 M sodium carbonate (0.49 mL, 0.494 mmol) was added and the reaction mixture heated at 50° C. for 9 h. The reaction mixture was allowed to cool to room temperature, evaporated to dryness, diluted with saturated aqueous NH₄Cl (20 mL) and extracted with 10% methanol in DCM (3×10 mL). The combined organic layers were dried over sodium sulfate, filtered and evaporated to dryness to afford a beige solid. The solid was purified twice by HPLC (Method 4) to give the title compound (60 mg, 53% Yield). $\delta_H$ (500 MHz, DMSO-d6) 12.06 (br s, 1H), 10.48 (br s, 1H), 9.18-8.15 (m, 2H), 7.14 (t, J=72.8 Hz, 1H), 5.68 (br s, 1H), 5.05-4.84 (m, 1H), 4.60-4.35 (m, 1H), 3.73-3.62 (m, 1H), 3.51 (br s, 3H), 3.41-3.20 (m, 1H; obs), 2.91-2.84 (m, 2H), 2.84-2.76 (m, 1H), 2.76-2.64 (m, 3H), 2.48-2.38 (m, 2H), 2.32-2.22 (m, 1H), 2.20-2.11 (m, 1H), 1.67-1.54 (m, 1H), 1.35-1.24 (m, 1H). LCMS [M+H]⁺ 637, RT 3.12 minutes (Method 10).

Example 326

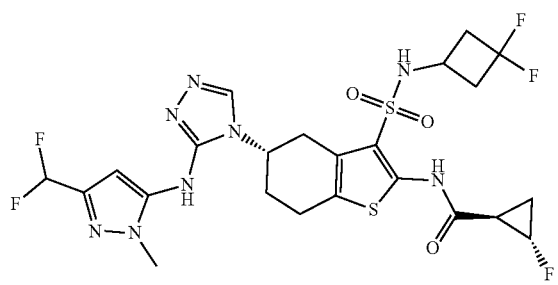 [SMILES: Cn1nc(C(F)F)cc1Nc1nncn1[C@H]1CCc2sc(NC(=O)[C@H]3C[C@@H]3F)c(S(=O)(=O)NC3CC(F)(F)C3)c2C1]

(1R,2S)—N-[(5S)-3-[(3,3-difluorocyclobutyl)sulfamoyl]-5-[3-[[5-(difluoromethyl)-2-methylpyrazol-3-yl]amino]-1,2,4-triazol-4-yl]-4,5,6,7-tetrahydro-1-benzothiophen-2-yl]-2-fluorocyclopropane-1-carboxamide A solution of formic hydrazide (36 mg, 0.599 mmol) in methanol (2 mL) was added to intermediate 480 (77%, 150 mg, 0.20 mmol) at room temperature and stirred for 30 min. The reaction mixture was diluted with methanol (3 mL) then 0.92 M sodium carbonate (0.60 mL, 0.599 mmol) was added and heated at 50° C. for 9 h. The reaction mixture was allowed to cool to room temperature, evaporated to dryness, diluted with saturated aqueous NH₄Cl (20 mL) then extracted with 10% methanol in DCM (3×10 mL). The combined organic layers were dried over sodium sulfate, filtered and evaporated to dryness to afford beige solid. The solid was purified twice by HPLC (Method 4) to give the title compound (33 mg, 26% Yield). $\delta_H$ (500 MHz, DMSO-d6) 12.08 (br s, 1H), 10.46 (br s, 1H), 9.18-8.02 (m, 2H), 6.99-6.59 (m, 1H), 6.59-6.10 (m, 1H), 5.06-4.84 (m, 1H), 4.59-4.41 (m, 1H), 3.73-3.58 (m, 4H), 3.40-3.16 (m, 1H), 2.87 (s, 21H), 2.84-2.78 (m, 1H), 2.78-2.64 (m, 3H), 2.48-2.38 (m, 2H), 2.34-2.23 (m, 1H), 2.22-2.12 (m, 1H), 1.69-1.53 (m, 1H), 1.37-1.25 (m, 1H). Comments: Tautomers 1H obscured under solvent peak. LCMS [M+H]⁺ 621, RT 3.02 minutes (Method 10).

Example 327

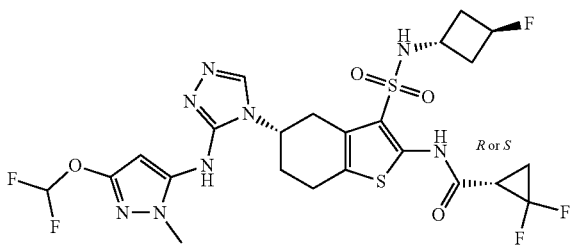 [SMILES: Cn1nc(OC(F)F)cc1Nc1nncn1[C@H]1CCc2sc(NC(=O)[C@@H]3CC3(F)F)c(S(=O)(=O)N[C@H]3C[C@H](F)C3)c2C1]

(1R*)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S)

A solution of formic hydrazide (90 mg, 1.50 mmol) in methanol (2 mL) was added to the intermediate 485 (70%, 423 mg, 0.498 mmol) at room temperature and stirred for 30 min. The reaction mixture was diluted with methanol (3 mL) then aqueous 0.92 M sodium carbonate (1.5 mL, 1.49 mmol) was added and heated at 50° C. for 9 h. The reaction mixture was cooled to room temperature, evaporated to dryness, diluted with saturated aqueous NH₄Cl (20 mL) and extracted with 10% methanol in DCM (3×10 mL). The combined organic layers were dried over sodium sulfate, filtered and evaporated to dryness. The crude material was purified by column chromatography (eluting with 0-10% methanol in DCM) to give a mixture of isomers of the title compound (135 mg, 43% Yield). The mixture was separated by SFC to give the title compound (6 mg, 4% Yield). $\delta_H$ (400 MHz, MeOH-d4) 11.92 (s, 1H), 10.48 (s, 1H), 8.76-7.98 (m, 2H), 7.12 (td, J=74.3, 73.8, 28.9 Hz, 1H), 5.80 (d, J=103.1 Hz, 1H), 5.11 (d, J=56.9 Hz, 1H), 4.49 (s, 2H), 3.90 (s, 1H), 3.55 (d, J=40.4 Hz, 3H), 3.35 (dd, J=16.4, 5.4 Hz, 1H), 3.24 (d, J=10.7 Hz, 1H), 2.88 (d, J=8.1 Hz, 3H), 2.35-2.14 (m, 6H), 2.06 (q, J=9.2 Hz, 2H). LCMS [M+H]⁺ 637, RT 1.71 minutes (Method 26). Chiral SFC** RT=4.56 minutes.
** Using chiral SFC Method 1

Example 328

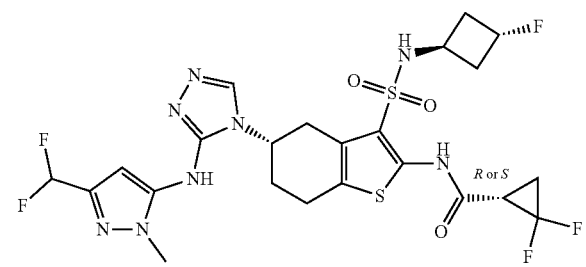 [SMILES: Cn1nc(C(F)F)cc1Nc1nncn1[C@H]1CCc2sc(NC(=O)[C@@H]3CC3(F)F)c(S(=O)(=O)N[C@H]3C[C@H](F)C3)c2C1]

(1R*)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S)

A solution of formic hydrazide (100 mg, 1.67 mmol) in methanol (5 mL) was added to intermediate 487 (322 mg, 0.557 mmol) at room temperature and stirred for 30 min. The reaction mixture was diluted with methanol (10 mL) then aqueous 0.92 M sodium carbonate (1.7 mL, 1.67 mmol) was added and the mixture was heated at 50° C. for 9 h. The reaction mixture was cooled to room temperature, evaporated to dryness, diluted with saturated aqueous NH$_4$Cl (50 mL) and extracted with 10% methanol in DCM (3×20 mL). The combined organic layers were dried over sodium sulfate, filtered and evaporated to dryness. The crude material was purified by column chromatography (eluting with 0-10% methanol in DCM) to give a mixture of isomers of the title compound (157 mg, 45% Yield). LCMS [M+H]$^+$ 621, RT 2.90 minutes (Method 10). The mixture was separated by chiral SFC to give the title compound (15 mg, 0.02 mmol, 10% Yield). δ$_H$ (400 MHz, MeOH-d4) 8.18 (s, 1H), 6.62 (t, J=55.2 Hz, 1H), 6.28 (s, 1H), 5.07 (dtt, J=56.5, 6.2, 3.1 Hz, 1H), 4.58 (tt, J=9.8, 5.1 Hz, 1H), 3.97 (dddd, J=14.2, 8.1, 6.1, 1.7 Hz, 1H), 3.73 (s, 3H), 3.51 (dd, J=16.3, 5.3 Hz, 1H), 3.04-2.87 (m, 4H), 2.49-2.17 (m, 6H), 2.12 (dtd, J=13.6, 7.7, 6.0 Hz, 1H), 1.96 (tdd, J=11.0, 7.9, 5.2 Hz, 1H). LCMS [M+H]$^+$ 621, RT 1.66 minutes (Method 26). Chiral SFC** RT=4.29 minutes.

** Using chiral SFC Method 1 Example 329

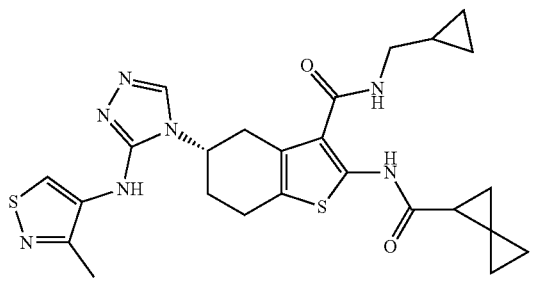 [SMILES: Cc1nscc1Nc1nncn1[C@H]1CCc2sc(NC(=O)C3CC34CC4)c(C(=O)NCC3CC3)c2C1]

(5S)—N-(cyclopropylmethyl)-5-[3-[(3-methyl-1,2-thiazol-4-yl)amino]-1,2,4-triazol-4-yl]-2-(spiro[2.2]pentane-2-carbonylamino)-4,5,6,7-tetrahydro-1-benzothiophene-3-carboxamide A solution of formic hydrazide (70 mg, 1.15 mmoL) in methanol (2 mL) was added to a solution of intermediate 504 (184 mg, 0.38 mmoL) in methanol (4 mL) and the resulting mixture was stirred at room temperature for 1 hour 15 minutes. 1 M sodium carbonate aqueous solution (1.2 mL, 1.2 mmol) was added and the mixture was stirred at 50° C. overnight. The reaction mixture was concentrated in vacuo, the residue was dissolved in ethyl acetate (20 mL) and washed with water (10 mL). The layers were separated and the aqueous phase was extracted with ethyl acetate (2×10 mL). The combined organic layers were washed with brine (10 mL), dried over magnesium sulfate, filtered and concentrated. The crude material was purified by flash column chromatography with a 0 to 100% ethyl acetate in heptane gradient, followed by a 0 to 20% methanol in ethyl acetate gradient. Further purification by HPLC (Method 4) afforded the title compound (10 mg, 5% yield). δ$_H$ (500 MHz, DMSO-d6) 11.16 (s, 1H), 8.82 (m, 1H), 8.37 (m, 1H), 8.26 (m, 1H), 7.61 (s, 1H), 4.62-4.50 (m, 1H), 3.18-3.04 (m, 3H), 3.04-2.92 (m, 1H), 2.91-2.77 (m, 2H), 2.38 (m, 31H), 2.28-2.14 (m, 3H), 1.46-1.38 (m, 1H), 1.40-1.35 (m, 1H), 1.01-0.89 (m, 3H), 0.91-0.84 (m, 1H), 0.82-0.75 (m, 1H), 0.37-0.29 (m, 2H), 0.16 (m, 2H). LCMS [M+H]$^+$ 524, RT 2.57 minutes (Method 10).

Example 330

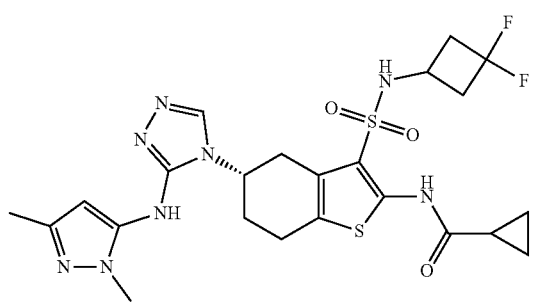 [SMILES: Cc1cc(Nc2nncn2[C@H]2CCc3sc(NC(=O)C4CC4)c(S(=O)(=O)NC4CC(F)(F)C4)c3C2)n(C)n1]

N-[(5S)-3-[(3,3-difluorocyclobutyl)sulfamoyl]-5-[3-[(2,5-dimethylpyrazol-3-yl)amino]-1,2,4-triazol-4-yl]-4,5,6,7-tetrahydro-1-benzothiophen-2-yl]cyclopropanecarboxamide A solution of formic hydrazide (34 mg, 0.57 mmol) in anhydrous methanol (1 mL) was added to a stirring solution of intermediate 508 (100 mg, 0.19 mmol) in anhydrous methanol (2 mL) and the resulting mixture was stirred at room temperature for 50 minutes. 1 M aqueous sodium carbonate (0.57 mL, 0.57 mmol) was added and the mixture was stirred at 50° C. overnight. The reaction mixture was concentrated in vacuo, the residue was dissolved in ethyl acetate (10 mL) and washed with water (5 mL). The layers were separated and the aqueous phase extracted with ethyl acetate (2×10 mL). The combined organics were washed with brine (10 mL), dried over magnesium sulfate, filtered and concentrated. The crude material was purified by flash column chromatography with a 0 to 100% ethyl acetate in heptane gradient, followed by a 0 to 20% methanol in ethyl acetate gradient. The isolated material was further purified by HPLC (Method 2) to afford the title compound (17 mg, 16% Yield). δ$_H$ (500 MHz, Methanol-d4) 8.25 (s, 1H), 5.91 (s, 1H), 4.59-4.50 (m, 1H), 3.70-3.64 (m, 1H), 3.64 (s, 3H), 3.49 (dd, J=15.8, 4.8 Hz, 1H), 2.98-2.86 (m, 3H), 2.85-2.69 (m, 2H), 2.55-2.38 (m, 2H), 2.37-2.30 (m, 2H), 2.19 (s, 3H), 1.87-1.79 (m, 1H), 1.08-0.96 (m, 4H). LCMS [M+H]$^+$ 567, RT 2.36 minutes (Method 10)

Example 331

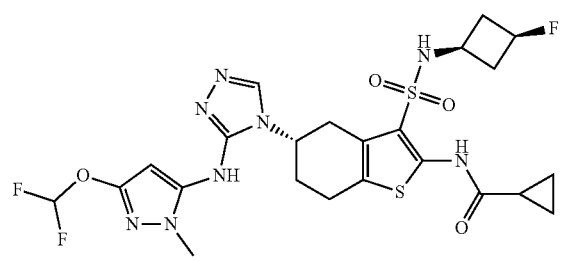 [SMILES: Cn1nc(OC(F)F)cc1Nc1nncn1[C@H]1CCc2sc(NC(=O)C3CC3)c(S(=O)(=O)N[C@H]3C[C@@H](F)C3)c2C1]

N-[(5S)-5-[3-[[5-(difluoromethoxy)-2-methylpyrazol-3-yl]amino]-1,2,4-triazol-4-yl]-3-[cis-(3-fluorocyclobutyl)sulfamoyl]-4,5,6,7-tetrahydro-1-benzothiophen-2-yl]cyclopropanecarboxamide A solution of formic hydrazide (45 mg, 0.75 mmol) in anhydrous methanol (3 mL) was added to a solution of intermediate 512 (140 mg, 0.25 mmol) in anhydrous methanol (4 mL) and the resulting mixture was stirred at room temperature for 1 hour. 1 M aqueous sodium carbonate (0.75 mL, 0.75 mmol) was added and the mixture was stirred at 50° C. overnight, then left stirring at room temperature for 2 days. The reaction mixture was concentrated in vacuo, the residue was dissolved in ethyl acetate (10 mL) and washed with water (5 mL). The layers were separated and the aqueous phase was extracted with ethyl acetate (2×10 mL). The combined organics were washed with brine (10 mL), dried over magnesium sulfate, filtered and concentrated. The crude material was purified by flash column chromatography with a 0 to 100% ethyl acetate in heptane gradient. The compound was further purified by HPLC (Method 4) to afford the title compound (45 mg, 30% yield). $\delta_H$ (500 MHz, DMSO-d6) 11.98 (br s, 1H), 10.42 (br s, 1H), 8.95-7.62 (m, 21H), 7.15 (t, J=74.1 Hz, 1H), 5.75 (s, 1H), 4.70 (dp, J=56.4, 6.8 Hz, 1H), 4.53-4.40 (m, 1H), 3.51 (s, 3H), 3.40-3.31 (m, 1H, obscured by water signal), 3.26-3.19 (m, 1H), 2.89-2.83 (m, 2H), 2.80 (dd, J=16.4, 10.5 Hz, 1H), 2.48-2.39 (m, 2H), 2.33-2.22 (m, 1H), 2.21-2.12 (m, 1H), 2.05-1.89 (m, 31H), 0.97-0.85 (m, 4H). LCMS [M+H]$^+$ 601, RT 2.93 minutes (Method 10)

Example 332

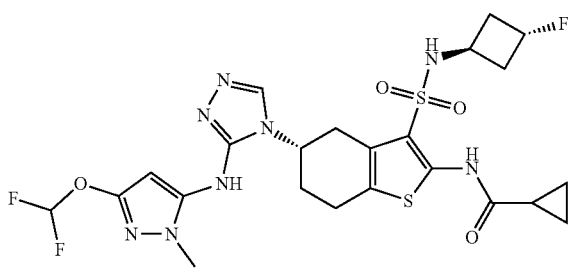 [SMILES: Cn1nc(OC(F)F)cc1Nc1nncn1[C@H]1CCc2sc(NC(=O)C3CC3)c(S(=O)(=O)N[C@H]3C[C@H](F)C3)c2C1]

N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]cyclopropanecarboxamide A solution of formic hydrazide (28 mg, 0.47 mmol) in anhydrous methanol (3 mL) was added to a solution of intermediate 516 (88 mg, 0.16 mmol) in anhydrous methanol (4 mL) and the resulting mixture was stirred at room temperature for 1 hour. 1 M aqueous sodium carbonate (0.47 mL, 0.47 mmol) was added and the mixture was stirred at 50° C. overnight, then left stirring at room temperature for 2 days. The reaction mixture was concentrated in vacuo, the residue was dissolved in ethyl acetate (10 mL) and washed with water (5 mL). The layers were separated and the aqueous phase was extracted with ethyl acetate (2×10 mL). The combined organic layers were washed with brine (10 mL), dried over magnesium sulfate, filtered and concentrated. The crude material was purified by flash column chromatography with a 0 to 100% ethyl acetate in heptane gradient, followed by HPLC (Method 4) to afford the title compound (35 mg, 37% Yield). $\delta_H$ (500 MHz, DMSO-d6) 12.05 (br s, 1H), 10.40 (s, 1H), 8.97-7.97 (m, 2H), 7.15 (t, J=74.4 Hz, 1H), 6.16-5.46 (m, 1H), 5.12 (dtt, J=56.9, 6.4, 3.3 Hz, 1H), 4.57-4.37 (m, 1H), 3.98-3.77 (m, 1H), 3.51 (s, 3H), 3.40-3.30 (m, 1H, obscured by water signal), 2.89-2.83 (m, 2H), 2.79 (dd, J=16.3, 10.5 Hz, 1H), 2.34-2.23 (m, 3H), 2.23-2.10 (m, 3H), 2.00-1.91 (m, 1H), 0.99-0.84 (m, 4H). LCMS [M+H]$^+$ 601, RT 2.94 minutes (Method 10)

Example 333

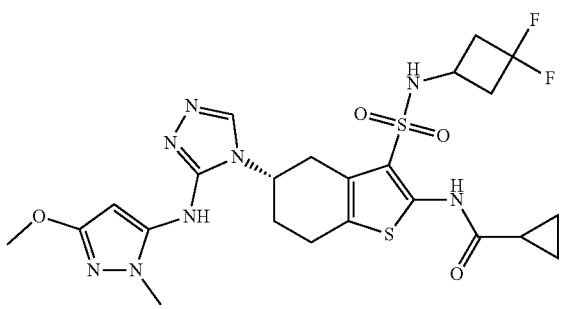 [SMILES: COc1cc(Nc2nncn2[C@H]2CCc3sc(NC(=O)C4CC4)c(S(=O)(=O)NC4CC(F)(F)C4)c3C2)n(C)n1]

N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]cyclopropanecarboxamide To a solution of intermediate 519 (92 mg, 0.16 mmol) in DMF (5 mL) was added formic hydrazide (29 mg, 0.48 mmol) followed by mercury dichloride (130 mg, 0.48 mmol) and triethylamine (0.07 mL, 0.48 mmol) and the resulting mixture was stirred at 90° C. for 3 hours. Celite was added to the stirring mixture and it was diluted with ethyl acetate (10 mL). The mixture was then filtered through a pad of celite, washing through with more ethyl acetate, and the solvent was evaporated in vacuo. The crude material was purified by reverse phase chromatography eluting with a gradient 10 to 100% of acetonitrile (0.1% formic acid) in water (0.1% formic acid) to afford the title compound (6.6 mg, 7% yield). $\delta_H$ (400 MHz, DMSO-d6) 11.84 (s, 1H), 10.43 (s, 1H), 8.70-7.97 (m, 2H), 5.77-5.26 (m, 1H), 4.62-4.34 (m, 1H), 3.70 (s, 3H), 3.67-3.57 (m, 1H), 3.54-3.37 (m, 4H), 2.91-2.82 (m, 2H), 2.81-2.67 (m, 3H), 2.49-2.39 (m, 2H, part. obs. by solvent), 2.29-2.20 (m, 1H), 2.19-2.10 (m, 1H), 2.00-1.91 (m, 1H), 0.98-0.84 (m, 4H)—Rotamers present. LCMS [M+H]$^+$ 583, RT 2.60 minutes (Method 10)

Example 334

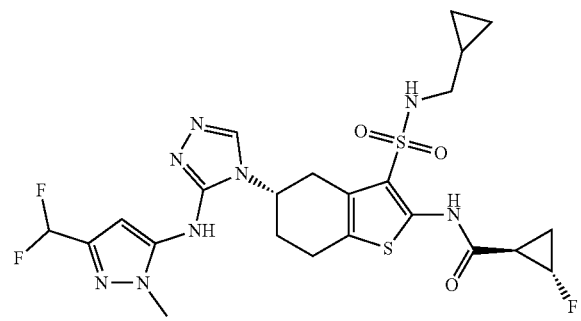 [SMILES: Cn1nc(C(F)F)cc1Nc1nncn1[C@H]1CCc2sc(NC(=O)[C@H]3C[C@@H]3F)c(S(=O)(=O)NCC3CC3)c2C1]

(1R,2S)—N-[(5S)-3-(cyclopropylmethylsulfamoyl)-
5-[3-[[5-(difluoromethyl)-2-methylpyrazol-3-yl]
amino]-1,2,4-triazol-4-yl]-4,5,6,7-tetrahydro-1-benzothiophen-2-yl]-2-fluorocyclopropane-1-carboxamide To a mixture of intermediate 522 (132 mg, 0.23 mmol) and triethylamine (0.1 mL, 0.69 mmol) in DCM (3 mL) at 0° C., methanesulfonyl chloride (19 μL, 0.25 mmol) was added. The mixture was stirred for 30 minutes, then further triethylamine (0.096 mL, 0.69 mmol) followed by methanesulfonyl chloride (19 μL, 0.25 mmol) were added and stirring was continued for 1 hour. The mixture was diluted with DCM (5 mL), washed with saturated aqueous NH₄Cl (5 mL), dried over magnesium sulfate, filtered and concentrated to afford the intermediate carbodiimide as a pale orange solid. A solution of formic hydrazide (41 mg, 0.69 mmol) in anhydrous methanol (1 mL) was added to a solution of the carbodiimide intermediate in methanol (2 mL) and the resulting mixture was stirred at room temperature for 1 hour. 1 M aqueous sodium carbonate (0.69 mL, 0.69 mmol) was added and the mixture was stirred at 40° C. overnight. The solvent was reduced in vacuo, the aqueous was taken up with ethyl acetate (20 mL) and the layers were separated. The aqueous was further extracted with ethyl acetate (20 mL), the combined organic layers were dried over magnesium sulfate, filtered and concentrated. The crude mixture was purified by HPLC (Method 4) to afford the title compound (45 mg, 33% yield). $\delta_H$ (500 MHz, Methanol-d4) 8.19 (s, 1H), 6.62 (t, J=55.2 Hz, 1H), 6.28 (s, 1H), 4.96-4.87 (m, 1H), 4.63-4.58 (m, 1H), 3.73 (s, 3H), 3.53 (dd, J=16.2, 5.3 Hz, 1H), 3.00 (dd, J=16.7, 9.7 Hz, 1H), 2.96-2.85 (m, 2H), 2.85-2.76 (m, 2H), 2.43-2.27 (m, 3H), 1.64-1.53 (m, 1H), 1.44-1.34 (m, 1H), 0.88-0.79 (m, 1H), 0.49-0.40 (m, 2H), 0.14-0.05 (m, 2H). LCMS [M+H]⁺ 585, RT 2.97 minutes (Method 10)

Example 335

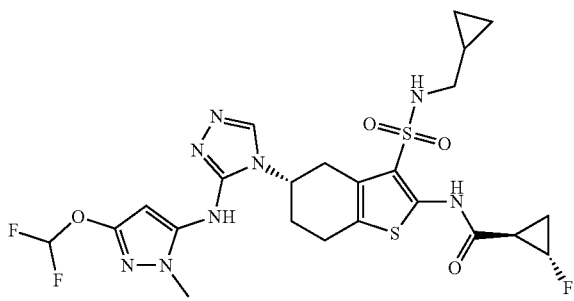 [SMILES: Cn1nc(OC(F)F)cc1Nc1nncn1[C@H]1CCc2sc(NC(=O)[C@H]3C[C@@H]3F)c(S(=O)(=O)NCC3CC3)c2C1]

(1R,2S)—N-[(5S)-3-(cyclopropylmethylsulfamoyl)-
5-[3-[[5-(difluoromethoxy)-2-methylpyrazol-3-yl]
amino]-1,2,4-triazol-4-yl]-4,5,6,7-tetrahydro-1-benzothiophen-2-yl]-2-fluorocyclopropane-1-carboxamide To a solution of intermediate 523 (137 mg, 0.23 mmol) and triethylamine (0.1 mL, 0.69 mmol) in DCM (3 mL) at 0° C., methanesulfonyl chloride (20 μL, 0.25 mmol) was added. The mixture was stirred for 30 minutes, then further triethylamine (0.097 mL, 0.69 mmol) followed by methanesulfonyl chloride (20 μL, 0.25 mmol) were added and stirring was continued for 1 hour. The mixture was diluted with DCM (5 mL), washed with saturated aqueous NH₄Cl (5 mL), dried over magnesium sulfate, filtered and concentrated to afford the intermediate carbodiimide as a pale orange solid. A solution of formic hydrazide (42 mg, 0.69 mmol) in anhydrous methanol (1 mL) was added to a solution of the carbodiimide intermediate in methanol (2 mL) and the resulting mixture was stirred at room temperature under nitrogen for 1 hour. 1 M aqueous sodium carbonate (0.69 mL, 0.69 mmol) was added and the mixture was stirred at 40° C. overnight. The solvent was reduced in vacuo, the aqueous was taken up with ethyl acetate (20 mL) and the layers were separated. The aqueous phase was further extracted with ethyl acetate (20 mL), the combined organic layers were then dried over magnesium sulfate, filtered and concentrated. The crude mixture was purified by HPLC (Method 4) to afford the title compound (33 mg, 22% yield). $\delta_H$ (500 MHz, Methanol-d4) 8.18 (s, 1H), 6.88 (t, J=73.9 Hz, 1H), 5.74 (s, 1H), 4.96-4.86 (m, 1H), 4.60-4.56 (m, 1H), 3.61 (s, 3H), 3.52 (dd, J=16.2, 5.2 Hz, 1H), 2.99 (dd, J=17.1, 9.6 Hz, 1H), 2.95-2.84 (m, 2H), 2.84-2.75 (m, 2H), 2.43-2.27 (m, 3H), 1.65-1.53 (m, 1H), 1.43-1.35 (m, 1H), 0.88-0.79 (m, 1H), 0.48-0.39 (m, 2H), 0.15-0.05 (m, 2H). LCMS [M+H]⁺ 601, RT 3.08 minutes (Method 10).

Example 336

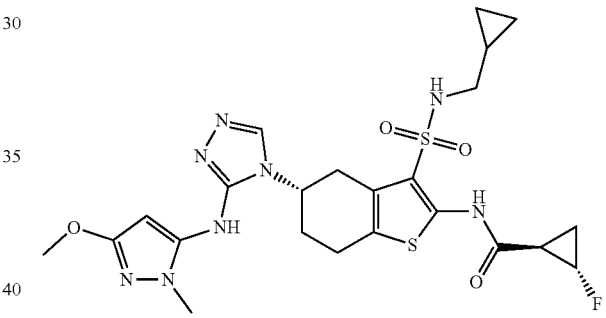

(1R,2S)—N-[(5S)-3-(cyclopropylmethylsulfamoyl)-
5-[3-[(5-methoxy-2-methylpyrazol-3-yl)amino]-1,2,4-triazol-4-yl]-4,5,6,7-tetrahydro-1-benzothiophen-2-yl]-2-fluorocyclopropane-1-carboxamide To a solution of intermediate 524 (100 mg, 0.17 mmol) and triethylamine (0.07 mL, 0.51 mmol) in DCM (3 mL) at 0° C., methanesulfonyl chloride (14 μL, 0.19 mmol) was added. The mixture was stirred for 30 minutes, then further triethylamine (0.071 mL, 0.51 mmol) and methanesulfonyl chloride (14 μL, 0.19 mmol) were added and stirring was continued for 1 hour. The mixture was diluted with DCM (5 mL), washed with saturated aqueous NH₄Cl (5 mL), dried over magnesium sulfate, filtered and concentrated to afford the intermediate carbodiimide as a pale orange oil. A solution of formic hydrazide (30 mg, 0.51 mmol) in anhydrous methanol (1 mL) was added to the carbodiimide intermediate, the resulting solution was further diluted with methanol (2 mL) and stirred at room temperature under nitrogen for 1 hour. 1 M aqueous sodium carbonate (0.51 mL, 0.51 mmol) was added and the mixture was stirred at 40° C. overnight. The solvent was reduced in vacuo, the aqueous was taken up with ethyl acetate (20 mL) and the layers were separated. The aqueous phase was further extracted with ethyl acetate (20 mL), the combined organic layers were then dried over magnesium sulfate, filtered and concentrated. The crude mixture was purified by HPLC (Method 4) to afford the title compound (17 mg, 17% yield). $\delta_H$ (400 MHz, Methanol-d4) 8.22 (br s, 1H), 4.96-4.90 (m, 1H, part. obs. by solvent), 4.55-4.49 (m, 1H), 3.81 (s, 3H), 3.56 (s, 3H), 3.51 (dd, J=16.5, 5.6 Hz, 1H), 2.99 (m, 1H), 2.95-2.84 (m, 2H), 2.80 (dd, J=7.0, 1.4 Hz, 2H), 2.45-2.26 (m, 3H), 1.68-1.51 (m, 1H), 1.45-1.32 (m, 1H), 0.90-0.76 (m, 1H), 0.50-0.36 (m, 2H), 0.10 (dt, J=4.9, 2.0 Hz, 2H), 3 exchangeable+1 aromatic protons missing. LCMS [M+H]$^+$ 565, RT 2.59 minutes (Method 10)

Example 337

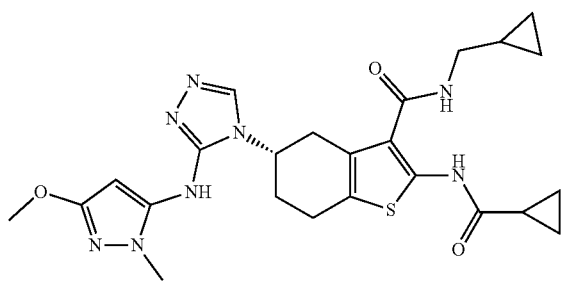 [SMILES: COc1cc(Nc2nncn2[C@H]2CCc3sc(NC(=O)C4CC4)c(C(=O)NCC4CC4)c3C2)n(C)n1]

(5S)-2-(cyclopropanecarbonylamino)-N-(cyclopropylmethyl)-5-[3-[(5-methoxy-2-methylpyrazol-3-yl)amino]-1,2,4-triazol-4-yl]-4,5,6,7-tetrahydro-1-benzothiophene-3-carboxamide To a mixture of intermediate 526 (90%, 631 mg, 1.13 mmol) and triethylamine (0.47 mL, 3.39 mmol) in DCM (14 mL) at 0° C., methanesulfonyl chloride (0.10 mL, 1.36 mmol) was added. The solution was stirred at 0° C. for 10 minutes. An additional portion of methanesulfonyl chloride (0.022 mL, 0.282 mmol) was added and the reaction was stirred for another 20 minutes. The reaction was diluted with DCM (10 mL) and washed with saturated NH$_4$Cl (20 mL). The organic layer was dried (MgSO$_4$) and the solvent removed to give the intermediate carbodiimide as a yellow oil. The oil was dissolved in a solution of formic hydrazide (204 mg, 3.39 mmol) in MeOH (5 mL) and then diluted with MeOH (15 mL). The reaction was stirred for 10 minutes. Another portion of formic hydrazide (100 mg, 1.70 mmol) in MeOH (2.5 mL) was added and the reaction was stirred for a further 10 minutes. 1 M sodium carbonate (3.4 mL, 3.39 mmol) was added to the solution and this was then heated at 40° C. for 21 hours. The solvent was removed and the residue partitioned between DCM (20 mL) and water (20 mL). The organic layer was separated, and the aqueous layer extracted with DCM (2×10 mL). The combined organic layers were dried (MgSO$_4$) and the solvent was removed. Purification of the residue by flash column chromatography eluting with 0 to 10% of methanol in DCM gradient gave the title compound (316 mg, 49% Yield). $\delta_H$ (500 MHz, DMSO-d6) 11.83 (s, 0.5H, rotamer), 11.24 (s, 0.5H, rotamer), 11.20 (s, 0.5H, rotamer), 8.54 (s, 0.5H, rotamer), 8.37 (s, 0.5H, rotamer), 8.14 (s, 0.5H, rotamer), 7.79-7.63 (m, 1H), 5.57 (s, 0.5H, rotamer), 5.39 (s, 0.5H, rotamer), 4.52-4.32 (m, 1H), 3.72 (s, 1.5H, rotamer), 3.69 (s, 1.5H, rotamer), 3.50 (s, 1.5H, rotamer), 3.44 (s, 1.5H, rotamer), 3.26-3.07 (m, 3H), 3.02-2.88 (m, 1H), 2.88-2.76 (m, 2H), 2.24-2.06 (m, 2H), 1.96-1.86 (m, 1H), 1.09-0.95 (m, 1H), 0.93-0.79 (m, 4H), 0.44-0.30 (m, 2H), 0.24-0.07 (m, 2H). LCMS [M+H]$^+$ 511, RT 2.27 minutes, Method 10.

Example 338

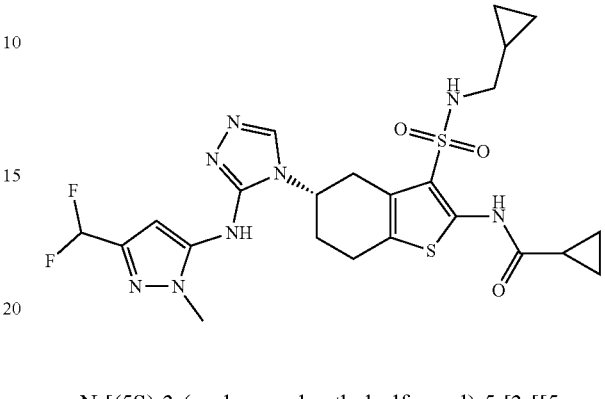

N-[(5S)-3-(cyclopropylmethylsulfamoyl)-5-[3-[[5-(difluoromethyl)-2-methylpyrazol-3-yl]amino]-1,2,4-triazol-4-yl]-4,5,6,7-tetrahydro-1-benzothiophen-2-yl]cyclopropanecarboxamide To a solution of intermediate 529 (1127 mg, 1.85 mmol) in DCM (25 mL) was added triethylamine (0.8 mL, 5.73 mmol). The solution was cooled to −20° C. then methanesulfonyl chloride (161.27 µl, 2069 µmol) was added, immediately after addition the reaction was kept at 0° C. for 10 minutes. The solution was cooled to −20° C. and another portion of methanesulfonyl chloride (49 µl, 628 µmol) was added and the solution stirred at 0° C. for 10 minutes. Saturated NH$_4$Cl solution (20 mL) was added to the reaction followed by DCM (10 mL). The DCM layer was separated, washed further with saturated NH$_4$Cl solution (10 mL), then was dried (MgSO4) and the solvent was removed to give the carbodiimide as a pale yellow foam. 1 M Formic hydrazide in MeOH (5.54 mL) was added to the carbodiimide followed by MeOH (4 mL). The reaction was stirred for 30 minutes. Another portion of 1 M formyl hydrazide (200 µL) was added and the mixture was stirred for 5 minutes. 10% Na$_2$CO$_3$ aqueous solution (5.8 mL, 5.54 mmol) was added to the solution which turned into a suspension followed by MeOH (5 mL). The reaction was then heated at 50° C. for 4.5 hours and then room temperature for 18 hours. The majority of the MeOH was removed and water (10 mL) was added. The mixture was extracted with 10% MeOH/DCM (2×30 mL). The solvent of the combined organic layers was removed to give a pale brown oil. Purification by flash column chromatography eluting with 0 to 10% of methanol in DCM gradient gave the racemate of the title compound (792 mg, 73% Yield). The racemate was separated using SFC conditions (Chiralpak IC 5 µm 250×30 mm, CO$_2$/EtOH+0.5% IPA 70/30, 70 g/min, 100° C., 100 bar) to give the title compound (454 mg, 40% Yield). $\delta_H$(500 MHz, DMSO-d6) 12.06 and 8.76 (2×s, 1H, rotamers), 10.47 (s, 1H), 8.46 and 8.23 (2×s, 1H, rotamers), 7.96 (s, 1H), 6.75 (t, J=54.4 Hz, 1H), 6.45 and 6.21 (2×s, 1H, rotamers), 4.60-4.38 (m, 1H), 3.76-3.55 (2×s, 3H, rotamers), 3.41-3.34 (m, 1H), 2.89-2.76 (m, 3H), 2.78-2.66 (m, 2H), 2.23 (d, J=41.2 Hz, 2H), 1.98-1.83 (m, 1H), 1.01-0.84 (m, 4H), 0.84-0.66 (m, 1H), 0.43-0.25 (m, 2H), 0.13-0.01 (m, 2H). LCMS [M+H]$^+$ 567, RT 2.93 minutes, Method 10.

Example 339

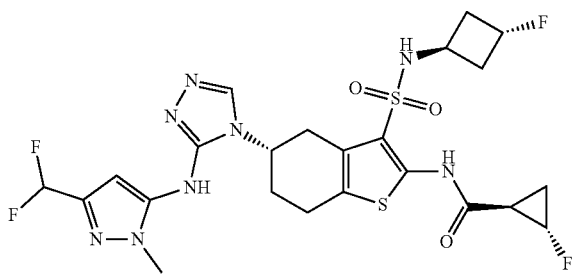 [SMILES: Cn1nc(C(F)F)cc1Nc1nncn1[C@H]1CCc2sc(NC(=O)[C@H]3C[C@@H]3F)c(S(=O)(=O)N[C@H]3C[C@H](F)C3)c2C1]

(1R,2S)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide To a solution of intermediate 533 (190 mg, 0.320 mmol) in DCM (8 mL) at 0° C. was added triethylamine (0.13 mL, 0.959 mmol) and methanesulfonyl chloride (0.030 mL, 0.383 mmol). The solution was stirred at 0° C. for 10 minutes. An additional portion of methanesulfonyl chloride (0.0030 mL, 0.0383 mmol) was added and the reaction was stirred for another 20 minutes. The reaction was diluted with DCM (10 mL) and washed with saturated aqueous $NH_4Cl$ (20 mL). The organic layer was dried ($MgSO_4$) and the solvent removed to give the intermediate carbodiimide as a yellow oil. The oil was dissolved in a solution of formic hydrazide (58 mg, 0.959 mmol) in MeOH (1 mL) and then diluted with MeOH (5 mL). The reaction was stirred for 15 minutes. 1 M sodium carbonate (0.96 mL, 0.959 mmol) was added to the solution and this was then heated at 40° C. for 18 hours. The solvent was removed and the residue partitioned between DCM (20 mL) and water (20 mL). The organic layer was separated and the aqueous layer was further extracted with DCM (2×10 mL). The combined organic layers were dried ($MgSO_4$) and the resulting residue purified by column chromatography (eluting with 0 to 5% of MeOH in DCM gradient) to give the title compound (100 mg, 50% Yield). $\delta_H$ (500 MHz, DMSO-d6) 12.08 and 8.76 (2×s, 1H, rotamers), 10.51 and 8.45 (2×s, 1H, rotamers), 8.25 (s, 1.5H), 6.98 and 6.75 (s and t, J=55.4 Hz, 1H, rotamers), 6.47 and 6.21 (2×s, 1H, rotamers), 5.17 and 4.89 (2×s, 1H, rotamers), 5.10-4.98 (m, 1H), 4.63-4.40 (m, 1H), 3.96-3.83 (m, 1H), 3.71 and 3.61 (2×s, 3H), 3.39-3.33 (m, 1H), 2.95-2.76 (m, 3H), 2.76-2.66 (m, 1H), 2.35-2.11 (m, 6H), 1.69-1.51 (m, 1H), 1.38-1.23 (m, 1H). LCMS [M+H]+ 603, RT 2.90 minutes (Method 10).

Example 340

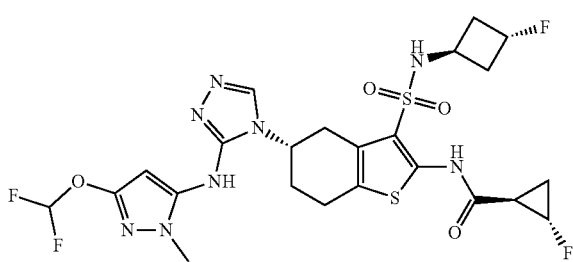 [SMILES: Cn1nc(OC(F)F)cc1Nc1nncn1[C@H]1CCc2sc(NC(=O)[C@H]3C[C@@H]3F)c(S(=O)(=O)N[C@H]3C[C@H](F)C3)c2C1]

(1R,2S)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide To a solution of intermediate 534 (213 mg, 0.349 mmol) in DCM (8 mL) at 0° C. was added triethylamine (0.15 mL, 1.05 mmol) and then methanesulfonyl chloride (0.032 mL, 0.419 mmol). The solution was stirred at 0° C. for 2 minutes. An additional portion of methanesulfonyl chloride (0.0040 mL, 0.0523 mmol) was added and the reaction was stirred for another 10 minutes. The reaction was diluted with DCM (15 mL) and washed with saturated aqueous $NH_4Cl$ solution (10 mL). The organic layer was dried ($MgSO_4$) and the solvent removed to give the intermediate carbodiimide as a yellow oil. The oil was dissolved in a solution of formic hydrazide (63 mg, 1.05 mmol) in MeOH (1.5 mL) and then this solution was diluted with MeOH (5 mL). The reaction was stirred for 20 minutes. 1 M sodium carbonate (1.0 mL, 1.05 mmol) was added to the solution and this was then heated at 40° C. for 6 hours. The reaction was left at room temperature for 18 hours. The solvent was removed and the residue partitioned between DCM (20 mL) and water (20 mL). The organic layer was separated and the aqueous layer was further extracted with 10% MeOH/DCM (2×10 mL). The solvent of the combined organic layers was removed to give an oil. Purification by flash column chromatography eluting with 0 to 5% of MeOH in DCM gradient gave the title compound (100 mg, 46% Yield): $\delta_H$ (500 MHz, Methanol-d4) 8.18 (br s, 1H), 6.89 (t, J=73.9 Hz, 1H), 5.74 (br s, 1H), 5.13 (tt, J=6.0, 3.0 Hz, 0.5H, rotamer), 5.02 (tt, J=6.1, 3.0 Hz, 0.5H, rotamer), 4.95 (ddd, J=6.1, 3.5, 1.6 Hz, 0.5H, rotamer), 4.83-4.76 (m, 0.5H, rotamer), 4.62-4.49 (m, 1H), 4.03-3.93 (m, 1H), 3.61 (s, 3H), 3.54-3.43 (m, 1H), 3.04-2.83 (m, 3H), 2.50-2.14 (m, 7H), 1.67-1.51 (m, 1H), 1.45-1.34 (m, 1H). LCMS [M+H]+ 619, RT 3.01 minutes, Method 10.

Example 341

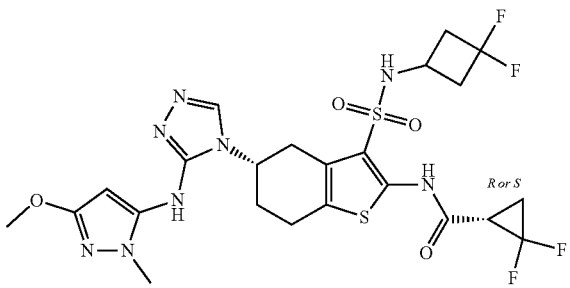 [SMILES: COc1cc(Nc2nncn2[C@H]2CCc3sc(NC(=O)[C@@H]4CC4(F)F)c(S(=O)(=O)NC4CC(F)(F)C4)c3C2)n(C)n1]

(1R*)—N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]-2,2-difluorocyclopropane-1-carboxamide (* or S)

To a solution of intermediate 542 (291 mg, 0.477 mmol) in DCM (6 mL) was added triethylamine (0.20 mL, 1.43 mmol). The solution was cooled to 0° C. then methanesulfonyl chloride (0.044 mL, 0.572 mmol) was added. The solution was stirred at 0° C. for 5 minutes. An additional portion of methanesulfonyl chloride (0.0055 mL, 0.0715 mmol) was added. The reaction was stirred for another 10 minutes at 0° C. The reaction was diluted with DCM (10 mL) and washed with saturated aqueous NH₄Cl solution (10 mL). The organic layer was dried (MgSO₄) and the solvent removed to give the intermediate carbodiimide as a yellow oil. The oil was dissolved in a solution of formic hydrazide (86 mg, 1.43 mmol) in MeOH (0.5 mL) and then this solution was diluted with MeOH (5 mL). The reaction was stirred for 35 minutes. 1 M aqueous sodium carbonate solution (1.4 mL, 1.43 mmol) was added to the solution and this was then heated at 40° C. for 18 hours. The solvent was removed, and the residue partitioned between 10% MeOH/DCM (15 mL) and water (20 mL). The organic layer was separated, and the aqueous layer was further extracted with 10% MeOH/DCM (2×10 mL). The solvent of the combined organic layers was removed to give an oil. Purification by flash column chromatography eluting with 0 to 5% of MeOH in DCM gradient gave the title compound as a mixture of isomers (70 mg, 21% yield). LCMS [M+H]⁺ 619, RT 2.68 minutes (Method 10). The mixture was separated by SFC to give the title compound (8 mg, 0.013 mmol, 20% Yield) δH (400 MHz, MeOH-d4) 8.27 (s, 1H), 5.55 (s, 1H), 4.61-4.45 (m, 1H), 3.81 (s, 3H), 3.68 (dt, J=9.1, 7.1 Hz, 1H), 3.57 (s, 3H), 3.50 (dd, J=16.3, 5.2 Hz, 1H), 3.01-2.88 (m, 4H), 2.76 (dtd, J=17.6, 12.9, 10.4, 6.6 Hz, 2H), 2.58-2.26 (m, 4H), 2.19-2.04 (m, 1H), 1.96 (tdd, J=12.0, 7.8, 5.1 Hz, 1H) LCMS [M+H]⁺ 619, RT 1.57 minutes (Method 26). Chiral SFC* RT 5.30 minutes.

* Using chiral SFC Method 1

Example 342

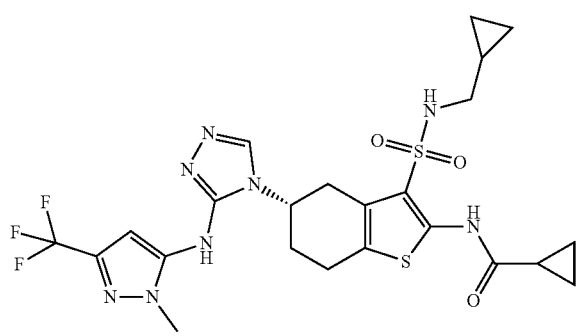 [SMILES: Cn1nc(C(F)(F)F)cc1Nc1nncn1[C@H]1CCc2sc(NC(=O)C3CC3)c(S(=O)(=O)NCC3CC3)c2C1]

N-[(5S)-3-(cyclopropylmethylsulfamoyl)-5-[3-[[2-methyl-5-(trifluoromethyl)pyrazol-3-yl]amino]-1,2,4-triazol-4-yl]-4,5,6,7-tetrahydro-1-benzothiophen-2-yl]cyclopropanecarboxamide To a solution of Intermediate 546 (1945 mg, 3.37 mmol) in DCM (20 mL) was added triethylamine (1.41 ml, 0.01 mol). The solution was cooled to −20° C. and methanesulfonyl chloride (294 μl, 3777 μmol) was added. After addition of the methanesulfonyl chloride the reaction was stirred at 0° C. for 10 minutes. Another portion of methanesulfonyl chloride (147 μl, 1888 μmol) was added at −20° C. and the solution was stirred for 10 minutes. Another portion of methanesulfonyl chloride (13 μl, 168 μmol) was added at −20° C. and the mixture was stirred for another 20 minutes. Saturated aqueous NH₄Cl solution (15 mL) was added to the reaction followed by DCM (5 mL). The DCM layer was separated, dried (MgSO₄) and the solvent was removed to give the intermediate carbodiimide as a pale yellow foam. 1 M formic hydrazide (10 mL) in MeOH was added to the carbodiimide intermediate followed by MeOH (5 mL). The reaction was stirred for 20 minutes. 10% Aq. Na₂CO₃ solution (10.7 ml, 10.12 mmol) was added followed by MeOH (5 mL). The reaction was heated at 50° C. for 4 hours and then stirred at room temperature for another 18 hours. The solvent was removed and then water (10 mL) and 10% MeOH/DCM (20 mL) were added. The organic layer was separated, and the aqueous layer extracted with 10% MeOH in DCM (2×10 mL). The combined organic layers were passed through a phase separator frit and the solvent was removed to give an oil. Purification by flash column chromatography eluting with 0 to 5% of MeOH in DCM gradient gave the racemic product as a white solid (1518 mg, 75% yield). The racemic product was separated using SFC conditions (Chiralpak IC 5 μm 250×30 mm, CO₂/(EtOH+0.5% IPA) 70/30, 70 g/min, 100° C., 100 bar) to give the title compound (537 mg). δH (500 MHz, DMSO-d6) 12.17 and 8.86 (s and br s, 1H, rotamers), 10.46 (s, 1H), 8.44 and 8.26 (br s and s, 1H, rotamers), 7.95 (s, 1H), 6.61 and 6.35 (br s and s, 1H, rotamers), 4.59-4.40 (m, 1H), 3.86-3.58 (m, 3H, rotamers), 3.45-3.33 (m, 1H), 2.94-2.77 (m, 5H), 2.74-2.67 (m, 3H), 2.32-2.12 (m, 3H), 1.99-1.85 (m, 2H), 0.97-0.84 (m, 6H), 0.84-0.65 (m, 2H), 0.42-0.26 (m, 3H), 0.11-−0.01 (m, 3H). LCMS [M+H]⁺ 585, RT 3.29 minutes (Method 10). Chiral SFC** RT=5.89 minutes.

** Chiral analysis was carried out using CHIRALPAK IC (25 cm column), eluting with a gradient of 70/30 CO₂/EtOH+0.5% isopropylamine, 1 mL/min, 200 bar.

Example 343

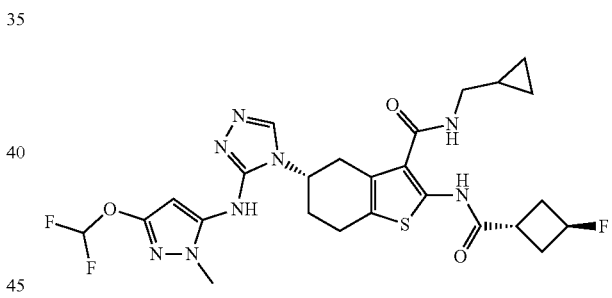

(5S)—N-(cyclopropylmethyl)-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide The title compound was obtained following general method 6 with intermediate 436 (48 mg, 0.09 mmol), trans-3-fluorocyclobutanecarboxylic acid (10.3 mg, 0.09 mmol), pyridine (35 μL, 0.44 mmol), T3P (104 μL, 0.17 mmol) and DCM (5 mL). Reaction duration: 16 hours. Reaction mixture was diluted with DCM (15 mL) then water (15 mL) was added and organic layer separated. The aqueous layer was extracted with DCM (2×10 mL) and the organic fractions combined, dried (Na₂SO₄) and concentrated under vacuum. Purification by revers phase HPLC eluting 5-95% Acetonitrile (0.1% formic acid) in Water (0.1% formic acid) gave the title compound (17 mg, 33.4% Yield). δH (500 MHz, MeOH-d4) 8.08 (br s, 1H), 6.65 (t, J=73.9 Hz, 1H), 5.56 (brts, 1H), 5.11-4.87 (m, 1H), 4.35-

4.24 (m, 1H), 3.37 (s, 3H), 3.07-2.98 (m, 3H), 2.97-2.89 (m, 1H), 2.88-2.60 (m, 3H), 2.48-2.22 (m, 4H), 2.19-2.00 (m, 2H), 0.87-0.73 (m, 1H), 0.38-0.19 (m, 2H), 0.11--0.06 (m, 2H). LCMS [M+H]⁺ 579, RT 2.91 minutes (Method 10).

Example 344

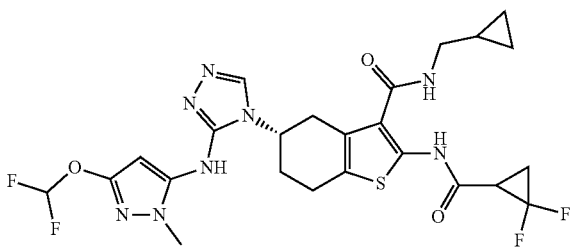 [SMILES: Cn1nc(OC(F)F)cc1Nc1nncn1[C@H]1CCc2sc(NC(=O)C3CC3(F)F)c(C(=O)NCC3CC3)c2C1]

(5S)—N-(cyclopropylmethyl)-2-[(2,2-difluorocyclopropanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 6 with intermediate 436 (95.0 mg, 0.17 mmol), 2,2-difluorocyclopropanecarboxylic acid (21.03 mg, 0.17 mmol), pyridine (69 μL, 0.86 mmol), T3P (205 μL, 0.34 mmol) and DCM (5 mL). Reaction duration: 16 hours. Reaction mixture was diluted with DCM (15 mL) then water (15 mL) was added and organic layer separated. The aqueous layer was extracted with DCM (2×10 mL) and the organic fractions combined, dried (Na₂SO₄) and concentrated under vacuum. Purification by revers phase HPLC eluting 5-95% Acetonitrile (0.1% formic acid) in Water (0.1% formic acid) gave the title compound (34 mg, 33% Yield). $\delta_H$ (500 MHz, MeOH-d4) 8.19 (br s, 1H), 6.88 (t, J=73.8 Hz, 1H), 5.73 (br s, 1H), 4.63-4.37 (m, 1H), 3.60 (s, 3H), 3.30-3.22 (m, 2H), 3.22-3.14 (m, 1H), 3.09-2.88 (m, 3H), 2.87-2.79 (m, 1H), 2.43-2.28 (m, 2H), 2.15-2.05 (m, 1H), 1.97-1.83 (m, 1H), 1.17-0.98 (m, 1H), 0.52-0.43 (m, 2H), 0.28-0.18 (m, 2H). LCMS [M+H]⁺ 583, RT 2.87 minutes (Method 10).

Example 345

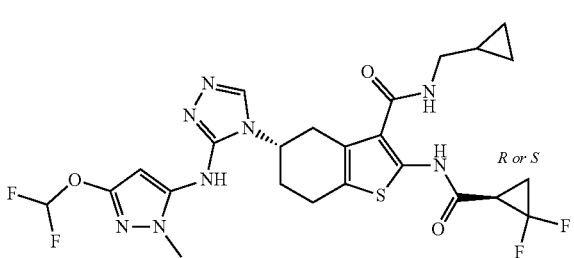 [SMILES: Cn1nc(OC(F)F)cc1Nc1nncn1[C@H]1CCc2sc(NC(=O)[C@H]3CC3(F)F)c(C(=O)NCC3CC3)c2C1]

(5S)—N-(cyclopropylmethyl)-2-[[(1R*)-2,2-difluorocyclopropanecarbonyl]amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide (* or S)

Example 344 (29.0 mg, 0.05 mmol) was separated by SFC (using 10% Methanol: 90% CO₂ with Chiralcel OJ-H 25 cm column at 15 mL/min) to give the title compound as a single isomer (6 mg, 21% Yield). $\delta_H$ (500 MHz, MeOH-d4) 8.23 (br s, 1H), 6.88 (t, J=73.9 Hz, 1H), 5.74 (br s, 1H), 4.60-4.39 (m, 1H), 3.60 (s, 3H), 3.35-3.31 (m, 1H), 3.30-3.23 (m, 1H), 3.18 (m, 1H), 3.11-2.86 (m, 3H), 2.85-2.73 (m, 1H), 2.40-2.28 (m, 2H), 2.14-2.03 (m, 1H), 1.97-1.83 (m, 1H), 1.13-1.01 (m, 1H), 0.52-0.44 (m, 2H), 0.27-0.21 (m, 2H). LCMS [M+H]⁺ 583, RT 2.88 minutes (Method 10). Chiral SFC** RT=29.57 minutes.

** Chiral analysis using Chiralcel OJ-H (4.6×250 mm 5 μm) column, flow rate 4 mL/min, eluting with 20% Methanol: 80% CO₂, 50 minutes run time.

Example 346

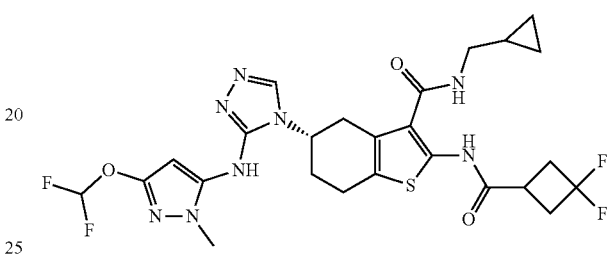

(5S)—N-(cyclopropylmethyl)-2-[(3,3-difluorocyclobutanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 6 with intermediate 436 (47 mg, 0.09 mmol), 3,3-difluorocyclobutanecarboxylic acid (11.6 mg, 0.09 mmol), pyridine (34 μL, 0.43 mmol), T3P (101 μL, 0.17 mmol), and DCM (5 mL). Reaction duration: 16 hours. Reaction mixture was diluted with DCM (20 mL) then water (15 mL) was added and organic layer separated. The aqueous layer was extracted with DCM (2×10 mL) and the organic fractions combined, dried (Na₂SO₄) and concentrated under vacuum. Purification by revers phase HPLC eluting 5-95% Acetonitrile (0.1% formic acid) in Water (0.1% formic acid) gave the title compound (18 mg, 35% Yield). $\delta_H$ (500 MHz, MeOH-d4) 8.33 and 7.90 (2×br s, 1H, rotamers), 7.20-6.58 (m, 1H), 5.82 and 5.57 (2×br s, 1H, rotamers), 4.57-4.45 (m, 1H), 3.61 (br s, 3H), 3.28-3.21 (m, 2H), 3.21-3.12 (m, 2H), 3.11-2.74 (m, 7H), 2.46-2.24 (m, 2H), 1.12-0.92 (m, 1H), 0.54-0.39 (m, 2H), 0.29-0.14 (m, 2H). LCMS [M+H]⁺ 597, RT 3.01 minutes (Method 10).

Example 347

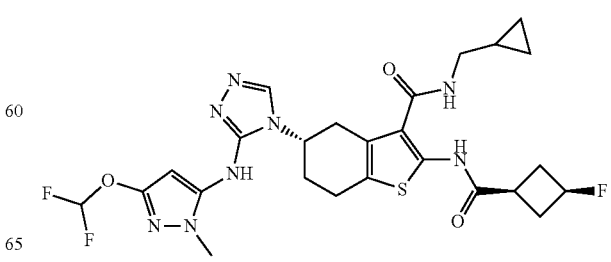

(5S)—N-(cyclopropylmethyl)-5-[3-[[5-(difluoromethoxy)-2-methylpyrazol-3-yl]amino]-1,2,4-triazol-4-yl]-2-[cis-(3-fluorocyclobutanecarbonyl)amino]-4,5,6,7-tetrahydro-1-benzothiophene-3-carboxamide The title compound was obtained following general method 6 with intermediate 436 (76.0 mg, 0.14 mmol), cis-3-fluorocyclobutanecarboxylic acid (16.28 mg, 0.14 mmol), pyridine (56 ⌐L, 0.69 mmol), T3P (164 ⌐L, 0.28 mmol), and DCM (5 mL). Reaction duration: 16 hours. Reaction mixture was diluted with DCM (15 ml) then water (15 ml) was added and organic layer separated. The aqueous layer was extracted with DCM (2×10 ml) and the organic fractions combined, dried (Na$_2$SO$_4$) and concentrated under vacuum. Purification by revers phase HPLC eluting 5-95% Acetonitrile (0.1% formic acid) in Water (0.1% formic acid) gave the title compound (42 mg, 53% Yield). $\delta_H$ (400 MHz, MeOH-d4) 8.18 (br s, 1H), 6.88 (t, J=73.8 Hz, 1H), 5.73 (br s, 1H), 5.10-4.86 (m, 1H), 4.61-4.44 (m, 1H), 3.60 (s, 3H), 3.36-3.32 (m, 1H), 3.28-3.21 (m, 1H), 3.20-3.12 (m, 1H), 3.12-2.86 (m, 3H), 2.85-2.73 (m, 1H), 2.69-2.56 (m, 2H), 2.53-2.26 (m, 4H), 1.13-0.97 (m, 1H), 0.54-0.41 (m, 2H), 0.30-0.16 (m, 2H). LCMS [M+H]$^+$ 579, RT 2.83 minutes (Method 10).

Example 348

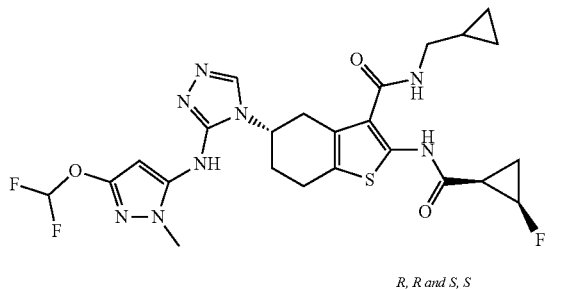

R, R and S, S

(5S)—N-(cyclopropylmethyl)-5-[3-[[5-(difluoromethoxy)-2-methylpyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide 1 M formic hydrazide (0.92 mL, 0.919 mmol) in MeOH was added to intermediate 548 (160 mg, 0.306 mmol). MeOH (3 mL) was added and the reaction mixture stirred for 30 mins. Then aqueous 0.92 M sodium carbonate (0.92 mL, 0.919 mmol) was added and reaction heated to 50° C. with stirring for 16 hours. Reaction allowed to cool to room temperature. MeOH was removed under reduced pressure and water (10 mL) added. The mixture was extracted with DCM (2×10 mL) and the combined organic layers dried (MgSO4) before concentration under reduced pressure. The residue was purified by reverse phase HPLC eluting with 5-95% Acetonitrile (0.1% formic acid) in Water (0.1% formic acid) to afford the title compound (70 mg, 40% Yield). $\delta_H$ (500 MHz, MeOH-d4) 8.34 and 7.91 (2×s, 1H, rotamers), 7.16-6.64 (m, 1H), 5.82 and 5.58 (2×s, 1H, rotamers), 5.01-4.76 (m, 1H), 4.62-4.39 (m, 1H), 3.60 (s, 3H), 3.29-3.22 (m, 2H), 3.18 (dd, J=13.9, 7.0 Hz, 1H), 3.12-2.81 (m, 3H), 2.49-2.21 (m, 2H), 2.12-1.99 (m, 1H), 1.86-1.65 (m, 1H), 1.36-1.19 (m, 1H), 1.15-0.88 (m, 1H), 0.57-0.38 (m, 2H), 0.32-0.13 (m, 2H). LCMS [M+H]$^+$ 565, RT 2.61 minutes (Method 10).

Example 349 & 350

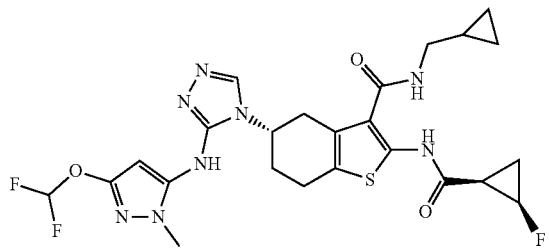

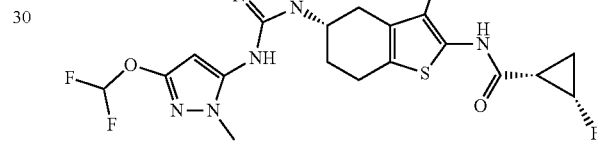

(5S)—N-(cyclopropylmethyl)-5-[3-[[5-(difluoromethoxy)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide

(5S)—N-(cyclopropylmethyl)-5-[3-[[5-(difluoromethoxy)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide Example 348 was separated by chiral SFC to give the title compounds:

Isomer 1 (4.5 mg, 7% Yield) $\delta_H$ (500 MHz, MeOH-d4) 8.19 (s, 1H), 6.88 (t, J=73.8 Hz, 1H), 5.74 (s, 1H), 4.99-4.89 (m, 1H), 4.57-4.51 (m, 1H), 3.60 (s, 3H), 3.35-3.32 (m, 1H), 3.29-3.24 (m, 1H), 3.19-3.13 (m, 1H), 3.10-3.02 (m, 1H), 3.01-2.86 (m, 2H), 2.38-2.30 (m, 2H), 2.10-1.98 (m, 1H), 1.82-1.68 (m, 1H), 1.31-1.23 (m, 1H), 1.13-1.01 (m, 1H), 0.52-0.42 (m, 2H), 0.29-0.21 (m, 2H). LCMS [M+H]$^+$ 565, RT 2.62 minutes (Method 10). Chiral SFC* RT=4.67 minutes.

Isomer 2 (21 mg, 36% Yield) $\delta_H$ (500 MHz, MeOH-d4) 8.17 (s, 1H), 6.88 (t, J=73.8 Hz, 1H), 5.74 (s, 1H), 4.98-4.90 (m, 1H), 4.61-4.47 (m, 1H), 3.60 (s, 3H), 3.35-3.31 (m, 1H), 3.28-3.21 (m, 1H), 3.22-3.14 (m, 1H), 3.06 (dd, J=15.5, 9.7 Hz, 1H), 3.00-2.84 (m, 2H), 2.40-2.27 (m, 2H), 2.13-1.97 (m, 1H), 1.80-1.66 (m, 1H), 1.31-1.23 (m, 1H), 1.12-1.01 (m, 1H), 0.51-0.43 (m, 2H), 0.27-0.20 (m, 2H). LCMS

[M+H]⁺ 565, RT 2.62 minutes (Method 10). Chiral SFC* RT=5.79 minutes.

* Chiral analysis using CHIRALPAK ID (4.6×250 mm 5 µm) column, flow rate 2.4 mL/min, eluting with CO₂/(MeOH+0.5% isopropylamine) 65/35%, 10 minutes run time on a SFC Berger.

Example 351

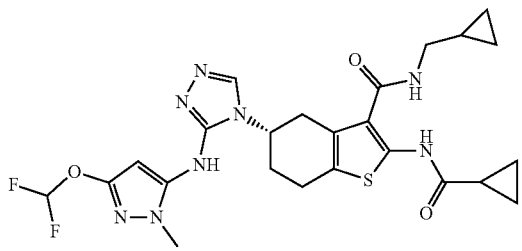

(5S)-2-(cyclopropanecarbonylamino)-N-(cyclopropylmethyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide 1 M formic hydrazide (0.23 mL, 0.23 mmol) in MeOH was added to intermediate 550 (38.0 mg, 0.08 mmol). MeOH (2 mL) was added and the reaction mixture stirred for 30 min. Then aqueous 0.92 M sodium carbonate (0.25 mL, 0.23 mmol) was added and reaction heated to 50° C. with stirring for 16 hours. Reaction allowed to cool to room temperature. The MeOH was removed under vacuum and water added (10 mL). The mixture was extracted with DCM (2×10 mL) and the combined organic layers dried (MgSO₄) before concentration under reduced pressure. The residue was purified by reverse phase HPLC eluting with 5-95% Acetonitrile (0.1% formic acid) in Water (0.1% formic acid) to give the title compound (16 mg, 38% Yield). $\delta_H$ (500 MHz, DMSO-d6) 12.03 (s, 1H, Major rotamer), 11.23 and 11.19 (2×s, 1H), 8.74 (s, 1H, minor rotamer), 8.40 and 8.19 (2×s, 1H), 7.81-7.54 (m, 1H), 7.45-6.87 (m, 1H), 5.90 and 5.65 (2×s, 1H), 4.62-4.27 (m, 1H), 3.57 and 3.48 (s, 3H), 3.24-3.02 (m, 3H), 3.03-2.89 (m, 1H), 2.89-2.78 (m, 2H), 2.28-2.12 (m, 2H), 1.98-1.87 (m, 1H), 1.07-0.95 (m, 1H), 0.90-0.80 (m, 4H), 0.40-0.31 (m, 2H), 0.23-0.15 (m, 2H). LCMS [M+H]⁺ 547, RT 2.78 minutes (Method 10).

Example 352

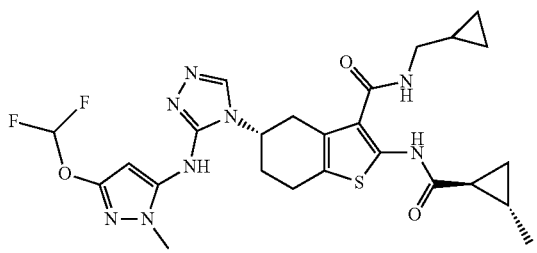

(5S)—N-(cyclopropylmethyl)-5-[3-[[5-(difluoromethoxy)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 6 with intermediate 436 (59.2 mg, 0.115 mmol), (1S,2S)-2-methylcyclopropanecarboxylic acid (12 µL), pyridine (50 µL, 0.61 mmol), T3P [50 mass % solution in EtOAc] (135 µL, 0.23 mmol), and DCM (3 mL). Reaction duration: 16 hours. Reaction mixture was diluted with brine (20 mL), water (20 mL), DCM (20 mL) and a few drops of methanol. The aqueous layer was extracted with DCM (2×35 mL) with a few drops of methanol. The organic fractions combined, dried and concentrated under vacuum. Purification by column chromatography eluting with 0-10% MeOH in DCM followed by reverse phase column chromatography eluting with 0-80% MeCN in H₂O (pH10, NH₃) gave the title compound (26 mg, 41% Yield) as a mixture of rotamers (7:3). $\delta_H$ (400 MHz, DMSO-d6) 12.04 (s, 0.7H), 11.31-11.14 (m, 1H), 8.75 (s, 0.3H), 8.47-8.15 (m, 1H), 7.82-7.65 (m, 1H), 7.46-6.88 (m, 1H), 6.05-5.53 (m, 1H), 4.61-4.24 (m, 1H), 3.62-3.43 (m, 3H), 3.23-3.04 (m, 3H), 3.05-2.90 (m, 1H), 2.83 (s, 2H), 2.31-2.12 (m, 21H), 1.68 (dt, J=8.3, 4.2 Hz, 1H), 1.30-1.19 (m, 1H), 1.09 (d, J=6.0 Hz, 3H), 1.07-0.95 (m, 21H), 0.73-0.66 (m, 1H), 0.36 (dt, J=9.4, 3.1 Hz, 2H), 0.24-0.13 (m, 2H). LCMS [M+H]⁺ 561, RT 1.76 minutes (Method 26)

Example 353

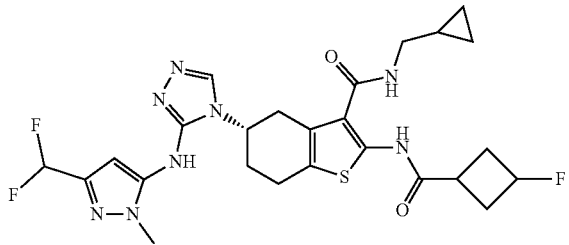

(5S)—N-(cyclopropylmethyl)-5-[3-[[5-(difluoromethyl)-2-methylpyrazol-3-yl]amino]-1,2,4-triazol-4-yl]-2-[(3-fluorocyclobutanecarbonyl)amino]-4,5,6,7-tetrahydro-1-benzothiophene-3-carboxamide The title compound was obtained following general method 6 with intermediate 425 (93 mg, 0.17 mmol), 3-fluorocyclobutanecarboxylic acid (15 µL, 0.17 mmol), pyridine (70 µL, 0.87 mmol), T3P (207 µL, 0.35 mmol), and DCM (10 mL). Reaction duration: 16 hours. Reaction mixture was diluted with DCM (30 mL) then water (15 mL) was added and organic layer separated. The aqueous layer was extracted with DCM (2×10 mL) and the organic fractions combined, dried (Na₂SO₄) and concentrated under vacuum. Purification by column chromatography eluting 0-100% EtOAc in heptane followed by revers phase HPLC eluting with 5-95% Acetonitrile (0.1% formic acid) in Water (0.1% formic acid) gave the title compound (51 mg, 51% Yield). $\delta_H$ (500 MHz, MeOH-d4) 8.31 (s, 1H), 6.61 (t, J=55.1 Hz, 1H), 6.33 (s, 1H), 5.34-5.12 (m, 1H), 4.64-4.43 (m, 1H), 3.72 (s, 3H), 3.36-3.32 (m, 2H), 3.25 (dd, J=13.8, 7.1 Hz, 1H), 3.16 (dd, J=13.8, 7.0 Hz, 1H), 3.11-2.84 (m, 3H), 2.67-2.46 (m, 4H), 2.41-2.29 (m, 2H), 1.14-0.97 (m, 1H), 0.53-0.41 (m, 2H), 0.29-0.20 (m, 2H). LCMS [M+H]⁺ 563, RT 2.81 minutes (Method 10).

Example 354

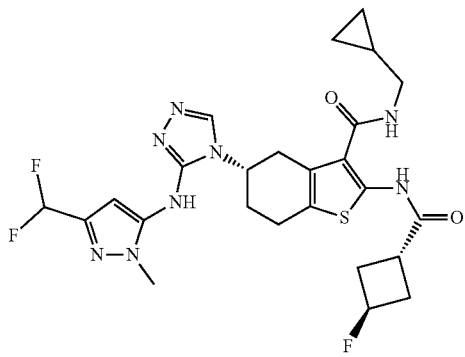

(5S)—N-(cyclopropylmethyl)-5-[3-[[5-(difluoromethyl)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide Example 353 (45 mg, 0.08 mmol) was separated by chiral SFC to give the title compound (26 mg, 57% Yield). δ$_H$ (500 MHz, MeOH-d4) 8.18 (s, 1H), 6.61 (t, J=55.2 Hz, 1H), 6.27 (s, 1H), 5.35-5.13 (m, 1H), 4.64-4.50 (m, 1H), 3.72 (s, 3H), 3.36-3.31 (m, 2H), 3.25 (dd, J=13.8, 7.1 Hz, 1H), 3.16 (dd, J=13.8, 7.0 Hz, 1H), 3.12-3.02 (m, 1H), 3.03-2.85 (m, 2H), 2.70-2.46 (m, 4H), 2.41-2.29 (m, 2H), 1.11-0.99 (m, 1H), 0.51-0.41 (m, 2H), 0.27-0.19 (m, 2H). LCMS [M+H]⁺ 563, RT 2.82 minutes (Method 10). Chiral SFC* RT=10.25 minutes.

* Chiral analysis using Chiralpak IC (4.6×250 mm 5 μm) column, flow rate 4 mL/min, eluting with 40% Ethanol: 60% CO₂, 15 minutes run time.

Example 355

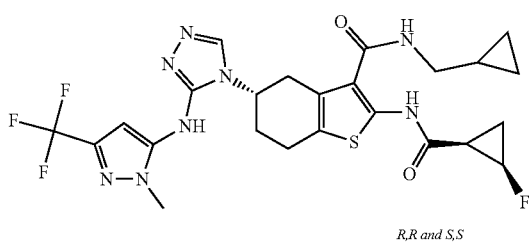 [SMILES: Cn1nc(C(F)(F)F)cc1Nc1nncn1[C@H]1CCc2sc(NC(=O)[C@H]3C[C@H]3F)c(C(=O)NCC3CC3)c2C1]

R,R and S,S (5S)—N-(cyclopropylmethyl)-2-[[(1RS,2RS)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide 1 M formic hydrazide (0.86 mL, 0.858 mmol) in MeOH was added to intermediate 552 (150 mg, 0.286 mmol). MeOH (3 mL) was added and the reaction stirred for 30 mins. Then aqueous 0.92 M sodium carbonate (0.86 mL, 0.858 mmol) was added and reaction heated to 50° C. with stirring for 16 hours. Reaction was allowed to cool to room temperature, MeOH was removed under vacuum and water added (10 mL). The mixture was extracted with DCM (2×10 mL) and the combined organic layers dried (MgSO₄) and concentration under reduced pressure. The residue was purified reverse phase HPLC eluting with 5-95% Acetonitrile (0.1% formic acid) in Water (0.1% formic acid) to afford the title compound (73 mg, 44% Yield). δ$_H$ (500 MHz, MeOH-d4) 8.34 and 7.95 (2×br s, 1H, isomers), 6.48 and 6.23 (2×br s, 1H, isomers), 5.01-4.88 and 4.81-4.72 (2×m, 1H, isomers), 4.67-4.47 (m, 1H), 3.76 (br s, 3H), 3.40-3.33 (m, 1H), 3.28-3.13 (m, 2H), 3.11-2.80 (m, 3H), 2.51-2.23 (m, 2H), 2.14-1.95 (m, 1H), 1.83-1.65 (m, 1H), 1.34-1.21 (m, 1H), 1.15-0.96 (m, 1H), 0.56-0.39 (m, 2H), 0.31-0.20 (m, 2H). LCMS [M+H]⁺ 567, RT 2.87 minutes (Method 10).

Example 356

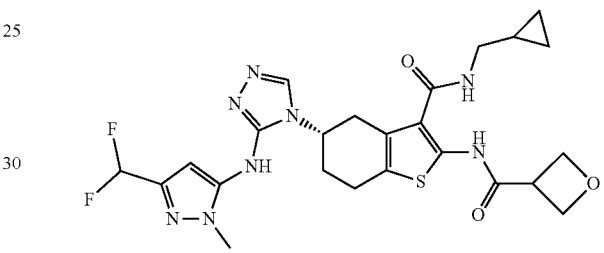

N-[(5S)-3-(cyclopropylmethylcarbamoyl)-5-[3-[[5-(difluoromethyl)-2-methylpyrazol-3-yl]amino]-1,2,4-triazol-4-yl]-4,5,6,7-tetrahydro-1-benzothiophen-2-yl]oxetane-3-carboxamide The title compound was obtained following general method 6 with intermediate 425 (45 mg, 0.08 mmol), oxetane-3-carboxylic acid (6 μL, 0.08 mmol), pyridine (34 μL, 0.42 mmol), T3P (100 μL, 0.17 mmol), and DCM (5 mL). Reaction duration: 16 hours. Reaction mixture was diluted with DCM (20 mL) then water (15 mL) was added and organic layer separated. The aqueous layer was extracted with DCM (2×10 mL) and the organic fractions combined, dried (Na₂SO₄) and concentrated under vacuum. Purification by revers phase HPLC eluting with 5-95% Acetonitrile (0.1% formic acid) in Water (0.1% formic acid) followed by revers phase HPLC eluting with 5-95% Acetonitrile (0.2% ammonium hydroxide) in Water (0.2% ammonium hydroxide) gave the title compound (3 mg, 6% Yield). δ$_H$ (500 MHz, MeOH-d4) 8.38 (br s, 1H), 6.61 (t, J=55.2 Hz, 1H), 6.28 (br s, 1H), 4.91-4.84 (m, 4H), 4.61-4.49 (m, 1H), 4.11-4.00 (m, 1H), 3.72 (s, 31H), 3.37-3.32 (m, 1H), 3.28-3.21 (m, 1H), 3.19-3.12 (m, 1H), 3.11-2.87 (m, 31H), 2.41-2.30 (m, 2H), 1.10-0.99 (m, 1H), 0.51-0.43 (m, 2H), 0.28-0.19 (m, 2H). LCMS [M+H]⁺ 547, RT 2.18 minutes (Method 10).

Example 357

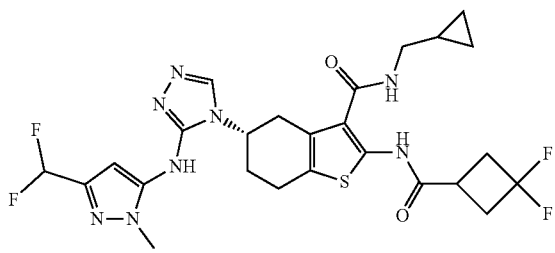

(5S)—N-(cyclopropylmethyl)-2-[(3,3-difluorocyclobutanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 6 with intermediate 425 (46 mg, 0.09 mmol), 3,3-difluorocyclobutanecarboxylic acid (15 μL, 0.09 mmol), pyridine (35 μL, 0.43 mmol), T3P (102 μL, 0.17 mmol), and DCM (5 mL). Reaction duration: 16 hours. Reaction mixture was diluted with DCM (20 mL) then water (15 mL) was added and organic layer separated. The aqueous layer was extracted with DCM (2×10 mL) and the organic fractions combined, dried ($Na_2SO_4$) and concentrated under vacuum. Purification by revers phase HPLC eluting with 5-95% Acetonitrile (0.1% formic acid) in Water (0.1% formic acid) gave the title compound (32 mg, 64% Yield). $\delta_H$ (500 MHz, DMSO-d6) 12.06 (s, 1H, major rotamer), 11.04 (s, 1H), 8.74 (s, 1H, minor rotamer), 8.39 and 8.19 (2×s, 1H), 7.89-7.67 (m, 1H), 7.03-6.49 (m, 1H), 6.40 and 6.20 (2×s, 1H), 4.63-4.30 (m, 1H), 3.70 and 3.60 (2×s, 3H), 3.29-3.24 (m, 1H), 3.21-3.02 (m, 3H), 3.02-2.71 (m, 7H), 2.31-2.11 (m, 2H), 1.04-0.92 (m, 1H), 0.41-0.30 (m, 2H), 0.24-0.11 (m, 2H). LCMS [M+H]$^+$ 581, RT 2.93 minutes (Method 10).

Example 358

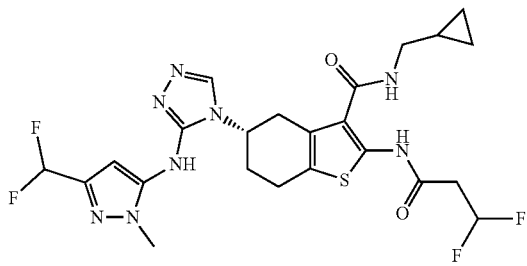

(5S)—N-(cyclopropylmethyl)-5-[3-[[5-(difluoromethyl)-2-methylpyrazol-3-yl]amino]-1,2,4-triazol-4-yl]-2-(3,3-difluoropropanoylamino)-4,5,6,7-tetrahydro-1-benzothiophene-3-carboxamide The title compound was obtained following general method 6 with intermediate 425 (45.0 mg, 0.08 mmol), 3,3-difluoropropanoic acid (15 μL, 0.08 mmol), pyridine (34 μL, 0.42 mmol), T3P (100 μL, 0.17 mmol), and DCM (5 mL). Reaction duration: 16 hours. Reaction mixture was diluted with DCM (30 mL) then water (15 mL) was added and organic layer separated. The aqueous layer was extracted with DCM (2×10 mL) and the organic fractions combined, dried ($Na_2SO_4$) and concentrated under vacuum. Purification by revers phase HPLC eluting with 5-95% Acetonitrile (0.1% formic acid) in Water (0.1% formic acid) gave the title compound (20 mg, 42% Yield). $\delta_H$ (500 MHz, DMSO-d6) 12.06 (s, 1H, major rotamer), 11.11 and 11.08 (2×s, 1H), 8.74 (s, 1H, minor rotamer), 8.39 and 8.19 (2×s, 1H), 7.90-7.66 (m, 1H), 7.05-6.58 (m, 1H), 6.40 (s, 1H, minor rotamer), 6.36 (tt, J=55.7, 4.6 Hz, 1H), 6.19 (s, 1H, major rotamer), 4.60-4.33 (m, 1H), 3.70 and 3.60 (2×s, 3H), 3.26-3.03 (m, 5H), 3.02-2.79 (m, 3H), 2.30-2.15 (m, 2H), 1.12-0.90 (m, 1H), 0.40-0.28 (m, 2H), 0.22-0.10 (m, 2H). LCMS [M+H]$^+$ 555, RT 2.61 minutes (Method 10).

Example 359

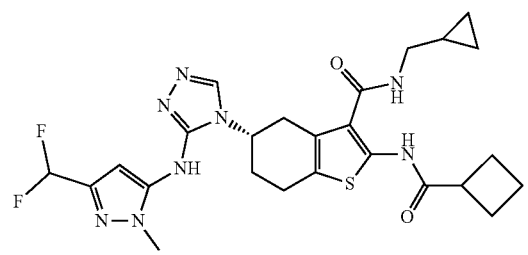

(5S)-2-(cyclobutanecarbonylamino)-N-(cyclopropylmethyl)-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 6 with intermediate 425 (70 mg, 0.13 mmol), cyclobutanecarboxylic acid (15 μL, 0.13 mmol), pyridine (53 μL, 0.65 mmol), T3P (156 μL, 0.26 mmol), and DCM (5 mL). Reaction duration: 16 hours. Reaction mixture was diluted with DCM (30 mL) then water (15 mL) was added and organic layer separated. The aqueous layer was extracted with DCM (2×10 mL) and the organic fractions combined, dried ($Na_2SO_4$) and concentrated under vacuum. Purification by revers phase HPLC eluting with 5-95% Acetonitrile (0.1% formic acid) in Water (0.1% formic acid) gave the title compound (36 mg, 49% Yield). $\delta_H$ (500 MHz, DMSO-d6) 12.07 (s, 1H, major rotamer), 11.09 and 11.05 (2×s, 1H), 8.73 (s, 1H, minor rotamer), 8.39 and 8.19 (2×s, 1H), 7.69-7.48 (m, 1H), 7.02-6.56 (m, 1H), 6.40 and 6.19 (2×s, 1H), 4.53-4.36 (m, 1H), 3.70 and 3.60 (2×s, 3H), 3.25-3.11 (m, 2H), 3.10-2.94 (m, 2H), 2.92-2.79 (m, 2H), 2.29-2.09 (m, 6H), 2.00-1.90 (m, 1H), 1.86-1.75 (m, 1H), 1.12-0.89 (m, 1H), 0.41-0.29 (m, 2H), 0.25-0.11 (m, 2H). 1H missing under the water. LCMS [M+H]$^+$ 545, RT 2.94 minutes (Method 10).

Example 360

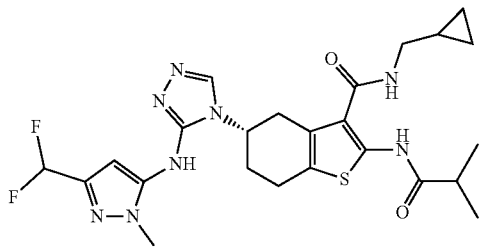

(5S)—N-(cyclopropylmethyl)-5-[3-[[5-(difluoromethyl)-2-methylpyrazol-3-yl]amino]-1,2,4-triazol-4-yl]-2-(2-methylpropanoylamino)-4,5,6,7-tetrahydro-1-benzothiophene-3-carboxamide The title compound was obtained following general method 6 with intermediate 425 (70 mg, 0.13 mmol), 2-methylpropanoic acid (98%, 15 μL, 0.13 mmol), pyridine (53 μL, 0.65 mmol), T3P (156 μL, 0.26 mmol), and DCM (5 mL). Reaction duration: 16 hours. Reaction mixture was diluted with DCM (30 mL) then water (15 mL) was added and organic layer separated. The aqueous layer was extracted with DCM (2×10 mL) and the organic fractions combined, dried (Na$_2$SO$_4$) and concentrated under vacuum. Purification by revers phase HPLC eluting with 5-95% Acetonitrile (0.1% formic acid) in Water (0.1% formic acid) gave the title compound (35 mg, 48% Yield). δ$_H$ (500 MHz, DMSO-d6) 12.07 (s, 1H, major rotamer), 11.25 and 11.20 (2×s, 1H), 8.74 (s, 1H, minor rotamer), 8.39 and 8.19 (2×s, 1H), 7.65-7.52 (m, 1H), 6.99-6.48 (m, 1H), 6.40 and 6.20 (2×s, 1H), 4.52-4.37 (m, 1H), 3.70 and 3.60 (2×s, 3H), 3.25-3.12 (m, 2H), 3.11-2.95 (m, 2H), 2.92-2.79 (m, 2H), 2.72-2.64 (m, 1H), 2.28-2.15 (m, 2H), 1.16-1.11 (m, 6H), 1.05-0.95 (m, 1H), 0.39-0.31 (m, 2H), 0.21-0.15 (m, 2H). LCMS [M+H]$^+$ 533, RT 2.83 minutes (Method 10).

Example 361

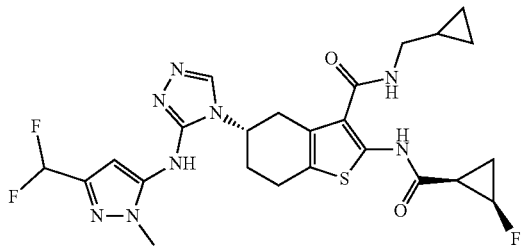

R,R and S,S (5S)—N-(cyclopropylmethyl)-5-[3-[[5-(difluoromethyl)-2-methylpyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide The title compound was obtained following general method 6 with intermediate 425 (160 mg, 0.3 mmol), cis-2-fluorocyclopropanecarboxylic acid (15 μL, 0.3 mmol), pyridine (120 μL, 1.49 mmol), T3P (356 μL, 0.6 mmol), and DCM (30 mL). Reaction duration: 16 hours. Reaction mixture was diluted with DCM (30 mL) then water (15 mL) was added and organic layer separated. The aqueous layer was extracted with DCM (2×10 mL) and the organic fractions combined, dried (Na$_2$SO$_4$) and concentrated under vacuum. Purification by column chromatography eluting with 0-100% EtOAc in heptane gave the title compound as a mixture of 2 cis diastereoisomers (105 mg, 61% Yield). δ$_H$ (500 MHz, Methanol-d4) 8.35 and 7.92 (2×s, 1H, isomers), 6.62 (t, J=55.6 Hz, 1H), 6.38 and 6.15 (2×s, 1H, isomers), 4.95 and 4.81 (2×m, 1H, isomers), 4.64-4.43 (m, 1H), 3.73 (s, 3H), 3.38-3.33 (m, 1H), 3.29-3.23 (m, 1H), 3.22-3.12 (m, 1H), 3.13-2.84 (m, 3H), 2.43-2.29 (m, 2H), 2.08-2.02 (m, 1H), 1.82-1.68 (m, 1H), 1.32-1.25 (m, 1H), 1.12-1.02 (m, 1H), 0.53-0.43 (m, 2H), 0.29-0.20 (m, 2H). LCMS [M+H]$^+$ 549, RT 2.51 minutes (Method 10).

Example 362 & 363

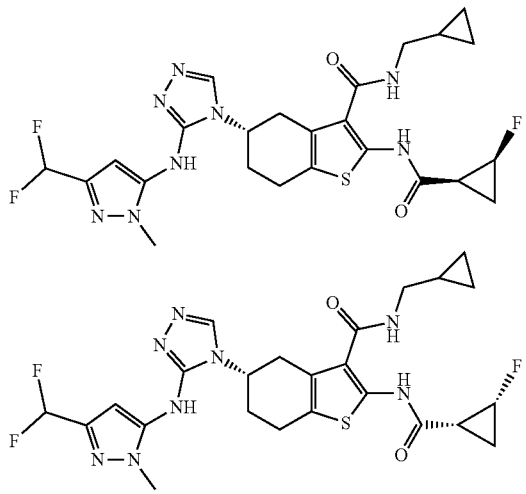

(5S)—N-(cyclopropylmethyl)-5-[3-[[5-(difluoromethyl)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide (362)

(5S)—N-(cyclopropylmethyl)-5-[3-[[5-(difluoromethyl)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide (363)

The title compound was prepared by chiral SFC purification of Example 361 (85 mg) using a Chiralcel OJ-H 250×21.2 mm 5 μm column, eluted with a gradient of 3 to 40% MeOH (+0.1% NH$_4$OH) in CO$_2$ with a flow rate of 100 mL/min on a Waters Prep 100-SQD2, to give the title compounds:

Peak 1 (38 mg, 45% Yield): δ$_H$ (400 MHz, DMSO-d6) 12.08 (s, 0.6H), 11.31 (s, 1H), 8.76 (s, 0.4H), 8.41 (s, 0.4H), 8.21 (s, 0.6H), 7.75 (s, 1H), 6.87 (t, J=55.5 Hz, 0.4H), 6.76 (t, J=55.5 Hz, 0.6H), 6.41 (s, 0.4H), 6.21 (s, 0.6H), 5.10-4.76 (m, 2H), 4.47 (m, 1H), 3.71 (s, 1.2H), 3.61 (s, 2.8H), 3.25-2.92 (m, 4H), 2.90-2.79 (m, 2H), 2.30-2.13 (m, 3H), 1.71-1.55 (m, 1H), 1.30-1.13 (m, 1H), 1.06-0.94 (m, 1H), 0.42-0.29 (m, 2H), 0.23-0.11 (m, 2H). LCMS [M+H]⁺ 549, RT 1.70 minutes (Method 26). Chiral SFC* RT 5.31 minutes.

Peak 2 (12 mg, 14% Yield). $\delta_H$ (400 MHz, DMSO-d6) 12.06 (s, 0.6H), 11.28 (s, 1H), 8.76 (s, 0.4H), 8.41 (s, 0.4H), 8.20 (s, 0.6H), 7.80-7.65 (m, 1H), 6.87 (d, J=55.5 Hz, 0.4H), 6.75 (t, J=55.5 Hz, 0.6H), 6.42 (s, 0.4H), 6.21 (s, 0.6H), 5.09-4.79 (m, 1H), 4.45 (m, 1H), 3.71 (s, 1.2H), 3.61 (s, 1.8H), 3.21-2.78 (m, 6H), 2.21 (m, 3H), 1.70-1.52 (m, 1H), 1.20 (s, 1H), 1.04-0.87 (m, 1H), 0.42-0.30 (m, 2H), 0.22-0.16 (m, 2H). LCMS [M+H]⁺ 549, RT 1.69 minutes (Method 26). Chiral SFC* RT 5.15 minutes.

\* Chiral analysis was carried out using a Chiral Art Cellulose SJ (4.6×150 mm 5 μm) column, flow rate 3 mL/min eluting with a gradient of 3 to 40% MeOH (+0.1% NH₄OH), using a 6.5 minutes run time on a Waters UPC2-QDa.

Example 364

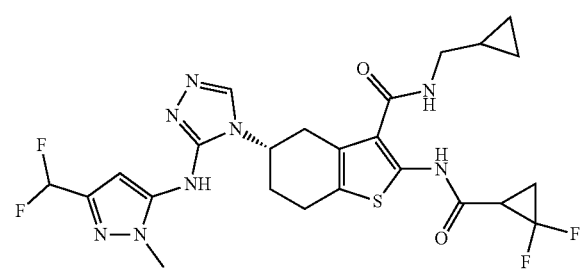 [SMILES: Cn1nc(C(F)F)cc1Nc1nncn1[C@H]1CCc2sc(NC(=O)C3CC3(F)F)c(C(=O)NCC3CC3)c2C1]

(5S)—N-(cyclopropylmethyl)-2-[(2,2-difluorocyclopropanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 6 with intermediate 425 (80 mg, 0.15 mmol), 2,2-difluorocyclopropanecarboxylic acid (15 ⍰L, 0.15 mmol), pyridine (60 ⍰L, 0.75 mmol), T3P (178 ⍰L, 0.3 mmol), and DCM (10 mL). Reaction duration: 16 hours. Reaction mixture was diluted with DCM (20 mL) then water (10 mL) was added and organic layer separated. The aqueous layer was extracted with DCM (2×10 mL) and the organic fractions combined, dried (Na₂SO₄) and concentrated under vacuum. Purification by revers phase HPLC eluting with 5-95% Acetonitrile (0.1% formic acid) in Water (0.1% formic acid) gave the title compound (55 mg, 65% Yield). $\delta_H$ (500 MHz, Methanol-d4) 8.34 and 7.91 (2×s, 1H, rotamers), 6.61 (t, J=55.2 Hz, 1H), 6.33 and 6.11 (2×s, 1H, rotamers), 4.65-4.46 (m, 1H), 3.73 (s, 3H), 3.35-3.32 (m, 1H), 3.28-3.22 (m, 1H), 3.22-3.14 (m, 1H), 3.11-2.88 (m, 3H), 2.88-2.76 (m, 1H), 2.44-2.29 (m, 21H), 2.16-2.05 (m, 1H), 1.97-1.85 (m, 1H), 1.12-1.02 (m, 1H), 0.52-0.43 (m, 2H), 0.29-0.19 (m, 21H). LCMS [M+H]⁺ 567, RT 2.77 minutes (Method 10).

Example 365

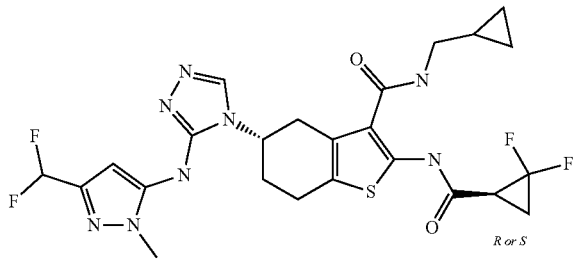 [SMILES: Cn1nc(C(F)F)cc1Nc1nncn1[C@H]1CCc2sc(NC(=O)[C@@H]3CC3(F)F)c(C(=O)NCC3CC3)c2C1]

(5S)—N-(cyclopropylmethyl)-2-[[(1R*)-2,2-difluorocyclopropanecarbonyl]amino]-5-[3-[[5-(difluoromethyl)-2-methylpyrazol-3-yl]amino]-1,2,4-triazol-4-yl]-4,5,6,7-tetrahydro-1-benzothiophene-3-carboxamide (* or S)

The title compound was obtained by chiral SFC purification of Example 364 (38 mg) using a gradient of 10 to 25% MeOH (+0.1% NH₄OH) in CO₂ using a Lux Cellulose-3 250×21.2 mm 5 μm column, with a flow rate of 100 mL/min on a Waters Prep 100-SQD2, to give the title compound (the first peak eluted) as a white solid (12 mg 32% Yield). $\delta_H$ (400 MHz, DMSO-d6) 12.08 (s, 0.6H), 11.31-11.21 (m, 1H), 8.76 (s, 0.4H), 8.41 (s, 0.4H), 8.20 (s, 0.6H), 7.96-7.82 (m, 1H), 6.87 (t, J=55.1 Hz, 0.4H), 6.75 (t, J=55.1 Hz, 0.6H), 6.41 (s, 0.4H), 6.20 (s, 0.6H), 4.54-4.41 (m, 1H), 3.71 (s, 1.2H), 3.61 (s, 1.8H), 3.23-2.76 (m, 7H), 2.31-2.14 (m, 2H), 2.10-1.96 (m, 2H), 1.05-0.95 (m, 1H), 0.40-0.32 (m, 2H), 0.22-0.13 (m, 2H). LCMS [M+H]⁺ 565, RT 1.86 minutes (Method 26). Chiral SFC** RT 4.72 minutes.

\*\* Chiral analysis was carried out using Lux Cellulose-3 (4.6×150 mm 3 μm) column, flow rate 3 mL/min eluting with a gradient of 10 to 25% MeOH (+0.1% NH40H), using a 6.5 minutes run time on a Waters UPC2-QDa

Example 366

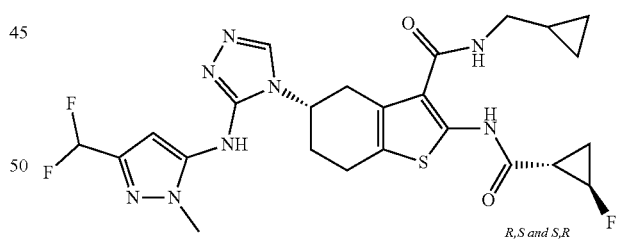

(5S)—N-(cyclopropylmethyl)-5-[3-[[5-(difluoromethyl)-2-methylpyrazol-3-yl]amino]-1,2,4-triazol-4-yl]-2-[[(1RS,2SR)-2-fluorocyclopropanecarbonyl]amino]-4,5,6,7-tetrahydro-1-benzothiophene-3-carboxamide The title compound was obtained following general method 6 with intermediate 425 (150 mg, 0.28 mmol), rac-(1S,2R)-2-fluorocyclopropanecarboxylic acid (15 ⍰L, 0.28 mmol), pyridine (113 ⍰L, 1.4 mmol), T3P (334 ⍰L, 0.56 mmol), and DCM (10 mL). Reaction duration: 16 hours. Reaction mixture was diluted with DCM (30 mL)

then water (15 mL) was added and organic layer separated. The aqueous layer was extracted with DCM (2×10 mL) and the organic fractions combined, dried (Na₂SO₄) and concentrated under vacuum. Purification by column chromatography eluting with 0-100% EtOAc in heptane to give the title compound as a mixture of two trans diastereoisomers (112 mg, 70% Yield). δ_H (500 MHz, Methanol-d4) 8.27 (br.s, 1H), 6.61 (t, J=55.2 Hz, 1H), 6.30 (br.s, 1H), 4.94-4.74 (m, 1H), 4.60-4.50 (m, 1H), 3.72 (s, 3H), 3.36-3.32 (m, 1H), 3.28-3.24 (m, 1H), 3.23-3.12 (m, 1H), 3.10-2.80 (m, 3H), 2.41-2.27 (m, 3H), 1.60-1.47 (m, 1H), 1.41-1.30 (m, 1H), 1.15-1.02 (m, 1H), 0.55-0.40 (m, 2H), 0.31-0.19 (m, 2H). LCMS [M+H]⁺ 549, RT 2.71 minutes (Method 10).

Example 367

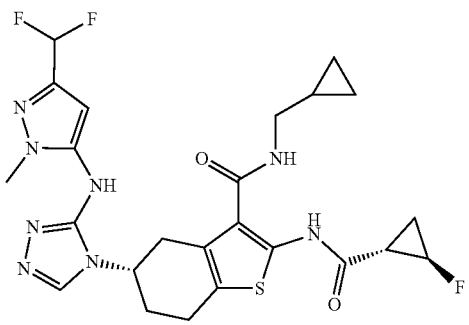 [SMILES: Cn1nc(C(F)F)cc1Nc1nncn1[C@H]1CCc2sc(NC(=O)[C@@H]3C[C@H]3F)c(C(=O)NCC3CC3)c2C1]

(5S)—N-(cyclopropylmethyl)-5-[3-[[5-(difluoromethyl)-2-methylpyrazol-3-yl]amino]-1,2,4-triazol-4-yl]-2-[[(1S,2R)-2-fluorocyclopropanecarbonyl]amino]-4,5,6,7-tetrahydro-1-benzothiophene-3-carboxamide The title compound was prepared by chiral SFC purification of Example 366 (105 mg) using a Lux Cellulose-3 250×21.2 mm 5 μm column, eluting with a gradient of 10 to 25% MeOH (+0.1% NH4OH) in CO₂, with a flow rate 100 mL/min on a Waters Prep 100-SQD2, to give the title product (the second peak eluted) as a white solid (31 mg, 31% Yield). δ_H (400 MHz, DMSO-d6) 12.07 (s, 0.6H), 11.20 (m, 1H), 8.76 (s, 0.4H), 8.40 (s, 0.4H), 8.19 (s, 0.6H), 7.89 (m, 1H), 6.87 (t, J=55.1 Hz, 0.4H), 6.75 (t, J=55.1 Hz, 0.6H), 6.41 (s, 0.4H), 6.20 (s, 0.6H), 5.04-4.70 (m, 1H), 4.54-4.32 (m, 1H), 3.71 (s, 1.2H), 3.61 (s, 2.8H), 3.23-3.02 (m, 3H), 3.00-2.73 (m, 3H), 2.64-2.55 (m, 1H), 2.30-2.12 (m, 2H), 1.63-1.41 (m, 1H), 1.30-1.19 (m, 1H), 1.06-0.93 (m, 1H), 0.41-0.32 (m, 2H), 0.23-0.14 (m, 2H). LCMS [M+H]⁺ 549, RT 1.83 minutes (Method 26). Chiral SFC* RT 5.71 minutes.

* Chiral analysis was carried out using Lux Cellulose-3 (4.6×150 mm 3 μm) column, flow rate 3 mL/min eluting with a gradient of 10 to 25% MeOH (+0.1% NH₄OH), using a 6.5 minutes run time on a Waters UPC2-QDa. LC, RT 5.71 minutes Example 368

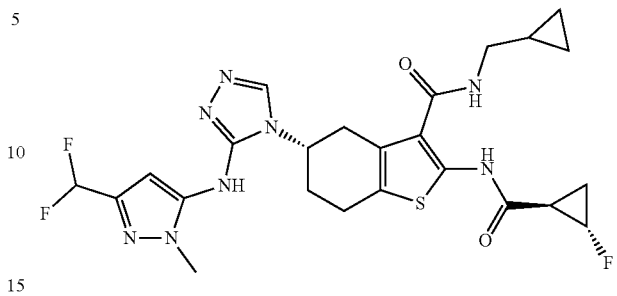

(5S)—N-(cyclopropylmethyl)-5-[3-[[5-(difluoromethyl)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide Synthesised in the same manner as example 229, intermediate 632 (785 mg, 1.12 mmol) and comparable stoichiometries of reagents. Purification by prep HPLC service gave the title compound (216 mg, 32% Yield). δ_H (400 MHz, MeOH-d4) 8.23 (s, 1H), 6.62 (t, J=55.1 Hz, 1H), 6.28 (s, 1H), 4.84 (dddd, J=64.2, 6.3, 3.4, 1.6 Hz, 1H), 4.55 (d, J=5.5 Hz, 1H), 3.72 (s, 3H), 3.37-3.22 (m, 2H), 3.18 (dd, J=13.8, 7.0 Hz, 1H), 3.11-2.84 (m, 3H), 2.42-2.28 (m, 3H), 1.62-1.46 (m, 1H), 1.36 (dq, J=12.9, 6.4 Hz, 1H), 1.14-0.99 (m, 1H), 0.54-0.41 (m, 2H), 0.31-0.20 (m, 2H).). LCMS [M+H]⁺ 549, RT 1.64 minutes (Method 26).

Example 369

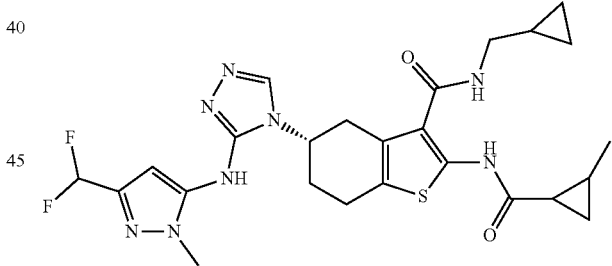

(5S)—N-(cyclopropylmethyl)-5-[3-[[5-(difluoromethyl)-2-methylpyrazol-3-yl]amino]-1,2,4-triazol-4-yl]-2-[(2-methylcyclopropanecarbonyl)amino]-4,5,6,7-tetrahydro-1-benzothiophene-3-carboxamide The title compound was obtained following general method 6 with intermediate 425 (50 mg, 0.09 mmol), 2-methylcyclopropanecarboxylic acid (9.3 mg, 0.09 mmol), pyridine (37.6 μL, 0.46 mmol), T3P (1110 μL, 0.18 mmol) and DCM (10 mL). Reaction duration: 16 hours. Reaction mixture was diluted with DCM (30 mL) then water (25 mL) was added and organic layer separated. The aqueous layer was extracted with DCM (2×20 mL) and the organic fractions combined, dried (Na₂SO₄) and concentrated under vacuum. Purification by HPLC (Method 4) gave the title compound (31 mg, 60% Yield). δ_H (500 MHz, Methanol-d4)

8.33 and 7.91 (2×s, 1H, rotamers), 6.81-6.46 (m, 1H), 6.36 and 6.11 (2×s, 1H, rotamers), 4.69-4.40 (m, 1H), 3.73 (s, 3H), 3.30-3.23 (m, 2H), 3.23-3.13 (m, 1H), 3.14-2.81 (m, 3H), 2.44-2.25 (m, 2H), 1.91-1.79 and 1.60-1.50 (2×m, 1H, rotamers), 1.47-1.35 (m, 1H), 1.25-1.15 (m, 4H, rotamer 1H), 1.13-1.03 (m, 1H, rotamer 1H), 0.99-0.90 and 0.83-0.75 (m, 1H, rotamers), 0.55-0.40 (m, 2H), 0.35-0.17 (m, 2H). LCMS [M+H]$^+$ 545, RT 2.94 minutes (Method 10).

Example 370

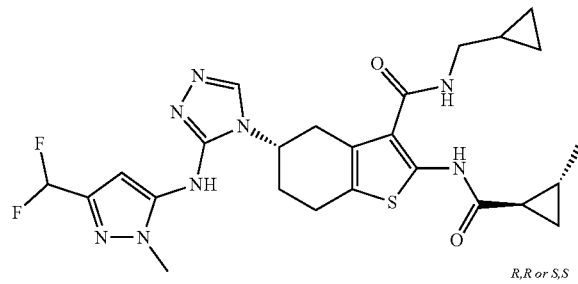

R,R or S,S (5S)—N-(cyclopropylmethyl)-5-[3-[[5-(difluoromethyl)-2-methylpyrazol-3-yl]amino]-1,2,4-triazol-4-yl]-2-[[(1R*,2R*)-2-methylcyclopropanecarbonyl]amino]-4,5,6,7-tetrahydro-1-benzothiophene-3-carboxamide (* or S)

The title compound was prepared by chiral SFC purification of Example 369 using a Chiralpak IG (20 mm×250 mm, 5 Om) column eluted with 50:50 IPA:CO$_2$ (0.2% v/v NH$_3$) at a rate of 50 mL/min at 150 Bar, to give the title product as (the second peak eluted) as a white solid after evaporation of solvent (51 mg, 25% Yield). $\delta_H$ (400 MHz, DMSO-d6) 12.08 (s, 0.6H), 11.24 (s, 0.4H), 11.19 (s, 0.6H), 8.75 (s, 0.4H), 8.41 (s, 0.4H), 8.20 (s, 0.6H), 7.79-7.66 (m, 1H), 6.87 (t, J=55.1 Hz, 0.4H), 6.75 (t, J=55.1 Hz, 0.6H), 6.41 (s, 0.4H), 6.20 (s, 0.6H), 4.54-4.39 (m, 1H), 3.71 (s, 1.2H), 3.61 (s, 1.8H), 3.24-2.91 (m, 4H), 2.91-2.79 (m, 2H), 2.30-2.13 (m, 2H), 1.69 (dt, J=8.3, 4.3 Hz, 1H), 1.33-1.21 (m, 1H), 1.10 (d, J=6.0 Hz, 3H), 1.10-0.95 (m, 2H), 0.77-0.67 (m, 1H), 0.40-0.31 (m, 2H), 0.23-0.15 (m, 2H). Tautomers. LCMS [M+H]$^+$ 543, RT 2.01 minutes (Method 26). Chiral SFC** RT 2.34 minutes.

** Chiral analysis was carried out using a Chiralpak IG (4.6 mm×250 mm, 5 μm) column, eluted with 50:50 IPA:CO$_2$ (0.2% v/v NH3) at a rate of 4 mL/min at 125 Bar.

Example 371

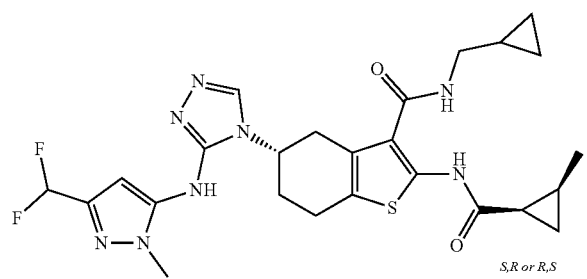 [SMILES: C[C@H]1C[C@H]1C(=O)Nc1sc2c(c1C(=O)NCC1CC1)C[C@@H](n1cnnc1Nc1cc(C(F)F)nn1C)CC2]

S,R or R,S (5S)—N-(cyclopropylmethyl)-5-[3-[[5-(difluoromethyl)-2-methylpyrazol-3-yl]amino]-1,2,4-triazol-4-yl]-2-[[(1R*,2S*)-2-methylcyclopropanecarbonyl]amino]-4,5,6,7-tetrahydro-1-benzothiophene-3-carboxamide (*1R,2S or 1S,2R)

The title compound was prepared by chiral SFC purification of intermediate Example 369 using a Chiralpak IG (20 mm×250 mm, 5 Ωm) column eluted with 50:50 IPA:CO$_2$ (0.2% v/v NH$_3$) at a rate of 50 mL/min at 150 Bar, to give the title product as (the first peak eluted) as a white solid after evaporation of solvent (12 mg, 6% Yield). $\delta_H$ (400 MHz, DMSO-d6) 12.08 (s, 0.6H), 11.30 (s, 0.4H), 11.26 (s, 0.6H), 8.75 (s, 0.4H), 8.41 (s, 0.4H), 8.21 (s, 0.6H), 7.73-7.61 (m, 1H), 6.87 (t, J=55.1 Hz, 0.4H), 6.75 (t, J=55.1 Hz, 0.6H), 6.41 (s, 0.4H), 6.21 (s, 0.6H), 4.54-4.40 (m, 1H), 3.71 (s, 1.2H), 3.61 (s, 1.8H), 3.24-2.92 (m, 4H), 2.91-2.79 (m, 2H), 2.27-2.14 (m, 2H), 1.98-1.89 (m, 1H), 1.27-1.21 (m, 2H), 1.09 (d, J=6.1 Hz, 3H), 1.06-0.96 (m, 1H), 0.85-0.78 (m, 1H), 0.39-0.32 (m, 2H), 0.22-0.14 (m, 2H). Tautomers. LCMS [M+H]$^+$ 543, RT 2.02 minutes (Method 26). Chiral SFC** RT 1.71 minutes.

** Chiral analysis was carried out using a Chiralpak IG (4.6 mm×250 mm 5 μm) column, eluted with 50:50 IPA:CO$_2$ (0.2% v/v NH$_3$) at a rate of 4 mL/min at 125 Bar.

Example 372

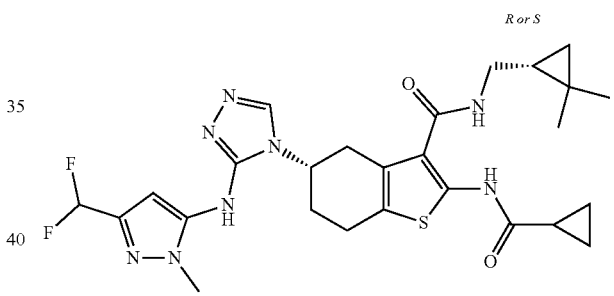

R or S (5S)-2-(cyclopropanecarbonylamino)-5-[3-[[5-(difluoromethyl)-2-methylpyrazol-3-yl]amino]-1,2,4-triazol-4-yl]-N-[[(1R*)-2,2-dimethylcyclopropyl]methyl]-4,5,6,7-tetrahydro-1-benzothiophene-3-carboxamide (* or S)

The title compound was obtained following general method 1 with intermediate 494 (29 mg, 0.0631 mmol), 2,2-dimethylcyclopropyl)methanamine hydrochloride (26 mg, 0.191 mmol), triethylamine (26 ΩL, 0.187 mmol), and DMF (1 mL). Reaction time: 1.5 hours at 140° C. The solution was concentrated under reduced pressure, then purified by flash column chromatography eluting with a 0-5% methanol in DCM gradient to give a mixture of isomers which were separated by chiral chromatography (70:30 Heptane:IPA with ChiralPAK AD-H 25 cm, 18 mL/min) to give the title compound (Peak 2, 3.5 mg, 9.8% Yield). $\delta_H$ (500 MHz, MeOH-d4) 8.20 (s, 1H), 6.61 (t, J=55.2 Hz, 1H), 6.27 (s, 1H), 4.61-4.50 (m, 1H), 3.72 (s, 3H), 3.51 (dd, J=14.0, 7.1 Hz, 1H), 3.36-3.32 (m, 1H), 3.20 (dd, J=14.0, 8.1 Hz, 1H), 3.10-2.88 (m, 3H), 2.41-2.32 (m, 2H), 1.84-1.78 (m, 1H), 1.09 (s, 3H), 1.01-0.86 (m, 8H), 0.44 (dd, J=8.6, 4.4 Hz, 1H), 0.15 (t, J=4.8 Hz, 1H). LCMS [M+H]+ 559, RT 3.19 minutes (Method 10). Chiral LC** RT=17.28 minutes.

** Chiral analysis was carried out using a ChiralPAK AD-H 4.6×250 mm, 5 μm column, flow rate 1 mL/min eluting with 70:30 Heptane:APA, using a 25 minute run time on a Waters 2795.

Example 373

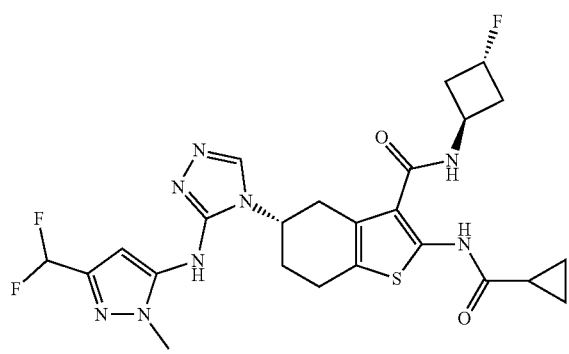 [SMILES: Cn1nc(C(F)F)cc1Nc1nncn1[C@H]1CCc2sc(NC(=O)C3CC3)c(C(=O)N[C@H]3C[C@H](F)C3)c2C1]

(5S)-2-(cyclopropanecarbonylamino)-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide The title compound was obtained following general method 1 with intermediate 494 (29 mg, 0.0631 mmol), trans-3-fluorocyclobutanamine hydrochloride (24 mg, 0.191 mmol), triethylamine (26 μL, 0.187 mmol), and DMF (1 mL). Reaction time: 1.5 hours at 140° C. The solution was concentrated under reduced pressure, then purified by flash column chromatography eluting with a 0-5% methanol in DCM gradient to give the title compound (8.5 mg, 22% Yield). $\delta_H$ (500 MHz, MeOH-d4) 8.44-7.79 (m, 1H), 6.62 (t, J=55.1 Hz, 1H), 6.44-6.03 (m, 1H), 5.25-5.09 (m, 1H), 4.67-4.59 (m, 1H), 4.58-4.50 (m, 1H), 3.72 (s, 3H), 3.30-3.25 (m, 1H), 3.05 (s, 1H), 2.99-2.91 (m, 1H), 2.90-2.83 (m, 1H), 2.66-2.54 (m, 2H), 2.49-2.37 (m, 2H), 2.36-2.28 (m, 2H), 1.85-1.77 (m, 1H), 1.04-0.89 (m, 4H). LCMS [M+H]+ 549, RT 2.54 minutes (Method 10).

Example 374 & 375

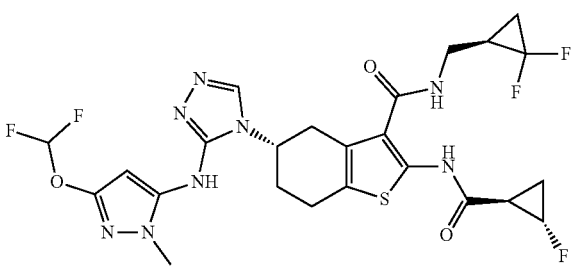

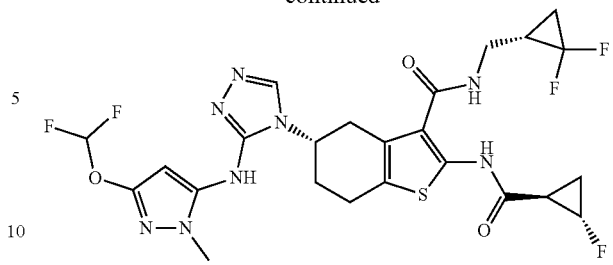

(5S)—N-[[(1R)-2,2-difluorocyclopropyl]methyl]-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-4,5,6,7-tetrahydro-1-benzothiophene-3-carboxamide (5S)—N-[[(1S)-2,2-difluorocyclopropyl]methyl]-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-4,5,6,7-tetrahydro-1-benzothiophene-3-carboxamide Propylphosphonic anhydride solution (50%, 308 μL, 0.53 mmol) was added drop wise to the stirred suspension of intermediate 461 (90 mg, 0.17 mmol) and pyridine (57 μL, 0.70 mmol) in dry DCM (4 mL) at room temperature and stirred for 24 h. The reaction mixture was diluted with water (10 mL) and extracted with DCM (2×10 mL), combined organic layers were dried (Na2SO4), filtered, evaporated to dryness. The resulting solid was dissolved in dry acetonitrile (2 mL) then added to a suspension of (2,2-difluorocyclopropyl)methanamine hydrochloride (75 mg, 0.522 mmol) and triethylamine (98 μL, 0.704 mmol) in acetonitrile (2 mL). The reaction mixture was heated at 70° C. for 30 min then evaporated to dryness, diluted water (10 mL) and extracted with DCM (2×10 mL). The combined organic layers were dried (Na2SO4), filtered, evaporated to dryness. The residual solid was purified by reverse phase column chromatography eluting with a gradient of 5-95% Acetonitrile (0.1% formic acid) in Water (0.1% formic acid). The product (a mixture of diastereomers) was separated by SFC (Lux i-C5, 250×21.2 mm, 5 μm, Mobile phase: Isocratic 45% MeOH (+0.2% NH3) in CO2, Flowrate: 50 mL/min, Temperature: 40° C., Pressure: 100 bar) to give the title compounds:

Isomer 1 (16 mg, 34% Yield) $\delta_H$ (400 MHz, MeOH-d4) 8.21 (s, 1H), 6.88 (t, J=73.8 Hz, 1H), 5.74 (s, 1H), 4.84 (dddd, J=64.2, 6.2, 3.4, 1.6 Hz, 1H), 4.51 (d, J=14.0 Hz, 1H), 3.60 (s, 4H), 3.43-3.24 (m, 2H), 3.03 (dd, J=25.8, 9.7 Hz, 1H), 2.93 (dd, J=14.6, 6.4 Hz, 2H), 2.44-2.28 (m, 3H), 2.01 (ddt, J=18.8, 14.8, 7.4 Hz, 1H), 1.52 (dtdd, J=28.1, 12.0, 7.2, 3.9 Hz, 2H), 1.41-1.17 (m, 2H). LCMS [M+H]+ 601, RT 2.68 minutes (Method Below). Chiral LC RT 2.07 minutes.

Isomer 2 (18 mg, 38% Yield) $\delta_H$ (400 MHz, MeOH-d4) 8.22 (s, 1H), 6.88 (t, J=73.8 Hz, 1H), 5.74 (s, 1H), 4.84 (dddd, J=64.2, 6.3, 3.4, 1.6 Hz, 1H), 4.62-4.44 (m, 1H), 3.60 (s, 3H), 3.55-3.40 (m, J=7.3 Hz, 2H), 3.27 (d, J=5.4 Hz, 1H), 3.03 (dd, J=15.5, 9.4 Hz, 1H), 2.93 (dd, J=15.2, 6.7 Hz, 2H), 2.41-2.28 (m, 3H), 1.99 (ddq, J=14.8, 11.5, 7.4 Hz, 1H), 1.51 (dtdd, J=28.2, 11.9, 7.2, 3.9 Hz, 2H), 1.36 (dq, J=12.9, 6.5

Hz, 1H), 1.24 (dtd, J=13.5, 7.7, 3.8 Hz, 1H). LCMS [M+H]+ 601, RT 2.40 minutes. Chiral LC* RT=2.07 minutes.

* Chiral analysis was performed using an Lux i-C5 column, 250×2.1 mm, 5 µm, eluted using an isocratic 50% MeOH (+0.2% NH₃) in CO₂ method, flow rate of 4 mL/min, 100 bar pressure and a 4.5 minute run time on a Waters UPC2-QDa LCMS method: Acquity CSH C18 column 50×2.1 mm, 1.7 µm, eluted with a gradient of 0-100% MeCN in Water (+0.1% TFA), flow rate of 0.6 mL/min, and a 4.5 min run time.

Example 376

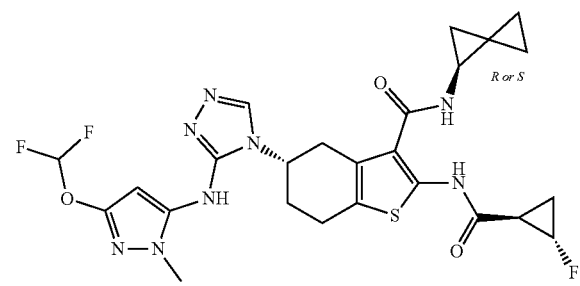 [SMILES: Cn1nc(OC(F)F)cc1Nc1nncn1[C@H]1CCc2sc(NC(=O)[C@H]3C[C@@H]3F)c(C(=O)N[C@H]3CC34CC4)c2C1]

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[(2R*)-spiro[2.2]pentan-2-yl]-4,5,6,7-tetrahydro-1-benzothiophene-3-carboxamide (* or S)

The title compound was obtained following general method 3 with intermediate 461 (100 mg, 0.196 mmol), DIPEA (137 µL, 0.782 mmol), spiro[2.2]pentan-2-amine hydrochloride (in 2 portions: 69 & 12 mg, 0.75 mmol), HATU (149 mg, 0.391 mmol) and DMF (2 mL). Reaction duration: 1 hour at room temperature followed by 2 hours at 70° C. The reaction mixture was diluted with saturated aqueous NH₄Cl (5 mL), and extracted with DCM (3×5 mL). The organic layers were combined, dried (Na₂SO₄), and evaporated to dryness. The crude material was purified by reverse phase column chromatography eluting with a gradient 5-95% Acetonitrile (0.2% ammonium hydroxide) in Water (0.2% ammonium hydroxide). The resulting product (a mixture of diastereomers) was separated using chiral column chromatography (Lux Cellulose-2, 370×76 mm, 20 µm, Mobile phase: Isocratic 50% EtOH in heptane, Flow-rate: 200 mL/min, Temperature: 35° C.) to give the title compound (7 mg, 16% Yield). δ$_H$ (400 MHz, MeOH-d4) 8.56-7.77 (m, 1H), 6.89 (t, J=73.6 Hz, 1H), 5.77 (s, 1H), 4.83 (dddd, J=64.1, 6.3, 3.4, 1.6 Hz, 1H), 4.59-4.45 (m, 1H), 3.60 (s, 3H), 3.26-3.17 (m, 1H), 3.06-2.79 (m, 3H), 2.43-2.24 (m, 3H), 1.62-1.46 (m, 1H), 1.41-1.25 (m, 3H), 1.08-0.98 (m, 2H), 0.94-0.81 (m, 2H), 0.80-0.72 (m, 1H). LCMS [M+H]+ 577, RT 1.63 minutes (Method 26). Chiral LC** RT 3.36 minutes.

** Chiral analysis was performed using a Lux Cellulose-2 (150×4.6 mm 3 µm) column, eluted using an isocratic 50% EtOH in heptane method, flow rate of 1.5 mL/min, 100 bar and an 8 minute run time on an Agilent Infinity II 1290.

Examples 377 & 378

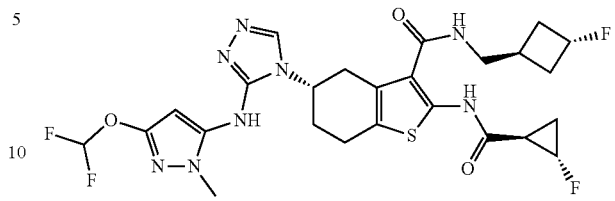

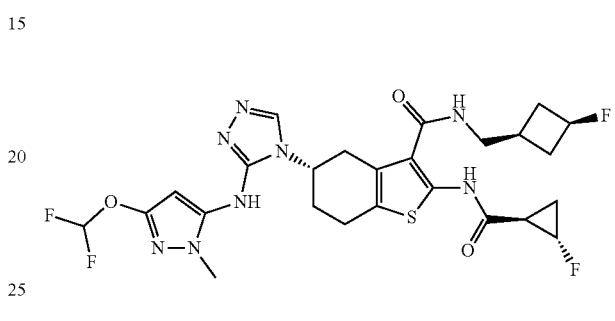

(5S)-5-[3-[[5-(difluoromethoxy)-2-methylpyrazol-3-yl]amino]-1,2,4-triazol-4-yl]-N-[cis-(3-fluorocyclobutyl)methyl]-2-[[(1R,2S)-2-fluorocyclopropanecarbonyl]amino]-4,5,6,7-tetrahydro-1-benzothiophene-3-carboxamide (5S)-5-[3-[[5-(difluoromethoxy)-2-methylpyrazol-3-yl]amino]-1,2,4-triazol-4-yl]-N-[trans-(3-fluorocyclobutyl)methyl]-2-[[(1R,2S)-2-fluorocyclopropanecarbonyl]amino]-4,5,6,7-tetrahydro-1-benzothiophene-3-carboxamide The title compound was obtained following general method 3 with intermediate 461 (60 mg, 0.117 mmol), DIPEA (82 ML, 0.469 mmol), (3-fluorocyclobutyl)methanamine hydrochloride (9:1 trans:Cis, in 2 portions: 48 & 10 mg, 0.415 mmol), HATU (89 mg, 0.235 mmol) and DMF (2 mL). Reaction duration: 1 hour at room temperature followed by 2 hours at 70° C. The reaction mixture was diluted with saturated aqueous NH₄Cl (5 mL), water (5 mL) and DCM (5 mL) and the aqueous phase extracted with DCM (2×5 mL). The organic layers were combined, dried (Na₂SO₄), and evaporated to dryness. The crude material was purified by reverse phase column chromatography eluting with a gradient of 5-95% Acetonitrile (0.2% ammonium hydroxide) in water (0.2% ammonium hydroxide). The resulting product (a mixture of diastereomers) was separated using chiral SFC (25% Methanol: 75% CO₂ with Chiralpak IC 25 cm column at 15 mL/min) to give the title compounds:

Cis Isomer (Peak 2, 1 mg, 2.5% Yield). δ$_H$ (500 MHz, MeOH-d4) 8.16 (br s, 1H), 6.88 (t, J=73.9 Hz, 1H), 5.73 (br s, 1H), 4.92-4.87 (m, 1H), 4.78-4.72 (m, 1H), 4.59-4.47 (m, 1H), 3.60 (s, 3H), 3.51 (dd, J=13.4, 6.4 Hz, 1H), 3.39-3.34 (m, 1H), 3.28-3.23 (m, 1H), 3.06-2.84 (m, 3H), 2.49-2.37 (m, 2H), 2.37-2.29 (m, 3H), 2.11-1.99 (m, 1H), 1.96-1.83 (m, 2H), 1.58-1.47 (m, 1H), 1.40-1.33 (m, 1H). LCMS [M+H]+ 597, RT 2.82 minutes (Method 10). Chiral SFC* RT=12.66 minutes.

Trans isomer (Peak 3, 10 mg, 25% Yield). δ$_H$ (500 MHz, MeOH-d4) 8.16 (br s, 1H), 6.88 (t, J=73.9 Hz, 1H), 5.73 (s, 1H), 5.24-5.00 (m, 1H), 4.95-4.72 (m, 1H), 4.62-4.46 (m, 1H), 3.60 (s, 3H), 3.46 (dd, J=13.5, 7.8 Hz, 1H), 3.36 (dd, J=13.6, 7.8 Hz, 1H), 3.29-3.21 (m, 1H), 3.06-2.84 (m, 3H), 2.64-2.51 (m, 1H), 2.48-2.04 (m, 7H), 1.61-1.46 (m, 1H), 1.40-1.31 (m, 1H). LCMS [M+H]$^+$ 597, RT 2.82 minutes (Method 10). Chiral SFC* RT=14.03 minutes.

* Chiral analysis was carried out using CHIRALPAK IC, 25 cm column, 15 mL/min, eluting with a gradient of 70/30 CO$_2$/MEOH, using a 20 minutes run time.

Example 379

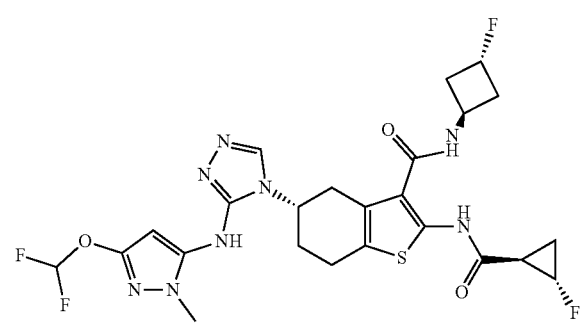 [SMILES: Cn1nc(OC(F)F)cc1Nc1nncn1[C@H]1CCc2sc(NC(=O)[C@H]3C[C@@H]3F)c(C(=O)N[C@H]3C[C@H](F)C3)c2C1]

(5S)-5-[3-[[5-(difluoromethoxy)-2-methylpyrazol-3-yl]amino]-1,2,4-triazol-4-yl]-N-(trans-3-fluorocyclobutyl)-2-[[(1R,2S)-2-fluorocyclopropanecarbonyl]amino]-4,5,6,7-tetrahydro-1-benzothiophene-3-carboxamide The title compound was obtained following general method 3 with intermediate 461 (100 mg, 0.196 mmol), DIPEA (137 μL, 0.782 mmol), trans-3-fluorocyclobutanamine hydrochloride (72 mg, 0.573 mmol), HATU (in two portions of 89 mg, 1.78 mmol) and DMF (3 mL). Reaction duration: 24 hours at room temperature followed by 1 hours at 70° C. The reaction mixture was diluted with saturated aqueous NH$_4$Cl (5 mL) and extracted with DCM (3×5 mL), combined organic layers were dried (Na$_2$SO$_4$), filtered and evaporated to dryness. The crude material was purified by reverse phase column chromatography eluting with a gradient of 5-95% Acetonitrile (0.2% ammonium hydroxide) in water (0.2% ammonium hydroxide). The resulting product (a mixture of diastereomers) was separated using chiral SFC (35% Methanol: 65% CO$_2$ with Chiralpak IC 25 cm column at 15 mL/min) to give the title compound (Peak 2, 23 mg, 96% Yield). δ$_H$ (500 MHz, MeOH-d4) 8.17 (br s, 1H), 6.88 (t, J=73.9 Hz, 1H), 5.73 (br s, 1H), 5.26-5.08 (m, 1H), 4.93-4.75 (m, 1H), 4.70-4.58 (m, 1H), 4.58-4.46 (m, 1H), 3.60 (s, 3H), 3.30-3.23 (m, 1H), 3.06-2.96 (m, 1H), 2.96-2.82 (m, 2H), 2.67-2.54 (m, 2H), 2.48-2.37 (m, 2H), 2.37-2.24 (m, 3H), 1.59-1.48 (m, 1H), 1.41-1.31 (m, 1H). LCMS [M+H]$^+$ 583, RT 2.70 minutes (Method 10). Chiral SFC* RT=6.34 minutes.

* CHIRALPAK IC, 25 cm column, 4 mL/min, eluting with a gradient of 65/35 CO$_2$/MEOH, using a 10 minutes run time.

Example 380

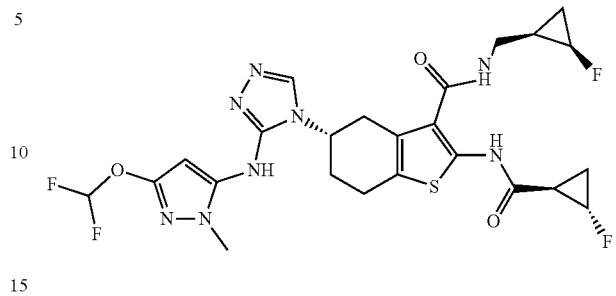

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1R,2R)-2-fluorocyclopropyl]methyl]-4,5,6,7-tetrahydro-1-benzothiophene-3-carboxamide The title compound was obtained following general method 3 with intermediate 461 (100 mg, 0.196 mmol), DIPEA (137 μL, 0.782 mmol), [(1R,2R)-2-fluorocyclopropyl]methanamine hydrochloride (73 mg, 0.577 mmol), HATU (149 mg, 0.391 mmol) and DMF (2 mL). Reaction duration: 1 hour at room temperature followed by 1 hours at 70° C. and o/n at room temperature. The reaction mixture diluted with saturated aqueous NH$_4$Cl (5 mL) and extracted with DCM (3×5 mL), combined organic layers were dried (Na$_2$SO$_4$), filtered and evaporated to dryness. The crude material was purified by HPLC (Method C) to give the title compound (50 mg, 44% Yield). δ$_H$ (500 MHz, MeOH-d4) 8.16 (br s, 1H), 6.88 (t, J=73.8 Hz, 1H), 5.74 (br s, 1H), 4.93-4.76 (m, 1H), 4.76-4.59 (m, 1H), 4.58-4.46 (m, 1H), 3.75-3.66 (m, 1H), 3.60 (s, 3H), 3.34-3.26 (m, 2H), 3.10-3.00 (m, 1H), 3.00-2.83 (m, 2H), 2.40-2.35 (m, 1H), 2.35-2.27 (m, 2H), 1.62-1.46 (m, 1H), 1.40-1.31 (m, 1H), 1.31-1.20 (m, 1H), 0.86-0.69 (m, 2H). LCMS [M+H]$^+$ 583, RT 2.76 minutes (Method 10).

Example 381

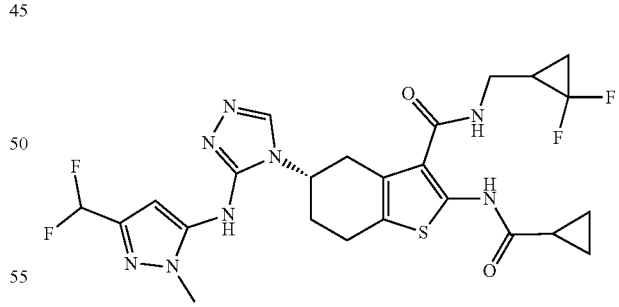

(5S)-2-(cyclopropanecarbonylamino)-N-[(2,2-difluorocyclopropyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 1 with intermediate 494 (29 mg, 0.06 mmol), (2,2-difluorocyclopropyl)methanamine hydrochloride (27 mg, 0.19 mmol), triethylamine (26 μL, 0.187 mmol) and DMF (1 mL). Reaction time: 2 h at 140° C. Once at room temperature the reaction mixture was concentrated under reduced pressure and purified by column chromatography eluting with a gradient of 0-100% (10% methanol in DCM) in DCM to give a mixture of isomers (25 mg, 70% Yield). δH (500 MHz, DMSO-d6) 8.55-7.77 (m, 1H), 6.63 (t, J=55.0 Hz, 1H), 6.33 (br s, 1H), 4.67-4.47 (m, 1H), 3.74 (s, 3H), 3.63-3.45 (m, 2H), 3.32-3.28 (m, 1H), 3.15-3.04 (m, 1H), 3.04-2.86 (m, 2H), 2.45-2.28 (m, 2H), 2.11-1.94 (m, 1H), 1.88-1.80 (m, 1H), 1.55-1.43 (m, 1H), 1.30-1.22 (m, 1H), 1.04-0.99 (m, 2H), 0.99-0.93 (m, 2H). LCMS [M+H]+ 567, RT 2.73 minutes (Method 10).

Examples 382 & 383

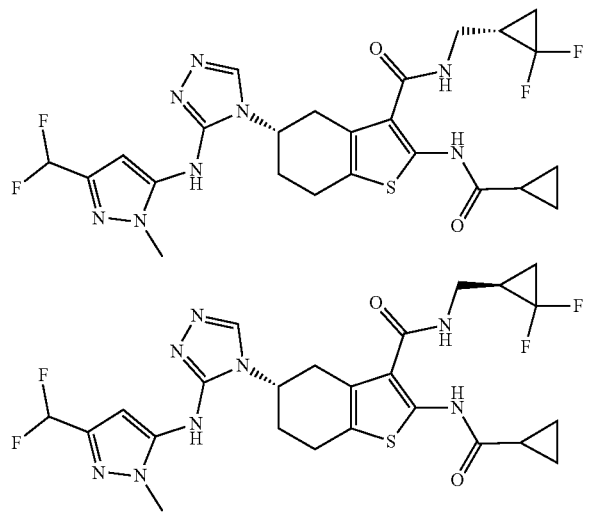

(5S)-2-(cyclopropanecarbonylamino)-N-[[(1R)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide (5S)-2-(cyclopropanecarbonylamino)-N-[[(1S)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide The title compounds were obtained by separating the two enantiomers of Example 381 by SFC (Chiralpak IC 5 μm 250×20 mm Mobile phase: CO2/MeOH+0.1% IPA 70/30, 50 mL/min, 40° C., 100 bar):
Isomer 1 (Peak 1, 4.3 mg, 20% Yield, 100% chiral purity). δH (500 MHz, DMSO-d6) 11.18 (br s, 1H), 8.60-7.74 (m, 2H), 7.02-6.61 (m, 1H), 6.27 (br s, 1H), 4.53-4.41 (m, 1H), 3.64 (s, 3H), 3.39-3.32 (m, 2H), 3.23-3.09 (m, 1H), 3.03-2.90 (m, 1H), 2.89-2.74 (m, 2H), 2.30-2.13 (m, 2H), 2.06-1.95 (m, 1H), 1.95-1.86 (m, 1H), 1.59-1.44 (m, 1H), 1.35-1.25 (m, 1H), 0.89-0.79 (m, 4H). LCMS [M+H]+ 567, RT 2.72 minutes (Method 10). Chiral SFC* RT=15.33
Isomer 2 (5.6 mg, 25% Yield, 95.7% chiral purity). δH (500 MHz, DMSO-d6) 11.19 (br s, 1H), 8.86-7.66 (m, 2H), 7.09-6.57 (m, 1H), 6.50-6.03 (m, 1H), 4.53-4.41 (m, 1H), 3.64 (s, 3H), 3.45-3.31 (m, 2H), 3.22-3.08 (m, 1H), 3.01-2.91 (m, 1H), 2.89-2.76 (m, 2H), 2.31-2.13 (m, 2H), 2.05-1.96 (m, 1H), 1.91 (s, 1H), 1.59-1.44 (m, 1H), 1.36-1.26 (m, 1H), 0.85 (d, J=4.7 Hz, 4H). LCMS [M+H]+ 567, RT 2.72 minutes (Method 10). Chiral SFC* RT=18.16

* CHIRALPAK IC (4.6×250 mm 5 μm) column, 2.4 mL/min, 100 Bar, eluting with a gradient of 70/30 CO2/MEOH+0.5% isopropylamine, using a 24 minutes run time on SFC BERGER.

Example 384

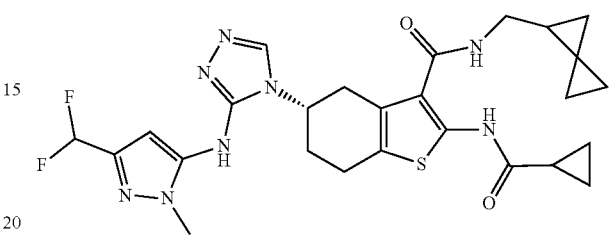

(5S)-2-(cyclopropanecarbonylamino)-5-[3-[[5-(difluoromethyl)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide The title compound was obtained following general method 1 with intermediate 494 (29 mg, 0.06 mmol), spiro[2.2]pentan-2-ylmethanamine (19 mg, 0.191 mmol), and DMF (1 mL). Reaction time: 2 h at 140° C. Once at room temperature the reaction mixture was concentrated under reduced pressure and purified by column chromatography eluting with a gradient of 0-100% (10% methanol in DCM) in DCM to give a the title compound (23 mg, 65% Yield). δH (500 MHz, Methanol-d4) 8.18 (br s, 1H), 6.63 (t, J=55.1 Hz, 1H), 6.31 (br s, 1H), 4.67-4.46 (m, 1H), 3.74 (s, 3H), 3.49-3.41 (m, 1H), 3.31-3.24 (m, 2H), 3.10-2.89 (m, 3H), 2.46-2.30 (m, 2H), 1.87-1.78 (m, 1H), 1.51-1.40 (m, 1H), 1.04-0.99 (m, 2H), 0.98-0.94 (m, 3H), 0.89-0.83 (m, 1H), 0.79-0.65 (m, 4H). LCMS [M+H]+ 557, RT 2.97 minutes (Method 10).

Examples 385 & 386

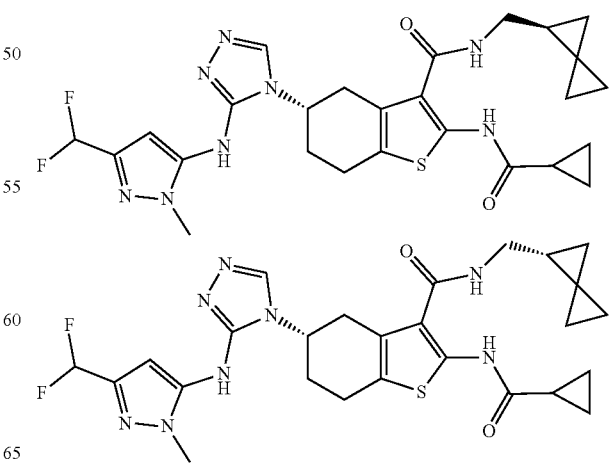

(5S)-2-(cyclopropanecarbonylamino)-5-[3-[[5-(difluoromethyl)-2-methylpyrazol-3-yl]amino]-1,2,4-triazol-4-yl]-N-[[(2R)-spiro[2.2]pentan-2-yl]methyl]-4,5,6,7-tetrahydro-1-benzothiophene-3-carboxamide (5S)-2-(cyclopropanecarbonylamino)-5-[3-[[5-(difluoromethyl)-2-methylpyrazol-3-yl]amino]-1,2,4-triazol-4-yl]-N-[[(2S)-spiro[2.2]pentan-2-yl]methyl]-4,5,6,7-tetrahydro-1-benzothiophene-3-carboxamide The title compounds were obtained by separating the two enantiomers of Example 384 (23 mg) using chiral column chromatography (80:20 Heptane: IPA with Chiralpak AD-H 25 cm column at 18 mL/min):

Isomer 1 (Peak 1, 1.1 mg, 4.7% Yield, 96% chiral purity; 4% other isomer). $\delta_H$ (500 MHz, Methanol-d4) 8.25 (br s, 1H), 6.61 (t, J=55.1 Hz, 1H), 6.29 (br s, 1H), 4.64-4.44 (m, 1H), 3.72 (s, 3H), 3.48-3.37 (m, 1H), 3.29-3.20 (m, 2H), 3.09-2.83 (m, 3H), 2.44-2.24 (m, 2H), 1.85-1.76 (m, 1H), 1.47-1.38 (m, 1H), 1.03-0.97 (m, 2H), 0.97-0.90 (m, 3H), 0.88-0.79 (m, 1H), 0.78-0.61 (m, 4H). LCMS [M+H]$^+$ 557, RT 2.96 minutes (Method 10). Chiral LC* RT=38.29 minutes Isomer 2 (3 mg, 13% Yield, 96% chiral purity; 3% other isomer). $\delta_H$ (500 MHz, Methanol-d4) 8.23 (br s, 1H), 6.61 (t, J=55.2 Hz, 1H), 6.30 (br s, 1H), 4.61-4.48 (m, 1H), 3.73 (s, 3H), 3.48-3.37 (m, 1H), 3.30-3.23 (m, 2H), 3.11-2.83 (m, 3H), 2.41-2.28 (m, 2H), 1.85-1.76 (m, 1H), 1.47-1.35 (m, 1H), 1.03-0.97 (m, 2H), 0.97-0.91 (m, 3H), 0.87-0.81 (m, 1H), 0.76-0.60 (m, 4H). LCMS [M+H]$^+$ 557, RT 2.96 minutes (Method 10). Chiral LC* RT=44.56 minutes

* Chiral analysis was carried out using CHIRALPAK AD-H, 25 cm column, 1 mL/min, eluting with a gradient of 80/20 Heptane:IPA+0.5% IPA, using a 60 minutes run time.

Example 387

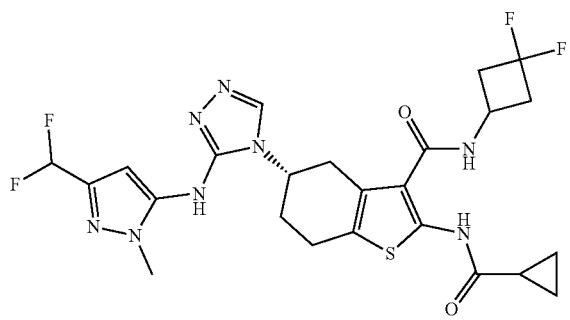 [SMILES: Cn1nc(C(F)F)cc1Nc1nncn1[C@H]1CCc2sc(NC(=O)C3CC3)c(C(=O)NC3CC(F)(F)C3)c2C1]

(5S)-2-(cyclopropanecarbonylamino)-N-(3,3-difluorocyclobutyl)-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 1 with intermediate 494 (80% purity, 70 mg, 0.122 mmol), 3,3-difluorocyclobutan-1-amine hydrochloride (53 mg, 0.368 mmol), triethylamine (50 µL, 0.362 mmol) and DMF (1.5 mL). Reaction time: 2 h at 140° C. Once at room temperature the reaction mixture was concentrated under reduced pressure and purified by reverse phase column chromatography eluting basic conditions to give the title compound (14 mg, 20% Yield). $\delta_H$ (500 MHz, DMSO-d6) 12.05 (br s, 1H, major rotamer), 10.96 (s, 1H), 8.73 (s, 1H, minor rotamer), 8.37 (s, 1H, minor rotamer), 8.27 (s, 1H), 8.15 (s, 1H, major rotamer), 7.05-6.55 (m, 1H), 6.40 and 6.20 (2×s, 1H, rotamers), 4.53-4.36 (m, 1H), 4.30-4.14 (m, 1H), 3.69 and 3.61 (2×s, 3H, rotamers), 3.19-3.07 (m, 1H), 2.98-2.78 (m, 5H), 2.76-2.60 (m, 2H), 2.29-2.11 (m, 2H), 2.01-1.83 (m, 1H), 0.92-0.74 (m, 4H). LCMS [M+H]$^+$ 567, RT 2.73 minutes (Method 10).

Example 388

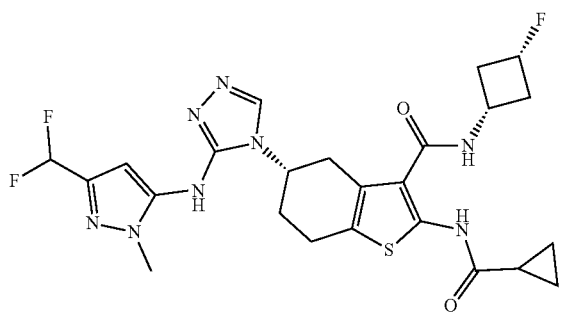 [SMILES: Cn1nc(C(F)F)cc1Nc1nncn1[C@H]1CCc2sc(NC(=O)C3CC3)c(C(=O)N[C@H]3C[C@@H](F)C3)c2C1]

(5S)-2-(cyclopropanecarbonylamino)-5-[3-[[5-(difluoromethyl)-2-methylpyrazol-3-yl]amino]-1,2,4-triazol-4-yl]-N-(cis-3-fluorocyclobutyl)-4,5,6,7-tetrahydro-1-benzothiophene-3-carboxamide The title compound was obtained following general method 1 with intermediate 494 (29 mg, 0.06 mmol), cis-3-fluorocyclobutanamine hydrochloride (24 mg, 0.19 mmol), triethylamine (26 µL, 0.187 mmol) and DMF (1 mL). Reaction time: 2 h at 140° C. Once at room temperature the reaction mixture was concentrated under reduced pressure and purified by column chromatography eluting with a gradient of 0-100% (10% methanol in DCM) in DCM to give the title compound (22 mg, 64% Yield). $\delta_H$ (500 MHz, Methanol-d4) 8.17 (br s, 1H), 6.64 (t, J=55.2 Hz, 1H), 6.31 (br s, 1H), 4.93-4.86 (m, 1H), 4.78 (p, J=6.8 Hz, 1H), 4.62-4.51 (m, 1H), 4.04 (p, J=7.9 Hz, 1H), 3.74 (s, 3H), 3.30 (d, J=5.1 Hz, 1H), 3.14-3.03 (m, 1H), 3.03-2.93 (m, 1H), 2.93-2.77 (m, 3H), 2.41-2.31 (m, 2H), 2.31-2.15 (m, 2H), 1.89-1.77 (m, 1H), 1.04-0.99 (m, 2H), 0.99-0.93 (m, 2H). LCMS [M+H]$^+$ 549, RT 2.52 minutes (Method 10).

Example 389

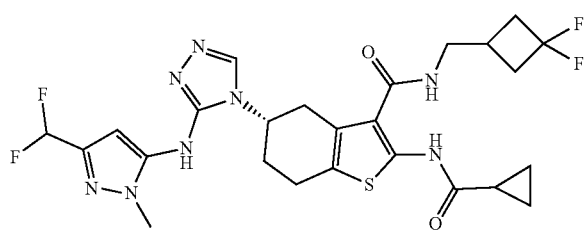 [SMILES: Cn1nc(C(F)F)cc1Nc1nncn1[C@H]1CCc2sc(NC(=O)C3CC3)c(C(=O)NCC3CC(F)(F)C3)c2C1]

(5S)-2-(cyclopropanecarbonylamino)-N-[(3,3-difluorocyclobutyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide The title compound was obtained following general method 1 with intermediate 494 (29 mg, 0.06 mmol), (3,3-difluorocyclobutyl)methanamine hydrochloride (30 mg, 0.191 mmol), triethylamine (26 ⌷L, 0.187 mmol) and DMF (1 mL). Reaction time: 2 h at 140° C. Once at room temperature the reaction mixture was concentrated under reduced pressure and purified by column chromatography eluting with a gradient of 0-100% (10% methanol in DCM) in DCM to give the title compound (20 mg, 55% Yield). $\delta_H$ (500 MHz, Methanol-d4) 8.19 (br s, J=83.4 Hz, 1H), 6.63 (t, J=55.2 Hz, 1H), 6.20 (br s, J=97.8 Hz, 1H), 4.65-4.42 (m, 1H), 3.74 (s, 3H), 3.55 (dd, J=13.6, 6.9 Hz, 1H), 3.44 (dd, J=13.7, 7.0 Hz, 1H), 3.32-3.24 (m, 1H), 3.12-3.01 (m, 1H), 3.01-2.87 (m, 2H), 2.69-2.56 (m, 2H), 2.53-2.42 (m, 1H), 2.42-2.28 (m, 4H), 1.88-1.78 (m, 1H), 1.04-0.99 (m, 2H), 0.99-0.94 (m, 2H). LCMS [M+H]$^+$ 581, RT 2.82 minutes (Method 10).

Example 390 & 391

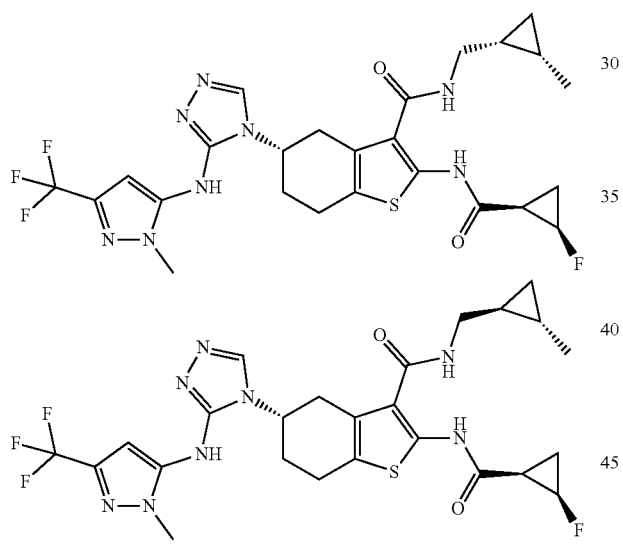

(5S)-2-[[(1R,2R)-2-fluorocyclopropanecarbonyl]amino]-N-[[1RS,2RS)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (cis)

(5S)-2-[[(1R,2R)-2-fluorocyclopropanecarbonyl]amino]-N-[[1RS,2SR)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (trans)

The title compound was obtained following general method 1 with intermediate 455 (77%, 180 mg, 0.28 mmol), 1-(2-methylcyclopropyl)methanamine hydrochloride (1:1 Cis:Trans, 102 mg, 0.839 mmol), DIPEA (147 ⌷L, 0.839 mmol), and acetonitrile (6 mL). Reaction time: 2 hours at 75° C. in a sealed tube. The solution was concentrated under reduced pressure, then purified by revers phase column chromatography eluting with 5-95% Acetonitrile (0.1% formic acid) in Water (0.1% formic acid) to give a mixture of isomers (115 mg). The mixture was separated by chiral column chromatography (70:30 Heptane: Ethanol with Chiralcel OD-H 25 cm column at 9 mL/min) to give two mixtures of diastereoisomers. These are assumed to be the cis and trans mixtures.

Diastereoisomer pair 1 (28 mg, 17% Yield) $\delta_H$ (500 MHz, MeOH-d4) 8.14 (s, 1H), 6.35 (s, 1H), 5.00-4.76 (m, 1H), 4.63-4.47 (m, 1H), 3.75 (s, 3H), 3.36-3.32 (m, 1H), 3.25 (dd, J=13.8, 7.3 Hz, 1H), 3.17 (dd, J=13.8, 6.8 Hz, 1H), 3.09-3.01 (m, 1H), 3.01-2.87 (m, 2H), 2.43-2.31 (m, 2H), 2.08-1.98 (m, 1H), 1.80-1.67 (m, 1H), 1.28-1.22 (m, 1H), 0.95 (d, J=6.0 Hz, 3H), 0.81-0.71 (m, 1H), 0.69-0.60 (m, 1H), 0.45-0.34 (m, 1H), 0.24-0.15 (m, 1H). LCMS [M+H]$^+$ 581, RT 3.06 minutes (Method 10). Chiral LC* RT=31.85 minutes.

Diastereoisomer pair 2 (32 m, 19% Yield). $\delta_H$ (500 MHz, MeOH-d4) 8.15 (s, 1H), 6.35 (s, 1H), 4.98-4.73 (m, 1H), 4.64-4.48 (m, 1H), 3.74 (s, 3H), 3.38-3.32 (m, 2H), 3.13-3.01 (m, 2H), 3.01-2.88 (m, 2H), 2.40-2.28 (m, 2H), 2.08-1.97 (m, 1H), 1.80-1.66 (m, 1H), 1.27-1.21 (m, 1H), 0.95 (d, J=6.0 Hz, 3H), 0.79-0.71 (m, 1H), 0.70-0.60 (m, 1H), 0.44-0.36 (m, 1H), 0.25-0.15 (m, 1H). LCMS [M+H]$^+$ 581, RT 3.06 minutes (Method 10). Chiral LC* RT=37.71 minutes.

* Chiral analysis using Chiralcel OD-H (4.6×250 mm 5 µm) column, flow rate 0.5 mL/min, eluting with 70:30 Heptane:Ethanol, 60 minutes run time on a Waters 2795

Example 392

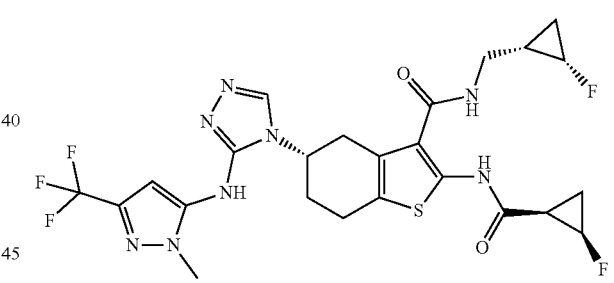

(5S)-2-[[(1R,2R)-2-fluorocyclopropanecarbonyl]amino]-N-[[(1S,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (77%, 90 mg, 0.14 mmol), [(1S,2S)-2-fluorocyclopropyl]methanamine hydrochloride (53 mg, 0.420 mmol), DIPEA (73 ⌷L, 0.420 mmol), and acetonitrile (6 mL). Reaction time: 2 hours at 75° C. in a sealed tube. The solution was concentrated under reduced pressure, then purified by revers phase column chromatography eluting with 5-95% Acetonitrile (0.1% formic acid) in Water (0.1% formic acid) to give the title compound (38 mg, 46% Yield). $\delta_H$ (500 MHz, MeOH-d4) 8.34 and 7.93 (2×br s, 1H), 6.50 and 6.21 (2×br s, 1H), 4.96-4.8 (m, 1H), 4.77-4.53 (m, 2H), 3.82-3.68 (m, 3H), 3.66-3.57 (m, 1H), 3.40 (dd, J=14.1, 7.9 Hz, 1H), 3.36-3.32 (m, 1H), 3.23-2.72

(m, 3H), 2.46-2.19 (m, 2H), 2.11-1.96 (m, 1H), 1.84-1.64 (m, 1H), 1.37-1.11 (m, 2H), 0.90-0.62 (m, 2H). LCMS [M+H]⁺ 585, RT 2.78 minutes (Method 10).

Example 393 & 394

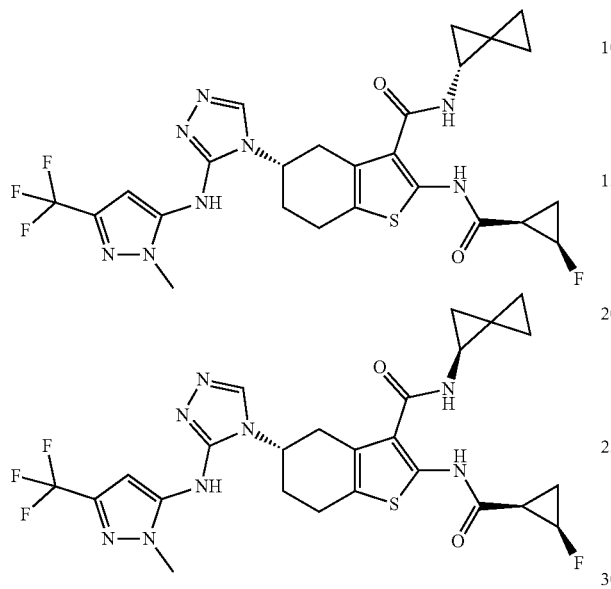

(5S)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-N-[(2R)-spiro[2.2]pentan-2-yl]-4,5,6,7-tetrahydro-1-benzothiophene-3-carboxamide (5S)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-N-[(2S)-spiro[2.2]pentan-2-yl]-4,5,6,7-tetrahydro-1-benzothiophene-3-carboxamide The title compound was obtained following general method 1 with intermediate 455 (77%, 90 mg, 0.14 mmol), spiro[2.2]pentan-2-amine hydrochloride (50 mg, 0.420 mmol), DIPEA (73 µL, 0.420 mmol), and acetonitrile (6 mL). Reaction time: 2 hours at 75° C. in a sealed tube. The solution was concentrated under reduced pressure, then purified by revers phase column chromatography eluting with 5-95% Acetonitrile (0.1% formic acid) in Water (0.1% formic acid) to give a mixture of diastereomers (115 mg). Chiral SFC (35% Ethanol: 65% CO₂ with Chiralpak IC, 25 cm column, at 15 mL/min) gave the title compounds.

Isomer 1 (7 mg, 8.6% Yield) $\delta_H$ (500 MHz, MeOH-d4) 8.30 and 7.93 (br s, 1H), 6.47 and 6.24 (br s, 1H), 4.99-4.75 (m, 1H), 4.63-4.47 (m, 1H), 3.74 (s, 3H), 3.30-3.24 (m, 1H), 3.22-3.17 (m, 1H), 3.07-2.80 (m, 3H), 2.40-2.27 (m, 2H), 2.10-1.97 (m, 1H), 1.83-1.64 (m, 1H), 1.32-1.19 (m, 2H), 1.09-0.95 (m, 2H), 0.89-0.79 (m, 2H), 0.78-0.70 (m, 1H). LCMS [M+H]⁺ 579, RT 2.93 minutes (Method 10). Chiral SFC* RT=6.98 minutes.

Isomer 2 (11 mg, 14% Yield) $\delta_H$ (500 MHz, MeOH-d4) 8.29 and 7.93 (2×br s, 1H), 6.46 and 6.25 (2×br s, 1H), 5.00-4.76 (m, 1H), 4.63-4.46 (m, 1H), 3.75 (s, 3H), 3.30-3.23 (m, 1H), 3.17-3.09 (m, 1H), 3.08-2.80 (m, 3H), 2.40-2.27 (m, 2H), 2.09-1.98 (m, 1H), 1.81-1.65 (m, 1H), 1.34-1.22 (m, 2H), 1.05-0.95 (m, 2H), 0.91-0.82 (m, 2H), 0.76-0.68 (m, 1H). LCMS [M+H]⁺ 579, RT 2.92 minutes (Method 10). Chiral SFC* RT=14.79 minutes.

* Chiral analysis using Chiralpak IC (4.6×250 mm 5 µm) column, flow rate 4 mL/min, eluting with 35% Ethanol: 65% CO₂, 20 minutes run time.

Example 395

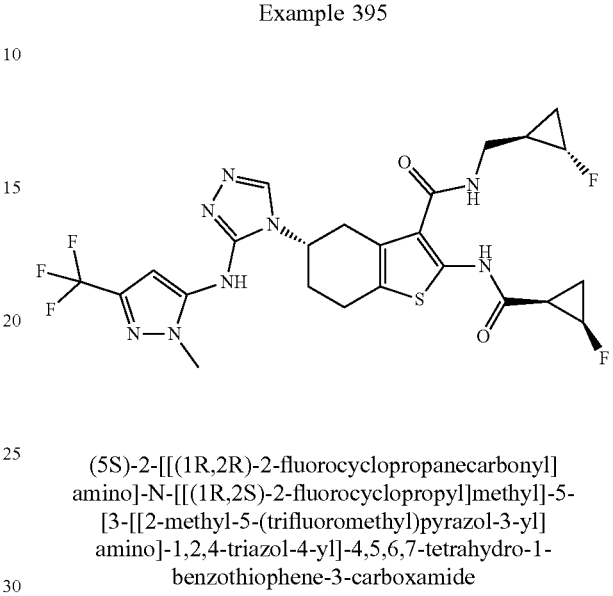

(5S)-2-[[(1R,2R)-2-fluorocyclopropanecarbonyl]amino]-N-[[(1R,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (77%, 40 mg, 0.06 mmol), intermediate 588 (6.6 mg, 0.07 mmol) (6% W/V in DMSO, 1 mL was used), and acetonitrile (1 mL). Reaction time: 2 hours at 75° C. in a sealed tube. The solution was concentrated under reduced pressure. Purification by revers phase column chromatography eluting with 5-95% Acetonitrile (0.1% formic acid) in Water (0.1% formic acid) followed by a second column (silica) eluting with a gradient of 50% to 100% EtOAc in heptane gave the title compound (7.3 mg, 20% Yield). $\delta_H$ (500 MHz, MeOH-d4) 8.36 and 7.94 (2×s, 1H, rotamers), 6.50 and 6.21 (2×s, 1H, rotamers), 5.10-4.73 (m, 1H), 4.67-4.36 (m, 2H), 3.78 and 3.71 (2×s, 3H, rotamers), 3.42-3.30 (m, 21H), 3.19-2.77 (m, 4H), 2.42-2.21 (m, 21H), 2.15-1.97 (m, 1H), 1.85-1.65 (m, 1H), 1.67-1.41 (m, 1H), 1.35-1.15 (m, 1H), 1.10-0.89 (m, 1H), 0.77-0.52 (m, 1H). LCMS [M+H]⁺ 585, RT 2.82 minutes (Method 10).

Example 396

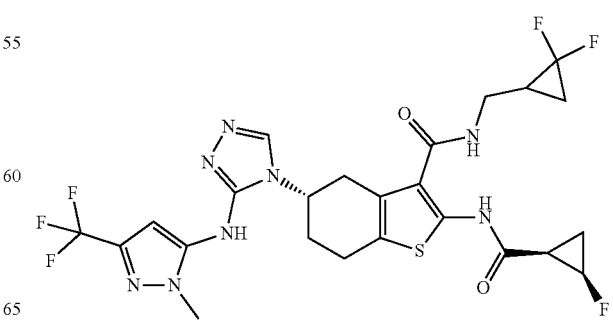

(5S)—N-[(2,2-difluorocyclopropyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (90%, 35 mg, 0.06 mmol), (2,2-difluorocyclopropyl)methanamine hydrochloride (27 mg, 0.191 mmol), DIPEA (33 ▒L, 0.191 mmol), and acetonitrile (3 mL). Reaction time: 2 hours at 75° C. in a sealed tube. The solution was concentrated under reduced pressure. Purification by revers phase column chromatography eluting with 5-95% Acetonitrile (0.1% formic acid) in Water (0.1% formic acid) gave the title compound (23 mg, 60% Yield). $\delta_H$ (500 MHz, MeOH-d4) 8.34 and 7.95 (2×s, 1H, rotamers), 6.49 and 6.22 (2×br s, 1H, rotamers), 5.02-4.73 (m, 1H), 4.63-4.46 (m, 1H), 3.75 (s, 3H), 3.64-3.35 (m, 1H), 3.50-3.44 (m, 1H), 3.35-3.32 (m, 1H), 3.15-2.82 (m, 3H), 2.45-2.27 (m, 2H), 2.12-1.90 (m, 2H), 1.83-1.66 (m, 1H), 1.53-1.40 (m, 1H), 1.36-1.14 (m, 2H). LCMS [M+H]$^+$ 603, RT 2.92 minutes (Method 10).

Example 397 & 398

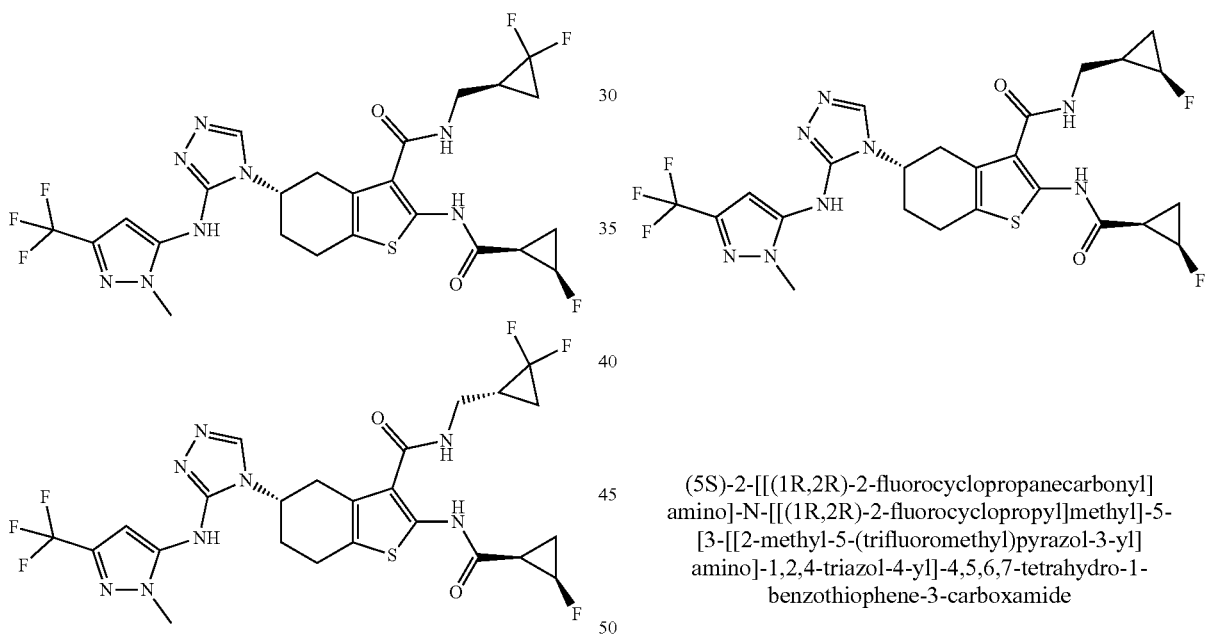

(5S)—N-[[(1R)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (5S)—N-[[(1S)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide Example 396 (65.0 mg, 0.11 mmol) was separated by chiral SFC (20% Methanol: 80% CO$_2$ with Chiralpak IC 25 cm column at 15 mL/min) to give the title compounds:

Isomer 1 (12.9 mg, 19.6% Yield) $\delta_H$ (500 MHz, MeOH-d4) 8.14 (s, 1H), 6.36 (s, 1H), 5.05-4.71 (m, 1H), 4.62-4.48 (m, 1H), 3.74 (s, 3H), 3.60-3.50 (m, 1H), 3.41-3.34 (m, 1H), 3.34-3.27 (m, 1H), 3.13-3.03 (m, 1H), 3.01-2.85 (m, 2H), 2.40-2.29 (m, 2H), 2.08-1.92 (m, 2H), 1.81-1.68 (m, 1H), 1.53-1.39 (m, 1H), 1.33-1.17 (m, 2H). LCMS [M+H]$^+$ 603, RT 2.95 minutes (Method 10). Chiral SFC* RT=20.41 minutes.

Isomer 2 (15.3 mg, 23.5% Yield) $\delta_H$ (500 MHz, MeOH-d4) 8.33 and 7.95 (2×br s, 1H), 6.48 and 6.24 (2×br s, 1H), 5.03-4.77 (m, 1H), 4.65-4.50 (m, 1H), 3.75 (s, 3H), 3.55-3.40 (m, 2H), 3.35-3.28 (m, 1H), 3.15-2.84 (m, 3H), 2.41-2.27 (m, 2H), 2.09-1.92 (m, 2H), 1.80-1.69 (m, 1H), 1.52-1.41 (m, 1H), 1.30-1.20 (m, 2H). LCMS [M+H]$^+$ 603, RT 2.94 minutes (Method 10). Chiral SFC* RT=24.85 minutes.

* Chiral analysis using Chiralpak IC (4.6×250 mm 5 μm) column, flow rate 4 mL/min, eluting with 20% Methanol: 80% CO$_2$, 30 minutes run time.

Example 399

(5S)-2-[[(1R,2R)-2-fluorocyclopropanecarbonyl]amino]-N-[[(1R,2R)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (77%, 90 mg, 0.14 mmol), [(1R,2R)-2-fluorocyclopropyl]methanamine hydrochloride (53 mg, 0.420 mmol), DIPEA (73 ▒L, 0.420 mmol), and acetonitrile (6 mL). Reaction time: 2 hours at 75° C. in a sealed tube. The solution was concentrated under reduced pressure. Purification by revers phase column chromatography eluting with 5-95% Acetonitrile (0.1% formic acid) in Water (0.1% formic acid) gave the title compound (32 mg, 39% Yield). $\delta_H$ (500 MHz, MeOH-d4) 8.33 and 794(2×br s, 1H), 6.48 and 6.24 (2×br s, 1H), 5.04-4.78 (m, 1H), 4.75-4.49 (m, 2H), 3.75 (s, 3H), 3.72-3.66 (m, 1H), 3.37-3.32 (m, 1H), 3.30-3.26 (m, 1H), 3.16-3.02 (m, 1H), 3.03-2.83 (m, 2H), 2.43-2.27 (m, 2H), 2.11-1.94 (m, 1H), 1.80-1.64 (m, 1H), 1.33-1.18 (m, 2H), 0.88-0.67 (m, 2H). LCMS [M+H]$^+$ 585, RT 2.81 minutes (Method 10).

Example 400

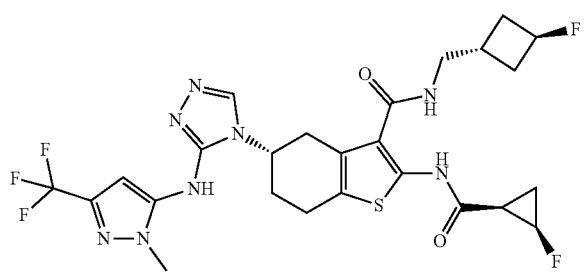 [SMILES: Cn1nc(C(F)(F)F)cc1Nc1nncn1[C@H]1CCc2sc(NC(=O)[C@H]3C[C@H]3F)c(C(=O)NC[C@H]3C[C@H](F)C3)c2C1]

(5S)—N-[trans-(3-fluorocyclobutyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (77%, 90 mg, 0.14 mmol), (3-fluorocyclobutyl)methanamine hydrochloride (9:1 trans:cis, 59 mg, 0.420 mmol), DIPEA (73 ⊠L, 0.420 mmol), and acetonitrile (6 mL). Reaction time: 2 hours at 75° C. in a sealed tube. The solution was concentrated under reduced pressure. Purification by revers phase column chromatography eluting with 5-95% Acetonitrile (0.1% formic acid) in Water (0.1% formic acid) gave a mixture of diastereoisomers (45 mg, 9:1, trans:cis). The mixture was separated by HPLC to give the title compound (19 mg, 21% Yield). $\delta_H$ (500 MHz, MeOH-d4) 8.56 (s, 1H), 8.11 (s, 1H), 6.34 (s, 1H), 5.08 (s, 1H), 4.84 (s, 1H), 4.62-4.52 (m, 1H), 3.75 (s, 3H), 3.50-3.42 (m, 1H), 3.38-3.33 (m, 1H), 3.29-3.24 (m, 1H), 3.09-2.85 (m, 3H), 2.64-2.51 (m, 1H), 2.43-2.10 (m, 6H), 2.09-1.97 (m, 1H), 1.83-1.67 (m, 1H), 1.36-1.18 (m, 1H). LCMS [M+H]$^+$ 599, RT 2.96 minutes (Method 10).

Example 401

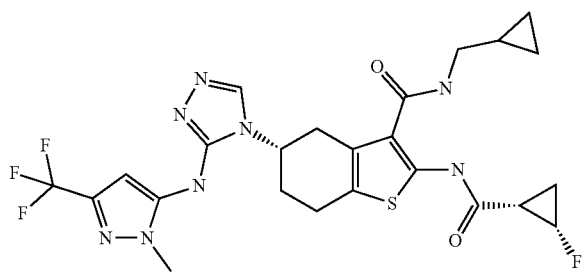 [SMILES: Cn1nc(C(F)(F)F)cc1Nc1nncn1[C@H]1CCc2sc(NC(=O)[C@@H]3C[C@@H]3F)c(C(=O)NCC3CC3)c2C1]

(5S)—N-(cyclopropylmethyl-2-[[(1S,2S)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide To a mixture of intermediate 432 (90 mg, 0.15 mmol), pyridine (37 ⊠L, 0.46 mmol) and cyclopropylmethanamine (16.5 mg, 0.23 mmol) in DCM (6 mL), 2,4,6-Tripropyl-1,3,5,2,4,6-trioxatriphosphorinane-2,4,6-trioxide (184 ⊠L, 0.31 mmol) was slowly added at 0° C. The reaction mixture was slowly allowed to warm to r.t. and stirred for 16 h. Reaction mixture was diluted with DCM (20 mL) then water (15 mL). The aqueous layer was extracted with DCM (2×10 mL) and the organic fractions combined, dried (Na$_2$SO$_4$) and concentrated under vacuum. The residue was dissolved in DMF (3 mL) and cyclopropylmethanamine (16 mg, 0.231 mmol) was added and reaction mixture heated at 100° C. for 2 hours. The reaction mixture was concentrated under reduced pressure and the residue purified using reverse phase column chromatography eluting with 5-95% Acetonitrile (0.1% formic acid) in Water (0.1% formic acid) to give the title compound (35 mg, 40% Yield). $\delta_H$ (500 MHz, MeOH-d4) 8.34 and 7.93 (2×s, 1H, rotamers), 6.49 and 6.22 (2×s, 1H, rotamers), 5.00-4.75 (m, 1H), 4.64-4.47 (m, 1H), 3.75 (s, 3H), 3.40-3.32 (m, 1H), 3.29-3.22 (m, 1H), 3.22-3.13 (m, 1H), 3.12-2.80 (m, 3H), 2.42-2.28 (m, 2H), 2.09-1.98 (m, 1H), 1.81-1.66 (m, 1H), 1.31-1.20 (m, 1H), 1.13-1.00 (m, 1H), 0.51-0.41 (m, 2H), 0.27-0.20 (m, 2H). LCMS [M+H]$^+$ 567, RT 2.86 minutes (Method 10).

Example 402

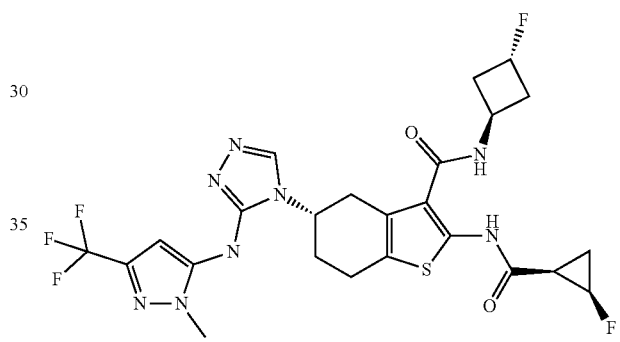

(5S)—N-(trans-3-fluorocyclobutyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide The title compound was obtained following general method 1 with intermediate 455 (77%, 90 mg, 0.14 mmol), trans-3-fluorocyclobutanamine hydrochloride (53 mg, 0.420 mmol), DIPEA (73 ⊠L, 0.420 mmol), and acetonitrile (6 mL). Reaction time: 2 hours at 75° C. in a sealed tube. The solution was concentrated under reduced pressure. Purification by revers phase column chromatography eluting with 5-95% Acetonitrile (0.1% formic acid) in water (0.1% formic acid) gave the title compound (45 mg, 55% Yield). $\delta_H$ (500 MHz, MeOH-d4) 8.11 (br s, 1H), 6.36 (br s, 1H), 5.26-5.06 (m, 1H), 5.00 j-4.75 (m, 1H), 4.70-4.49 (m, 2H), 3.75 (s, 3H), 3.30-3.25 (m, 1H), 3.07-3.00 (m, 1H), 2.99-2.82 (m, 2H), 2.65-2.50 (m, 2H), 2.49-2.36 (m, 2H), 2.36-2.27 (m, 2H), 2.10-1.97 (m, 1H), 1.81-1.66 (m, 1H), 1.31-1.19 (m, 1H). LCMS [M+H]$^+$ 585, RT 2.76 minutes (Method 10).

Example 403

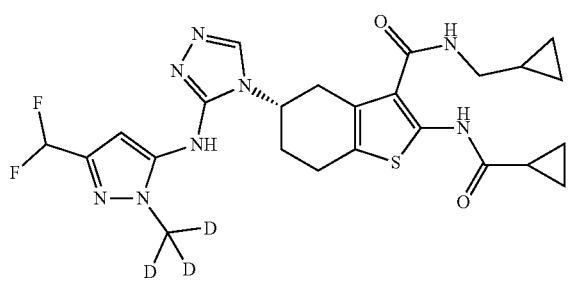 [SMILES: [2H]C([2H])([2H])n1nc(C(F)F)cc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[[5-(difluoromethyl)-2-(trideuteriomethyl)pyrazol-3-yl]amino]-1,2,4-triazol-4-yl]-4,5,6,7-tetrahydrobenzothiophene-3-carboxamide The title compound was prepared by a method analogous to that used to prepare Example 108, using intermediate 573, intermediate 117, and formyl hydrazine. Crystallization of the crude material from methanol afforded the title compound (2.96 g, 47% Yield). $\delta_H$ (400 MHz, DMSO-d6) 12.07 and 8.74 (s, 1H rotamer), 11.26 and 11.21 (s, 1H rotamer), 8.40 and 8.19 (s, 1H rotamers 40:60), 7.73 (m, 1H), 6.86 and 6.75 (t, 1H rotamer), 6.41 and 6.20 (s, 1H rotamer), 4.46 (m, 1H), 3.13 (m, 2H), 2.99 (m, 2H), 2.85 (m, 2H), 2.20 (m, 2H), 1.93 (m, 1H), 1.00 (m, 1H), 0.85 (m, 4H), 0.36 (m, 2H), 0.19 (m, 2H). HRMS [M+H+]$^+$ 534.2290 ($C_{24}H_{25}D_3F_2N_8O_2S$=533.1789).

Example 404

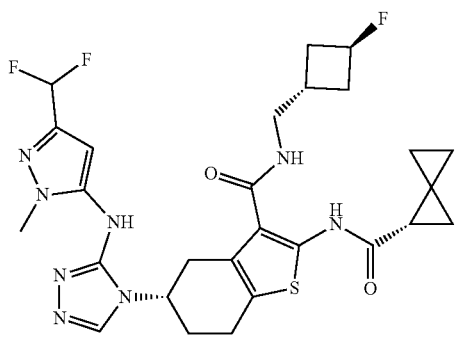 [SMILES: Cn1nc(C(F)F)cc1Nc1nncn1[C@H]1CCc2sc(NC(=O)[C@H]3CC34CC4)c(C(=O)NC[C@H]3C[C@H](F)C3)c2C1]

(5S)-5-[3-[[5-(Difluoromethyl)-2-methylpyrazol-3-yl]amino]-1,2,4-triazol-4-yl]-N-[trans-(3-fluorocyclobutyl)methyl]-2-[[(2S)-spiro[2.2]pentane-2-carbonyl]amino]-4,5,6,7-tetrahydro-1-benzothiophene-3-carboxamide The title compound was obtained following general method 1 with intermediate 578 (30 mg, 0.06 mmol), trans-(3-fluorocyclobutyl)methanamine hydrochloride (27 mg, 3 equivalents), DIPEA (3.5 equivalents), and MeCN (1 mL). Reaction time: 30 min at 70° C. Filtration and purification using column chromatography eluting with a gradient of 0-15% MeOH in DCM gave the title compound (21 mg, 59% Yield). $\delta_H$ (300 MHz, DMSO-d6) 12.08 (s, 0.6H), 11.09 (s, 0.4H), 11.04 (s, 0.6H), 8.74 (s, 0.4H), 8.39 (s, 0.4H), 8.19 (s, 0.6H), 7.76-7.56 (m, 1H), 7.05-6.57 (m, 1H), 6.41 (s, 0.4H), 6.20 (s, 0.6H), 5.25-5.14 (m, 0.6H), 5.05-4.97 (m, 0.4H), 4.54-4.36 (m, 1H), 3.71 (s, 1.2H), 3.61 (s, 1.8H), 3.38-3.05 (m, 4H), 3.03-2.71 (m, 3H), 2.30-2.05 (m, 7H), 1.47-1.34 (m, 2H), 1.01-0.75 (m, 4H) [Note: contained 2 tautomers in an approximate ratio of 0.6:0.4]. LCMS [M+H]$^+$ 589, RT 1.76 minutes (Method 25).

Example 405

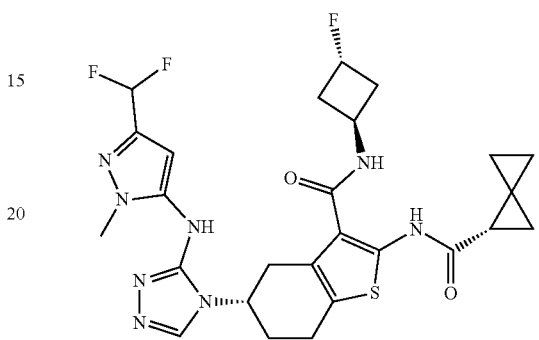

(5S)-5-[3-[[5-(Difluoromethyl)-2-methylpyrazol-3-yl]amino]-1,2,4-triazol-4-yl]-N-(trans-3-fluorocyclobutyl)-2-[[(2S)-spiro[2.2]pentane-2-carbonyl]amino]-4,5,6,7-tetrahydro-1-benzothiophene-3-carboxamide The title compound was obtained following general method 1 with intermediate 578 (30 mg, 0.06 mmol), trans-3-fluorocyclobutanamine hydrochloride (24 mg, 3 equivalents), DIPEA (3.5 equivalents), and MeCN (1 mL). Reaction time: 30 min at 70° C. Filtration and purification using column chromatography eluting with a gradient of 0-15% MeOH in DCM gave the title compound (23 mg, 66% Yield). $\delta_H$ (300 MHz, DMSO-d6) 12.07 (s, 0.6H), 10.88 (s, 0.4H), 10.84 (s, 0.6H), 8.74 (s, 0.4H), 8.37 (s, 0.4H), 8.15 (s, 0.6H), 8.08-7.95 (m, 1H), 7.05-6.57 (m, 1H), 6.41 (s, 0.4H), 6.21 (s, 0.6H), 5.35-5.25 (m, 0.6H), 5.15-5.07 (m, 0.4H), 4.58-4.37 (m, 2H), 3.71 (s, 1.2H), 3.62 (s, 1.8H), 3.21-2.71 (m, 4H), 2.47-2.10 (m, 7H), 1.47-1.20 (m, 2H), 1.00-0.72 (m, 4H) [Note: contained 2 tautomers in an approximate ratio of 0.6:0.4]. LCMS [M+H]$^+$ 575, RT 1.67 minutes (Method 25).

Example 406

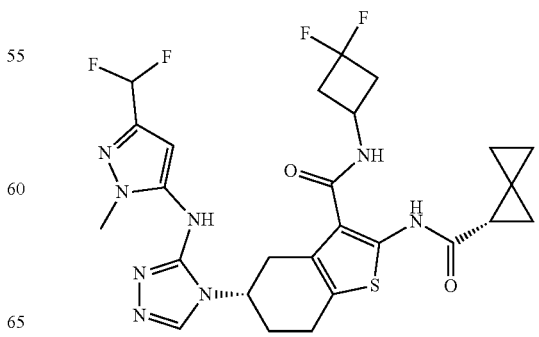

733

(5S)—N-(3,3-Difluorocyclobutyl)-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide The title compound was obtained following general method 1 with intermediate 578 (30 mg, 0.06 mmol), 3,3-difluorocyclobutanamine hydrochloride (27 mg, 3 equivalents), DIPEA (3.5 equivalents), and MeCN (1 mL). Reaction time: 30 min at 70° C. Filtration and purification using column chromatography eluting with a gradient of 0-15% MeOH in DCM gave the title compound (20 mg, 54% Yield). $\delta_H$ (300 MHz, DMSO-d6) 12.08 (s, 0.6H), 10.89 (s, 0.4H), 10.86 (s, 0.6H), 8.74 (s, 0.4H), 8.37 (s, 0.4H), 8.21-8.09 (m, 1.6H), 7.06-6.57 (m, 1H), 6.41 (s, 0.4H), 6.21 (s, 0.6H), 4.51-4.38 (m, 1H), 4.27-4.13 (m, 1H), 3.71 (s, 1.2H), 3.61 (s, 1.8H), 3.21-2.58 (m, 8H), 2.30-2.11 (m, 3H), 1.48-1.35 (m, 2H), 0.98-0.76 (m, 4H) [Note: contained 2 tautomers in an approximate ratio of 0.6:0.4]. LCMS [M+H]$^+$ 593, RT 1.76 minutes (Method 25).

Example 407

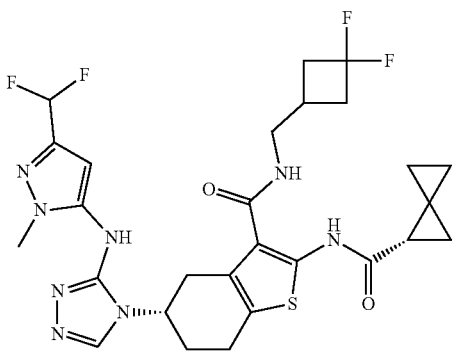 [SMILES: Cn1nc(C(F)F)cc1Nc1nncn1[C@H]1CCc2sc(NC(=O)[C@H]3CC34CC4)c(C(=O)NCC3CC(F)(F)C3)c2C1]

(5S)—N-[(3,3-Difluorocyclobutyl)methyl]-5-[3-[[5-(difluoromethyl)-2-methylpyrazol-3-yl]amino]-1,2,4-triazol-4-yl]-2-[[(2S)-spiro[2,2]pentane-2-carbonyl]amino]-4,5,6,7-tetrahydro-1-benzothiophene-3-carboxamide The title compound was obtained following general method 1 with intermediate 578 (30 mg, 0.06 mmol), (3,3-difluorocyclobutyl)methanamine hydrochloride (29 mg, 3 equivalents), DIPEA (3.5 equivalents), and MeCN (1 mL). Reaction time: 30 min at 70° C. Filtration and purification using column chromatography eluting with a gradient of 0-15% MeOH in DCM gave the title compound (30 mg, 81% Yield). $\delta_H$ (300 MHz, DMSO-d6) 12.07 (s, 0.6H), 11.08 (s, 0.4H), 11.03 (s, 0.6H), 8.73 (s, 0.4H), 8.38 (s, 0.4H), 8.17 (s, 0.6H), 7.80-7.70 (m, 1H), 7.05-6.57 (m, 1H), 6.40 (s, 0.4H), 6.20 (s, 0.6H), 4.53-4.38 (m, 1H), 3.71 (s, 1.2H), 3.61 (s, 1.8H), 3.46-3.25 (m, 3H), 3.20-2.77 (m, 4H), 2.64-2.12 (m, 7H), 1.50-1.35 (m, 2H), 1.01-0.75 (m, 4H) [Note: contained 2 tautomers in an approximate ratio of 0.6:0.4]. LCMS [M+H]$^+$ 607, RT 1.83 minutes (Method 25).

734

Example 408

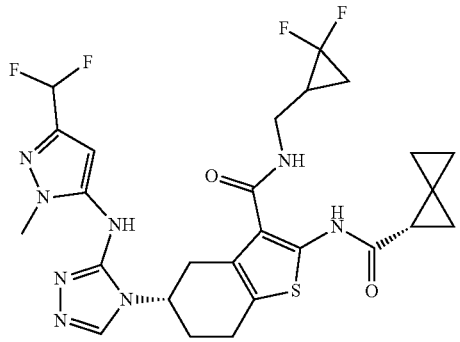 [SMILES: Cn1nc(C(F)F)cc1Nc1nncn1[C@H]1CCc2sc(NC(=O)[C@H]3CC34CC4)c(C(=O)NCC3CC3(F)F)c2C1]

(5S)—N-[(2,2-Difluorocyclopropyl)methyl]-5-[3-[[5-(difluoromethyl)-2-methylpyrazol-3-yl]amino]-1,2,4-triazol-4-yl]-2-[[(2S)-spiro [2.2]pentane-2-carbonyl]amino]-4,5,6,7-tetrahydro-1-benzothiophene-3-carboxamide The title compound was obtained following general method 1 with intermediate 578 (60 mg, 0.12 mmol), (2,2-difluorocyclopropyl)methanamine hydrochloride (53 mg, 3 equivalents), DIPEA (3.5 equivalents), and MeCN (2 mL). Reaction time: 30 min at 70° C. Filtration and purification using column chromatography eluting with a gradient of 0-15% MeOH in DCM gave the title compound (38 mg, 52% Yield). $\delta_H$ (300 MHz, DMSO-d6) 12.07 (s, 0.6H), 11.17-11.09 (m, 1H), 8.74 (s, 0.4H), 8.40 (s, 0.4H), 8.19 (s, 0.6H), 7.91-7.77 (m, 1H), 7.05-6.57 (m, 1H), 6.41 (s, 0.4H), 6.20 (s, 0.6H), 4.55-4.38 (m, 1H), 3.71 (s, 1.2H), 3.61 (s, 1.8H), 3.45-2.77 (m, 7H), 2.32-2.12 (m, 3H), 2.09-1.90 (m, 1H), 1.59-1.22 (m, 3H), 1.01-0.76 (m, 4H) [Note: contained 2 tautomers in an approximate ratio of 0.6:0.4]. LCMS [M+H]$^+$ 593, RT 1.78 minutes (Method 25).

Example 409 & 410

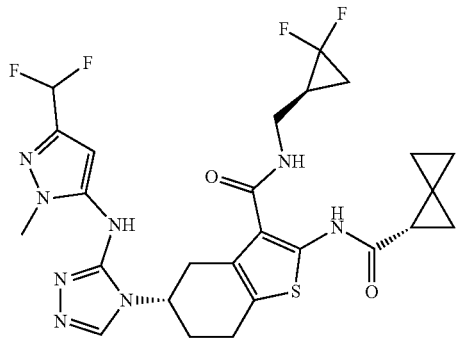

-continued

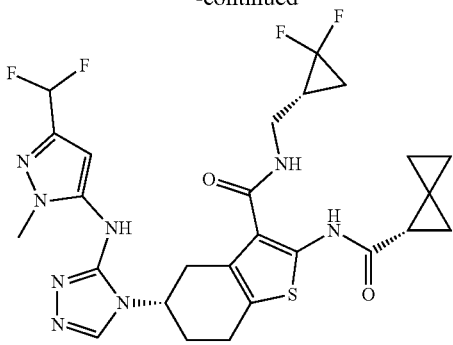

(5S)—N-[[(1S)-2,2-Difluorocyclopropyl]methyl]-5-
[3-[[5-(difluoromethyl)-2-methyl-pyrazol-3-yl]
amino]-1,2,4-triazol-4-yl]-2-[[(2S)-spiro[2.2]pen-
tane-2-carbonyl]amino]-4,5,6,7-
tetrahydrobenzothiophene-3-carboxamide (5S)—N-[[(1R)-2,2-difluorocyclopropyl]methyl]-5-
[3-[[5-(difluoromethyl)-2-methyl-pyrazol-3-yl]
amino]-1,2,4-triazol-4-yl]-2-[[(2S)-spiro[2.2]pen-
tane-2-carbonyl]amino]-4,5,6,7-
tetrahydrobenzothiophene-3-carboxamide The title compounds were obtained by chiral chromatography of Example 408 (31.5 mg) to give:
Isomer 1 (9.4 mg, 30% Yield) δ$_H$ (300 MHz, DMSO-d6) 12.07 (s, 0.6H), 11.17-11.03 (m, 1H), 8.74 (s, 0.4H), 8.39 (s, 0.4H), 8.19 (s, 0.6H), 7.91-7.78 (m, 1H), 7.05-6.57 (m, 1H), 6.41 (s, 0.4H), 6.20 (s, 0.6H), 4.55-4.35 (m, 1H), 3.71 (s, 1.2H), 3.61 (s, 1.8H), 3.45-2.77 (m, 7H), 2.31-2.13 (m, 3H), 2.07-1.90 (m, 1H), 1.58-1.20 (m, 3H), 1.02-0.75 (m, 4H) [Note: contained 2 tautomers in an approximate ratio of 0.6:0.4]. LCMS [M+H]$^+$ 593, RT 1.79 minutes (Method 25). Chiral LC* RT=4.27 minutes.
Isomer 2 (7.4 mg, 24% Yield) δ$_H$ (300 MHz, DMSO-d6) 12.08 (s, 0.6H), 11.18-11.07 (m, 1H), 8.74 (s, 0.4H), 8.40 (s, 0.4H), 8.19 (s, 0.6H), 7.90-7.79 (m, 1H), 7.05-6.57 (m, 1H), 6.41 (s, 0.4H), 6.20 (s, 0.6H), 4.54-4.38 (m, 1H), 3.71 (s, 1.2H), 3.61 (s, 1.8H), 3.48-2.75 (m, 7H), 2.30-2.14 (m, 3H), 2.09-1.90 (m, 1H), 1.59-1.22 (m, 3H), 1.01-0.75 (m, 4H) [Note: contained 2 tautomers in an approximate ratio of 0.6:0.4]. LCMS [M+H]$^+$ 593, RT 1.79 minutes (Method 25). Chiral LC* RT=4.96 minutes.

* Chiral analysis performed using a Chiralpak IG-3 (150×4.6 mm 3 μm) column, eluted using an isocratic 50% heptane in EtOAc (+0.1% DEA) method, flow rate of 1.5 mL/min, 100 bar and a 8 minute run time minute run time on an Agilent Infinity II 1290.

Example 411

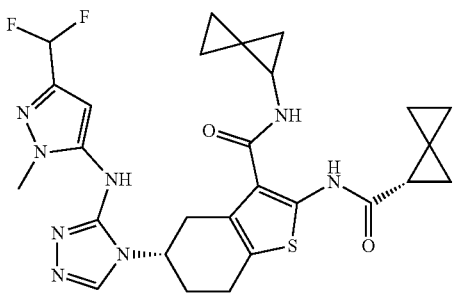 [SMILES: Cn1nc(C(F)F)cc1Nc1nncn1[C@H]1CCc2sc(NC(=O)[C@H]3CC34CC4)c(C(=O)NC3CC34CC4)c2C1]

(5S)-5-[3-[[5-(Difluoromethyl)-2-methylpyrazol-3-
yl]amino]-1,2,4-triazol-4-yl]-2-[[(2S)-spiro[2.2]pen-
tane-2-carbonyl]amino]-N-spiro[2.2]pentan-2-yl-4,5,
6,7-tetrahydro-1-benzothiophene-3-carboxamide The title compound was obtained following general method 1 with intermediate 578 (60 mg, 0.12 mmol), spiro[2.2]pentan-2-amine hydrochloride (44 mg, 3 equivalents), DIPEA (3.5 equivalents), and MeCN (2 mL). Reaction time: 30 min at 70° C. Filtration and purification using column chromatography eluting with a gradient of 0-15% MeOH in DCM gave the title compound (49 mg, 70% Yield). δ$_H$ (300 MHz, DMSO-d6) 12.08 (s, 0.6H), 10.97-10.85 (m, 1H), 8.73 (s, 0.4H), 8.35 (s, 0.4H), 8.17-8.12 (m, 0.6H), 7.80-7.70 (m, 1H), 7.05-6.57 (m, 1H), 6.41 (s, 0.4H), 6.21 (s, 0.6H), 4.53-4.35 (m, 1H), 3.71 (s, 1.2H), 3.61 (s, 1.8H), 3.21-2.75 (m, 5H), 2.32-2.12 (m, 3H), 1.48-1.15 (m, 4H), 1.01-0.55 (m, 8H) [Note: contained 2 tautomers in an approximate ratio of 0.6:0.4]. LCMS [M+H]$^+$ 569, RT 1.78 minutes (Method 25).

Example 412

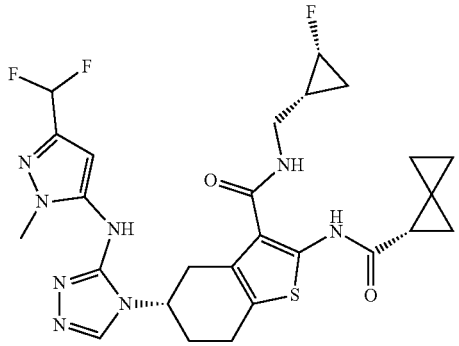 [SMILES: Cn1nc(C(F)F)cc1Nc1nncn1[C@H]1CCc2sc(NC(=O)[C@H]3CC34CC4)c(C(=O)NC[C@H]3C[C@H]3F)c2C1]

(5S)-5-[3-[[5-(Difluoromethyl)-2-methylpyrazol-3-
yl]amino]-1,2,4-triazol-4-yl]-N-[[(1R,2R)-2-fluoro-
cyclopropyl]methyl]-2-[[(2S)-spiro[2.2]pentane-2-
carbonyl]amino]-4,5,6,7-tetrahydro-1-
benzothiophene-3-carboxamide The title compound was obtained following general method 1 with intermediate 578 (30 mg, 0.06 mmol), [(1R,2R)-2-fluorocyclopropyl]methanamine hydrochloride (23 mg, 3 equivalents), DIPEA (3.5 equivalents), and MeCN (1 mL). Reaction time: 30 min at 70° C. Filtration and purification using column chromatography eluting with a gradient of 0-15% MeOH in DCM gave the title compound (22 mg, 61% Yield). δ$_H$ (300 MHz, DMSO-d6) 12.07 (s, 0.6H), 11.29-11.09 (m, 1H), 8.74 (s, 0.4H), 8.40 (s, 0.4H), 8.19 (s, 0.6H), 7.83-7.70 (m, 1H), 7.05-6.57 (m, 1H), 6.41 (s, 0.4H), 6.21 (s, 0.6H), 4.86-4.59 (m, 1H), 4.56-4.38 (m, 1H), 3.71 (s, 1.2H), 3.61 (s, 1.8H), 3.46-3.11 (m, 2H), 3.08-2.77 (m, 3H), 2.33-2.14 (m, 3H), 1.49-1.36 (m, 2H), 1.32-1.13 (m, 2H), 1.02-0.64 (m, 6H) [Note: contained 2 tautomers in an approximate ratio of 0.6:0.4]. LCMS [M+H]$^+$ 575, RT 1.69 minutes (Method 25).

Example 413

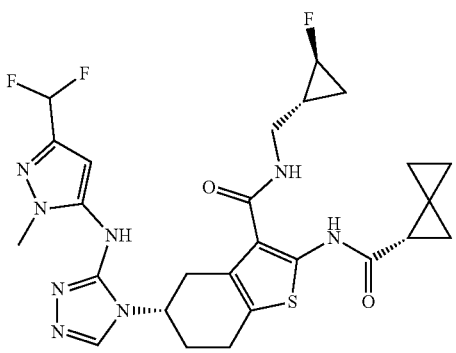 [SMILES: Cn1nc(C(F)F)cc1Nc1nncn1[C@H]1CCc2sc(NC(=O)[C@H]3CC34CC4)c(C(=O)NC[C@H]3C[C@@H]3F)c2C1]

(5S)-5-[3-[[5-(Difluoromethyl)-2-methylpyrazol-3-yl]amino]-1,2,4-triazo-4-yl]-N-[[(1R,2S)-2-fluorocyclopropyl]methyl]-2-[[(2S)-spiro[2.2]pentane-2-carbonyl]amino]-4,5,6,7-tetrahydro-1-benzothiophene-3-carboxamide The title compound was obtained following general method 1 with intermediate 578 (30 mg, 0.06 mmol), intermediate 588 (3 equivalents), DIPEA (3.5 equivalents), and MeCN (1 mL). Reaction time: 30 min at 70° C. Filtration and purification using HPLC (Method 5) gave the title compound (4 mg, 12% Yield). $\delta_H$ (300 MHz, DMSO-d6) 12.07 (s, 0.6H), 11.22-11.08 (m, 1H), 8.74 (s, 0.4H), 8.40 (s, 0.4H), 8.19 (s, 0.6H), 7.78-7.64 (m, 1H), 7.05-6.57 (m, 1H), 6.42 (s, 0.41H), 6.21 (s, 0.6H), 4.75-4.38 (m, 2H), 3.71 (s, 1.2H), 3.61 (s, 1.81H), 3.27-2.76 (m, 6H), 2.32-2.12 (m, 3H), 1.59-1.34 (m, 3H), 1.03-0.75 (m, 5H), 0.68-0.55 (m, 1H) [Note: contained 2 tautomers in an approximate ratio of 0.6:0.4]. LCMS [M+H]⁺ 575, RT 1.78 minutes (Method 25).

Example 414 & 415

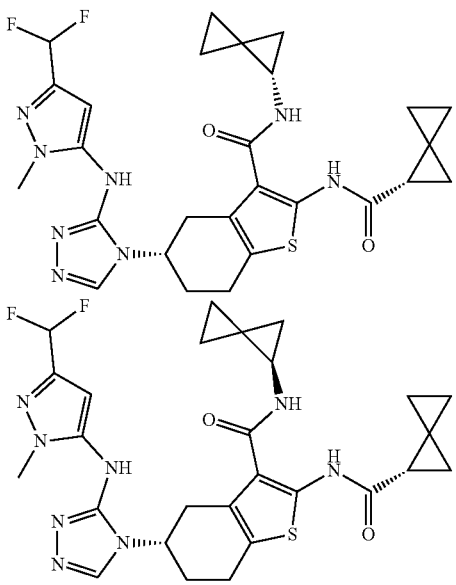

(5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2S)-spiro[2.2]pentan-2-yl]-4,5,6,7-tetrahydrobenzothiophene-3-carboxamide (5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2R)-spiro[2.2]pentan-2-yl]-4,5,6,7-tetrahydrobenzothiophene-3-carboxamide Example 411 (41.5 mg) was separated by chiral SFC (Chiracel OJ column, 250×20 mm, 5 μm, Isocratic 15% MeOH (+0.1% ammonium hydroxide) in CO₂, 100 mL/min, 20 minutes, 40° C. and 120 bar) to give the title compounds:

Isomer 1 (Peak 1, 8 mg, 19% Yield) $\delta_H$ (300 MHz, DMSO-d6) 12.08 (s, 0.6H), 11.00-10.83 (m, 1H), 8.74 (s, 0.4H), 8.35 (s, 0.4H), 8.15 (s, 0.6H), 7.88-7.63 (m, 1H), 7.03-6.58 (m, 1H), 6.41 (s, 0.4H), 6.21 (s, 0.6H), 4.51-4.34 (m, 1H), 3.70 (s, 1.2H), 3.61 (s, 1.8H), 3.24-2.75 (m, 5H), 2.31-2.09 (m, 3H), 1.44-1.15 (m, 4H), 0.99-0.57 (m, 8H) [Note: contained 2 tautomers in an approximate ratio of 0.6:0.4]. LCMS [M+H]⁺ 569, RT 1.76 minutes (Method 25).

Isomer 2 (Peak 2, 5 mg, 13% Yield) $\delta_H$ (300 MHz, DMSO-d6) 12.07 (s, 0.6H), 11.01-10.81 (m, 1H), 8.73 (s, 0.4H), 8.35 (s, 0.4H), 8.15 (s, 0.6H), 7.85-7.71 (m, 1H), 7.05-6.58 (m, 1H), 6.41 (s, 0.4H), 6.20 (s, 0.6H), 4.53-4.35 (m, 1H), 3.71 (s, 1.2H), 3.61 (s, 1.8H), 3.26-2.75 (m, 5H), 2.29-2.09 (m, 3H), 1.46-1.13 (m, 4H), 1.01-0.61 (m, 8H) [note: contained 2 tautomers in an approximate ratio of 0.6:0.4]. LCMS [M+H]⁺ 569, RT 1.77 minutes (Method 25).

Example 416

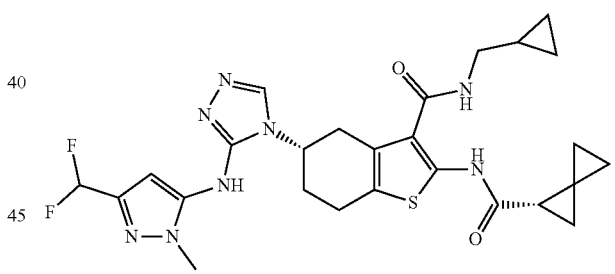

(5S)—N-(Cyclopropylmethyl)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide The title compound was obtained following general method 1 with intermediate 578 (16 mg, 0.03 mmol), cyclopropylmethanamine (9.4 mg, 0.132 mmol, 4 equivalents), and MeCN (1 mL). Reaction time: 1 hour at 90° C. Purification using column chromatography eluting with a gradient of 0-15% MeOH in DCM gave the title compound (9.7 mg, 53% Yield). $\delta_H$ (300 MHz, DMSO-d6) 12.08 (s, 0.6H), 11.23-11.10 (m, 1H), 8.74 (s, 0.4H), 8.40 (s, 0.4H), 8.20 (s, 0.6H), 7.69-7.57 (m, 1H), 7.00-6.62 (m, 1H), 6.41 (s, 0.4H), 6.20 (s, 0.6H), 4.53-4.39 (m, 1H), 3.71 (s, 1.21H), 3.61 (s, 1.8H), 3.25-2.77 (m, 6H), 2.28-2.14 (m, 3H), 1.47-1.36 (m, 2H), 1.05-0.77 (m, 5H), 0.39-0.32 (m, 2H), 0.23-0.15 (m, 2H) [Note: contained 2 tautomers in an approximate ratio of 0.6:0.4]. LCMS [M+H]+ 557, RT 1.78 minutes (Method 25).

Example 417a & 417

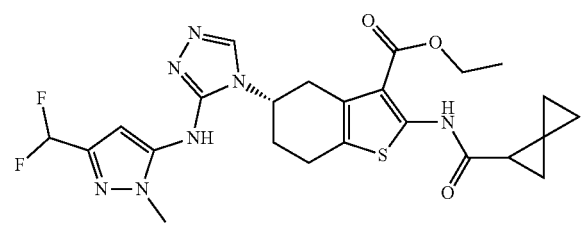

Ethyl (5S)-5-[3-[[5-(difluoromethyl)-2-methyl-pyrazol-3-yl]amino]-1,2,4-triazol-4-yl]-2-(spiro[2.2]pentane-2-carbonylamino)-4,5,6,7-tetrahydrobenzothiophene-3-carboxylate (417a)

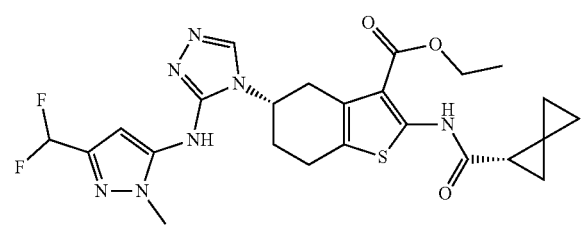

Ethyl (5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxylate (417)

Example 417a was synthesised using general method 8, intermediate 576 (6.65 g, 12.7 mmol) and comparable stoichiometries of reagents. The product was purified by flash chromatography eluting with 1-10% MeOH/DCM to afford the title compound (3.82 g, 57%) as a colourless powder. LCMS [M+H]+ 532, RT 1.87 minutes (Method 25).

Example 417 was obtained by chiral chromatography of Example 417a (3.46 g, 6.51 mmol) to give:

Peak 1 (1.49 g, 43% Yield). $δ_H$ (300 MHz, DMSO-d6) 12.07 (s, 0.7H), 11.05 (s, 1H), 8.74 (s, 0.3H), 8.43 (s, 0.31H), 8.19 (s, 0.7H), 7.05-7.58 (m, 1H), 6.40 (s, 0.3H), 6.21 (s, 0.7H), 4.55-4.41 (m, 1H), 4.29 (q, J=7.0 Hz, 2H), 3.71 (s, 0.9H), 3.62 (s, 2.1H), 3.43-3.33 (m, 1H), 3.03-2.75 (m, 3H), 2.37-2.08 (m, 3H), 1.55-1.41 (m, 2H), 1.26 (t, J=7.0 Hz, 3H), 1.05-0.80 (m, 4H) [Note: contained 2 tautomers in an approximate ratio of 0.7:0.3]. LCMS [M+H]+ 532, RT 1.99 minutes (Method 25). Chiral LC* RT=2.78 minutes.

* Chiral analysis performed using a Chiralpak IA-3 column, 150×4.6 mm, 3 μm, eluted using an isocratic 50% EtOH in heptane (+0.1% DEA) method, flow rate of 1.5 mL/min, 100 bar pressure and a 8 minute run time minute run time on an Agilent Infinity II 1290.

Example 418

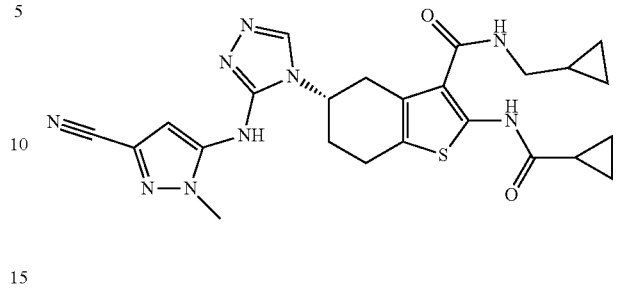

(5S)-5-[3-[(5-Cyano-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide Synthesised using general procedure general method 8, using intermediate 581 (500 mg, 1.01 mmol) and comparable stoichiometries of reagents. The product was purified by flash chromatography eluting with 0-15% MeOH/DCM to afford the title compound (8 mg, 1.6%) as a colourless powder. $δ_H$ (400 MHz, DMSO-d6) 11.48-10.95 (m, 2H), 8.23 (s, 1H), 7.99-7.56 (m, 1H), 6.54 (s, 1H), 4.52-4.37 (m, 1H), 3.66 (s, 3H), 3.25-3.04 (m, 3H), 2.98-2.71 (m, 4H), 2.28-2.09 (m, 3H), 1.94-1.77 (m, 1H), 1.05-0.91 (m, 1H), 0.90-0.68 (m, 4H), 0.43-0.30 (m, 1H), 0.25-0.14 (m, 1H). LCMS [M+H]+ 506, RT 1.80 minutes (Method 25).

Example 419

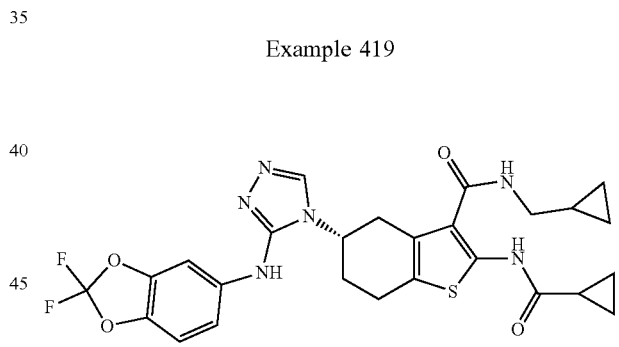

(5S)-2-(Cyclopropanecarbonylamino)-N-(cyclopropylmethyl)-5-[3-[(2,2-difluoro-1,3-benzodioxol-5-yl)amino]-1,2,4-triazol-4-yl]-4,5,6,7-tetrahydrobenzothiophene-3-carboxamide Synthesised using general procedure general method 8, using intermediate 583 (431 mg, 0.786 mmol) and comparable stoichiometries of reagents. The product was purified by flash chromatography eluting with 0-10% MeOH/DCM to afford the title compound (149 mg, 34% Yield) as a colourless powder. $δ_H$ (300 MHz, DMSO-d6) 11.26 (s, 1H), 8.85 (s, 1H), 8.41 (s, 1H), 7.81 (s, 1H), 7.69 (t, J=5.7 Hz, 1H), 7.40-7.25 (m, 2H), 4.58-4.43 (m, 1H), 3.21-2.80 (m, 6H), 2.35-2.12 (m, 2H), 1.94 (p, J=6.5 Hz, 1H), 1.03-0.78 (m, 5H), 0.36-0.25 (m, 2H), 0.19-0.10 (m, 2H). LCMS [M+H]+ 557, RT 2.44 minutes (Method 25).

Example 420

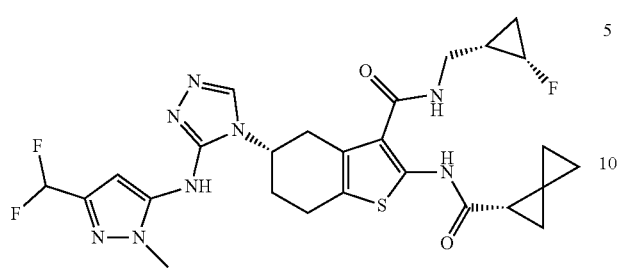

(5S)-5-[3-[[5-(Difluoromethyl)-2-methyl-pyrazol-3-yl]amino]-1,2,4-triazol-4-yl]-N-[[(1S,2S)-2-fluoro-cyclopropyl]methyl]-2-[[(2S)-spiro[2.2]pentane-2-carbonyl]amino]-4,5,6,7-tetrahydrobenzothiophene-3-carboxamide The title compound was obtained following general method 1 with intermediate 578 (30 mg, 0.06 mmol), [(1S,2S)-2-fluorocyclopropyl]methylammonium chloride (23 mg, 3 equivalents), DIPEA (3.5 equivalents), and MeCN (1 mL). Reaction time: 3 h at 70° C. The product was purified by flash chromatography eluting with 0-20% MeOH/DCM to afford the title compound (30 mg, 85% yield) as a colourless powder. $\delta_H$ (300 MHz, DMSO-d6) 12.08 (s, 0.6H), 11.15-11.10 (m, 1H), 8.74 (s, 0.4H), 8.40 (s, 0.4H), 8.19 (s, 0.6H), 7.81-7.69 (m, 1H), 7.05-6.57 (m, 1H), 6.42 (s, 0.4H), 6.21 (s, 0.6H), 4.87-4.80 (m, 0.6H), 4.65-4.58 (m, 0.6H), 4.54-4.40 (m, 1.4H), 4.17-4.12 (m, 0.4H), 3.71 (s, 1.2H), 3.60 (s, 1.8H), 3.39-2.85 (m, 6H), 2.32-2.13 (m, 3H), 1.54-1.05 (m, 4H), 1.02-0.62 (m, 4H) [Note: contained 2 tautomers in an approximate ratio of 0.6:0.4]. LCMS [M+H]$^+$ 575, RT 1.73 minutes (Method 25).

Example 421

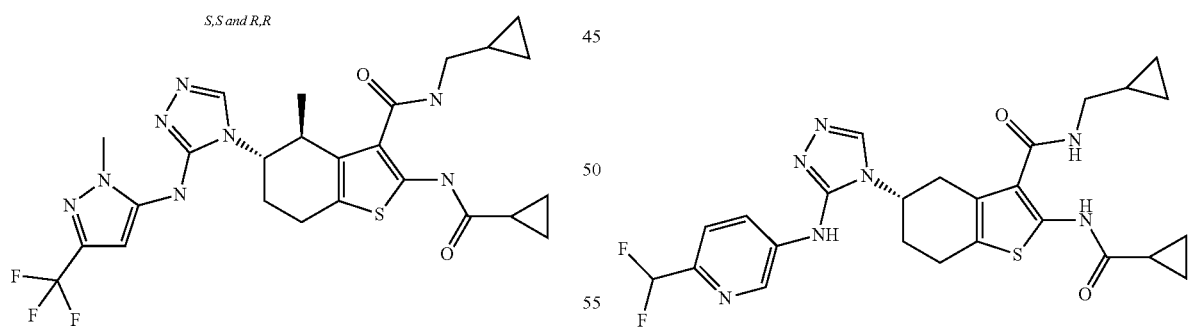

(4RS,5RS)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide Synthesised in the same manner as Example 229, using intermediate 598 (95 mg, 0.17 mmol) and comparable stoichiometries of reagents. The product was purified by HPLC to afford the title compound (27 mg, 27% Yield). $\delta_H$ (400 MHz, DMSO-d6) 12.16 (s, 1H), 10.65 (s, 1H), 8.35-8.12 (m, 1H), 8.12-7.78 (m, 1H), 6.47-6.22 (m, 1H), 4.29 (ddd, J=8.9, 6.1, 2.9 Hz, 1H), 3.67 (s, 3H), 3.43 (s, 1H), 3.11 (qt, J=13.4, 6.2 Hz, 2H), 2.83-2.70 (m, 1H), 2.62-2.54 (m, 1H), 2.31-2.20 (m, 1H), 2.12-1.89 (m, 2H), 1.16 (d, J=6.8 Hz, 3H), 1.07-0.94 (m, 1H), 0.93-0.70 (m, 5H), 0.44-0.35 (m, 2H), 0.25-0.17 (m, 2H). LCMS [M+H]$^+$ 563, RT 1.73 minutes (Method 26).

Example 422

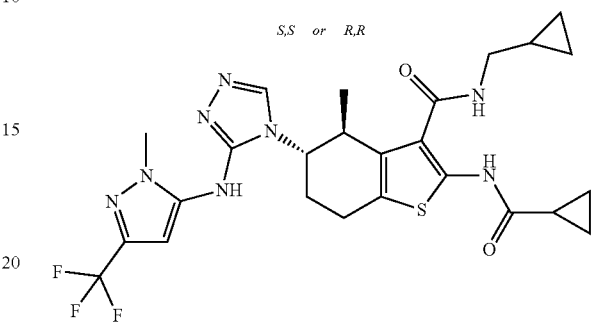

(4R*,5R*)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide Chiral separation by SFC of Example 421 (20 mg) afforded the title compound (6 mg, 6% Yield) as a colourless powder. $\delta_H$ (400 MHz, DMSO-d6) 12.16 (s, 1H), 10.64 (s, 1H), 8.20 (s, 1H), 7.95 (s, 1H), 6.36 (s, 1H), 4.36-4.21 (m, 1H), 3.67 (s, 3H), 3.42 (s, 1H), 3.11 (qt, J=13.4, 6.2 Hz, 2H), 2.84-2.72 (m, 1H), 2.61-2.55 (m, 1H), 2.29-2.20 (m, 1H), 2.13-1.91 (m, 2H), 1.22-1.07 (m, 3H), 1.07-0.94 (m, 1H), 0.92-0.71 (m, 5H), 0.46-0.31 (m, 2H), 0.24-0.13 (m, 2H). LCMS [M+H]$^+$ 563, RT 1.73 minutes (Method 26). Chiral SFC* RT=4.93 minutes

* Using chiral SFC Method 1 with a Chiralpak IB column.

Example 423

(5S)-2-(cyclopropanecarbonylamino)-N-(cyclopropylmethyl)-5-[3-[[6-(difluoromethyl)-3-pyridyl]amino]-1,2,4-triazol-4-yl]-4,5,6,7-tetrahydrobenzothiophene-3-carboxamide Synthesised in the same manner as Example 229, using intermediate 599 (403 mg, 0.78 mmol) and comparable stoichiometries of reagents. The product was purified by HPLC (Method 5) to afford the title compound (140 mg, 34% Yield). $\delta_H$ (300 MHz, DMSO-d6) 11.26 (s, 1H), 9.20 (s, 1H), 8.82 (d, J=2.6 Hz, 1H), 8.47 (s, 1H), 8.30 (dd, J=8.6, 2.6 Hz, 1H), 7.68 (t, J=5.7 Hz, 1H), 7.63 (d, J=8.7 Hz, 1H), 6.87 (t, J=55.4 Hz, 1H), 4.69-4.44 (m, 1H), 3.22-2.79 (m, 6H), 2.38-2.12 (m, 2H), 2.03-1.83 (m, 1H), 1.02-0.79 (m, 5H), 0.28 (dt, J=8.3, 2.8 Hz, 21H), 0.18-0.10 (m, 2H). LCMS [M+H]⁺ 528, RT 1.92 minutes (Method 26).

Example 424

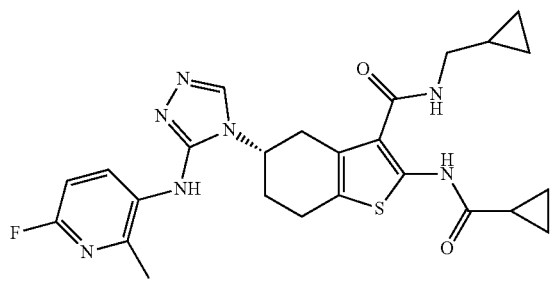 [SMILES: Cc1nc(F)ccc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(6-fluoro-2-methyl-3-pyridyl)amino]-1,2,4-triazol-4-yl]-4,5,6,7-tetrahydrobenzothiophene-3-carboxamide Synthesised in the same manner as Example 229, using intermediate 600 (446 mg, 0.89 mmol) and comparable stoichiometries of reagents. The product was purified by HPLC (Method 5) to afford the title compound (100 mg, 22% Yield). $\delta_H$ (300 MHz, DMSO-d6) 11.22 (s, 1H), 8.39 (s, 1H), 7.94 (s, 1H), 7.85 (dd, J=8.6, 7.5 Hz, 1H), 7.73 (t, J=5.7 Hz, 1H), 6.94 (dd, J=8.6, 3.6 Hz, 1H), 4.49 (dt, J=9.8, 4.9 Hz, 1H), 3.23-2.91 (m, 4H), 2.91-2.76 (m, 2H), 2.33 (s, 3H), 2.31-2.13 (m, 2H), 1.93 (dt, J=12.5, 6.5 Hz, 1H), 1.06-0.92 (m, 1H), 0.90-0.81 (m, 4H), 0.42-0.28 (m, 21H), 0.25-0.10 (m, 21H). LCMS [M+H]⁺ 510, RT 1.84 minutes (Method 26).

Example 425

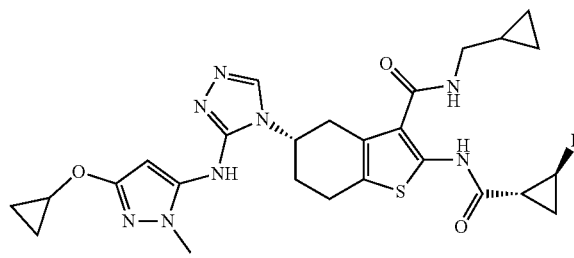

(5S)-5-[3-[[5-(cyclopropoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide Synthesised in the same manner as Example 229, using intermediate 606 (90 mg, 0.16 mmol) and comparable stoichiometries of reagents. Purification by HPLC afforded the title compound (2 mg, 2% Yield). $\delta_H$ (400 MHz, Methanol-d4) 8.36-8.12 (m, 1H), 5.75-5.60 (m, 1H), 4.84 (dddd, J=64.3, 6.3, 3.4, 1.6 Hz, 1H), 4.56-4.46 (m, 1H), 3.92-3.84 (m, 1H), 3.56 (s, 3H), 3.29-3.14 (m, 2H), 3.11-2.83 (m, 2H), 2.43-2.25 (m, 3H), 1.60-1.46 (m, 1H), 1.41-1.26 (m, 2H), 1.13-1.01 (m, 1H), 0.96-0.83 (m, 1H), 0.74-0.65 (m, 4H), 0.54-0.45 (m, 2H), 0.29-0.21 (m, 2H). LCMS [M+H]⁺ 555, RT 1.61 minutes (Method 26).

Example 426

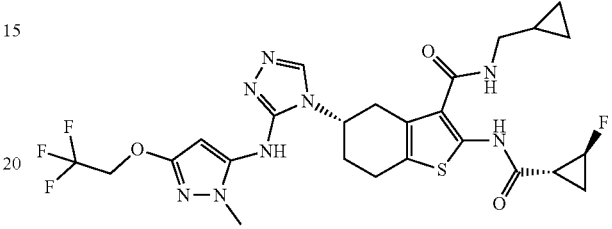

(5S)—N-(cyclopropylmethyl)-2-[[(1R,2S)-2-fluorocyclopropanecarbonyl]amino]-5-[3-[[2-methyl-5-(2,2,2-trifluoroethoxy)pyrazol-3-yl]amino]-1,2,4-triazol-4-yl]-4,5,6,7-tetrahydrobenzothiophene-3-carboxamide Synthesised in the same manner as Example 229, using Intermediate 612 (93 mg, 0.16 mmol) and comparable stoichiometries of reagents. The product was purified HPLC to afford the title compound (5 mg, 5% Yield). $\delta_H$ (400 MHz, Methanol-d4) 8.42-8.05 (m, 1H), 5.67-5.50 (m, 1H), 4.84 (dddd, J=64.2, 6.3, 3.4, 1.6 Hz, 1H), 4.62-4.47 (m, 3H), 3.57 (s, 3H), 3.30-3.15 (m, 3H), 3.10-2.83 (m, 2H), 2.40-2.28 (m, 3H), 1.53 (dddd, J=21.7, 10.2, 6.6, 3.4 Hz, 1H), 1.40-1.25 (m, 1H), 1.12-1.01 (m, 1H), 0.94-0.84 (m, 1H), 0.52-0.45 (m, 2H), 0.25 (dt, J=5.9, 4.5 Hz, 2H). LCMS [M+H]⁺ 597, RT 1.84 minutes (Method 26).

Example 427

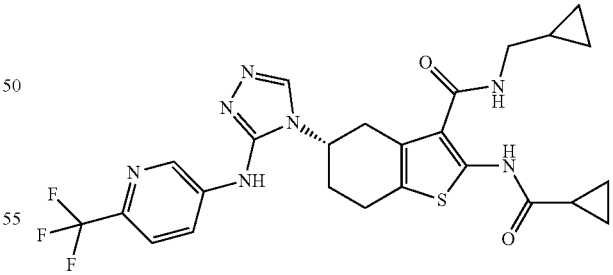

(5S)-2-(cyclopropanecarbonylamino)-N-(cyclopropylmethyl)-5-[3-[[6-(trifluoromethyl)-3-pyridyl]amino]-1,2,4-triazol-4-yl]-4,5,6,7-tetrahydrobenzothiophene-3-carboxamide Synthesised in the same manner as Example 229, using Intermediate 614 (78 mg) and comparable stoichiometries of reagents. The product was purified by SFC to afford the title compound (3 mg) as a colourless powder. $\delta_H$ (400 MHz, Methanol-d4) 8.74 (d, J=2.6 Hz, 1H), 8.45 (s, 1H), 8.20 (dd, J=8.8, 2.6 Hz, 1H), 7.73 (d, J=8.7 Hz, 1H), 4.67-4.56 (m, 1H), 3.30-2.84 (m, 6H), 2.42-2.30 (m, 2H), 1.85-1.75 (m, 1H), 1.07-0.84 (m, 5H), 0.46-0.36 (m, 2H), 0.25-0.16 (m, 2H). LCMS [M+H]$^+$ 546, RT 2.13 minutes (Method 26).

Example 428

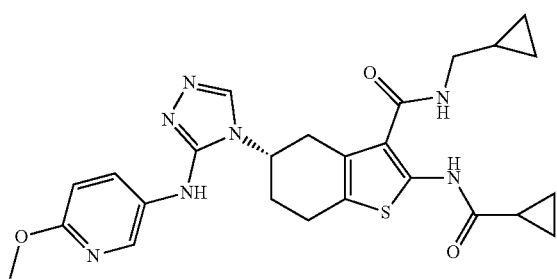 [SMILES: COc1ccc(Nc2nncn2[C@H]2CCc3sc(NC(=O)C4CC4)c(C(=O)NCC4CC4)c3C2)cn1]

(5S)-2-(cyclopropanecarbonylamino)-N-(cyclopropylmethyl)-5-[3-[(6-methoxy-3-pyridyl)amino]-1,2,4-triazol-4-yl]-4,5,6,7-tetrahydrobenzothiophene-3-carboxamide Synthesised in the same manner as Example 229, using intermediate 616 (80 mg) and comparable stoichiometries of reagents. The product was purified by HPLC to afford the title compound (9 mg) as a colourless powder. $\delta_H$ (300 MHz, Methanol-d4) 8.31 (s, 1H), 8.21 (d, J=2.8 Hz, 1H), 7.84 (dd, J=8.9, 2.9 Hz, 1H), 6.84-6.72 (m, 1H), 4.63-4.44 (m, 1H), 3.88 (s, 3H), 3.30-2.86 (m, 6H), 2.42-2.28 (m, 2H), 1.92-1.73 (m, 1H), 1.19-0.83 (m, 5H), 0.56-0.35 (m, 2H), 0.22 (dt, J=6.1, 4.5 Hz, 2H). LCMS [M+H]$^+$ 508, RT 1.86 minutes (Method 26).

Example 429

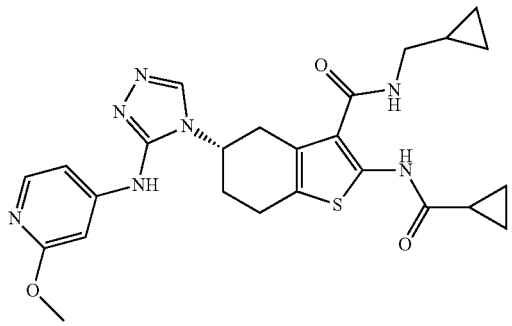 [SMILES: COc1cc(Nc2nncn2[C@H]2CCc3sc(NC(=O)C4CC4)c(C(=O)NCC4CC4)c3C2)ccn1]

(5S)-2-(cyclopropanecarbonylamino)-N-(cyclopropylmethyl)-5-[3-[(2-methoxy-4-pyridyl)amino]-1,2,4-triazol-4-yl]-4,5,6,7-tetrahydrobenzothiophene-3-carboxamide Synthesised in the same manner as Example 229, using intermediate 618 (11 mg) and comparable stoichiometries of reagents. The product was purified by HPLC to afford the title compound (2 mg) as a colourless powder. $\delta_H$ (300 MHz, Methanol-d4) 8.47 (s, 1H), 7.89 (d, J=5.9 Hz, 1H), 6.89 (dd, J=5.9, 2.0 Hz, 1H), 6.81 (d, J=1.9 Hz, 1H), 4.55 (dq, J=9.8, 5.8, 5.3 Hz, 1H), 3.86 (s, 3H), 3.30-2.87 (m, 6H), 2.44-2.24 (m, 2H), 1.86-1.73 (m, 1H), 1.06-0.87 (m, 5H), 0.49-0.36 (m, 2H), 0.20 (dt, J=6.1, 4.4 Hz, 2H). LCMS [M+H]$^+$ 508, RT 1.80 minutes (Method 26).

Example 430

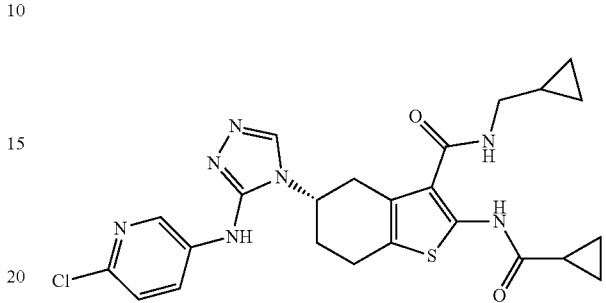

(5S)-5-[3-[(6-chloro-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide Synthesised in the same manner as Example 229, using Intermediate 620 (62 mg) and comparable stoichiometries of reagents. The product was purified by HPLC (Method 5) to afford the title compound (19 mg) as a colourless powder. $\delta_H$ (300 MHz, Methanol-d4) 8.49 (dd, J=3.0, 0.6 Hz, 1H), 8.40 (s, 1H), 8.03 (dd, J=8.7, 3.0 Hz, 1H), 7.37 (dd, J=8.7, 0.6 Hz, 1H), 4.66-4.48 (m, 1H), 3.30-2.85 (m, 6H), 2.44-2.29 (m, 2H), 1.92-1.73 (m, 1H), 1.11-0.86 (m, 5H), 0.50-0.33 (m, 2H), 0.21 (dt, J=6.1, 4.4 Hz, 2H). LCMS [M+H]$^+$ 512, RT 1.95 minutes (Method 26).

Example 431

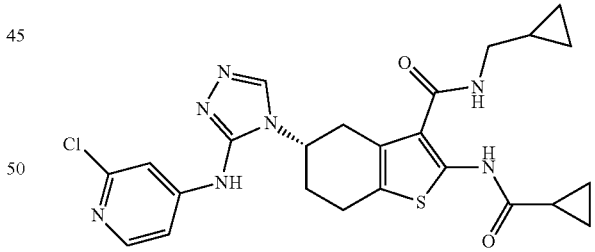

(5S)-5-[3-[(2-chloro-4-pyridyl)amino]-1,2,4-triazol-4-yl]-2-(cyclopropanecarbonylamino)-N-(cyclopropylmethyl)-4,5,6,7-tetrahydrobenzothiophene-3-carboxamide Synthesised in the same manner as Example 229, using Intermediate 622 (59 mg) and comparable stoichiometries of reagents. The product was HPLC (Method 5) to afford the title compound (7 mg) as a colourless glass. $\delta_H$ (400 MHz, DMSO-d6) 11.26 (s, 1H), 9.50 (s, 1H), 8.53 (s, 1H), 8.14 (d, J=5.7 Hz, 1H), 7.72 (d, J=2.0 Hz, 1H), 7.67 (t, J=5.7 Hz, 1H), 7.41 (dd, J=5.8, 2.0 Hz, 1H), 4.62-4.44 (m, 1H), 3.19-2.90 (m, 4H), 2.90-2.82 (m, 2H), 2.31-2.15 (m, 2H), 1.99-1.86 (m, 1H), 1.00-0.90 (m, 1H), 0.90-0.79 (m, 4H), 0.36-0.24 (m, 2H), 0.20-0.07 (m, 2H). LCMS [M+H]+ 512, RT 1.82 minutes (Method 26).

Example 432

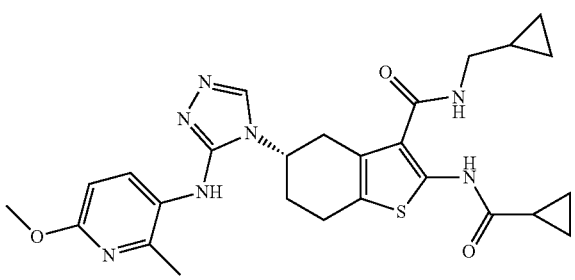 [SMILES: COc1ccc(Nc2nncn2[C@H]2CCc3sc(NC(=O)C4CC4)c(C(=O)NCC4CC4)c3C2)c(C)n1]

(5S)-2-(cyclopropanecarbonylamino)-N-(cyclopropylmethyl)-5-[3-[(6-methoxy-2-methyl-3-pyridyl)amino]-1,2,4-triazol-4-yl]-4,5,6,7-tetrahydrobenzothiophene-3-carboxamide Synthesised in the same manner as Example 229, using Intermediate 624 (47 mg) and comparable stoichiometries of reagents. The product was purified by HPLC to afford the title compound (7 mg) as a colourless powder. δ$_H$ (400 MHz, Methanol-d4) 7.66-7.48 (m, 1H), 6.85-6.72 (m, 1H), 4.07-3.98 (m, 1H), 3.96 (s, 3H), 3.26-3.13 (m, 3H), 2.91-2.74 (m, 2H), 2.69-2.54 (m, 1H), 2.29-2.15 (m, 4H), 1.99-1.69 (m, 2H), 1.17-1.03 (m, 1H), 1.03-0.89 (m, 4H), 0.57-0.39 (m, 2H), 0.34-0.19 (m, 2H). LCMS [M+H]+ 522, RT 1.92 minutes (Method 26).

Example 433

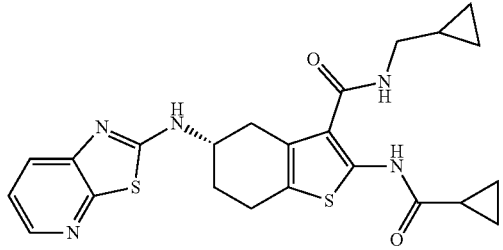 [SMILES: O=C(NCC1CC1)c1c(NC(=O)C2CC2)sc2c1C[C@@H](Nc1nc3cccnc3s1)CC2]

(5S)-2-(cyclopropanecarbonylamino)-N-(cyclopropylmethyl)-5-[3-[(2-fluoro-3-pyridyl)amino]-1,2,4-triazol-4-yl]-4,5,6,7-tetrahydrobenzothiophene-3-carboxamide Synthesised in the same manner as Example 229, using intermediate 626 (25 mg) and comparable stoichiometries of reagents. The product was purified by HPLC (Method 5) to afford the title compound (31 mg). δ$_H$ (400 MHz, DMSO-d6) 11.11 (s, 1H), 8.47 (d, J=6.9 Hz, 1H), 8.10 (dd, J=4.8, 1.5 Hz, 1H), 7.73 (t, J=5.7 Hz, 1H), 7.68 (dd, J=8.0, 1.5 Hz, 1H), 7.25 (dd, J=8.1, 4.8 Hz, 1H), 4.28-4.17 (m, 1H), 3.21-3.08 (m, 3H), 2.87-2.75 (m, 2H), 2.70 (dd, J=16.1, 7.4 Hz, 1H), 2.18-2.08 (m, 1H), 1.98-1.85 (m, 2H), 1.06-0.95 (m, 1H), 0.92-0.79 (m, 4H), 0.36 (dt, J=8.6, 2.8 Hz, 2H), 0.28-0.12 (m, 2H). LCMS [M+H]+ 468, RT 2.16 minutes (Method 26).

Example 434

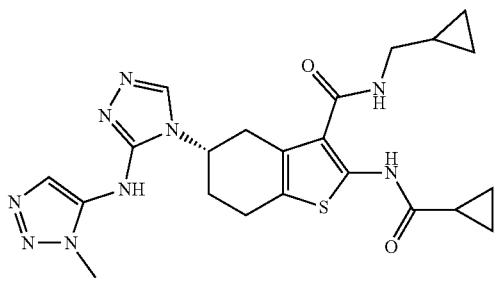 [SMILES: Cn1nncc1Nc1nncn1[C@H]1CCc2sc(NC(=O)C3CC3)c(C(=O)NCC3CC3)c2C1]

(5S)-2-(cyclopropanecarbonylamino)-N-(cyclopropylmethyl)-5-[3-[(3-methyltriazol-4-yl)amino]-1,2,4-triazol-4-yl]-4,5,6,7-tetrahydrobenzothiophene-3-carboxamide Synthesised in the same manner as Example 229, using intermediate 628 (210 mg, 0.44 mmol) and comparable stoichiometries of reagents. The product was purified by HPLC (Method 5) to afford the title compound (78 mg, 16% Yield) as a colourless powder. δ$_H$ (300 MHz, DMSO-d6) 12.11 (s, 1H), 11.29-11.13 (m, 1H), 8.23 (d, J=1.1 Hz, 1H), 7.80-7.67 (m, 1H), 7.45 (s, 1H), 4.57-4.39 (m, 1H), 3.88-3.71 (m, 3H), 3.22-2.79 (m, 6H), 2.29-2.08 (m, 2H), 1.99-1.86 (m, 1H), 1.06-0.93 (m, 1H), 0.91-0.75 (m, 4H), 0.43-0.27 (m, 2H), 0.17 (dt, J=6.0, 4.3 Hz, 2H). LCMS [M+H]+ 482, RT 1.62 minutes (Method 26).

Example 435

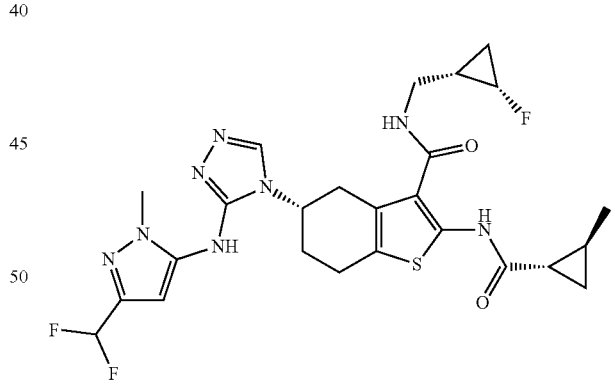

(5S)-5-[3-[[5-(difluoromethyl)-2-methylpyrazol-3-yl]amino]-1,2,4-triazol-4-yl]-N-[[(1S,2S)-2-fluorocyclopropyl]methyl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), [(1S,2S)-2-fluorocyclopropyl]methylammonium chloride (27 mg, 0.2 mmol), triethylamine (0.05 mL) and DMF (0.5 mL). Reaction time: 1 h at 70° C. Filtration and purification using HPLC (method 5) gave the title compound (41 mg, 69% Yield). δ$_H$ (300 MHz, DMSO-d6) 12.07 (s, 1H), 11.26-11.08 (m, 1H), 8.83-8.32 (m, 1H), 8.19 (s, 1H), 7.95-7.71 (m, 1H), 7.09-6.52 (m, 1H), 6.48-6.11 (m, 1H), 4.94-4.57 (m, 1H), 4.57-4.32 (m, 1H), 3.78-3.51 (m, 3H), 3.40-3.33 (m, 1H), 3.23-2.90 (m, 21H), 2.90-2.75 (m, 2H), 2.33-2.09 (m, 3H), 1.69 (dt, J=8.3, 4.3 Hz, 1H), 1.35-1.13 (m, 1H), 1.12-1.01 (m, 4H), 0.80-0.62 (m, 3H). LCMS [M+H]$^+$ 563, RT 1.66 minutes (Method 26).

Example 436

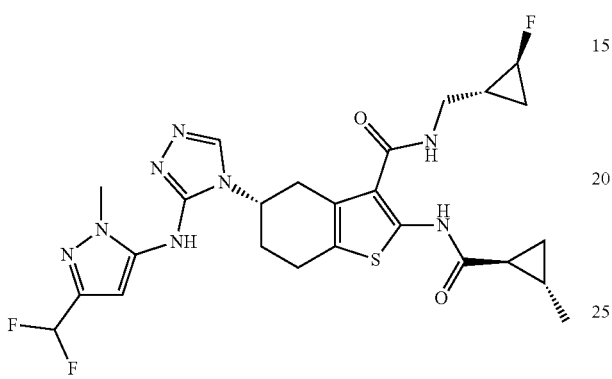

(5S)-5-[3-[[5-(difluoromethyl)-2-methylpyrazol-3-yl]amino]-1,2,4-triazol-4-yl]-N-[[(1R,2S)-2-fluorocyclopropyl]methyl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), intermediate 588 (3 equivalents), triethylamine (0.05 mL), and DMF (0.5 mL). Reaction time: 30 min at 75° C. Filtration and purification using HPLC (Method 5) gave the title compound (18 mg). δ$_H$ (400 MHz, MeOH-d4) 8.19 (s, 1H), 6.61 (t, J=55.1 Hz, 1H), 6.28 (s, 1H), 4.64-4.39 (m, 2H), 3.77-3.60 (m, 3H), 3.33-3.25 (m, 2H), 3.16-2.84 (m, 4H), 2.34 (h, J=5.5 Hz, 2H), 1.63-1.48 (m, 2H), 1.39 (dtd, J=8.6, 6.2, 3.9 Hz, 1H), 1.23-1.17 (m, 1H), 1.16 (d, J=6.1 Hz, 3H), 1.00 (dddd, J=21.5, 11.0, 7.0, 2.6 Hz, 1H), 0.78 (ddd, J=8.0, 6.4, 4.0 Hz, 1H), 0.63 (dq, J=10.3, 6.7 Hz, 1H). LCMS [M+H]$^+$ 563, RT 1.67 minutes (Method 26).

Example 437

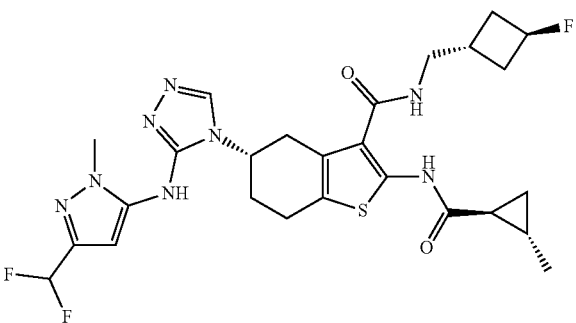 [SMILES: C[C@H]1C[C@@H]1C(=O)Nc1sc2c(c1C(=O)NC[C@H]1C[C@H](F)C1)C[C@@H](n1cnnc1Nc1cc(C(F)F)nn1C)CC2]

(5S)-5-[3-[[5-(difluoromethyl)-2-methylpyrazol-3-yl]amino]-1,2,4-triazol-4-yl]-N-[trans-(3-fluorocyclobutyl)methyl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), trans-(3-fluorocyclobutyl)methanamine hydrochloride (3 equivalents), triethylamine (0.05 mL), and DMF (0.5 mL). Reaction time: 30 min at 75° C. Filtration and purification using HPLC (Method 5) gave the title compound (31 mg). δ$_H$ (400 MHz, MeOH-d4) 8.18 (s, 1H), 6.62 (t, J=55.1 Hz, 1H), 6.28 (s, 1H), 5.20-4.98 (m, 1H), 4.58-4.48 (m, 1H), 3.76-3.68 (m, 3H), 3.50-3.32 (m, 2H), 3.27 (dd, J=15.6, 5.4 Hz, 2H), 3.07-2.84 (m, 3H), 2.66-2.50 (m, 1H), 2.38-2.10 (m, 5H), 1.54 (dt, J=8.2, 4.3 Hz, 1H), 1.39 (dtd, J=8.8, 6.2, 3.8 Hz, 1H), 1.22-1.11 (m, 4H), 0.78 (ddd, J=8.0, 6.3, 4.0 Hz, 1H). LCMS [M+H]$^+$ 577, RT 1.71 minutes (Method 26).

Example 438

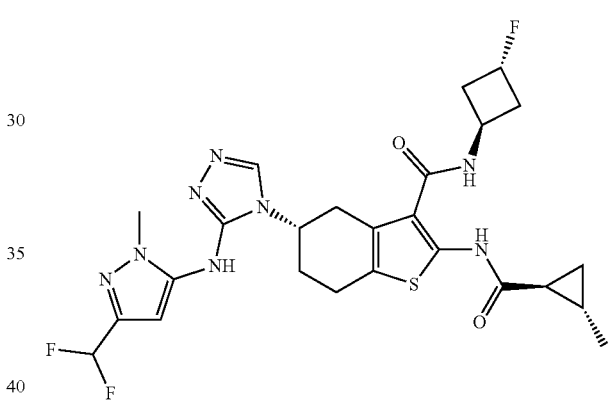

(5S)-5-[3-[[5-(difluoromethyl)-2-methylpyrazol-3-yl]amino]-1,2,4-triazol-4-yl]-N-(trans-3-fluorocyclobutyl)-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), trans-3-fluorocyclobutanamine hydrochloride (3 equivalents), triethylamine (0.05 mL), and DMF (0.5 mL). Reaction time: 30 min at 75° C. Filtration and purification using HPLC (Method 5) gave the title compound (27 mg). δ$_H$ (400 MHz, MeOH-d4) 8.16 (s, 1H), 6.62 (t, J=55.1 Hz, 1H), 6.28 (s, 1H), 5.17 (dtt, J=56.5, 6.4, 3.3 Hz, 1H), 4.68-4.48 (m, 2H), 3.72 (s, 3H), 3.30-3.23 (m, 1H), 3.10-2.81 (m, 3H), 2.68-2.51 (m, 2H), 2.51-2.24 (m, 4H), 1.54 (dt, J=8.3, 4.3 Hz, 1H), 1.44-1.30 (m, 1H), 1.21-1.10 (m, 4H), 0.78 (ddd, J=7.9, 6.3, 4.0 Hz, 1H). LCMS [M+H]$^+$ 563, RT 1.62 minutes (Method 26).

Example 439

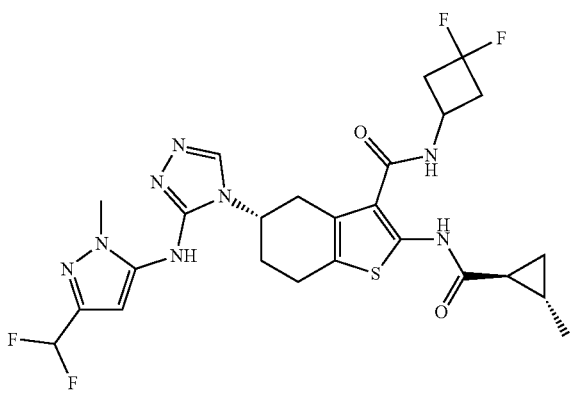 [SMILES: C[C@H]1C[C@@H]1C(=O)Nc1sc2c(c1C(=O)NC1CC(F)(F)C1)C[C@@H](n1cnnc1Nc1cc(C(F)F)nn1C)CC2]

(5S)—N-(3,3-difluorocyclobutyl)-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), 3,3-difluorocyclobutanamine hydrochloride (3 equivalents), triethylamine (0.05 mL), and DMF (0.5 mL). Reaction time: 30 min at 75° C. Filtration and purification using HPLC (Method 5) gave the title compound (28 mg). $\delta_H$ (400 MHz, MeOH-d4) 8.16 (s, 1H), 6.62 (t, J=55.1 Hz, 1H), 6.28 (s, 1H), 4.53 (td, J=8.9, 4.2 Hz, 1H), 4.35-4.24 (m, 1H), 3.72 (s, 3H), 3.30-3.22 (m, 1H), 3.11-2.80 (m, 4H), 2.75-2.57 (m, 2H), 2.32 (td, J=8.3, 7.9, 5.0 Hz, 2H), 1.54 (dt, J=8.2, 4.3 Hz, 1H), 1.37 (dtd, J=8.7, 6.2, 3.9 Hz, 1H), 1.22-1.10 (m, 4H), 0.77 (ddd, J=8.0, 6.3, 3.9 Hz, 1H). LCMS [M+H]$^+$ 581, RT 1.71 minutes (Method 26).

Example 440

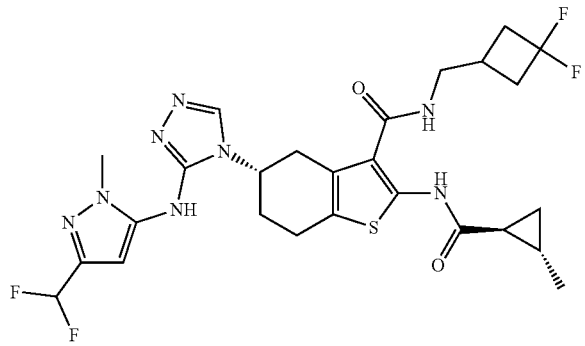 [SMILES: C[C@H]1C[C@@H]1C(=O)Nc1sc2c(c1C(=O)NCC1CC(F)(F)C1)C[C@@H](n1cnnc1Nc1cc(C(F)F)nn1C)CC2]

(5S)—N-[(3,3-difluorocyclobutyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), (3,3-difluorocyclobutyl)methanamine hydrochloride (3 equivalents), triethylamine (0.05 mL), and DMF (0.5 mL). Reaction time: 30 min at 75° C. Filtration and purification using HPLC (Method 5) gave the title compound (32 mg). $\delta_H$ (400 MHz, MeOH-d4) 8.17 (s, 1H), 6.61 (t, J=55.1 Hz, 1H), 6.28 (s, 1H), 4.60-4.47 (m, 1H), 3.72 (s, 31H), 3.59-3.37 (m, 21H), 3.30-3.22 (m, 1H), 3.10-2.81 (m, 31H), 2.60 (ddt, J=14.0, 11.6, 8.2 Hz, 2H), 2.51-2.25 (m, 5H), 1.54 (dt, J=8.2, 4.3 Hz, 1H), 1.38 (dtd, J=8.7, 6.2, 3.9 Hz, 1H), 1.21-1.11 (m, 4H), 0.78 (ddd, J=8.0, 6.4, 3.9 Hz, 1H). LCMS [M+H]$^+$ 595, RT 1.78 minutes (Method 26).

Example 441

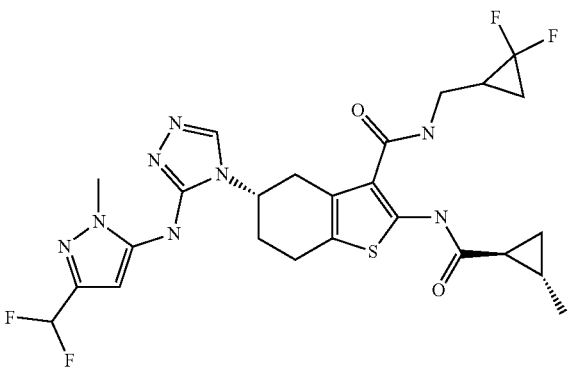 [SMILES: C[C@H]1C[C@@H]1C(=O)Nc1sc2c(c1C(=O)NCC1CC1(F)F)C[C@@H](n1cnnc1Nc1cc(C(F)F)nn1C)CC2]

(5S)—N-[(2,2-difluorocyclopropyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), (2,2-difluorocyclopropyl)methanamine hydrochloride (3 equivalents), triethylamine (0.05 mL), and DMF (0.5 mL). Reaction time: 30 min at 75° C. Filtration and purification using HPLC (Method 5) gave the title compound (28 mg). $\delta_H$ (400 MHz, MeOH-d4) 8.18 (s, 1H), 6.62 (t, J=55.1 Hz, 1H), 6.28 (s, 1H), 4.59-4.48 (m, 1H), 3.72 (s, 3H), 3.61-3.34 (m, 2H), 3.29-3.24 (m, 1H), 3.12-2.83 (m, 3H), 2.39-2.29 (m, 2H), 2.09-1.91 (m, 1H), 1.60-1.34 (m, 3H), 1.28-1.17 (m, 2H), 1.16 (d, J=6.0 Hz, 3H), 0.78 (ddd, J=8.0, 6.3, 3.9 Hz, 1H). LCMS [M+H]$^+$ 581, RT 1.73 minutes (Method 26).

Example 442

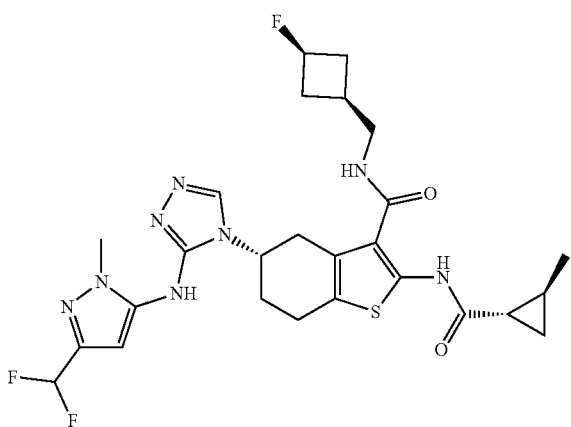 [SMILES: C[C@H]1C[C@@H]1C(=O)Nc1sc2c(c1C(=O)NC[C@H]1C[C@@H](F)C1)C[C@@H](n1cnnc1Nc1cc(C(F)F)nn1C)CC2]

(5S)-5-[3-[[5-(difluoromethyl)-2-methylpyrazol-3-yl]amino]-1,2,4-triazol-4-yl]-N-[cis-(3-fluorocyclobutyl)methyl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), cis-(3-fluorocyclobutyl)methanamine hydrochloride (16 mg, 1.1 equivalents), triethylamine (0.05 mL), and DMF (2 mL). Reaction time: 15 min at 70° C. Filtration and purification using HPLC (Method 5) gave the title compound (32 mg, 53% yield). $\delta_H$ (400 MHz, DMSO-d6) 12.07 (s, 1H), 11.19-11.03 (m, 1H), 8.77-8.30 (m, 1H), 8.18 (s, 1H), 7.83-7.66 (m, 1H), 7.07-6.49 (m, 1H), 6.42-6.14 (m, 1H), 4.97-4.66 (m, 1H), 4.52-4.36 (m, 1H), 3.76-3.51 (m, 3H), 3.44-3.18 (m, 21H), 3.18-3.03 (m, 1H), 3.04-2.75 (m, 3H), 2.32 (dtt, J=11.2, 7.0, 3.4 Hz, 2H), 2.26-2.11 (m, 2H), 2.03-1.72 (m, 3H), 1.69 (dt, J=8.4, 4.3 Hz, 1H), 1.34-1.17 (m, 1H), 1.13-0.96 (m, 4H), 0.77-0.63 (m, 1H). LCMS [M+H]$^+$ 577, RT 1.72 minutes (Method 26).

Example 443

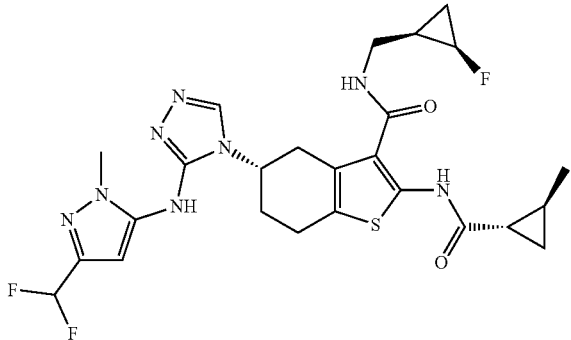 [SMILES: C[C@H]1C[C@@H]1C(=O)Nc1sc2c(c1C(=O)NC[C@H]1C[C@H]1F)C[C@@H](n1cnnc1Nc1cc(C(F)F)nn1C)CC2]

(5S)-5-[3-[[5-(difluoromethyl)-2-methylpyrazol-3-yl]amino]-1,2,4-triazol-4-yl]-N-[[(1R,2R)-2-fluorocyclopropyl]methyl]-2-[[(1S,2S)-2-methylcyclopropanecarbonyl]amino]-4,5,6,7-tetrahydro-1-benzothiophene-3-carboxamide The title compound was obtained following general method 1 with intermediate 645 (50 mg, 0.10 mmol), intermediate 631 (18 mg, 1.3 equivalents), triethylamine (0.05 mL), and DMF (2 mL). Reaction time: 35 min at 75° C. Filtration and purification using HPLC (Method 5) gave the title compound (32 mg, 53% yield). $\delta_H$ (400 MHz, DMSO-d6) 12.07 (s, 1H), 11.30-11.07 (m, 1H), 8.77-8.35 (m, 1H), 8.19 (s, 1H), 7.91-7.78 (m, 1H), 7.05-6.48 (m, 1H), 6.44-6.11 (m, 1H), 4.85-4.57 (m, 1H), 4.52-4.38 (m, 1H), 3.77-3.55 (m, 3H), 3.46-3.26 (m, 1H), 3.21-3.07 (m, 1H), 3.06-2.90 (m, 1H), 2.91-2.75 (m, 2H), 2.30-2.10 (m, 2H), 1.75-1.62 (m, 1H), 1.35-1.13 (m, 2H), 1.13-0.99 (m, 4H), 0.80-0.63 (m, 3H). LCMS [M+H]$^+$ 563, RT 1.66 minutes (Method 26).

Example 444

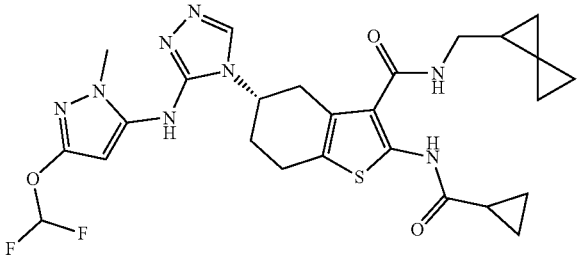 [SMILES: Cn1nc(OC(F)F)cc1Nc1nncn1[C@H]1CCc2sc(NC(=O)C3CC3)c(C(=O)NCC3CC34CC4)c2C1]

(5S)-2-(cyclopropanecarbonylamino)-5-[3-[[5-(difluoromethoxy)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide The title compound was obtained following general method 1 with intermediate 646 (20 mg, 0.04 mmol), spiro[2.2]pentan-1-ylmethanamine (40 mg, 0.411 mmol, ~10 equivalents), triethylamine (0.017 mL, 3 equivalents), and DMF (0.67 mL). Reaction time: 45 min at 140° C. The cooled reaction mixture was diluted with water (1 mL) and DCM (2 mL). The organic phase was partitioned and dried over Na$_2$SO$_4$ then concentrated under reduced pressure. The crude product was then purified using achiral SFC purification to give the title compound (15 mg). $\delta_H$ (400 MHz, DMSO-d6) 12.03 (s, 1H), 11.12 (s, 1H), 8.87-8.09 (m, 1H), 7.91-7.56 (m, 1H), 7.46-6.86 (m, 1H), 6.04-5.49 (m, 1H), 4.53-4.28 (m, 1H), 3.63-3.43 (m, 3H), 3.42-3.33 (m, 1H), 3.26-3.17 (m, 1H), 3.14-3.01 (m, 1H), 2.99-2.74 (m, 3H), 2.28-2.07 (m, 2H), 2.01-1.77 (m, 1H), 1.41-1.29 (m, 1H), 0.96-0.71 (m, 6H), 0.71-0.49 (m, 4H). LCMS [M+H]$^+$ 573, RT 1.78 minutes (Method 26).

Example 445

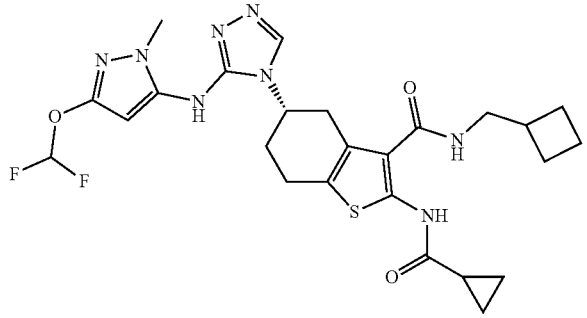 [SMILES: Cn1nc(OC(F)F)cc1Nc1nncn1[C@H]1CCc2sc(NC(=O)C3CC3)c(C(=O)NCC3CCC3)c2C1]

(5S)—N-(cyclobutylmethyl)-2-(cyclopropanecarbonylamino)-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 1 with intermediate 646 (20 mg, 0.04 mmol), cyclobutylmethanamine hydrochloride (20 mg, 0.16 mmol, 4 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using achiral SFC purification to give the title compound (5 mg). $\delta_H$ (400 MHz, DMSO-d6) 12.03 (s, 1H), 11.12 (s, 1H), 8.84-8.11 (m, 1H), 7.82-7.50 (m, 1H), 7.43-6.90 (m, 1H), 5.98-5.55 (m, 1H), 4.56-4.27 (m, 1H), 3.64-3.40 (m, 3H), 3.24-3.03 (m, 1H), 3.00-2.69 (m, 3H), 2.47-2.44 (m, 2H), 2.29-2.09 (m, 3H), 2.03-1.83 (m, 2H), 1.83-1.56 (m, 4H), 0.97-0.64 (m, 4H). LCMS [M+H]+ 561, RT 1.72 minutes (Method 26).

Example 446

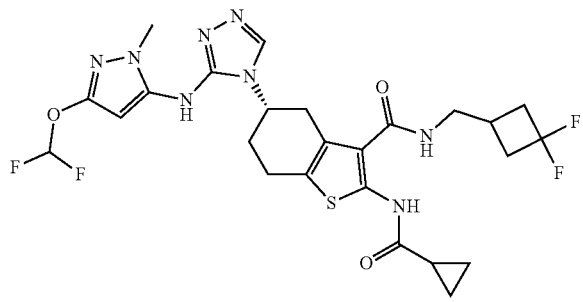 [SMILES: Cn1nc(OC(F)F)cc1Nc1nncn1[C@H]1CCc2sc(NC(=O)C3CC3)c(C(=O)NCC3CC(F)(F)C3)c2C1]

(5S)-2-(cyclopropanecarbonylamino)-N-[(3,3-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 1 with intermediate 646 (20 mg, 0.04 mmol), (3,3-difluorocyclobutyl)methanamine hydrochloride (20 mg, 0.126 mmol, ~3 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using achiral SFC purification to give the title compound (6 mg). $\delta_H$ (400 MHz, DMSO-d6) 12.02 (s, 1H), 11.10 (s, 1H), 8.86-8.06 (m, 1H), 8.06-7.68 (m, 1H), 7.45-6.92 (m, 1H), 6.06-5.44 (m, 1H), 4.49-4.30 (m, 1H), 3.62-3.44 (m, 3H), 3.44-3.35 (m, 2H), 3.23-2.98 (m, 1H), 3.03-2.73 (m, 3H), 2.60-2.53 (m, 2H), 2.41-2.27 (m, 3H), 2.26-2.09 (m, 2H), 2.04-1.79 (m, 1H), 0.95-0.71 (m, 4H). LCMS [M+H]+ 597, RT 1.67 minutes (Method 26).

Example 447

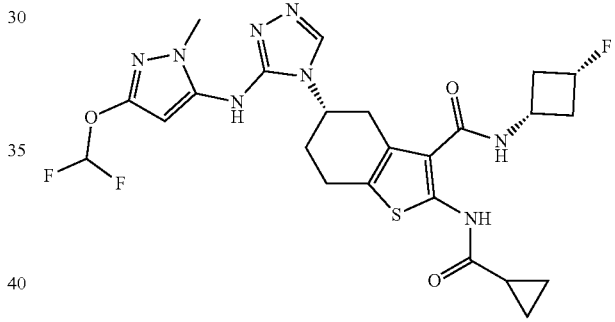

(5S)-2-(cyclopropanecarbonylamino)-5-[3-[[5-(difluoromethoxy)-2-methylpyrazol-3-yl]amino]-1,2,4-triazol-4-yl]-N-(cis-3-fluorocyclobutyl)-4,5,6,7-tetrahydro-1-benzothiophene-3-carboxamide The title compound was obtained following general method 1 with intermediate 646 (20 mg, 0.04 mmol), cis-3-fluorocyclobutanamine hydrochloride (20 mg, 0.16 mmol, ~4 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using achiral SFC purification to give the title compound (7 mg). $\delta_H$ (400 MHz, DMSO-d6) 10.98 (s, 1H), 8.48-7.89 (m, 2H), 7.15 (t, J=74.3 Hz, 1H), 6.56 (s, 1H), 5.99-5.47 (m, 1H), 4.83 (dp, J=56.5, 6.8 Hz, 1H), 4.53-4.35 (m, 1H), 3.98-3.79 (m, 1H), 3.61-3.42 (m, 3H), 3.27-3.02 (2H, m), 2.97-2.68 (m, 4H), 2.28-2.07 (m, 4H), 2.01-1.78 (m, 1H), 0.91-0.69 (m, 4H). LCMS [M+H]+ 565, RT 1.50 minutes (Method 26).

Example 448

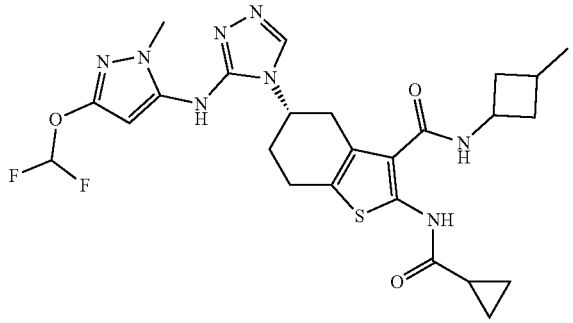 [SMILES: CC1CC(NC(=O)c2c(NC(=O)C3CC3)sc3c2C[C@@H](n2cnnc2Nc2cc(OC(F)F)nn2C)CC3)C1]

(5S)-2-(cyclopropanecarbonylamino)-5-[3-[[5-(difluoromethoxy)-2-methylpyrazol-3-yl]amino]-1,2,4-triazol-4-yl]-N-(3-methylcyclobutyl)-4,5,6,7-tetrahydro-1-benzothiophene-3-carboxamide The title compound was obtained following general method 1 with intermediate 646 (20 mg, 0.04 mmol), 3-methylcyclobutanamine hydrochloride (40 mg, 0.328 mmol, ~8 equivalents), triethylamine (0.017 mL, 3 equivalents), and DMF (0.67 mL). Reaction time: 45 min at 140° C. The cooled reaction mixture was diluted with water (1 mL) and DCM (2 mL). The organic phase was partitioned and dried over $Na_2SO_4$ then concentrated under reduced pressure. The crude product was then purified using achiral SFC purification to give the title compound (17 mg). $\delta_H$ (400 MHz, DMSO-d6) 12.04 (s, 1H), 11.09-10.83 (m, 1H), 8.77-8.13 (m, 1H), 8.00-7.81 (m, 1H), 7.49-6.85 (m, 1H), 5.99-5.50 (m, 1H), 4.57-4.28 (m, 1H), 4.23-4.08 (m, 1H), 3.61-3.42 (m, 3H), 3.20-2.73 (m, 4H), 2.40-2.34 (m, 1H), 2.30-2.04 (m, 3H), 2.04-1.80 (m, 3H), 1.55 (q, J=10.0 Hz, 1H), 1.13-0.96 (m, 3H), 0.90-0.77 (m, 4H). LCMS [M+H]+ 561, RT 1.72 minutes (Method 26).

Example 449

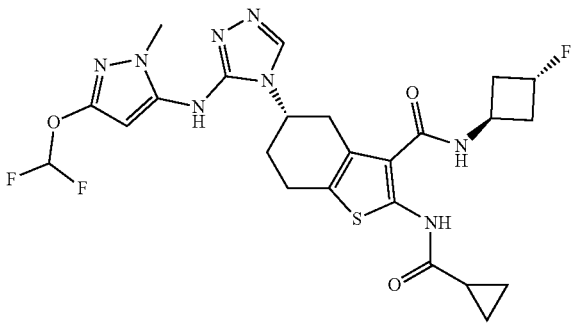 [SMILES: Cn1nc(OC(F)F)cc1Nc1nncn1[C@H]1CCc2sc(NC(=O)C3CC3)c(C(=O)N[C@H]3C[C@H](F)C3)c2C1]

(5S)-2-(cyclopropanecarbonylamino)-5-[3-[[5-(difluoromethoxy)-2-methylpyrazol-3-yl]amino]-1,2,4-triazol-4-yl]-N-(trans-3-fluorocyclobutyl)-4,5,6,7-tetrahydro-1-benzothiophene-3-carboxamide The title compound was obtained following general method 1 with intermediate 646 (20 mg, 0.04 mmol), trans-3-fluorocyclobutanamine hydrochloride (20 mg, 0.16 mmol, ~4 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using achiral SFC purification to give the title compound (5 mg). $\delta_H$ (400 MHz, DMSO-d6) 11.83 (br s, 1H), 10.95 (s, 1H), 8.73 (s, 1H), 8.51-7.85 (m, 2H), 7.15 (t, J=74.1 Hz, 1H), 6.03-5.50 (m, 1H), 5.20 (dtt, J=56.9, 6.5, 3.8 Hz, 1H), 4.46 (ddt, J=33.8, 13.1, 7.0 Hz, 2H), 3.51 (s, 3H), 3.19-3.04 (m, 1H), 2.96-2.71 (m, 3H), 2.47-2.29 (m, 3H), 2.27-2.08 (m, 2H), 1.93 (p, J=5.2, 4.2 Hz, 1H), 0.90-0.77 (m, 4H). LCMS [M+H]+ 565, RT 1.51 minutes (Method 26).

Example 450

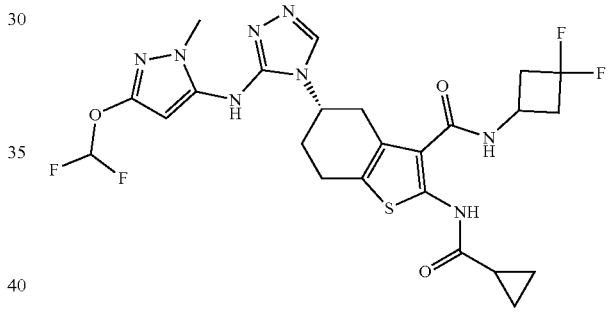

(5S)-2-(cyclopropanecarbonylamino)-N-(3,3-difluorocyclobutyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 1 with intermediate 646 (20 mg, 0.04 mmol), 3,3-difluorocyclobutanamine hydrochloride (20 mg, 0.139 mmol, ~3.5 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using achiral SFC purification to give the title compound (6 mg). $\delta_H$ (400 MHz, DMSO-d6) 11.03-10.87 (m, 1H), 8.51-7.93 (m, 1H), 7.14 (t, J=74.4 Hz, 1H), 6.54 (s, 1H), 6.14-5.29 (m, 1H), 4.48-4.35 (m, 1H), 4.27-4.14 (m, 1H), 3.63-3.40 (m, 3H), 3.20-3.01 (m, 1H), 3.00-2.76 (m, 5H), 2.77-2.59 (m, 1H), 2.28-2.11 (m, 2H), 2.01-1.82 (m, 1H), 0.96-0.66 (m, 4H). LCMS [M+H]+ 583, RT 1.60 minutes (Method 26).

Example 451

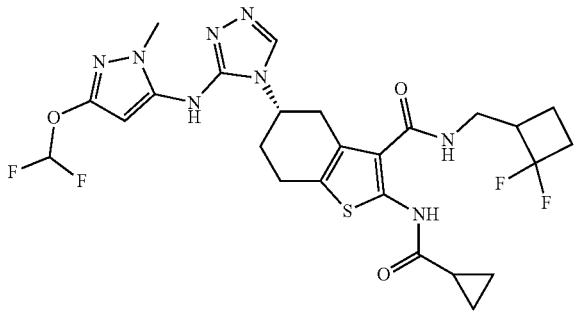 [SMILES: Cn1nc(OC(F)F)cc1Nc1nncn1[C@H]1CCc2sc(NC(=O)C3CC3)c(C(=O)NCC3CCC3(F)F)c2C1]

(5S)-2-(cyclopropanecarbonylamino)-N-[(2,2-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 1 with intermediate 646 (20 mg, 0.04 mmol), (2,2-difluorocyclobutyl)methanamine (40 mg, 0.33 mmol, ~8 equivalents), triethylamine (0.017 mL, 3 equivalents), and DMF (0.67 mL). Reaction time: 45 min at 140° C. The cooled reaction mixture was diluted with water (1 mL) and DCM (2 mL). The organic phase was partitioned and dried over $Na_2SO_4$ then concentrated under reduced pressure. The crude product was then purified using achiral SFC purification to give the title compound (7 mg). $\delta_H$ (400 MHz, DMSO-d6) 12.03 (s, 1H), 11.32-10.85 (m, 1H), 8.97-8.04 (m, 1H), 7.81 (s, 1H), 7.49-6.79 (m, 1H), 5.99-5.48 (m, 1H), 4.57-4.21 (m, 1H), 3.62-3.43 (m, 3H), 3.44-3.35 (m, 1H), 3.17-2.98 (m, 1H), 2.99-2.69 (m, 3H), 2.46-2.35 (m, 2H), 2.30-2.12 (m, 2H), 2.00-1.73 (m, 1H), 1.47 (p, J=9.1 Hz, 1H), 0.96-0.66 (m, 4H). LCMS $[M+H]^+$ 597, RT 1.65 minutes (Method 26).

Example 452

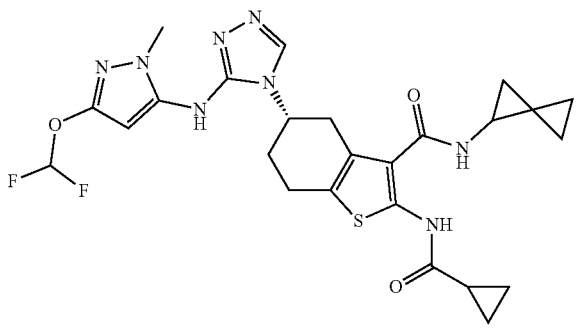 [SMILES: Cn1nc(OC(F)F)cc1Nc1nncn1[C@H]1CCc2sc(NC(=O)C3CC3)c(C(=O)NC3CC34CC4)c2C1]

(5S)-2-(cyclopropanecarbonylamino)-5-[3-[[5-(difluoromethoxy)-2-methylpyrazol-3-yl]amino]-1,2,4-triazol-4-yl]-N-spiro[2.2]pentan-2-yl-4,5,6,7-tetrahydro-1-benzothiophene-3-carboxamide The title compound was obtained following general method 1 with intermediate 646 (20 mg, 0.04 mmol), spiro[2.2]pentan-2-amine (40 mg, 0.48 mmol, 12 equivalents), triethylamine (0.017 mL, 3 equivalents), and DMF (0.67 mL). Reaction time: 45 min at 140° C. The cooled reaction mixture was diluted with water (1 mL) and DCM (2 mL). The organic phase was partitioned and dried over $Na_2SO_4$ then concentrated under reduced pressure. The crude product was then purified using achiral SFC purification to give the title compound (9 mg). $\delta_H$ (400 MHz, DMSO-d6) 12.55-10.68 (m, 2H), 8.47-8.02 (m, 1H), 8.06-7.63 (m, 1H), 7.16 (t, J=74.1 Hz, 1H), 6.07-5.50 (m, 1H), 4.53-4.23 (m, 1H), 3.61-3.43 (m, 3H), 3.19-3.00 (m, 1H), 2.96-2.70 (m, 3H), 2.12 (d, J=35.7 Hz, 2H), 1.90 (s, 1H), 1.27-1.12 (m, 1H), 1.03-0.74 (m, 8H), 0.73-0.51 (m, 1H). LCMS $[M+H]^+$ 559, RT 1.61 minutes (Method 26).

Example 453

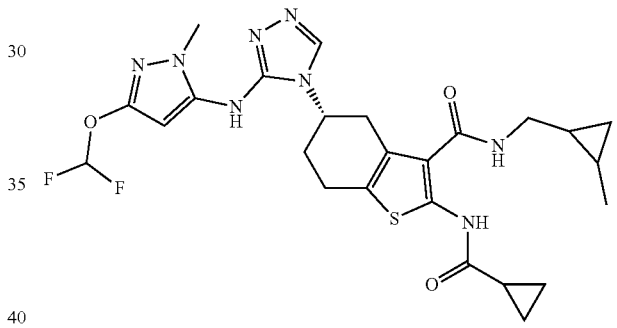

(5S)-2-(cyclopropanecarbonylamino)-5-[3-[[5-(difluoromethoxy)-2-methylpyrazol-3-yl]amino]-1,2,4-triazol-4-yl]-N-[(2-methylcyclopropyl)methyl]-4,5,6,7-tetrahydro-1-benzothiophene-3-carboxamide The title compound was obtained following general method 1 with intermediate 646 (20 mg, 0.04 mmol), (2-methylcyclopropyl)methanamine hydrochloride (60 mg, 0.49 mmol, ~12 equivalents), triethylamine (0.017 mL, 3 equivalents), and DMF (0.67 mL). Reaction time: 45 min at 140° C. The cooled reaction mixture was diluted with water (1 mL) and DCM (3 mL). The organic phase was partitioned and dried over $Na_2SO_4$ then concentrated under reduced pressure. The crude product was then purified using achiral SFC purification to give the title compound (26 mg). $\delta_H$ (400 MHz, DMSO-d6) 11.92 (s, 1H), 11.17 (s, 1H), 8.55-8.00 (m, 1H), 7.75 (s, 1H), 7.14 (t, J=74.2 Hz, 1H), 6.06-5.50 (m, 1H), 4.61-4.27 (m, 1H), 3.60-3.41 (m, 3H), 3.27-3.03 (m, 2H), 3.02-2.74 (m, 3H), 2.30-2.11 (m, 2H), 1.92 (p, J=6.5 Hz, 1H), 0.89 (dd, J=5.9, 1.4 Hz, 3H), 0.87-0.79 (m, 4H), 0.76-0.64 (m, 1H), 0.65-0.50 (m, 1H), 0.38-0.28 (m, 1H), 0.16-0.05 (m, 1H). LCMS $[M+H]^+$ 561, RT 1.72 minutes (Method 26).

Example 454

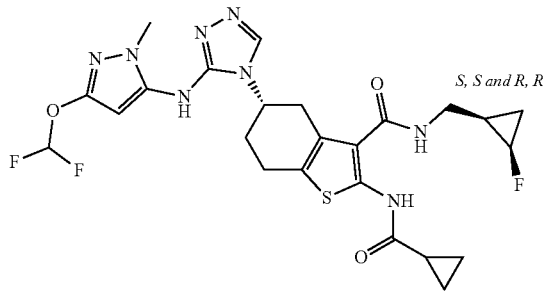 [SMILES: Cn1nc(OC(F)F)cc1Nc1nncn1[C@H]1CCc2sc(NC(=O)C3CC3)c(C(=O)NC[C@H]3C[C@H]3F)c2C1]

(5S)-2-(cyclopropanecarbonylamino)-5-[3-[[5-(difluoromethoxy)-2-methylpyrazol-3-yl]amino]-1,2,4-triazol-4-yl]-N-[[(1RS,2RS)-2-fluorocyclopropyl]methyl]-4,5,6,7-tetrahydro-1-benzothiophene-3-carboxamide The title compound was obtained following general method 1 with intermediate 646 (20 mg, 0.04 mmol), cis-2-fluorocyclopropyl]methanamine (20 mg, 0.22 mmol, ~5.5 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using column chromatography eluting with a 40-100% gradient of EtOAc in isohexane, followed by 0-10% MeOH in EtOAc. Product-containing fractions were combined and concentrated in vacuo to give the title compound (14 mg). $\delta_H$ (400 MHz, DMSO-d6) 12.04 (s, 1H), 11.26-11.12 (m, 1H), 8.81-8.14 (m, 1H), 7.93-7.75 (m, 1H), 7.42-6.92 (m, 1H), 5.97-5.57 (m, 1H), 4.90-4.58 (m, 1H), 4.55-4.34 (m, 1H), 3.62-3.45 (m, 3H), 3.40-3.32 (m, 2H), 3.21-2.77 (m, 4H), 2.29-2.11 (m, 2H), 1.98-1.88 (m, 1H), 1.26-1.11 (m, 1H), 0.91-0.78 (m, 4H), 0.78-0.61 (m, 2H). LCMS [M+H]+ 565, RT 1.52 minutes (Method 26).

Example 455

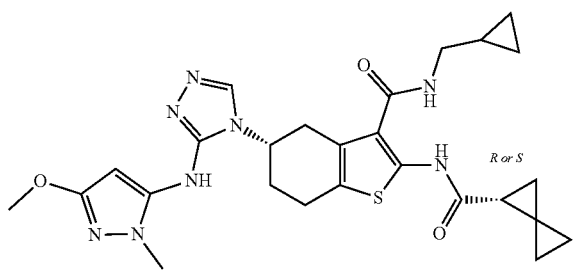 [SMILES: COc1cc(Nc2nncn2[C@H]2CCc3sc(NC(=O)[C@@H]4CC45CC5)c(C(=O)NCC4CC4)c3C2)n(C)n1]

(5S)—N-(cyclopropylmethyl)-5-[3-[(5-methoxy-2-methyl-pyrazol-3-yl)amino]-1,2,4-triazo-4-yl]-2-[[(2R*)-spiro[2.2]pentane-2-carbonyl]amino]-4,5,6,7-tetrahydrobenzothiophene-3-carboxamide (* or S)

To a stirring solution of intermediate 488 (270 mg, 0.51 mmol) in anhydrous DMF (6 mL) was added formic hydrazide (92 mg, 1.53 mmol) followed by mercury dichloride (416 mg, 1.53 mmol) and triethylamine (0.21 mL, 1.53 mmol), and the resulting mixture was stirred at 90° for 4 hours. Celite was added to the stirring mixture and it was diluted with ethyl acetate (10 mL). The mixture was filtered through a pad of celite, washing through with more ethyl acetate, and the solvent was evaporated in vacuo. The crude material was purified by flash column chromatography eluting with a 0 to 10% methanol in DCM gradient to afford a white solid. The title compound was afforded by separating the two diastereoisomers by chiral chromatography (50:50 Ethanol: Methanol with Cellulose-4 25 cm column at 7 mL/min).

Isomer 2—Peak 2 (17 mg, 99% chiral purity). $\delta_H$ (500 MHz, Methanol-d4) 8.27 (s, 1H), 4.59-4.48 (m, 1H), 3.82 (s, 3H), 3.57 (s, 3H), 3.34-3.32 (m, 1H), 3.29-3.22 (m, 1H), 3.20-3.13 (m, 1H), 3.12-3.03 (m, 1H), 3.02-2.86 (m, 2H), 2.40-2.30 (m, 2H), 2.16 (dd, J=7.1, 4.8 Hz, 1H), 1.53-1.48 (m, 2H), 1.10-1.03 (m, 2H), 1.03-0.97 (m, 1H), 0.98-0.89 (m, 2H), 0.54-0.44 (m, 2H), 0.27-0.21 (m, 2H), 3 exchangeable+1 aromatic protons missing. LCMS [M+H]+ 537, RT 2.58 minutes (Method 10). Chiral LC** RT=14.56 minutes.
** Chiral analysis using Cellulose-4 4.6×250 mm, 5 μm column, flow rate 0.5 mL/min, eluting with 50:50 Ethanol:Methanol, 20 minutes run time on a Waters 2795.

Example 456

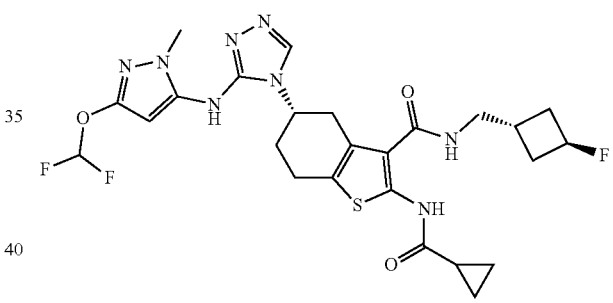

(5S)-2-(cyclopropanecarbonylamino)-5-[3-[[5-(difluoromethoxy)-2-methylpyrazol-3-yl]amino]-1,2,4-triazol-4-yl]-N-[trans-(3-fluorocyclobutyl)methyl]-4,5,6,7-tetrahydro-1-benzothiophene-3-carboxamide The title compound was obtained following general method 1 with intermediate 646 (20 mg, 0.04 mmol), trans-(3-fluorocyclobutyl)methanamine hydrochloride (20 mg, 0.143 mmol, 3.5 equivalents), triethylamine (0.017 mL, 3 equivalents), and DMF (0.67 mL). Reaction time: 45 min at 140° C. The cooled reaction mixture was diluted with water (1 mL) and DCM (1 mL). The organic phase was partitioned and dried over $Na_2SO_4$ then concentrated under reduced pressure. The crude product was then purified using column chromatography eluting with a 40-100% gradient of EtOAc in isohexane, followed by 0-10% MeOH in EtOAc. Product-containing fractions were combined and concentrated in vacuo to give the title compound (11 mg). $\delta_H$ (400 MHz, DMSO-d6) 12.04 (s, 1H), 11.21-11.03 (m, 1H), 8.77-8.15 (m, 1H), 8.15-7.98 (m, 1H), 7.85-7.69 (m, 1H), 7.46-6.87 (m, 1H), 5.95-5.56 (m, 1H), 5.25-4.98 (m, 2H), 4.53-4.33 (m, 1H), 3.63-3.43 (m, 3H), 3.28-3.20 (m, 1H), 3.17-3.03 (m, 2H), 3.00-2.76 (m, 2H), 2.43-2.34 (m, 1H), 2.29-2.03 (m, 5H), 1.99-1.84 (m, 1H), 0.92-0.75 (m, 4H). LCMS [M+H]⁺ 579, RT 1.60 minutes (Method 26).

Example 457

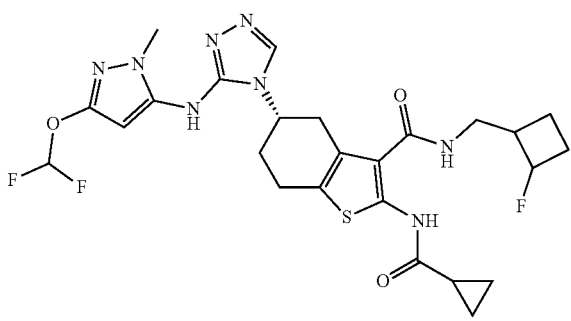 [SMILES: Cn1nc(OC(F)F)cc1Nc1nncn1[C@H]1CCc2sc(NC(=O)C3CC3)c(C(=O)NCC3CCC3F)c2C1]

(5S)-2-(cyclopropanecarbonylamino)-5-[3-[[5-(difluoromethoxy)-2-methylpyrazol-3-yl]amino]-1,2,4-triazol-4-yl]-N-[(2-fluorocyclobutyl)methyl]-4,5,6,7-tetrahydro-1-benzothiophene-3-carboxamide The title compound was obtained following general method 1 with intermediate 646 (20 mg, 0.04 mmol), (2-fluorocyclobutyl)methanamine hydrochloride (60 mg, 0.43 mmol, ~10 equivalents), triethylamine (0.017 mL, 3 equivalents), and DMF (0.67 mL). Reaction time: 45 min at 140° C. The cooled reaction mixture was diluted with water (1 mL) and DCM (3 mL). The organic phase was partitioned and dried over Na₂SO₄ then concentrated under reduced pressure. The crude product was then purified using column chromatography eluting with a 40-100% gradient of EtOAc in isohexane, followed by 0-10% MeOH in EtOAc. Product-containing fractions were combined and concentrated in vacuo to give the title compound (24 mg). δ$_H$ (400 MHz, DMSO-d6) 12.03 (s, 1H), 11.23-11.05 (m, 1H), 8.81-8.15 (m, 1H), 7.84-7.60 (m, 1H), 7.43-6.91 (m, 1H), 5.96-5.61 (m, 1H), 5.23-4.94 (m, 1H), 4.51-4.30 (m, 1H), 3.61-3.35 (m, 3H), 3.19-2.98 (m, 1H), 2.99-2.70 (m, 4H), 2.31-2.10 (m, 4H), 1.97-1.88 (m, 1H), 1.69-1.51 (m, 1H), 0.91-0.77 (m, 4H). LCMS [M+H]⁺ 579, RT 1.62 minutes (Method 26).

Example 458

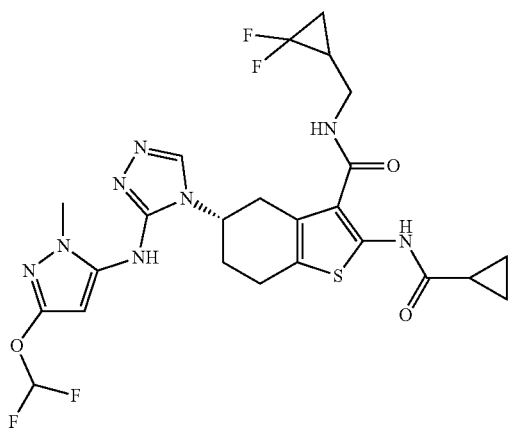 [SMILES: Cn1nc(OC(F)F)cc1Nc1nncn1[C@H]1CCc2sc(NC(=O)C3CC3)c(C(=O)NCC3CC3(F)F)c2C1]

(5S)-2-(cyclopropanecarbonylamino)-N-[(2,2-difluorocyclopropyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide The title compound was obtained following general method 1 with intermediate 646 (30 mg, 0.06 mmol), (2,2-difluorocyclopropyl)methanamine hydrochloride (27 mg, 0.189 mmol, 3 equivalents), triethylamine (0.02 mL, 3 equivalents), and DMF (1 mL). Reaction time: 15 min at 140° C. in a sealed vial. The cooled reaction mixture was diluted DCM (3 mL) and washed with water (2 mL). The organic phase was partitioned and dried over Na₂SO₄ then concentrated under reduced pressure. The crude product was then purified using column chromatography eluting with a 0-100% gradient of EtOAc in isohexane followed by 0-10% MeOH in EtOAc. Product-containing fractions were combined and concentrated under reduced pressure to afford the title compound (12.5 mg, 34% Yield). δ$_H$ (300 MHz, DMSO-d6) 12.03 (s, 1H), 11.26-11.10 (m, 1H), 8.78-8.13 (m, 1H), 8.07-7.90 (m, 1H), 7.57-6.85 (m, 1H), 6.00-5.56 (m, 1H), 4.53-4.34 (m, 1H), 3.62-3.45 (m, 3H), 3.39-3.27 (m, 1H), 3.21-3.06 (m, 1H), 3.04-2.75 (m, 3H), 2.25-2.10 (m, 2H), 2.10-1.87 (m, 2H), 1.62-1.42 (m, 1H), 1.40-1.20 (m, 1H), 1.00-0.73 (m, 4H). LCMS [M+H]⁺ 583, RT 1.62 minutes (Method 26).

Examples 459 & 460

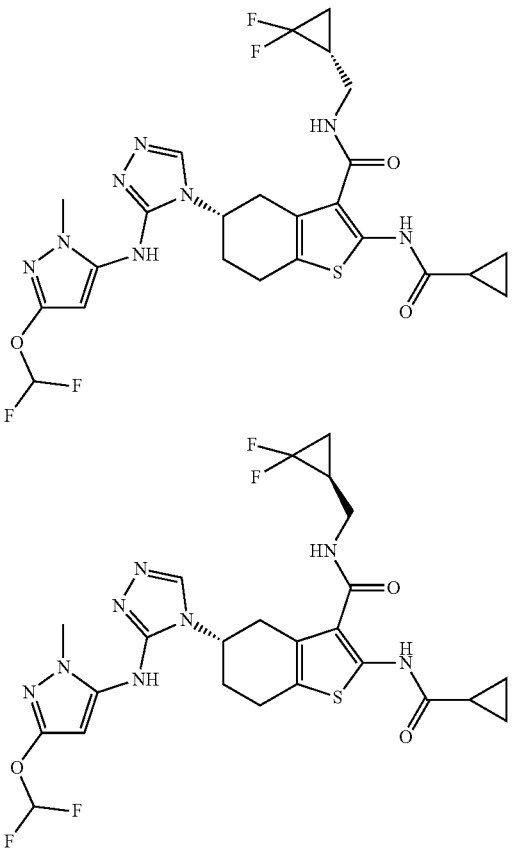 [SMILES: Cn1nc(OC(F)F)cc1Nc1nncn1[C@H]1CCc2sc(NC(=O)C3CC3)c(C(=O)NC[C@H]3CC3(F)F)c2C1 ; Cn1nc(OC(F)F)cc1Nc1nncn1[C@H]1CCc2sc(NC(=O)C3CC3)c(C(=O)NC[C@@H]3CC3(F)F)c2C1]

(5S)-2-(cyclopropanecarbonylamino)-N-[[(1R)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide (5S)-2-(cyclopropanecarbonylamino)-N-[[(1S)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide Example 458 was purified chiral SFC to give the two isomers titled above:
Peak 1: δ$_H$ (400 MHz, Methanol-d4) 8.46-7.81 (m, 1H), 6.89 (t, J=73.9 Hz, 1H), 5.95-5.51 (m, 1H), 4.62-4.41 (m, 1H), 3.62 (s, 3H), 3.52-3.41 (m, 2H), 3.30-3.25 (m, 1H), 3.12-2.80 (m, 3H), 2.42-2.26 (m, 2H), 2.11-1.90 (m, 1H), 1.86-1.76 (m, 1H), 1.55-1.40 (m, 1H), 1.35-1.11 (m, 2H), 1.04-0.87 (m, 3H). LCMS [M+H]$^+$ 583, RT 1.64 minutes (Method 26). Chiral SFC* RT=5.49 minutes
Peak 2: δ$_H$ (400 MHz, Methanol-d4) 8.54-7.74 (m, 1H), 6.88 (t, J=73.7 Hz, 1H), 6.02-5.47 (m, 1H), 4.65-4.38 (m, 1H), 3.68-3.50 (m, 4H), 3.43-3.23 (m, 2tH), 3.12-2.80 (m, 3H), 2.42-2.24 (m, 2H), 2.09-1.93 (m, 1H), 1.87-1.76 (m, 1H), 1.54-1.42 (m, 1H), 1.40-1.12 (m, 2H), 1.07-0.80 (m, 3H). LCMS [M+H]$^+$ 583, RT 1.64 minutes (Method 26). Chiral SFC* RT=6.19 minutes

* Chiral analysis was performed using an Amylose-C column, 250×2.1 mm, 5 μm, eluted using an isocratic 25% IPA (+0.2% NH$_3$) in CO$_2$ method, flow rate of 4 mL/min, 125 bar and a 4.5 minute run time on a Waters UPC2-QDa.

Example 461

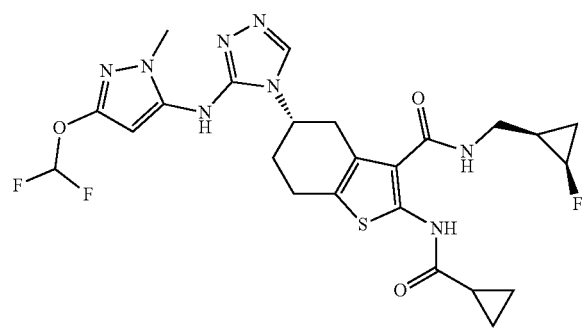 [SMILES: Cn1nc(OC(F)F)cc1Nc1nncn1[C@H]1CCc2sc(NC(=O)C3CC3)c(C(=O)NC[C@H]3C[C@H]3F)c2C1]

(5S)-2-(cyclopropanecarbonylamino)-5-[3-[[5-(difluoromethoxy)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide The title compound was obtained following general method 1 with intermediate 646 (50 mg, 0.10 mmol), [(1R,2R)-2-fluorocyclopropyl]methylammonium chloride (17.7 mg, 0.137 mmol, 1.3 equivalents), triethylamine (0.04 mL), and DMF (2 mL). Reaction time: 15 min at 70° C. Filtration and purification using HPLC (Method 5) gave the title compound (1.7 mg, 2.9% Yield). δ$_H$ (400 MHz, DMSO-d6) 12.04 (s, 1H), 11.27-11.13 (m, 1H), 8.79-8.35 (m, 1H), 8.19 (s, 1H), 7.93-7.78 (m, 1H), 7.46-6.92 (m, 1H), 5.96-5.62 (m, 1H), 4.72 (dd, J=65.9, 4.1 Hz, 1H), 4.51-4.34 (m, 1H), 3.62-3.45 (m, 3H), 3.44-3.28 (m, 1H), 3.22-3.03 (m, 1H), 3.05-2.89 (m, 1H), 2.88-2.77 (m, 2H), 2.28-2.09 (m, 21H), 2.00-1.86 (m, 1H), 1.26-1.11 (m, 1H), 0.91-0.78 (m, 4H), 0.78-0.63 (m, 21H). LCMS [M+H]$^+$ 565, RT 1.55 minutes (Method 26).

Example 462

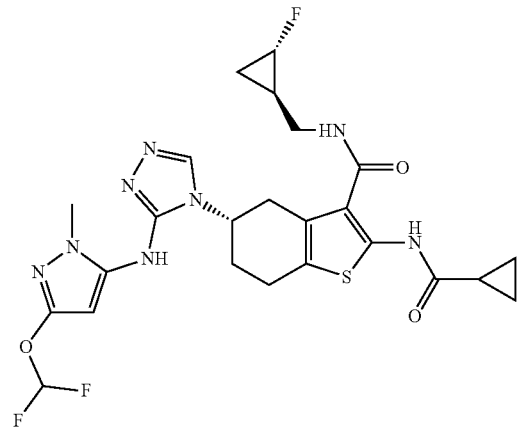 [SMILES: Cn1nc(OC(F)F)cc1Nc1nncn1[C@H]1CCc2sc(NC(=O)C3CC3)c(C(=O)NC[C@H]3C[C@@H]3F)c2C1]

(5S)-2-(cyclopropanecarbonylamino)-5-[3-[[5-(difluoromethoxy)-2-methylpyrazol-3-yl]amino]-1,2,4-triazol-4-yl]-N-[[(1R,2S)-2-fluorocyclopropyl]methyl]-4,5,6,7-tetrahydro-1-benzothiophene-3-carboxamide The title compound was obtained following general method 1 with intermediate 646 (50 mg, 0.10 mmol), intermediate 588 (3 equivalents), triethylamine (0.04 mL), and DMF (2 mL). Reaction time: 15 min at 70° C. Filtration and purification using column chromatography eluting with a 50-100% gradient of EtOAc in isohexane followed by 0-10% MeOH in EtOAc. Product-containing fractions were combined and concentrated under reduced pressure to afford the title compound (29 mg, 0.05 mmol, 49% Yield). δ$_H$ (300 MHz, DMSO-d6) 12.03 (s, 1H), 11.30-11.11 (m, 1H), 8.46-8.13 (m, 1H), 7.90-7.70 (m, 1H), 7.48-6.86 (m, 1H), 5.97-5.58 (m, 1H), 4.61 (ddt, J=64.7, 6.1, 2.3 Hz, 1H), 4.48-4.34 (m, 1H), 3.62-3.43 (m, 3H), 3.20-3.01 (m, 3H), 2.89-2.75 (m, 2H), 2.24-2.06 (m, 2H), 2.01 20-1.86 (m, 1H), 1.61-1.39 (m, 1H), 1.05-0.88 (m, 1H), 0.89-0.81 (m, 4H), 0.61 (dq, J=10.7, 6.7 Hz, 1H). LCMS [M+H]$^+$ 565, RT 1.65 minutes (Method 26).

Examples 463 &464

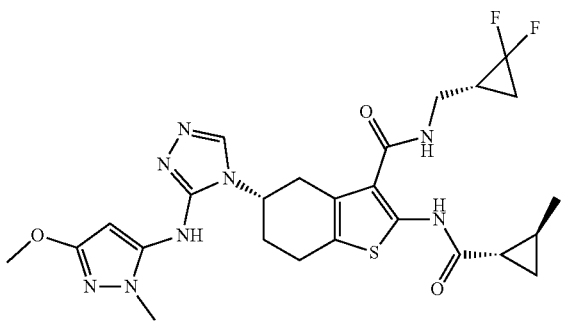

767
-continued

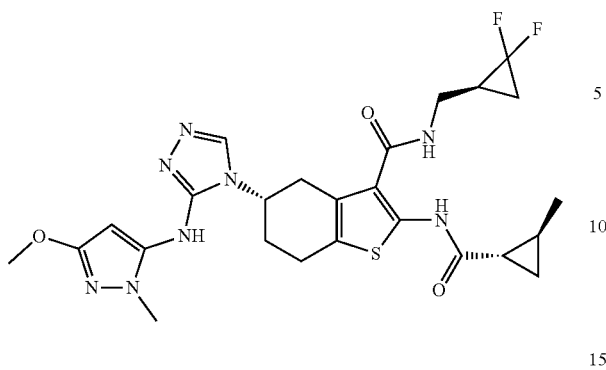

(5S)—N-[[(1R)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide (5S)—N-[[(1S)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide The title compounds were obtained following general method 1 with intermediate 647 (108 mg, 0.238 mmol), (2,2-difluorocyclopropyl)methanamine hydrochloride (51 mg, 0.36 mmol, 1.5 equivalents), DIPEA (0.062 mL, 0.36 mmol, 1.5 equivalents) and MeCN (2 mL). Reaction time: 2.5 hours at 70° C. Concentration gave a crude mixture of two diastereoisomers (167 mg). Purification by chiral chromatography gave the title compounds:

Isomer 1 (Peak 1, 4 mg, 3% Yield): $\delta_H$ (400 MHz, DMSO-d6) (contained 2 tautomers in an approximate ratio of 1:1) 11.82 (s, 0.5H), 11.19 (s, 0.5H), 11.14 (s, 0.5H), 8.54 (s, 0.5H), 8.38 (s, 0.5H), 8.14 (s, 0.5H), 8.01-7.88 (m, 1H), 5.57 (s, 0.5H), 5.39 (s, 0.51H), 4.48-4.35 (m, 1H), 3.72 (s, 1.5H), 3.69 (s, 1.5H), 3.50 (s, 1.5H), 3.43 (s, 1.5H), 3.40-3.28 (obs. m, 2H), 3.17-3.04 (m, 1H), 3.01-2.74 (m, 3H), 2.28-2.10 (m, 2H), 2.07-1.93 (m, 1H), 1.74-1.64 (m, 1H), 1.58-1.47 (m, 1H), 1.37-1.20 (m, 2H), 1.14-1.00 (m, 4H), 0.77-0.66 (m, 1H). LCMS [M+H]+ 561, RT 1.61 minutes (Method 26). Chiral LC* RT=4.07 minutes.

Isomer 2 (Peak 2, 3 mg, 2% Yield): $\delta_H$ (400 MHz, DMSO-d6) (contained 2 tautomers in an approximate ratio of 1:1) 11.83 (s, 0.5H), 11.17 (s, 0.5H), 11.12 (s, 0.5H), 8.54 (s, 0.5H), 8.37 (s, 0.5H), 8.14 (s, 0.5H), 8.02-7.88 (m, 1H), 5.57 (s, 0.5H), 5.39 (s, 0.51H), 4.50-4.33 (m, 1H), 3.72 (s, 1.5H), 3.69 (s, 1.5H), 3.50 (s, 1.5H), 3.43 (s, 1.5H), 3.39-3.27 (obs. m, 2H), 3.18-3.05 (m, 1H), 3.00-2.75 (m, 3H), 2.27-2.11 (m, 2H), 2.06-1.92 (m, 1H), 1.75-1.65 (m, 1H), 1.58-1.46 (m, 1H), 1.36-1.19 (m, 2H), 1.14-1.00 (m, 4H), 0.77-0.67 (m, 1H). LCMS [M+H]+ 561, RT 1.61 minutes (Method 26). Chiral LC* RT 5.04 minutes.

* Chiral analysis performed using a Chiralpak IC-3 column, 150×4.6 mm, 3 μm, eluted using an isocratic 10% EtOH in EtOAc (+0.1% DEA) method, flow rate of 1.5 mL/min, 100 bar and a 8 minute run time minute run time on an Agilent Infinity II 1290.

768

Example 465

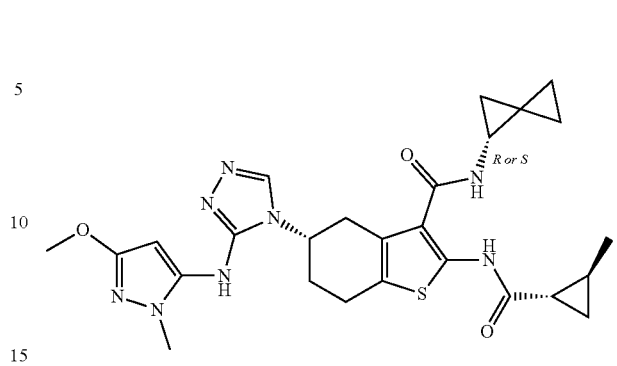

(5S)-5-[3-[(5-methoxy-2-methyl-pyrazol-3-yl)amino]-1,2,4-triazol-4-yl]-2-[[(1S,2S)-2-methylcyclopropanecarbonyl]amino]-N-[(2R*)-spiro[2.2]pentan-2-yl]-4,5,6,7-tetrahydrobenzothiophene-3-carboxamide [* or S]

The title compound was obtained following general method 1 with intermediate 647 (108 mg, 0.238 mmol), spiro[2.2]pentan-2-ylammonium chloride (43 mg, 0.36 mmol, 1.5 equivalents), DIPEA (0.062 mL, 0.36 mmol, 1.5 equivalents) and MeCN (2 mL). Reaction time: 2.5 hours at 70° C. Concentration gave a crude mixture of two diastereoisomers (177 mg). Purification by chiral SFC (Chiralpak IB column, 250×20 mm, 5 μm, Isocratic 25% MeOH (+0.1% ammonium hydroxide) in CO2, 100 mL/min, 14 minutes, 40° C. and 120 bar) gave the title compound (Peak 1 of 2, 4 mg, 3% Yield). $\delta_H$ (300 MHz, DMSO-d6) (contained 2 tautomers in an approximate ratio of 0.5:0.5) 11.81 (s, 0.5H), 8.54 (s, 0.5H), 8.48 (s, 0.5H), 8.34 (s, 0.5H), 8.11 (s, 0.5H), 5.57 (s, 0.5H), 5.39 (s, 0.5H), 4.46-4.30 (m, 1H), 3.72 (s, 1.5H), 3.70 (s, 1.5H), 3.50 (s, 1.5H), 3.44 (s, 1.5H), 3.18-3.09 (m, 1H), 2.96-2.66 (m, 3H), 2.24-2.03 (m, 2H), 1.33-0.79 (m, 13H), 0.77-0.67 (m, 1H). LCMS [M+H]+ 537, RT 1.58 minutes (Method 26).

Example 466

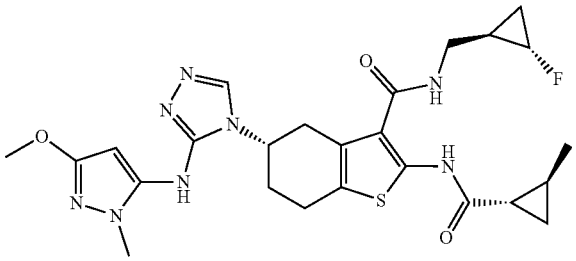

(5S)—N-[[(1R,2S)-2-fluorocyclopropyl]methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 647 (54 mg, 0.12 mmol), intermediate 588 (314 mg, 0.211 mmol, 6 mass %, solution in DMSO, ~1.7 equivalents), DIPEA (0.062 mL, 0.36 mmol, 1.5 equivalents) and MeCN (0.7 mL). Reaction time: 2.5 hours at 70° C. Concentration under reduced pressure followed by purification using HPLC (Method 5) gave the title compound (6.6 mg, 0.012 mmol, 10% Yield). δ$_H$ (300 MHz, d-Chloroform) 11.93 (s, 1H), 7.68 (s, 1H), 6.47 (s, 1H), 5.49 (s, 1H), 4.78-4.40 (m, 2H), 3.88 (s, 3H), 3.74-3.44 (m, 4H), 3.47-3.14 (m, 2H), 3.08-2.78 (m, 3H), 2.40-2.18 (m, 2H), 1.73-1.47 (m, 2H), 1.46-1.26 (m, 2H), 1.17 (d, J=6.0 Hz, 3H), 1.13-1.00 (m, 1H), 0.84-0.74 (m, 1H), 0.72-0.58 (m, 1H). LCMS [M+H]$^+$ 543, RT 1.59 minutes (Method 26).

Example 467

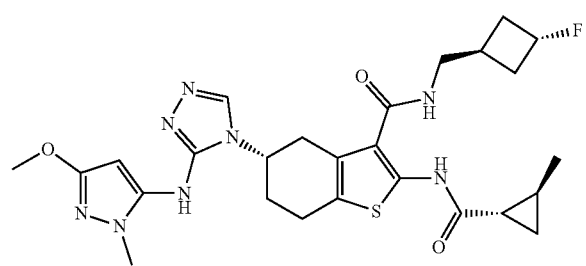 [SMILES: COc1cc(Nc2nncn2[C@H]2CCc3sc(NC(=O)[C@H]4C[C@@H]4C)c(C(=O)NC[C@H]4C[C@H](F)C4)c3C2)n(C)n1]

(5S)—N-[trans-(3-fluorocyclobutyl)methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 647 (54 mg, 0.12 mmol), trans-(3-fluorocyclobutyl)methanamine hydrochloride (52 mg, 0.36 mmol, 96% mass, 1.5 equivalents), DIPEA (0.062 mL, 0.36 mmol, 1.5 equivalents) and MeCN (1 mL). Reaction time: 1 hour at 70° C. Concentration under reduced pressure followed by purification using HPLC (Method 5) gave the title compound (29 mg, 44% Yield). δ$_H$ (300 MHz, d-Chloroform) 11.93 (s, 1H), 7.57 (s, 1H), 6.03 (s, 1H), 5.31 (s, 1H), 5.14 (dp, J=55.4, 6.1 Hz, 1H), 4.74-4.52 (m, 1H), 3.86 (s, 3H), 3.62 (s, 3H), 3.54-3.34 (m, 3H), 3.03-2.77 (m, 3H), 2.71-2.53 (m, 1H), 2.45-2.08 (m, 6H), 1.58-1.46 (m, 1H), 1.41 (dt, J=8.2, 4.3 Hz, 1H), 1.32 (dt, J=8.6, 4.2 Hz, 1H), 1.17 (d, J=6.0 Hz, 3H), 0.83-0.71 (m, 1H). LCMS [M+H]$^+$ 557, RT 1.64 minutes (Method 26).

Example 468

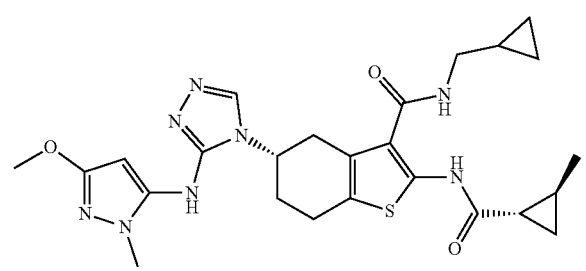

(5S)—N-(cyclopropylmethyl)-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide The title compound was obtained following general method 1 with intermediate 647 (32 mg, 0.071 mmol), cyclopropylmethanamine (0.018 mL, 0.21 mmol) and MeCN (0.7 mL). Reaction time: 1 hours at 70° C. Concentration under reduced pressure followed by purification using HPLC (Method 5) gave the title compound (7.7 mg, 21% Yield). δ$_H$ (400 MHz d-chloroform) 12.03 (s, 1H), 7.52 (s, 1H), 5.84 (s, 1H), 5.24 (s, 1H), 4.74-4.54 (m, 1H), 3.88 (s, 3H), 3.63 (s, 3H), 3.52-3.38 (m, 1H), 3.36-3.18 (m, 2H), 3.04-2.74 (m, 3H), 2.46-2.30 (m, 1H), 2.30-2.21 (m, 1H), 1.58-1.46 (m, 1H), 1.42 (dt, J=8.3, 4.3 Hz, 1H), 1.33 (dt, J=8.6, 4.3 Hz, 1H), 1.16 (d, J=6.0 Hz, 3H), 1.13-1.00 (m, 1H), 0.78 (ddd, J=7.8, 6.4, 4.0 Hz, 1H), 0.59-0.51 (m, 2H), 0.29-0.23 (m, 2H). LCMS [M+H]$^+$ 525, RT 1.62 minutes (Method 26).

Examples 469 & 470

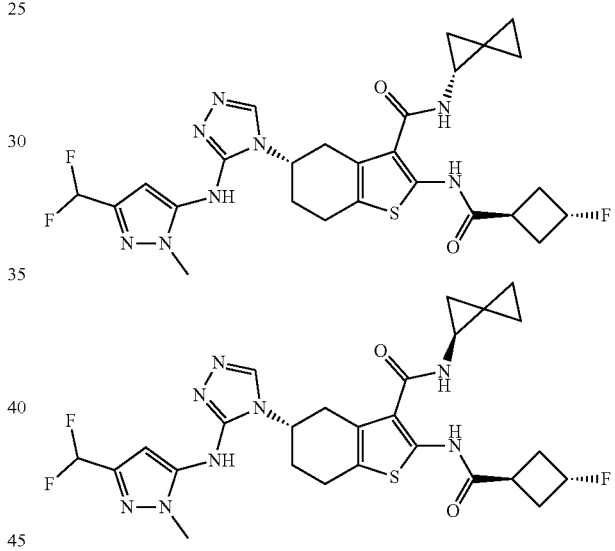

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide (5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide Triethylamine (0.030 mL, 0.21 mmol) was added to a suspension of intermediate 650 (105 mg, 0.206 mmol) and spiro[2.2]pentan-2-amine hydrochloride (27 mg, 0.22 mmol) in DCM (1.5 mL). N-(3-Dimethylaminopropyl)-N'-ethylcarbodiimide hydrochloride (42 mg, 0.22 mmol) was then added and the reaction mixture stirred at r.t. for 22.5 hours. A second portion of N-(3-dimethylaminopropyl)-N'-ethylcarbodiimide hydrochloride (4.0 mg, 0.021 mmol) was added and the reaction stirred for a further 3 hours at room temperature. MeCN (1.5 mL) was added and the reaction was stirred at 75° C. for 7 hours and then left to stand at room temperature overnight. Another portion of spiro[2.2]pentan-2-amine hydrochloride (5.2 mg, 0.041 mmol, 95% mass) was then added and the reaction mixture stirred for a further 3.5 hours at 75° C. The reaction mixture was cooled to room temperature, concentrated in vacuo and dissolved in DCM (20 mL). Water (20 mL) was added, the layers separated and the aqueous layer extracted with DCM (2×10 mL). The combined organic layers were dried and concentrated in vacuo to give the crude product as a mixture of isomers. Purification by chiral SFC to give the title compounds:

Trans-Isomer 1—Peak 2 (9 mg, 8% Yield): $\delta_H$ (400 MHz, d-Chloroform) 11.92 (s, 1H), 7.50 (s, 1H), 6.60 (t, J=55.3 Hz, 1H), 6.03 (s, 1H), 5.97 (s, 1H), 5.33 (dp, J=56.0, 6.3 Hz, 1H), 4.78 (s, 1H), 3.77 (s, 3H), 3.45 (dd, J=15.0, 5.4 Hz, 1H), 3.34-3.18 (m, 2H), 3.07-2.93 (m, 1H), 2.93-2.79 (m, 2H), 2.78-2.66 (m, 2H), 2.66-2.49 (m, 2H), 2.45-2.32 (m, 1H), 2.32-2.19 (m, 1H), 1.41 (t, J=6.0 Hz, 1H), 1.06 (dt, J=9.4, 4.8 Hz, 1H), 1.00-0.91 (m, 2H), 0.84-0.66 (m, 2H). $\delta_F$ (282 MHz, d-Chloroform) −111.27 (d, J=52.0 Hz), −165.13−−165.59 (m). LCMS [M+H]$^+$ 575, RT 1.6 minutes (Method 26). Chiral SFC* RT=4.50 minutes.

Trans-Isomer 2—Peak 3 (9 mg, 8% Yield): $\delta_H$ (400 MHz, d-Chloroform) 11.95 (s, 1H), 7.49 (s, 1H), 6.60 (t, J=55.4 Hz, 1H), 6.00 (s, 1H), 5.89 (s, 1H), 5.34 (dp, J=56.0, 6.2 Hz, 1H), 4.79-4.66 (m, 1H), 3.76 (s, 3H), 3.42 (dd, J=14.8, 5.4 Hz, 1H), 3.33-3.19 (m, 2H), 3.04-2.93 (m, 1H), 2.92-2.82 (m, 2H), 2.78-2.67 (m, 2H), 2.67-2.48 (m, 2H), 2.44-2.32 (m, 1H), 2.32-2.21 (m, 1H), 1.41 (t, J=5.9 Hz, 1H), 1.07 (dt, J=9.3, 4.7 Hz, 1H), 1.00-0.92 (m, 2H), 0.81 (dt, J=8.9, 4.7 Hz, 1H), 0.75 (dt, J=9.4, 4.7 Hz, 1H). $\delta_F$ (282 MHz, d-Chloroform) −111.23 (d, J=55.4 Hz), −165.11−−165.56 (m). LCMS [M+H]$^+$ 575, RT 1.6 minutes (Method 26). Chiral SFC* RT=5.01 minutes.

* Using chiral SFC Method 1 with a Chiral Art SJ column

Example 471

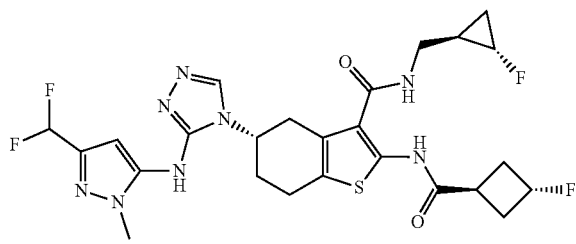 [SMILES: Cn1nc(C(F)F)cc1Nc1nncn1[C@H]1CCc2sc(NC(=O)[C@H]3C[C@H](F)C3)c(C(=O)NC[C@H]3C[C@@H]3F)c2C1]

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide N-(3-dimethylaminopropyl)-N'-ethylcarbodiimide hydrochloride (22 mg, 0.11 mmol) was added to a suspension of intermediate 650 (55 mg, 0.11 mmol) and intermediate 588 (192 mg, 0.129 mmol, 6% mass, solution in DMSO) in DCM (0.8 mL). The reaction mixture was stirred at room temperature for 16.5 hours. A second portion of N-(3-dimethylaminopropyl)-N'-ethylcarbodiimide hydrochloride (5 mg, 0.03 mmol) was added and the reaction stirred for a further 2 hours at room temperature. MeCN (0.8 mL) was added and the reaction was stirred at 75° C. for 5 hours before adding more intermediate 588 (80 mg, 0.054 mmol, 6% mass, solution in DMSO) and N-(3-dimethylaminopropyl)-N'-ethylcarbodiimide hydrochloride (1 mg, 0.005 mmol) and stirring at 75° C. for a further 6 hours. The reaction mixture was left to stand at room temperature overnight before concentrating in vacuo. The residue was dissolved in DCM (20 mL) and water (20 mL) was added. The layers were separated and the aqueous layer was extracted with DCM (2×10 mL). Organics combined, dried and concentrated under reduced pressure. The crude residue was then purified by HPLC to give the title compound (17 mg, 27% Yield). $\delta_H$ (400 MHz, d-Chloroform) 11.83 (s, 1H), 7.56 (s, 1H), 6.59 (t, J=55.4 Hz, 1H), 6.09 (s, 1H), 6.03 (s, 1H), 5.34 (dp, J=56.0, 6.3 Hz, 1H), 4.79-4.69 (m, 1H), 4.53 (ddt, J=63.8, 6.3, 2.4 Hz, 1H), 3.77 (s, 3H), 3.49 (dd, J=16.7, 5.3 Hz, 1H), 3.36-3.16 (m, 3H), 3.07-2.84 (m, 3H), 2.79-2.67 (m, 2H), 2.67-2.51 (m, 2H), 2.45-2.34 (m, 1H), 2.34-2.24 (m, 1H), 1.64-1.49 (m, 1H), 1.11 (dddd, J=21.1, 10.9, 7.2, 2.5 Hz, 1H), 0.65 (dq, J=10.3, 6.8 Hz, 1H). $\delta_F$ (282 MHz, d-Chloroform) −111.26 (d, J=55.5 Hz), −165.23−−165.69 (m). LCMS [M+H]$^+$ 581, RT 1.56 minutes (Method 26).

Example 472

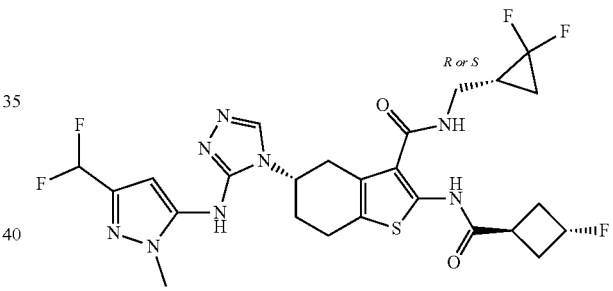

(5S)—N-[[(1R*)-2,2-difluorocyclopropyl]methyl]-5-[3-[[5-(difluoromethyl)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxamide [* or S]

Triethylamine (0.031 mL, 0.22 mmol) was added to a suspension of intermediate 650 (107 mg, 0.211 mmol) and (2,2-difluorocyclopropyl)methanamine hydrochloride (34 mg, 0.22 mmol) in DCM (1.6 mL). N-(3-dimethylaminopropyl)-N'-ethylcarbodiimide hydrochloride (42 mg, 0.22 mmol) was then added and the reaction mixture stirred at room temperature for 22.5 hours. A second portion of N-(3-dimethylaminopropyl)-N'-ethylcarbodiimide hydrochloride (4 mg, 0.02 mmol) was added and the reaction stirred for a further 3 hours. More MeCN (1.6 mL) was added and the reaction was stirred for 7 hours at 75° C. and then left to stand at room temperature overnight. The residue was dissolved in DCM (20 mL) and water (20 mL) was added. The layers were separated and the aqueous layer was extracted with DCM (2×10 mL). Organics combined, dried and concentrated under reduced pressure. The crude residue was then purified by chiral SFC to give the title compound (Peak 1, 7 mg, 6% Yield). $\delta_H$ (400 MHz, d-Chloroform) 11.93 (s, 1H), 7.46 (s, 1H), 6.60 (t, J=55.4 Hz, 1H), 5.96 (s, 1H), 5.91 (s, 1H), 5.35 (dp, J=56.0, 6.4 Hz, 1H), 4.78-4.53 (m, 1H), 3.98-3.88 (m, 1H), 3.76 (s, 3H), 3.41 (dd, J=14.8, 5.4 Hz, 1H), 3.34-3.14 (m, 2H), 3.06-2.82 (m, 3H), 2.81-2.68 (m, 2H), 2.68-2.52 (m, 2H), 2.46-2.33 (m, 1H), 2.33-2.24 (m, 1H), 2.04-1.90 (m, 1H), 1.52 (tdd, J=11.9, 8.0, 4.5 Hz, 1H), 1.20 (dtd, J=15.3, 7.7, 3.6 Hz, 1H). $\delta_F$ (282 MHz, d-Chloroform) −111.15 (d, J=55.4 Hz), −129.05 (dt, J=160.8, 12.9 Hz), −143.94 (ddd, J=160.7, 14.1, 5.6 Hz), −165.25--165.71 (m). LCMS [M+H]⁺ 599, RT 1.62 minutes (Method 26). Chiral SFC** RT=7.53 minutes.

** Using chiral SFC Method 1 with a Chiralpak IC-3 column with an isocratic 20% MeOH (+0.1% ammonium hydroxide) method and a 10 minute run time.

Example 473

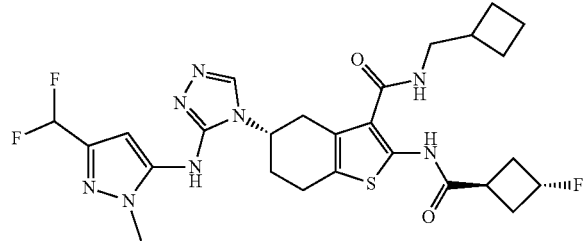 [SMILES: Cn1nc(C(F)F)cc1Nc1nncn1[C@H]1CCc2sc(NC(=O)[C@H]3C[C@H](F)C3)c(C(=O)NCC3CCC3)c2C1]

(5S)—N-(cyclobutylmethyl)-5-[3-[[5-(difluoromethyl)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide N-(3-dimethylaminopropyl)-N'-ethylcarbodiimide hydrochloride (9 mg, 0.05 mmol) was added to a suspension of intermediate 650 (20 mg, 0.039 mmol) in MeCN (0.6 mL). The suspension was stirred at 50° C. for 3 hours then at room temperature overnight. Cyclobutylmethanamine hydrochloride (7.2 mg, 0.059 mmol) was then added followed by triethylamine (0.015 mL, 0.11 mmol). The reaction mixture was heated at 75° C. for 30 min then concentrated under reduced pressure. The residue was dissolved in DCM (20 mL). Water (20 mL) was added and the layers separated. The aqueous layer was extracted with DCM (2×10 mL). Organics combined, dried and concentrated under reduced pressure. The crude residue was then purified by HPLC to give the title compound (9 mg, 40% Yield). $\delta_H$ (400 MHz, d-Chloroform) 12.02 (s, 1H), 9.17 (s, 1H), 7.43 (s, 1H), 6.60 (t, J=55.4 Hz, 1H), 5.94 (s, 1H), 5.62 (s, 1H), 5.34 (dq, J=56.1, 6.3 Hz, 1H), 4.66 (s, 1H), 3.75 (s, 3H), 3.53-3.35 (m, 3H), 3.32-3.19 (m, 1H), 3.06-2.82 (m, 3H), 2.80-2.67 (m, 2H), 2.67-2.49 (m, 3H), 2.46-2.33 (m, 1H), 2.33-2.24 (m, 1H), 2.11-2.00 (m, 2H), 1.99-1.81 (m, 2H), 1.76-1.64 (m, 2H). $\delta_F$ (282 MHz, d-Chloroform) −111.02 (d, J=55.3 Hz), −165.16 to −165.62 (m). LCMS [M+H]⁺ 577, RT 1.73 minutes (Method 26).

Examples 474 & 475

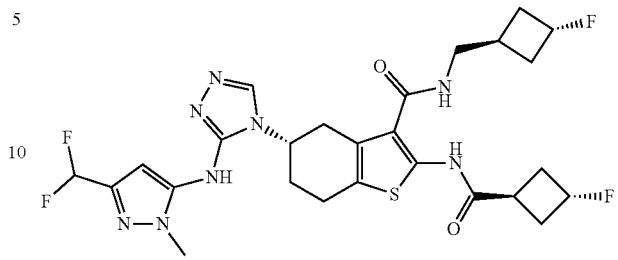

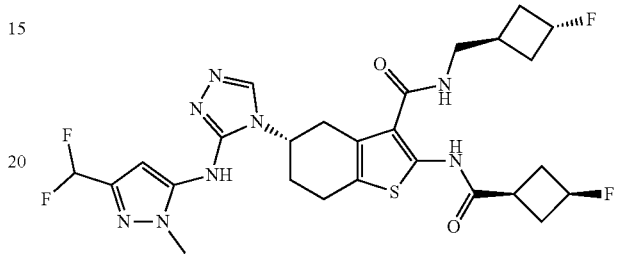

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide (474)

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-[trans-(3-fluorocyclobutyl)methyl]-4,5,6,7-tetrahydro-1-benzothiophene-3-carboxamide (475)

Triethylamine (0.015 mL, 0.11 mmol) was added to a suspension of intermediate 650 (54 mg, 0.11 mmol) and trans-(3-fluorocyclobutyl)methanamine hydrochloride (16 mg, 0.11 mmol) in DCM (0.8 mL). N-(3-dimethylaminopropyl)-N'-ethylcarbodiimide hydrochloride (21 mg, 0.11 mmol) was then added and the reaction mixture stirred at room temperature for 6 hours. A second portion of N-(3-dimethylaminopropyl)-N'-ethylcarbodiimide hydrochloride (4 mg, 0.02 mmol) was then added and the reaction mixture stirred at room temperature overnight. MeCN (0.8 mL) was then added and the reaction mixture stirred at 75° C. for 6 hours and 15 minutes. The reaction mixture was cooled to room temperature then concentrated under reduced pressure. The residue was dissolved in DCM (20 mL). Water (20 mL) was added and the layers separated. The aqueous layer was extracted with DCM (2×10 mL). Organics combined, dried and concentrated under reduced pressure. The crude residue was then purified by HPLC to give the title compounds:

Example 475 (cis): Peak 1 (10 mg, 16% Yield). $\delta_H$ (400 MHz, d-Chloroform) 11.70 (s, 1H), 7.62 (s, 1H), 6.60 (t, J=55.4 Hz, 1H), 6.18 (s, 1H), 6.10 (s, 1H), 5.25-4.87 (m, 2H), 4.87-4.74 (m, 1H), 3.81 (s, 3H), 3.56-3.38 (m, 3H), 3.10-2.97 (m, 1H), 2.97-2.80 (m, 2H), 2.74-2.55 (m, 6H), 2.48-2.27 (m, 4H), 2.26-2.09 (m, 2H). $\delta_F$ (282 MHz, d-Chloroform) −111.28 (d, J=55.5 Hz), −163.07--163.50 (m), −169.60--169.98 (m). LCMS [M+H]⁺ 595, RT 1.67 minutes (Method 26).

Example 474 (trans): Peak 2 (16 mg, 26% Yield). $\delta_H$ (400 MHz, d-Chloroform) 11.98 (s, 1H), 9.18 (s, 1H), 7.44 (s, 1H), 6.61 (t, J=55.4 Hz, 1H), 5.95 (s, 1H), 5.68 (t, J=5.8 Hz, 1H), 5.34 (dq, J=55.9, 6.2 Hz, 1H), 5.14 (dq, J=55.4, 5.6 Hz, 1H), 4.66 (s, 1H), 3.75 (s, 3H), 3.48 (dd, J=7.9, 5.8 Hz, 2H), 3.40 (dd, J=14.6, 5.4 Hz, 1H), 3.32-3.21 (m, 1H), 3.06-2.94 (m, 1H), 2.95-2.82 (m, 2H), 2.81-2.67 (m, 2H), 2.68-2.51 (m, 3H), 2.48-2.23 (m, 4H), 2.24-2.09 (m, 2H). $\delta_F$ (282 MHz, d-Chloroform) −111.06 (d, J=55.1 Hz), −165.23-−165.68 (m), −169.61-−170.08 (m). LCMS [M+H]$^+$ 595, RT 1.72 minutes (Method 26).

Examples 476 & 477

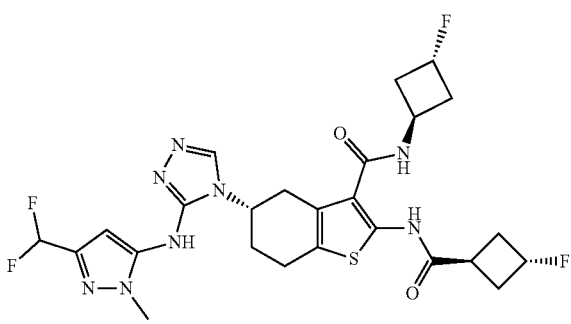

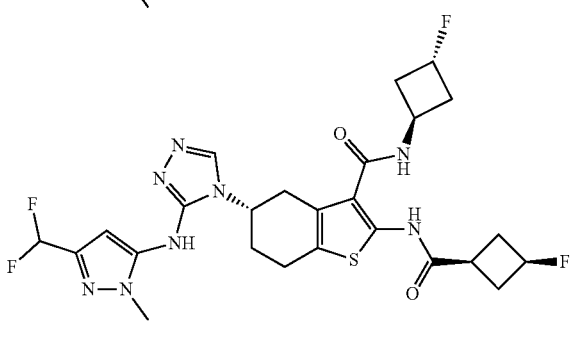

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide (476)

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-(trans-3-fluorocyclobutyl)-4,5,6,7-tetrahydro-1-benzothiophene-3-carboxamide (477)

Pyridine (0.024 mL, 0.29 mmol) was added to a solution of intermediate 650 (32 mg, 0.062 mmol) in DMF (0.93 mL, 12 mmol) under an atmosphere of N$_2$ and cooled to 0° C. Trans-3-fluorocyclobutanamine hydrochloride (8.9 mg, 0.068 mmol) was then added followed by 2,4,6-Tripropyl-1,3,5,2,4,6-trioxatriphosphorinane-2,4,6-trioxide solution (0.069 mL, 0.12 mmol, 50 mass %, solution in EtOAc). The solution was stirred for 17.5 hours with warming to room temperature (allowed the ice bath to melt). The reaction mixture was heated at 75° C. for 2 hours 15 mins. Triethylamine (0.069 mL, 0.49 mmol) was then added followed by a second portion of trans-3-fluorocyclobutanamine hydrochloride (8.9 mg, 0.068 mmol). The reaction mixture was heated for a further 1 hour and 45 mins at 75° C. then cooled to room temperature. Water (10 mL) was then added and the aqueous layer was extracted with EtOAc (3×10 mL). Organics combined, washed with brine (10 mL) and concentrated under reduced pressure. The crude residue was then purified by HPLC to give the title compounds:

Example 477 (cis): Peak 1 (4 mg, 11% Yield). $\delta_H$ (400 MHz, d-Chloroform) 11.96 (s, 1H), 7.44 (s, 1H), 6.61 (t, J=55.4 Hz, 1H), 5.95 (s, 1H), 5.76 (d, J=6.2 Hz, 1H), 5.33-5.13 (m, 1H), 5.10-4.88 (m, 1H), 4.73-4.64 (m, 2H), 3.76 (s, 3H), 3.40 (dd, J=14.5, 5.4 Hz, 1H), 3.06-2.84 (m, 3H), 2.82-2.55 (m, 7H), 2.47-2.31 (m, 3H), 2.31-2.21 (m, 1H). $\delta_F$ (282 MHz, d-Chloroform) −111.10 (d, J=56.0 Hz), −163.04-−163.43 (m), −177.94-−178.37 (m). LCMS [M+H]$^+$ 581, RT 1.57 minutes (Method 26).

Example 476 (trans): Peak 2 (6 mg, 17% Yield) $\delta_H$ (400 MHz, d-Chloroform) 11.80 (s, 1H), 7.52 (s, 1H), 6.60 (t, J=55.4 Hz, 1H), 6.06 (s, 1H), 6.02 (s, 1H), 5.44-5.13 (m, 2H), 4.80-4.71 (m, 1H), 4.71-4.62 (m, 1H), 3.77 (s, 3H), 3.47 (dd, J=14.8, 5.3 Hz, 1H), 3.31-3.21 (m, 1H), 3.05-2.84 (m, 3H), 2.82-2.66 (m, 4H), 2.66-2.50 (m, 2H), 2.48-2.33 (m, 3H), 2.32-2.21 (m, 1H). $\delta_F$ (282 MHz, d-Chloroform) −111.20 (d, J=55.4 Hz), −165.16-−165.61 (m), −178.01 (dt, J=55.9, 20.8 Hz). LCMS [M+H]$^+$ 581, RT 1.61 minutes (Method 26).

Example 478

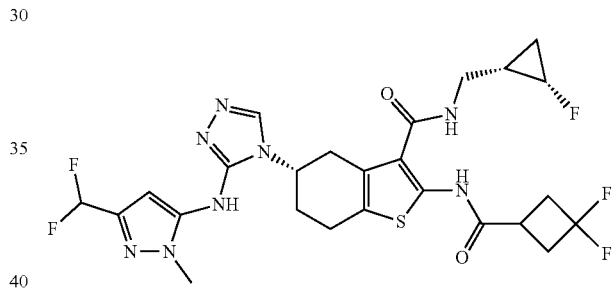

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1S,2S)-2-fluorocyclopropyl]methyl]-4,5,6,7-tetrahydro-1-benzothiophene-3-carboxamide The title compound was obtained following general method 3 with intermediate 653 (30 mg, 0.05 mmol), DIPEA (60 µL, 0.34 mmol), [(1S,2S)-2-fluorocyclopropyl]methylammonium chloride (30 mg, 0.24 mmol), HATU (50 mg, 0.13 mmol) and DMF (0.5 mL). Reaction duration: 1 hour and 50 min at 70° C. Once at room temperature the reaction mixture was purified using HPLC (Method 5) to give the title compound (8.4 mg, 29%). $\delta_H$ (400 MHz, d-Methanol) 8.21 (s, 1H), 6.62 (t, J=55.1 Hz, 1H), 6.28 (s, 1H), 4.67 (dtd, J=65.6, 5.9, 2.6 Hz, 1H), 4.55 (s, 1H), 3.72 (s, 3H), 3.68-3.58 (m, 1H), 3.37 (dd, J=14.1, 7.8 Hz, 2H), 3.17 (pd, J=8.4, 2.9 Hz, 1H), 3.10-3.00 (m, 1H), 3.01-2.71 (m, 6H), 2.34 (t, J=7.0 Hz, 2H), 1.28-1.15 (m, 1H), 0.87-0.62 (m, 2H). LCMS [M+H]$^+$ 599, RT 1.62 minutes (Method 26).

Example 479

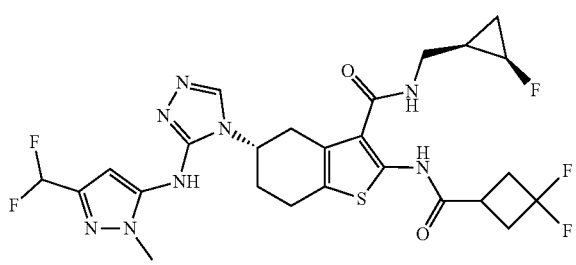 [SMILES: Cn1nc(C(F)F)cc1Nc1nncn1[C@H]1CCc2sc(NC(=O)C3CC(F)(F)C3)c(C(=O)NC[C@H]3C[C@H]3F)c2C1]

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide The title compound was obtained following general method 3 with intermediate 653 (30 mg, 0.05 mmol), DIPEA (in 2 portions of 50 µL, 0.29 mmol), [(1R,2R)-2-fluorocyclopropyl]methylammonium chloride (in 2 portions: 25 & 20 mg, 0.31 mmol), HATU (60 mg, 0.16 mmol) and DMF (0.5 mL). Reaction duration: 1 hour and 10 min at 70° C. Once at room temperature the reaction mixture was purified using HPLC (Method 5) to give the title compound (12 mg, 42% Yield). $\delta_H$ (400 MHz, d-Methanol) 8.21 (s, 1H), 6.62 (t, J=55.1 Hz, 1H), 6.28 (s, 1H), 4.67 (dtd, J=65.6, 5.9, 2.7 Hz, 2H), 3.80-3.63 (m, 4H), 3.38-3.22 (m, 2H), 3.18 (td, J=9.0, 8.5, 3.0 Hz, 1H), 3.12-2.97 (m, 1H), 2.98-2.75 (m, 6H), 2.34 (q, J=8.6, 7.8 Hz, 2H), 1.22 (td, J=14.8, 13.4, 9.1 Hz, 1H), 0.90-0.64 (m, 2H). LCMS [M+H]+ 599, RT 1.63 minutes (Method 26).

Example 480

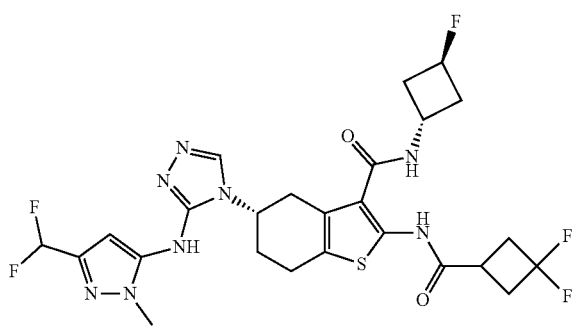 [SMILES: Cn1nc(C(F)F)cc1Nc1nncn1[C@H]1CCc2sc(NC(=O)C3CC(F)(F)C3)c(C(=O)N[C@H]3C[C@H](F)C3)c2C1]

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide The title compound was obtained following general method 3 with intermediate 653 (35 mg, 0.05 mmol), DIPEA (50 µL, 0.29 mmol), trans-3-fluorocyclobutanamine hydrochloride (in 2 portions of 30 mg, 0.23 mmol), HATU (in two portions of 30 mg, 0.08 mmol) and DMF (1 mL). Reaction duration: 1 hour 20 min at 70° C. Once at room temperature the reaction mixture was purified using HPLC (Method 5) to give the title compound (11 mg, 33% Yield). $\delta_H$ (400 MHz, d-Methanol) 8.18 (s, 1H), 6.55 (d, J=55.2 Hz, 1H), 6.28 (s, 1H), 5.16 (dtt, J=56.6, 6.4, 3.3 Hz, 1H), 4.67-4.51 (m, 2H), 3.72 (s, 3H), 3.31 (p, J=1.6 Hz, 1H), 3.23-3.10 (m, 1H), 3.04 (dd, J=16.6, 10.0 Hz, 1H), 2.98-2.74 (m, 6H), 2.67-2.51 (m, 2H), 2.48-2.24 (m, 4H). LCMS [M+H]+ 599, RT 1.59 minutes (Method 26).

Example 481

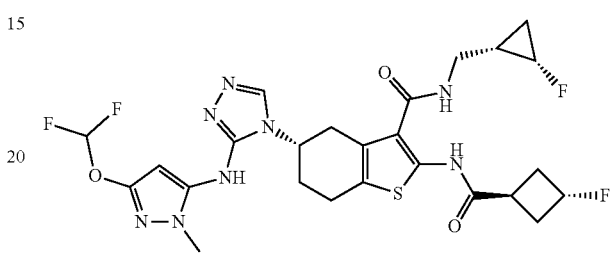

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1S,2S)-2-fluorocyclopropyl]methyl]-4,5,6,7-tetrahydro-1-benzothiophene-3-carboxamide The title compound was obtained following general method 3 with intermediate 530 (50 mg, 0.09 mmol), DIPEA (60 µL, 0.34 mmol), [(1S,2S)-2-fluorocyclopropyl]methylammonium chloride (30 mg, 0.24 mmol), HATU (50 mg, 0.13 mmol) and DMF (0.5 mL). Reaction duration: 1 hour 50 min at 70° C. The reaction mixture was diluted with EtOAc (30 mL) and washed with brine (50 mL). The aqueous phase was extracted with EtOAc (30 mL). The organic phases were combined and concentrated under reduced pressure. Purification by HPLC gave the title compound (8 mg, 14% Yield). $\delta_H$ (400 MHz, d-Methanol) 8.17 (s, 1H), 6.89 (t, J=73.8 Hz, 1H), 5.74 (s, 1H), 5.23 (ddt, J=56.2, 7.2, 6.2 Hz, 1H), 4.68 (dtd, J=65.6, 5.9, 2.6 Hz, 1H), 4.56-4.43 (m, 1H), 3.66-3.57 (m, 4H), 3.41-3.34 (m, 1H), 3.31 (dq, J=3.3, 1.6 Hz, 2H), 3.10-2.86 (m, 3H), 2.71-2.43 (m, 4H), 2.34 (q, J=7.7, 5.8 Hz, 2H), 1.29-1.15 (m, 1H), 0.86-0.66 (m, 2H). LCMS [M+H]+ 597, RT 1.61 minutes (Method 26).

Example 482

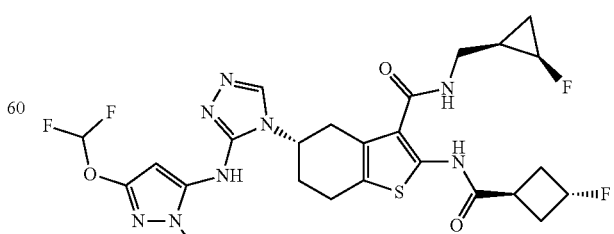

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2R)-2-fluorocyclopropyl]methyl]-4,5,6,7-tetrahydro-1-benzothiophene-3-carboxamide The title compound was obtained following general method 3 with intermediate 530 (40 mg, 0.07 mmol), DIPEA (70 µL, 0.40 mmol), intermediate 631 (30 mg, 0.23 mmol), HATU (60 mg, 0.16 mmol) and DMF (0.5 mL). Reaction duration: 1 hour 30 min at 70° C. The reaction mixture was diluted with EtOAc (30 mL) and washed with brine (50 mL). The aqueous phase was extracted with EtOAc (30 mL). The organic phases were combined and concentrated under reduced pressure. Purification by HPLC gave the title compound (6 mg, 11% Yield). δ$_H$ (400 MHz, d-Methanol) 8.27 (s, 1H), 6.89 (t, J=73.8 Hz, 1H), 5.76 (s, 1H), 5.36-5.12 (m, 1H), 4.67 (dtd, J=65.6, 6.0, 2.6 Hz, 1H), 4.51 (d, J=15.3 Hz, 1H), 3.70 (dd, J=14.0, 7.0 Hz, 1H), 3.60 (s, 3H), 3.31 (p, J=1.6 Hz, 3H), 3.14-3.00 (m, 1H), 2.96 (dd, J=15.4, 6.9 Hz, 2H), 2.72-2.44 (m, 4H), 2.34 (d, J=6.3 Hz, 2H), 1.25 (td, J=14.3, 6.9 Hz, 1H), 0.86-0.66 (m, 2H). LCMS [M+H]$^+$ 597, RT 1.61 minutes (Method 26).

Example 483

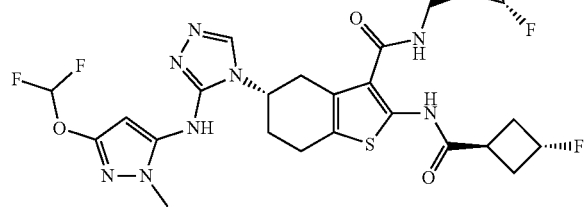

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide The title compound was obtained following general method 3 with intermediate 530 (50 mg, 0.09 mmol), DIPEA (80 µL, 0.46 mmol), intermediate 588 (6 wt % solution in DMSO) (in 2 portions: 220 & 100 mg, 0.22 mmol), HATU (two portions: 43 & 15 mg, 0.15 mmol) and DMF (1 mL). Reaction duration: 2 hours 50 min at 70° C. The reaction mixture was diluted with EtOAc (30 mL) and washed with brine (30 mL). The aqueous phase was extracted with EtOAc (2×30 mL). The organic phases were combined and concentrated under reduced pressure. Purification by HPLC gave the title compound (15 mg, 26% Yield). δ$_H$ (400 MHz, d-Chloroform) 11.83 (s, 1H), 7.58-7.43 (m, 1H), 6.79 (t, J=73.7 Hz, 1H), 6.01 (s, 1H), 5.49-5.19 (m, 2H), 4.68 (s, 1H), 4.51 (ddt, J=63.9, 6.3, 2.4 Hz, 1H), 3.62 (s, 3H), 3.45 (dd, J=14.8, 5.4 Hz, 1H), 3.34-3.13 (m, 3H), 3.03-2.80 (m, 3H), 2.78-2.64 (m, 2H), 2.56 (dddd, J=19.6, 13.7, 10.0, 5.7 Hz, 3H), 2.43-2.18 (m, 2H), 1.60-1.47 (m, 1H), 1.16-1.02 (m, 1H), 0.63 (dq, J=10.3, 6.7 Hz, 1H). LCMS [M+H]$^+$ 574, RT 1.61 minutes (Method 26).

Example 484 & 485

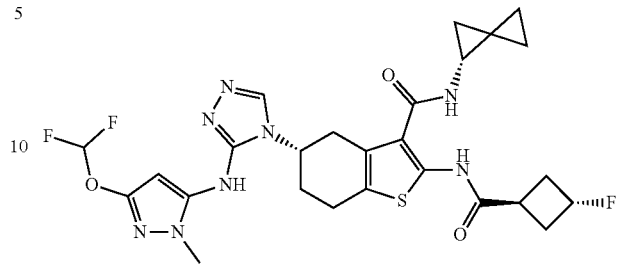

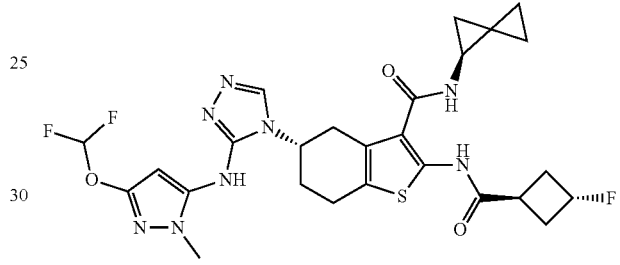

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide (5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide The title compound was obtained following general method 3 with intermediate 530 (in 2 portions: 25 & 60 mg, 0.16 mmol), DIPEA (in 2 portions: 40 & 80 µL, 0.69 mmol), spiro[2.2]pentan-2-amine (in 3 portions: 15, 30 & 30 mg, 0.86 mmol), HATU (in 3 portions: 30, 60 & 60 mg, 0.39 mmol) and DMF (0.5 mL). Reaction duration: 2 hours 30 min at 70° C. The reaction mixture was diluted with EtOAc (20 mL) and washed with a mixture of brine (50 mL) and water (20 mL). The aqueous phase was extracted with EtOAc (2×20 mL). The organic phases were combined, dried and concentrated under reduced pressure. Purification by chiral SFC gave the title compounds:

Isomer 1 (Peak 1, 0.7 mg, 2% Yield). LCMS [M+H]$^+$ 591, RT 1.72 minutes (Method 26). Chiral LC* RT=4.64 minutes Isomer 2 (Peak 2, 1 mg, 3.5% Yield). LCMS [M+H]$^+$ 591, RT 1.73 minutes (Method 26). Chiral LC* RT=5.01 minutes.

* Using chiral SFC Method 1 with a Chiralcel OJ-3 column.

Example 486

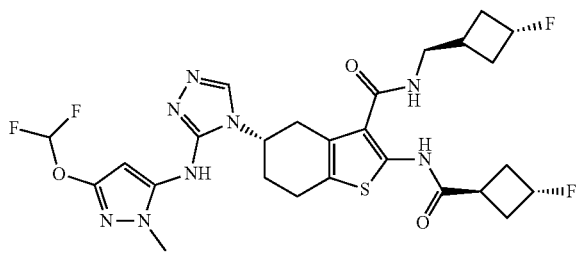

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide The title compound was obtained following general method 3 with intermediate 530 (46 mg, 0.09 mmol), DIPEA (80 µL, 0.46 mmol), trans-(3-fluorocyclobutyl)methanamine hydrochloride (in 2 portions: 25 & 5 mg, 0.20 mmol), HATU (in 2 portions: 40 & 10 mg, 0.13 mmol) and DMF (1 mL). Reaction duration: 6 hours 20 min at 70° C. The reaction mixture left to stand at room temperature overnight, then diluted with EtOAc (50 mL) and washed with a mixture of brine (50 mL) and water (10 mL). The aqueous phase was extracted with EtOAc (2×30 mL). The organic phases were combined, dried and concentrated under reduced pressure. Purification by HPLC gave the title compound (14 mg, 26% Yield). δ$_H$ (400 MHz, Methanol-d4) 8.17 (s, 1H), 6.88 (t, J=73.8 Hz, 1H), 5.73 (s, 1H), 5.39-4.95 (m, 2H), 4.60-4.44 (m, 1H), 3.60 (s, 3H), 3.45 (dd, J=13.5, 7.9 Hz, 1H), 3.36-3.23 (m, 2H), 3.07-2.85 (m, 3H), 2.71-2.44 (m, 5H), 2.38-2.11 (m, 7H). LCMS [M+H]$^+$ 611, RT 1.73 minutes (Method 26).

Example 487

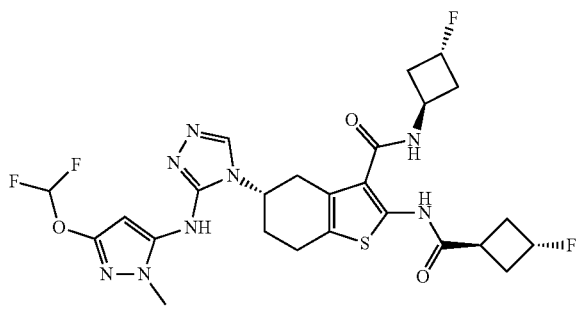 [SMILES: Cn1nc(OC(F)F)cc1Nc1nncn1[C@H]1CCc2sc(NC(=O)[C@H]3C[C@H](F)C3)c(C(=O)N[C@H]3C[C@H](F)C3)c2C1]

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide The title compound was obtained following general method 3 with intermediate 530 (40 mg, 0.07 mmol), DIPEA (80 µL, 0.46 mmol), trans-3-fluorocyclobutanamine hydrochloride (in 2 portions: 24 & 5 mg, 0.21 mmol), HATU (in 2 portions: 40 & 10 mg, 0.12 mmol) and DMF (1 mL). Reaction duration: 6 hours 45 min at 70° C. The reaction mixture left to stand at room temperature overnight, then diluted with EtOAc (50 mL) and washed with brine (50 mL). The aqueous phase was diluted with water (10 mL) and extracted with EtOAc (2×50 mL). The organic phases were combined, dried and concentrated under reduced pressure. Purification by HPLC gave the title compound (12 mg, 26% Yield). δ$_H$ (400 MHz, Methanol-d4) 8.14 (s, 1H), 6.88 (t, J=73.8 Hz, 1H), 5.73 (s, 1H), 5.37-5.03 (m, 2H), 4.62 (td, J=7.3, 6.2, 2.3 Hz, 1H), 4.54 (tq, J=9.4, 5.2, 4.5 Hz, 1H), 3.60 (s, 3H), 3.29-3.25 (m, 1H), 3.11-2.82 (m, 3H), 2.68-2.26 (m, 11H). LCMS [M+H]$^+$ 597, RT 1.63 minutes (Method 26).

Example 488 & 489

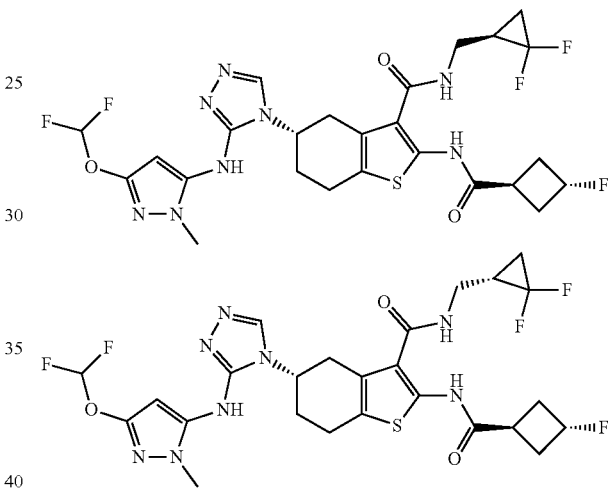

(5S)—N-[[(1R)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide (5S)—N-[[(1S)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide The title compound was obtained following general method 3 with intermediate 530 (100 mg, 0.19 mmol), DIPEA (170 µL, 0.97 mmol), (2,2-difluorocyclopropyl)methanamine hydrochloride (in 3 portions: 60, 12 mg & 12 mg, 0.56 mmol), HATU (in 3 portions: 105, 20 & 20 mg, 0.38 mmol) and DMF (2 mL). Reaction duration: 3 hours at 70° C. Once at room temperature the reaction mixture was diluted with EtOAc (50 mL) and washed with a mixture of brine (50 mL) and water (10 mL). The aqueous phase was extracted with EtOAc (2×30 mL). The organic phases were combined, dried and concentrated under reduced pressure. Purification by chiral SFC gave the title compounds:

Isomer 1 (Peak 1, 8 mg, 6.8% Yield). $\delta_H$ (400 MHz, Methanol-d4) 8.48-7.87 (m, 1H), 6.88 (t, J=73.8 Hz, 1H), 5.77 (s, 1H), 5.41-5.10 (m, 1H), 4.53 (s, 1H), 3.60 (s, 4H), 3.31 (p, J=1.6 Hz, 2H), 3.15-2.87 (m, 3H), 2.69-2.45 (m, 5H), 2.35 (t, J=7.6 Hz, 2H), 1.99 (ddd, J=13.7, 11.4, 7.4 Hz, 1H), 1.47 (tdd, J=12.0, 7.8, 4.5 Hz, 1H), 1.23 (dtd, J=13.5, 7.7, 3.8 Hz, 1H). LCMS [M+H]+ 615, RT 1.68 minutes (Method 26). Chiral SFC* RT=5.39 minutes Isomer 2 (Peak 2, 9 mg, 7.7% Yield). $\delta_H$ (400 MHz, Methanol-d4) 8.27 (s, 1H), 7.10-6.64 (m, 1H), 5.76 (s, 1H), 5.38-5.12 (m, 1H), 4.54 (s, 1H), 3.60 (s, 3H), 3.53-3.39 (m, 2H), 3.31 (p, J=1.6 Hz, 1H), 3.14-2.86 (m, 3H), 2.72-2.46 (m, 5H), 2.40-2.24 (m, 2H), 1.97 (ddq, J=14.8, 11.4, 7.6 Hz, 1H), 1.47 (tdd, J=12.0, 7.8, 4.5 Hz, 1H), 1.22 (dtd, J=13.4, 7.7, 3.7 Hz, 1H). LCMS [M+H]+ 615, RT 1.67 minutes (Method 26). Chiral SFC* RT=6.02 minutes

* Using chiral SFC Method 1 with an isocratic 25% MeOH (+0.1% NH₄OH) and a 10 minutes run time.

Example 490

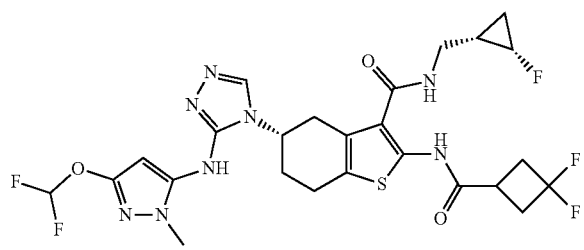 [SMILES: Cn1nc(OC(F)F)cc1Nc1nncn1[C@H]1CCc2sc(NC(=O)C3CC(F)(F)C3)c(C(=O)NC[C@@H]3C[C@@H]3F)c2C1]

(5S)-2-[(3,3-difluorocyclobutanecarbonyl)amino]-5-
[3-[[5-(difluoromethoxy)-2-methylpyrazol-3-yl]
amino]-1,2,4-triazol-4-yl]-N-[[(1S,2S)-2-fluorocyclopropyl]methyl]-4,5,6,7-tetrahydro-1-benzothiophene-3-carboxamide The title compound was obtained following general method 3 with intermediate 657 (30 mg, 0.05 mmol), DIPEA (60 µL, 0.34 mmol), [(1S,2S)-2-fluorocyclopropyl]methylammonium chloride (30 mg, 0.24 mmol), HATU (50 mg, 0.13 mmol) and DMF (0.5 mL). Reaction duration: 1 hour and 50 minutes. Once at room temperature the reaction mixture was purified using HPLC (Method 5) to give the title (6.3 mg, 19% Yield). $\delta_H$ (400 MHz, Methanol-d4) 8.38 (s, 1H), 6.89 (t, J=73.8 Hz, 1H), 5.74 (s, 1H), 4.68 (dtd, J=65.5, 5.9, 2.6 Hz, 1H), 4.58-4.45 (m, 1H), 3.66-3.60 (m, 1H), 3.60 (s, 3H), 3.37 (dd, J=14.1, 8.0 Hz, 1H), 3.31 (p, J=1.6 Hz, 1H), 3.24-3.11 (m, 1H), 3.04 (dd, J=16.5, 10.4 Hz, 1H), 3.00-2.74 (m, 6H), 2.44-2.27 (m, 2H), 1.27-1.15 (m, 1H), 0.94-0.65 (m, 2H). LCMS [M+H]+ 615, RT 1.67 minutes (Method 26).

Example 491

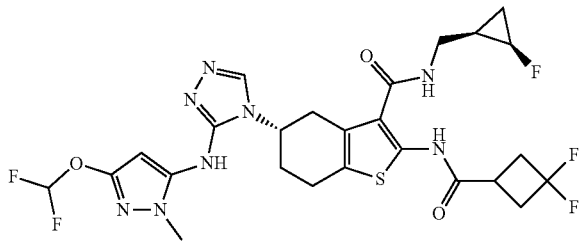 [SMILES: Cn1nc(OC(F)F)cc1Nc1nncn1[C@H]1CCc2sc(NC(=O)C3CC(F)(F)C3)c(C(=O)NC[C@H]3C[C@H]3F)c2C1]

(5S)-2-[(3,3-difluorocyclobutanecarbonyl)amino]-5-
[3-[[5-(difluoromethoxy)-2-methylpyrazol-3-yl]
amino]-1,2,4-triazol-4-yl]-N-[[(1R,2R)-2-fluorocyclopropyl]methyl]-4,5,6,7-tetrahydro-1-benzothiophene-3-carboxamide The title compound was obtained following general method 3 with intermediate 657 (30 mg, 0.05 mmol), DIPEA (50 µL, 0.29 mmol), intermediate 631 (in 2 portions: 30 & 10 mg, 0.32 mmol), HATU (50 mg, 0.13 mmol) and DMF (0.5 mL). Reaction duration: 1 hour and 20 minutes. Once at room temperature the reaction mixture was purified using HPLC (Method 5) to give the title (7.9 mg, 23% Yield). $\delta_H$ (400 MHz, Methanol-d4) 8.28 (s, 1H), 6.89 (t, J=73.8 Hz, 1H), 5.76 (s, 1H), 4.67 (dtd, J=65.6, 5.9, 2.7 Hz, 1H), 4.52 (q, J=7.0, 6.5 Hz, 1H), 3.74-3.66 (m, 2H), 3.60 (s, 3H), 3.28 (dd, J=13.3, 7.2 Hz, 2H), 3.16 (qd, J=8.3, 3.1 Hz, 1H), 3.04 (dd, J=21.9, 8.6 Hz, 1H), 2.99-2.77 (m, 6H), 2.34 (d, J=5.6 Hz, 4H). LCMS [M+H]+ 615, RT 1.73 minutes (Method 26).

Example 492

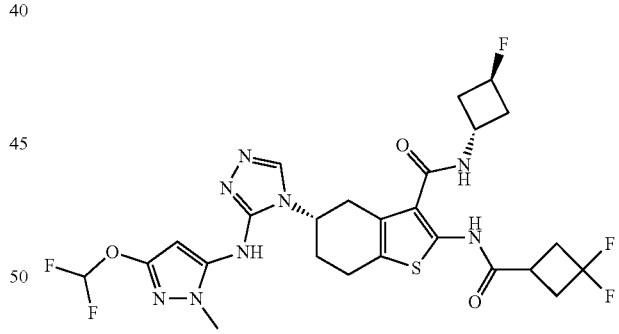

(5S)-2-[(3,3-difluorocyclobutanecarbonyl)amino]-5-
[3-[[5-(difluoromethoxy)-2-methylpyrazol-3-yl]
amino]-1,2,4-triazol-4-yl]-N-(trans-3-fluorocyclobutyl)-4,5,6,7-tetrahydro-1-benzothiophene-3-carboxamide The title compound was obtained following general method 3 with intermediate 657 (30 mg, 0.05 mmol), DIPEA (50 µL, 0.29 mmol), trans-(3-fluorocyclobutyl)ammonium chloride (in 2 portions: 30 & 10 mg, 0.32 mmol), HATU (50 mg, 0.13 mmol) and DMF (0.5 mL). Reaction duration: 1 hour and 20 minutes. Once at room temperature the reaction mixture was purified using HPLC (Method 5) to give the title compound (7.9 mg, 23% Yield). δ$_H$ (400 MHz, Methanol-d4) 8.28 (s, 1H), 6.89 (t, J=73.8 Hz, 1H), 5.76 (s, 1H), 4.67 (dtd, J=65.6, 5.9, 2.7 Hz, 1H), 4.52 (q, J=7.0, 6.5 Hz, 1H), 3.74-3.66 (m, 2H), 3.60 (s, 3H), 3.28 (dd, J=13.3, 7.2 Hz, 2H), 3.16 (qd, J=8.3, 3.1 Hz, 1H), 3.04 (dd, J=21.9, 8.6 Hz, 1H), 2.99-2.77 (m, 6H), 2.34 (d, J=5.6 Hz, 4H). LCMS [M+H]⁺ 615, RT 1.73 minutes (Method 26).

Example 493

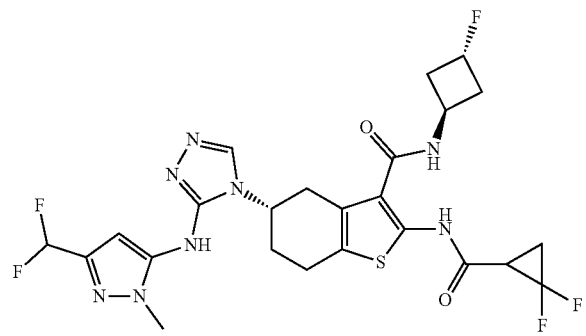 [SMILES: Cn1nc(C(F)F)cc1Nc1nncn1[C@H]1CCc2sc(NC(=O)C3CC3(F)F)c(C(=O)N[C@H]3C[C@H](F)C3)c2C1]

(5S)-2-[(2,2-difluorocyclopropanecarbonyl)amino]-5-[3-[[5-(difluoromethyl)-2-methyl-pyrazol-3-yl]amino]-1,2,4-triazol-4-yl]-N-(trans-3-fluorocyclobutyl)-4,5,6,7-tetrahydrobenzothiophene-3-carboxamide To a stirring mixture of intermediate 349 (50.0 mg, 0.1 mmol), pyridine (31 μL, 0.39 mmol) and trans-(3-fluorocyclobutyl)ammonium chloride (18 mg, 0.15 mmol) in DCM (3 mL) cooled to 0° C. was added T3P (116 μL, 0.19 mmol) and the resulting yellow/orange solution was allowed to gently warm to room temperature overnight. Triethylamine (54 μL, 0.39 mmol) was added and stirring was continued for 1 hour. HATU (44 mg, 0.12 mmol) was added and stirring was continued at room temperature for 3 days, then the mixture was diluted with DCM (10 mL), followed by water (5 mL) and sat. aq. NH₄Cl solution (5 mL). The layers were separated and the aqueous was extracted with more DCM (20 mL). The combined organics were washed with brine (5 mL), dried over magnesium sulfate, filtered and concentrated to afford a yellow gum. This residue was dissolved in anhydrous DMF (2 mL), (3-fluorocyclobutyl) ammonium chloride (27 mg, 0.21 mmol) followed by triethylamine (39 mL, 0.28 mmol) were added and the resulting mixture was heated at 70° C. for 3 hours. The mixture was diluted with ethyl acetate (10 mL) and washed with water (5 mL) followed by sat. aq. NH₄Cl solution (5 mL). The layers were separated and the aqueous was further extracted with ethyl acetate (20 mL). The combined organics were washed with water (5 mL), sat. aq. NH₄Cl solution (5 mL), brine (5 mL), then dried over magnesium sulfate, filtered and concentrated in vacuo. The crude material was purified by reverse phase column chromatography (Method 4), then freeze dried to afford the title compound (15 mg, 25% yield) as a mixture of two isomers. δ$_H$ (400 MHz, Methanol-d4) 8.19 (s, 1H), 6.62 (t, J=55.1 Hz, 1H), 6.27 (s, 1H), 5.17 (ddt, J=56.6, 6.3, 3.1 Hz, 1H), 4.67-4.59 (m, 1H), 4.57-4.51 (m, 1H), 3.73 (s, 3H), 3.34-3.32 (m, 1H), 3.09-2.89 (m, 3H), 2.87-2.74 (m, 1H), 2.67-2.52 (m, 2H), 2.49-2.38 (m, 2H), 2.38-2.28 (m, 2H), 2.16-2.01 (m, 1H), 1.97-1.83 (m, 1H). LCMS [M+H]⁺ 585, RT 2.65 minutes (Method 10).

Examples 494, 495 & 496

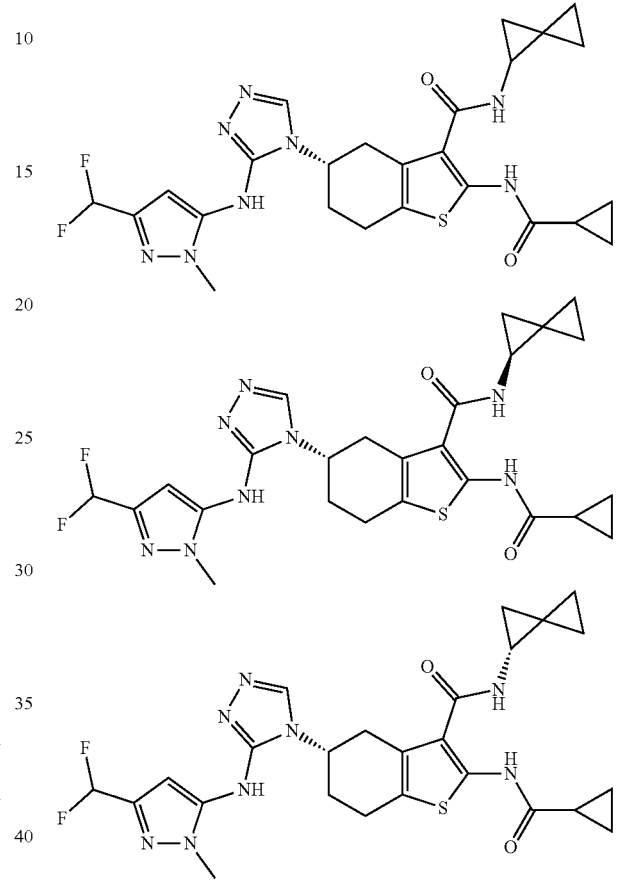

(5S)-2-cyclopropaneamido-5-(3-{[3-(difluoromethyl)-1-methyl-1H-pyrazol-5-yl]amino}-4H-1,2,4-triazol-4-yl)-N-{spiro[2.2]pentan-1-yl}-4,5,6,7-tetrahydro-1-benzothiophene-3-carboxamide (494)

(5S)-2-(cyclopropanecarbonylamino)-5-[3-[[5-(difluoromethyl)-2-methyl-pyrazol-3-yl]amino]-1,2,4-triazol-4-yl]-N-[(2S)-spiro[2.2]pentan-2-yl]-4,5,6,7-tetrahydrobenzothiophene-3-carboxamide (5S)-2-(cyclopropanecarbonylamino)-5-[3-[[5-(difluoromethyl)-2-methyl-pyrazol-3-yl]amino]-1,2,4-triazol-4-yl]-N-[(2R)-spiro[2.2]pentan-2-yl]-4,5,6,7-tetrahydrobenzothiophene-3-carboxamide To a solution of intermediate 494 (29 mg, 0.063 mmol) in dry N,N-dimethylformamide (0.5 mL) at 140° C. was introduced (dropwise) a solution of spiro[2.2]pentan-1-amine hydrochloride (23 mg, 0.191 mmol) and triethylamine (19 mg, 0.186 mmol) in dry N,N-dimethylformamide (0.5 mL). After 2 h at 140° C. under an atmosphere of nitrogen, the reaction mixture was cooled to room temperature and the solution concentrated in-vacuo. The residue was purified by flash column chromatography (0-10% gradient of methanol in dichloromethane) to furnish example 494 as a mixture of epimers (16.9 mg, 0.031 mmol, 49% Yield); δ$_H$ (500 MHz, d$_4$-methanol) 8.06 (br s, 1H), 6.52 (t, J=55.1 Hz, 1H), 6.22 (br s, 1H), 4.53-4.34 (m, 1H), 3.62 (s, 31H), 3.20-3.00 (m, 21H), 2.99-2.70 (m, 31H), 2.29-2.15 (m, 21H), 1.76-1.66 (m, 1H), 1.27-1.14 (m, 1H), 0.96-0.87 (m, 4H), 0.87-0.81 (m, 21H), 0.80-0.72 (m, 2H), 0.70-0.59 (m, 1H); LCMS [M+H]$^+$ 543, RT 2.68 mins, MET-uPLC-AB-101 (7 min, low pH).

The mixture of epimers was resolved by chiral SFC (Chiralcel OJ-H 25 cm column using 25% methanol in CO$_2$ at 15 mL/minute) to furnish the title compounds (Examples 495 & 496):

Diastereomer 1 (Peak 1, 2.5 mg, 0.005 mmol) δ$_H$ (500 MHz, d$_4$-methanol) 8.17 (s, 1H), 6.62 (t, J=55.2 Hz, 1H), 6.27 (s, 1H), 4.53 (dt, J=14.2, 7.9 Hz, 1H), 3.72 (s, 3H), 3.27 (dd, J=16.0, 5.6 Hz, 1H), 3.15 (d, J=10.1 Hz, 1H), 3.06-2.82 (m, 3H), 2.33 (q, J=8.1 Hz, 2H), 1.81 (ddd, J=12.6, 7.8, 4.7 Hz, 1H), 1.34-1.26 (m, 1H), 1.03-0.92 (m, 6H), 0.90-0.84 (m, 2H), 0.74 (q, J=6.7, 6.2 Hz, 1H); LCMS [M+H]$^+$ 543, RT 2.67 mins (Method 10). Chiral SFC* RT=3.82 mins.

Diastereomer 2 (Peak 2, 2.5 mg, 0.005 mmol) δ$_H$ (500 MHz, d$_4$-methanol) 8.15 (s, 1H), 6.61 (t, J=55.2 Hz, 1H), 6.28 (s, 1H), 4.53 (dt, J=14.1, 6.5 Hz, 1H), 3.72 (s, 3H), 3.30-3.24 (m, 1H), 3.20 (dd, J=6.9, 3.3 Hz, 1H), 3.06-2.82 (m, 3H), 2.33 (q, J=8.0, 7.5 Hz, 2H), 1.80 (ddd, J=12.6, 7.9, 4.7 Hz, 1H), 1.36-1.25 (m, 1H), 1.05-0.81 (m, 8H), 0.80-0.73 (m, 1H); LCMS [M+H]$^+$ 543, RT 2.68 mins (Method 10). Chiral SFC* RT=4.65 mins

* Chiral analysis using Cellulose-3 4.6×250 mm, 5 µm column, flow rate 4 mL/min, eluting with 40% methanol in CO$_2$, 6 min run time on a WatersThar Resolution.

Example 497

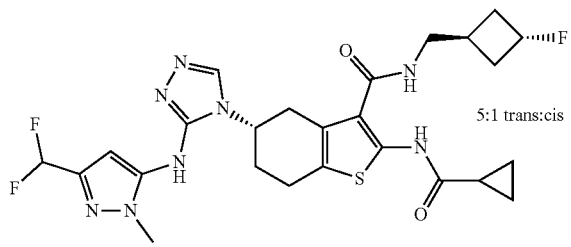 [SMILES: Cn1nc(C(F)F)cc1Nc1nncn1[C@H]1CCc2sc(NC(=O)C3CC3)c(C(=O)NC[C@H]3C[C@H](F)C3)c2C1]

(5S)-2-(cyclopropanecarbonylamino)-5-[3-[[5-(difluoromethyl)-2-methyl-pyrazol-3-yl]amino]-1,2,4-triazol-4-yl]-N-[(3-fluorocyclobutyl)methyl]-4,5,6,7-tetrahydrobenzothiophene-3-carboxamide To a solution of intermediate 494 (29 mg, 0.063 mmol) in dry N,N-dimethylformamide (0.5 mL) at 140° C. was introduced (dropwise) a solution of [3-fluorocyclobutyl]methanamine hydrochloride (27 mg, 0.191 mmol, a 9:1 mixture of trans:cis-isomers) and triethylamine (19 mg, 0.186 mmol) in dry N,N-dimethylformamide (0.5 mL). After 2 h at 140° C. under an atmosphere of nitrogen, the reaction mixture was cooled to room temperature and the solution concentrated in-vacuo. The residue was purified by flash column chromatography (0-10% gradient of methanol in dichloromethane) to furnish the title compound (as a 85:15 mixture of trans:cis-isomers) as a beige solid (2.7 mg, 8% Yield); δ$_H$ (500 MHz, d$_4$-methanol) 8.40 (br. s, 1H), 6.63 (t, J=55.2 Hz, 1H), 6.48-5.98 (m, 1H), 5.11 (dp, J=55.3, 6.2 Hz, 1H), 4.65-4.44 (m, 1H), 3.74 (s, 3H), 3.48 (dd, J=13.5, 7.8 Hz, 1H), 3.37 (dd, J=13.5, 7.8 Hz, 1H), 3.32-3.24 (m, 1H), 3.13-2.86 (m, 3H), 2.67-2.54 (m, 1H), 2.49-2.14 (m, 6H), 1.87-1.78 (m, 1H), 1.04-0.99 (m, 2H), 0.99-0.93 (m, 2H); LCMS [M+H]$^+$ 563, RT 2.66 mins (cis-isomer) and 2.70 mins (trans-isomer) (Method 10).

Example 498

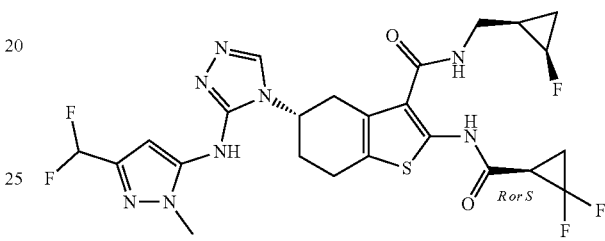

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[[(1R,2R)-2-fluorocyclopropyl]methyl]-4,5,6,7-tetrahydrobenzothiophene-3-carboxamide (* or S)

To a suspension of intermediate 631 (59 mg, 0.467 mmol) and intermediate 349 (80 mg, 0.156 mmol) in DCM (3 mL) was added N-ethyl-N-isopropyl-propan-2-amine (82 µL, 0.467 mmol) and 1-[bis(dimethylamino)methylidene]-1H-[1,2,3]triazolo[4,5-b]pyridin-1-ium 3-oxide hexafluorophosphate (89 mg, 0.234 mmol). The solution was stirred at room temperature for 2 h. DCM was removed under a stream of nitrogen gas and the residue was dissolved in acetonitrile (2 mL) and heated at 40° C. for 2 h. Solvent was removed under a stream of nitrogen gas and the residue was purified by flash column chromatography eluting with a 0-5% methanol in DCM gradient followed by reverse phase HPLC (Method 4) followed by chiral SFC (Chiralpak IG 5 µm, 250×30 mm, CO$_2$:Methanol+0.5% isopropylamine 70:30, a flow rate of 70 mL/min, 125 bar at 40° C.) to give the title compound (5.2 mg, 6% Yield) as a white solid. δ$_H$ (500 MHz, DMSO-d$_6$,2:1 rotameric mixture) 12.05 (m, 1H, RotA), 11.23 (m, 1H), 8.73 (s, 1H, RotB), 8.40 (s, 1H, RotB), 8.18 (s, 1H, RotA), 8.02 (m, 1H), 6.74 (t, J=55.1 Hz, 1H), 6.41 (s, 1H, RotB), 6.20 (s, 1H, RotA), 4.83-4.59 (m, 1H), 4.54-4.36 (m, 1H), 3.70 (s, 3H, RotB), 3.60 (s, 3H, RotA), 3.45-3.38 (m, 1H), 3.26-3.20 (m, 1H), 3.20-3.03 (m, 2H), 2.99-2.75 (m, 3H), 2.28-2.11 (m, 2H), 2.07-1.95 (m, 2H), 1.20-1.12 (m, 1H), 0.80-0.63 (m, 2H). LCMS [M+H]$^+$ 585, RT 2.66 minutes (Method 10). Chiral SFC** RT=6.87 minutes

** Chiral analysis using CHIRALPAK IG (250 mm×4.6 mm 5 µm) column, flow rate 2.4 mL/min, eluting with 70:30 CO2/(Ethanol+0.5% IPA), 12 minutes run time on a Berger SFC.

Example 499

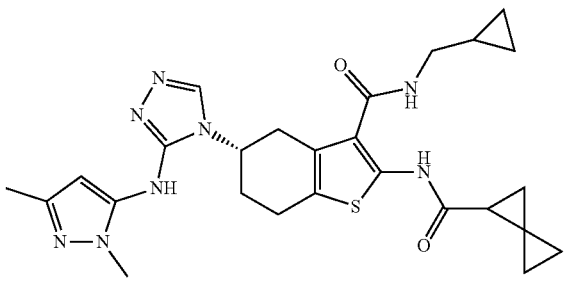 [SMILES: Cc1cc(Nc2nncn2[C@H]2CCc3sc(NC(=O)C4CC45CC5)c(C(=O)NCC4CC4)c3C2)n(C)n1]

(5S)—N-(cyclopropylmethyl)-5-[3-[(2,5-dimethylpyrazol-3-yl)amino]-1,2,4-triazol-4-yl]-2-(spiro[2.2]pentane-2-carbonylamino)-4,5,6,7-tetrahydrobenzothiophene-3-carboxamide A solution of formic hydrazide (75 mg, 1.25 mmol) in anhydrous methanol (3 mL) was added to a solution of intermediate 665 (200 mg, 0.42 mmol) in anhydrous methanol (4 mL) and the resulting mixture was stirred at room temperature under nitrogen for 45 minutes. 1 M aqueous sodium carbonate (1.3 mL, 1.3 mmol) was added and the mixture was stirred at 50° C. overnight. The reaction mixture was concentrated in vacuo, the residue was dissolved in ethyl acetate (20 mL) and washed with water (5 mL). The layers were separated and the aqueous was extracted with ethyl acetate (2×10 mL). The combined organics were washed with brine (10 mL), dried over magnesium sulfate, filtered and concentrated. The crude material was purified by flash column chromatography with a 0 to 100% ethyl acetate in heptane gradient, followed by a 0 to 20% methanol in ethyl acetate gradient. The compound was further purified by reverse phase column chromatography (Method 2), then freeze dried to afford the title compound (24 mg, 10% yield). $\delta_H$ (500 MHz, DMSO-d6) 11.73 (s, 1H, Rotamer 1), 11.14 (m, 1H), 8.41 (m, 1H, Rotamer 2), 8.33 (m, 1H, Rot 2), 8.10 (m, 1H, Rot 1), 7.61 (s, 1H), 5.89 (m, 1H, Rot 2), 5.70 (s, 1H, Rot 1), 4.48-4.32 (m, 1H), 3.54 (m, 3H, Rot 2), 3.48 (m, 3H, Rot 1), 3.20-3.05 (m, 3H), 3.05-2.92 (m, 1H), 2.90-2.78 (m, 2H), 2.26-2.12 (m, 3H), 2.07 (s, 3H, Rot 2), 2.04 (s, 3H, Rot 1), 1.48-1.40 (m, 1H), 1.40-1.35 (m, 1H), 1.02-0.97 (m, 1H), 0.97-0.91 (m, 2H), 0.91-0.86 (m, 1H), 0.84-0.74 (m, 1H), 0.43-0.30 (m, 2H), 0.24-0.13 (m, 2H). LCMS [M+H]⁺ 521, RT 2.34 minutes (Method 10)

Example 500

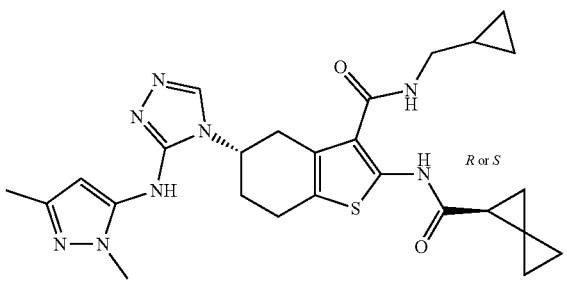 [SMILES: Cc1cc(Nc2nncn2[C@H]2CCc3sc(NC(=O)[C@H]4CC45CC5)c(C(=O)NCC4CC4)c3C2)n(C)n1]

(5S)—N-(cyclopropylmethyl)-5-[3-[(2,5-dimethylpyrazol-3-yl)amino]-1,2,4-triazol-4-yl]-2-[[(2S*)-spiro[2.2]pentane-2-carbonyl]amino]-4,5,6,7-tetrahydrobenzothiophene-3-carboxamide (* or R)

Prepared as described for Example 499. The title compound was obtained by separating the two diastereoisomers by chiral chromatography (85:15 Heptane: Ethanol with Chiralcel OD-H 25 cm column at 18 mL/min).

Isomer 1—Peak 1 (7 mg, 99% chiral purity) $\delta_H$ (500 MHz, DMSO-d6) 11.73 (s, 1H, Rotamer 1), 11.23-11.05 (m, 1H), 8.41 (s, 1H, Rotamer 2), 8.33 (s, 1H, Rot 2), 8.10 (s, 1H, Rot 1), 7.61 (s, 1H), 5.89 (s, 1H, Rot 2), 5.70 (s, 1H, Rot 1), 4.49-4.31 (m, 1H), 3.55 (s, 3H, Rot 2), 3.48 (s, 3H, Rot 1), 3.21-3.05 (m, 3H), 3.03-2.91 (m, 1H), 2.90-2.76 (m, 2H), 2.28-2.12 (m, 3H), 2.07 (s, 3H, Rot 2), 2.04 (s, 3H, Rot 1), 1.47-1.40 (m, 1H), 1.40-1.35 (m, 1H), 1.03-0.90 (m, 3H), 0.91-0.84 (m, 1H), 0.82-0.73 (m, 1H), 0.40-0.32 (m, 2H), 0.23-0.12 (m, 2H). LCMS [M+H]⁺ 521, RT 2.34 minutes (Method 10). Chiral LC** RT=20.49 minutes.

** Chiral analysis using Chiralcel OD-H 4.6×250 mm, 5 µm column, flow rate 1 mL/min, eluting with 85:15 Heptane: Ethanol, 40 minutes run time on a Waters 2795.

Example 501

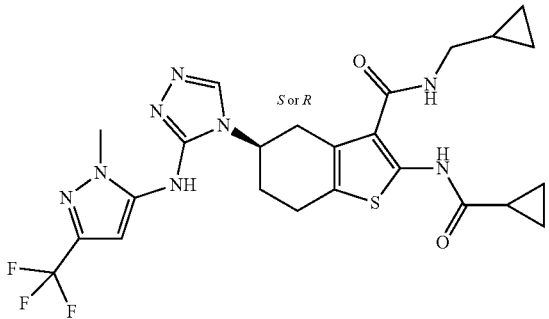 [SMILES: Cn1nc(C(F)(F)F)cc1Nc1nncn1[C@@H]1CCc2sc(NC(=O)C3CC3)c(C(=O)NCC3CC3)c2C1]

(3R*)-6-(cyclopropanecarbonylamino)-N-(cyclopropylmethyl)-3-[3-[[2-methyl-5-(trifluoromethyl)pyrazol-3-yl]amino]-1,2,4-triazol-4-yl]-3,4-dihydro-2H-thieno[2,3-b]pyran-5-carboxamide (* or S)

To a stirred solution of intermediate 673 (200 mg, 0.37 mmol) in DCM (10 mL) at 0° C. under nitrogen was added triethylamine (0.15 mL, 1.10 mmol) and methanesulfonyl chloride [124-63-0] (0.03 mL, 0.39 mmol). The reaction mixture was stirred at 0° C. for 1 h and then treated with a solution of formic acid hydrazide [624-84-0] (46 mg, 0.74 mmol) in DMF (1.5 mL). Stirring was continued at 0° C. for 1.5 h. The organic layer was washed with water and dried over Na₂SO₄. Volatiles were removed in vacuo and the resulting mixture diluted with DMF (1.5 mL) and treated with sodium carbonate (97 mg, 0.92 mmol). The mixture stirred at 45° C. under nitrogen for 5 h then allowed to cool to room temperature. The reaction mixture was filtered and concentrated in vacuo. The crude product was purified by column chromatography eluting with a 0-100% gradient of DCM in isohexane followed by 0-10% MeOH in DCM. Product-containing fractions were concentrated and purified by HPLC (Method 5) to afford a racemic mixture of the title compound (33 mg). Chiral separation employing SFC with a 10-25% gradient of MeOH (+0.1% NH₄OH) in CO₂, on a CHIRALCEL OJ-H column (20×250 mm 5 mm, 100 mL/min) gave the title compound (Peak 2, 11.5 mg, 5.7% yield). $\delta_H$ (400 MHz, DMSO-d6) 12.24 (s, 1H), 11.27 (s, 1H), 7.89 (s, 1H), 7.81-7.49 (m, 1H), 6.37 (s, 1H), 4.96-4.70 (m, 1H), 4.62-4.24 (m, 2H), 3.69 (s, 3H), 3.30-3.20 (m, 1H), 3.18-2.96 (m, 31H), 2.01-1.78 (m, 1H), 1.09-0.96 (m, 1H), 0.93-0.72 (m, 4H), 0.44-0.34 (m, 2H), 0.24-0.16 (m, 2H). LCMS [M+H]+ 551, RT 2.02 minutes (Method 3). Chiral SFC** RT=5.71 minutes.
** Chiral analysis using CHIRALCEL OJ-H (4.6×150 mm 3 μm) column, eluting 10-25% gradient of MeOH (+0.1% NH$_4$OH) in CO$_2$, flow rate 1 mL/min.

Y131A FRET Assay

Protocol for Preparation of IgE-Tb Reagent 86 nmoles of IgE-Fc (N265Q, N371Q) (Young et al., 1995) at 172 uM in 100 mM NaHCO$_3$, pH 9.5 was added to 1 mg of LanthaScreen™ Amine Reactive Tb Chelate (ThermoFisher catalogue number PV3583) and incubated for 16 hours at 20° C. The material was then buffer exchanged into Phosphate Buffered Saline (being, 137 mM NaCl, 2.7 mM KCl, 10 mM Na$_2$HPO$_4$, 1.8 mM KH$_2$HPO$_4$, pH 7.4) and the material quantified and the degree of Tb conjugation determined by measuring the absorption at 280 nm and 343 nm.

The integrity of the conjugated material was determined by analytical size exclusion chromatography on a S200 HR 10×300 column (GE Healthcare). Typical conjugation ratios were 4:1 Tb:IgE-Fc.

Young R J., Owens, R J., MacKay G A., Chan C M W., Shi J., Hide M., Francis D M., Henry A J., Sutton B J., and Gould H J (1995) Protein Engineering 8:193-199

Protocol for Preparation of sFcεRIα-Y131A-AF488 Reagent 400 nmoles FcεRIα (Y131A mutant) (Cook et al., 1997) at 400 uM in 100 mM NaOAc pH 5.5 was reacted with 1 mM sodium periodate (in 100 mM NaOAc, pH 5.5) for 60 minutes at 22° C. Oxidation was quenched with the addition of 40 uL of ethanediol and incubation for 60 minutes at 22° C. The protein was buffer exchanged in to conjugation buffer (50 mM NaHCO$_3$ 150 mM NaCl, pH 9.5) and concentrated to 750 uM.

175 nmoles of protein was added to 1 mg of Alexa Fluor™ 488 hydrazide (Invitrogen) and incubated for 16 hours at 22° C. Sodium cyanoborohydride (at 100 mM in conjugation buffer) was added to a final concentration of 1 mM and incubated for 60 minutes on ice. The protein was buffer exchanged into Phosphate Buffered Saline (being, 137 mM NaCl, 2.7 mM KCl, 10 mM Na$_2$HPO$_4$, 1.8 mM KH$_2$HPO$_4$, pH 7.4) and the material quantified and the degree of Alexa Fluor™ 488 conjugation determined by measuring the absorption at 280 nm and 495 nm.

The integrity of the conjugated material was determined by analytical size exclusion chromatography on a S200 HR 10×300 column (GE Healthcare). Typical conjugation ratios were 2:1 Alexa Fluor™ 488: FcεRIα

Cook J P D., Henry A J., McDonnell J M., Owens R J., Sutton B J., and Gould H J (1997) Biochemistry 36:15579-15588

In Vitro Biochemical Assay:

The aim was to measure binding of IgE-Tb to receptor, and the inhibition thereof by compounds, using an in vitro Fluorescence Resonance Energy Transfer (FRET) Assay.

Reagents

FRET reagents used were IgE labelled with Terbium (FRET donor), and soluble IgE receptor FcεRIα with a Y131A mutation, labelled with Alexa Fluor™ 488 (FRET acceptor). Unlabelled FcεRIα was also used to generate a background control. The assay buffer consisted of 20 mM Tris pH7.2, 150 mM NaCl, and 0.002% Tween.

Assay Reaction

Examples 1-233

For examples 1 to 233, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by diluting 10-fold in assay buffer. For the assay, 5 μl of diluted compound was added to 10 μl of, followed by addition of 10 μl FcεRIα-Y131A-AF488. FRET reagents FACs were 5 nM IgE-Tb, 25 nM FcεRIα-Y131A-AF488. Usually the top FAC of compound in the assay was 10 μM. The final DMSO concentration was 2%. The minimum signal (MIN) was measured by adding 5l unlabelled FcεRIα at 1 μM (FAC=200 nM) to the FRET reagents. The maximum FRET signal (MAX) was measured in wells containing FRET reagents but no compound. The assay was incubated for 2 hours at room temperature, protected from light and evaporation, and with gentle agitation.

FRET Measurement

Measurement of FRET for each well was carried out by exciting at 330 nm and measuring emission at 495/520 nm using an Envision plate reader (Perkin Elmer). FRET ratio was calculated as follows:

Emission at 520/Emission at 495×1000.

The FRET ratio was used for the data analysis.

Data Analysis

Z' was calculated as follows (σ=standard deviation and μ=mean):

$1-((3\times\sigma_{MAX})+(3\times\sigma_{MIN}))/(\mu_{MAX}-\mu_{MIN})$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Examples 234-501

For examples 234 to 501, the assay was conducted according to the following: Each assay reaction was conducted in a volume of 25 μl in a 384-well half-volume plate. 10 point compound serial dilutions (3-fold) were generated in DMSO at a concentration of ×50 that of the final assay concentration (FAC). Compound solutions were then prepared by diluting 10-fold in assay buffer. For the assay, 5l of diluted compound was added to 10 μl of IgE-Tb and incubated for 30 minutes before the addition of 10 μl sFcεRIα-Y131A-AF488. FRET reagents FACs were 5 nM IgE-Tb, 25 nM sFcεRIα-Y131A-AF488. Usually the top FAC of compound in the assay was 10 μM. The final DMSO concentration was 2%. The minimum signal (MIN) was measured by adding 5 μl unlabelled sFcεR1a at 1 μM (FAC=200 nM) to the FRET reagents. The maximum FRET signal (MAX) was measured in wells containing FRET reagents but no compound.

The assay was incubated for 18 hours at room temperature, protected from light and evaporation, and with gentle agitation.

FRET Measurement

Measurement of FRET for each well was carried out by exciting at 337 nm and measuring emission at 490/520 nm using a PHERAstar FSX plate reader (BMG Labtech). FRET ratio was calculated as follows:

Emission at 520/7Emission at 490×1000.

The FRET ratio was used for the data analysis.

Data Analysis

Z' was calculated as follows (σ=standard deviation and μ=mean):

$1-((3\times\sigma_{MAX})+(3\times\sigma_{MIN}))/(\mu_{MAX}-\mu_{MIN})$

Z' above 0.5 was considered a good assay.

Background signal (MIN) was subtracted from all wells. Using the background subtracted values, the percent inhibition by compound in each test-well was calculated as follows:

100−Test-well FRET ratio/MAX FRET ratio×100.

Percent inhibition was plotted against compound concentration. IC50 values for each compound were determined using four parameter logistic fit model using the XLFIT5 software package. The results are as follows:

The invention claimed is:

1. A compound of formula (I) or a pharmaceutically acceptable salt thereof:

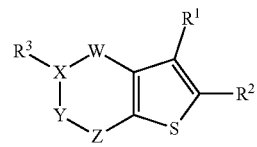

(I)

wherein

X represents CH or C—$R^4$, wherein $R^3$ and $R^4$ together with the carbon to which they are attached optionally form a 4-6 membered cycloalkyl or heterocyclic ring, wherein each 4-6 membered cycloalkyl or heterocyclic ring is optionally substituted by one or more substituents selected from halogen, =O, OH, SMe, $C_1$-$C_2$ alkoxy, O—$C_1$-$C_2$ haloalkyl, $C_1$-$C_2$alkyl, $C_1$-$C_2$ heteroalkyl, $C_1$-$C_2$haloalkyl, $NH_2$, NHMe, $NMe_2$, aryl and heteroaryl, with aryl and heteroaryl optionally substituted by one or more substituents

| Example Number | Y131A FRET $IC_{50}$ range |
|---|---|
| 2, 3, 4, 5, 7, 8, 9, 10, 11, 12, 14, 40, 55, 56, 69, 74, 79, 87, 88, 98, 102, 103, 109, 146, 174. | 10-50 micromolar |
| 1, 6, 13, 18, 20, 22, 27, 29, 38, 39, 58, 60, 64, 65, 66, 68, 70, 71, 72, 73, 75, 76, 77, 78, 80, 81, 82, 84, 85, 89, 90, 91, 92, 93, 95, 97, 107, 129, 151, 157, 163, 170, 173, 177, 179, 194, 196, 199, 201, 202, 204, 205, 206, 211, 214. | 1-10 micromolar |
| 15, 16, 17, 19, 21, 23, 24, 25, 26, 28, 30, 31, 32, 33, 34, 35, 36, 37, 41, 42, 43, 44, 45, 46, 47, 48, 49, 50, 51, 52, 53, 54, 57, 59, 61, 62, 63, 67, 86, 94, 100, 104, 105, 106, 108, 110, 111, 112, 113, 114, 115, 116, 117, 118, 119, 120, 121, 122, 123, 124, 125, 126, 127, 128, 130, 131, 132, 133, 134, 135, 136, 137, 138, 139, 140, 141, 142, 143, 144, 145, 147, 148, 149, 150, 152, 153, 154, 155, 156, 158, 159, 160, 161, 162, 164, 165, 166, 167, 168, 169, 171, 172, 175, 176, 178, 180, 181, 182, 183, 184, 185, 186, 187, 188, 189, 190, 191, 192, 193, 195, 197, 198, 200, 203, 207, 208, 209, 210, 212, 213, 215, 216, 217, 218, 219, 220, 221, 222, 223, 224, 225, 226, 227, 228, 229, 230, 231, 232, 233, 247, 260, 278, 356, 358, 367, 378, 391, 396, 398, 399, 421, 447, 450, 451, 462, 465, 475, 477, 486, 487, 490, 493, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 279, 280, 281, 282, 283, 284, 285, 286, 287, 288, 289, 290, 291, 292, 293, 294, 295, 296, 297, 298, 299, 300, 301, 302, 303, 304, 305,, 306, 307, 308, 309, 310, 311, 312, 313, 322, 329, 337, 343, 344, 345, 346, 347, 348, 349, 350, 351, 352, 353, 354, 355, 357, 359, 360, 361, 362, 363, 364, 365, 366, 368, 369, 370, 371, 372, 373, 374, 375, 376, 377, 378, 379, 380, 381, 382, 383, 384, 385, 386, 387, 388, 389, 390, 392, 393, 394, 395, 397, 400, 401, 402, 403, 404, 405, 406, 407, 408, 409, 410, 411, 412, 413, 414, 415, 416, 417, 417a, 418, 419, 420, 422, 423, 424, 425, 426, 427, 428, 429, 430, 431, 432, 433, 434, 435, 436, 437, 438, 439, 440, 441, 442, 443, 444, 445, 446, 448, 449, 452, 453, 454, 455, 456, 457, 458, 459, 460, 461, 463, 464, 466, 467, 468, 469, 470, 471, 472, 473, 474, 476, 479, 480, 481, 482, 483, 484, 485, 488, 489, 491, 492, 494, 495, 496, 497, 498, 499, 500, 501. | 0-1 micromolar | selected from halogen, OH, $C_1$-$C_6$ alkyl, $C_1$-$C_6$ alkoxy and $C_1$-$C_2$ haloalkyl;

W, Y and Z are CH
and each is optionally substituted by 1 or 2 groups which are independently selected from H, halogen, $SF_5$, =O, =NOH, —OH, —CN, —C(O)Me, —C(O)OH, —C(O)$NH_2$, NH—C(O)O—$C_1$-$C_4$ alkyl, —$NO_2$, $NH_2$, NHMe, $NMe_2$, SH, SMe, SOMe, $SO_2$Me, $C_1$-$C_4$ alkyl, $C_3$-$C_4$ cycloalkyl, $C_1$-$C_4$ alkoxy, heterocycle, and $C_1$-$C_4$ heteroalkyl, each of which is optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, and $NMe_2$;

$R^1$ is

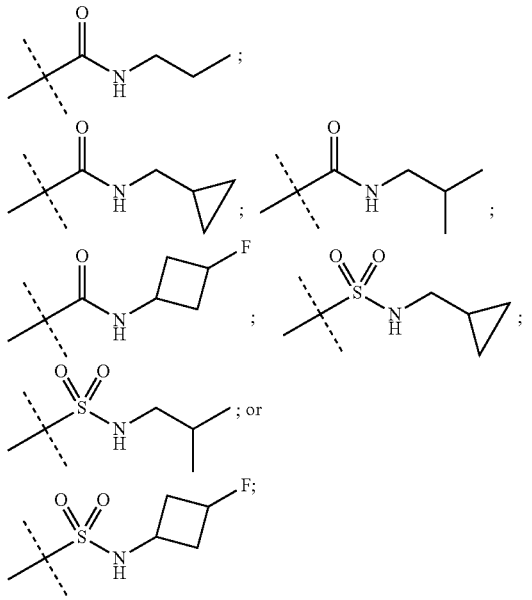

$R^2$ represents —N($R^{12}$)C(O)$R^{13}$;
$R^3$ is selected from —OH, —N$R^dR^c$, —NH-$R^{14}$—NH—$R^a$, —NMe-$R^{14}$—NH—$R^a$, —NH-$R^{14}$—NMe-$R^a$, —CO—N$R^dR^c$, —NH—COO—$R^c$, —NH—CO—$R^c$, —COOH, —COO—$C_1$-$C_8$ alkyl, —CO—$C_1$-$C_8$ alkyl, —$C_1$-$C_8$ alkylene-COO—$C_1$-$C_8$ alkyl, —$C_1$-$C_8$ alkylene-N$R^a$—COO—$C_1$-$C_8$ alkyl, —$C_1$-$C_8$ alkylene-N$R^dR^c$, —$C_1$-$C_8$ alkylene-NH-$R^{14}$—NH—$R^a$, heteroaryl, —CN, —CH=N—OH, —$CF_3$, alkylamino, amino, —NH—SO—$C_1$-$C_8$ alkyl, —NH—$SO_2$—$C_1$-$C_8$ alkyl, heteroalkyl-amino, aryl, heterocycle, $C_3$-$C_6$ cycloalkyl, —NHS(O)(=NH)Me, —$SO_2$—$C_1$-$C_8$ alkyl, —NH—C($CH_3$)=N-CN, —NH—CH=N—CN, and —NH—S(=O)(=N)—$C_1$-$C_2$ alkyl,
each of which is optionally substituted by one or more substituents selected from halogen, —OH, =O, —COOH, —COH, —CN, SMe, —N$R^dR^c$, —O$R^c$, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $C_1$-$C_2$ alkylene-O—$C_1$-$C_2$ alkyl, $C_1$-$C_2$alkylene-$C_3$-$C_4$ cycloalkyl, heterocycle, $C_3$-$C_6$ cycloalkyl, aryl, heteroaryl, $C_3$-$C_6$ cycloalkyl-amino, heterocyclo-amino, arylamino, heteroaryl-amino, —CONR$^d$R$^c$, —NHCO—R$^a$, —NHCOO—$C_1$-$C_4$ alkyl, —CO—$C_1$-$C_2$ alkyl, and —COO—R$^a$, or wherein each of —CONR$^d$R$^c$ and —NR$^d$R$^c$ optionally forms a seven-membered ring fused to a six-membered aryl group;
wherein each aryl, heteroaryl, heterocycle and cycloalkyl is optionally substituted by one or more substituents selected from halogen oxo, cyano, OH, —NOOH, $C_1$-$C_6$ alkyl, $C_1$-$C_6$ alkoxy, halo-$C_1$-$C_6$ alkoxy, $C_3$-$C_6$-cycloalkyl-$C_1$-$C_3$-alkoxy, —O—CO—$C_1$-$C_6$ alkyl, $C_3$-$C_6$ cycloalkyl, $C_1$-$C_2$haloalkyl, $C_2$-$C_4$ heterocycle, acetyl, acetylphenyl, —CONR$^d$R$^c$, COO—$C_1$-$C_8$ alkyl, —S(O)NH-$C_1$-$C_2$-alkyl, —S(O)$_n$—$C_1$-$C_2$-alkyl, and heteroaryl, wherein each heteroaryl is optionally substituted with one or more halogen group or $C_1$-$C_2$-alkyl,
with n equal 0, 1 or 2;

$R^4$ is selected from halogen, OH, CN, $NO_2$, $NH_2$, NHMe, $NMe_2$, SH, SMe, SOMe, $SO_2$Me, $C_1$-$C_4$ alkyl, $C_3$-$C_4$ cycloalkyl, $C_1$-$C_3$ alkoxy, $C_1$-$C_3$ heteroalkyl, heterocycle, each of which is optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl $NH_2$, NHMe, and $NMe_2$;

$R^{12}$ is selected from H and $C_1$-$C_3$ alkyl, each of which is optionally substituted by 1 to 7 halogen;

$R^{13}$ is selected from $C_1$-$C_7$ alkyl, $C_1$-$C_6$ heteroalkyl, $C_3$-$C_8$ cycloalkyl, —$C_1$-$C_2$ alkylene-$C_3$-$C_6$ cycloalkyl, $C_3$-$C_5$ heterocycle,
wherein cycloalkyl includes spirocyclic carbocyclic rings;
each of which $R^{13}$ groups is optionally substituted by one or more substituents selected from halogen, =O, OH, SMe, $C_1$-$C_2$ alkoxy, O—$C_1$-$C_2$ haloalkyl, $C_1$-$C_2$ alkyl, $C_1$-$C_2$ heteroalkyl, $C_1$-$C_2$ haloalkyl, $NH_2$, NHMe, and $NMe_2$;

$R^{14}$ is C=O, C=S, C=N-OH, C=NR$^b$, C=CH-$NO_2$, $SO_2$, and $C_3$-$C_6$ cycloalkenyl which may be substituted with 1 or 2 =O;

$R^a$ is selected from H, $C_1$-$C_8$ alkyl, heteroalkyl, $C_1$-$C_8$ alkoxy, heterocycle, $C_3$-$C_8$ cycloalkyl, heteroaryl and aryl,
each of which is optionally substituted by one or more substituents selected from halogen, =O, OH, SMe, $C_1$-$C_2$ alkoxy, —O—$C_1$-$C_2$haloalkyl, $C_1$-$C_2$ alkyl, $C_3$-$C_6$ cycloalkyl, $C_3$-$C_6$ heterocycloalkyl, $C_1$-$C_2$heteroalkyl, $C_1$-$C_2$ haloalkyl, aryl, heteroaryl, $NH_2$, NHMe, and $NMe_2$;

$R^b$ is selected from CN, aryl, heteroaryl, —$NO_2$, —O—$C_1$-$C_2$ alkyl, and —CO—O—$C_1$-$C_2$ alkyl, wherein each aryl and heteroaryl is optionally substituted by one or more $C_1$-$C_2$ alkyl;

$R^c$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, and $C_1$-$C_4$ alkylene-$C_3$-$C_6$ cycloalkyl;
each of which is optionally substituted by one or more substituents selected from C(O)(R$^g$), C(O)N(R$^f$)(R$^g$), halogen, $SF_5$, OH, =O, —COH, —COOH, —CO—O—R$^a$, CN, SMe, $SO_2$Me, $SO_2$R$^g$, $C_1$-$C_4$ alkoxy, O—$C_1$-$C_4$haloalkyl, $C_1$-$C_4$ alkyl, $C_1$-$C_2$ heteroalkyl, $C_1$-$C_4$haloalkyl, N(R$^f$)(R$^g$), N(R$^f$)$SO_2$(R$^g$), $SO_2NH_2$, $SO_2$NHMe, $SO_2NMe_2$, S(O)(NR$^f$)R$^g$, $C_3$-$C_6$ cycloalkyl, heterocycle, $C_1$-$C_4$ alkylene-$C_3$-$C_6$ cycloalkyl, aryl and heteroaryl,
wherein each aryl, heteroaryl, heterocycle and cycloalkyl is optionally substituted by one or more substituents selected from halogen, =O, =NH, =NMe, OH, $C_1$-$C_2$ alkyl, $C_1$-$C_2$ alkoxy, —COOH, —COO—$C_1$-$C_2$ alkyl, $SO_2R^a$, $COR^a$, $SOR^a$, $S(O)(NH)R^a$, and $CONHR^a$;

$R^d$ represents H or $C_1$-$C_4$ alkyl;

or $R^c$ and $R^d$ together with a nitrogen atom to which they are linked form a 5-7 membered heterocyclic group containing at least one nitrogen ring atom;

$R^f$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, and $C_1$-$C_4$ alkylene-$C_3$-$C_6$ cycloalkyl,
each of which is optionally substituted by one or more substituents selected from halogen, =O, =NH, =NMe, OH, aryl, heteroaryl, $C_1$-$C_2$ alkyl, $C_1$-$C_2$haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, $S(O)(NH)R^a$, and $CONHR^a$;

$R^g$ is selected from H, aryl, heteroaryl, $C_3$-$C_6$ cycloalkenyl, $C_3$-$C_8$ cycloalkyl, heterocycle, $C_1$-$C_8$ alkyl, $C_1$-$C_8$ heteroalkyl, and $C_1$-$C_4$ alkylene-$C_3$-$C_6$ cycloalkyl,
each of which is optionally substituted by one or more substituents selected from halogen, =O, =NH, =NMe, OH, aryl, heteroaryl, $C_1$-$C_2$ alkyl, $C_1$-$C_2$haloalkyl, $C_1$-$C_2$ alkoxy, O—$C_1$-$C_2$ haloalkyl, —COOH, —COO—$C_1$-$C_2$ alkyl, $SO_2R^a$, $COR^a$, $SOR^a$, and $S(O)(NH)R^a$, $CONHR^a$.

2. A compound according to claim 1, or a pharmaceutically acceptable salt thereof, which is a compound of formula (II):

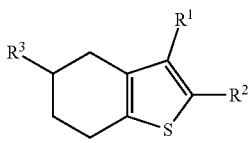

(II)

3. A compound according to claim 1 or a pharmaceutically acceptable salt thereof, wherein $R^1$ is

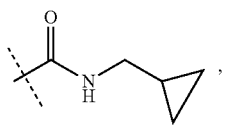

and $R^2$ is

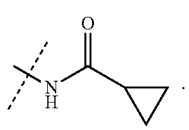

4. A compound according to claim 1, wherein $R^1$ is selected from N-methylaminocarbonyl, (cyclopropylmethyl)aminocarbonyl, cyclopropylcarbonylamino, cyclopropylcarbamoyl, propyl-sulfamoyl, isobutyl-sulfamoyl, [(2-hydroxy-2-methyl)propyl]sulfamoyl, 2-hydroxypropylsulfamoyl, 3-pyrrolidin-1-ylsulfonyl, (3-fluorocyclobutyl)-sulfamoyl, butylsulfonyl, butylsulfinyl, cyclopropylmethylsulfamoyl, butylsulfonimidoyl, 3-fluoropyrrolidine-1-carbonyl, 3-fluoroazetidine-1-carbonyl, piperidine-1-carbonyl, cyclopropylmethoxycarbonyl, ethoxycarbonyl, isobutyl-aminocarbonyl, 5-azaspiro[2.4]heptane-5-carbonyl, (3,3-difluorocyclobutyl)carbamoyl, (3-fluorocyclobutyl)carbamoyl, (2-fluoro-2-methyl-propyl)carbamoyl, isobutylcarbamoyl, 3-methylpyrrolidine-1-carbonyl, and propylcarbamoyl.

5. A compound according to claim 1 or a pharmaceutically acceptable salt thereof, wherein $R^2$ is selected from cyclopropanecarbonylamino, 2-methylpropanoylamino, cyclobutanecarbonylamino, and (2-methylcyclopropanecarbonyl)amino.

6. A compound according to claim 1 or a pharmaceutically acceptable salt thereof, wherein X is C or N and $R^3$ is selected from OH, amino, methylsulfonyl, acetyl, 2-methoxyacetyl, 2-phenylacetyl, 2-(tert-butoxycarbonylamino)ethyl, 2-phenylethyl, pyrimidin-2-ylamino, methanesufonamido, (4-methoxyphenyl)carbamothioylamino, (4-Methoxyphenyl)carbamoylamino, ethylcarbamoyl, [N'-Cyano-N-(p-tolyl)carbamimidoyl]amino, [N'-Cyano-N-ethyl-carbamimidoyl]amino, (1-oxoisoindolin-5-yl)carbamoyl, (3-sulfamoylphenyl)carbamoyl, (3-methylsulfonylphenyl)carbamoyl, 3-isoxazol-5-ylanilino, (2-ethoxy-3,4-dioxo-cyclobuten-1-yl)amino, ethylcarbonyl, carboxy, (1-oxoisoindolin-5-yl)aminocarbonyl, [(5-oxopyrrolidin-3-yl)phenyl]aminocarbonyl, [3-(3-methyl-5-oxo-4H-pyrazol-1-yl)phenyl]carbonylamino, (1H-indazol-4-yl)carbonylamino, 1H-imidazo[4,5-b]pyrazin-2-yl, indan-2-yl, [2-(4-methoxyphenyl)ethylaminocarbonyl, quinoxalin-6-yl, (thiazol-2-yl)aminocarbonyl, (1H-tetrazol-5-yl)aminocarbonyl, (4-pyridyl)aminocarbonyl, pyrazin-2-ylaminocarbonyl, (3-pyridyl)aminocarbonyl, 3-hydroxyazetidine-1-carbonyl, 1,1-dioxo-1,4-thiazinane-4-carbonyl, 2-(4-hydroxyphenyl)ethylaminocarbonyl, hydroxyiminomethyl, [(4-ethyl-1,2,4-triazol-3-yl)amino]methyl, (4-methylanilino)methyl, 2-Amino-3-pyridyl, 5-(p-tolyl)-1H-imidazol-2-yl, cyano, trifluoromethyl, 4-methyloxazol-2-yl, aminomethyl, (p-tolylcarbamoylamino)methyl, 3-methyl-1,2,4-oxadiazol-5-yl, 5-methyl-1,3,4-oxadiazol-2-yl, pyrrolidine-1-carbonyl, 3-pyridylcarbamothioylamino, 3-(3-pyridylamino)-1,2,4-triazol-4-yl, 1H-pyrazol-3-yl, 5-Amino-4-cyano-imidazol-1-yl, 3-(2,2-dimethylpropylamino)-1,2,4-triazol-4-yl, 3-[(2,5-dimethylpyrazol-3-yl)amino]-1,2,4-triazol-4-yl, 4-(2,5-dimethylpyrazol-3-yl)-1,2,4-triazol-3-yl]amino, [(2,5-dimethylpyrazol-3-yl)amino]-1,2,4-triazol-4-yl, N'-Cyano-N-phenyl-carbamimidoylamino, 3-(isobutylamino)-1,2,4-triazol-4-yl, 3-[(1-methylcyclopropyl)methylamino]-1,2,4-triazol-4-yl, 5-Acetamidoimidazol-1-yl, 3-[(5-methyl-3-pyridyl)amino]-1,2,4-triazol-4-yl, 3-(4-pyridylamino)-1,2,4-triazol-4-yl, N'-Cyano-N-(3,4-dimethoxyphenyl)carbamimidoyl]amino, 4-ethoxycarbony-5-(ethylamino)imidazole-1-yl, 3-(2-morpholinoethylamino)-1,2,4-triazol-4-yl, (5-oxo-4H-1,2,4-oxadiazol-3-yl)amino, 2-(ethylamino)-3,4-dioxo-cyclobuten-1-yl]amino, [N'-cyano-N-(2,2,2-trifluoroethyl)carbamimidoyl]amino, 3-(ethylamino)-1,2,4-triazol-4-yl, (N-ethyl-N'-nitro-carbamimidoyl)amino, 3-(3-pyridylamino)-1,2,4-triazol-4-yl, 3-[(1-oxidopyridin-1-ium-3-yl)amino, [N'-nitro-N-(p-tolyl)carbamimidoyl]amino, 2-(3-pyridylamino)imidazol-1-yl, 3-(3-pyridylamino)-1,2,4-triazol-4-yl, 3-(cyclopropylmethylamino, (2,5-dimethylpyrazol-3-yl)carbamothioylamino, 3-(pyrimidin-5-ylamino)-1,2,4-triazol-4-yl, 2-(cyclopropylmethylamino)imidazol-1-yl, [4-(ethylamino)-1,1-dioxo-1,2,5-thiadiazol-3-yl]amino, [1-(4-methylanilino)-2-nitro-vinyl]amino, (N'-cyano-N-ethyl-carbamimidoyl)-methyl-amino, [2-(4-methylanilino)-3,4-dioxo-cyclobuten-1-yl]amino, 3-(2-pyridylamino)-1,2,4-triazol-4-yl, 2-Acetamidoimidazol-1-yl, 5-(N-tert-butyloxycarbonylamino)-triazol-1-yl, 5-(3-pyridylamino)triazol-1-yl, ethylcarbamothioylamino, 3-[[(3S)-tetrahydrofuran-3-yl]amino]-1,2,4-triazol-4-yl, [(E)-N-ethyl-N'-nitro-carbamimidoyl]amino, 2-(ethylamino)imidazol-1-yl, 3-[(3,5-dimethylisoxazol-4-yl)amino], [[N'-ethoxycarbonyl-N-(p-tolyl)carbamimidoyl]amino], [2-[(2-methyl-3-pyridyl)amino]imidazol-1-yl, 1-[(ethylamino)-2-nitro-vinyl]amino], (4-methyl-6-oxo-1H-pyrimidin-2-yl)amino, 5-amino-4-(methylcarbamoyl)imidazol-1-yl, 5-amino-4-carbamoyl-imidazol-1-yl, 2-Anilinoimidazol-1-yl, ethylcarbamoylamino, (4-oxo-1H-pyridin-2-yl)amino, [6-(5-methyl-1,3,4-oxadiazol-2-yl)-3-pyridyl]amino, 5-(ethylamino)tetrazol-1-yl, 1H-1,2,4-triazol-3-ylamino, 4-(1-methylpyrazol-4-yl)-1,2,4-triazol-3-yl]amino, 4-(ethyloxycarbonyl)imidazol-1-yl, [4-(4-fluorophenyl)-1,2,4-triazol-3-yl]amino, 1H-imidazol-2-ylamino, N'-methoxy-N-(p-tolyl)carbamimidoyl]amino, [4-(4-methylanilino)-1,1-dioxo-1,2,5-thiadiazol-3-yl]amino, [1-(3-pyridyl)imidazol-2-yl]amino, 5-aminotriazol-1-yl, (2-methoxyphenyl)carbamoylamino, 4-pyridine-carbonylamino, benzylamino, 1H-Benzimidazol-2-ylamino, [N'-hydroxycarbamimidoyl]amino, [N'-(1-methylpyrazol-3-yl)-N-(p-tolyl)carbamimidoyl]amino, 3-[(3,5-dimethylpyrazin-2-yl)amino, 3-(ethylamino)-5-(methoxymethyl)-1,2,4-triazol-4-yl, [5-(3-pyridyl)-1H-1,2,4-triazol-3-yl]amino, p-tolyl-carbonylamino, quinazolin-2-ylamino, 1,3-Benzoxazol-2-ylamino, 3-(ethylamino)-5-(hydroxymethyl)-1,2,4-triazol-4-yl, 2-aminoimidazol-1-yl, 3-amino-5-oxo-1,2,4-oxadiazol-4-yl, 3-(ethylamino)-5-methyl-1,2,4-triazol-4-yl, (2-ethyl-3,4-dioxo-cyclobuten-1-yl)amino, 1,3,4-oxadiazol-2-ylamino, 5-oxo-1-(p-tolyl)-4H-imidazol-2-yl]amino, [2-[ethyl(methyl)amino]-3,4-dioxo-cyclobuten-1-yl]amino, (methylsulfonimidoyl)amino, [N-Cyano-C-methyl-carbonimidoyl]amino, tetrazol-1-yl, methanesulfinamido, morpholino, 3-(ethylamino)-5-(trifluoromethyl)-1,2,4-triazol-4-yl, (4-oxo-1H-pyrimidin-2-yl)amino, isopropylsulfamoylamino, N'-Cyano-N-morpholino-carbamimidoyl]amino, acetamido, methanesulfonamido, [N'-Cyano-N-methoxy-carbamimidoyl]amino, (4-methoxyphenyl)carbamoylamino, [4-oxo-6-(trifluoromethyl)-1H-pyrimidin-2-yl]amino, [4-(trifluoromethoxy)phenyl]carbamoylamino, 3-(2-methylpropanoylamino)-1,2,4-triazol-4-yl, 3-[(2,5-dimethylpyrazol-3-yl)-methyl-amino]-1,2,4-triazol-4-yl, 5-amino-4-(5-methyl-1,3,4-oxadiazol-2-yl)imidazol-1-yl, 3-[(3-methyl-1H-pyrazol-5-yl)amino]-1,2,4-triazol-4-yl, 3-[(1,3-dimethylpyrazol-4-yl)amino]-1,2,4-triazol-4-yl-[(5-cyclopropyl-2-methyl-pyrazol-3-yl)amino]-1,2,4-triazol-4-yl, 3-[(5-isopropyl-2-methyl-pyrazol-3-yl)amino]-1,2,4-triazol-4-yl, 3-[[2-methyl-5-(trifluoromethyl)pyrazol-3-yl]amino]-1,2,4-triazol-4-yl, 3-[(2-isopropyl-5-methyl-pyrazol-3-yl)amino, 3-[(5-methyl-2-tetrahydrofuran-3-yl-pyrazol-3-yl)amino]-1,2,4-triazol-4-yl, 3-[(2-methylpyrazol-3-yl)amino]-1,2,4-triazol-4-yl, 3-[(2-ethyl-5-methyl-pyrazol-3-yl)amino]-1,2,4-triazol-4-yl, 3-[(2-cyclopropyl-5-methyl-pyrazol-3-yl)amino]-1,2,4-triazol-4-yl, 3-[(3-methoxy-1-methyl-pyrazol-4-yl)amino]-1,2,4-triazol-4-yl, 3-[(5-ethyl-2-methyl-pyrazol-3-yl)amino]-1,2,4-triazol-4-yl, 3-[[5-(difluoromethyl)-2-methyl-pyrazol-3-yl]amino, 3-[(1,4-dimethylpyrazol-3-yl)amino]-1,2,4-triazol-4-yl, [3-[(5-methoxycarbonyl-2-methyl-pyrazol-3-yl)amino]-1,2,4-triazol-4-yl], 2-[[2-methyl-5-(trifluoromethyl)pyrazol-3-yl]amino]imidazol-1-yl, and [3-[(5-carboxy-2-methyl-pyrazol-3-yl)amino]-1,2,4-triazol-4-yl].

7. A compound according to claim 1 or a pharmaceutically acceptable salt thereof, wherein W, X, Y, and Z are C and Z is optionally substituted with a methyl group.

8. A compound according to claim 1 or a pharmaceutically acceptable salt thereof, wherein $R^1$ is selected from (cyclopropylmethyl)carbamoyl, (3-fluorocyclobutylmethyl)carbamoyl, (2-fluorocyclopropyl)methyl-carbamoyl, (2,2-difluorocyclopropyl)methyl-carbamoyl, (2,2-dimethylcyclopropyl)methylcarbamoyl, (spiro[2.2]pentan-2-yl)carbamoyl, (spiro[2.2]pentan-2-yl)methyl-carbamoyl, (3,3-difluorocyclobutyl)carbamoyl, (3-fluorocyclobutyl)carbamoyl, (2-methylcyclopropyl)methylcarbamoyl, (3,3-difluorocyclobutyl)methyl-carbamoyl, ethoxycarbonyl, (3-fluorocyclobutyl)methyl-carbamoyl, (cyclobutyl)methyl-carbamoyl, (3-methylcyclobutyl)carbamoyl, (2,2-difluorocyclobutyl)methyl-carbamoyl, (3-fluorocyclobutyl)methyl-carbamoyl, (2-fluorocyclobutyl)methyl-per carbamoyl, and (spiro[2.2]pentan-2-yl)carbamoyl.

9. A compound according to claim 1 or a pharmaceutically acceptable salt thereof, wherein $R^2$ is selected from (cyclopropyl)acetylamino, (spiro[2.2]pentan-2-yl)carbonylamino, (2-fluorocyclopropyl)carbonylamino, (2,2-difluorocyclopropyl)carbonylamino, (2-methylcyclopropyl)carbonylamino, (3-fluorocyclobutyl)carbonylamino, (3,3-difluorocyclobutyl)carbonylamino, (oxetan-3-yl)carbonylamino, 3,3-difluoropropanoylamino, (cyclobutyl)carbonylamino, and 2-(methylpropanoyl)amino.

10. A compound according to claim 1 or a pharmaceutically acceptable salt thereof, wherein $R^3$ is selected from (1,1-dioxothiolan-3-yl)amino-1,2,4-triazol-4-yl, 3-[3-[methylsulfonimidoyl]anilino]-1,2,4-triazol-4-yl, 3-[(1-acetyl-3-methylpyrrolidin-3-yl)amino]-4H-1,2,4-triazol-4-yl, 3-{[1-(6-methylpyridazin-3-yl)pyrrolidin-3-yl]amino}-4H-1,2,4-triazol-4-yl, 3-[[-1-pyrazin-2-ylpyrrolidin-3-yl]amino]-1,2,4-triazol-4-yl, 3-[(4-methyl-1-methylsulfonyl-pyrrolidin-3-yl)amino]-1,2,4-triazol-4-yl, 3-[(1-oxo-2,3-dihydro-1H-isoindol-4-yl)amino]-4H-1,2,4-triazol-4-yl, 3-[[-1-(6-fluoropyridazin-3-yl)pyrrolidin-3-yl]amino]-1,2,4-triazol-4-yl, 3-[[1-pyrimidin-2-ylpyrrolidin-3-yl]amino]-1,2,4-triazol-4-yl, 5-amino-4-(2-methoxyethoxycarbonyl)imidazol-1-yl, 5-amino-4-(2-morpholinethoxycarbonyl)imidazol-1-yl, 3-(3-methylsulfanylanilino)-1,2,4-triazol-4-yl, 3-(3-methylsulfonylanilino)-1,2,4-triazol-4-yl, 3-(3-methylsulfinylanilino)-1,2,4-triazol-4-yl, 3-[3-(methylsulfonimidoyl)anilino]-1,2,4-triazol-4-yl, 3-[(6-methylsulfinyl-2-pyridyl)amino]-1,2,4-triazol-4-yl, 3-[(6-methylsulfonyl-2-pyridyl)amino]-1,2,4-triazol-4-yl, 8-methoxy-4-oxo-5,10-dihydroimidazo[4,5-c][1,5]benzodiazepin-1-yl, 8-methoxy-5-methyl-4-oxo-10H-imidazo[4,5-c][1,5]benzodiazepin-1-yl, 5-amino-4-[(2S)-2-methylpyrrolidine-1-carbonyl]imidazol-1-yl, 5-amino-4-[(3R)-3-hydroxypyrrolidine-1-carbonyl]imidazol-1-yl, 5-amino-4-[(2S)-2-methylpyrrolidine-1-carbonyl]imidazol-1-yl, 5-[[4-(dihydroxyamino)-2,5-dimethyl-3H-pyrazol-3-yl]amino]-4-ethoxycarbonyl-imidazol-1-yl, 5-[[4-(dihydroxyamino)-2,5-dimethyl-3H-pyrazol-3-yl]amino]-4-ethoxycarbonyl-imidazol-1-yl, 3-(2-methyl-3-methylsulfinyl-anilino)-1,2,4-triazol-4-yl, 3-(2-methyl-3-methylsulfonyl-anilino)-1,2,4-triazol-4-yl, 3-[(2-methyl-5-oxazol-yl-pyrazol-3-yl)amino]-1,2,4-triazol-4-yl, 1-acetylpyrrolidin-3-yl]amino]-1,2,4-triazol-4-yl, 1-methylsulfonylpyrrolidin-3-yl]amino]-1,2,4-triazol-4-yl, 3-[(2-methylcyclohexyl)amino]-1,2,4-triazol-4-yl, 3-[(5-oxopyrrolidin-3-yl)amino]-1,2,4-triazol-4-yl, 3-[(2-oxo-4-piperidyl)amino]-1,2,4-triazol-4-yl, 3-[(1-acetyl-2-methyl-pyrrolidin-3-yl)amino]-1,2,4-triazol-4-yl, 3-[(2-methyl-1-methylsulfonyl-pyrrolidin-3-yl)amino]-1,2,4-triazol-4-yl, -[3-[[3-(6-methyl-3-pyridyl)cyclobutyl]amino]-1,2,4-triazol-4-yl, 3-[[5-(difluoromethoxy)-2-methyl-pyrazol-3-yl]amino]-1,2,4-triazol-4-yl, [[1-benzoyl-4,4-difluoro-pyrrolidin-3-yl]amino]-1,2,4-triazol-4-yl, 3-[(1-acetyl-4-piperidyl)amino]-1,2,4-triazol-4-yl, 3-[(1-methoxycarbonylpyrrolidin-3-yl)amino]-1,2,4-triazol-4-yl, 3-[[1-(ethylcarbamoyl)pyrrolidin-3-yl]amino]-1,2,4-triazol-4-yl, 3-{[2-(pyrimidin-2-yl)-2-azaspiro[4.4]nonan-7-yl]amino}-4H-1,2,4-triazol-4-yl, 3-[[2-methyl-5-(trifluoromethoxy)pyrazol-3-yl]amino]-1,2,4-triazol-4-yl, 3-[[5-[chloro(difluoro)methoxy]-2-methyl-pyrazol-3-yl]amino]-1,2,4-triazol-4-yl, 3-{1-methyl-3-(5-methyl-1,3,4-oxadiazol-2-yl)-1H-pyrazol-5-yl]amino}-4H-1,2,4-triazol-4-yl, 3-[(5-methoxy-3-methyl-pyrazin-2-yl)amino]-1,2,4-triazol-4-yl, (5-methylthiazolo[5,4-b]pyridin-2-yl)amino, 3-[(5-cyano-2-methyl-3-pyridyl)amino]-1,2,4-triazol-4-yl, 3-[(6-cyano-2-methyl-3-pyridyl)amino]-1,2,4-triazol-4-yl, 3-[(1-methyl-2-oxo-4-pyridyl)amino]-1,2,4-triazol-4-yl, 3-[(6-chloro-2-methyl-3-pyridyl)amino]-1,2,4-triazol-4-yl, 3-[[2-methyl-6-(trifluoromethyl)-3-pyridyl]amino]-1,2,4-triazol-4-yl, 3-[(3-methylpyridazin-4-yl)amino]-1,2,4-triazol-4-yl, 3-[(5-chloro-2-methyl-pyrazol-3-yl)amino]-1,2,4-triazol-4-yl, 3-[(3-methylisothiazol-4-yl)amino]-1,2,4-triazol-4-yl, 3-[(3-methylisoxazol-4-yl)amino]-1,2,4-triazol-4-yl, 3-[[5-(cyclopropylmethoxy)-2-methyl-pyrazol-3-yl]amino]-1,2,4-triazol-4-yl, 3-[(5-ethoxy-2-methyl-pyrazol-3-yl)amino]-1,2,4-triazol-4-yl, 3-[(2,5-dimethylpyrazol-3-yl)amino]-1,2,4-triazol-4-yl, (5-amino-4-ethoxycarbonyl-imidazol-1-yl), 3-[[5-(difluoromethoxy)-2-methylpyrazol-3-yl]amino]-1,2,4-triazol-4-yl, 3-[[5-(difluoromethyl)-2-methylpyrazol-3-yl]amino]-1,2,4-triazol-4-yl, 3-[(5-methoxy-2-methylpyrazol-3-yl)amino]-1,2,4-triazol-4-yl, 3-[[5-(difluoromethyl)-2-(trideuteriomethyl)pyrazol-3-yl]amino, 3-[(5-Cyano-2-methyl-pyrazol-3-yl)amino]-1,2,4-triazol-4-yl, 3-[(2,2-difluoro-1,3-benzodioxol-5-yl)amino]-1,2,4-triazol-4-yl, 3-[(5-methoxy-2-methyl-pyrazol-3-yl)amino]-1,2,4-triazol-4-yl, 3-[[5-(difluoromethyl)-2-(trideuteriomethyl)pyrazol-3-yl]amino]-1,2,4-triazol-4-yl, 3-[(6-fluoro-2-methyl-3-pyridyl)amino]-1,2,4-triazol-4-yl, 3-[[5-(cyclopropoxy)-2-methyl-pyrazol-3-yl]amino]-1,2,4-triazol-4-yl, 3-[[2-methyl-5-(2,2,2-trifluoroethoxy)pyrazol-3-yl]amino]-1,2,4-triazol-4-yl, 3-[[6-(trifluoromethyl)-3-pyridyl]amino]-1,2,4-triazol-4-yl, 3-[(6-methoxy-3-pyridyl)amino]-1,2,4-triazol-4-yl, 3-[(2-methoxy-4-pyridyl)amino]-1,2,4-triazol-4-yl, 3-[(6-chloro-3-pyridyl)amino]-1,2,4-triazol-4-yl, 3-[(2-chloro-4-pyridyl)amino]-1,2,4-triazol-4-yl, 3-[(6-methoxy-2-methyl-3-pyridyl)amino]-1,2,4-triazol-4-yl, thiazolo[5,4-b]pyridin-2-ylamino, and 3-[(3-methyltriazol-4-yl)amino]-1,2,4-triazol-4-yl.

11. A compound according to claim 1, which is:
(4R)-2-(Cyclopropanecarbonylamino)-N-(cyclopropylmethyl)-4-methyl-5,6-dihydro-4H-cyclopenta[b]thiophene-3-carboxamide;
(4S)-2-(Cyclopropanecarbonylamino)-N-(cyclopropylmethyl)-4-methyl-5,6-dihydro-4H-cyclopenta[b]thiophene-3-carboxamide;
N-[3-(Cyclopropylmethylsulfamoyl)-4,5,6,7-tetrahydrobenzothiophen-2-yl]cyclopropanecarboxamide;
N-[3-(Propylsulfamoyl)-4,5,6,7-tetrahydrobenzothiophen-2-yl]cyclopropanecarboxamide;
N-[3-(Isobutylsulfamoyl)-4,5,6,7-tetrahydrobenzothiophen-2-yl]cyclopropanecarboxamide;
N-[3-[(2-Hydroxy-2-methyl-propyl)sulfamoyl]-4,5,6,7-tetrahydrobenzothiophen-2-yl]cyclopropanecarboxamide;
N-[3-(2-Hydroxypropylsulfamoyl)-4,5,6,7-tetrahydrobenzothiophen-2-yl]cyclopropanecarboxamide;
N-(3-Pyrrolidin-1-ylsulfonyl-4,5,6,7-tetrahydrobenzothiophen-2-yl)cyclopropanecarboxamide;
N-[3-[(3-Fluorocyclobutyl)sulfamoyl]-4,5,6,7-tetrahydrobenzothiophen-2-yl]cyclopropanecarboxamide;
N-(3-Butylsulfonyl-4,5,6,7-tetrahydrobenzothiophen-2-yl)cyclopropanecarboxamide;
N-[3-(Isobutylsulfamoyl)-5-(pyrimidin-2-ylamino)-4,5,6,7-tetrahydrobenzothiophen-2-yl]cyclopropanecarboxamide;
N-[3-(Isobutylsulfamoyl)-5-(methanesulfonamido)-4,5,6,7-tetrahydrobenzothiophen-2-yl]cyclopropanecarboxamide;
N-[5-[(4-Methoxyphenyl)carbamothioylamino]-3-(propylsulfamoyl)-4,5,6,7-tetrahydrobenzothiophen-2-yl]cyclopropanecarboxamide;
N-[5-[(4-Methoxyphenyl)carbamoylamino]-3-(propylsulfamoyl)-4,5,6,7-tetrahydrobenzothiophen-2-yl]cyclopropanecarboxamide;
2-(Cyclopropanecarbonylamino)-N-ethyl-3-(isobutylsulfamoyl)-4,5,6,7-tetrahydrobenzothiophene-7-carboxamide;
2-(Cyclopropanecarbonylamino)-N-ethyl-3-(isobutylsulfamoyl)-4,5,6,7-tetrahydrobenzothiophene-5-carboxamide;
N-(3-Butylsulfinyl-4,5,6,7-tetrahydrobenzothiophen-2-yl)cyclopropanecarboxamide;
N-[5-[[N'-Cyano-N-(p-tolyl)carbamimidoyl]amino]-3-(cyclopropylmethylsulfamoyl)-4,5,6,7-tetrahydrobenzothiophen-2-yl]cyclopropanecarboxamide;
N-[5-[[N'-Cyano-N-ethyl-carbamimidoyl]amino]-3-(cyclopropylmethylsulfamoyl)-4,5,6,7-tetrahydrobenzothiophen-2-yl]cyclopropanecarboxamide;
2-(Cyclopropanecarbonylamino)-3-(cyclopropylmethylsulfamoyl)-N-(1-oxoisoindolin-5-yl)-4,5,6,7-tetrahydrobenzothiophene-5-carboxamide;
2-(Cyclopropanecarbonylamino)-3-(cyclopropylmethylsulfamoyl)-N-(3-sulfamoylphenyl)-4,5,6,7-tetrahydrobenzothiophene-5-carboxamide;
2-(Cyclopropanecarbonylamino)-3-(cyclopropylmethylsulfamoyl)-N-(3-methylsulfonylphenyl)-4,5,6,7-tetrahydrobenzothiophene-5-carboxamide;
2-(Cyclopropanecarbonylamino)-3-(cyclopropylmethylsulfamoyl)-N-(3-isoxazol-5-ylphenyl)-4,5,6,7-tetrahydrobenzothiophene-5-carboxamide;
N-[3-(Cyclopropylmethylsulfamoyl)-5-[(2-ethoxy-3,4-dioxo-cyclobuten-1-yl)amino]-4,5,6,7-tetrahydrobenzothiophen-2-yl]cyclopropanecarboxamide;
N-[3-(Cyclopropylmethylsulfamoyl)-5-[[2-(ethylamino)-3,4-dioxo-cyclobuten-1-yl]amino]-4,5,6,7-tetrahydrobenzothiophen-2-yl]cyclopropanecarboxamide;
N-[3-(Butylsulfonimidoyl)-4,5,6,7-tetrahydrobenzothiophen-2-yl]cyclopropanecarboxamide;
Ethyl 2-(cyclopropanecarbonylamino)-3-(cyclopropylmethylcarbamoyl)-4,5,6,7-tetrahydrobenzothiophene-5-carboxylate;
2-(Cyclopropanecarbonylamino)-3-(cyclopropylmethylcarbamoyl)-4,5,6,7-tetrahydrobenzothiophene-5-carboxylic acid;
2-(Cyclopropanecarbonylamino)-N3-(cyclopropylmethyl)-N5-(1-oxoisoindolin-5-yl)-4,5,6,7-tetrahydrobenzothiophene-3,5-dicarboxamide;
2-(Cyclopropanecarbonylamino)-N3-(cyclopropylmethyl)-N5-[3-(5-oxopyrrolidin-3-yl)phenyl]-4,5,6,7-tetrahydrobenzothiophene-3,5-dicarboxamide;
2-(Cyclopropanecarbonylamino)-N3-(cyclopropylmethyl)-N5-[3-(3-methyl-5-oxo-4H-pyrazol-1-yl)phenyl]-4,5,6,7-tetrahydrobenzothiophene-3,5-dicarboxamide;

2-(Cyclopropanecarbonylamino)-N3-(cyclopropylmethyl)-N5-(1H-indazol-4-yl)-4,5,6,7-tetrahydrobenzothiophene-3,5-dicarboxamide;2,2,2-trifluoroacetic acid;

2-(Cyclopropanecarbonylamino)-N3-(cyclopropylmethyl)-N5-(1H-indazol-5-yl)-4,5,6,7-tetrahydrobenzothiophene-3,5-dicarboxamide;2,2,2-trifluoroacetic acid;

2-(Cyclopropanecarbonylamino)-N-(cyclopropylmethyl)-5-(1H-imidazo[4,5-b]pyrazin-2-yl)-4,5,6,7-tetrahydrobenzothiophene-3-carboxamide;

2-(Cyclopropanecarbonylamino)-N3-(cyclopropylmethyl)-N5-indan-2-yl-4,5,6,7-tetrahydrobenzothiophene-3,5-dicarboxamide;

2-(Cyclopropanecarbonylamino)-N3-(cyclopropylmethyl)-N5-[2-(4-methoxyphenyl)ethyl]-4,5,6,7-tetrahydrobenzothiophene-3,5-dicarboxamide;

2-(Cyclopropanecarbonylamino)-N3-(cyclopropylmethyl)-N5-quinoxalin-6-yl-4,5,6,7-tetrahydrobenzothiophene-3,5-dicarboxamide;

2-(Cyclopropanecarbonylamino)-N3-(cyclopropylmethyl)-N5-thiazol-2-yl-4,5,6,7-tetrahydrobenzothiophene-3,5-dicarboxamide;

2-(Cyclopropanecarbonylamino)-N3-(cyclopropylmethyl)-N5-(1H-tetrazol-5-yl)-4,5,6,7-tetrahydrobenzothiophene-3,5-dicarboxamide;

2-(Cyclopropanecarbonylamino)-N3-(cyclopropylmethyl)-N5-(4-pyridyl)-4,5,6,7-tetrahydrobenzothiophene-3,5-dicarboxamide;

2-(Cyclopropanecarbonylamino)-N3-(cyclopropylmethyl)-N5-pyrazin-2-yl-4,5,6,7-tetrahydrobenzothiophene-3,5-dicarboxamide;

2-(Cyclopropanecarbonylamino)-N3-(cyclopropylmethyl)-N5-(3-pyridyl)-4,5,6,7-tetrahydrobenzothiophene-3,5-dicarboxamide;

2-(Cyclopropanecarbonylamino)-N-(cyclopropylmethyl)-5-(3-hydroxy azetidine-1-carbonyl)-4,5,6,7-tetrahydrobenzothiophene-3-carboxamide;

2-(Cyclopropanecarbonylamino)-N-(cyclopropylmethyl)-5-(1,1-dioxo-1,4-thiazinane-4-carbonyl)-4,5,6,7-tetrahydrobenzothiophene-3-carboxamide;

2-(Cyclopropanecarbonylamino)-N3-(cyclopropylmethyl)-N5-[2-(4-hydroxyphenyl)ethyl]-4,5,6,7-tetrahydrobenzothiophene-3,5-dicarboxamide;

2-(cyclopropanecarbonylamino)-N-(cyclopropylmethyl)-5-(hydroxyiminomethyl)-4,5,6,7-tetrahydrobenzothiophene-3-carboxamide;

2-(Cyclopropanecarbonylamino)-N-(cyclopropylmethyl)-5-[[(4-ethyl-1,2,4-triazol-3-yl)amino]methyl]-4,5,6,7-tetrahydrobenzothiophene-3-carboxamide;

2-(Cyclopropanecarbonylamino)-N-(cyclopropylmethyl)-5-hydroxy-5-[(4-methylanilino)methyl]-6,7-dihydro-4H-benzothiophene-3-carboxamide;

2-(Cyclopropanecarbonylamino)-N-(cyclopropylmethyl)-2'-oxo-3'-(p-tolyl)spiro[6,7-dihydro-4H-benzothiophene-5,5'-oxazolidine]-3-carboxamide;

5-(2-Amino-3-pyridyl)-2-(cyclopropanecarbonylamino)-N-(cyclopropylmethyl)-4,5,6,7-tetrahydrobenzothiophene-3-carboxamide;

2-(Cyclopropanecarbonylamino)-N-(cyclopropylmethyl)-5-[5-(p-tolyl)-1H-imidazol-2-yl]-4,5,6,7-tetrahydrobenzothiophene-3-carboxamide;

5-Cyano-2-(cyclopropanecarbonylamino)-N-(cyclopropylmethyl)-4,5,6,7-tetrahydrobenzothiophene-3-carboxamide;

7-Cyano-2-(cyclopropanecarbonylamino)-N-(cyclopropylmethyl)-4,5,6,7-tetrahydrobenzothiophene-3-carboxamide;

(5R)-2-(Cyclopropanecarbonylamino)-N-(cyclopropylmethyl)-5-(trifluoromethyl)-4,5,6,7-tetrahydrobenzothiophene-3-carboxamide;

(5S)-2-(Cyclopropanecarbonylamino)-N-(cyclopropylmethyl)-5-(trifluoromethyl)-4,5,6,7-tetrahydrobenzothiophene-3-carboxamide;

2-(Cyclopropanecarbonylamino)-N-(cyclopropylmethyl)-5-(4-methyloxazol-2-yl)-4,5,6,7-tetrahydrobenzothiophene-3-carboxamide;

5-(Aminomethyl)-2-(cyclopropanecarbonylamino)-N-(cyclopropylmethyl)-5-hydroxy-6,7-dihydro-4H-benzothiophene-3-carboxamide;

2-(Cyclopropanecarbonylamino)-N-(cyclopropylmethyl)-5-hydroxy-5-[(p-tolylcarbamoylamino)methyl]-6,7-dihydro-4H-benzothiophene-3-carboxamide;

2-(Cyclopropanecarbonylamino)-N-(cyclopropylmethyl)-5-(3-methyl-1,2,4-oxadiazol-5-yl)-4,5,6,7-tetrahydrobenzothiophene-3-carboxamide;

2-(Cyclopropanecarbonylamino)-N-(cyclopropylmethyl)-5-(5-methyl-1,3,4-oxadiazol-2-yl)-4,5,6,7-tetrahydrobenzothiophene-3-carboxamide;

2-(Cyclopropanecarbonylamino)-N-(cyclopropylmethyl)-5-(pyrrolidine-1-carbonyl)-4,5,6,7-tetrahydrobenzothiophene-3-carboxamide;

2-(Cyclopropanecarbonylamino)-N-(cyclopropylmethyl)-5-hydroxy-5-methyl-6,7-dihydro-4H-benzothiophene-3-carboxamide;

N-[3-[(3R)-3-Fluoropyrrolidine-1-carbonyl]-4,5,6,7-tetrahydrobenzothiophen-2-yl]cyclopropanecarboxamide;

N-[3-(3-Fluoroazetidine-1-carbonyl)-4,5,6,7-tetrahydrobenzothiophen-2-yl]cyclopropanecarboxamide;

N-[3-(Piperidine-1-carbonyl)-4,5,6,7-tetrahydrobenzothiophen-2-yl]cyclopropanecarboxamide;

2-(Cyclopropanecarbonylamino)-7-hydroxy-N-methyl-4,5,6,7-tetrahydrobenzothiophene-3-carboxamide;

2-(Cyclopropanecarbonylamino)-N-(cyclopropylmethyl)-4-methyl-4,5,6,7-tetrahydrobenzothiophene-3-carboxamide;

2-(Cyclopropanecarbonylamino)-N-(cyclopropylmethyl)-5,7-dimethyl-4,5,6,7-tetrahydrobenzothiophene-3-carboxamide;

2-(Cyclopropanecarbonylamino)-N-(cyclopropylmethyl)-5-methyl-4,5,6,7-tetrahydrobenzothiophene-3-carboxamide;

2-(cyclopropanecarbonylamino)-N-(cyclopropylmethyl)-7-methyl-4,5,6,7-tetrahydrobenzothiophene-3-carboxamide;

2-(Cyclopropanecarbonylamino)-N-(cyclopropylmethyl)-5,5-dimethyl-6,7-dihydro-4H-benzothiophene-3-carboxamide;

2-(Cyclopropanecarbonylamino)-N-(cyclopropylmethyl)-5-methyl-7-oxo-5,6-dihydro-4H-benzothiophene-3-carboxamide;

2'-(Cyclopropanecarbonylamino)-N-(cyclopropylmethyl)spiro[1,3-dioxolane-2,5'-6,7-dihydro-4H-benzothiophene]-3'-carboxamide;

N-(Cyclopropylmethyl)-2-(2-methylpropanoylamino)-4,5,6,7-tetrahydrobenzothiophene-3-carboxamide;

2-(Cyclobutanecarbonylamino)-N-(cyclopropylmethyl)-4,5,6,7-tetrahydrobenzothiophene-3-carboxamide;

2-(Cyclopropanecarbonylamino)-N-(cyclopropylmethyl)-4,5-dimethyl-4,5,6,7-tetrahydrobenzothiophene-3-carboxamide;

2-(Cyclopropanecarbonylamino)-4,5-dimethyl-4,5,6,7-tetrahydrobenzothiophene-3-carboxylic acid;

N-(cyclopropylmethyl)-2-[(2-methylcyclopropanecarbonyl)amino]-4,5,6,7-tetrahydrobenzothiophene-3-carboxamide—Diastereomer 1;

N-(cyclopropylmethyl)-2-[(2-methylcyclopropanecarbonyl)amino]-4,5,6,7-tetrahydrobenzothiophene-3-carboxamide—Diastereomer 2;

2-(Cyclopropanecarbonylamino)-N-(cyclopropylmethyl)-2',5'-dioxo-spiro[6,7-dihydro-4H-benzothiophene-5,4'-imidazolidine]-3-carboxamide;

Cyclopropylmethyl 2-(cyclopropanecarbonylamino)-5-(3-pyridylcarbamothioylamino)-4,5,6,7-tetrahydrobenzothiophene-3-carboxylate;

Cyclopropylmethyl 2-(cyclopropanecarbonylamino)-5-[3-(3-pyridylamino)-1,2,4-triazol-4-yl]-4,5,6,7-tetrahydrobenzothiophene-3-carboxylate;

2-(Cyclopropanecarbonylamino)-N,5-dimethyl-4,5,6,7-tetrahydrobenzothiophene-3-carboxamide;

2-(Cyclopropanecarbonylamino)-N,7-dimethyl-4,5,6,7-tetrahydrobenzothiophene-3-carboxamide;

tert-Butyl N-[2-(cyclopropanecarbonylamino)-3-(cyclopropylmethylcarbamoyl)-4,5,6,7-tetrahydrobenzothiophen-7-yl]carbamate;

2-(Cyclopropanecarbonylamino)-N3-(cyclopropylmethyl)-N7-ethyl-4,5,6,7-tetrahydrobenzothiophene-3,7-dicarboxamide;

2-(Cyclopropanecarbonylamino)-N-(cyclopropylmethyl)-5-(1H-pyrazol-3-yl)-4,5,6,7-tetrahydrobenzothiophene-3-carboxamide;

2-(Cyclopropanecarbonylamino)-N-(cyclopropylmethyl)-7-(1H-pyrazol-3-yl)-4,5,6,7-tetrahydrobenzothiophene-3-carboxamide;

N-Methyl-2-[(2-methylcyclopropanecarbonyl)amino]-4,5,6,7-tetrahydrobenzothiophene-3-carboxamide;

Ethyl 2-(cyclopropanecarbonylamino)-7-hydroxy-4,5,6,7-tetrahydrobenzothiophene-3-carboxylate;

(5S)-5-(5-Amino-4-cyano-imidazol-1-yl)-2-(cyclopropanecarbonylamino)-N-(cyclopropylmethyl)-4,5,6,7-tetrahydrobenzothiophene-3-carboxamide;

(5S)-2-(Cyclopropanecarbonylamino)-N-(cyclopropylmethyl)-5-[3-(2,2-dimethylpropylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[[4-(2,5-dimethylpyrazol-3-yl)-1,2,4-triazol-3-yl]amino]-4,5,6,7-tetrahydrobenzothiophene-3-carboxamide;

(5S)-2-(Cyclopropanecarbonylamino)-5-[3-[(2,5-dimethylpyrazol-3-yl)amino]-1,2,4-triazol-4-yl]-N-isobutyl-4,5,6,7-tetrahydrobenzothiophene-3-carboxamide;

5-Amino-2-(cyclopropanecarbonylamino)-N-(cyclopropylmethyl)-4,5,6,7-tetrahydrobenzothiophene-3-carboxamide;

5-[[N'-Cyano-N-phenyl-carbamimidoyl]amino]-2-(cyclopropanecarbonylamino)-N-(cyclopropylmethyl)-4,5,6,7-tetrahydrobenzothiophene-3-carboxamide;

(5S)-2-(Cyclopropanecarbonylamino)-N-(cyclopropylmethyl)-5-[3-(isobutylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[(1-methylcyclopropyl)methylamino]-1,2,4-triazol-4-yl]-4,5,6,7-tetrahydrobenzothiophene-3-carboxamide;

(5S)-5-(5-Acetamidoimidazol-1-yl)-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(5-methyl-3-pyridyl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-(4-pyridylamino)-1,2,4-triazol-4-yl]-4,5,6,7-tetrahydrobenzothiophene-3-carboxamide;

5-[[N'-Cyano-N-(3,4-dimethoxyphenyl)carbamimidoyl]amino]-2-(cyclopropanecarbonylamino)-N-(cyclopropylmethyl)-4,5,6,7-tetrahydrobenzothiophene-3-carboxamide;

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate;

(5S)-2-(Cyclopropanecarbonylamino)-N-(cyclopropylmethyl)-5-[3-(2-morpholinoethylamino)-1,2,4-triazol-4-yl]-4,5,6,7-tetrahydrobenzothiophene-3-carboxamide;

2-(Cyclopropanecarbonylamino)-N-(cyclopropylmethyl)-5-[(5-oxo-4H-1,2,4-oxadiazol-3-yl)amino]-4,5,6,7-tetrahydrobenzothiophene-3-carboxamide;

2-(Cyclopropanecarbonylamino)-N-(cyclopropylmethyl)-5-[[2-(ethylamino)-3,4-dioxo-cyclobuten-1-yl]amino]-4,5,6,7-tetrahydrobenzothiophene-3-carboxamide;

5-[[N'-cyano-N-(2,2,2-trifluoroethyl)carbamimidoyl]amino]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-(ethylamino)-1,2,4-triazol-4-yl]-4,5,6,7-tetrahydrobenzothiophene-3-carboxamide;

2-(cyclopropanecarbonylamino)-N-(cyclopropylmethyl)-5-[(N-ethyl-N'-nitro-carbamimidoyl)amino]-4,5,6,7-tetrahydrobenzothiophene-3-carboxamide;

(5S)-2-(Cyclopropanecarbonylamino)-N-(cyclopropylmethyl)-5-[3-(3-pyridylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[(1-oxidopyridin-1-ium-3-yl)amino]-1,2,4-triazol-4-yl]-4,5,6,7-tetrahydrobenzothiophene-3-carboxamide;

2-(cyclopropanecarbonylamino)-N-(cyclopropylmethyl)-5-[[N'-nitro-N-(p-tolyl)carbamimidoyl]amino]-4,5,6,7-tetrahydrobenzothiophene-3-carboxamide;

(5S)-2-(Cyclopropanecarbonylamino)-N-(cyclopropylmethyl)-5-[2-(3-pyridylamino)imidazol-1-yl]-4,5,6,7-tetrahydrobenzothiophene-3-carboxamide;

N-[(5S)-3-(5-azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide;

N-[(5R)-3-(5-Azaspiro[2.4]heptane-5-carbonyl)-5-[3-(3-pyridylamino)-1,2,4-triazol-4-yl]-4,5,6,7-tetrahydrobenzothiophen-2-yl]cyclopropanecarboxamide;

(5S)-2-(Cyclopropanecarbonylamino)-N-(cyclopropylmethyl)-5-[3-(cyclopropylmethylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[(2,5-dimethylpyrazol-3-yl)carbamothioylamino]-4,5,6,7-tetrahydrobenzothiophene-3-carboxamide;

(5S)-2-(Cyclopropanecarbonylamino)-N-(cyclopropylmethyl)-5-[3-(pyrimidin-5-ylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[2-(cyclopropylmethylamino)imidazol-1-yl]-4,5,6,7-tetrahydrobenzothiophene-3-carboxamide;

2-(Cyclopropanecarbonylamino)-N-(cyclopropylmethyl)-5-[[4-(ethylamino)-1,1-dioxo-1,2,5-thiadiazol-3-yl]amino]-4,5,6,7-tetrahydrobenzothiophene-3-carboxamide;

2-(cyclopropanecarbonylamino)-N-(cyclopropylmethyl)-5-[[1-(4-methylanilino)-2-nitro-vinyl]amino]-4,5,6,7-tetrahydrobenzothiophene-3-carboxamide;

(5S)-5-[(N'-cyano-N-ethyl-carbamimidoyl)-methyl-amino]-2-(cyclopropanecarbonylamino)-N-(cyclopropylmethyl)-4,5,6,7-tetrahydrobenzothiophene-3-carboxamide;

2-(Cyclopropanecarbonylamino)-N-(cyclopropylmethyl)-5-[[2-(4-methylanilino)-3,4-dioxo-cyclobuten-1-yl]amino]-4,5,6,7-tetrahydrobenzothiophene-3-carboxamide;

(5S)-2-(Cyclopropanecarbonylamino)-N-(cyclopropylmethyl)-5-[3-(2-pyridylamino)-1,2,4-triazol-4-yl]-4,5,6,7-tetrahydrobenzothiophene-3-carboxamide;

(5S)-5-(2-Acetamidoimidazol-1-yl)-2-(cyclopropanecarbonylamino)-N-(cyclopropylmethyl)-4,5,6,7-tetrahydrobenzothiophene-3-carboxamide;

tert-Butyl N-[3-[2-(cyclopropanecarbonylamino)-3-(cyclopropylmethylcarbamoyl)-4,5,6,7-tetrahydrobenzothiophen-5-yl]triazol-4-yl]carbamate;

2-(Cyclopropanecarbonylamino)-N-(cyclopropylmethyl)-5-[5-(3-pyridylamino)triazol-1-yl]-4,5,6,7-tetrahydrobenzothiophene-3-carboxamide;

2-(Cyclopropanecarbonylamino)-N-(cyclopropylmethyl)-5-(ethylcarbamothioylamino)-4,5,6,7-tetrahydrobenzothiophene-3-carboxamide;

(5S)-2-(cyclopropanecarbonylamino)-N-(cyclopropylmethyl)-5-[3-[[(3S)-tetrahydrofuran-3-yl]amino]-1,2,4-triazol-4-yl]-4,5,6,7-tetrahydrobenzothiophene-3-carboxamide;

5-[[N'-Cyano-N-ethyl-carbamimidoyl]amino]-2-(cyclopropanecarbonylamino)-N-(cyclopropylmethyl)-4,5,6,7-tetrahydrobenzothiophene-3-carboxamide;

(5S)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide;

(5R)-2-(Cyclopropanecarbonylamino)-N-(cyclopropylmethyl)-5-[[(E)-N-ethyl-N'-nitro-carbamimidoyl]amino]-4,5,6,7-tetrahydrobenzothiophene-3-carboxamide;

(5S)-2-(Cyclopropanecarbonylamino)-N-(cyclopropylmethyl)-5-[2-(ethylamino)imidazol-1-yl]-4,5,6,7-tetrahydrobenzothiophene-3-carboxamide;

(5S)-2-(Cyclopropanecarbonylamino)-N-(cyclopropylmethyl)-5-[3-[(3,5-dimethylisoxazol-4-yl)amino]-1,2,4-triazol-4-yl]-4,5,6,7-tetrahydrobenzothiophene-3-carboxamide;

ethyl N-[[[2-(cyclopropanecarbonylamino)-3-(cyclopropylmethylcarbamoyl)-4,5,6,7-tetrahydrobenzothiophen-5-yl]amino]-(4-methylanilino)methylene]carbamate;

(5S)-2-(Cyclopropanecarbonylamino)-N-(cyclopropylmethyl)-5-[2-[(2-methyl-3-pyridyl)amino]imidazol-1-yl]-4,5,6,7-tetrahydrobenzothiophene-3-carboxamide;

2-(cyclopropanecarbonylamino)-N-(cyclopropylmethyl)-5-[[1-(ethylamino)-2-nitro-vinyl]amino]-4,5,6,7-tetrahydrobenzothiophene-3-carboxamide;

2-(Cyclopropanecarbonylamino)-N-(cyclopropylmethyl)-5-[[(4-methyl-6-oxo-1H-pyrimidin-2-yl)amino]-4,5,6,7-tetrahydrobenzothiophene-3-carboxamide;

5-amino-1-[(5S)-2-cyclopropaneamido-3-[(cyclopropylmethyl)carbamoyl]-4,5,6,7-tetrahydro-1-benzothiophen-5-yl]-N-methyl-1H-imidazole-4-carboxamide;

5-amino-1-[(5S)-2-cyclopropaneamido-3-[(cyclopropylmethyl)carbamoyl]-4,5,6,7-tetrahydro-1-benzothiophen-5-yl]-1H-imidazole-4-carboxamide;

5-(2-Anilinoimidazol-1-yl)-2-(cyclopropanecarbonylamino)-N-(cyclopropylmethyl)-4,5,6,7-tetrahydrobenzothiophene-3-carboxamide;

(5S)-5-[[N'-cyano-N-ethyl-carbamimidoyl]amino]-2-(cyclopropanecarbonylamino)-N-(cyclopropylmethyl)-4,5,6,7-tetrahydrobenzothiophene-3-carboxamide;

2-(Cyclopropanecarbonylamino)-N-(cyclopropylmethyl)-5-(ethylcarbamoylamino)-4,5,6,7-tetrahydrobenzothiophene-3-carboxamide;

2-(Cyclopropanecarbonylamino)-N-(cyclopropylmethyl)-5-[(4-oxo-1H-pyridin-2-yl)amino]-4,5,6,7-tetrahydrobenzothiophene-3-carboxamide;

(5S)-2-(cyclopropanecarbonylamino)-N-(cyclopropylmethyl)-5-[[6-(5-methyl-1,3,4-oxadiazol-2-yl)-3-pyridyl]amino]-4,5,6,7-tetrahydrobenzothiophene-3-carboxamide;

2-(Cyclopropanecarbonylamino)-N-(cyclopropylmethyl)-5-[5-(ethylamino)tetrazol-1-yl]-4,5,6,7-tetrahydrobenzothiophene-3-carboxamide;

2-(Cyclopropanecarbonylamino)-N-(cyclopropylmethyl)-5-(1H-1,2,4-triazol-3-ylamino)-4,5,6,7-tetrahydrobenzothiophene-3-carboxamide;

(5R)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[[4-(1-methylpyrazol-4-yl)-1,2,4-triazol-3-yl]amino]-4,5,6,7-tetrahydrobenzothiophene-3-carboxamide;

ethyl 1-[(5S)-2-cyclopropaneamido-3-[(cyclopropylmethyl)carbamoyl]-4,5,6,7-tetrahydro-1-benzothiophen-5-yl]-1H-imidazole-4-carboxylate;

2-(Cyclopropanecarbonylamino)-N-(cyclopropylmethyl)-5-[[4-(4-fluorophenyl)-1,2,4-triazol-3-yl]amino]-4,5,6,7-tetrahydrobenzothiophene-3-carboxamide;

(5S)-2-(Cyclopropanecarbonylamino)-N-(cyclopropylmethyl)-5-(1H-imidazol-2-ylamino)-4,5,6,7-tetrahydrobenzothiophene-3-carboxamide;

N-[3-(isopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide;

2-(Cyclopropanecarbonylamino)-N-(cyclopropylmethyl)-5-[[N'-methoxy-N-(p-tolyl)carbamimidoyl]amino]-4,5,6,7-tetrahydrobenzothiophene-3-carboxamide;

2-(Cyclopropanecarbonylamino)-N-(cyclopropylmethyl)-5-[[4-(4-methylanilino)-1,1-dioxo-1,2,5-thiadiazol-3-yl]amino]-4,5,6,7-tetrahydrobenzothiophene-3-carboxamide;

(5S)-2-(Cyclopropanecarbonylamino)-N-(cyclopropylmethyl)-5-[[1-(3-pyridyl)imidazol-2-yl]amino]-4,5,6,7-tetrahydrobenzothiophene-3-carboxamide;

5-(5-Aminotriazol-1-yl)-2-(cyclopropanecarbonylamino)-N-(cyclopropylmethyl)-4,5,6,7-tetrahydrobenzothiophene-3-carboxamide;

2-(Cyclopropanecarbonylamino)-N-(cyclopropylmethyl)-5-[(2-methoxyphenyl)carbamoylamino]-4,5,6,7-tetrahydrobenzothiophene-3-carboxamide;
N-[2-(Cyclopropanecarbonylamino)-3-(cyclopropylethylcarbamoyl)-4,5,6,7-tetrahydrobenzothiophen-5-yl]pyridine-4-carboxamide;
5-(Benzylamino)-2-(cyclopropanecarbonylamino)-N-(cyclopropylmethyl)-4,5,6,7-tetrahydrobenzothiophene-3-carboxamide;
5-(1H-Benzimidazol-2-ylamino)-2-(cyclopropanecarbonylamino)-N-(cyclopropylmethyl)-4,5,6,7-tetrahydrobenzothiophene-3-carboxamide;
2-(Cyclopropanecarbonylamino)-N-(cyclopropylmethyl)-5-[[N'-hydroxycarbamimidoyl]amino]-4,5,6,7-tetrahydrobenzothiophene-3-carboxamide;
2-(Cyclopropanecarbonylamino)-N-(cyclopropylmethyl)-5-[[N'-(1-methylpyrazol-3-yl)-N-(p-tolyl)carbamimidoyl]amino]-4,5,6,7-tetrahydrobenzothiophene-3-carboxamide;formic acid;
(5S)-2-(Cyclopropanecarbonylamino)-N-(cyclopropylmethyl)-5-[3-[(3,5-dimethylpyrazin-2-yl)amino]-1,2,4-triazol-4-yl]-4,5,6,7-tetrahydrobenzothiophene-3-carboxamide;
2-(Cyclopropanecarbonylamino)-N-(cyclopropylmethyl)-5-[3-(ethylamino)-5-(methoxymethyl)-1,2,4-triazol-4-yl]-4,5,6,7-tetrahydrobenzothiophene-3-carboxamide;
2-(Cyclopropanecarbonylamino)-N-(cyclopropylmethyl)-5-[[5-(3-pyridyl)-1H-1,2,4-triazol-3-yl]amino]-4,5,6,7-tetrahydrobenzothiophene-3-carboxamide;
p-Tolyl N-[2-(cyclopropanecarbonylamino)-3-(cyclopropylmethylcarbamoyl)-4,5,6,7-tetrahydrobenzothiophen-5-yl]carbamate;
2-(Cyclopropanecarbonylamino)-N-(cyclopropylmethyl)-5-(quinazolin-2-ylamino)-4,5,6,7-tetrahydrobenzothiophene-3-carboxamide;
5-(1,3-Benzoxazol-2-ylamino)-2-(cyclopropanecarbonylamino)-N-(cyclopropylmethyl)-4,5,6,7-tetrahydrobenzothiophene-3-carboxamide;
2-(Cyclopropanecarbonylamino)-N-(cyclopropylmethyl)-5-[3-(ethylamino)-5-(hydroxymethyl)-1,2,4-triazol-4-yl]-4,5,6,7-tetrahydrobenzothiophene-3-carboxamide;
2-(cyclopropanecarbonylamino)-N-(3,3-difluorocyclobutyl)-5-[3-[(2,5-dimethylpyrazol-3-yl)amino]-1,2,4-triazol-4-yl]-4,5,6,7-tetrahydrobenzothiophene-3-carboxamide;
(5S)-5-(2-Aminoimidazol-1-yl)-2-(cyclopropanecarbonylamino)-N-(cyclopropylmethyl)-4,5,6,7-tetrahydrobenzothiophene-3-carboxamide;
5-(3-Amino-5-oxo-1,2,4-oxadiazol-4-yl)-2-(cyclopropanecarbonylamino)-N-(cyclopropylmethyl)-4,5,6,7-tetrahydrobenzothiophene-3-carboxamide;
2-(Cyclopropanecarbonylamino)-N-(cyclopropylmethyl)-5-[3-(ethylamino)-5-methyl-1,2,4-triazol-4-yl]-4,5,6,7-tetrahydrobenzothiophene-3-carboxamide;
(5R)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide;
(5S)-2-(Cyclopropanecarbonylamino)-N-(cyclopropylmethyl)-5-[(2-ethyl-3,4-dioxo-cyclobuten-1-yl)amino]-4,5,6,7-tetrahydrobenzothiophene-3-carboxamide;
2-(Cyclopropanecarbonylamino)-N-(cyclopropylmethyl)-5-(pyrimidin-2-ylamino)-4,5,6,7-tetrahydrobenzothiophene-3-carboxamide;
2-(Cyclopropanecarbonylamino)-N-(cyclopropylmethyl)-5-(1,3,4-oxadiazol-2-ylamino)-4,5,6,7-tetrahydrobenzothiophene-3-carboxamide;
2-(cyclopropanecarbonylamino)-5-[3-[(2,5-dimethylpyrazol-3-yl)amino]-1,2,4-triazol-4-yl]-N-(3-fluorocyclobutyl)-4,5,6,7-tetrahydrobenzothiophene-3-carboxamide;
2-(Cyclopropanecarbonylamino)-N-(cyclopropylmethyl)-5-[5-oxo-1-((p-tolyl)-4H-imidazol-2-yl]amino]-4,5,6,7-tetrahydrobenzothiophene-3-carboxamide;
2-(Cyclopropanecarbonylamino)-N-(cyclopropylmethyl)-5-[[2-[ethyl(methyl)amino]-3,4-dioxo-cyclobuten-1-yl]amino]-4,5,6,7-tetrahydrobenzothiophene-3-carboxamide;
2-(Cyclopropanecarbonylamino)-N-(cyclopropylmethyl)-5-[(methylsulfonimidoyl)amino]-4,5,6,7-tetrahydrobenzothiophene-3-carboxamide;
5-[[N-Cyano-C-methyl-carbonimidoyl]amino]-2-(cyclopropanecarbonylamino)-N-(cyclopropylmethyl)-4,5,6,7-tetrahydrobenzothiophene-3-carboxamide;
2-(Cyclopropanecarbonylamino)-N-(cyclopropylmethyl)-5-(tetrazol-1-yl)-4,5,6,7-tetrahydrobenzothiophene-3-carboxamide;
2-(Cyclopropanecarbonylamino)-N-(cyclopropylmethyl)-5-(methanesulfinamido)-4,5,6,7-tetrahydrobenzothiophene-3-carboxamide;
2-(cyclopropanecarbonylamino)-5-[3-[(2,5-dimethylpyrazol-3-yl)amino]—1,2,4-triazol-4-yl]-N-(2-fluoro-2-methyl-propyl)-4,5,6,7-tetrahydrobenzothiophene-3-carboxamide;
2-(Cyclopropanecarbonylamino)-N-(cyclopropylmethyl)-5-morpholino-4,5,6,7-tetrahydrobenzothiophene-3-carboxamide;
2-(Cyclopropanecarbonylamino)-N-(cyclopropylmethyl)-5-[3-(ethylamino)-5-(trifluoromethyl)-1,2,4-triazol-4-yl]-4,5,6,7-tetrahydrobenzothiophene-3-carboxamide;
2-(Cyclopropanecarbonylamino)-N-(cyclopropylmethyl)-5-[(4-oxo-1H-pyrimidin-2-yl)amino]-4,5,6,7-tetrahydrobenzothiophene-3-carboxamide;
2-(Cyclopropanecarbonylamino)-N-(cyclopropylmethyl)-5-(isopropylsulfamoylamino)-4,5,6,7-tetrahydrobenzothiophene-3-carboxamide;
5-[[N'-Cyano-N-morpholino-carbamimidoyl]amino]-2-(cyclopropanecarbonylamino)-N-(cyclopropylmethyl)-4,5,6,7-tetrahydrobenzothiophene-3-carboxamide;
5-Acetamido-2-(cyclopropanecarbonylamino)-N-(cyclopropylmethyl)-4,5,6,7-tetrahydrobenzothiophene-3-carboxamide;
2-(Cyclopropanecarbonylamino)-N-(cyclopropylmethyl)-5-(methanesulfonamido)-4,5,6,7-tetrahydrobenzothiophene-3-carboxamide;
5-[[N'-Cyano-N-methoxy-carbamimidoyl]amino]-2-(cyclopropanecarbonylamino)-N-(cyclopropylmethyl)-4,5,6,7-tetrahydrobenzothiophene-3-carboxamide;
2-(Cyclopropanecarbonylamino)-N-isobutyl-5-[(4-methoxyphenyl)carbamoylamino]-4,5,6,7-tetrahydrobenzothiophene-3-carboxamide;
2-(Cyclopropanecarbonylamino)-N-(cyclopropylmethyl)-5-[[4-oxo-6-(trifluoromethyl)-1H-pyrimidin-2-yl]amino]-4,5,6,7-tetrahydrobenzothiophene-3-carboxamide;
N-[5-(Methanesulfonamido)-3-(3-methylpyrrolidine-1-carbonyl)-4,5,6,7-tetrahydrobenzothiophen-2-yl]cyclopropanecarboxamide;

2-(Cyclopropanecarbonylamino)-N-propyl-5-[[4-(trifluoromethoxy)phenyl]carbamoylamino]-4,5,6,7-tetrahydrobenzothiophene-3-carboxamide;

(5S)-2-(cyclopropanecarbonylamino)-N-(cyclopropylmethyl)-5-[3-(2-methylpropanoylamino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2,5-dimethylpyrazol-3-yl)-methylamino]-1,2,4-triazol-4-yl]-4,5,6,7-tetrahydrobenzothiophene-3-carboxamide;

N-[(5S)-3-(cyclopropylmethylsulfamoyl)-5-[3-[(2,5-dimethylpyrazol-3-yl)amino]-1,2,4-triazol-4-yl]-4,5,6,7-tetrahydrobenzothiophen-2-yl]cyclopropanecarboxamide;

(5S)-5-[5-amino-4-(5-methyl-1,3,4-oxadiazol-2-yl)imidazol-1-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(3-methyl-1H-pyrazol-5-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(1,3-dimethylpyrazol-4-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-isopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-isopropyl-5-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-methyl-2-tetrahydrofuran-3-yl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methylpyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-ethyl-5-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-cyclopropyl-5-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methoxy-1-methyl-pyrazol-4-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[(1,4-dimethylpyrazol-3-yl)amino]-1,2,4-triazol-4-yl]-4,5,6,7-tetrahydrobenzothiophene-3-carboxamide;

Methyl 5-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylate;

(5S)-2-(Cyclopropanecarbonylamino)-N-(cyclopropylmethyl)-5-[2-[[2-methyl-5-(trifluoromethyl)pyrazol-3-yl]amino]imidazol-1-yl]-4,5,6,7-tetrahydrobenzothiophene-3-carboxamide;

5-[[4-[(5S)-2-(Cyclopropanecarbonylamino)-3-(cyclopropylmethylcarbamoyl)-4,5,6,7-tetrahydrobenzothiophen-5-yl]-1,2,4-triazol-3-yl]amino]-1-methyl-pyrazole-3-carboxylic acid; or an enantiomer or a pharmaceutically acceptable salt thereof.

12. A compound according to claim 1 or a pharmaceutically acceptable salt thereof, wherein the compound is selected from:

(5S)-2-(cyclopropanecarbonylamino)-N-(cyclopropylmethyl)-5-[3-[[(3S*)-1,1-dioxothiolan-3-yl]amino]-1,2,4-triazol-4-yl]-4,5,6,7-tetrahydrobenzothiophene-3-carboxamide [*or R];

(5S)-2-cyclopropaneamido-N-(cyclopropylmethyl)-5-[3-({3-[imino(methyl)oxo-lambda6-sulfanyl]-2-methylphenyl}amino)-4H-1,2,4-triazol-4-yl]-4,5,6,7-tetrahydro-1-benzothiophene-3-carboxamide;

(5S)-2-(cyclopropanecarbonylamino)-N-(cyclopropylmethyl)-5-[3-[2-methyl-3-[(S)-methylsulfonimidoyl]anilino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[2-methyl-3-[(R)-methylsulfonimidoyl]anilino]-1,2,4-triazol-4-yl]-4,5,6,7-tetrahydrobenzothiophene-3-carboxamide;

(5S)-5-{3-[(1-acetyl-3-methylpyrrolidin-3-yl)amino]-4H-1,2,4-triazol-4-yl}-2-cyclopropaneamido-N-(cyclopropylmethyl)-4,5,6,7-tetrahydro-1-benzothiophene-3-carboxamide;

(5S)-5-[3-[[(3S*)-1-acetyl-3-methyl-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R];

(5S)-2-cyclopropaneamido-N-(cyclopropylmethyl)-5-(3-{[(3 S)-1-(6-methylpyridazin-3-yl)pyrrolidin-3-yl]amino}-4H-1,2,4-triazol-4-yl)-4,5,6,7-tetrahydro-1-benzothiophene-3-carboxamide;

(5S)-2-(cyclopropanecarbonylamino)-N-(cyclopropylmethyl)-5-[3-[[(3S)-1-pyrazin-2-ylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(4-methyl-1-methylsulfonyl-pyrrolidin-3-yl)amino]-1,2,4-triazol-4-yl]-4,5,6,7-tetrahydrobenzothiophene-3-carboxamide;

(5S)-2-cyclopropaneamido-N-(cyclopropylmethyl)-5-{3-[(1-oxo-2,3-dihydro-1H-isoindol-4-yl)amino]-4H-1,2,4-triazol-4-yl}-4,5,6,7-tetrahydro-1-benzothiophene-3-carboxamide;

(5S)-2-(cyclopropanecarbonylamino)-N-(cyclopropylmethyl)-5-[3-[[(3S)-1-(6-fluoropyridazin-3-yl)pyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[(3S)-1-pyrimidin-2-ylpyrrolidin-3-yl]amino]-1,2,4-triazol-4-yl]-4,5,6,7-tetrahydro-1-benzothiophene-3-carboxamide;

2-methoxyethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate;

2-morpholin-4-ylethyl 5-amino-1-[(5S)-2-(cyclopropanecarbonylamino)-3-(cyclopropylmethylcarbamoyl)-4,5,6,7-tetrahydro-1-benzothiophen-5-yl]imidazole-4-carboxylate;

(5S)-2-(cyclopropanecarbonylamino)-N-(cyclopropylmethyl)-5-[3-(3-methylsulfanylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(3-methylsulfonylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(3-methylsulfinylanilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[3-(methylsulfonimidoyl)anilino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[3-[(S)-methylsulfonimidoyl]anilino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[3-[(R)-methylsulfonimidoyl]anilino]-1,2,4-triazol-4-yl]-4,5,6,7-tetrahydrobenzothiophene-3-carboxamide;

(5S)—N-(cyclopropylmethyl)-5-[3-[(6-methylsulfinyl-2-pyridyl)amino]-1,2,4-triazol-4-yl]-2-(spiro[2.2]pentane-2-carbonylamino)-4,5,6,7-tetrahydrobenzothiophene-3-carboxamide;

(5S)—N-(cyclopropylmethyl)-5-[3-[(6-methylsulfonyl-2-pyridyl)amino]-1,2,4-triazol-4-yl]-2-[[(2S*)-spiro[2.2]pentane-2-carbonyl]amino]-4,5,6,7-tetrahydrobenzothiophene-3-carboxamide;

(5S)-2-(cyclopropanecarbonylamino)-N-(cyclopropylmethyl)-5-(8-methoxy-4-oxo-5,10-dihydroimidazo[4,5-c][1,5]benzodiazepin-1-yl)-4,5,6,7-tetrahydrobenzothiophene-3-carboxamide;

(5S)-2-(cyclopropanecarbonylamino)-N-(cyclopropylmethyl)-5-(8-methoxy-5-methyl-4-oxo-10H-imidazo[4,5-c][1,5]benzodiazepin-1-yl)-4,5,6,7-tetrahydrobenzothiophene-3-carboxamide;

(5S)-5-[5-amino-4-[(2S)-2-methylpyrrolidine-1-carbonyl]imidazol-1-yl]-N-(cyclopropylmethyl)-2-[[(1R*,2R*)-2-fluorocyclopropanecarbonyl]amino]-4,5,6,7-tetrahydrobenzothiophene-3-carboxamide [* or 1S,2S];

(5S)-5-[5-amino-4-[(3R)-3-hydroxypyrrolidine-1-carbonyl]imidazol-1-yl]-2-(cyclopropanecarbonylamino)-N-(cyclopropylmethyl)-4,5,6,7-tetrahydrobenzothiophene-3-carboxamide;

(5S)-5-[5-amino-4-[(2S)-2-methylpyrrolidine-1-carbonyl]imidazol-1-yl]-2-(cyclopropanecarbonylamino)-N-(cyclopropylmethyl)-4,5,6,7-tetrahydrobenzothiophene-3-carboxamide;

Ethyl 1-[(5S)-2-(cyclopropanecarbonylamino)-3-(cyclopropylmethylcarbamoyl)-4,5,6,7-tetrahydrobenzothiophen-5-yl]-5-[(2,5-dimethyl-4-nitro-pyrazol-3-yl)amino]imidazole-4-carboxylate;

(5S)-2-(cyclopropanecarbonylamino)-N-(cyclopropylmethyl)-5-[3-(2-methyl-3-methylsulfinyl-anilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-(2-methyl-3-methylsulfonyl-anilino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methyl-5-oxazol-2-yl-pyrazol-3-yl)amino]-1,2,4-triazol-4-yl]-4,5,6,7-tetrahydrobenzothiophene-3-carboxamide;

(5S)-5-[3-[[(3S)-1-acetylpyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[[(3S)-1-methylsulfonylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[(3R)-1-methylsulfonylpyrrolidin-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methylcyclohexyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-oxopyrrolidin-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[(3R*)-5-oxopyrrolidin-3-yl]amino]-1,2,4-triazol-4-yl]-4,5,6,7-tetrahydrobenzothiophene-3-carboxamide (*or S);

5S)-2-(cyclopropanecarbonylamino)-N-(cyclopropylmethyl)-5-[3-[(2-oxo-4-piperidyl)amino]-1,2,4-triazol-4-yl]-4,5,6,7-tetrahydrobenzothiophene-3-carboxamide;

(5S)-5-[3-[(1-acetyl-2-methyl-pyrrolidin-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(2-methyl-1-methylsulfonyl-pyrrolidin-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamide (5S)-2-(cyclopropanecarbonylamino)-N-(cyclopropylmethyl)-5-[3-[[3-(6-methyl-3-pyridyl)cyclobutyl]amino]-1,2,4-triazol-4-yl]-4,5,6,7-tetrahydrobenzothiophene-3-carboxamide;

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [*or S];

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-(trans-3-fluorocyclobutyl)-4,5,6,7-tetrahydrobenzothiophene-3-carboxamide (* or S);

(5S)-2-[[(1R*)-2,2-difluorocyclopropanecarbonyl]amino]-5-[3-[[5-(difluoromethoxy)-2-methyl-pyrazol-3-yl]amino]-1,2,4-triazol-4-yl]-N-[trans-(3-fluorocyclobutyl)methyl]-4,5,6,7-tetrahydrobenzothiophene-3-carboxamide [* or S];

(5S)-2-[[(1S*)-2,2-difluorocyclopropanecarbonyl]amino]-5-[3-[[5-(difluoromethoxy)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R];

(5S)-2-[(2,2-difluorocyclopropanecarbonyl)amino]-N-[(2,2-difluorocyclopropyl)methyl]-5-[3-[[5-(difluoromethyl)-2-methyl-pyrazol-3-yl]amino]-1,2,4-triazol-4-yl]-4,5,6,7-tetrahydrobenzothiophene-3-carboxamide;

(5S)-2-[[(1S*)-2,2-difluorocyclopropanecarbonyl]amino]-5-[3-[[5-(difluoromethyl)-2-methyl-pyrazol-3-yl]amino]-1,2,4-triazol-4-yl]-N-[[(1S,2S)-2-fluorocyclopropyl]methyl]-4,5,6,7-tetrahydrobenzothiophene-3-carboxamide [* or R];

(5S)-5-[3-[[(3S*)-1-benzoyl-4,4-difluoro-pyrrolidin-3-yl]amino]-1,2,4-triazol-4-yl]-2-(cyclopropanecarbonylamino)-N-(cyclopropylmethyl)-4,5,6,7-tetrahydrobenzothiophene-3-carboxamide [* or R];

(5S)-5-[3-[(1-acetyl-4-piperidyl)amino]-1,2,4-triazol-4-yl]-2-(cyclopropanecarbonylamino)-N-(cyclopropylmethyl)-4,5,6,7-tetrahydrobenzothiophene-3-carboxamide;

Methyl (3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]pyrrolidine-1-carboxylate;

(3S)-3-[[4-[(5S)-2-(cyclopropanecarbonylamino)-3-(cyclopropylmethylcarbamoyl)-4,5,6,7-tetrahydrobenzothiophen-5-yl]-1,2,4-triazol-3-yl]amino]-N-ethyl-pyrrolidine-1-carboxamide;

(5S)-2-cyclopropaneamido-N-(cyclopropylmethyl)-5-(3-{[2-(pyrimidin-2-yl)-2-azaspiro[4.4]nonan-7-yl]amino}-4H-1,2,4-triazol-4-yl)-4,5,6,7-tetrahydro-1-benzothiophene-3-carboxamide;

(5S)—N-(cyclopropylmethyl)-2-[[(1R,2R)-2-fluorocyclopropanecarbonyl]amino]-5-[3-[[2-methyl-5-(trifluoromethoxy)pyrazol-3-yl]amino]-1,2,4-triazol-4-yl]-4,5,6,7-tetrahydrobenzothiophene-3-carboxamide;

(5S)-5-[3-[[5-[chloro(difluoro)methoxy]-2-methyl-pyrazol-3-yl]amino]-1,2,4-triazol-4-yl]-N-(cyclopropylmethyl)-2-[[(1R,2R)-2-fluorocyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethoxy)pyrazol-3-yl]amino]-1,2,4-triazol-4-yl]-4,5,6,7-tetrahydrobenzothiophene-3-carboxamide;

(5S)-5-[3-[[5-[chloro(difluoro)methoxy]-2-methyl-pyrazol-3-yl]amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-cyclopropaneamido-N-(cyclopropylmethyl)-5-(3-{[1-methyl-3-(5-methyl-1,3,4-oxadiazol-2-yl)-1H-pyrazol-5-yl]amino}-4H-1,2,4-triazol-4-yl)-4,5,6,7-tetrahydro-1-benzothiophene-3-carboxamide;

(5S)-2-(cyclopropanecarbonylamino)-N-(cyclopropylmethyl)-5-[3-[(5-methoxy-3-methyl-pyrazin-2-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[(5-methylthiazolo[5,4-b]pyridin-2-yl)amino]-4,5,6,7-tetrahydrobenzothiophene-3-carboxamide;

(5S)-5-[3-[(5-cyano-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-5-[3-[(6-cyano-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(1-methyl-2-oxo-4-pyridyl)amino]-1,2,4-triazol-4-yl]-4,5,6,7-tetrahydrobenzothiophene-3-carboxamide;

(5S)-5-[3-[(6-chloro-2-methyl-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[[2-methyl-6-(trifluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methylpyridazin-4-yl)amino]-1,2,4-triazol-4-yl]-4,5,6,7-tetrahydrobenzothiophene-3-carboxamide;

(5S)-5-[3-[(5-chloro-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1S,2R)-2-methylcyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[(3-methylisothiazol-4-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methylisoxazol-4-yl)amino]-1,2,4-triazol-4-yl]-4,5,6,7-tetrahydrobenzothiophene-3-carboxamide;

(5S)-5-[3-[[5-(cyclopropylmethoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide;

(5S)—N-(cyclopropylmethyl)-5-[3-[(5-ethoxy-2-methyl-pyrazol-3-yl)amino]-1,2,4-triazol-4-yl]-2-[[(1R,2S)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(2R*)-spiro[2.2]pentane-2-carbonyl]amino]-4,5,6,7-tetrahydrobenzothiophene-3-carboxamide [* or S];

(5S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide;

N-[(5S)-3-(cyclopropylmethylsulfamoyl)-5-[3-[(2,5-dimethylpyrazol-3-yl)amino]-1,2,4-triazol-4-yl]-4,5,6,7-tetrahydro-1-benzothiophen-2-yl]cyclopropanecarboxamide;

ethyl 5-amino-1-[(5S*)-2-(cyclopropanecarbonylamino)-3-(cyclopropylmethylsulfamoyl)-4,5,6,7-tetrahydrobenzothiophen-5-yl]imidazole-4-carboxylate (* or R);

N-[(5S*)-3-(cyclopropylmethylsulfamoyl)-5-[3-[[5-(difluoromethoxy)-2-methyl-pyrazol-3-yl]amino]-1,2,4-triazol-4-yl]-4,5,6,7-tetrahydrobenzothiophen-2-yl]cyclopropanecarboxamide (* or R);

N-[(5S*)-3-(cyclopropylmethylsulfamoyl)-5-[3-[(2-methylpyrazol-3-yl)amino]-1,2,4-triazol-4-yl]-4,5,6,7-tetrahydrobenzothiophen-2-yl]cyclopropanecarboxamide (* or R);

(1R,2S)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluoro-cyclopropanecarboxamide;

(1R,2S)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2-fluoro-cyclopropanecarboxamide;

(1S*)—N-[(5S)-5-[3-[[5-(difluoromethoxy)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R];

(1S*)—N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]-2,2-difluoro-cyclopropanecarboxamide [* or R];

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1S,2S)-2-fluorocyclopropyl]methyl]-4,5,6,7-tetrahydro-1-benzothiophene-3-carboxamide;

N-[(5S)-5-[3-[[5-(difluoromethyl)-2-methyl-pyrazol-3-yl]amino]-1,2,4-triazol-4-yl]-3-[cis-(3-fluorocyclobutyl)sulfamoyl]-4,5,6,7-tetrahydrobenzothiophen-2-yl]cyclopropanecarboxamide;

N-[(5S)-5-[3-[[5-(difluoromethyl)-2-methyl-pyrazol-3-yl]amino]-1,2,4-triazol-4-yl]-3-[trans-(3-fluorocyclobutyl)sulfamoyl]-4,5,6,7-tetrahydrobenzothiophen-2-yl]cyclopropanecarboxamide;

(1R,2S)—N-[(5S)-3-[(3,3-difluorocyclobutyl)sulfamoyl]-5-[3-[[5-(difluoromethoxy)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R,2S)—N-[(5S)-3-[(3,3-difluorocyclobutyl)sulfamoyl]-5-[3-[[5-(difluoromethyl)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R*)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S);

(1R*)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2,2-difluorocyclopropane-1-carboxamide (* or S);

(5S)—N-(cyclopropylmethyl)-5-[3-[(3-methyl-1,2-thiazol-4-yl)amino]-1,2,4-triazol-4-yl]-2-(spiro[2.2]pentane-2-carbonylamino)-4,5,6,7-tetrahydro-1-benzothiophene-3-carboxamide;

N-[(5S)-3-[(3,3-difluorocyclobutyl)sulfamoyl]-5-[3-[(2,5-dimethylpyrazol-3-yl)amino]-1,2,4-triazol-4-yl]-4,5,6,7-tetrahydro-1-benzothiophen-2-yl]cyclopropanecarboxamide;

N-[(5S)-5-[3-[[5-(difluoromethoxy)-2-methylpyrazol-3-yl]amino]-1,2,4-triazol-4-yl]-3-[cis-(3-fluorocyclobutyl)sulfamoyl]-4,5,6,7-tetrahydro-1-benzothiophen-2-yl]cyclopropanecarboxamide;

N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]cyclopropanecarboxamide;

N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]cyclopropanecarboxamide;

(1R,2S)—N-[(5S)-3-(cyclopropylmethylsulfamoyl)-5-[3-[[5-(difluoromethyl)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R,2S)—N-[(5S)-3-(cyclopropylmethylsulfamoyl)-5-[3-[[5-(difluoromethoxy)-2-methylpyrazol-3-yl]amino]-1,2,4-triazol-4-yl]-4,5,6,7-tetrahydro-1-benzothiophen-2-yl]-2-fluorocyclopropane-1-carboxamide;

(1R,2S)—N-[(5S)-3-(cyclopropylmethylsulfamoyl)-5-[3-[(5-methoxy-2-methylpyrazol-3-yl)amino]-1,2,4-triazol-4-yl]-4,5,6,7-tetrahydro-1-benzothiophen-2-yl]-2-fluorocyclopropane-1-carboxamide;

(5S)-2-(cyclopropanecarbonylamino)-N-(cyclopropylmethyl)-5-[3-[(5-methoxy-2-methylpyrazol-3-yl)amino]-1,2,4-triazol-4-yl]-4,5,6,7-tetrahydro-1-benzothiophene-3-carboxamide;

N-[(5S)-3-(cyclopropylmethylsulfamoyl)-5-[3-[[5-(difluoromethyl)-2-methylpyrazol-3-yl]amino]-1,2,4-triazol-4-yl]-4,5,6,7-tetrahydro-1-benzothiophen-2-yl]cyclopropanecarboxamide;

(1R,2S)—N-[(5S)-5-[3-[[5-(difluoromethyl)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide;

(1R,2S)—N-[(5S)-5-[3-[[5-(difluoromethoxy)-2-methylpyrazol-3-yl]amino]-1,2,4-triazol-4-yl]-3-[trans-(3-fluorocyclobutyl)sulfamoyl]-4,5,6,7-tetrahydro-1-benzothiophen-2-yl]-2-fluorocyclopropane-1-carboxamide;

(1R*)—N-[(5S)-3-[(3,3-difluorocyclobutyl)sulfamoyl]-5-[3-[(5-methoxy-2-methylpyrazol-3-yl)amino]-1,2,4-triazol-4-yl]-4,5,6,7-tetrahydro-1-benzothiophen-2-yl]-2,2-difluorocyclopropane-1-carboxamide (* or S);

N-[(5S)-3-(cyclopropylmethylsulfamoyl)-5-[3-[[2-methyl-5-(trifluoromethyl)pyrazol-3-yl]amino]-1,2,4-triazol-4-yl]-4,5,6,7-tetrahydro-1-benzothiophen-2-yl]cyclopropanecarboxamide;

(5S)—N-(cyclopropylmethyl)-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)—N-(cyclopropylmethyl)-2-[(2,2-difluorocyclopropanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-2-[[(1R*)-2,2-difluorocyclopropanecarbonyl]amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide (* or S);

(5S)—N-(cyclopropylmethyl)-2-[(3,3-difluorocyclobutanecarbonyl)amino]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[cis-(3-fluorocyclobutanecarbonyl)amino]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethoxy)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide;

(5S)-2-(cyclopropanecarbonylamino)-N-(cyclopropylmethyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethoxy)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[(3-fluorocyclobutanecarbonyl)amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)—N-(cyclopropylmethyl)-2-[[(1RS,2RS)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

N-[(5S)-3-(cyclopropylmethylcarbamoyl)-5-[3-[[5-(difluoromethyl)-2-methylpyrazol-3-yl]amino]-1,2,4-triazol-4-yl]-4,5,6,7-tetrahydro-1-benzothiophen-2-yl]oxetane-3-carboxamide;

(5S)—N-(cyclopropylmethyl)-2-[(3,3-difluorocyclobutanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-(3,3-difluoropropanoylamino)-4,5,6,7-tetrahydro-1-benzothiophene-3-carboxamide;

(5S)-2-(cyclobutanecarbonylamino)-N-(cyclopropylmethyl)-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-(2-methylpropanoylamino)-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[[(1RS,2RS)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(1S,2S)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(1R,2R)-2-fluorocyclopropanecarbonyl]amino]-4,5,6,7-tetrahydrobenzothiophene-3-carboxamide;

(5S)—N-(cyclopropylmethyl)-2-[(2,2-difluorocyclopropanecarbonyl)amino]-5-[3-[[5-(difluoromethyl)-2-methylpyrazol-3-yl]amino]-1,2,4-triazol-4-yl]-4,5,6,7-tetrahydro-1-benzothiophene-3-carboxamide (5S)—N-(cyclopropylmethyl)-2-[[(1R*)-2,2-difluorocyclopropanecarbonyl]amino]-5-[3-[[5-(difluoromethyl)-2-methylpyrazol-3-yl]amino]-1,2,4-triazol-4-yl]-4,5,6,7-tetrahydro-1-benzothiophene-3-carboxamide (* or S);

(5S)—N-(cyclopropylmethyl)-5-[3-[[5-(difluoromethyl)-2-methylpyrazol-3-yl]amino]-1,2,4-triazol-4-yl]-2-[[(1RS,2SR)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[[(1S,2R)-2-fluorocyclopropanecarbonyl]amino]-4,5,6,7-tetrahydro-1-benzothiophene-3-carboxamide;

(5S)—N-(cyclopropylmethyl)-5-[3-[[5-(difluoromethyl)-2-methyl-pyrazol-3-yl]amino]-1,2,4-triazol-4-yl]-2-[[(1R,2S)-2-fluorocyclopropanecarbonyl]amino]-4,5,6,7-tetrahydrobenzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[(2-methylcyclopropanecarbonyl)amino]-4,5,6,7-tetrahydro-1-benzothiophene-3-carboxamide;

(5S)—N-(cyclopropylmethyl)-5-[3-[[5-(difluoromethyl)-2-methylpyrazol-3-yl]amino]-1,2,4-triazol-4-yl]-2-[[(1R*,2R*)-2-methylcyclopropanecarbonyl]amino]-4,5,6,7-tetrahydro-1-benzothiophene-3-carboxamide (* or S);

(5S)—N-(cyclopropylmethyl)-5-[3-[[5-(difluoromethyl)-2-methylpyrazol-3-yl]amino]-1,2,4-triazol-4-yl]-2-[[(1R*,2S*)-2-methylcyclopropanecarbonyl]amino]-4,5,6,7-tetrahydro-1-benzothiophene-3-carboxamide (*1R,2S or 1S,2R);

(5S)-2-(cyclopropanecarbonylamino)-5-[3-[[5-(difluoromethyl)-2-methylpyrazol-3-yl]amino]-1,2,4-triazol-4-yl]-N-[[(1R*)-2,2-dimethylcyclopropyl]methyl]-4,5,6,7-tetrahydro-1-benzothiophene-3-carboxamide (* or S);

(5S)-2-(cyclopropanecarbonylamino)-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)—N-[[(1R)-2,2-difluorocyclopropyl]methyl]-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-4,5,6,7-tetrahydro-1-benzothiophene-3-carboxamide;

(5S)—N-[[(1S)-2,2-difluorocyclopropyl]methyl]-5-[3-[[5-(difluoromethoxy)-2-methylpyrazol-3-yl]amino]-

1,2,4-triazol-4-yl]-2-[[(1R,2S)-2-fluorocyclopropanecarbonyl]amino]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[[(1R,2S)-2-fluorocyclopropanecarbonyl]amino]-N-[(2R*)-spiro[2.2]pentan-2-yl]-4,5,6,7-tetrahydro-1-benzothiophene-3-carboxamide (* or S);

(5S)-5-[3-[[5-(difluoromethoxy)-2-methylpyrazol-3-yl]amino]-1,2,4-triazol-4-yl]-N-[cis-(3-fluorocyclobutyl)methyl]-2-[[(1R,2S)-2-fluorocyclopropanecarbonyl]amino]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-N-[trans-(3-fluorocyclobutyl)methyl]-2-[[(1R,2S)-2-fluorocyclopropanecarbonyl]amino]-4,5,6,7-tetrahydro-1-benzothiophene-3-carboxamide;

(5S)-5-[33-[[5-(difluoromethoxy)-2-methylpyrazol-3-yl]amino]-1,2,4-triazol-4-yl]-N-(trans-3-fluorocyclobutyl)-2-[[(1R,2S)-2-fluorocyclopropanecarbonyl]amino]-4,5,6,7-tetrahydro-1-benzothiophene-3-carboxamide;

(5S)-5-[33-[[5-(difluoromethoxy)-2-methylpyrazol-3-yl]amino]-1,2,4-triazol-4-yl]-2-[[(1R,2S)-2-fluorocyclopropanecarbonyl]amino]-N-[[(1R,2R)-2-fluorocyclopropyl]methyl]-4,5,6,7-tetrahydro-1-benzothiophene-3-carboxamide;

(5S)-2-(cyclopropanecarbonylamino)-N-[(2,2-difluorocyclopropyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[[(1R)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[[(1S)-2,2-difluorocyclopropyl]methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethyl)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide;

(5S)-2-(cyclopropanecarbonylamino)-5-[3-[[5-(difluoromethyl)-2-methylpyrazol-3-yl]amino]-1,2,4-triazol-4-yl]-N-[[(2R)-spiro[2.2]pentan-2-yl]methyl]-4,5,6,7-tetrahydro-1-benzothiophene-3-carboxamide;

(5S)-2-(cyclopropanecarbonylamino)-5-[3-[[5-(difluoromethyl)-2-methylpyrazol-3-yl]amino]-1,2,4-triazol-4-yl]-N-[[(2S)-spiro[2.2]pentan-2-yl]methyl]-4,5,6,7-tetrahydro-1-benzothiophene-3-carboxamide;

(5S)-2-(cyclopropanecarbonylamino)-N-(3,3-difluorocyclobutyl)-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethyl)-2-methylpyrazol-3-yl]amino]-1,2,4-triazol-4-yl]-N-(cis-3-fluorocyclobutyl)-4,5,6,7-tetrahydro-1-benzothiophene-3-carboxamide;

(5S)-2-(cyclopropanecarbonylamino)-N-[(3,3-difluorocyclobutyl)methyl]-5-[3-[[5-(difluoromethyl)-2-methylpyrazol-3-yl]amino]-1,2,4-triazol-4-yl]-4,5,6,7-tetrahydro-1-benzothiophene-3-carboxamide;

(5S)-2-[[(1R,2R)-2-fluorocyclopropanecarbonyl]amino]-N-[[(1RS,2RS)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (cis);

(5S)-2-[[(1R,2R)-2-fluorocyclopropanecarbonyl]amino]-N-[[(1RS,2SR)-2-methylcyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide (trans);

5S)-2-[[(1R,2R)-2-fluorocyclopropanecarbonyl]amino]-N-[[(1S,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-N-[(2R)-spiro[2.2]pentan-2-yl]-4,5,6,7-tetrahydro-1-benzothiophene-3-carboxamide;

5S)-2-[[(1R,2R)-2-fluorocyclopropanecarbonyl]amino]-N-[[(1R,2S)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-[(2,2-difluorocyclopropyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-[[(1R)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-[[(1S)-2,2-difluorocyclopropyl]methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)-2-[[(1R,2R)-2-fluorocyclopropanecarbonyl]amino]-N-[[(1R,2R)-2-fluorocyclopropyl]methyl]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-[trans-(3-fluorocyclobutyl)methyl]-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-(cyclopropylmethyl)-2-[[(1S,2S)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)—N-(trans-3-fluorocyclobutyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydro-1-benzothiophene-3-carboxamide;

(5S)-2-(cyclopropanecarbonylamino)-N-(cyclopropylmethyl)-5-[3-[[5-(difluoromethyl)-2-(trideuteriomethyl)pyrazol-3-yl]amino]-1,2,4-triazol-4-yl]-4,5,6,7-tetrahydrobenzothiophene-3-carboxamide;

(5S)-5-[3-[[5-(Difluoromethyl)-2-methylpyrazol-3-yl]amino]-1,2,4-triazol-4-yl]-N-[trans-(3-fluorocyclobutyl)methyl]-2-[[(2S)-spiro[2.2]pentane-2-carbonyl]amino]-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-(trans-3-fluorocyclobutyl)-2-[[(2S)-spiro[2.2]pentane-2-carbonyl]amino]-4,5,6,7-tetrahydro-1-benzothiophene-3-carboxamide;

(5S)—N-(3,3-Difluorocyclobutyl)-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[(3,3-Difluorocyclobutyl)methyl]-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[(2,2-Difluorocyclopropyl)methyl]-5-[3-[[5-(difluoromethyl)-2-methylpyrazol-3-yl]amino]-1,2,4-triazol-4-yl]-2-[[(2S)-spiro[2.2]pentane-2-carbonyl]amino]-4,5,6,7-tetrahydro-1-benzothiophene-3-carboxamide;

(5S)—N-[[(1S)-2,2-Difluorocyclopropyl]methyl]-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide;

(5S)—N-[[(1R)-2,2-difluorocyclopropyl]methyl]-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide;

(5S)-5-[3-[[5-(Difluoromethyl)-2-methylpyrazol-3-yl]amino]-1,2,4-triazol-4-yl]-2-[[(2S)-spiro[2.2]pentane-2-carbonyl]amino]-N-spiro[2.2]pentan-2-yl-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-[[(1R,2R)-2-fluorocyclopropyl]methyl]-2-[[(2S)-spiro[2.2]pentane-2-carbonyl]amino]-4,5,6,7-tetrahydro-1-benzothiophene-3-carboxamide;

(5S)-5-[3-[[5-(Difluoromethyl)-2-methylpyrazol-3-yl]amino]-1,2,4-triazol-4-yl]-N-[[(1R,2S)-2-fluorocyclopropyl]methyl]-2-[[(2S)-spiro[2.2]pentane-2-carbonyl]amino]-4,5,6,7-tetrahydro-1-benzothiophene-3-carboxamide;

(5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2S)-spiro[2.2]pentan-2-yl]-4,5,6,7-tetrahydrobenzothiophene-3-carboxamide;

(5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-N-[(2R)-spiro[2.2]pentan-2-yl]-4,5,6,7-tetrahydrobenzothiophene-3-carboxamide;

(5S)—N-(Cyclopropylmethyl)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxamide;

Ethyl (5S)-5-[3-[[5-(difluoromethyl)-2-methyl-pyrazol-3-yl]amino]-1,2,4-triazol-4-yl]-2-(spiro[2.2]pentane-2-carbonylamino)-4,5,6,7-tetrahydrobenzothiophene-3-carboxylate;

Ethyl (5S)-5-[3-[[5-(difluoromethyl)-2-methyl-pyrazol-3-yl]amino]-1,2,4-triazol-4-yl]-2-[[(2S)-spiro[2.2]pentane-2-carbonyl]amino]-4,5,6,7-tetrahydrobenzothiophene-3-carboxylate;

(5S)-5-[13-[(5-Cyano-2-methyl-pyrazol-3-yl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(Cyclopropanecarbonylamino)-N-(cyclopropylmethyl)-5-[3-[(2,2-difluoro-1,3-benzodioxol-5-yl)amino]-1,2,4-triazol-4-yl]-4,5,6,7-tetrahydrobenzothiophene-3-carboxamide;

(5S)-5-[3-[[5-(Difluoromethyl)-2-methyl-pyrazol-3-yl]amino]-1,2,4-triazol-4-yl]-N-[[(1S,2S)-2-fluorocyclopropyl]methyl]-2-[[(2S)-spiro[2.2]pentane-2-carbonyl]amino]-4,5,6,7-tetrahydrobenzothiophene-3-carboxamide;

(4RS,5RS)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide;

(4R*,5R*)-2-(cyclopropanecarbonylamino)-N-(cyclopropylmethyl)-4-methyl-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[6-(difluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(6-fluoro-2-methyl-3-pyridyl)amino]-1,2,4-triazol-4-yl]-4,5,6,7-tetrahydrobenzothiophene-3-carboxamide;

(5S)-5-[3-[[5-(cyclopropoxy)-2-methyl-pyrazol-3-yl]amino]-1,2,4-triazol-4-yl]-N-(cyclopropylmethyl)-2-[[(1R,2S)-2-fluorocyclopropanecarbonyl]amino]-4,5,6,7-tetrahydrobenzothiophene-3-carboxamide;

(5S)—N-(cyclopropylmethyl)-2-[[(1R,2S)-2-fluorocyclopropanecarbonyl]amino]-5-[3-[[2-methyl-5-(2,2,2-trifluoroethoxy)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[6-(trifluoromethyl)-3-pyridyl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(6-methoxy-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methoxy-4-pyridyl)amino]-1,2,4-triazol-4-yl]-4,5,6,7-tetrahydrobenzothiophene-3-carboxamide;

(5S)-5-[3-[(6-chloro-3-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-5-[3-[(2-chloro-4-pyridyl)amino]-1,2,4-triazol-4-yl]-2-(cyclopropanecarbonylamino)-N-(cyclopropylmethyl)-4,5,6,7-tetrahydrobenzothiophene-3-carboxamide;

(5S)-2-(cyclopropanecarbonylamino)-N-(cyclopropylmethyl)-5-[3-[(6-methoxy-2-methyl-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-fluoro-3-pyridyl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(3-methyltriazol-4-yl)amino]-1,2,4-triazol-4-yl]-4,5,6,7-tetrahydrobenzothiophene-3-carboxamide;

(5S)-5-[3-[[5-(difluoromethyl)-2-methylpyrazol-3-yl]amino]-1,2,4-triazol-4-yl]-N-[[(1S,2S)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[[(1R,2S)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[trans-(3-fluorocyclobutyl)methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-(trans-3-fluorocyclobutyl)-2-[[(1S,2S)-2-methylcyclopropanecarbonyl]amino]-4,5,6,7-tetrahydro-1-benzothiophene-3-carboxamide;

(5S)—N-(3,3-difluorocyclobutyl)-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[(3,3-difluorocyclobutyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[(2,2-difluorocyclopropyl)methyl]-5-[3-[[5-(difluoromethyl)-2-methylpyrazol-3-yl]amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[cis-(3-fluorocyclobutyl)methyl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-N-[[(1R,2R)-2-fluorocyclopropyl]methyl]-2-[[(1S,2S)-2-methylcyclopropanecarbonyl]amino]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(spiro[2.2]pentan-2-ylmethyl)-4,5,6,7-tetrahydro-1-benzothiophene-3-carboxamide;

(5S)—N-(cyclobutylmethyl)-2-(cyclopropanecarbonylamino)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[(3,3-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(cis-3-fluorocyclobutyl)-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(3-methylcyclobutyl)-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-2-(cyclopropanecarbonylamino)-N-(3,3-difluorocyclobutyl)-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[(2,2-difluorocyclobutyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-spiro[2.2]pentan-2-yl-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[(2-methylcyclopropyl)methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[[(1RS,2RS)-2-fluorocyclopropyl]methyl]-4,5,6,7-tetrahydro-1-benzothiophene-3-carboxamide;

(5S)—N-(cyclopropylmethyl)-5-[3-[(5-methoxy-2-methyl-pyrazol-3-yl)amino]-1,2,4-triazol-4-yl]-2-[[(2R*)-spiro [2.2]pentane-2-carbonyl]amino]-4,5,6,7-tetrahydrobenzothiophene-3-carboxamide (* or S);

(5S)-2-(cyclopropanecarbonylamino)-5-[3-[[5-(difluoromethoxy)-2-methylpyrazol-3-yl]amino]-1,2,4-triazol-4-yl]-N-[trans-(3-fluorocyclobutyl)methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[(2-fluorocyclobutyl)methyl]-4,5,6,7-tetrahydro-1-benzothiophene-3-carboxamide;

(5S)-2-(cyclopropanecarbonylamino)-N-[(2,2-difluorocyclopropyl)methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-N-[[(1R)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide; &

(5S)-2-(cyclopropanecarbonylamino)-N-[[(1S)-2,2-difluorocyclopropyl]methyl]-5-[3-[[5-(difluoromethoxy)-2-methylpyrazol-3-yl]amino]-1,2,4-triazol-4-yl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-(cyclopropanecarbonylamino)-5-[3-[[5-(difluoromethoxy)-2-methylpyrazol-3-yl]amino]-1,2,4-triazol-4-yl]-N-[[(1R,2S)-2-fluorocyclopropyl]methyl]-4,5,6,7-tetrahydro-1-benzothiophene-3-carboxamide;

(5S)—N-[[(1R)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide;

(5S)—N-[[(1S)-2,2-difluorocyclopropyl]methyl]-5-[3-[(5-methoxy-2-methyl-pyrazol-3-yl)amino]-1,2,4-triazol-4-yl]-2-[[(1S,2S)-2-methylcyclopropanecarbonyl]amino]-4,5,6,7-tetrahydrobenzothiophene-3-carboxamide;

(5S)-5-[3-[(5-methoxy-2-methyl-pyrazol-3-yl)amino]-1,2,4-triazol-4-yl]-2-[[(1S,2S)-2-methylcyclopropanecarbonyl]amino]-N-[(2R*)-spiro[2.2]pentan-2-yl]-4,5,6,7-tetrahydrobenzothiophene-3-carboxamide [* or S];

(5S)—N-[[(1R,2S)-2-fluorocyclopropyl]methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-[trans-(3-fluorocyclobutyl)methyl]-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)—N-(cyclopropylmethyl)-5-[3-[(5-methoxy-2-methylpyrazol-3-yl)amino]-1,2,4-triazol-4-yl]-2-[[(1S,2S)-2-methylcyclopropanecarbonyl]amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide (5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide;

(5S)—N-[[(1R*)-2,2-difluorocyclopropyl]methyl]-5-[3-[[5-(difluoromethyl)-2-methyl-pyrazol-3-yl]amino]-1,2,4-triazol-4-yl]-2-[trans-(3-fluorocyclobutanecarbonyl)amino]-4,5,6,7-tetrahydrobenzothiophene-3-carboxamide [* or S];

(5S)—N-(cyclobutylmethyl)-5-[3-[[5-(difluoromethyl)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide;

(5S)-5-[3-[[5-(difluoromethyl)-2-methylpyrazol-3-yl]amino]-1,2,4-triazol-4-yl]-2-[cis-(3-fluorocyclobutanecarbonyl)amino]-N-(trans-3-fluorocyclobutyl)-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1S,2S)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethyl)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1S,2S)-2-fluorocyclopropyl]methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2R)-2-fluorocyclopropyl]methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[[(1R,2S)-2-fluorocyclopropyl]methyl]-4,5,6,7-tetrahydro-1-benzothiophene-3-carboxamide;

(5S)-5-[33-[[5-(difluoromethoxy)-2-methylpyrazol-3-yl]amino]-1,2,4-triazol-4-yl]-2-[trans-(3-fluorocyclobutanecarbonyl)amino]-N-[(2R)-spiro[2.2]pentan-2-yl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[(2S)-spiro[2.2]pentan-2-yl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-[trans-(3-fluorocyclobutyl)methyl]-4,5,6,7-tetrahydro-1-benzothiophene-3-carboxamide;

(5S)-5-[3-[[5-(difluoromethoxy)-2-methylpyrazol-3-yl]amino]-1,2,4-triazol-4-yl]-2-[trans-(3-fluorocyclobutanecarbonyl)amino]-N-(trans-3-fluorocyclobutyl)-4,5,6,7-tetrahydro-1-benzothiophene-3-carboxamide;

(5S)—N-1[[(1R)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)—N-[[(1S)-2,2-difluorocyclopropyl]methyl]-5-[3-[[5-(difluoromethoxy)-2-methylpyrazol-3-yl]amino]-1,2,4-triazol-4-yl]-2-[trans-(3-fluorocyclobutanecarbonyl)amino]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-[[(1S,2S)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-[[(1R,2R)-2-fluorocyclopropyl]methyl]-4,5,6,7-tetrahydro-1-benzothiophene-3-carboxamide;

(5S)-2-[(3,3-difluorocyclobutanecarbonyl)amino]-5-[3-[[5-(difluoromethoxy)-2-methylpyrazol-3-yl]amino]-1,2,4-triazol-4-yl]-N-(trans-3-fluorocyclobutyl)-4,5,6,7-tetrahydro-1-benzothiophene-3-carboxamide;

(5S)-2-[(2,2-difluorocyclopropanecarbonyl)amino]-5-[3-[[5-(difluoromethyl)-2-methyl-pyrazol-3-yl]amino]-1,2,4-triazol-4-yl]-N-(trans-3-fluorocyclobutyl)-4,5,6,7-tetrahydrobenzothiophene-3-carboxamide;

(5S)-2-cyclopropaneamido-5-(3-{[3-(difluoromethyl)-1-methyl-1H-pyrazol-5-yl]amino}-4H-1,2,4-triazol-4- yl)-N-{spiro[2.2]pentan-1-yl}-4,5,6,7-tetrahydro-1-benzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(2S)-spiro[2.2]pentan-2-yl]-4,5,6,7-tetrahydrobenzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(2R)-spiro[2.2]pentan-2-yl]-4,5,6,7-tetrahydrobenzothiophene-3-carboxamide;

(5S)-2-(cyclopropanecarbonylamino)-5-[3-[[5-(difluoromethyl)-2-methyl-pyrazol-3-yl]amino]-1,2,4-triazol-4-yl]-N-[(3-fluorocyclobutyl)methyl]-4,5,6,7-tetrahydrobenzothiophene-3-carboxamide;

(5S)-2-[[(1R*)-2,2-difluorocyclopropanecarbonyl]amino]-5-[3-[[5-(difluoromethyl)-2-methyl-pyrazol-3-yl]amino]-1,2,4-triazol-4-yl]-N-[[(1R,2R)-2-fluorocyclopropyl]methyl]-4,5,6,7-tetrahydrobenzothiophene-3-carboxamide (* or S);

(5S)—N-(cyclopropylmethyl)-5-[3-[(2,5-dimethylpyrazol-3-yl)amino]-1,2,4-triazol-4-yl]-2-(spiro[2.2]pentane-2-carbonylamino)-4,5,6,7-tetrahydrobenzothiophene-3-carboxamide;

(5S)—N-(cyclopropylmethyl)-5-[3-[(2,5-dimethylpyrazol-3-yl)amino]-1,2,4-triazol-4-yl]-2-[[(2S*)-spiro[2.2]pentane-2-carbonyl]amino]-4,5,6,7-tetrahydrobenzothiophene-3-carboxamide (* or R); and (3R*)-6-(cyclopropanecarbonylamino)-N-(cyclopropylmethyl)-3-[3-[[2-methyl-5-(trifluoromethyl)pyrazol-3-yl]amino]-1,2,4-triazol-4-yl]-3,4-dihydro-2H-thieno[2,3-b]pyran-5-carboxamide (* or S).

13. A compound according to claim 1 or a pharmaceutically acceptable salt thereof, wherein the compound is selected from:

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide;

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate;

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-isopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide;

(5S)—N-(cyclopropylmethyl)-5-[3-[(5-ethoxy-2-methyl-pyrazol-3-yl)amino]-1,2,4-triazol-4-yl]-2-[[(1R,2S)-2-fluorocyclopropanecarbonyl]amino]-4,5,6,7-tetrahydrobenzothiophene-3-carboxamide;

(5S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-2-[[(1R,2R)-2-fluorocyclopropanecarbonyl]amino]-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)—N-(cyclopropylmethyl)-5-[3-[(5-methoxy-2-methyl-pyrazol-3-yl)amino]-1,2,4-triazol-4-yl]-2-[[(2R*)-spiro[2.2]pentane-2-carbonyl]amino]-4,5,6,7-tetrahydrobenzothiophene-3-carboxamide (* or S); and (5S)—N-(cyclopropylmethyl)-5-[3-[(5-methoxy-2-methyl-pyrazol-3-yl)amino]-1,2,4-triazol-4-yl]-2-[[(2R*)-spiro[2.2]pentane-2-carbonyl]amino]-4,5,6,7-tetrahydrobenzothiophene-3-carboxamide (* or S).

14. A pharmaceutical composition comprising a compound according to claim 1 or a pharmaceutically acceptable salt thereof.

15. A compound according to claim 1 or a pharmaceutically acceptable salt thereof, wherein the compound is selected from:

(5S)-2-(Cyclopropanecarbonylamino)-N-(cyclopropylmethyl)-5-[3-[(2,5-dimethylpyrazol-3-yl)amino]-1,2,4-triazol-4-yl]-4,5,6,7-tetrahydrobenzothiophene-3-carboxamide;

Ethyl 5-amino-1-[(5S)-2-(cyclopropanecarbonylamino)-3-(cyclopropylmethylcarbamoyl)-4,5,6,7-tetrahydrobenzothiophen-5-yl]imidazole-4-carboxylate;

(5S)-2-(cyclopropanecarbonylamino)-N-(cyclopropylmethyl)-5-[3-(ethylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-(3-pyridylamino)-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-(cyclopropylmethylamino)-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-cyclopropyl-2-methyl-pyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[[2-methyl-5-(trifluoromethyl)pyrazol-3-yl]amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(2-methylpyrazol-3-yl)amino]-1,2,4-triazol-4-yl]-4,5,6,7-tetrahydrobenzothiophene-3-carboxamide;

(5S)-2-(cyclopropanecarbonylamino)-N-(cyclopropylmethyl)-5-[3-[(5-ethyl-2-methyl-pyrazol-3-yl)amino]-1,2,4-triazol-4-yl]-4,5,6,7-tetrahydrobenzothiophene-3-carboxamide;

(5S)-2-(Cyclopropanecarbonylamino)-N-(cyclopropylmethyl)-5-[3-[[5-(difluoromethyl)-2-methyl-pyrazol-3-yl]amino]-1,2,4-triazol-4-yl]-4,5,6,7-tetrahydrobenzothiophene-3-carboxamide; and (5S)-2-(cyclopropanecarbonylamino)-N-(cyclopropylmethyl)-5-[3-[5-(difluoromethoxy)-2-methylpyrazol-3-yl]amino]-1,2,4-triazol-4-yl]-4,5,6,7-tetrahydro-1-benzothiophene-3-carboxamide.

* * * * *